United States Patent
Kim et al.

(10) Patent No.: US 11,192,884 B2
(45) Date of Patent: Dec. 7, 2021

(54) HETEROCYCLIC COMPOUND AND ORGANIC LIGHT-EMITTING DEVICE COMPRISING SAME

(71) Applicant: LG CHEM, LTD., Seoul (KR)

(72) Inventors: Minjun Kim, Daejeon (KR); Kongkyeom Kim, Daejeon (KR); Hyok Joon Kwon, Daejeon (KR); Young Seok Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 378 days.

(21) Appl. No.: 16/339,868

(22) PCT Filed: Mar. 27, 2018

(86) PCT No.: PCT/KR2018/003621
§ 371 (c)(1),
(2) Date: Apr. 5, 2019

(87) PCT Pub. No.: WO2018/182300
PCT Pub. Date: Oct. 4, 2018

(65) Prior Publication Data
US 2020/0048226 A1    Feb. 13, 2020

(30) Foreign Application Priority Data
Mar. 27, 2017    (KR) .................. 10-2017-0038539

(51) Int. Cl.
*C07D 403/14*    (2006.01)
*C07D 407/14*    (2006.01)
(Continued)

(52) U.S. Cl.
CPC ......... *C07D 403/14* (2013.01); *C07D 407/14* (2013.01); *C07D 409/14* (2013.01);
(Continued)

(58) Field of Classification Search
CPC .. C07D 403/14; C07D 407/14; C07D 409/14; H01L 51/0067; H01L 51/0072
See application file for complete search history.

(56) References Cited

U.S. PATENT DOCUMENTS

| 2014/0231783 A1 | 8/2014 | Bae et al. |
| 2016/0260906 A1 | 9/2016 | Shin et al. |

(Continued)

FOREIGN PATENT DOCUMENTS

| CN | 103772268 A | 5/2014 |
| CN | 105980520 A | 9/2016 |

(Continued)

*Primary Examiner* — Vu A Nguyen
(74) *Attorney, Agent, or Firm* — Dentons US LLP

(57) ABSTRACT

The present specification relates to a heterocyclic compound of Chemical Formula 1, and an organic light emitting device comprising the same. The heterocyclic compound as a material of an organic material layer of the organic light
(Continued)

emitting device provides enhanced efficiency, low driving voltage and increased lifetime.

[Chemical Formula 1]

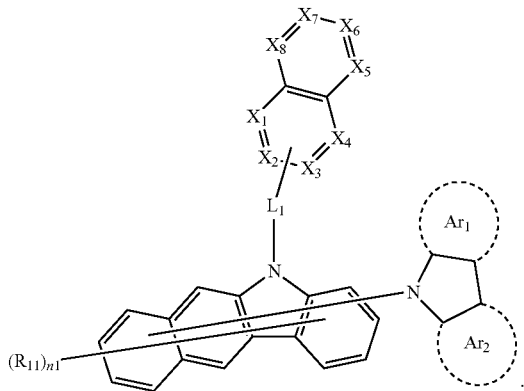

9 Claims, 4 Drawing Sheets

(51) Int. Cl.
C07D 409/14 (2006.01)
H01L 51/00 (2006.01)
H01L 51/50 (2006.01)

(52) U.S. Cl.
CPC ...... H01L 51/0054 (2013.01); H01L 51/0067 (2013.01); H01L 51/0072 (2013.01); H01L 51/0073 (2013.01); H01L 51/0074 (2013.01); H01L 51/5056 (2013.01); H01L 51/5072 (2013.01)

(56) References Cited

U.S. PATENT DOCUMENTS

2016/0336518 A1* 11/2016 Chun .................. H01L 51/0054
2017/0012217 A1    1/2017  Chun et al.
2017/0117485 A1    4/2017  Cho et al.
2018/0182973 A1    6/2018  Kim et al.

FOREIGN PATENT DOCUMENTS

| | | | |
|---|---|---|---|
| CN | 105980521 A | 9/2016 | |
| CN | 106068267 A | 11/2016 | |
| CN | 107635964 A | 1/2018 | |
| CN | 110024155 A | 7/2019 | |
| JP | 2015-221780 A | 12/2015 | |
| KR | 10-2012-0030009 A | 3/2012 | |
| KR | 10-2013-0055198 A | 5/2013 | |
| KR | 10-2013-0055216 A | 5/2013 | |
| KR | 10-2014-0103393 A | 8/2014 | |
| KR | 10-2014-0105633 A | 9/2014 | |
| KR | 10-2015-0114009 A | 10/2015 | |
| KR | 10-2016-0029721 A | 3/2016 | |
| KR | 10-2016-0059413 A | 5/2016 | |
| WO | 2015-053575 A1 | 4/2015 | |
| WO | WO-2016036171 A1 * | 3/2016 | ........... C07D 519/00 |

* cited by examiner

[FIG. 1]
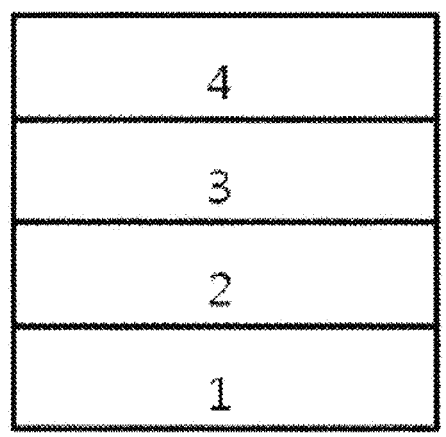

[FIG. 2]
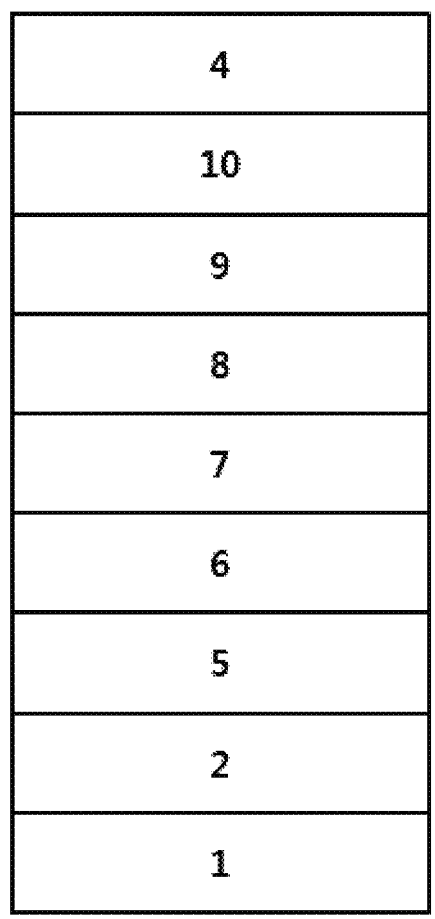

[FIG. 3]
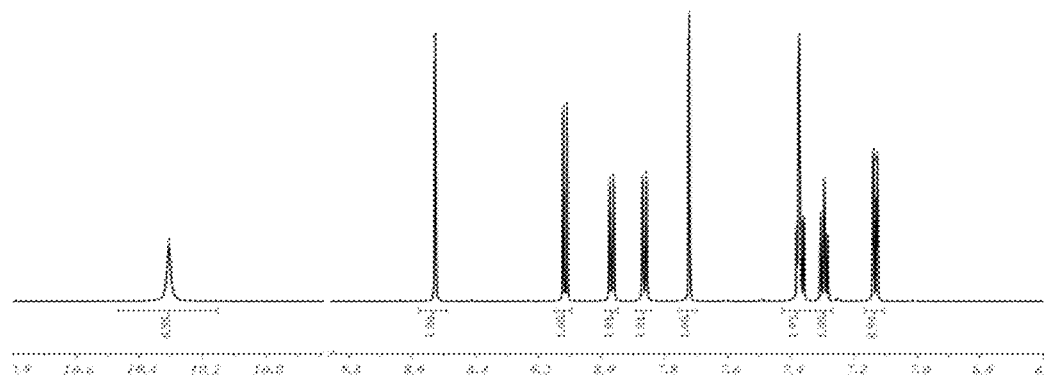
[FIG. 4]
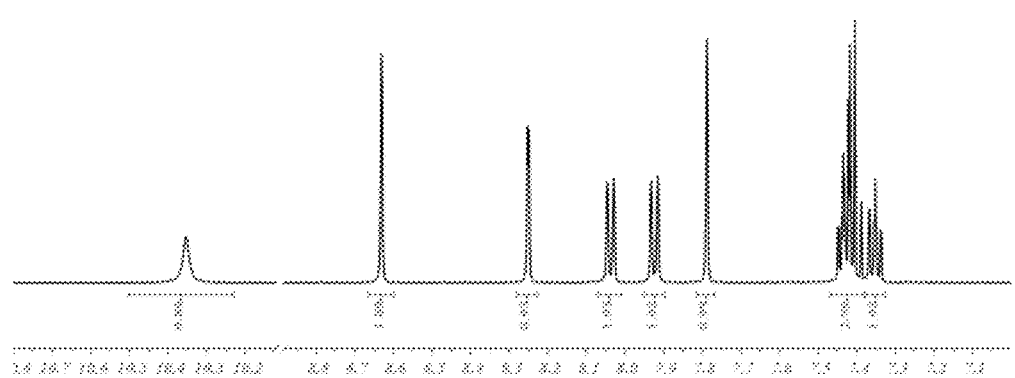

【FIG. 5】
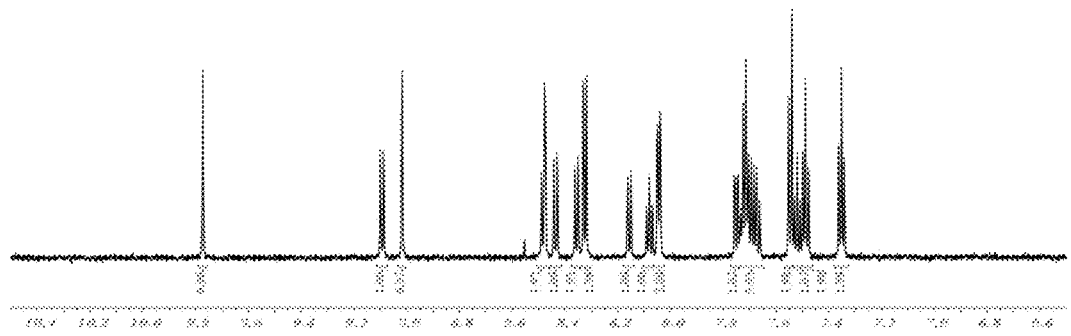
【FIG. 6】
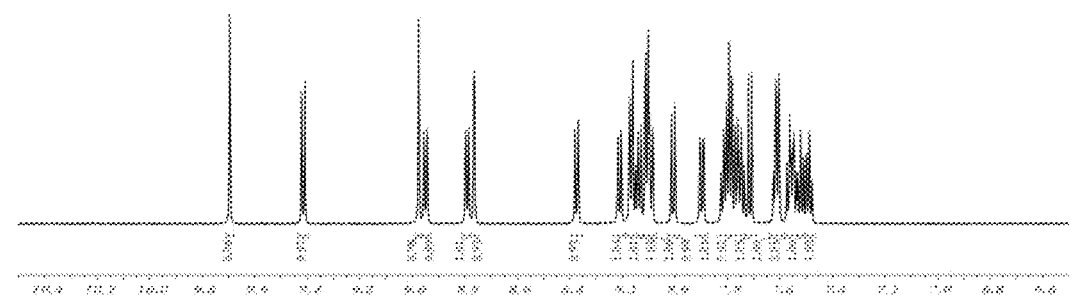

HETEROCYCLIC COMPOUND AND ORGANIC LIGHT-EMITTING DEVICE COMPRISING SAME

TECHNICAL FIELD

This application the National Phase of PCT International Application No. PCT/KR2018/003621, filed on Mar. 27, 2018, which claims priority to Korean Patent Application No. 10-2017-0038539, filed Mar. 27, 2017, the entire contents of which are incorporated herein by reference.

The present specification relates to a heterocyclic compound and an organic light emitting device comprising the same.

BACKGROUND ART

An organic light emitting device has a structure disposing an organic thin film between two electrodes. When a voltage is applied to an organic light emitting device having such a structure, electrons and holes injected from the two electrodes bind in the organic thin film to form a pair, and light emits as they disappear. The organic thin film may be formed in a single layer or a multilayer as necessary.

Materials used in organic light emitting devices are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and electrochemically stable when oxidized, are generally used. Meanwhile, as the electron injection material or the electron transfer material, organic materials having an n-type property, that is, organic materials readily reduced and electrochemically stable when reduced, are generally used. As the light emitting layer material, materials having both a p-type property and an n-type property, that is, materials having a stable form in both oxidized and reduced states, are preferred, and materials having high light emission efficiency converting, when excitons generated by the holes and the electrons recombining in the light emitting layer are formed, the excitons to light are preferred.

In order to enhance performance, lifetime or efficiency of an organic light emitting device, development of organic thin film materials has been consistently required.

DISCLOSURE

Technical Problem

The present specification is directed to providing a heterocyclic compound and an organic light emitting device comprising the same.

Technical Solution

One embodiment of the present specification provides a heterocyclic compound represented by the following Chemical Formula 1.

[Chemical Formula 1]

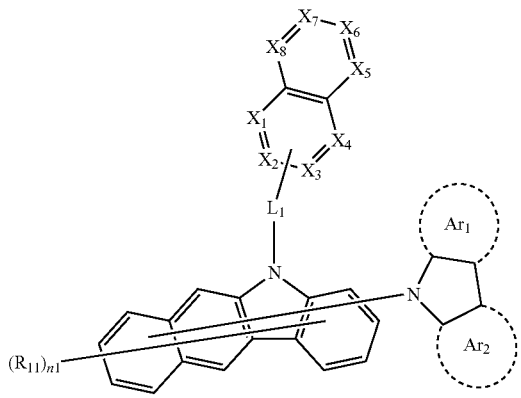

In Chemical Formula 1, $Ar_1$ and $Ar_2$ are the same as or different from each other and each independently substituted or unsubstituted benzene; or substituted or unsubstituted naphthalene, and any one of $Ar_1$ and $Ar_2$ is substituted or unsubstituted benzene, $X_1$ to $X_4$ are the same as or different from each other, and each independently N, CH, CRa, or C linked to $L_1$, $X_5$ to $X_8$ are the same as or different from each other, and each independently N, CH or CRa, at least one of $X_1$ to $X_8$ is CRa, Ra is a substituted or unsubstituted aryl group having 6 to 60 carbon atoms; or a substituted or unsubstituted heterocyclic group having 2 to 60 carbon atoms, $L_1$ is a direct bond; or a substituted or unsubstituted arylene group having 6 to 60 carbon atoms, $R_{11}$ is hydrogen or deuterium, and n1 is an integer of 0 to 9, and provided that n1 is 2 or greater, two or more $R_{11}$s is are the same as or different from each other.

Another embodiment of the present specification provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A heterocyclic compound described in the present specification can be used as a material of an organic material layer of an organic light emitting device. A compound according to at least one embodiment is capable of enhancing efficiency, obtaining a low driving voltage and/or enhancing lifetime properties in an organic light emitting device. A compound described in the present specification can be used as a material of a hole injection layer, a hole transfer layer, a hole injection layer and hole transfer layer, an electron blocking layer, a light emitting layer, a hole blocking layer, an electron transfer layer or an electron injection layer.

DESCRIPTION OF DRAWINGS

FIG. 1 illustrates an example of an organic light emitting device formed with a substrate (1), an anode (2), a light emitting layer (3) and a cathode (4).

FIG. 2 illustrates an example of an organic light emitting device formed with a substrate (1), an anode (2), a hole injection layer (5), a hole transfer layer (6), an electron blocking layer (7), a light emitting layer (8), a hole blocking layer (9), an electron injection and transfer layer (10) and a cathode (4).

FIG. 3 shows a graph measuring 1H-NMR of Chemical Formula a.

FIG. 4 shows a graph measuring 1H-NMR of Chemical Formula b.

FIG. 5 shows a graph measuring 1H-NMR of Compound 547.

FIG. 6 shows a graph measuring 1H-NMR of Compound 1057.

1: Substrate
2: Anode
3: Light Emitting Layer
4: Cathode
5: Hole Injection Layer
6: Hole Transfer Layer
7: Electron Blocking Layer
8: Light Emitting Layer
9: Hole Blocking Layer
10: Electron Injection and Transfer Layer

MODE FOR DISCLOSURE

Hereinafter, the present specification will be described in more detail.

The present specification provides a heterocyclic compound represented by Chemical Formula 1. When using the heterocyclic compound represented by Chemical Formula 1 in an organic material layer of an organic light emitting device, efficiency of the organic light emitting device is enhanced, and a low driving voltage and excellent lifetime properties are obtained as well.

In the present specification, a description of a certain part "comprising" certain constituents means capable of further comprising g other constituents, and does not exclude other constituents unless particularly stated on the contrary.

In the present specification, a description of one member being placed "on" another member comprises not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted alkylamine group; a substituted or unsubstituted arylamine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may comprise a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, examples of the halogen group may comprise fluorine (F), chlorine (Cl), bromine (Br) or iodine (I).

In the present specification, the silyl group may be represented by a chemical formula of $-SiY_aY_bY_c$, and $Y_a$, $Y_b$ and $Y_c$ may each be hydrogen; a substituted or unsubstituted alkyl group; or a substituted or unsubstituted aryl group. Specific examples of the silyl group may comprise a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the boron group may be represented by a chemical formula of $-BY_dY_e$, and $Y_d$ and $Y_d$ may each be hydrogen; a substituted or unsubstituted alkyl group; or a substituted or unsubstituted aryl group. Specific examples of the boron group may comprise a trimethylboron group, a triethylboron group, a t-butyldimethylboron group, a triphenylboron group, a phenylboron group and the like, but are not limited thereto.

In the present specification, the alkylamine group preferably has, although not particularly limited thereto, 1 to 40 carbon atoms. Specific examples of the alkylamine group may comprise a methylamine group, a dimethylamine group, an ethylamine group, a diethylamine group and the like, but are not limited thereto.

In the present specification, examples of the arylamine group comprise a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group comprising two or more aryl groups may comprise monocyclic aryl groups, polycyclic aryl groups, or both monocyclic aryl groups and polycyclic aryl groups.

Specific examples of the arylamine group may comprise phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, the alkyl group may be linear or branched, and although not particularly limited thereto, the number of carbon atoms is preferably from 1 to 60. According to one embodiment, the number of carbon atoms of the alkyl group is from 1 to 40. According to another embodiment, the number of carbon atoms of the alkyl group is from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the cycloalkyl group is not particularly limited, but preferably has 3 to 60 carbon atoms. According to one embodiment, the number of carbon atoms of the cycloalkyl group is from 3 to 40. According to another embodiment, the number of carbon atoms of the cycloalkyl group is from 1 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may be linear, branched or cyclic. The number of carbon atoms of the alkoxy group is not particularly limited, but is preferably from 1 to 30. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

In the present specification, the alkenyl group may be linear or branched, and although not particularly limited thereto, the number of carbon atoms is preferably from 2 to 30. Specific examples thereof may comprise vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl and the like, but are not limited thereto.

In the present specification, the aryl group is not particularly limited, but preferably has 6 to 60 carbon atoms, and may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may comprise a phenyl group, a biphenyl group, a terphenyl group and the like, but are not limited thereto. Examples of the polycyclic aryl group may comprise a naphthyl group, an anthracenyl group, a phenanthrenyl group, a pyrenyl group, a perylenyl group, a triphenylene group, a chrysenyl group, a fluorenyl group and the like, but are not limited thereto.

In the present specification, the fluorenyl group may be substituted, and adjacent substituents may bond to each other to form a ring.

When the fluorenyl group is substituted,

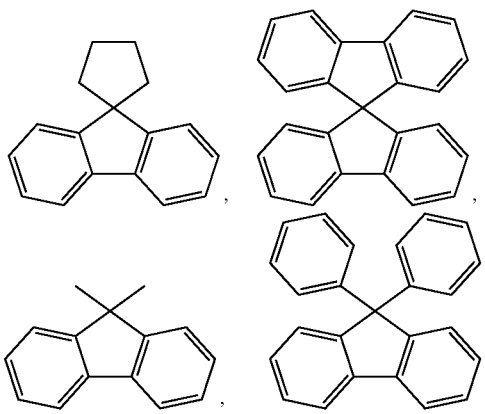

and the like may be included. However, the structure is not limited thereto.

In the present specification, the heterocyclic group is a heterocyclic group comprising one or more of N, O, P, S, Si and Se as a heteroatom, and although not particularly limited thereto, the number of carbon atoms is preferably from 2 to 60. According to one embodiment, the number of carbon atoms of the heterocyclic group is from 2 to 30. Examples of the heterocyclic group may comprise a pyridyl group, a pyrrole group, a pyrimidyl group, a pyridazinyl group, a furanyl group, a thiophenyl group, an imidazole group, a pyrazole group, an oxazole group, an isoxazole group, a thiazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophenyl group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In the present specification, descriptions on the heterocyclic group provided above may be applied to the heteroaryl group except for being aromatic.

In the present specification, descriptions on the aryl group provided above may be applied to the arylene group except for being divalent.

In the present specification, the "ring" in the substituted or unsubstituted ring formed by adjacent groups bonding to each other means a substituted or unsubstituted hydrocarbon ring; or a substituted or unsubstituted heteroring.

In the present specification, the hydrocarbon ring may be aromatic, aliphatic or a fused ring of aromatic and aliphatic, and may be selected from among examples of the cycloalkyl group or the aryl group except for those that are divalent.

In the present specification, descriptions on the aryl group may be applied to the aromatic hydrocarbon ring except for being divalent for those that are divalent.

In the present specification, the heteroring comprises one or more atoms that are not carbon, that is, heteroatoms, and specifically, the heteroatom may comprise one or more atoms selected from the group consisting of O, N, Se, S and the like. The heteroring may be monocyclic or polycyclic, aromatic, aliphatic or a fused ring of aromatic and aliphatic, and the aromatic heteroring may be selected from among examples of the heteroaryl group except for those that are not monovalent.

According to one embodiment of the present specification, $Ar_1$ and $Ar_2$ are the same as or different from each other and each independently substituted or unsubstituted benzene; or substituted or unsubstituted naphthalene, and any one of $Ar_1$ and $Ar_2$ is substituted or unsubstituted benzene.

According to another embodiment, $Ar_1$ and $Ar_2$ are the same as or different from each other and each independently benzene; or naphthalene, and any one of $Ar_1$ and $Ar_2$ is benzene.

According to another embodiment, any one of $Ar_1$ and $Ar_2$ is substituted or unsubstituted benzene, and the remaining one is substituted or unsubstituted benzene; or substituted or unsubstituted naphthalene. The naphthalene may be any one of the following structures.

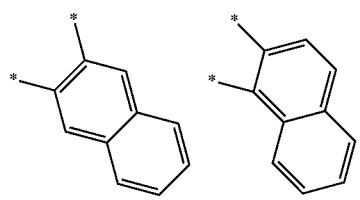

In the structures, "*" means a site bonding to Chemical Formula 1.

In another embodiment, any one of $Ar_1$ and $Ar_2$ is benzene, and the remaining one is benzene; or naphthalene. The naphthalene may be any one of the following structures.

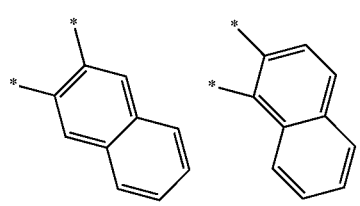

In one embodiment of the present specification, Chemical Formula 1 may be represented by any one of the following Chemical Formulae 2 to 5.

[Chemical Formula 2]

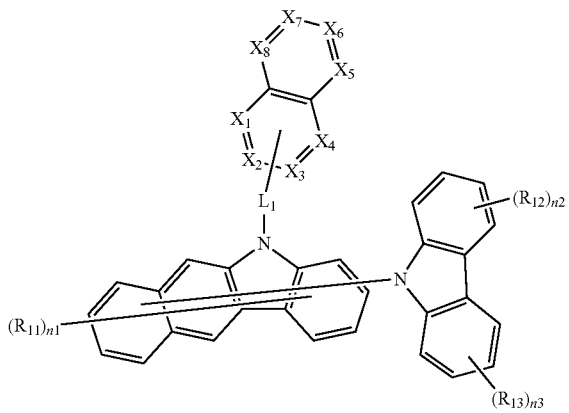

[Chemical Formula 3]

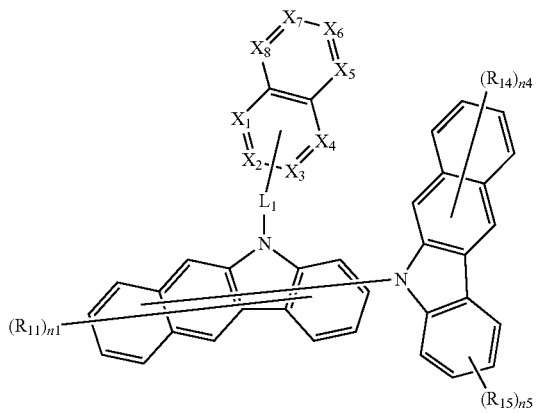

[Chemical Formula 4]

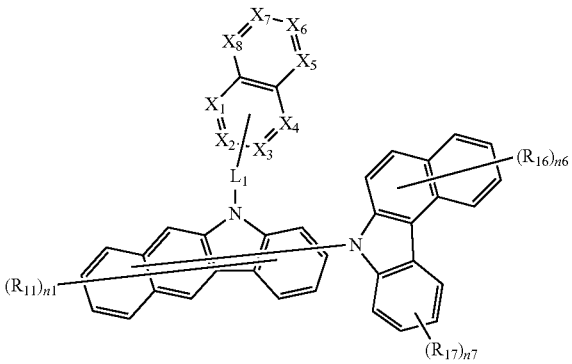

[Chemical Formula 5]

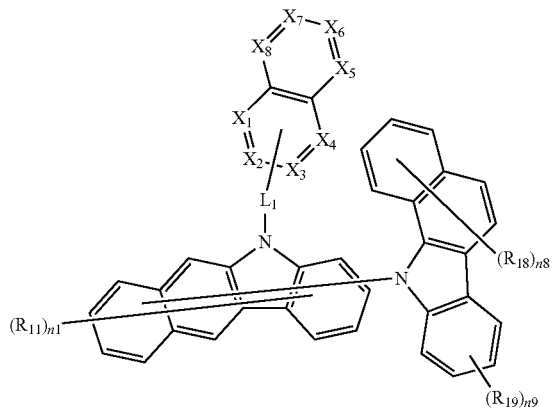

In Chemical Formulae 2 to 5, $X_1$ to $X_8$, $R_{11}$, n1 and $L_1$ have the same definitions as in Chemical Formula 1, $R_{12}$ to $R_{19}$ are the same as or different from each other, and each independently hydrogen; deuterium; a halogen group; a nitrile group; a substituted or unsubstituted alkyl group; a substituted or unsubstituted alkenyl group; a substituted or unsubstituted alkoxy group; a substituted or unsubstituted cycloalkyl group; a substituted or unsubstituted alkylamine group; a substituted or unsubstituted arylamine group; a substituted or unsubstituted aryl group; or a substituted or unsubstituted heterocyclic group, n2, n3, n5, n7 and n9 are each an integer of 0 to 4, n4, n6 and n8 are each an integer of 0 to 6, and provided that n2 to n9 are each 2 or greater, substituents in the parentheses are the same as or different from each other.

According to one embodiment of the present specification, $R_{11}$ is hydrogen or deuterium, n1 is an integer of 0 to 9, and when n1 is 2 or greater, two or more $R_{11}$s are the same as or different from each other.

In another embodiment, $R_{11}$ is hydrogen.

According to another embodiment, $R_{11}$ is deuterium.

According to one embodiment of the present specification, $L_1$ is a direct bond; or a substituted or unsubstituted arylene group having 6 to 60 carbon atoms.

According to another embodiment, $L_1$ is a direct bond; or a substituted or unsubstituted arylene group having 6 to 30 carbon atoms.

In another embodiment, $L_1$ is a direct bond; substituted or unsubstituted phenylene; or substituted or unsubstituted naphthylene.

According to another embodiment, $L_1$ is a direct bond; phenylene; or naphthylene.

According to one embodiment of the present specification, $X_1$ to $X_4$ are the same as or different from each other and each independently N, CH, CRa, or C linked to $L_1$, two or more of $X_1$ to $X_4$ are N, any one of $X_1$ to $X_4$ is C linked to $L_1$, $X_5$ to $X_8$ are the same as or different from each other and each independently N, CH or CRa, and at least one of $X_1$ to $X_8$ is CRa.

According to another embodiment, $X_1$ to $X_4$ are the same as or different from each other and each independently N, CH, CRa, or C linked to $L_1$, two or more of $X_1$ to X4 are N, any one of $X_1$ to $X_4$ is C linked to $L_1$, $X_5$ to $X_8$ are the same as or different from each other and each independently N, CH or CRa, and at least one of $X_1$ to $X_8$ is CRa.

In another embodiment, $X_1$ to $X_4$ are the same as or different from each other and each independently N, CH, CRa, or C linked to $L_1$, two of $X_1$ to $X_4$ are N, any one of $X_1$ to $X_4$ is C linked to $L_1$, $X_5$ to $X_8$ are the same as or different from each other and each independently N, CH or CRa, one of $X_1$ to $X_8$ is CRa, and the rest are CH.

According to another embodiment, two of $X_1$ to $X_4$ are N, any one of $X_1$ to $X_4$ is C linked to $L_1$, the remaining one is CRa, and $X_5$ to $X_8$ are CH.

According to one embodiment of the present disclosure, Ra is a substituted or unsubstituted aryl group having 6 to 60 carbon atoms; or a substituted or unsubstituted heterocyclic group having 2 to 60 carbon atoms.

According to another embodiment, Ra is a substituted or unsubstituted aryl group having 6 to 30 carbon atoms; or a substituted or unsubstituted heterocyclic group having 2 to 30 carbon atoms.

In another embodiment, Ra is an aryl group having 6 to 30 carbon atoms unsubstituted or substituted with an alkyl group having 1 to 20 carbon atoms or an aryl group having 6 to 30 carbon atoms; or a heterocyclic group having 2 to 30 carbon atoms unsubstituted or substituted with an alkyl group having 1 to 20 carbon atoms or an aryl group having 6 to 30 carbon atoms.

In another embodiment, Ra is a substituted or unsubstituted phenyl group; a substituted or unsubstituted naphthyl group; a substituted or unsubstituted biphenyl group; a substituted or unsubstituted terphenyl group; a substituted or unsubstituted triphenylene group; a substituted or unsubstituted fluoranthene group; a substituted or unsubstituted fluorenyl group; a substituted or unsubstituted phenanthrenyl group; a substituted or unsubstituted dibenzofuranyl group; a substituted or unsubstituted dibenzothiophenyl group; or a substituted or unsubstituted carbazole group.

According to another embodiment, Ra is a phenyl group unsubstituted or substituted with an alkyl group having 1 to 20 carbon atoms or an aryl group having 6 to 30 carbon atoms; a naphthyl group unsubstituted or substituted with an alkyl group having 1 to 20 carbon atoms or an aryl group having 6 to 30 carbon atoms; a biphenyl group unsubstituted or substituted with an alkyl group having 1 to 20 carbon atoms or an aryl group having 6 to 30 carbon atoms; a terphenyl group unsubstituted or substituted with an alkyl group having 1 to 20 carbon atoms or an aryl group having 6 to 30 carbon atoms; a triphenylene group unsubstituted or substituted with an alkyl group having 1 to 20 carbon atoms or an aryl group having 6 to carbon atoms; a fluoranthene group unsubstituted or substituted with an alkyl group having 1 to 20 carbon atoms or an aryl group having 6 to 30 carbon atoms; a fluorenyl group unsubstituted or substituted with an alkyl group having 1 to 20 carbon atoms or an aryl group having 6 to 30 carbon atoms; a phenanthrenyl group unsubstituted or substituted with an alkyl group having 1 to 20 carbon atoms or an aryl group having 6 to 30 carbon atoms; a dibenzofuranyl group unsubstituted or substituted with an alkyl group having 1 to 20 carbon atoms or an aryl group having 6 to 30 carbon atoms; a dibenzothiophenyl group unsubstituted or substituted with an alkyl group having 1 to 20 carbon atoms or an aryl group having 6 to 30 carbon atoms; or a carbazole group unsubstituted or substituted with an alkyl group having 1 to 20 carbon atoms or an aryl group having 6 to 30 carbon atoms.

In another embodiment, Ra is a phenyl group; a naphthyl group; a biphenyl group; a terphenyl group; a triphenylene group; a fluoranthene group; a fluorenyl group substituted with a methyl group; a phenanthrenyl group; a dibenzofuranyl group; a dibenzothiophenyl group; or a carbazole group substituted with a phenyl group.

According to one embodiment of the present specification,

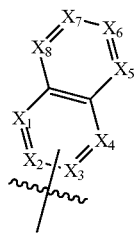

may be any one of the following structures.

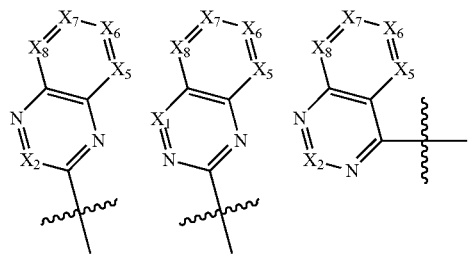

In the structures, $X_1$, $X_2$ and $X_5$ to $X_8$ have the same definitions as in Chemical Formula 1, and

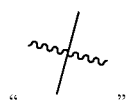

" "

means bonding to $L_1$ of Chemical Formula 1.

In one embodiment of the present specification, Chemical Formula 1 may be represented by any one of the following Chemical Formulae 1-1 to 1-3.

[Chemical Formula 1-1]

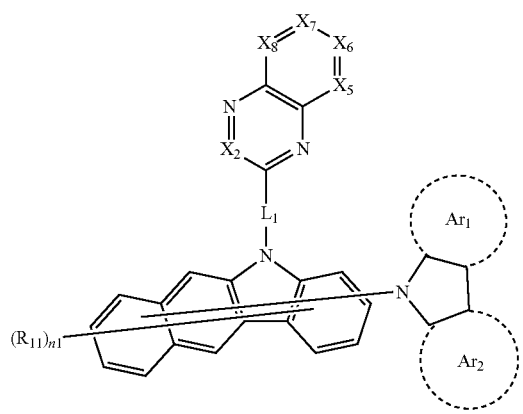

[Chemical Formula 1-2]

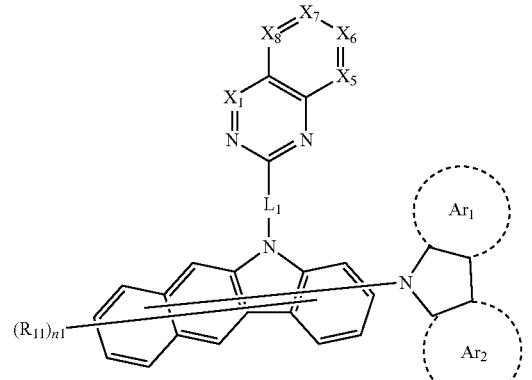

[Chemical Formula 1-3]

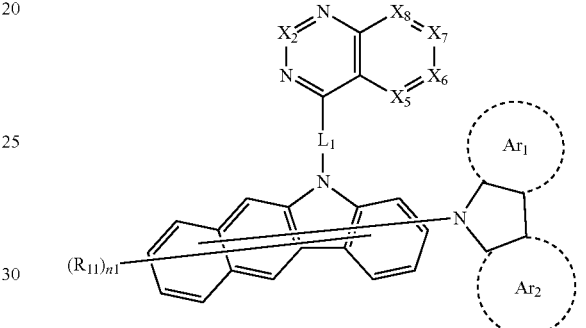

In Chemical Formulae 1-1 to 1-3, $X_1$, $X_2$, $X_5$ to $X_8$, $R_{11}$, n1, $L_1$, $Ar_1$ and $Ar_2$ have the same definitions as in Chemical Formula 1.

According to another embodiment,

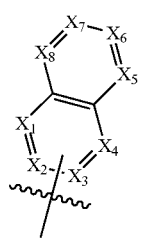

may be any one of the following structures.

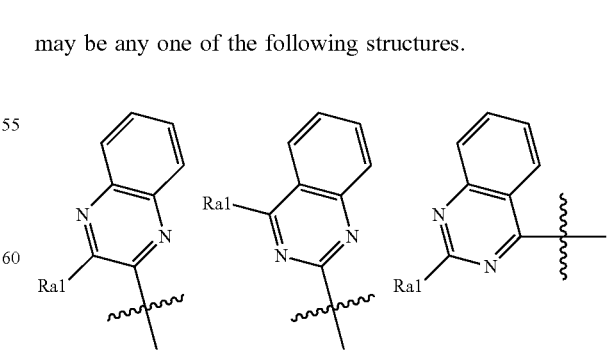

In the structures, Ra1 has the same definition as Ra in Chemical Formula 1.

In one embodiment of the present specification, Chemical Formula 1 may be represented by any one of the following Chemical Formulae 1-1-1 to 1-1-3.

[Chemical Formula 1-1-1]

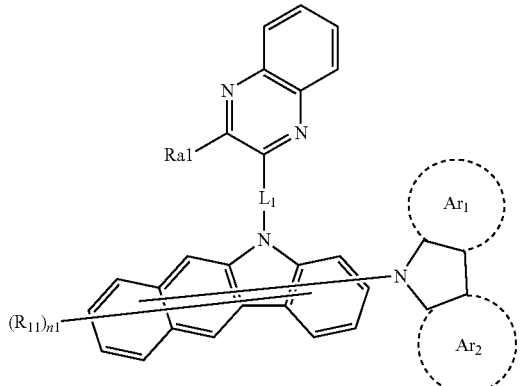

[Chemical Formula 1-1-2]

[Chemcial Formula 1-1-3]

In Chemical Formulae 1-1-1 to 1-1-3, $R_{11}$, n1, $L_1$, $Ar_1$ and $Ar_2$ have the same definitions as in Chemical Formula 1, Ra1 is a substituted or unsubstituted aryl group having 6 to 60 carbon atoms; or a substituted or unsubstituted heterocyclic group having 2 to 60 carbon atoms.

According to one embodiment of the present specification, Chemical Formula 2 may be represented by any one of the following Chemical Formulae 2-1 to 2-3.

[Chemical Formula 2-1]

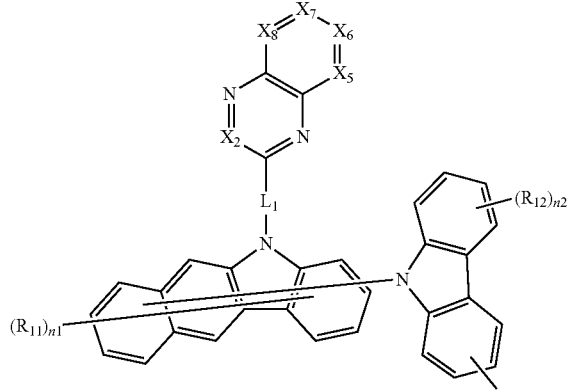

[Chemical Formula 2-2]

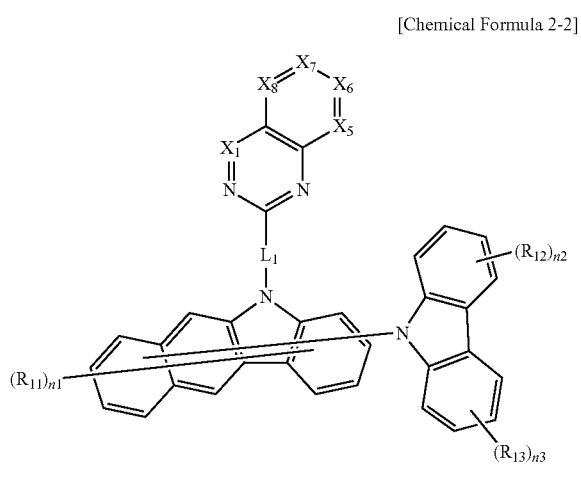

[Chemical Formula 2-3]

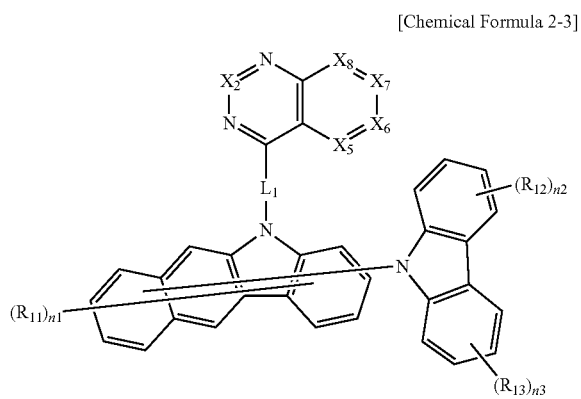

In Chemical Formulae 2-1 to 2-3, $X_1$, $X_2$, $X_5$ to $X_8$, $L_1$, $R_{11}$ to $R_{13}$ and n1 to n3 have the same definitions as in Chemical Formula 2.

According to one embodiment of the present specification, Chemical Formula 3 may be represented by any one of the following Chemical Formulae 2-4 to 2-6.

[Chemical Formula 2-4]

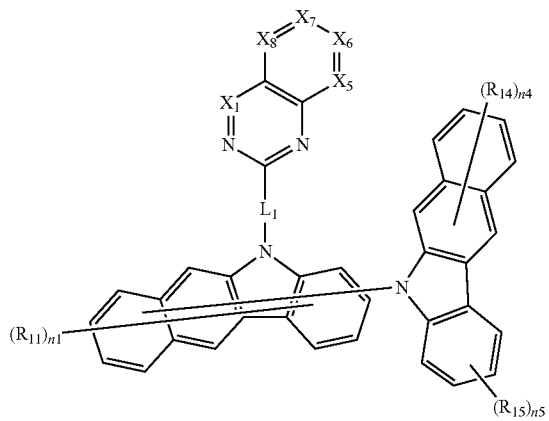

[Chemical Formula 2-5]

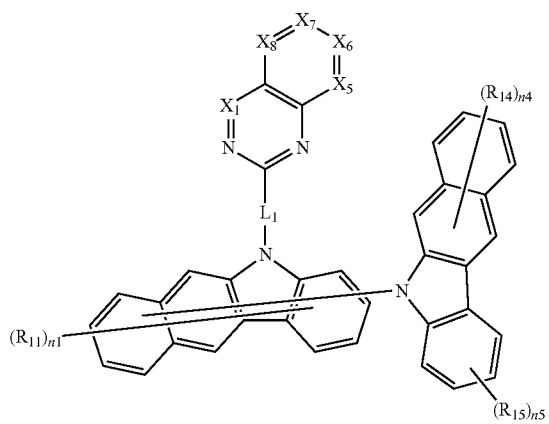

[Chemical Formula 2-6]

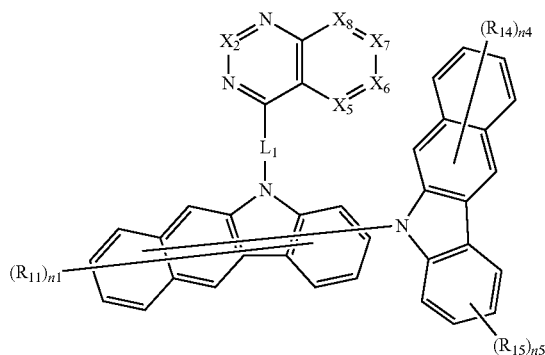

In Chemical Formulae 2-4 to 2-6, $X_1$, $X_2$, $X_5$ to $X_8$, $L_1$, $R_{11}$, $R_{14}$, $R_{15}$, n1, n4 and n5 have the same definitions as in Chemical Formula 3.

According to one embodiment of the present specification, Chemical Formula 4 may be represented by any one of the following Chemical Formulae 2-7 to 2-9.

[Chemical Formula 2-7]

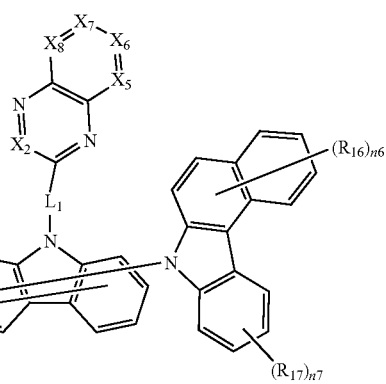

[Chemical Formula 2-8]

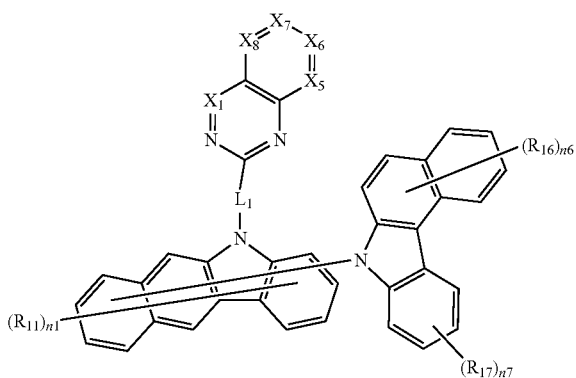

[Chemical Formula 2-9]

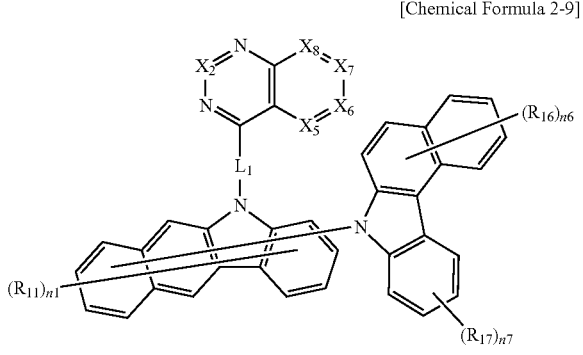

In Chemical Formulae 2-7 to 2-9, $X_1$, $X_2$, $X_5$ to $X_8$, $L_1$, $R_{11}$, $R_{16}$, $R_{17}$, n1, n6 and n7 have the same definitions as in Chemical Formula 4.

According to one embodiment of the present specification, Chemical Formula 5 may be represented by any one of the following Chemical Formulae 2-10 to 2-12.

[Chemical Formula 2-10]

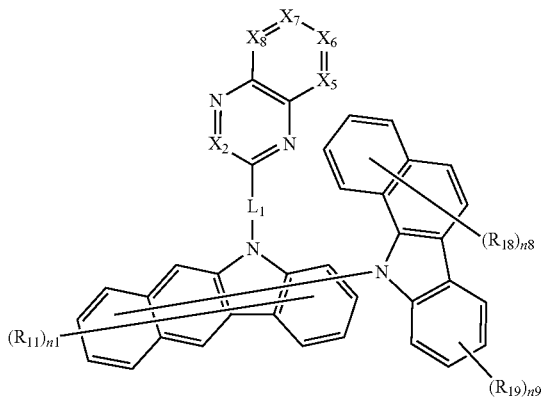

[Chemical Formula 2-11]

[Chemical Formula 2-12]

In Chemical Formulae 2-10 to 2-12, $X_1$, $X_2$, $X_5$ to $X_8$, $L_1$, $R_{11}$, $R_{18}$, $R_{19}$, n1, n8 and n9 have the same definitions as in Chemical Formula 5.

According to one embodiment of the present specification, Chemical Formula 2 may be represented by any one of the following Chemical Formulae 2-1-1 to 2-1-3.

[Chemical Formula 2-1-1]

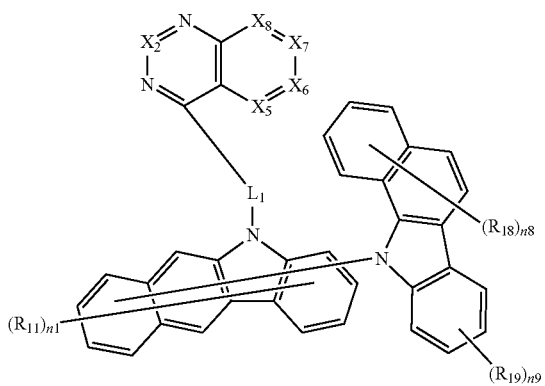

[Chemical Formula 2-1-2]

[Chemical Formula 2-1-3]

In Chemical Formulae 2-1-1 to 2-1-3, $L_1$, $R_{11}$ to $R_{13}$ and n1 to n3 have the same definitions as in Chemical Formula 2, and Ra1 is a substituted or unsubstituted aryl group having 6 to 60 carbon atoms; or a substituted or unsubstituted heterocyclic group having 2 to 60 carbon atoms.

According to one embodiment of the present specification, Chemical Formula 3 may be represented by any one of the following Chemical Formulae 2-1-4 to 2-1-6.

[Chemical Formula 2-1-4]

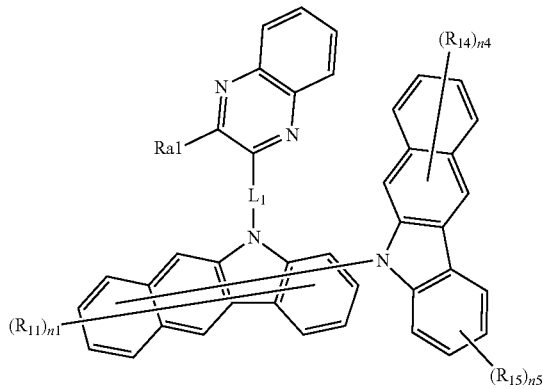

[Chemical Formula 2-1-7]

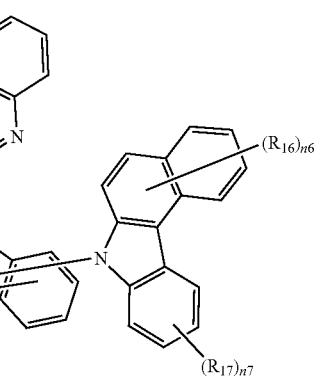

[Chemical Formula 2-1-5]

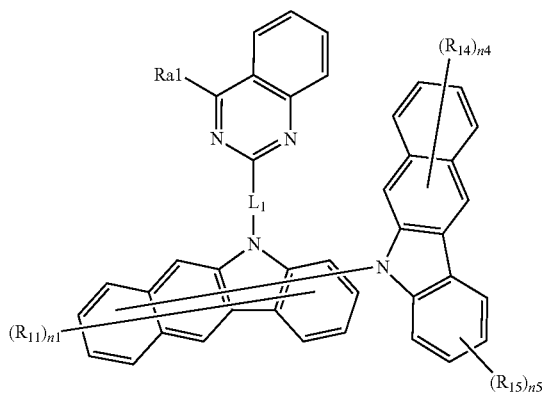

[Chemical Formula 2-1-8]

[Chemical Formula 2-1-6]

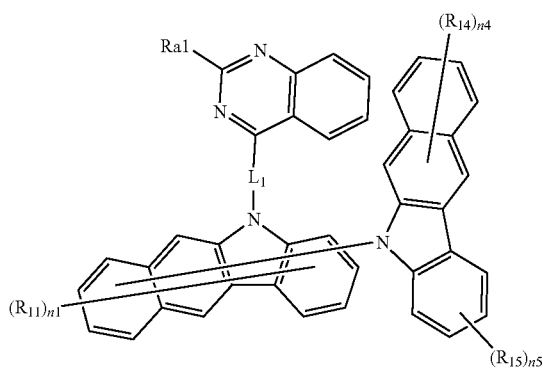

[Chemical Formula 2-1-9]

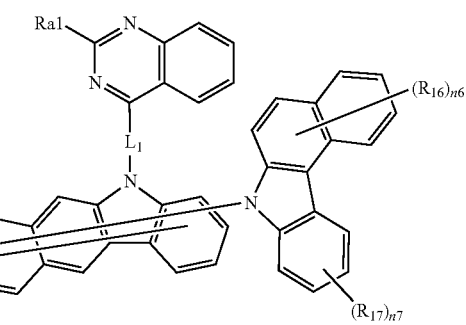

In Chemical Formulae 2-1-4 to 2-1-6, $L_1$, $R_{11}$, $R_{14}$, $R_{15}$, n1, n4 and n5 have the same definitions as in Chemical Formula 3, and Ra1 is a substituted or unsubstituted aryl group having 6 to 60 carbon atoms; or a substituted or unsubstituted heterocyclic group having 2 to 60 carbon atoms.

According to one embodiment of the present specification, Chemical Formula 4 may be represented by any one of the following Chemical Formulae 2-1-7 to 2-1-9.

In Chemical Formulae 2-1-7 to 2-1-9, $L_1$, $R_{11}$, $R_{16}$, $R_{17}$, n1, n6 and n7 have the same definitions as in Chemical Formula 4, and Ra1 is a substituted or unsubstituted aryl group having 6 to 60 carbon atoms; or a substituted or unsubstituted heterocyclic group having 2 to 60 carbon atoms.

According to one embodiment of the present specification, Chemical Formula 5 may be represented by any one of the following Chemical Formulae 2-1-10 to 2-1-12.

[Chemical Formula 2-1-10]

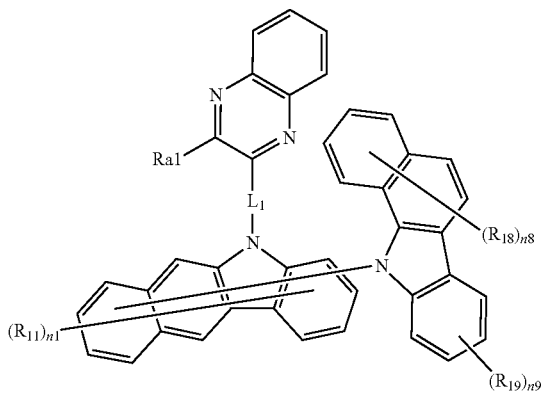

[Chemical Formula 2-1-11]

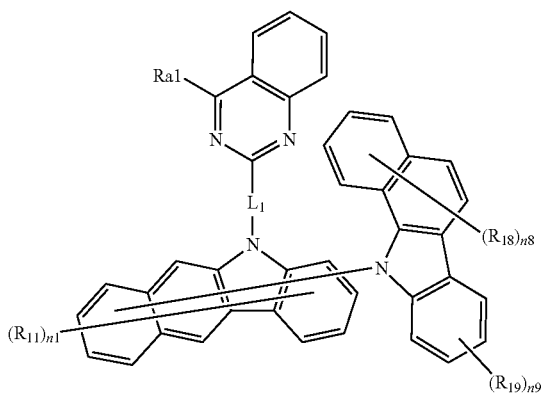

[Chemical Formula 2-1-12]

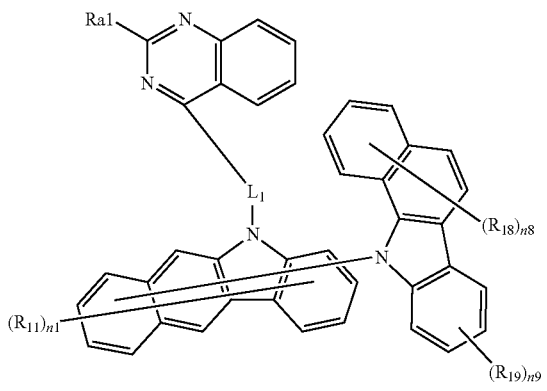

In Chemical Formulae 2-1-10 to 2-1-12, $L_1$, $R_{11}$, $R_{18}$, $R_{19}$, n1, n8 and n9 have the same definitions as in Chemical Formula 5, and Ra1 is a substituted or unsubstituted aryl group having 6 to 60 carbon atoms; or a substituted or unsubstituted heterocyclic group having 2 to 60 carbon atoms.

In one embodiment of the present disclosure, Ra1 is a substituted or unsubstituted aryl group having 6 to 60 carbon atoms; or a substituted or unsubstituted heterocyclic group having 2 to 60 carbon atoms.

According to another embodiment, Ra1 is a substituted or unsubstituted aryl group having 6 to 30 carbon atoms; or a substituted or unsubstituted heterocyclic group having 2 to 30 carbon atoms.

In another embodiment, Ra1 is an aryl group having 6 to 30 carbon atoms unsubstituted or substituted with an alkyl group having 1 to 20 carbon atoms or an aryl group having 6 to 30 carbon atoms; or a heterocyclic group having 2 to 30 carbon atoms unsubstituted or substituted with an alkyl group having 1 to 20 carbon atoms or an aryl group having 6 to 30 carbon atoms.

In another embodiment, Ra1 is a substituted or unsubstituted phenyl group; a substituted or unsubstituted naphthyl group; a substituted or unsubstituted biphenyl group; a substituted or unsubstituted terphenyl group; a substituted or unsubstituted triphenylene group; a substituted or unsubstituted fluoranthene group; a substituted or unsubstituted fluorenyl group; a substituted or unsubstituted phenanthrenyl group; a substituted or unsubstituted dibenzofuranyl group; a substituted or unsubstituted dibenzothiophenyl group; or a substituted or unsubstituted carbazole group.

According to another embodiment, Ra1 is a phenyl group unsubstituted or substituted with an alkyl group having 1 to 20 carbon atoms or an aryl group having 6 to 30 carbon atoms; a naphthyl group unsubstituted or substituted with an alkyl group having 1 to 20 carbon atoms or an aryl group having 6 to 30 carbon atoms; a biphenyl group unsubstituted or substituted with an alkyl group having 1 to 20 carbon atoms or an aryl group having 6 to 30 carbon atoms; a terphenyl group unsubstituted or substituted with an alkyl group having 1 to 20 carbon atoms or an aryl group having 6 to 30 carbon atoms; a triphenylene group unsubstituted or substituted with an alkyl group having 1 to 20 carbon atoms or an aryl group having 6 to carbon atoms; a fluoranthene group unsubstituted or substituted with an alkyl group having 1 to 20 carbon atoms or an aryl group having 6 to 30 carbon atoms; a fluorenyl group unsubstituted or substituted with an alkyl group having 1 to 20 carbon atoms or an aryl group having 6 to 30 carbon atoms; a phenanthrenyl group unsubstituted or substituted with an alkyl group having 1 to 20 carbon atoms or an aryl group having 6 to carbon atoms; a dibenzofuranyl group unsubstituted or substituted with an alkyl group having 1 to 20 carbon atoms or an aryl group having 6 to 30 carbon atoms; a dibenzothiophenyl group unsubstituted or substituted with an alkyl group having 1 to 20 carbon atoms or an aryl group having 6 to 30 carbon atoms; or a carbazole group unsubstituted or substituted with an alkyl group having 1 to 20 carbon atoms or an aryl group having 6 to 30 carbon atoms.

In another embodiment, Ra1 is a phenyl group; a naphthyl group; a biphenyl group; a terphenyl group; a triphenylene group; a fluoranthene group; a fluorenyl group substituted with a methyl group; a phenanthrenyl group; a dibenzofuranyl group; a dibenzothiophenyl group; or a carbazole group substituted with a phenyl group.

In one embodiment of the present specification, the heterocyclic compound represented by Chemical Formula 1 may be any one selected from among the following compounds.

1
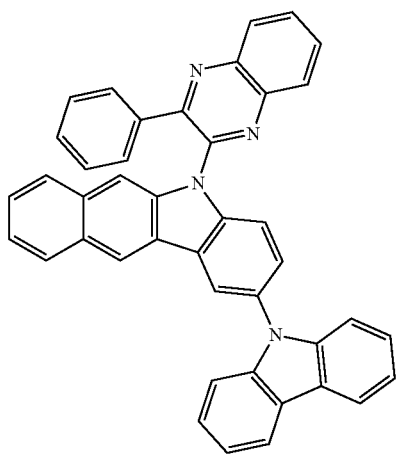
2
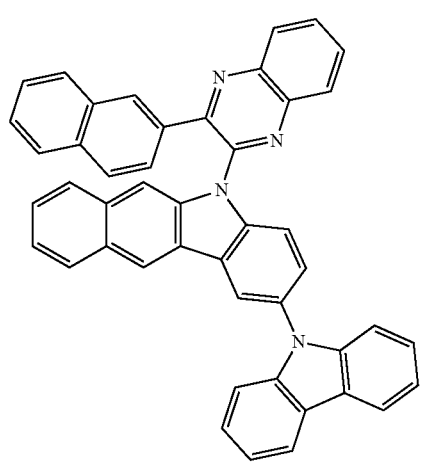
3
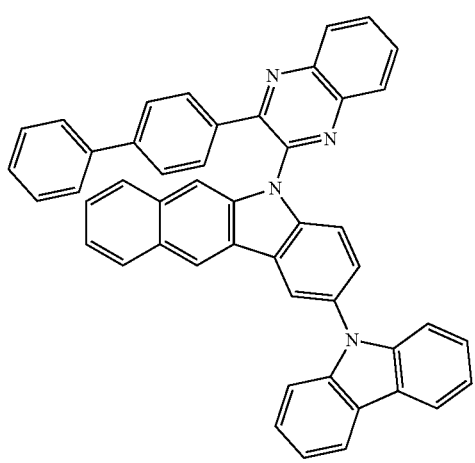
4
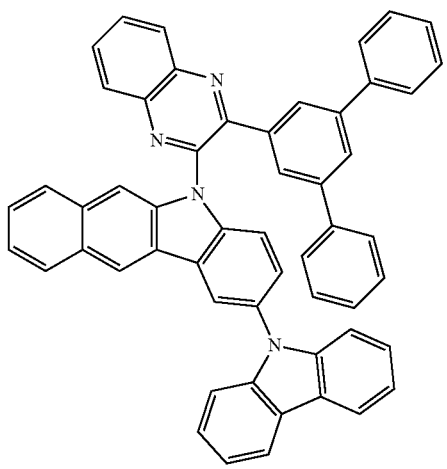
5
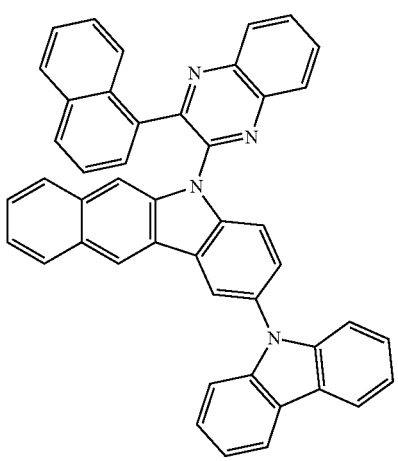
6
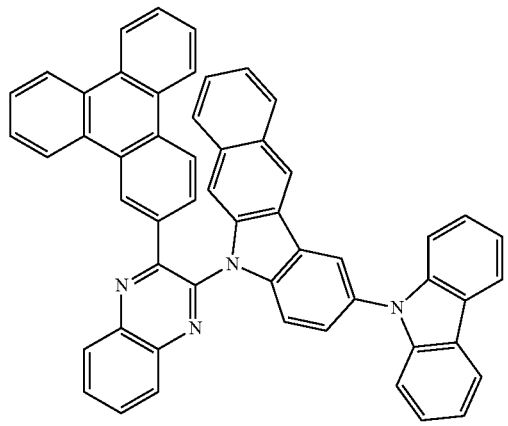

7
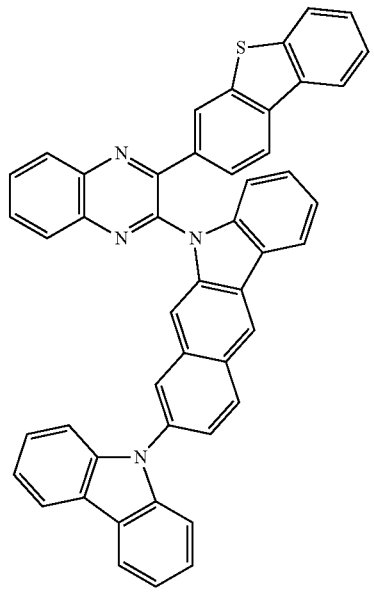
9
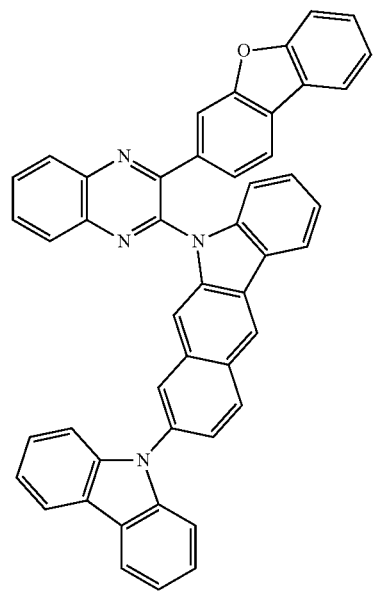
8
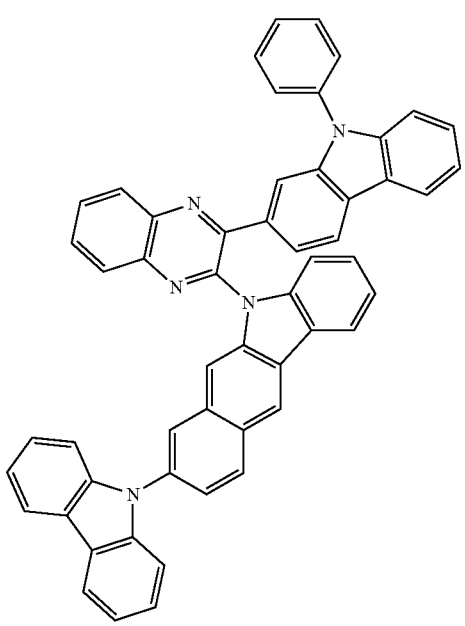
10

11
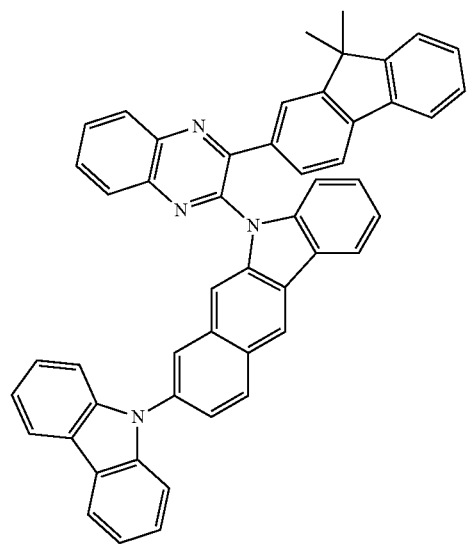
12
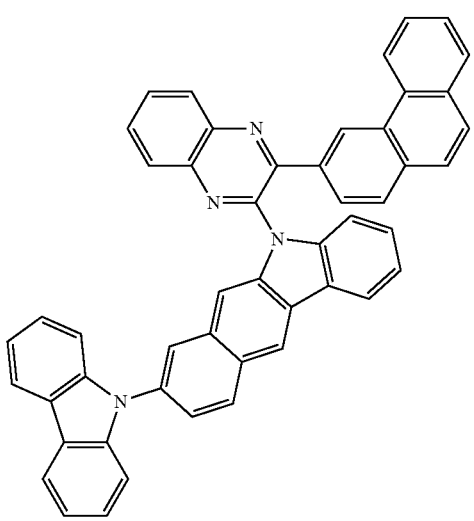
13
14
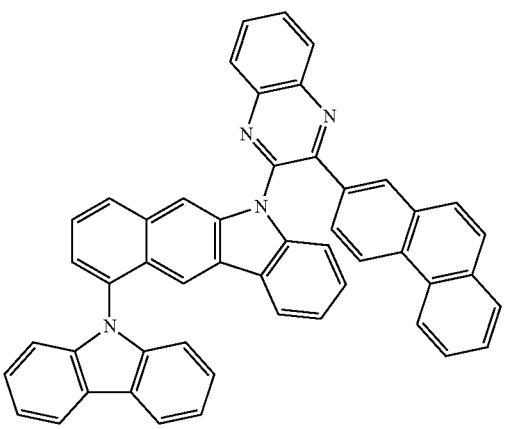
15
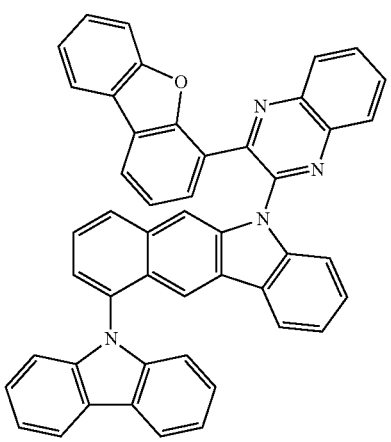
16
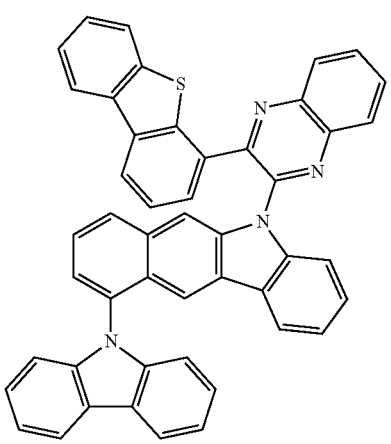

-continued
17
18
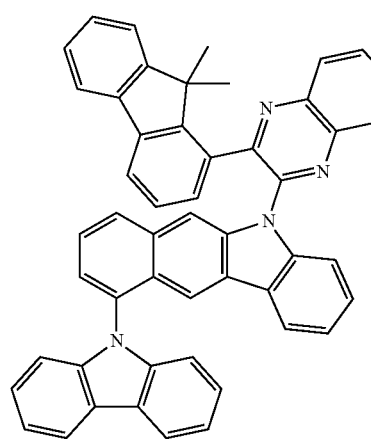
19
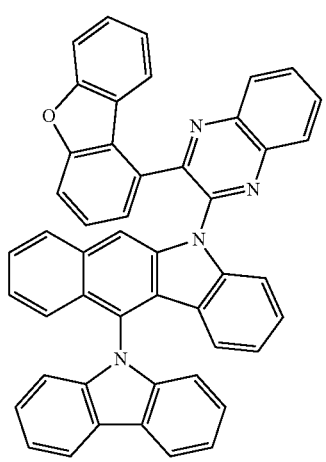
-continued
20
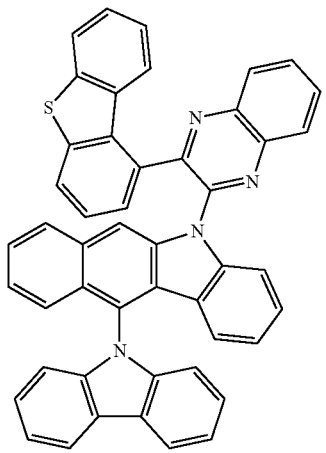
21
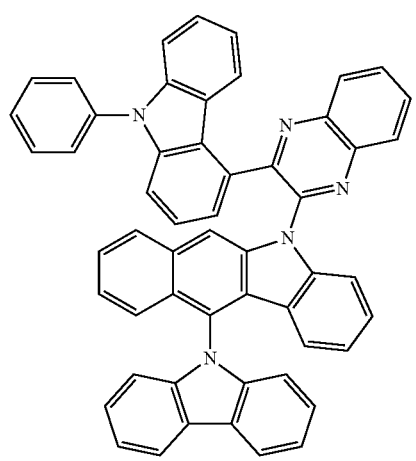
22
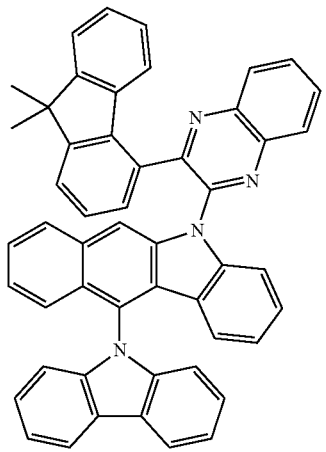

-continued
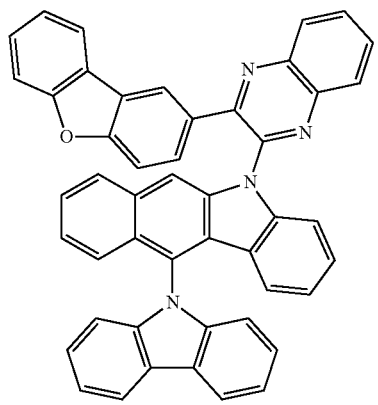
23
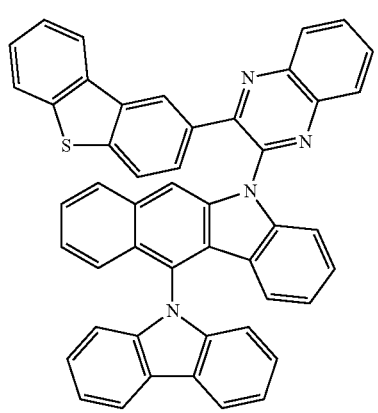
24
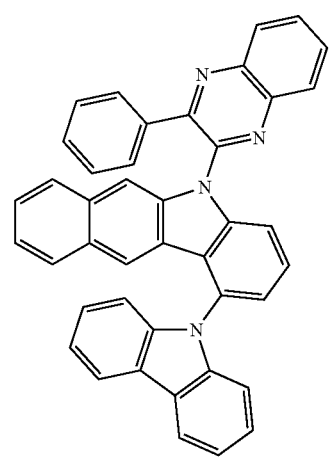
25
-continued
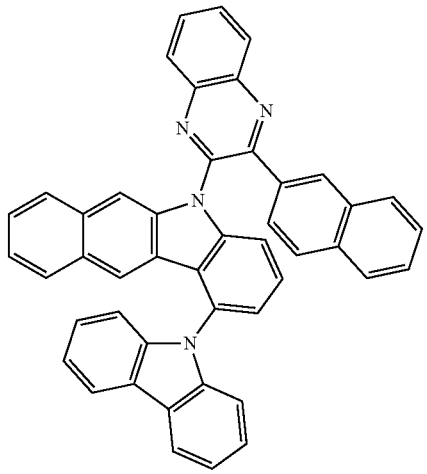
26
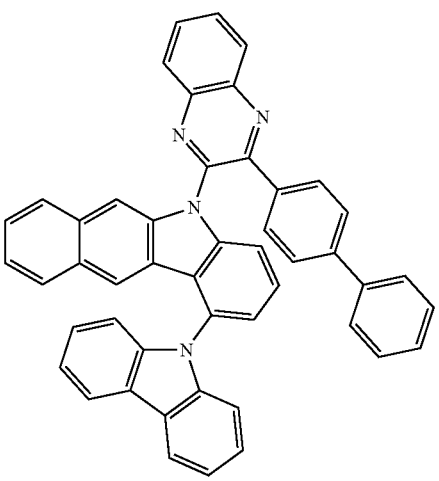
27
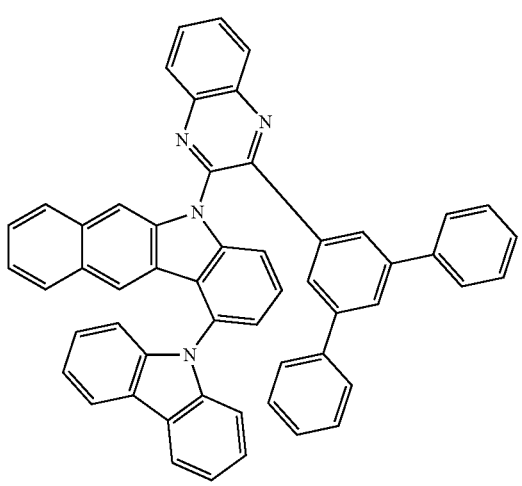
28

29
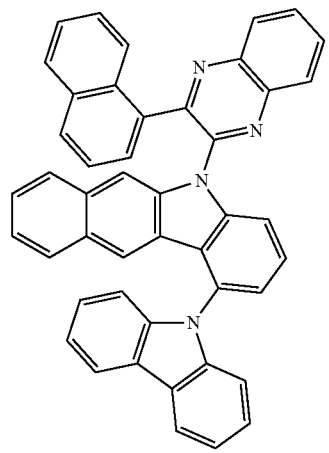
30
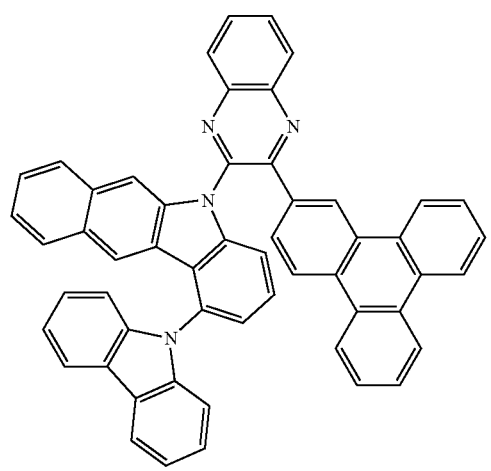
31
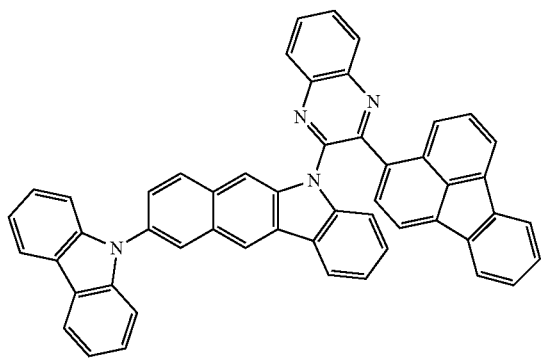
32
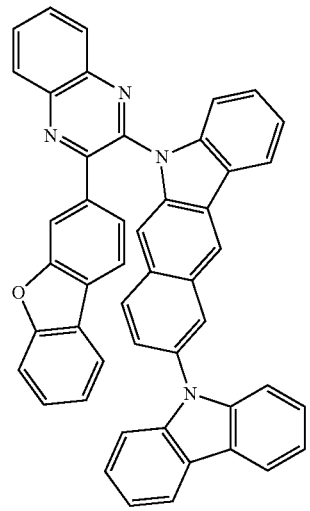
33
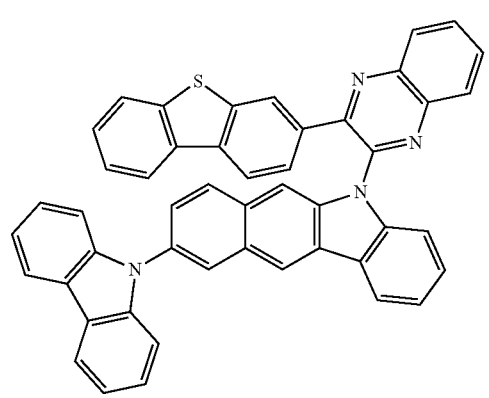
34
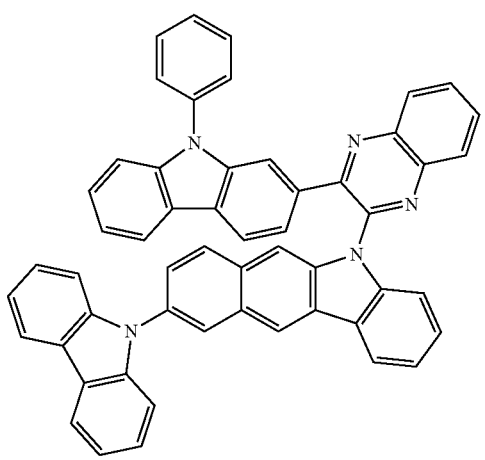

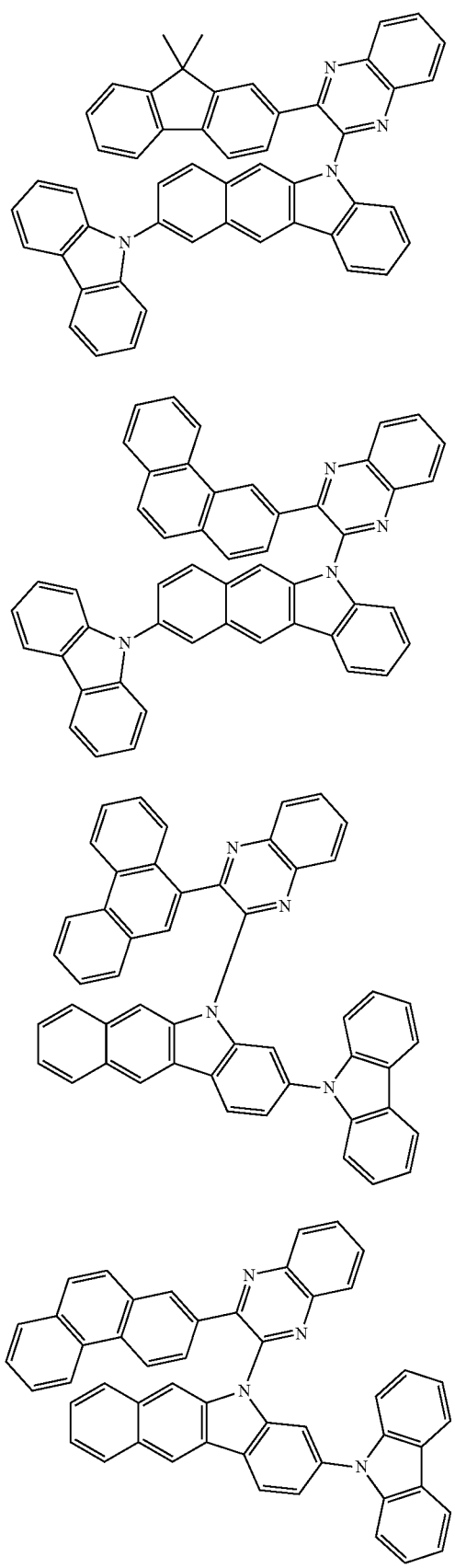
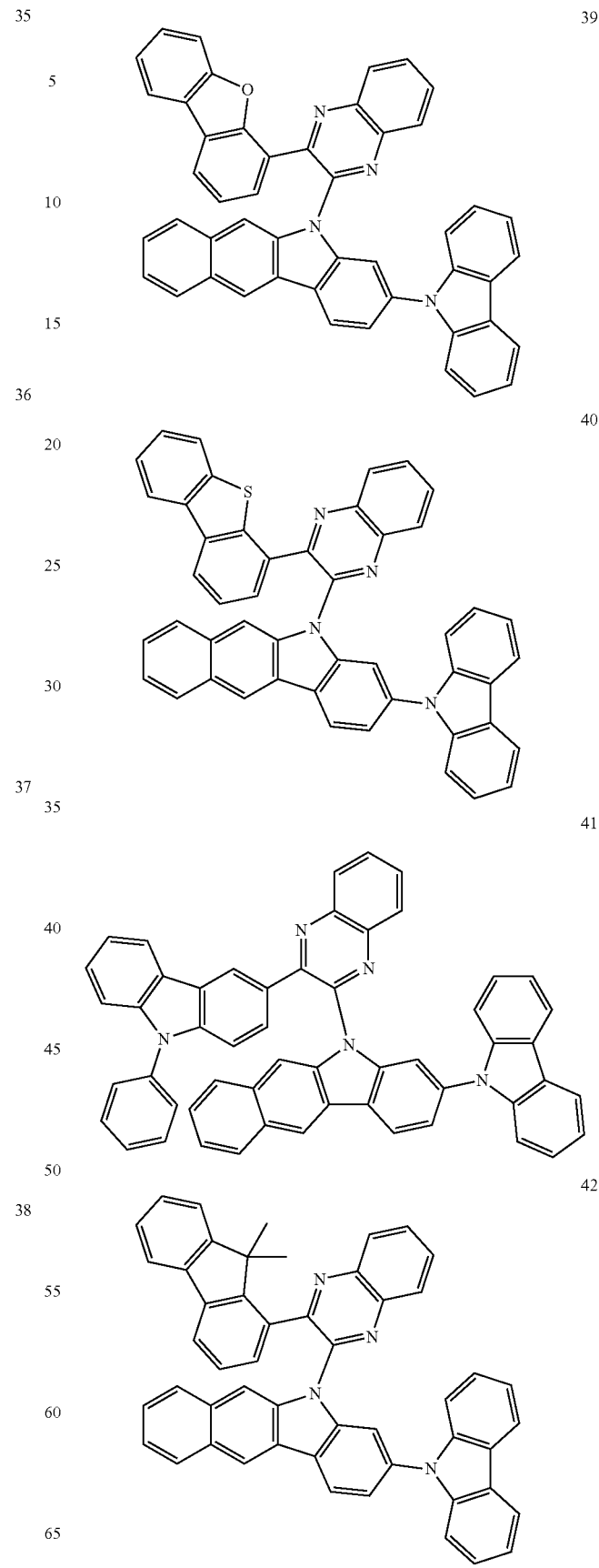

43
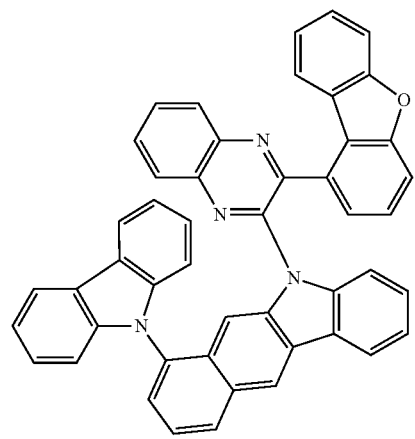
44
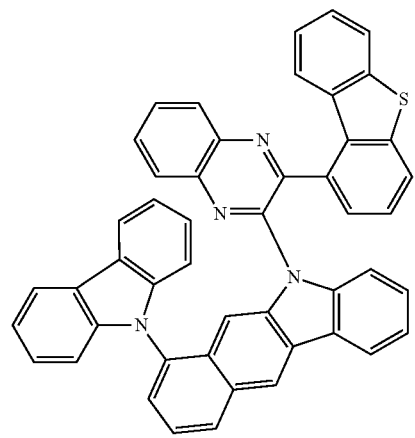
45
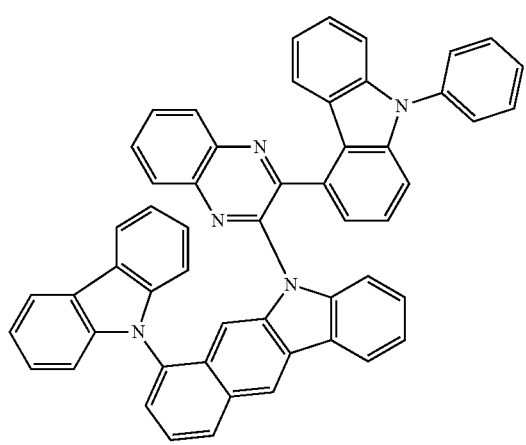
46
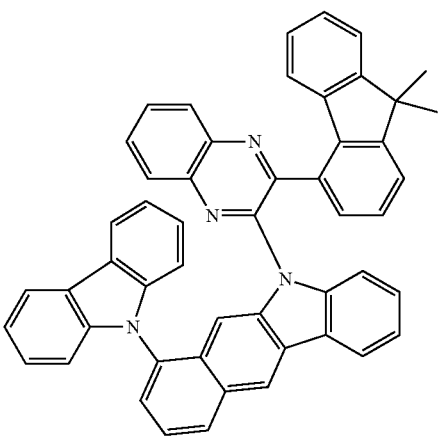
47
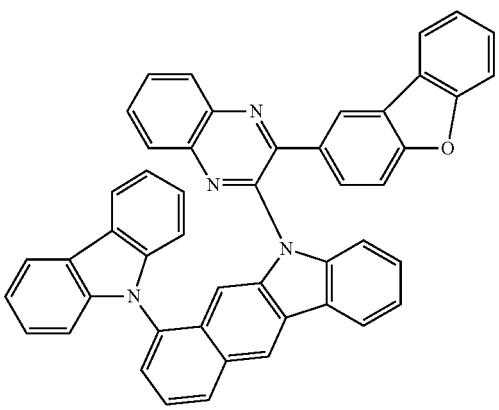
48
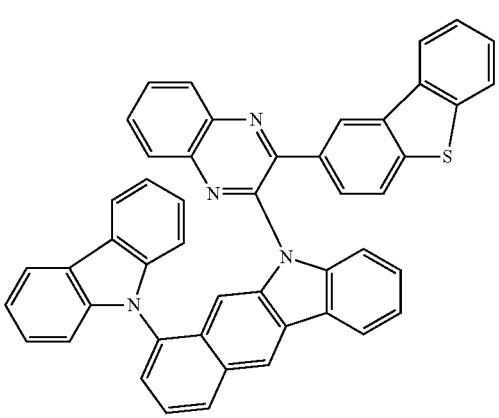

-continued
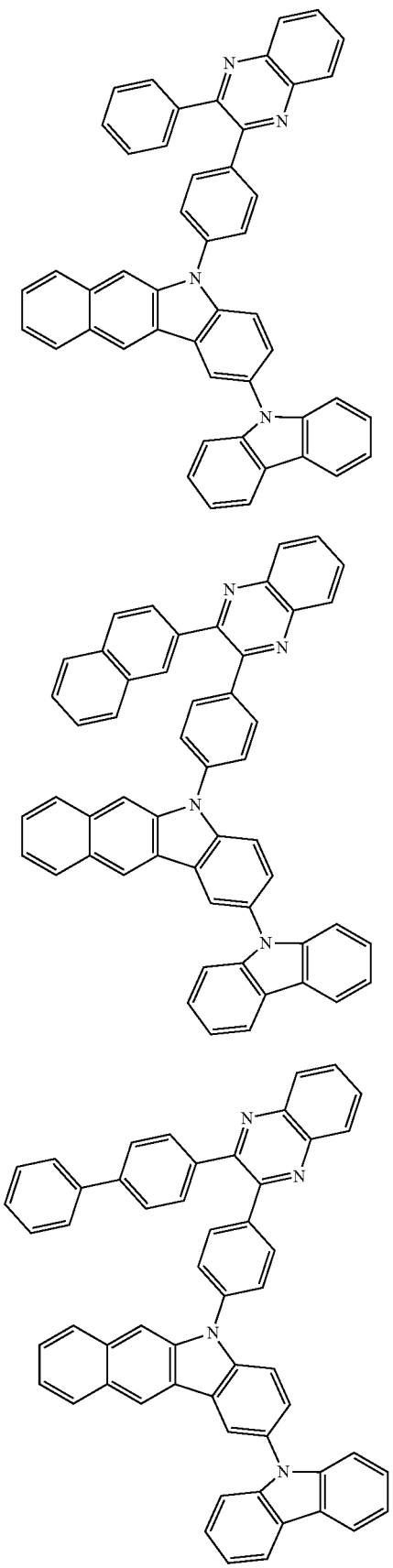
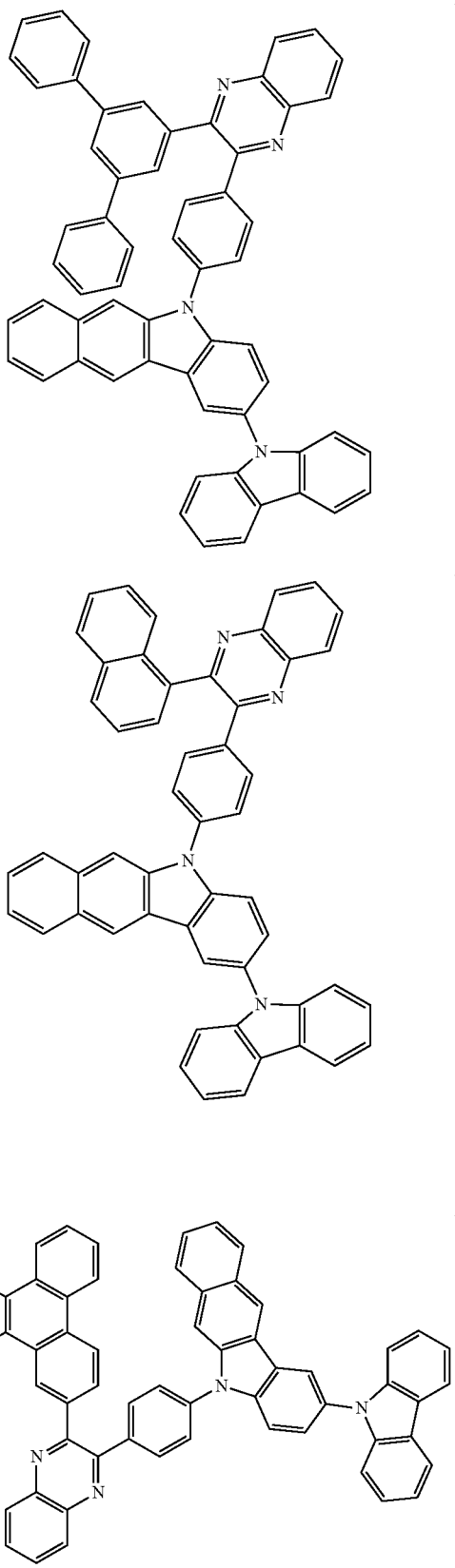

-continued
55
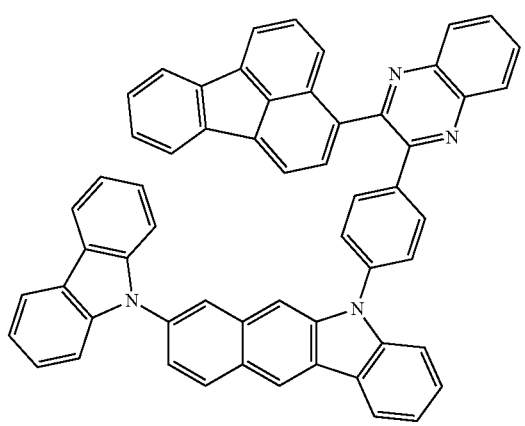
56
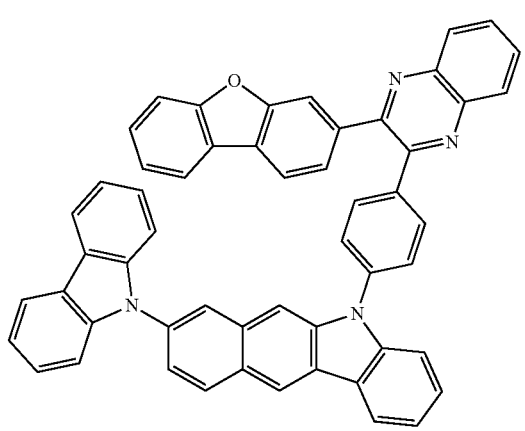
57
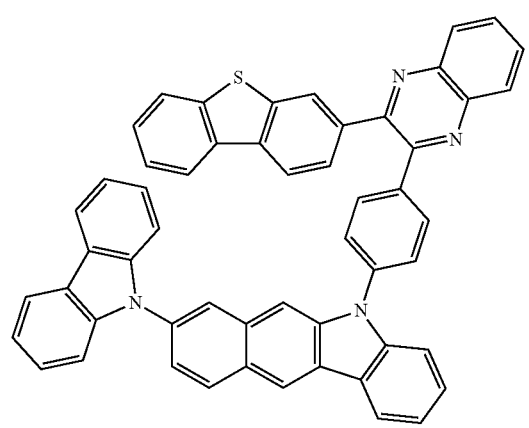
-continued
58
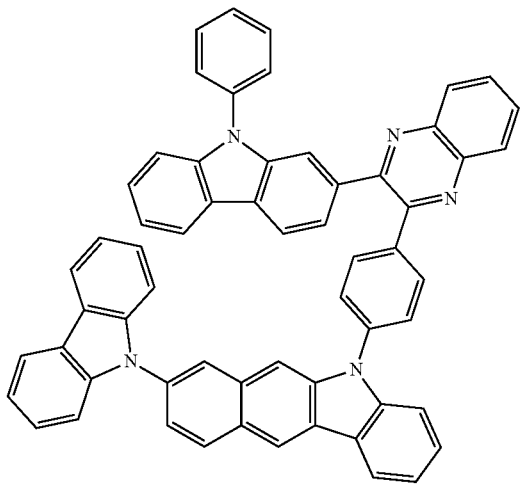
59
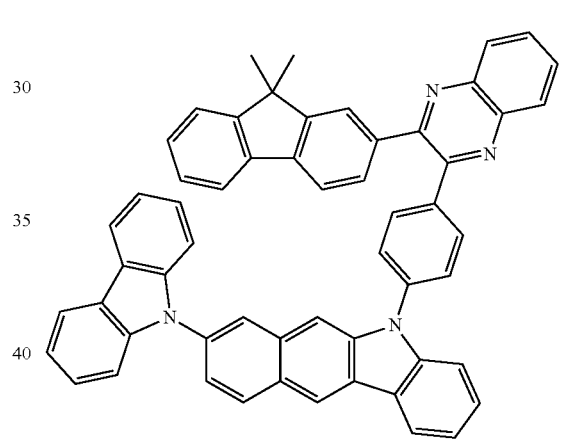
60
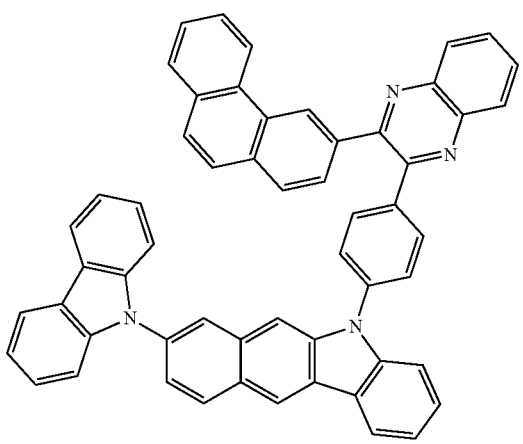

61
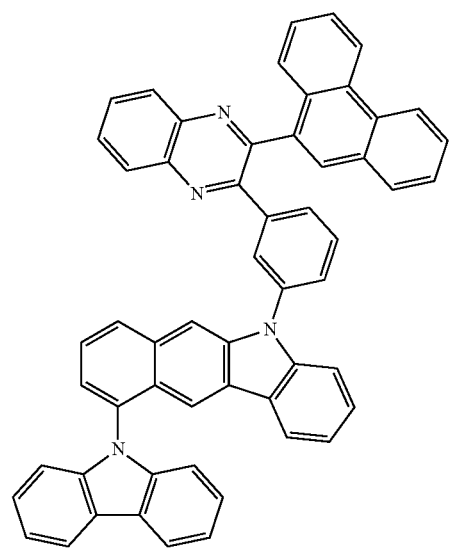
63
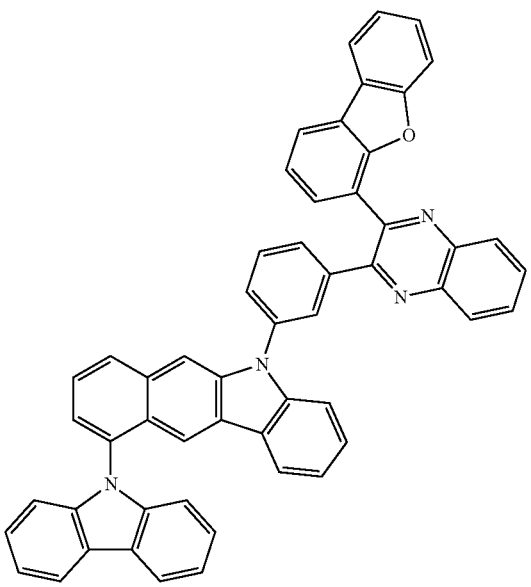
62
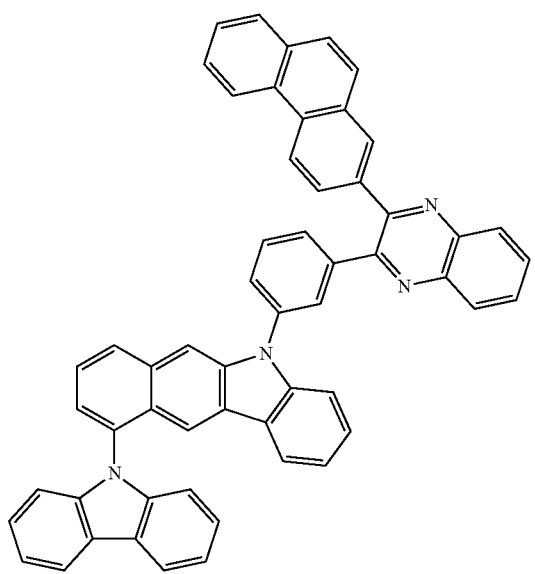
64
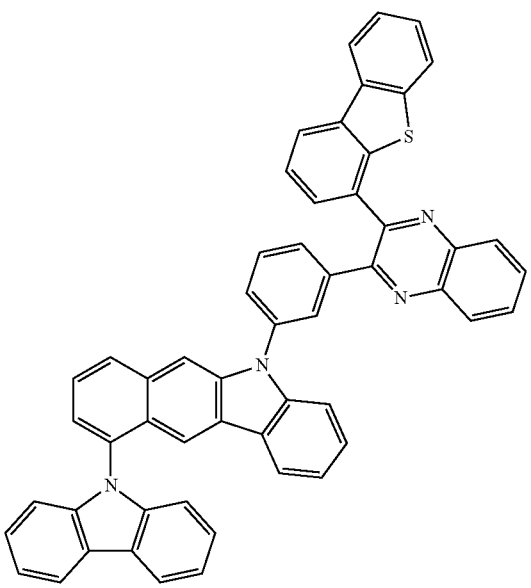

65
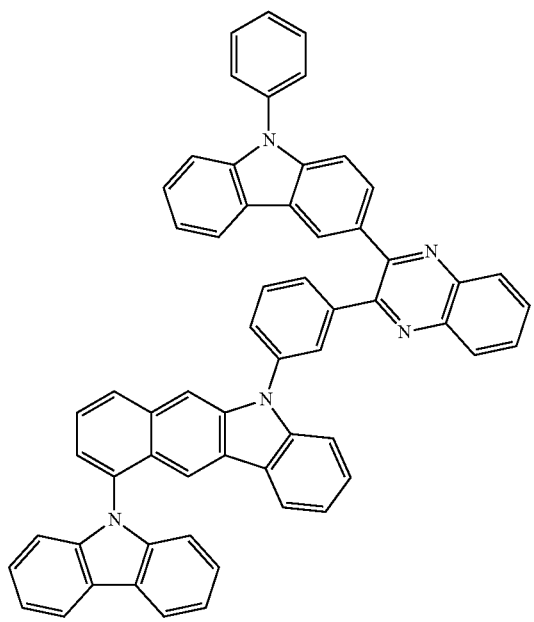
66
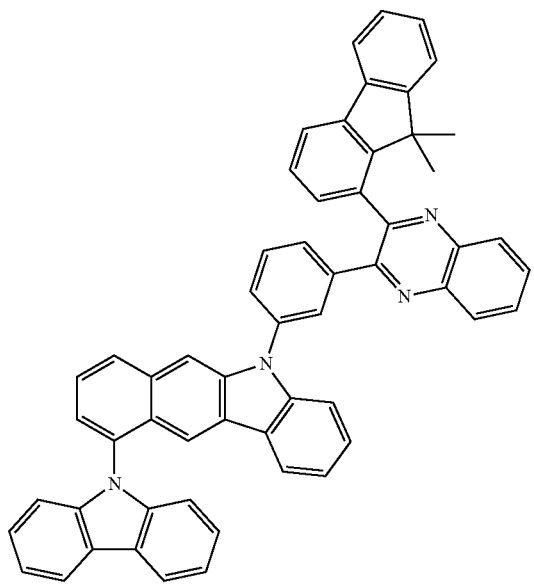
67
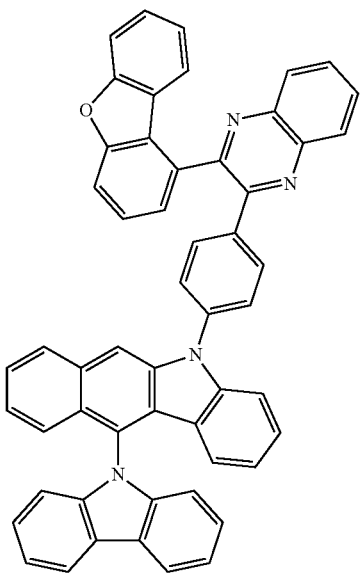
68
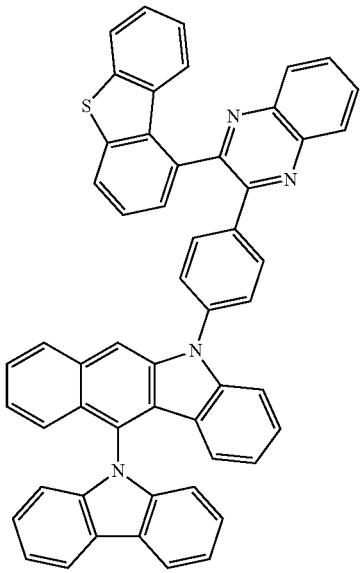

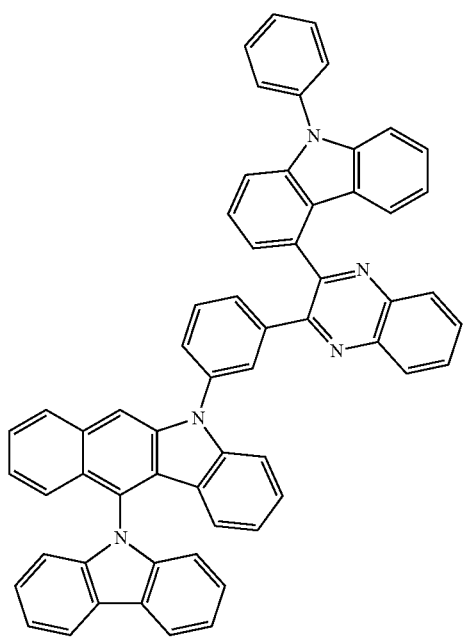
69
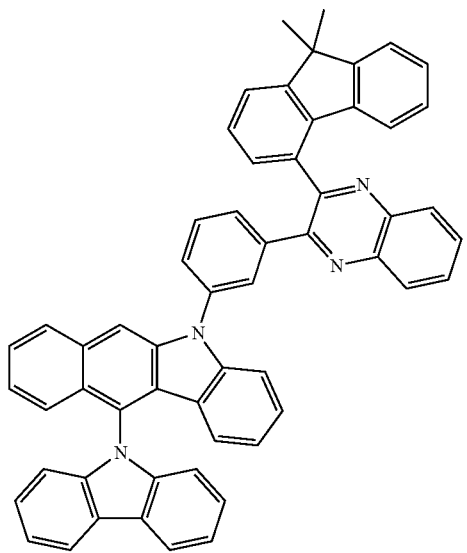
70
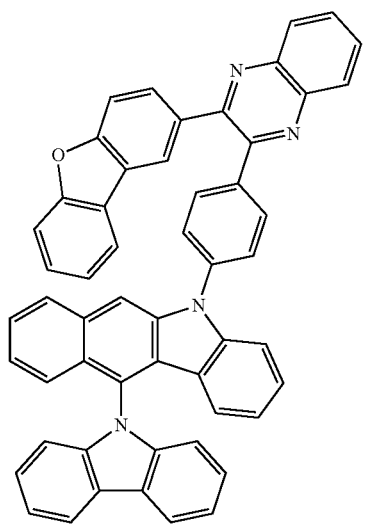
71
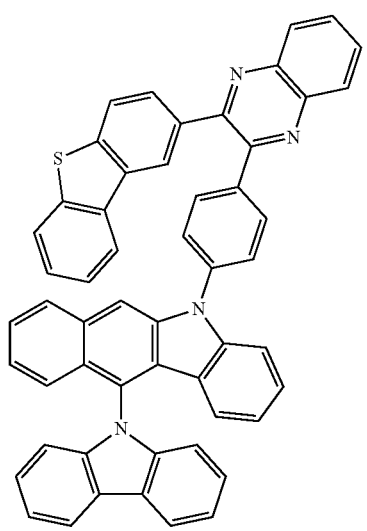
72
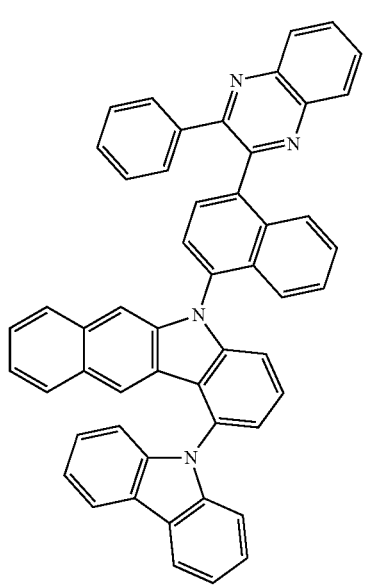
73

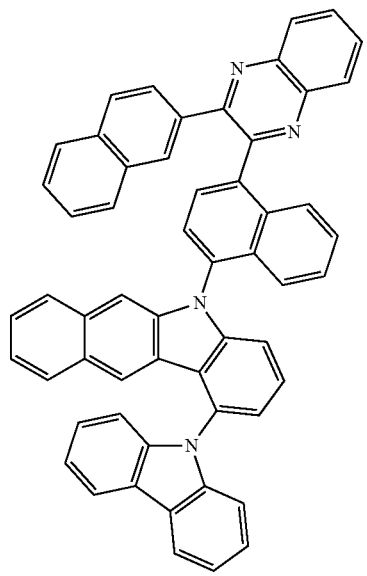
74
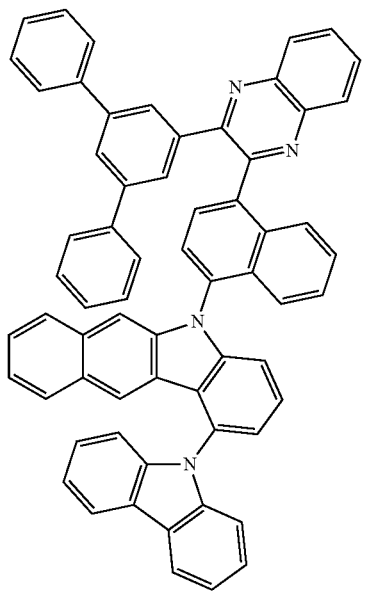
76
75
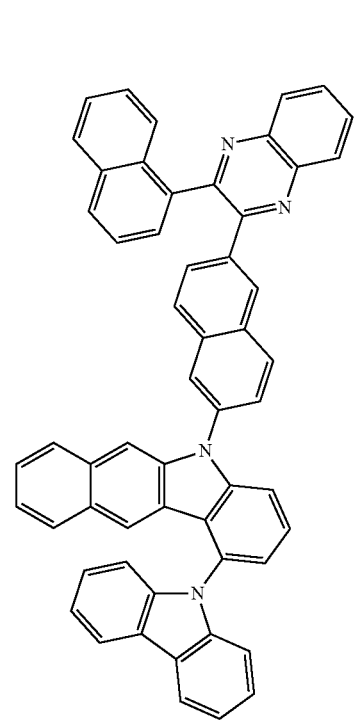
77

78
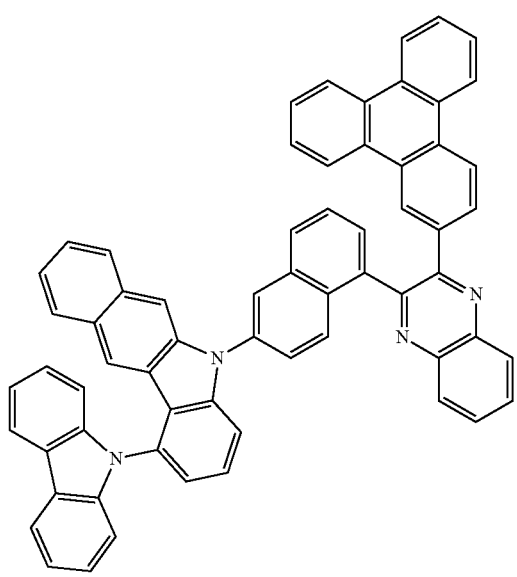
79
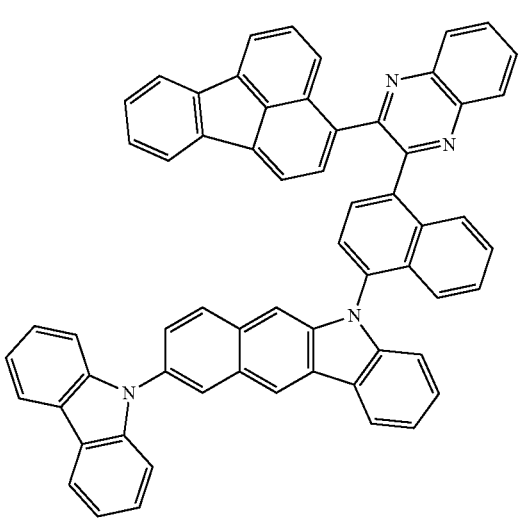
80
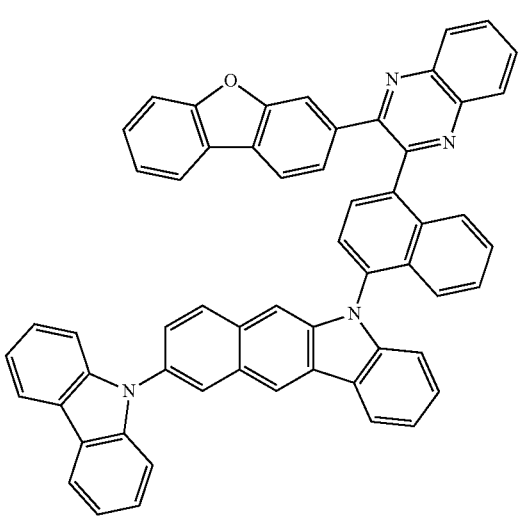
81
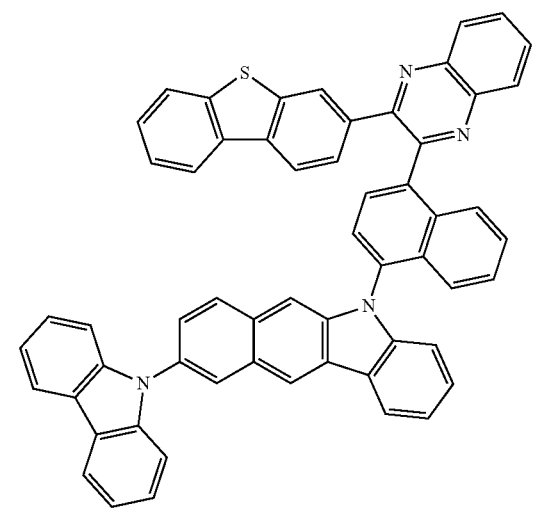
82
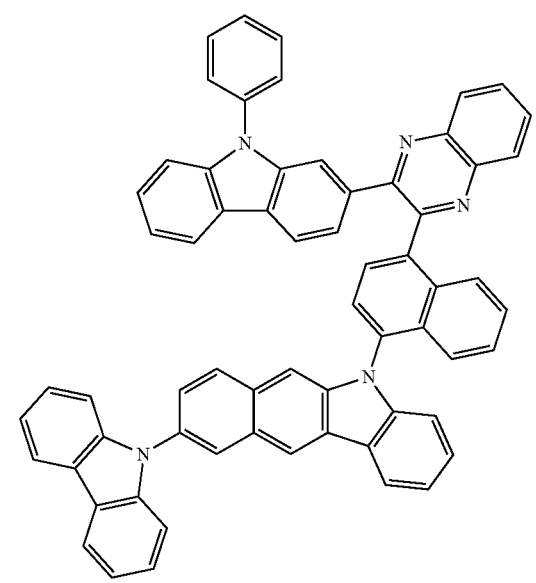
83
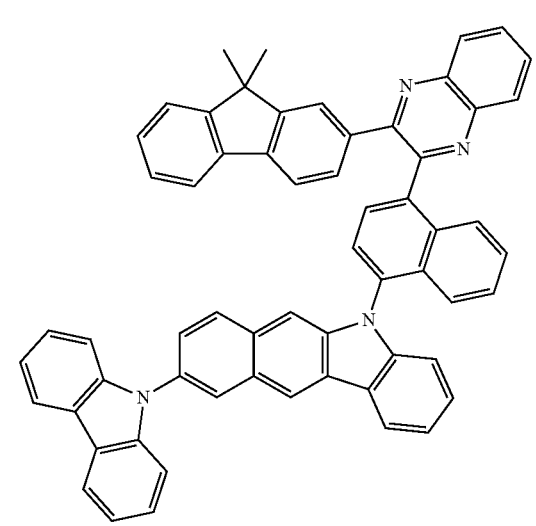

84
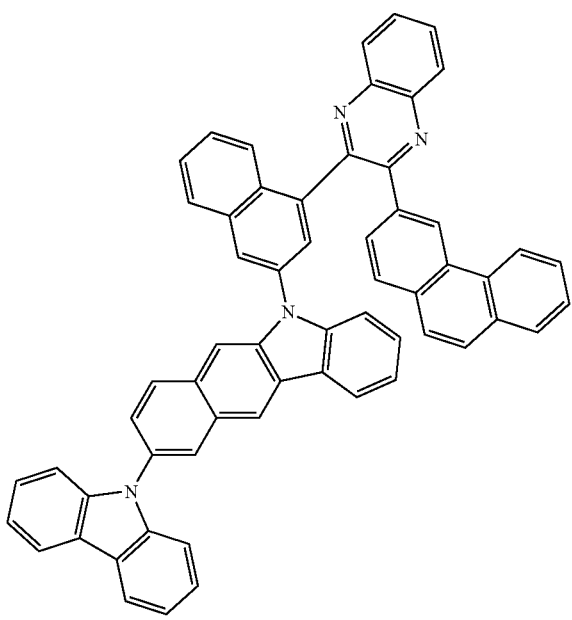
85
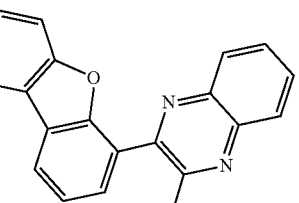
86
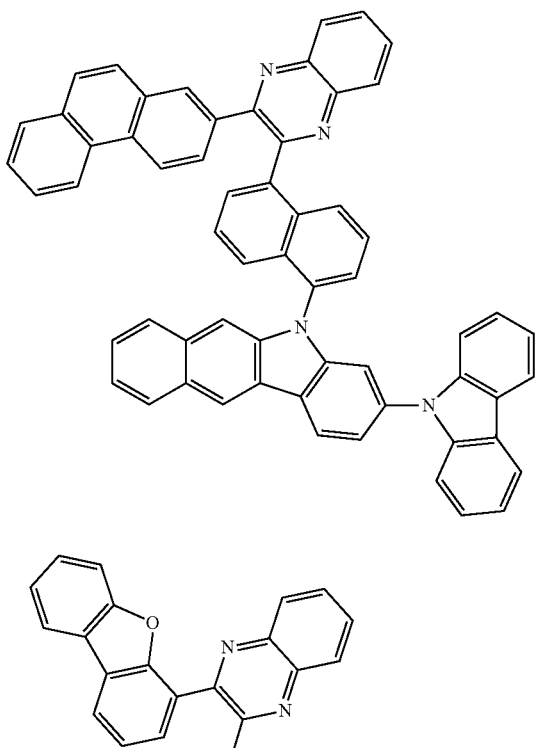
87
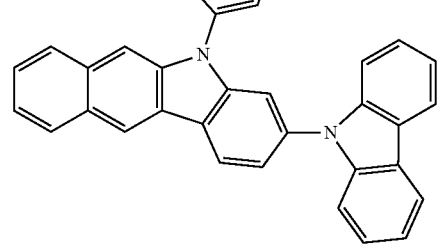
88
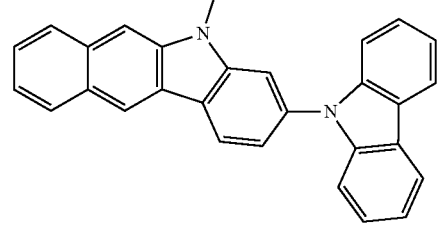

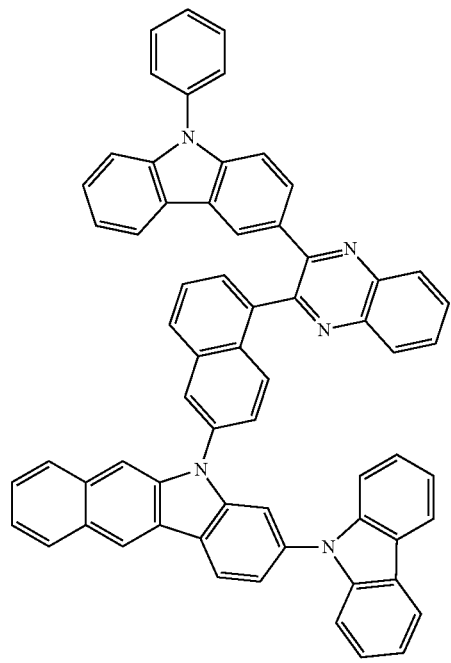
89
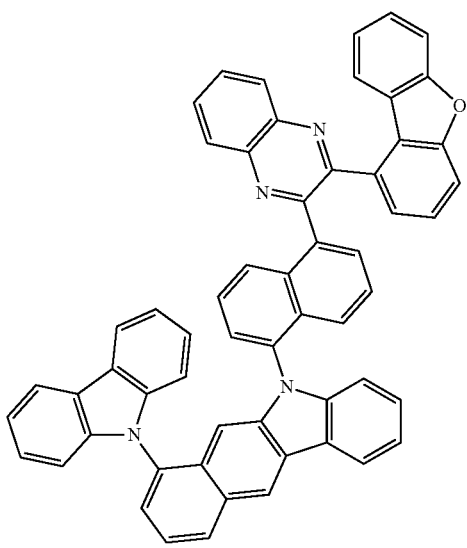
91
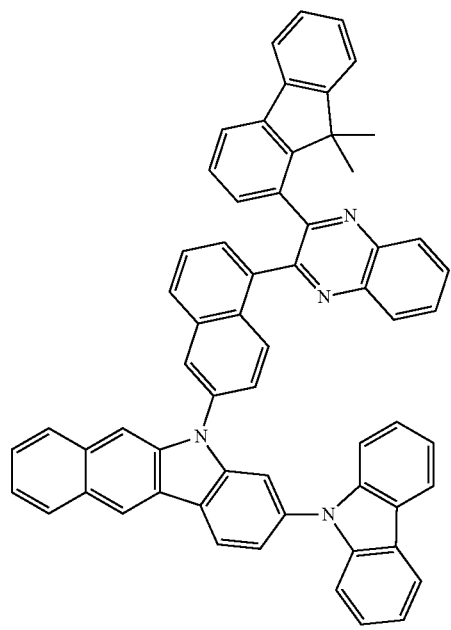
90
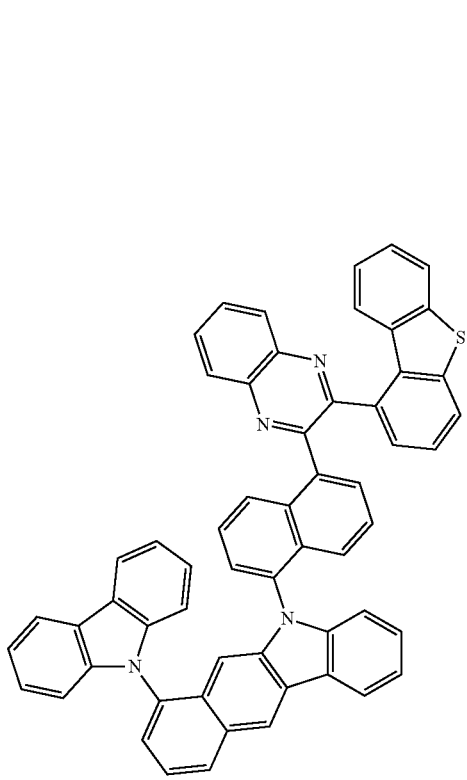
92

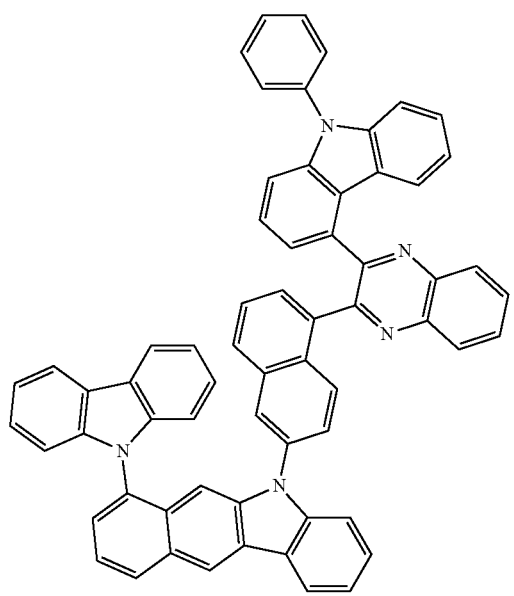
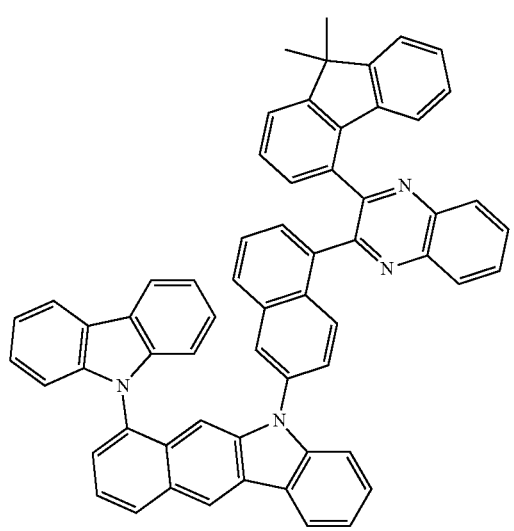
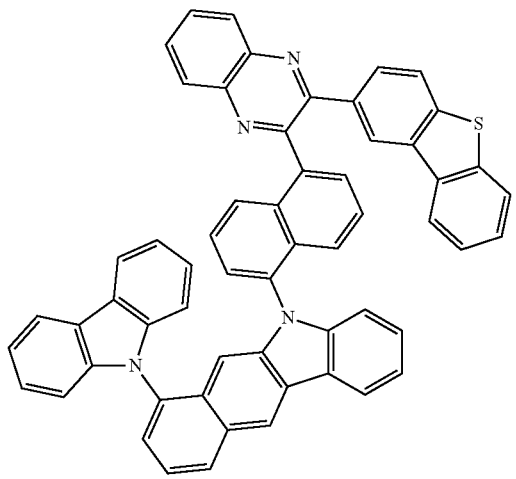
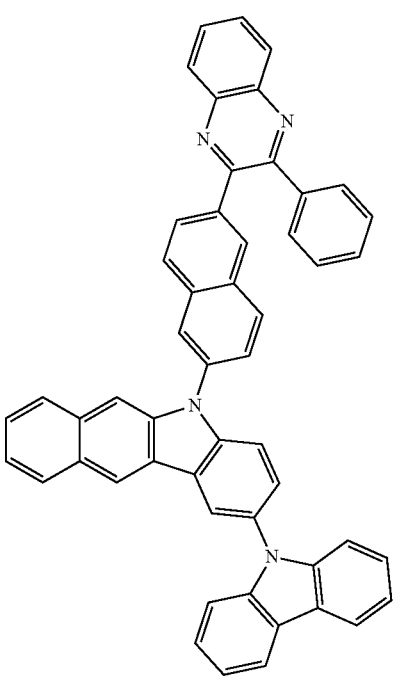

98
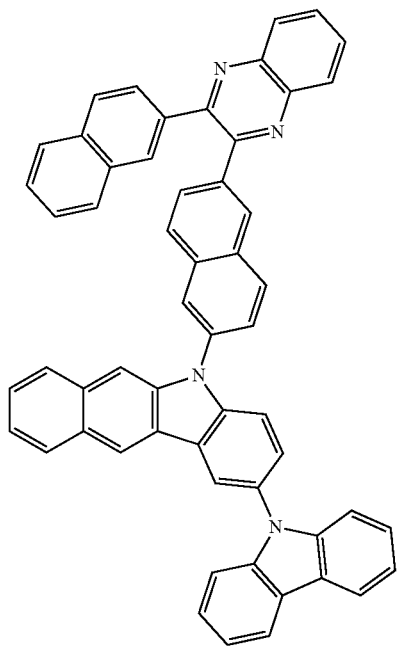
100
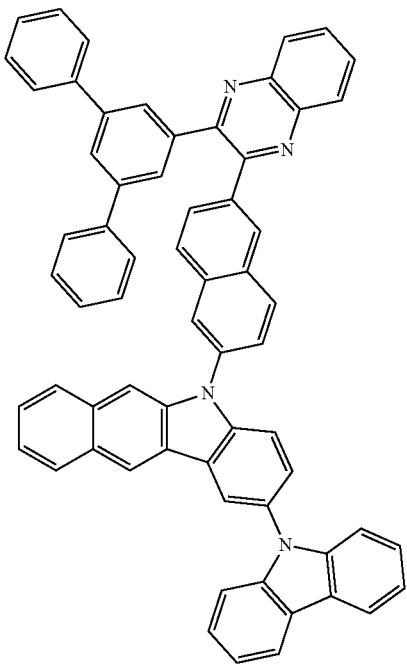
99
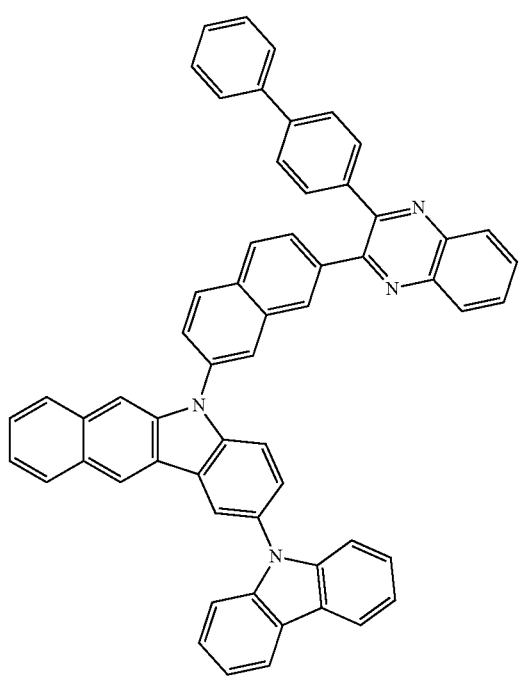
101
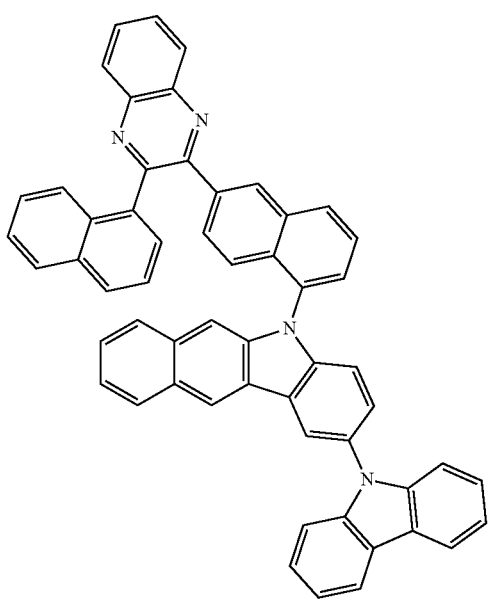

102
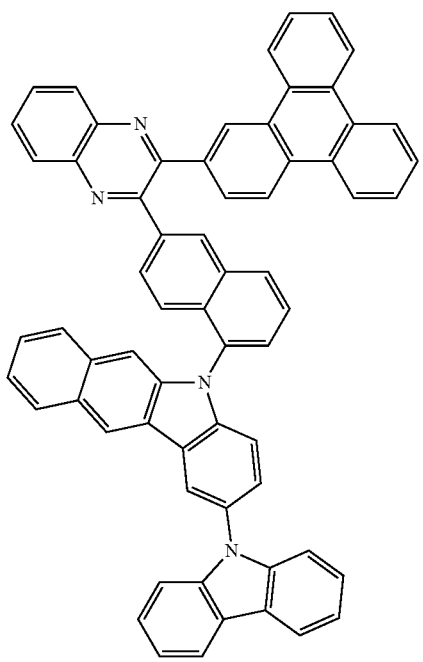
103
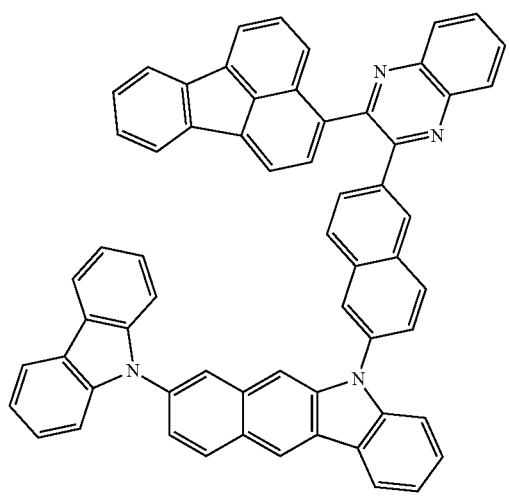
104
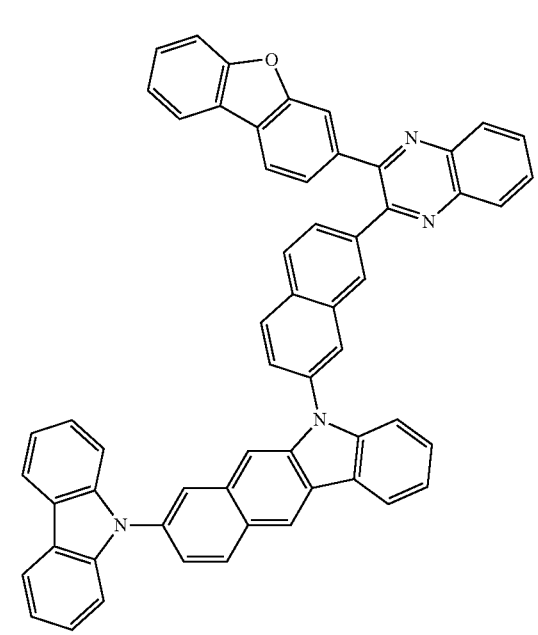
105
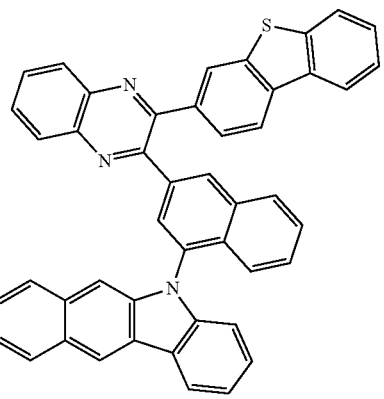

106
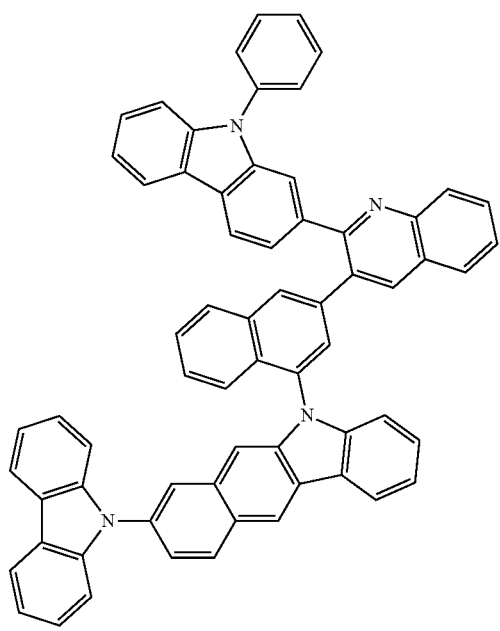
107
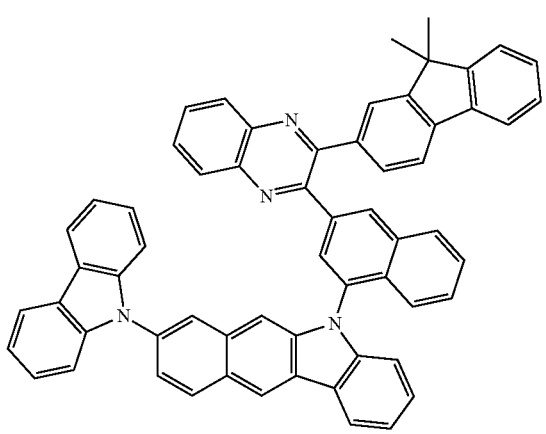
108
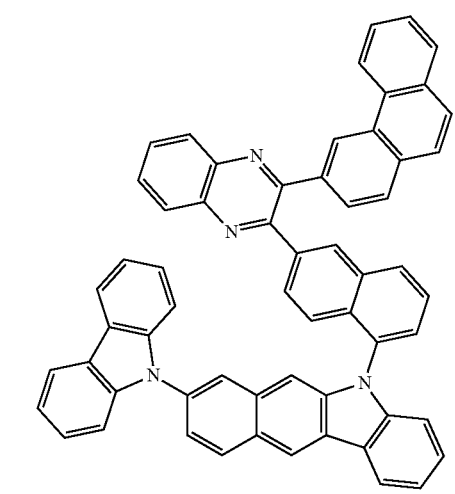
109
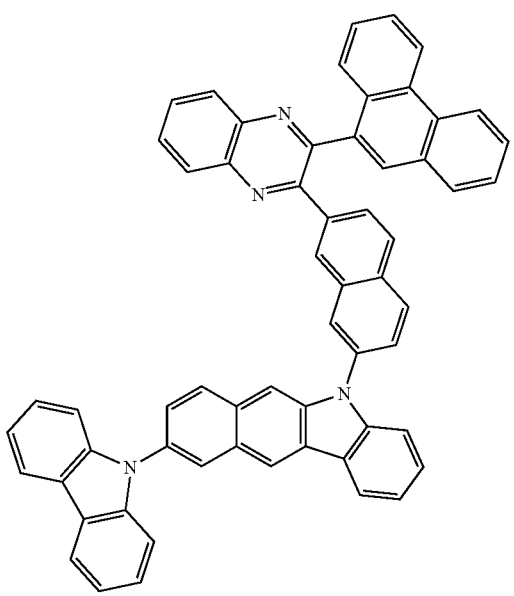
110
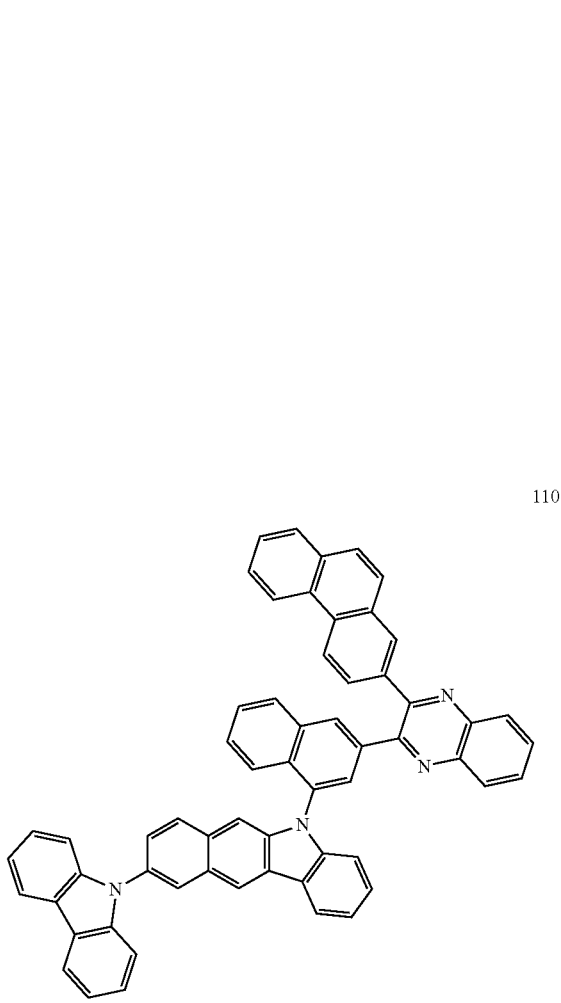

111
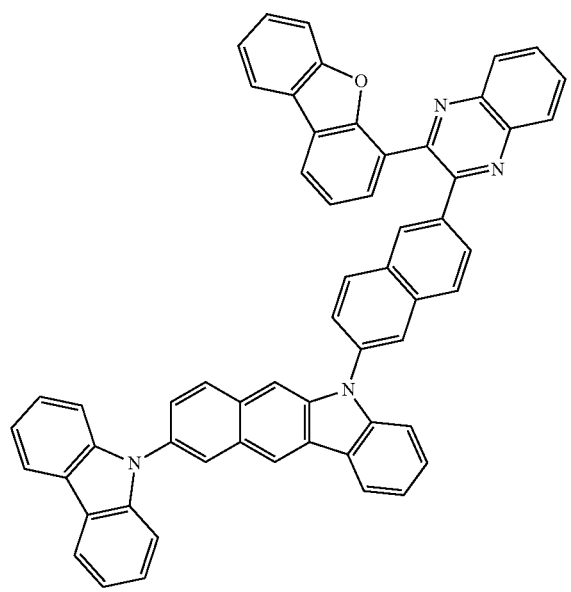
113
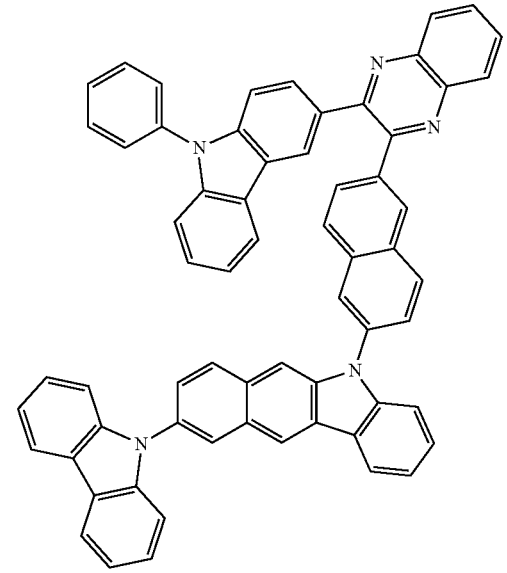
112
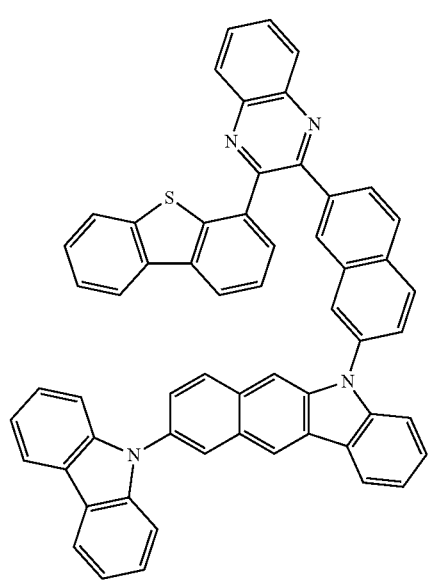
114
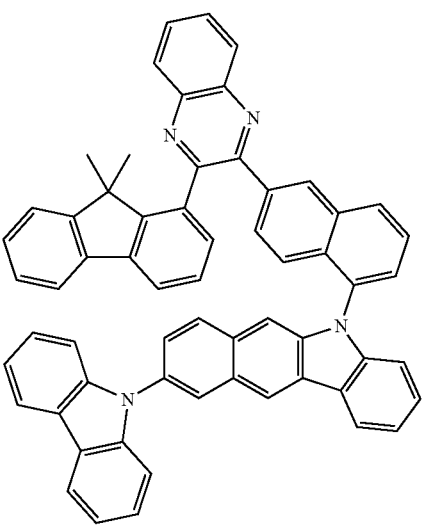

-continued
115
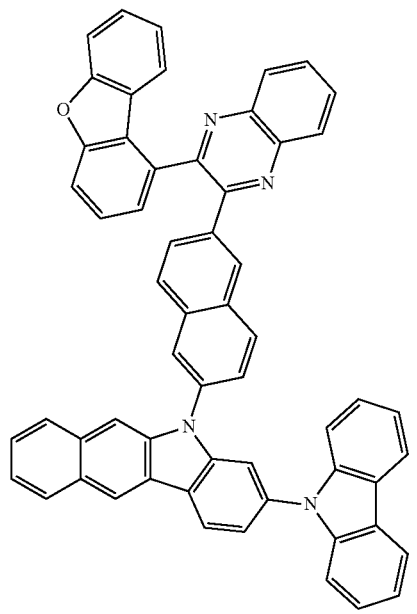
116
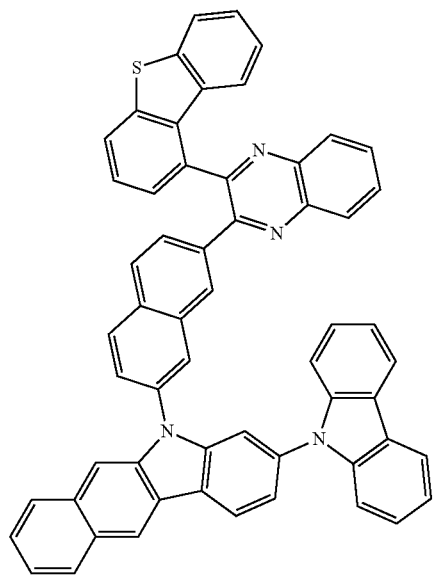
-continued
117
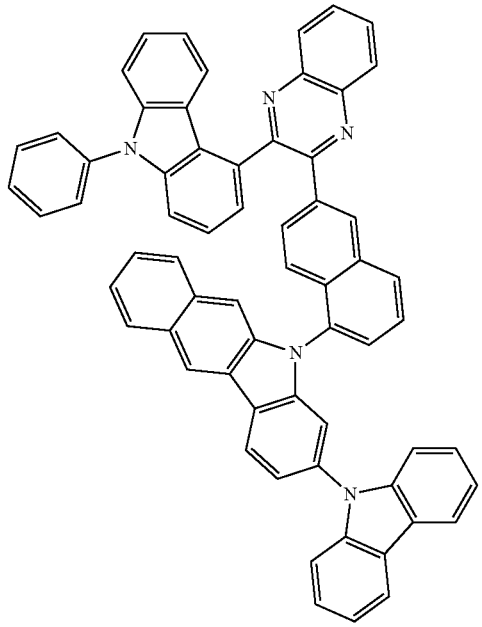
118
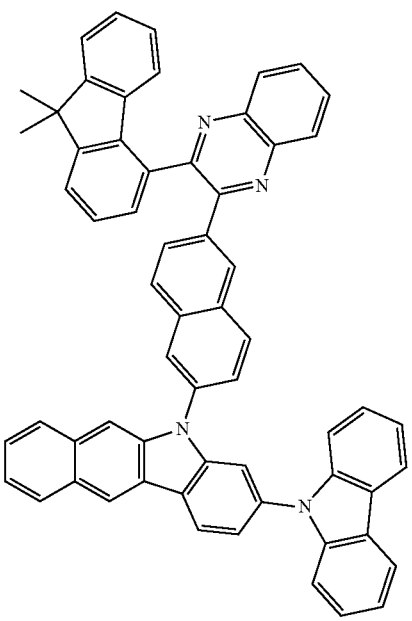

US 11,192,884 B2
69
-continued
119
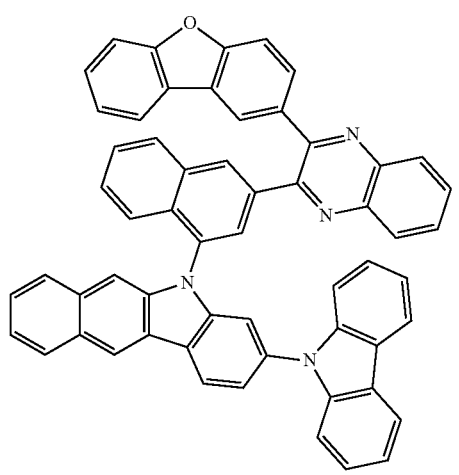
120
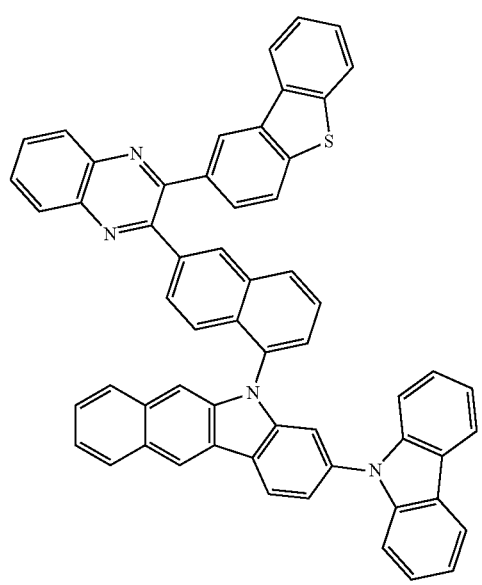
121
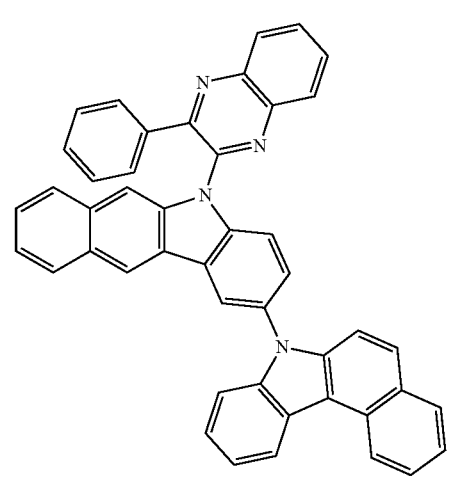
70
-continued
122
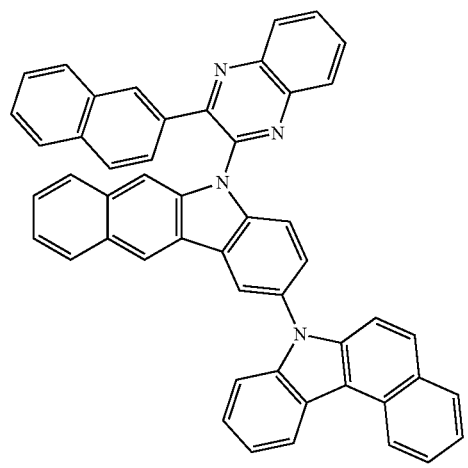
123
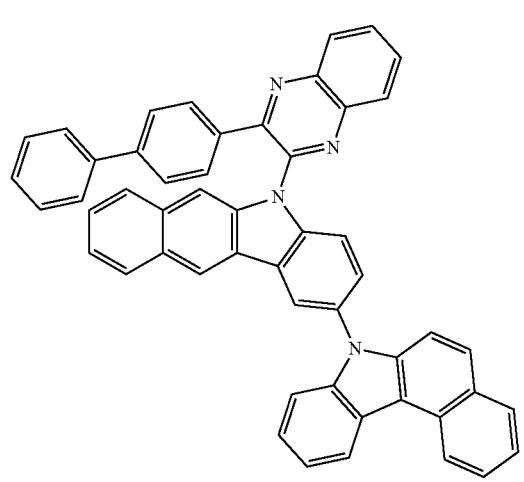
124
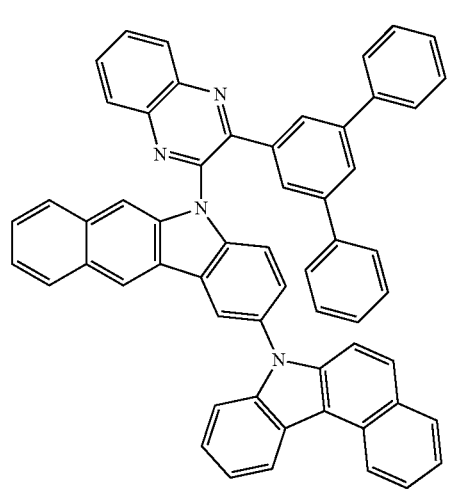

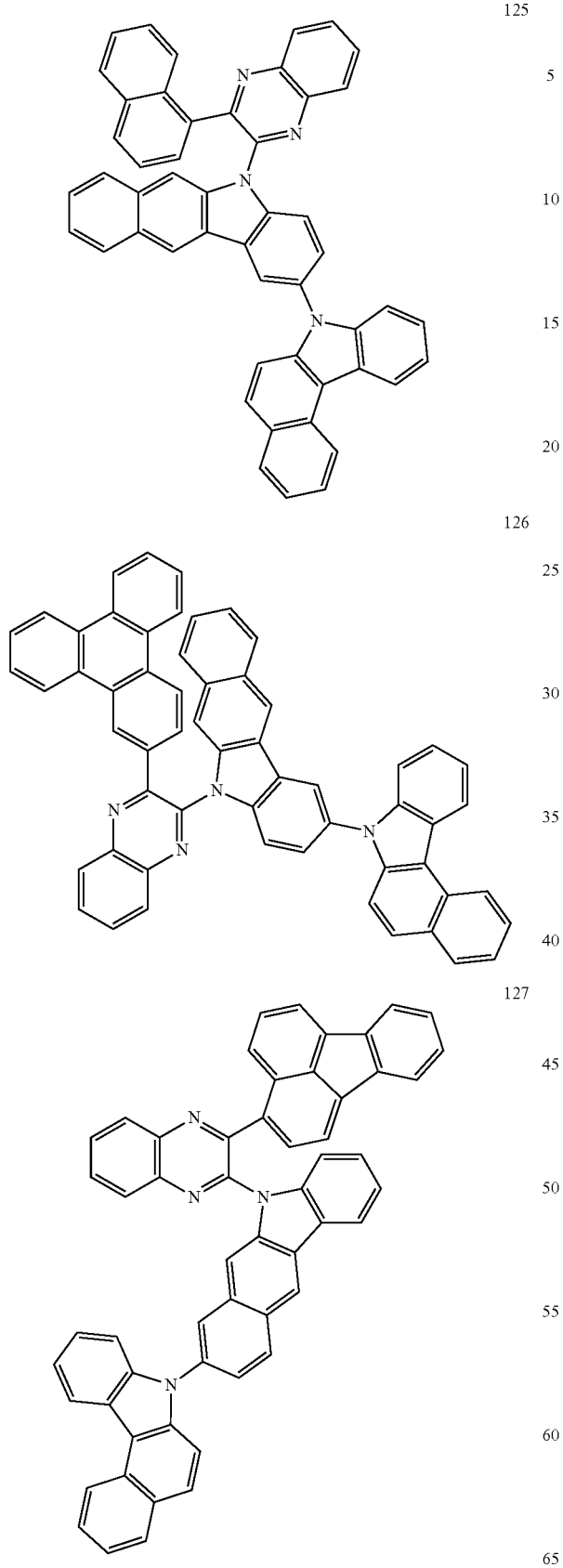
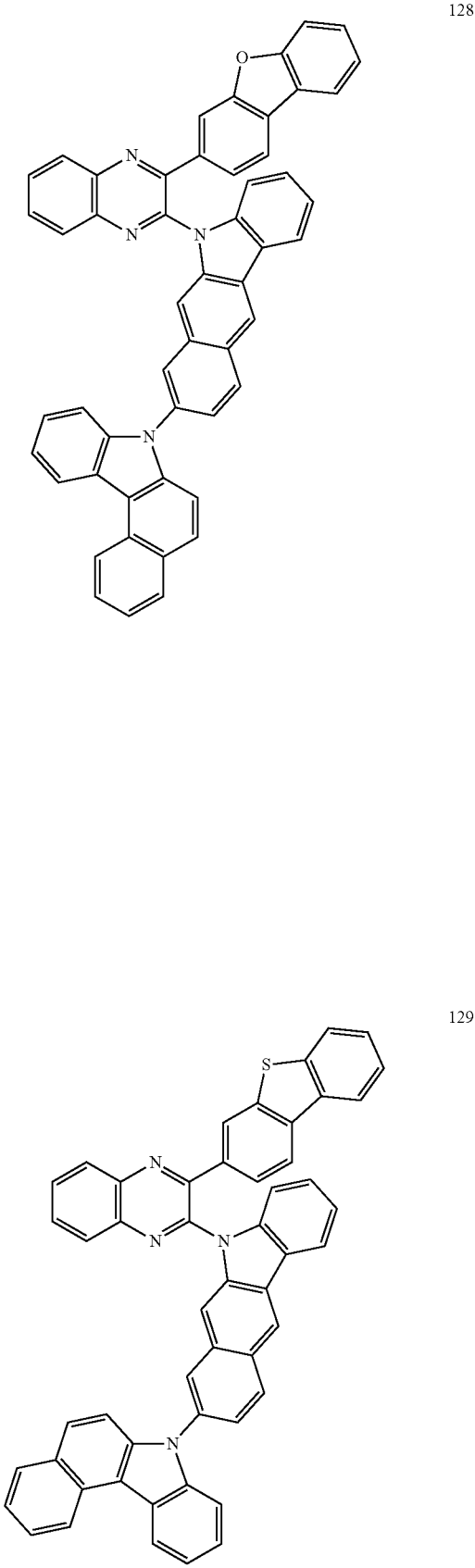

130
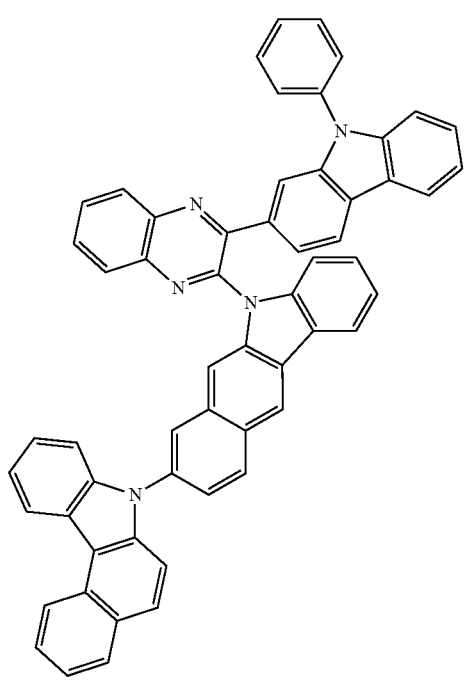
131
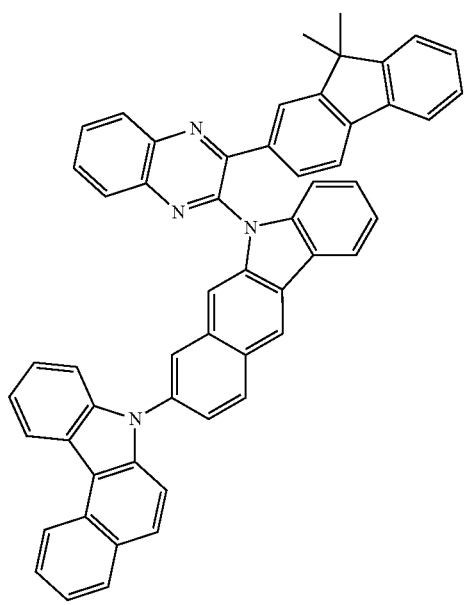
132
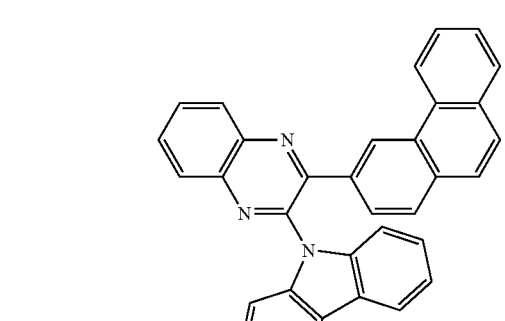
133
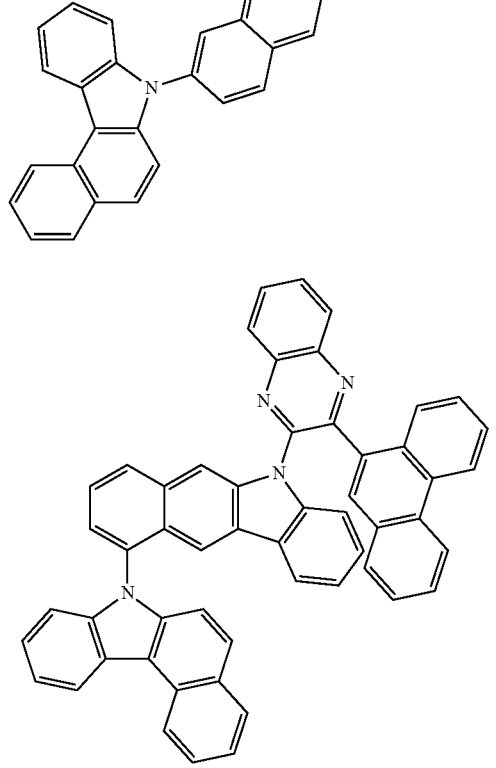
134
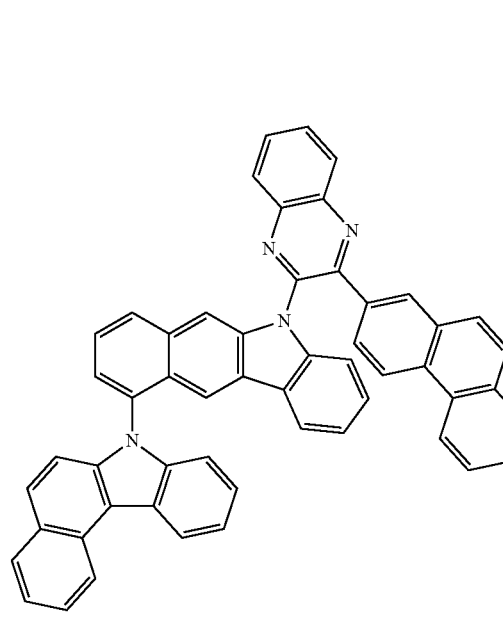

135
136
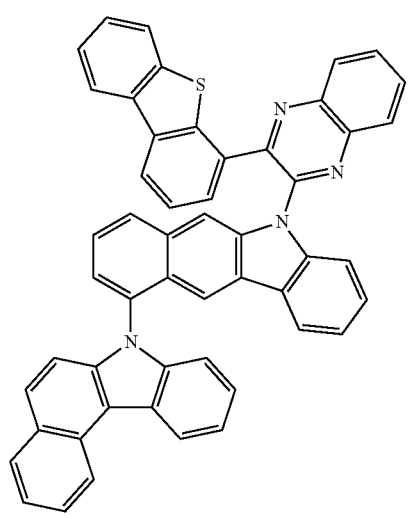
137
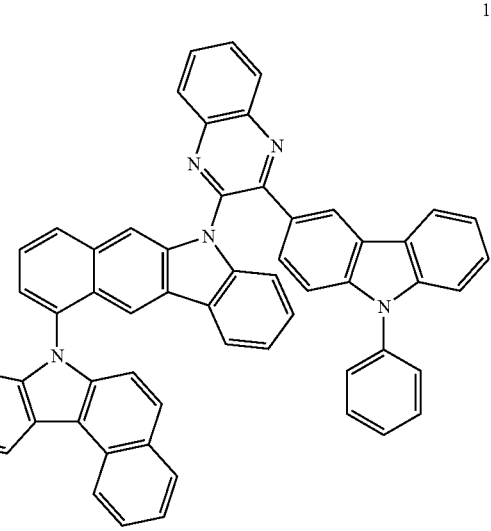
138
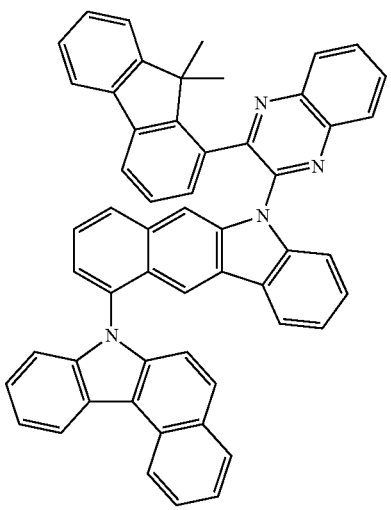
139
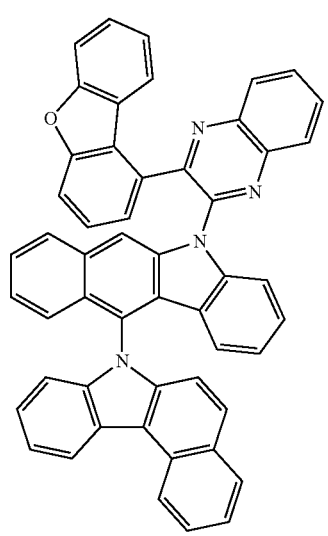
140
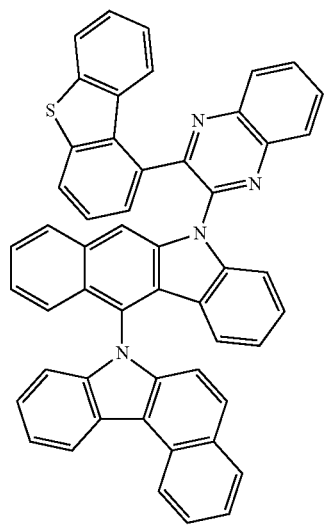

141
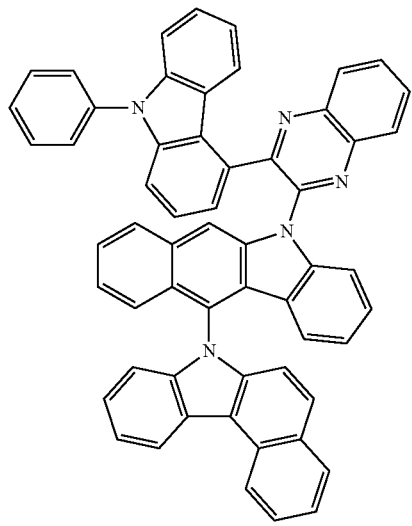
142
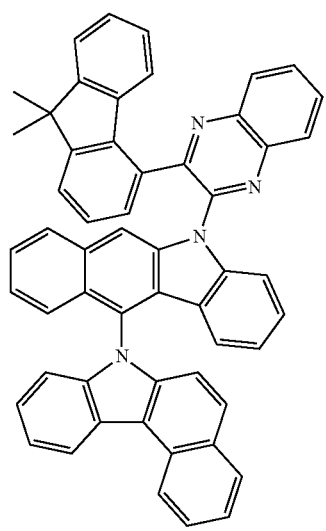
143
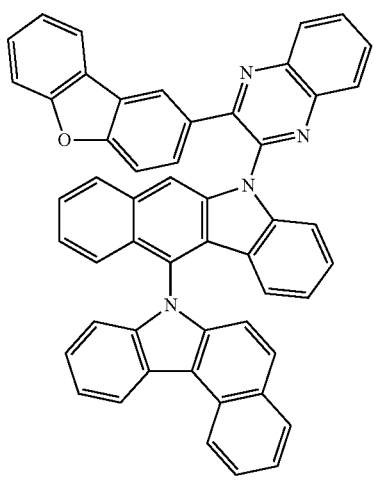
144
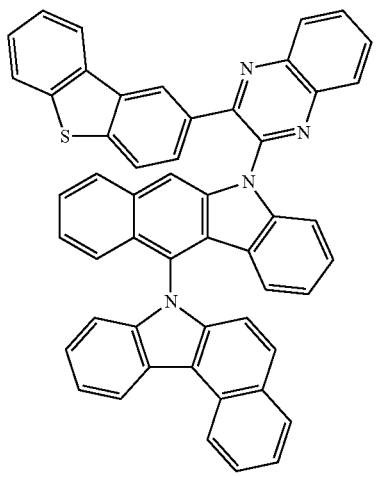
145
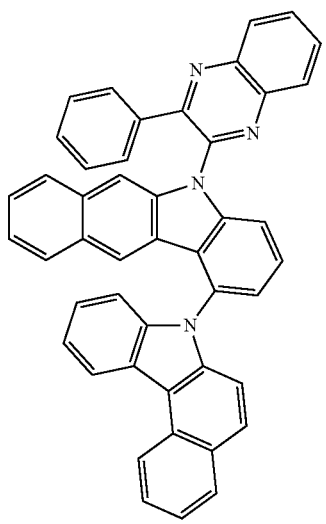
146
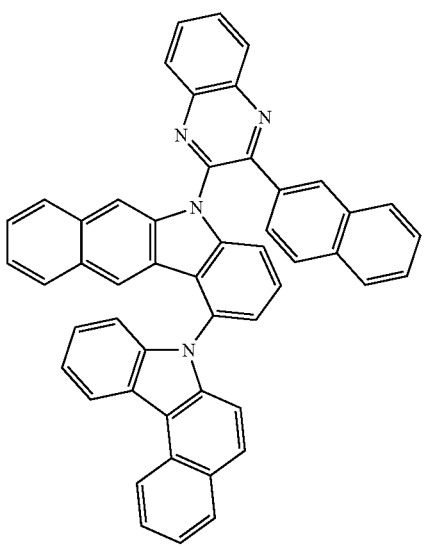

147
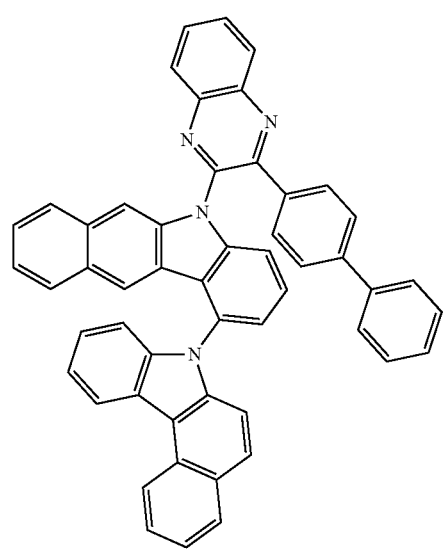
148
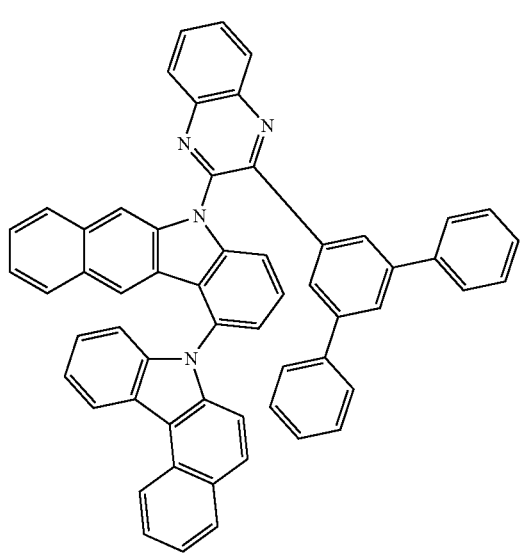
149
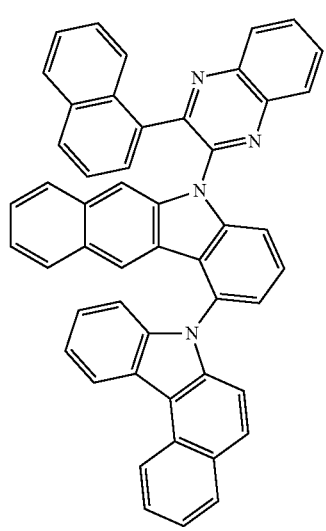
150
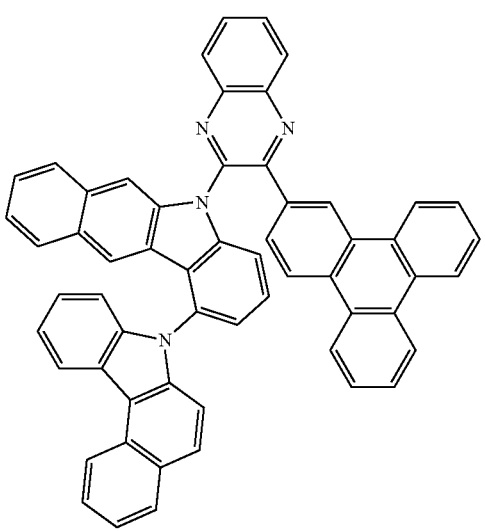
151
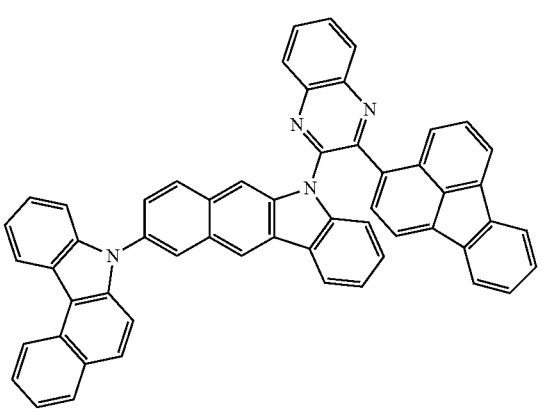
152
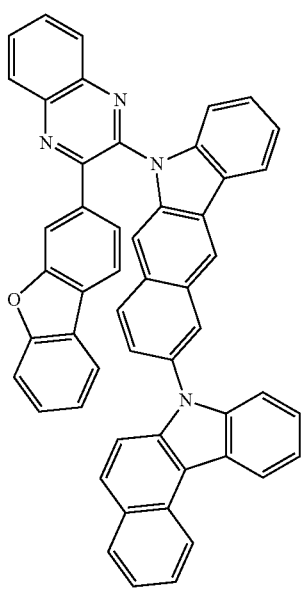

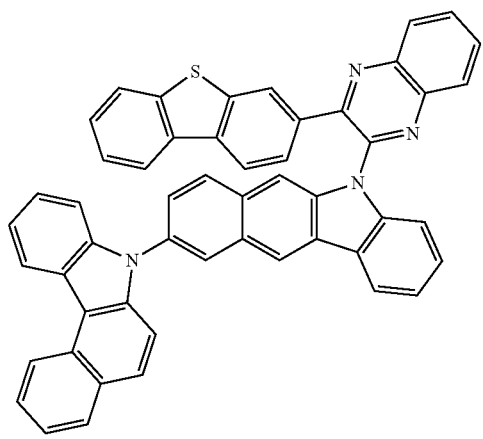
153
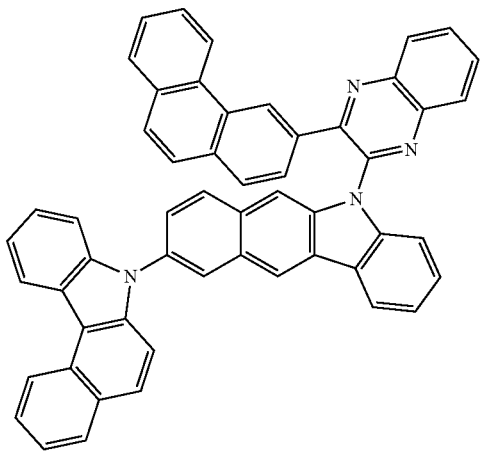
156
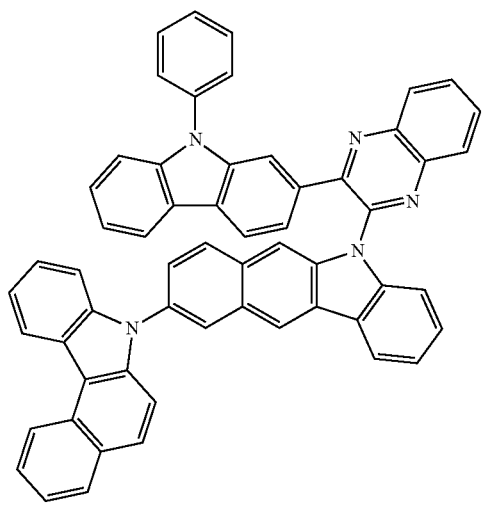
154
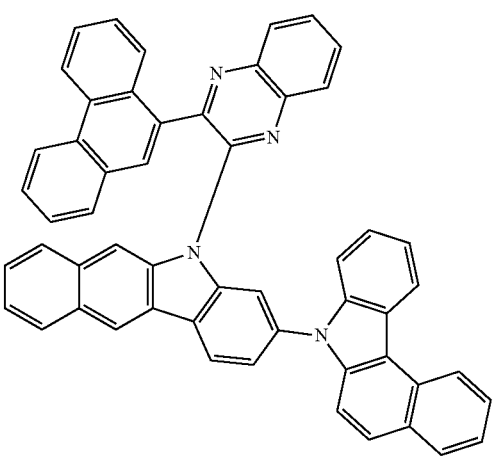
157
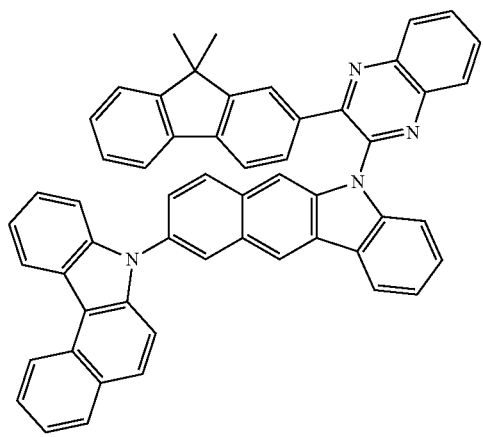
155
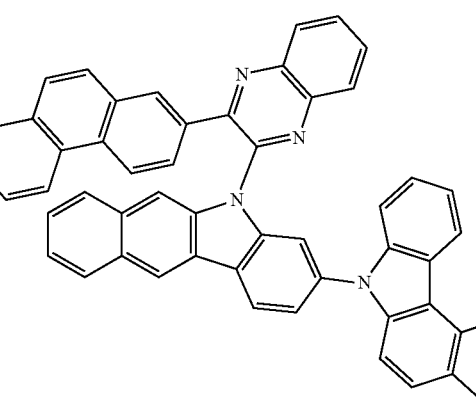
158

-continued
159
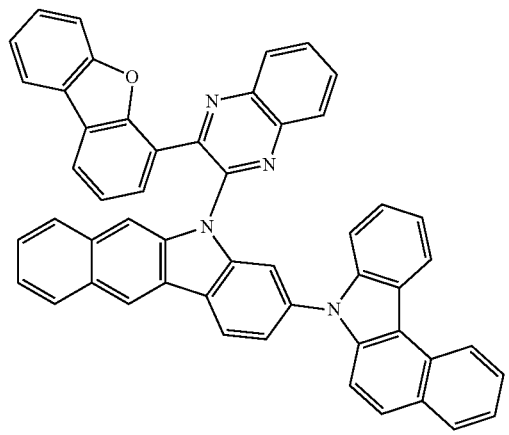
160
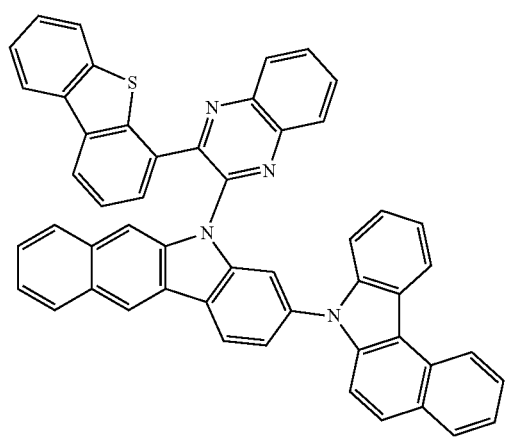
161
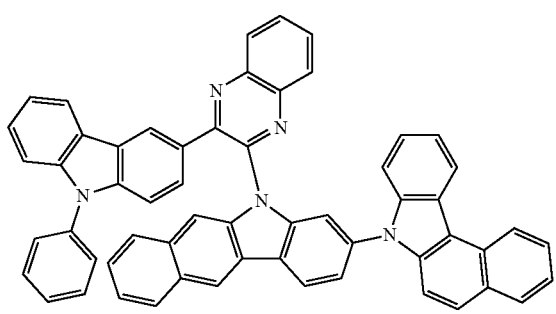
162
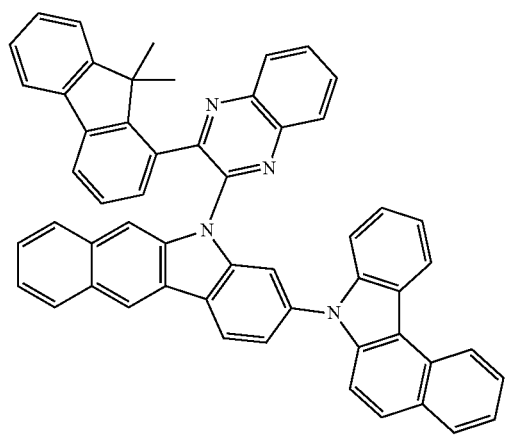
-continued
163
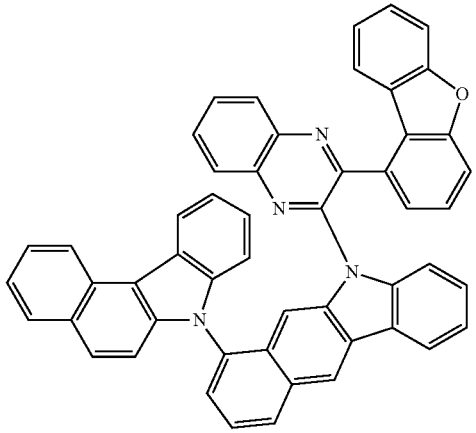
164
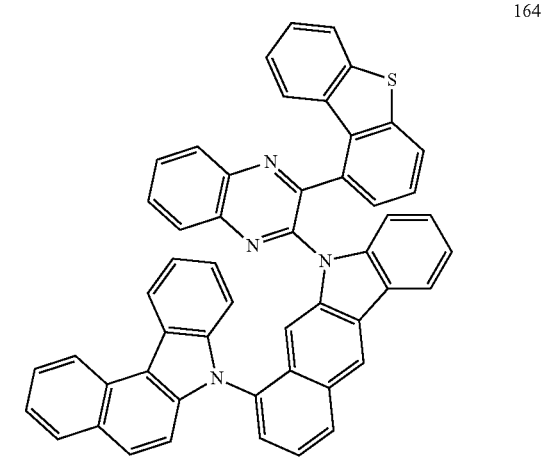
165
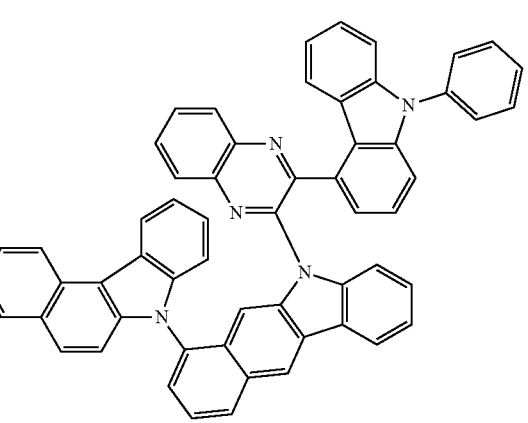

166
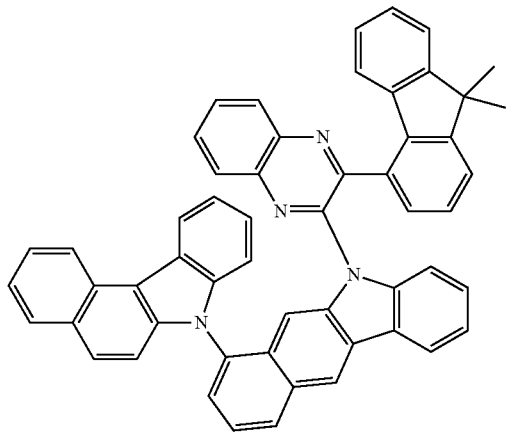
167
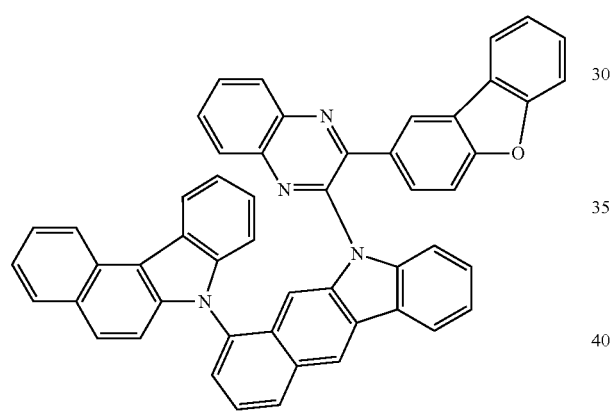
168
169
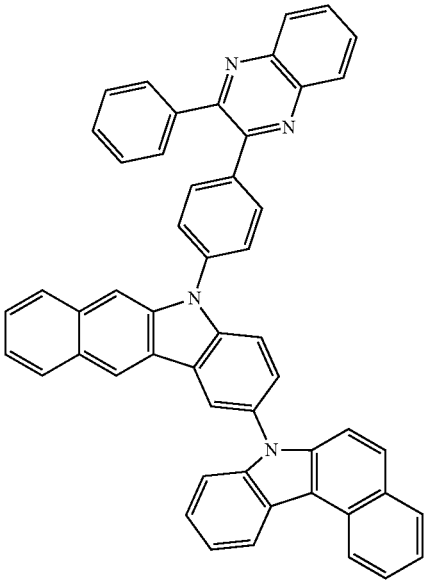
170
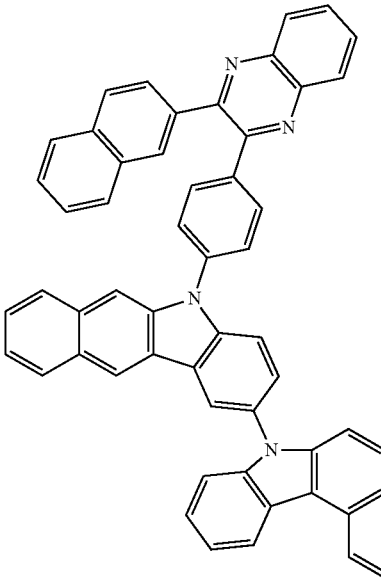

171
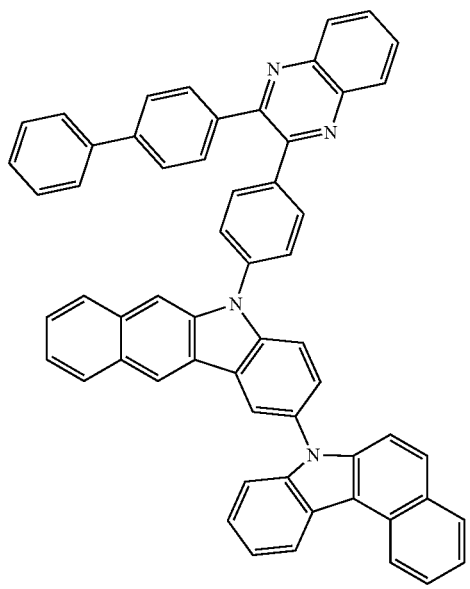
172
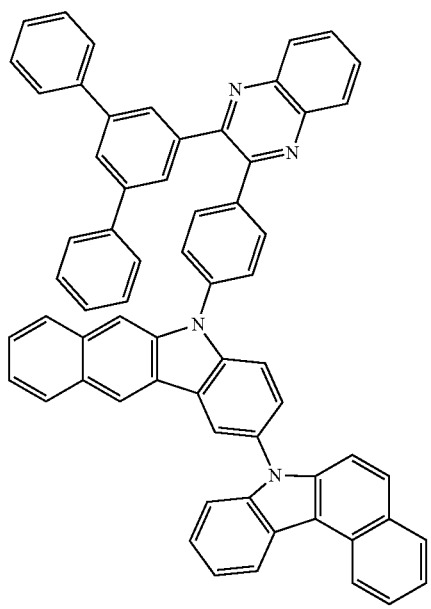
173
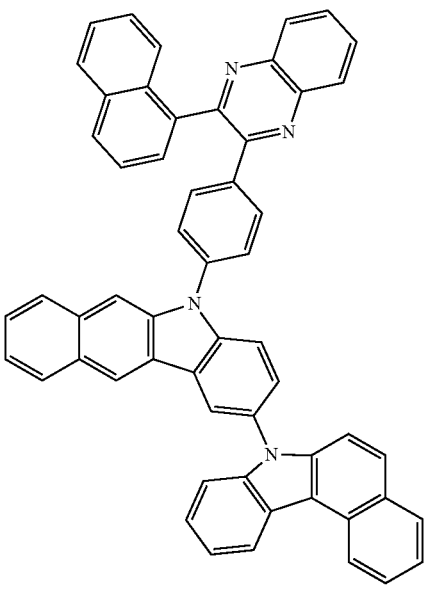
174
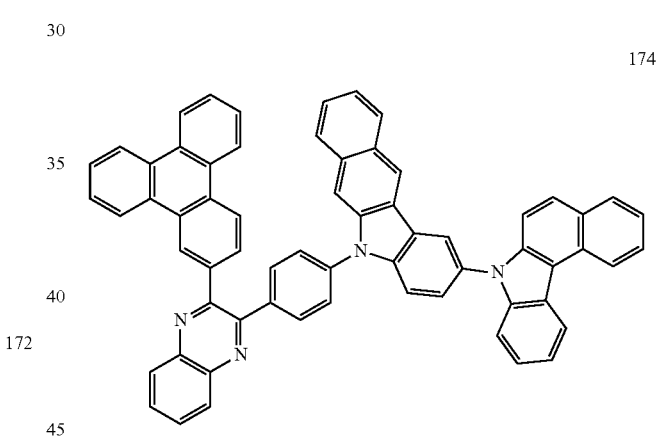
175
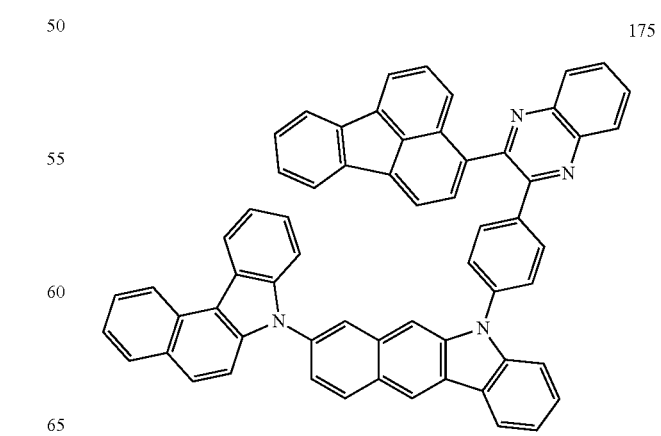

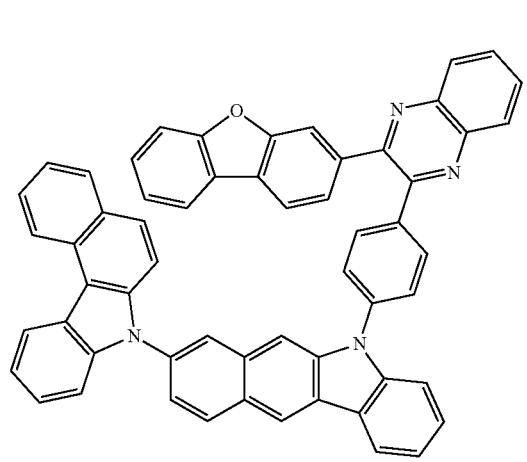
176
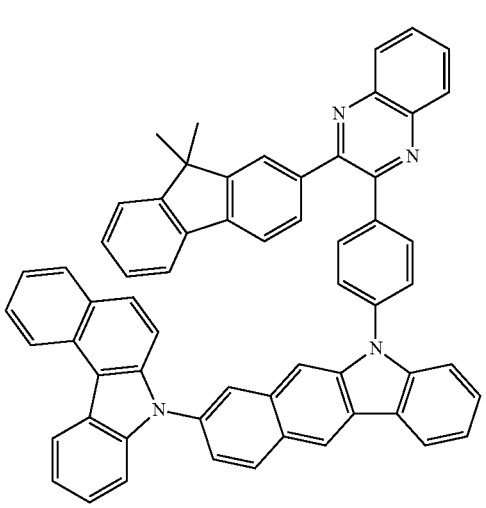
179
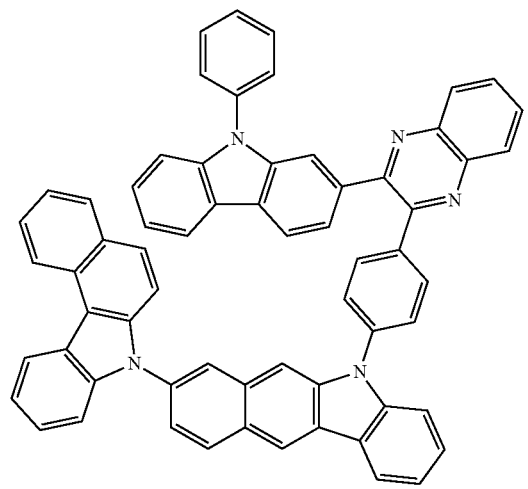
177
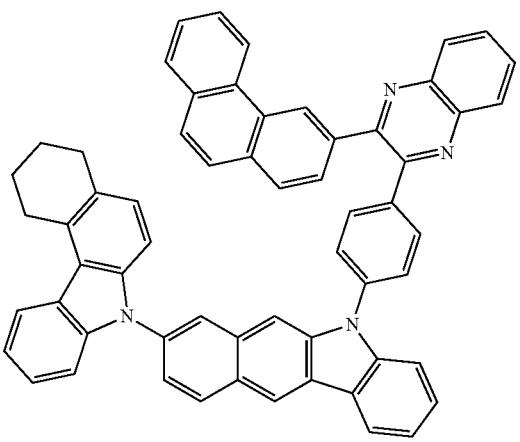
180
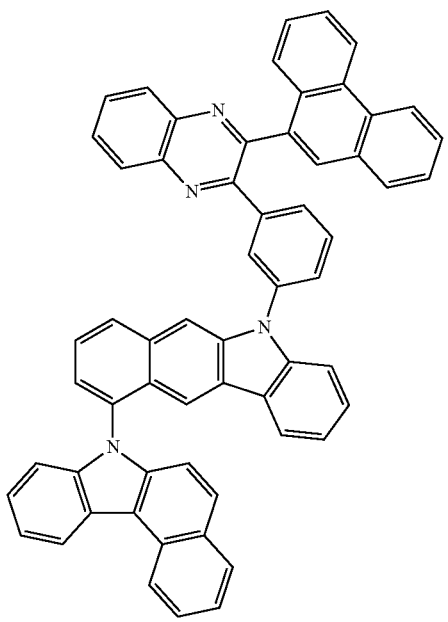
181
178

182
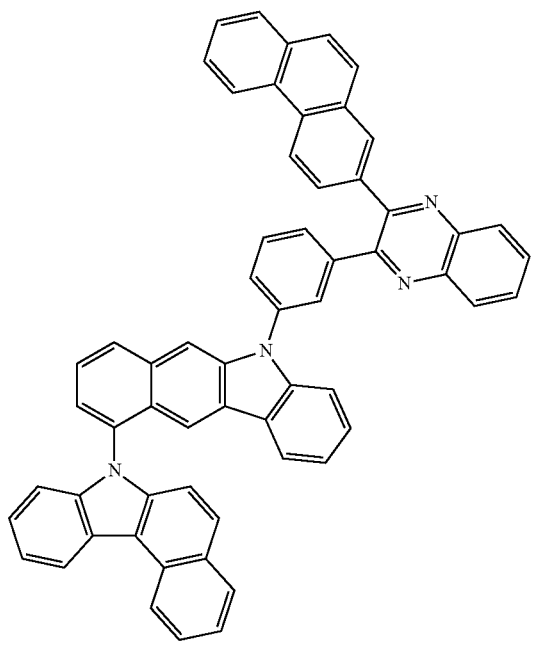
183
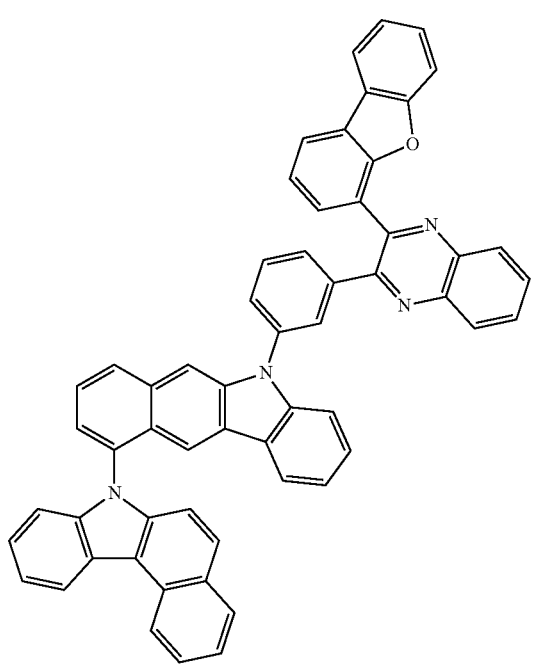
184
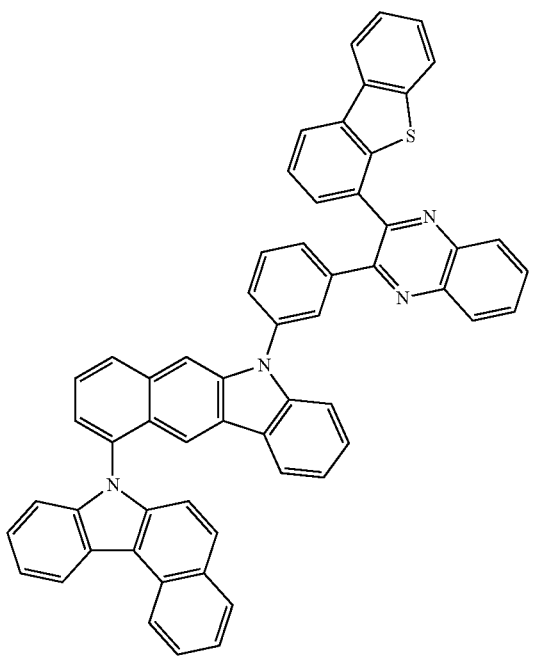
185
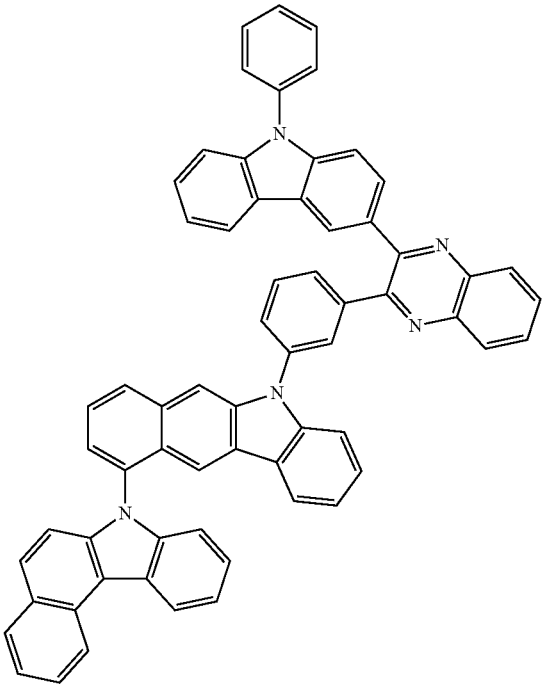

186
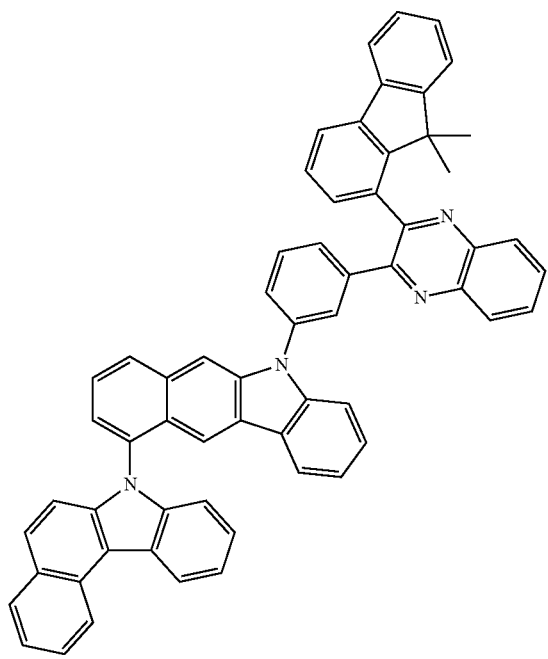
187
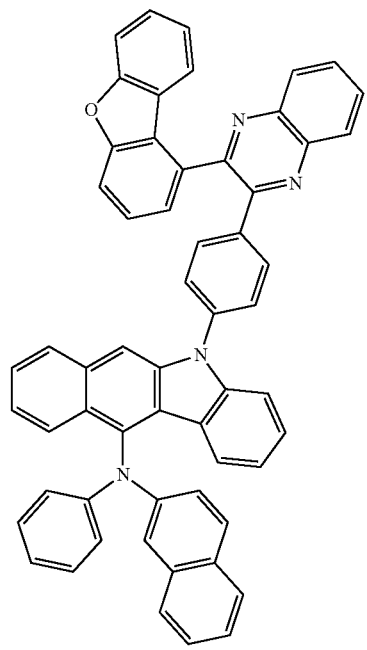
188
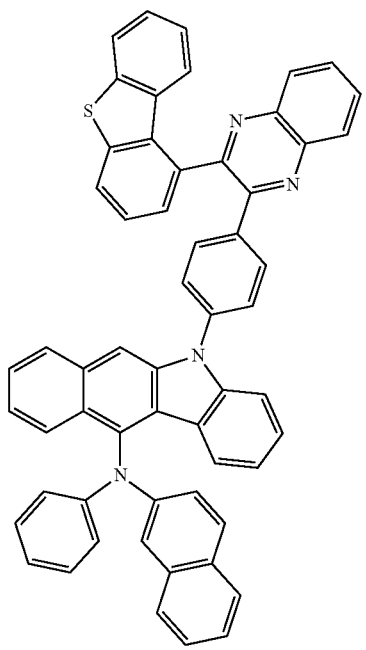
189
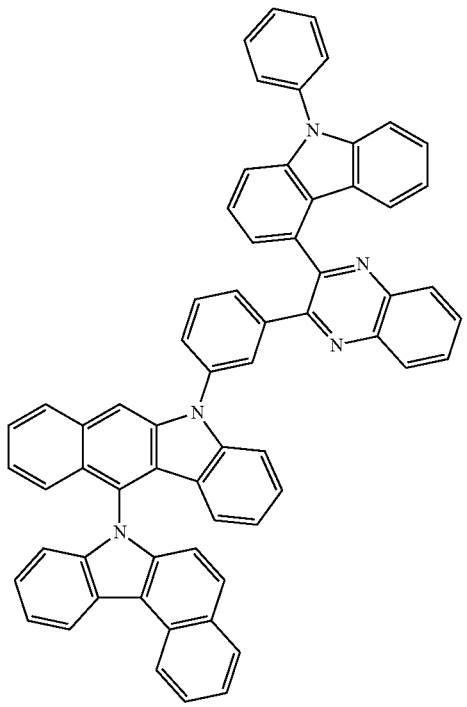

190
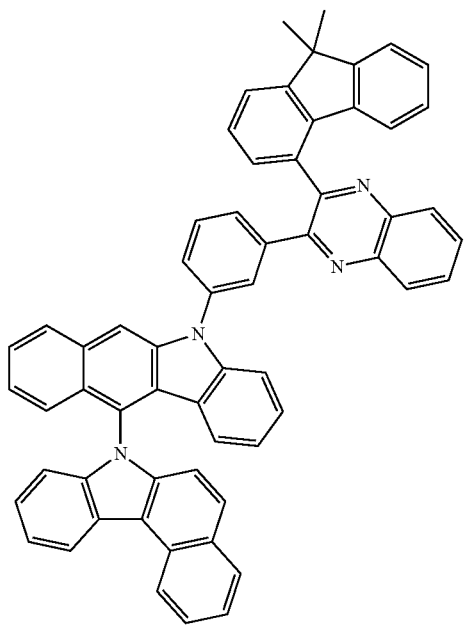
191
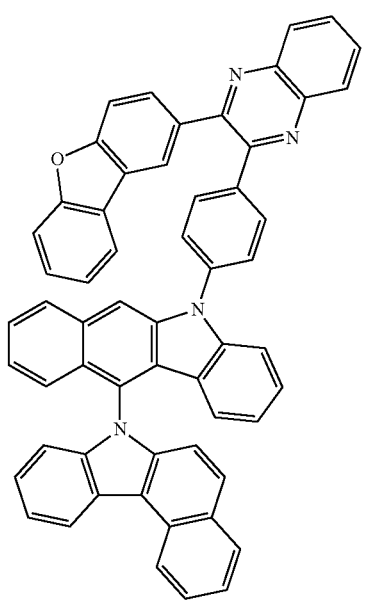
192
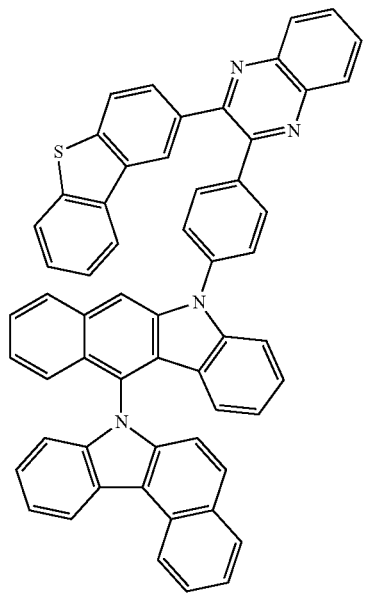
193
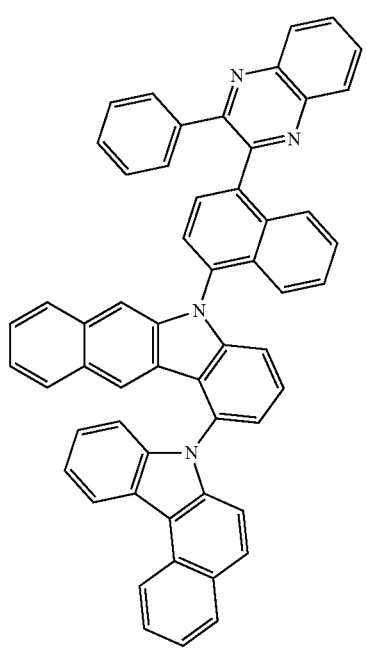

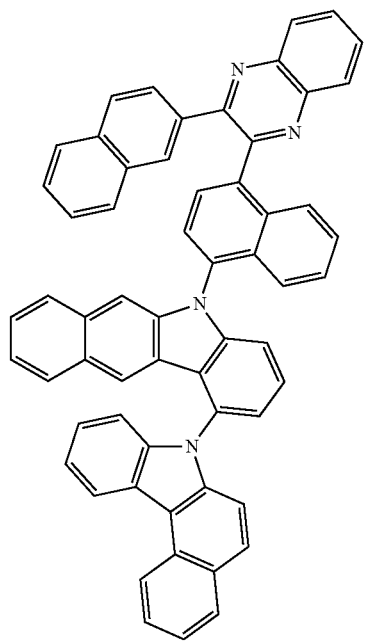
194
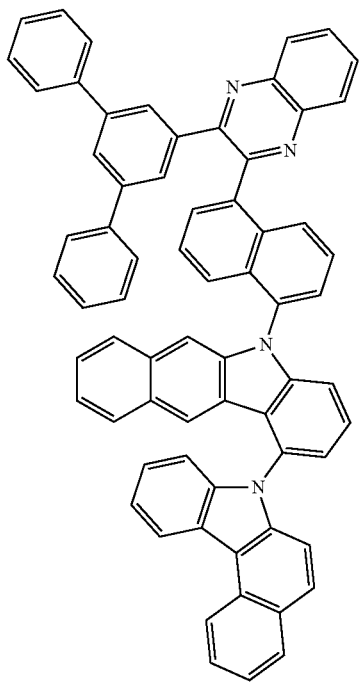
196
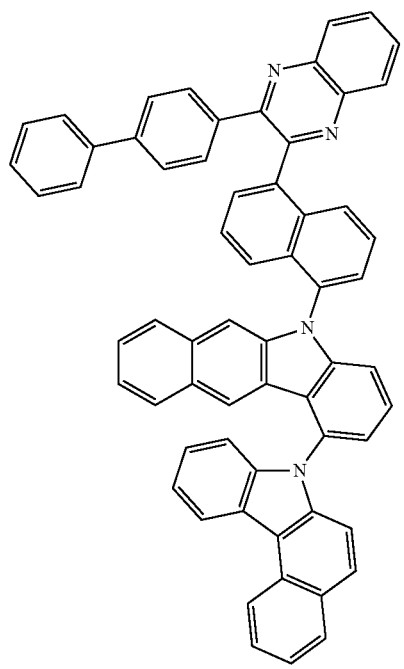
195
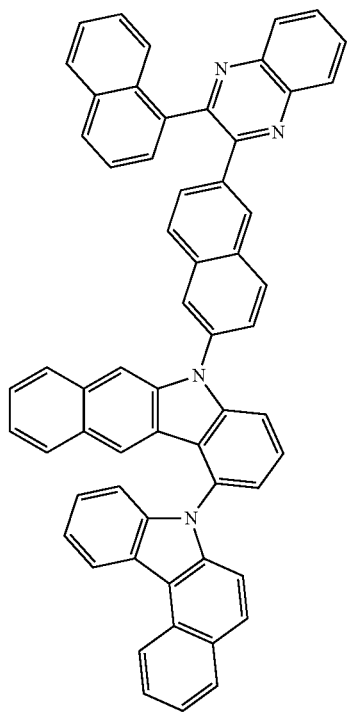
197

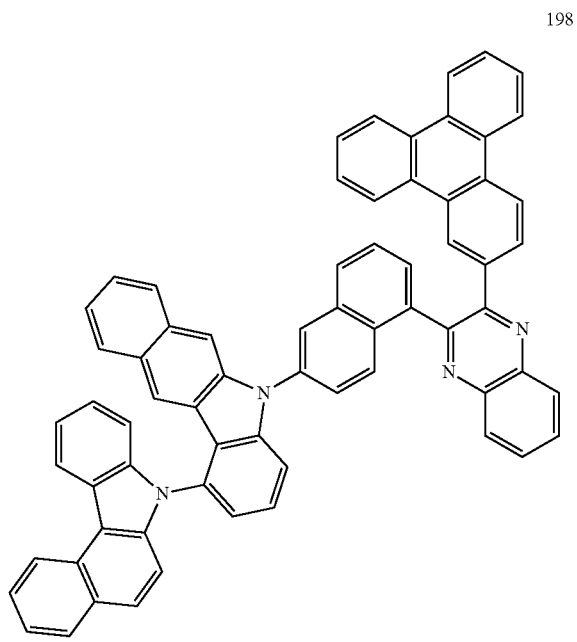
198
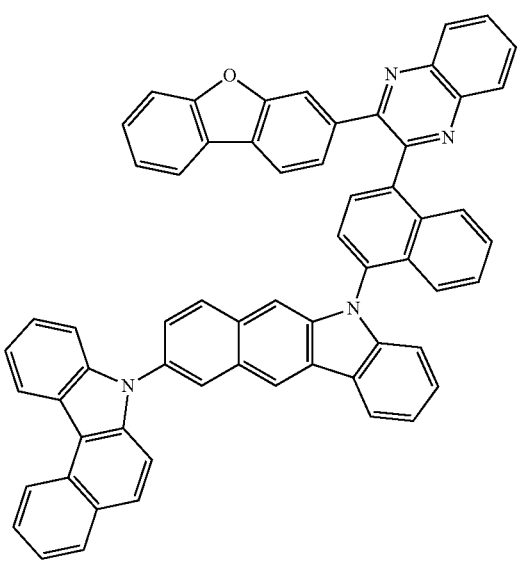
200
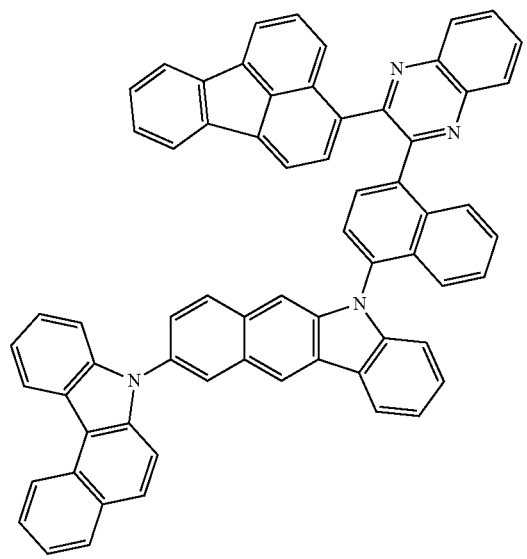
199
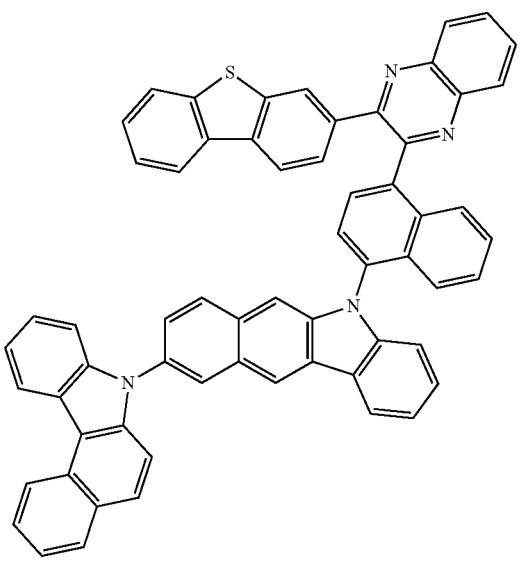
201

-continued
202
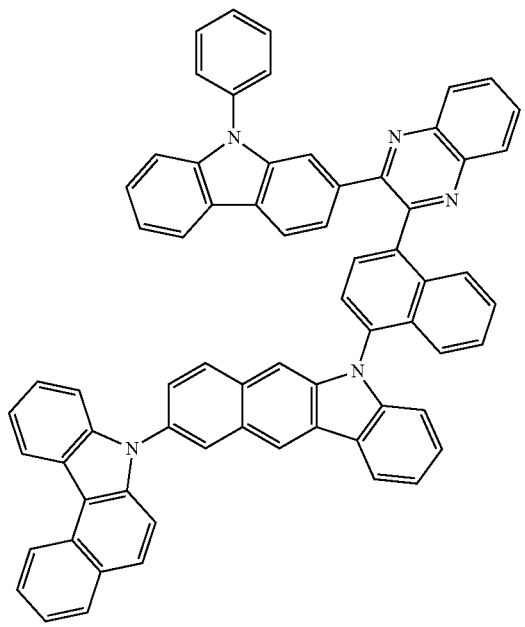
203
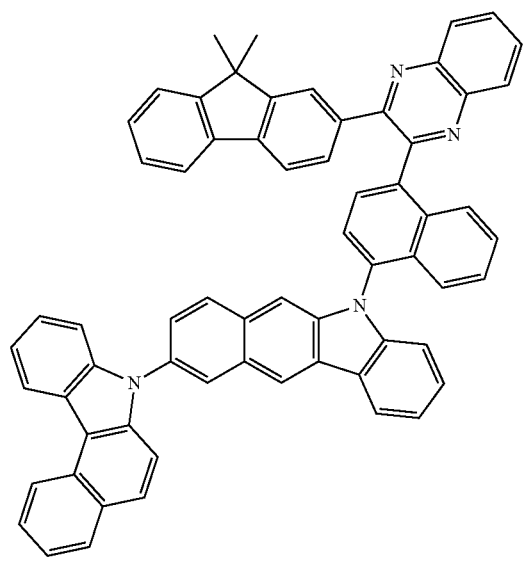
-continued
204
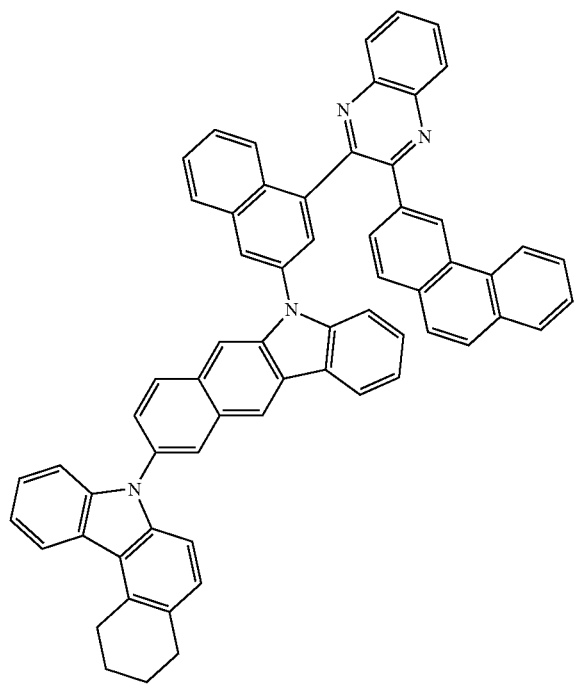
205
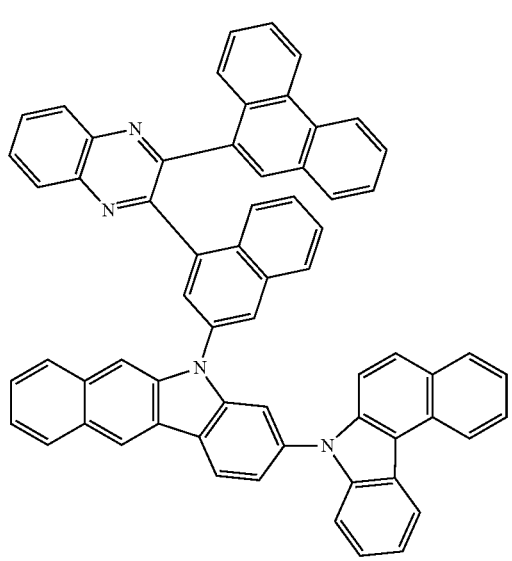

103
-continued
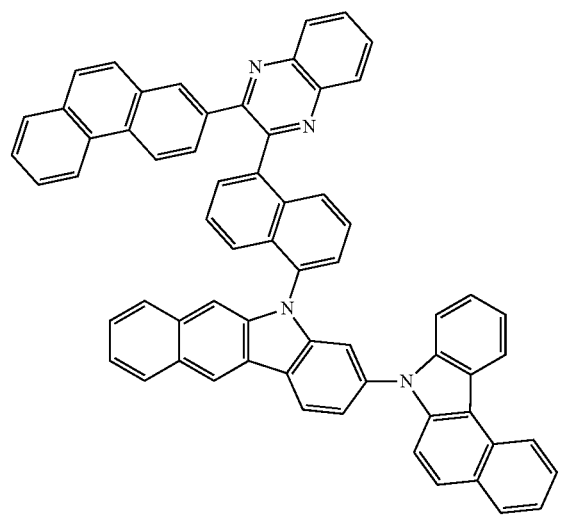
206
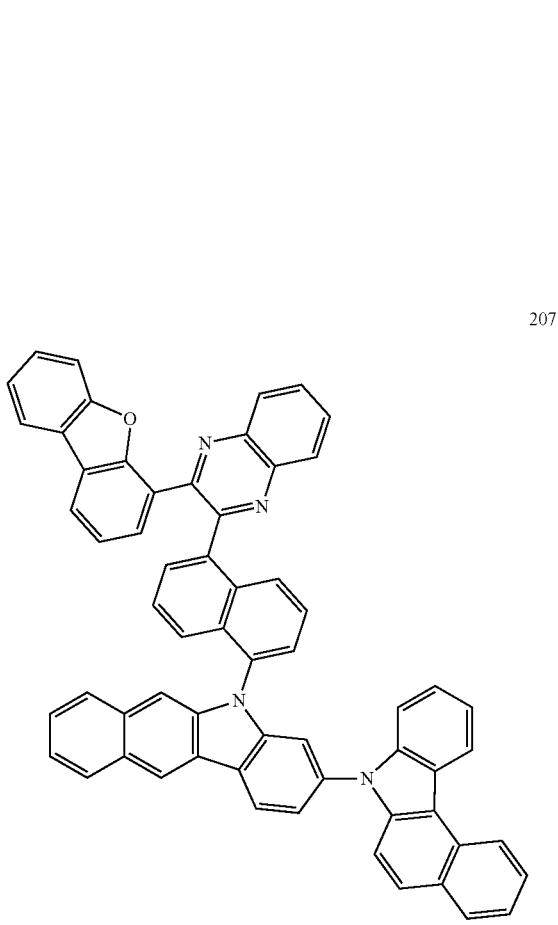
207
104
-continued
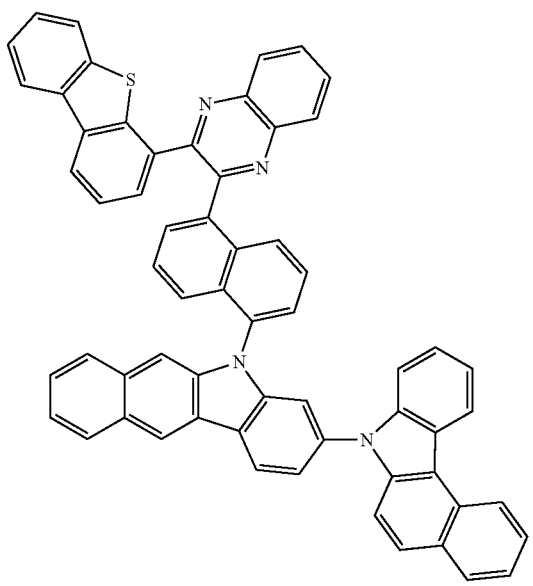
208
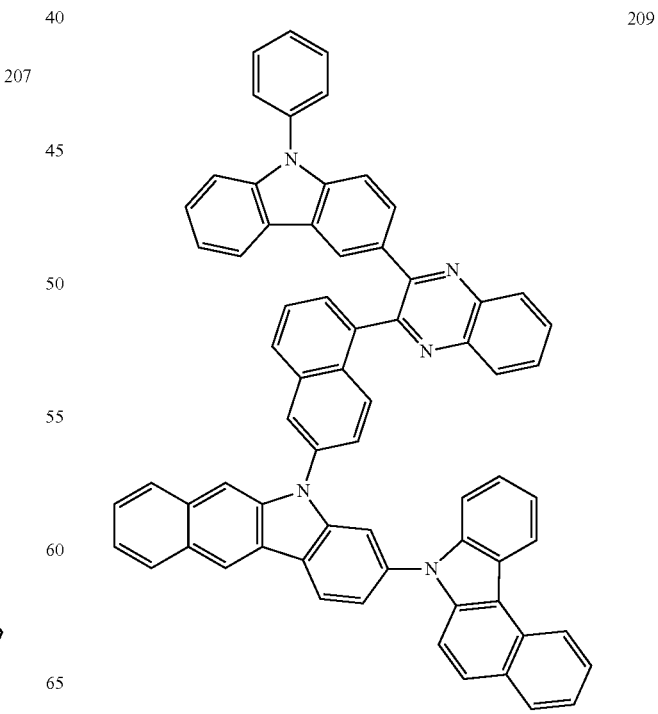
209

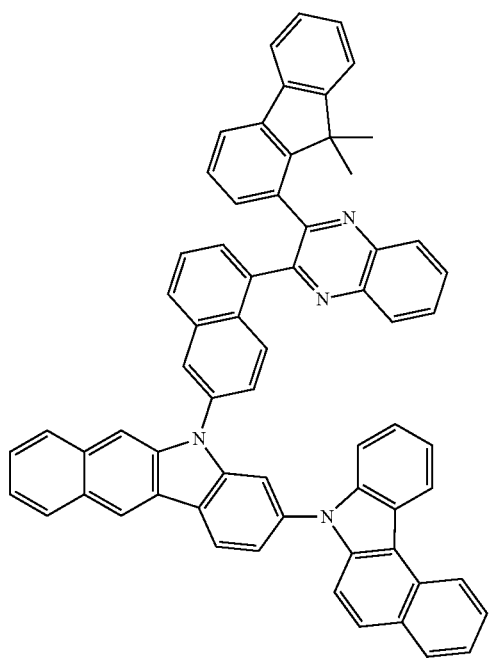
210
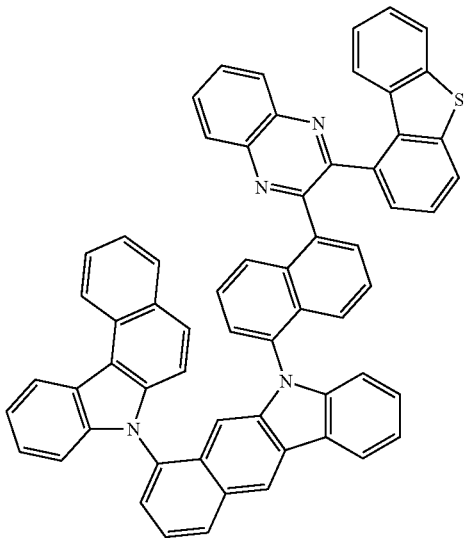
212
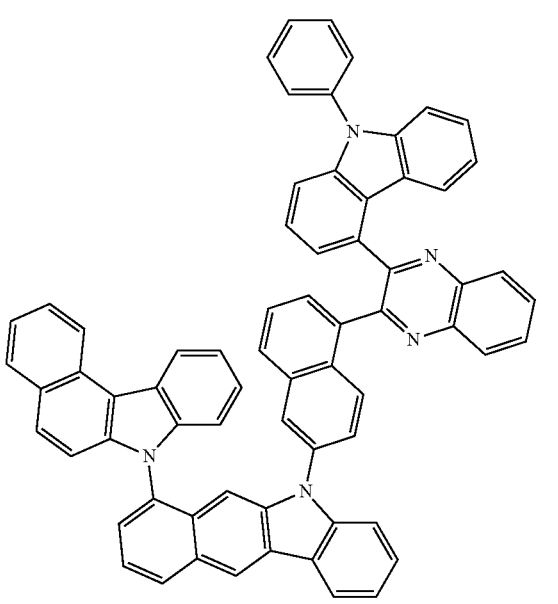
213

214
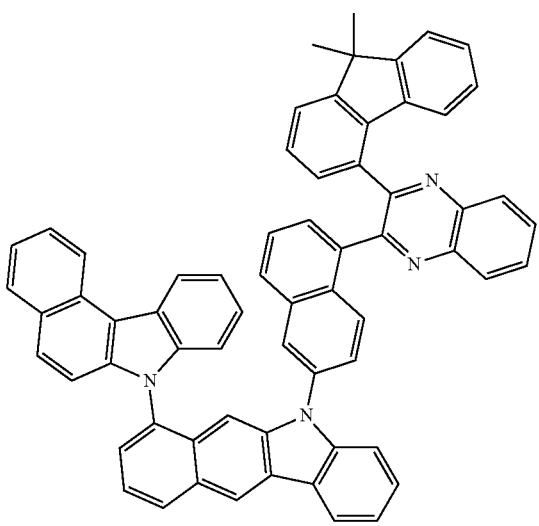
215
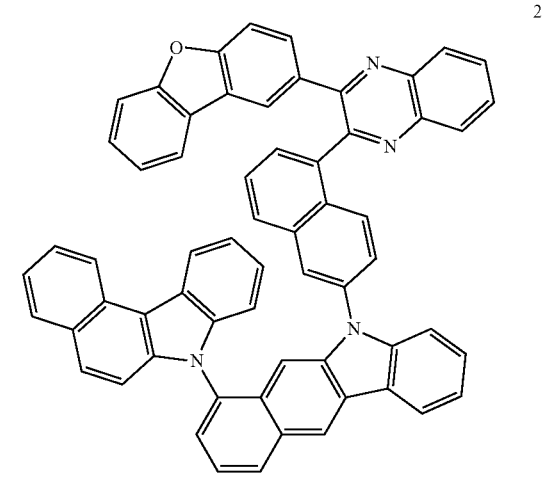
216

217
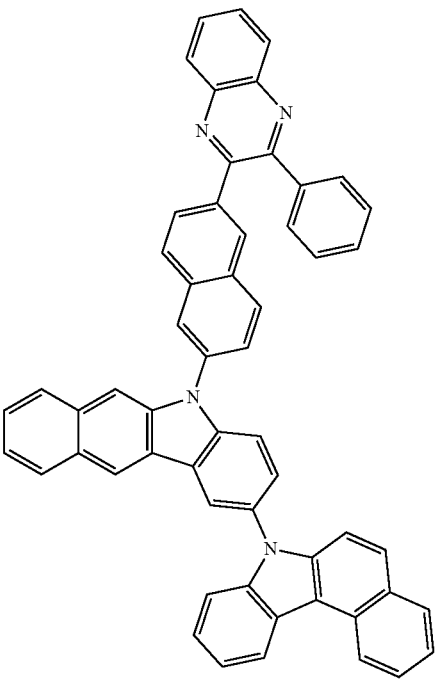
218
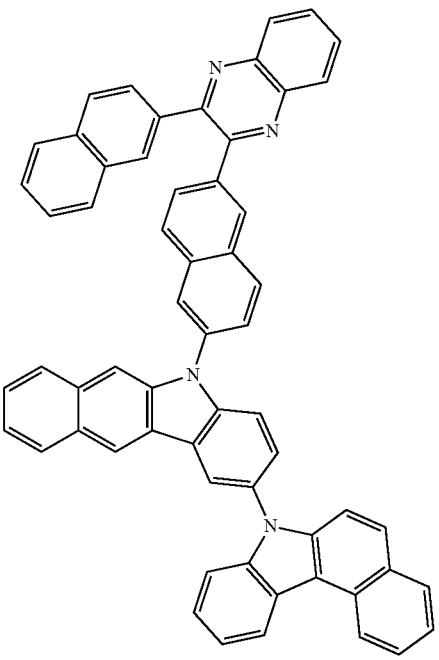

219
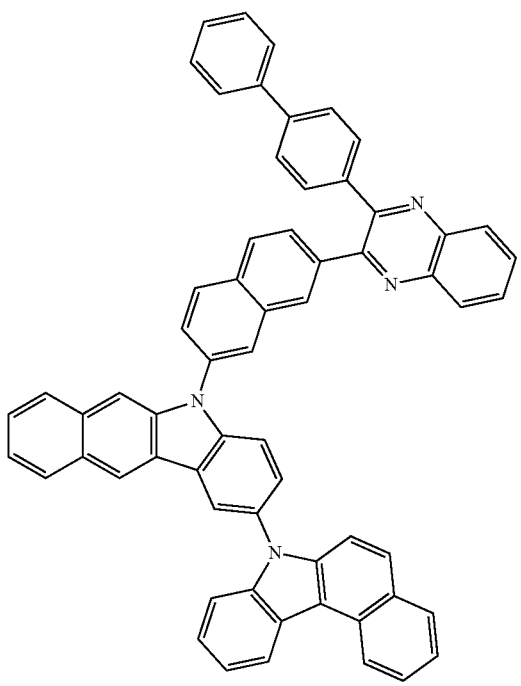
221
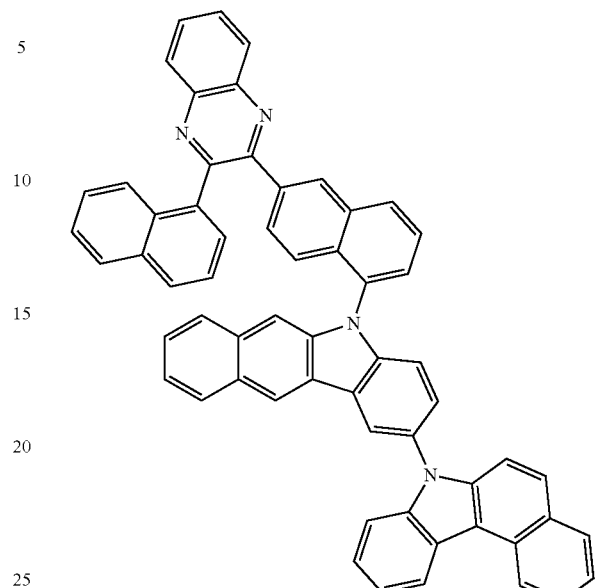
220
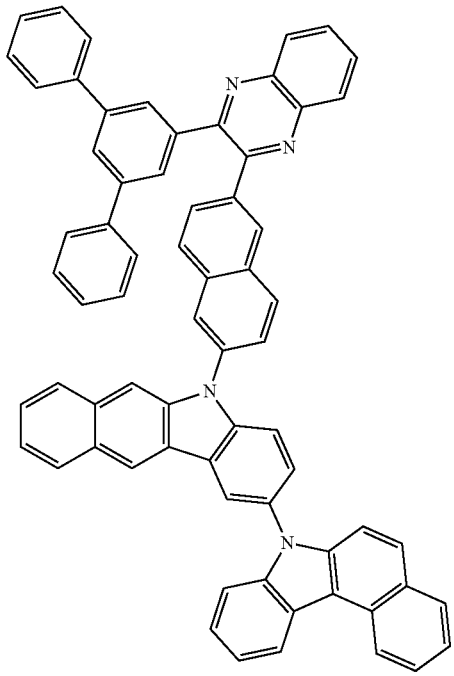
222
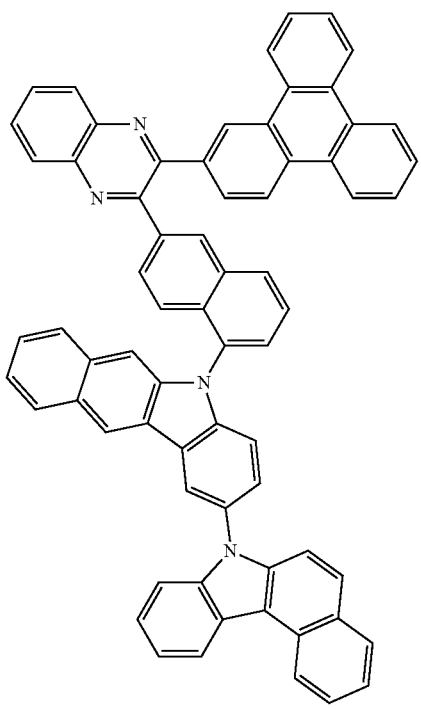

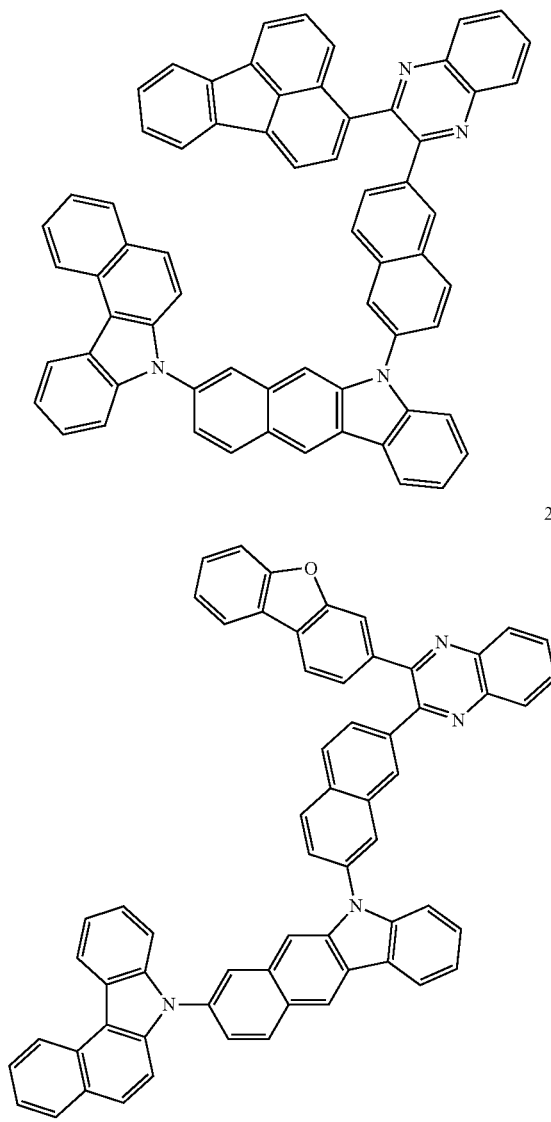
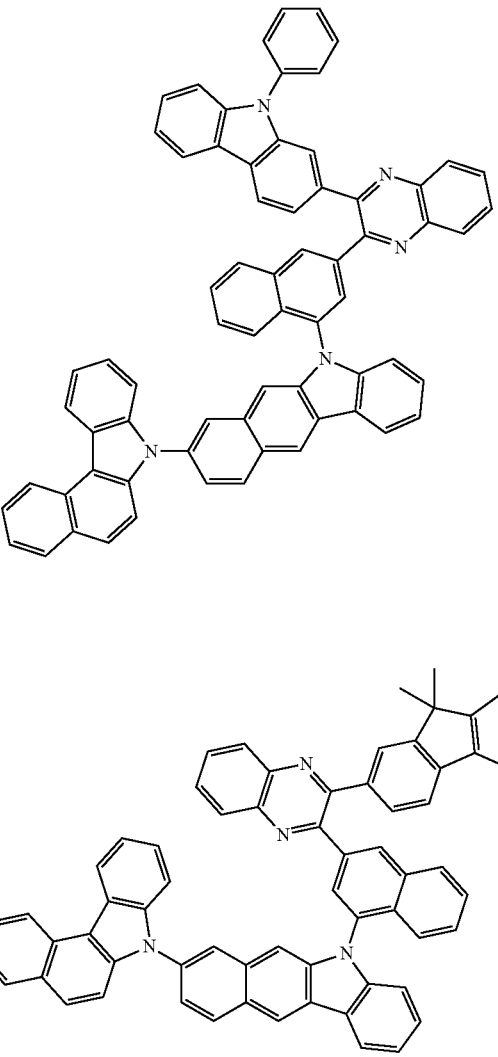
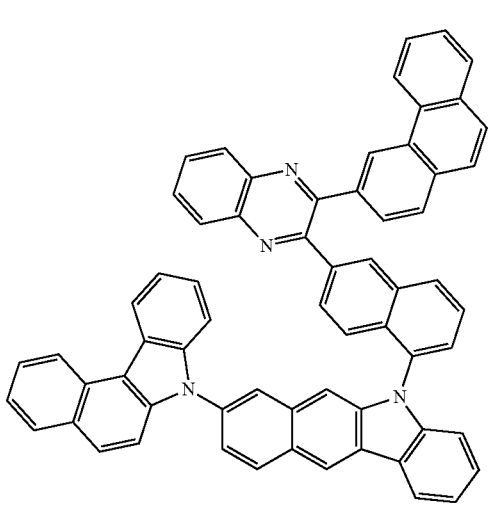

229
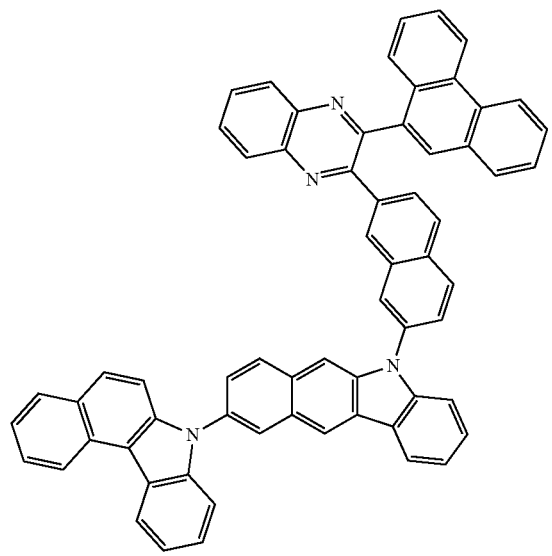
231
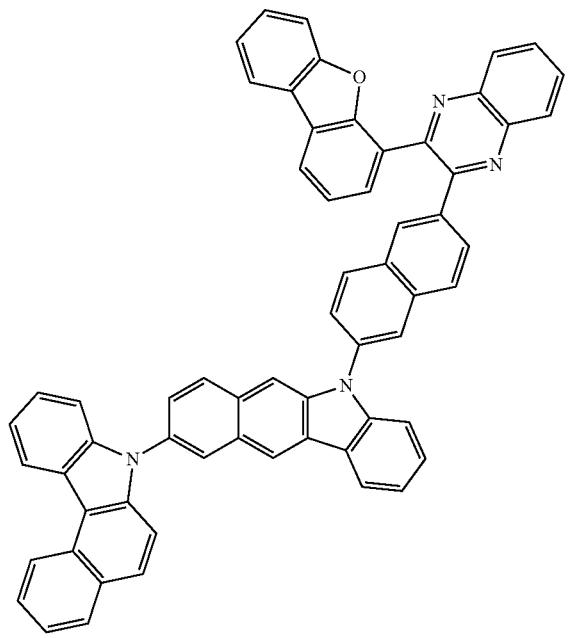
230
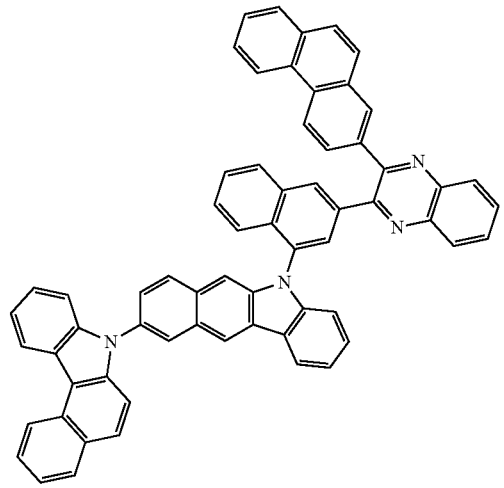
232
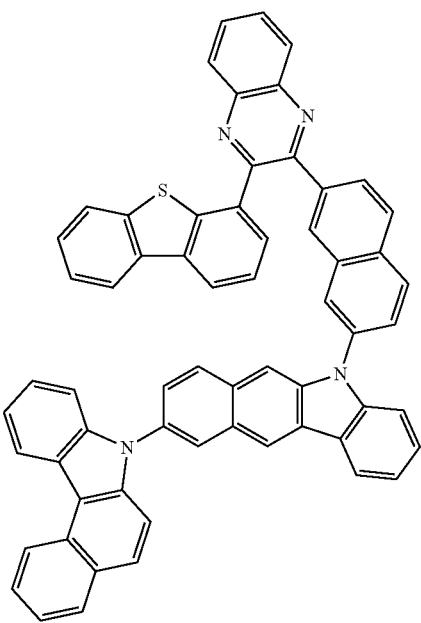

233
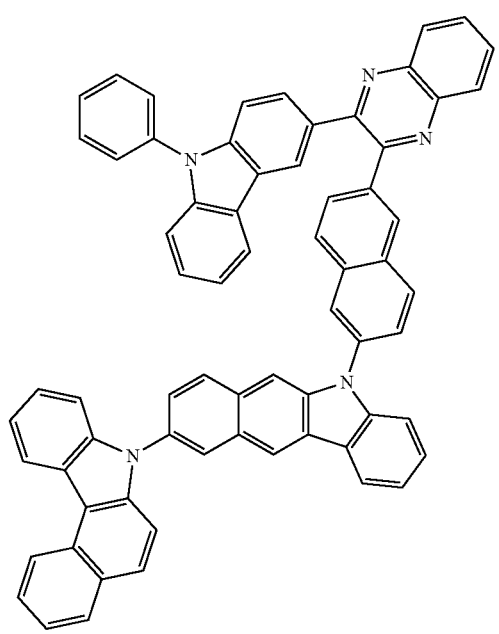
235
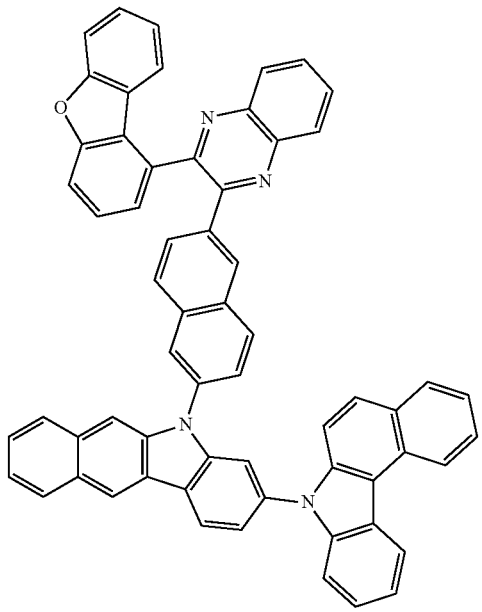
234
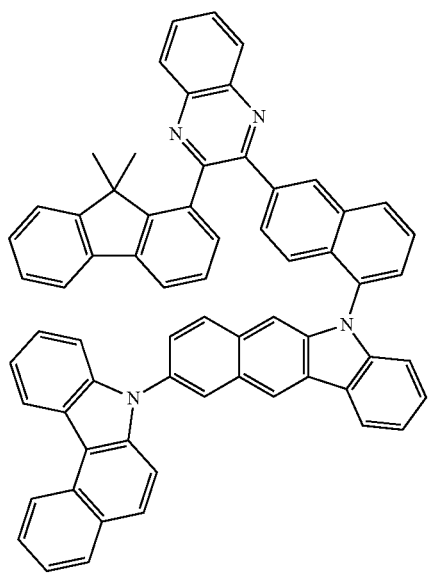
236
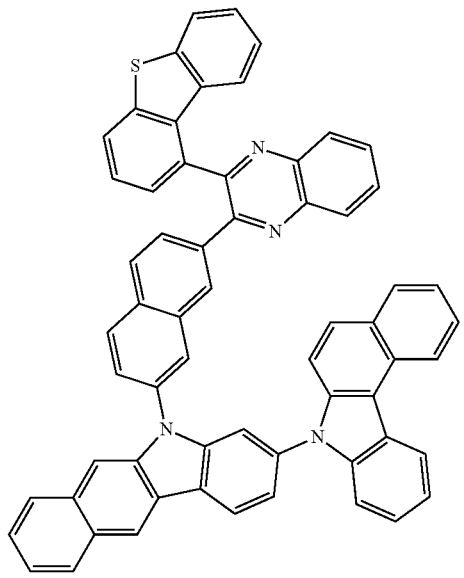

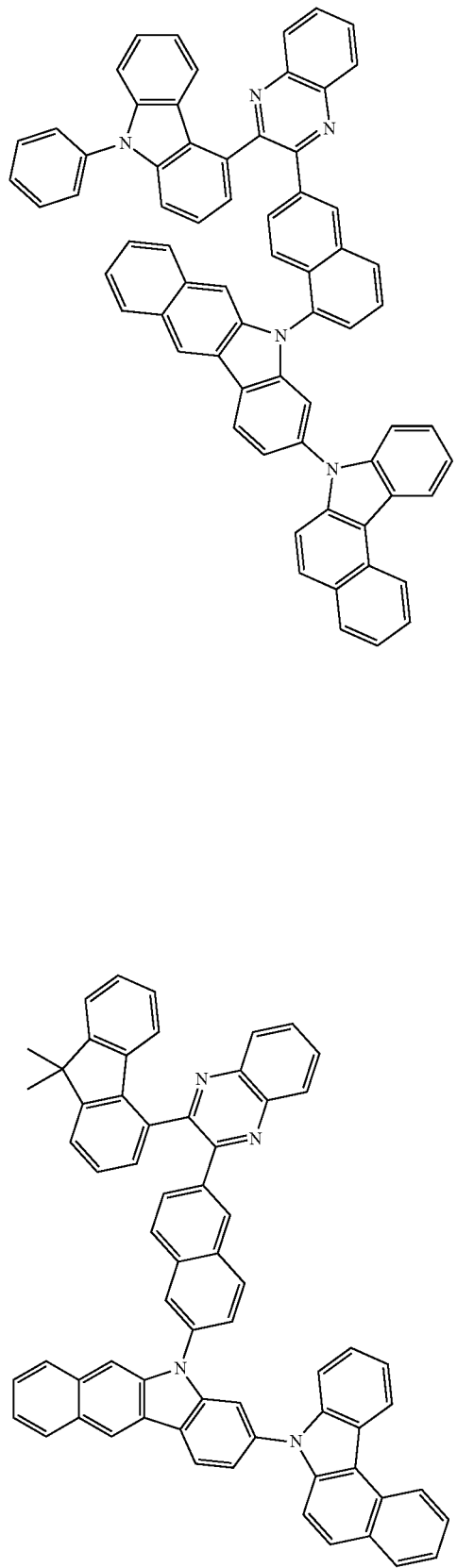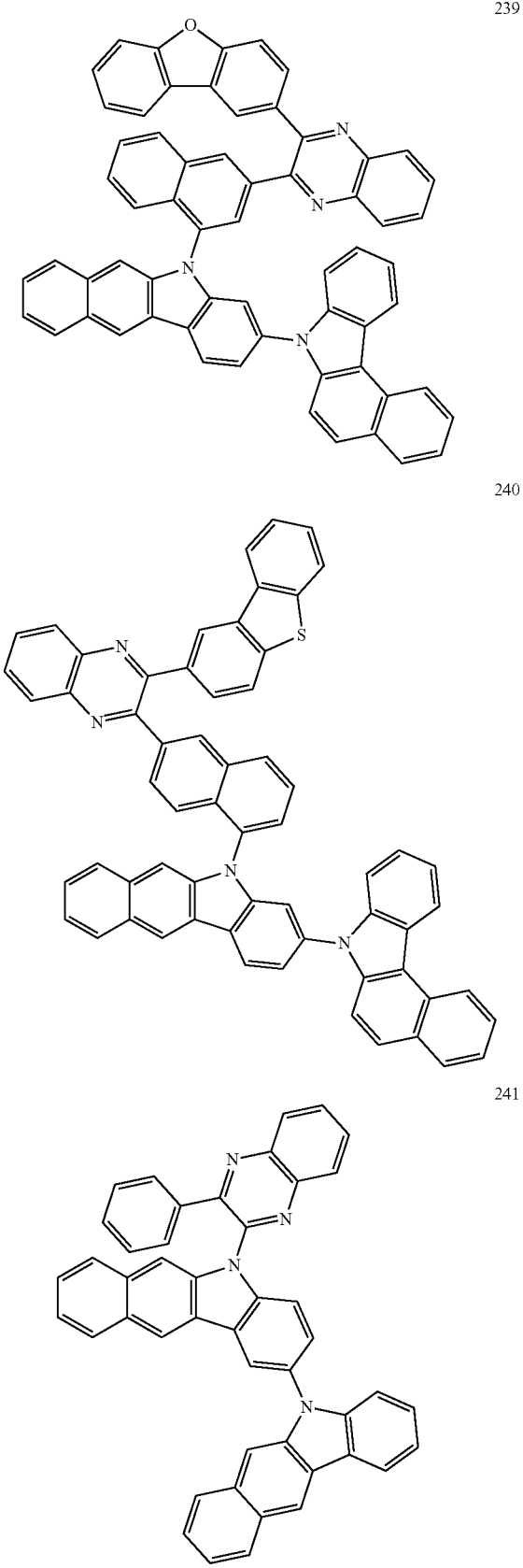

242
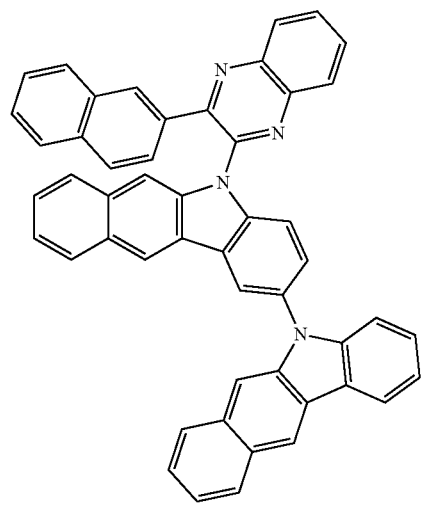
243
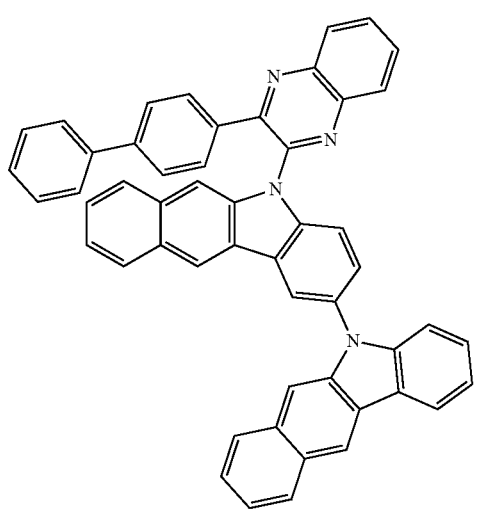
244
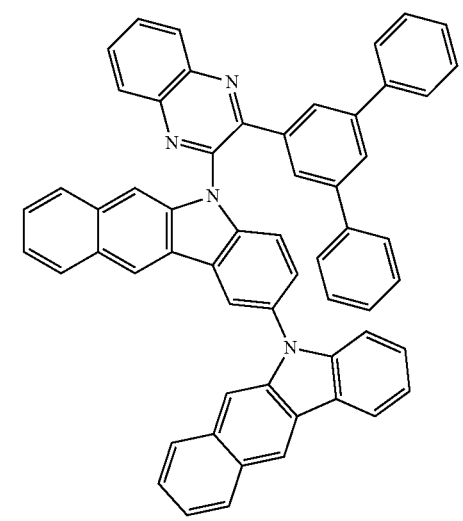
245
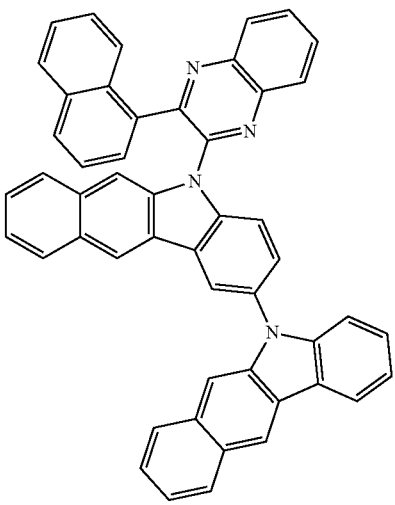
246
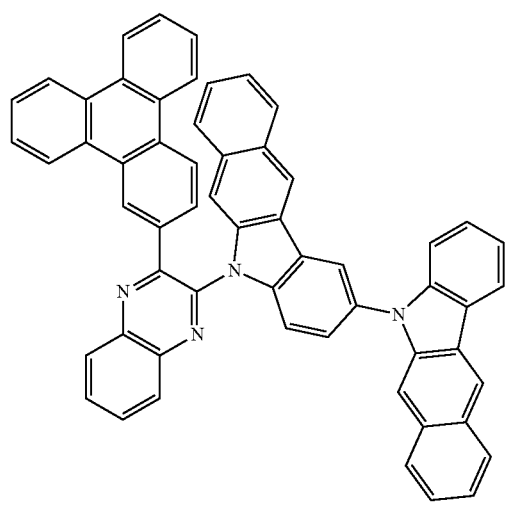
247
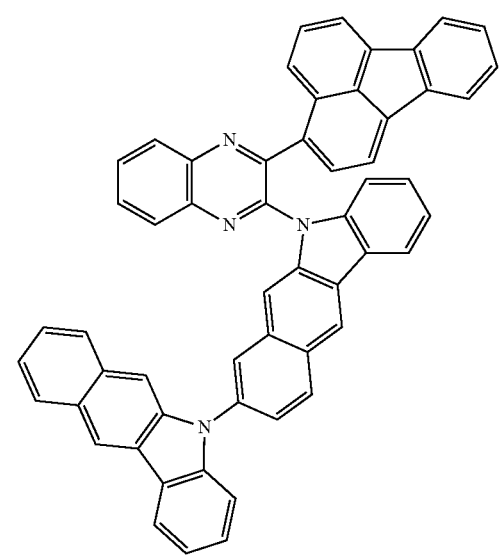

248
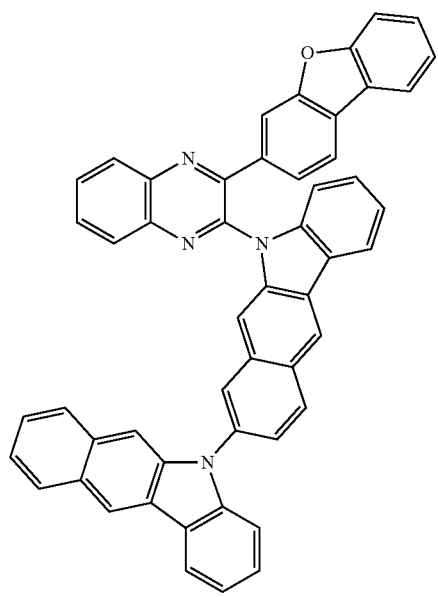
249
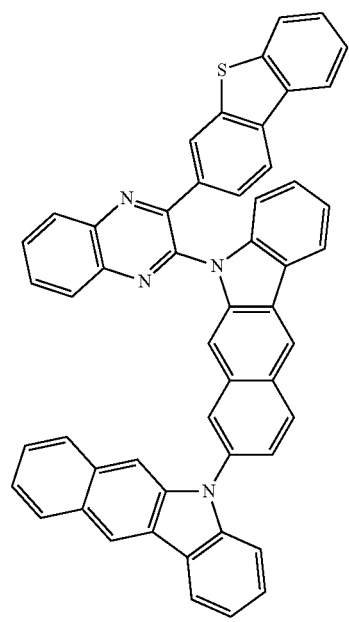
250
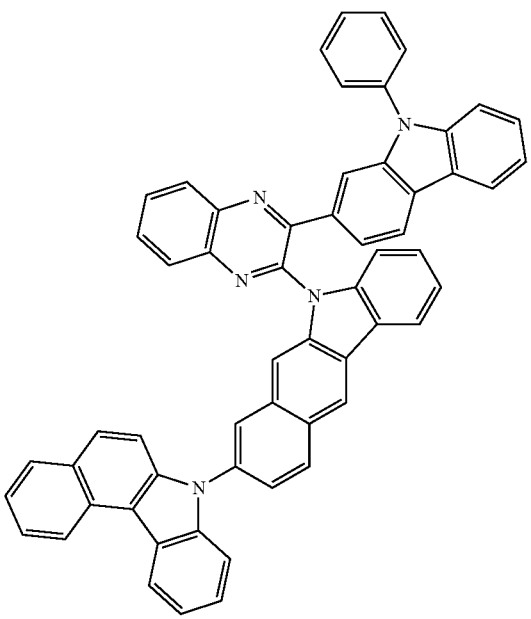
251
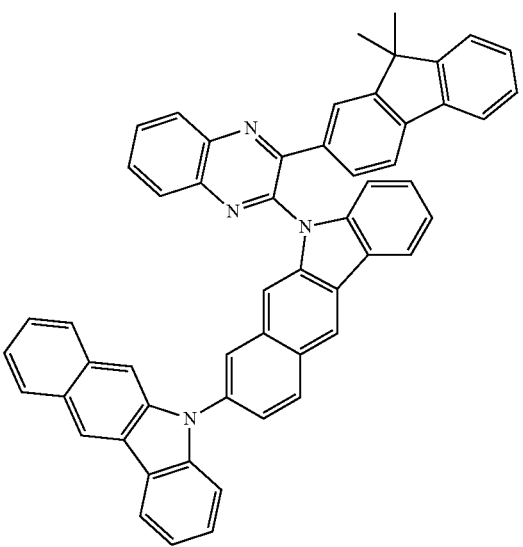

-continued
252
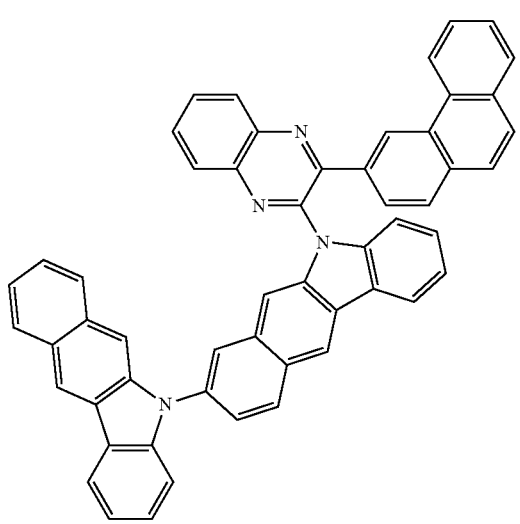
255
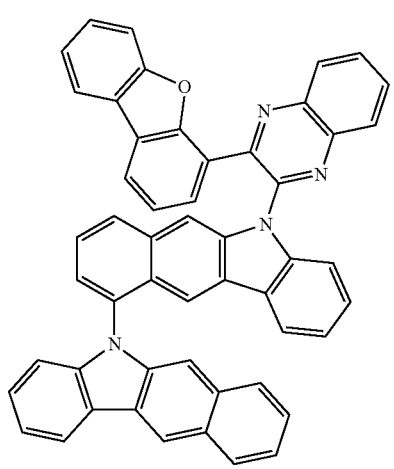
253
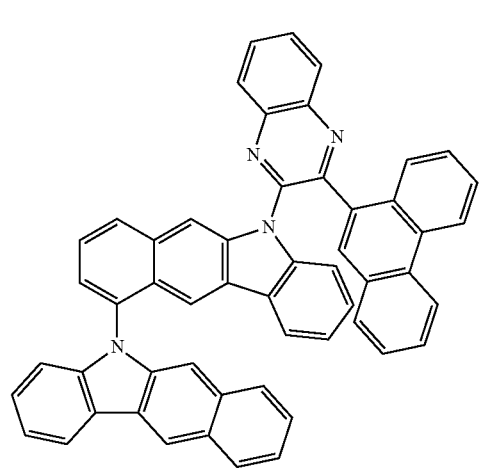
256
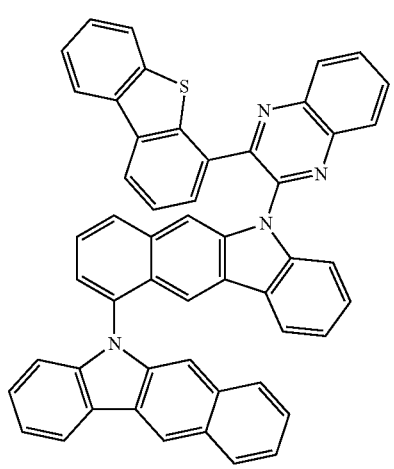
254
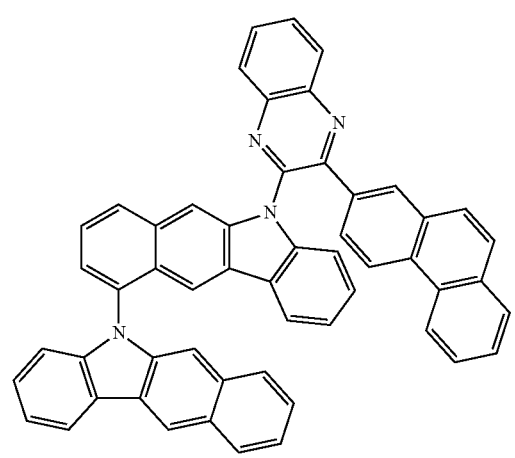
257
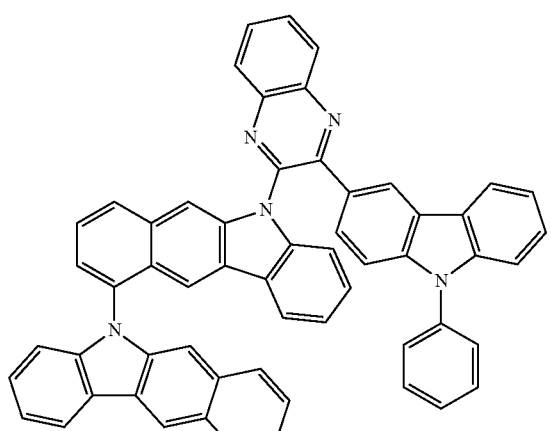

258
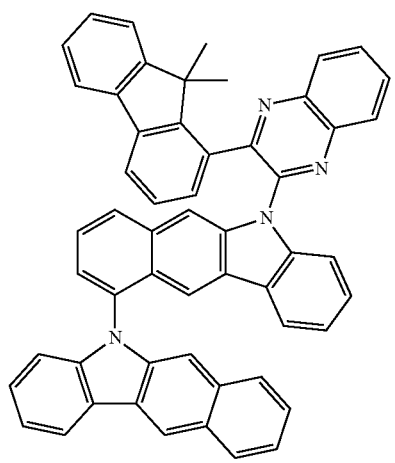
259
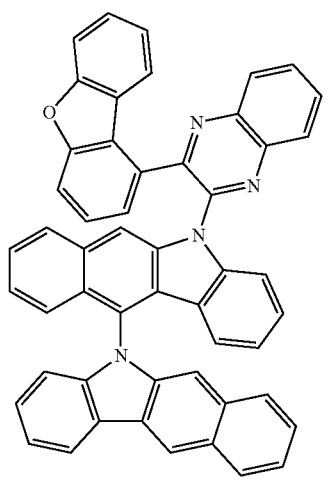
260
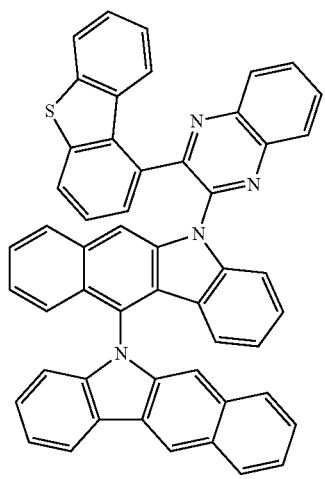
261
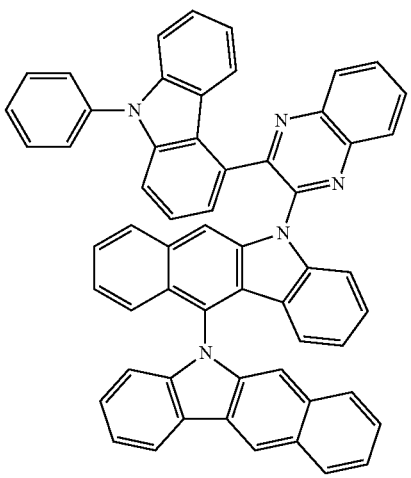
262
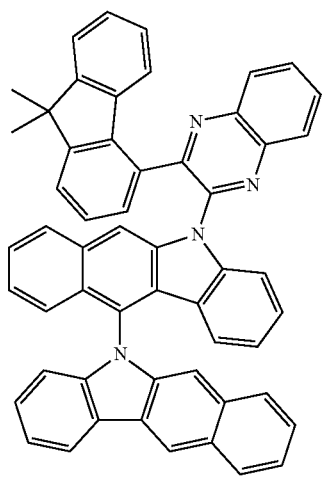
263
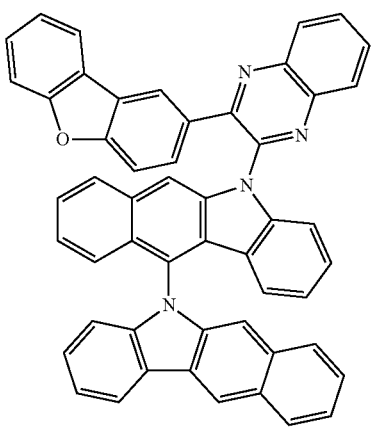

-continued
264
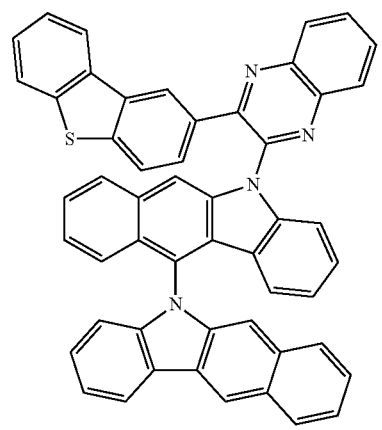
265
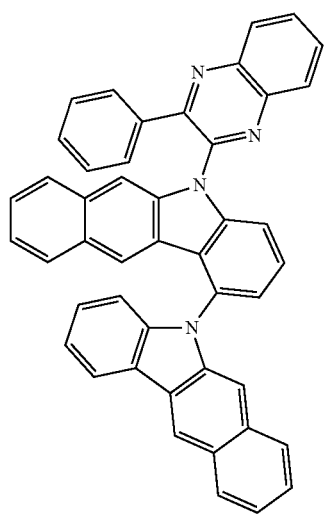
266
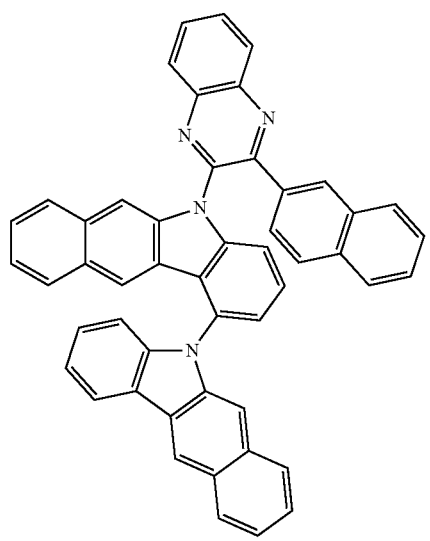
-continued
267
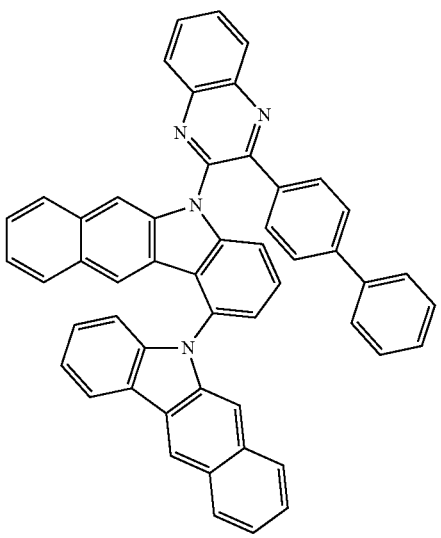
268
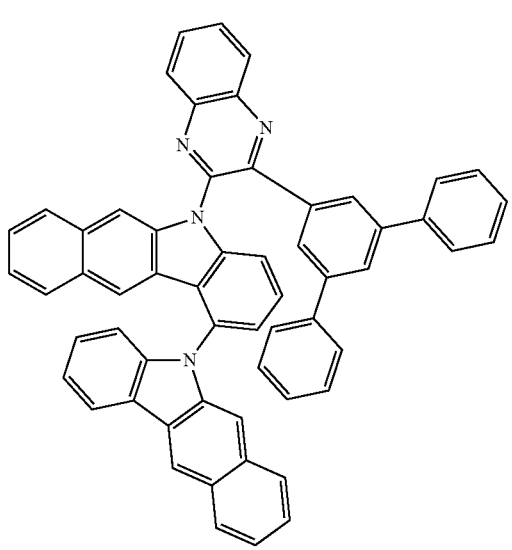
269
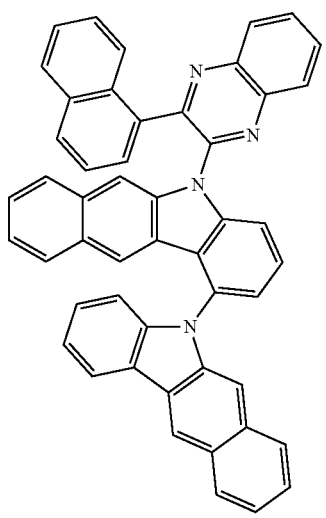

-continued
270
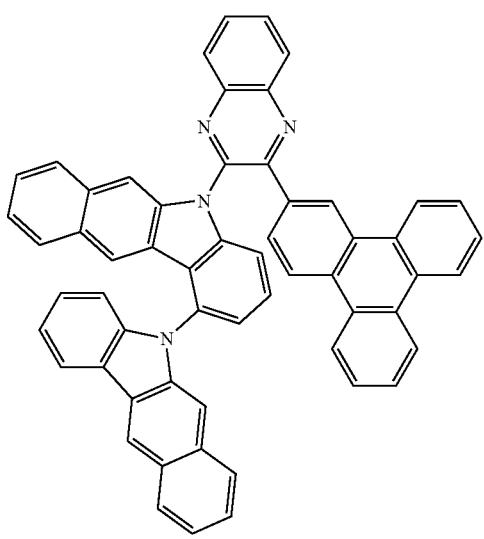
271
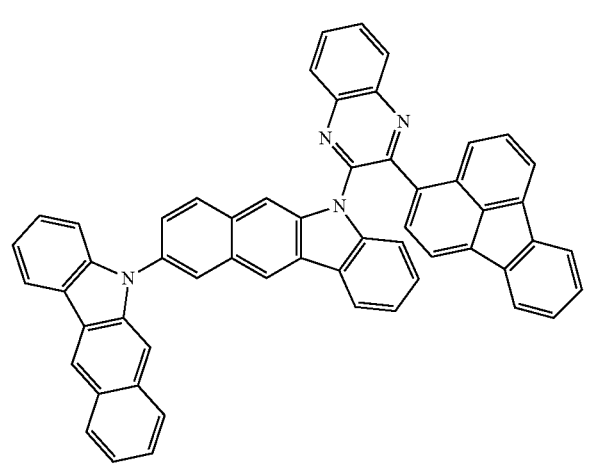
272
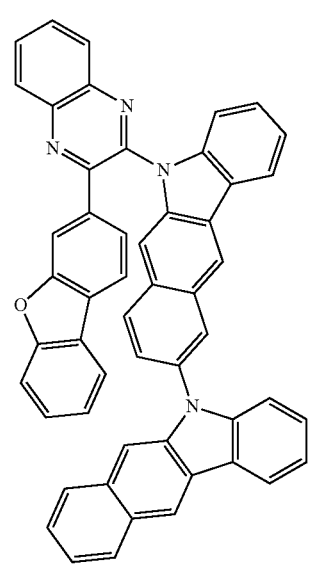
-continued
273
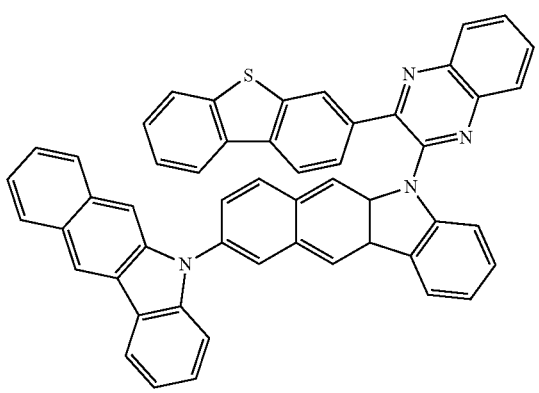
274
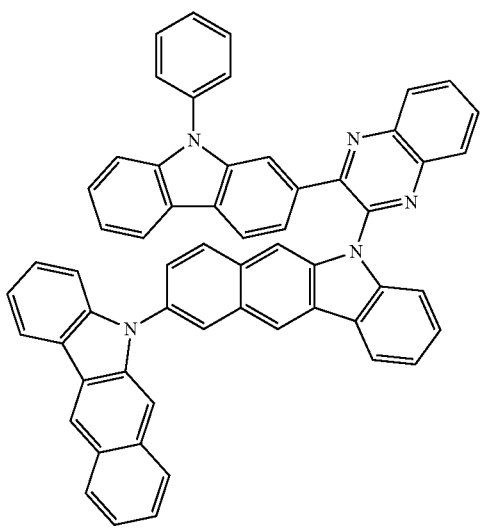
275
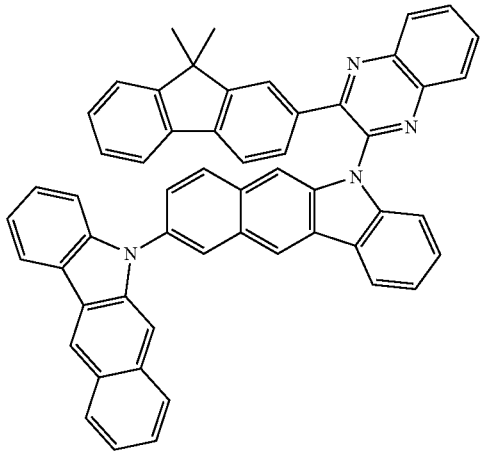

276
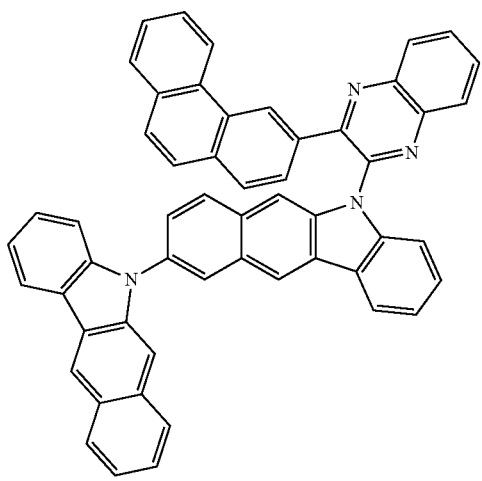
279
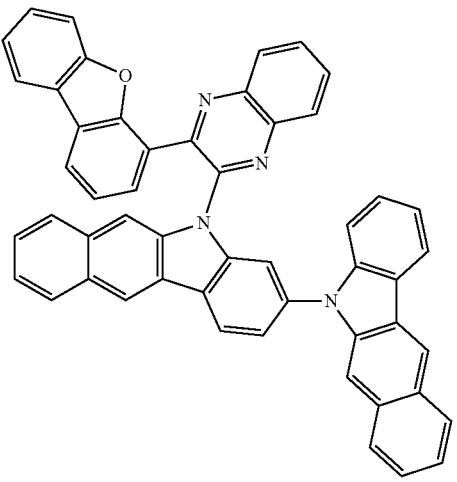
277
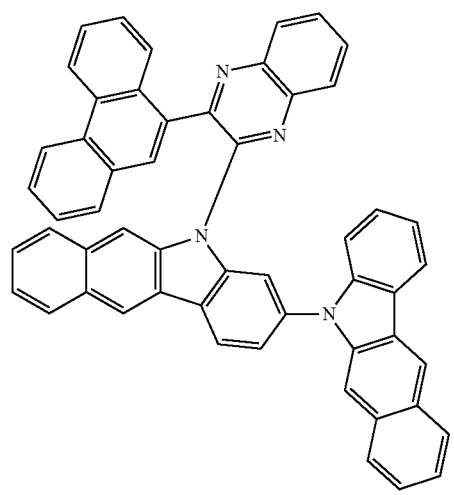
280
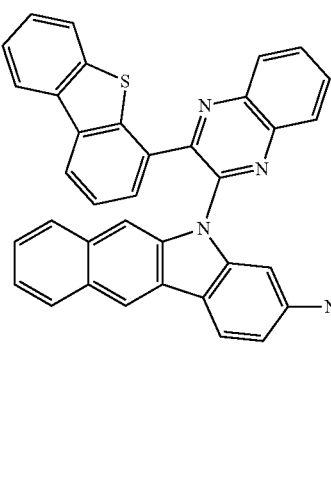
278
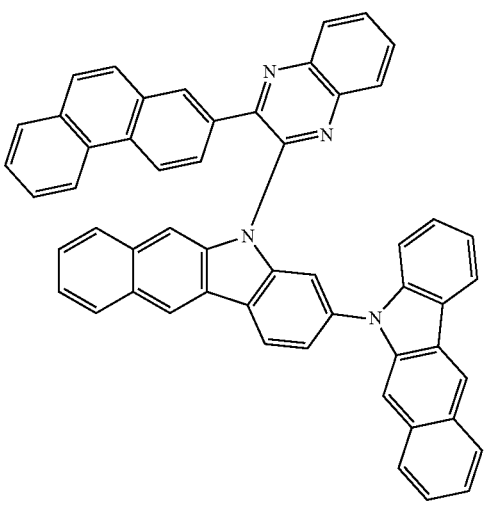
281
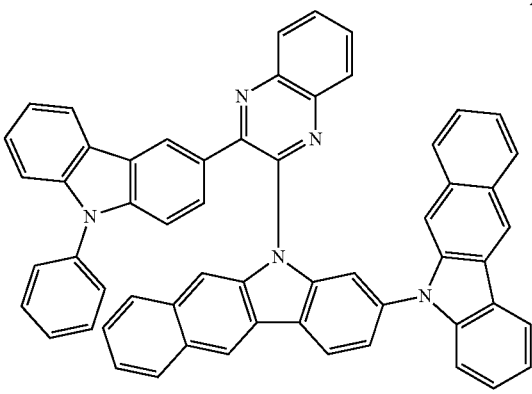

282
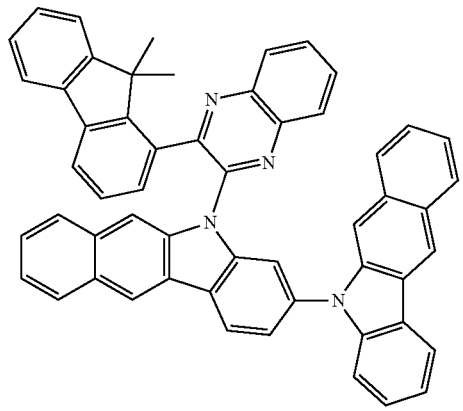
285
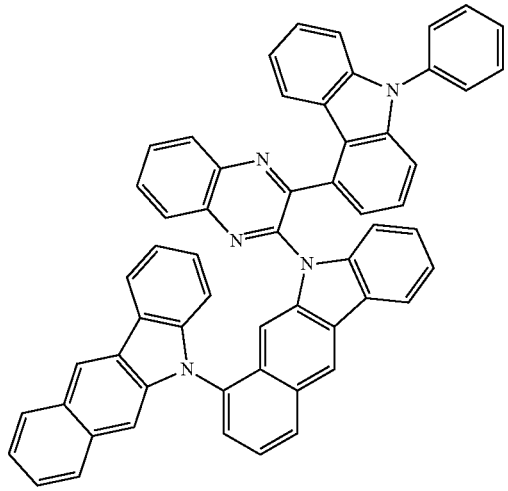
283
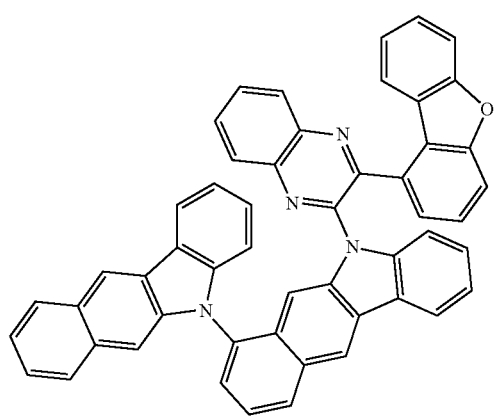
286
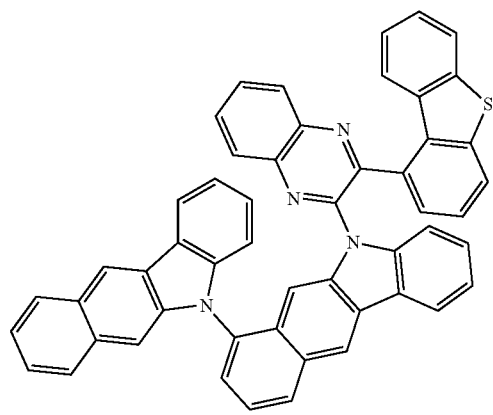
284
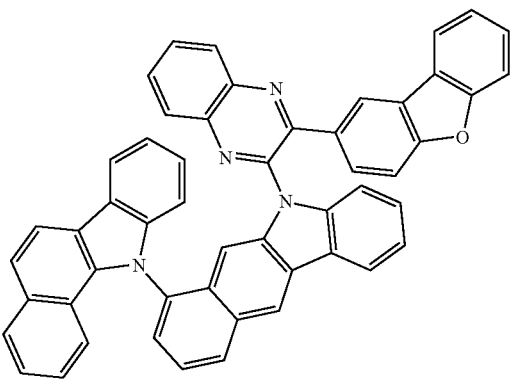
287

288
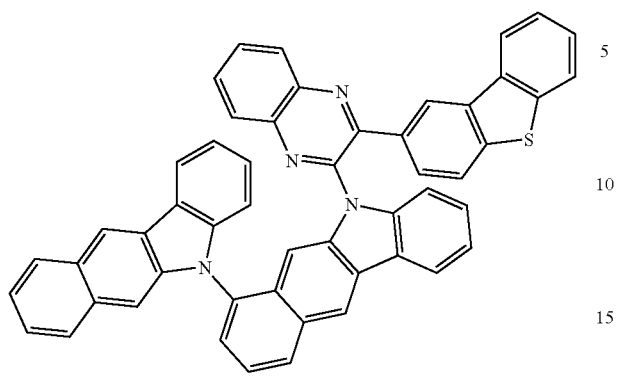
289
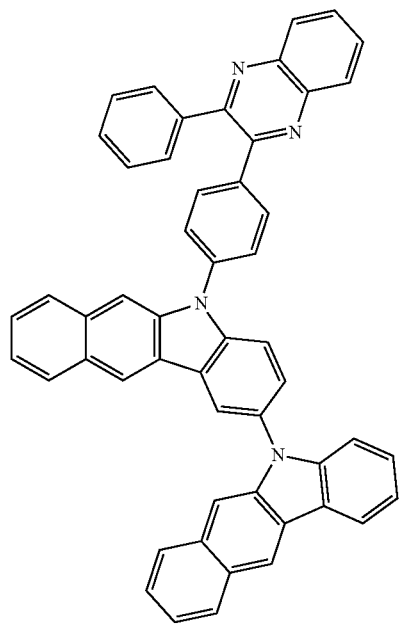
290
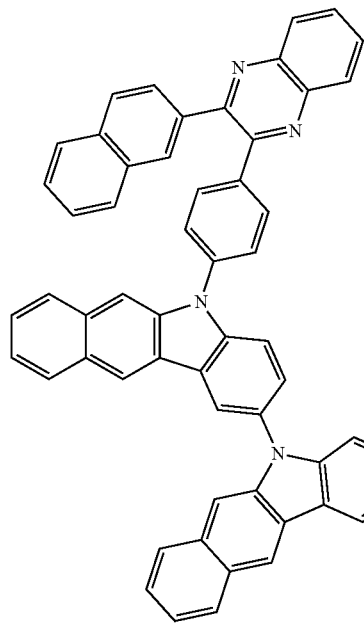
291
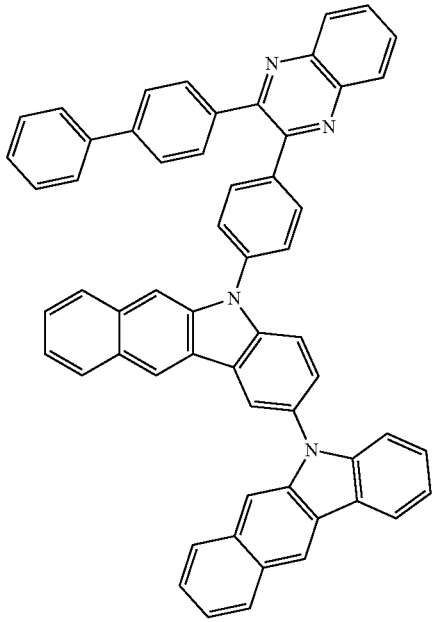
292
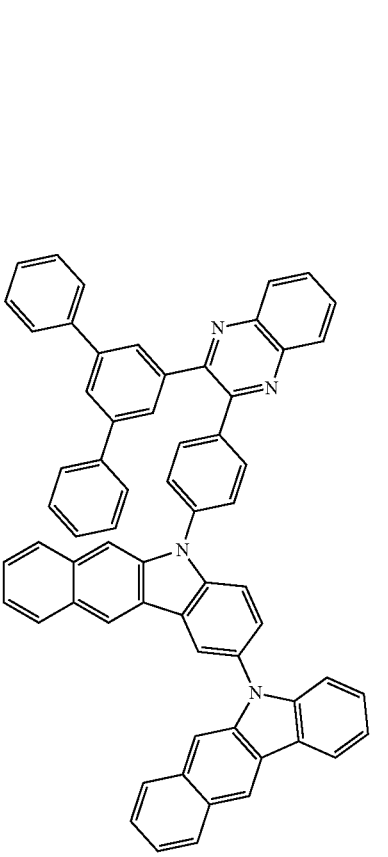

293
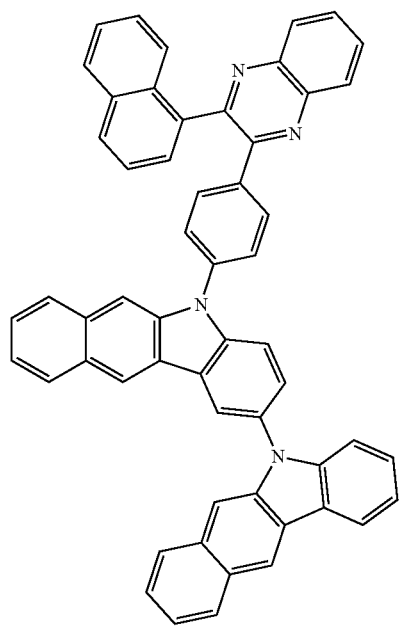
296
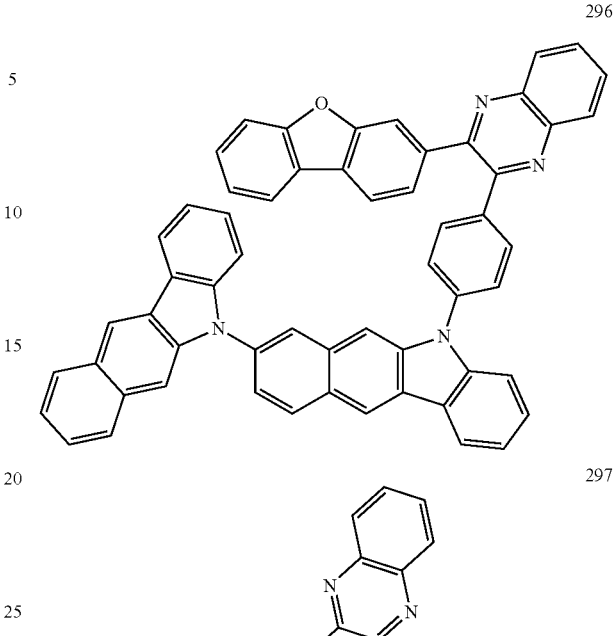
294
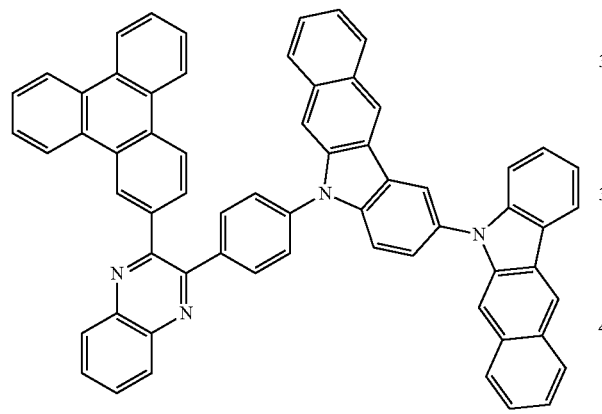
297
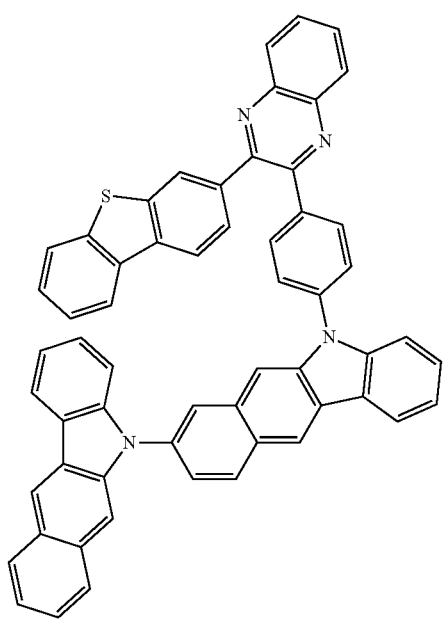
295
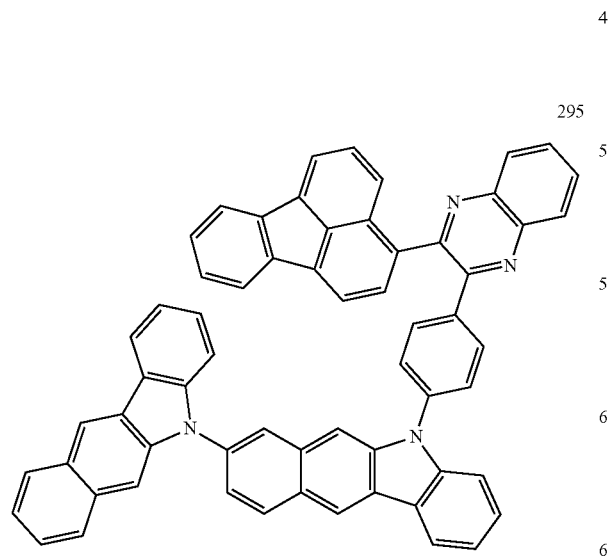
298
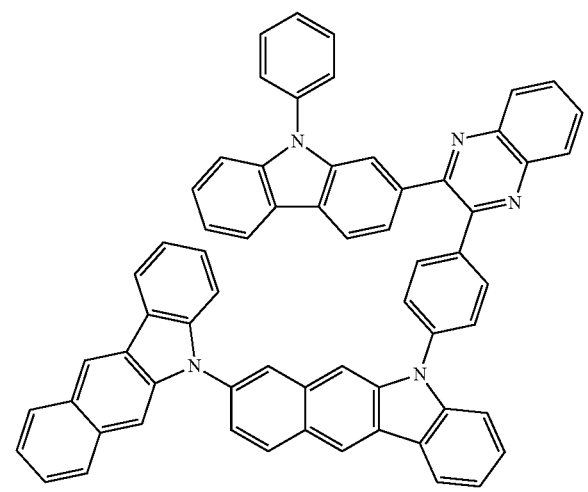

299
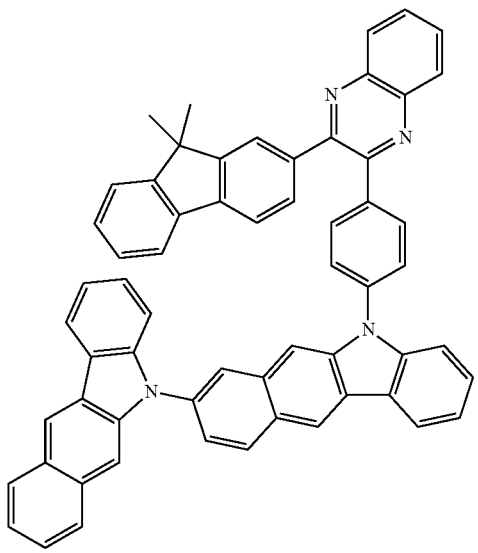
300
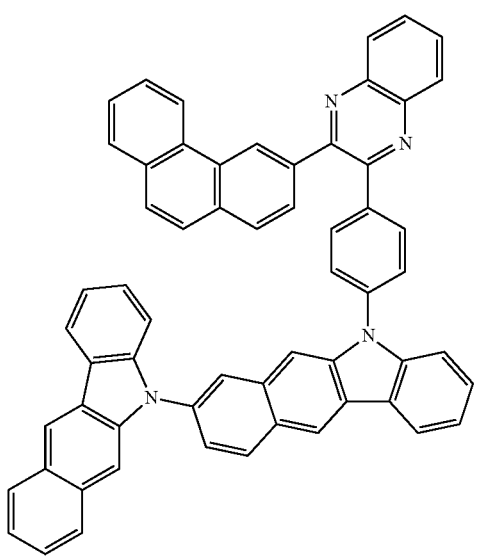
301
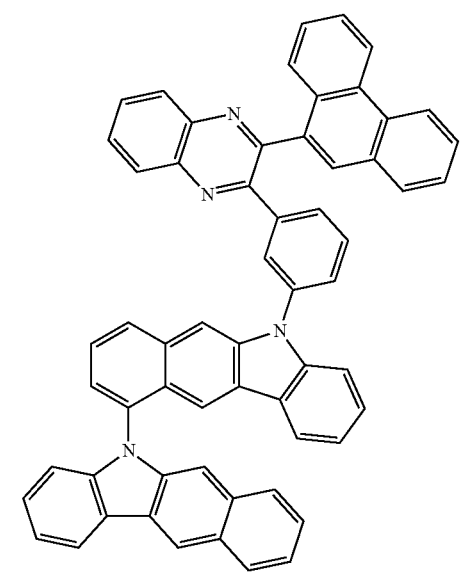
302
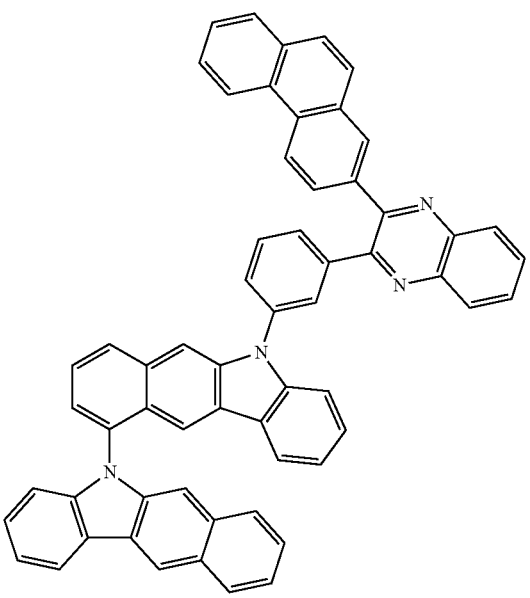
303
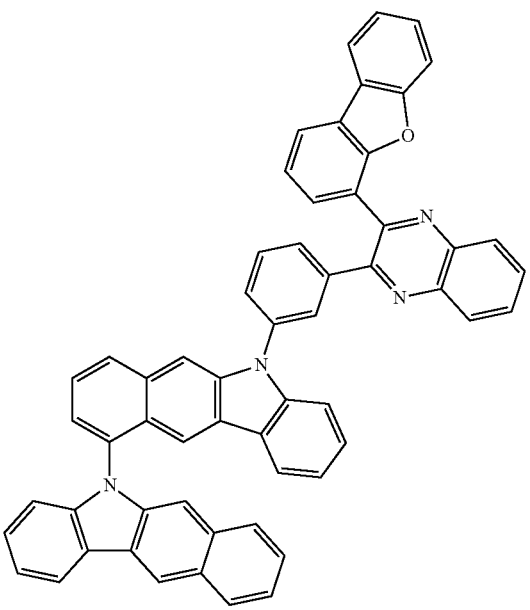

304
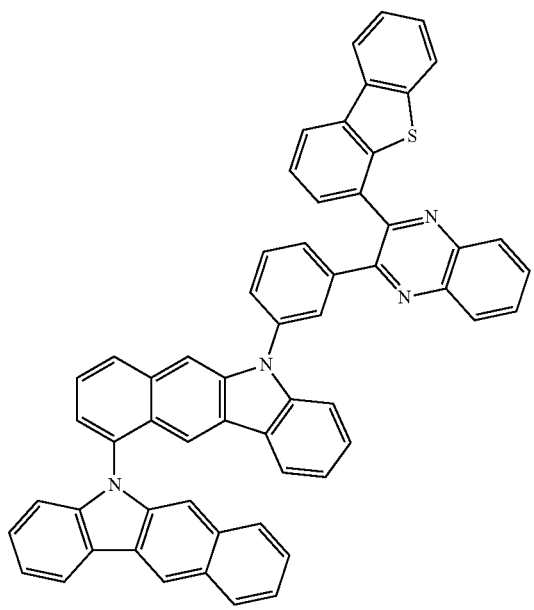
305
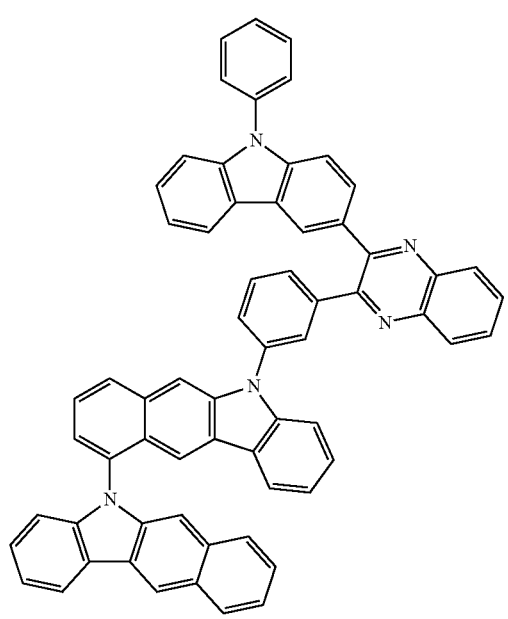
306
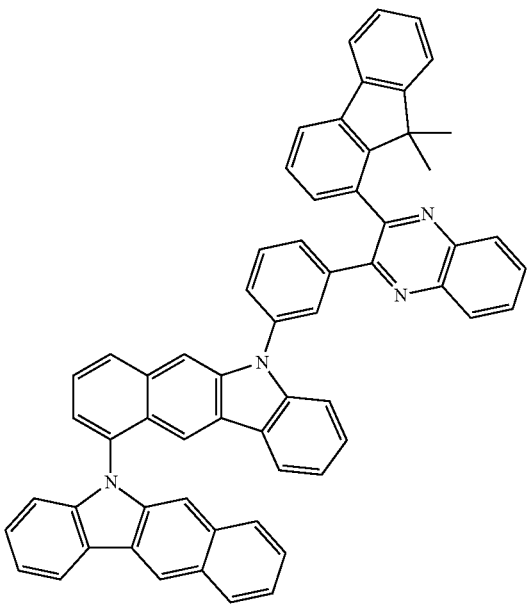
307
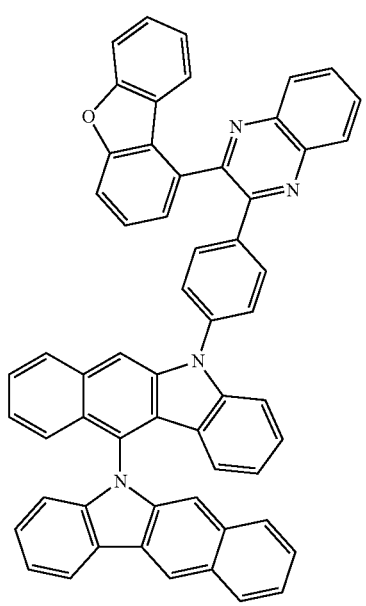

-continued
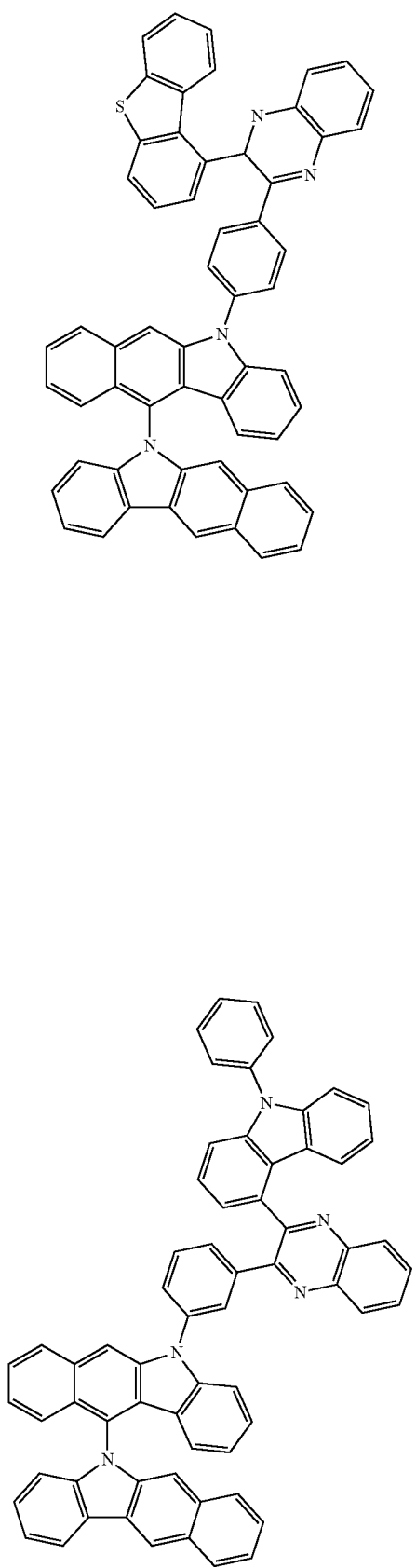
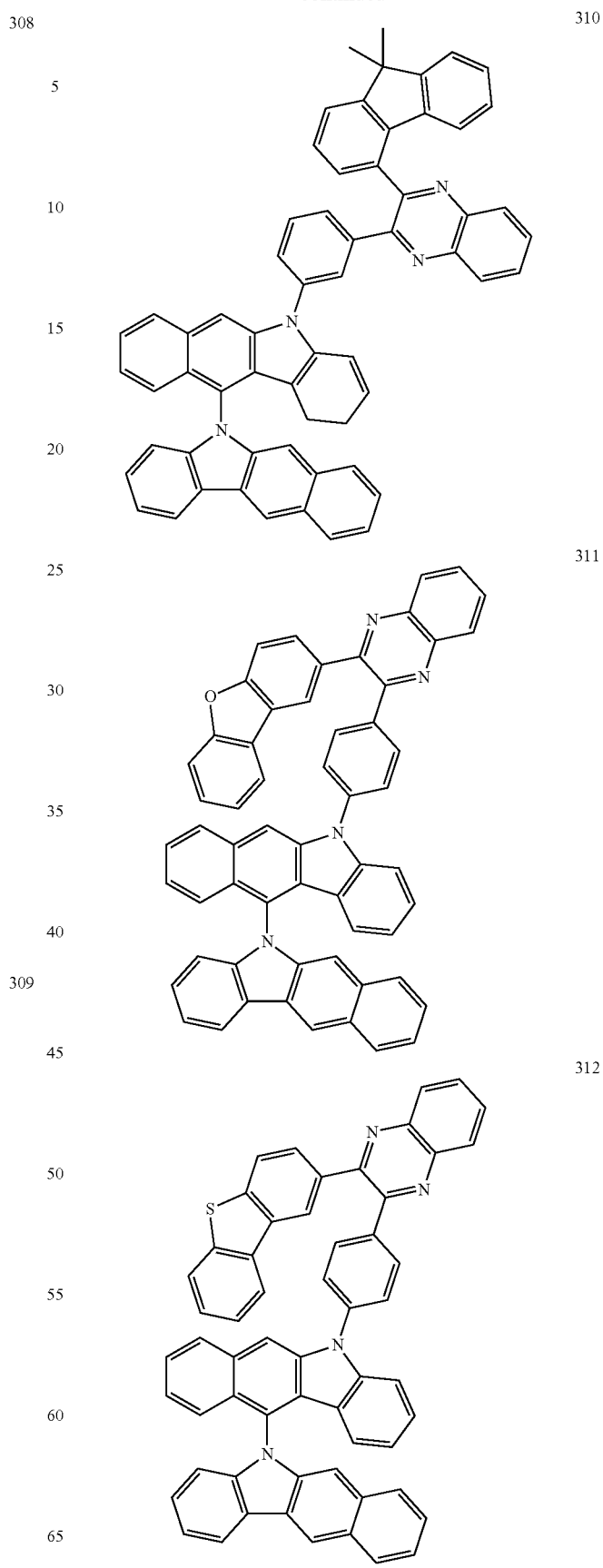

145
-continued
313
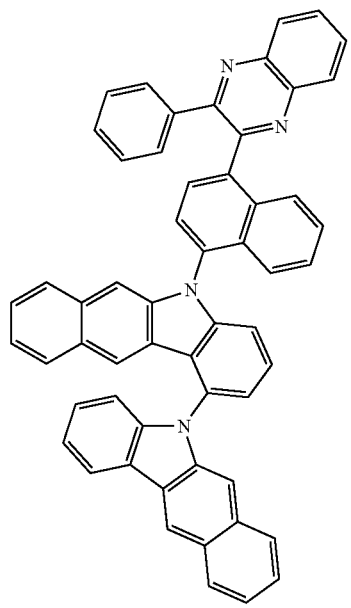
314
146
-continued
315
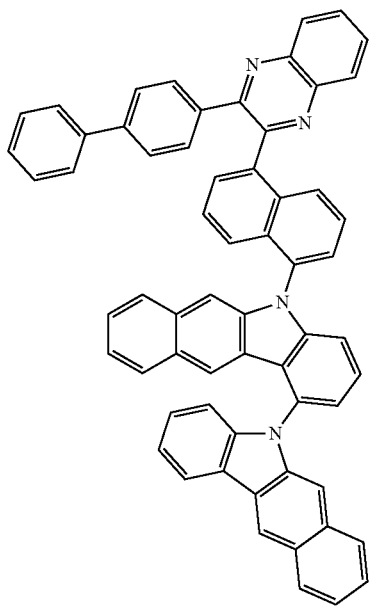
316
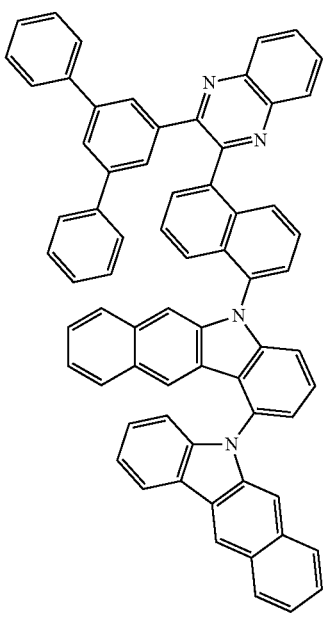

147
-continued
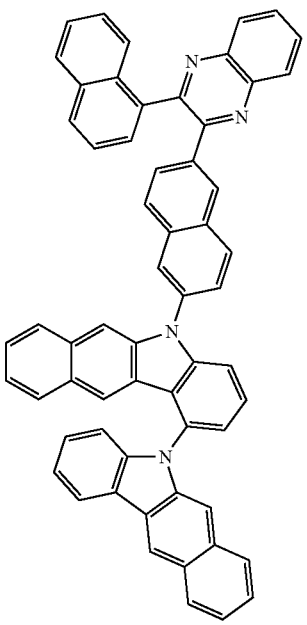
317
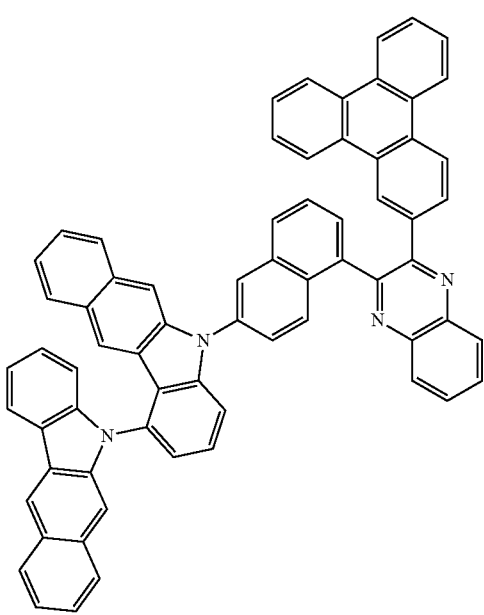
318
148
-continued
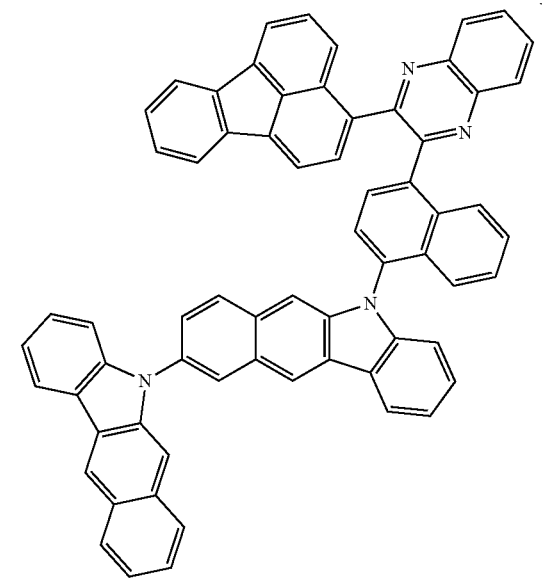
319
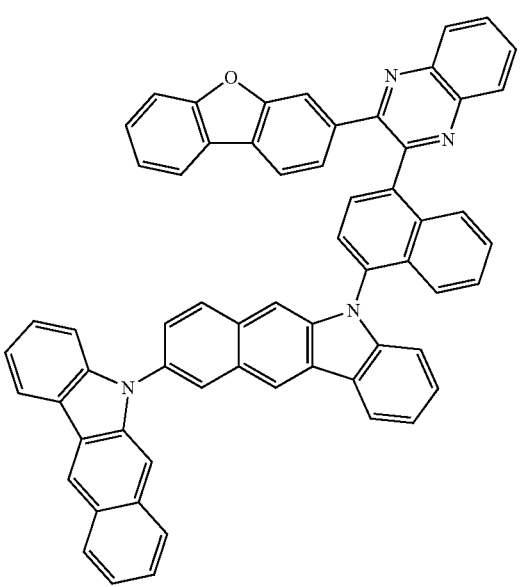
320

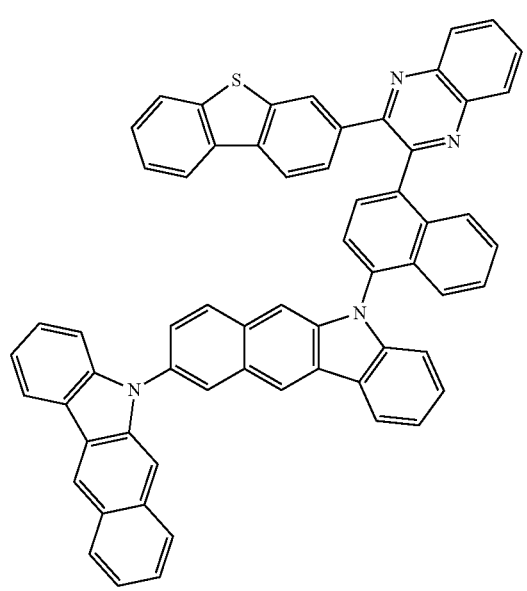
321
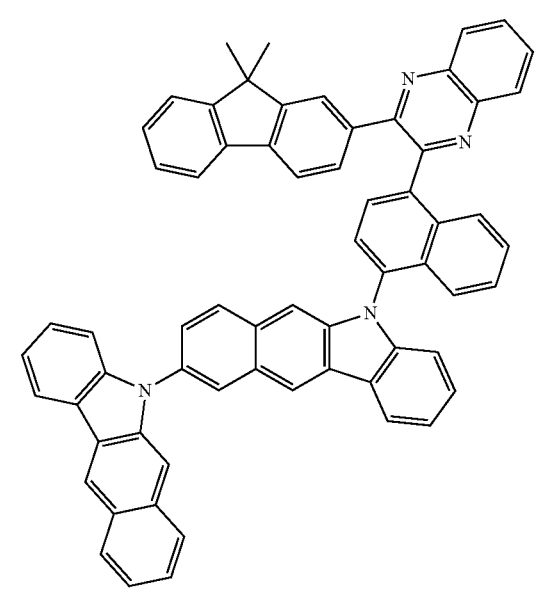
323
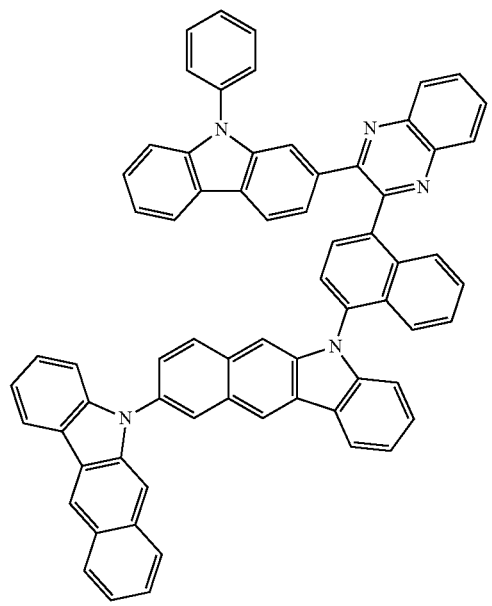
322
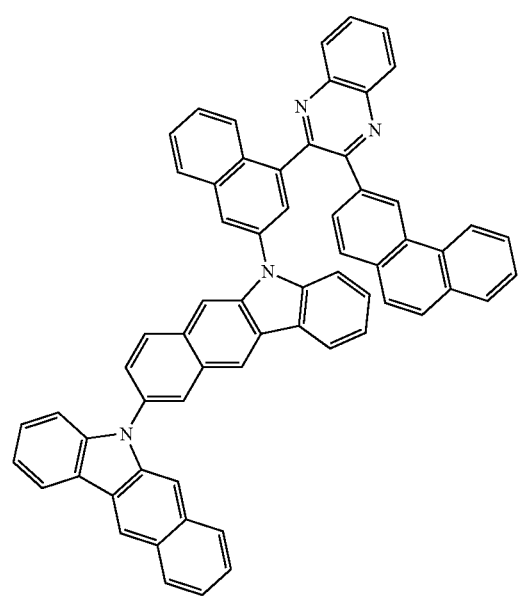
324

151
-continued
325
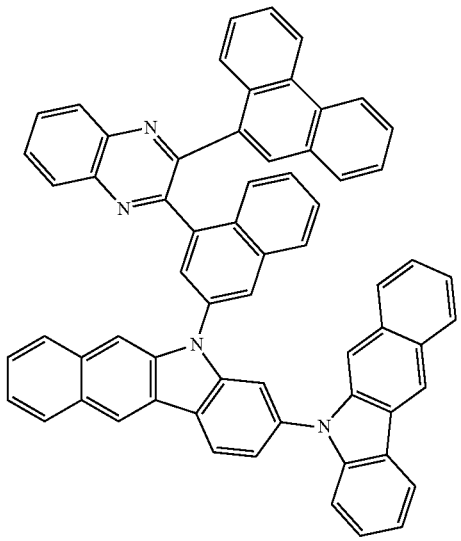
326
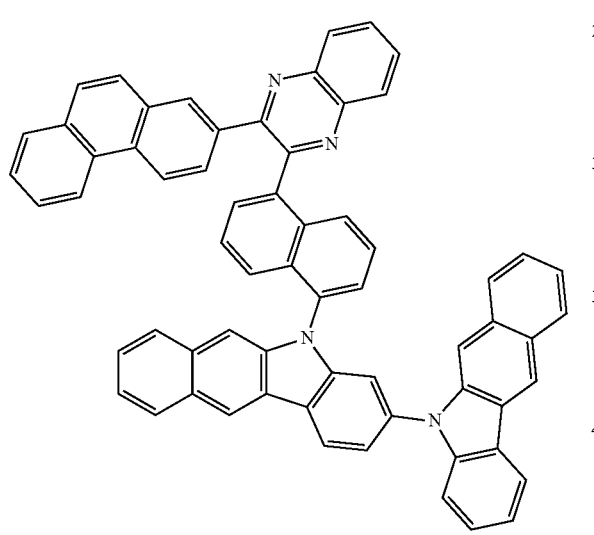
327
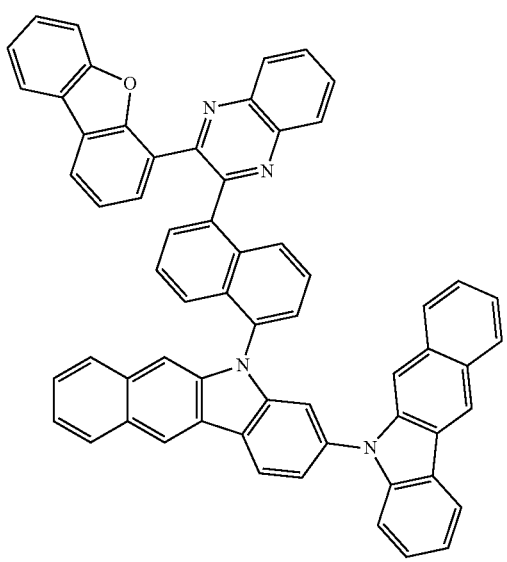
152
-continued
328
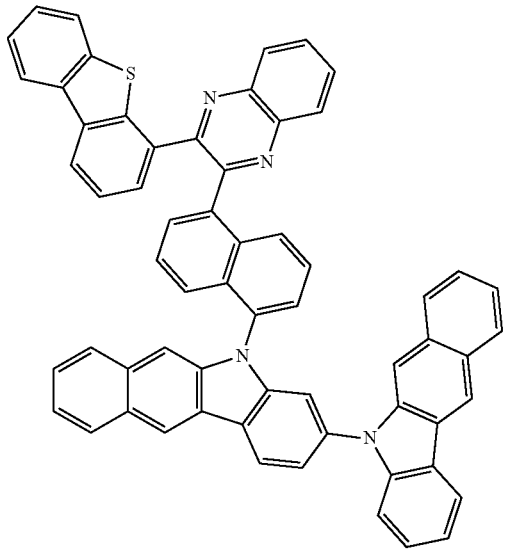
329
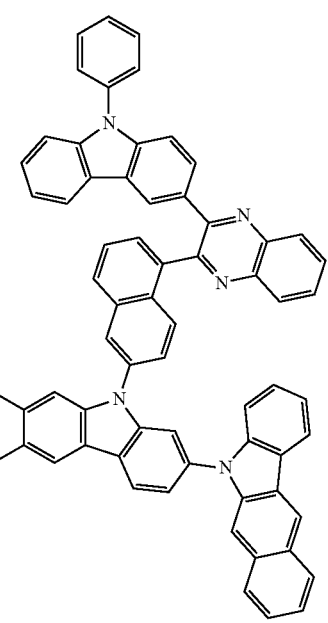

153
-continued
330
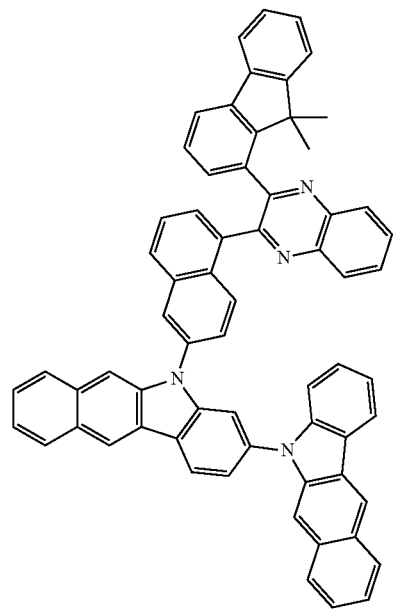
331
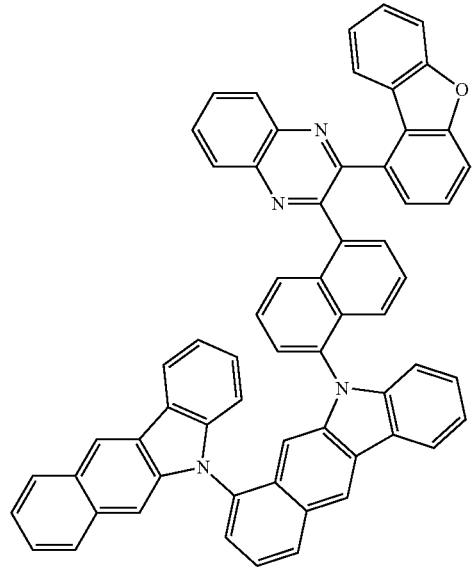
154
-continued
332
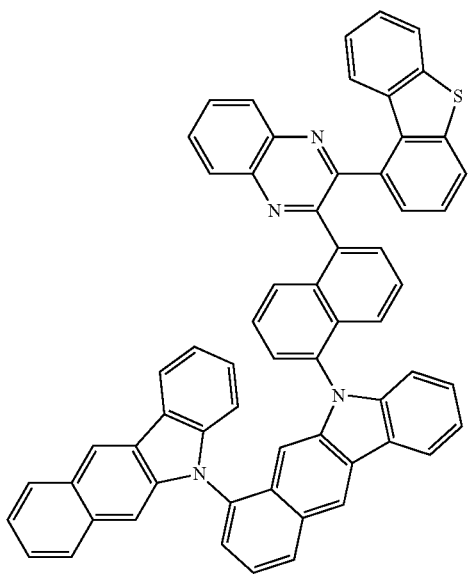
333
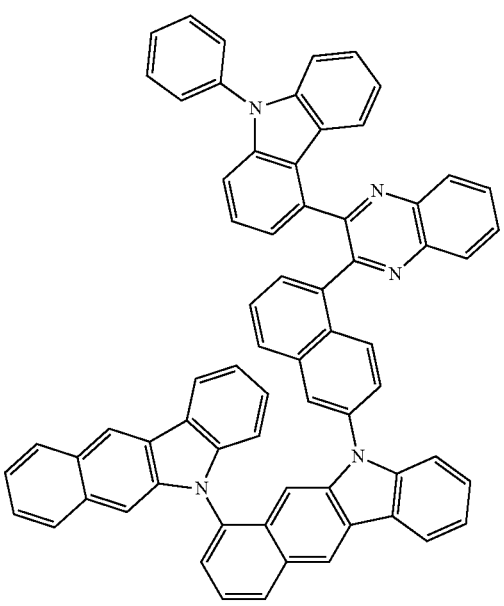

-continued
334
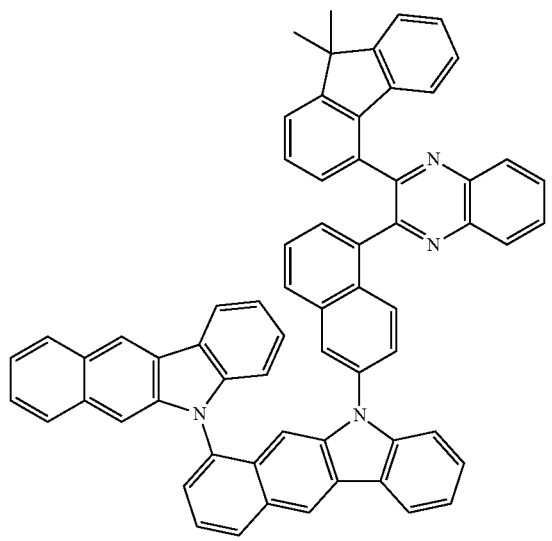
335
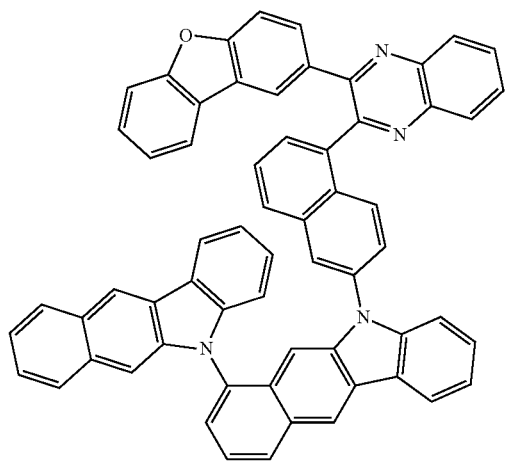
336
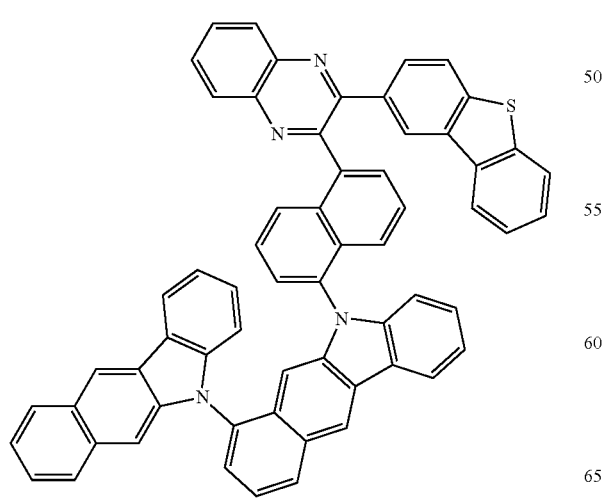
-continued
337
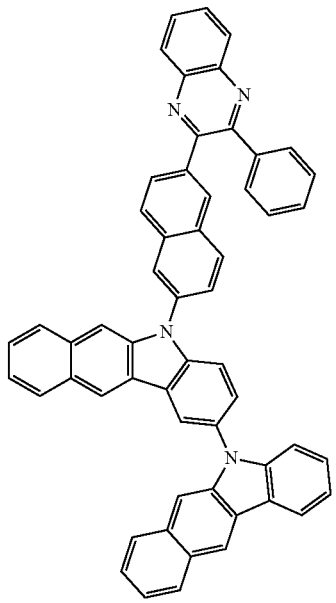
338
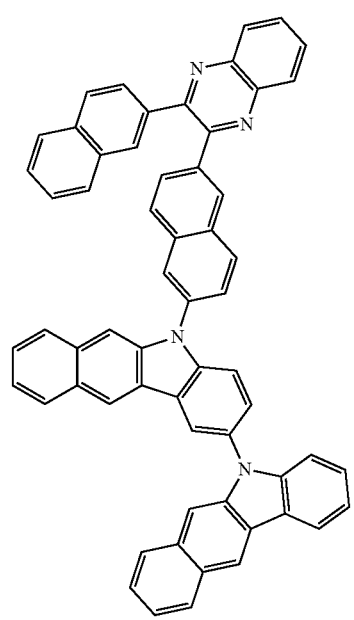

339
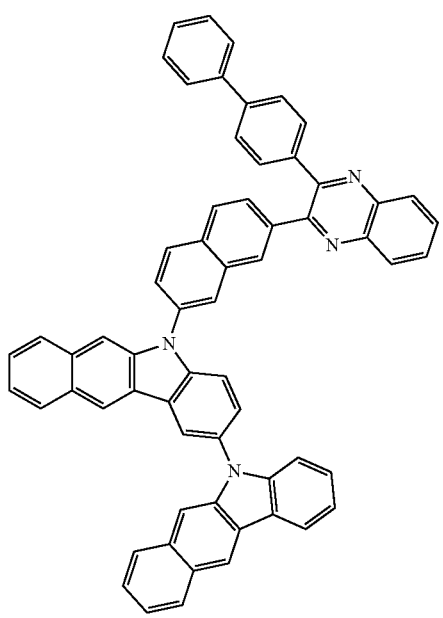
340
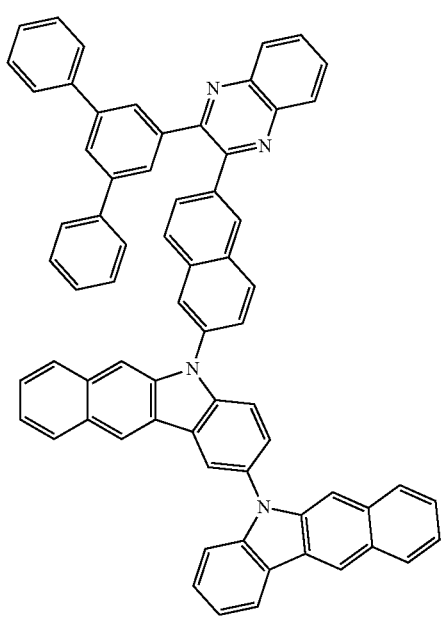
341
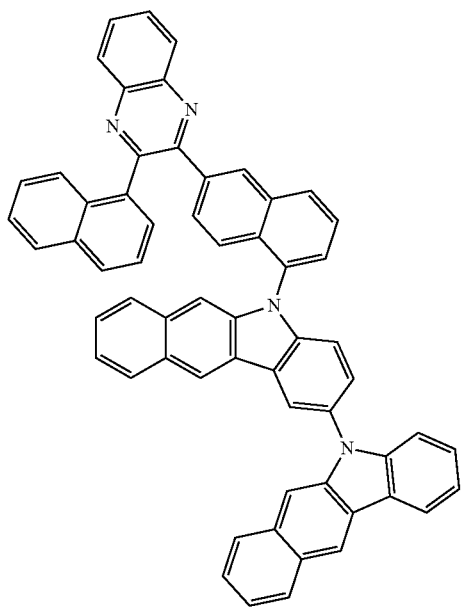
342

-continued
343
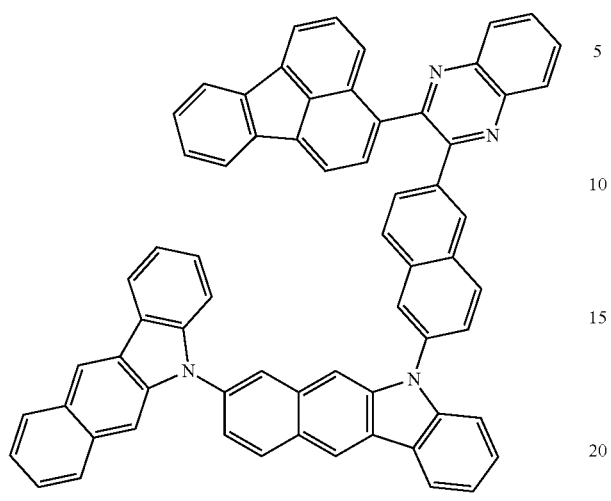
344
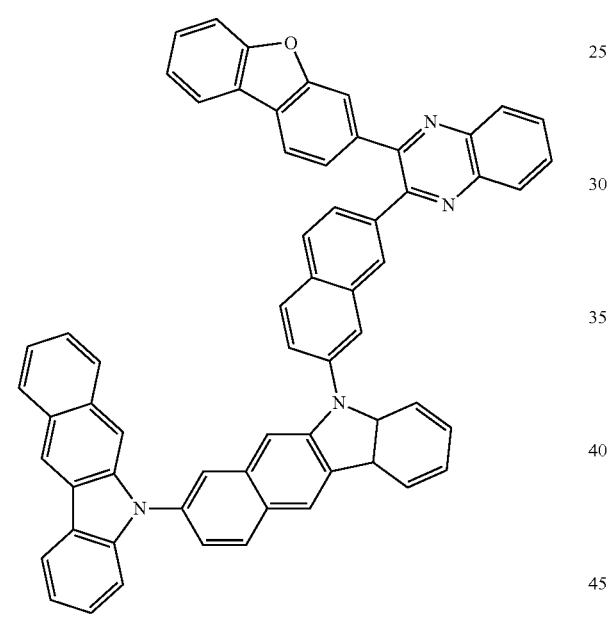
345
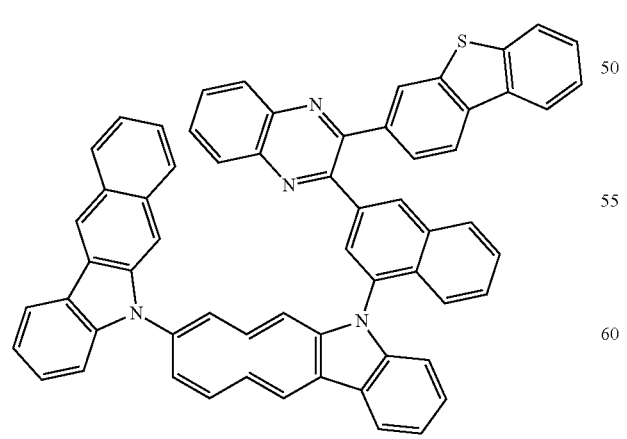
-continued
346
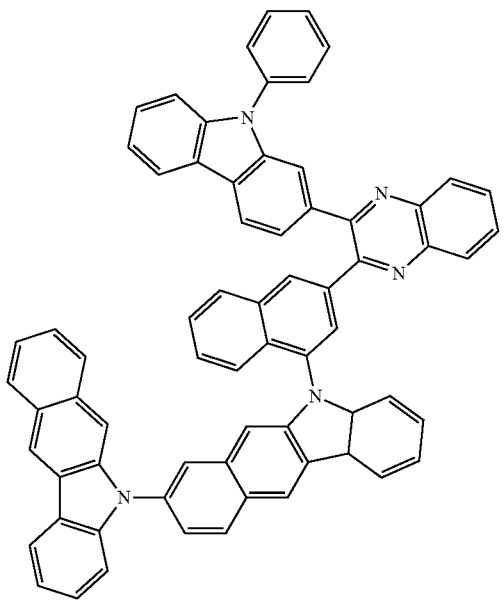
347
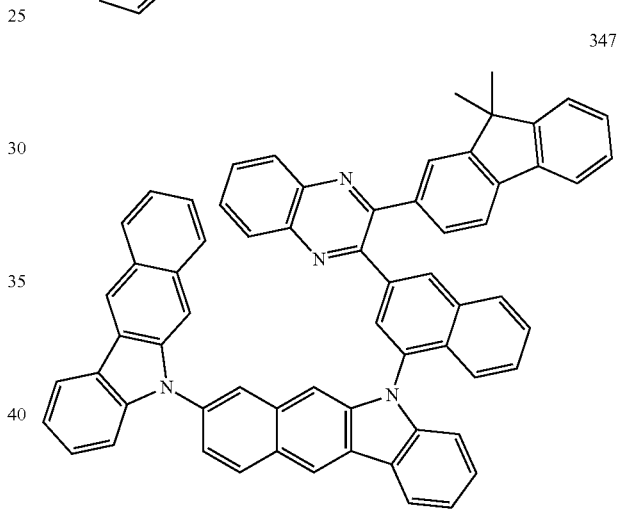
348
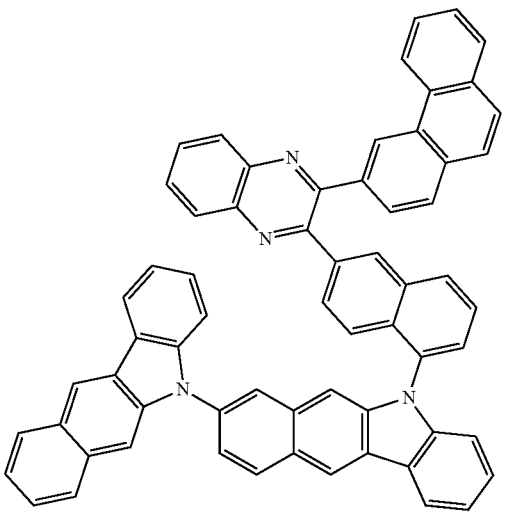

161
-continued
349
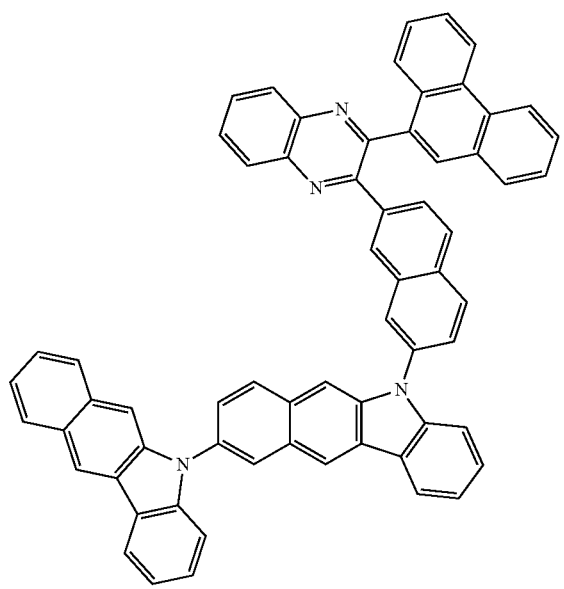
350
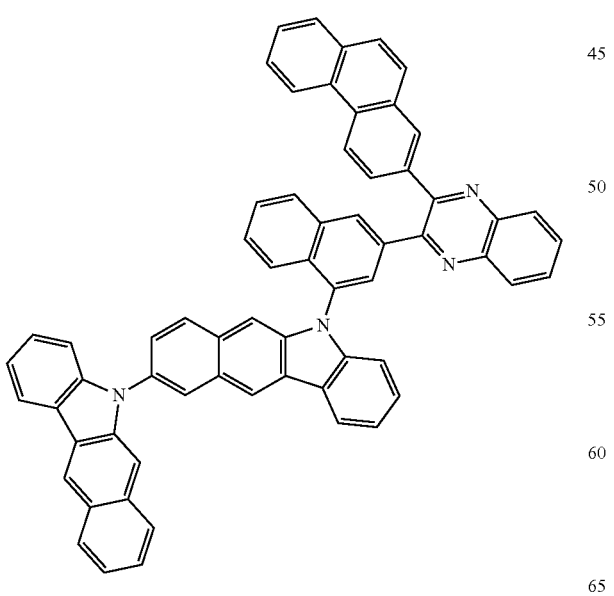
162
-continued
351
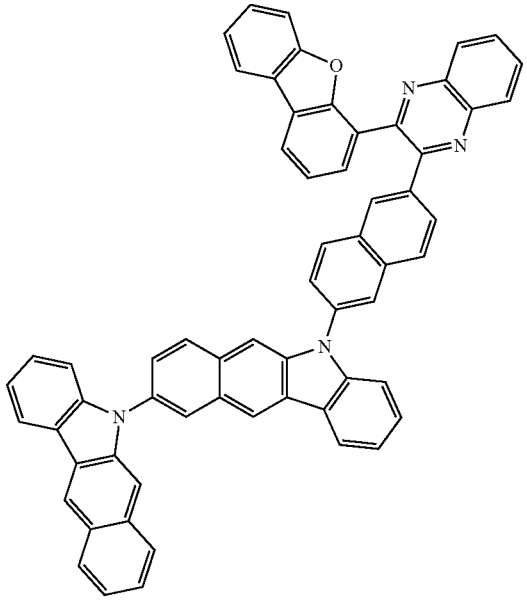
352
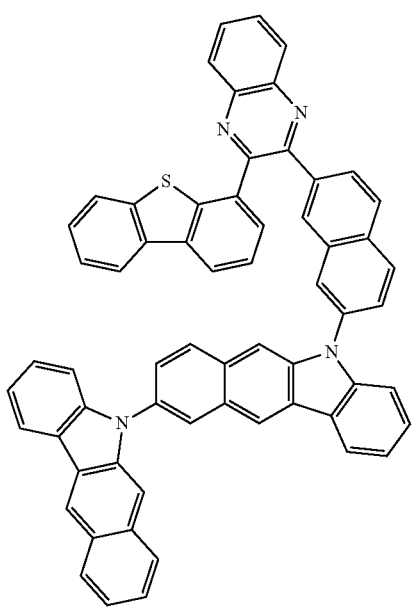

-continued
353
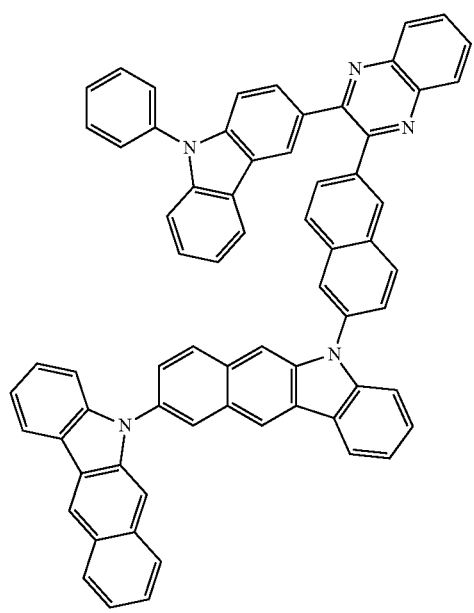
354
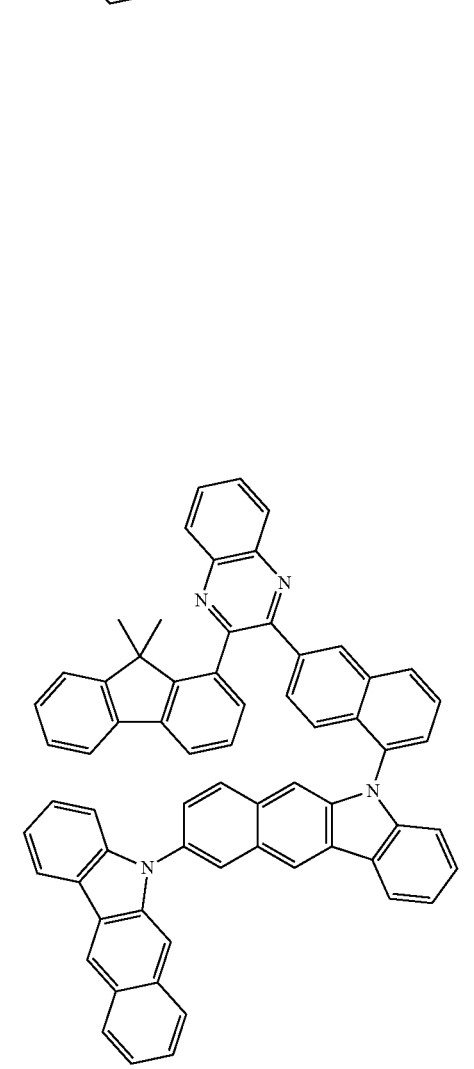
355
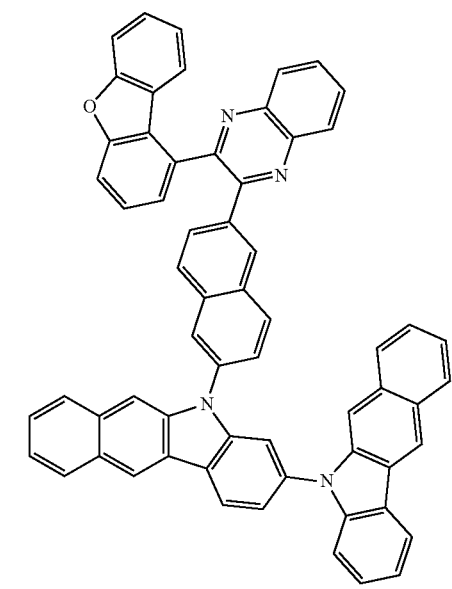
356
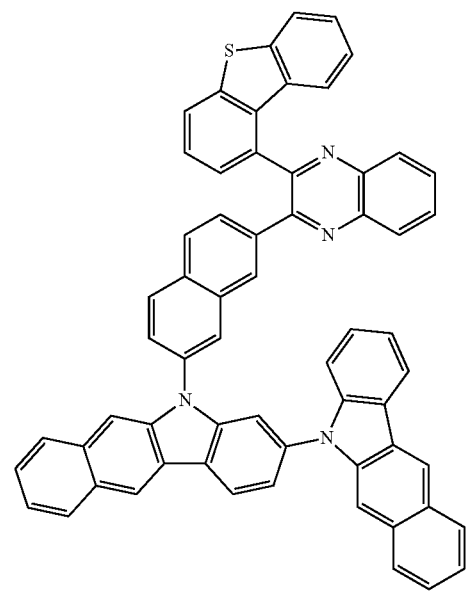

-continued
357
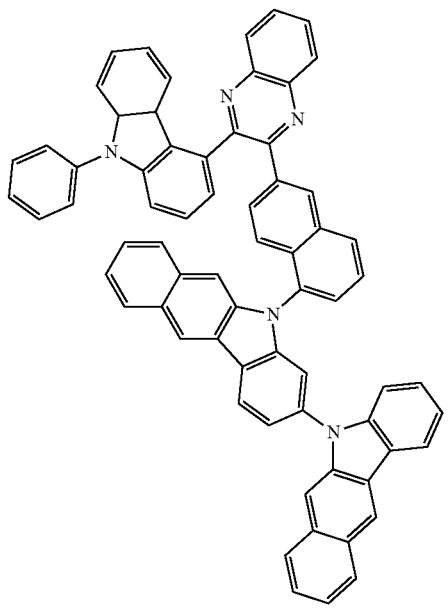
358
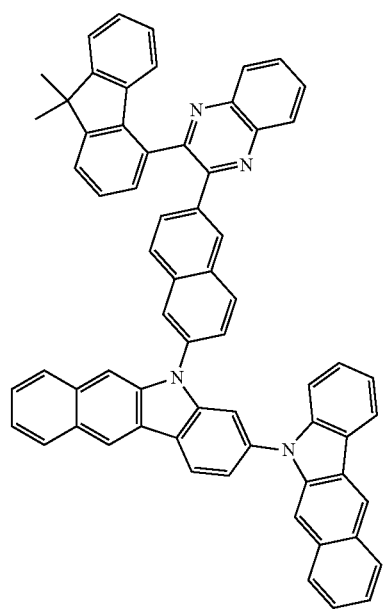
359
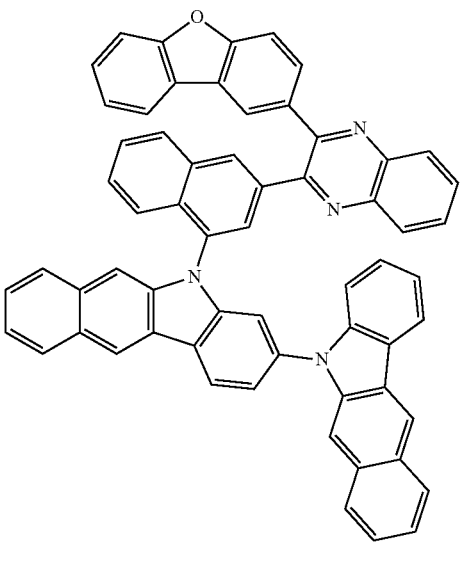
360
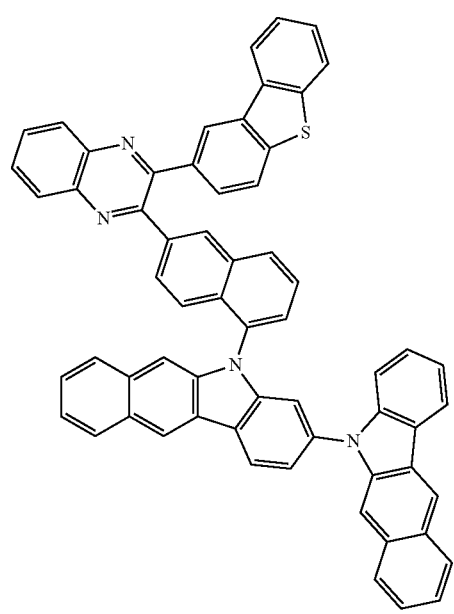
361
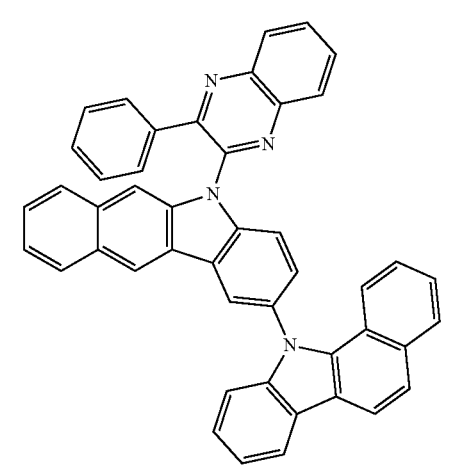

362
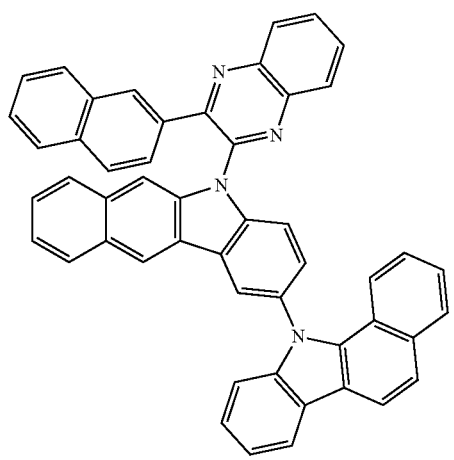
363
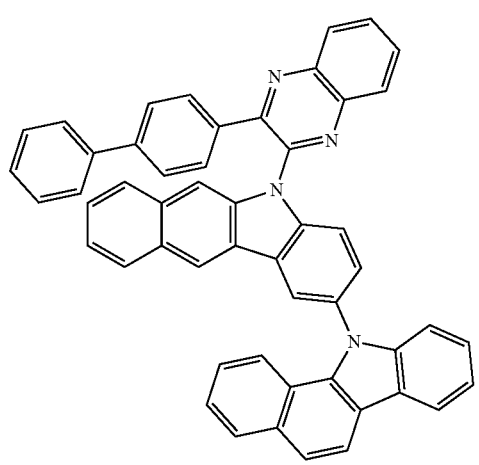
364
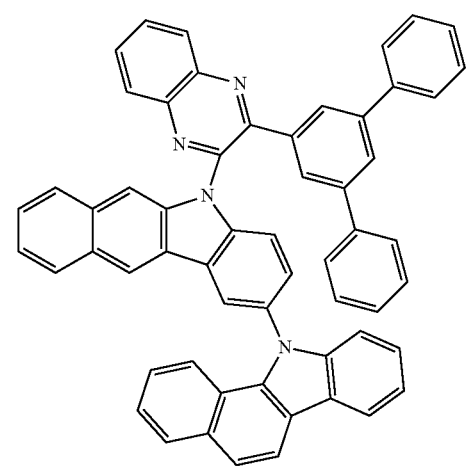
365
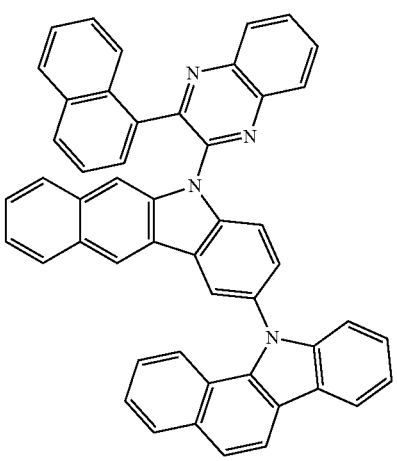
366
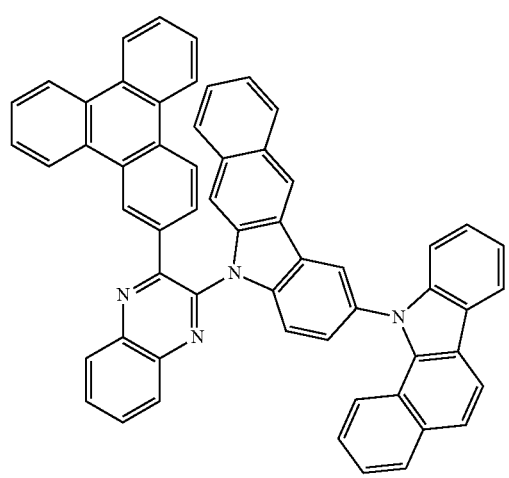
367
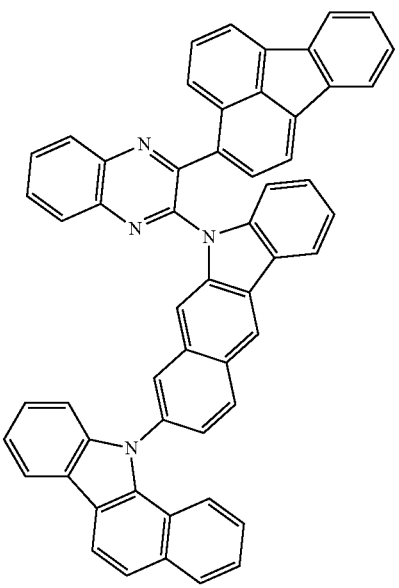

169
-continued
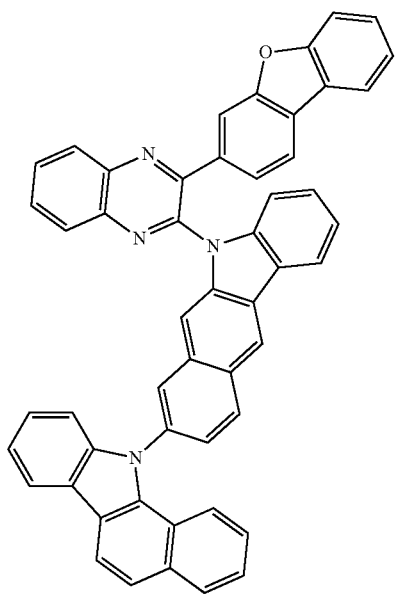
368
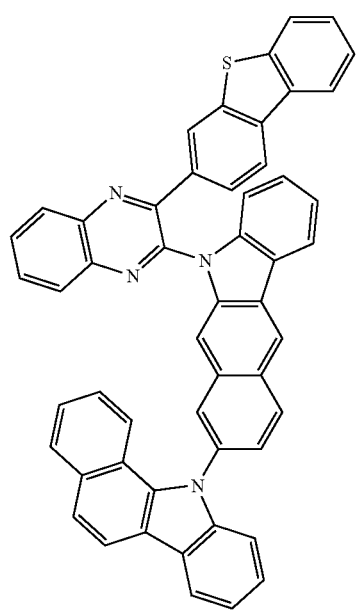
369
170
-continued
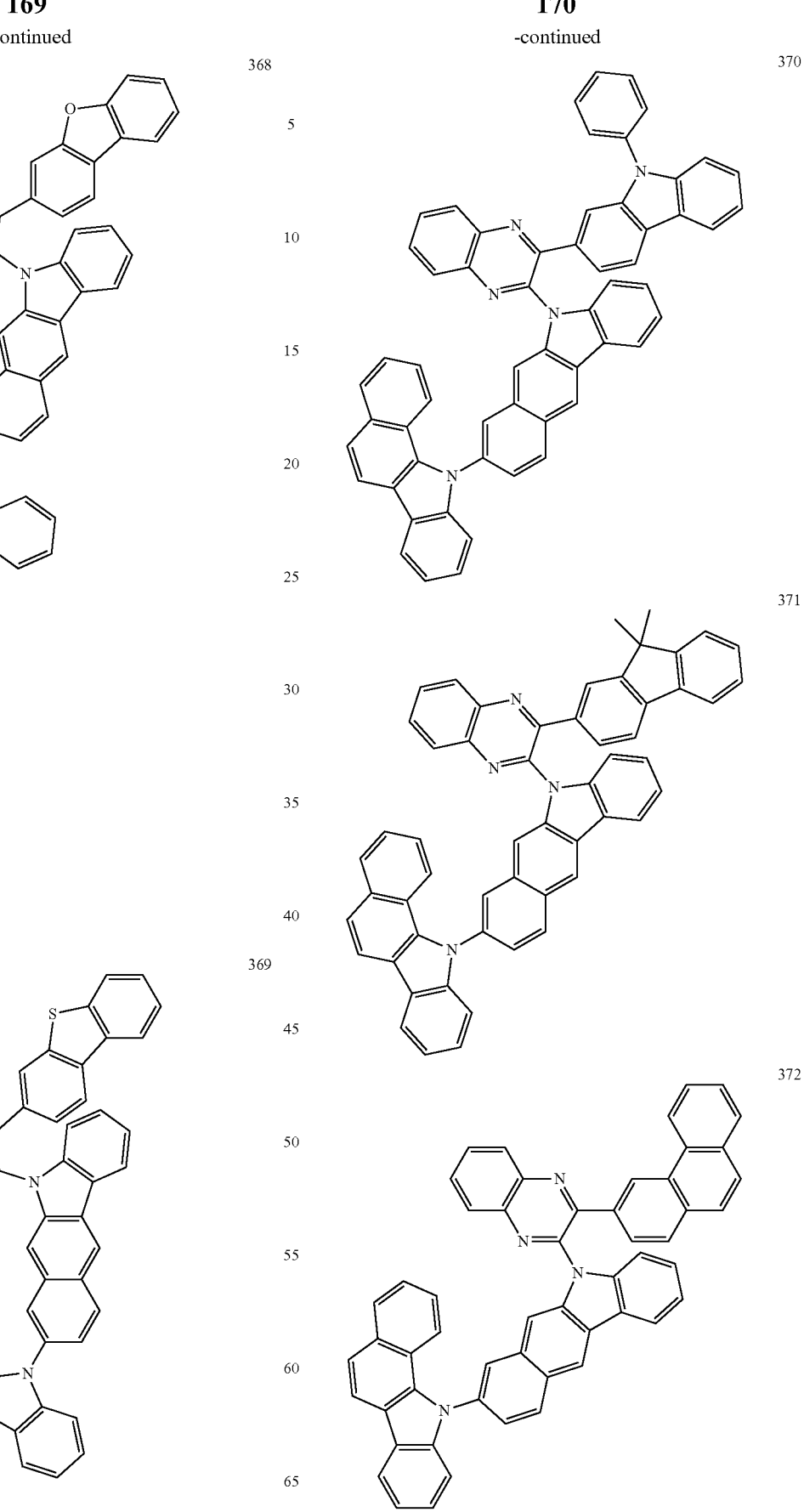
370
371
372

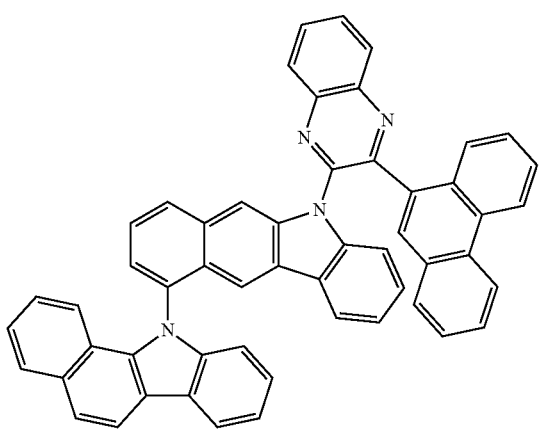
373
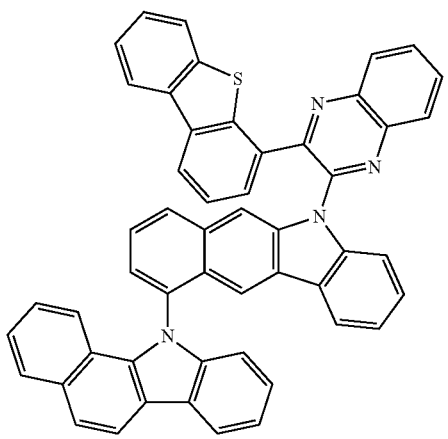
376
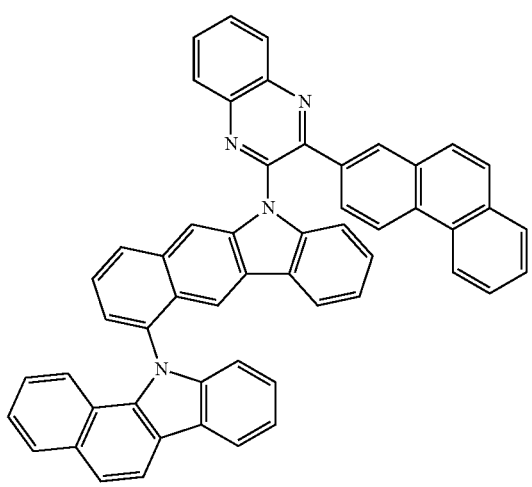
374
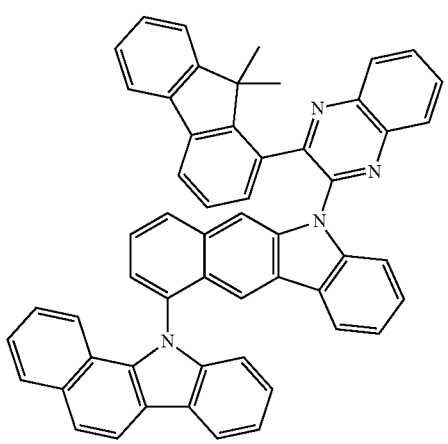
378
377
375

379
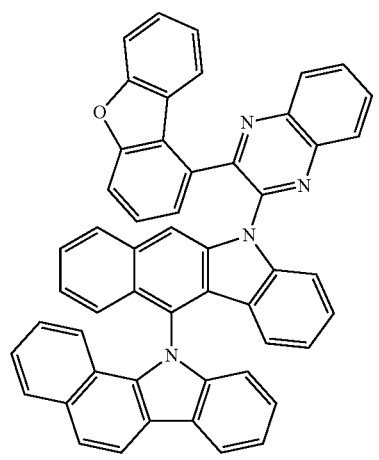
380
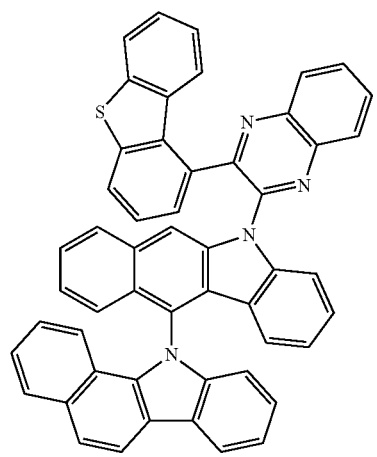
381
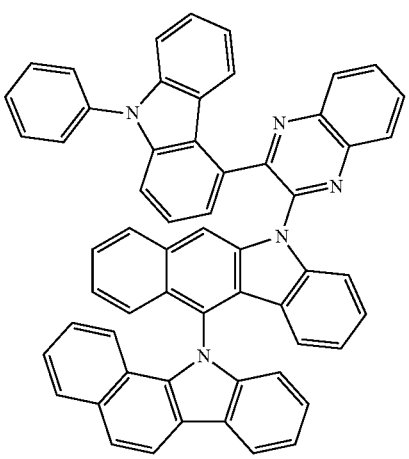
382
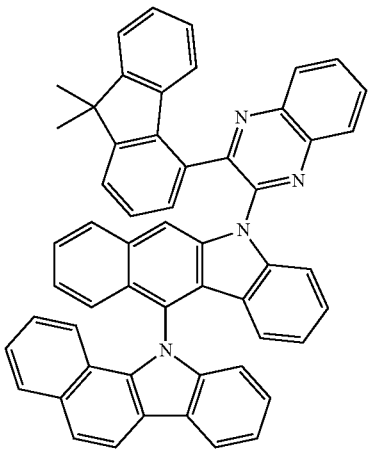
383
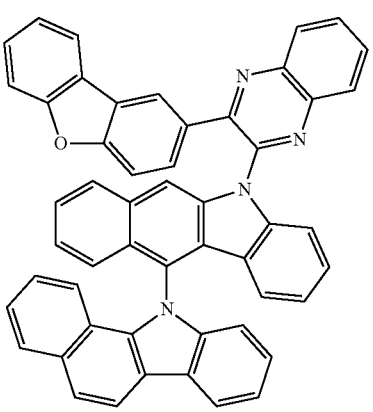
384
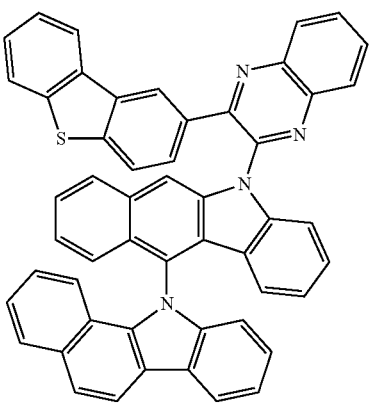

385
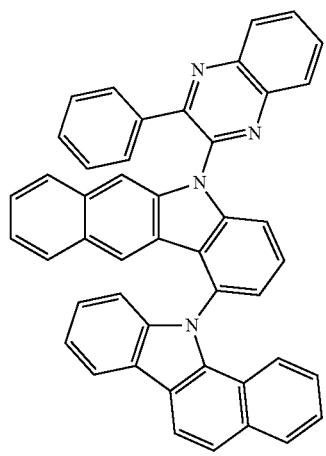
386
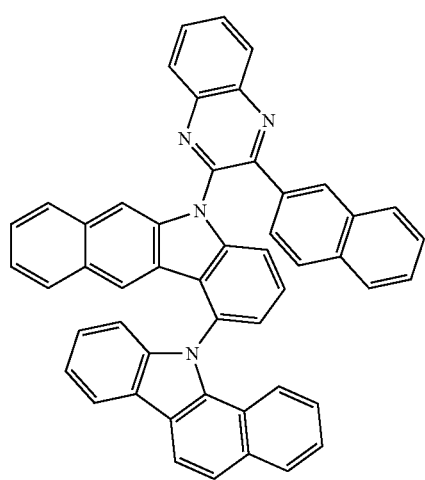
387
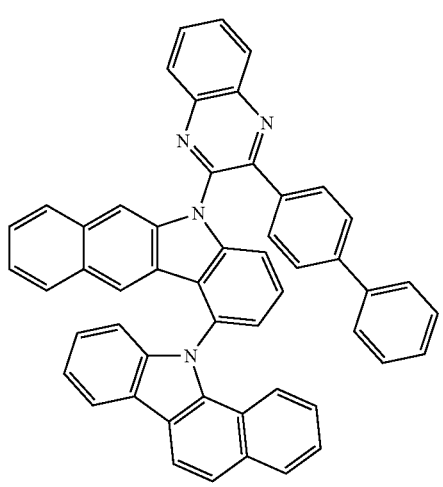
388
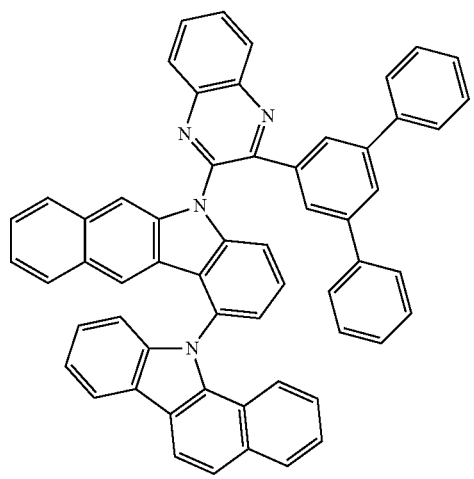
389
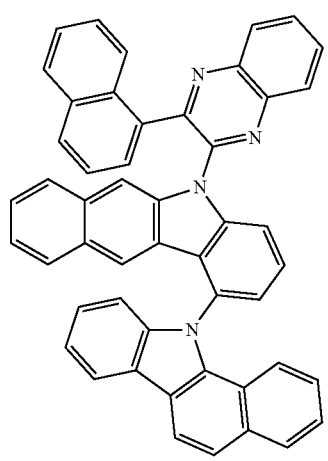
390
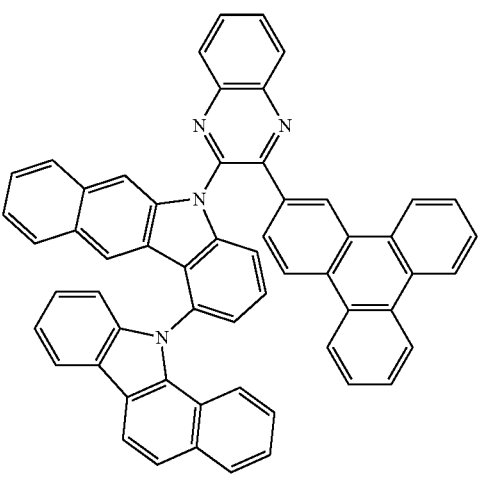

-continued
391
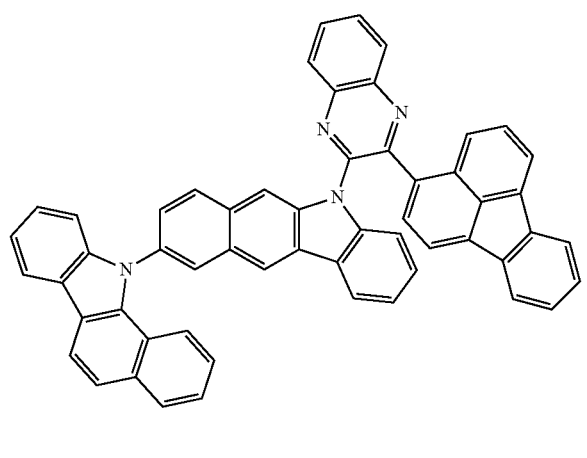
392
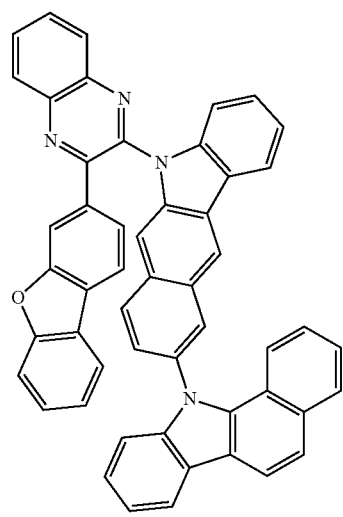
393
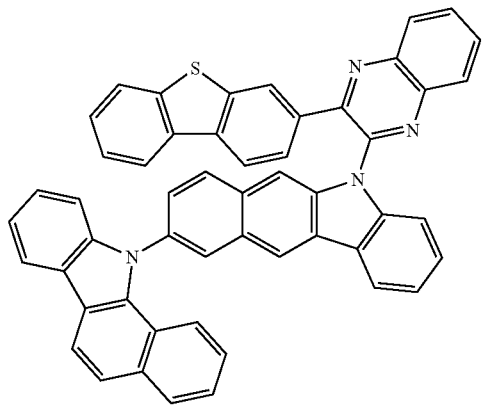
-continued
394
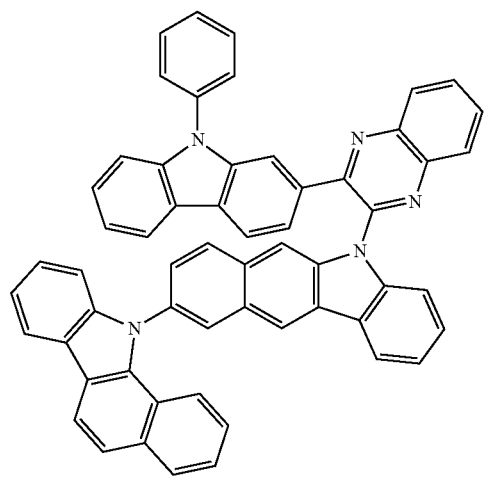
395
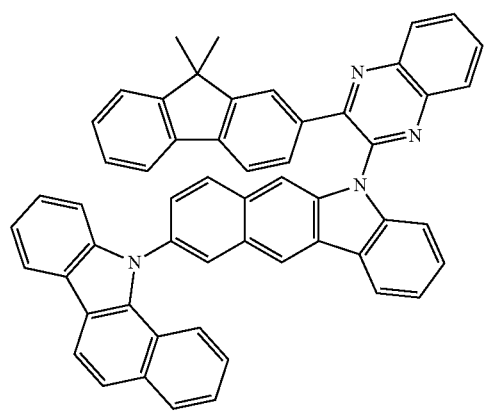
396
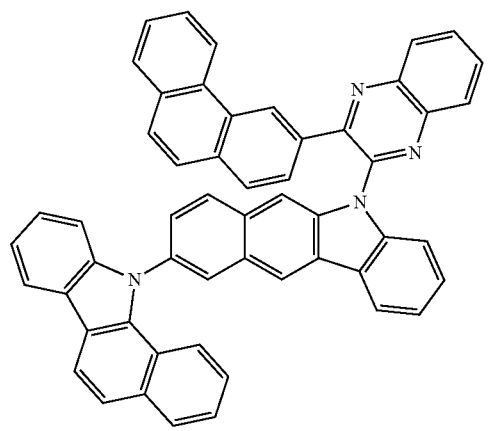

397
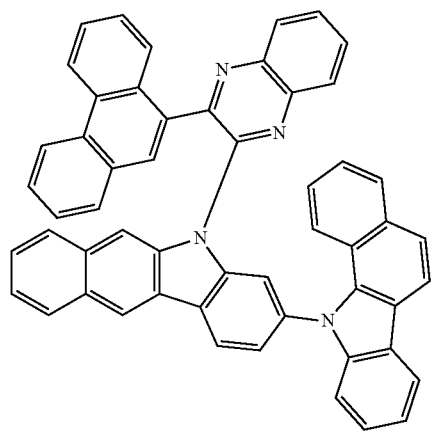
398
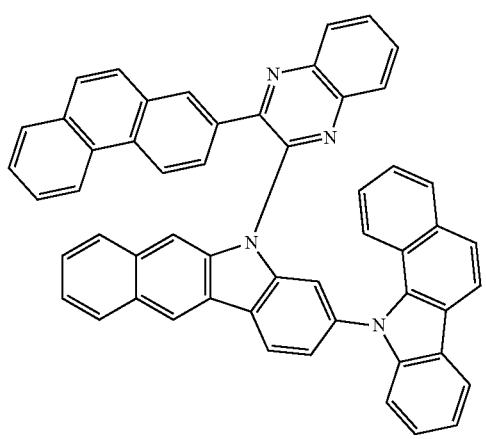
399
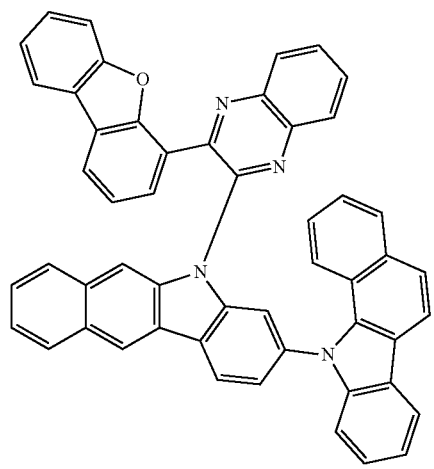
400
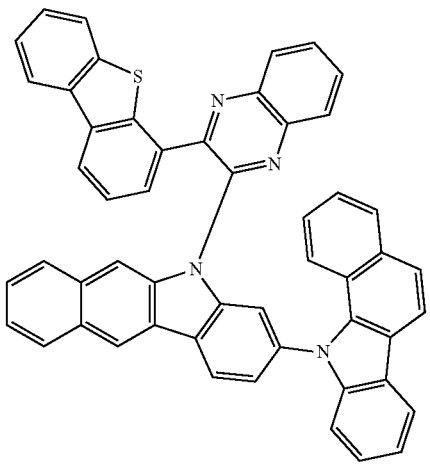
401
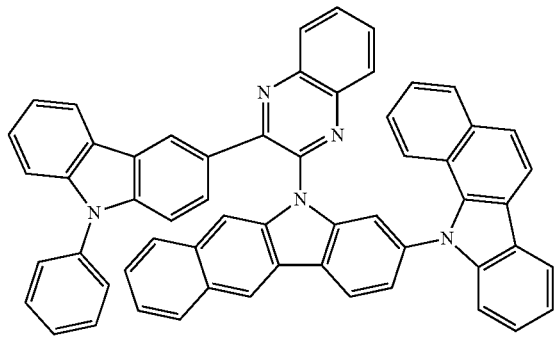
402
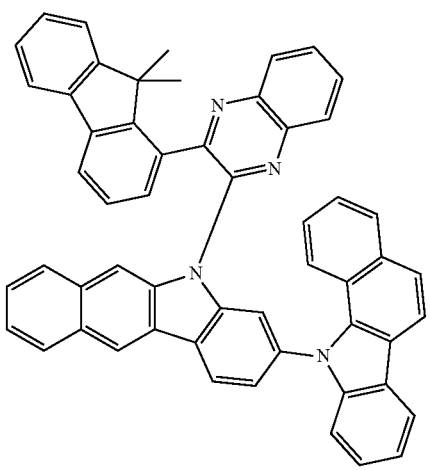

-continued
403
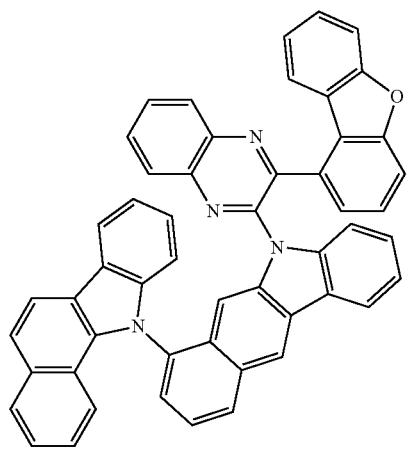
404
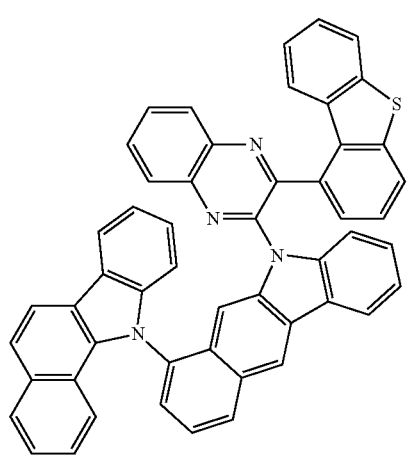
405
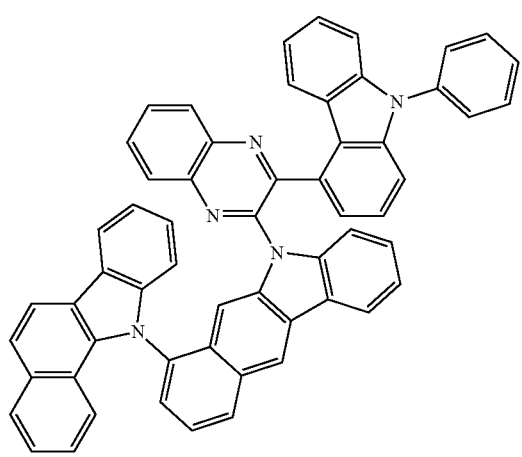
-continued
406
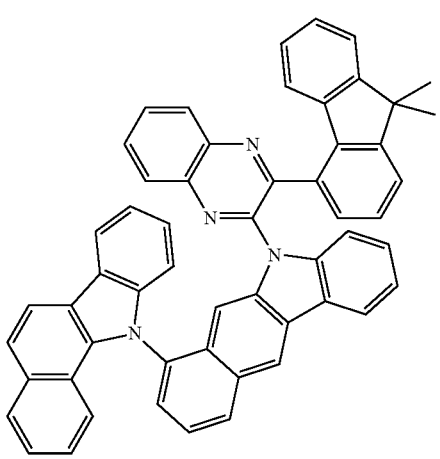
407
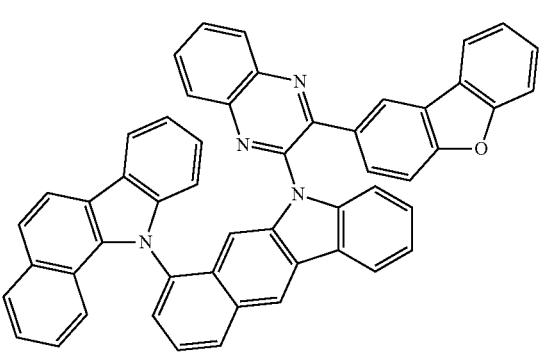
408
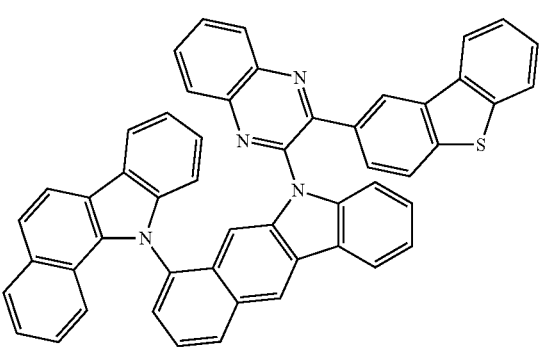

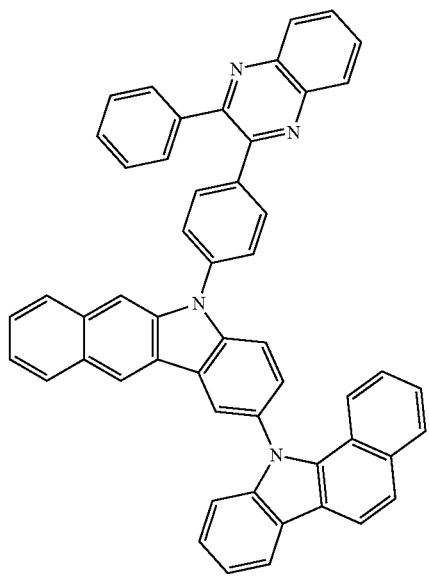
409
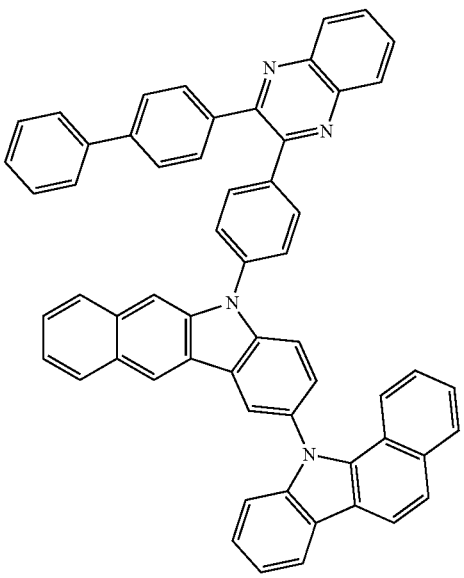
411
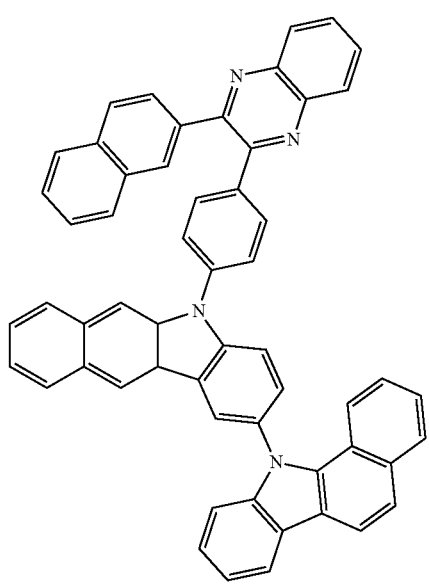
410
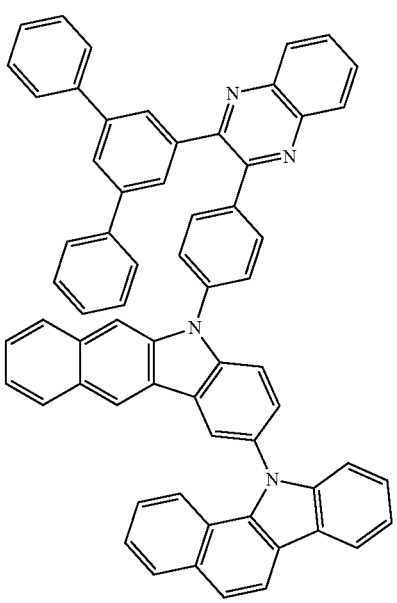
412

413
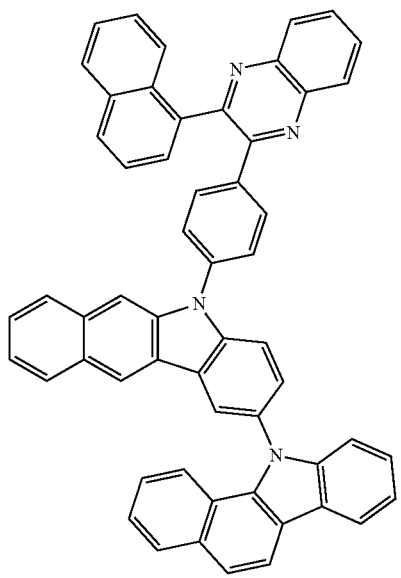
414
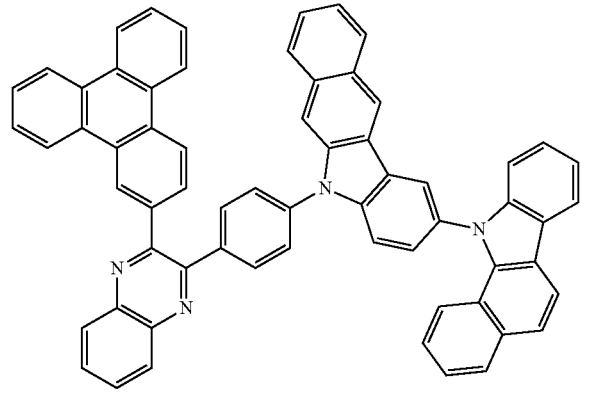
415
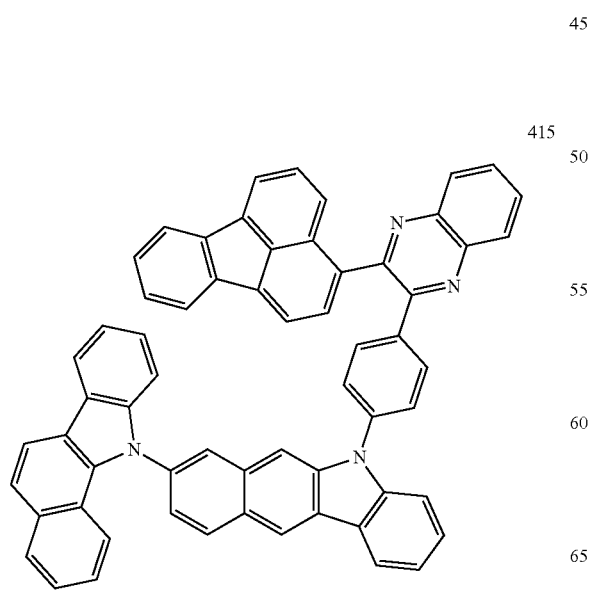
416
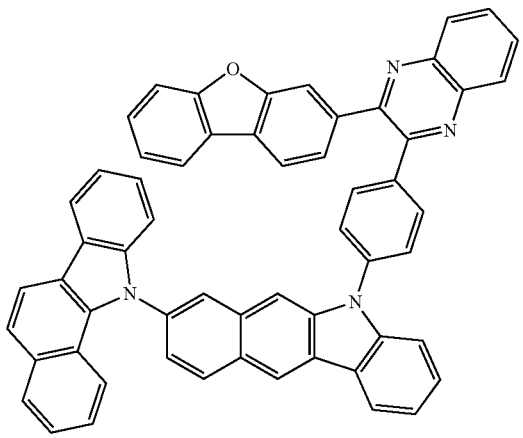
417
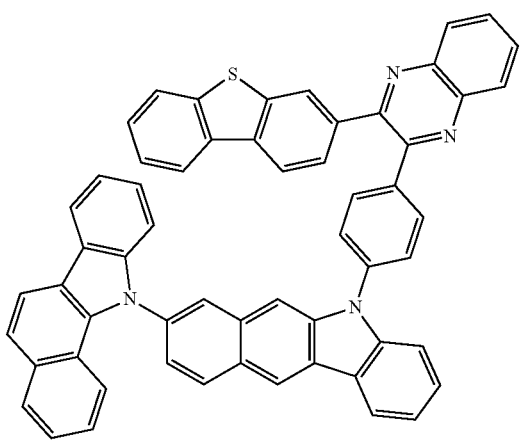
418
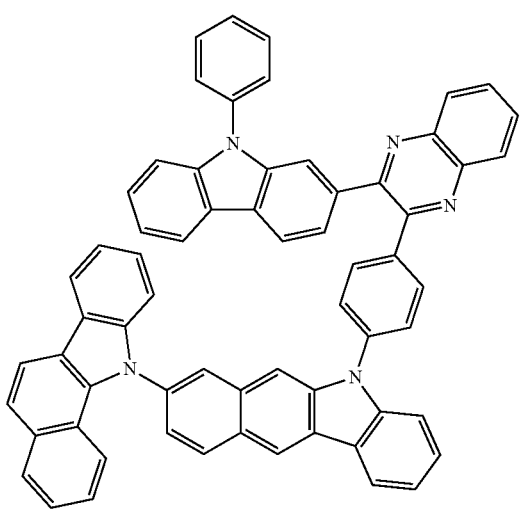

419
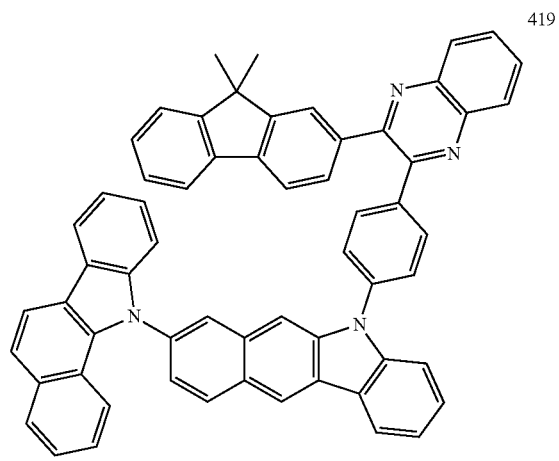
420
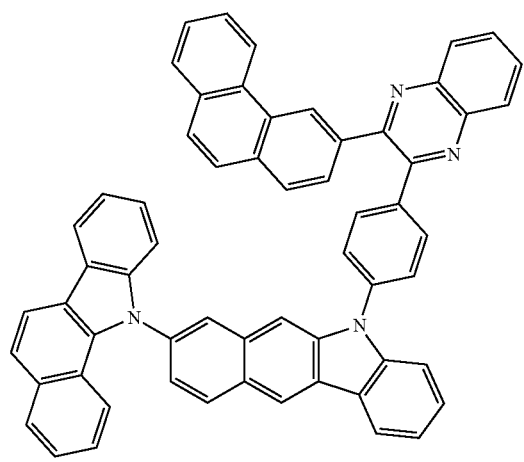
421
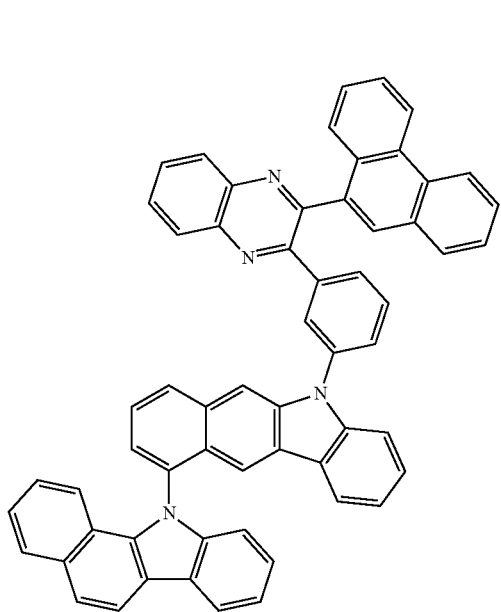
422
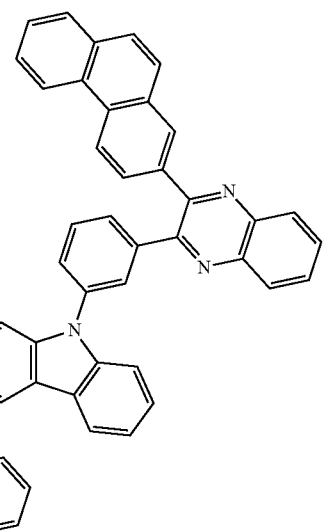
423
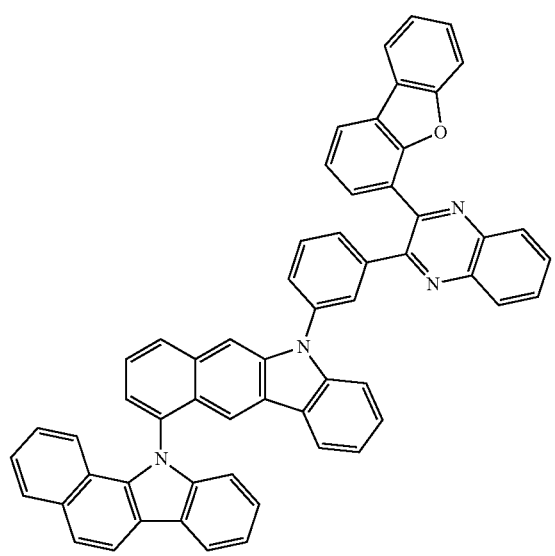

-continued
424
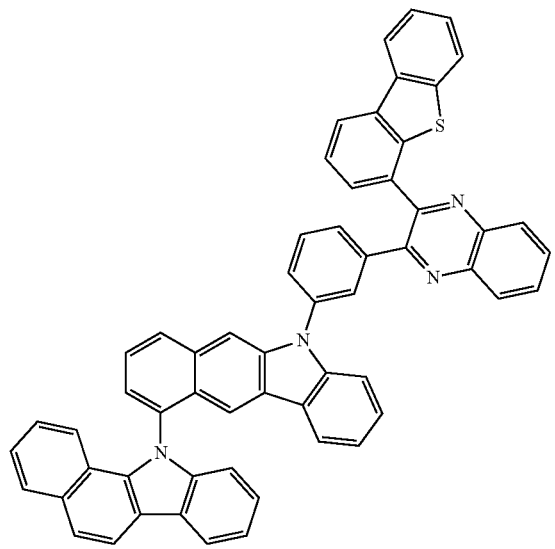
425
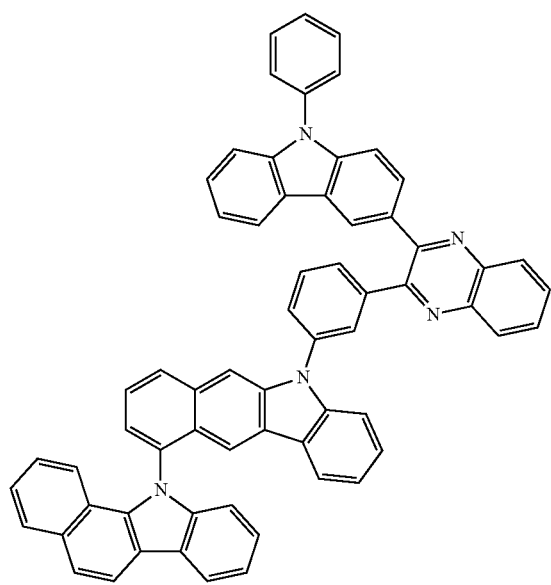
-continued
426
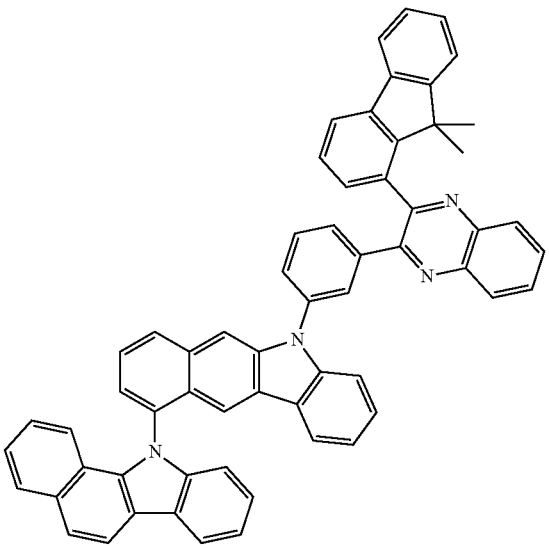
427
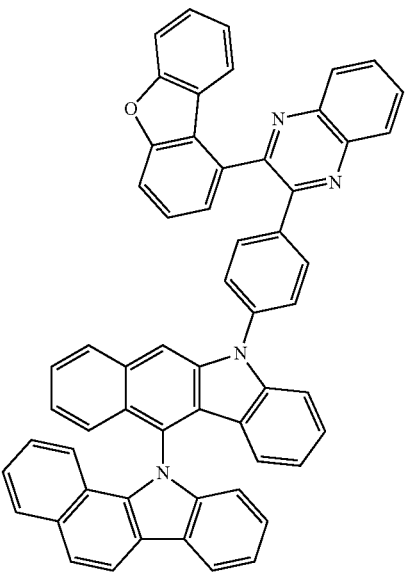

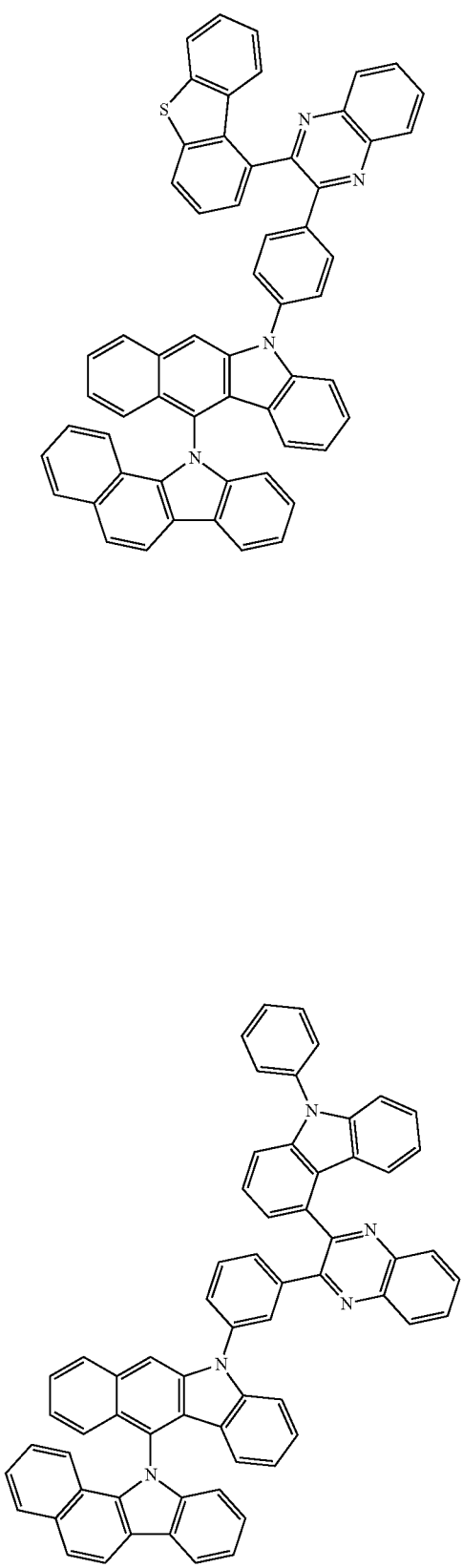
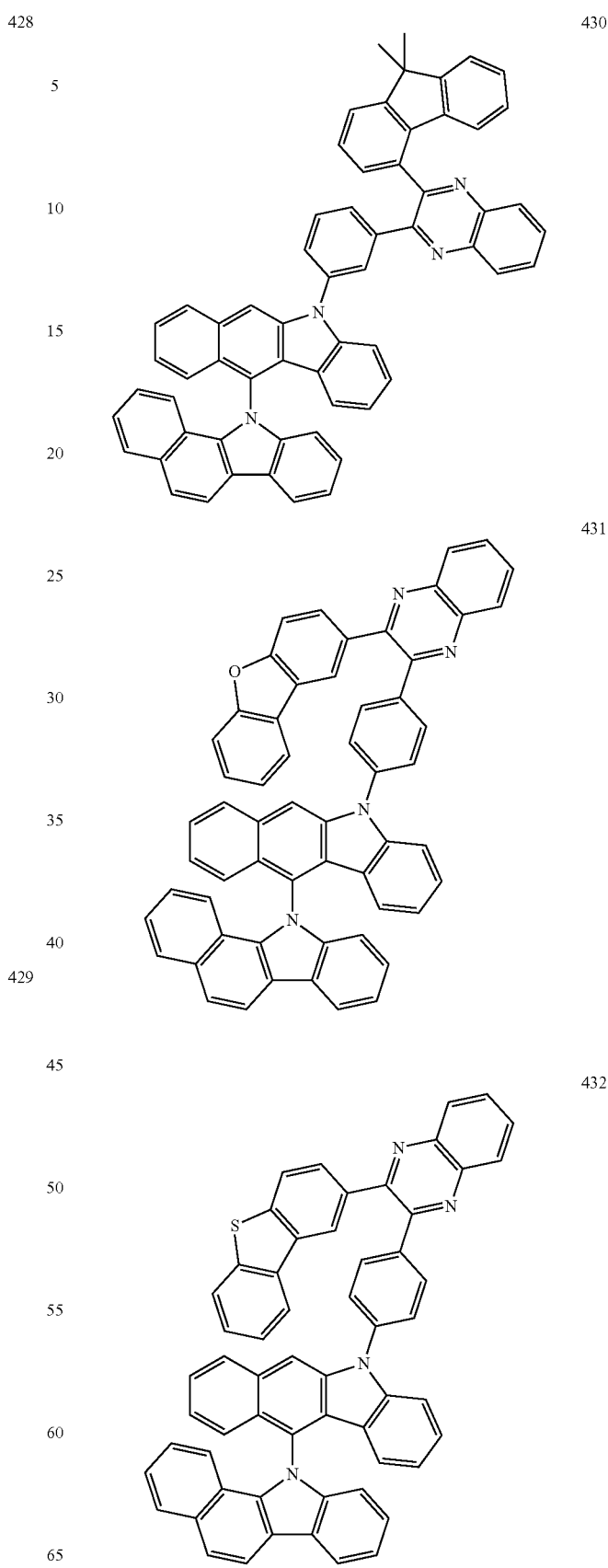

193
-continued
433
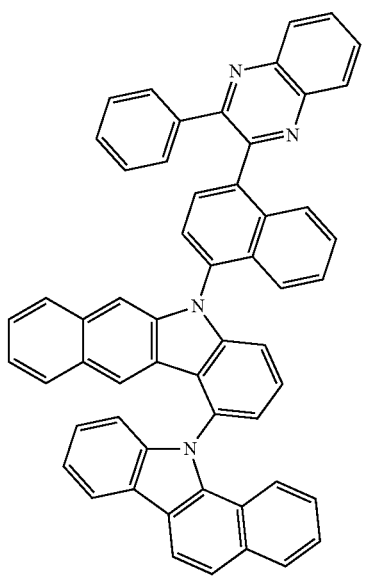
434
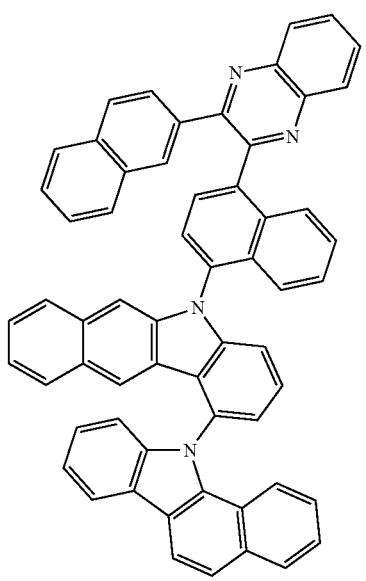
194
-continued
435
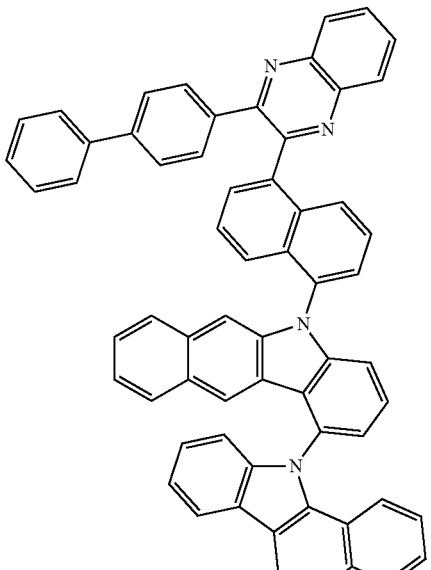
436
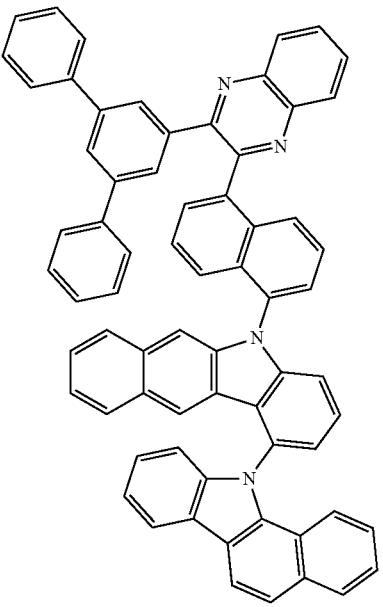

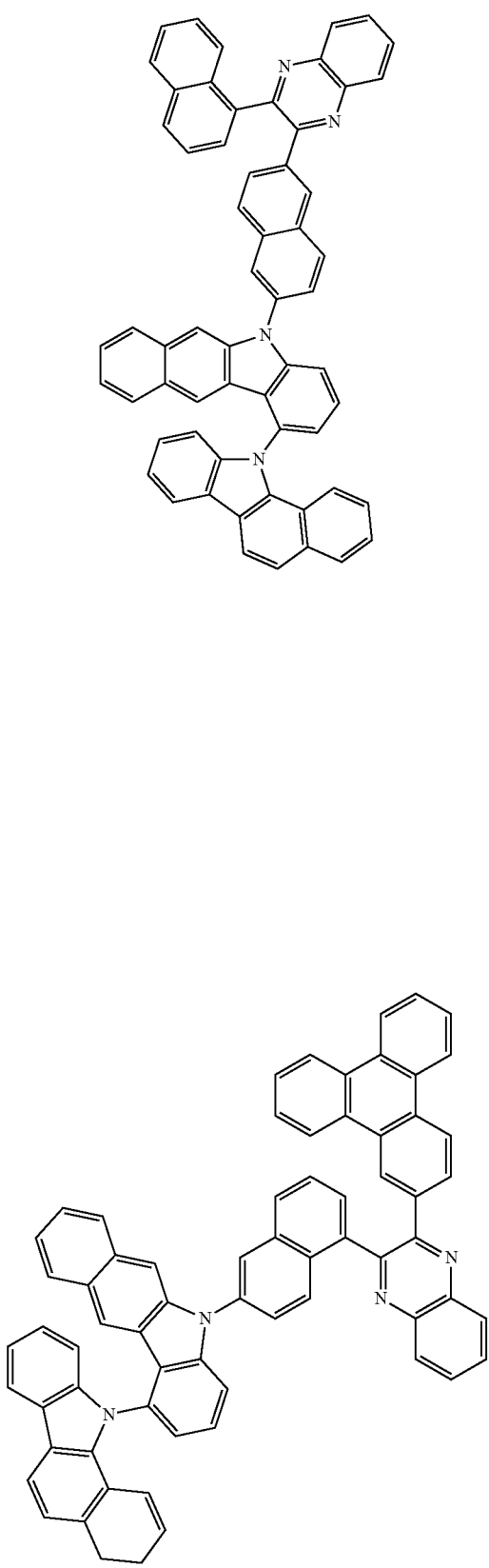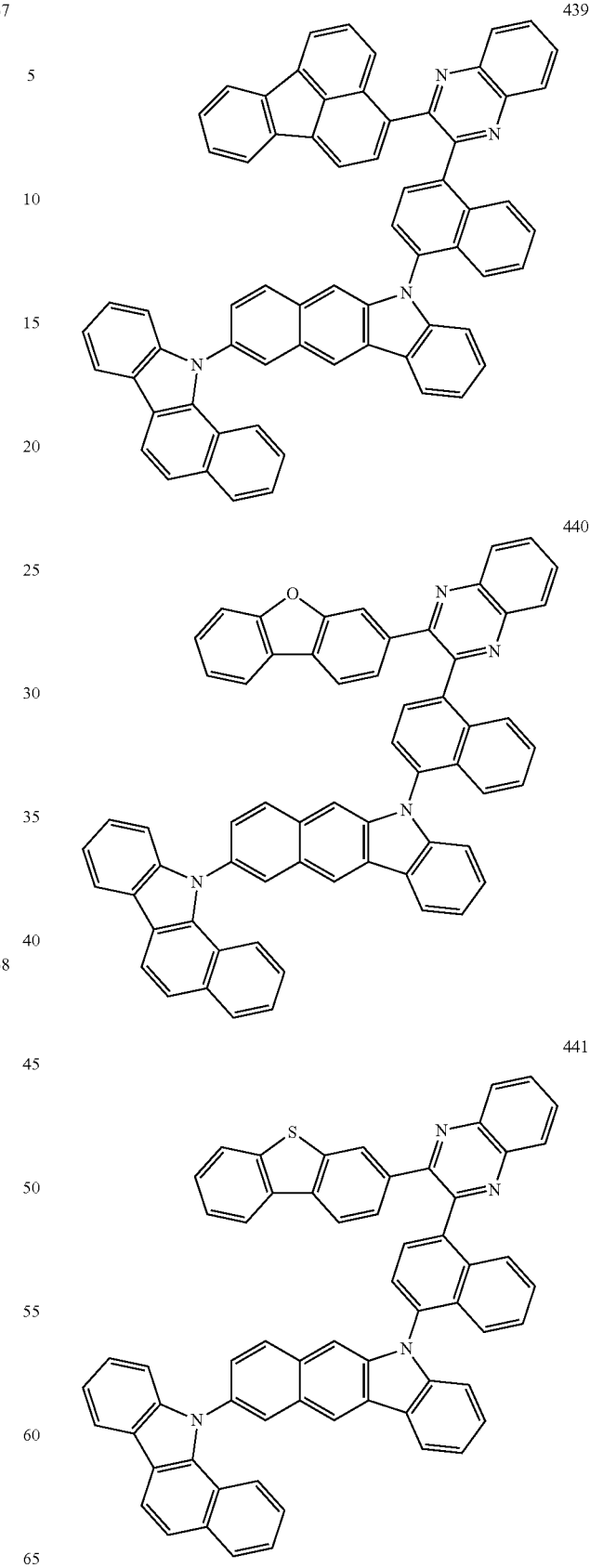

197
-continued
442
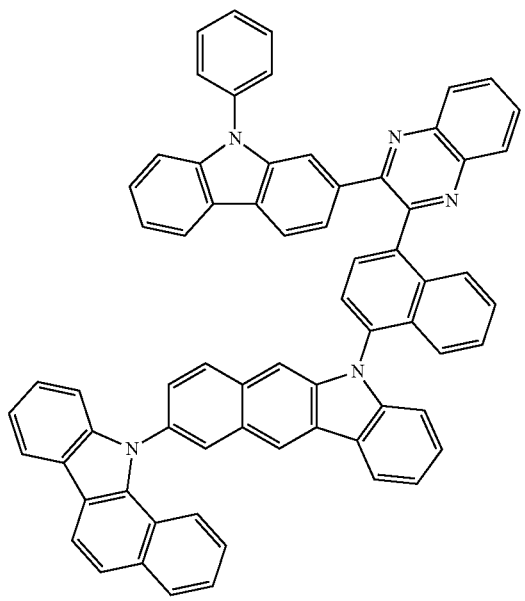
443
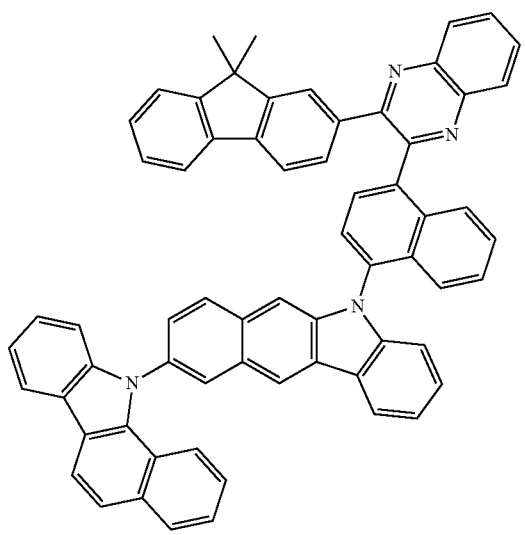
198
-continued
444
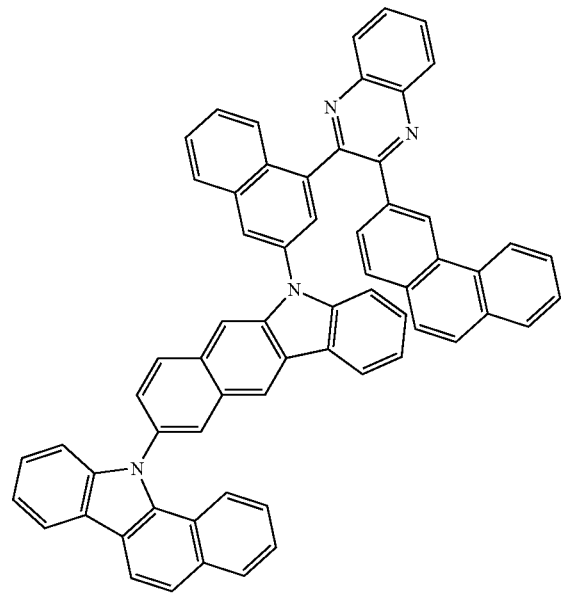
445
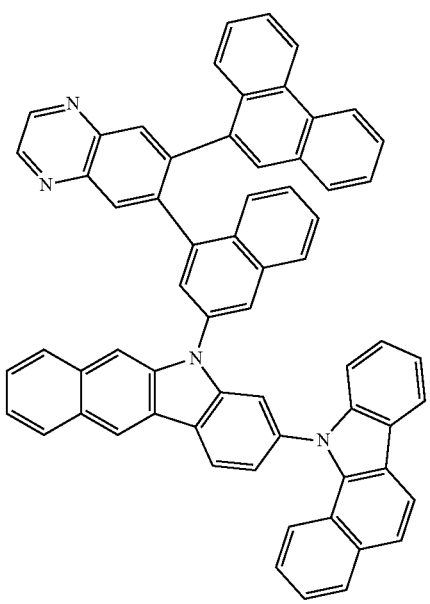

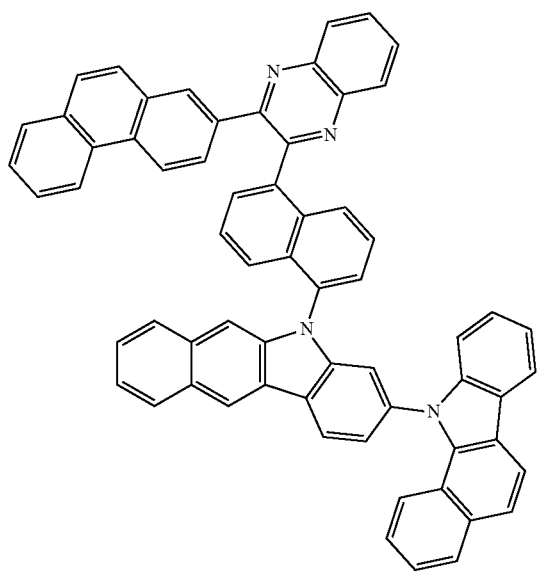
446
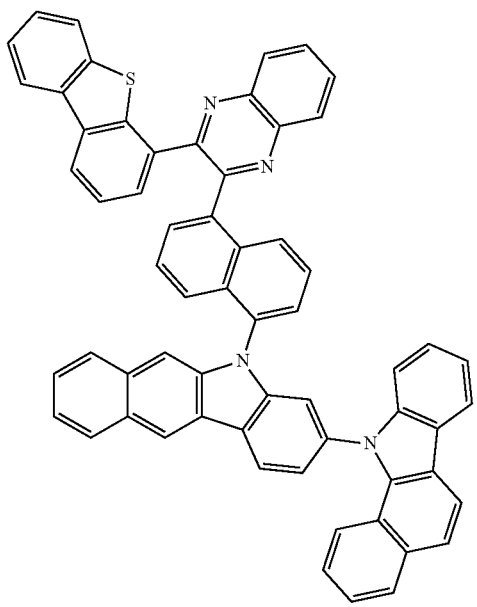
448
447
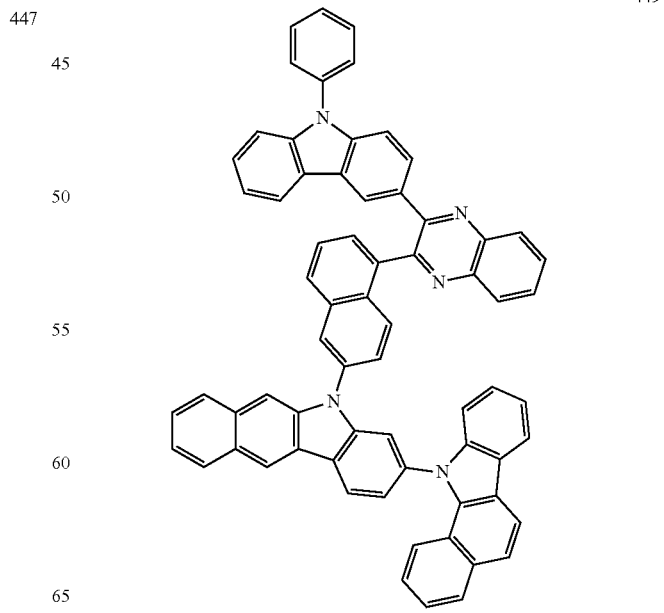
449

201
-continued
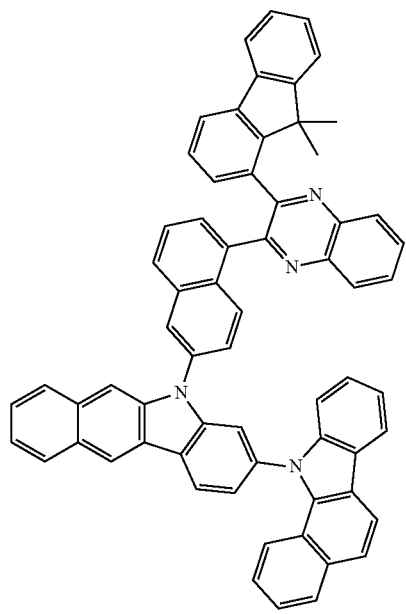
450
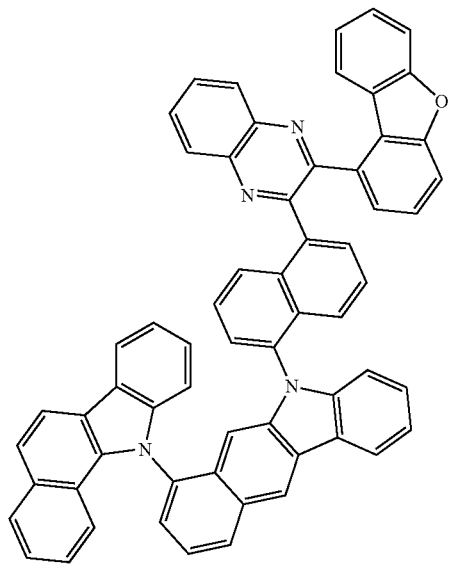
451
202
-continued
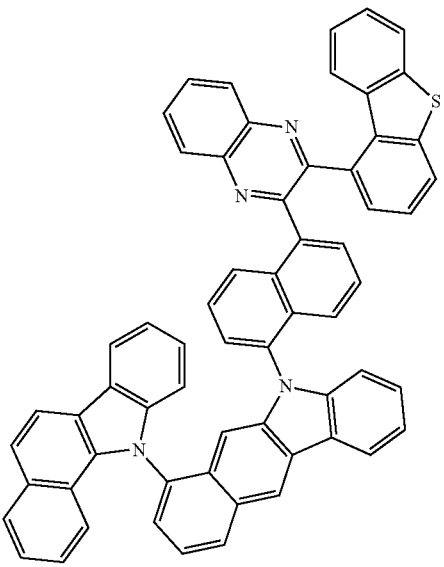
452
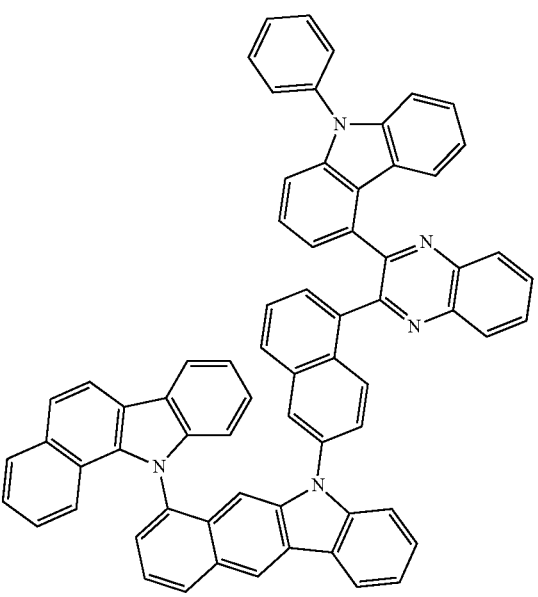
453

454
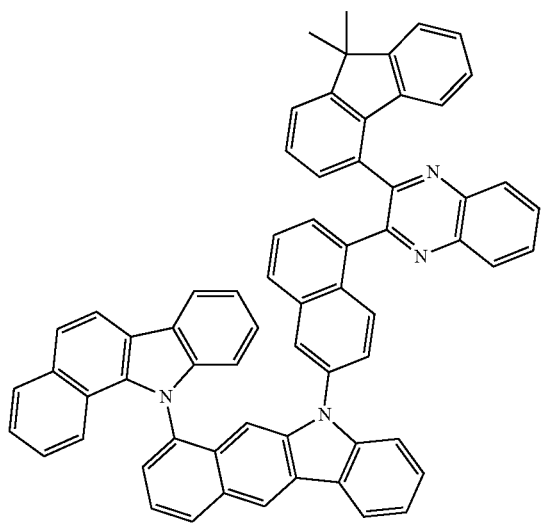
455
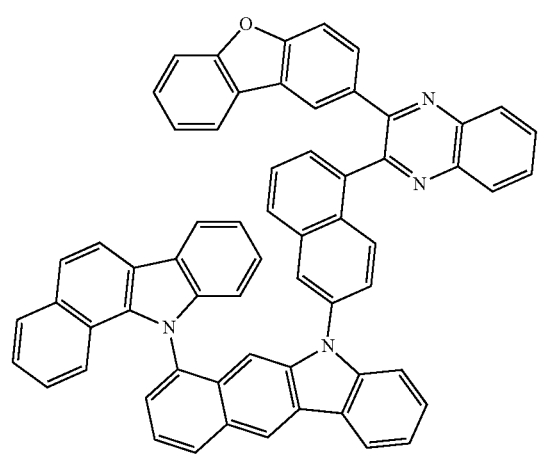
456
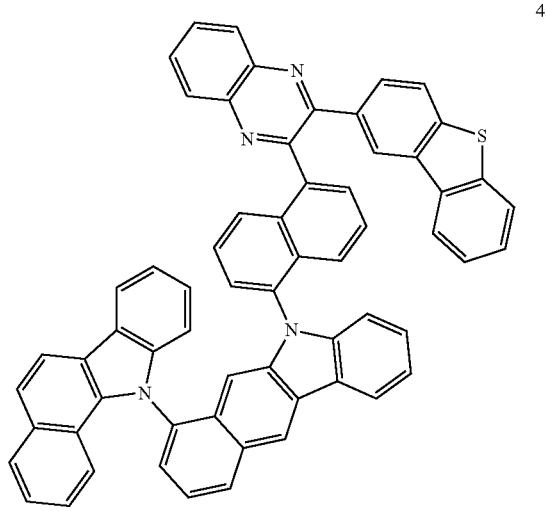
457
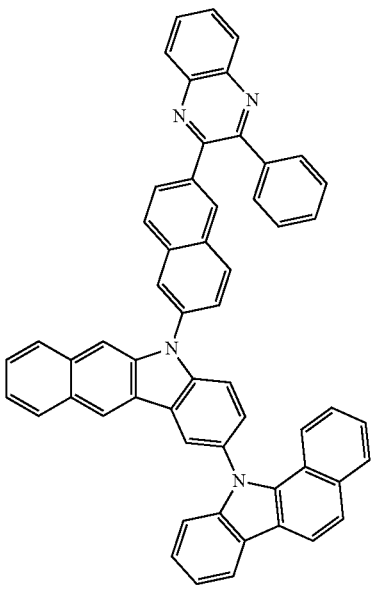
458
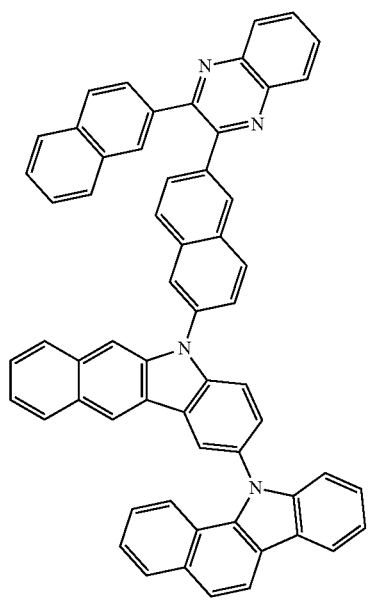

205
-continued
459
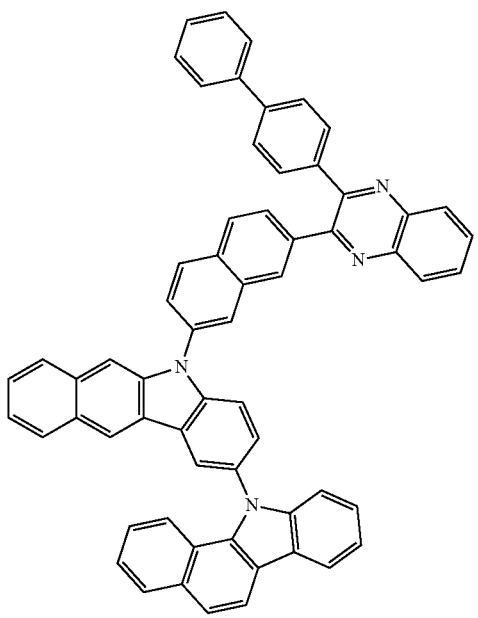
460
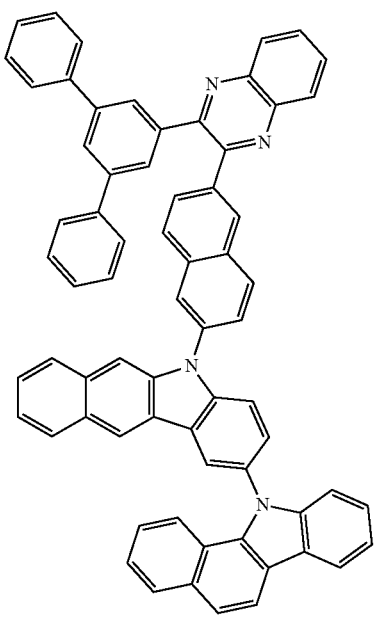
206
-continued
461
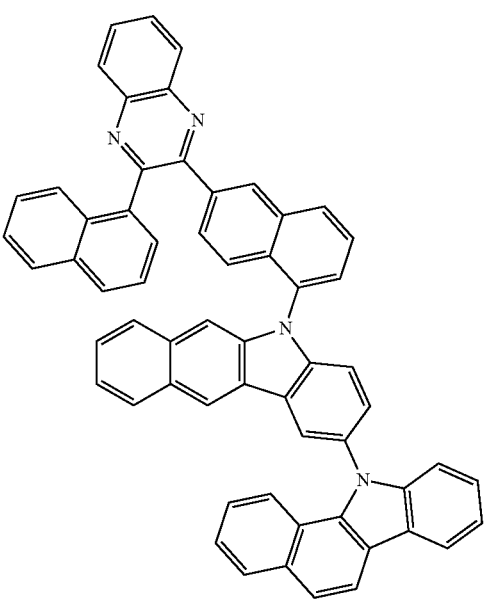
462
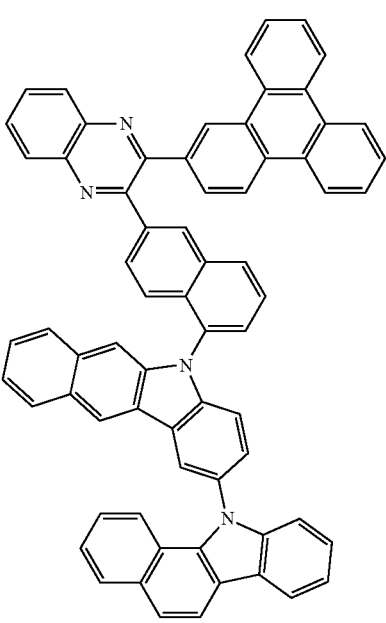

-continued

209
-continued
469
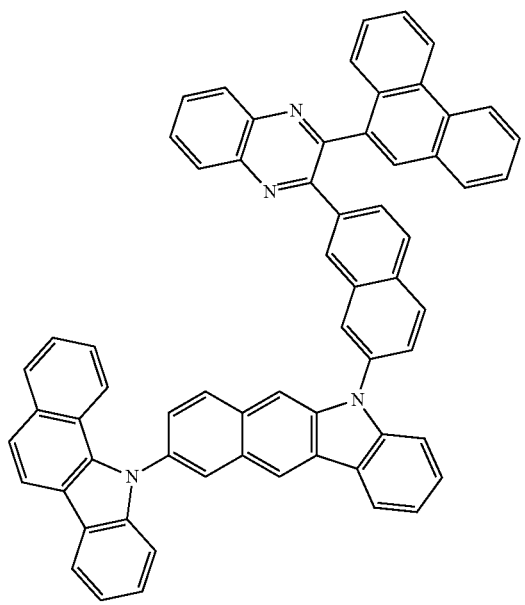
470
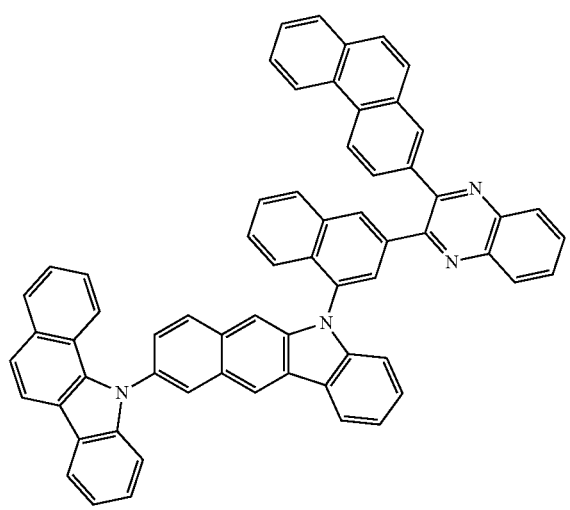
210
-continued
471
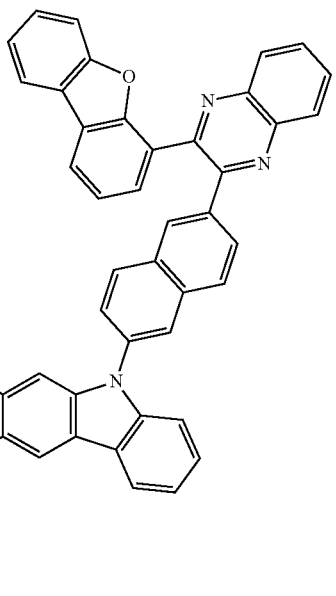
472
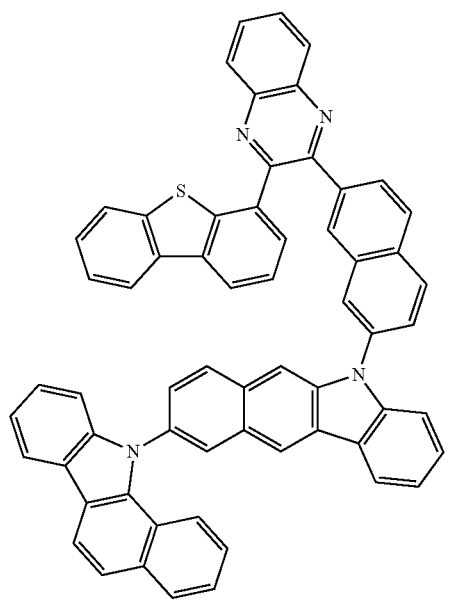

211
-continued
473
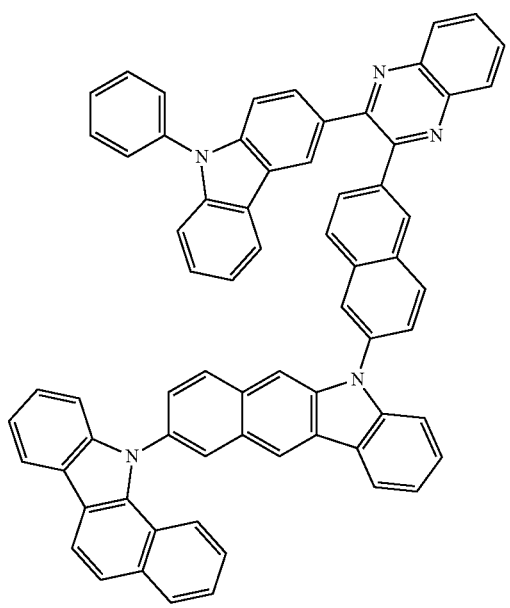
212
-continued
475
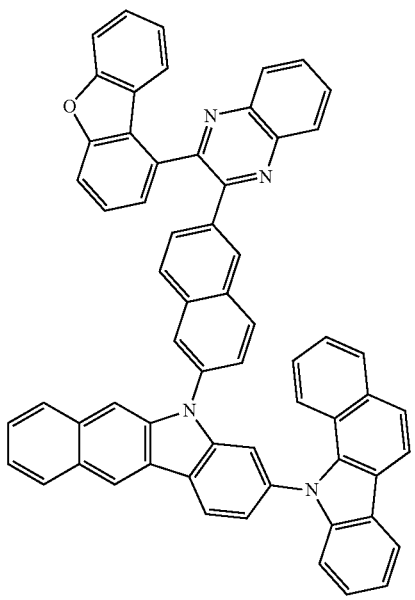
474
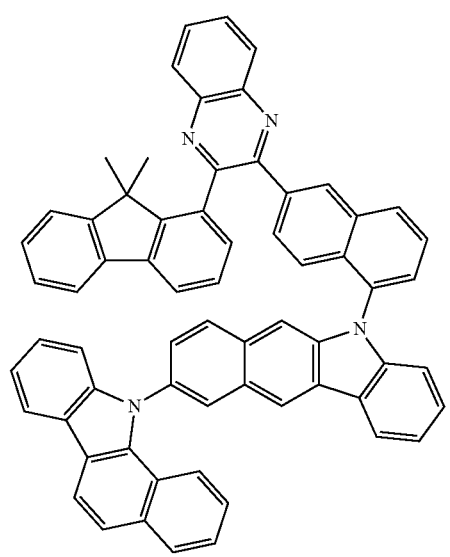
476
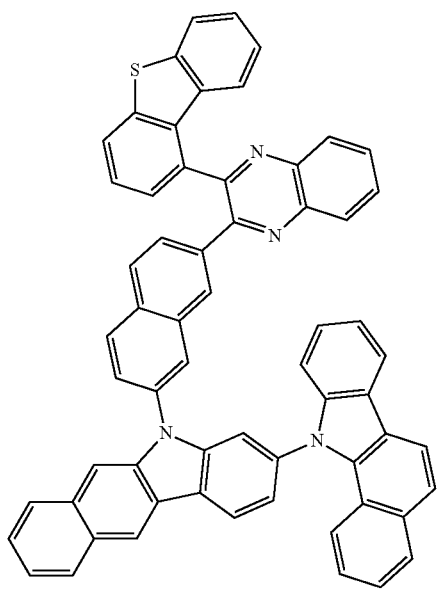

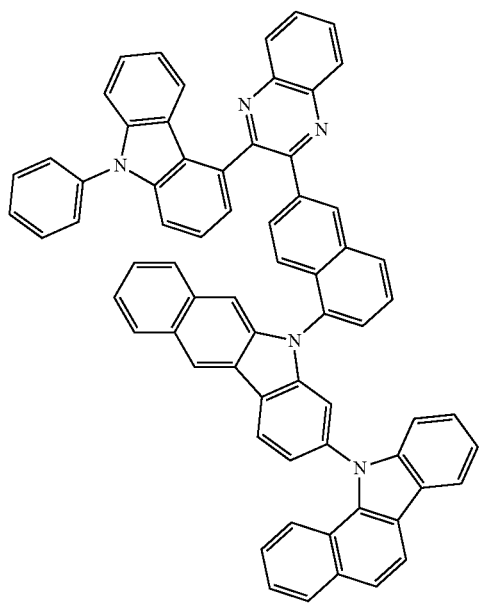
477
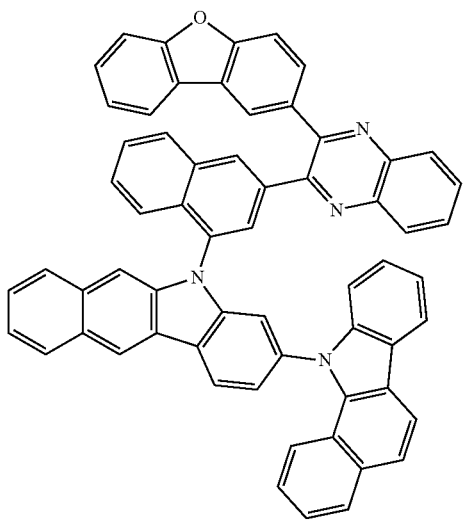
479
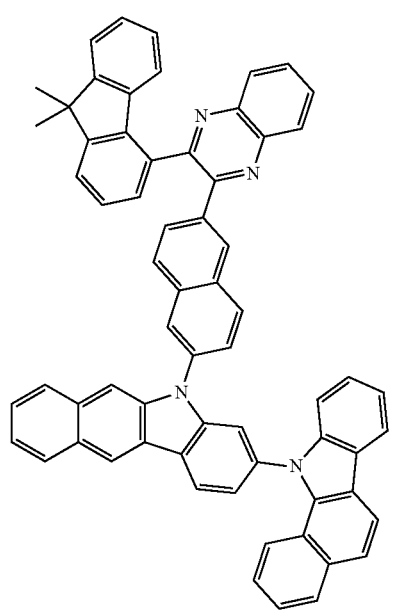
478
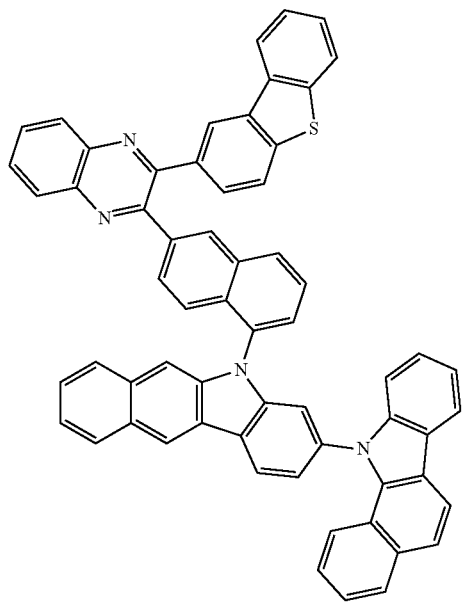
480

215
-continued
216
-continued
481
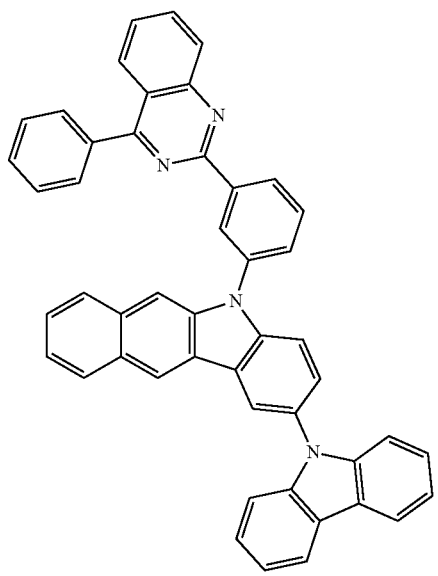
483
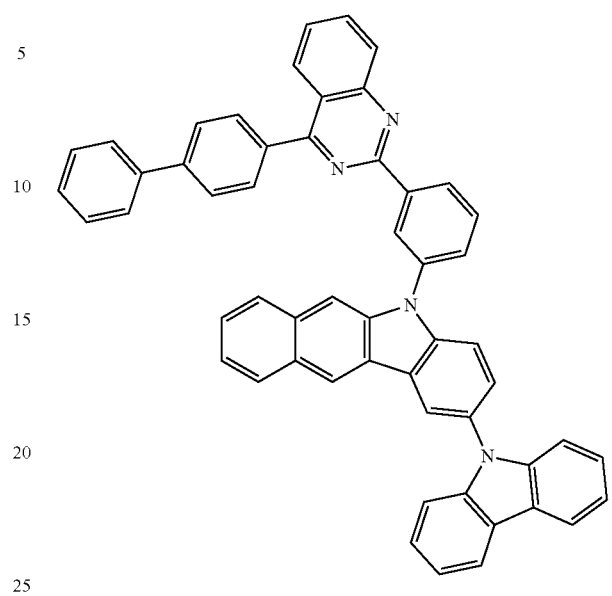
482
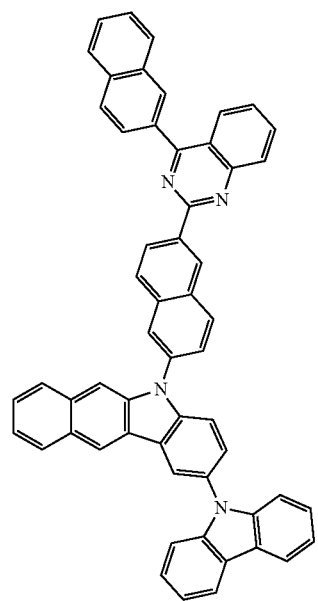
484
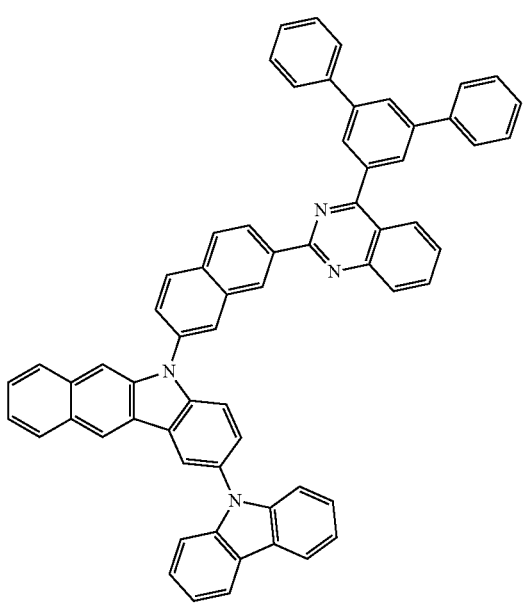

485
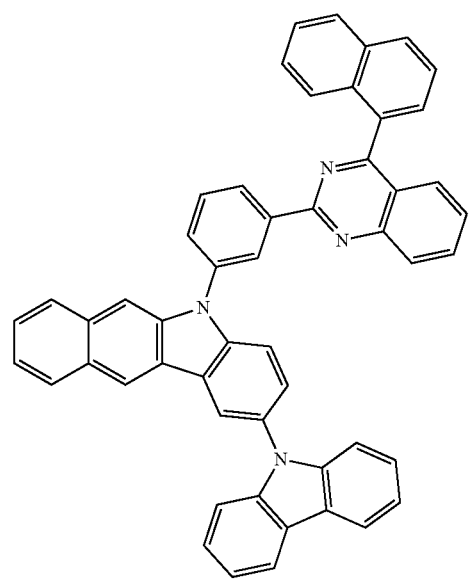
486
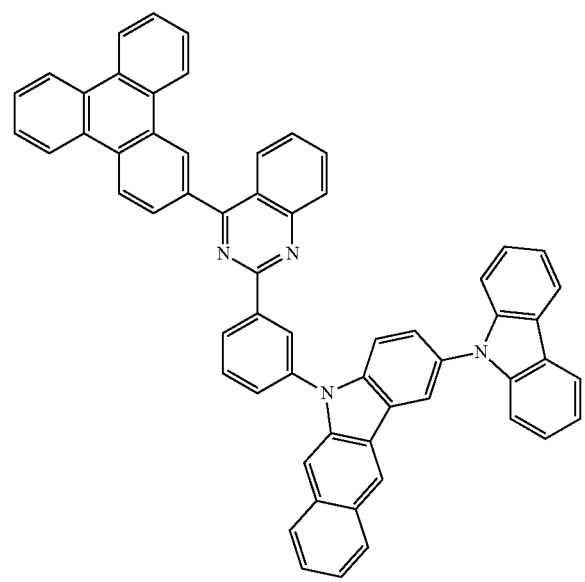
487
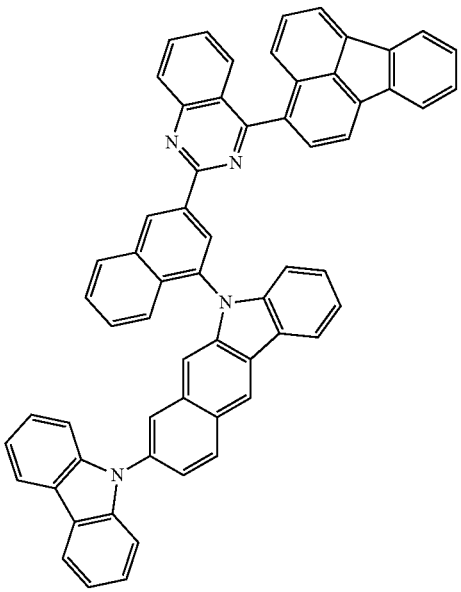
488
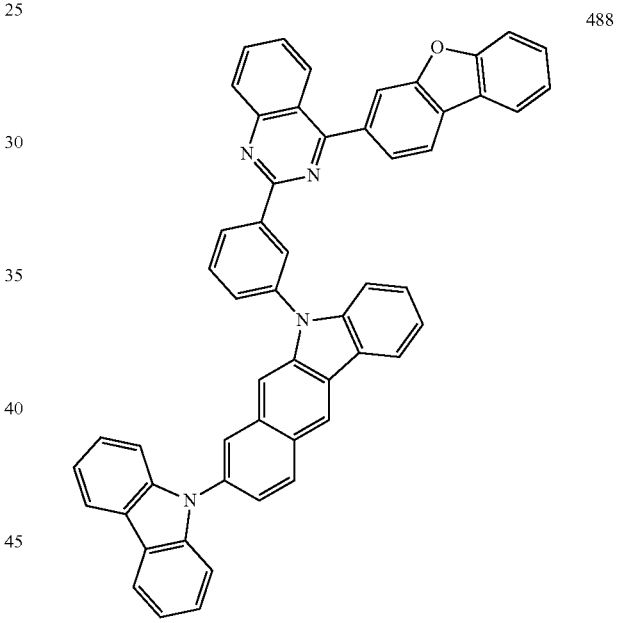
489
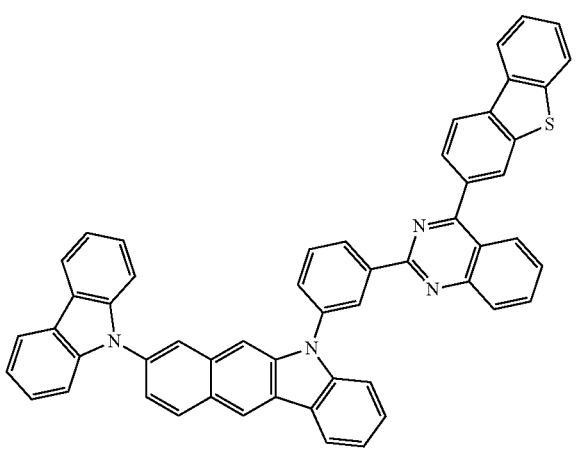

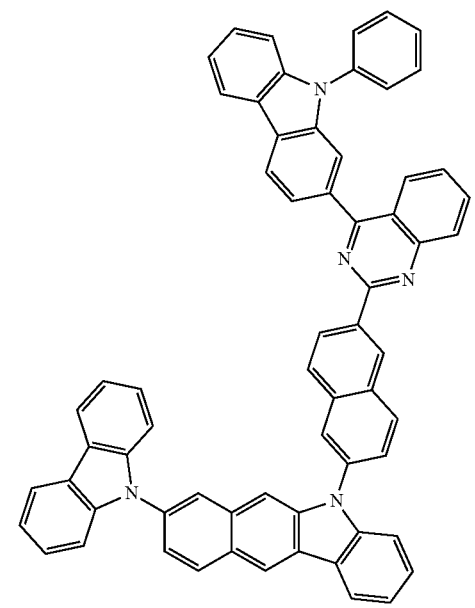
490
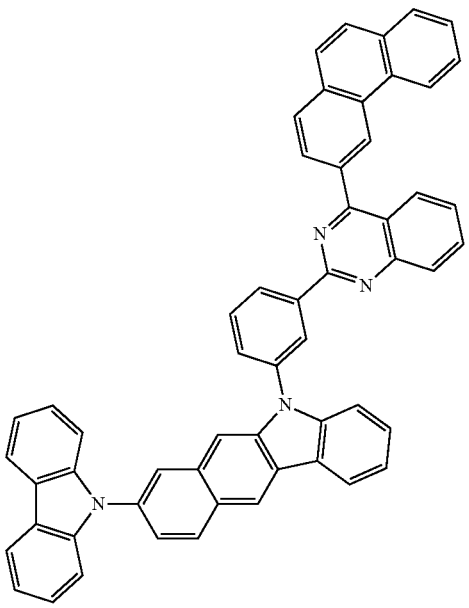
492
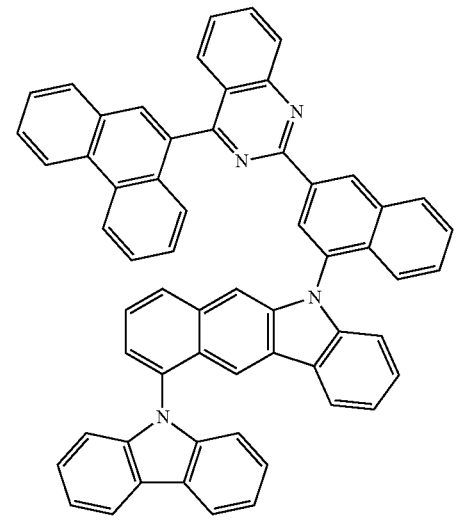
493
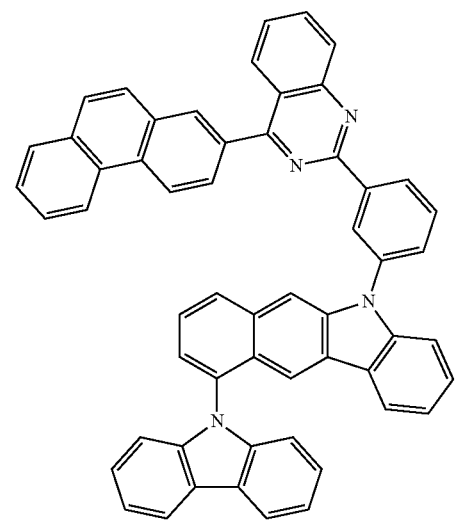
494

221
495
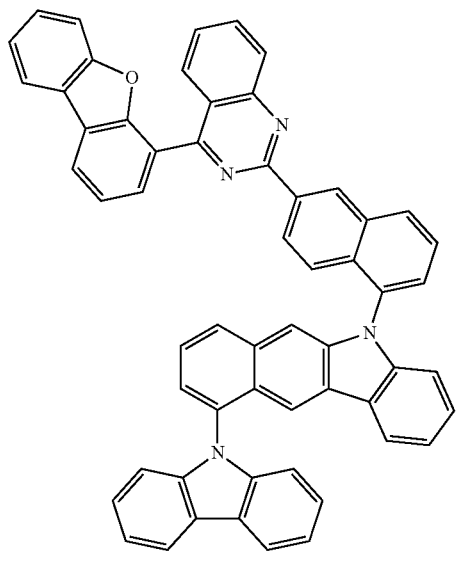
496
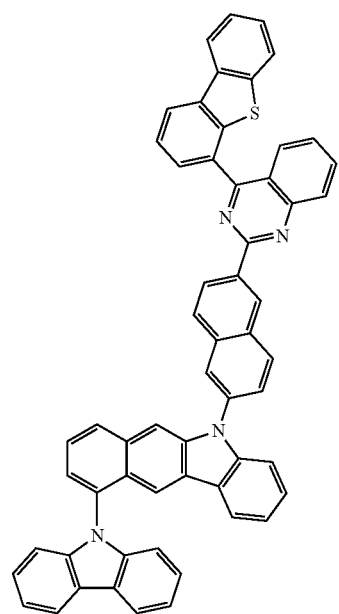
222
497
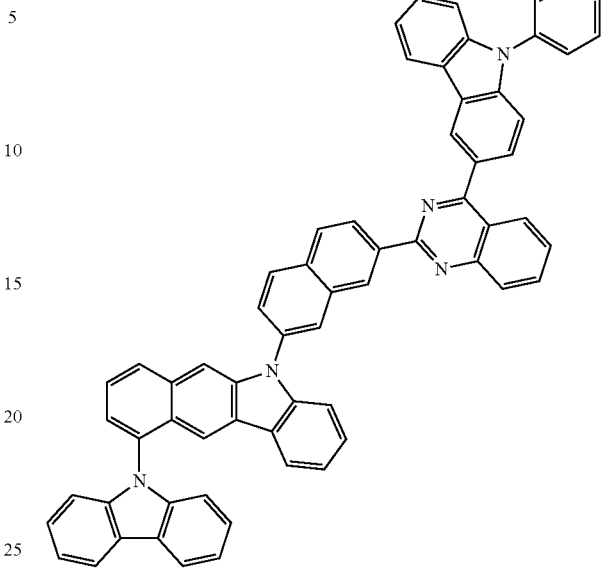
498
499
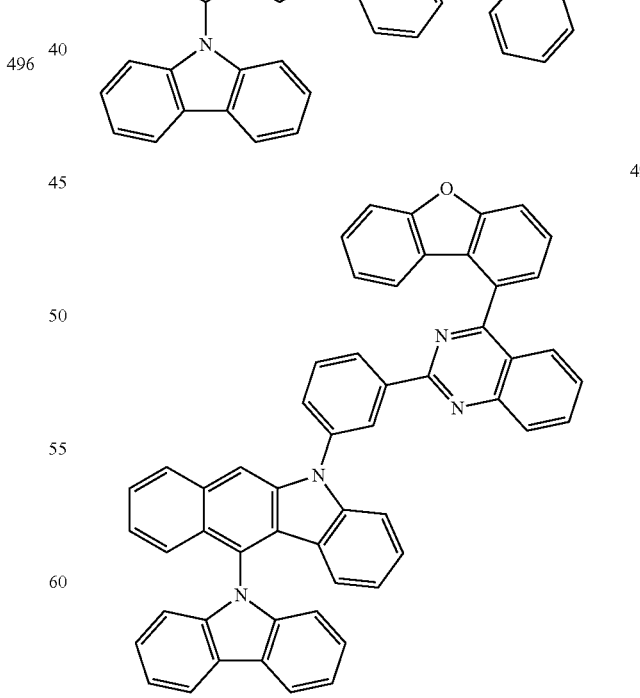

223
-continued
224
-continued
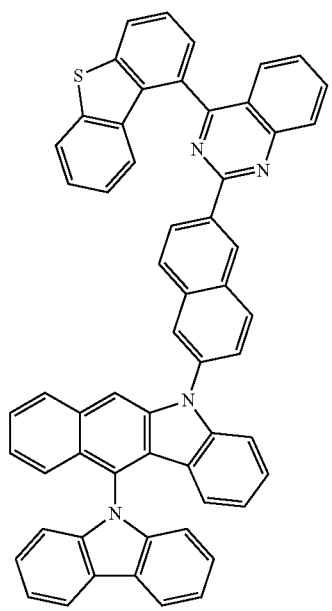
500
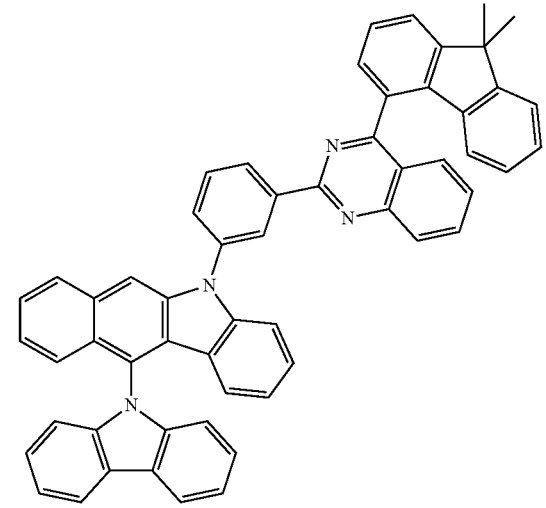
502
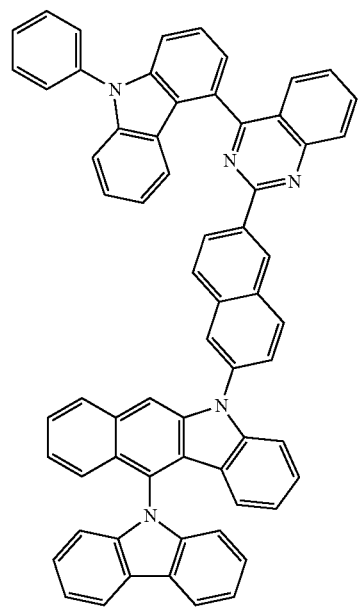
501
503

225
-continued
504
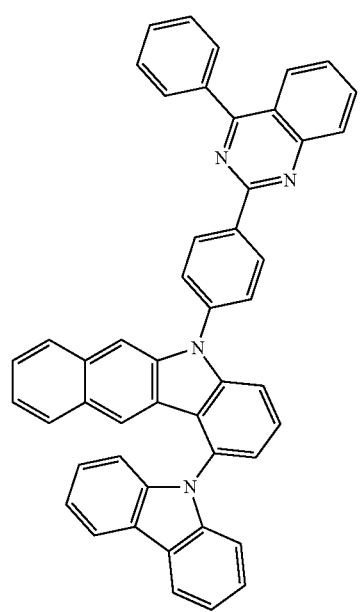
505
226
-continued
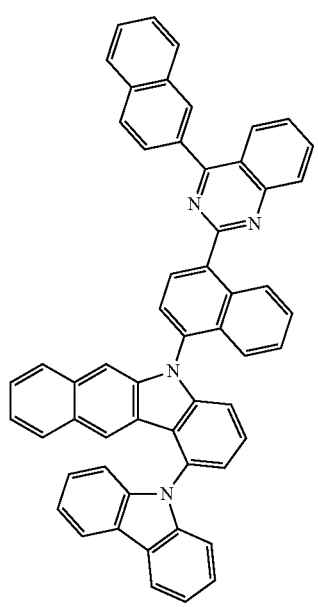
506
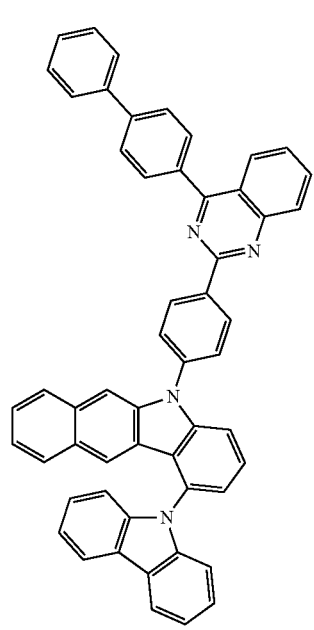
507

227
-continued
508
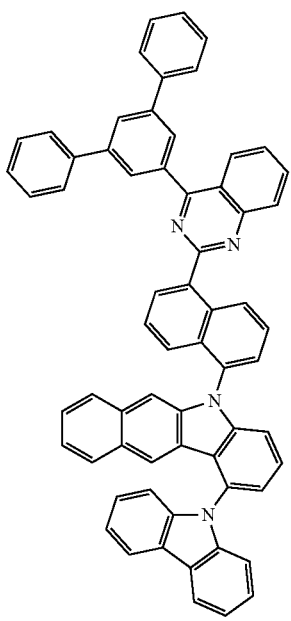
509
228
-continued
510
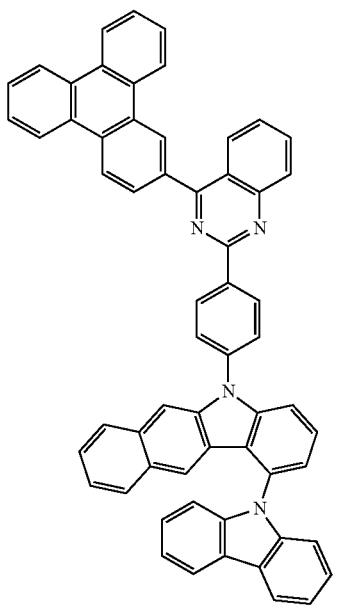
511
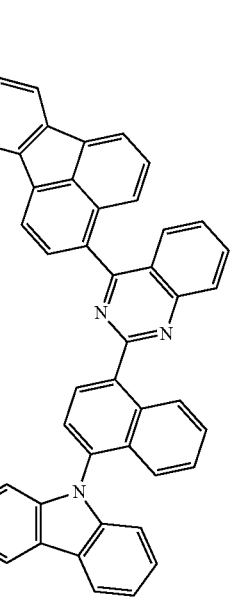

229
-continued
512
513
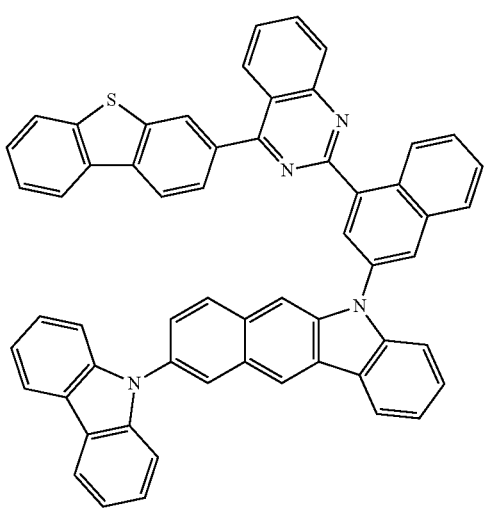
230
-continued
514
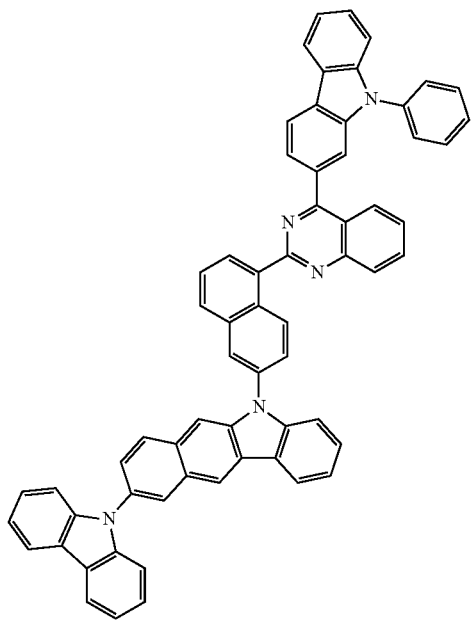
515
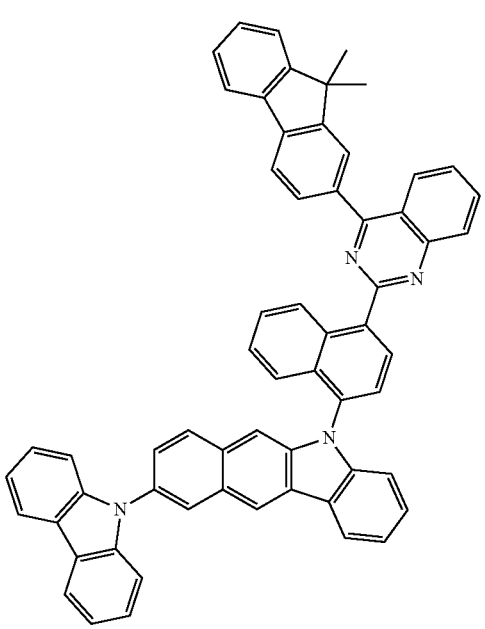

-continued
516
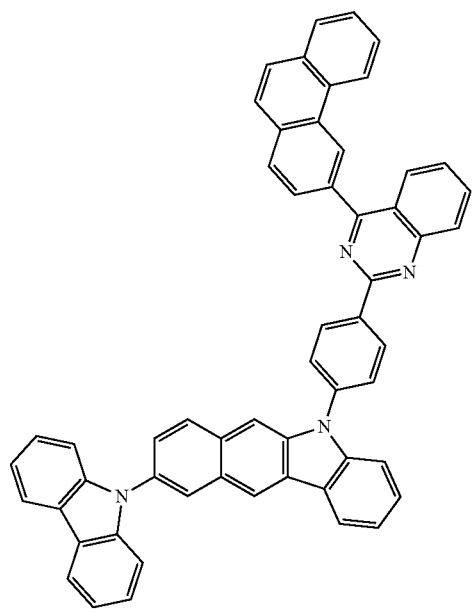
517
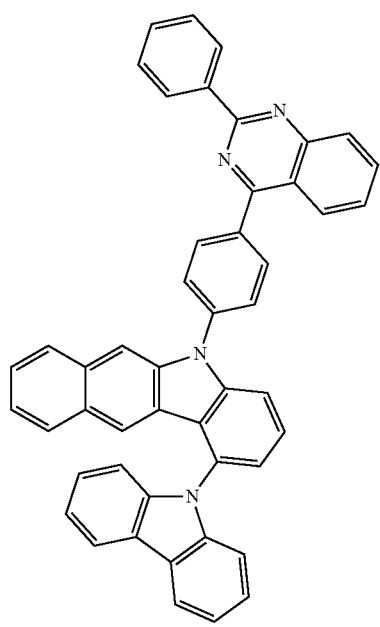
-continued
518
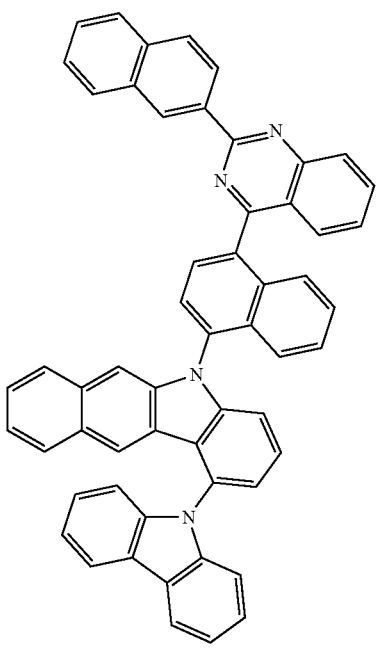
519
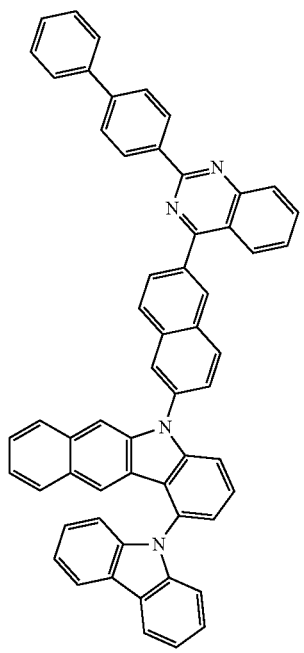

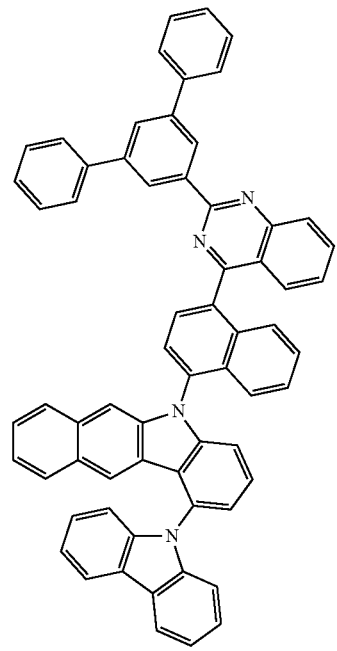
520
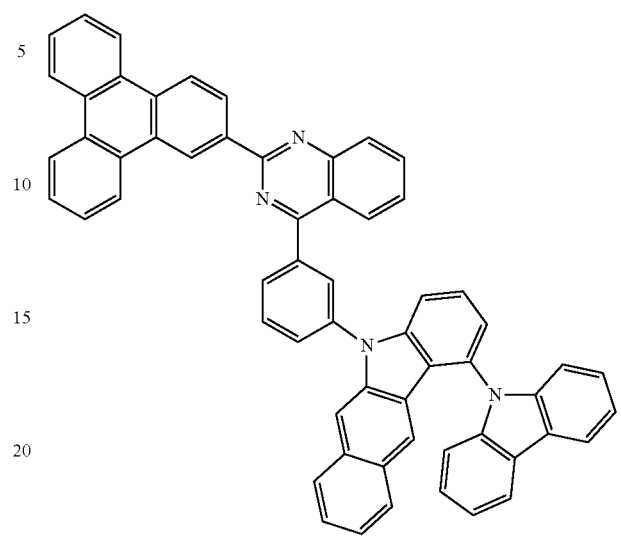
522
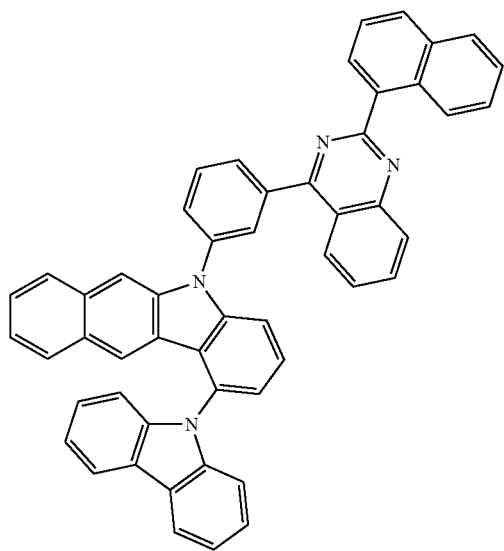
521
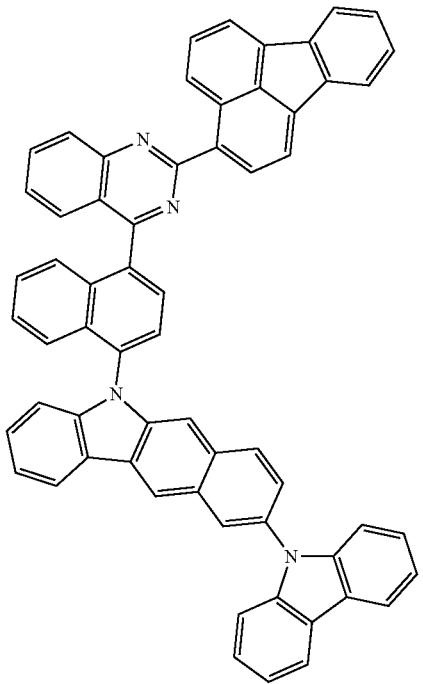
523

524
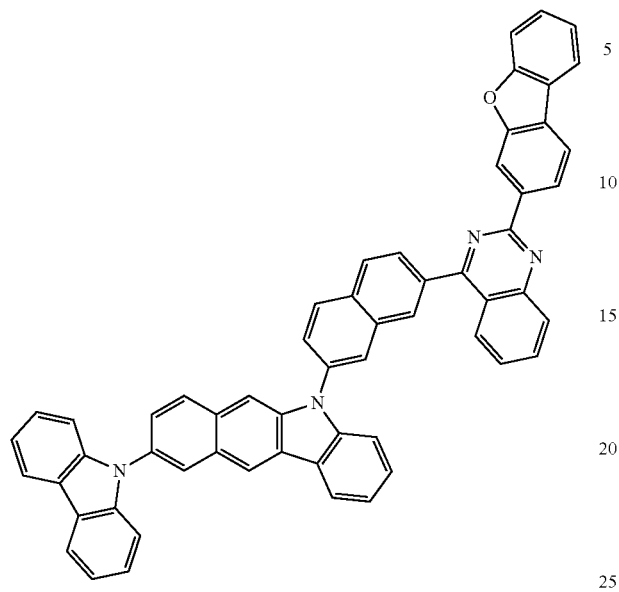
525
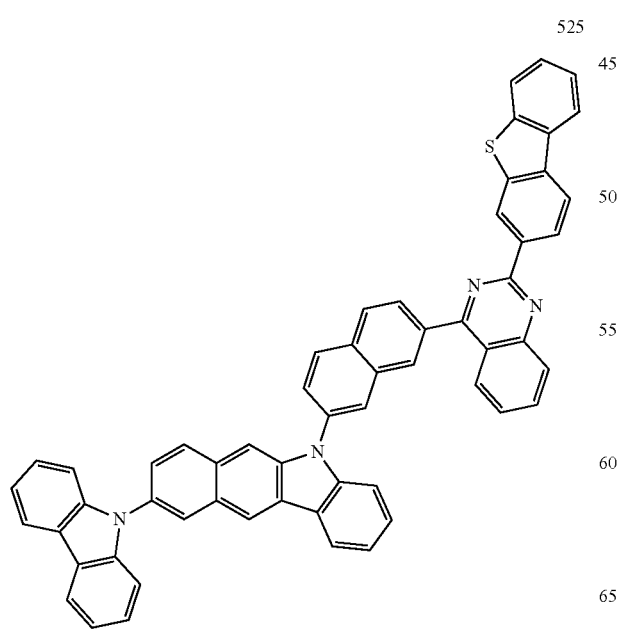
526
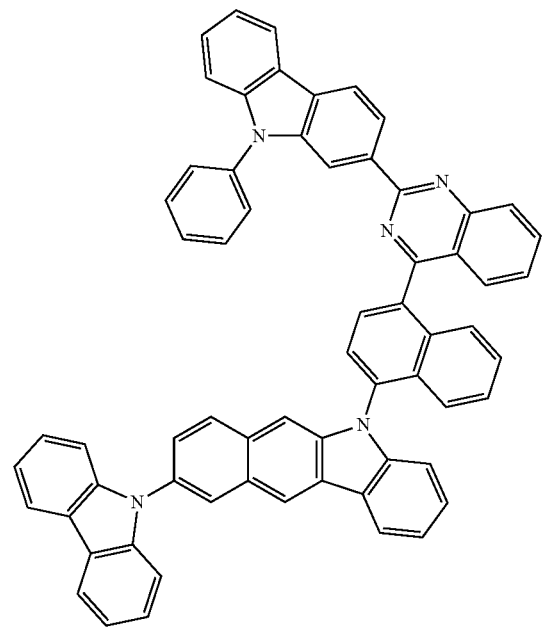
527
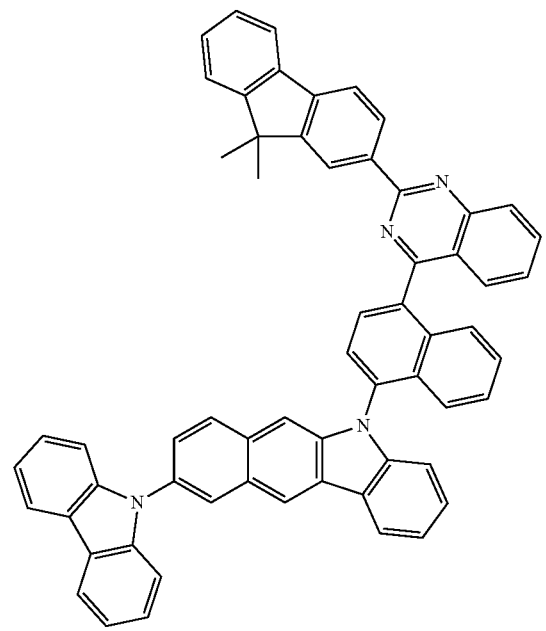

528
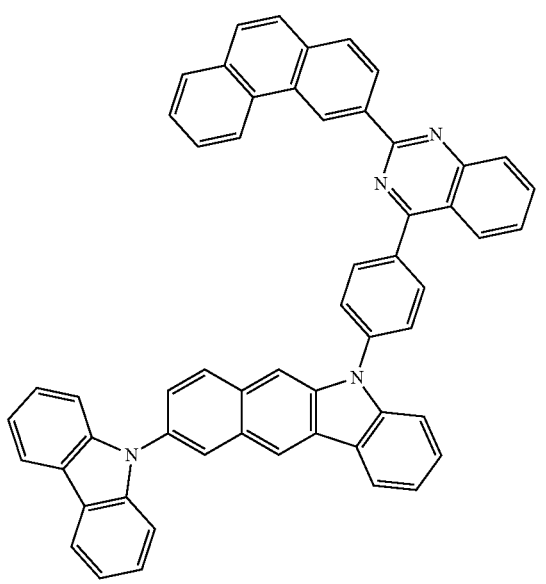
529
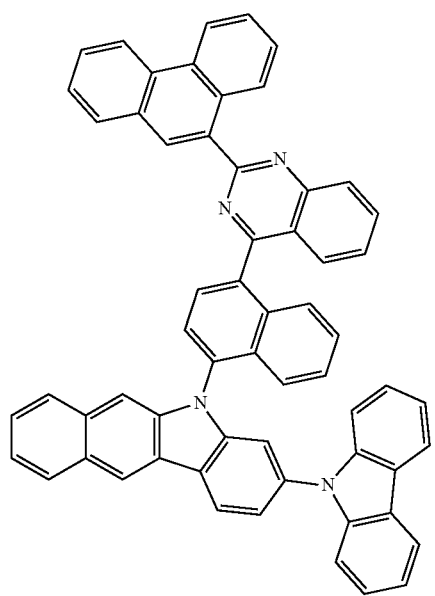
530
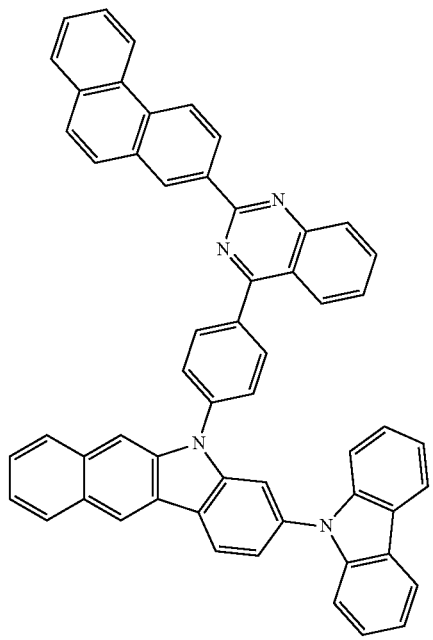
531
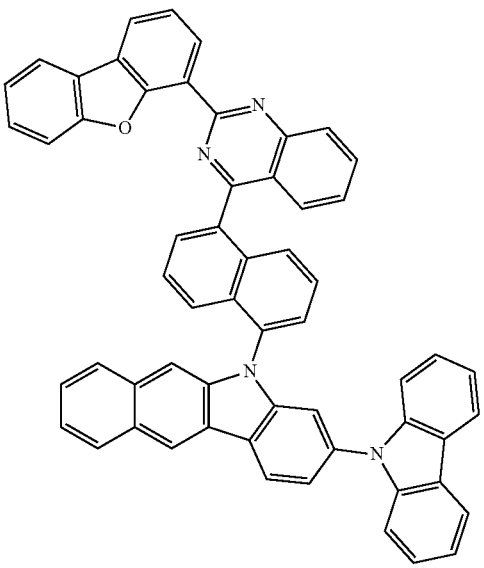

239
-continued
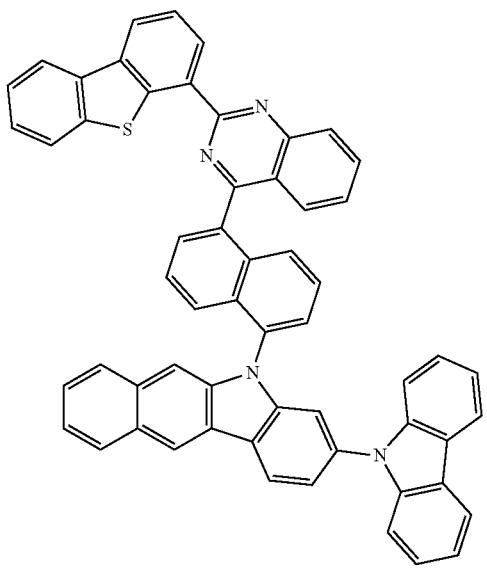
532
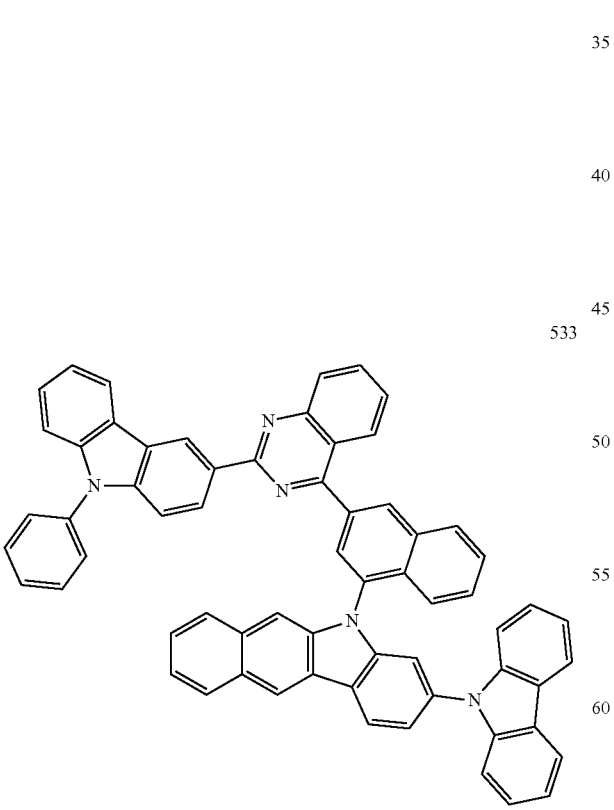
533
240
-continued
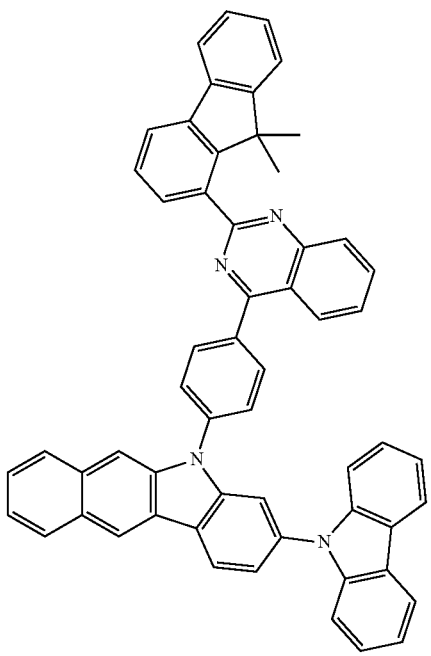
534
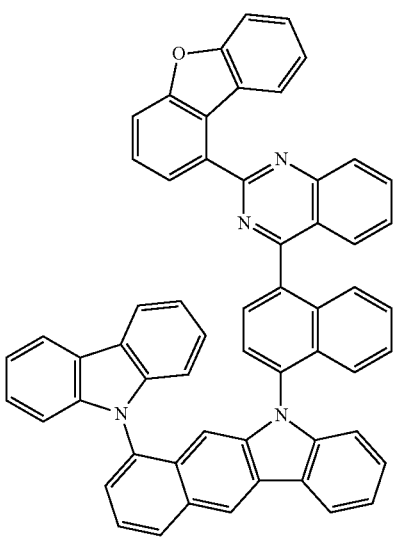
535

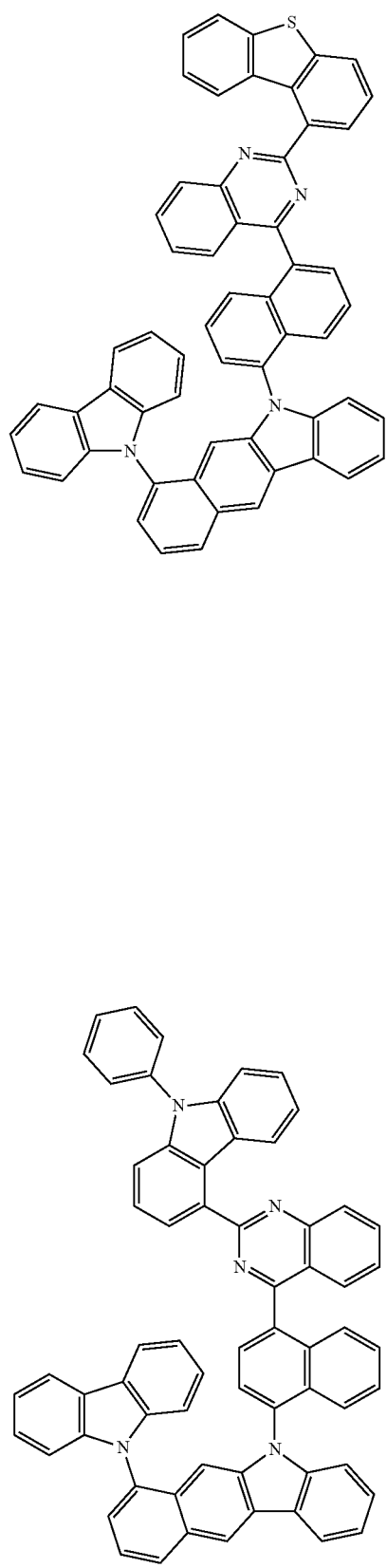
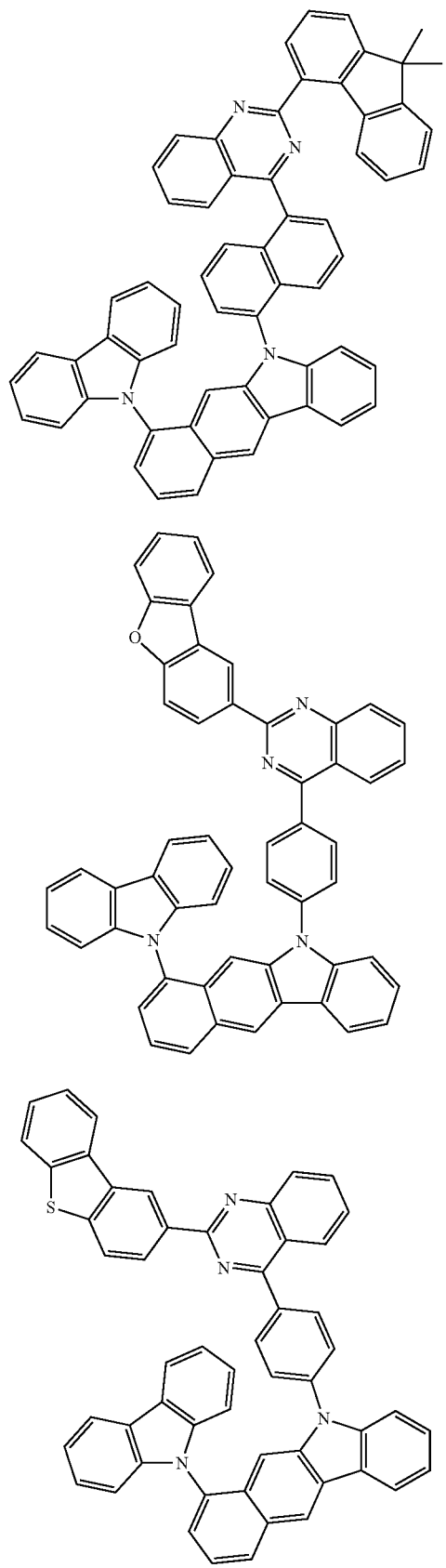

541
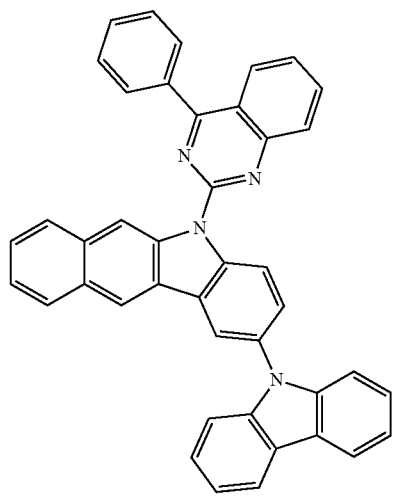
542
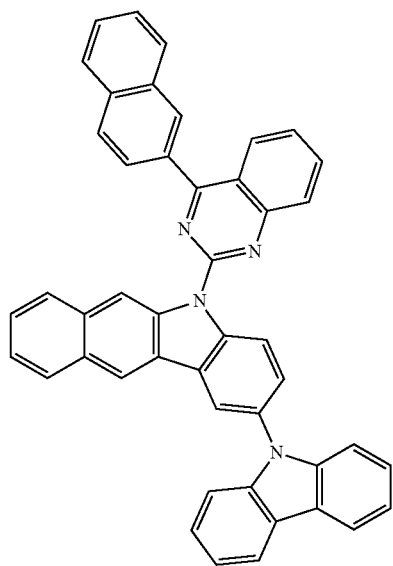
543
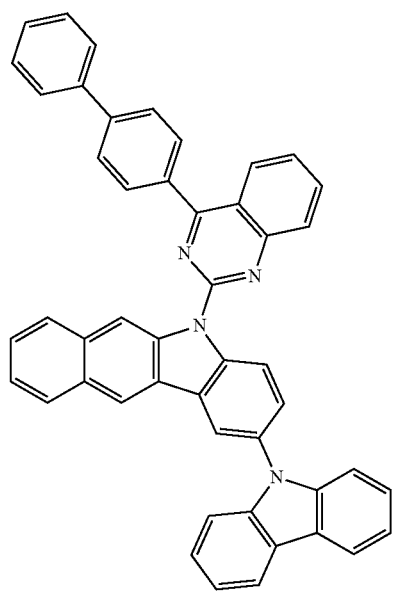
544
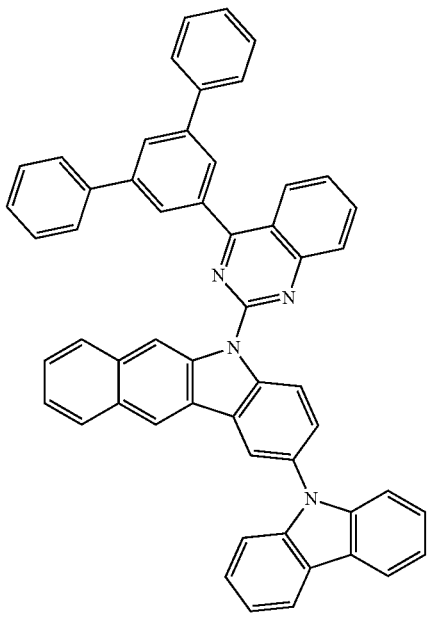
545
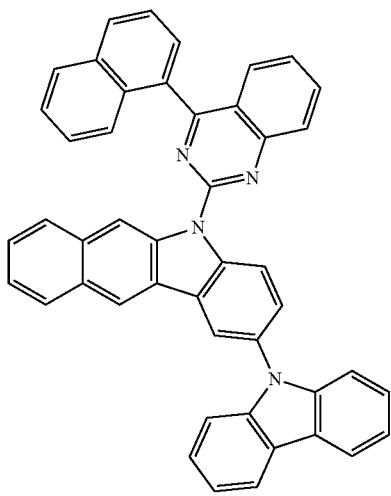

546
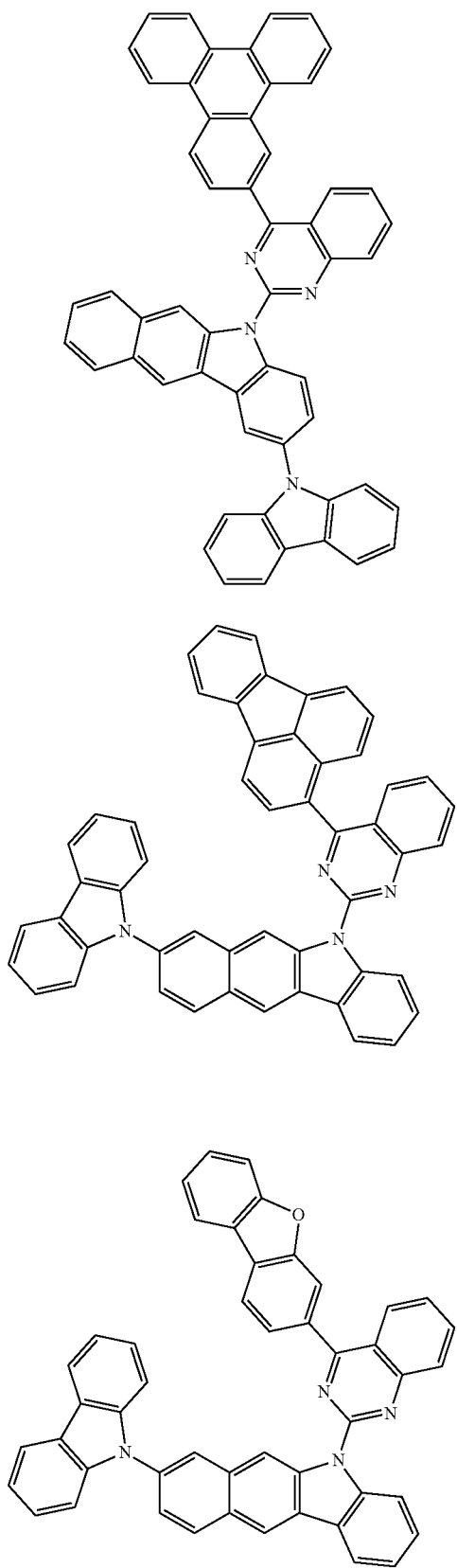
547
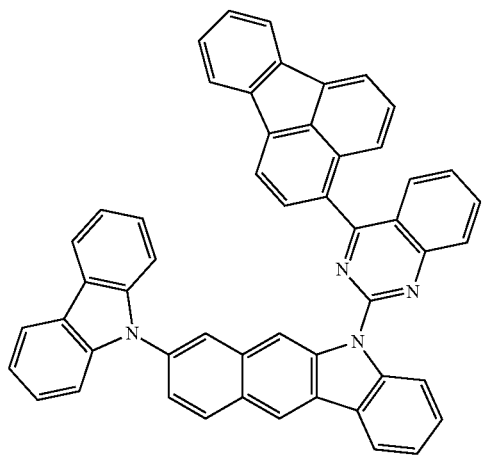
548
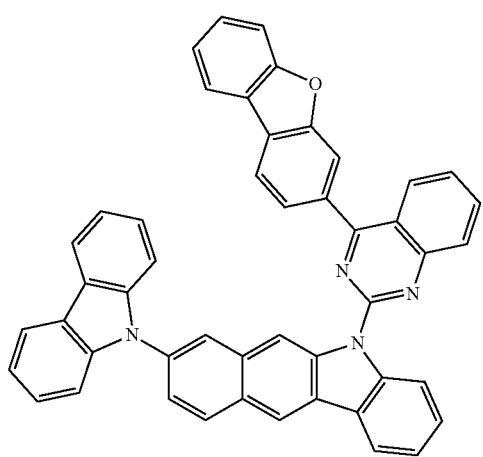
549
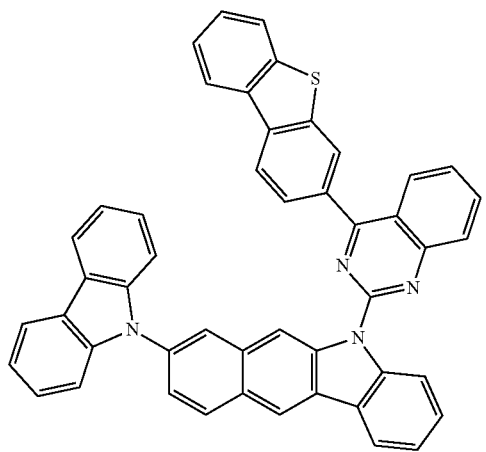
550
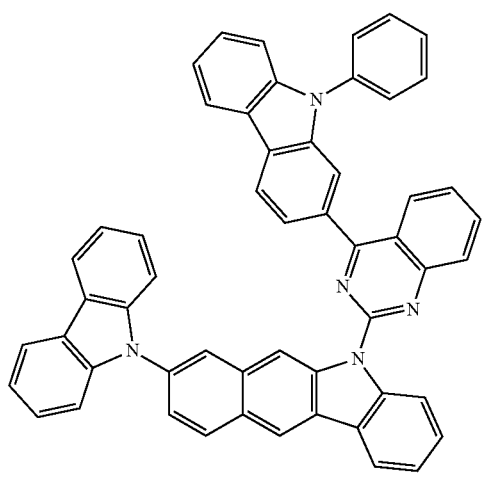
551
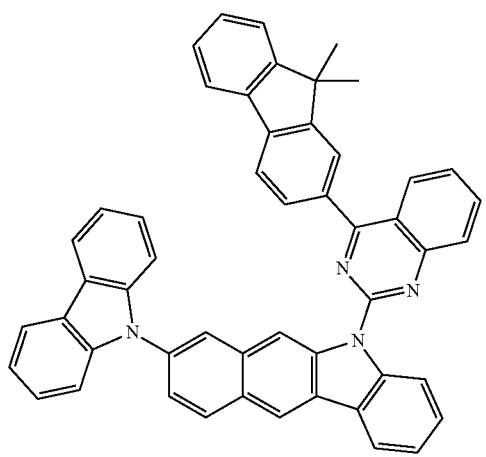

552
553
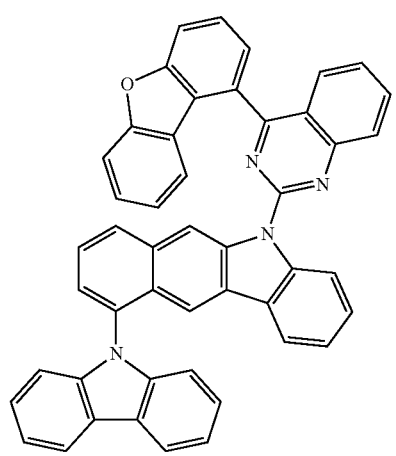
554
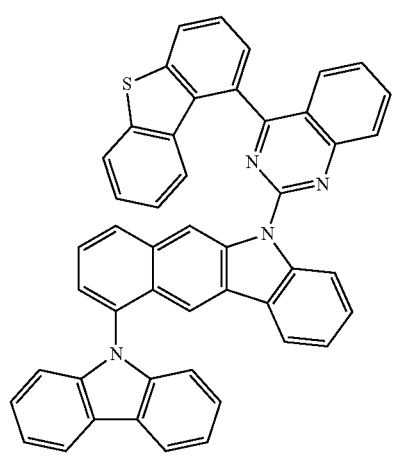
555
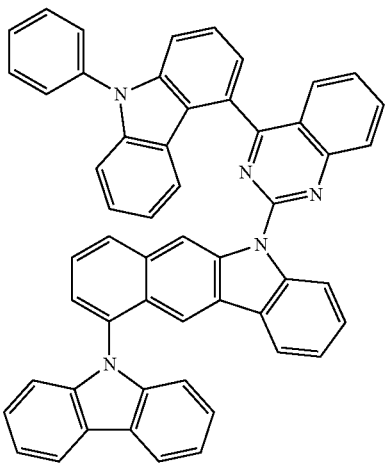
556
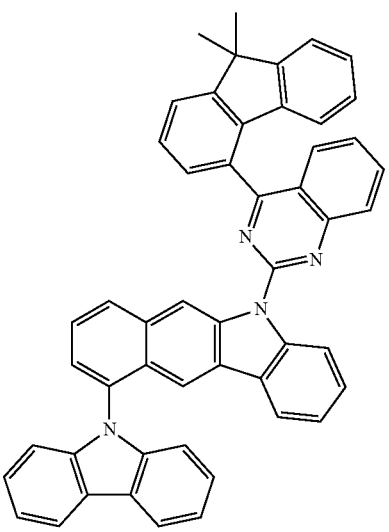
557
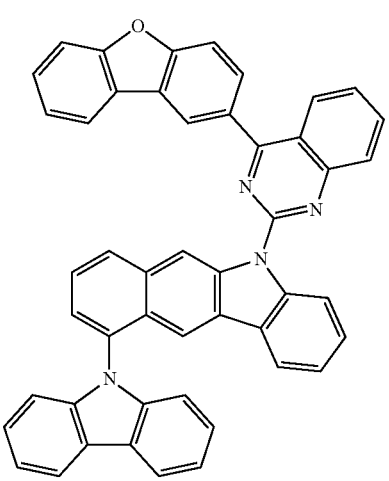

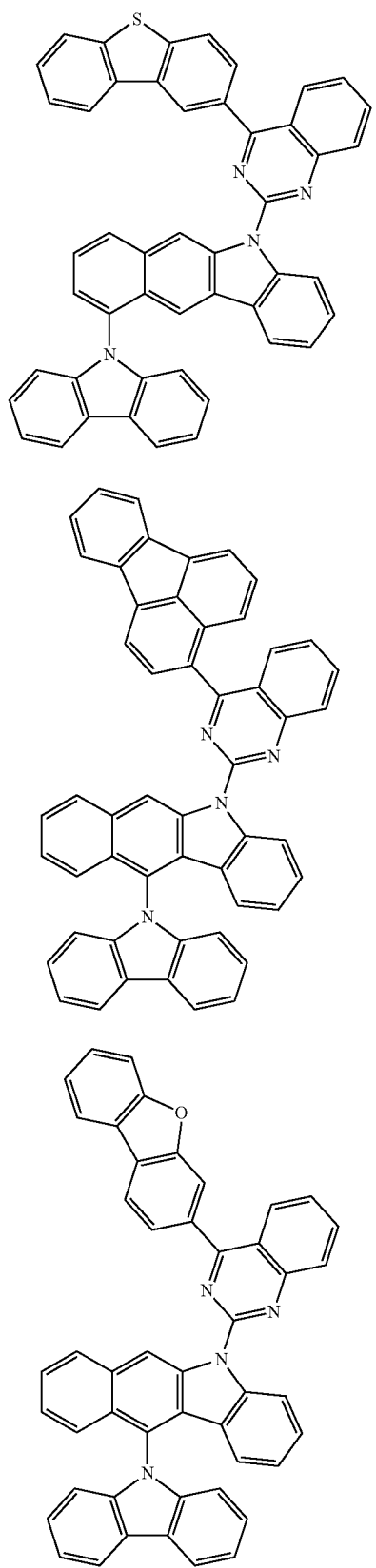

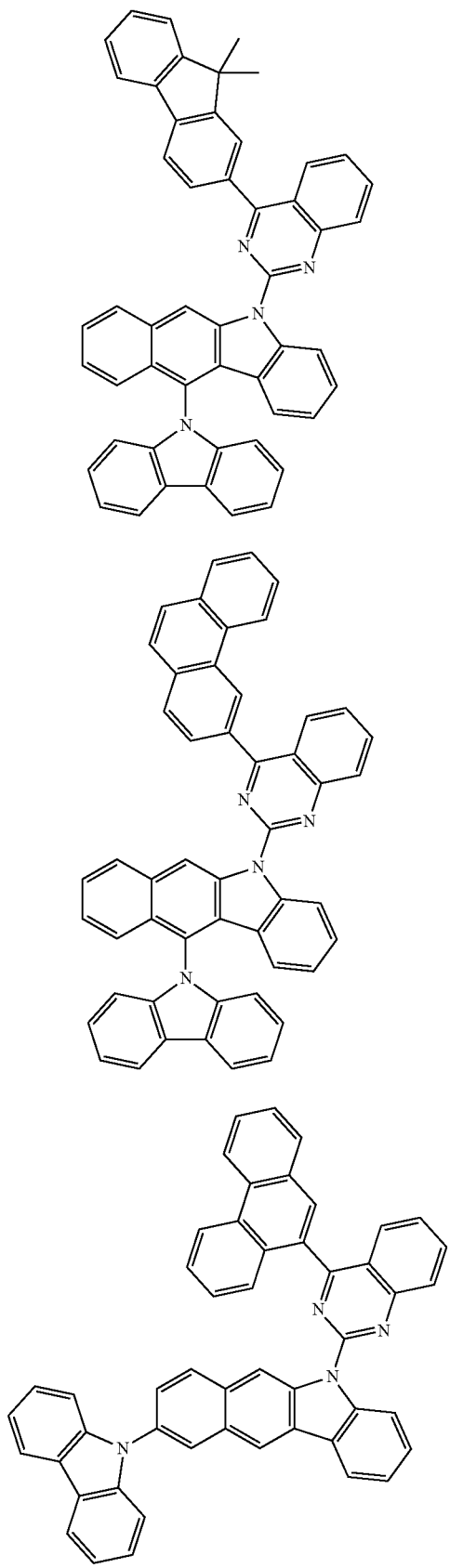
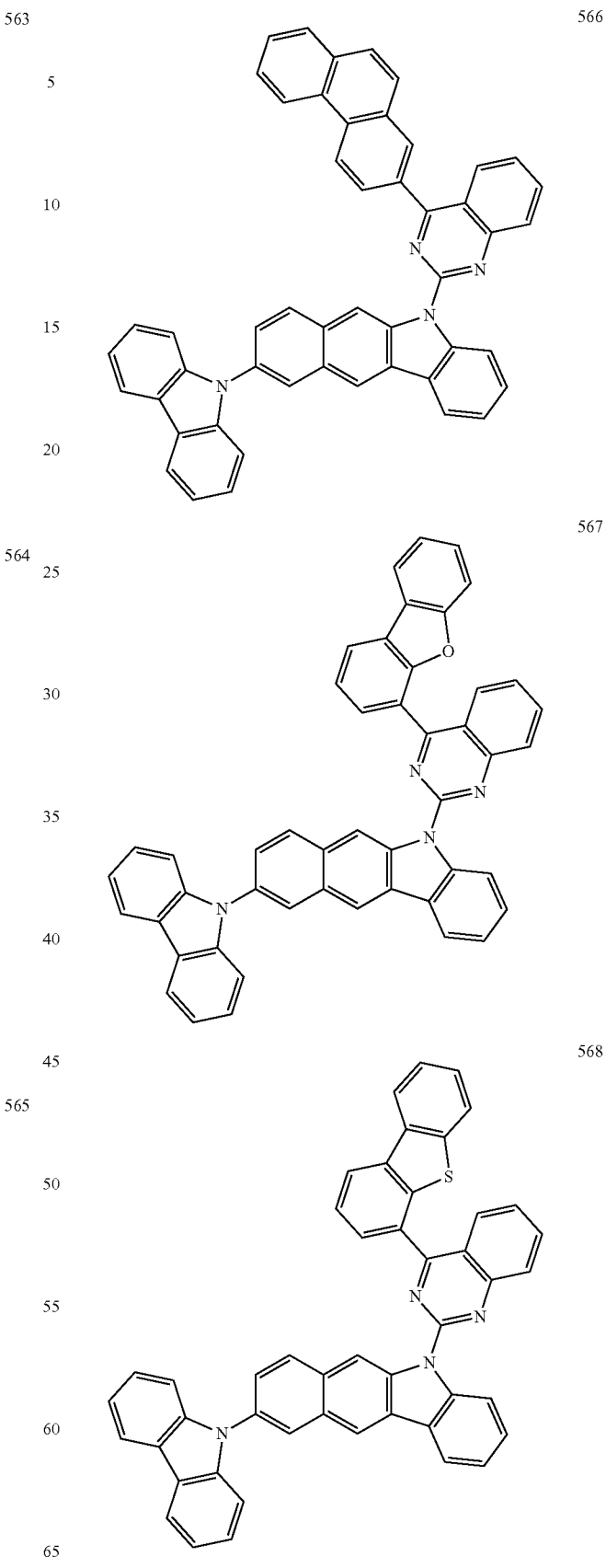

-continued
569
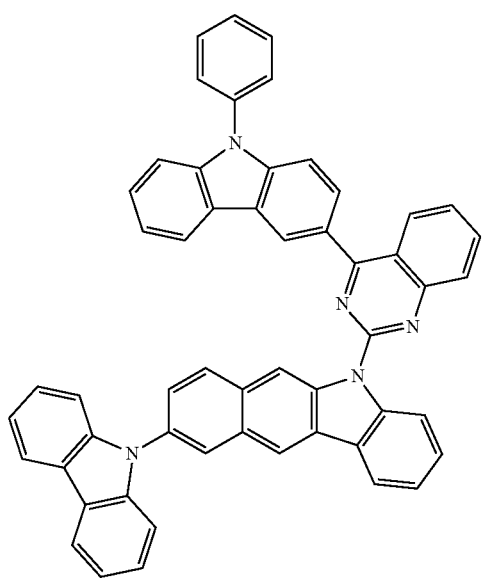
570
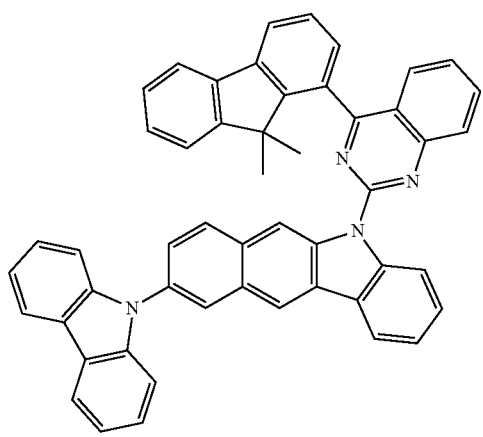
571
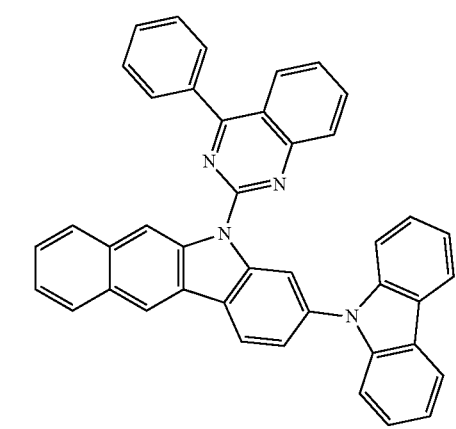
-continued
572
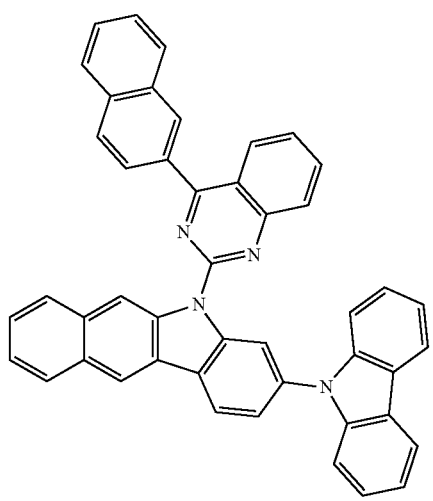
573
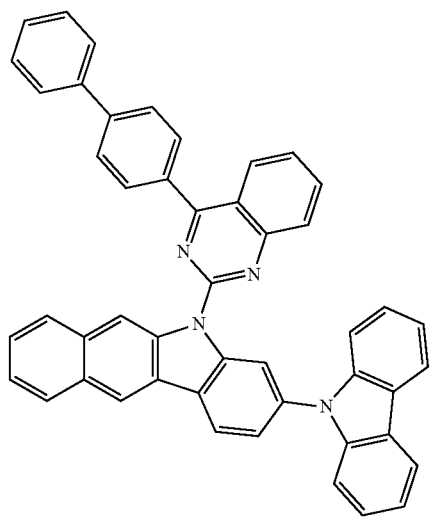
574
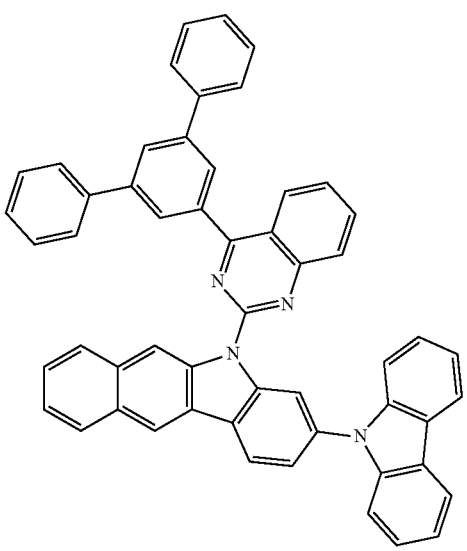

575 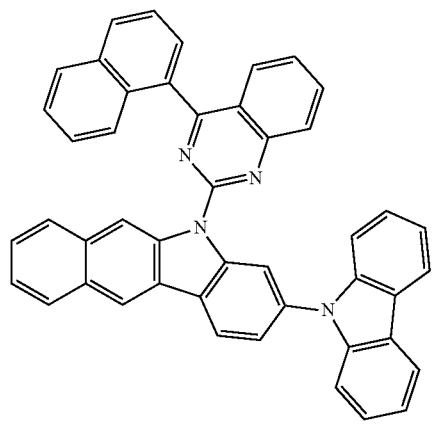
578 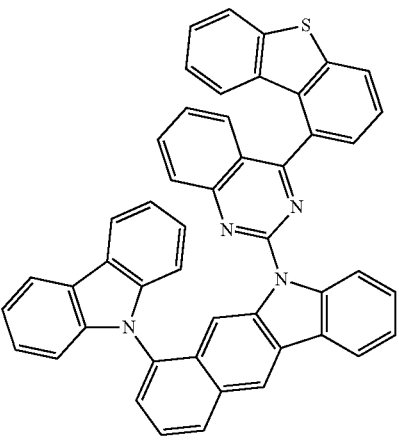
576 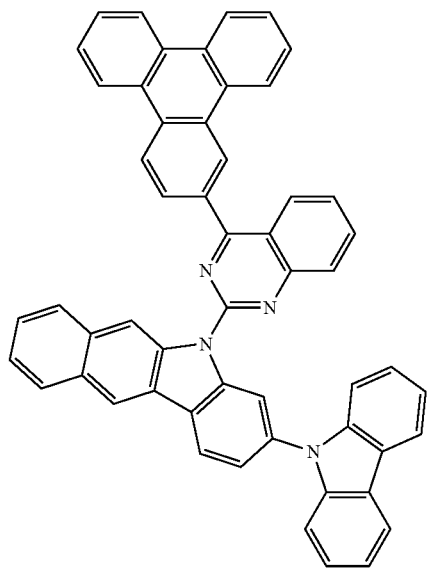
579 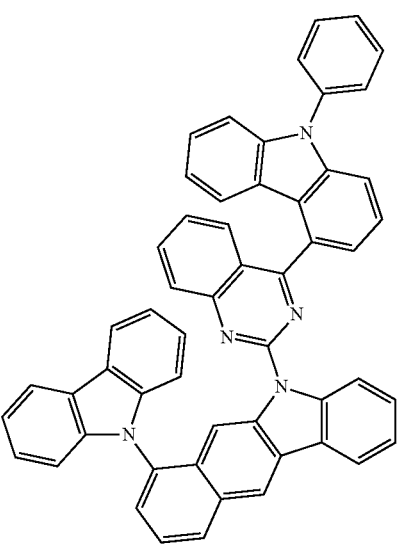
577 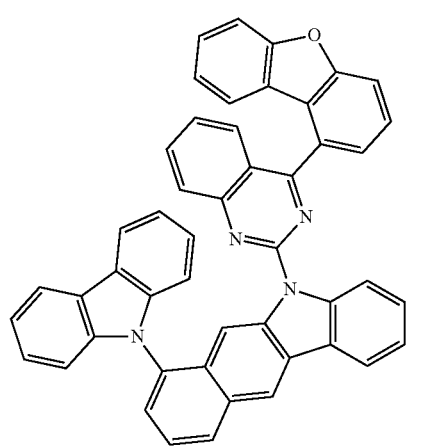
580 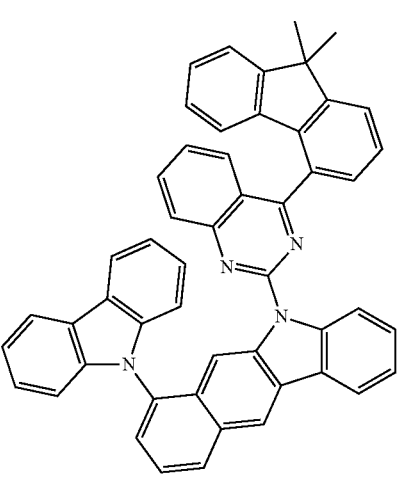

581
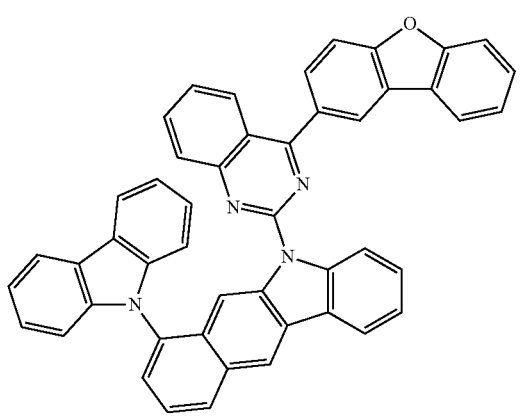
582
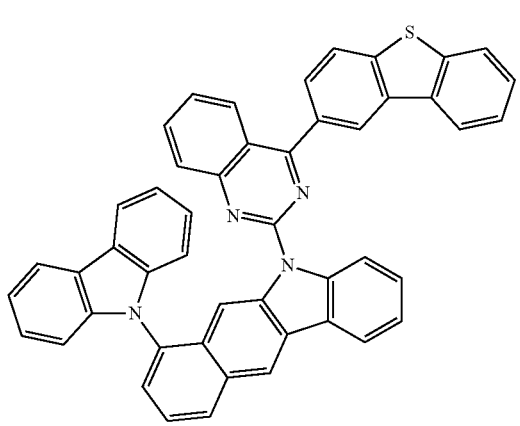
583
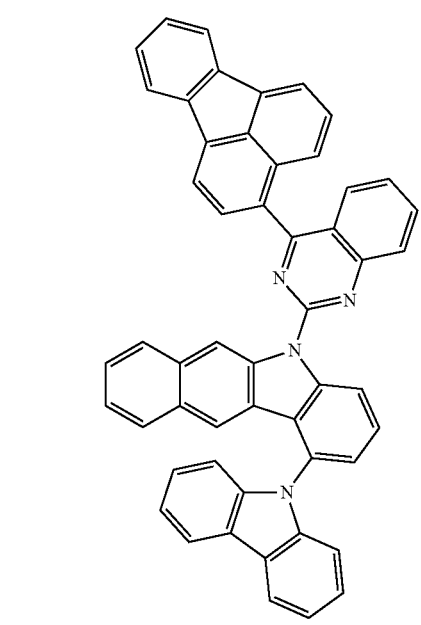
584
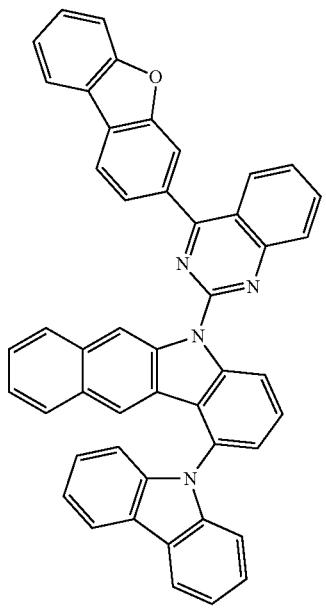
585
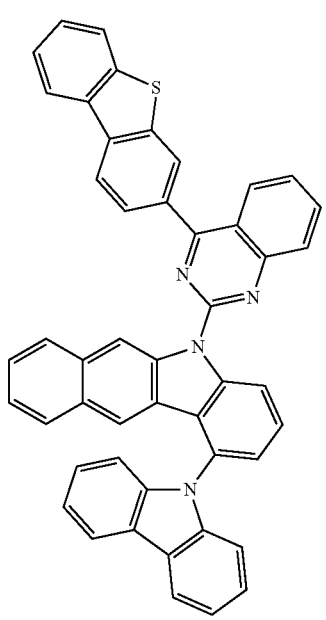

259
-continued
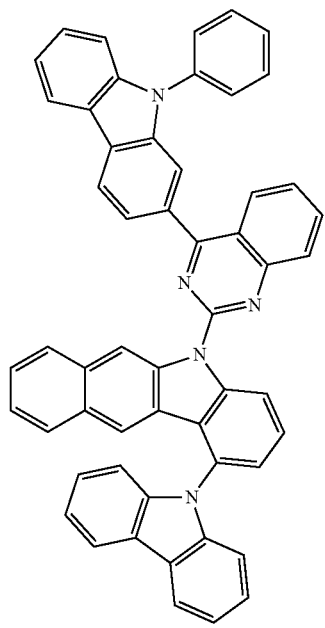
586
260
-continued
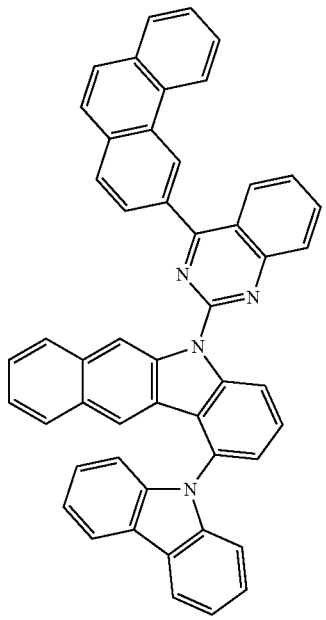
588
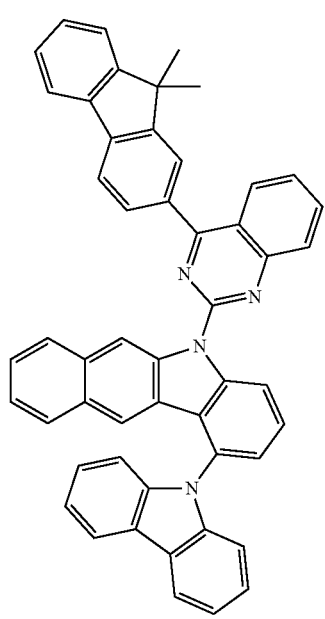
587
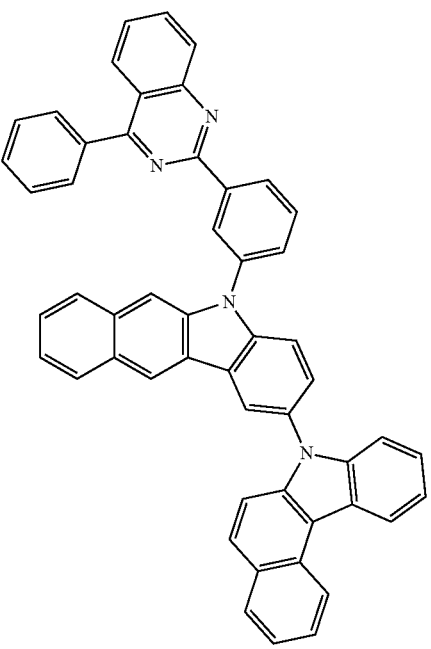
589

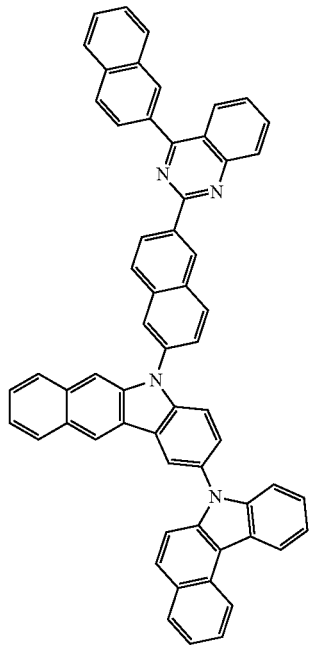
590
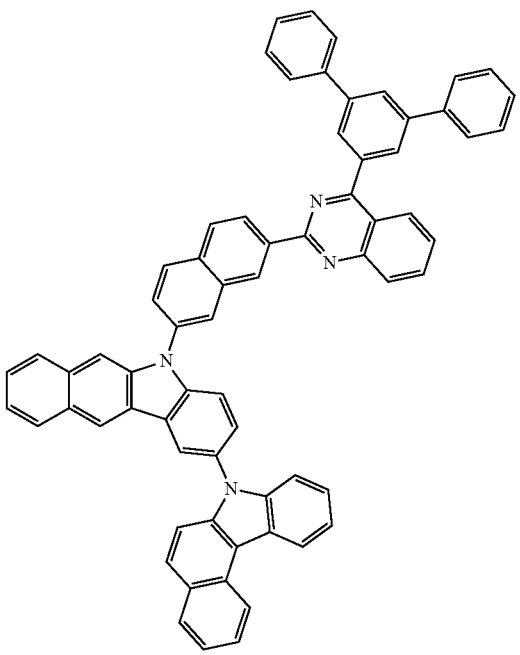
592
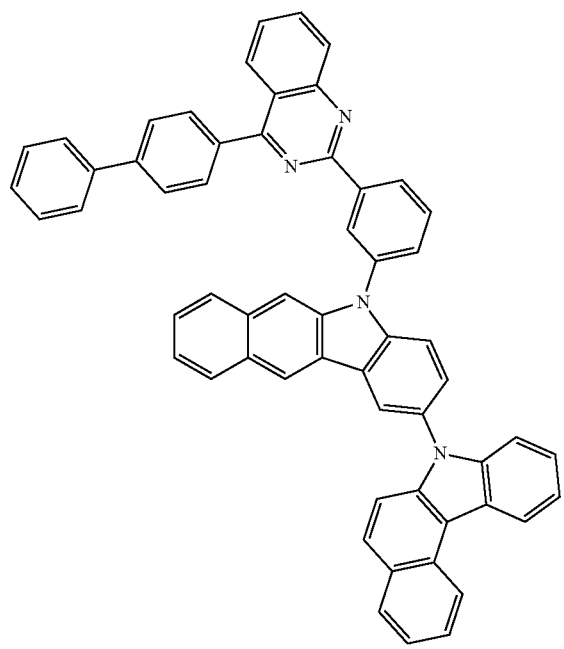
591
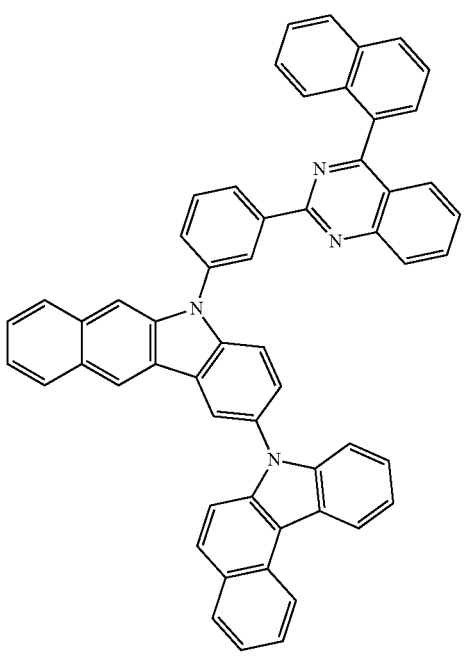
593

-continued
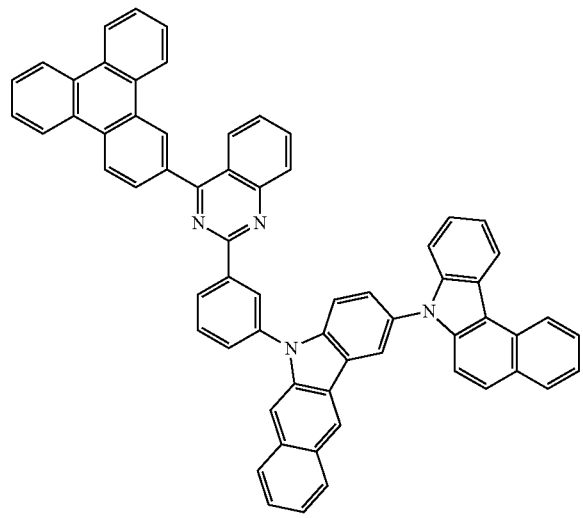
594
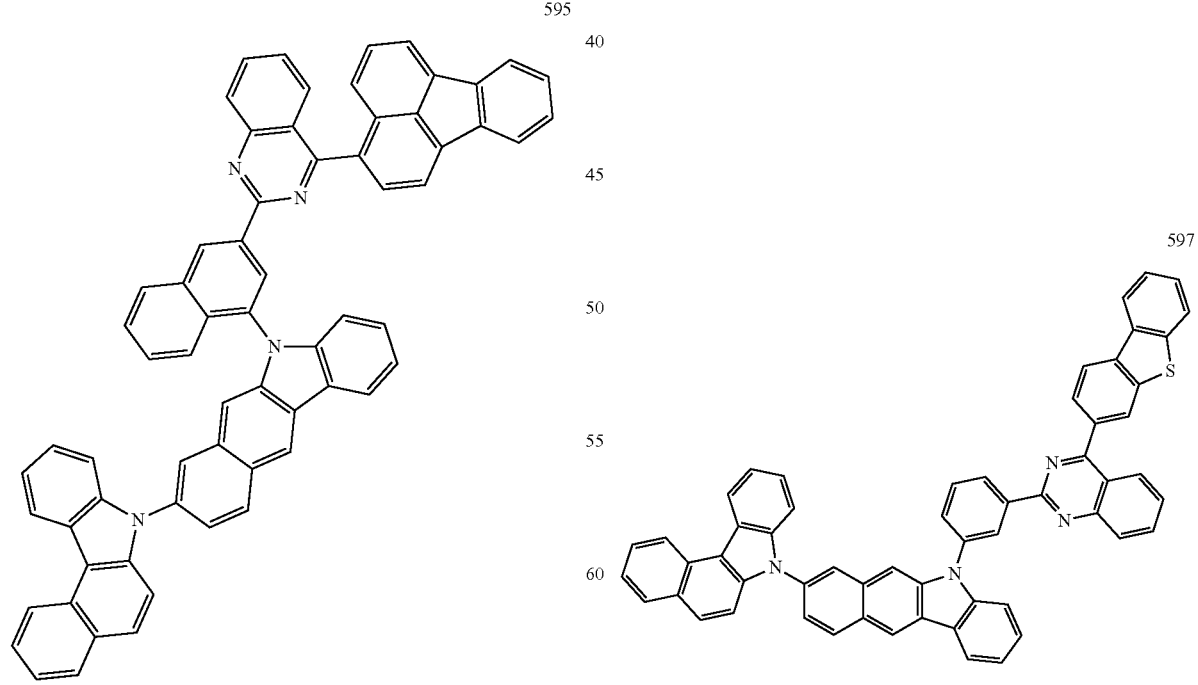
595
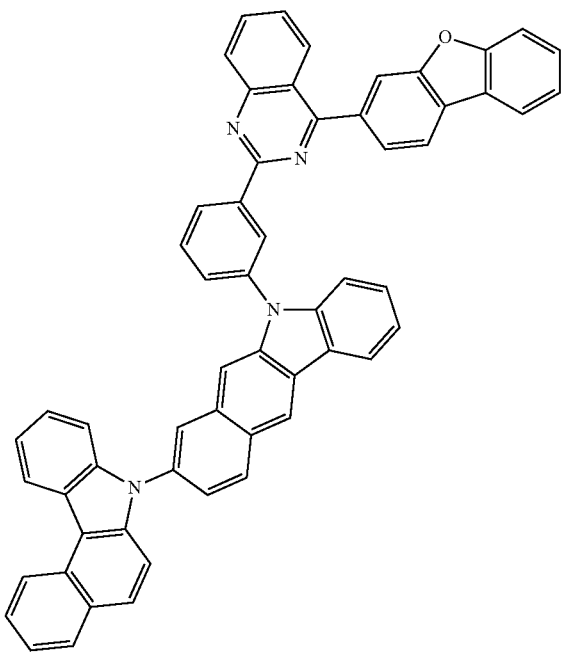
596
597

598
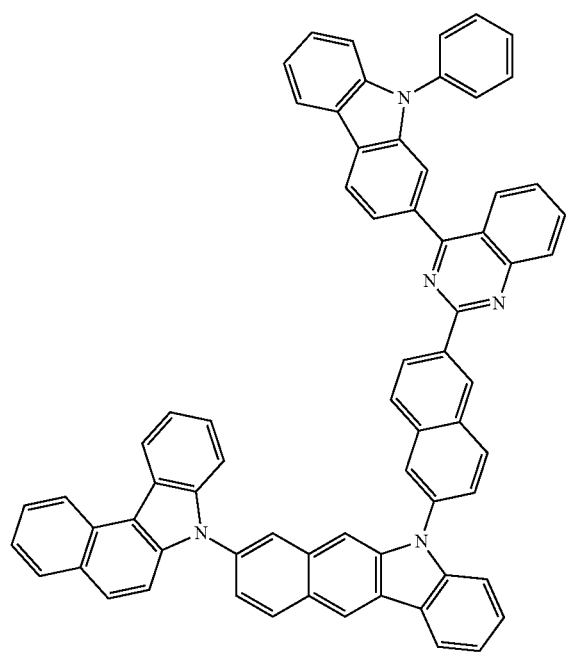
599
600
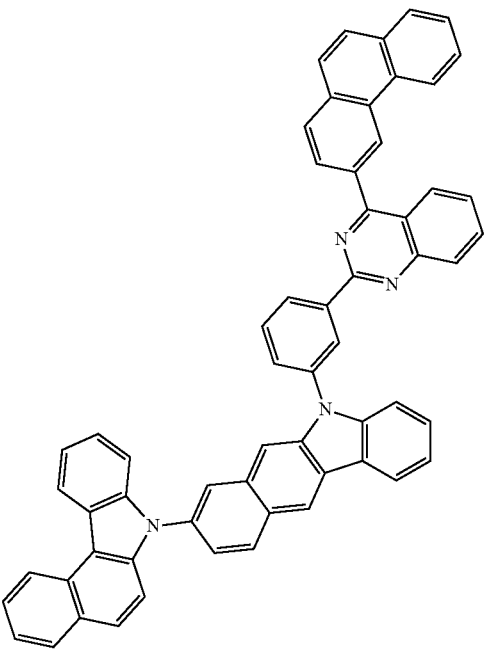
601
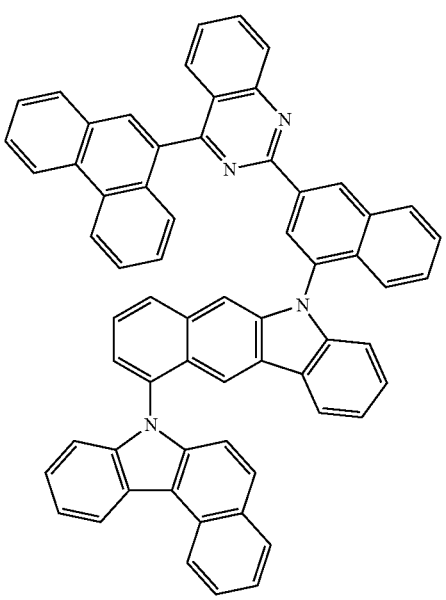

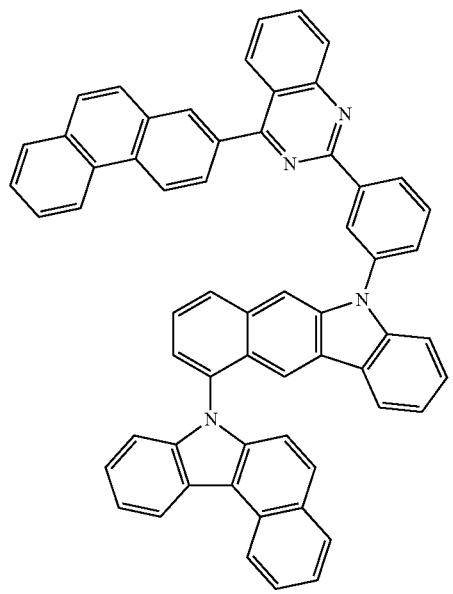
602
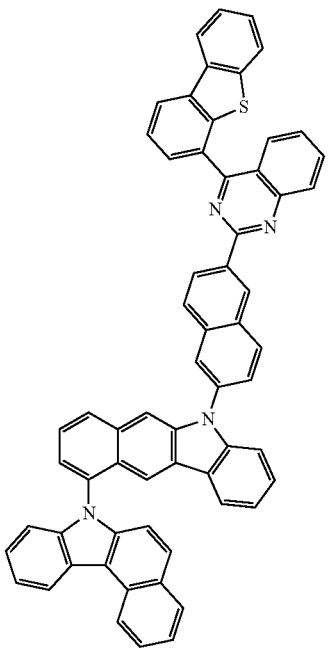
604
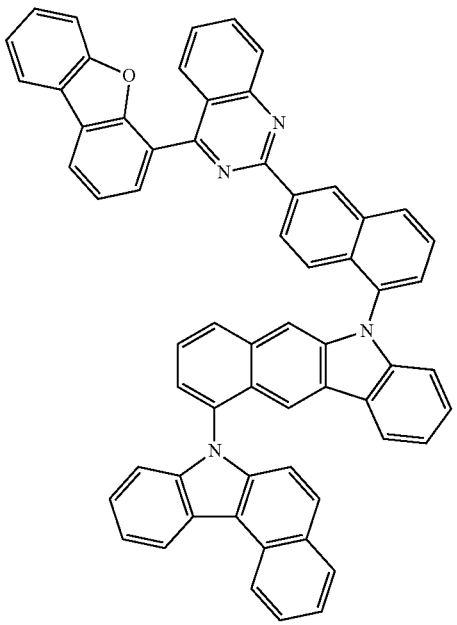
603
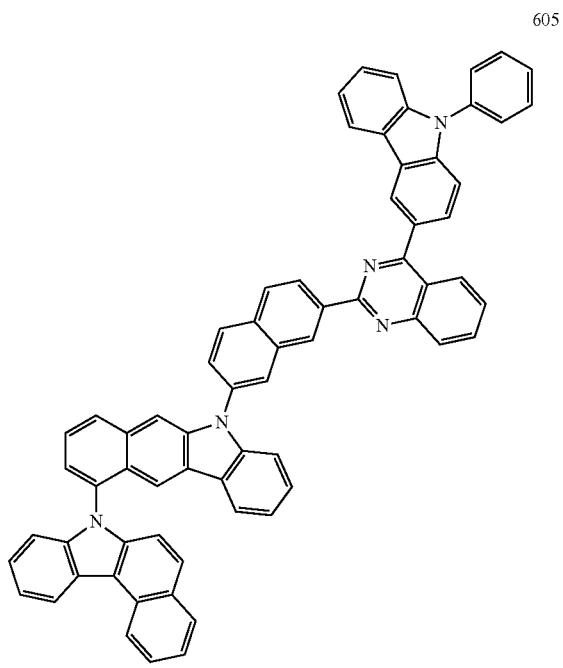
605

-continued
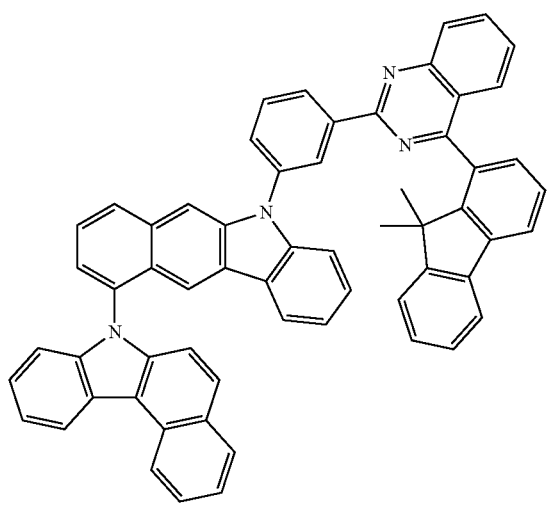
606
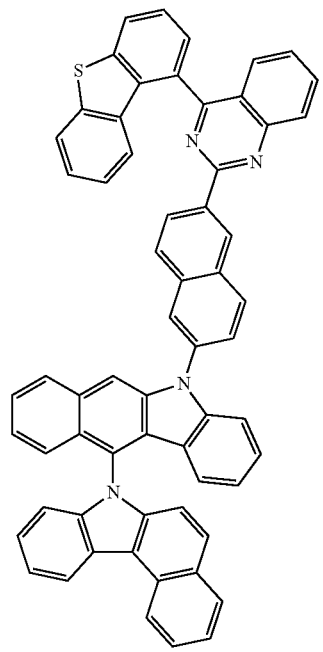
608
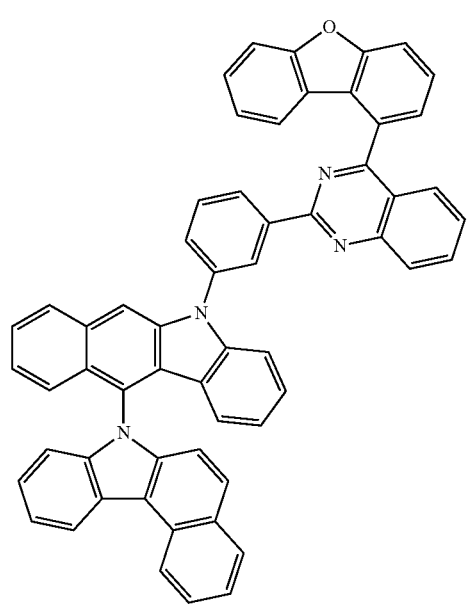
607
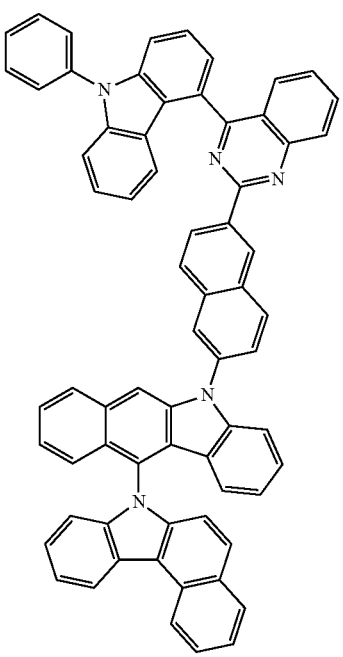
609

271
-continued
610
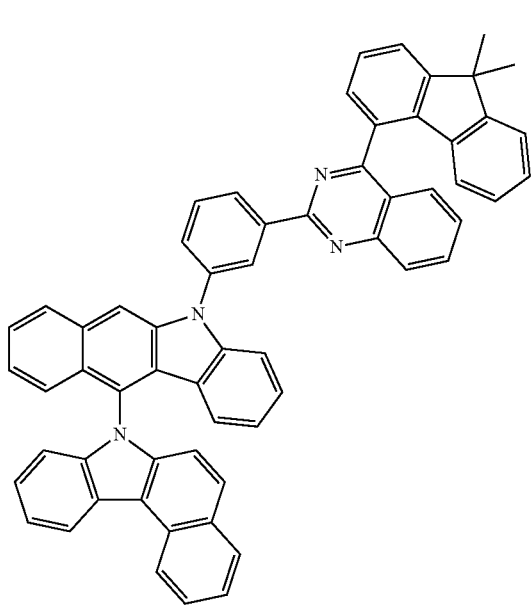
611
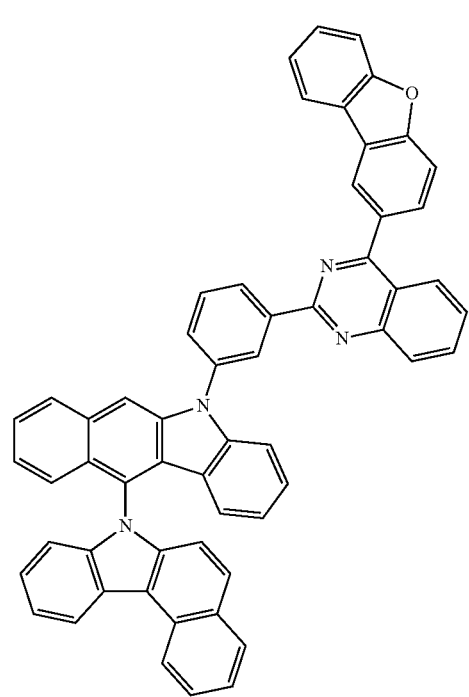
272
-continued
612
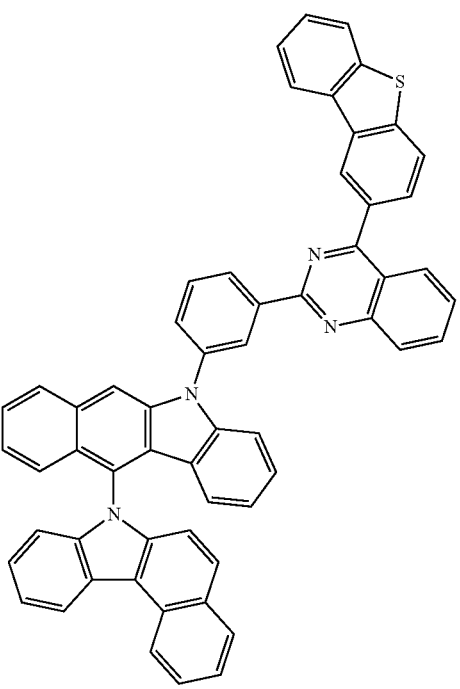
613
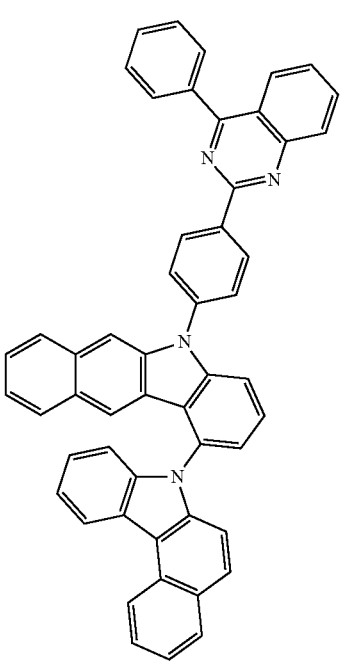

614
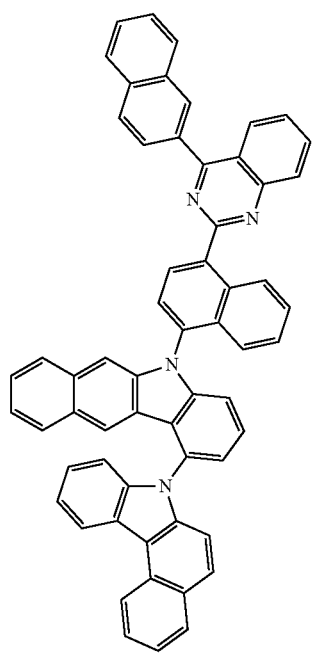
615
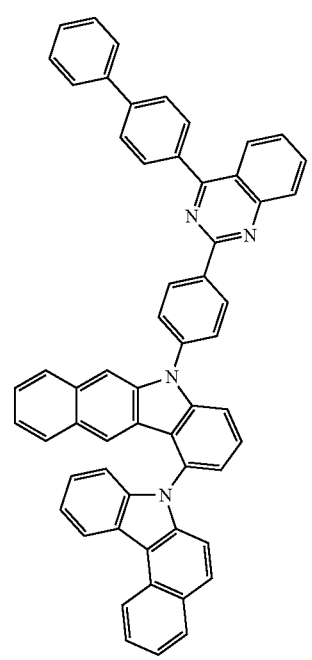
616
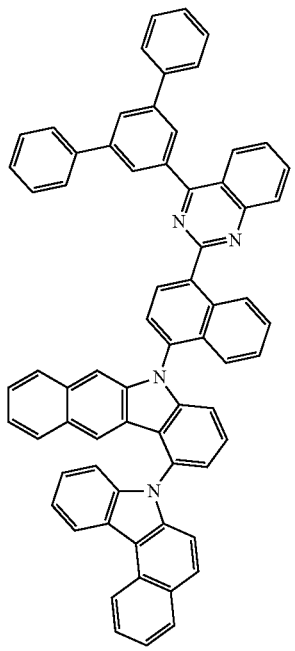
617
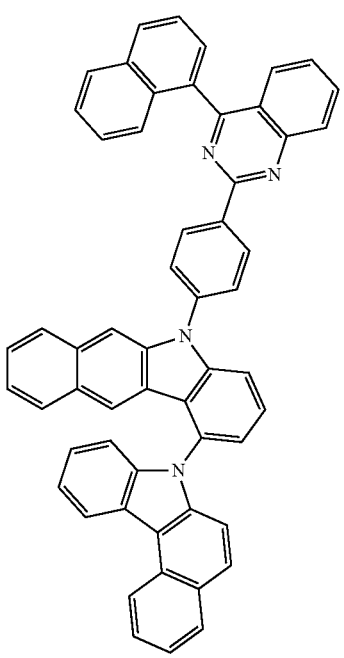

-continued
618
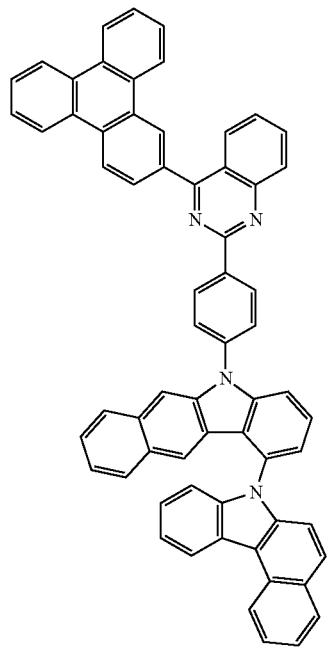
619
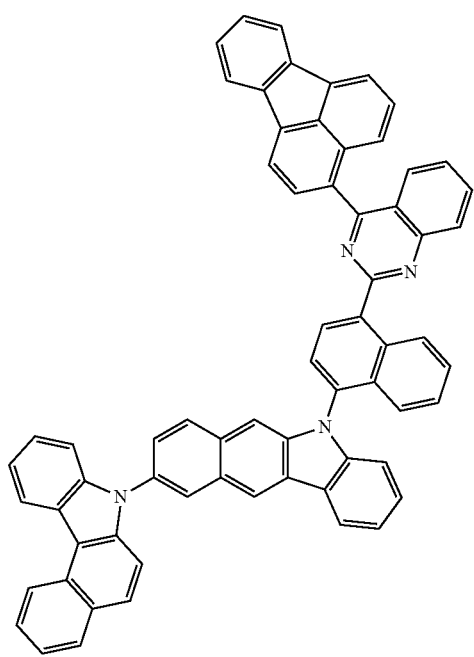
-continued
620
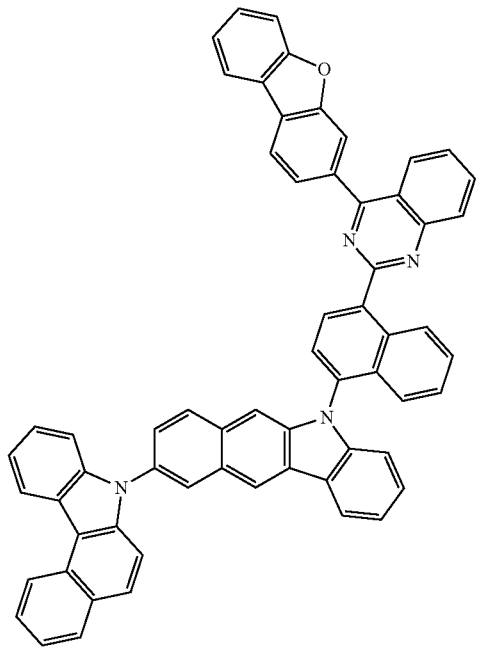
621
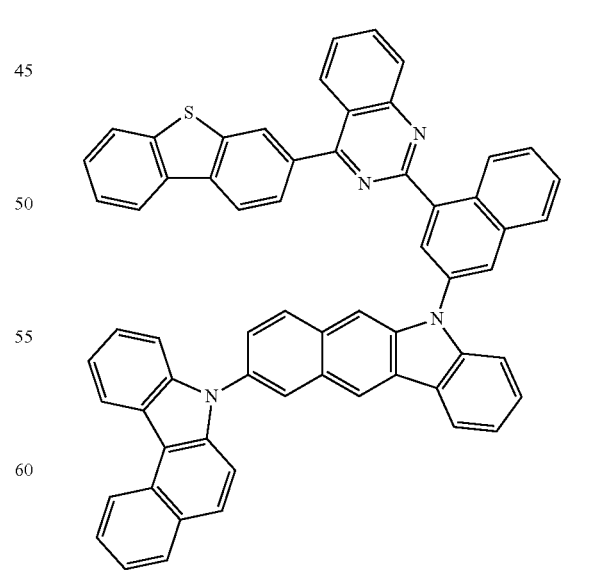

277
-continued
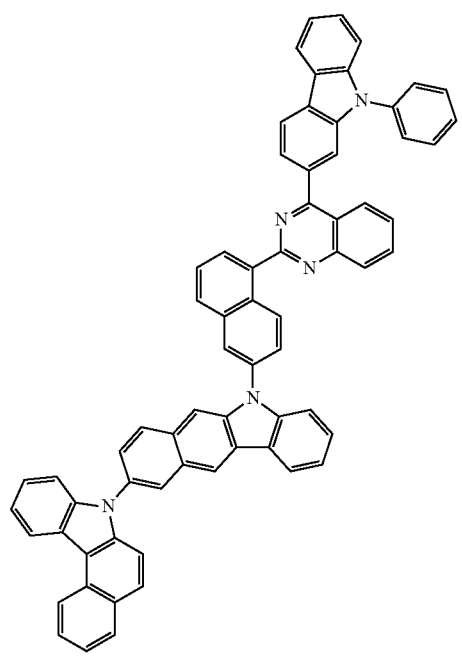
622
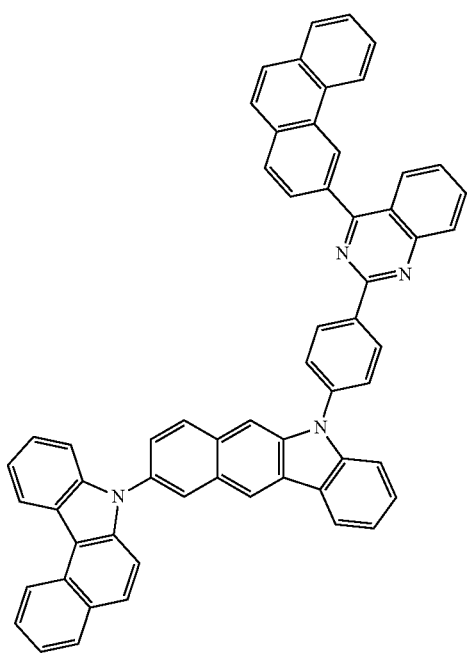
624
623
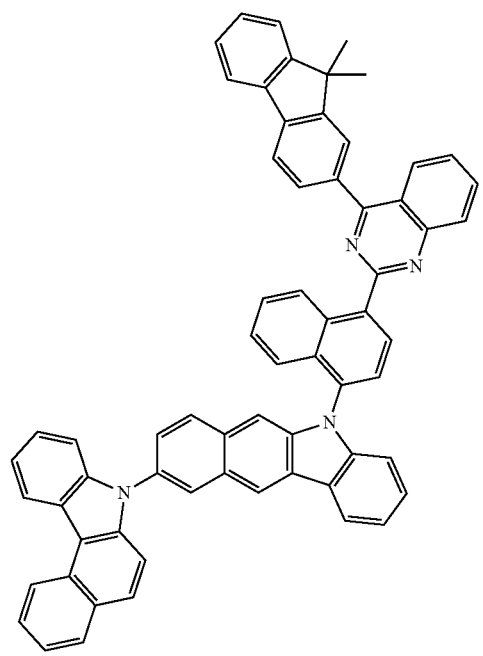
278
-continued
625
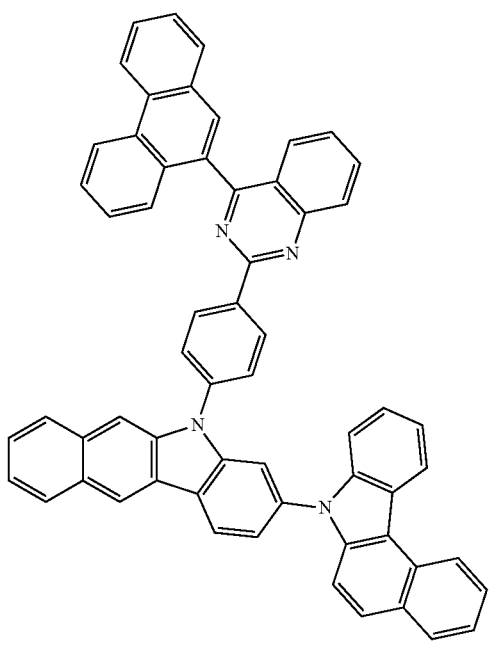

626
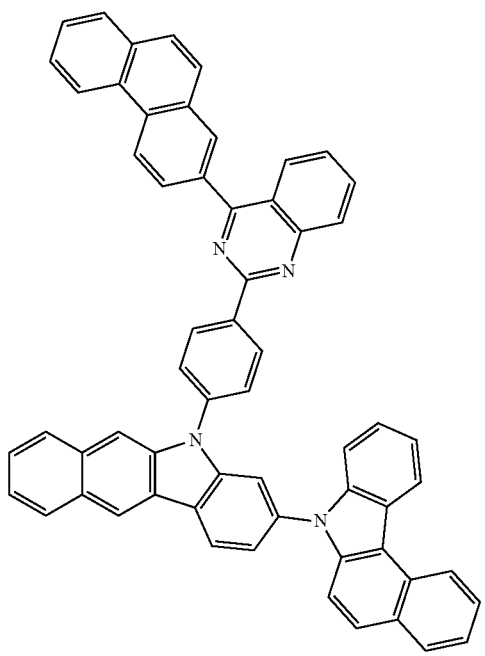
627
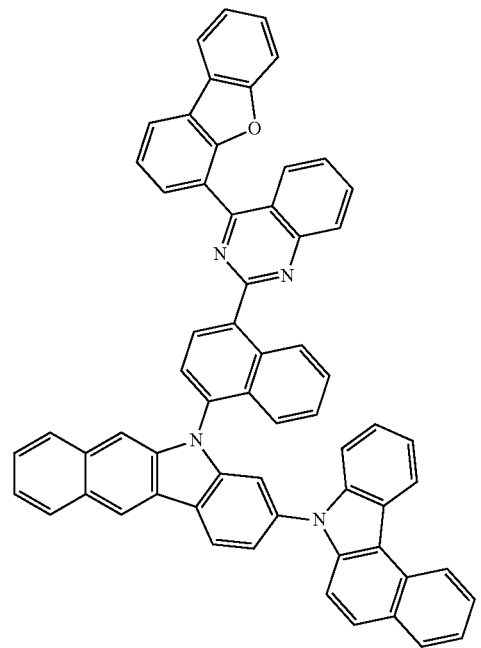
628
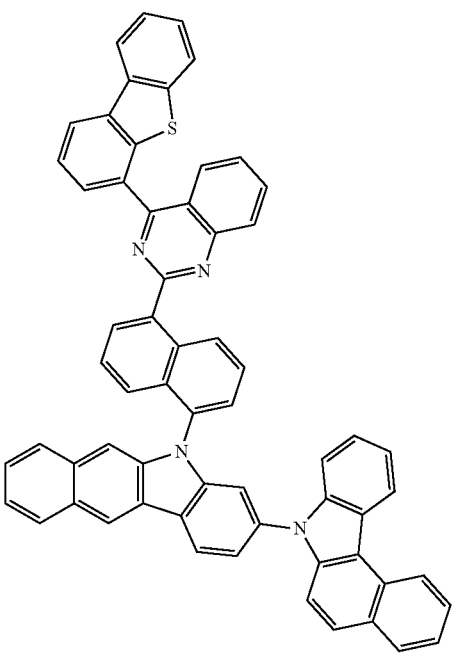
629
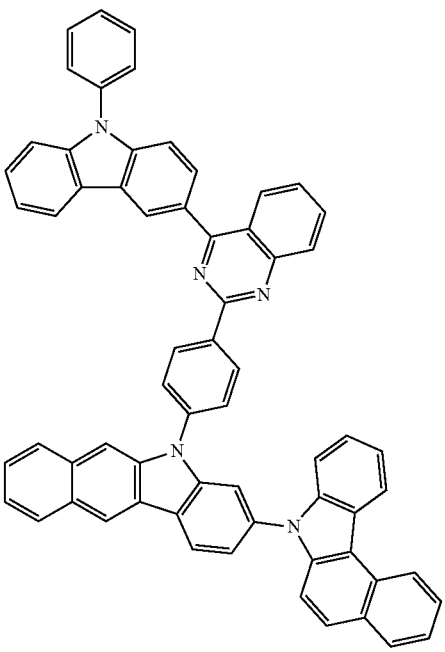

281
-continued
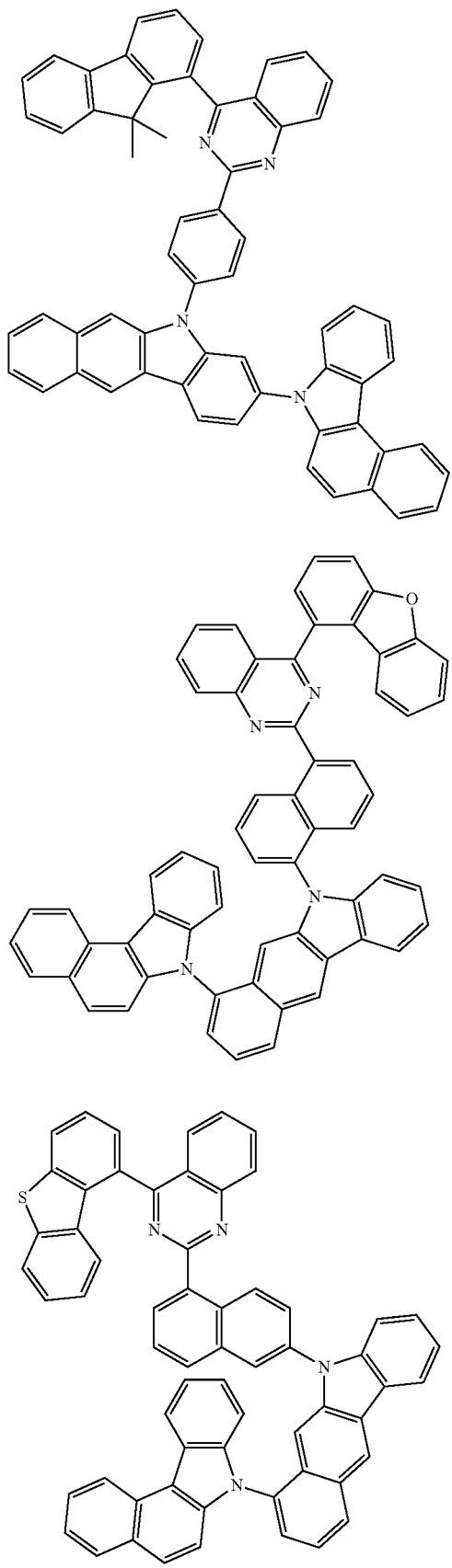
282
-continued
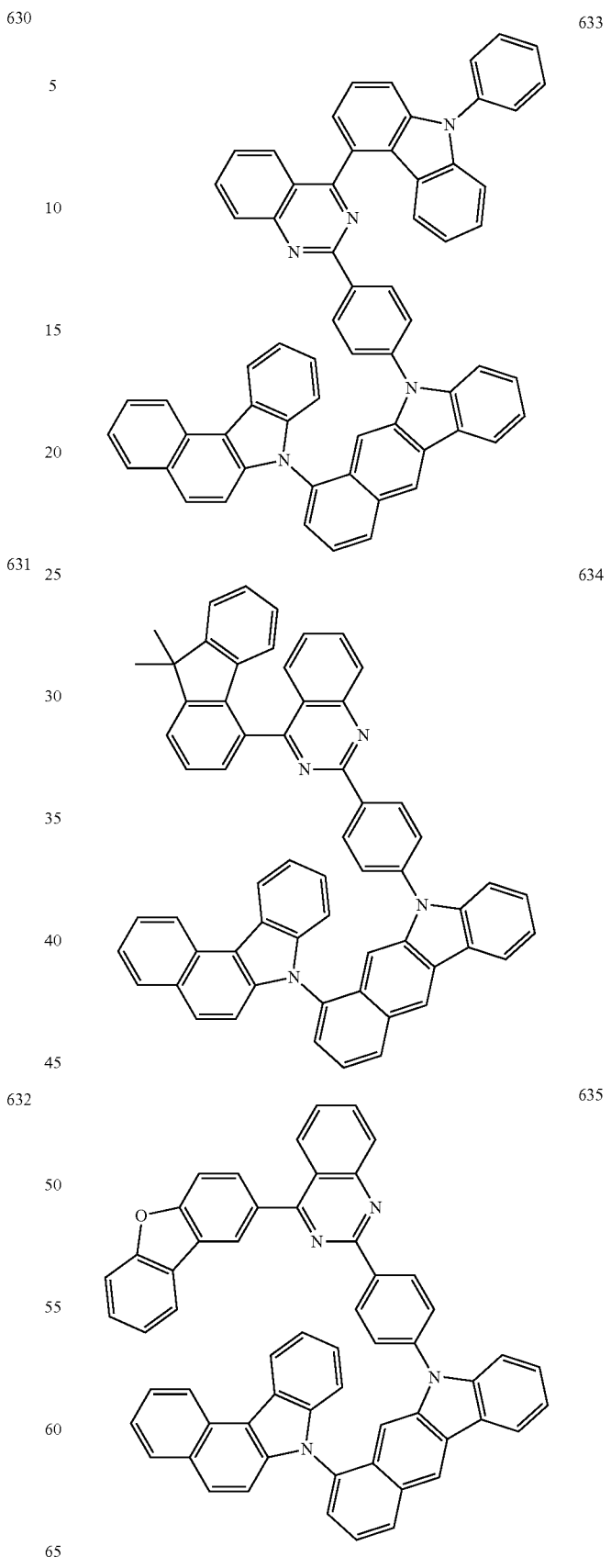

636
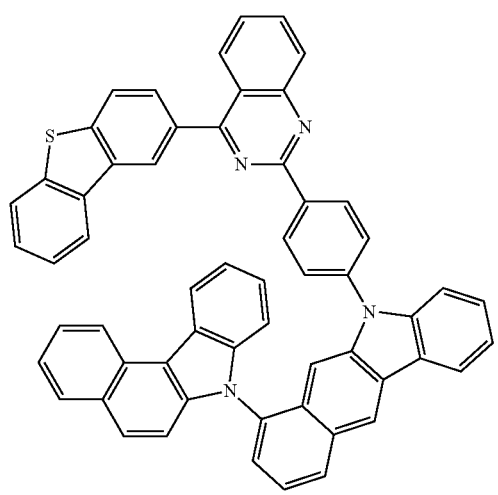
637
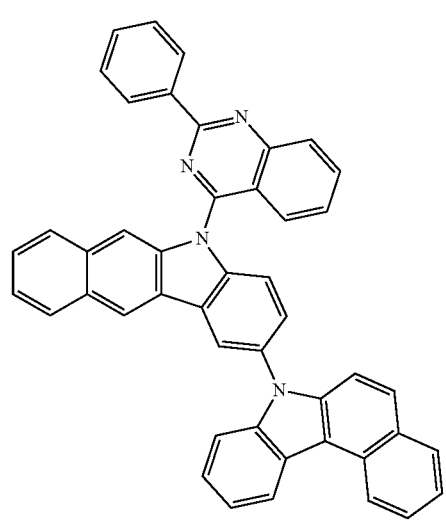
638
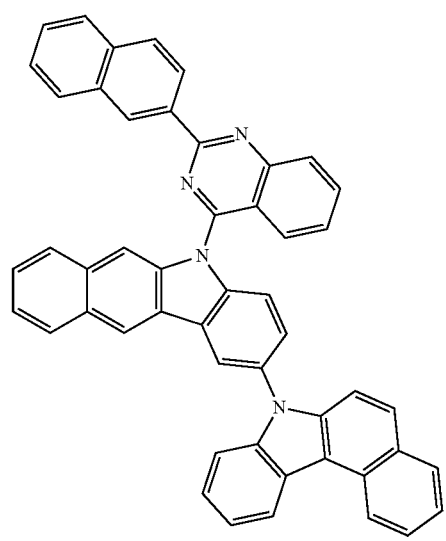
639
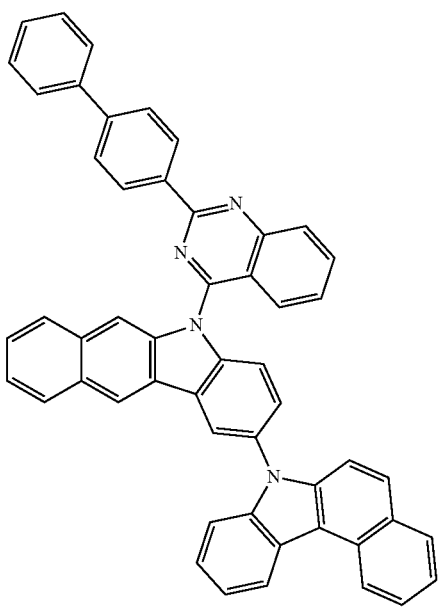
640
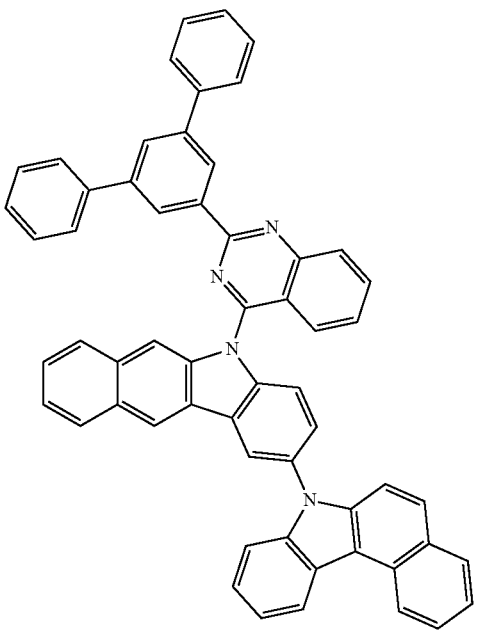

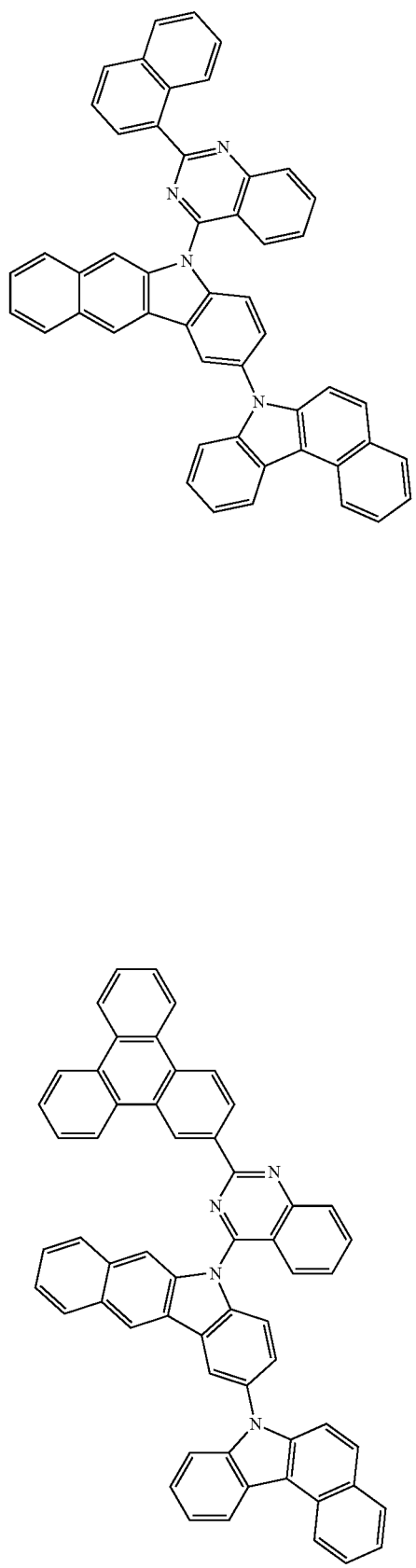
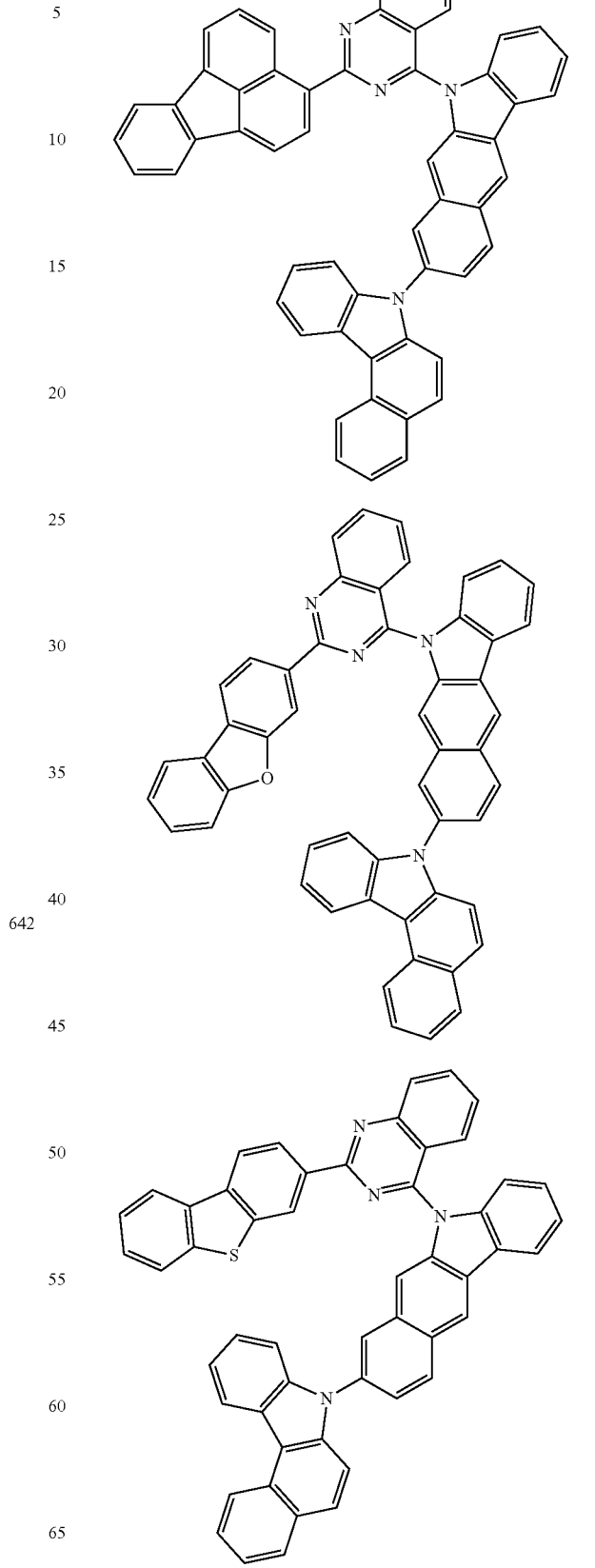

287
-continued
646
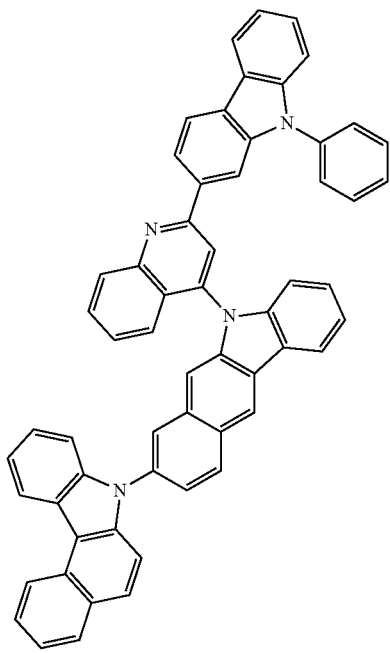
647
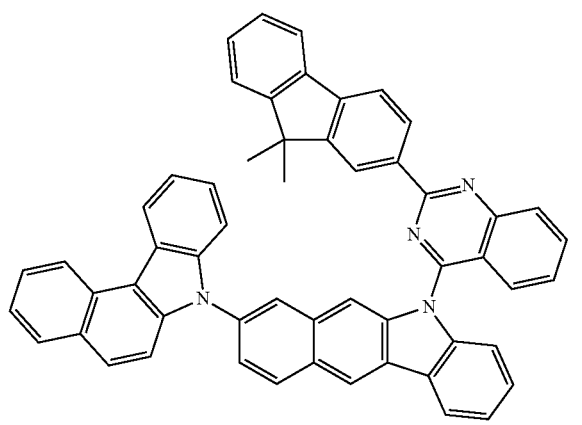
648
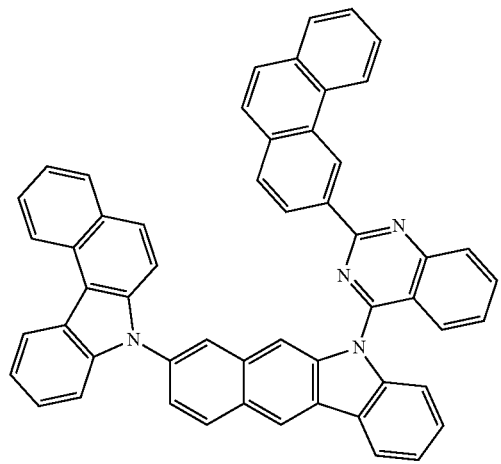
288
-continued
649
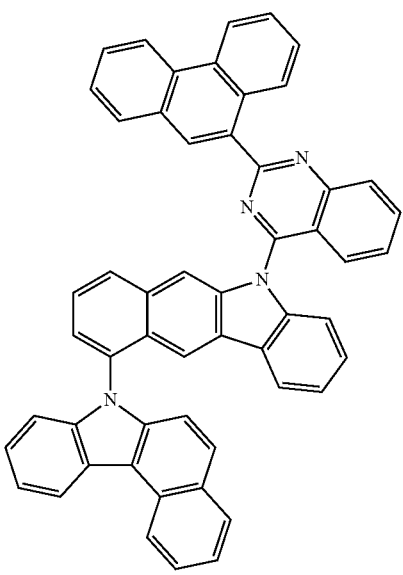
650
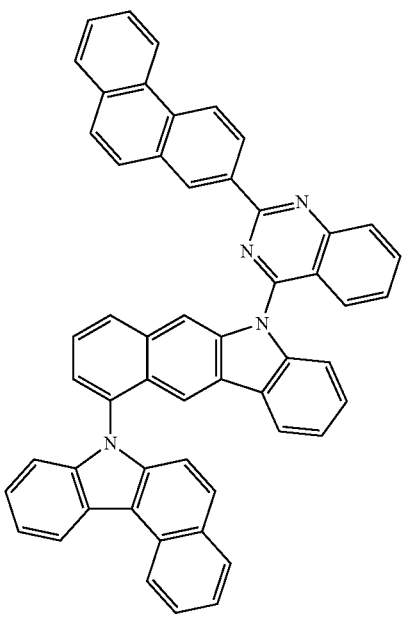

289
-continued
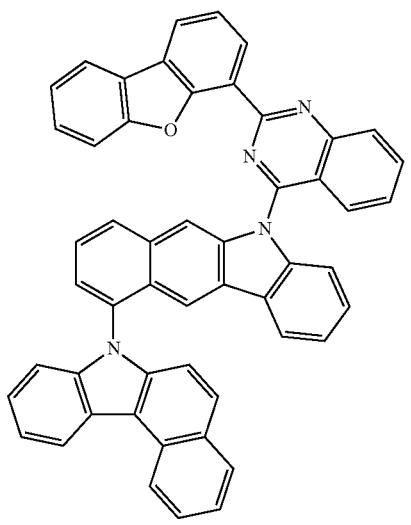
651
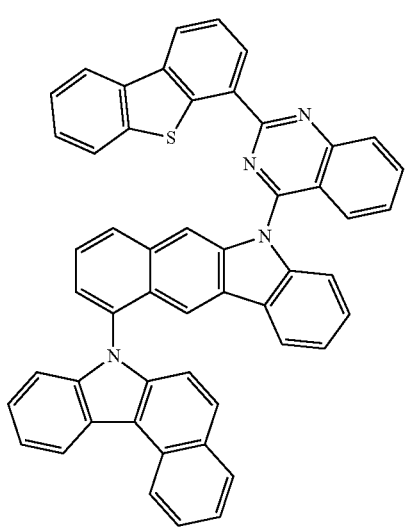
652
290
-continued
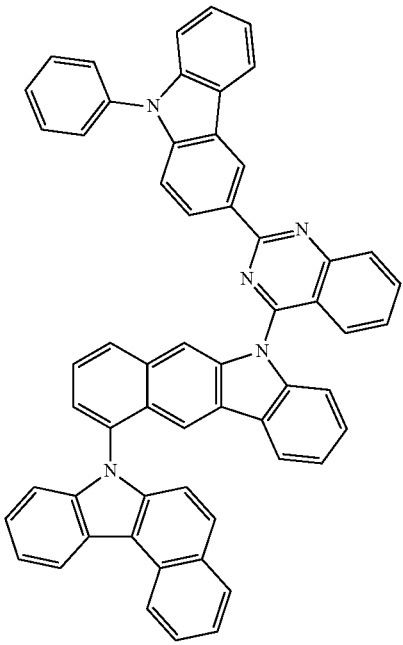
653
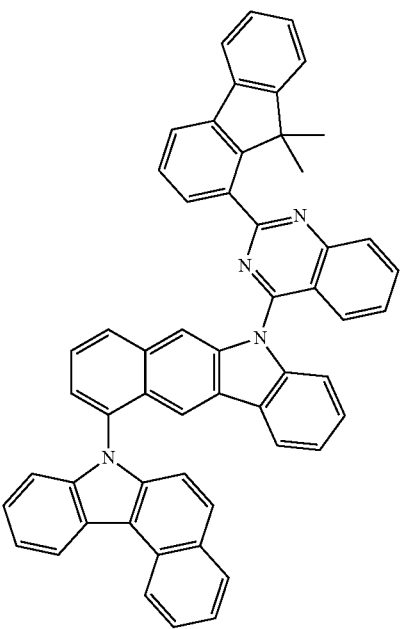
654

291
-continued
655
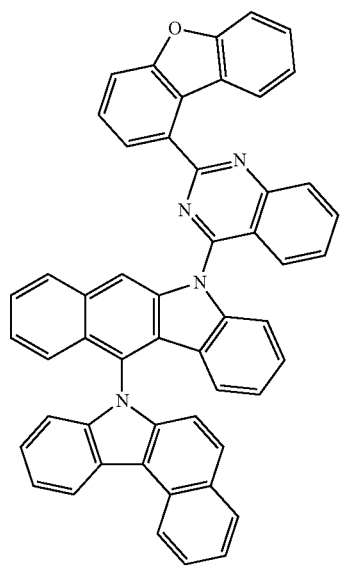
656
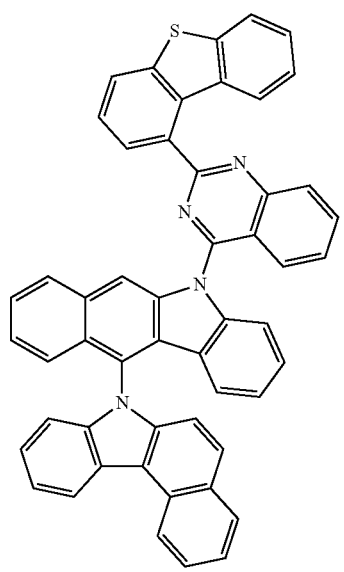
292
-continued
657
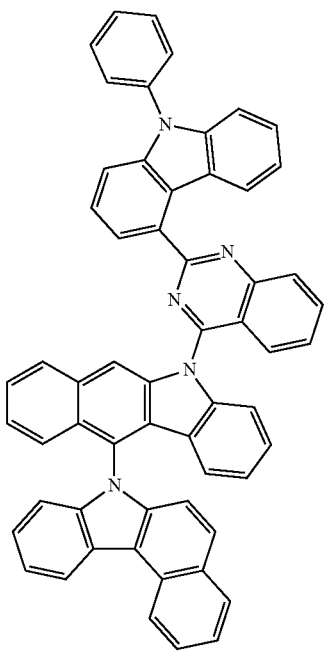
658

293
-continued
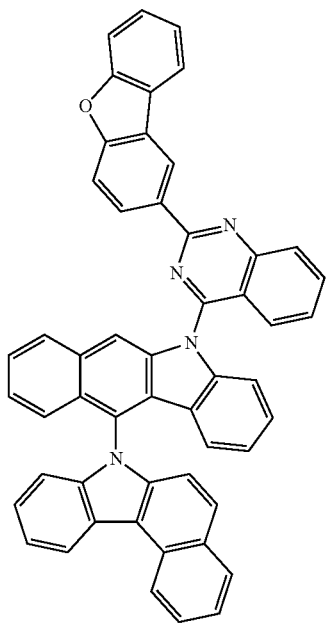
659
294
-continued
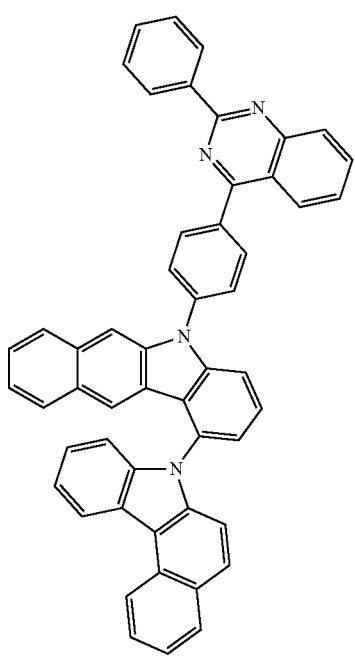
661
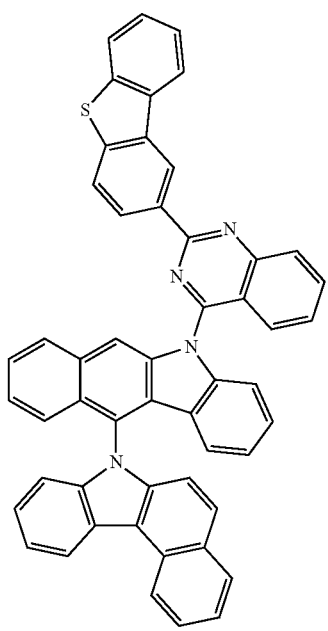
660
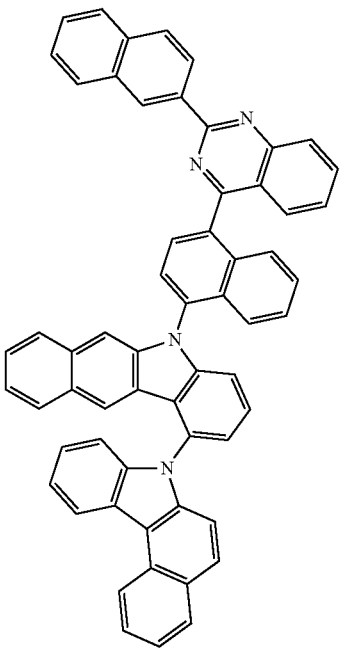
662

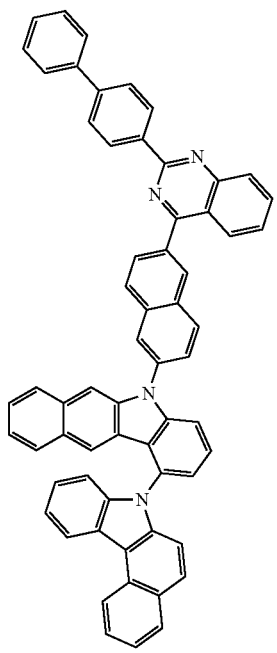
663
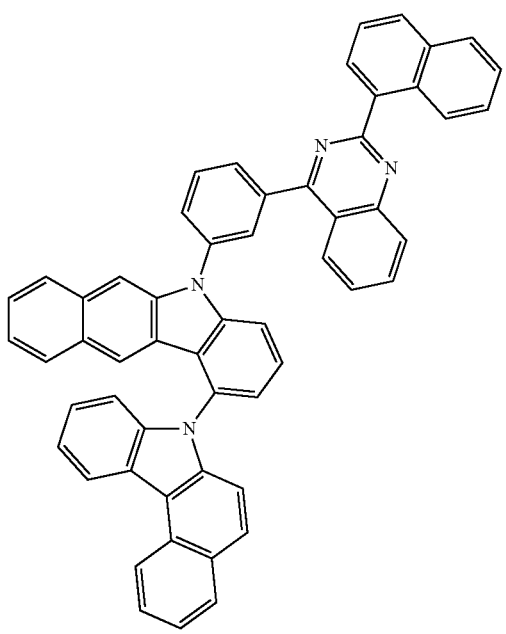
665
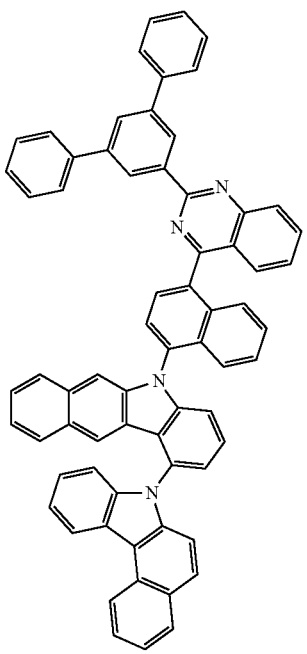
664
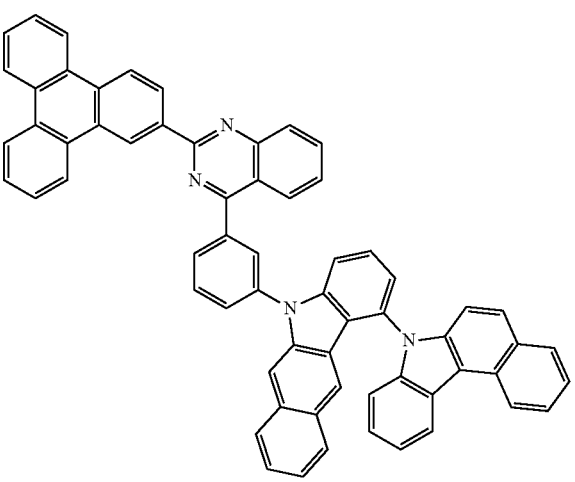
666

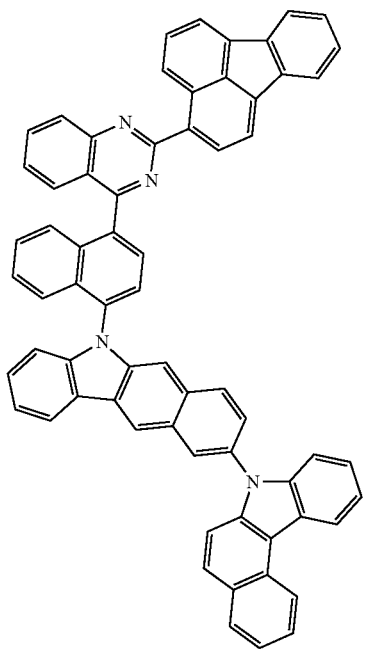
667
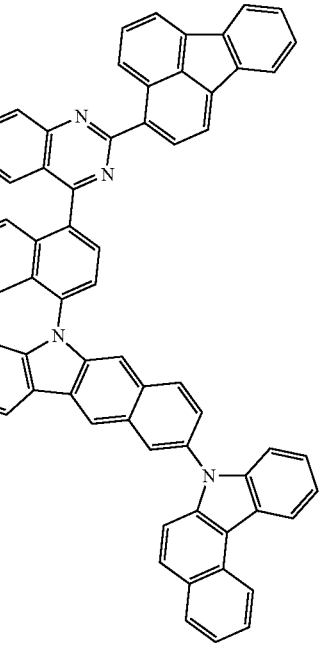
668
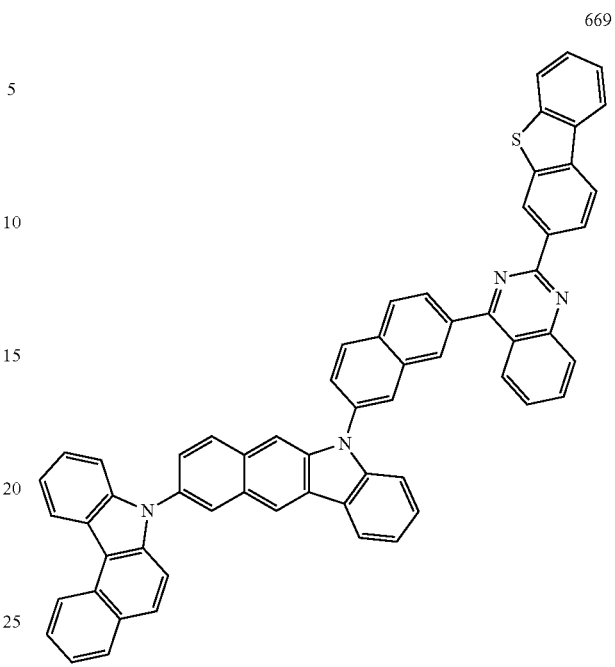
669
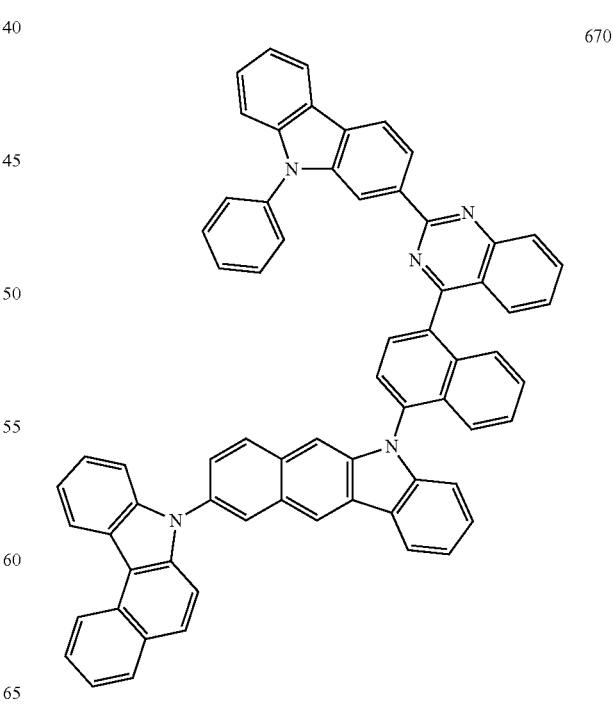
670

299
-continued
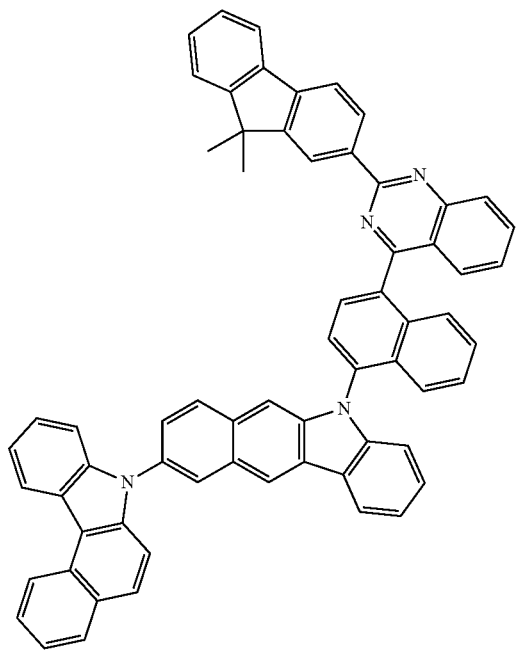
671
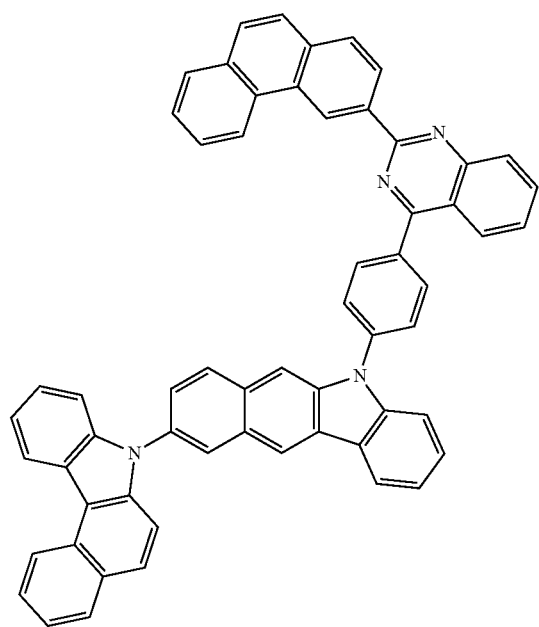
672
300
-continued
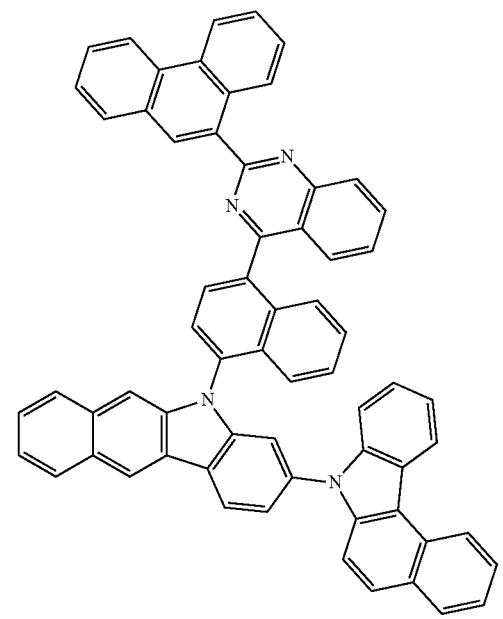
673
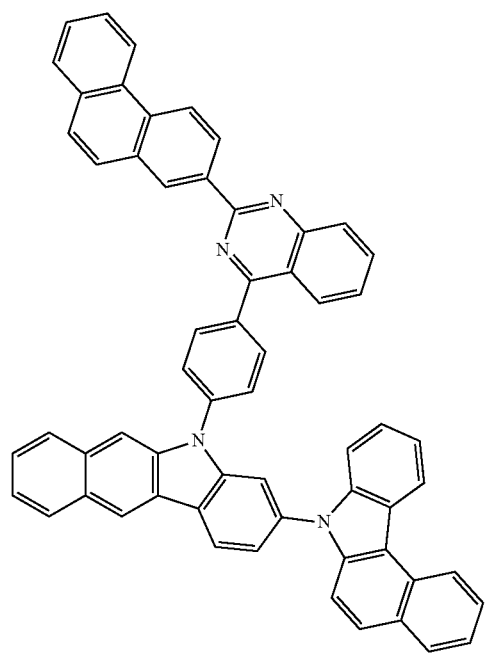
674

301
-continued
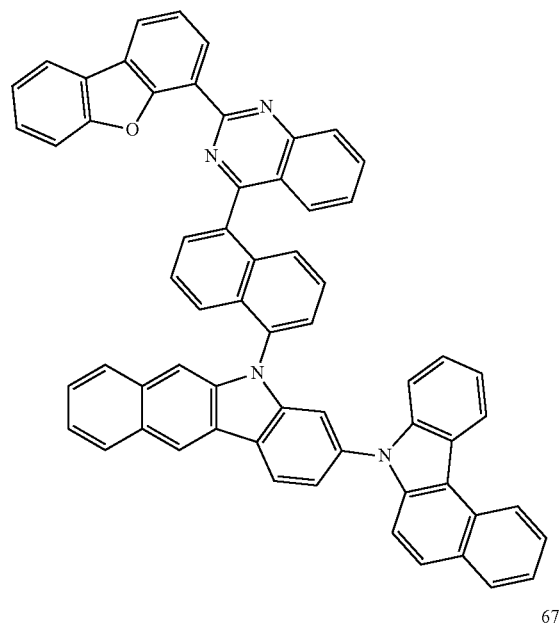
675
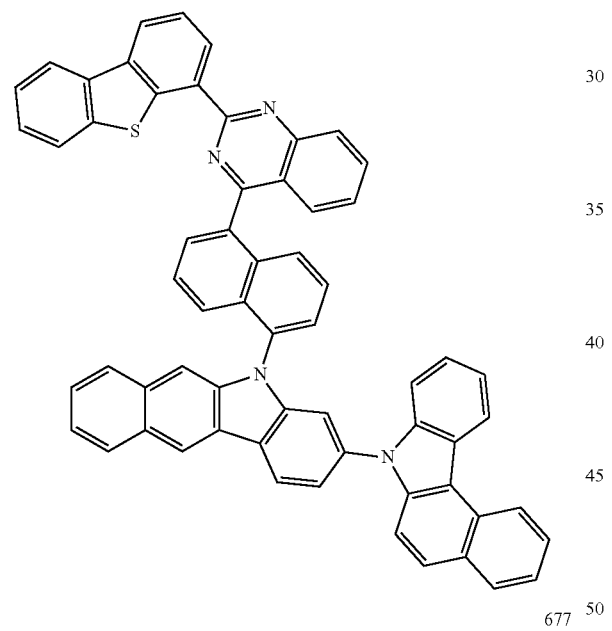
676
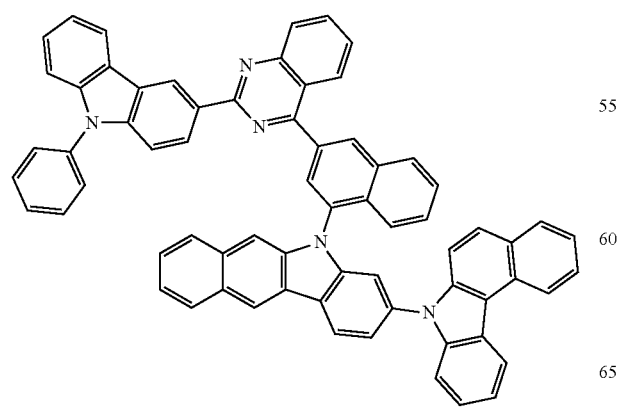
677
302
-continued
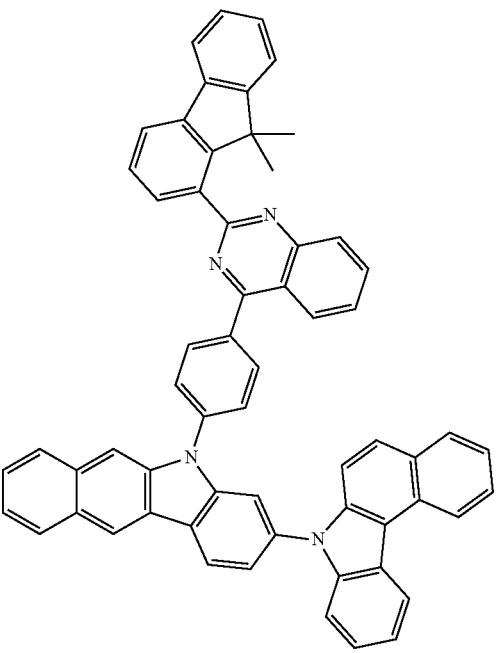
678
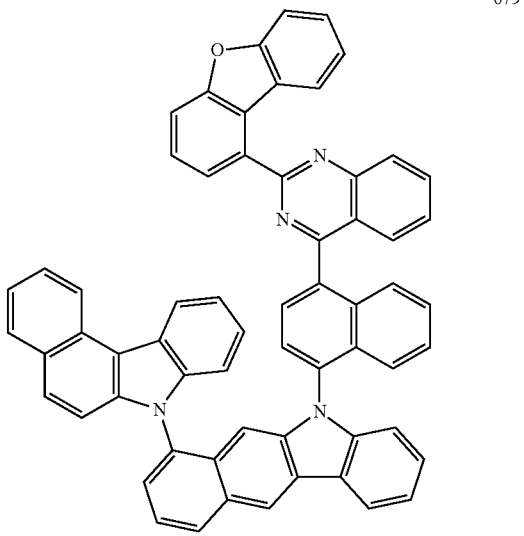
679

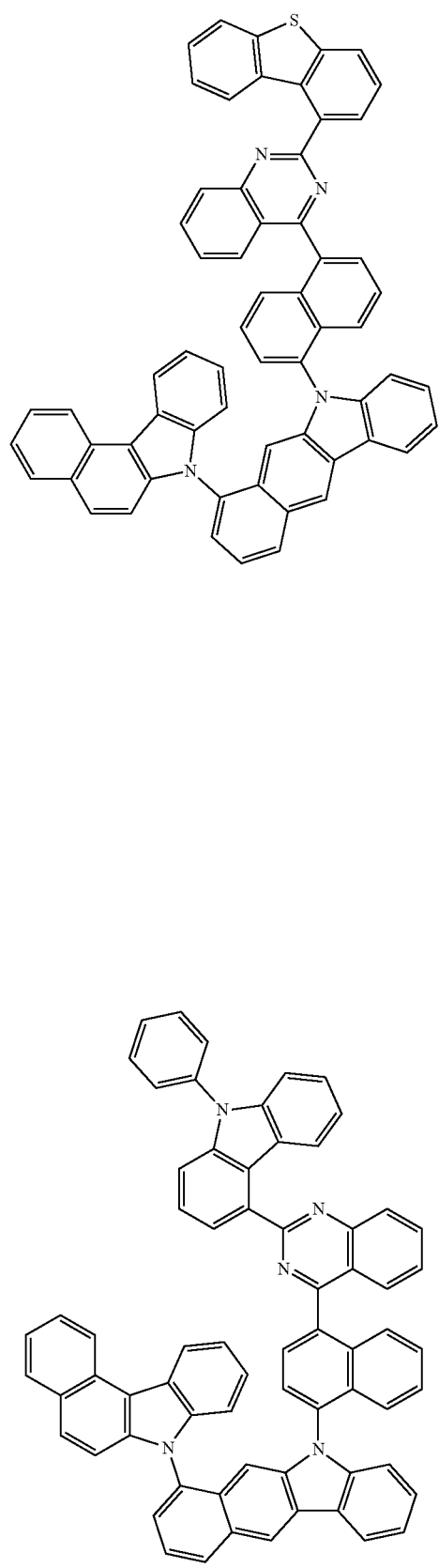
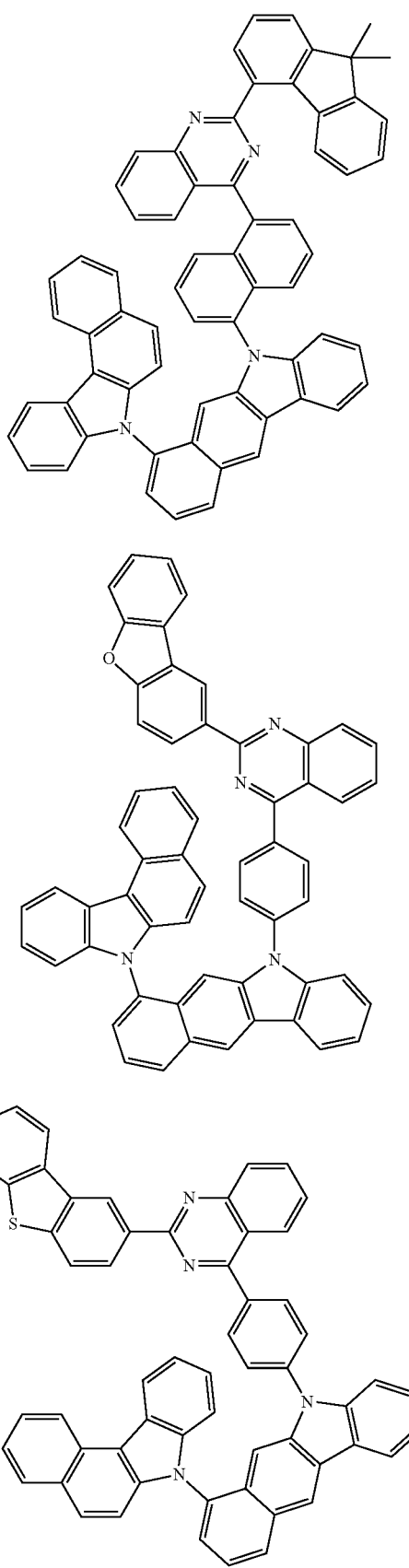

305
-continued
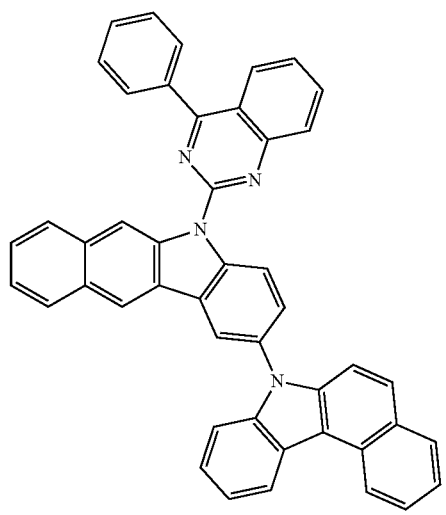
685
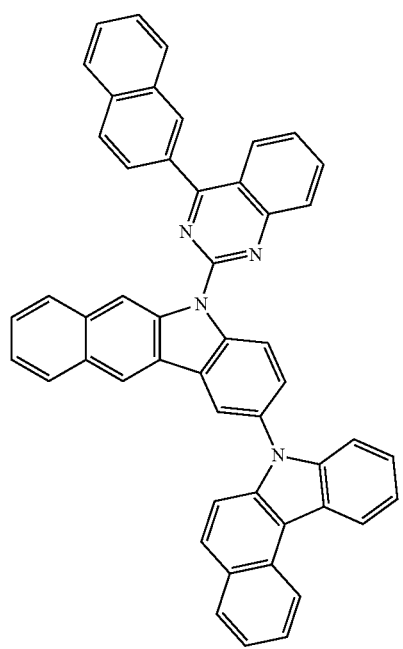
686
306
-continued
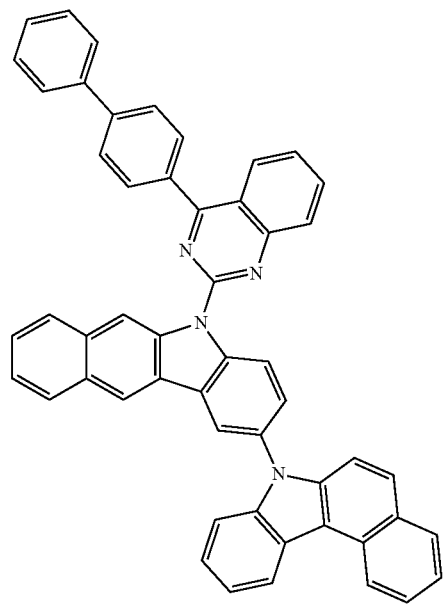
687
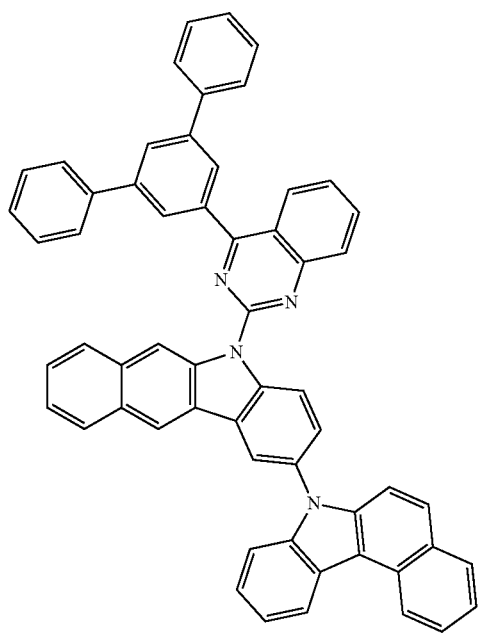
688

307
-continued
689
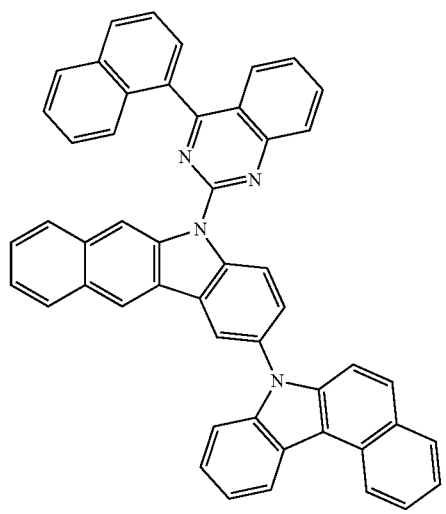
690
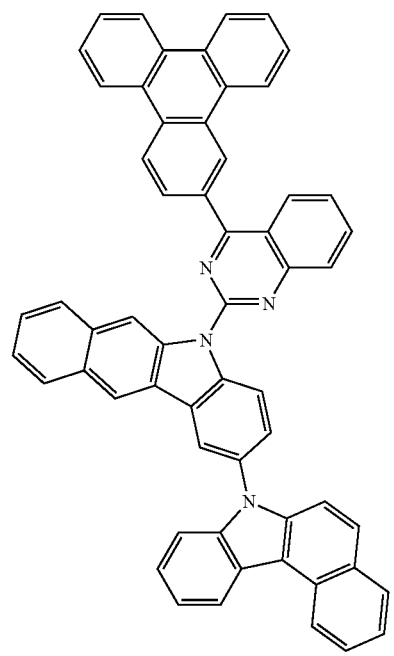
691
308
-continued
692
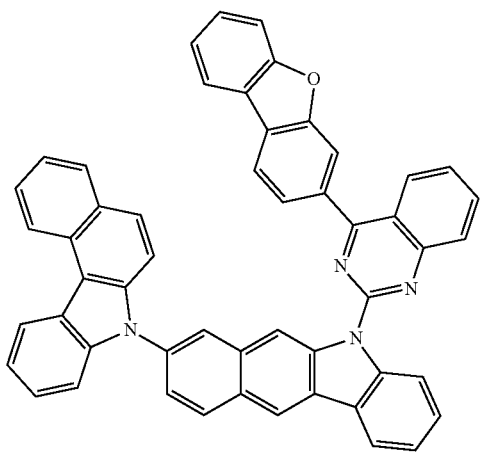
693
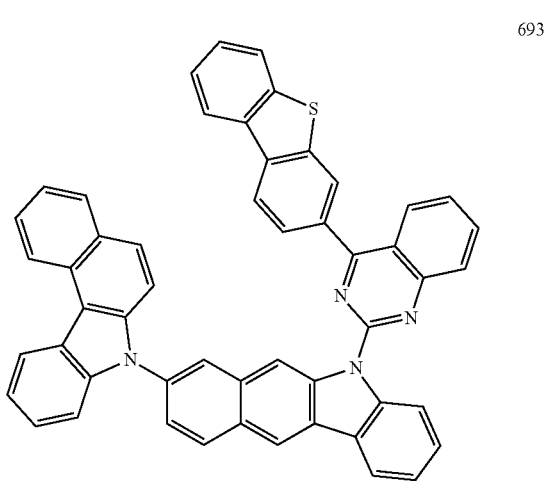
694
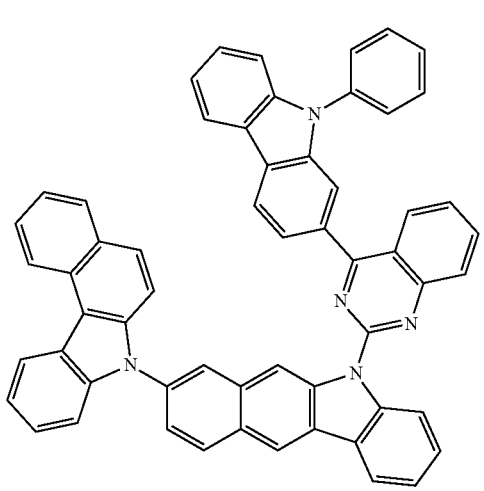

309
-continued
695
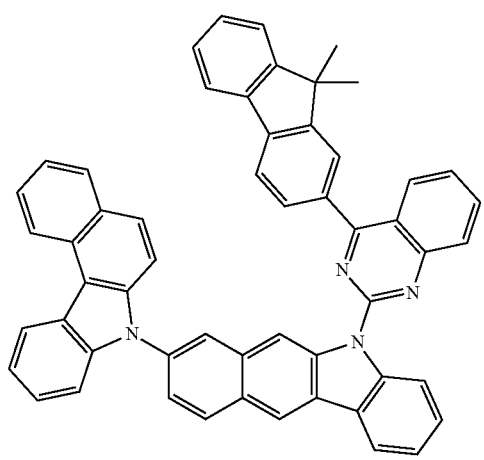
696
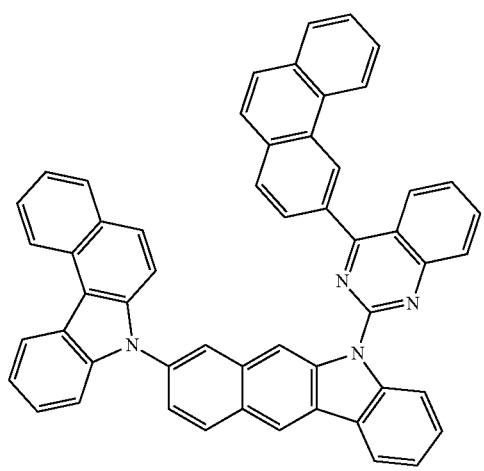
697
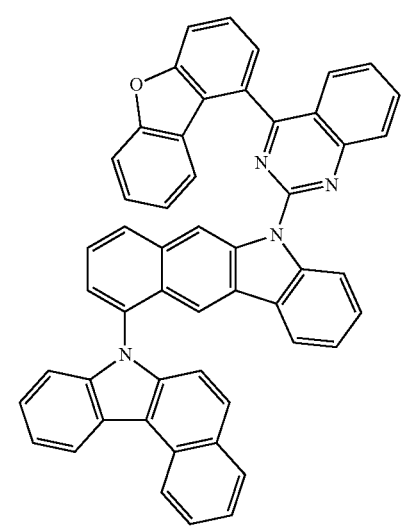
310
-continued
698
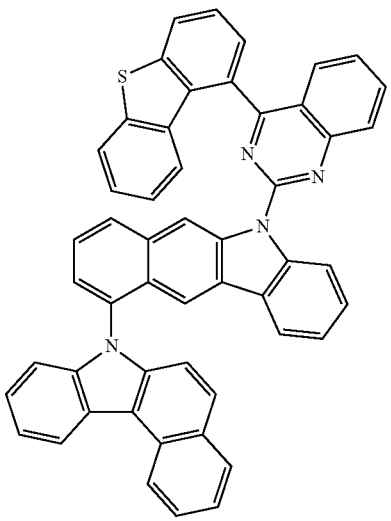
699
700
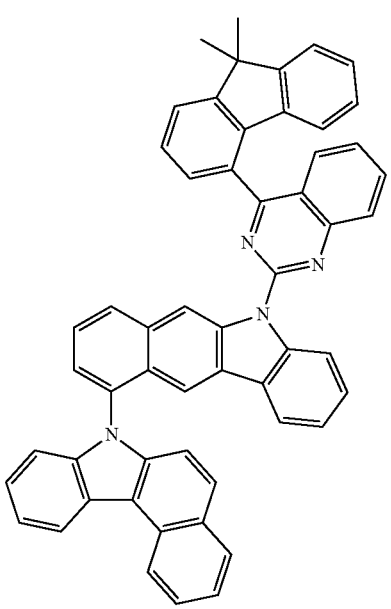

311
-continued
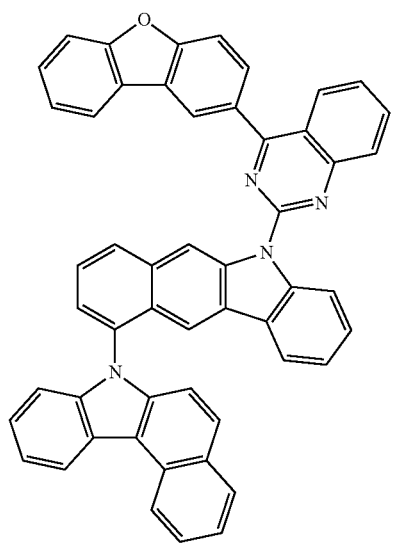
701
312
-continued
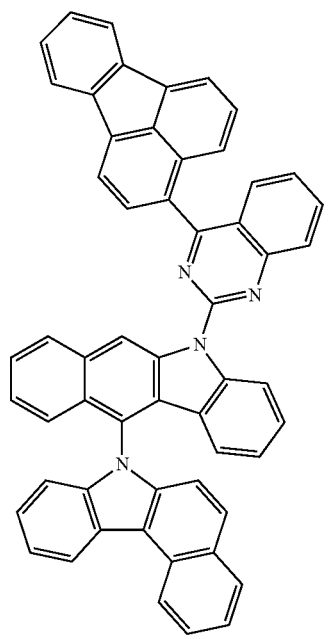
703
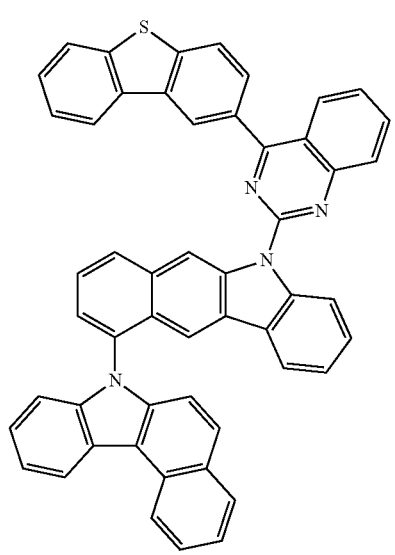
702
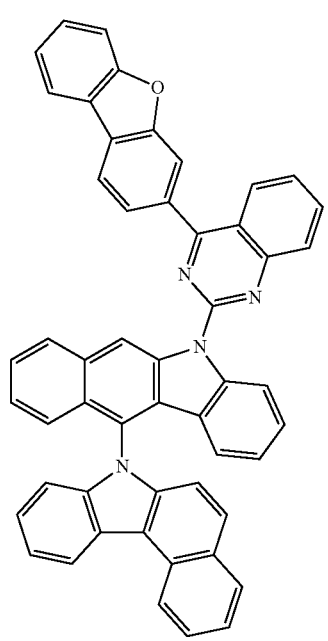
704

313
-continued
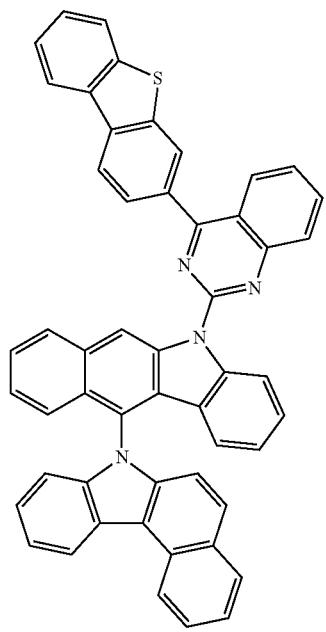
705
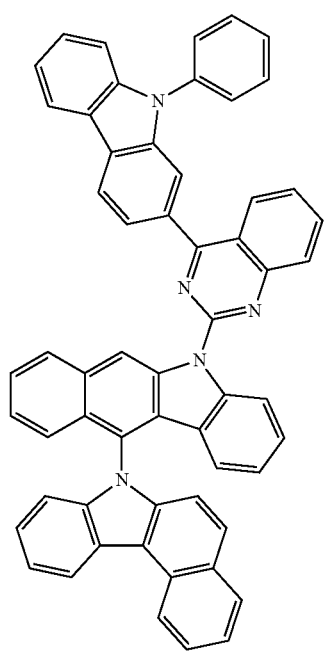
706
314
-continued
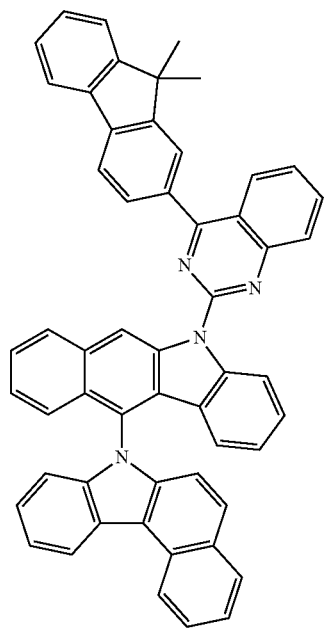
707
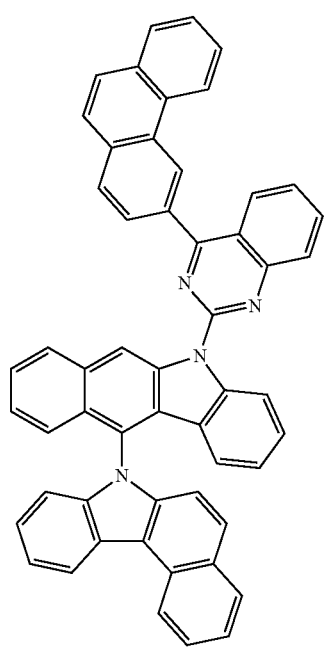
708

315
-continued
709
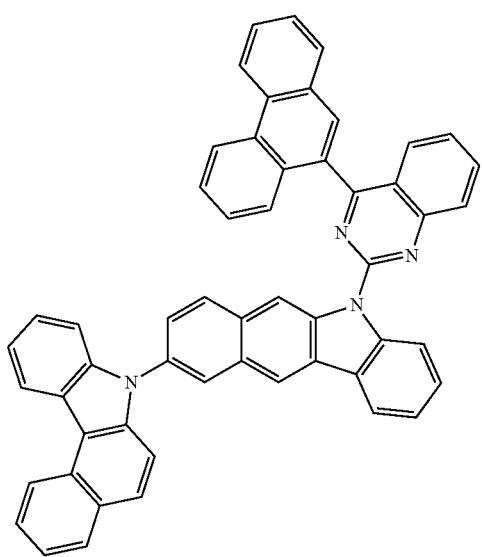
710
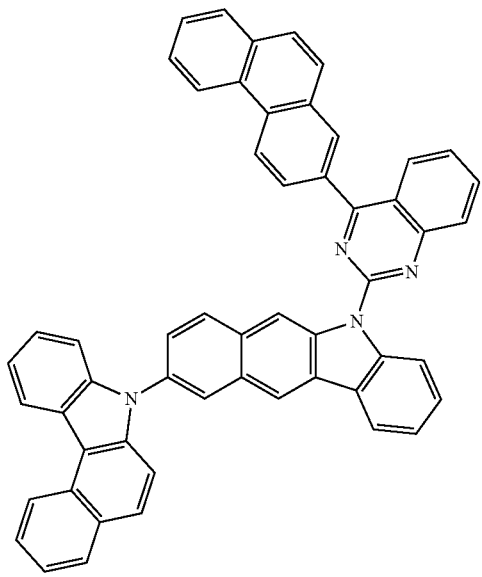
316
-continued
711
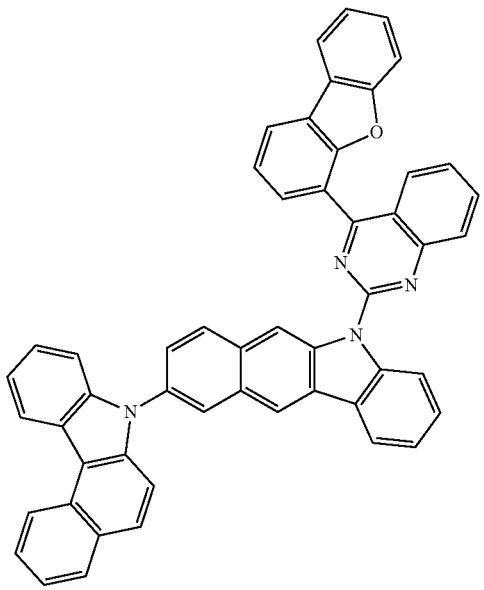
712
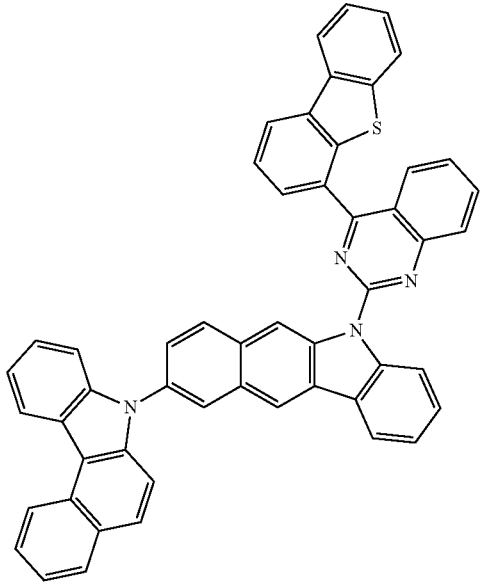

713
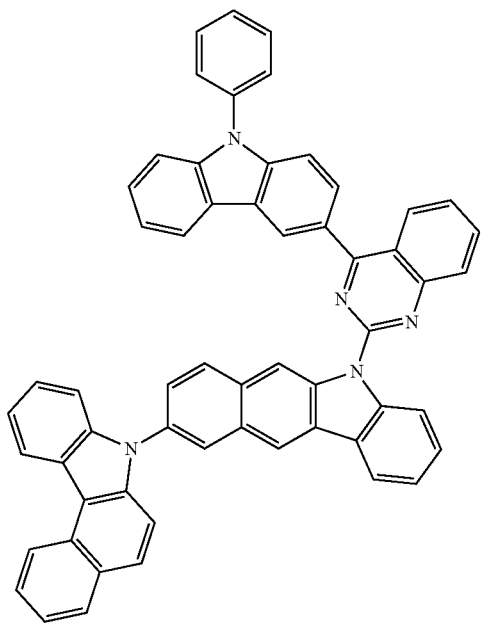
714
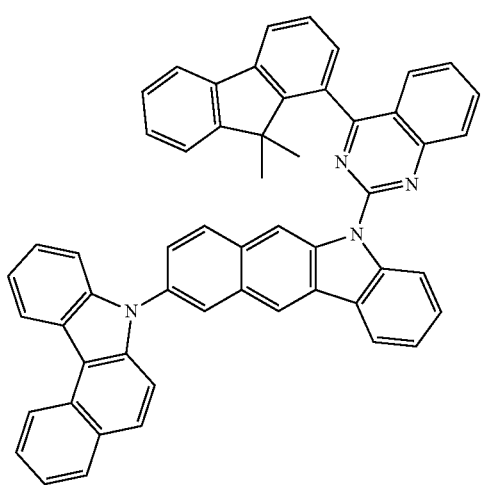
715
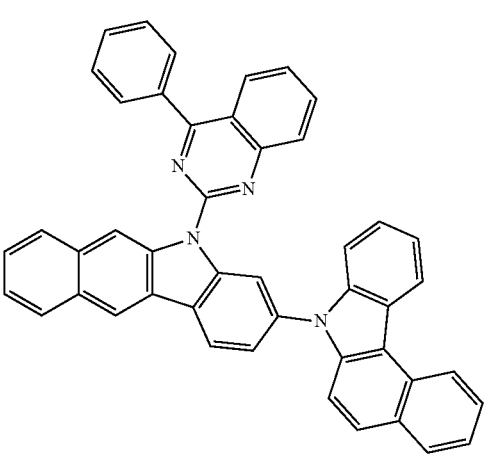
716
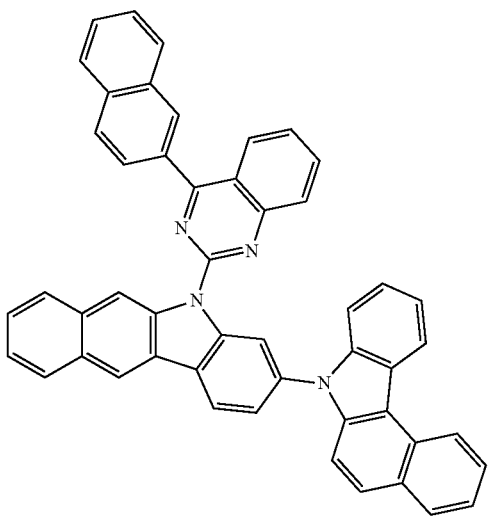
717
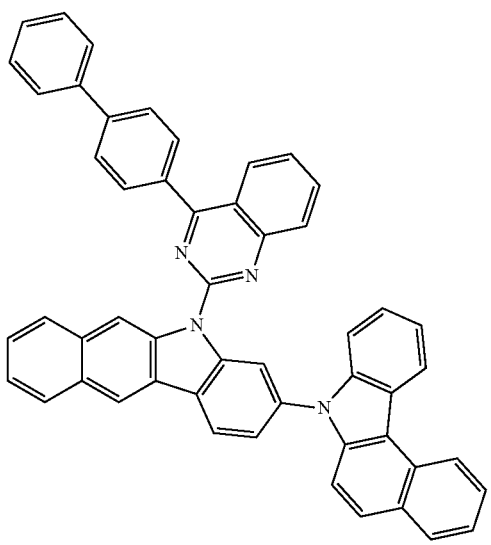
718
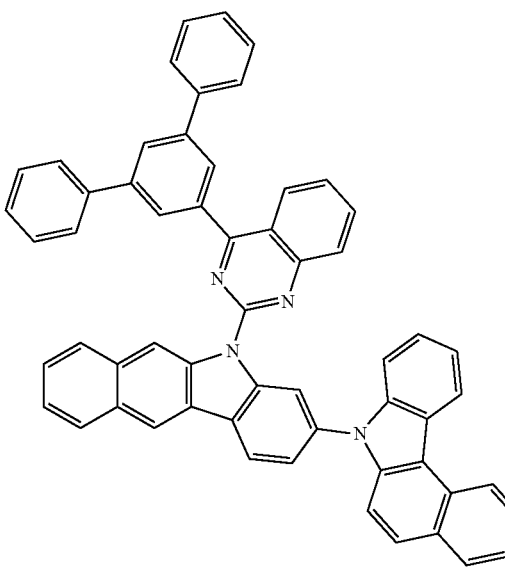

-continued
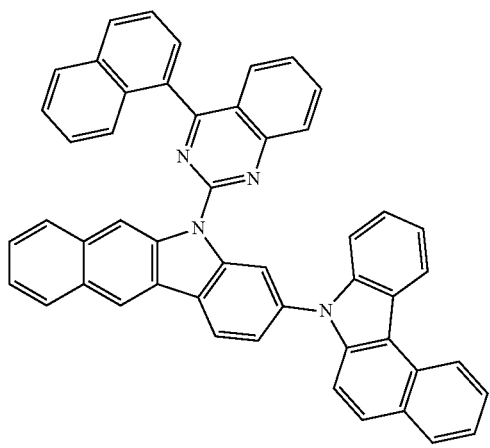
719
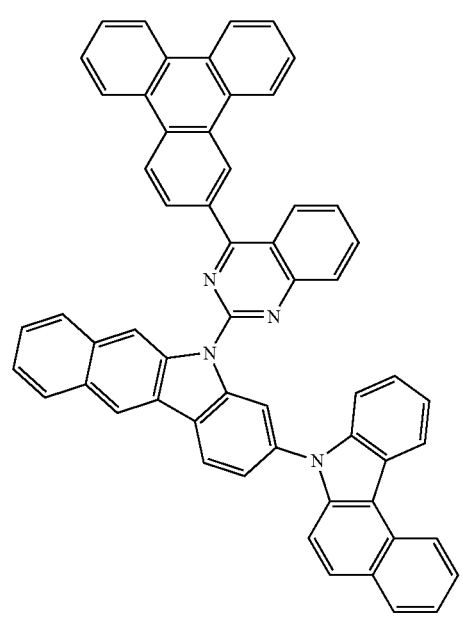
720
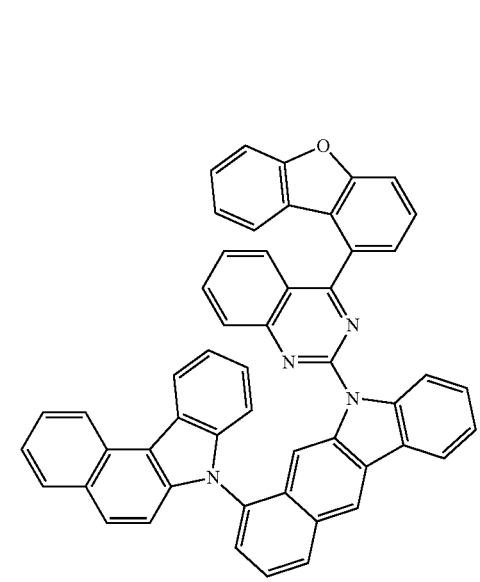
721
-continued
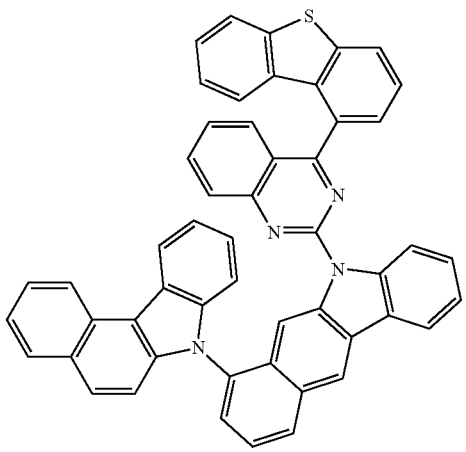
722
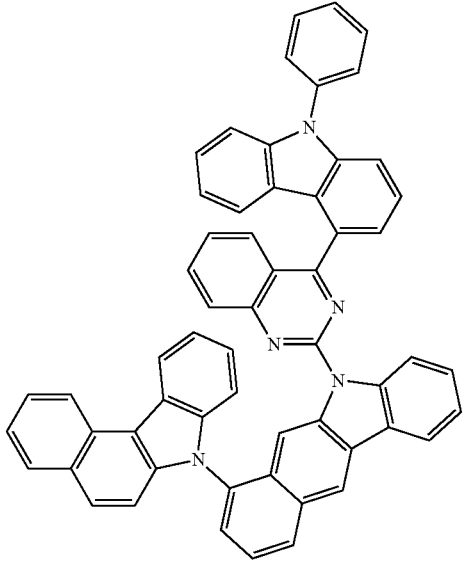
723
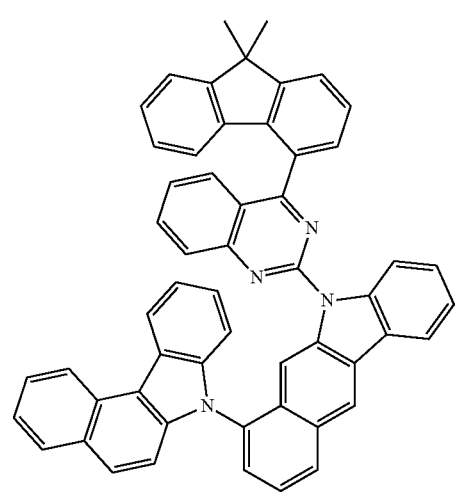
724

321
-continued
725
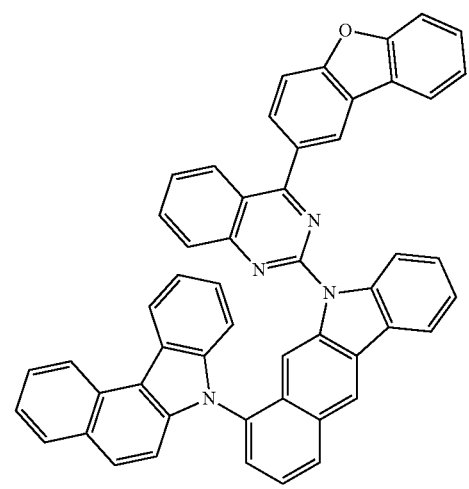
726
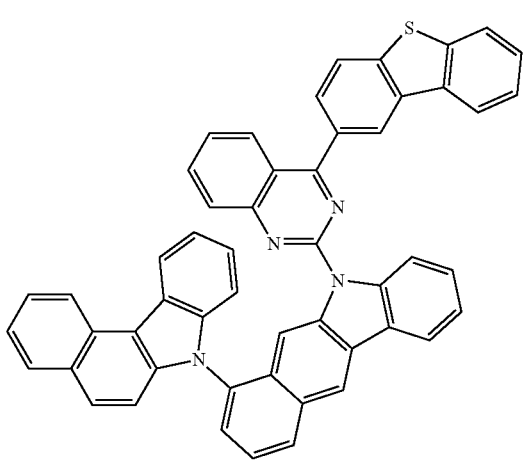
727
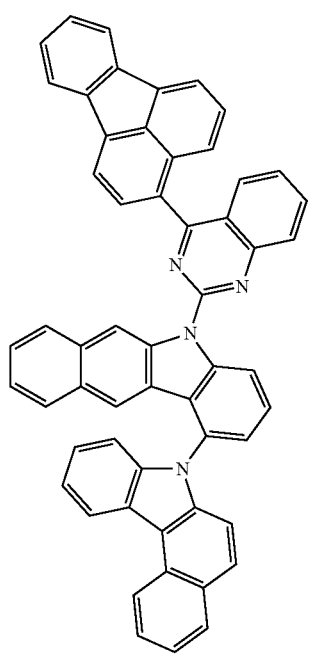
322
-continued
728
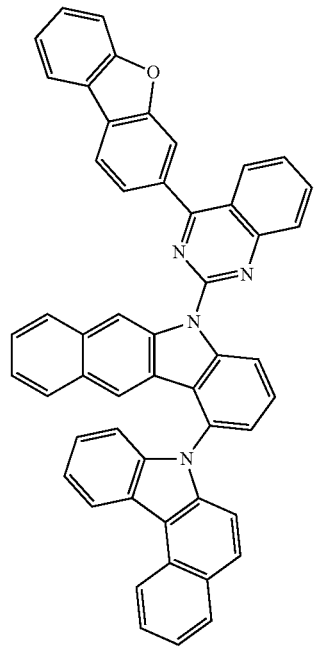
729
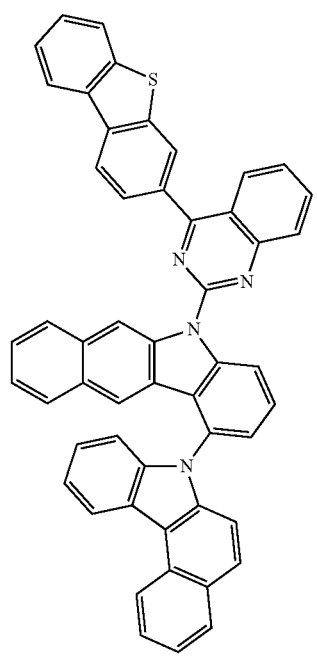

323
-continued
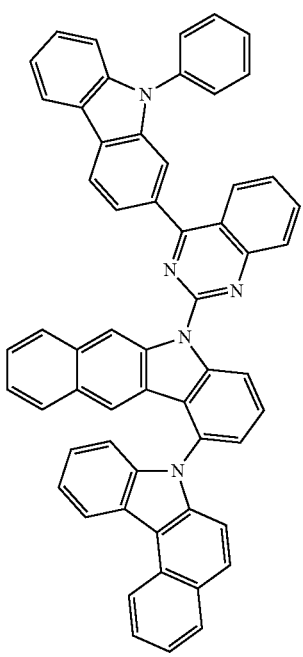
730
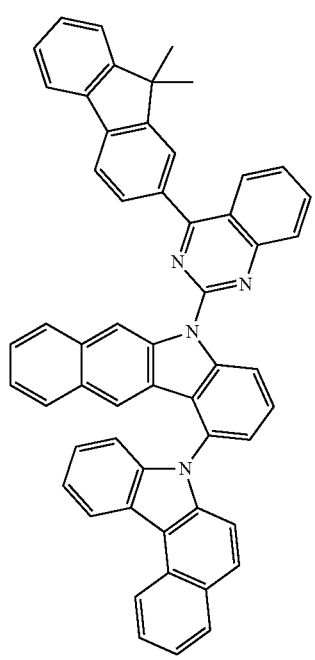
731
324
-continued
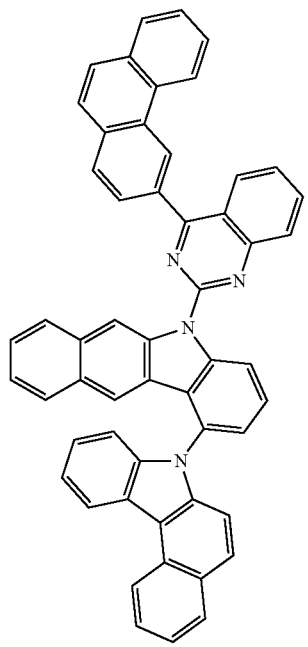
732
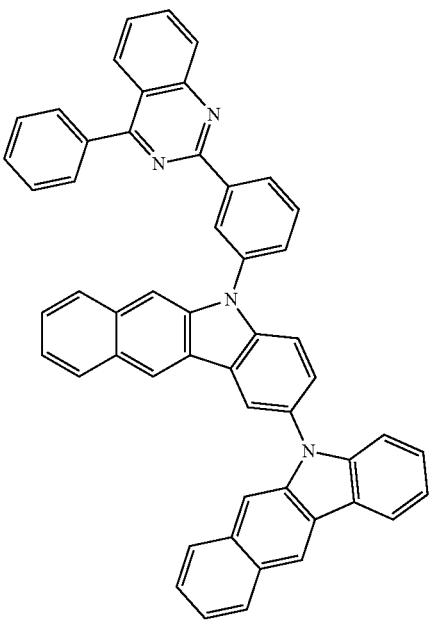
733

325
-continued
734
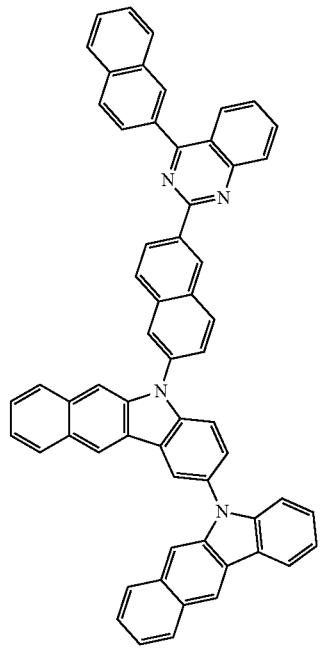
735
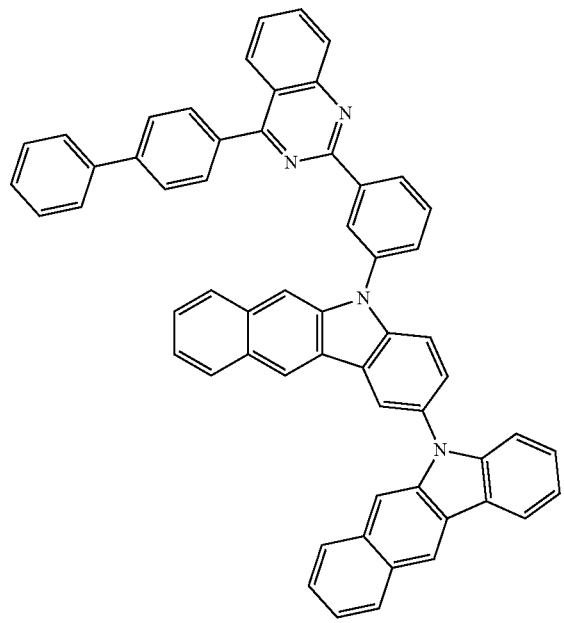
326
-continued
736
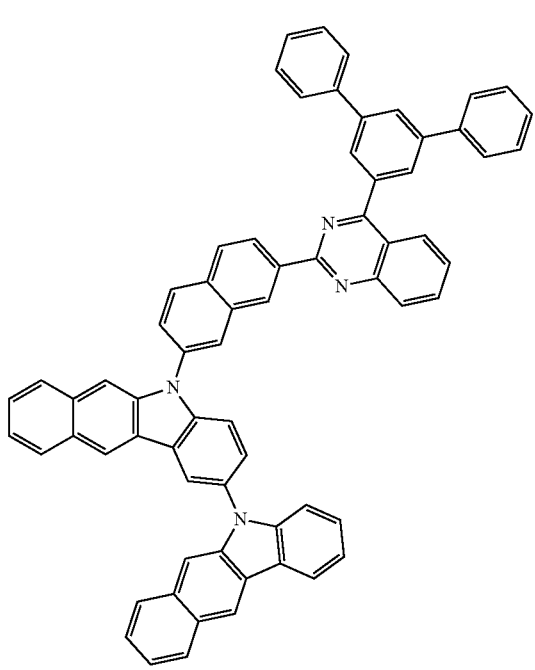
737
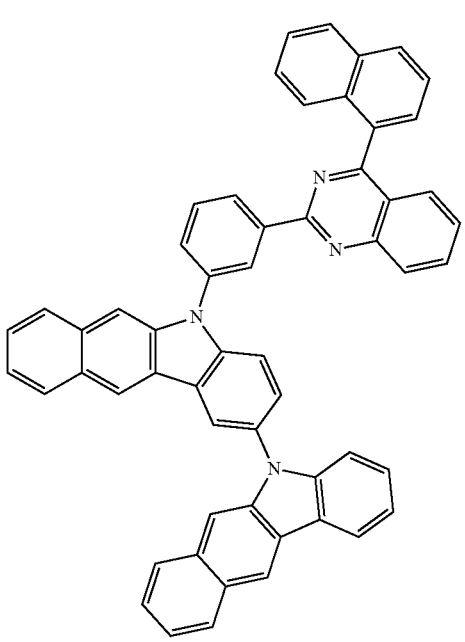

327
-continued
738
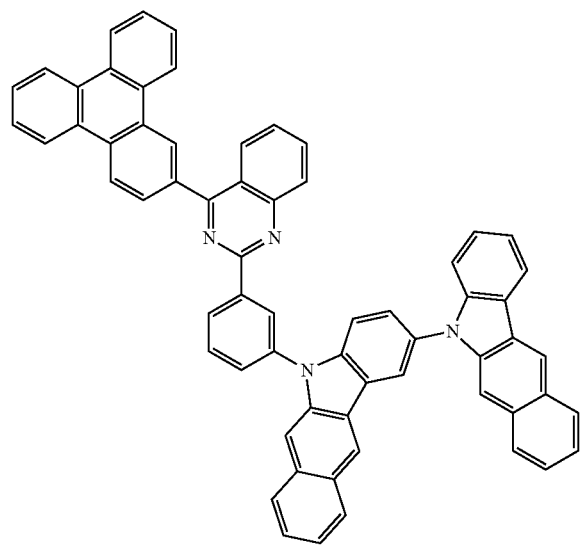
328
-continued
740
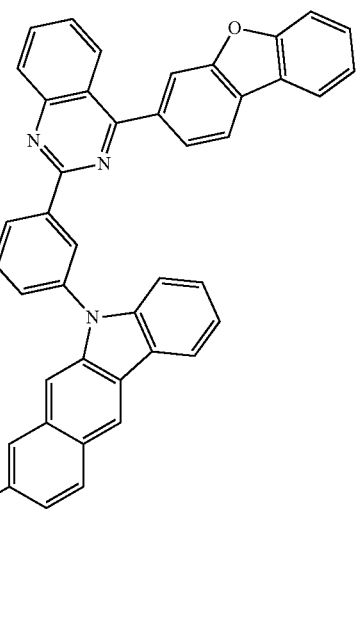
739
741
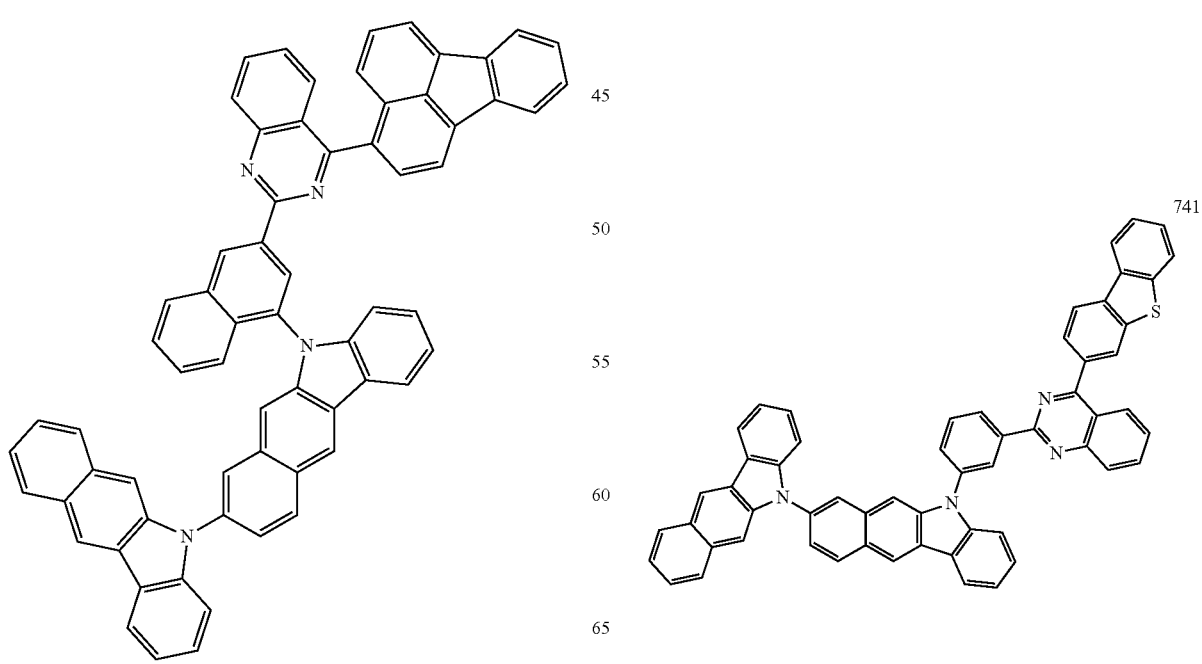

329
-continued
742
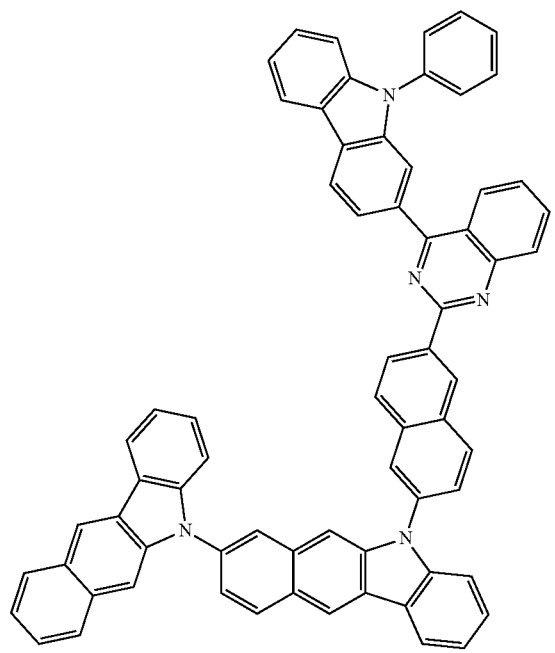
743
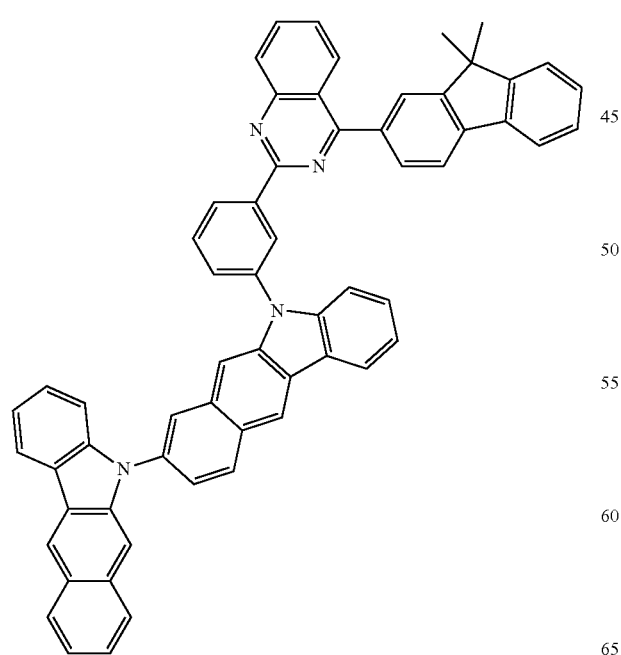
330
-continued
744
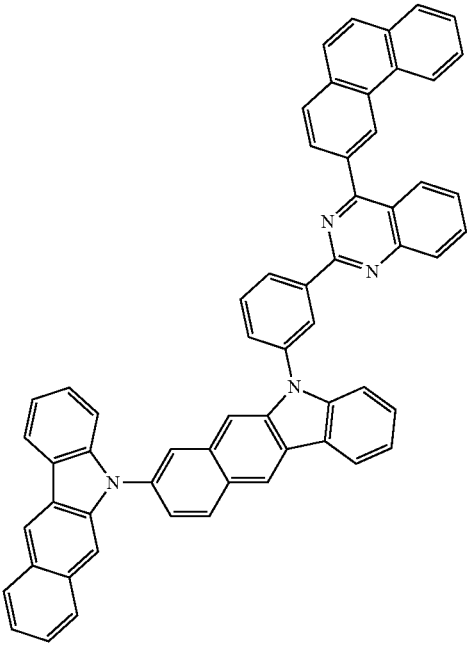
745
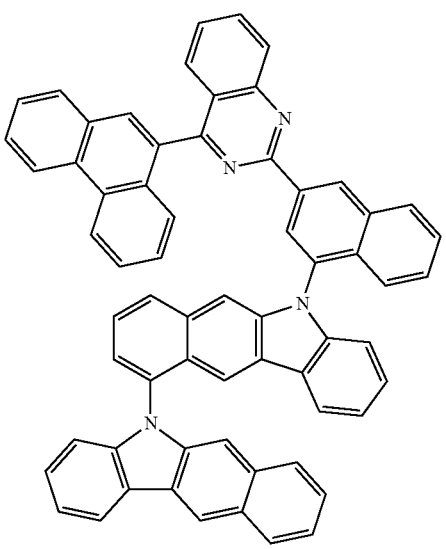

331
-continued
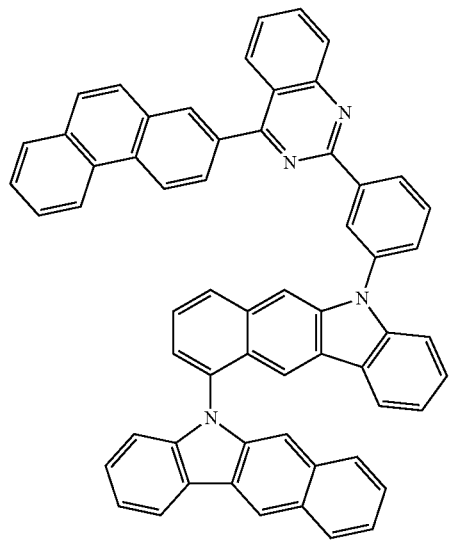
746
332
-continued
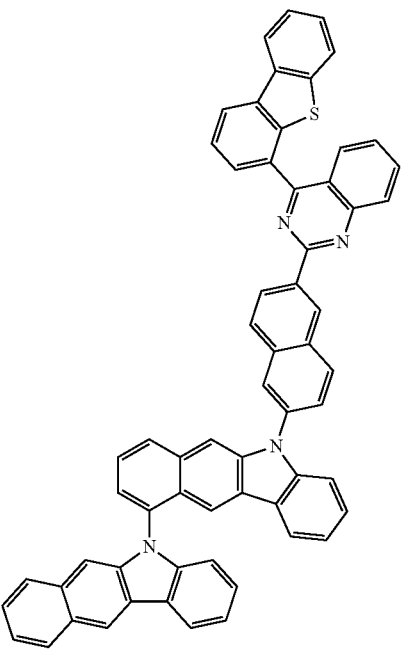
748
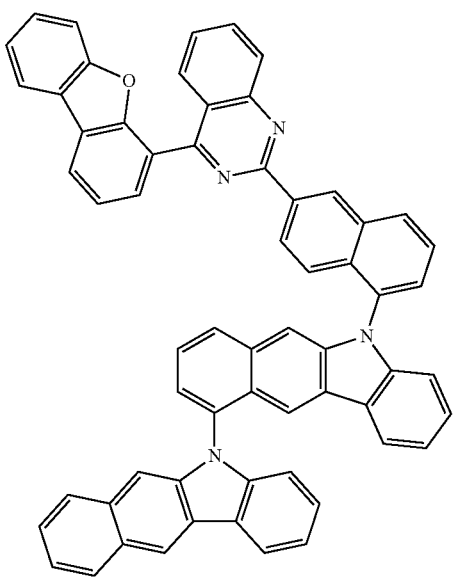
747
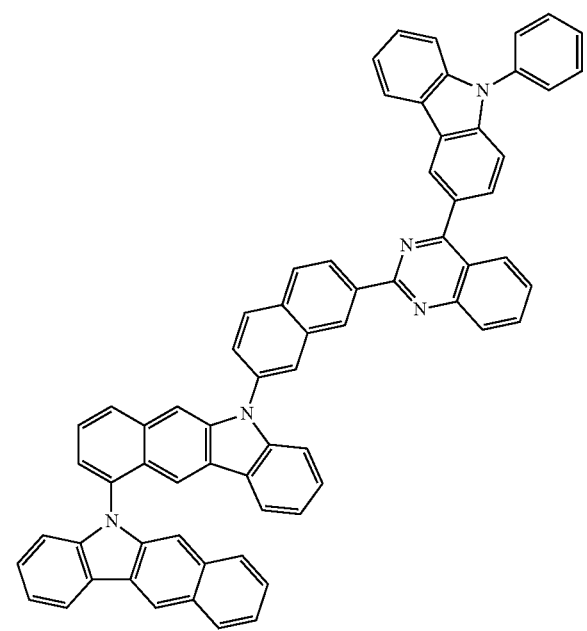
749

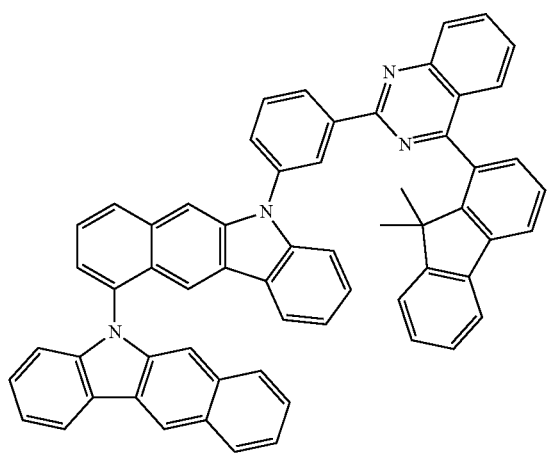
750
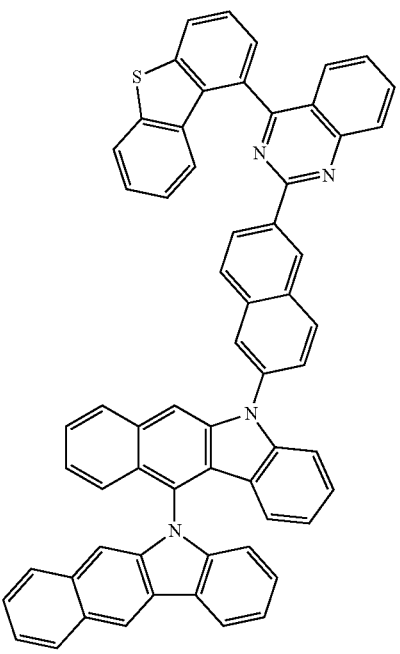
752
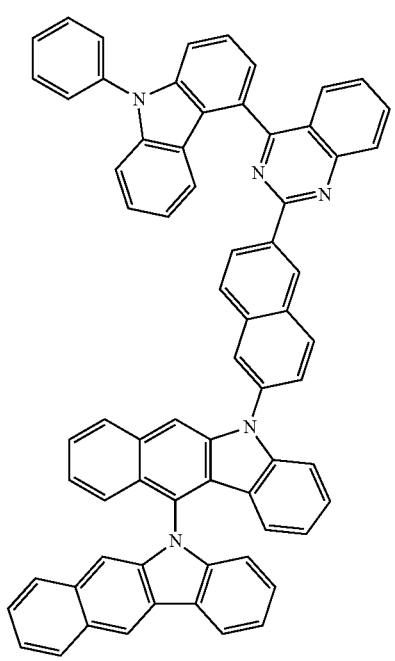
753
751

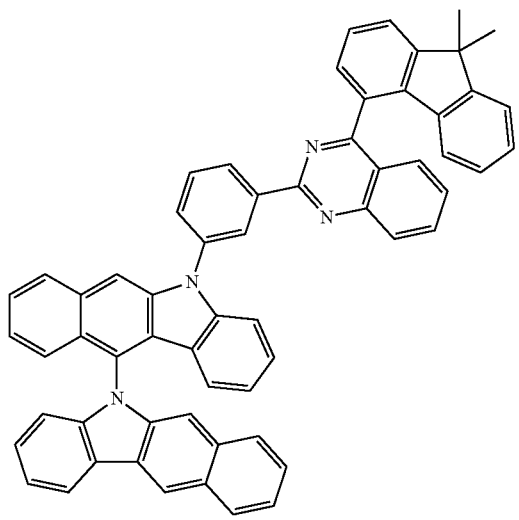
754
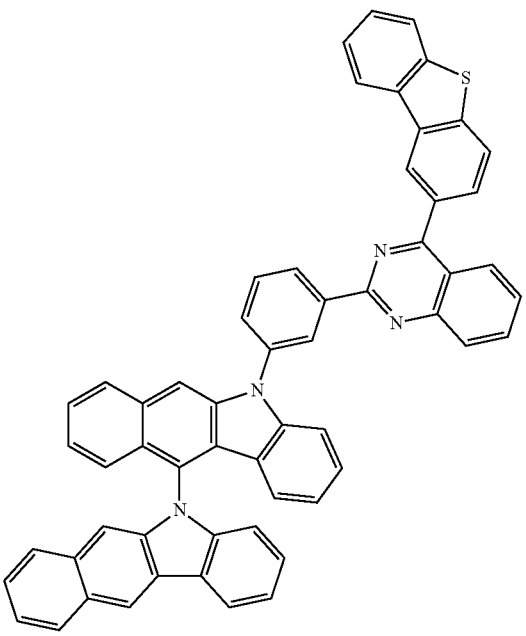
756
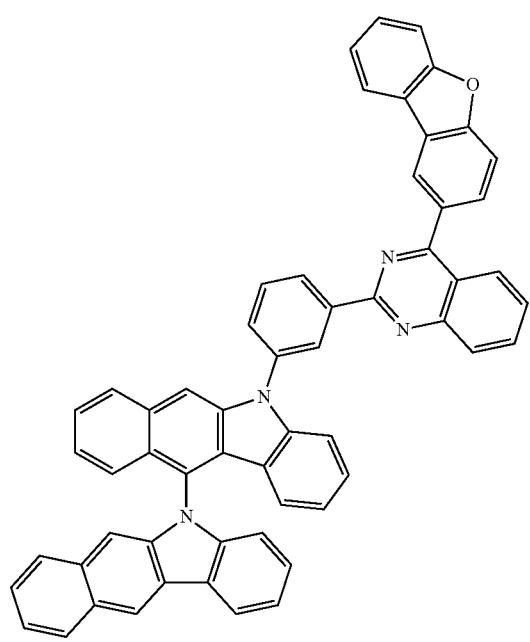
755
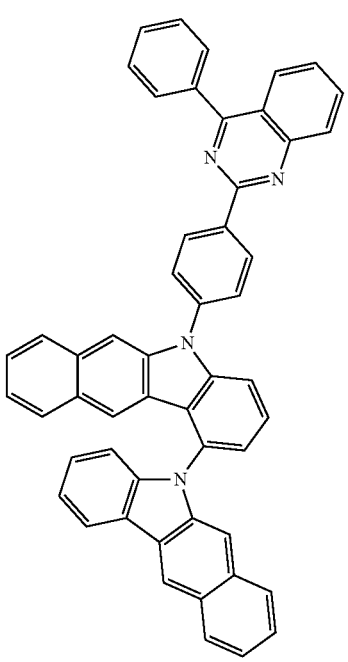
757

337
-continued
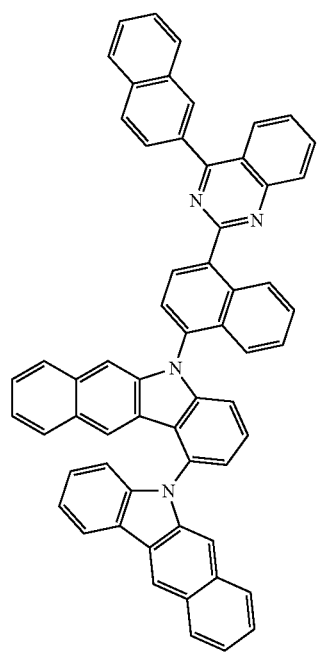
758
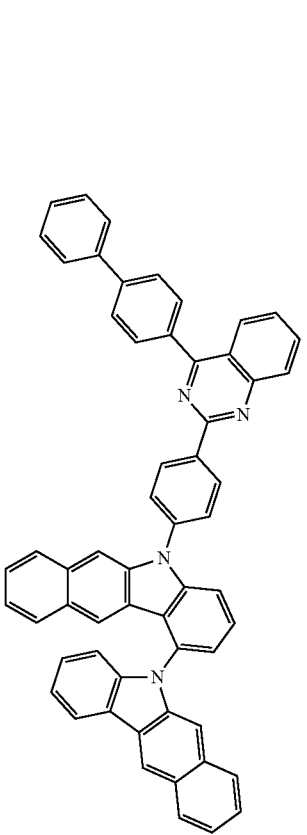
759
338
-continued
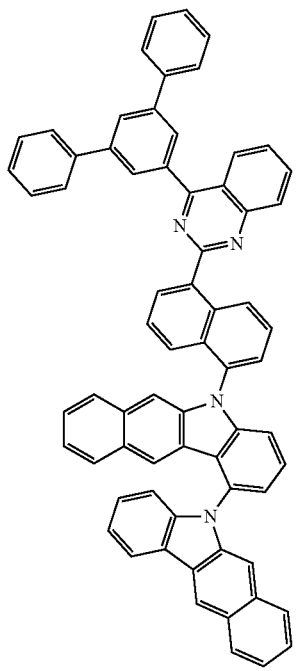
760
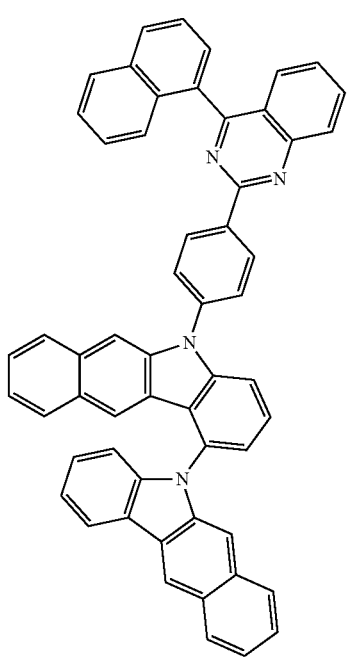
761

339
-continued
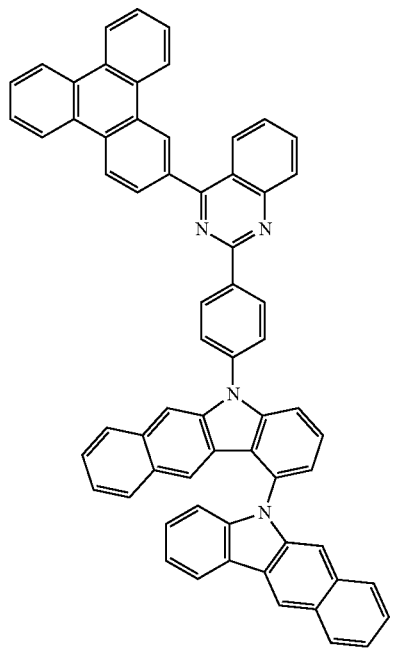
762
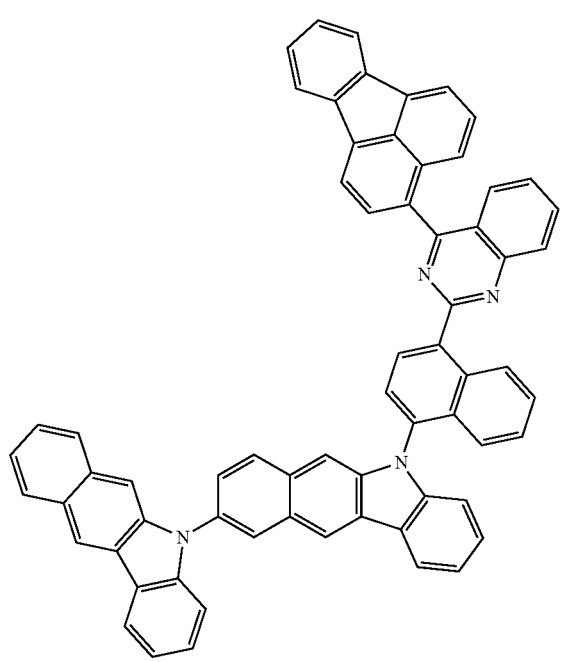
763
340
-continued
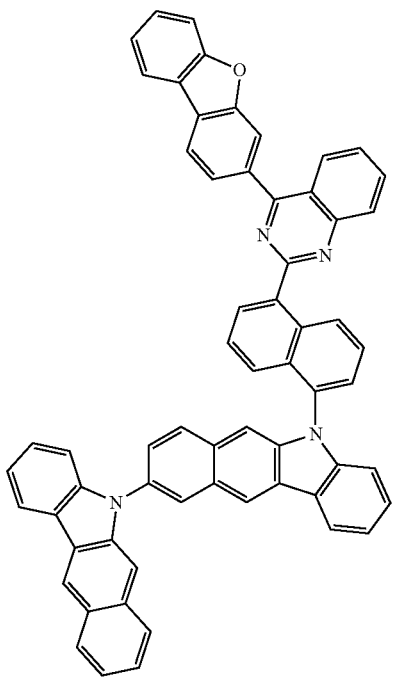
764
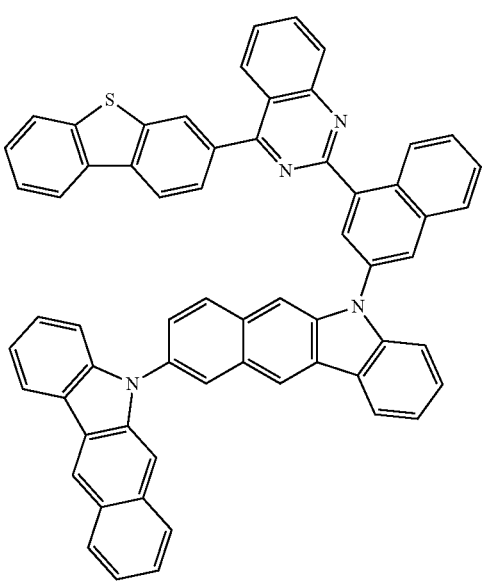
765

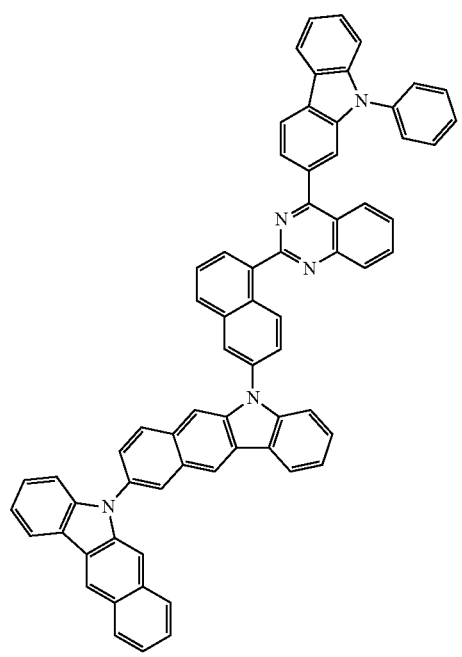
766
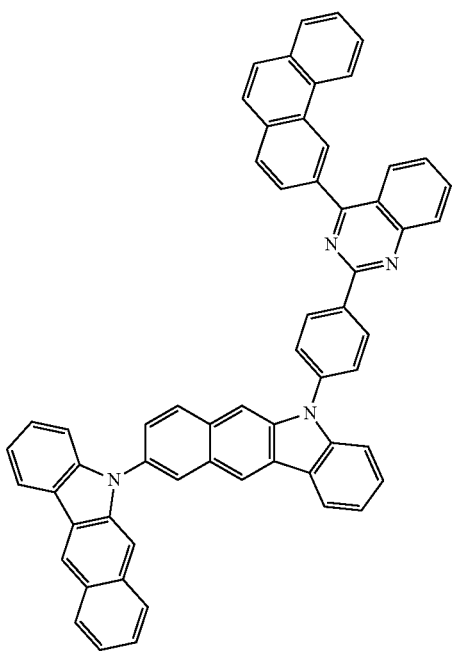
768
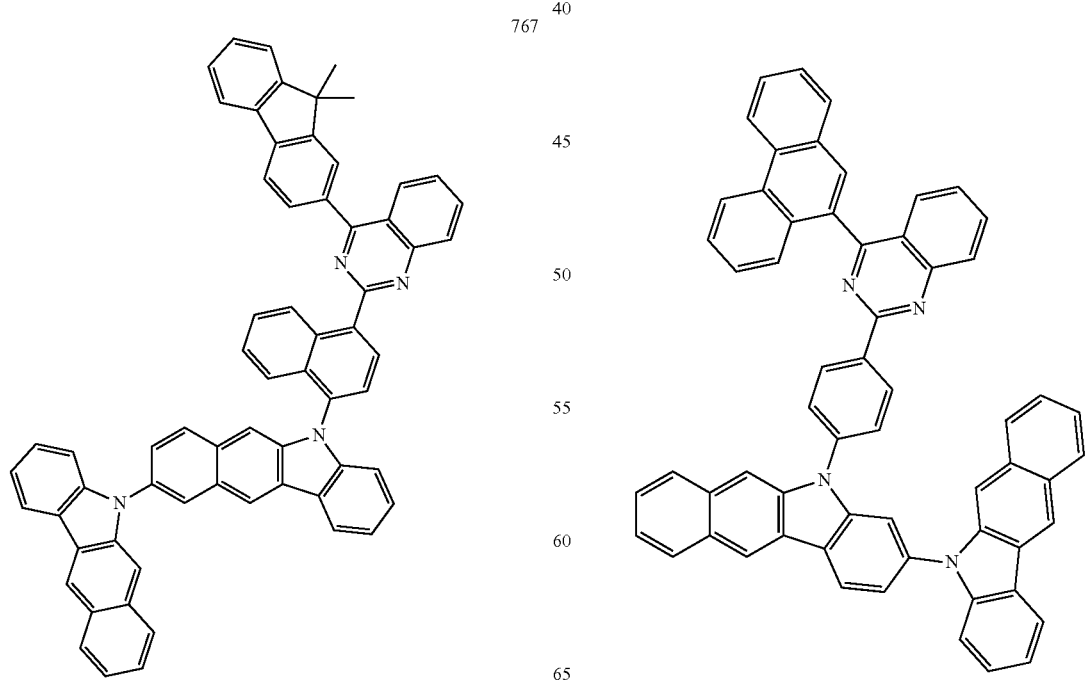
767
769

343
-continued
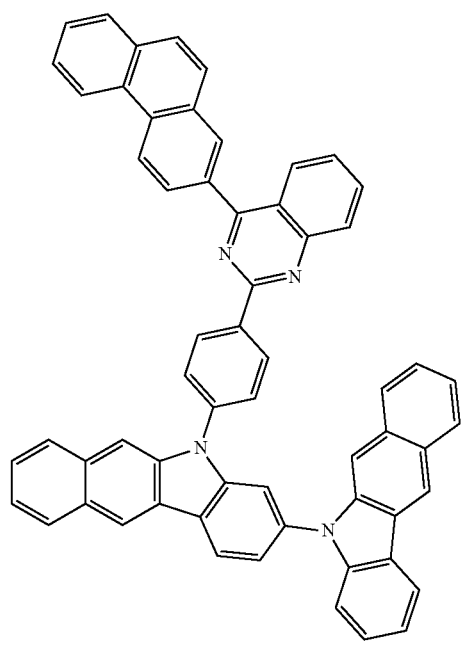
770
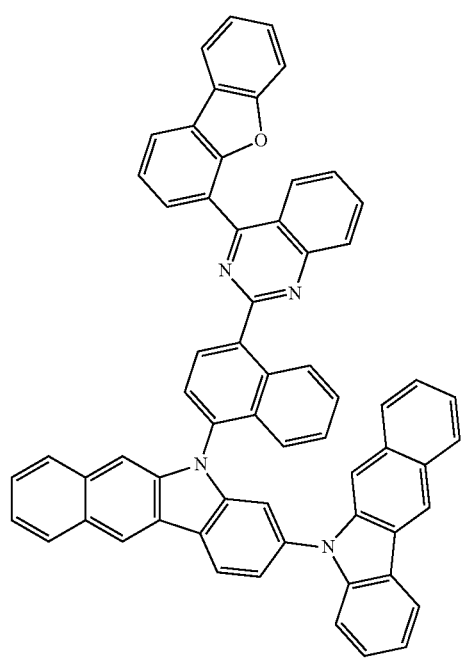
771
344
-continued
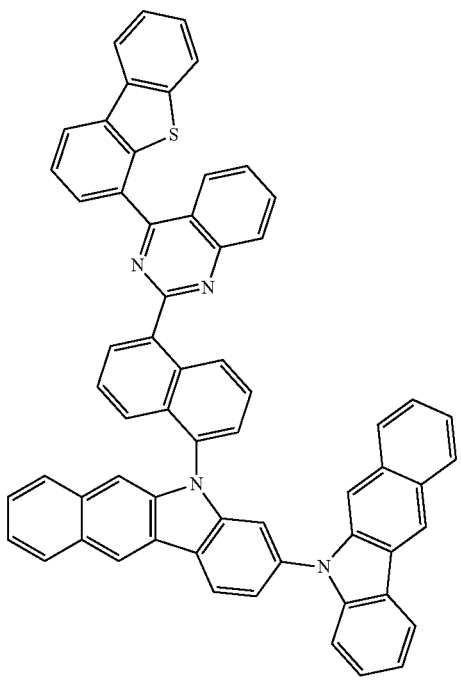
772
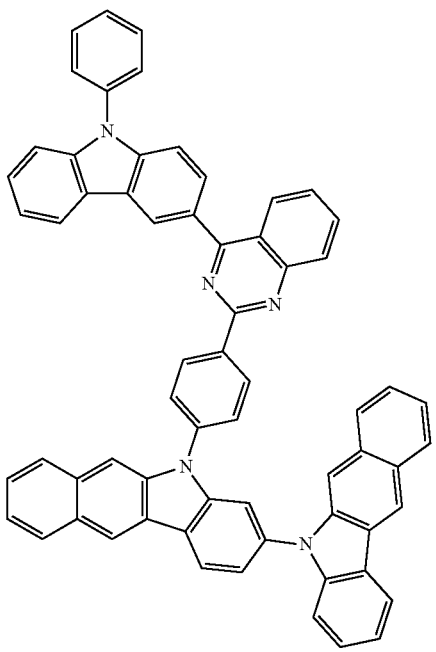
773

345
-continued
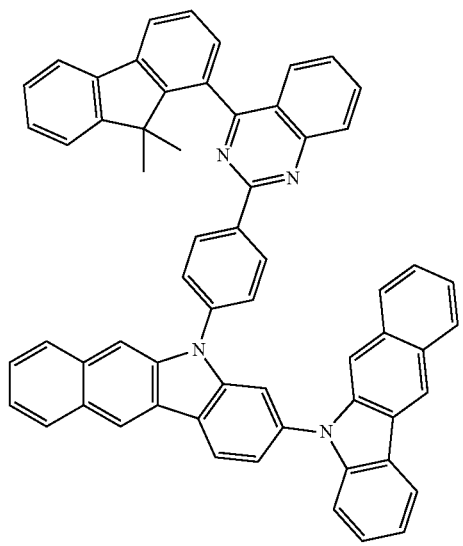
774
346
-continued
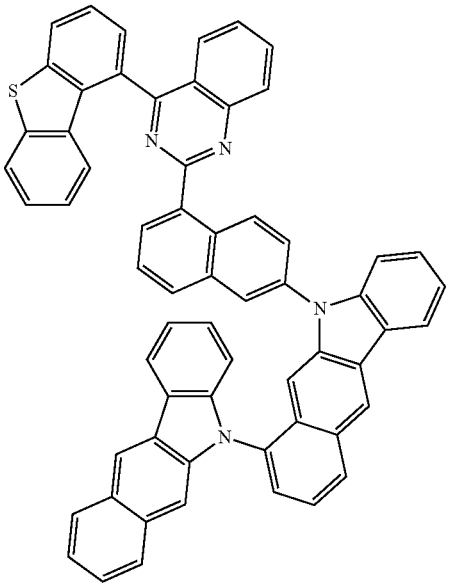
776
775
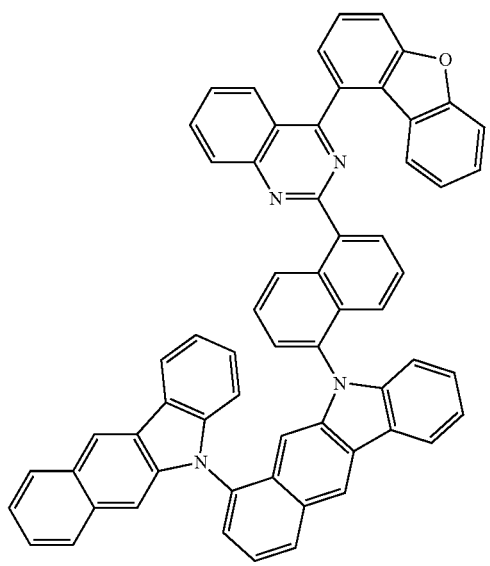
777
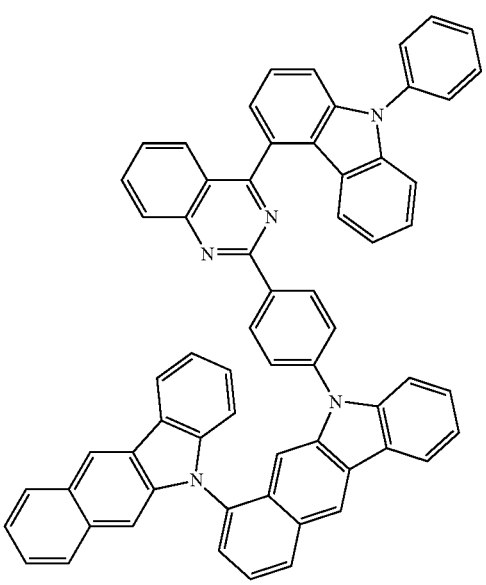

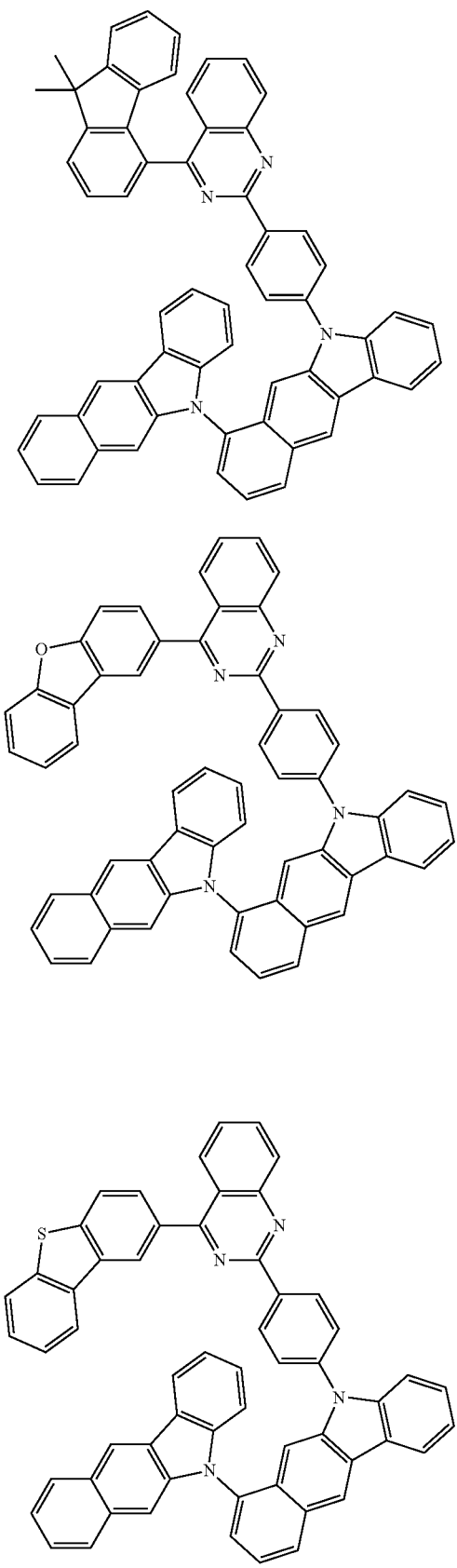
778
779
780
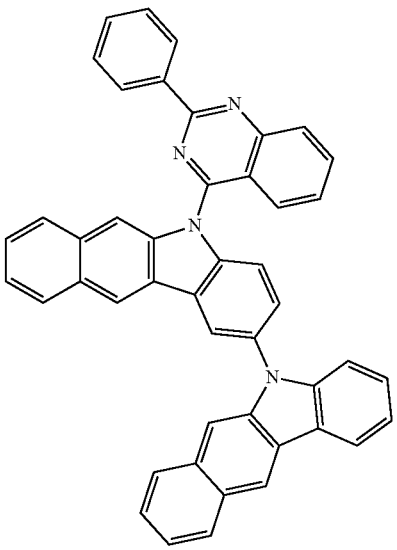
781
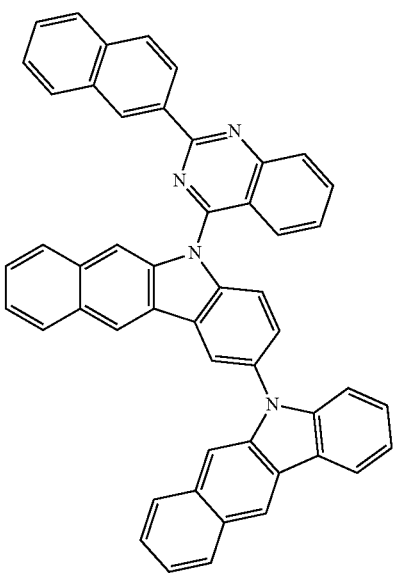
782

349
-continued
783
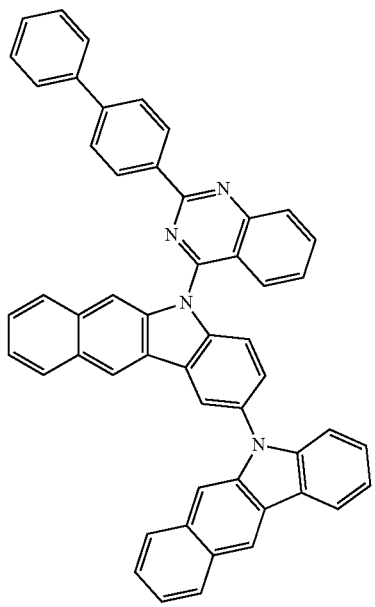
784
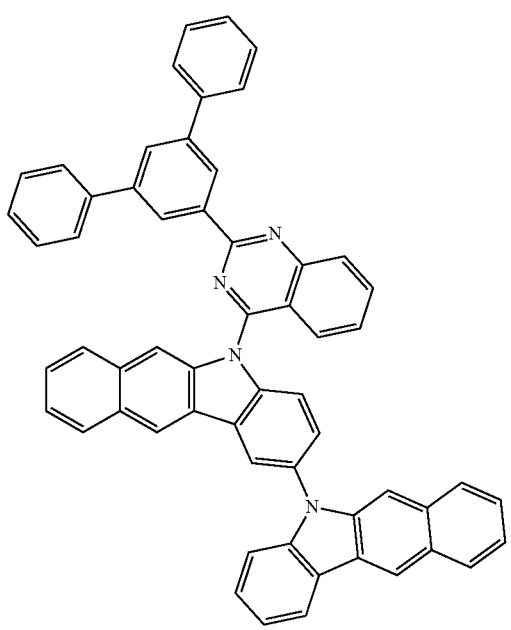
350
-continued
785
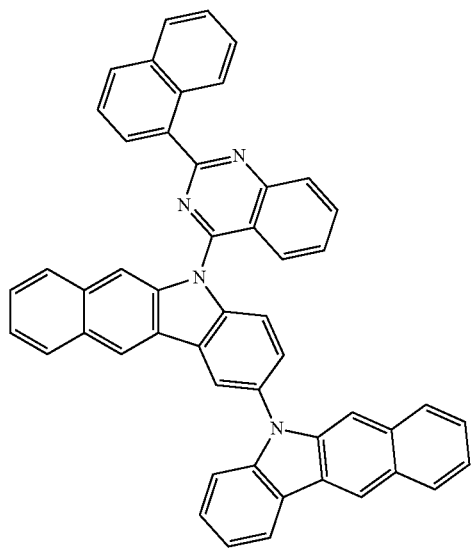
786
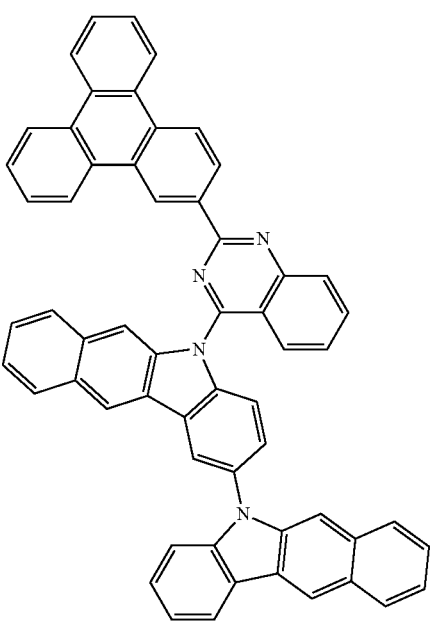

351
-continued
787
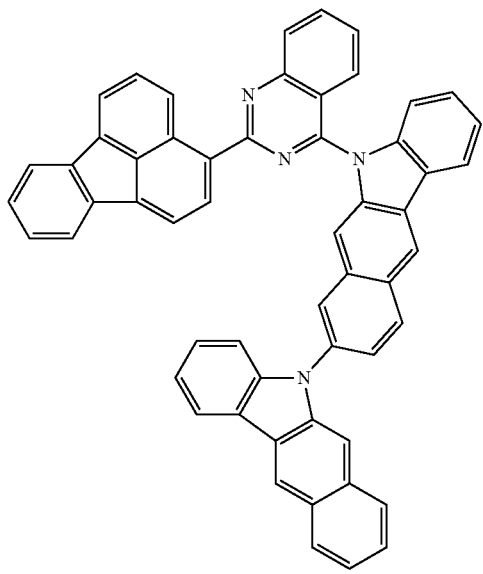
788
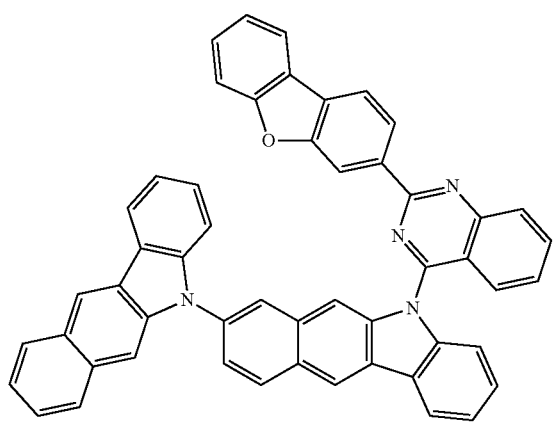
789
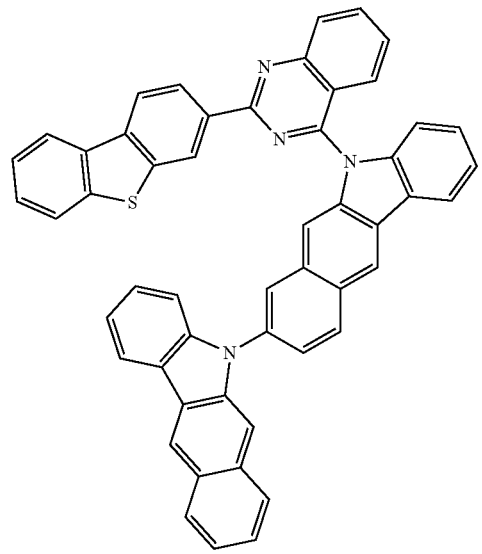
352
-continued
790
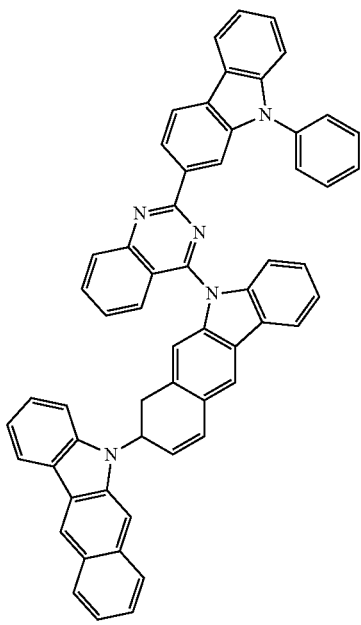
791
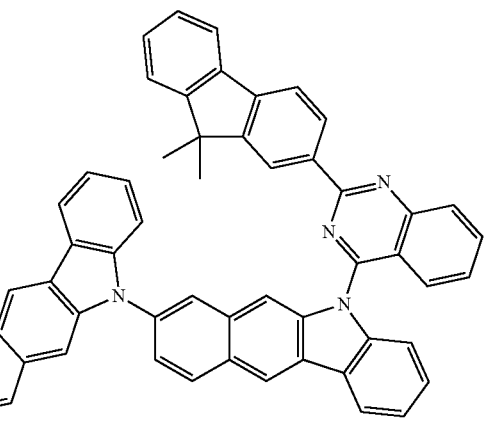
792
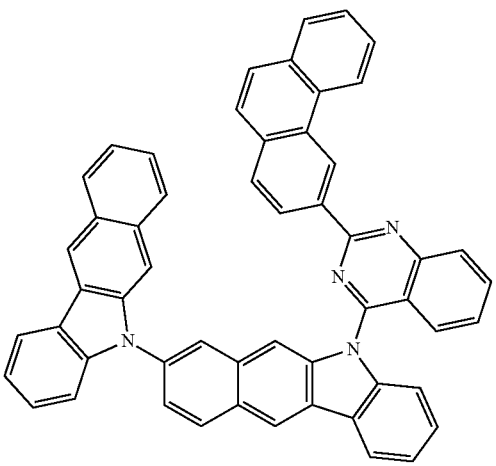

793 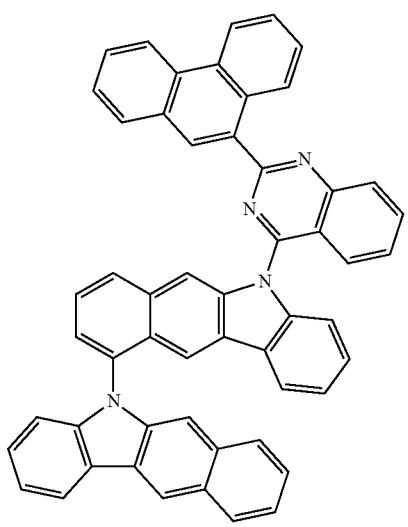
794 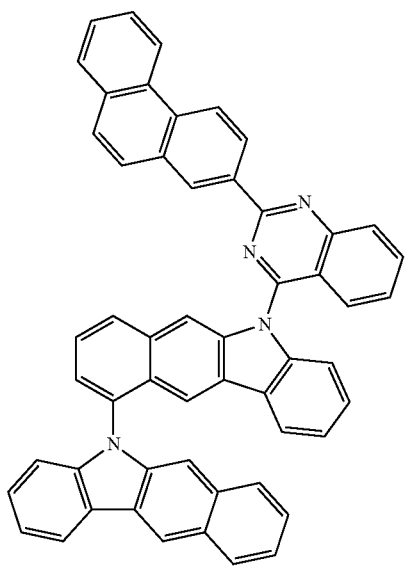
795 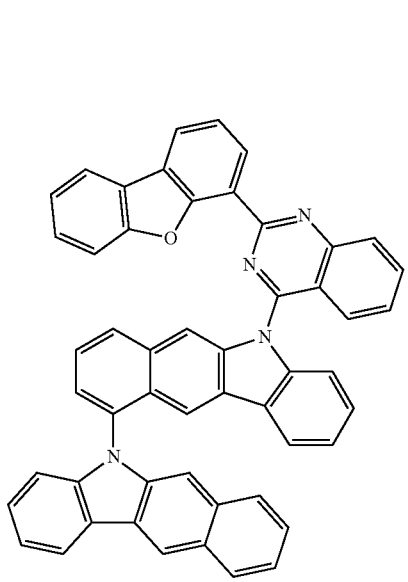
796 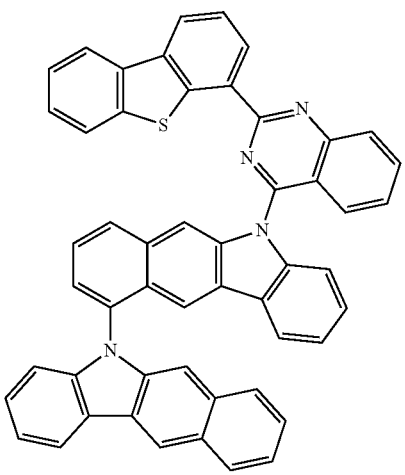
797 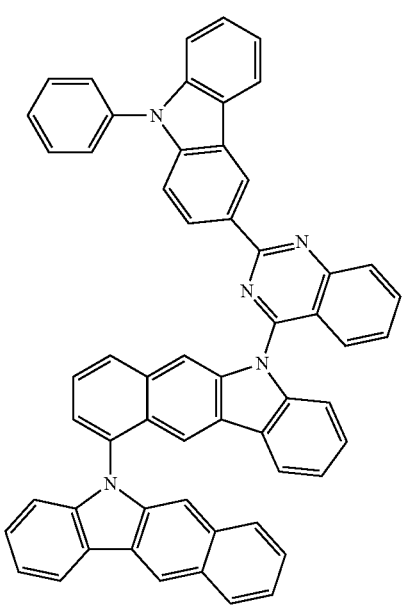
798 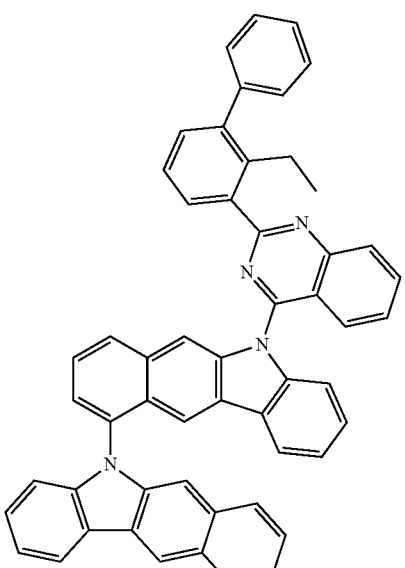

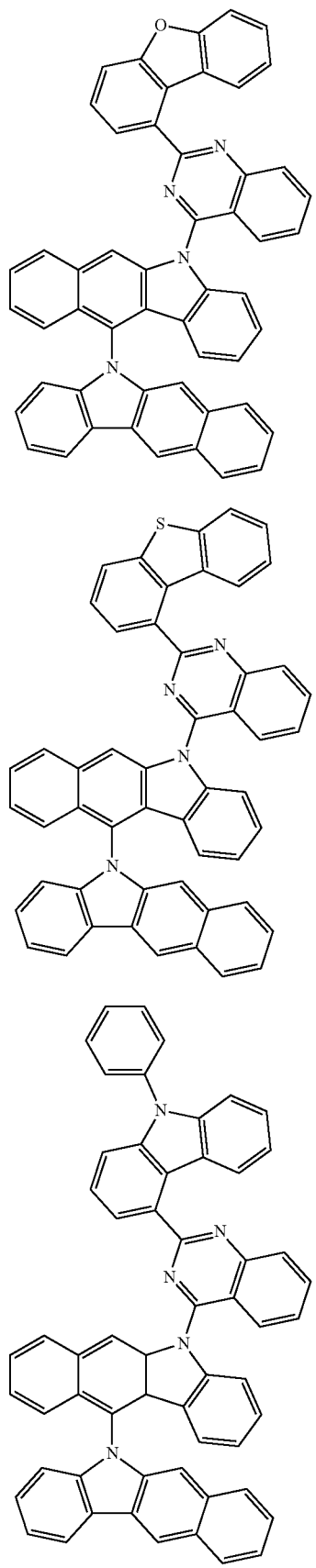
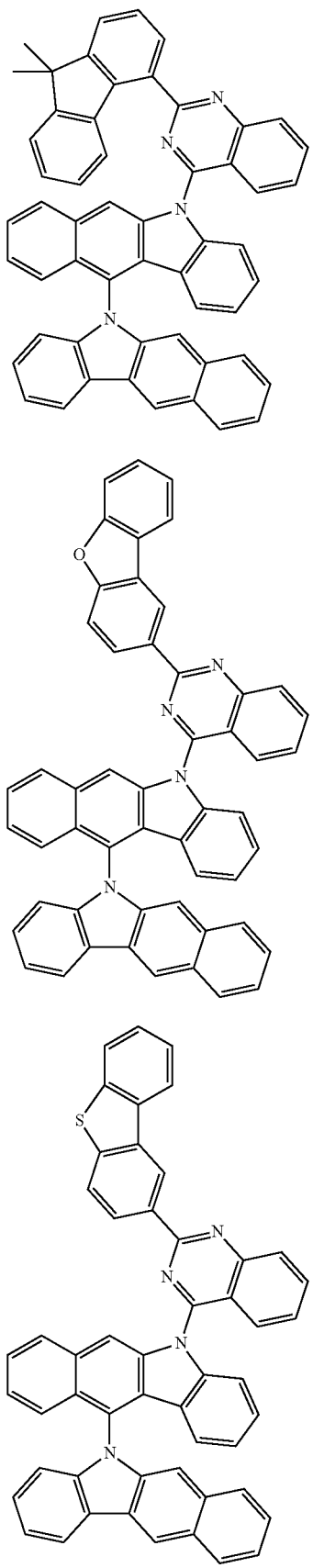

805 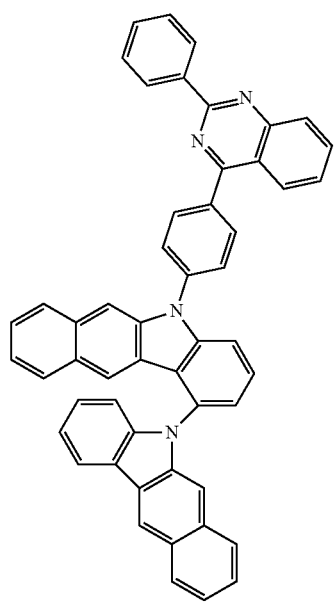
806 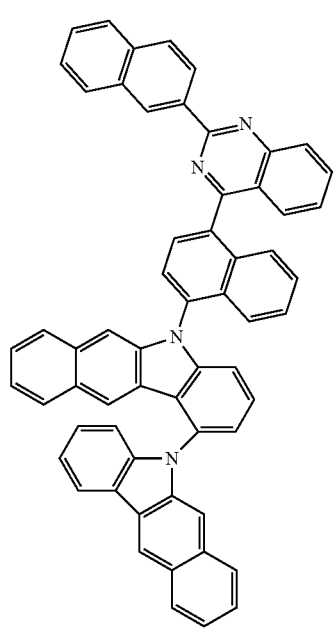
807 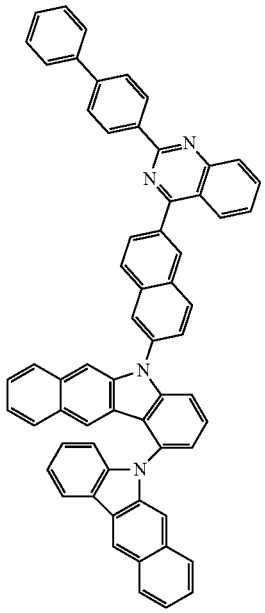
808 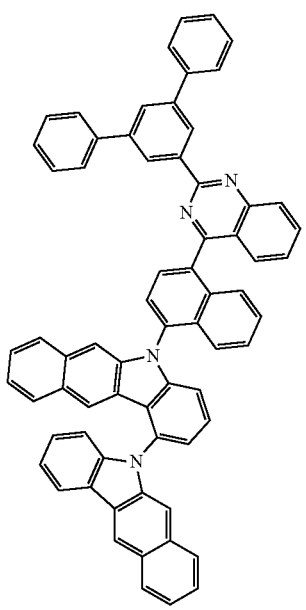

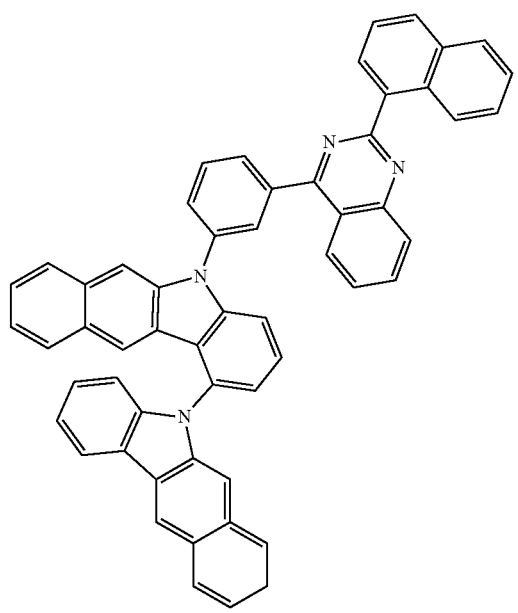
809
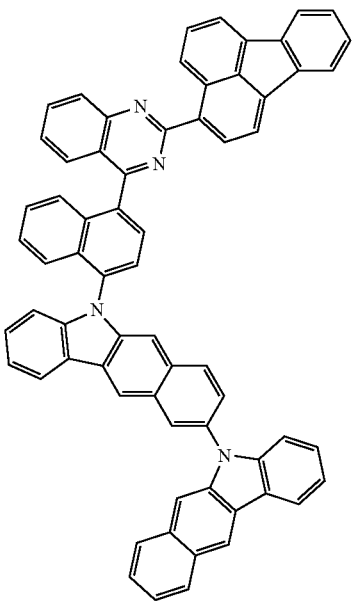
811
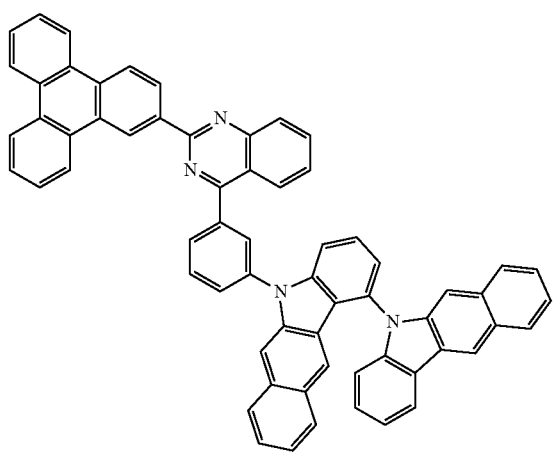
810
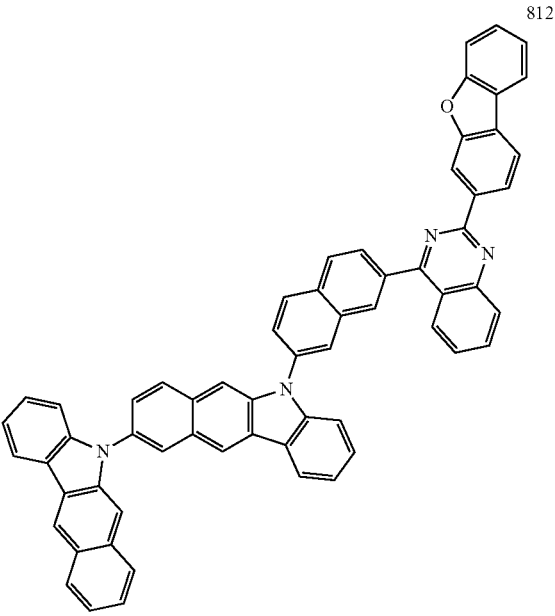
812

361
-continued
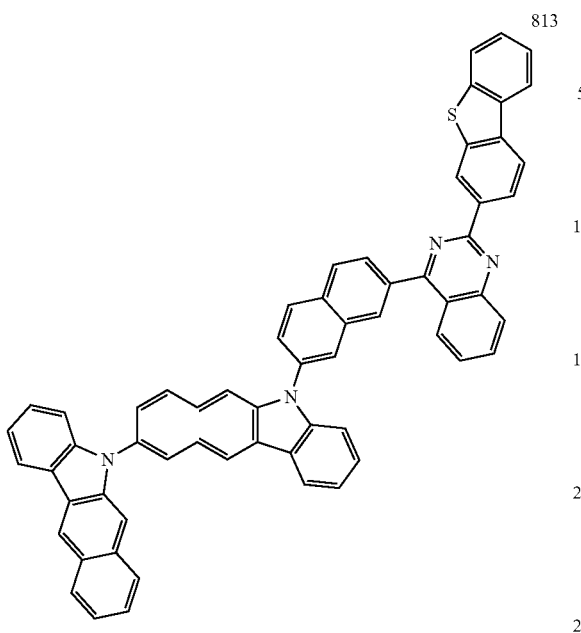
813
362
-continued
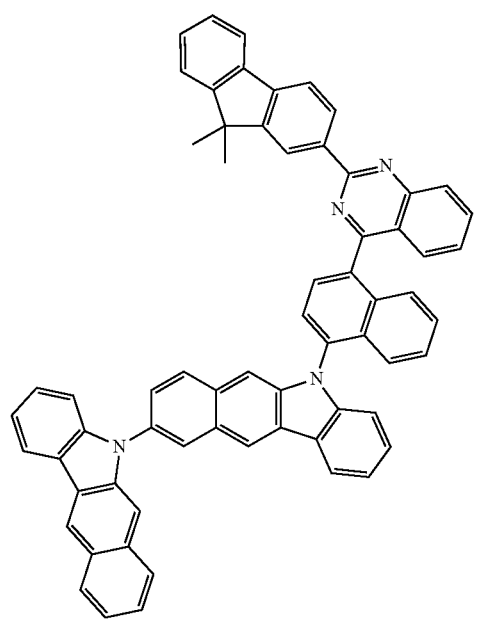
815
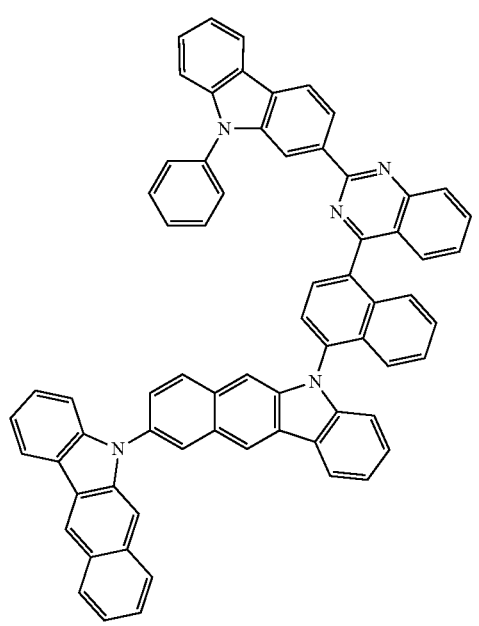
814
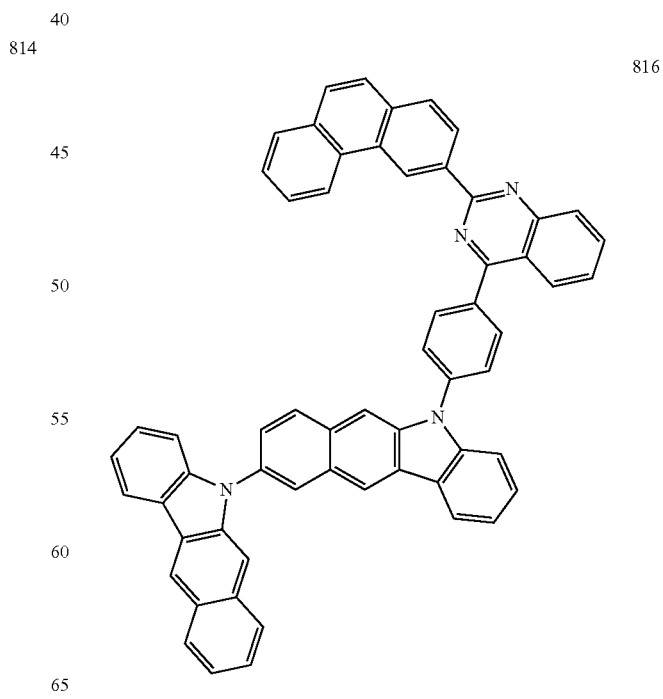
816

363
-continued
817
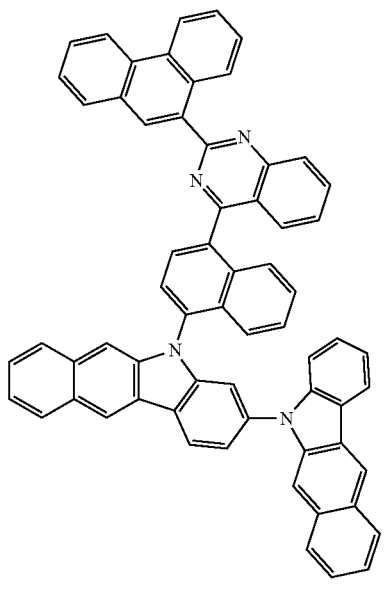
818
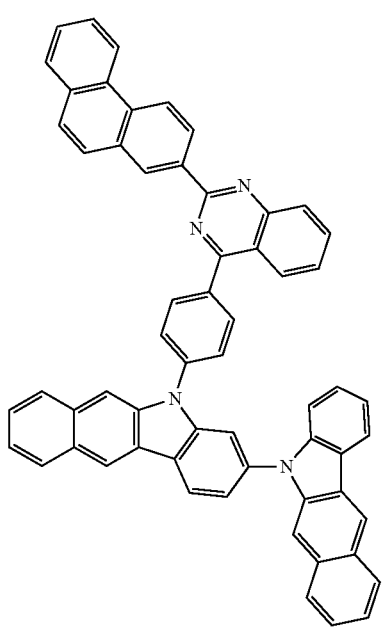
364
-continued
819
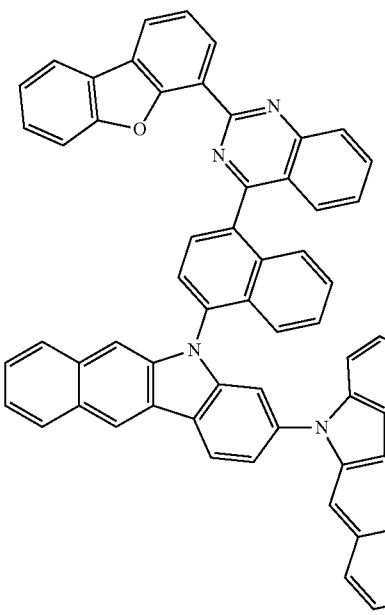
820
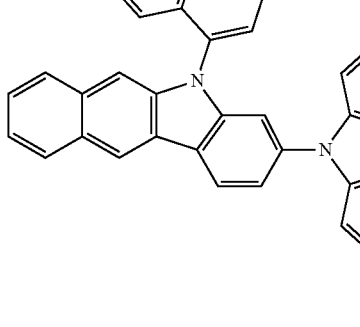

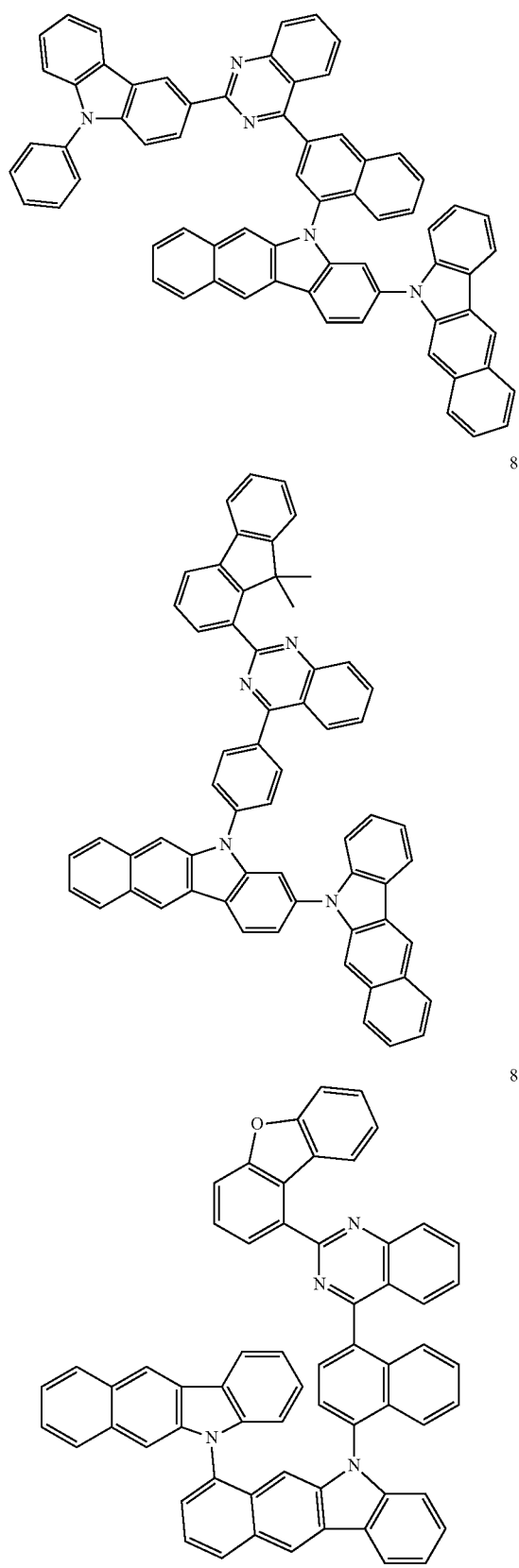
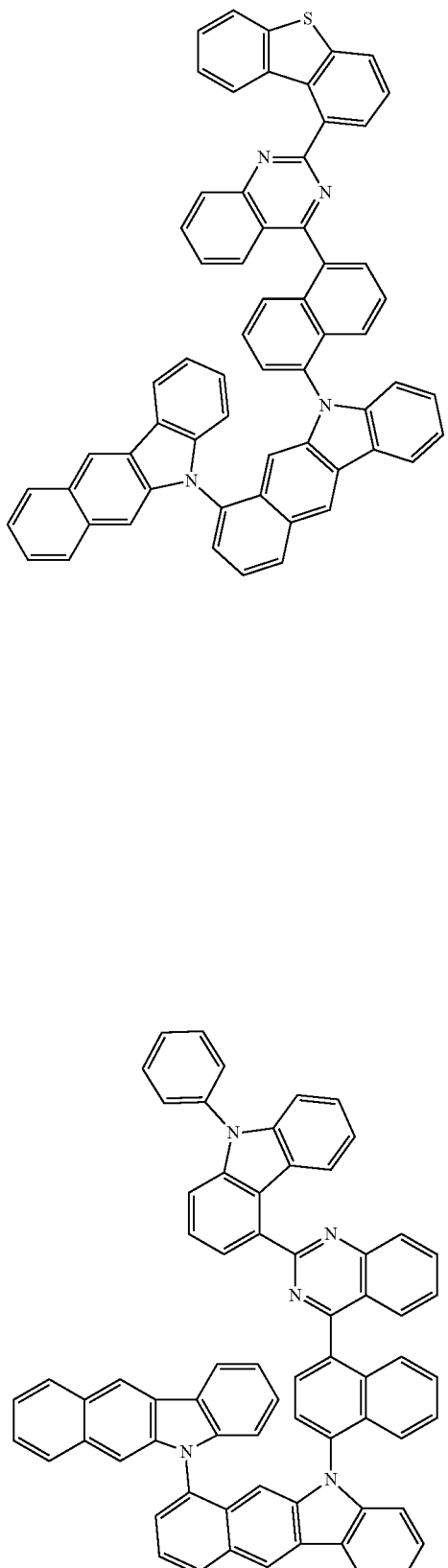

367
-continued
826
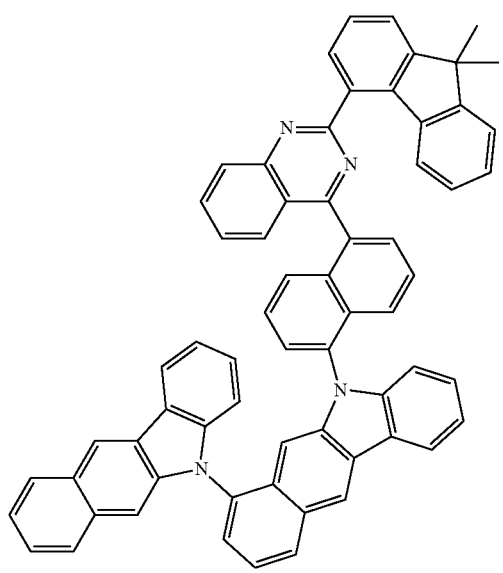
827
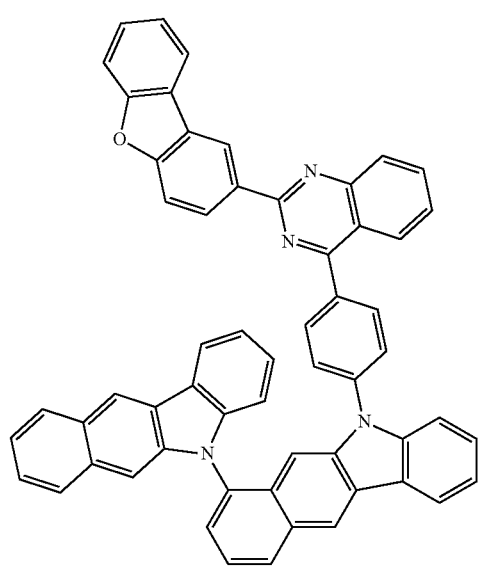
828
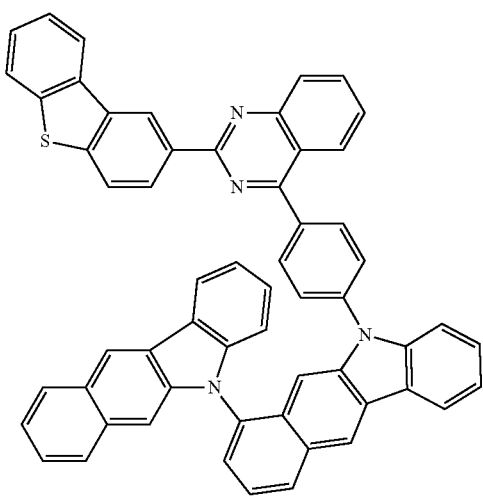
368
-continued
829
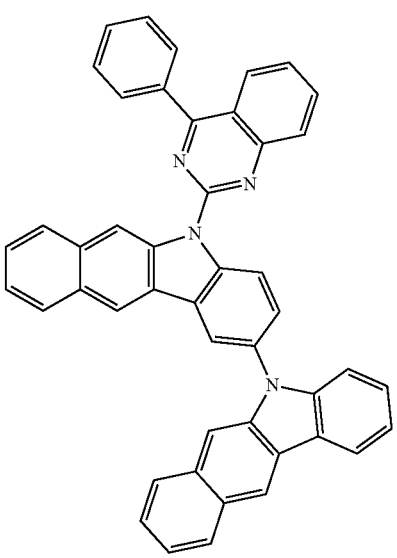
830
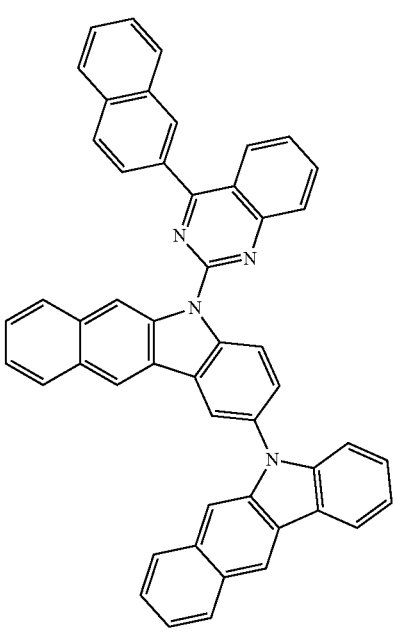

369
-continued
370
-continued
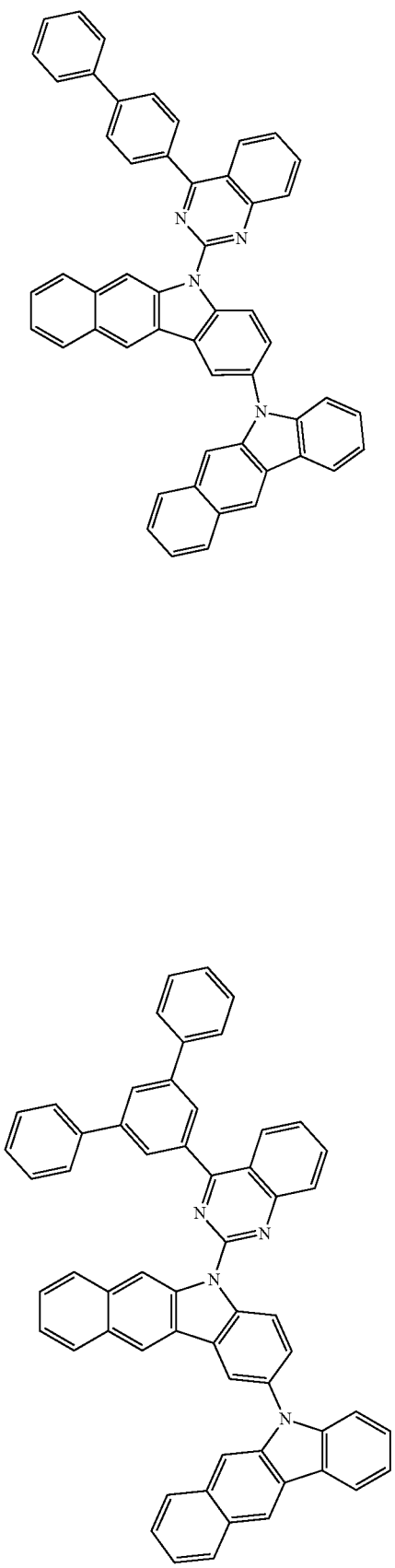
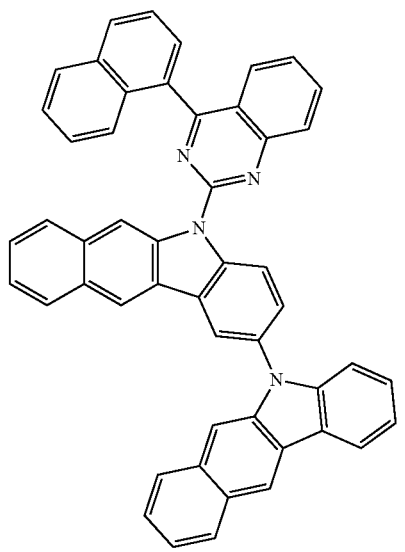
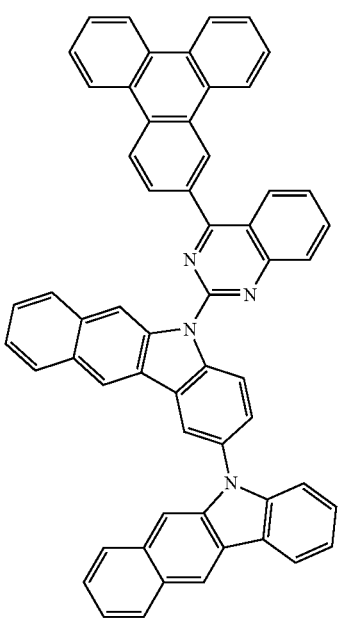
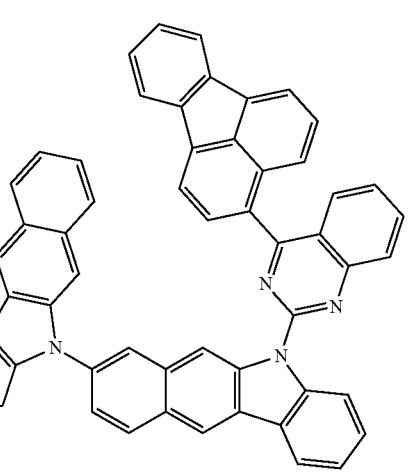

| 836 | 839 |
|---|---|
| 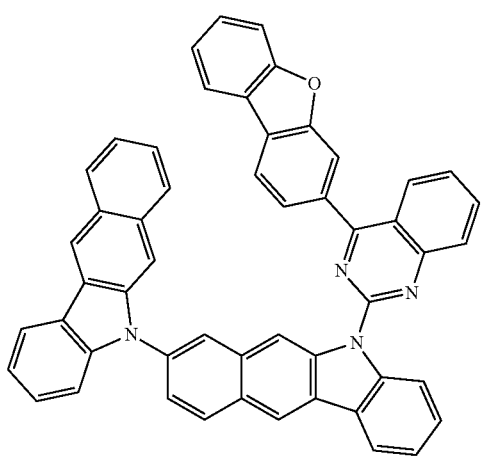 | 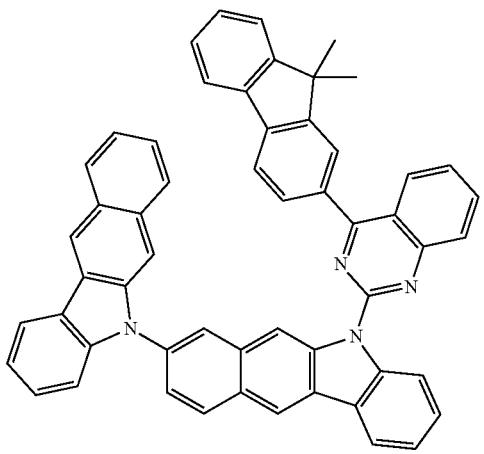 |
| 837 | 840 |
|---|---|
| 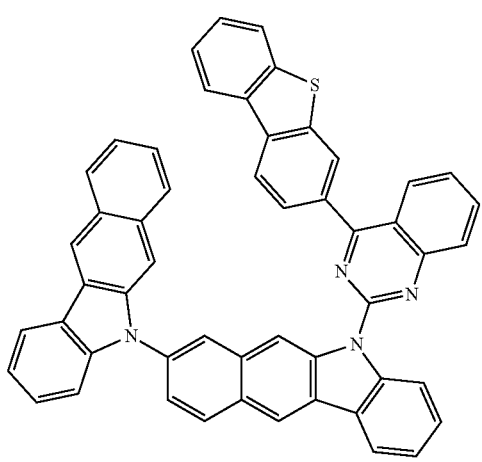 | 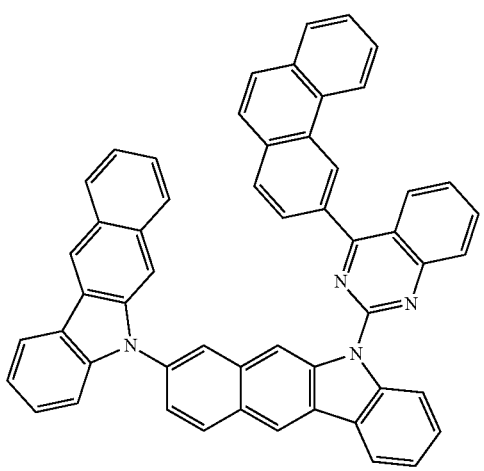 |
| 838 | 841 |
|---|---|
| 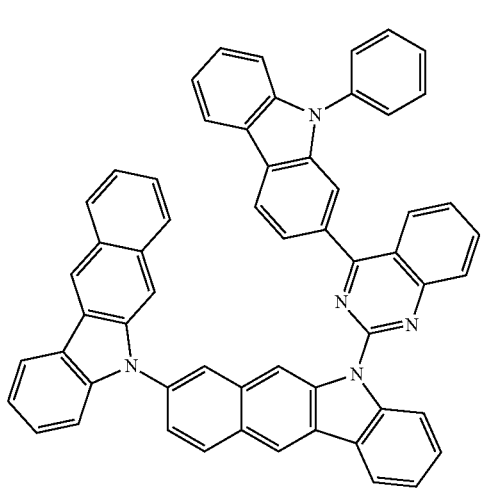 | 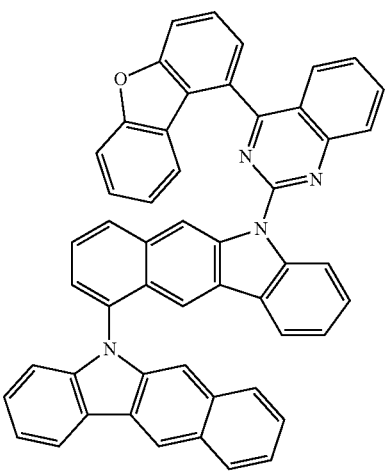 |

842
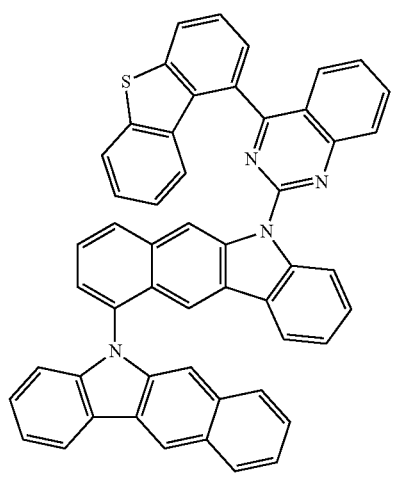
843
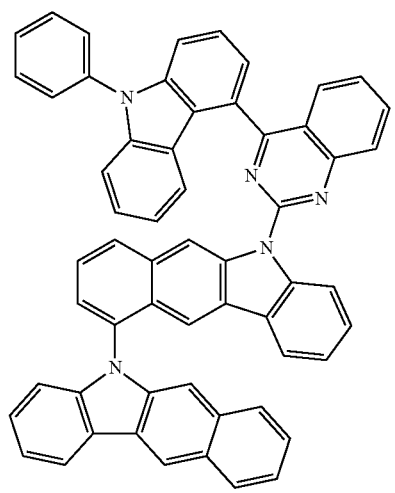
844
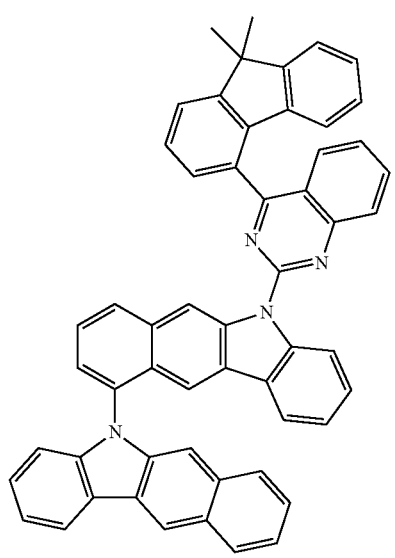
845
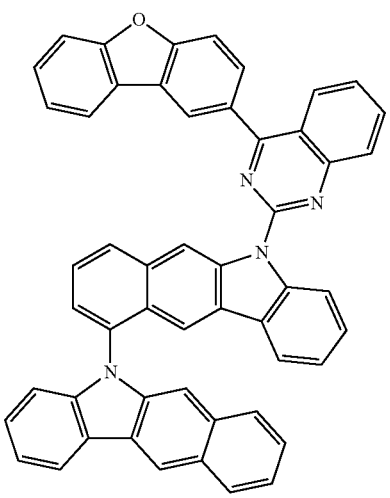
846
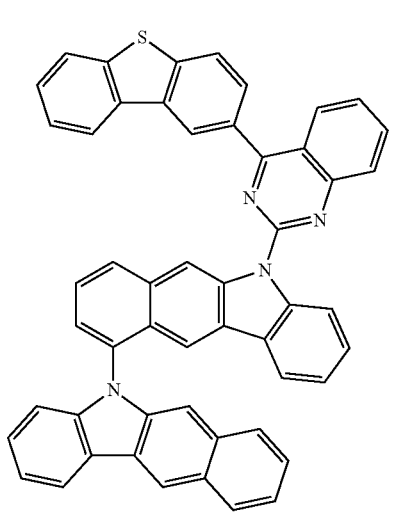
847
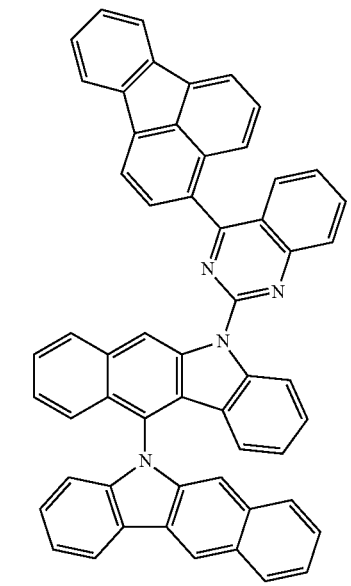

375
-continued
848
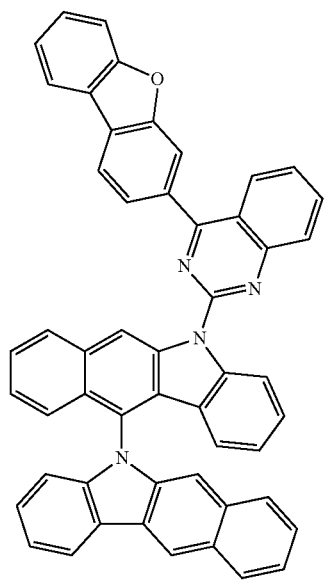
849
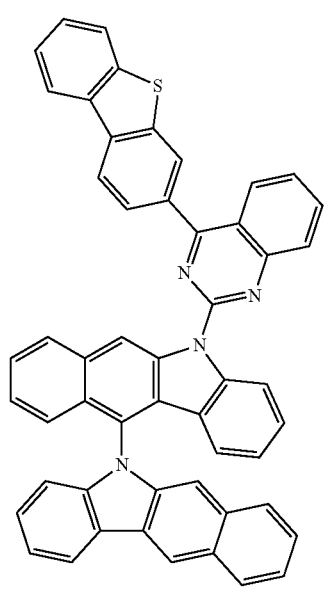
376
-continued
850
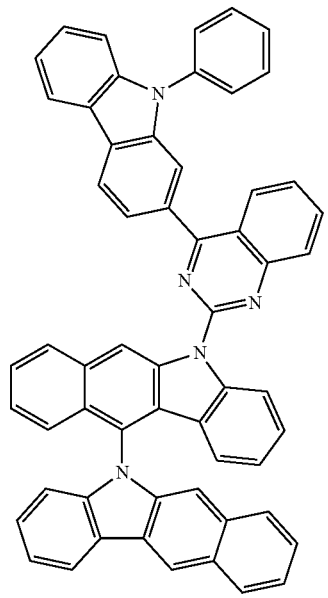
851
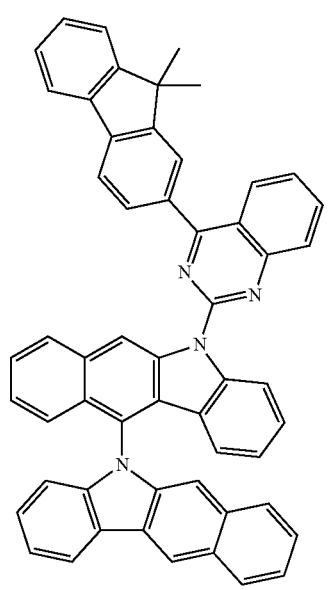

-continued
852
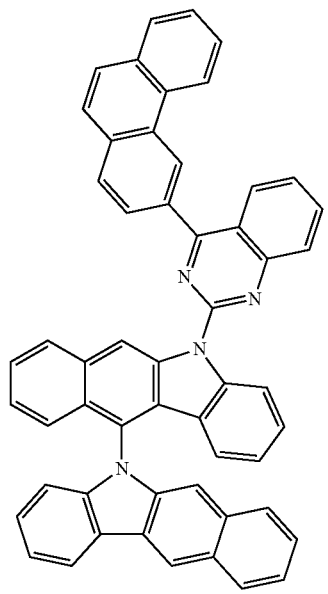
853
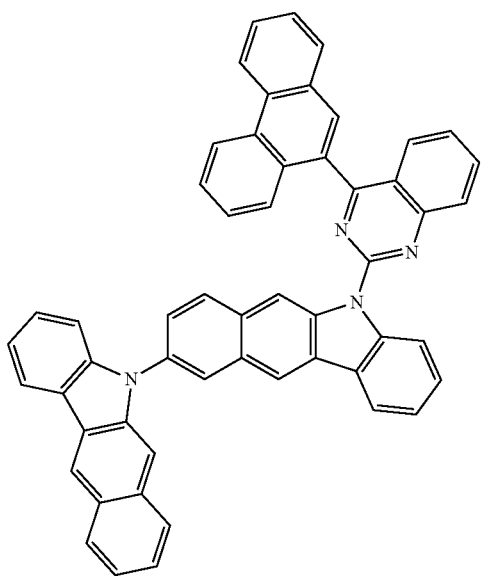
-continued
854
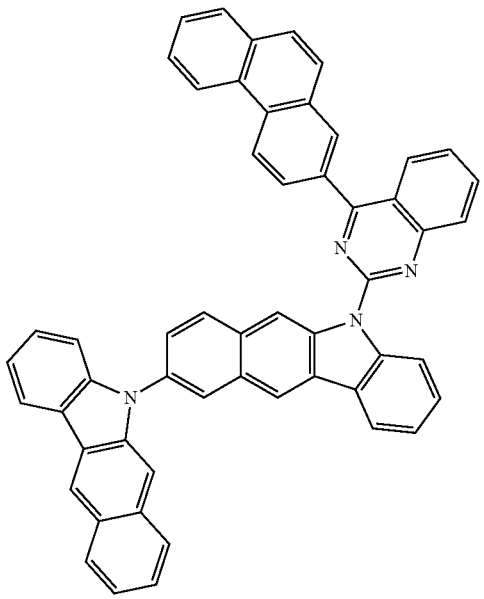
855
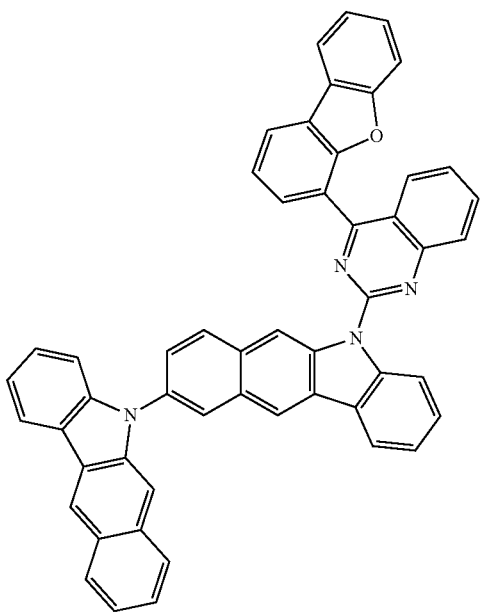

856
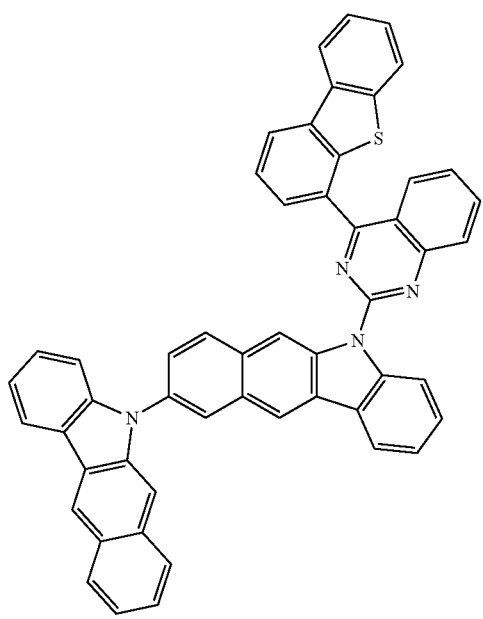
857
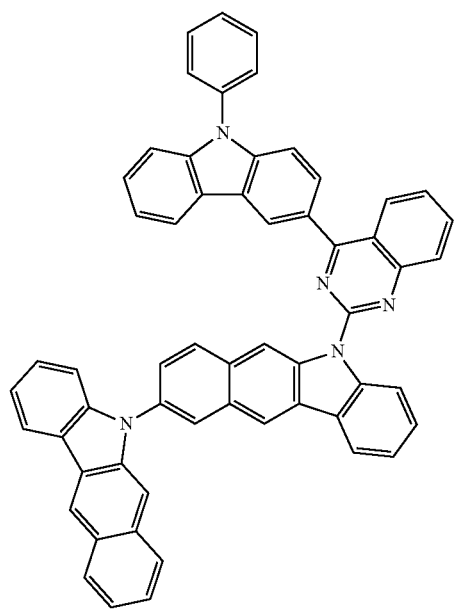
858
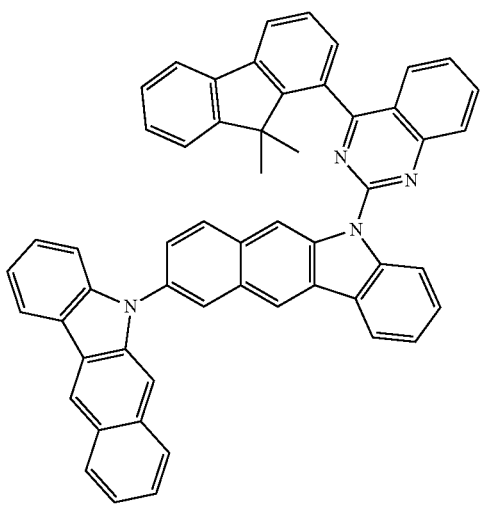
859
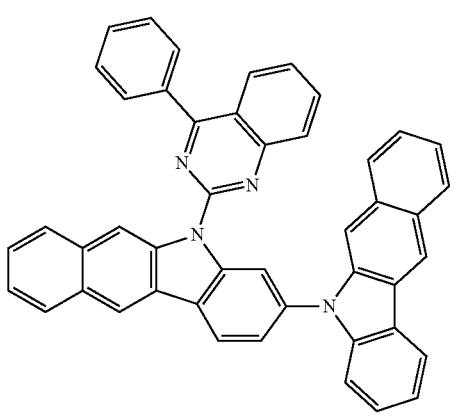
860
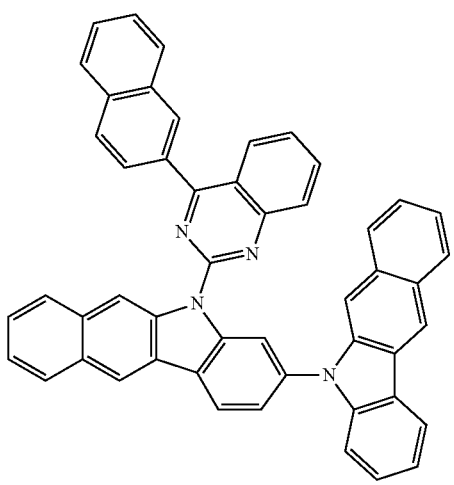

381
-continued
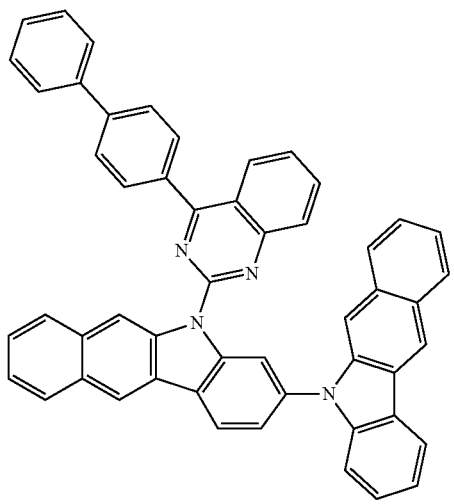
861
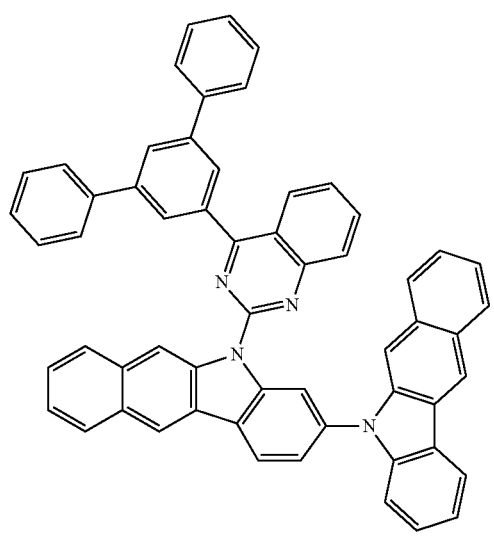
862
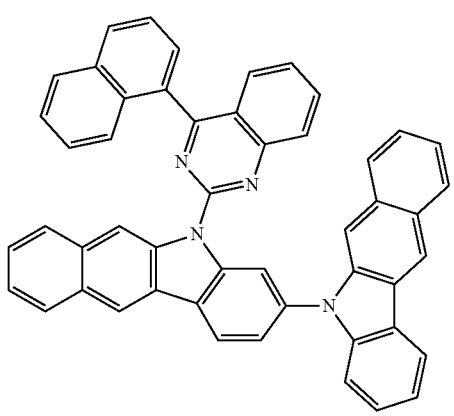
863
382
-continued
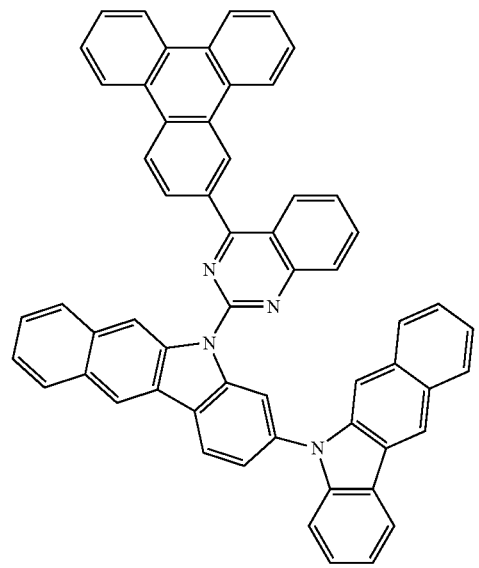
864
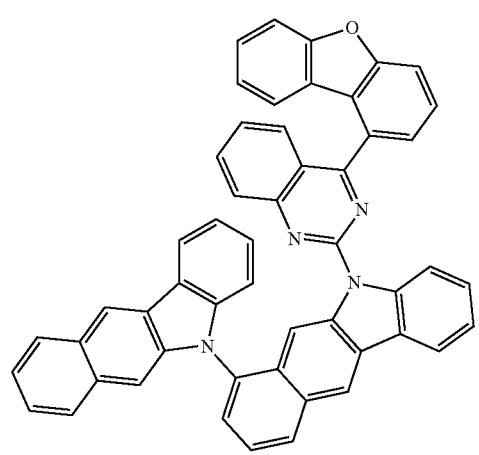
865
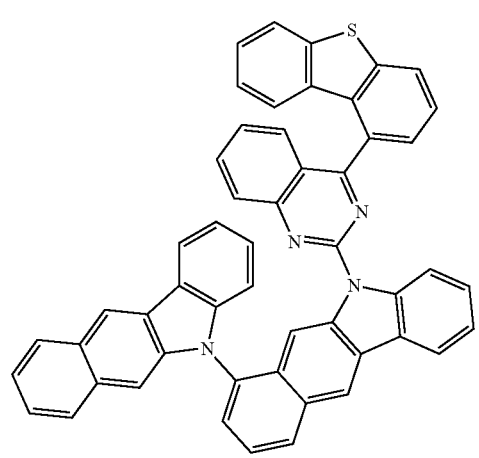
866

383
-continued
867
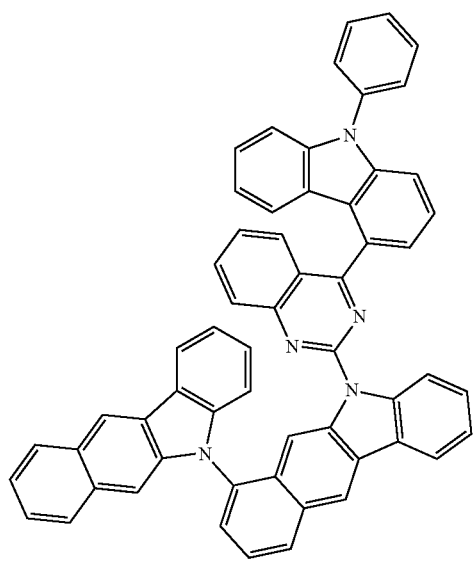
868
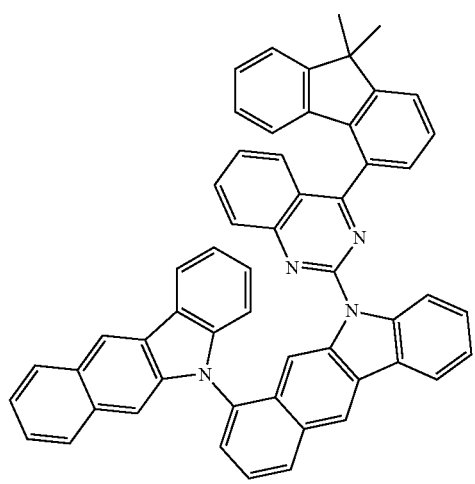
869
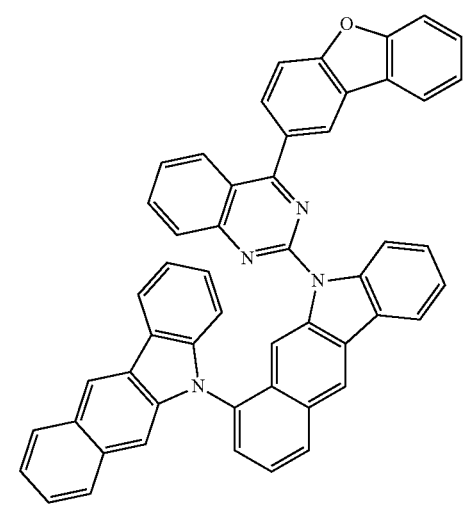
384
-continued
870
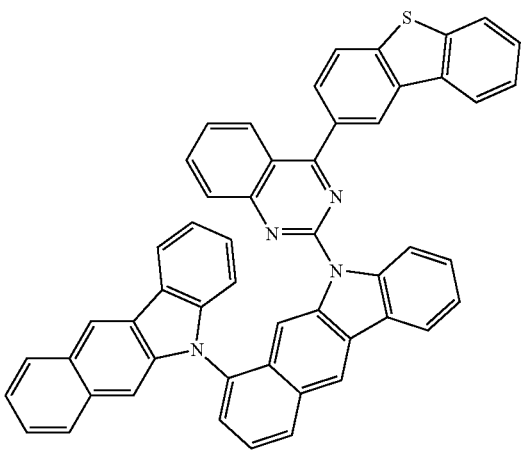
871
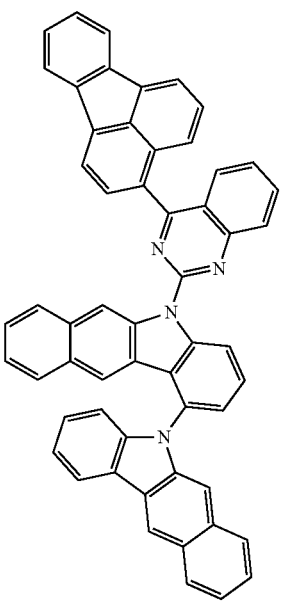

385
-continued
872
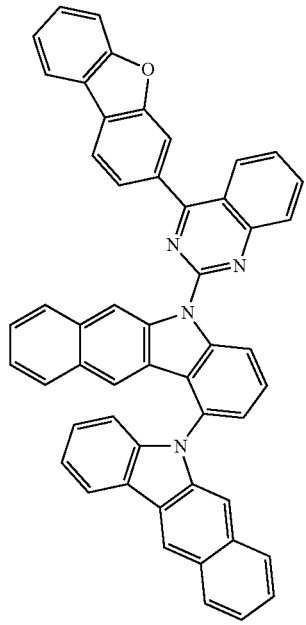
873
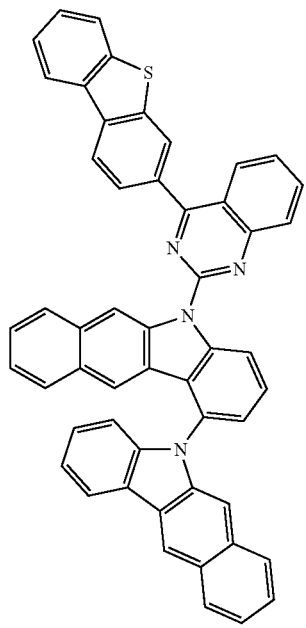
386
-continued
874
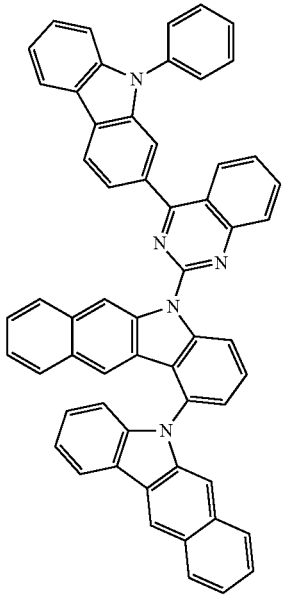
875
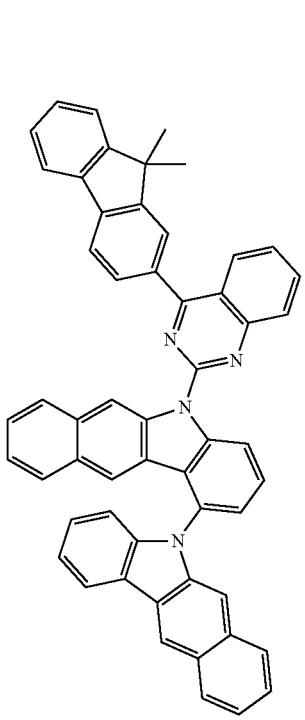

387
-continued
876
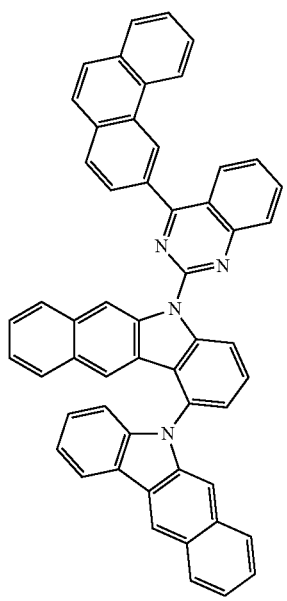
388
-continued
878
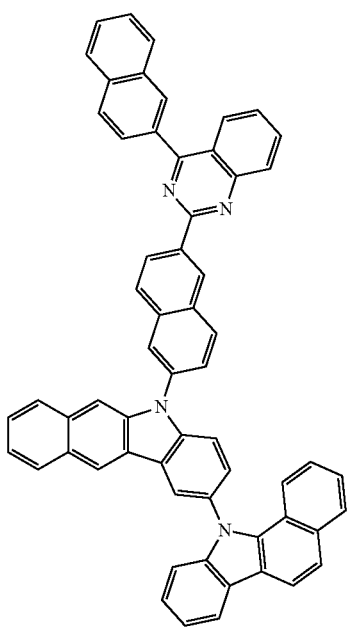
877
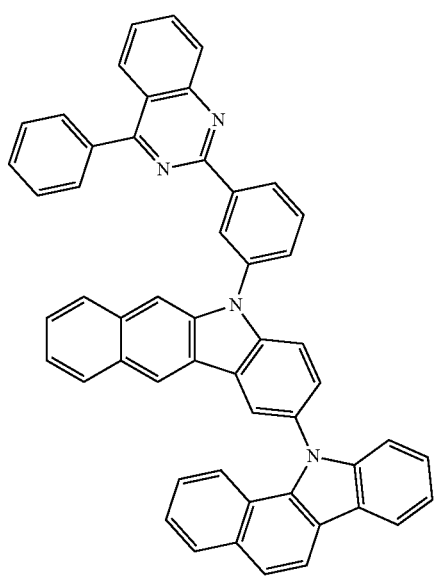
879
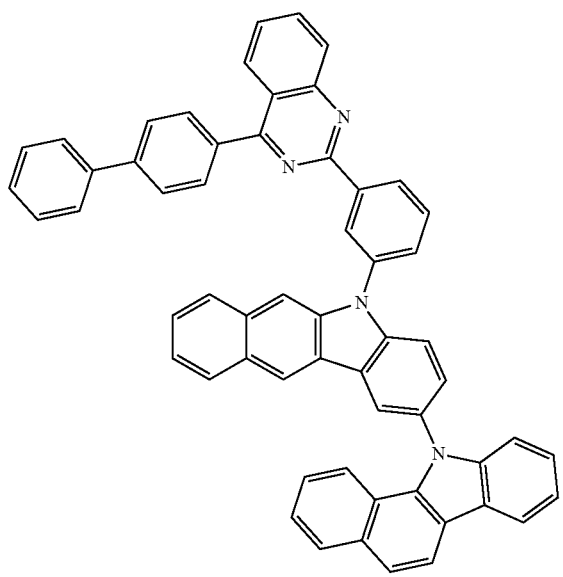

389
-continued
880
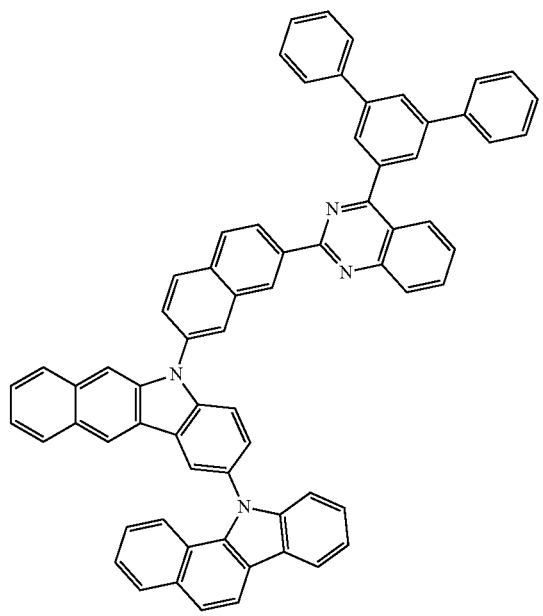
881
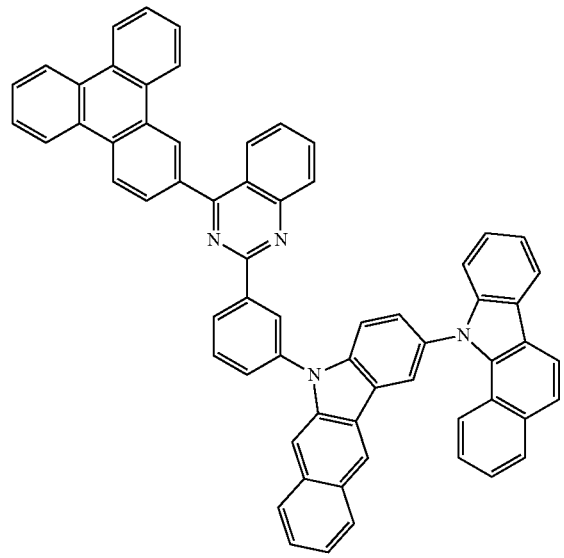
390
-continued
882
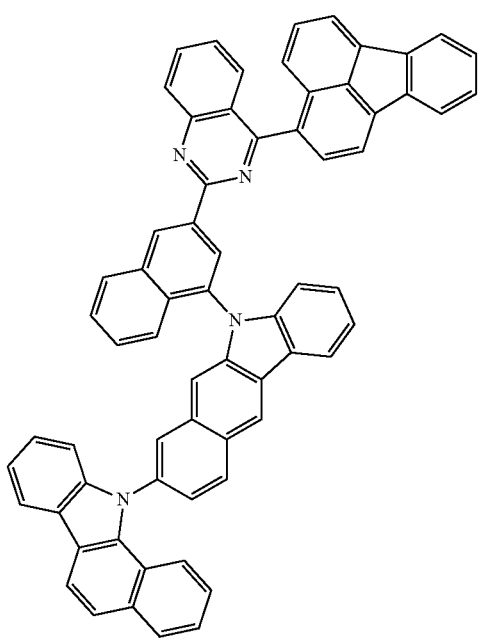
883

391
-continued
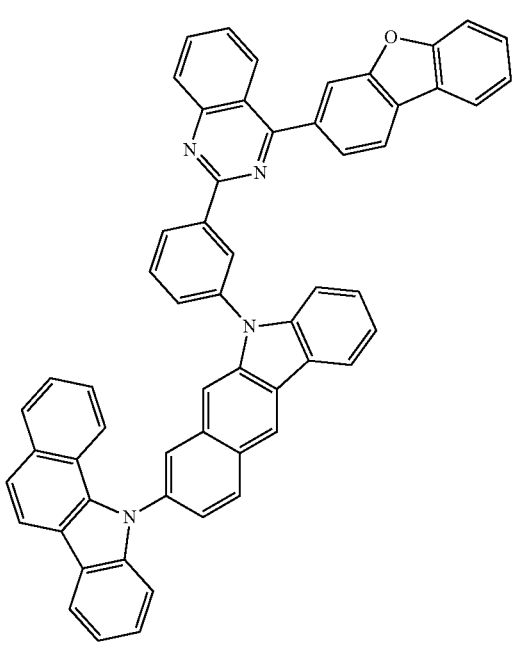
884
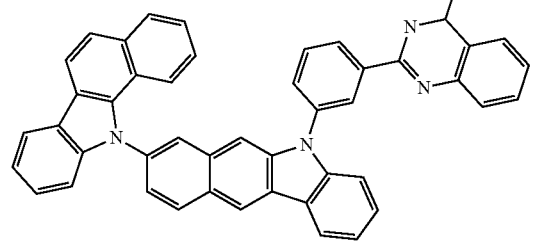
885
392
-continued
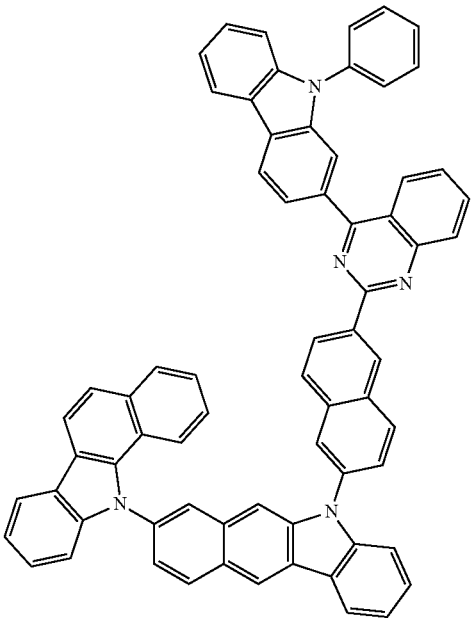
886
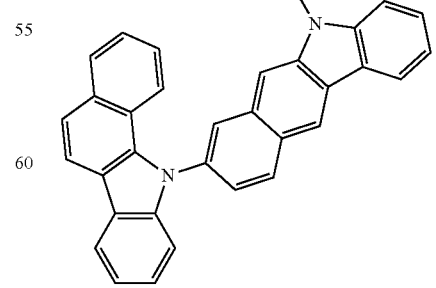
887

393
-continued
888
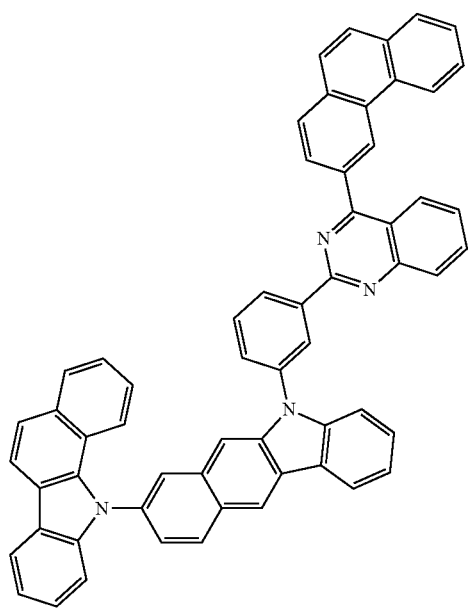
889
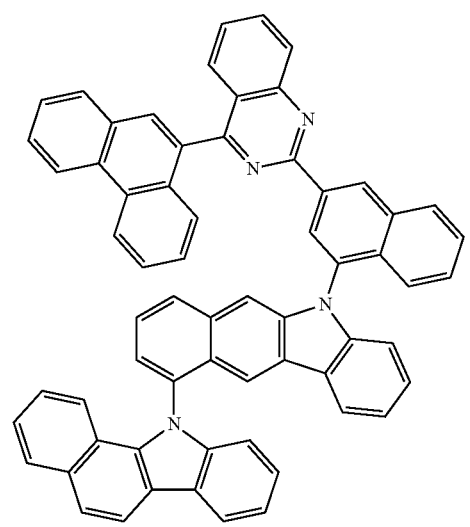
890
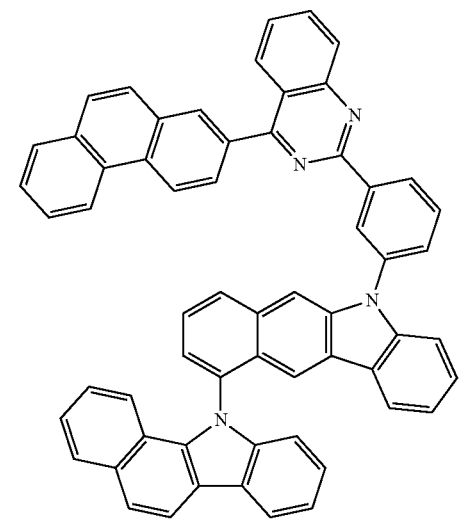
394
-continued
891
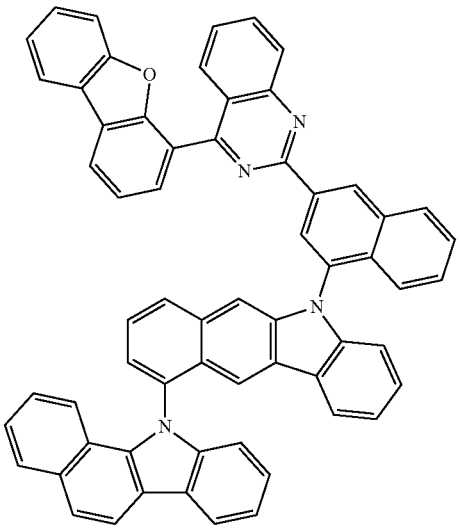
892
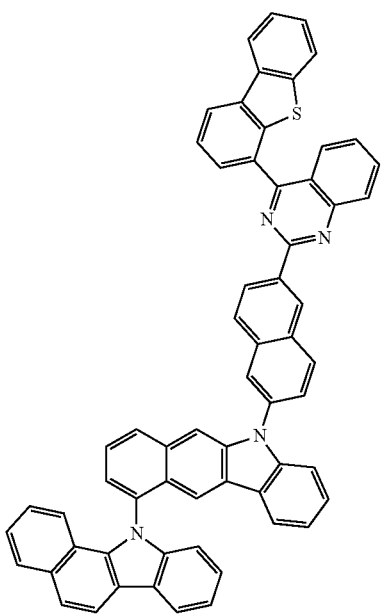

395
-continued
893
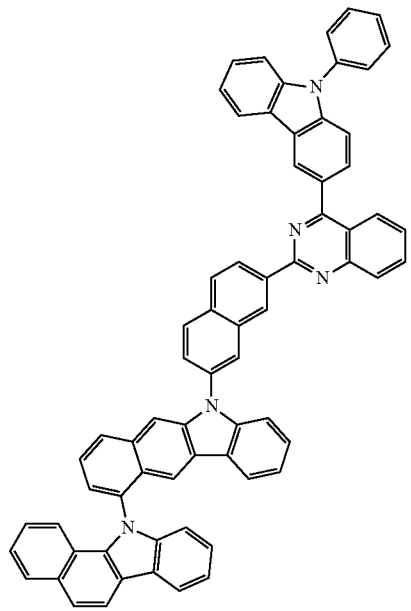
894
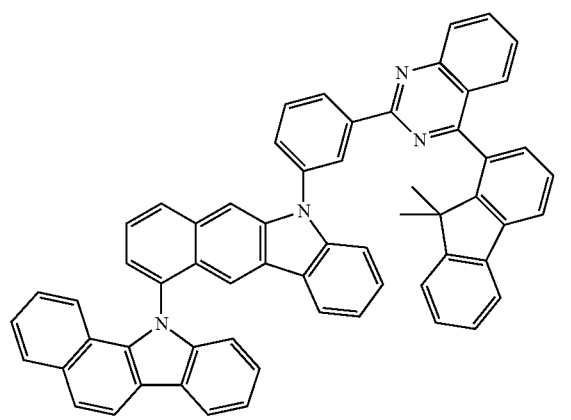
895
396
-continued
896
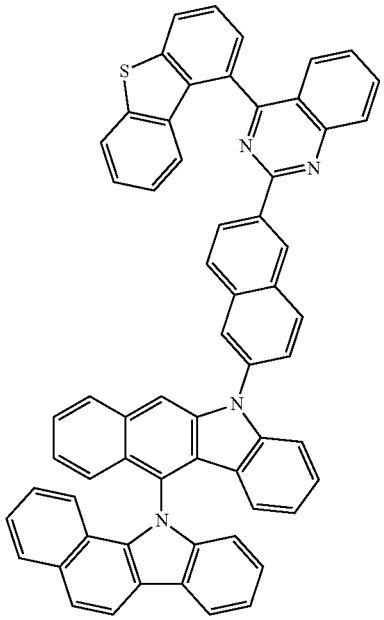
897
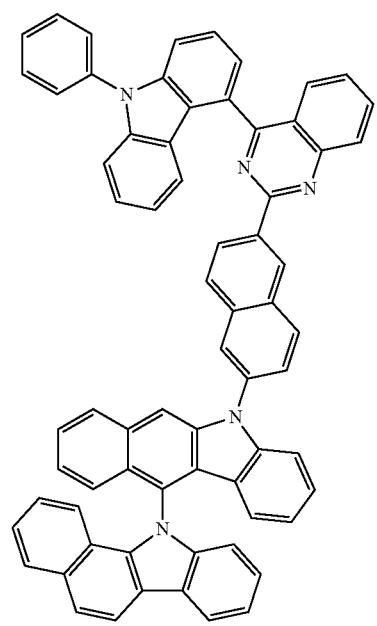

397
-continued
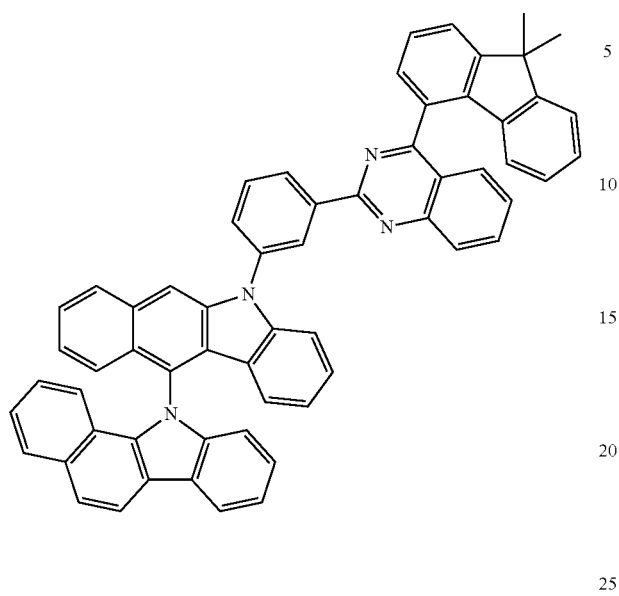
898
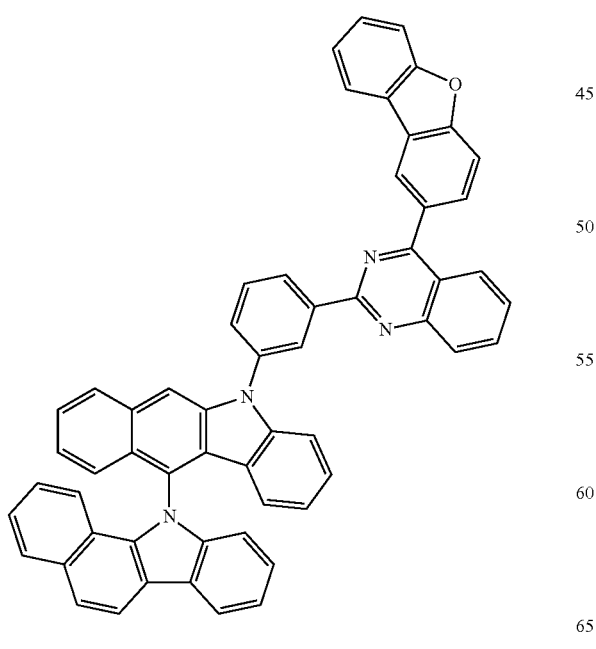
899
398
-continued
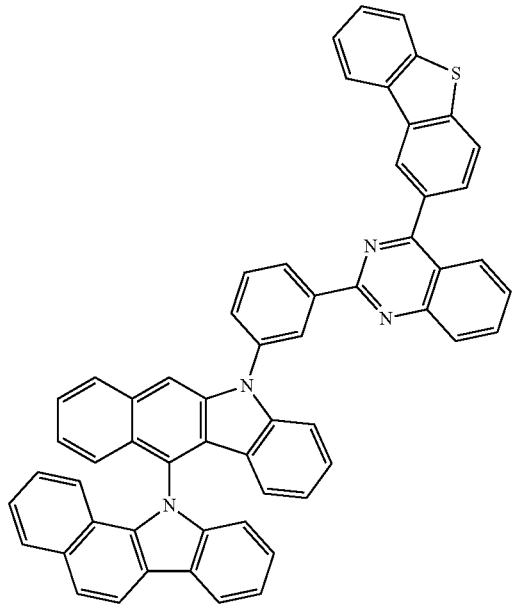
900
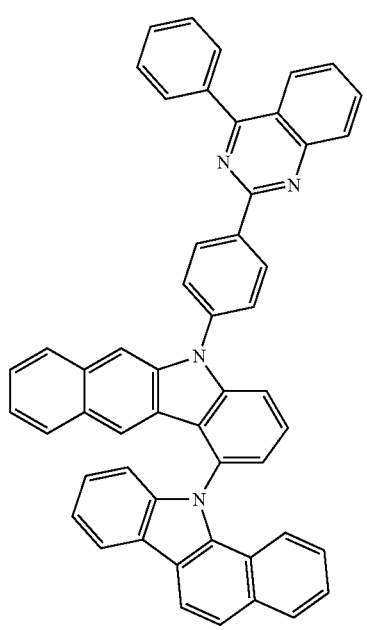
901

399
-continued
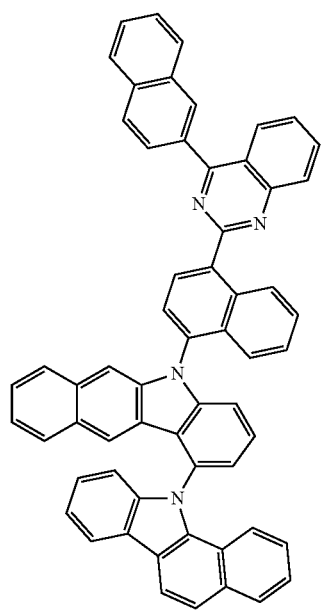
902
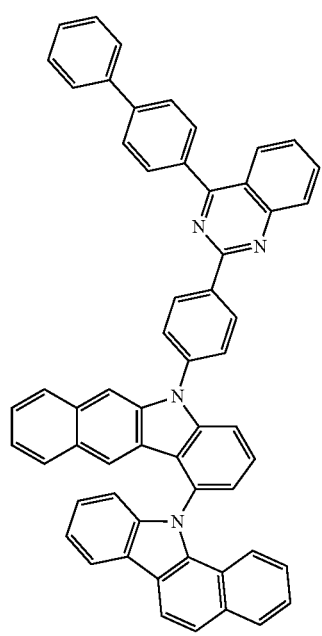
903
400
-continued
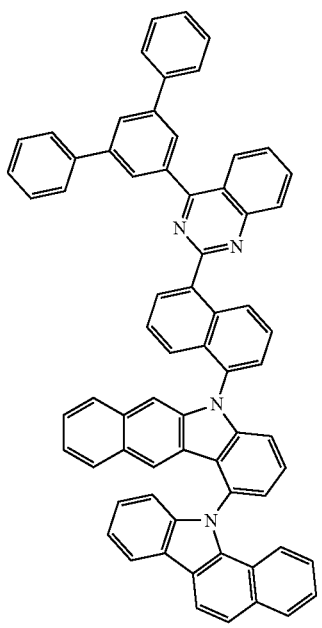
904
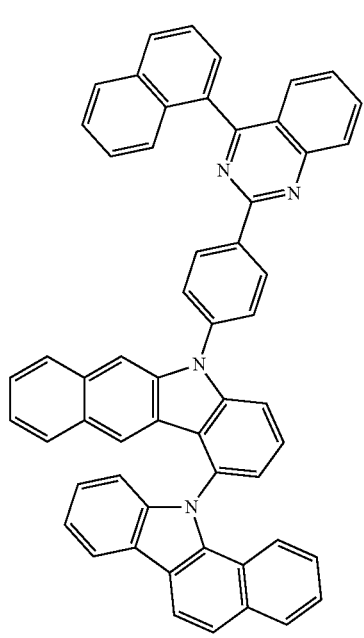
905

401
-continued
402
-continued
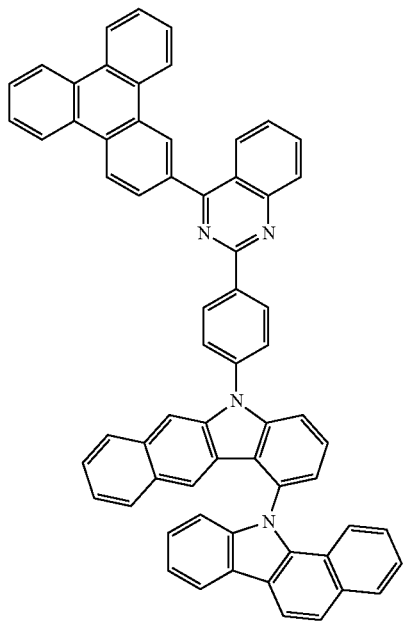
906
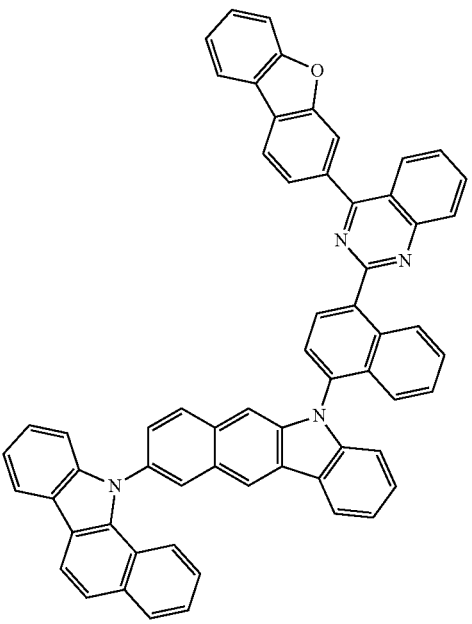
908
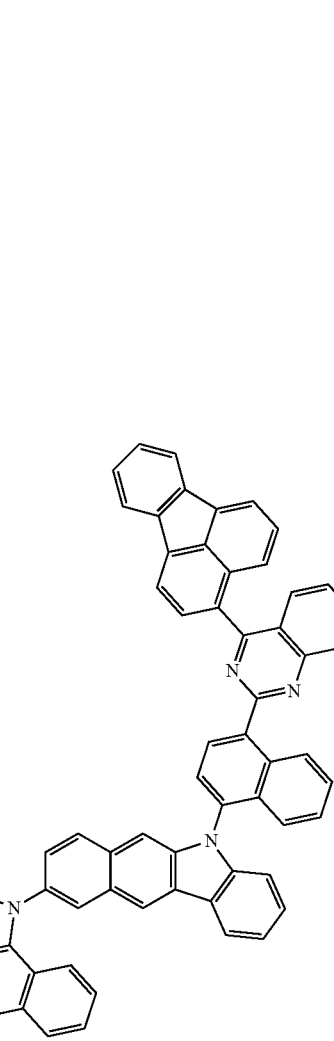
907
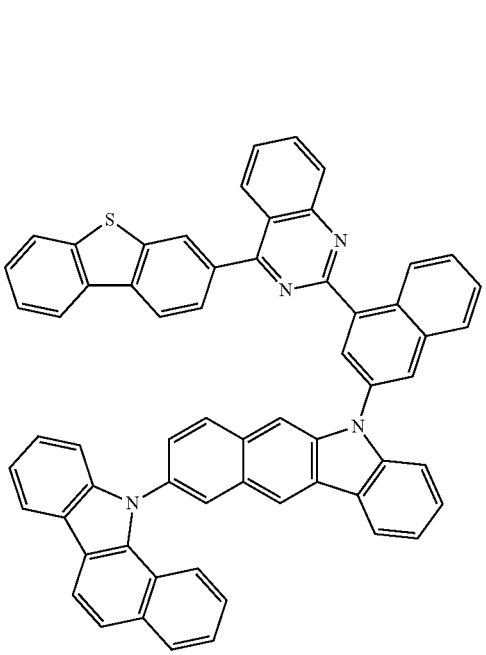
909

403
-continued
910
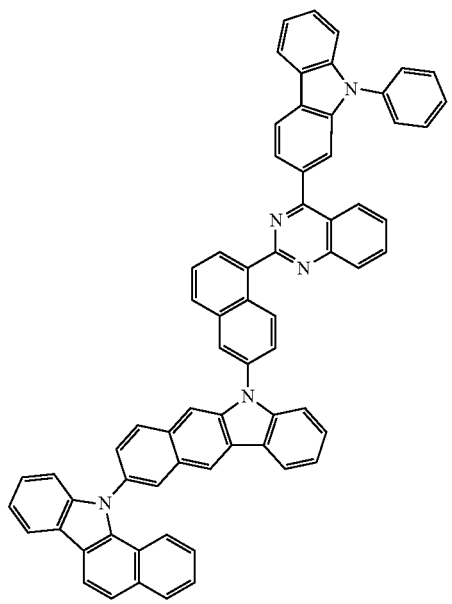
911
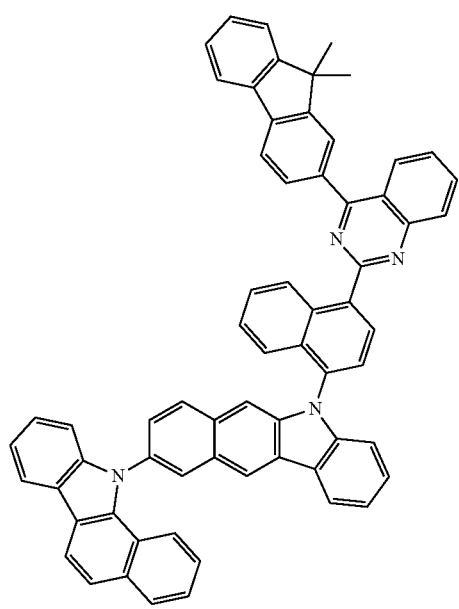
404
-continued
912
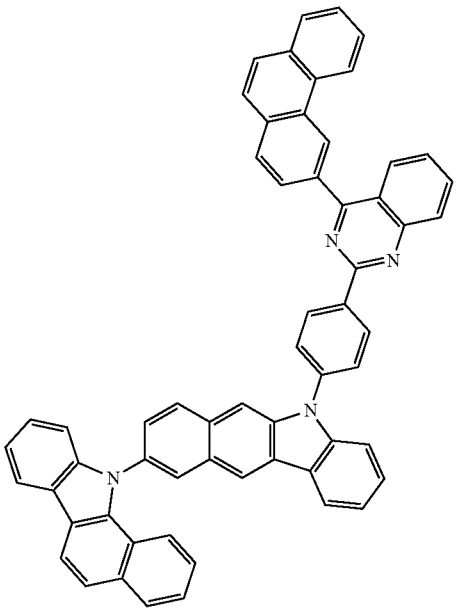
913
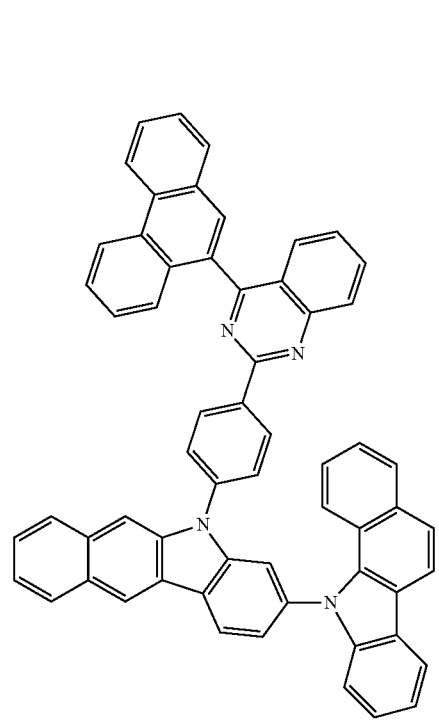

405
-continued
406
-continued
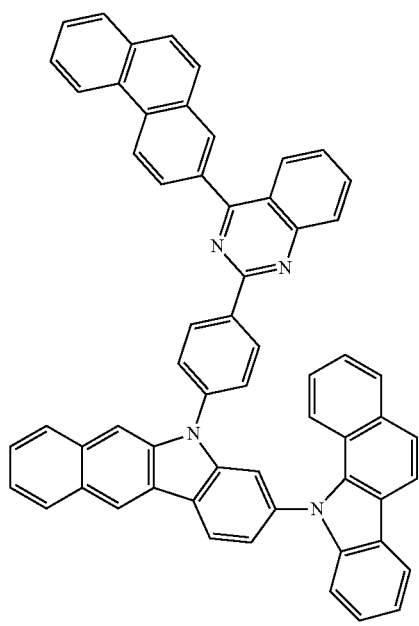
914
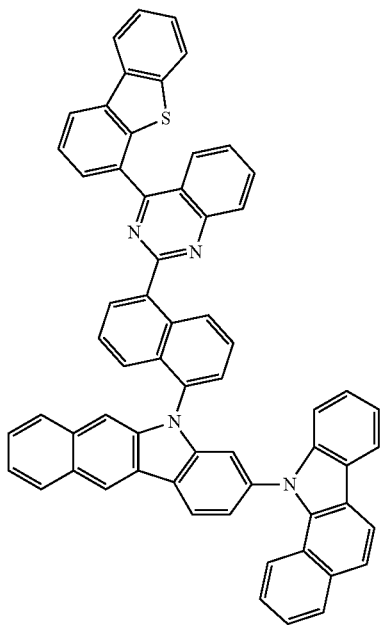
916
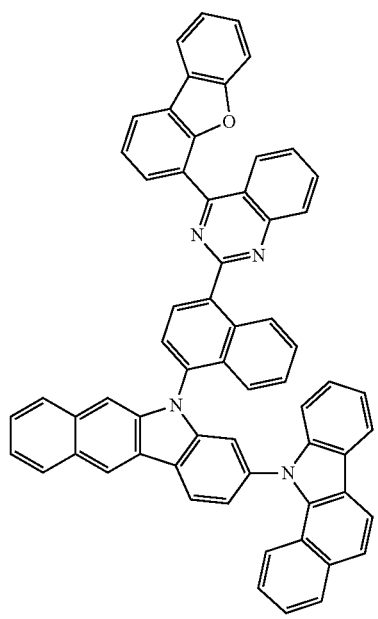
915
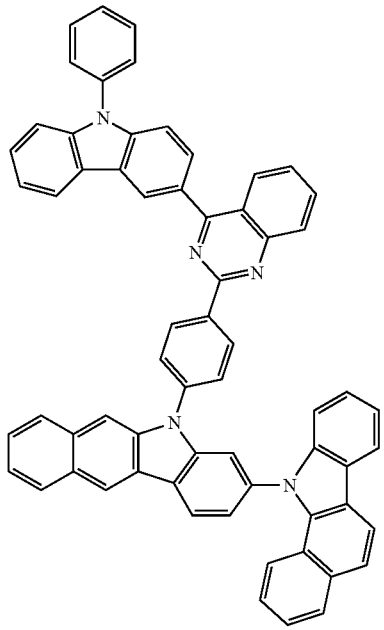
917

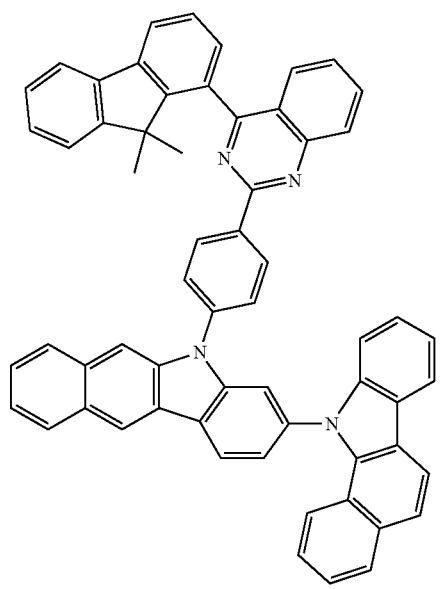
918
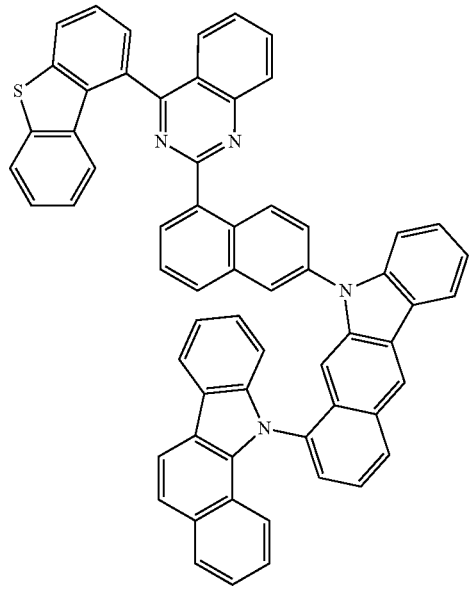
920
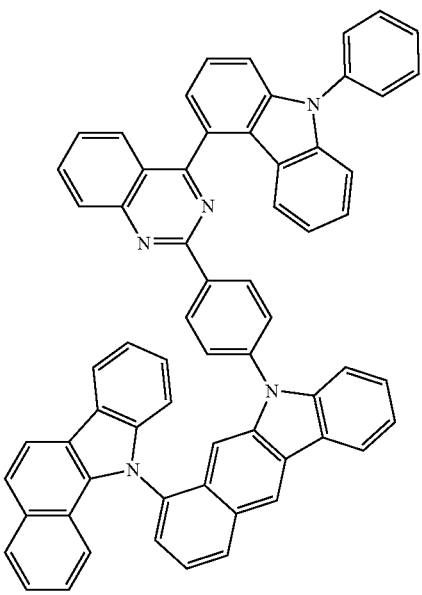
919

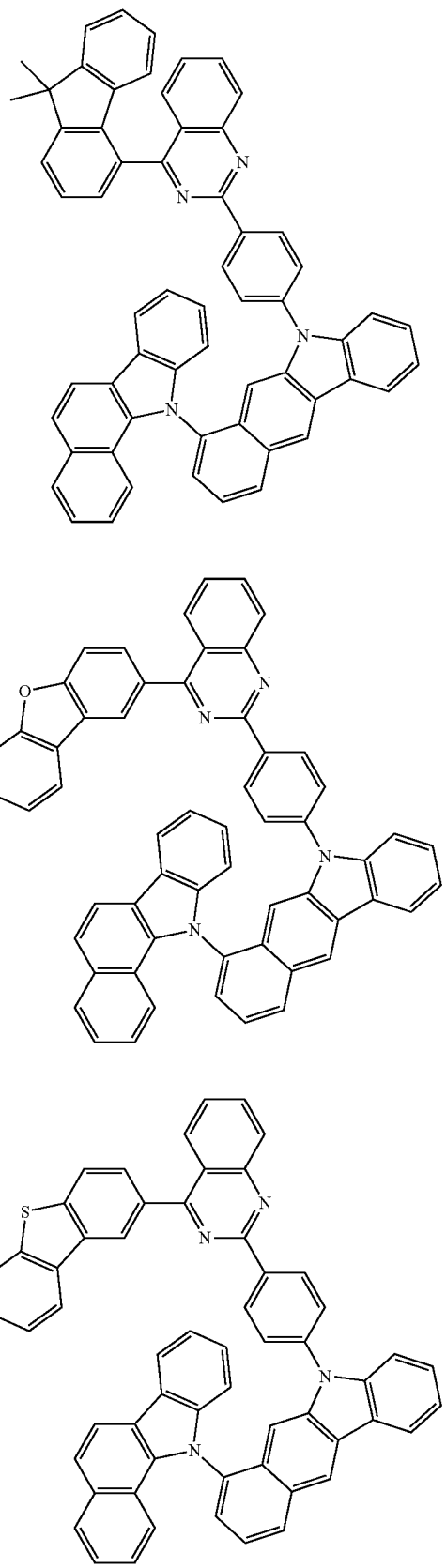
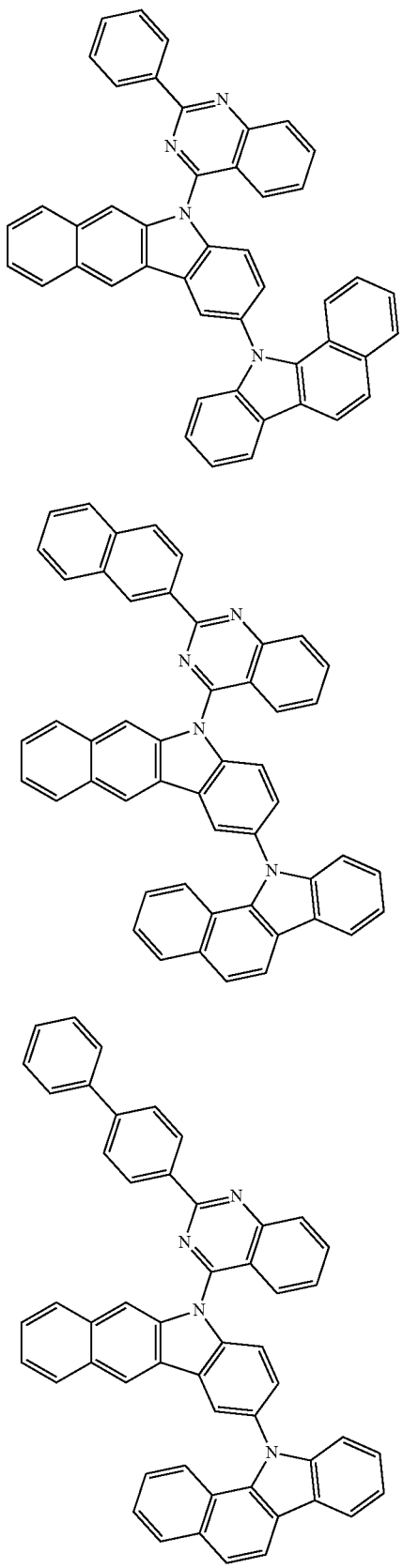

411
-continued
928
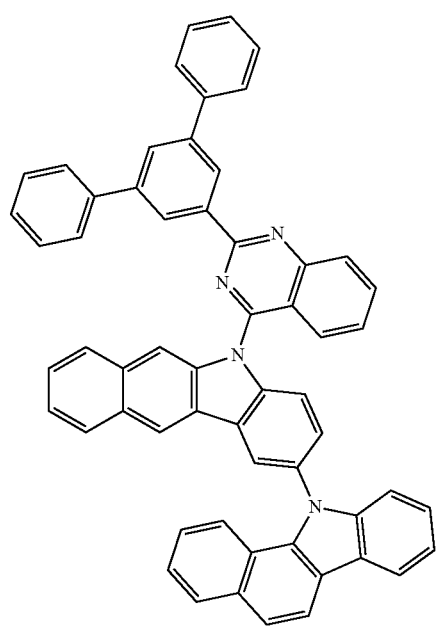
929
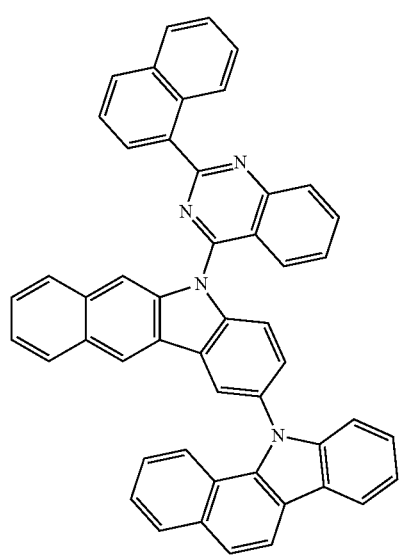
412
-continued
930
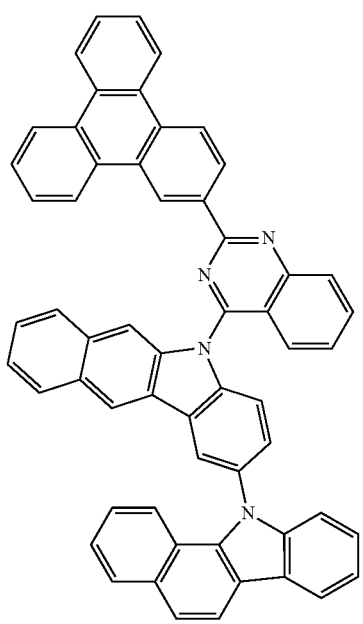
931
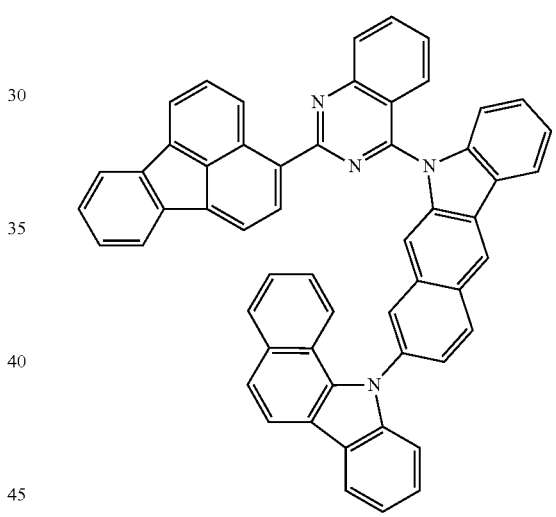
932
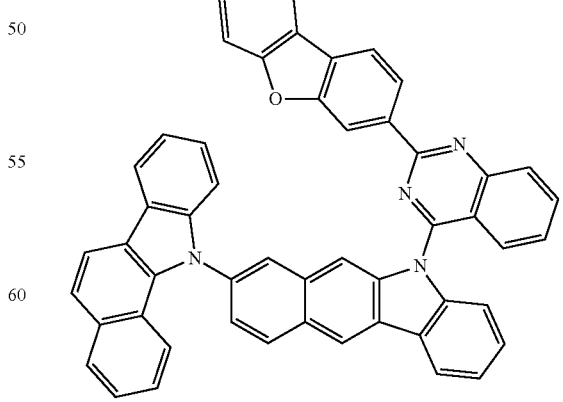

413
-continued
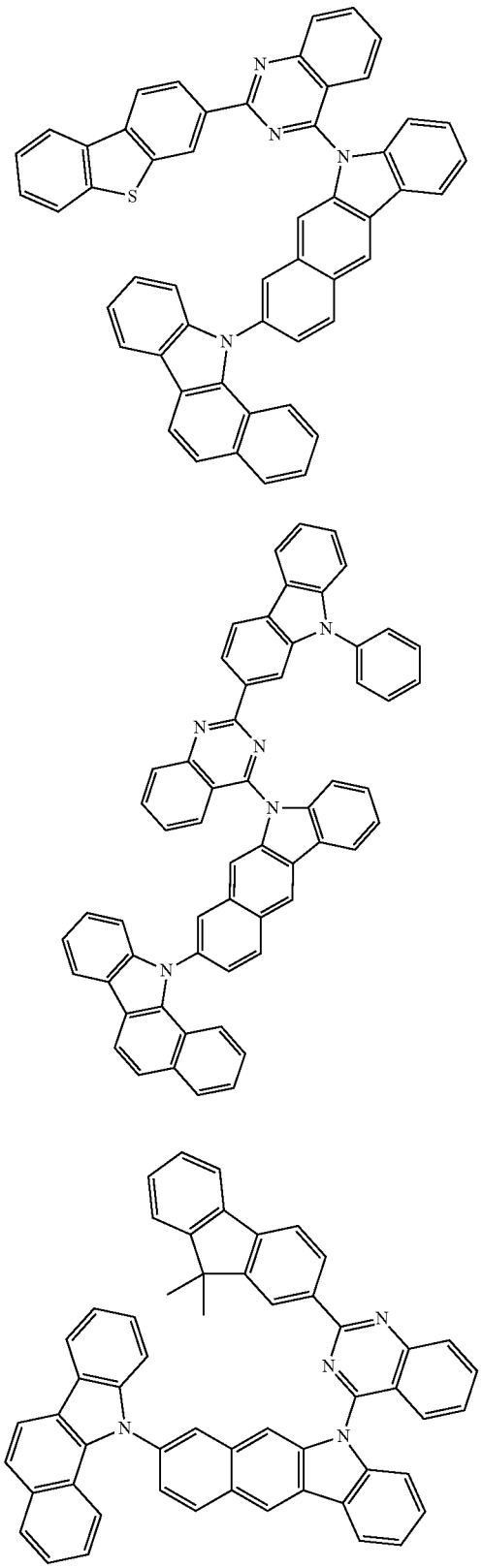
933
934
935
414
-continued
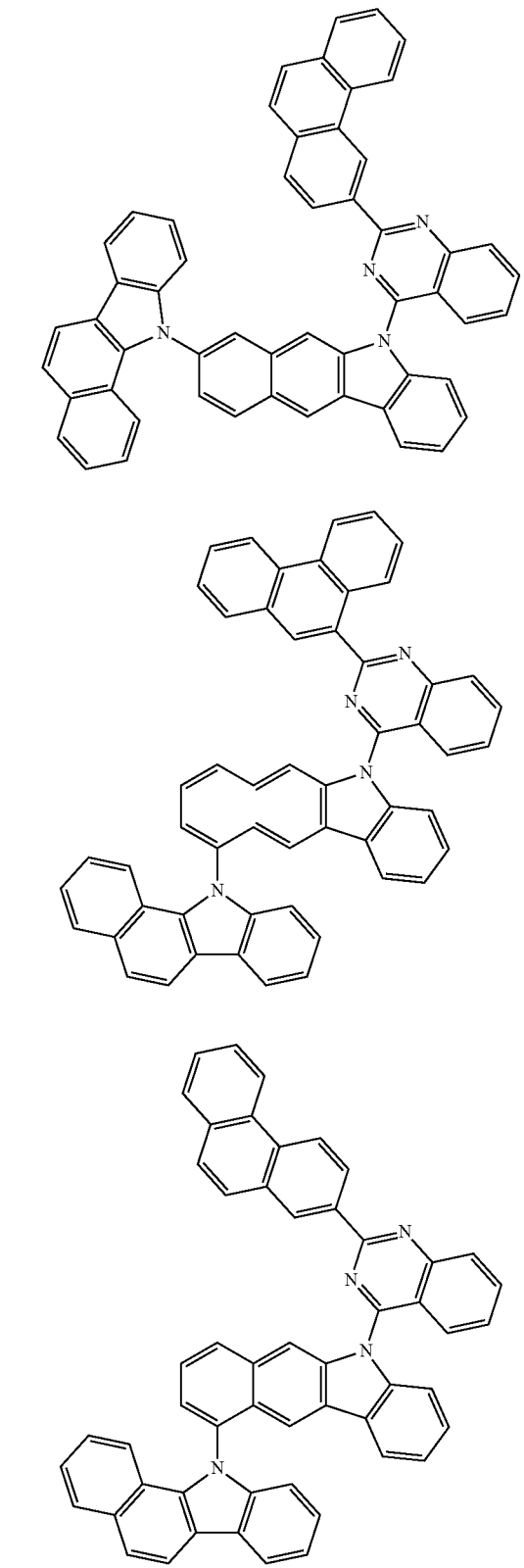
936
937
938

939
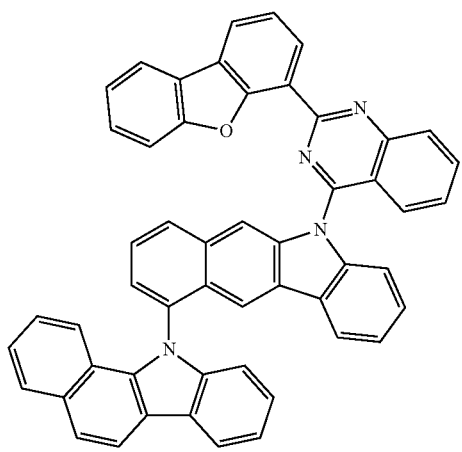
940
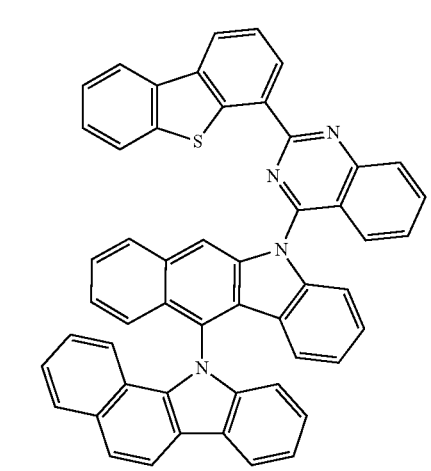
941
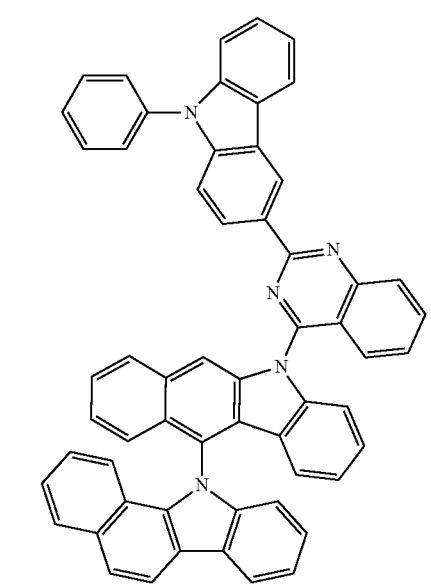
942
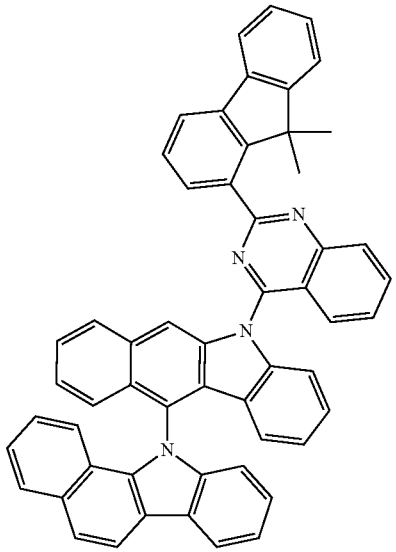
943
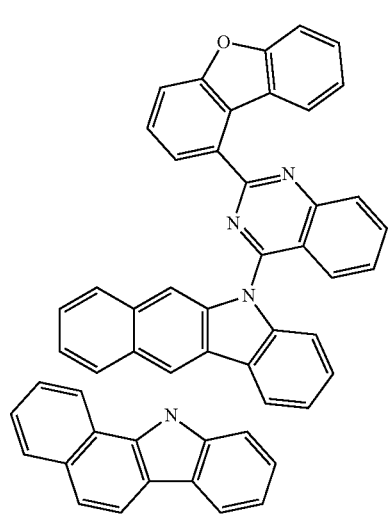
944
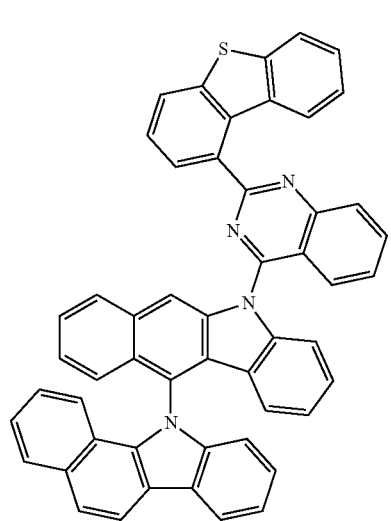

945
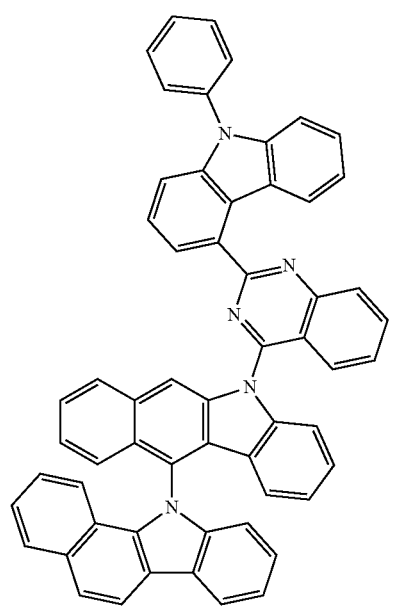
946
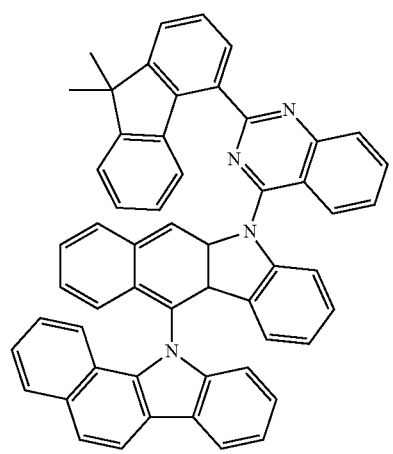
947
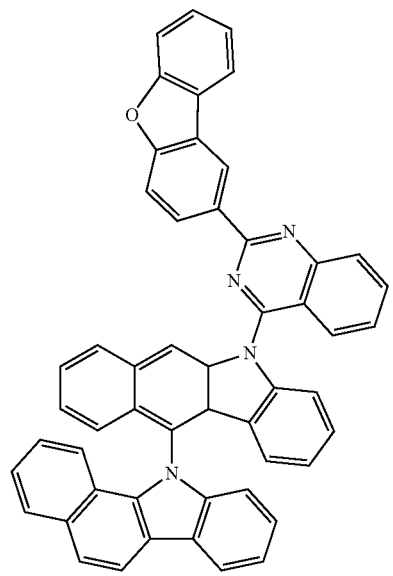
948
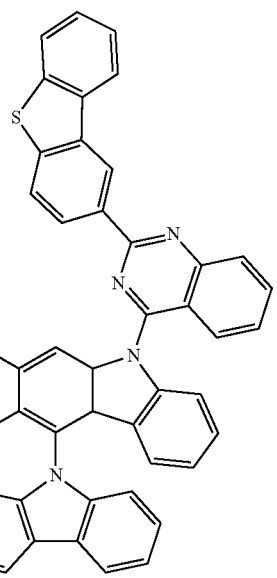
949
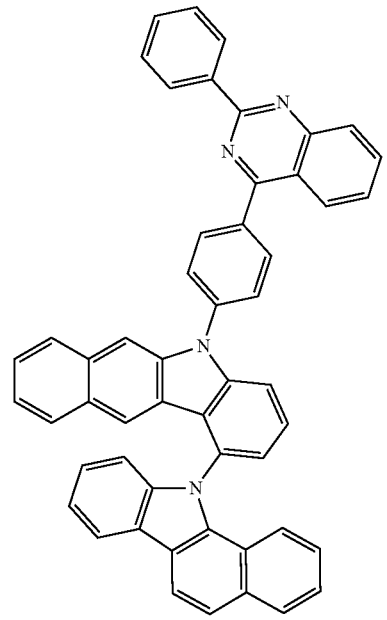

419
-continued
950
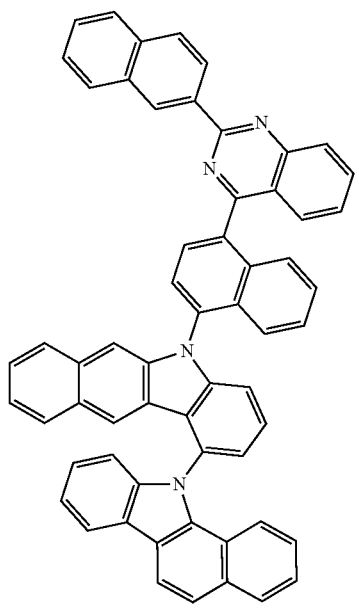
951
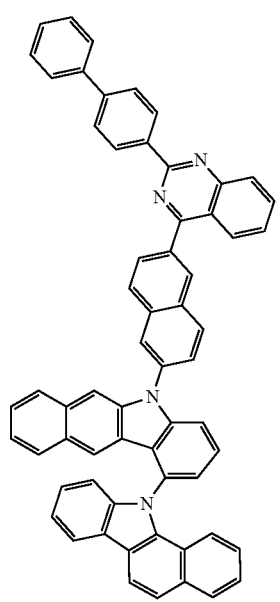
420
-continued
952
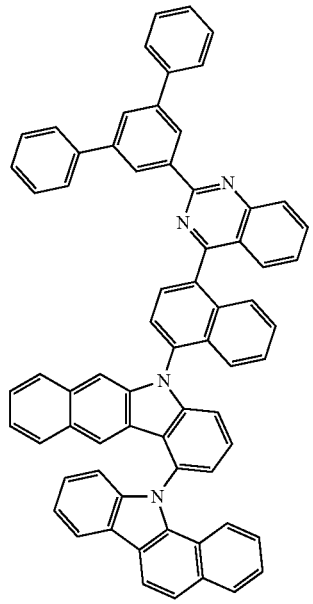
953
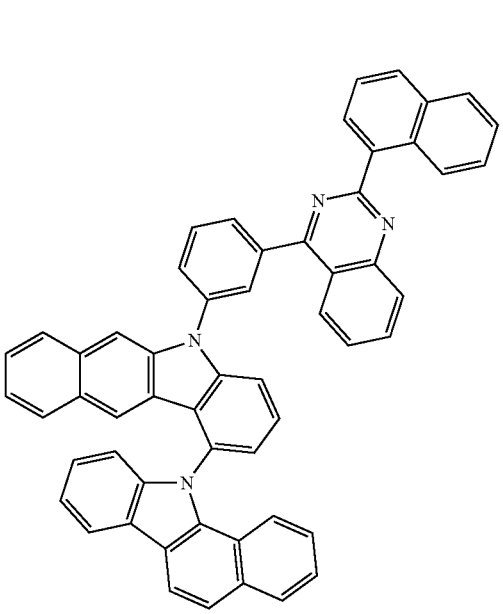

421
-continued
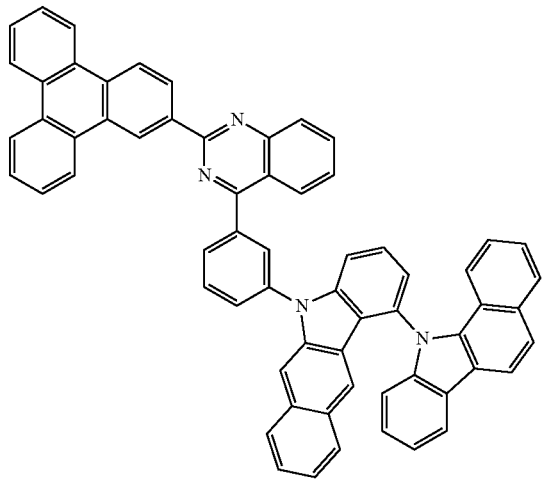
954
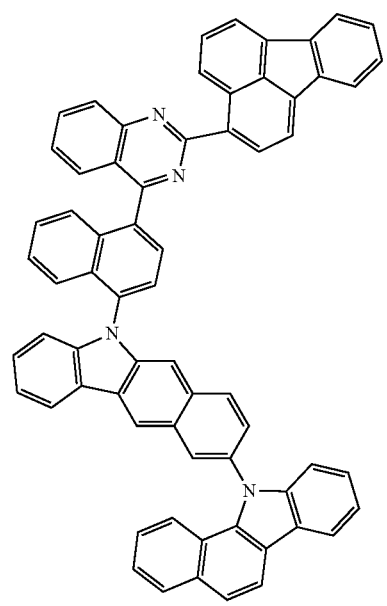
955
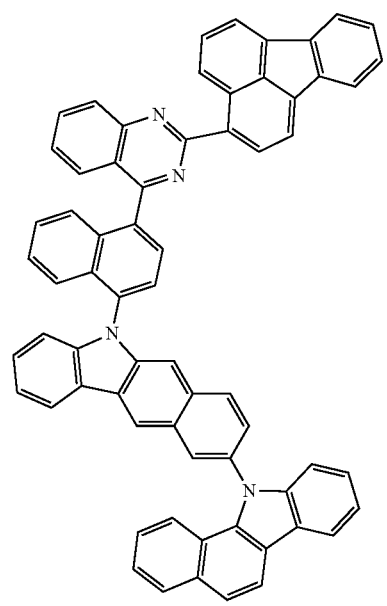
956
422
-continued
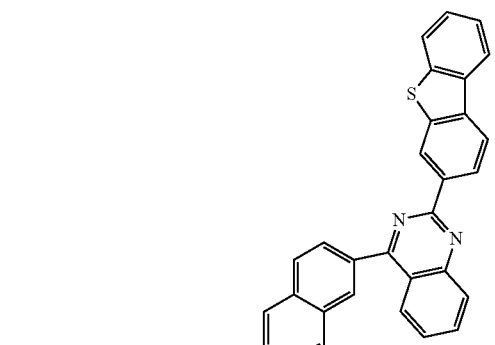
957
958

423
-continued
959
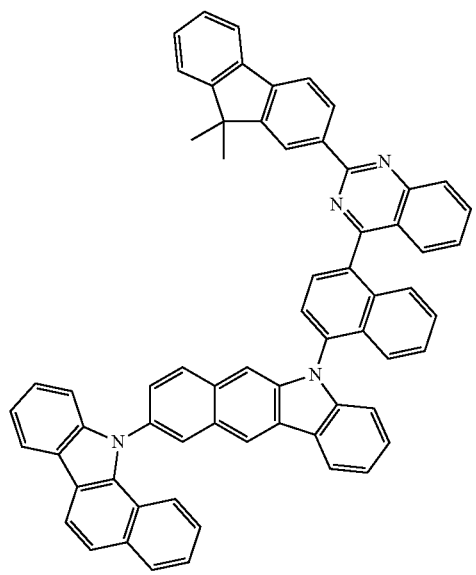
960
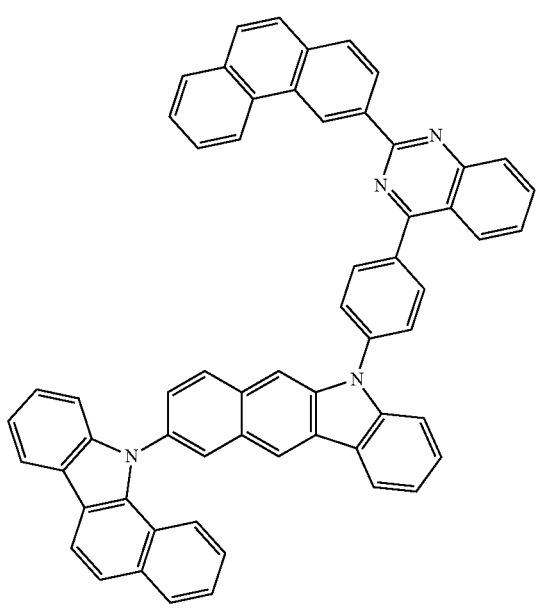
424
-continued
961
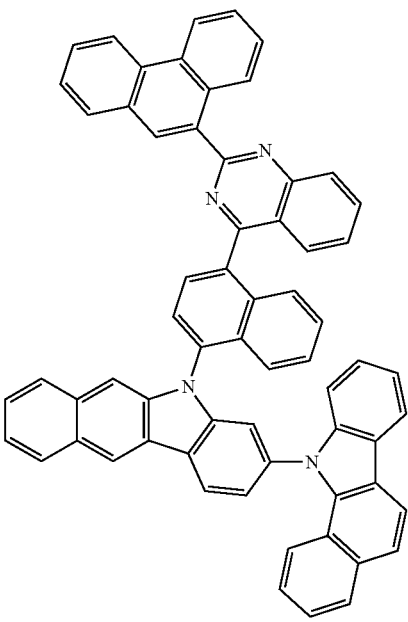
962
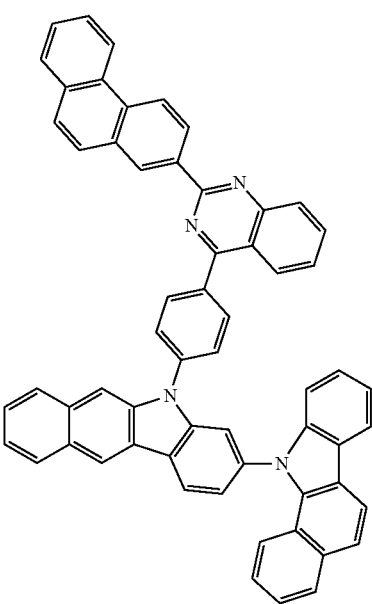

425
-continued
426
-continued
963
964
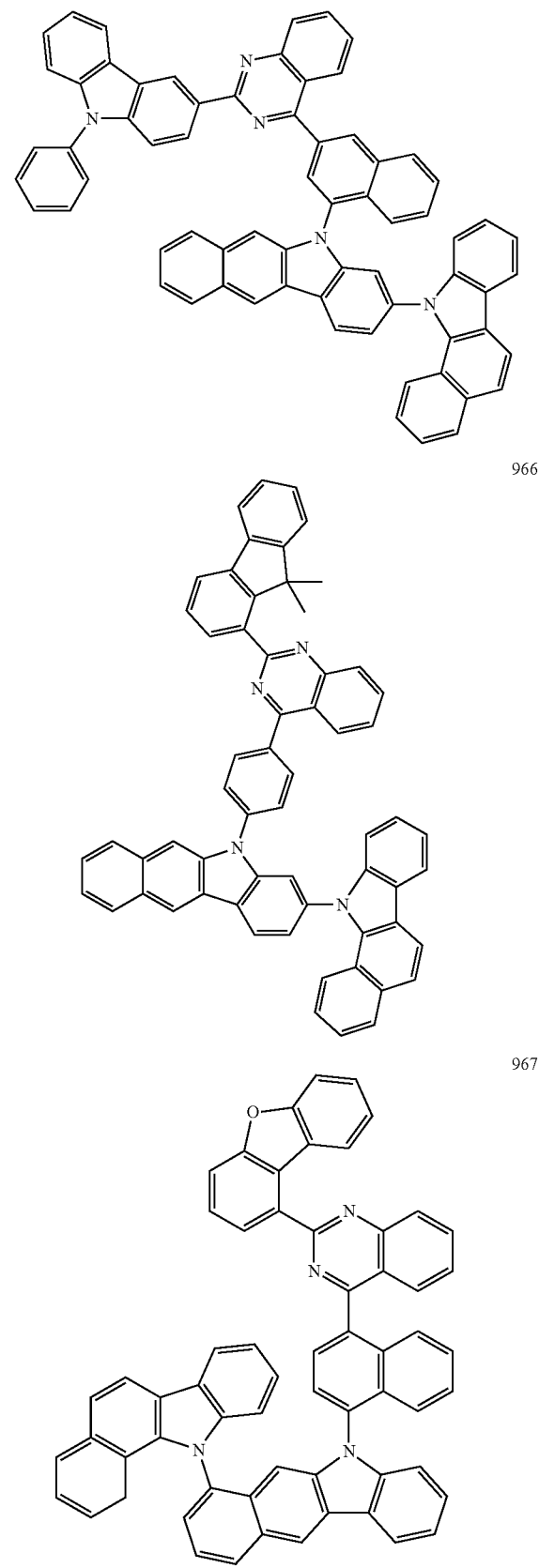
965
966
967

427
-continued
428
-continued
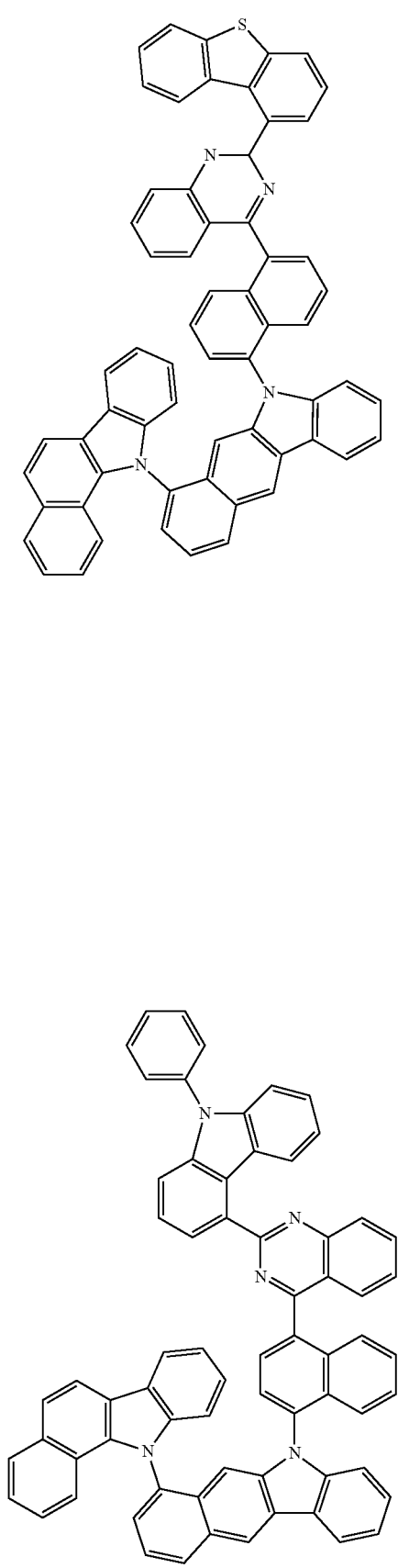
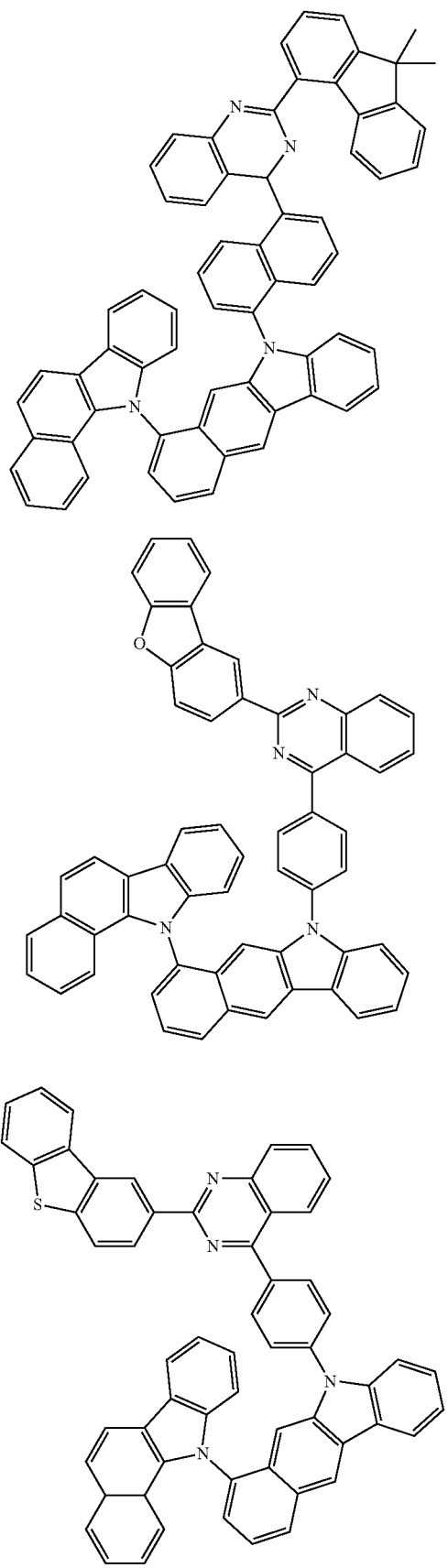

429
-continued
430
-continued
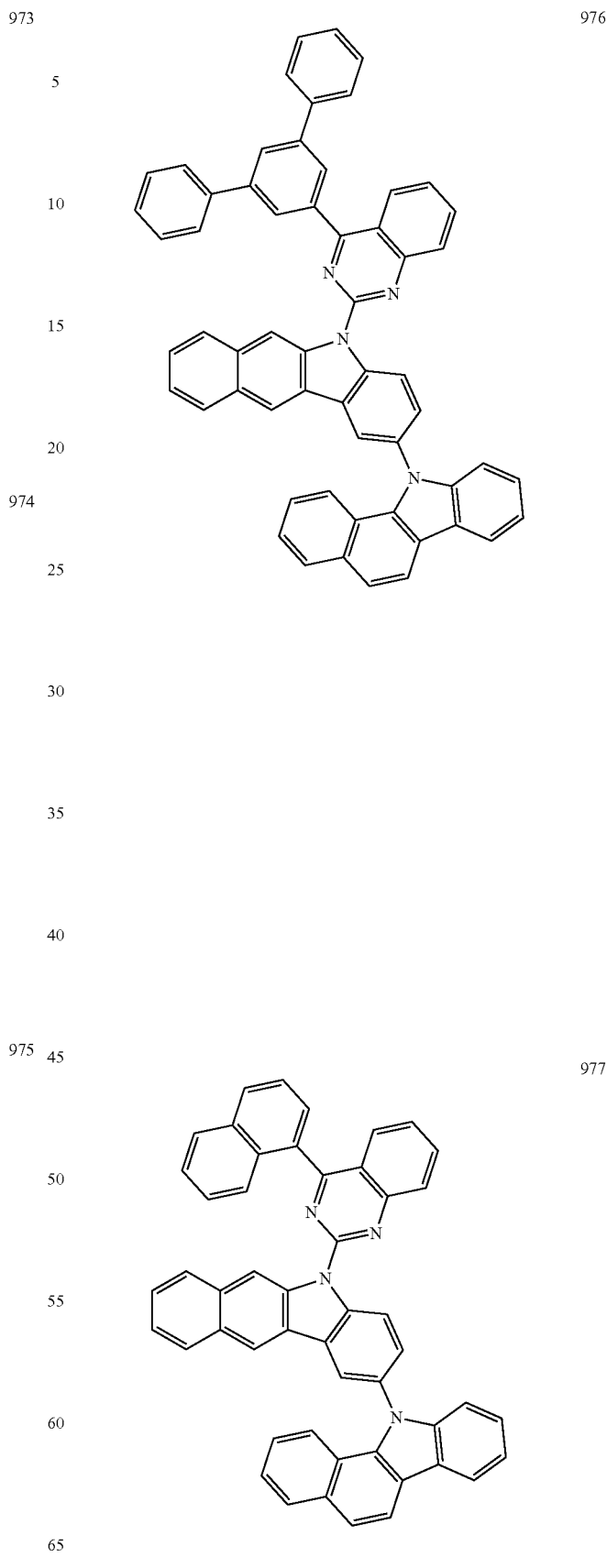

431
-continued
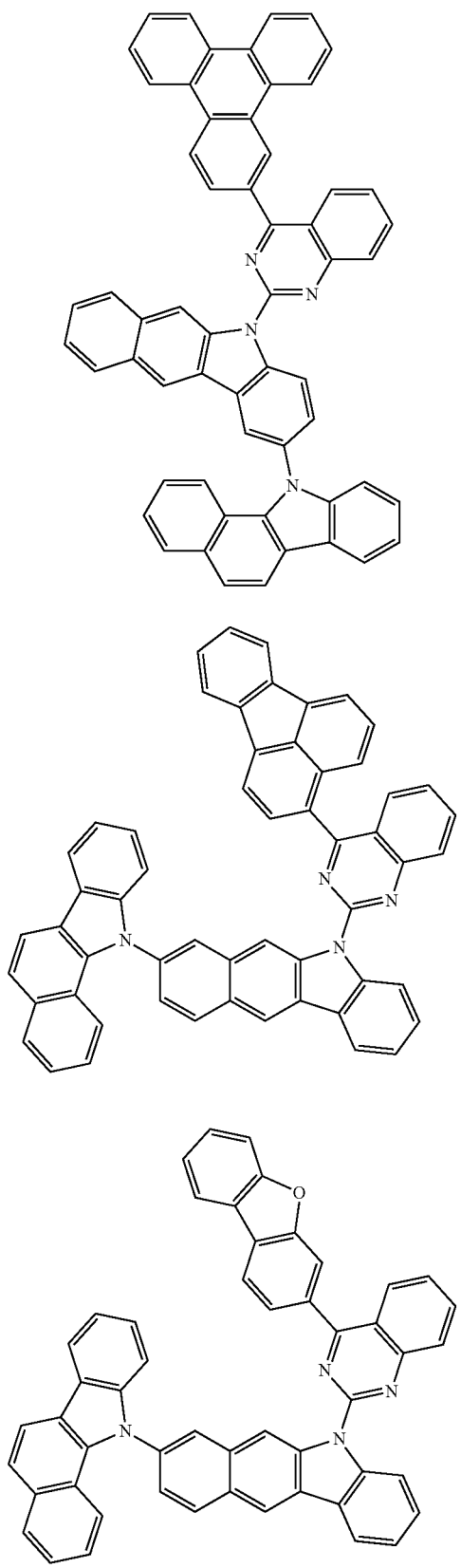
432
-continued
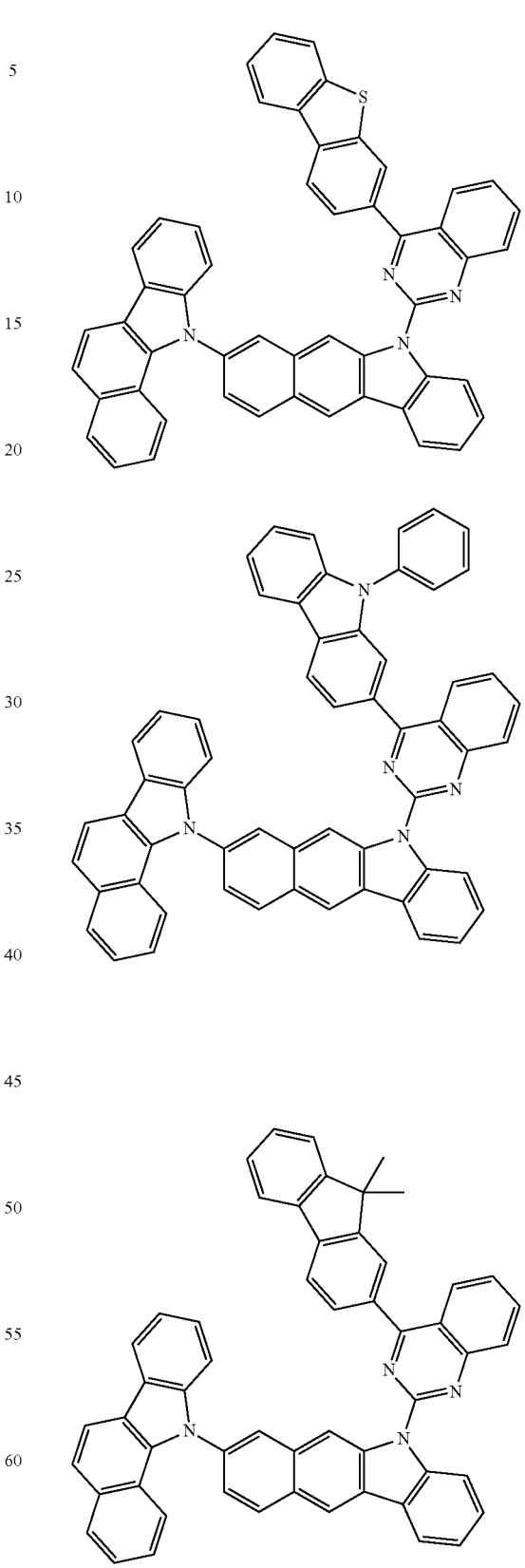

-continued
984
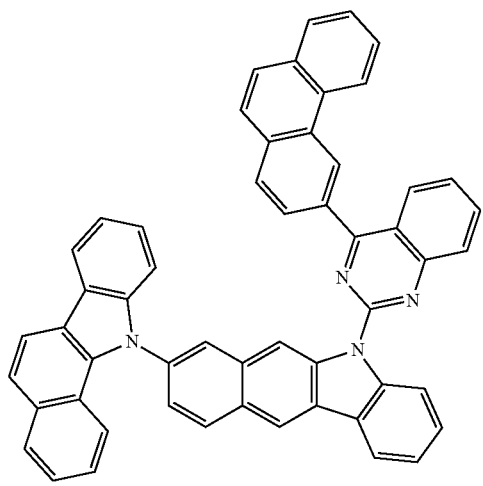
985
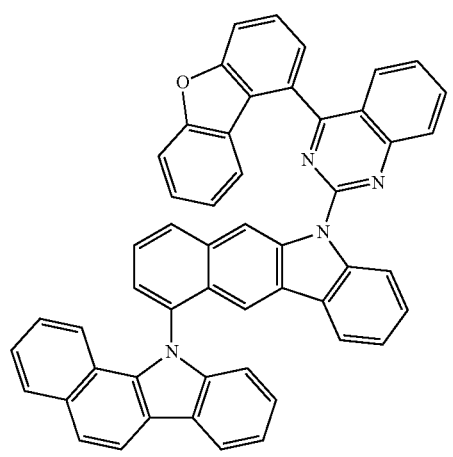
986
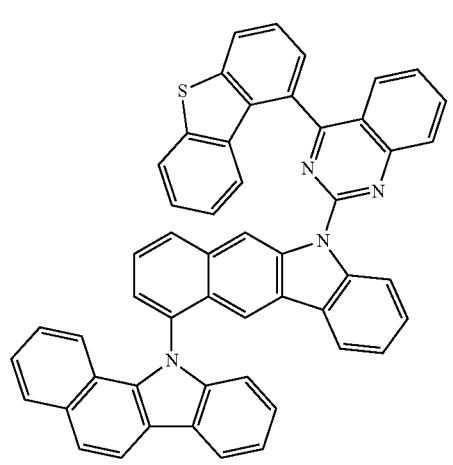
-continued
987
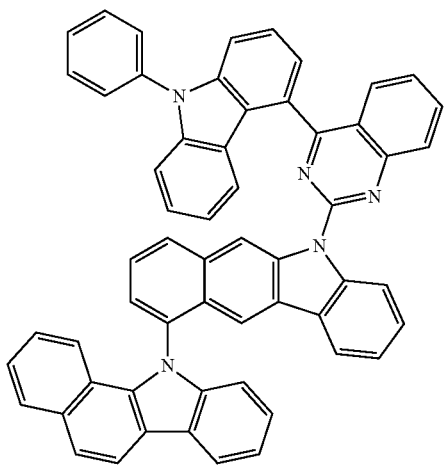
988
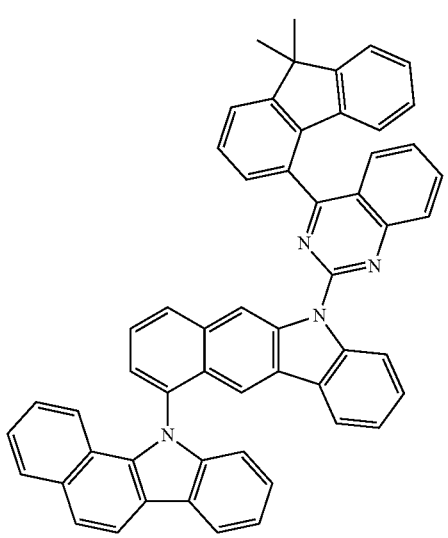
989
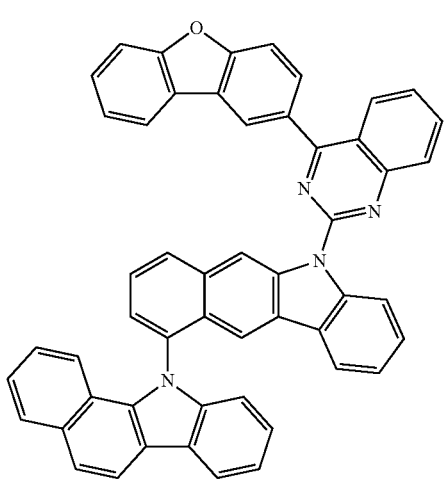

435
-continued
436
-continued
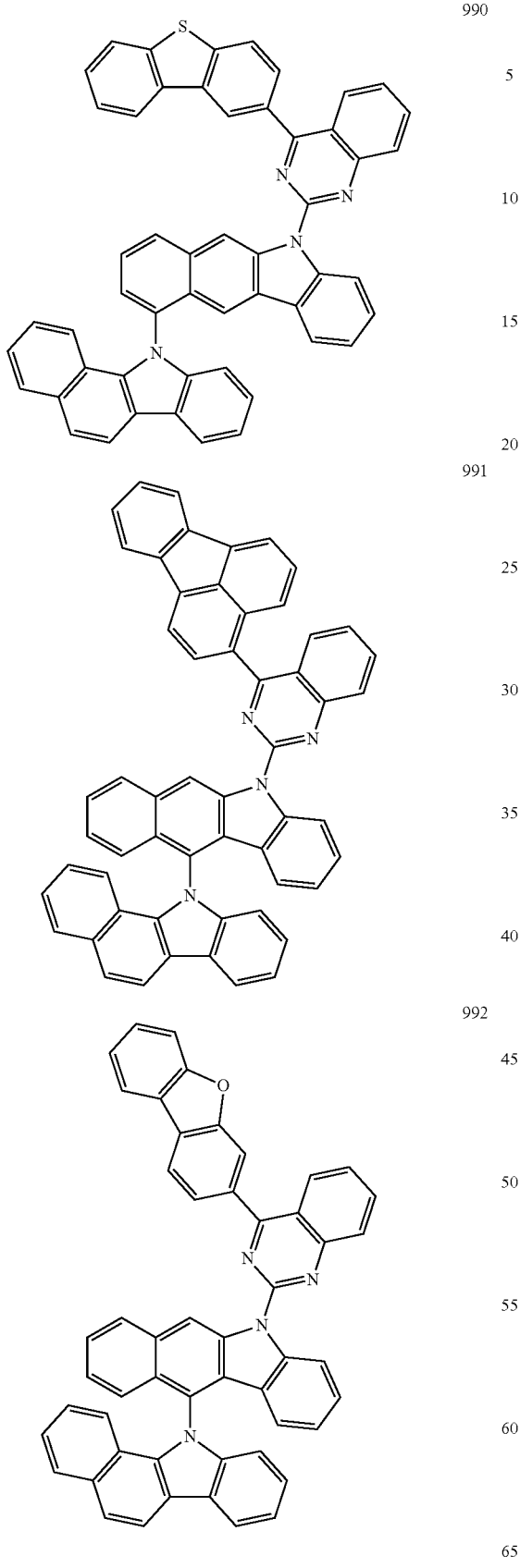

437
-continued
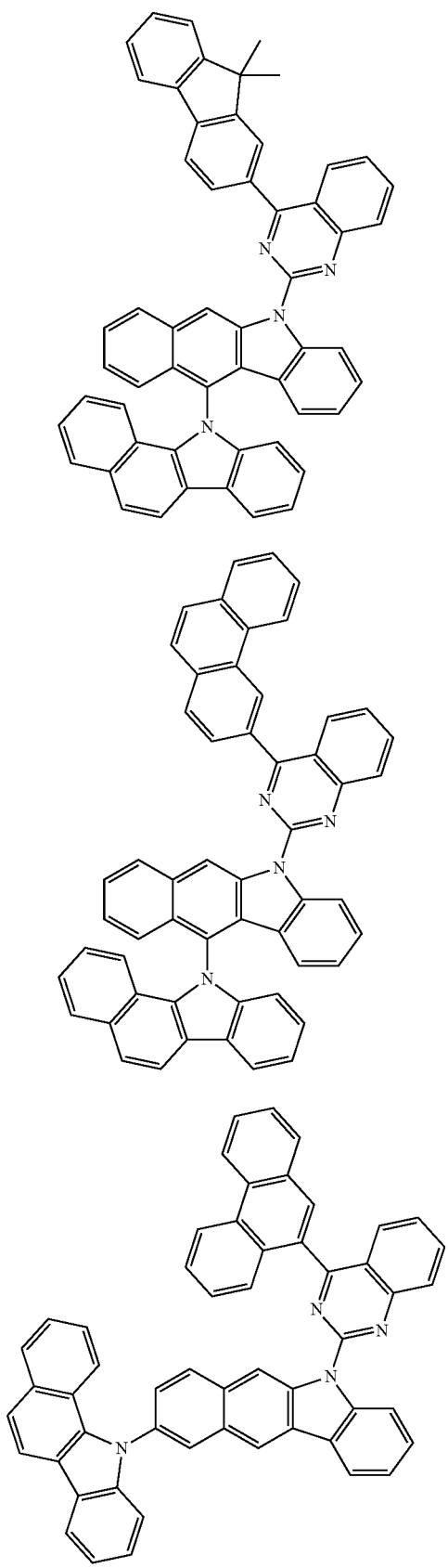
438
-continued
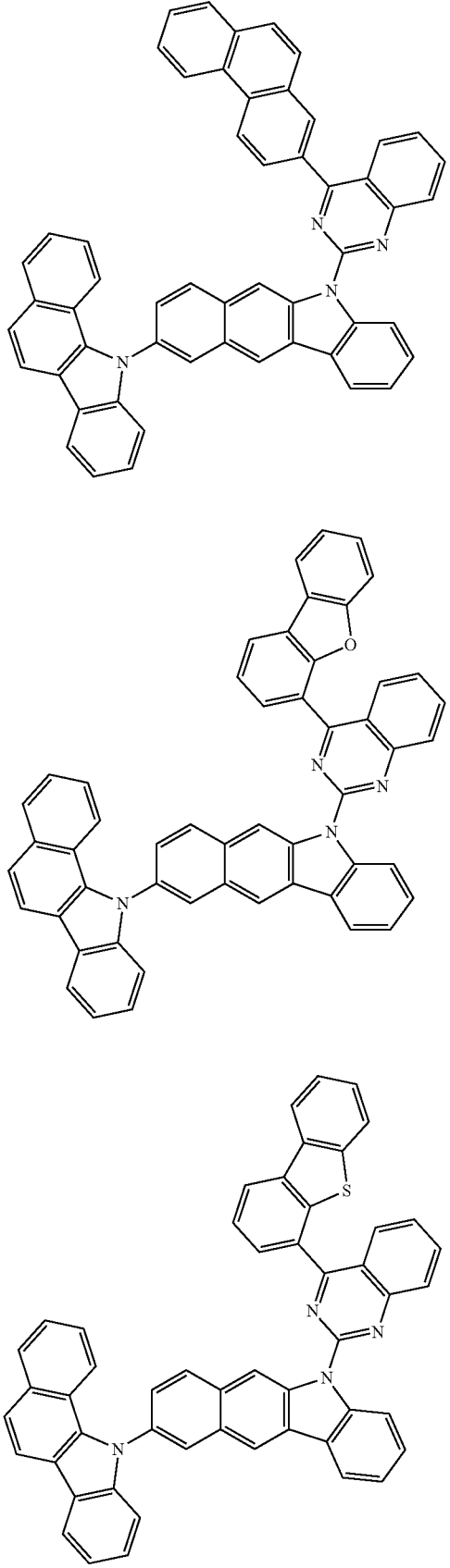

439
-continued
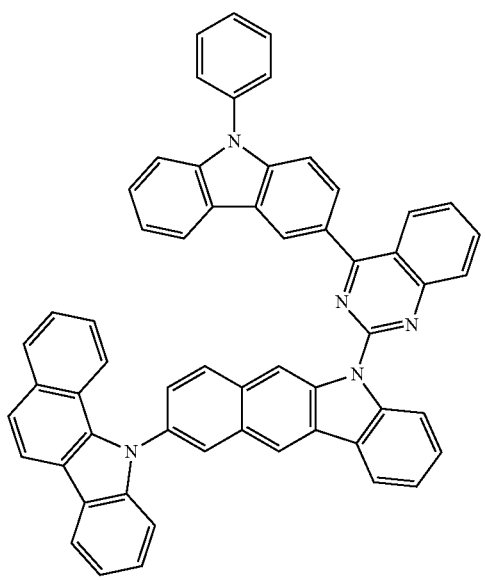
1001
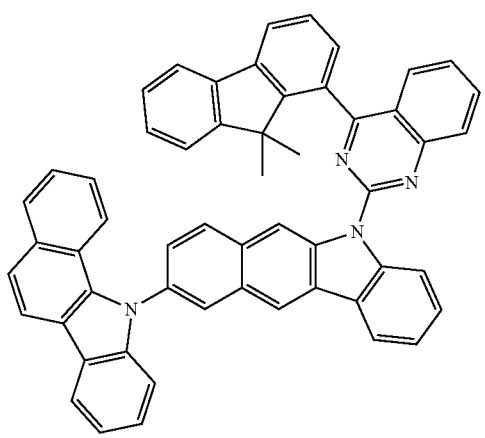
1002
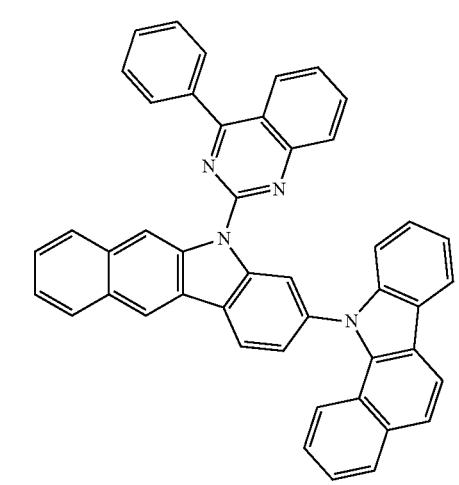
1003
440
-continued
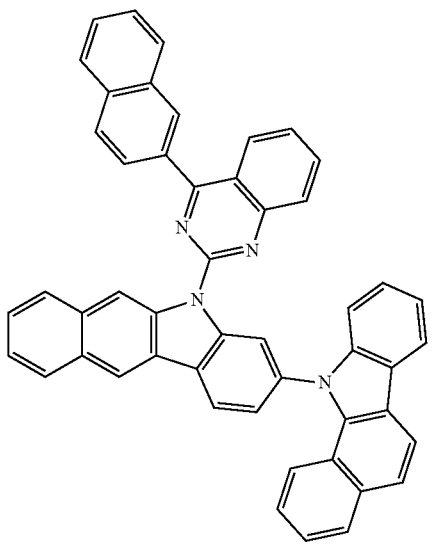
1004
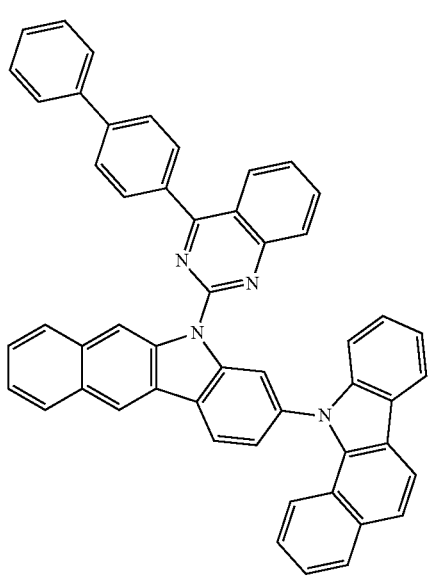
1005

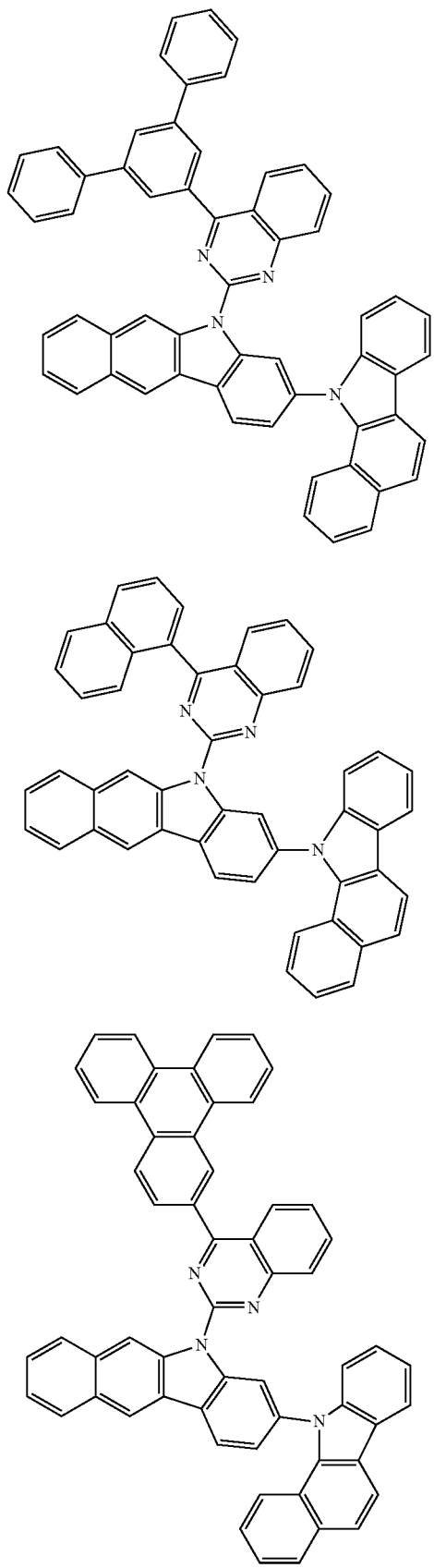
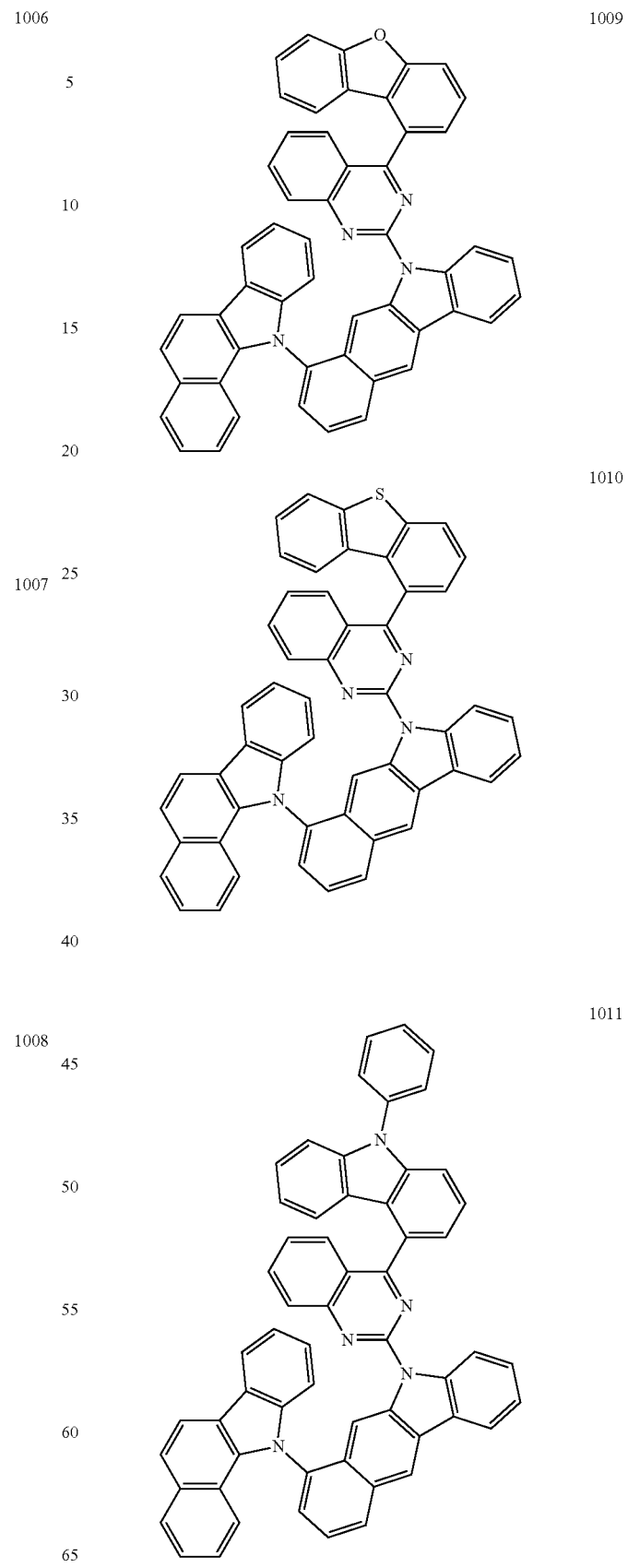

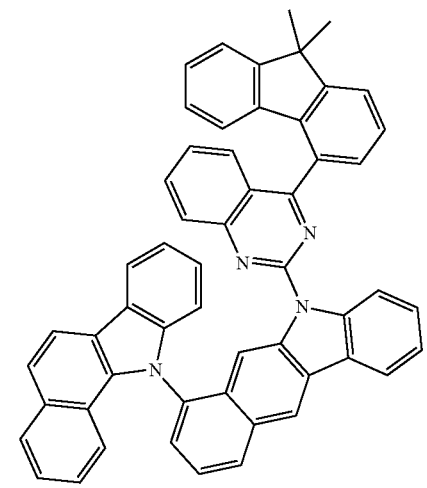
1012
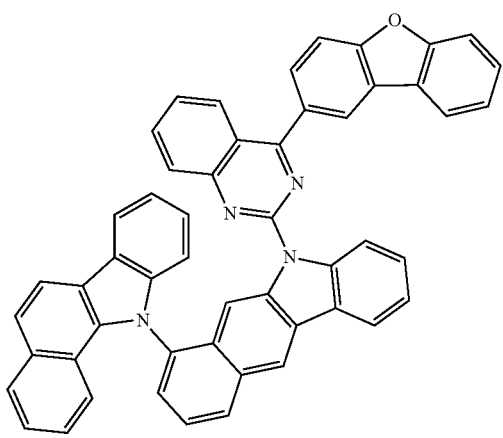
1013
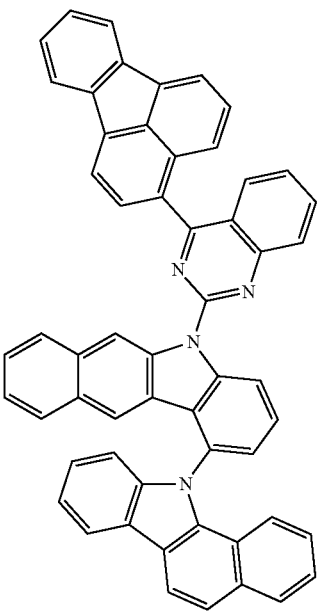
1015
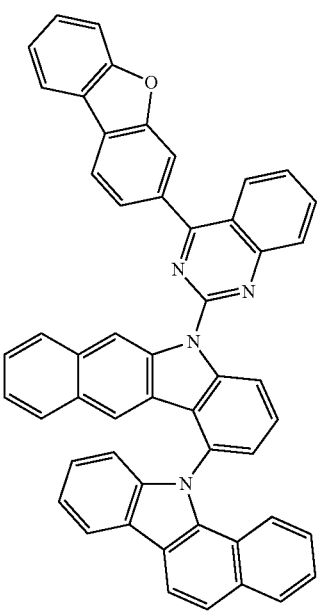
1016

1017
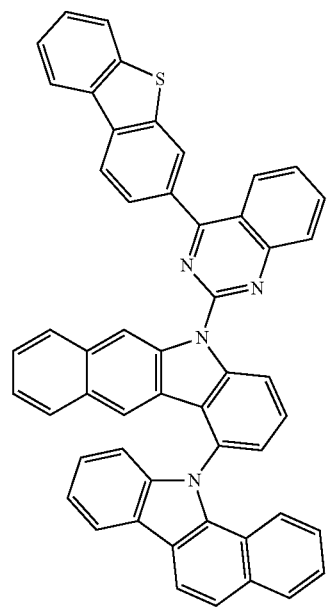
1018
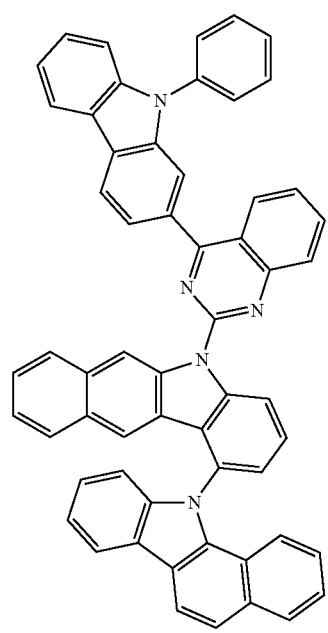
1019
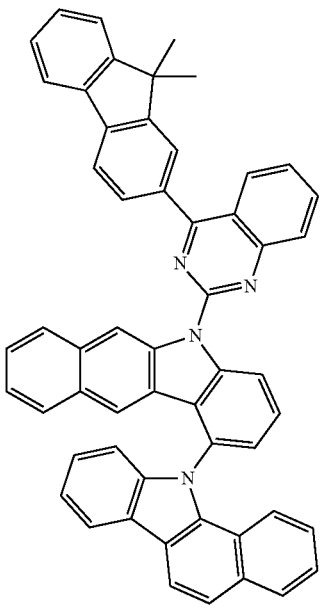
1020
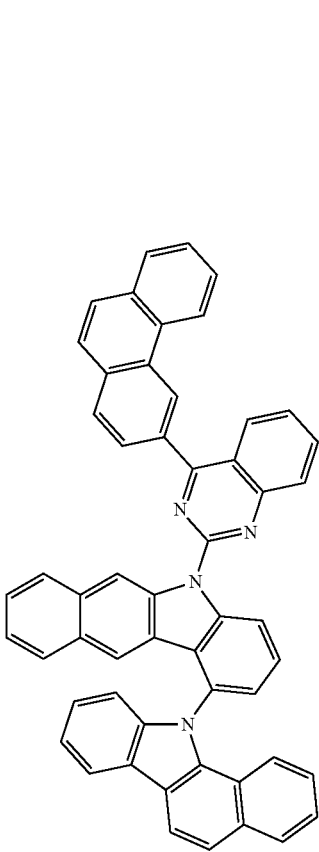

447
-continued
1021
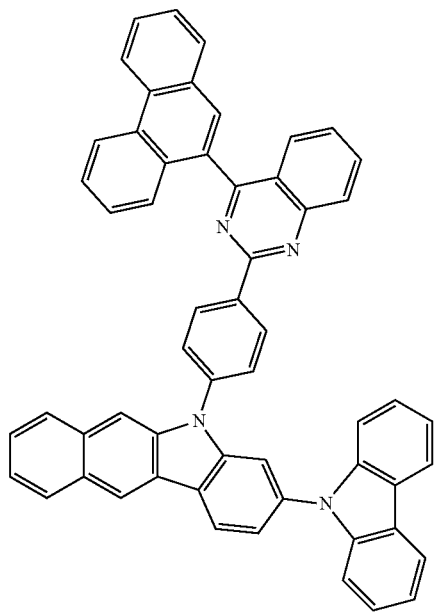
1022
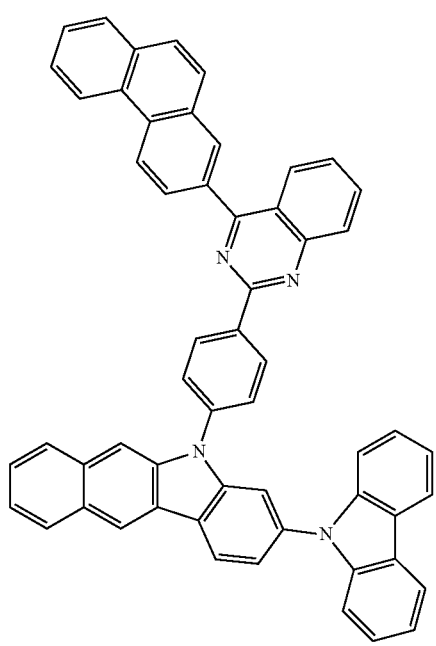
448
-continued
1023
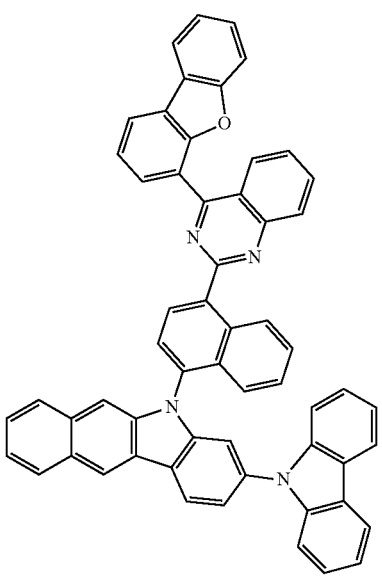
1024
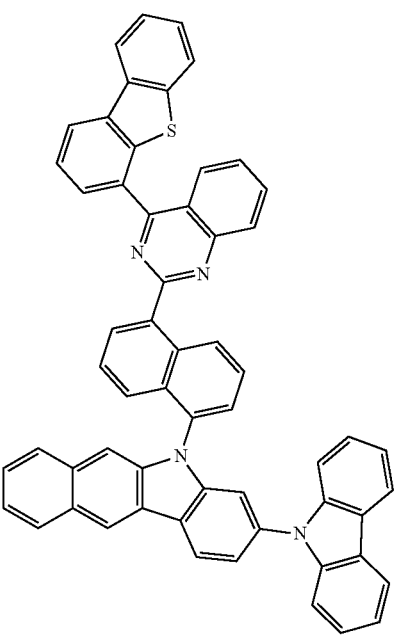

449
-continued
1025
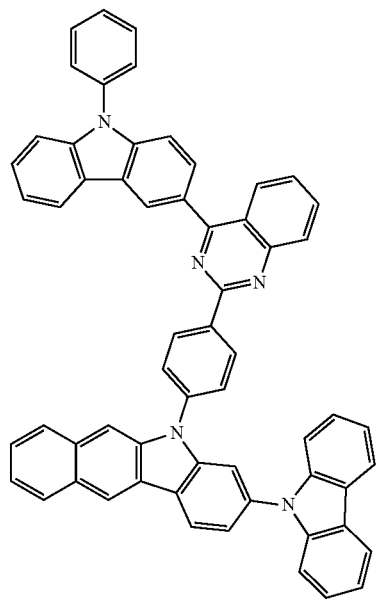
1026
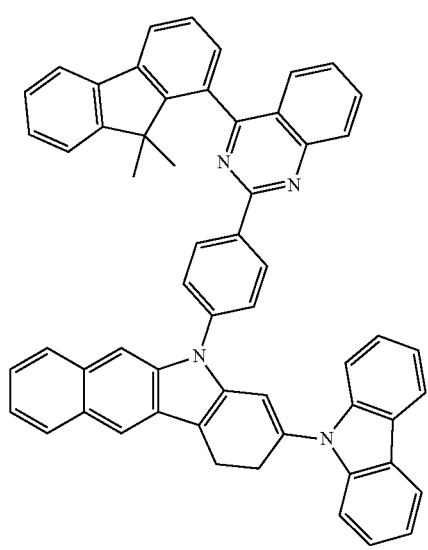
450
-continued
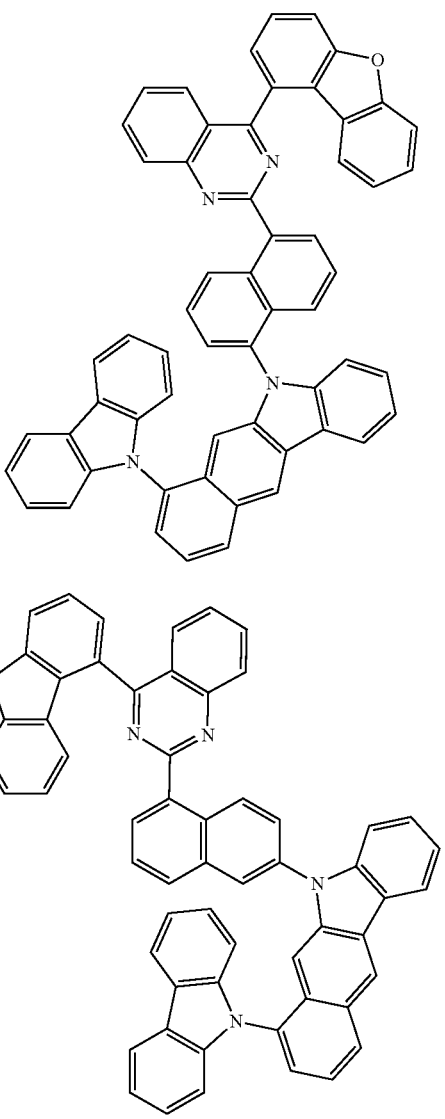
1027
1028
1029
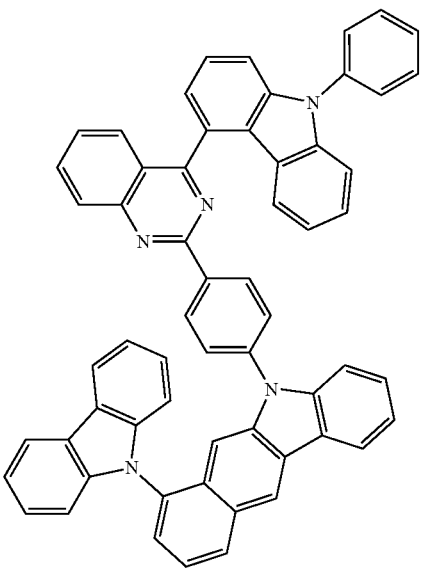

451
-continued
1030
1031
1032
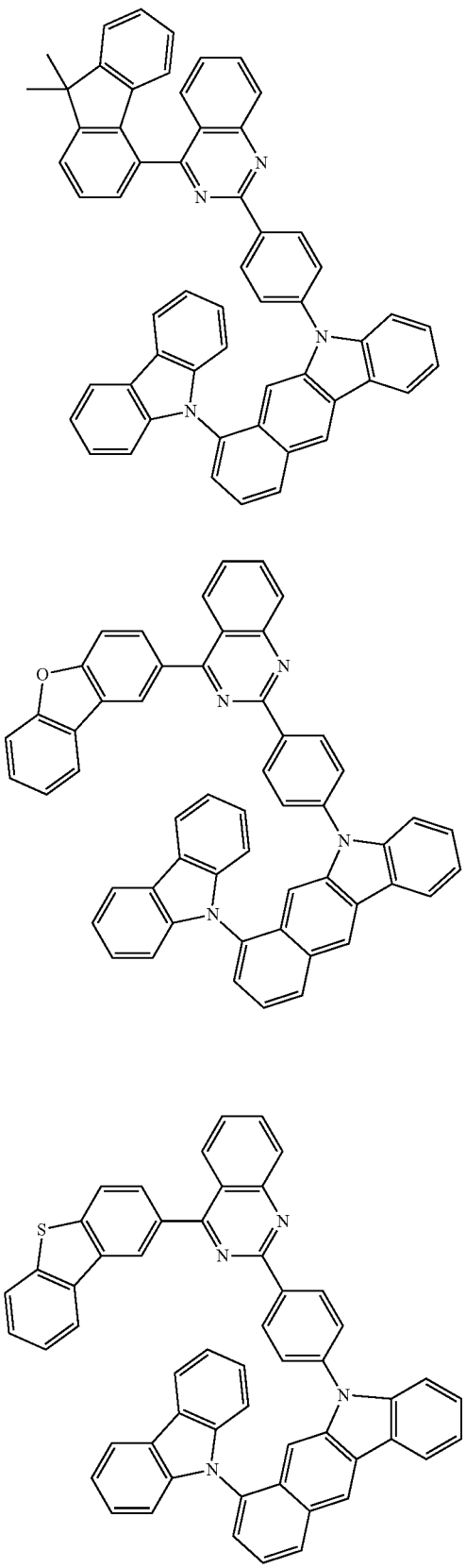
452
-continued
1033
1034
1035
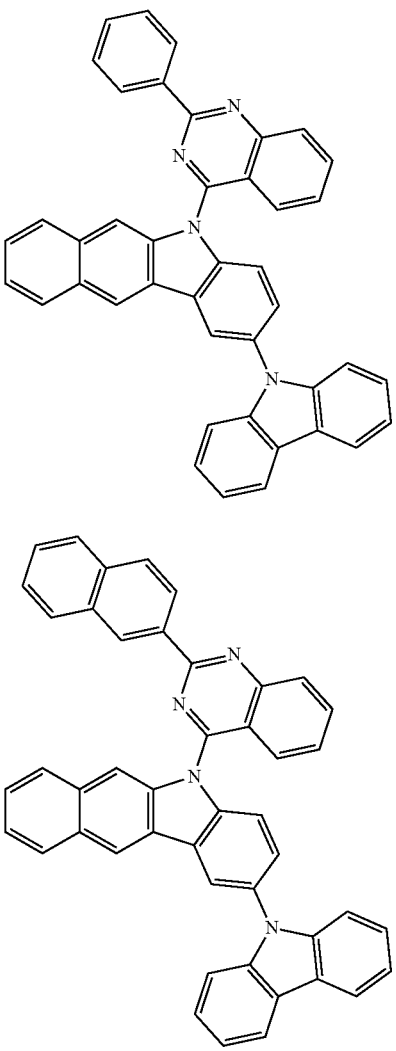

-continued
1036
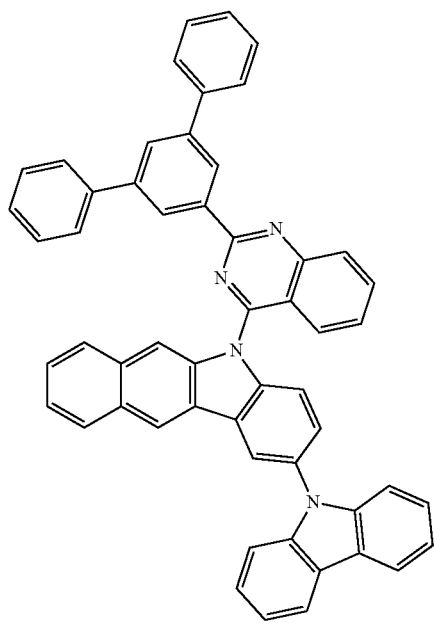
1037
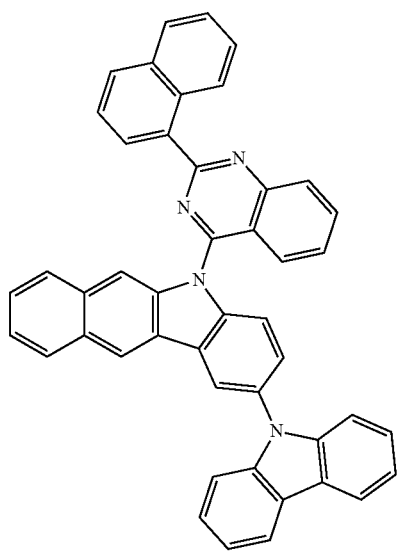
-continued
1038
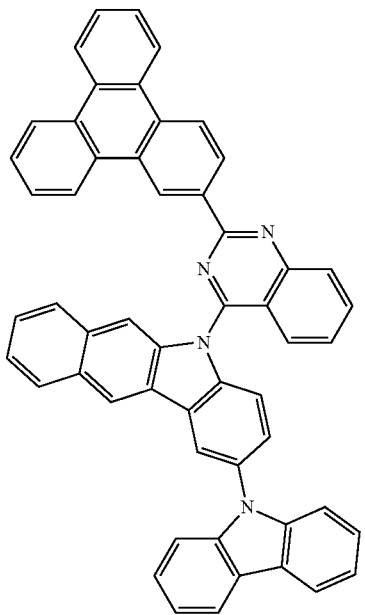
1039
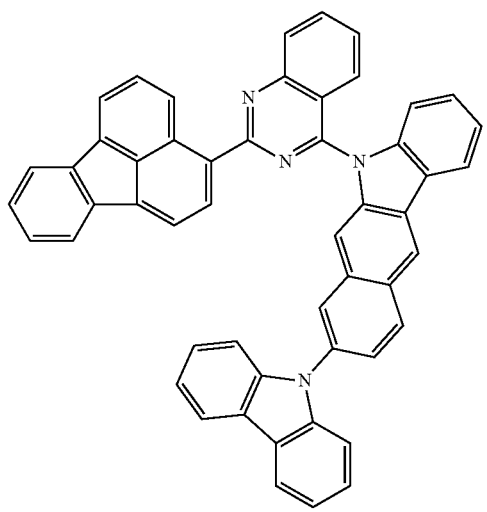
1040
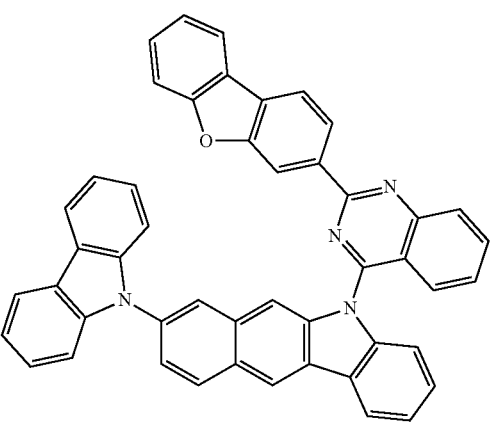

1041
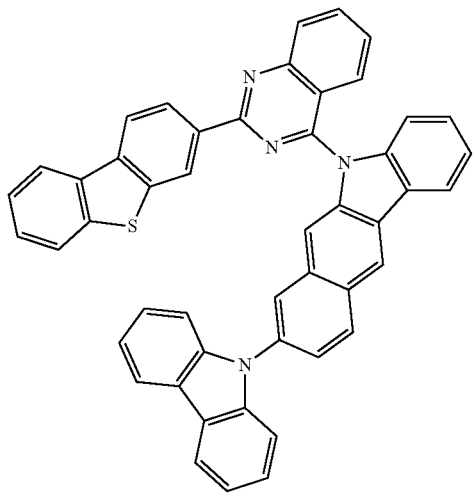
1042
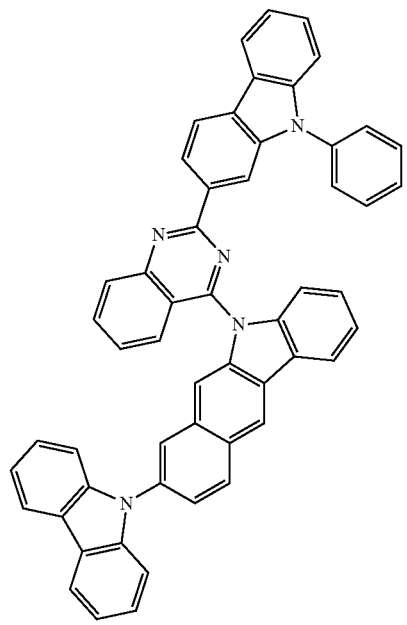
1043
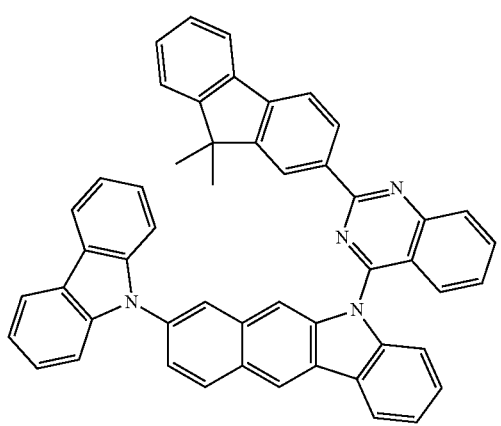
1044
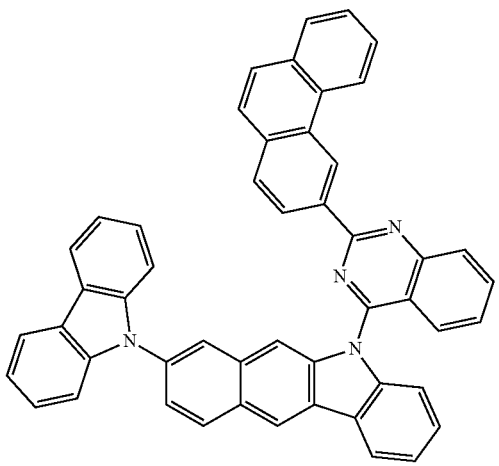
1045
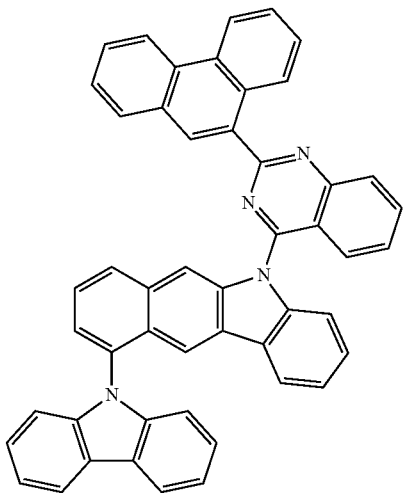
1046
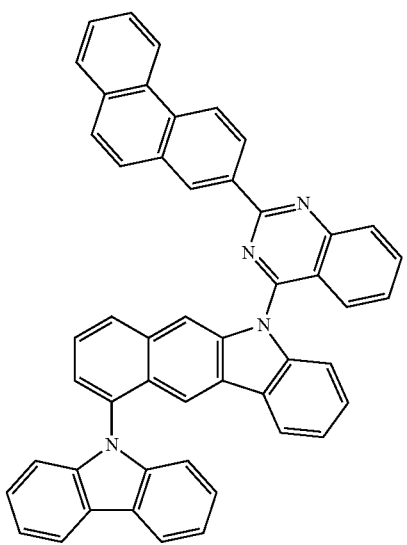

-continued
1047
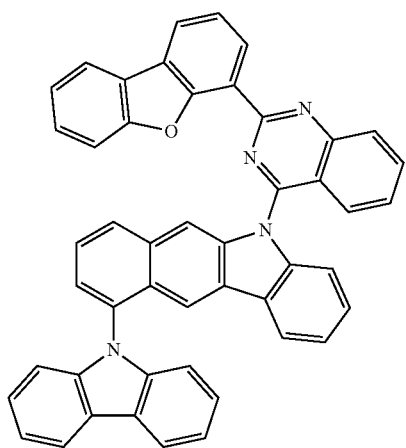
1048
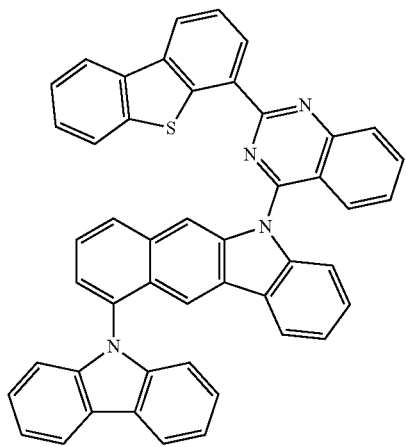
1049
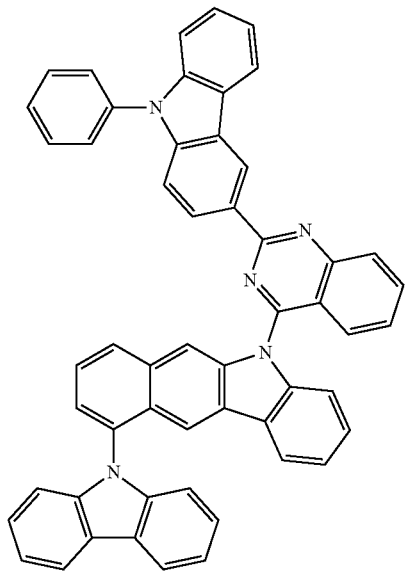
-continued
1050
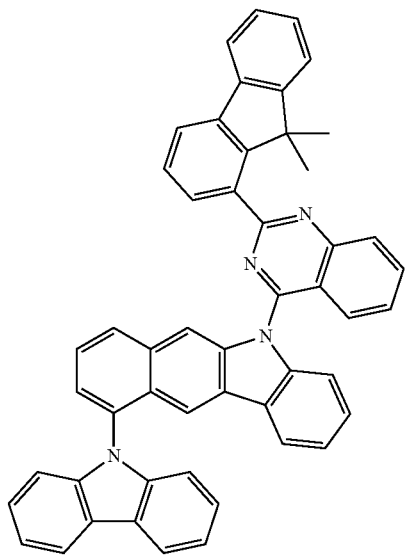
1051
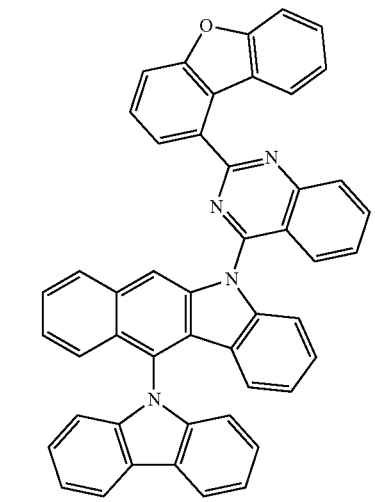
1052
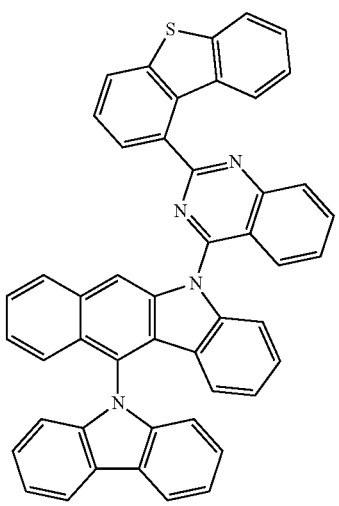

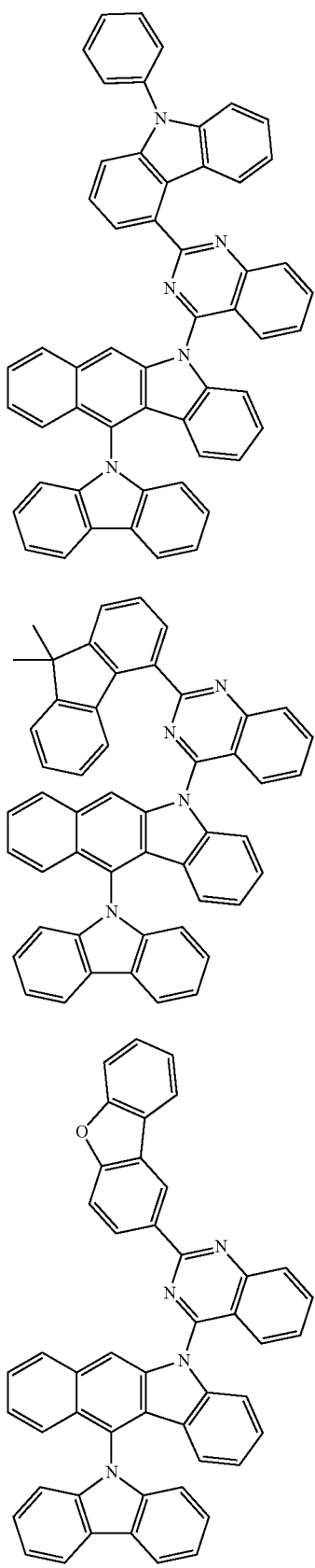

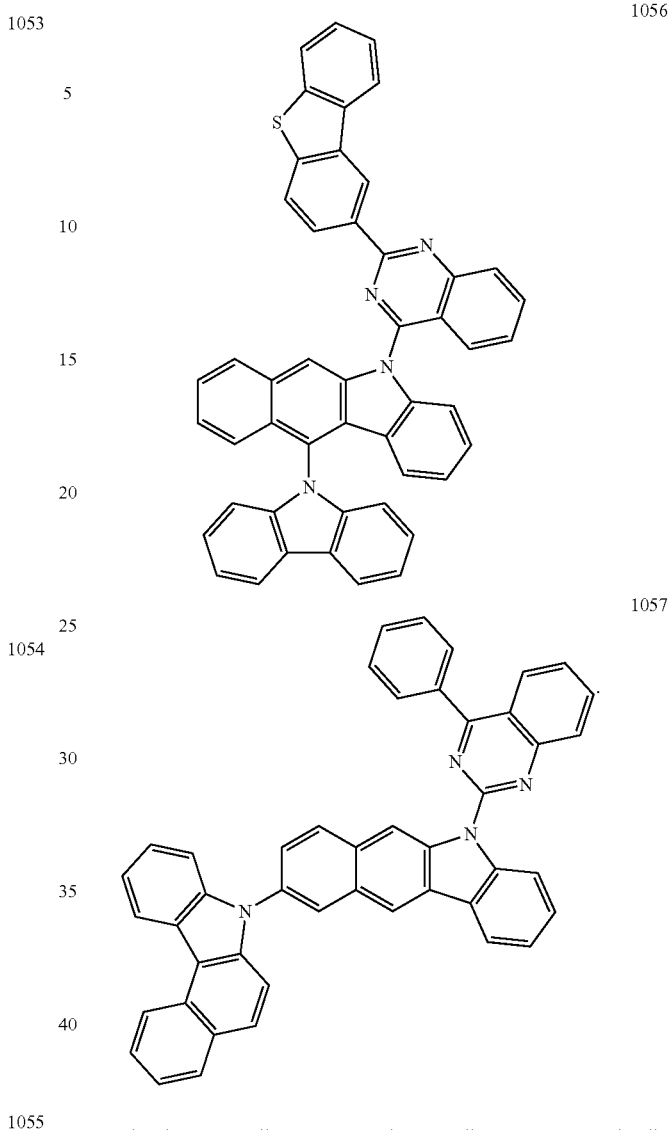

The heterocyclic compound according to one embodiment of the present specification may be prepared using a preparation method to describe below.

For example, the heterocyclic compound of Chemical Formula 1 may have its core structure prepared as in the following reaction formula. Substituents may bond using methods known in the art, and types, positions or the number of the substituents may vary depending on technologies known in the art.

The heterocyclic compound of the present disclosure may be prepared using, as typical reactions, a Buchwald-Hartwig coupling reaction, a Heck coupling reaction, a Suzuki coupling reaction and the like.

Reaction Formula

Reaction Forumla 1.

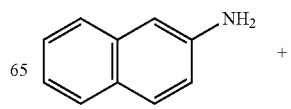

+

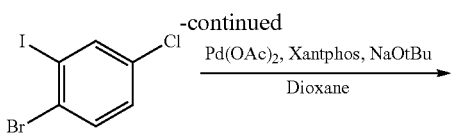

-continued

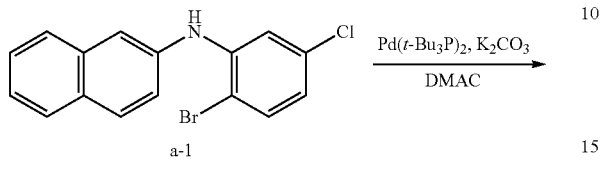

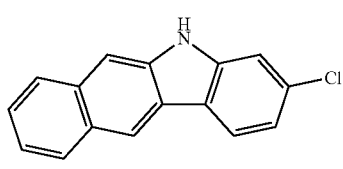

a

1) Preparation of Chemical Formula a-1

Naphthalene-2-amine (200.0 g, 1.0 eq.), 1-bromo-4-chloro-2-iodobenzene (443.25 g, 1.0 eq.) and NaOtBu (201.3 g, 1.5 eq.), Pd(OAc)$_2$ (3.13 g, 0.01 eq.) and Xantphos (8.08 g, 0.01 eq.) are dissolved in 1,4-dioxane (4 L), and the result is stirred under reflux. When the reaction is terminated after 3 hours, the solvent is removed under vacuum. After that, the result is completely dissolved in ethyl acetate, washed with water, and approximately 70% of the solvent is removed under vacuum again. Under reflux again, crystals are dropped while adding hexane thereto, and the result is cooled and then filtered. This goes through column chromatography to obtain Compound a-1 (283.41 g, yield 61%). [M+H]=333

2) Preparation of Chemical Formula a (3-chloro-5H-benzo[b]carbazole)

Pd(t-Bu$_3$P)$_2$ (3.90 g, 0.01 eq.) and K$_2$CO$_3$ (211.11 g, 2.00 eq.) are added to Chemical Formula a-1 (283.41 g, 1.0 eq.) in dimethylacetamide (2 L), and the result is stirred under reflux. After 3 hours, the reaction material is poured into water to drop crystals, and the result is filtered. The filtered solids are completely dissolved in 1,2-dichlorobenzene, then washed with water, and the solution in which a product is dissolved is vacuum concentrated to drop crystals, and the result is cooled and filtered. This is purified using column chromatography to obtain Chemical Formula a (3-chloro-5H-benzo[b]carbazole) (74.97 g, yield 39%). A graph measuring 1H-NMR of Chemical Formula a is shown in FIG. 3. [M+H]=252

Reaction Formula 2. Preparation of Chemical Formula b (2-chloro-5H-benzo[b]carbazole)

2-Chloro-5H-benzo[b]carbazole is synthesized in the same manner as in the method preparing Chemical Formula a using 2-bromo-4-chloro-1-iodobenzene instead of 1-bromo-4-chloro-2-iodobenzene. A graph measuring 1H-NMR of Chemical Formula b is shown in FIG. 4. [M+H]=252

Reaction Formula 3. Preparation of Chemical Formula c (1-chloro-5H-benzo[b]carbazole)

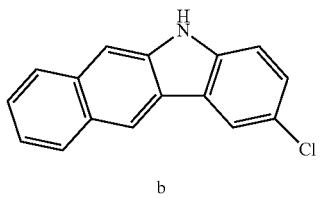

b

1-Chloro-5H-benzo[b]carbazole is synthesized in the same manner as in the method preparing Chemical Formula a using 2-bromo-1-chloro-3-iodobenzene instead of 1-bromo-4-chloro-2-iodobenzene.

Reaction Formula 4. Preparation of Chemical Formula d (11-chloro-5H-benzo[b]carbazole)

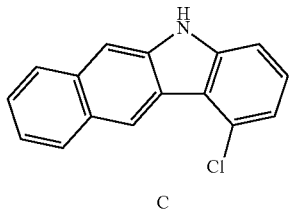

c

11-Chloro-5H-benzo[b]carbazole is synthesized in the same manner as in the method preparing Chemical Formula a using 4-chloronaphthalene-2-amine instead of naphthalene-2-amine, and 1-bromo-2-iodobenzene instead of 1-bromo-4-chloro-2-iodobenzene.

Reaction Formula 5. Preparation of Chemical Formula e (10-chloro-5H-benzo[b]carbazole)

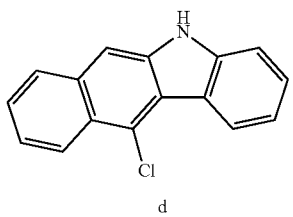

d

10-Chloro-5H-benzo[b]carbazole is synthesized in the same manner as in the method preparing Chemical Formula a using 5-chloronaphthalene-2-amine instead of naphthalene-2-amine, and 1-bromo-2-iodobenzene instead of 1-bromo-4-chloro-2-iodobenzene.

Reaction Formula 6. Preparation of Chemical Formula f
(9-chloro-5H-benzo[b]carbazole)

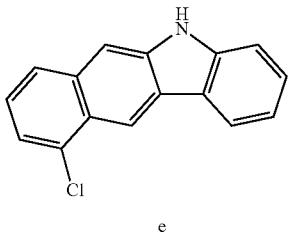

e

9-Chloro-5H-benzo[b]carbazole is synthesized in the same manner as in the method preparing Chemical Formula a using 6-chloronaphthalene-2-amine instead of naphthalene-2-amine, and 1-bromo-2-iodobenzene instead of 1-bromo-4-chloro-2-iodobenzene.

Reaction Formula 7. Preparation of Chemical Formula g
(8-chloro-5H-benzo[b]carbazole)

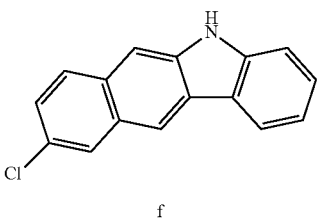

f

8-Chloro-5H-benzo[b]carbazole is synthesized in the same manner as in the method preparing Chemical Formula a using 7-chloronaphthalene-2-amine instead of naphthalene-2-amine, and 1-bromo-2-iodobenzene instead of 1-bromo-4-chloro-2-iodobenzene.

Reaction Formula 8. Preparation of Chemical Formula h
(7-chloro-5H-benzo[b]carbazole)

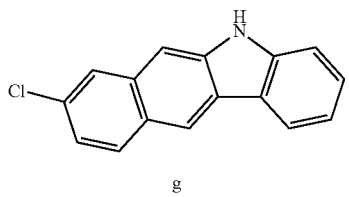

g

7-Chloro-5H-benzo[b]carbazole is synthesized in the same manner as in the method preparing Chemical Formula a using 8-chloronaphthalene-2-amine instead of naphthalene-2-amine, and 1-bromo-2-iodobenzene instead of 1-bromo-4-chloro-2-iodobenzene.

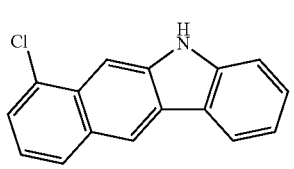

h

A conjugation length of a compound and an energy band gap thereof are closely related. Specifically, as a conjugation length of a compound increases, an energy band gap thereof decreases.

By introducing various substituents to the core structure as above, compounds having various energy band gaps may be synthesized in the present disclosure. In addition, by introducing various substituents to the core structure having structures as above, HOMO and LUMO energy levels of the compound may also be controlled in the present disclosure.

In addition, by introducing various substituents to the core structure having structures as above, compounds having unique properties of the introduced substituents may be synthesized. For example, by introducing substituents normally used as a hole injection layer material, a material for hole transfer, a light emitting layer material and an electron transfer layer material used for manufacturing an organic light emitting device to the core structure, materials satisfying needs required from each organic material layer may be synthesized.

In addition, an organic light emitting device according to the present disclosure comprises a first electrode; a second electrode provided opposite to the first electrode; and one or more organic material layers provided between the first electrode and the second electrode, wherein one or more layers of the organic material layers comprise the heterocyclic compound of Chemical Formula 1.

The organic light emitting device of the present disclosure may be prepared using common methods and materials for preparing an organic light emitting device except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a hole injection and transfer layer, an electron blocking layer, a light emitting layer, an electron transfer layer, an electron injection layer, a hole blocking layer, an electron injection and transfer layer and the like as the organic material layer. However, the structure of the organic light emitting device is not limited thereto, and may comprise less numbers of organic material layers or more numbers of organic material layers.

In the organic light emitting device of the present disclosure, the organic material layer may comprise an electron transfer layer or an electron injection layer, and the electron transfer layer or the electron injection layer may comprise the heterocyclic compound represented by Chemical Formula 1.

In the organic light emitting device of the present disclosure, the organic material layer may comprise a hole injection layer or a hole transfer layer, and the hole injection layer or the hole transfer layer may comprise the heterocyclic compound represented by Chemical Formula 1.

In another embodiment, the organic material layer comprises a light emitting layer, and the light emitting layer comprises the heterocyclic compound represented by Chemical Formula 1. As one example, the heterocyclic compound represented by Chemical Formula 1 may be included as a dopant of the light emitting layer.

In one embodiment of the present specification, the organic light emitting device is a green organic light emitting device in which the light emitting layer comprises the heterocyclic compound represented by Chemical Formula 1.

According to one embodiment of the present specification, the organic light emitting device is a red organic light emitting device in which the light emitting layer comprises the heterocyclic compound represented by Chemical Formula 1.

In another embodiment, the organic light emitting device is a blue organic light emitting device in which the light emitting layer comprises the heterocyclic compound represented by Chemical Formula 1.

As another example, the organic material layer comprising the heterocyclic compound represented by Chemical Formula 1 comprises the heterocyclic compound represented by Chemical Formula 1 as a dopant, and may comprise a fluorescent host or a phosphorescent host.

In another embodiment, the organic material layer comprising the heterocyclic compound represented by Chemical Formula 1 comprises the heterocyclic compound represented by Chemical Formula 1 as a dopant, comprises a fluorescent host or a phosphorescent host, and may comprise other organic compounds, metals or metal compounds as a dopant.

As another example, the organic material layer comprising the heterocyclic compound represented by Chemical Formula 1 comprises the heterocyclic compound represented by Chemical Formula 1 as a dopant, comprises a fluorescent host or a phosphorescent host, and may be used together with an iridium (Ir)-based dopant.

According to one embodiment of the present disclosure, the organic light emitting device comprises a light emitting layer, and the light emitting layer may comprise the heterocyclic compound represented by Chemical Formula 1 as a host of the light emitting layer.

According to another embodiment, the organic light emitting device comprises the heterocyclic compound represented by Chemical Formula 1 as a host of the light emitting layer, and may further comprise a dopant.

In another embodiment, the organic light emitting device comprises the heterocyclic compound represented by Chemical Formula 1 as a host of the light emitting layer, and may further comprise an iridium (Ir)-based dopant. Herein, a weight ratio of the host and the dopant (host:dopant) may be from 90:10 to 99:1, but is not limited thereto.

The structure of the organic light emitting device of the present disclosure may be as illustrated in FIG. 1 and FIG. 2, but is not limited thereto.

FIG. 1 illustrates a structure of the organic light emitting device in which an anode (2), a light emitting layer (3) and a cathode (4) are consecutively laminated on a substrate (1). In such a structure, the compound may be included in the light emitting layer (3).

The organic light emitting device may have, for example, a laminated structure as below, however, the structure is not limited thereto.

(1) Anode/hole transfer layer/light emitting layer/cathode
(2) Anode/hole injection layer/hole transfer layer/light emitting layer/cathode
(3) Anode/hole injection layer/hole buffer layer/hole transfer layer/light emitting layer/cathode
(4) Anode/hole transfer layer/light emitting layer/electron transfer layer/cathode
(5) Anode/hole transfer layer/light emitting layer/electron transfer layer/electron injection layer/cathode
(6) Anode/hole injection layer/hole transfer layer/light emitting layer/electron transfer layer/cathode
(7) Anode/hole injection layer/hole transfer layer/light emitting layer/electron transfer layer/electron injection layer/cathode
(8) Anode/hole injection layer/hole buffer layer/hole transfer layer/light emitting layer/electron transfer layer/cathode
(9) Anode/hole injection layer/hole buffer layer/hole transfer layer/light emitting layer/electron transfer layer/electron injection layer/cathode
(10) Anode/hole transfer layer/electron blocking layer/light emitting layer/electron transfer layer/cathode
(11) Anode/hole transfer layer/electron blocking layer/light emitting layer/electron transfer layer/electron injection layer/cathode
(12) Anode/hole injection layer/hole transfer layer/electron blocking layer/light emitting layer/electron transfer layer/cathode
(13) Anode/hole injection layer/hole transfer layer/electron blocking layer/light emitting layer/electron transfer layer/electron injection layer/cathode
(14) Anode/hole transfer layer/light emitting layer/hole blocking layer/electron transfer layer/cathode
(15) Anode/hole transfer layer/light emitting layer/hole blocking layer/electron transfer layer/electron injection layer/cathode
(16) Anode/hole injection layer/hole transfer layer/light emitting layer/hole blocking layer/electron transfer layer/cathode
(17) Anode/hole injection layer/hole transfer layer/light emitting layer/hole blocking layer/electron transfer layer/electron injection layer/cathode
(18) Anode/hole injection layer/hole transfer layer/electron blocking layer/light emitting layer/hole blocking layer/electron injection and transfer layer/cathode FIG. 2 illustrates a structure of the organic light emitting device in which an anode (2), a hole injection layer (5), a hole transfer layer (6), an electron blocking layer (7), a light emitting layer (7), a hole blocking layer (9), an electron injection and transfer layer (10) and a cathode (4) are consecutively laminated on a substrate (1). In such a structure, the heterocyclic compound may be included in the hole injection layer (5), the hole transfer layer (6) or the light emitting layer (8).

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer comprising a hole injection layer, a hole transfer layer, an electron blocking layer, a light emitting layer, a hole blocking layer, and an electron injection and transfer layer thereon, and then depositing a material capable of being used as a cathode thereon. In addition to such a method, the organic light emitting device may also be manufactured by consecutively depositing a cathode material, an organic material layer and an anode material on a substrate.

The organic material layer may have a multilayer structure comprising a hole injection layer, a hole transfer layer, a light emitting layer, an electron transfer layer and the like, however, the structure is not limited thereto, and the organic material layer may have a single layer structure. In addition, the organic material layer may be prepared to have less numbers of layers through a solvent process such as spin coating, dip coating, doctor blading, screen printing, inkjet printing or a thermal transfer method instead of a deposition method using various polymer materials.

As the anode material, materials having large work function are normally preferred so that hole injection to an organic material layer is smooth. Specific examples of the anode material capable of being used in the present disclosure comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material comprise metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto, and additional compounds capable of p-doping may be further included.

The hole transfer material is a material capable of receiving holes from an anode or a hole injection layer and transferring the holes to a light emitting layer, and materials having high mobility for the holes are suited. Specific examples thereof comprise arylamine-based organic materials, conductive polymers, block copolymers having conjugated parts and non-conjugated parts together, and the like, but are not limited thereto.

An electron blocking layer may be provided between the hole transfer layer and the light emitting layer. As the electron blocking layer, materials known in the art such as arylamine-based organic materials may be used.

The light emitting layer may emit light of red, green or blue, and may be formed with phosphorescent materials or fluorescent materials. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof comprise 8-hydroxyquinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly (p-phenylenevinylene) (PPV)-based polymers; spiro compounds; polyfluorene, rubrene, and the like, but are not limited thereto.

The host material of the light emitting layer comprises fused aromatic ring derivatives, heteroring-containing compounds or the like. Specifically, the fused aromatic ring derivative comprises anthracene derivatives, pyrene derivatives, naphthalene derivatives, pentacene derivatives, phenanthrene compounds, fluoranthene compounds and the like, and the heteroring-containing compound comprises carbazole derivatives, dibenzofuran derivatives, ladder-type furan compounds, pyrimidine derivatives and the like, however, the material is not limited thereto.

The iridium-based complex used as a dopant of the light emitting layer is as follows, but is not limited thereto.

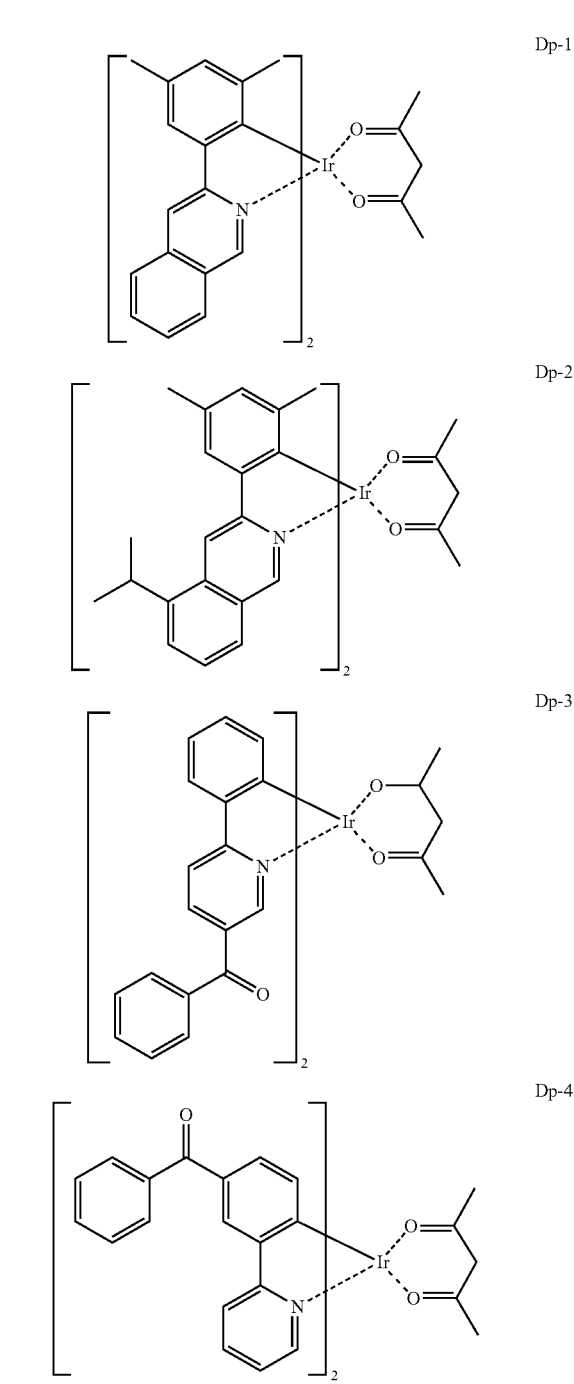

Dp-5
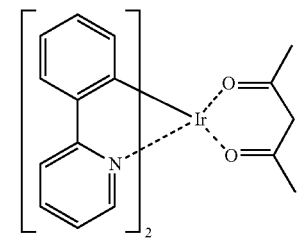
Dp-6
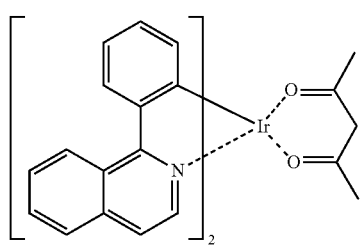
Dp-7
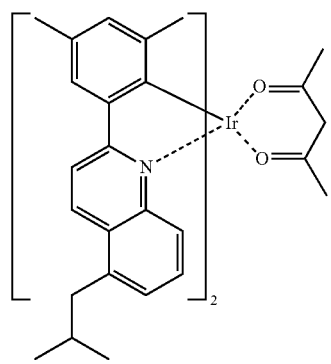
Dp-8
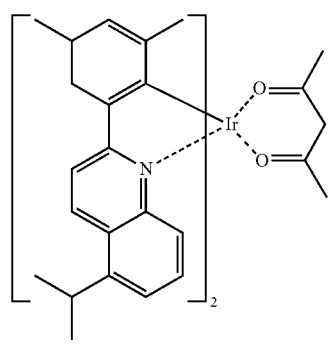
Dp-9
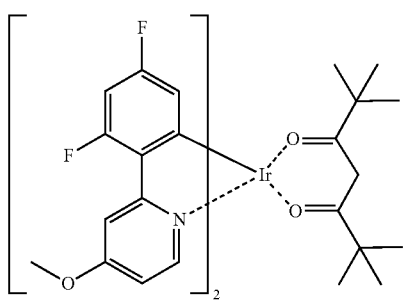
Dp-10
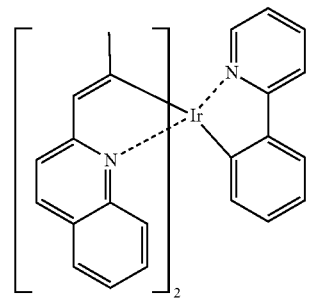
Dp-11
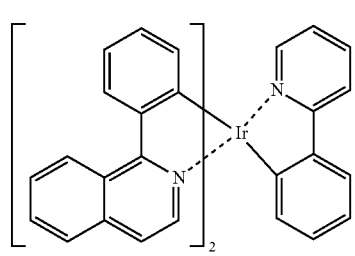
Dp-12
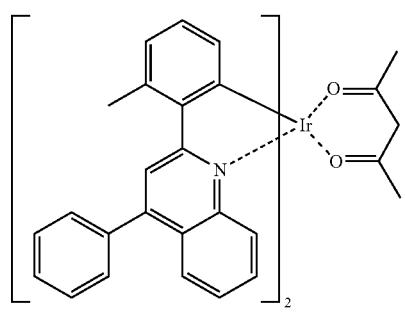
Dp-13
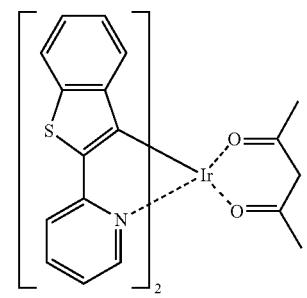
Dp-14
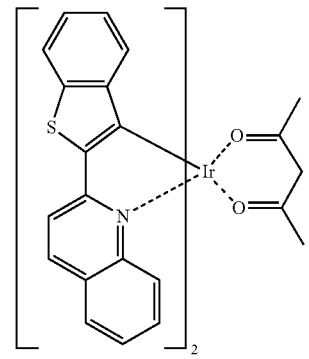

Dp-15
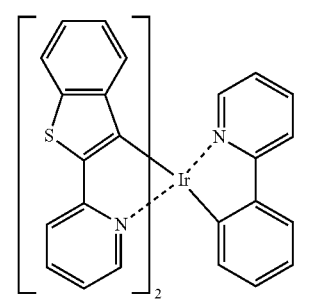
Dp-16
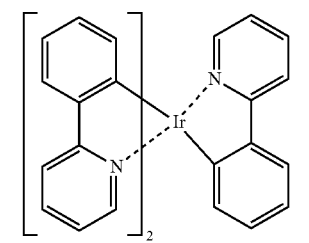
Dp-17
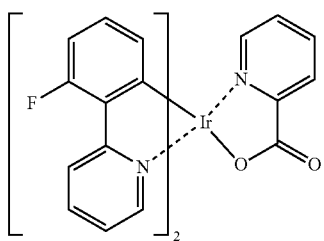
Dp-18
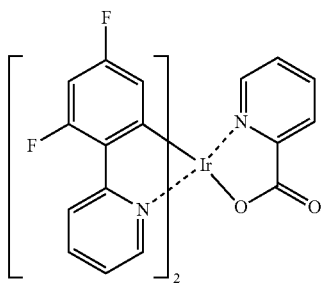
Dp-19
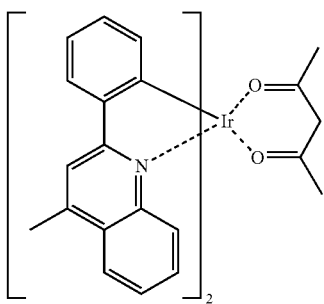
Dp-20
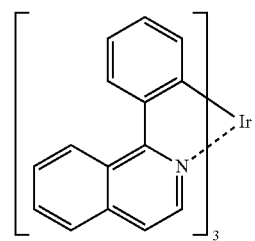
Dp-21
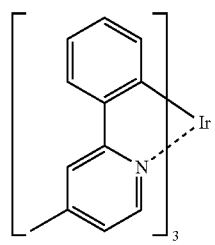
Dp-22
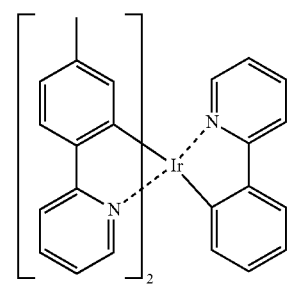
Dp-23
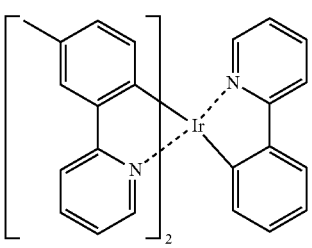
Dp-24
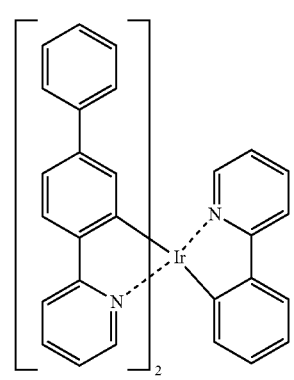
Dp-25
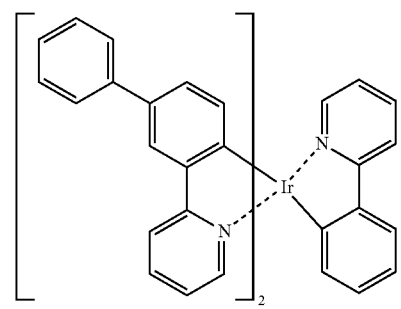

Dp-26 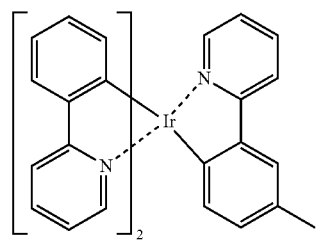
Dp-27 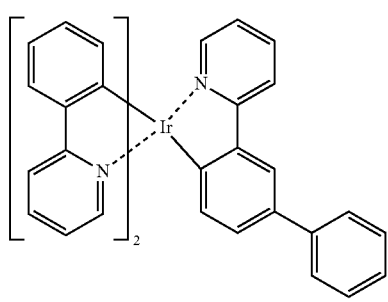
Dp-28 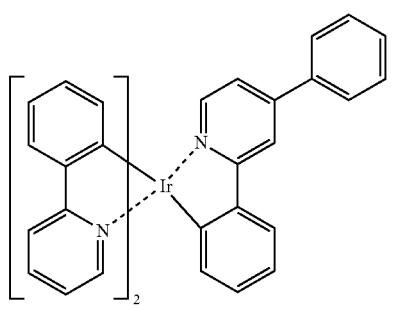
Dp-29 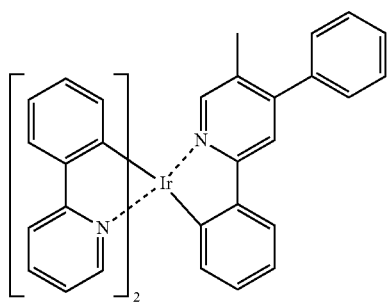
Dp-30 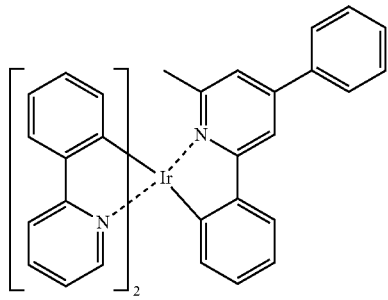
Dp-31 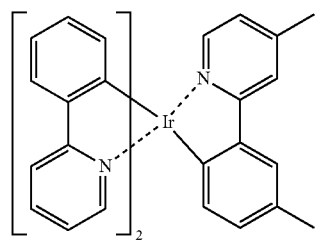
Dp-32 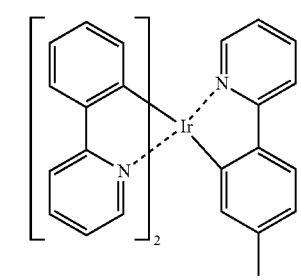
Dp-33 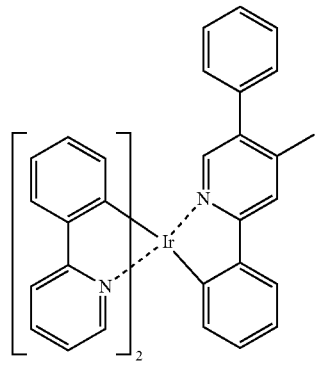
Dp-34 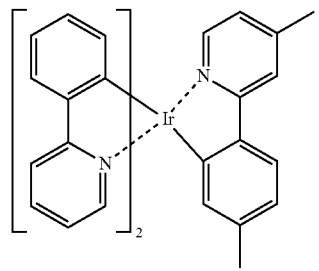
Dp-35 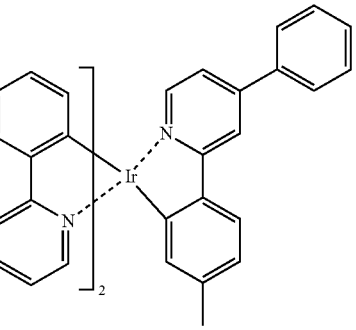

-continued

Dp-36
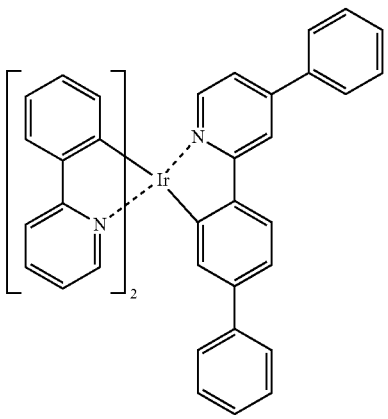

Dp-37
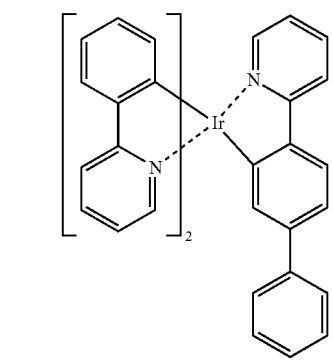

Dp-38
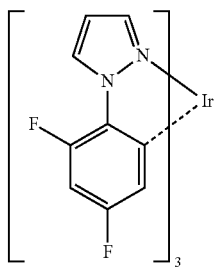

A hole blocking layer may be provided between the electron transfer layer and the light emitting layer, and materials known in the art such as triazine-based compounds may be used.

The electron transfer layer may perform a role of facilitating electron transfer. The electron transfer material is a material favorably receiving electrons from a cathode and transferring the electrons to a light emitting layer, materials having high mobility for the electrons are suited. Specific examples thereof comprise Al complexes of 8-hydroxyquinoline; complexes comprising $Alq_3$; organic radical compounds; hydroxyflavon-metal complexes, and the like, but are not limited thereto. The electron transfer layer may have a thickness of 1 nm to 50 nm. The electron transfer layer having a thickness of 1 nm or greater has an advantage of preventing decline in the electron transfer properties, and the thickness being 50 nm or less has an advantage of preventing an increase in the driving voltage for enhancing electron migration caused by the electron transfer layer being too thick.

The electron injection layer may perform a role of facilitating electron injection. The electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof comprise fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, examples according to the present specification may be modified to various different forms, and the scope of the present specification is not to be construed as being limited to the examples described below. Examples of the present specification are provided in order to more fully describe the present specification to those having average knowledge in the art.

Synthesis Example

Synthesis Example 1

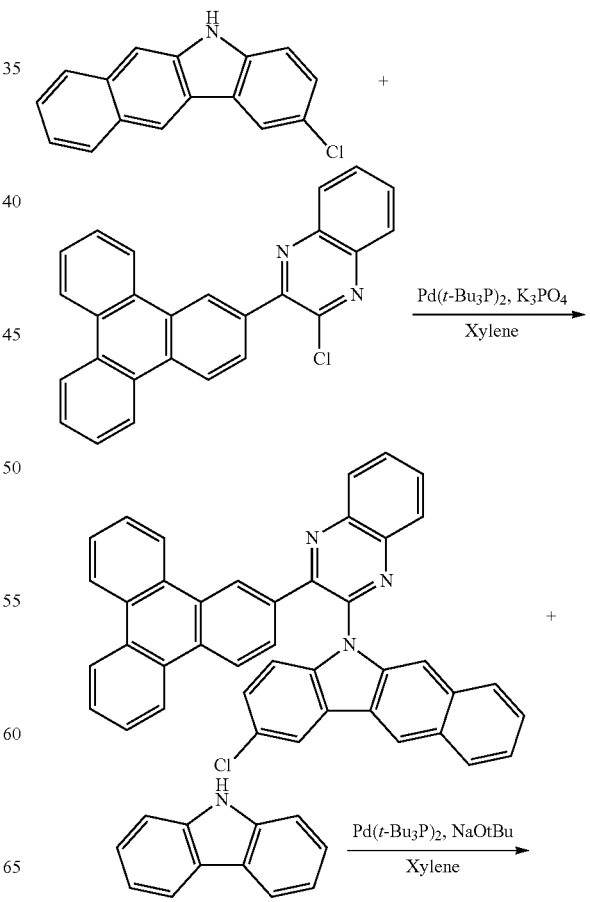

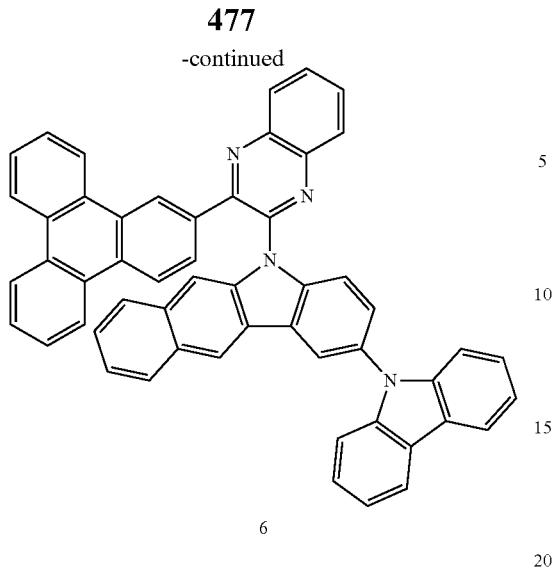

6

Chemical Formula b (10.0 g, 1.0 eq.), 2-chloro-3-(triphenylen-2-yl)quinoxaline (15.52 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 6-1 (15.17 g, yield 63%). [M+H]=607

Chemical Formula 6-1 (15.17 g, 1.0 eq.), 9H-carbazole (4.60 g, 1.1 eq.), $Pd(t-Bu_3P)_2$ (0.13 g, 0.01 eq.) and NaOtBu (4.81 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 6 (13.09 g, yield 71%). [M+H]=737

Synthesis Example 2

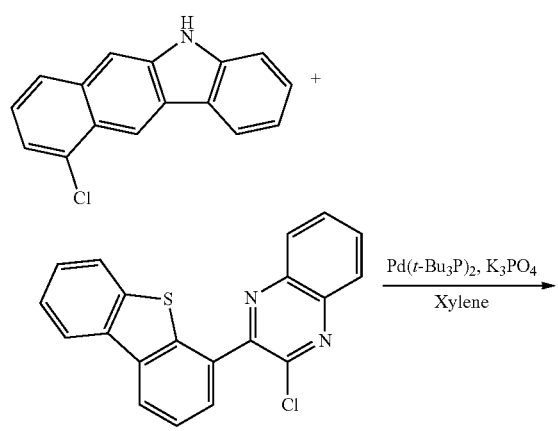

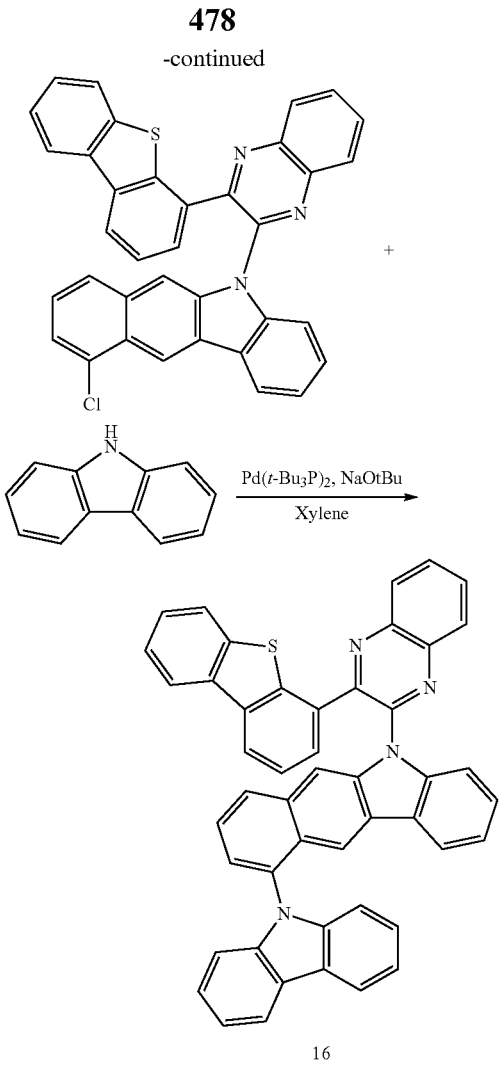

16

Chemical Formula e (10.0 g, 1.0 eq.), 2-chloro-3-(dibenzo[b,d]thiophen-4-yl)quinoxaline (13.78 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 16-1 (14.96 g, yield 67%). [M+H]=563

Chemical Formula 16-1 (14.96 g, 1.0 eq.), 9H-carbazole (4.89 g, 1.1 eq.), Pd(t-Bu3P)2 (0.13 g, 0.01 eq.) and NaOtBu (5.11 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 16 (12.90 g, yield 70%). [M+H]=693

Synthesis Example 3

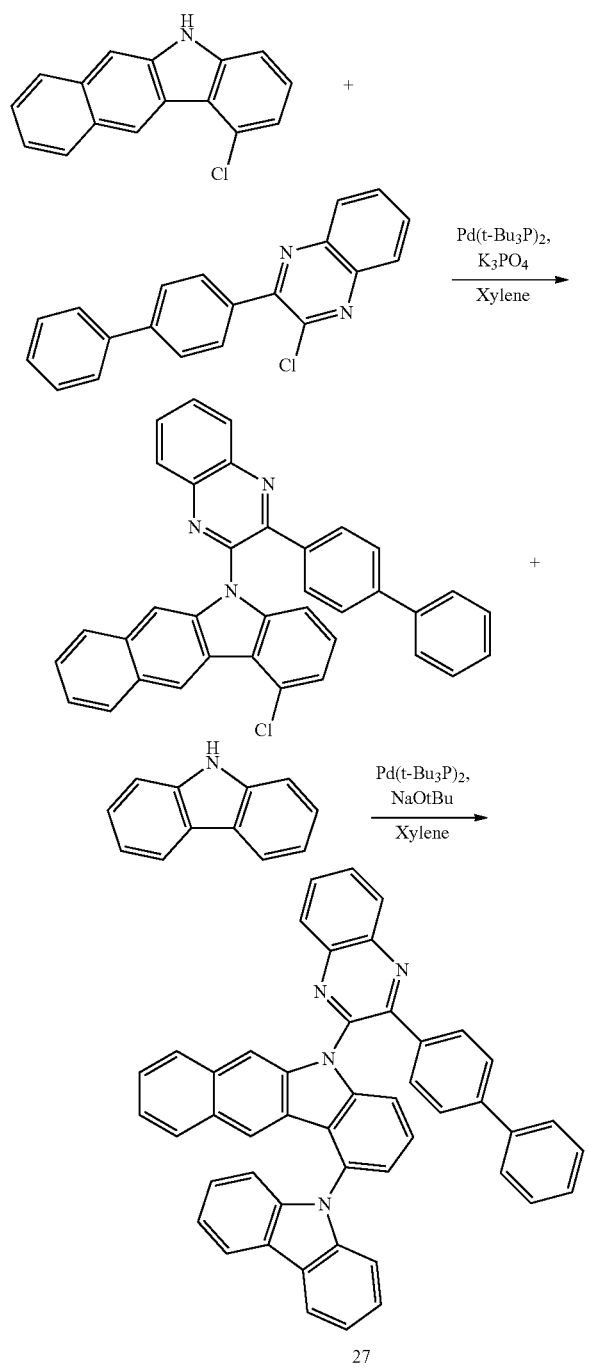

Chemical Formula c (10.0 g, 1.0 eq.), 2-([1,1'-biphenyl]-4-yl)-3-chloroquinoxaline (12.58 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 27-1 (14.79 g, yield 70%). [M+H]=533

Chemical Formula 27-1 (14.79 g, 1.0 eq.), 9H-carbazole (5.11 g, 1.1 eq.), Pd(t-Bu₃P)₂ (0.14 g, 0.01 eq.) and NaOtBu (5.34 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 27 (12.52 g, yield 68%). [M+H]=663

Synthesis Example 4

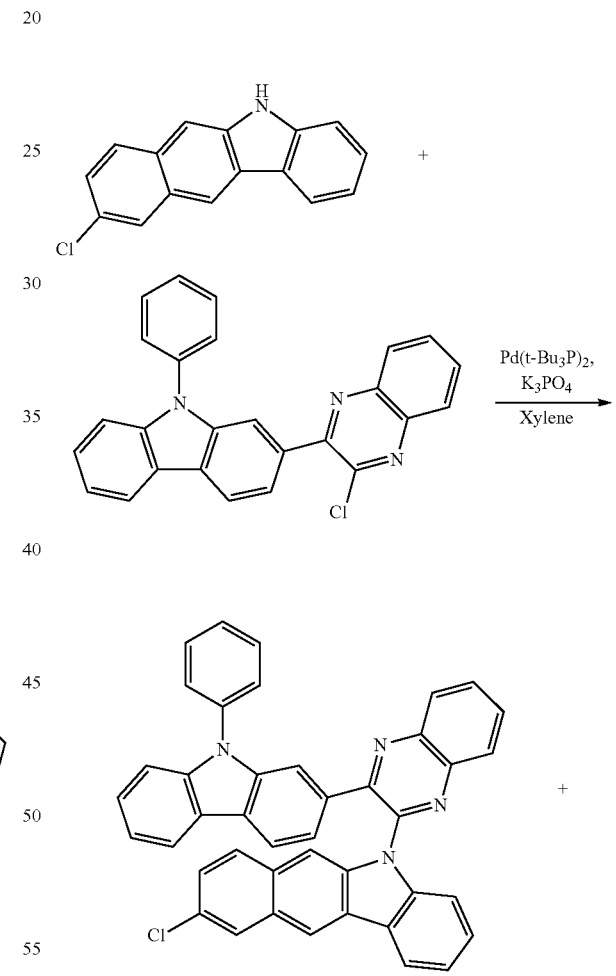

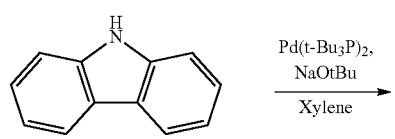

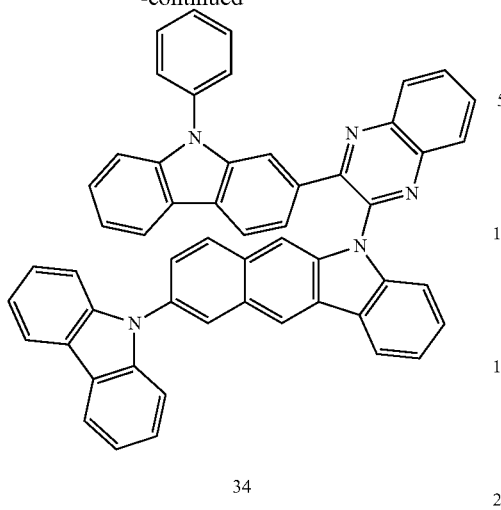

34

Chemical Formula f (10.0 g, 1.0 eq.), 2-(3-chloroquinoxalin-2-yl)-9-phenyl-9H-carbazole (16.12 g, 1.1 eq.), $K_3PO_4$ (16.86 g, 2.0 eq.) and Pd(t-Bu$_3$P) (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 34-1 (16.78 g, yield 68%). [M+H]= 622

Chemical Formula 34-1 (16.78 g, 1.0 eq.), 9H-carbazole (4.96 g, 1.1 eq.), Pd(t-Bu$_3$P)$_2$ (0.13 g, 0.01 eq.) and NaOtBu (5.19 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 34 (14.82 g, yield 73%). [M+H]=752

Synthesis Example 5

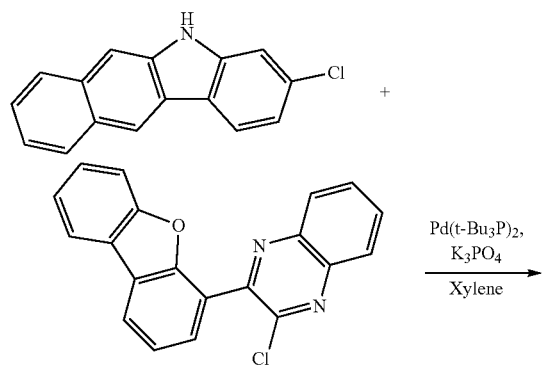

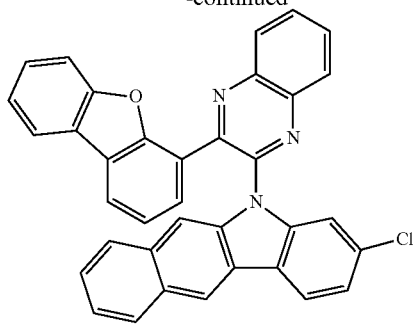

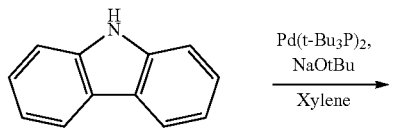

39

Chemical Formula a (10.0 g, 1.0 eq.), 2-chloro-3-(dibenzo[b,d]furan-4-yl)quinoxaline (13.14 g, 1.1 eq.), $K_3PO_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 39-1 (14.10 g, yield 65%). [M+H] =547

Chemical Formula 39-1 (14.10 g, 1.0 eq.), 9H-carbazole (4.79 g, 1.1 eq.), Pd(t-Bu$_3$P)$_2$ (0.13 g, 0.01 eq.) and NaOtBu (4.96 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 39 (12.23 g, yield 70%). [M+H]=677

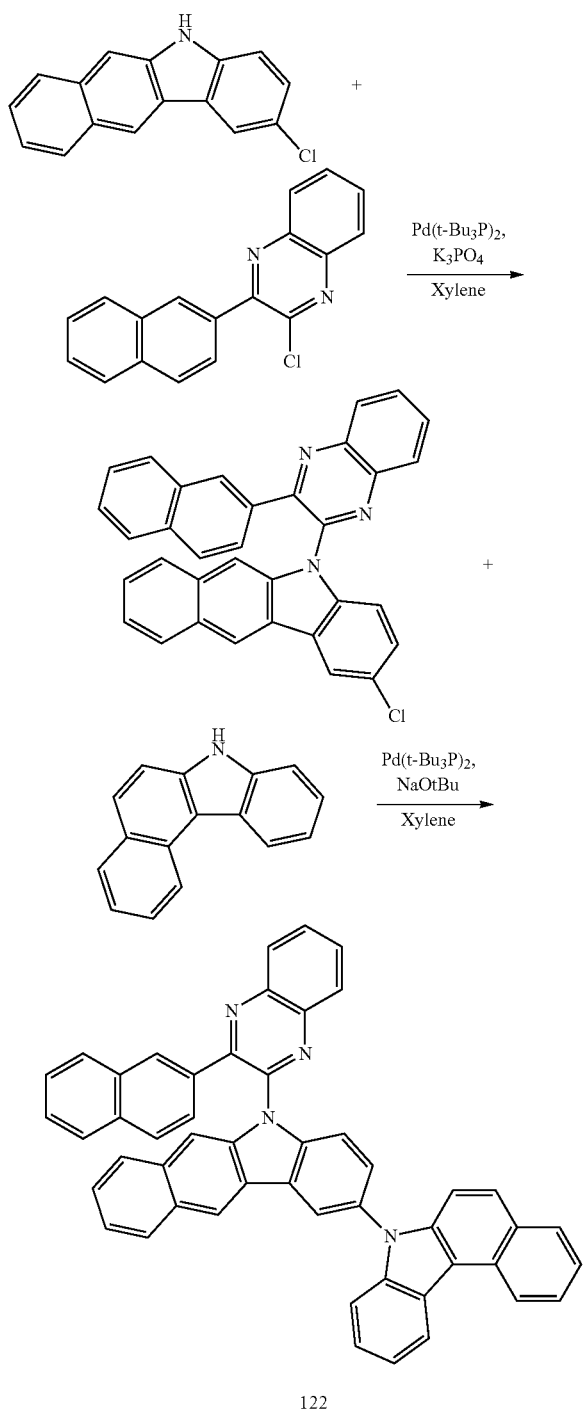

122

Synthesis Example 6

Chemical Formula b (10.0 g, 1.0 eq.), 2-chloro-3-(naphthalen-2-yl)quinoxaline (11.55 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 122-1 (13.46 g, yield 67%). [M+H]=507

Chemical Formula 122-1 (13.46 g, 1.0 eq.), 7H-benzo[c]carbazole (6.35 g, 1.1 eq.), Pd(t-Bu₃P)₂ (0.13 g, 0.01 eq.) and NaOtBu (5.11 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 122 (11.87 g, yield 65%). [M+H]=687

Synthesis Example 7

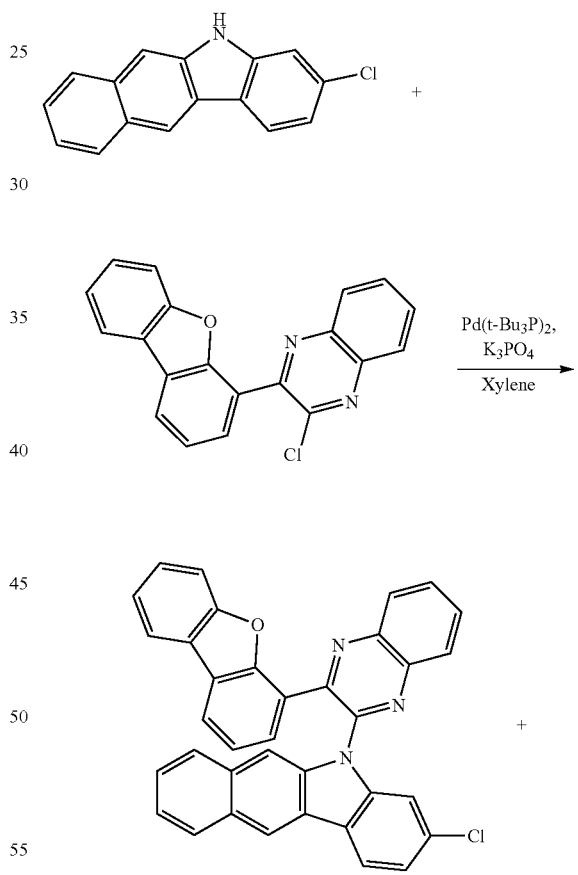

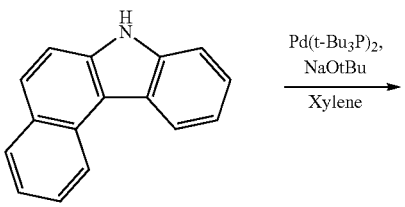

-continued

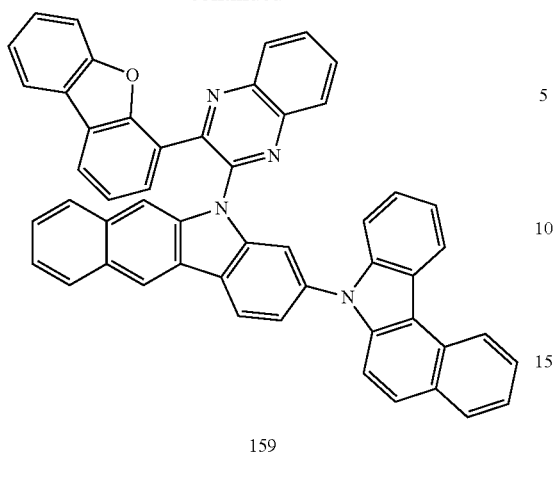

159

Chemical Formula a (10.0 g, 1.0 eq.), 2-chloro-3-(dibenzo[b,d]furan-4-yl)quinoxaline (13.14 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 159-1 (14.96 g, yield 69%). [M+H]=547

Chemical Formula 159-1 (14.96 g, 1.0 eq.), 7H-benzo[c]carbazole (6.54 g, 1.1 eq.), $Pd(t-Bu_3P)_2$ (0.14 g, 0.01 eq.) and NaOtBu (5.26 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 159 (12.94 g, yield 65%). [M+H]=727

Synthesis Example 8

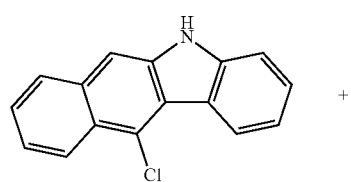 +

-continued

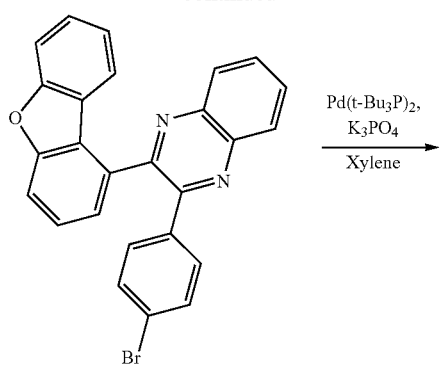

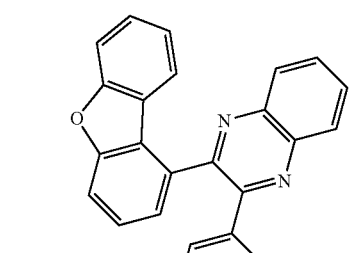

+

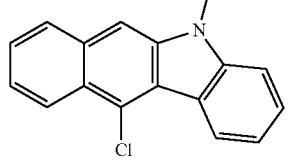

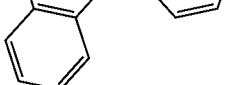

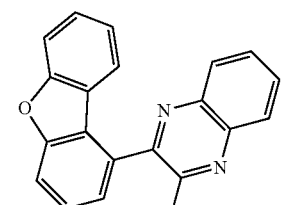

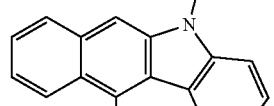

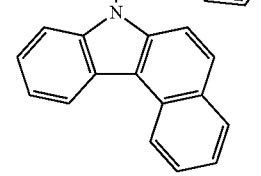

187

Chemical Formula d (10.0 g, 1.0 eq.), 2-(4-bromophenyl)-3-(dibenzo[b,d]furan-1-yl)quinoxaline (17.93 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 187-1 (18.28 g, yield 74%). [M+H]=623

Chemical Formula 187-1 (18.28 g, 1.0 eq.), 7H-benzo[c]carbazole (7.02 g, 1.1 eq.), Pd(t-Bu$_3$P)$_2$ (0.15 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 187 (16.27 g, yield 69%). [M+H]=803

Synthesis Example 9

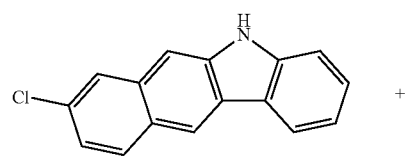
+
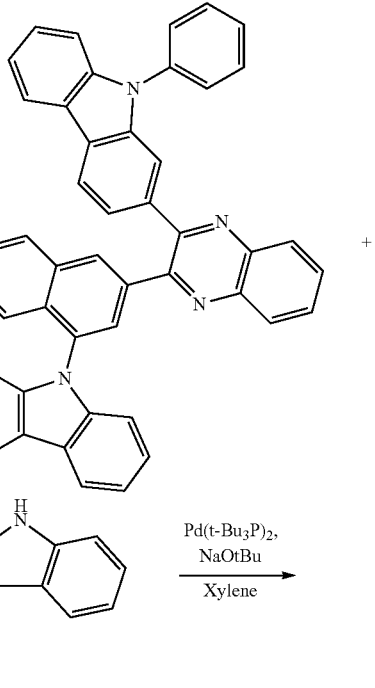

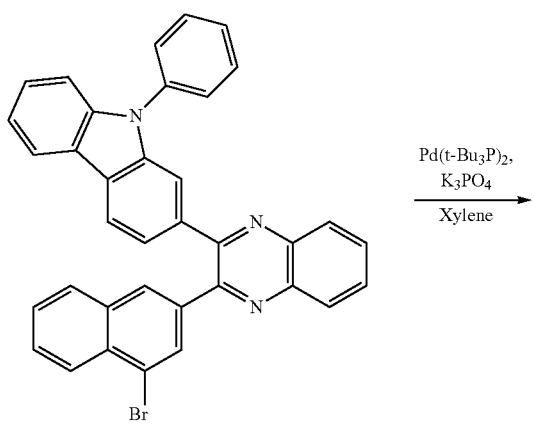

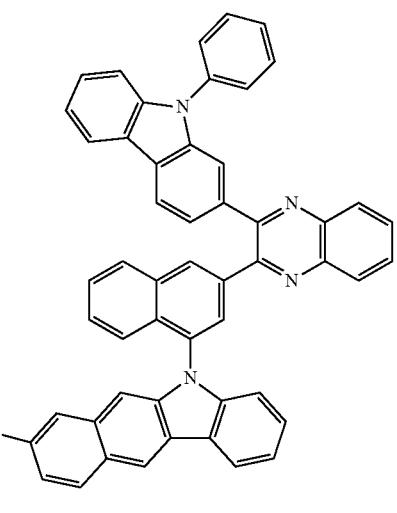

226

Chemical Formula g (10.0 g, 1.0 eq.), 2-(3-(4-bromonaphthalen-2-yl)quinoxalin-2-yl)-9-phenyl-9H-carbazole (22.90 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 226-1 (21.07 g, yield 71%). [M+H]=748

Chemical Formula 226-1 (21.07 g, 1.0 eq.), 7H-benzo[c]carbazole (6.73 g, 1.1 eq.), Pd(t-Bu$_3$P)$_2$ (0.14 g, 0.01 eq.) and NaOtBu (5.41 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 226 (17.00 g, yield 65%). [M+H]=929

Synthesis Example 10

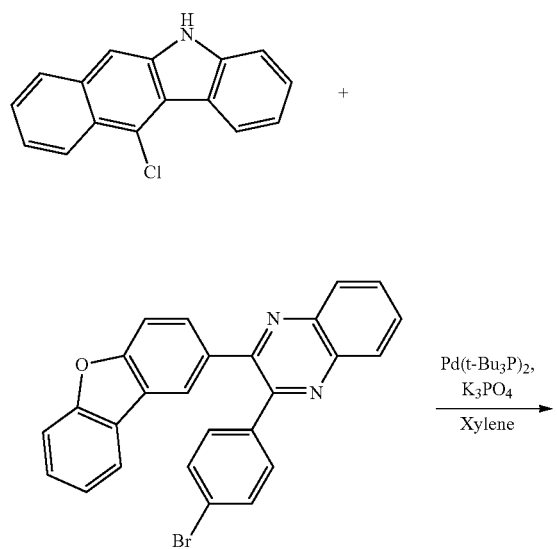

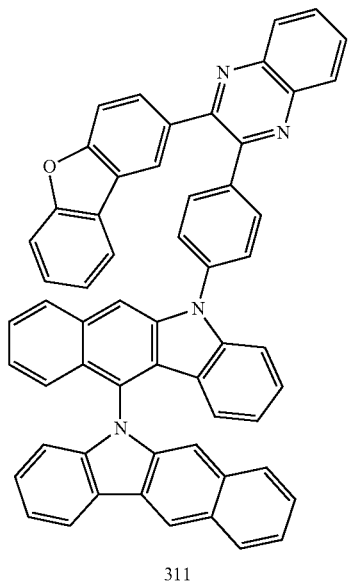

311

Chemical Formula d (10.0 g, 1.0 eq.), 2-(4-bromophenyl)-3-(dibenzo[b,d]furan-2-yl)quinoxaline (17.93 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 311-1 (19.03 g, yield 77%). [M+H]=623

Chemical Formula 311-1 (19.03 g, 1.0 eq.), 5H-benzo[b]carbazole (7.31 g, 1.1 eq.), Pd(t-Bu₃P)₂ (0.15 g, 0.01 eq.) and NaOtBu (5.87 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 311 (16.70 g, yield 68%). [M+H]=803

Synthesis Example 11

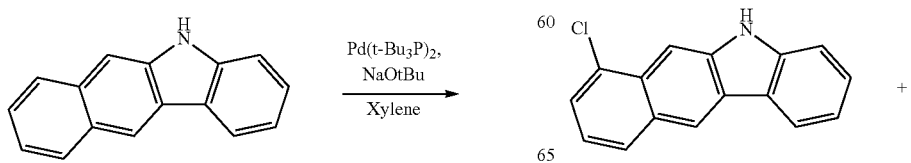

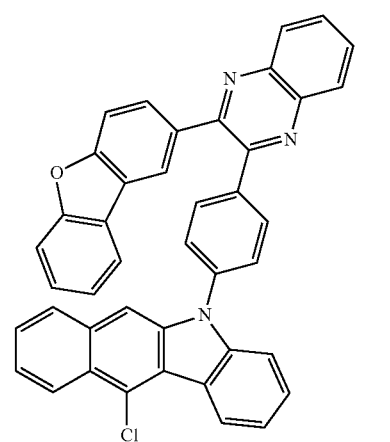

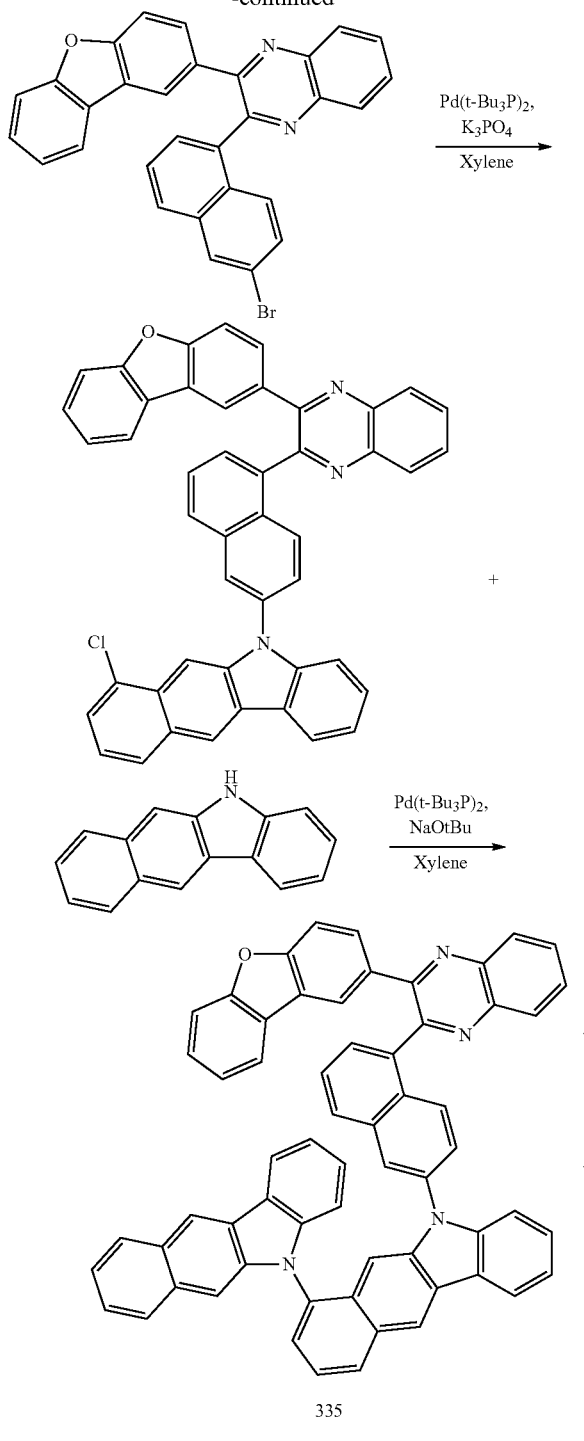

335

Chemical Formula h (10.0 g, 1.0 eq.), 2-(6-bromonaphthalen-1-yl)-3-(dibenzo[b,d]furan-2-yl)quinoxaline (19.91 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 335-1 (19.23 g, yield 77%). [M+H]=673

Chemical Formula 335-1 (19.23 g, 1.0 eq.), 5H-benzo[b]carbazole (6.83 g, 1.1 eq.), $Pd(t-Bu_3P)_2$ (0.14 g, 0.01 eq.) and NaOtBu (5.49 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 335 (16.34 g, yield 67%). [M+H]=854

Synthesis Example 12

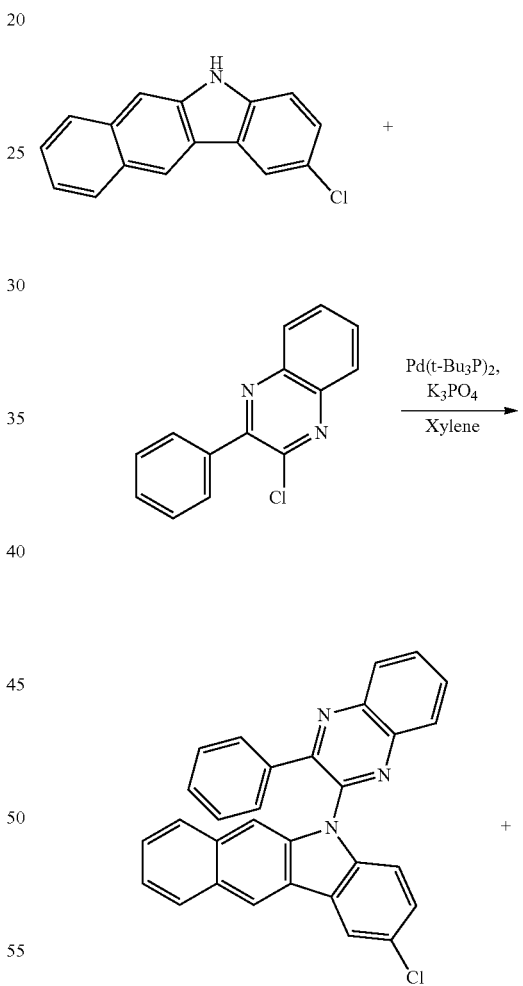

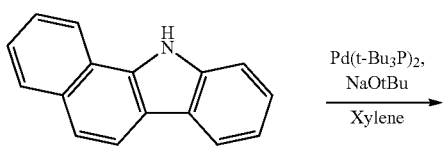

-continued

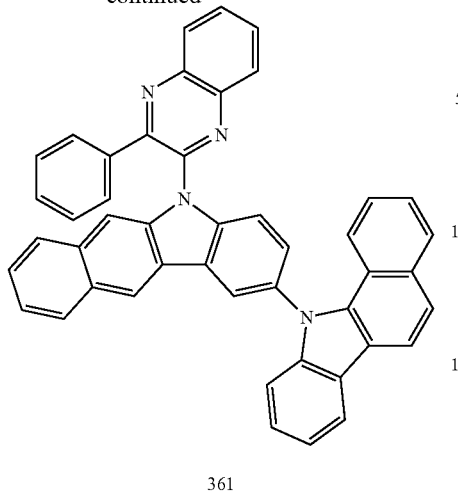

361

Chemical Formula b (10.0 g, 1.0 eq.), 2-chloro-3-phenylquinoxaline (9.56 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 361-1 (12.67 g, yield 70%). [M+H]=456

Chemical Formula 361-1 (12.67 g, 1.0 eq.), 11H-benzo[a]carbazole (6.64 g, 1.1 eq.), $Pd(t-Bu_3P)_2$ (0.14 g, 0.01 eq.) and NaOtBu (5.34 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 361 (12.03 g, yield 68%). [M+H]=637

Synthesis Example 13

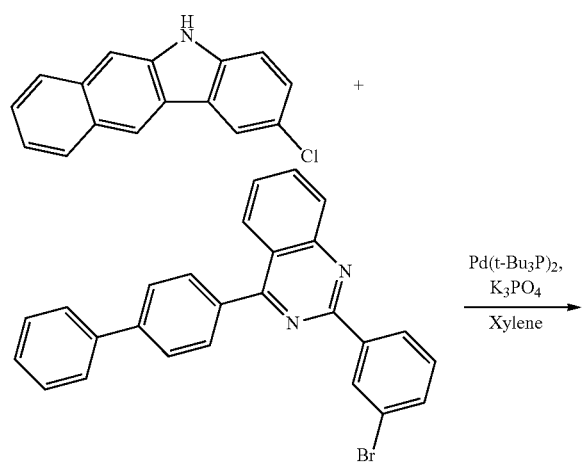

-continued

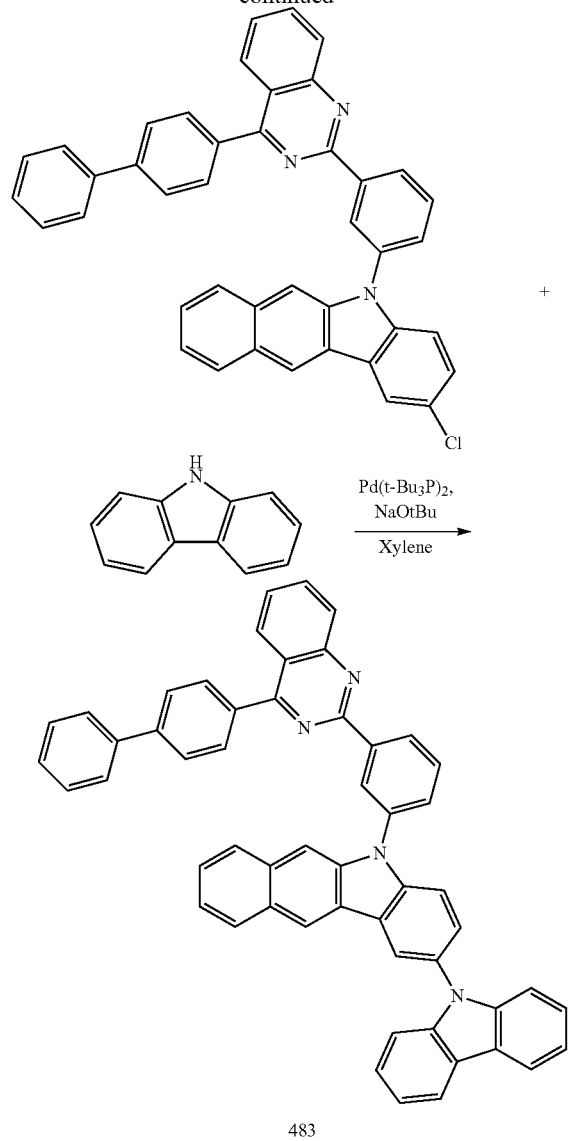

483

Chemical Formula b (10.0 g, 1.0 eq.), 4-([1,1'-biphenyl]-4-yl)-2-(3-bromophenyl)quinazoline (17.37 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 483-1 (16.91 g, yield 70%). [M+H]=609

Chemical Formula 483-1 (16.91 g, 1.0 eq.), 9H-carbazole (5.11 g, 1.1 eq.), $Pd(t-Bu_3P)_2$ (0.14 g, 0.01 eq.) and NaOtBu (5.34 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 483 (13.56 g, yield 66%). [M+H]=739

Synthesis Example 14

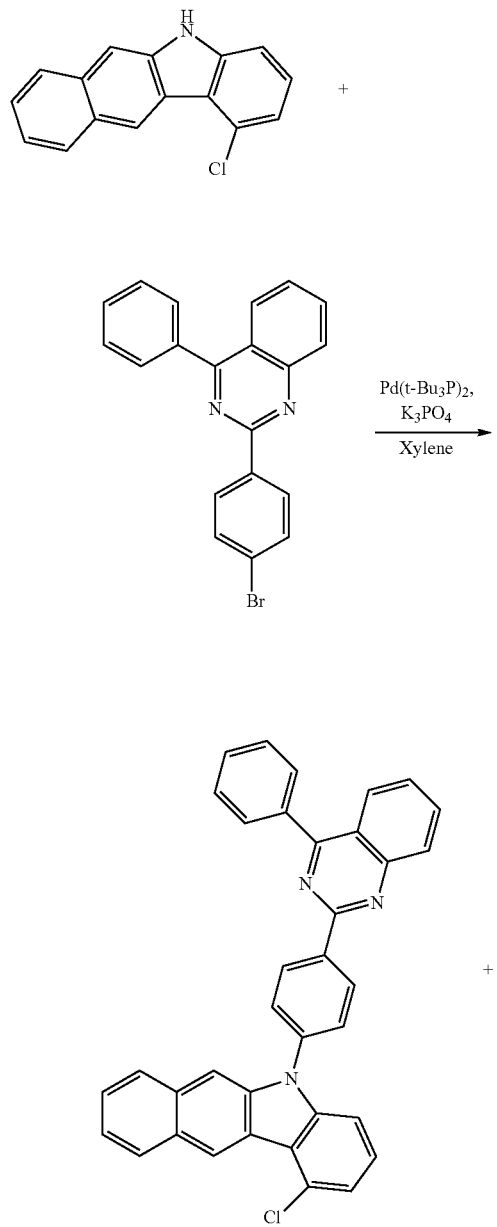

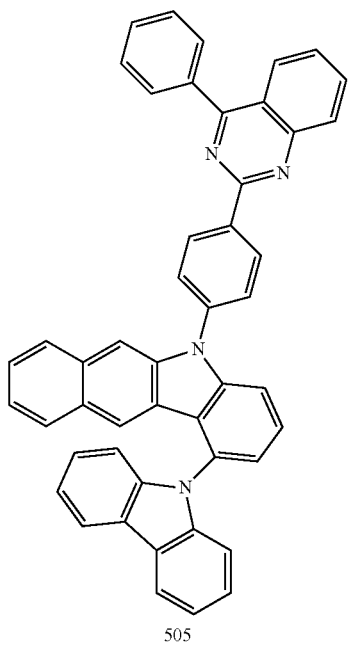

505

Chemical Formula c (10.0 g, 1.0 eq.), 2-(4-bromophenyl)-4-phenylquinazoline (14.35 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 505-1 (15.64 g, yield 74%). [M+H]=532

Chemical Formula 505-1 (15.64 g, 1.0 eq.), 9H-carbazole (5.40 g, 1.1 eq.), Pd(t-Bu₃P)₂ (0.15 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 505 (13.44 g, yield 69%). [M+H]=663

Synthesis Example 15

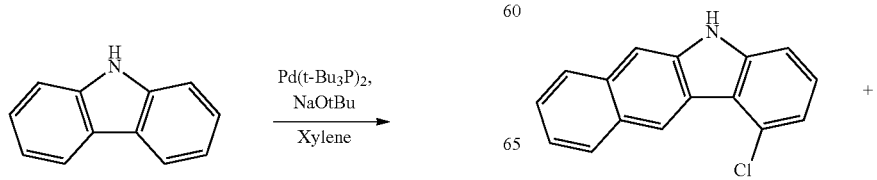

-continued

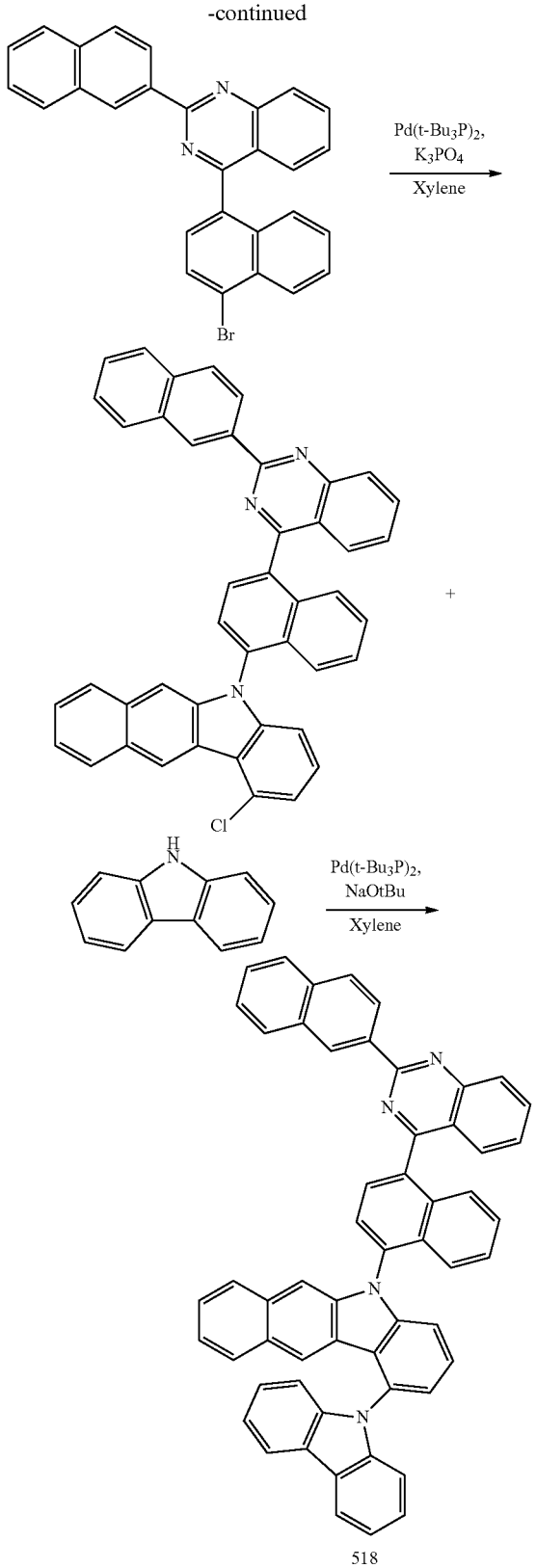

Chemical Formula c (10.0 g, 1.0 eq.), 4-(4-bromonaphthalen-1-yl)-2-(naphthalen-2-yl)quinazoline (18.32 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 518-1 (17.58 g, yield 70%). [M+H]=633

Chemical Formula 518-1 (17.58 g, 1.0 eq.), 9H-carbazole (5.11 g, 1.1 eq.), Pd(t-Bu₃P)₂ (0.14 g, 0.01 eq.) and NaOtBu (5.34 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 518 (13.36 g, yield 63%). [M+H]=763

Synthesis Example 16

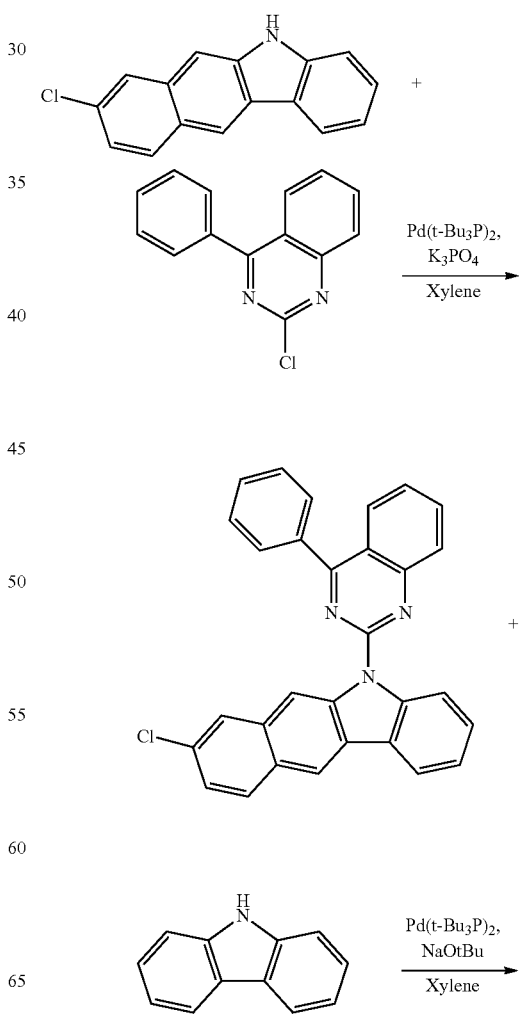

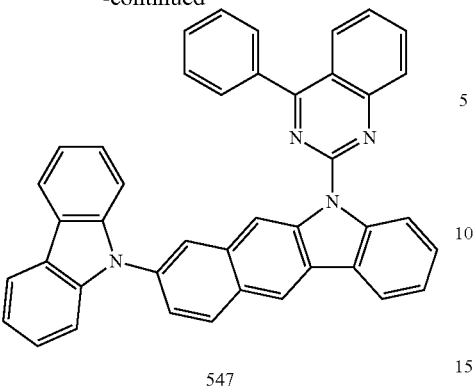

547

Chemical Formula g (10.0 g, 1.0 eq.), 2-chloro-4-phenylquinazoline (9.56 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 547-1 (13.22 g, yield 73%). [M+H]=456

Chemical Formula 547-1 (13.22 g, 1.0 eq.), 9H-carbazole (5.33 g, 1.1 eq.), Pd(t-Bu$_3$P)$_2$ (0.14 g, 0.01 eq.) and NaOtBu (5.57 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 547 (11.73 g, yield 69%). A graph measuring 1H-NMR of Compound 547 is shown in FIG. 5. [M+H]=587

Synthesis Example 17

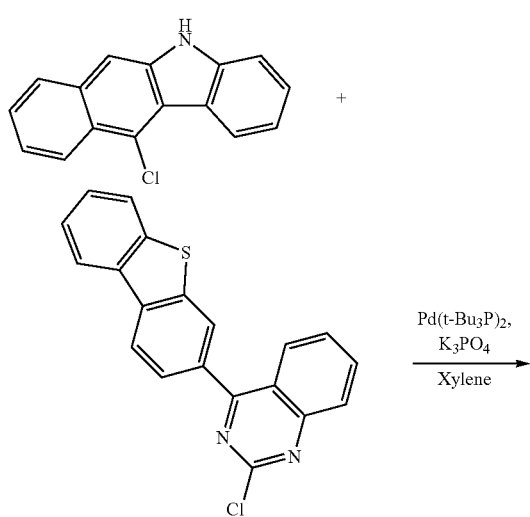

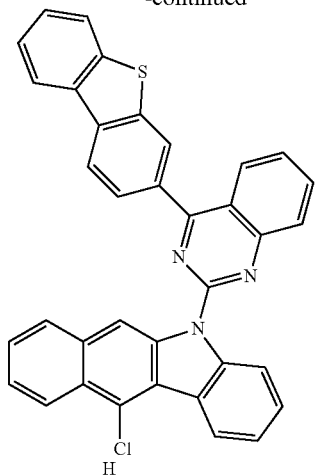

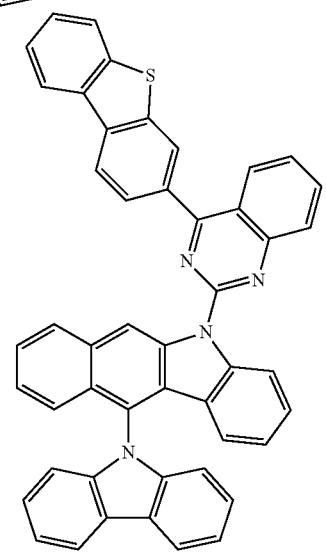

561

Chemical Formula d (10.0 g, 1.0 eq.), 2-chloro-4-(dibenzo[b,d]thiophen-3-yl)quinazoline (13.77 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 561-1 (16.74 g, yield 75%). [M+H]=563

Chemical Formula 561-1 (16.74 g, 1.0 eq.), 9H-carbazole (5.47 g, 1.1 eq.), Pd(t-Bu$_3$P)$_2$ (0.14 g, 0.01 eq.) and NaOtBu (5.72 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 561 (12.58 g, yield 61%). [M+H]=693

Synthesis Example 18

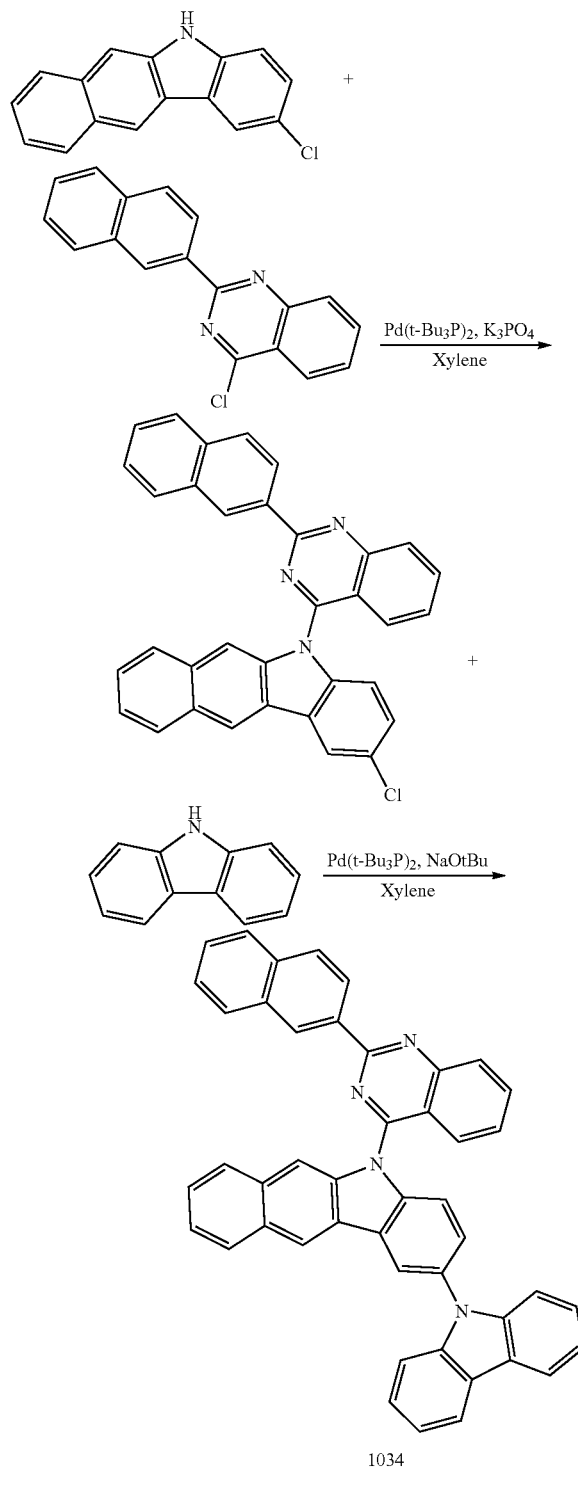

1034

Chemical Formula b (10.0 g, 1.0 eq.), 4-chloro-2-(naphthalen-2-yl)quinazoline (11.55 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 1034-1 (14.87 g, yield 74%). [M+H]=507

Chemical Formula 1034-1 (14.87 g, 1.0 eq.), 9H-carbazole (5.40 g, 1.1 eq.), $Pd(t-Bu_3P)_2$ (0.14 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 1034 (12.91 g, yield 69%) [M+H]=637

Synthesis Example 19

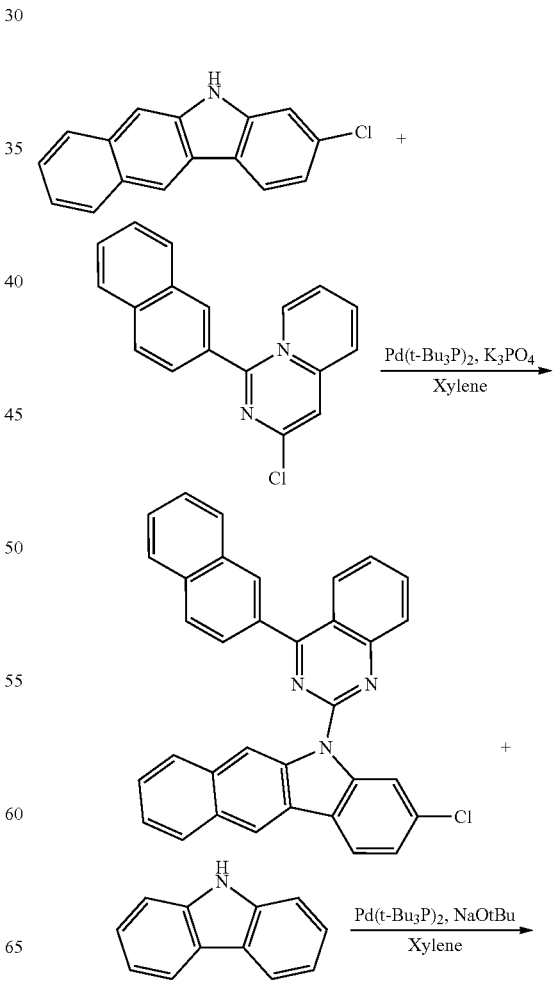

-continued

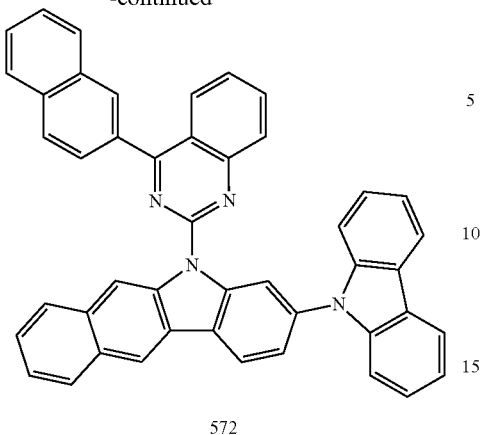

572

Chemical Formula a (10.0 g, 1.0 eq.), 2-chloro-4-(naphthalen-2-yl)quinazoline (11.55 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 572-1 (14.47 g, yield 72%). [M+H]=507

Chemical Formula 572-1 (14.47 g, 1.0 eq.), 9H-carbazole (5.40 g, 1.1 eq.), Pd(t-Bu$_3$P)$_2$ (0.14 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 572 (12.74 g, yield 70%). [M+H]=637

Synthesis Example 20

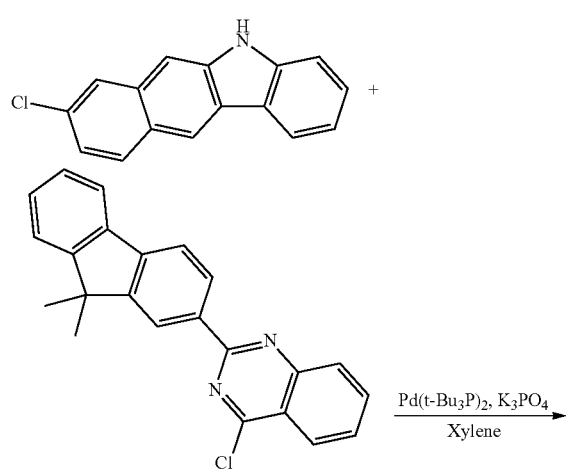

-continued

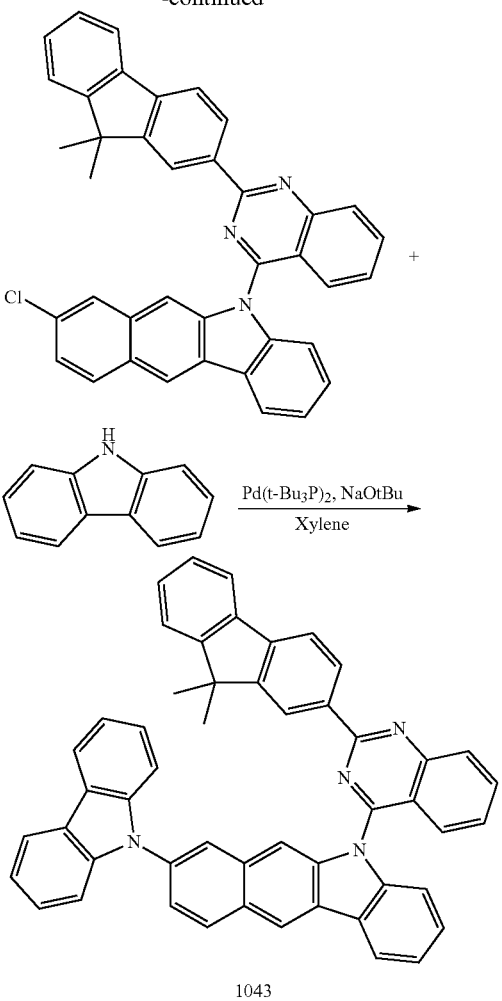

1043

Chemical Formula g (10.0 g, 1.0 eq.), 4-chloro-2-(9,9-dimethyl-9H-fluoren-2-yl)quinazoline (14.25 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1043-1 (15.91 g, yield 70%). [M+H]=573

Chemical Formula 1043-1 (15.91 g, 1.0 eq.), 9H-carbazole (5.11 g, 1.1 eq.), Pd(t-Bu$_3$P)$_2$ (0.14 g, 0.01 eq.) and NaOtBu (5.34 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1043 (14.07 g, yield 72%). [M+H]=703

Synthesis Example 21

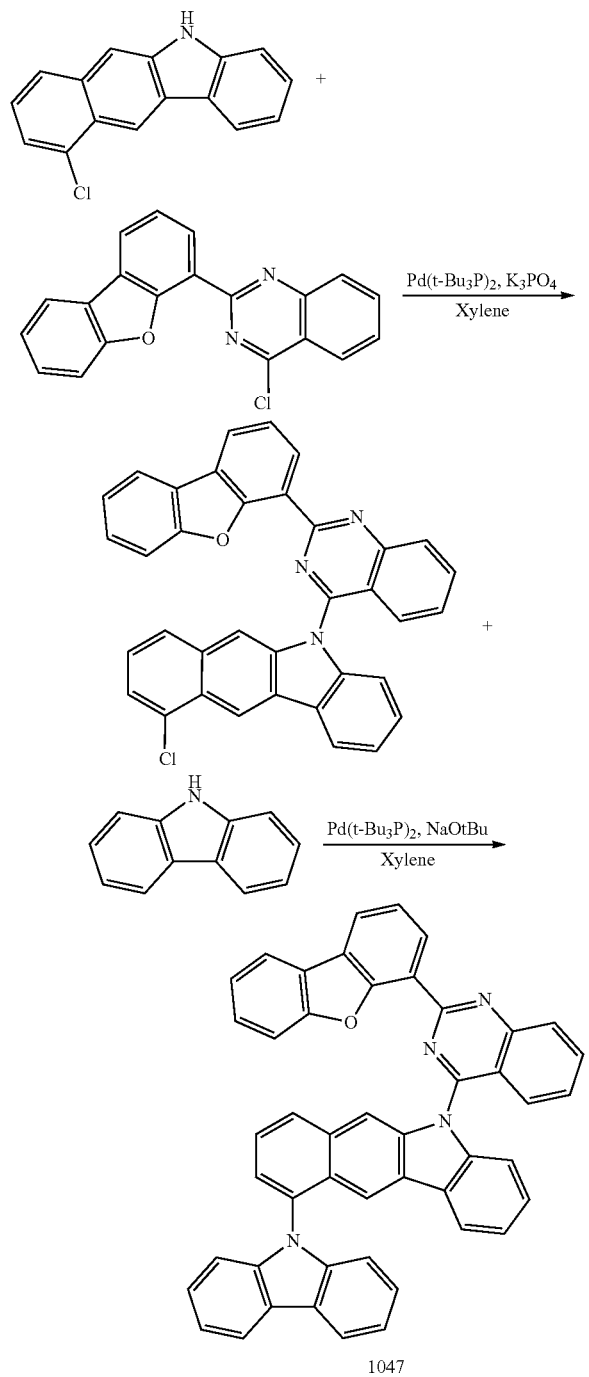

1047

Chemical Formula e (10.0 g, 1.0 eq.), 4-chloro-2-(dibenzo[b,d]furan-4-yl)quinazoline (13.14 g, 1.1 eq.), $K_3PO_4$ (16.86 g, 2.0 eq.) and Pd(t-Bu$_3$P)$_2$ (0.05 g, 0.002 eq.) were reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1047-1 (15.18 g, yield 70%). [M+H]=547

Chemical Formula 1047-1 (15.18 g, 1.0 eq.), 9H-carbazole (5.35 g, 1.1 eq.), Pd(t-Bu$_3$P)$_2$ (0.14 g, 0.01 eq.) and NaOtBu (5.60 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1047 (13.80 g, yield 70%). [M+H]=677

Synthesis Example 22

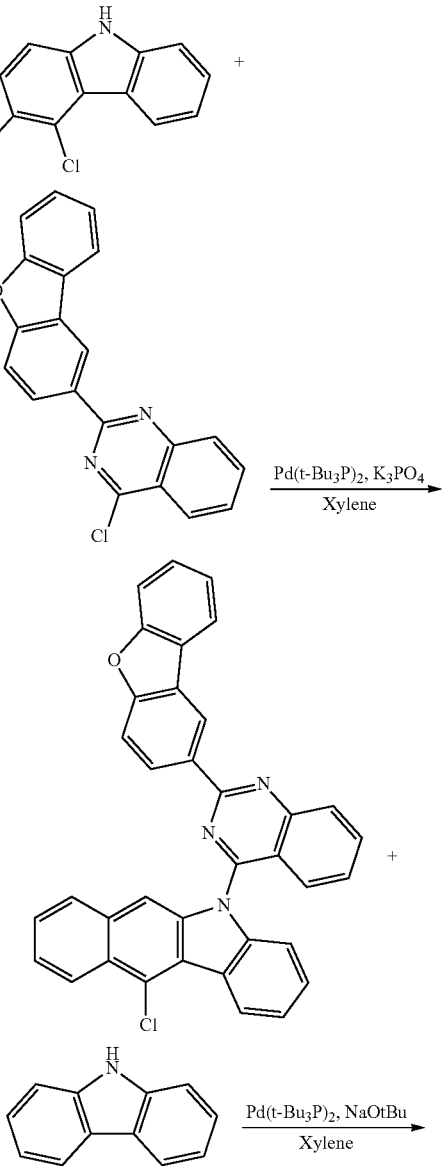

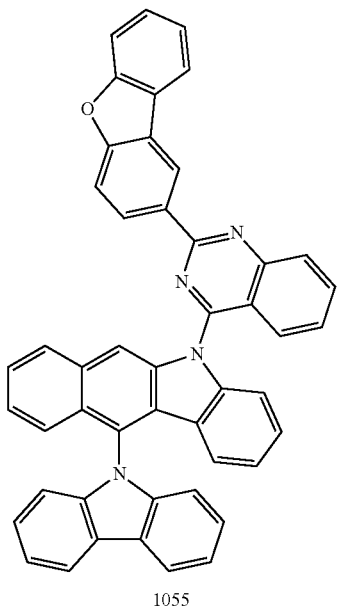

1055

Chemical Formula d (10.0 g, 1.0 eq.), 4-chloro-2-(dibenzo[b,d]furan-2-yl)quinazoline (13.14 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1055-1 (15.61 g, yield 72%). [M+H]=547

Chemical Formula 1055-1 (15.61 g, 1.0 eq.), 9H-carbazole (5.25 g, 1.1 eq.), Pd(t-Bu₃P)₂ (0.14 g, 0.01 eq.) and NaOtBu (5.49 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1055 (13.54 g, yield 70%). [M+H]=677

Synthesis Example 23

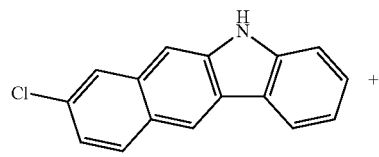

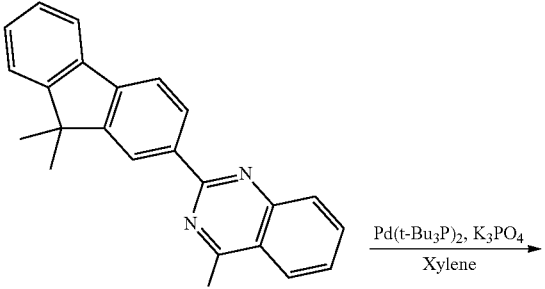

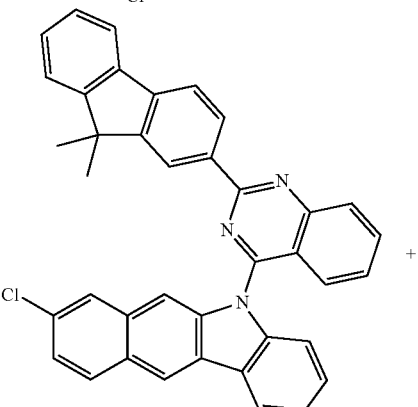

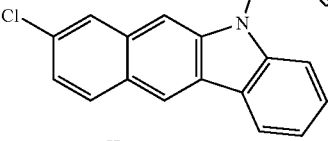

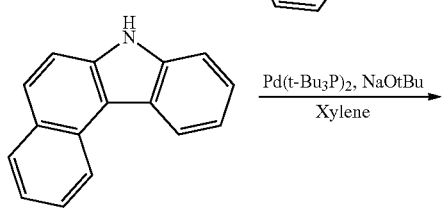

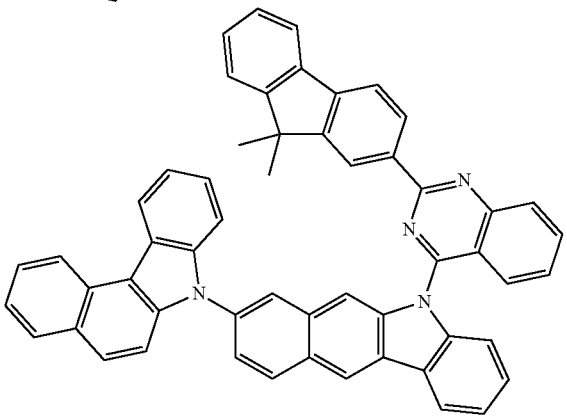

647

Chemical Formula g (10.0 g, 1.0 eq.), 4-chloro-2-(9,9-dimethyl-9H-fluoren-2-yl)quinazoline (14.17 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 647-1 (15.45 g, yield 68%). [M+H]=573

Chemical Formula 647-1 (15.45 g, 1.0 eq.), 7H-benzo[c]carbazole (6.52 g, 1.1 eq.), Pd(t-Bu₃P)₂ (0.14 g, 0.01 eq.) and NaOtBu (5.49 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 647 (13.14 g, yield 64%). [M+H]=753

Synthesis Example 24

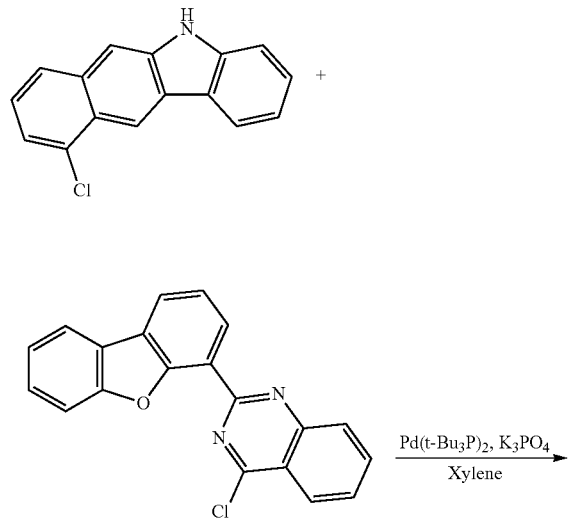

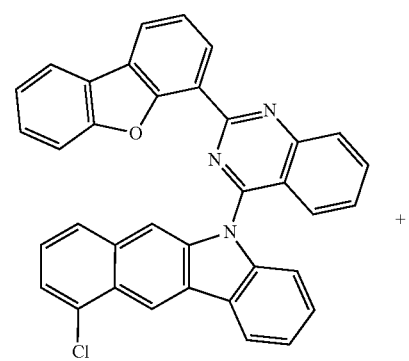

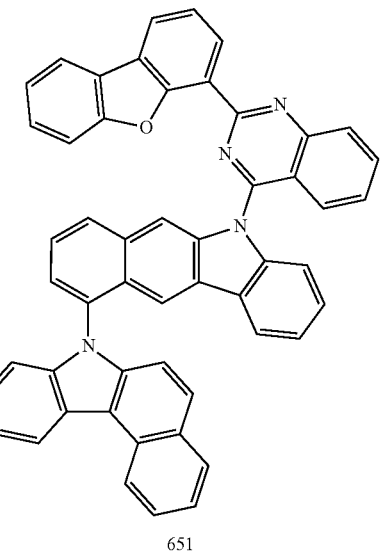

651

Chemical Formula e (10.0 g, 1.0 eq.), 4-chloro-2-(dibenzo[b,d]furan-4-yl)quinazoline (13.14 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 651-1 (14.75 g, yield 68%). [M+H]=547

Chemical Formula 651-1 (14.75 g, 1.0 eq.), 7H-benzo[c]carbazole (6.45 g, 1.1 eq.), Pd(t-Bu₃P)₂ (0.14 g, 0.01 eq.) and NaOtBu (5.19 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 651 (12.95 g, yield 66%). [M+H]=727

Synthesis Example 25

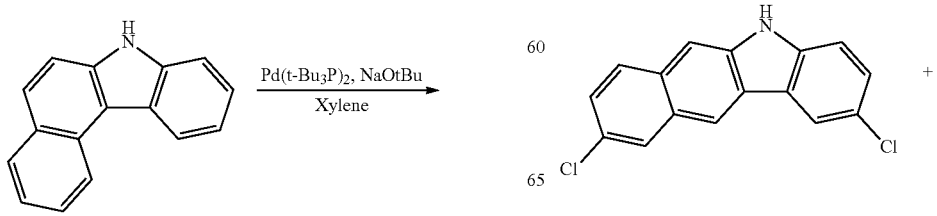

511
-continued

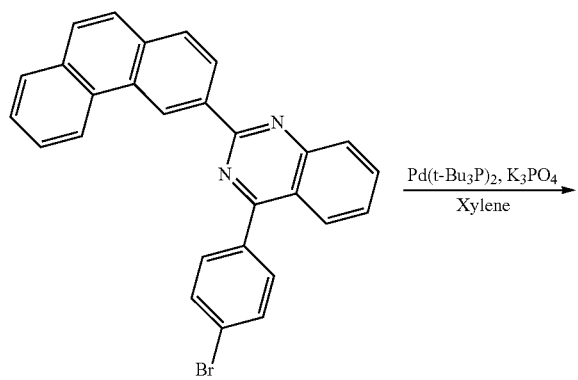

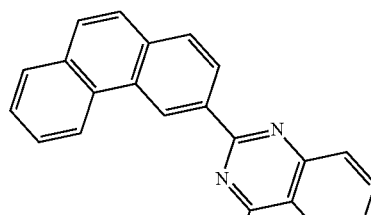

512
-continued

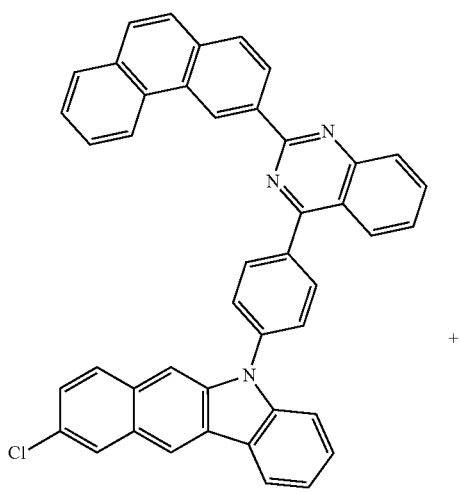

672

Chemical Formula f (10.0 g, 1.0 eq.), 4-(4-bromophenyl)-2-(phenanthren-3-yl)quinazoline (18.32 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 672-1 (16.82 g, yield 67%). [M+H]=633

Chemical Formula 672-1 (16.82 g, 1.0 eq.), 7H-benzo[c]carbazole (6.35 g, 1.1 eq.), $Pd(t-Bu_3P)_2$ (0.14 g, 0.01 eq.) and NaOtBu (5.11 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 672 (14.92 g, yield 69%). [M+H]=813

Synthesis Example 26

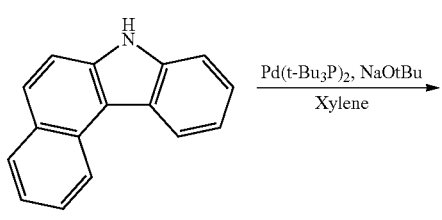

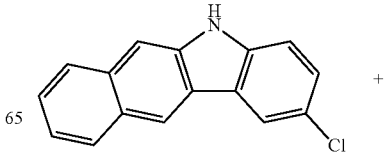

+

-continued

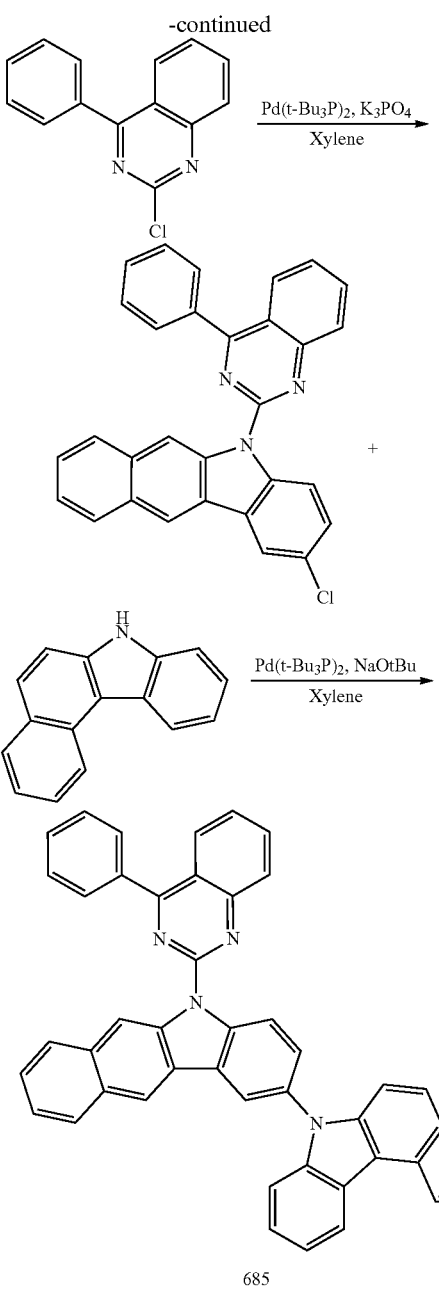

685

Chemical Formula b (10.0 g, 1.0 eq.), 2-chloro-4-phenylquinazoline (9.56 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 685-1 (13.22 g, yield 73%). [M+H]=456

Chemical Formula 685-1 (13.22 g, 1.0 eq.), 7H-benzo[c]carbazole (6.92 g, 1.1 eq.), Pd(t-Bu₃P)₂ (0.14 g, 0.01 eq.) and NaOtBu (5.57 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 685 (12.55 g, yield 68%). [M+H]=637

Synthesis Example 27

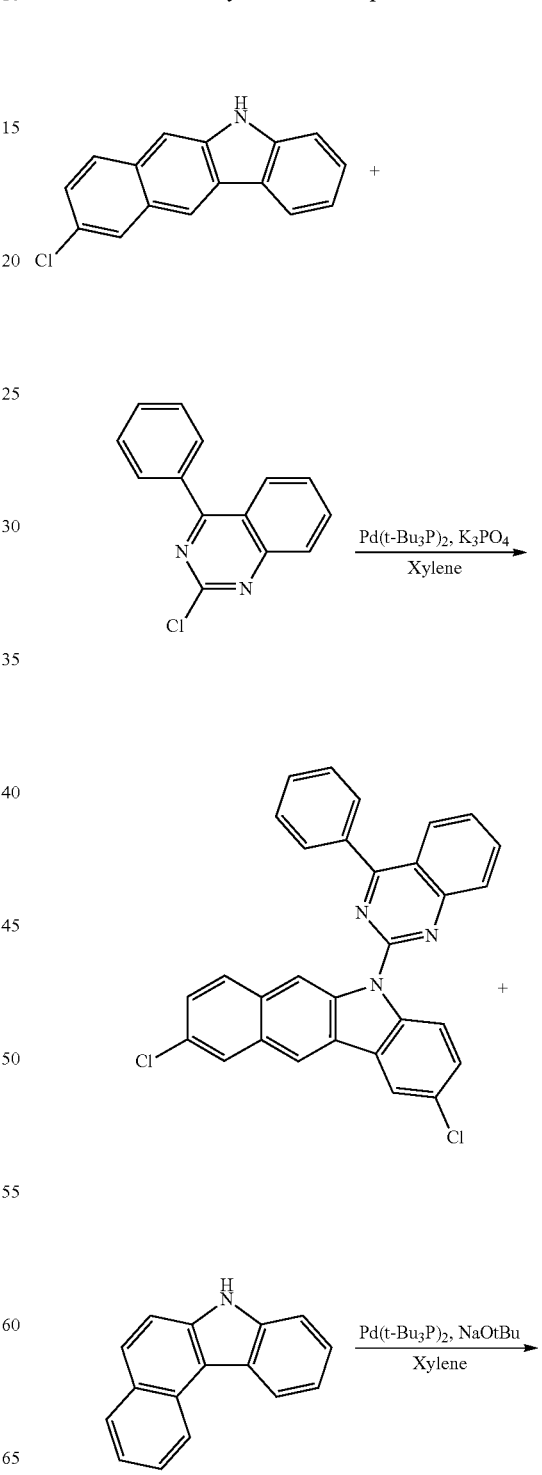

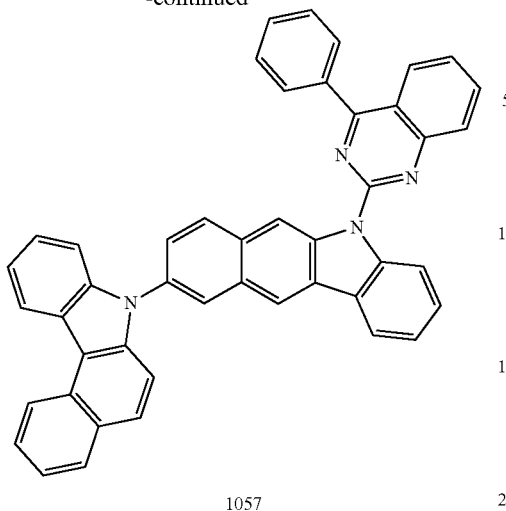

1057

Chemical Formula f (10.0 g, 1.0 eq.), 2-chloro-4-phenylquinazoline (9.56 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1057-1 (13.58 g, yield 75%). [M+H]=456

Chemical Formula 1057-1 (13.58 g, 1.0 eq.), 7H-benzo[c]carbazole (7.11 g, 1.1 eq.), Pd(t-Bu₃P)₂ (0.14 g, 0.01 eq.) and NaOtBu (5.72 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1057 (12.70 g, yield 67%). A graph measuring 1H-NMR of Compound 1057 is shown in FIG. 6. [M+H]=637

Synthesis Example 28

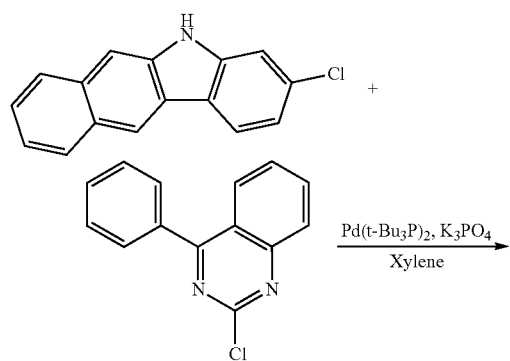

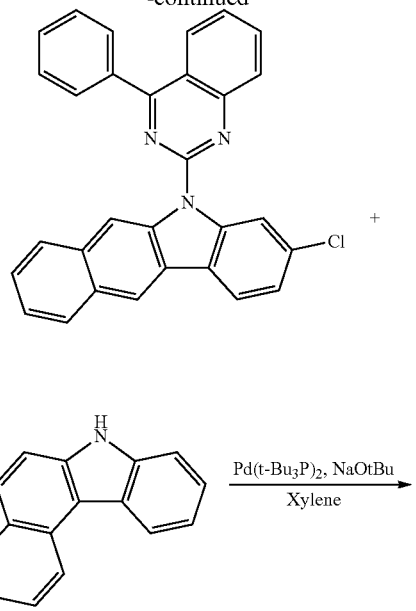

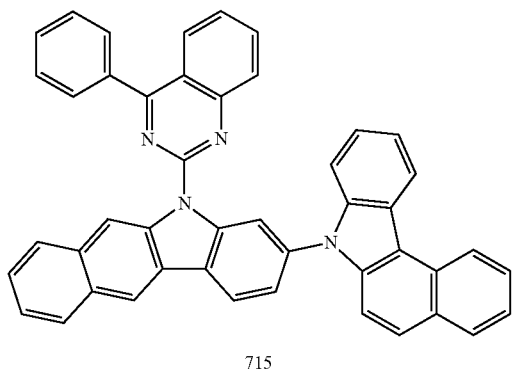

715

Chemical Formula a (10.0 g, 1.0 eq.), 2-chloro-4-phenylquinazoline (9.56 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 715-1 (13.40 g, yield 74%). [M+H]=456

Chemical Formula 715-1 (13.40 g, 1.0 eq.), 7H-benzo[c]carbazole (7.02 g, 1.1 eq.), Pd(t-Bu₃P)₂ (0.14 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 715 (13.09 g, yield 70%). [M+H]=637

Synthesis Example 29

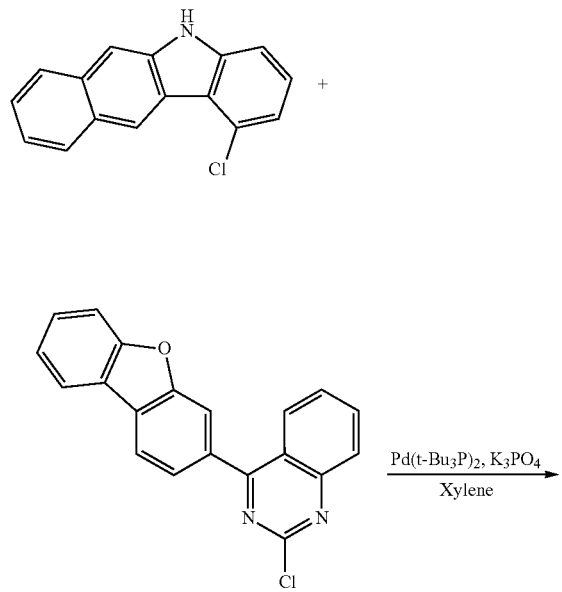

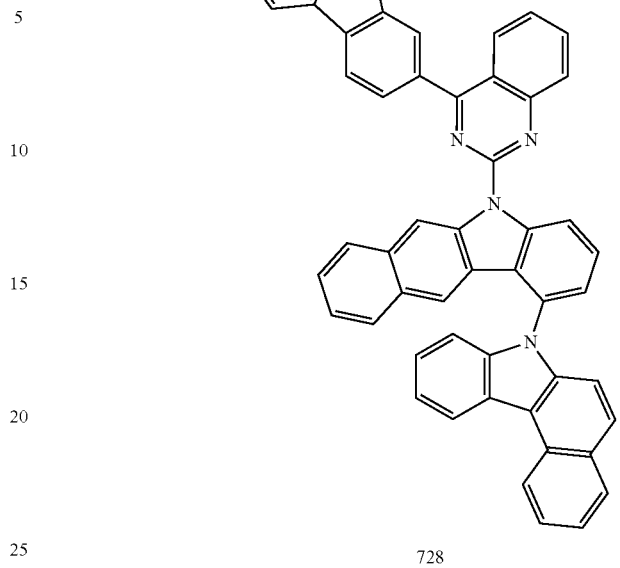

Chemical Formula c (10.0 g, 1.0 eq.), 2-chloro-4-(dibenzo[b,d]furan-3-yl)quinazoline (13.14 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 728-1 (15.40 g, yield 71%). [M+H]=547

Chemical Formula 728-1 (15.40 g, 1.0 eq.), 7H-benzo[c]carbazole (6.74 g, 1.1 eq.), Pd(t-Bu₃P)₂ (0.14 g, 0.01 eq.) and NaOtBu (5.42 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 728 (13.93 g, yield 68%). [M+H]=727

Synthesis Example 30

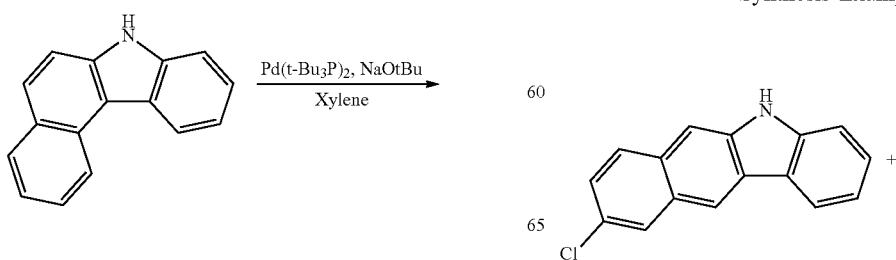

519
-continued

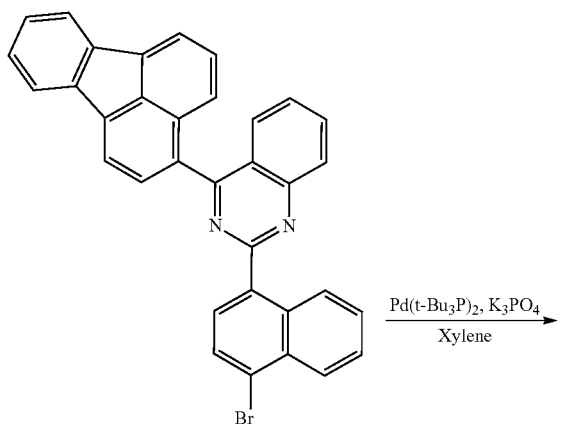

Pd(t-Bu₃P)₂, K₃PO₄
———————→
Xylene

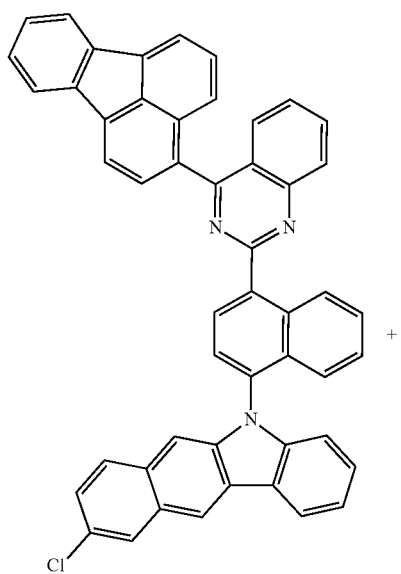

+

520
-continued

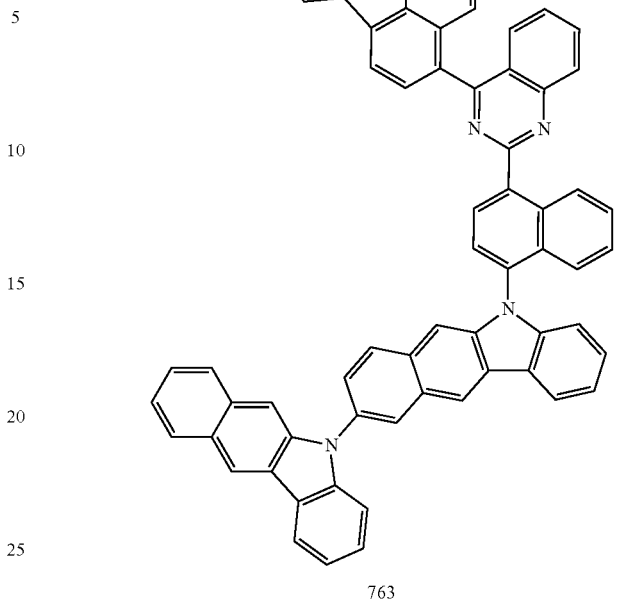

763

Chemical Formula f (10.0 g, 1.0 eq.), 2-(4-bromonapthalen-1-yl)-4-(fluoranthen-3-yl)quinazoline (23.39 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 763-1 (20.76 g, yield 74%). [M+H]=707

Chemical Formula 763-1 (20.76 g, 1.0 eq.), 5H-benzo[b]carbazole (7.02 g, 1.1 eq.), Pd(t-Bu₃P)₂ (0.14 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 763 (19.03 g, yield 73%). [M+H]=888

Synthesis Example 31

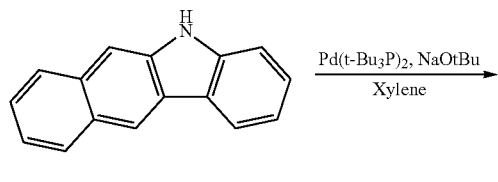

Pd(t-Bu₃P)₂, NaOtBu
———————→
Xylene

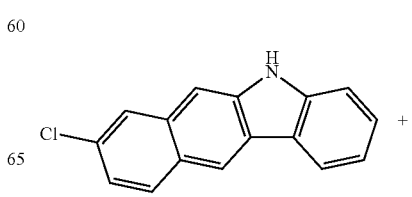

+

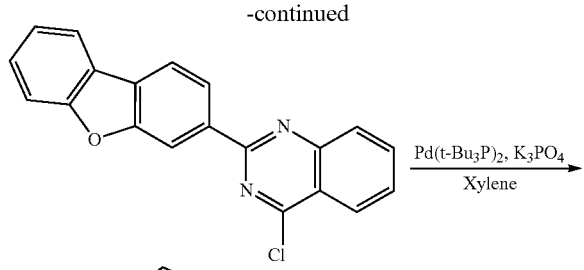

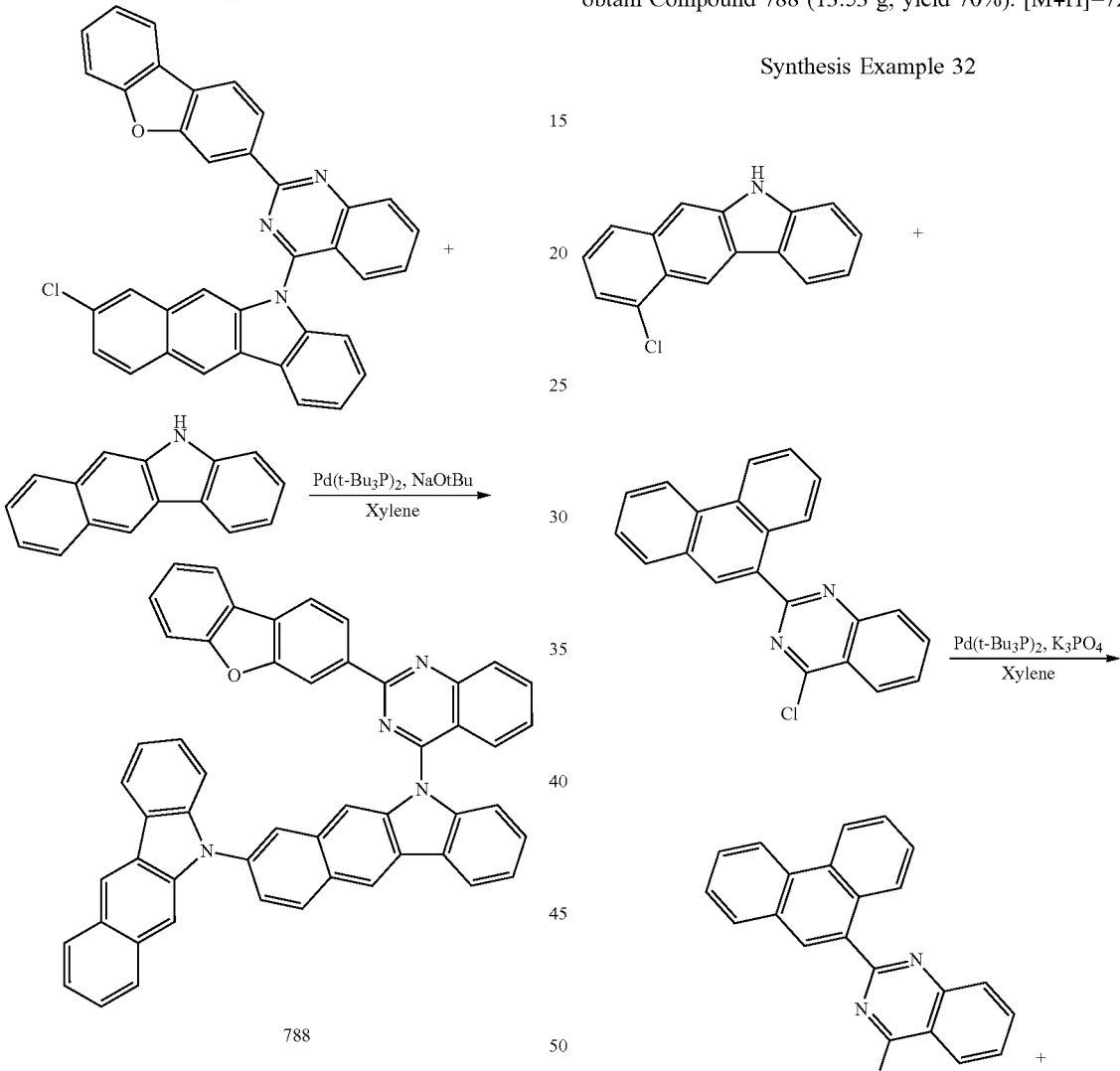

Chemical Formula g (10.0 g, 1.0 eq.), 4-chloro-2-(dibenzo[b,d]furan-3-yl)quinazoline (14.45 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 788-1 (14.53 g, yield 67%). [M+H]=547

Chemical Formula 788-1 (14.53 g, 1.0 eq.), 5H-benzo[b]carbazole (6.35 g, 1.1 eq.), Pd(t-Bu₃P)₂ (0.14 g, 0.01 eq.) and NaOtBu (5.11 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 788 (13.53 g, yield 70%). [M+H]=727

Synthesis Example 32

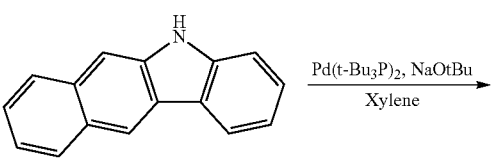

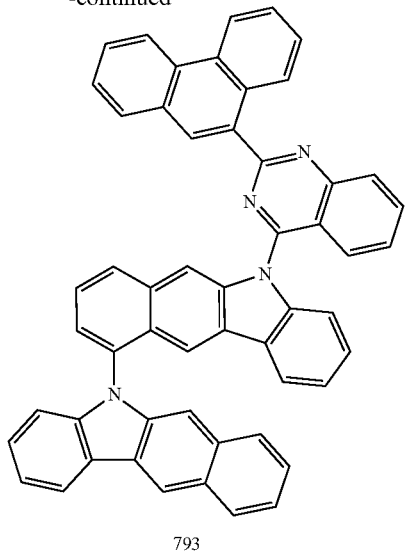

793

Chemical Formula e (10.0 g, 1.0 eq.), 4-chloro-2-(phenanthren-9-yl)quinazoline (14.89 g, 1.1 eq.), K₃PO₄ (16.86 in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 793-1 (15.24 g, yield 67%). [M+H]=557

Chemical Formula 793-1 (15.24 g, 1.0 eq.), 5H-benzo[b]carbazole (6.55 g, 1.1 eq.), Pd(t-Bu₃P)₂ (0.14 g, 0.01 eq.) and NaOtBu (5.26 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 793 (13.53 g, yield 67%). [M+H]=737

Synthesis Example 33

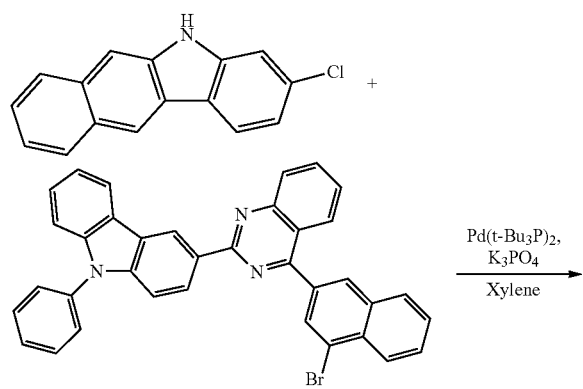

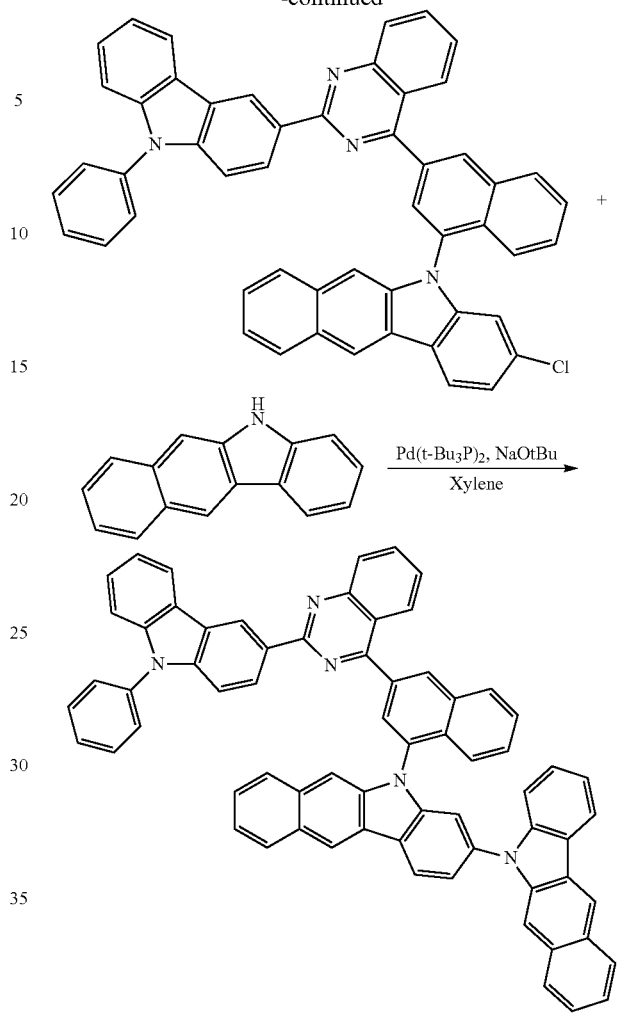

821

Chemical Formula a (10.0 g, 1.0 eq.), 3-(4-(4-bromonaphthalen-2-yl)quinazolin-2-yl)-9-phenyl-9H-carbazole (25.19 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 821-1 (21.96 g, yield 74%). [M+H]=748

Chemical Formula 821-1 (21.96 g, 1.0 eq.), 5H-benzo[b]carbazole (7.02 g, 1.1 eq.), Pd(t-Bu₃P)₂ (0.15 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 821 (17.72 g, yield 65%). [M+H]=929

Synthesis Example 34

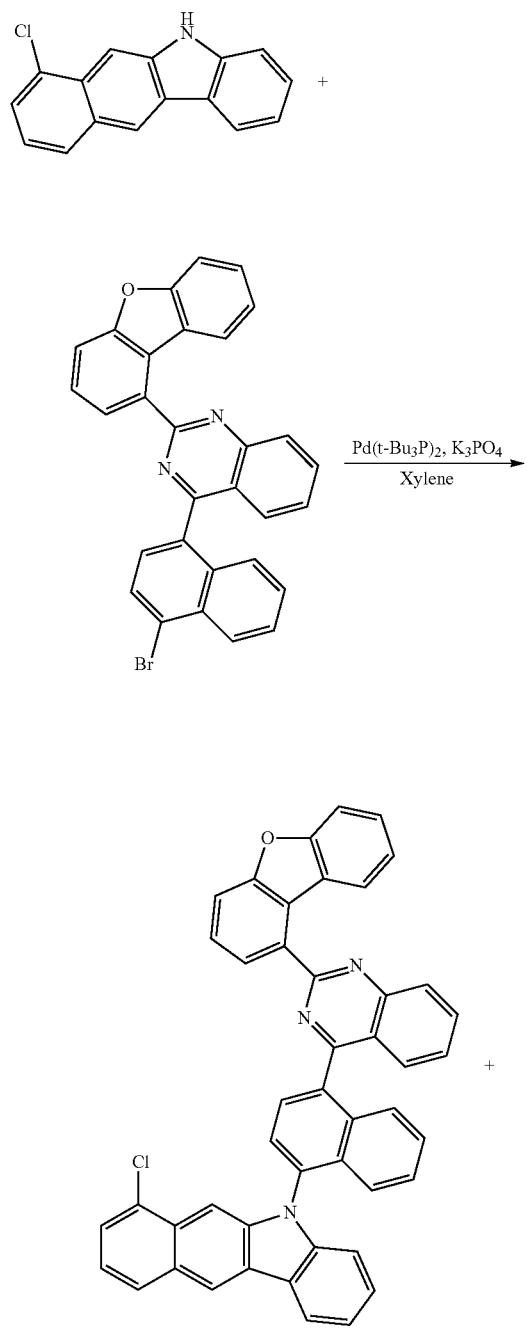

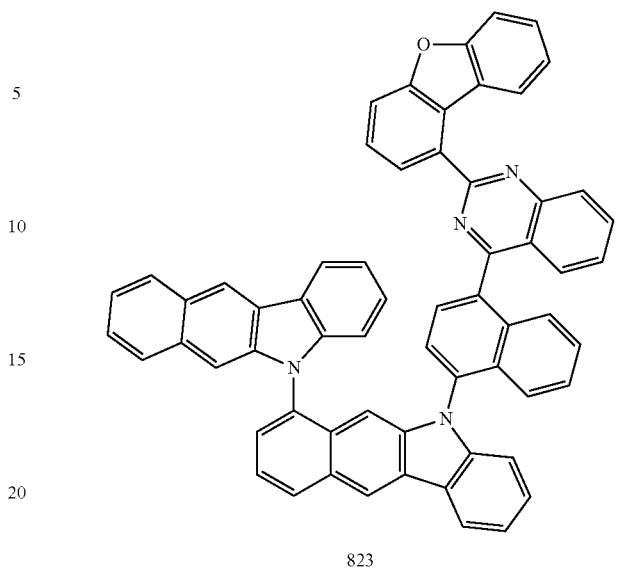

823

Chemical Formula h (10.0 g, 1.0 eq.), 4-(4-bromonaphthalen-1-yl)-2-(dibenzo[b,d]furan-1-yl) quinazoline (21.91 g, 1.1 eq.), K₃PO₄ (16.86 g, 2.0 eq.) and Pd(t-Bu₃P) 2 (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 823-1 (18.69 g, yield 70%). [M+H]=673

Chemical Formula 823-1 (18.69 g, 1.0 eq.), 5H-benzo[b] carbazole (6.64 g, 1.1 eq.), Pd(t-Bu₃P)₂ 0.15 g, 0.01 eq.) and NaOtBu (5.34 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 823 (14.46 g, yield 61%). [M+H]=854

Synthesis Example 35

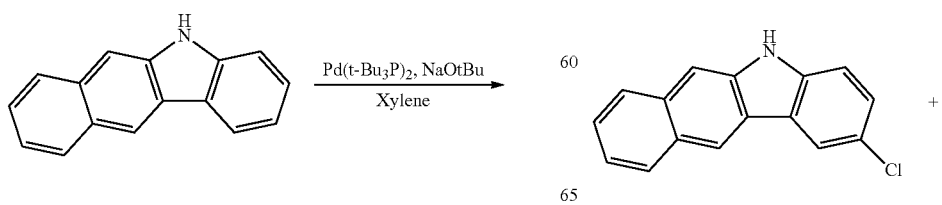

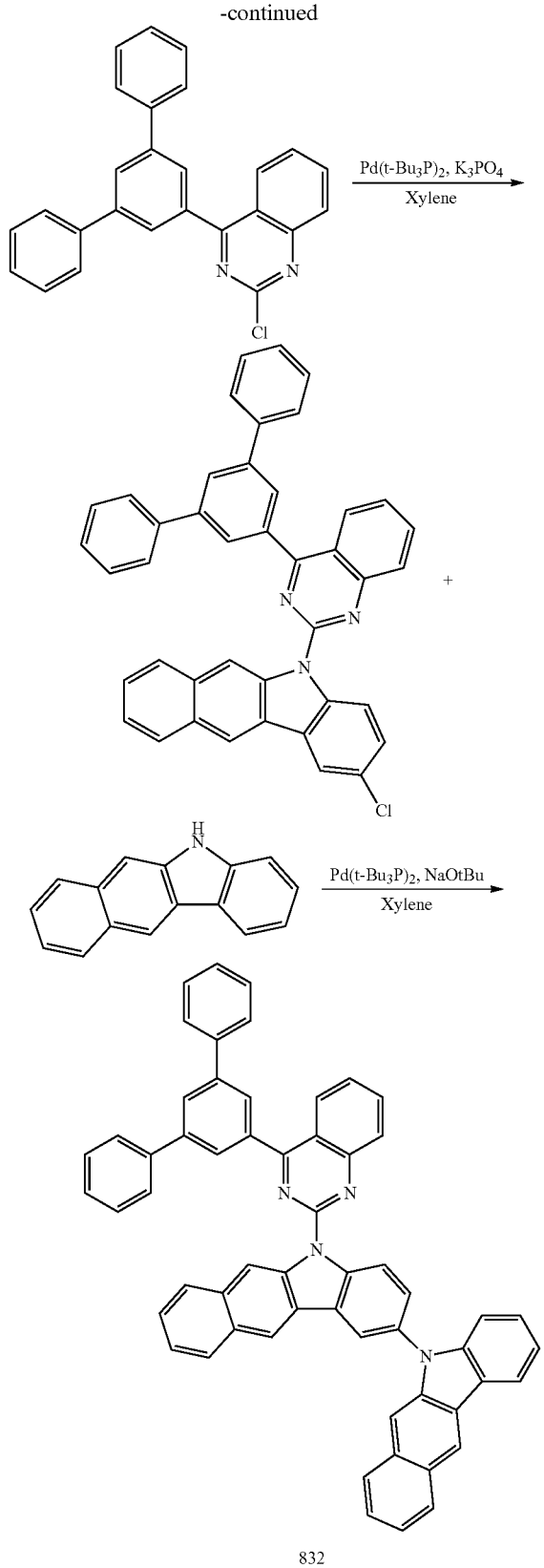

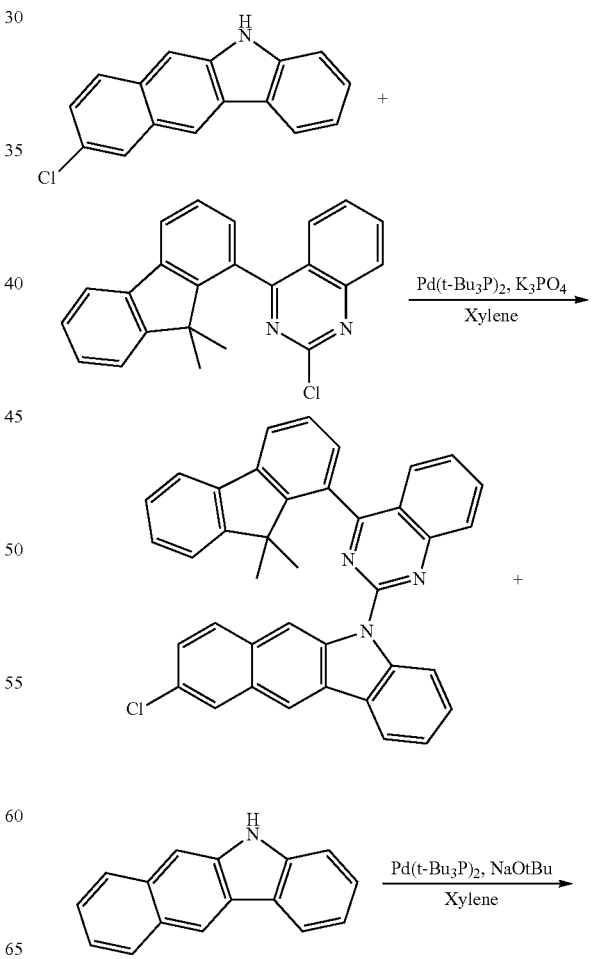

were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 832-1 (17.87 g, yield 74%). [M+H]=609

Chemical Formula 832-1 (17.87 g, 1.0 eq.), 5H-benzo[b] carbazole (7.02 g, 1.1 eq.), Pd(t-Bu₃P)₂ (0.15 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 832 (15.53 g, yield 67%). [M+H]=789

Synthesis Example 36

Chemical Formula b (10.0 g, 1.0 eq.), 4-([1,1':3',1''-terphenyl]-5'-yl)-2-chloroquinazoline (17.16 g, 1.1 eq.), K₃PO₄ (16.86 g, 2.0 eq.) and Pd(t-Bu₃P)₂ (0.05 g, 0.002 eq.)

-continued

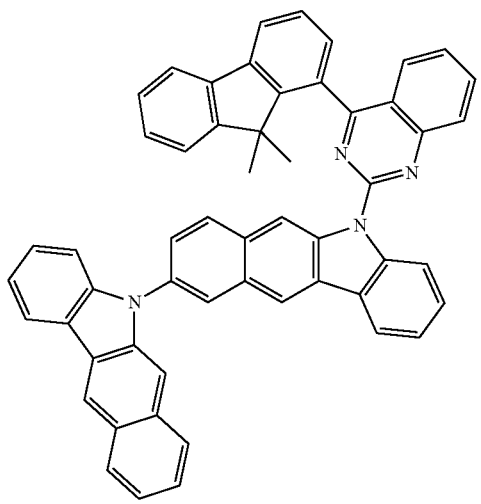

858

Chemical Formula f (10.0 g, 1.0 eq.), 2-chloro-4-(9,9-dimethyl-9H-fluoren-1-yl)quinazoline (15.59 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 858-1 (16.13 g, yield 71%). [M+H]=573

Chemical Formula 858-1 (16.13 g, 1.0 eq.), 5H-benzo[b] carbazole (6.73 g, 1.1 eq.), Pd(t-Bu$_3$P)$_2$ (0.15 g, 0.01 eq.) and NaOtBu (5.64 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 858 (14.64 g, yield 69%). [M+H]=753

Synthesis Example 37

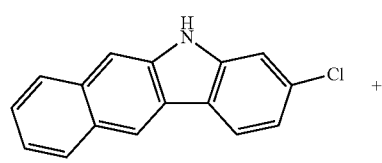 +

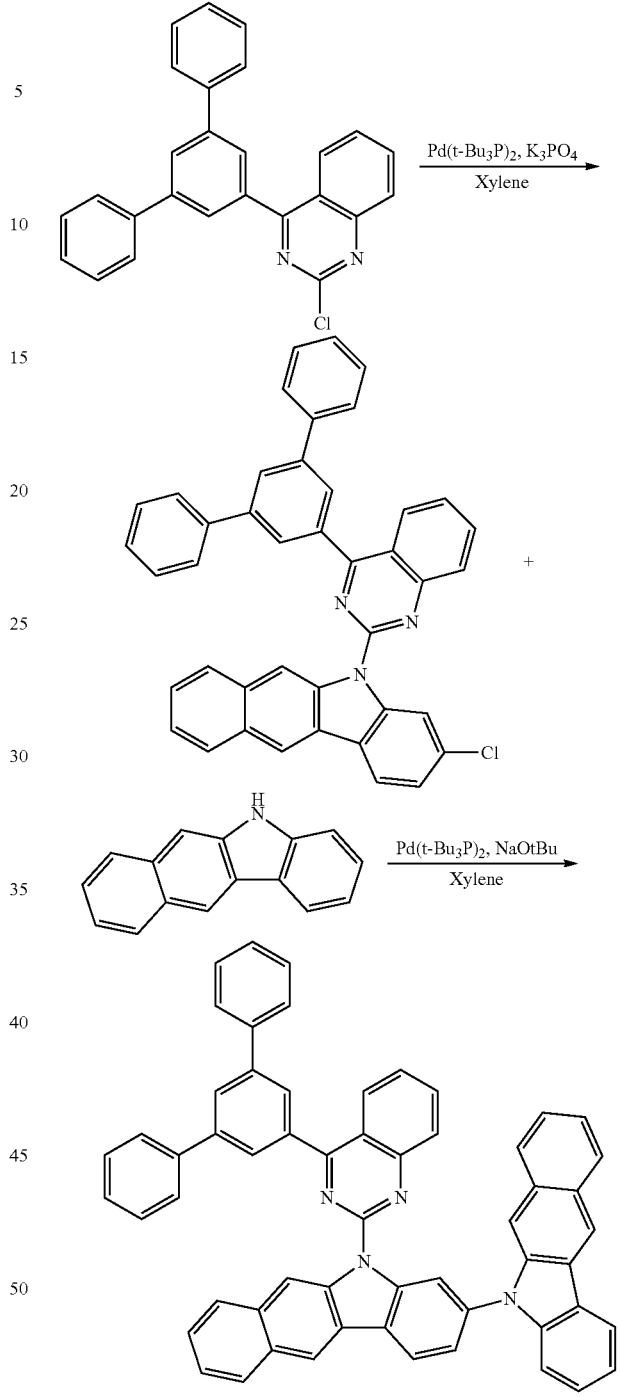

862

Chemical Formula a (10.0 g, 1.0 eq.), 4-([1,1':3',1''-terphenyl]-5'-yl)-2-chloroquinazoline (17.16 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 862-1 (17.63 g, yield 73%). [M+H]=609

Chemical Formula 862-1 (17.63 g, 1.0 eq.), 5H-benzo[b]carbazole (6.92 g, 1.1 eq.), Pd(t-Bu₃P)₂ (0.15 g, 0.01 eq.) and NaOtBu (5.57 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 862 (15.78 g, yield 69%). [M+H]=789

Synthesis Example 38

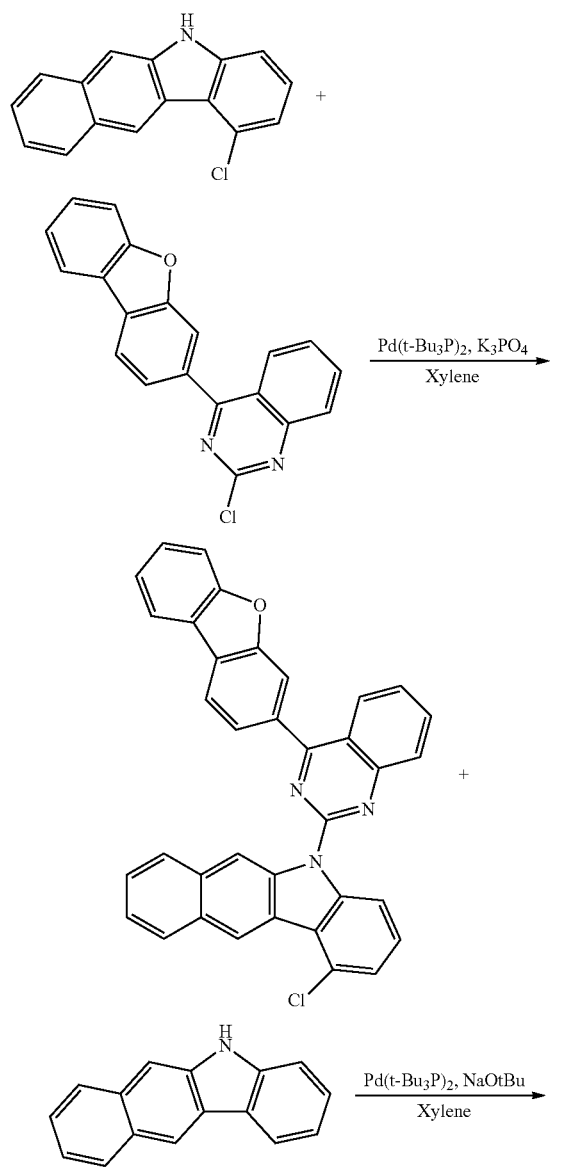

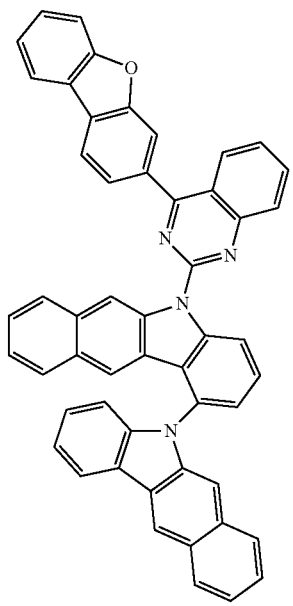

872

Chemical Formula c (10.0 g, 1.0 eq.), 2-chloro-4-(dibenzo[b,d]furan-3-yl)quinazoline (14.45 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 872-1 (16.26 g, yield 75%). [M+H]=547

Chemical Formula 872-1 (16.26 g, 1.0 eq.), 5H-benzo[b]carbazole (7.11 g, 1.1 eq.), Pd(t-Bu₃P)₂ (0.15 g, 0.01 eq.) and NaOtBu (5.72 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 872 (13.63 g, yield 63%). [M+H]=727

Synthesis Example 39

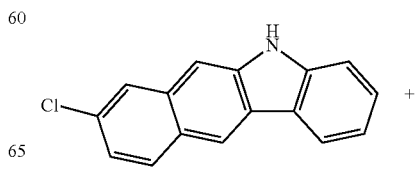

-continued

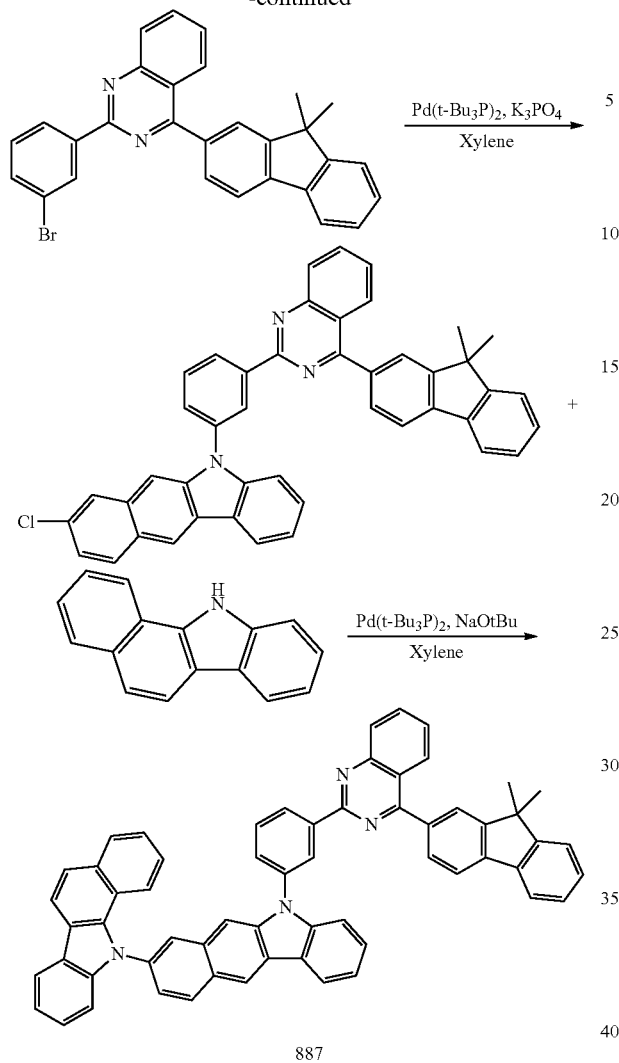

887

Chemical Formula g (10.0 g, 1.0 eq.), 2-(3-bromophenyl)-4-(9,9-dimethyl-9H-fluoren-2-yl)quinazoline (20.86 g, 1.1 eq.), $K_3PO_4$ (16.86 g, 2.0 eq.) and $Pd(t-Bu_3P)_2$ (0.05 g, 0.002 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 887-1 (18.79 g, yield 73%). [M+H]=649

Chemical Formula 887-1 (18.79 g, 1.0 eq.), 11H-benzo[a]carbazole (6.92 g, 1.1 eq.), $Pd(t-Bu_3P)_2$ (0.15 g, 0.01 eq.) and NaOtBu (5.57 g, 2.0 eq.) were introduced to xylene (250 ml), and the result was stirred under reflux. When the reaction was terminated after 2 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 887 (16.10 g, yield 67%). [M+H]=830

Synthesis Example 40

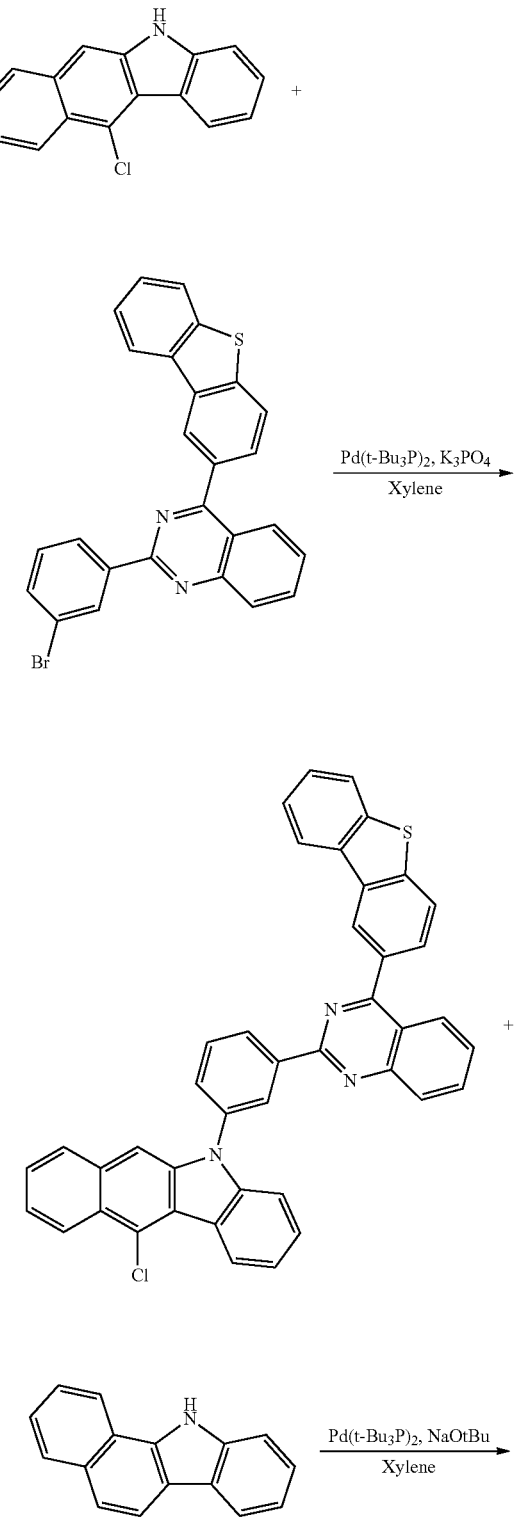

535
-continued

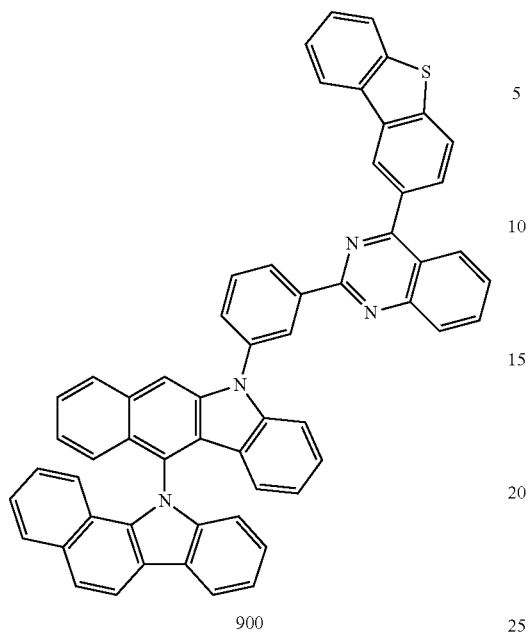

900

536
-continued

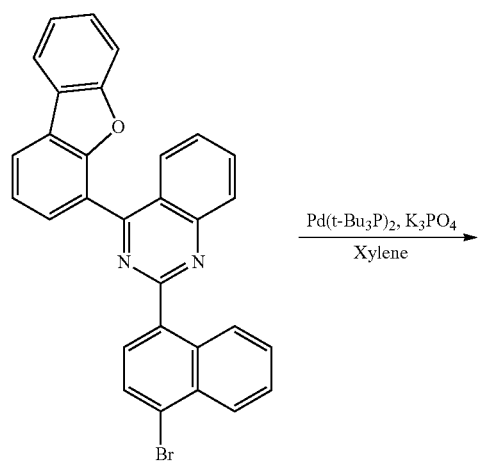

Chemical Formula d (10.0 g, 1.0 eq.), 2-(3-bromophenyl)-4-(dibenzo[b,d]thiophen-2-yl)quinazoline (20.42 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 900-1 (19.46 g, yield 77%). [M+H]=637

Chemical Formula 900-1 (19.46 g, 1.0 eq.), 11H-benzo[a]carbazole (7.31 g, 1.1 eq.), Pd(t-Bu$_3$P)$_2$ (0.15 g, 0.01 eq.) and NaOtBu (5.87 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 900 (15.28 g, yield 61%). [M+H]=820

Synthesis Example 41

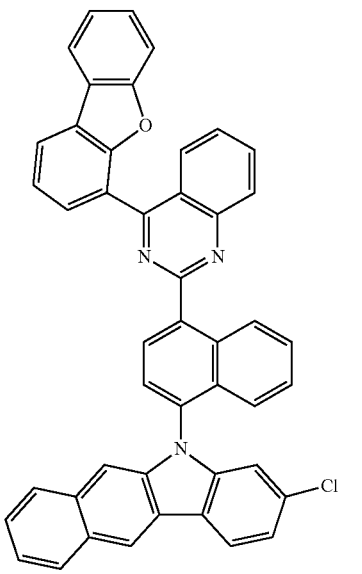

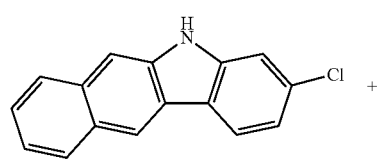

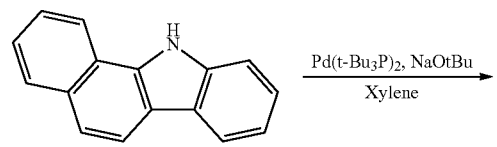

-continued

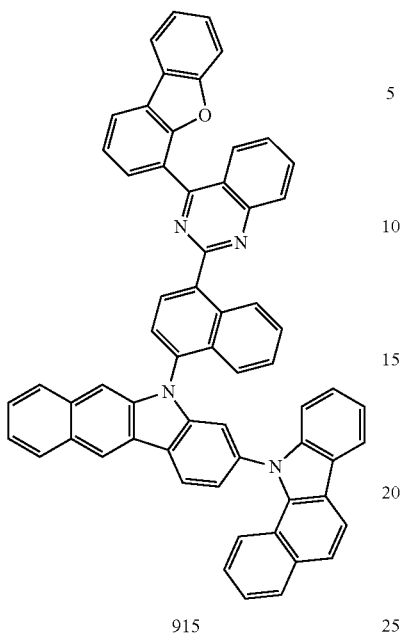

915

Chemical Formula a (10.0 g, 1.0 eq.), 2-(4-bromonaphthalen-1-yl)-4-(dibenzo[b,d]furan-4-yl)quinazoline (21.91 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 915-1 (19.76 g, yield 74%). [M+H]=673

Chemical Formula 915-1 (19.76 g, 1.0 eq.), 11H-benzo[a]carbazole (7.02 g, 1.1 eq.), Pd(t-Bu$_3$P)$_2$ (0.15 g, 0.01 eq.) and NaOtBu (5.65 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 915 (16.04 g, yield 64%). [M+H]=853

Synthesis Example 42

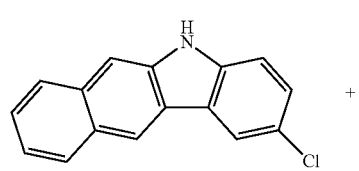 +

-continued

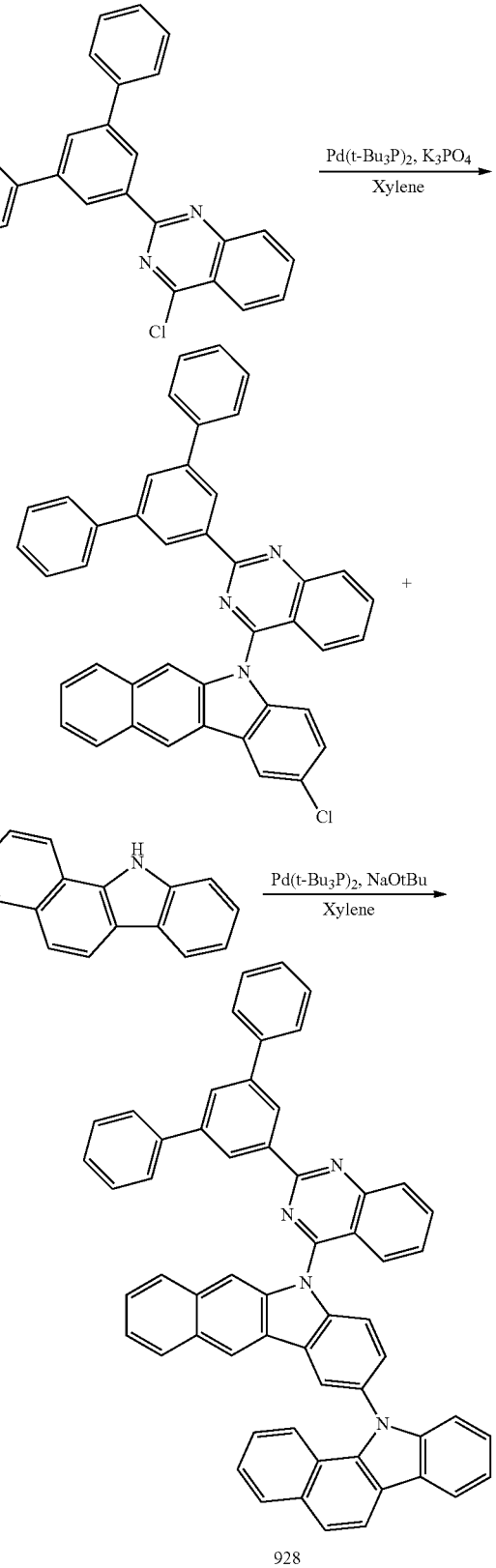

928

Chemical Formula b (10.0 g, 1.0 eq.), 2-([1,1':3',1''-terphenyl]-5'-yl)-4-chloroquinazoline (17.16 g, 1.1 eq.), K$_3$PO$_4$ (16.86 g, 2.0 eq.) and Pd(t-Bu$_3$P)$_2$ (0.05 g, 0.002 eq.)

were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 928-1 (16.42 g, yield 68%). [M+H]=609

Chemical Formula 928-1 (16.42 g, 1.0 eq.), 11H-benzo[a]carbazole (6.45 g, 1.1 eq.), Pd(t-Bu$_3$P)$_2$ (0.15 g, 0.01 eq.) and NaOtBu (5.18 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 928 (13.20 g, yield 62%). [M+H]=789

Synthesis Example 43

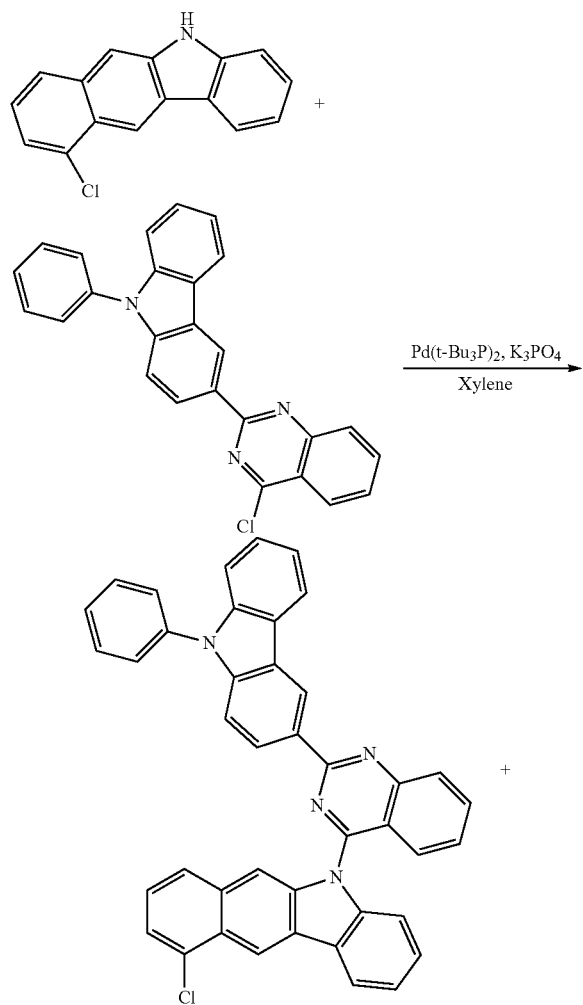

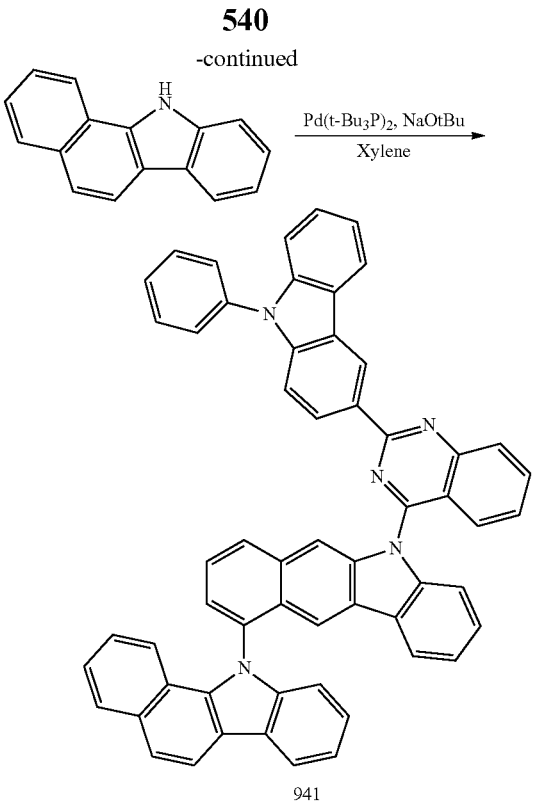

Chemical Formula e (10.0 g, 1.0 eq.), 3-(4-chloroquinazolin-2-yl)-9-phenyl-9H-carbazolee (17.73 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 941-1 (15.79 g, yield 64%). [M+H]=622

Chemical Formula 941-1 (15.79 g, 1.0 eq.), 11H-benzo[a]carbazole (6.07 g, 1.1 eq.), Pd(t-Bu$_3$P)$_2$ (0.15 g, 0.01 eq.) and NaOtBu (4.88 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 941 (12.84 g, yield 63%). [M+H]=802

Synthesis Example 44

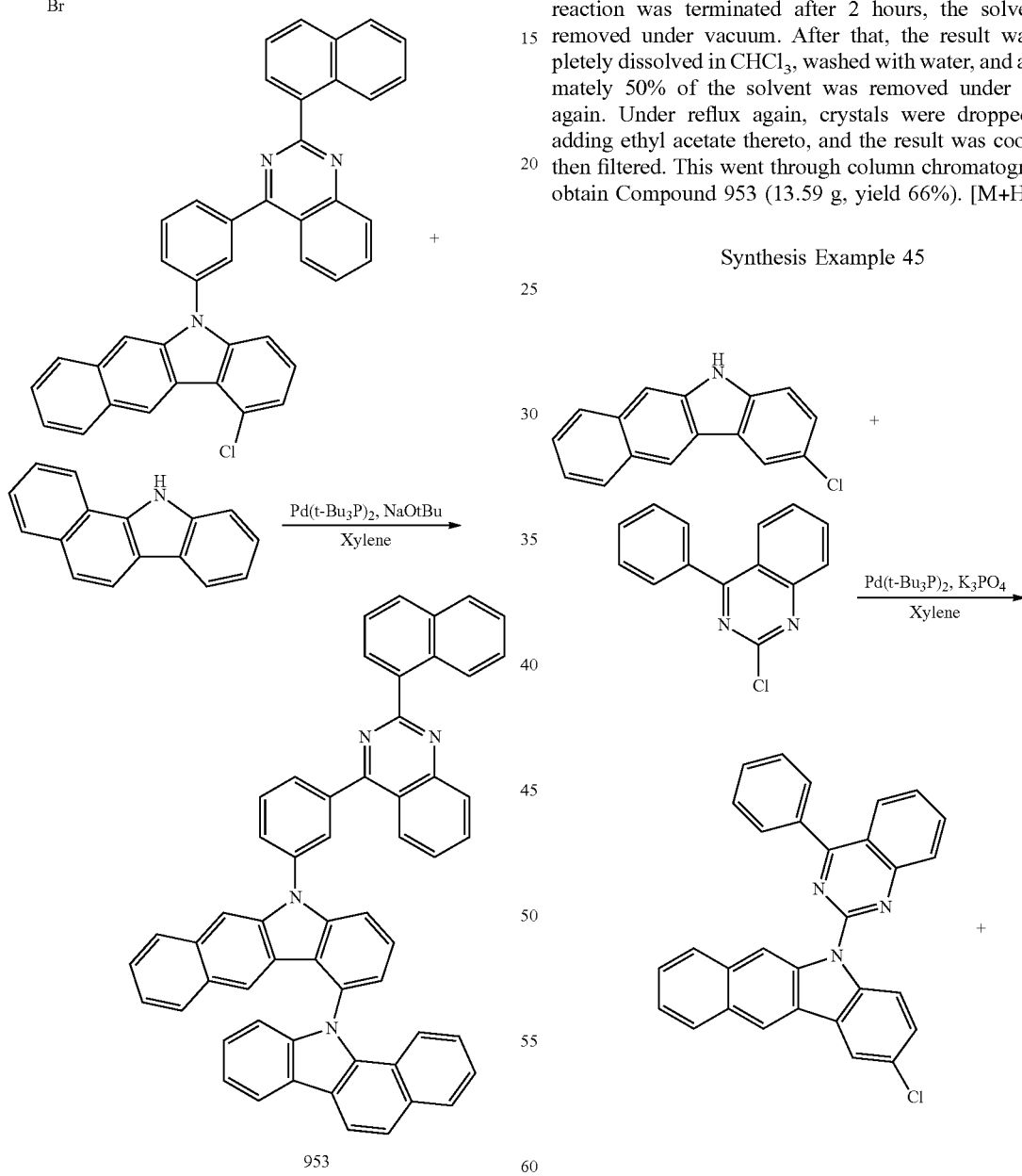

Chemical Formula c (10.0 g, 1.0 eq.), 4-(3-bromophenyl)-2-(naphthalen-1-yl)quinazoline (17.97 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 953-1 (15.72 g, yield 68%). [M+H]=583

Chemical Formula 953-1 (15.72 g, 1.0 eq.), 11H-benzo[a]carbazole (6.45 g, 1.1 eq.), Pd(t-Bu₃P)₂ (0.15 g, 0.01 eq.) and NaOtBu (5.19 g, 2.0 eq.) were introduced to xylene (250 ml), and the result was stirred under reflux. When the reaction was terminated after 2 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 953 (13.59 g, yield 66%). [M+H]=763

Synthesis Example 45

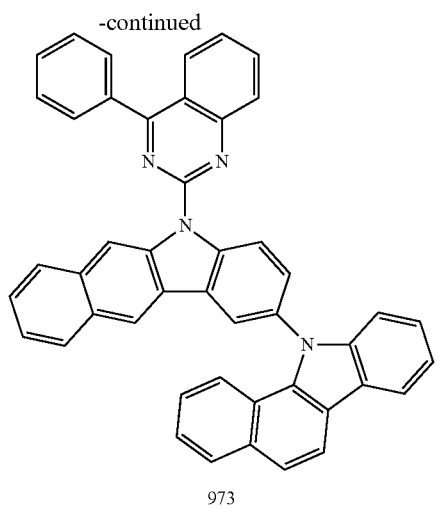

973

Chemical Formula b (10.0 g, 1.0 eq.), 2-chloro-4-phenylquinazoline (10.51 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 973-1 (13.58 g, yield 75%). [M+H]=456

Chemical Formula 973-1 (13.58 g, 1.0 eq.), 11H-benzo[a]carbazole (7.11 g, 1.1 eq.), Pd(t-Bu$_3$P)$_2$ (0.15 g, 0.01 eq.) and NaOtBu (5.72 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 973 (12.13 g, yield 64%). [M+H]=637

Synthesis Example 46

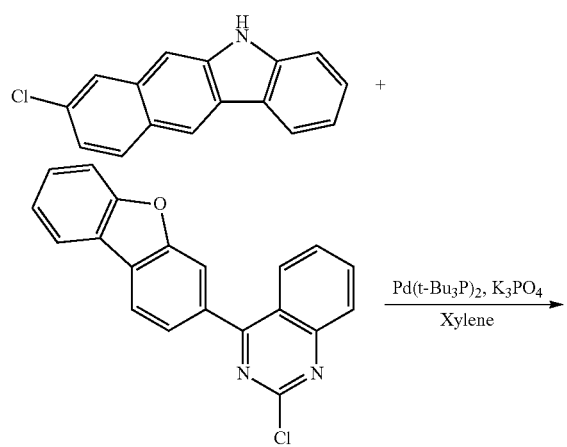

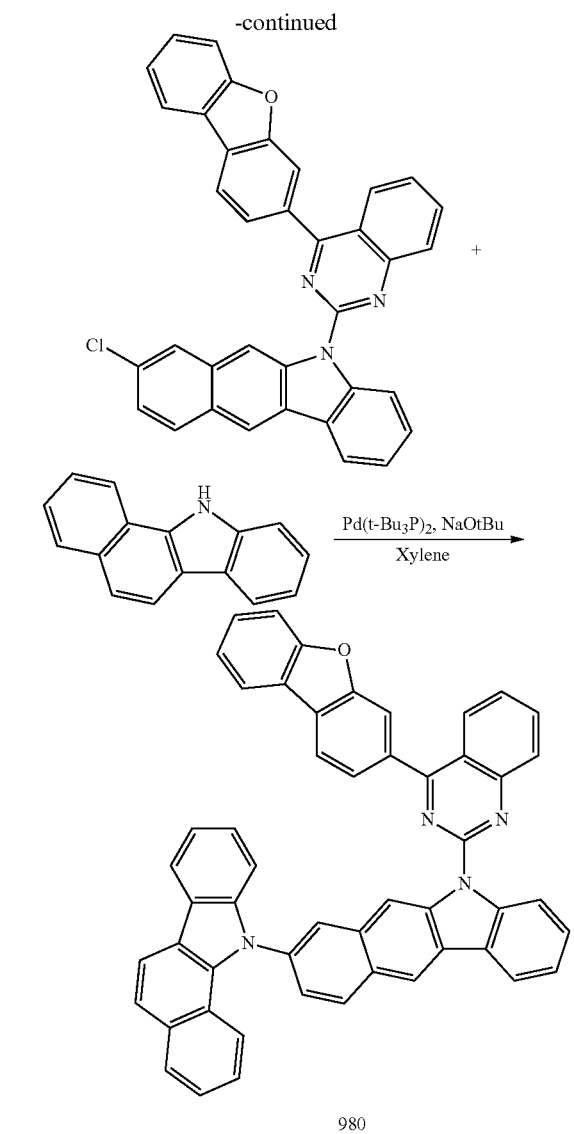

980

Chemical Formula g (10.0 g, 1.0 eq.), 2-chloro-4-(dibenzo[b,d]furan-3-yl)quinazoline (14.45 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 980-1 (16.26 g, yield 75%). [M+H]=547

Chemical Formula 980-1 (16.26 g, 1.0 eq.), 11H-benzo[a]carbazole (7.11 g, 1.1 eq.), Pd(t-Bu$_3$P)$_2$ (0.15 g, 0.01 eq.) and NaOtBu (5.72 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 980 (14.06 g, yield 65%). [M+H]=727

Synthesis Example 47

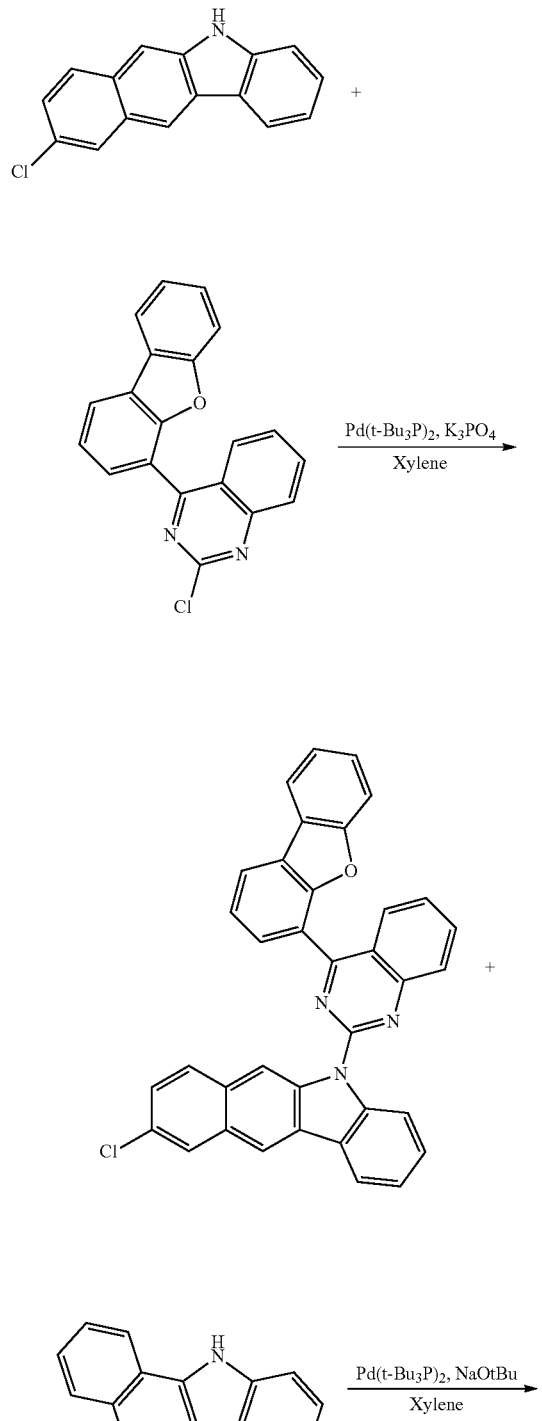

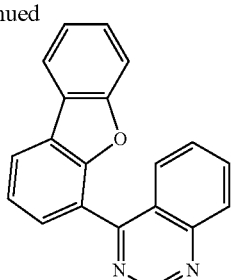

999

Chemical Formula f (10.0 g, 1.0 eq.), 2-chloro-4-(dibenzo[b,d]furan-4-yl)quinazoline (14.45 g, 1.1 eq.), K$_3$PO$_4$ (16.86 g, 2.0 eq.) and Pd(t-Bu$_3$P)$_2$ (0.05 g, 0.002 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 999-1 (16.48 g, yield 76%). [M+H]=547

Chemical Formula 980-1 (16.48 g, 1.0 eq.), 11H-benzo[a]carbazole (7.21 g, 1.1 eq.), Pd(t-Bu$_3$P)$_2$ (0.15 g, 0.01 eq.) and NaOtBu (5.80 g, 2.0 eq.) were introduced to xylene (250 ml), and the result was stirred under reflux. When the reaction was terminated after 2 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 999 (13.60 g, yield 62%). [M+H]=727

Experimental Example

Comparative Example 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, the following HI-1 Compound was formed to a thickness of 1150 Å as a hole injection layer with the following A-1 Compound being p-doped in a concentration of 1.5%. A hole transfer layer having a film thickness of 800 Å was formed by vacuum depositing the following HT-1 Compound on the hole injection layer. Subsequently, an electron blocking layer was formed by vacuum depositing the following EB-1 Compound on the hole transfer layer to a film thickness of 150 Å. Then, on the EB-1 deposited film, a red light emitting layer having a thickness of 400 Å was formed by vacuum depositing the following RH-1 Compound and the following Dp-7 Compound in a weight ratio of 98:2. On the light emitting layer, a hole blocking layer was formed by vacuum depositing the following HB-1 Compound to a film thickness of 30 Å. Then, on the hole blocking layer, an electron injection and transfer layer was formed to a thickness of 300 Å by vacuum depositing the following ET-1 Compound and the following LiQ Compound in a weight ratio of 2:1. A cathode was formed on the electron injection and transfer layer by depositing lithium fluoride (LiF) to a thickness of 12 Å and aluminum to a thickness of 1,000 Å in consecutive order.

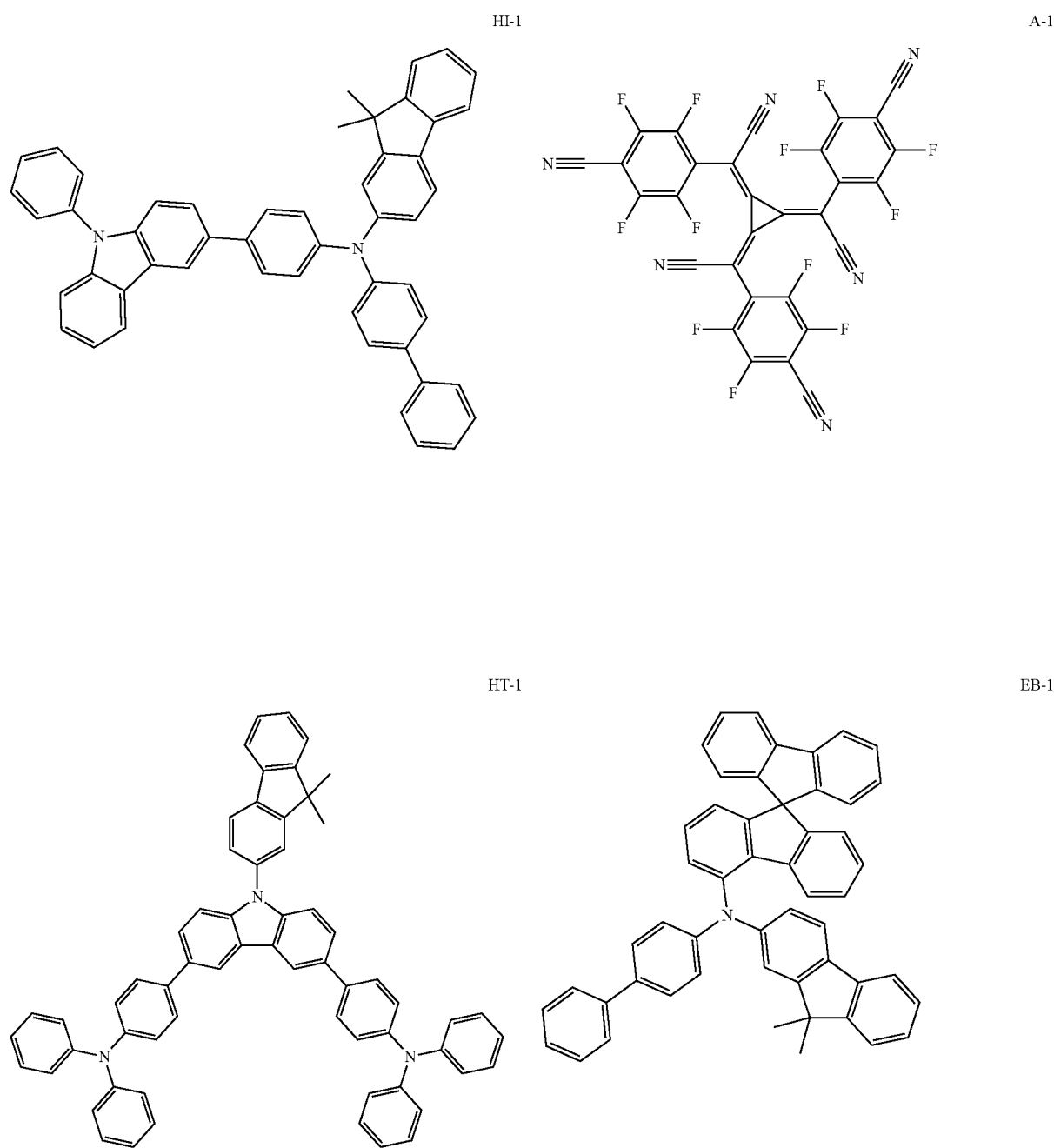

-continued
RH-1
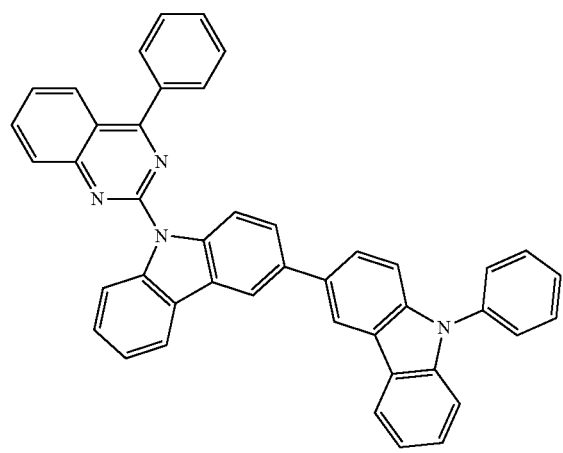
Dp-7
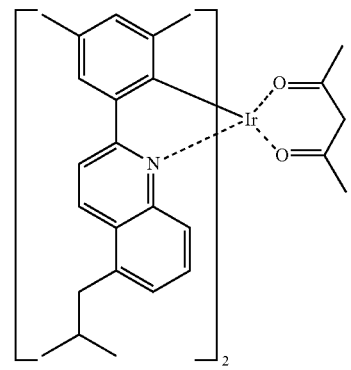
HB-1
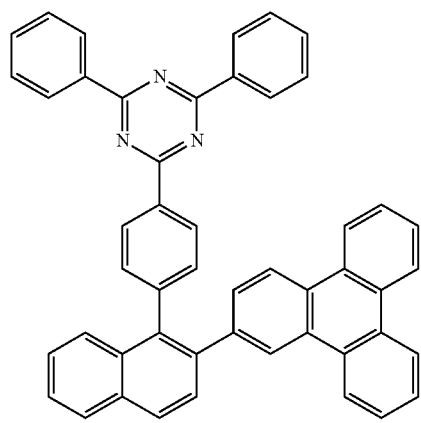
ET-1
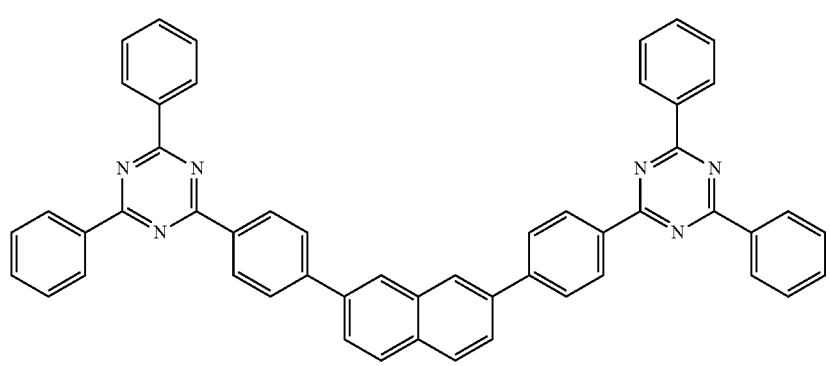
LiQ
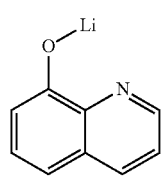
RH-2
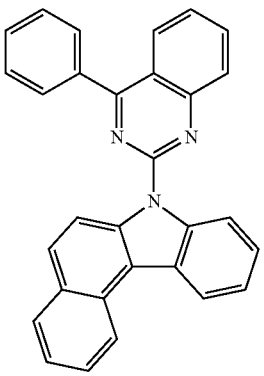

-continued
| | |
|---|---|
| RH-3 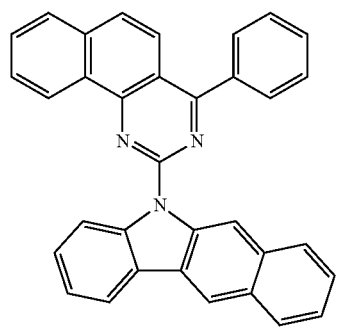 | RH-4 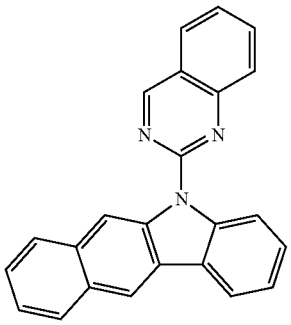 |
| RH-5 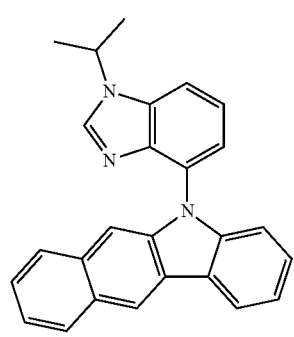 | RH-6 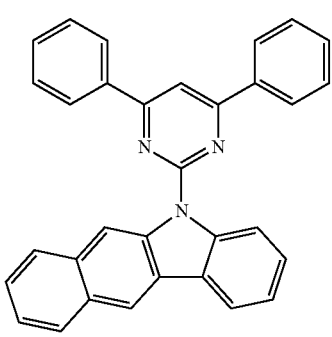 |
| RH-7 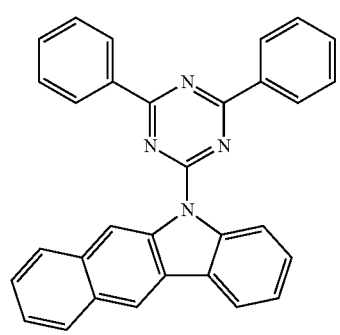 | RH-8 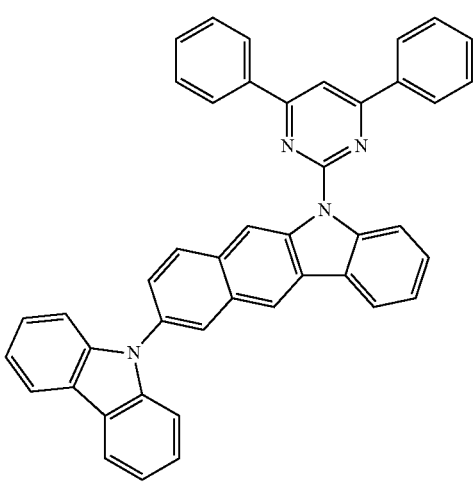 |
| RH-9 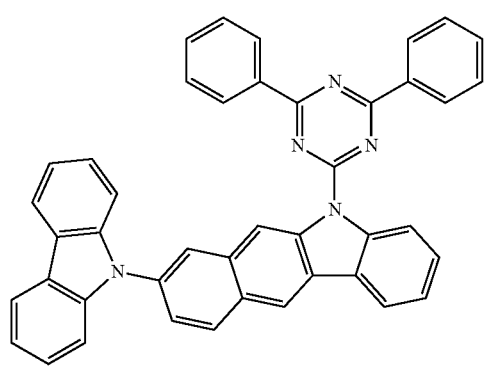 | RH-10 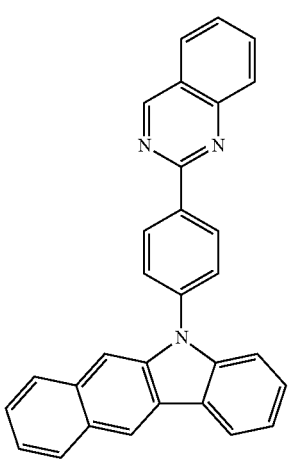 |

-continued
RH-11
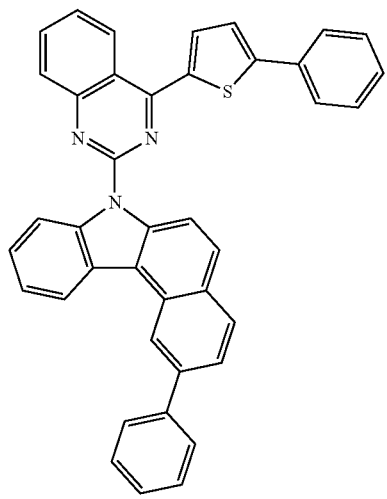
RH-12
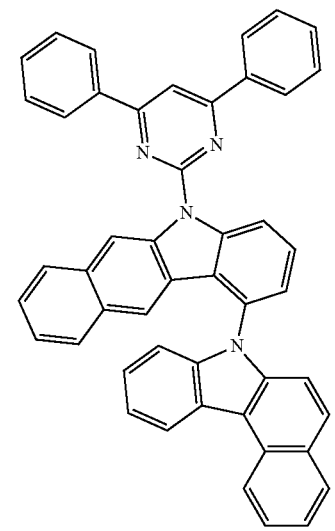
RH-13
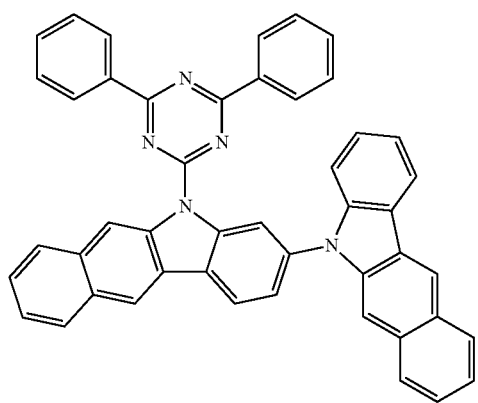
RH-14
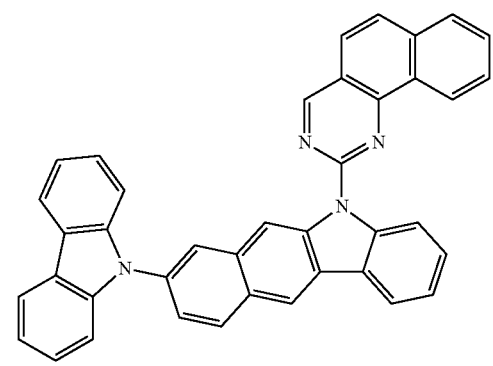
RH-15
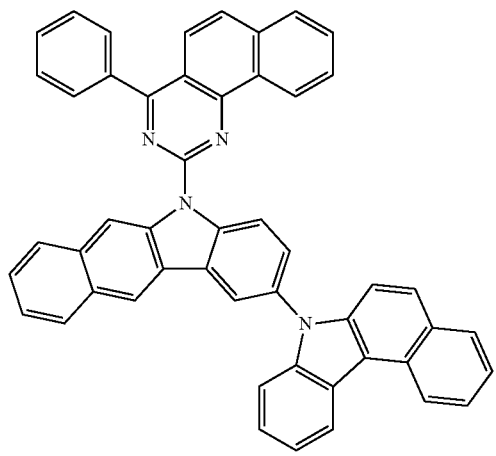
RH-16
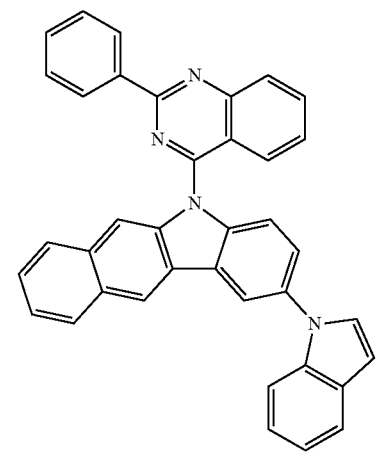

-continued
RH-17
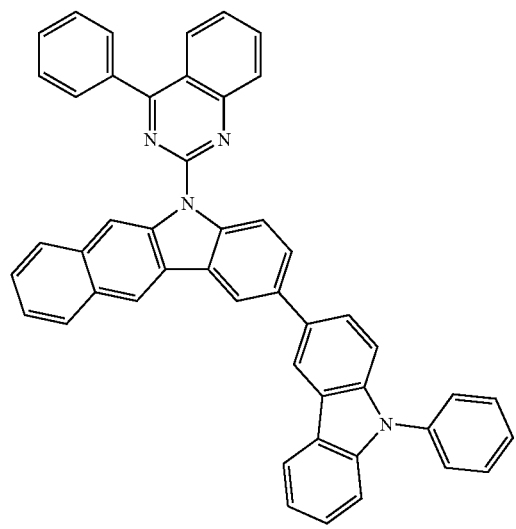
RH-18
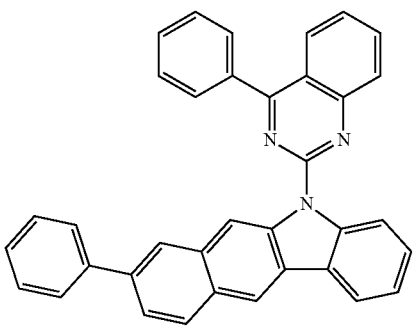
RH-19
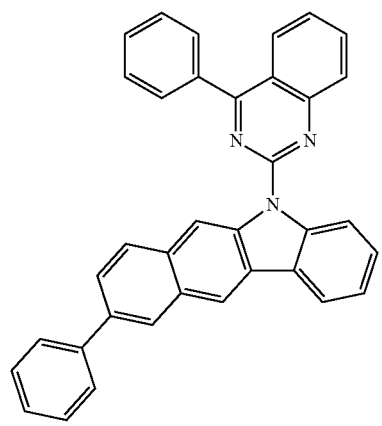
RH-20
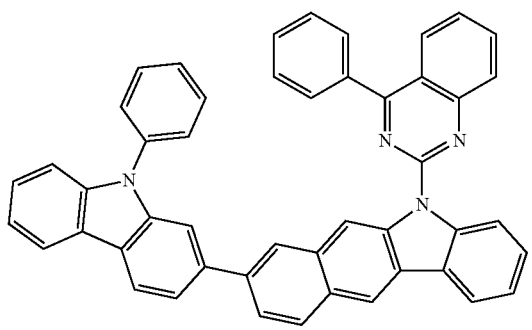
RH-21
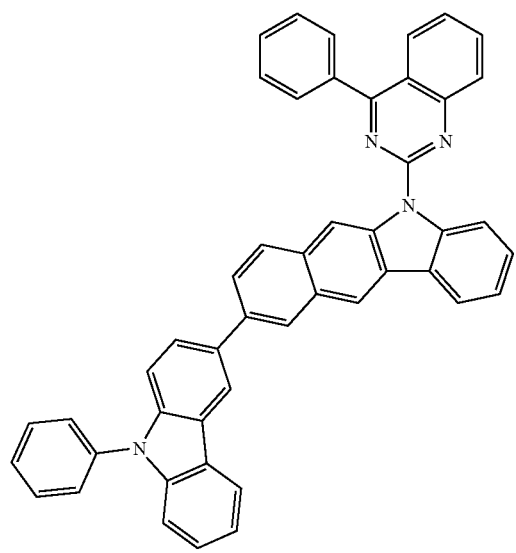
RH-22
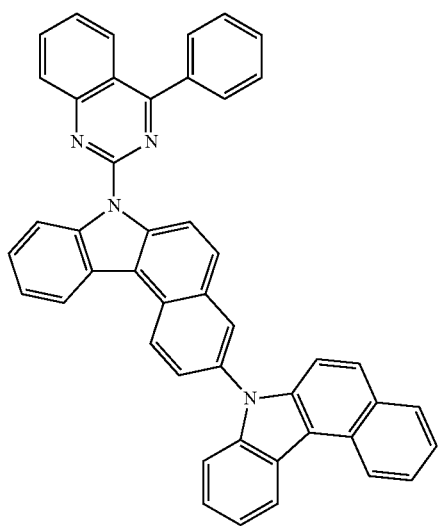

-continued
RH-23
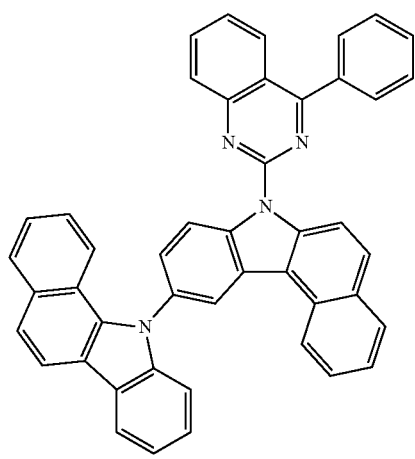
RH-24
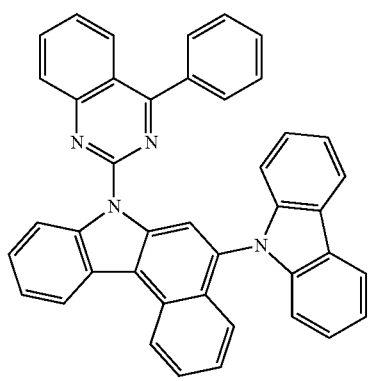
RH-25
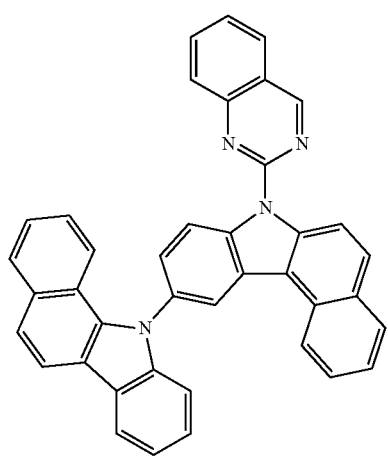
RH-26
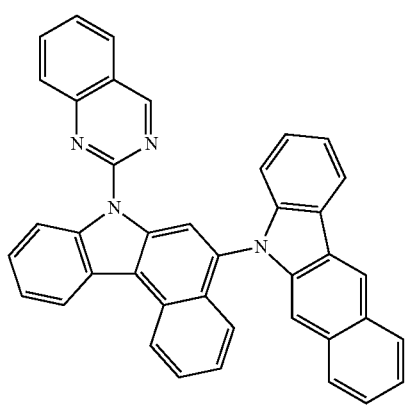
RH-27
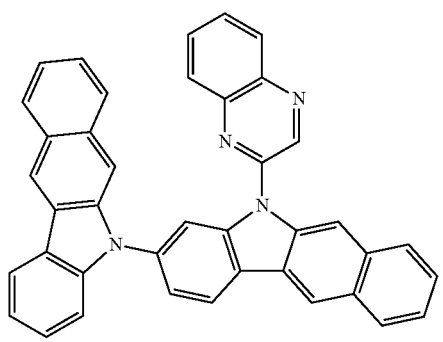
RH-28
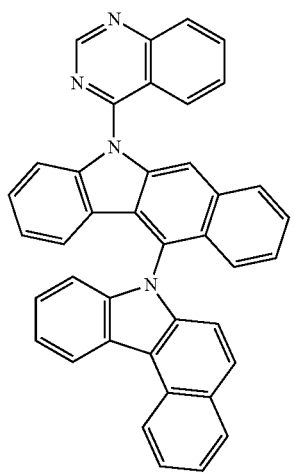

RH-29

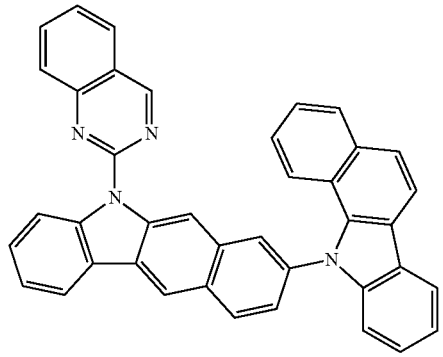

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 1 to Example 47

Organic light emitting devices were manufactured in the same manner as in Comparative Example 1 except that, in the organic light emitting device of Comparative Example 1, compounds described in the following Table 1 were used instead of RH-1.

Comparative Example 2 to Comparative Example 29

Organic light emitting devices were manufactured in the same manner as in Comparative Example 1 except that, in the organic light emitting device of Comparative Example 1, compounds described in the following Table 1 were used instead of RH-1.

When a current was applied to the organic light emitting devices manufactured in Example 1 to Example 47, and Comparative Example 1 to Comparative Example 29, a voltage, efficiency and a lifetime were measured, and the results are shown in the following Table 1. T95 means time taken for the luminance decreasing to 95% from its initial luminance (5000 nit).

TABLE 1

| Category | Material | Driving Voltage (V) | Efficiency (cd/A) | Lifetime T95 (hr) | Light Emitting Color |
|---|---|---|---|---|---|
| Comparative Example 1 | RH-1 | 4.48 | 33.5 | 173 | Red |
| Example 1 | Compound 6 | 4.19 | 35.5 | 232 | Red |
| Example 2 | Compound 16 | 4.27 | 34.7 | 213 | Red |
| Example 3 | Compound 27 | 3.98 | 37.8 | 267 | Red |
| Example 4 | Compound 34 | 3.93 | 39.7 | 271 | Red |
| Example 5 | Compound 39 | 3.98 | 38.3 | 260 | Red |
| Example 6 | Compound 122 | 4.05 | 37.5 | 247 | Red |

TABLE 1-continued

| Category | Material | Driving Voltage (V) | Efficiency (cd/A) | Lifetime T95 (hr) | Light Emitting Color |
|---|---|---|---|---|---|
| Example 7 | Compound 159 | 4.09 | 36.4 | 240 | Red |
| Example 8 | Compound 187 | 4.10 | 38.0 | 211 | Red |
| Example 9 | Compound 226 | 4.13 | 38.9 | 231 | Red |
| Example 10 | Compound 311 | 4.12 | 38.3 | 247 | Red |
| Example 11 | Compound 335 | 4.17 | 37.1 | 240 | Red |
| Example 12 | Compound 361 | 4.01 | 36.5 | 251 | Red |
| Example 13 | Compound 483 | 4.18 | 38.4 | 267 | Red |
| Example 14 | Compound 505 | 4.12 | 39.0 | 260 | Red |
| Example 15 | Compound 518 | 4.03 | 39.7 | 245 | Red |
| Example 16 | Compound 547 | 4.18 | 39.5 | 293 | Red |
| Example 17 | Compound 561 | 4.11 | 39.1 | 314 | Red |
| Example 18 | Compound 1034 | 4.08 | 38.0 | 253 | Red |
| Example 19 | Compound 572 | 3.95 | 40.3 | 353 | Red |
| Example 20 | Compound 1043 | 4.05 | 37.3 | 281 | Red |
| Example 21 | Compound 1047 | 3.91 | 38.5 | 294 | Red |
| Example 22 | Compound 1055 | 3.99 | 38.0 | 277 | Red |
| Example 23 | Compound 647 | 4.05 | 38.3 | 271 | Red |
| Example 24 | Compound 651 | 4.00 | 37.9 | 260 | Red |
| Example 25 | Compound 672 | 4.04 | 40.9 | 284 | Red |
| Example 26 | Compound 685 | 3.93 | 41.3 | 339 | Red |
| Example 27 | Compound 1057 | 3.98 | 40.7 | 357 | Red |
| Example 28 | Compound 715 | 4.07 | 39.4 | 371 | Red |
| Example 29 | Compound 728 | 4.19 | 39.9 | 341 | Red |
| Example 30 | Compound 763 | 4.03 | 41.7 | 314 | Red |
| Example 31 | Compound 788 | 4.14 | 41.2 | 263 | Red |
| Example 32 | Compound 793 | 4.17 | 40.7 | 250 | Red |
| Example 33 | Compound 821 | 4.04 | 37.7 | 232 | Red |

TABLE 1-continued

| Category | Material | Driving Voltage (V) | Efficiency (cd/A) | Lifetime T95 (hr) | Light Emitting Color |
|---|---|---|---|---|---|
| Example 34 | Compound 823 | 3.88 | 43.4 | 277 | Red |
| Example 35 | Compound 832 | 3.94 | 41.9 | 344 | Red |
| Example 36 | Compound 858 | 3.97 | 40.5 | 314 | Red |
| Example 37 | Compound 862 | 3.88 | 40.1 | 325 | Red |
| Example 38 | Compound 872 | 3.95 | 40.9 | 318 | Red |
| Example 39 | Compound 887 | 4.09 | 39.7 | 284 | Red |
| Example 40 | Compound 900 | 4.13 | 38.1 | 267 | Red |
| Example 41 | Compound 915 | 4.04 | 39.3 | 277 | Red |
| Example 42 | Compound 928 | 3.95 | 40.5 | 223 | Red |
| Example 43 | Compound 941 | 3.90 | 42.5 | 218 | Red |
| Example 44 | Compound 953 | 3.94 | 41.5 | 203 | Red |
| Example 45 | Compound 973 | 3.99 | 40.1 | 295 | Red |
| Example 46 | Compound 980 | 4.07 | 40.5 | 270 | Red |
| Example 47 | Compound 999 | 4.01 | 41.8 | 284 | Red |
| Comparative Example 2 | RH-2 | 4.61 | 31.5 | 153 | Red |
| Comparative Example 3 | RH-3 | 4.21 | 38.5 | 183 | Red |
| Comparative Example 4 | RH-4 | 4.61 | 32.5 | 104 | Red |
| Comparative Example 5 | RH-5 | 4.64 | 31.1 | 97 | Red |
| Comparative Example 6 | RH-6 | 4.31 | 36.5 | 143 | Red |
| Comparative Example 7 | RH-7 | 4.17 | 38.7 | 151 | Red |
| Comparative Example 8 | RH-8 | 4.34 | 37.5 | 153 | Red |
| Comparative Example 9 | RH-9 | 4.27 | 39.5 | 160 | Red |
| Comparative Example 10 | RH-10 | 4.58 | 29.5 | 88 | Red |
| Comparative Example 11 | RH-11 | 4.49 | 30.3 | 94 | Red |
| Comparative Example 12 | RH-12 | 4.35 | 37.0 | 155 | Red |
| Comparative Example 13 | RH-13 | 4.24 | 38.5 | 168 | Red |
| Comparative Example 14 | RH-14 | 4.41 | 37.4 | 112 | Red |
| Comparative Example 15 | RH-15 | 4.31 | 38.0 | 193 | Red |
| Comparative Example 16 | RH-16 | 4.51 | 34.0 | 117 | Red |
| Comparative Example 17 | RH-17 | 4.38 | 35.5 | 193 | Red |
| Comparative Example 18 | RH-18 | 4.58 | 32.5 | 143 | Red |
| Comparative Example 19 | RH-19 | 4.51 | 32.3 | 157 | Red |
| Comparative Example 20 | RH-20 | 4.45 | 33.5 | 193 | Red |
| Comparative Example 21 | RH-21 | 4.37 | 34.7 | 181 | Red |
| Comparative Example 22 | RH-22 | 4.40 | 37.9 | 150 | Red |
| Comparative Example 23 | RH-23 | 4.35 | 37.9 | 142 | Red |
| Comparative Example 24 | RH-24 | 4.27 | 38.9 | 174 | Red |
| Comparative Example 25 | RH-25 | 4.52 | 36.3 | 91 | Red |
| Comparative Example 26 | RH-26 | 4.46 | 35.1 | 103 | Red |
| Comparative Example 27 | RH-27 | 4.34 | 36.4 | 117 | Red |
| Comparative Example 28 | RH-28 | 4.27 | 37.9 | 87 | Red |
| Comparative Example 29 | RH-29 | 4.38 | 36.7 | 98 | Red |

When applying a current to the organic light emitting devices manufactured in Examples 1 to 47 and Comparative Examples 1 to 29, results of Table 1 were obtained. The red organic light emitting device of Comparative Example 1 used materials that have been widely used in the art, and had a structure using Compound [EB-1] as an electron blocking layer and using RH-1/Dp-7 as a red light emitting layer. Comparative Examples 2 to 29 manufactured organic light emitting devices using RH-2 to RH-29 instead of RH-1. When examining the results of Table 1, it was seen that, when using the compound of the present disclosure as a host of a red light emitting layer, energy transfer from a host to a red dopant was well achieved from the fact that a driving voltage decreased closer to as much as 30% and efficiency increased by 25% or greater compared to the materials in the comparative examples. In addition, it was seen that lifetime properties were greatly improved by a factor of two or more while maintaining high efficiency. This may ultimately be due to the fact that the compounds of the present disclosure have higher stability for electrons and holes compared to the compounds of the comparative examples. As a result, it can be identified that, when using the compound of the present disclosure as a host of a red light emitting layer, a driving voltage, light emission efficiency and lifetime properties of an organic light emitting device are improved.

The invention claimed is:
1. A heterocyclic compound represented by the following Chemical Formula 1:

[Chemical Formula 1]

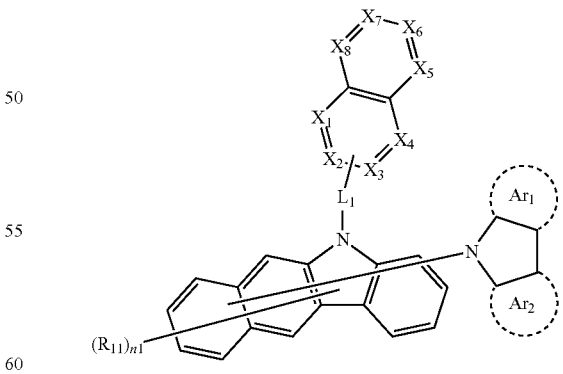

wherein, in Chemical Formula 1,
$Ar_1$ and $Ar_2$ are the same as or different from each other and each independently substituted or unsubstituted benzene; or substituted or unsubstituted naphthalene, and any one of $Ar_1$ and $Ar_2$ is substituted or unsubstituted benzene, $X_1$ to $X_4$ are the same as or different from each other, and each independently N, CH, CRa, or C linked to $L_1$, two or more of $X_1$ to $X_4$ are N, and any one of $X_1$ to $X_4$ is C linked to $L_1$, $X_5$ to $X_8$ are the same as or different from each other, and each independently N, CH or CRa, at least one of $X_1$ to $X_8$ is CRa, Ra is a substituted or unsubstituted aryl group having 6 to 60 carbon atoms; or a substituted or unsubstituted heterocyclic group having 2 to 60 carbon atoms, $L_1$ is a direct bond; or a substituted or unsubstituted arylene group having 6 to 60 carbon atoms, $R_{11}$ is hydrogen or deuterium, and n1 is an integer of 0 to 9, and provided that when n1 is 2 or greater, two or more $R_{11}$s is are the same as or different from each other.

2. The heterocyclic compound of claim 1, wherein Chemical Formula 1 is represented by any one of the following Chemical Formula 2 to Chemical Formula 5:

[Chemical Formula 2]

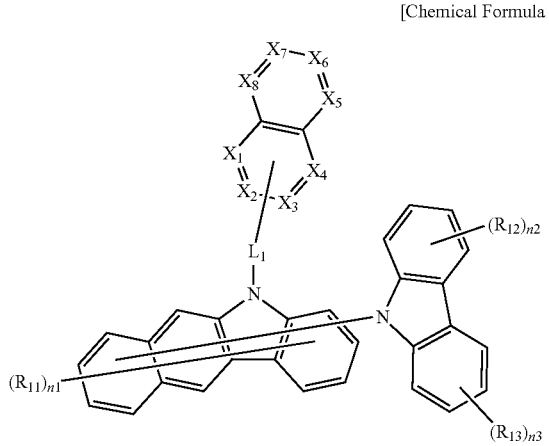

[Chemical Formula 3]

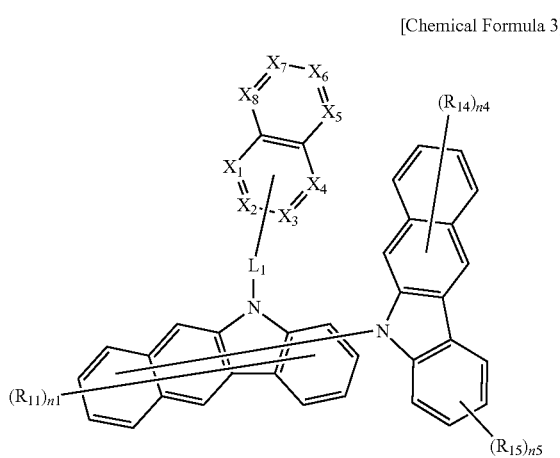

[Chemical Formula 4]

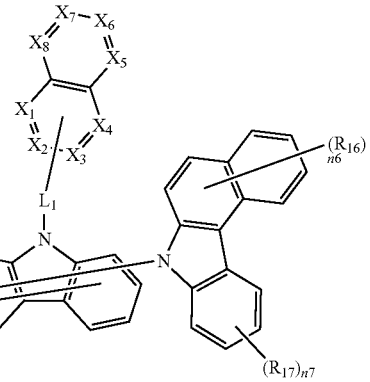

[Chemical Formula 5]

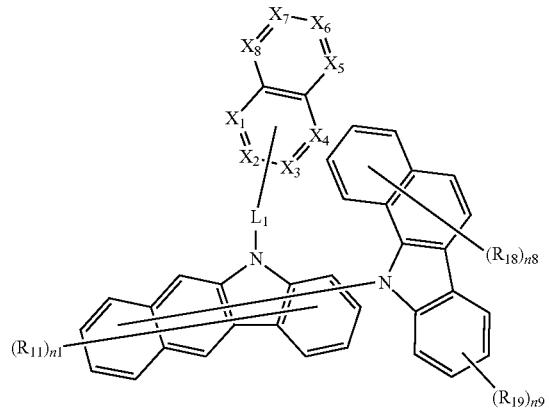

in Chemical Formulae 2 to 5, $X_1$ to $X_8$, $R_{11}$, n1 and $L_1$ have the same definitions as in Chemical Formula 1, $R_{12}$ to $R_{19}$ are the same as or different from each other, and each independently hydrogen; deuterium; a halogen group; a nitrile group; a substituted or unsubstituted alkyl group; a substituted or unsubstituted alkenyl group; a substituted or unsubstituted alkoxy group; a substituted or unsubstituted cycloalkyl group; a substituted or unsubstituted alkylamine group; a substituted or unsubstituted arylamine group; a substituted or unsubstituted aryl group; or a substituted or unsubstituted heterocyclic group, n2, n3, n5, n7 and n9 are each an integer of 0 to 4, n4, n6 and n8 are each an integer of 0 to 6, and provided that when n2 to n9 are each 2 or greater, substituents in the parentheses are the same as or different from each other.

3. The heterocyclic compound of claim 1, wherein Ra is a substituted or unsubstituted aryl group having 6 to 30 carbon atoms; or a substituted or unsubstituted heterocyclic group having 2 to 30 carbon atoms.

4. The heterocyclic compound of claim 1, wherein Chemical Formula 1 is represented by any one of the following Chemical Formulae 1-1 to 1-3:

[Chemical Formula 1-1]
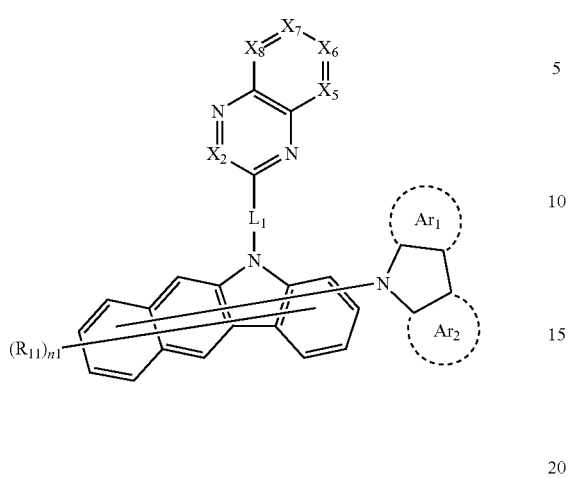
[Chemical Formula 1-2]
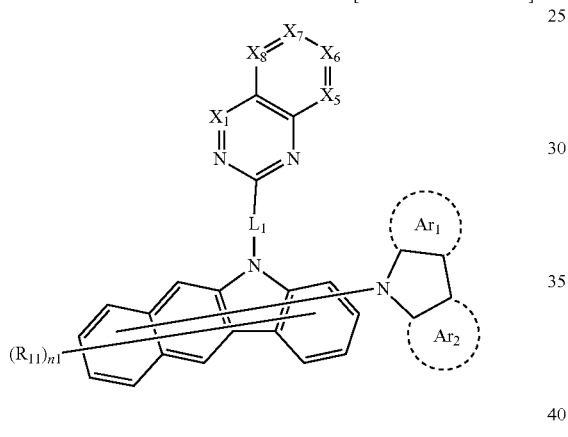
[Chemical Formula 1-3]
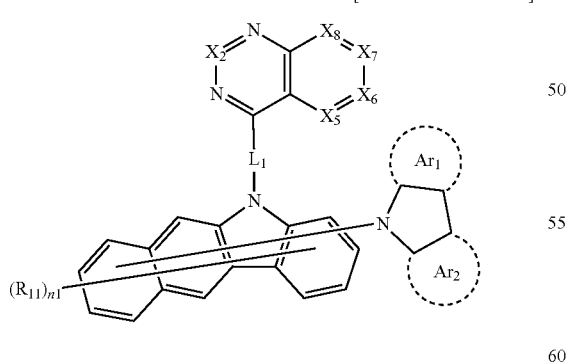
in Chemical Formulae 1-1 to 1-3,
$X_1$, $X_2$, $X_5$ to $X_8$, $R_{11}$, n1, $L_1$, $Ar_1$ and $Ar_2$ have the same definitions as in Chemical Formula 1.
5. The heterocyclic compound of claim 1, wherein Chemical Formula 1 is selected from among the following compounds:
1
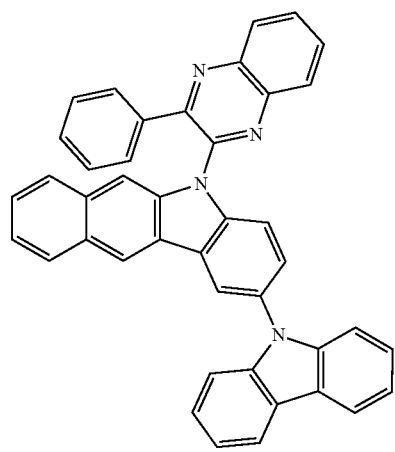
2
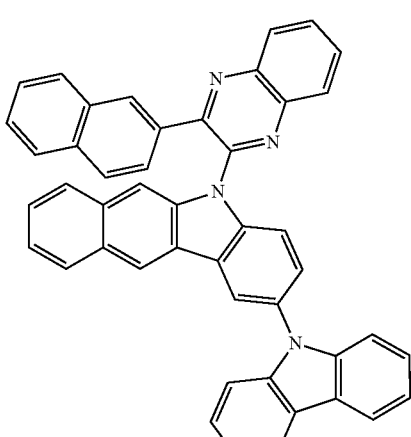
3
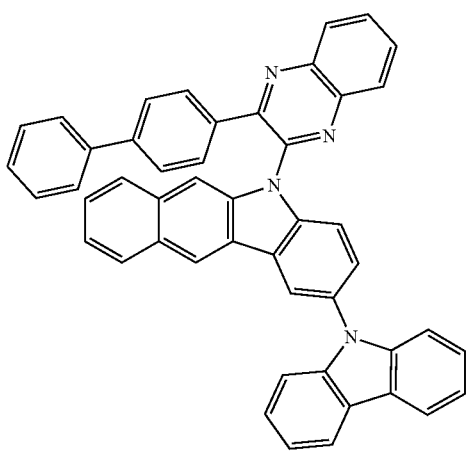

567
-continued
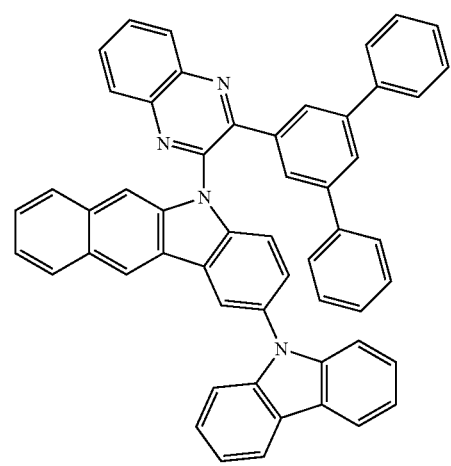
4
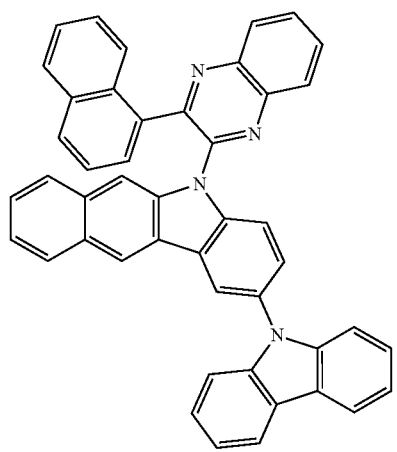
5
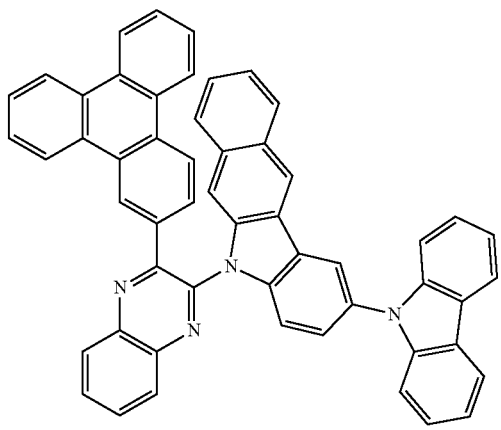
6
568
-continued
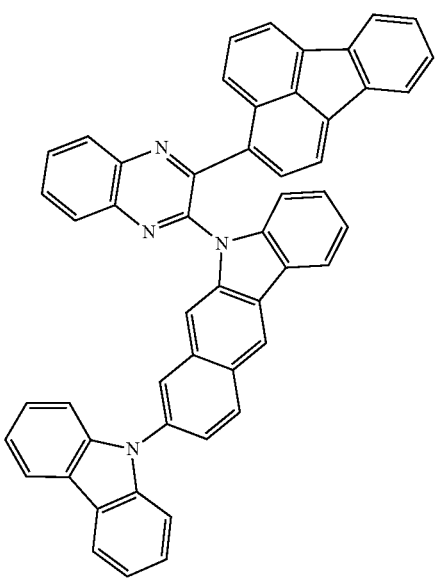
7
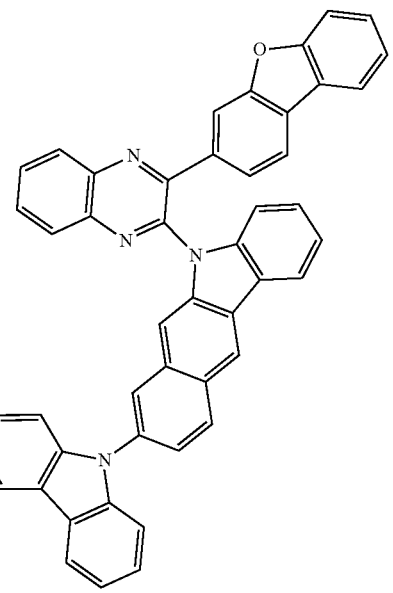
8

569
-continued
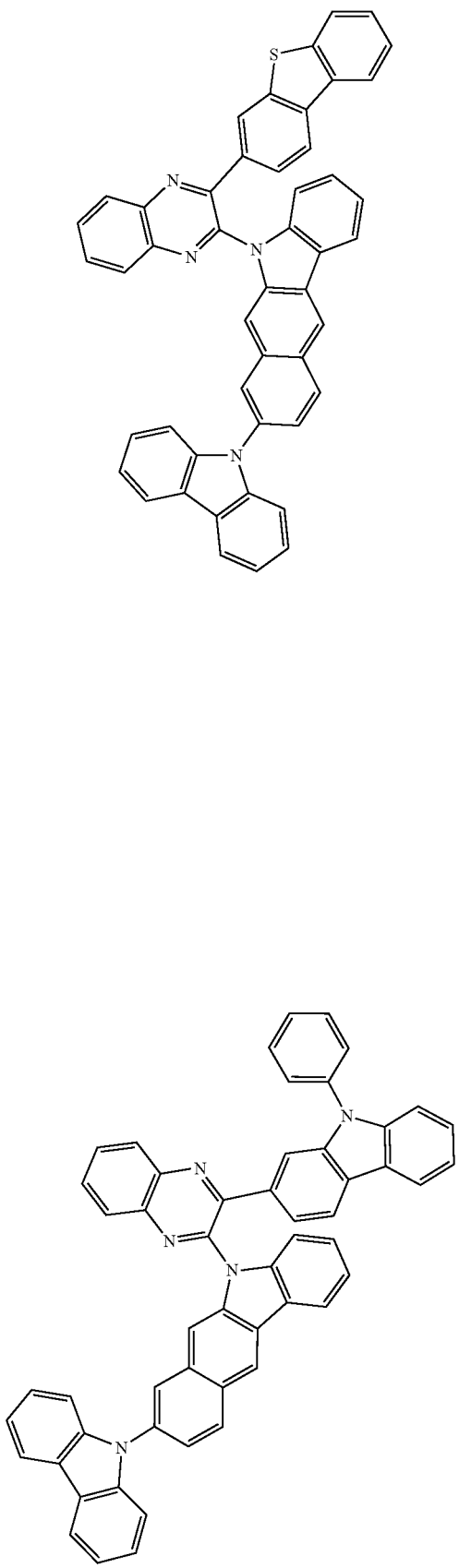
570
-continued
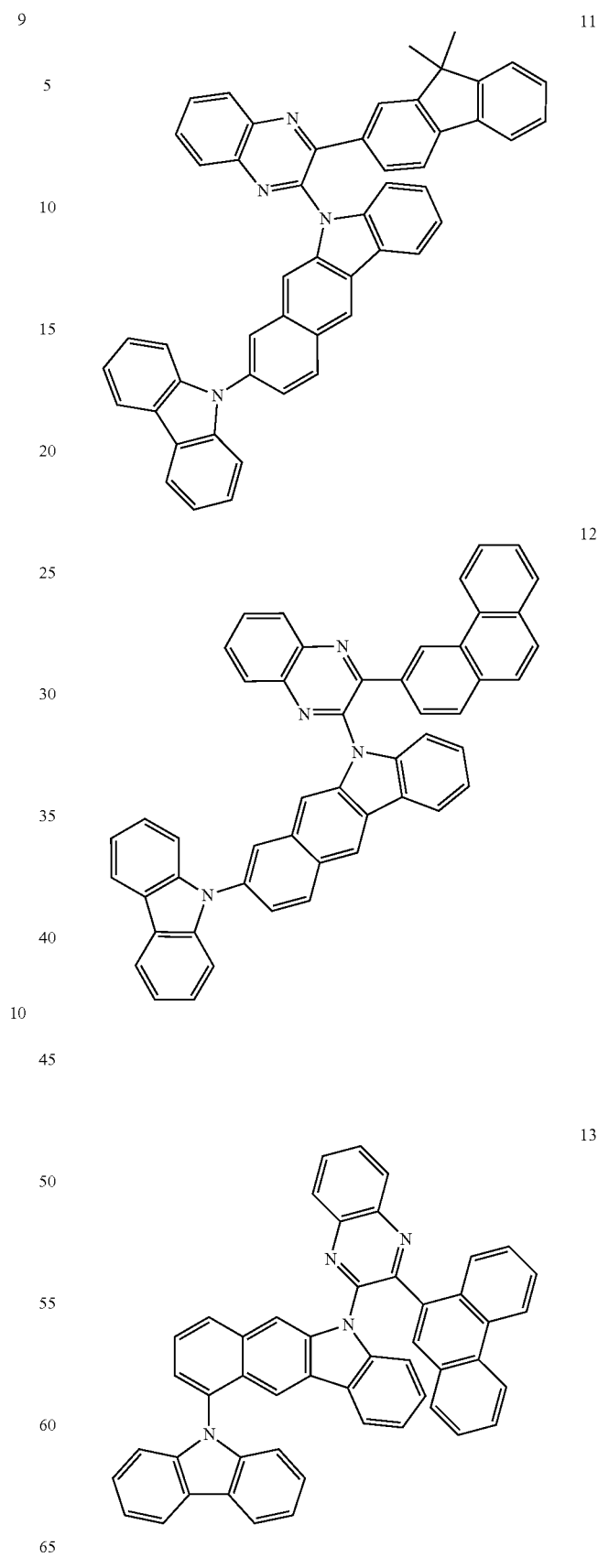

-continued
14
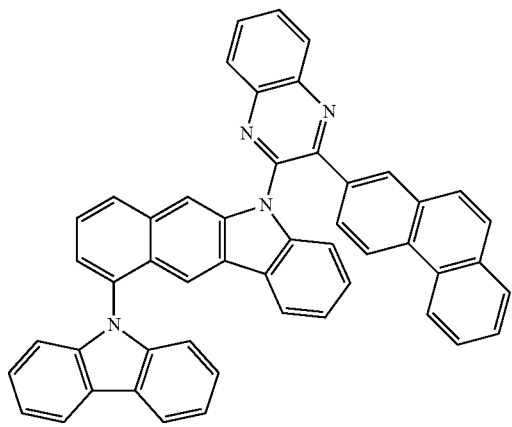
15
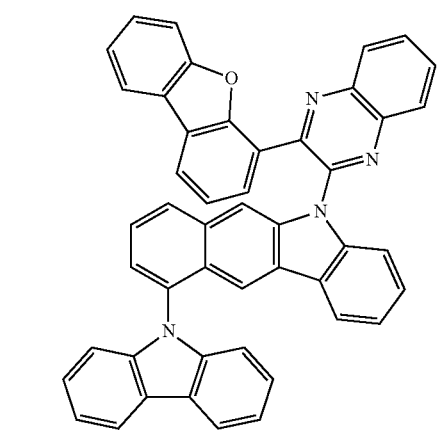
16
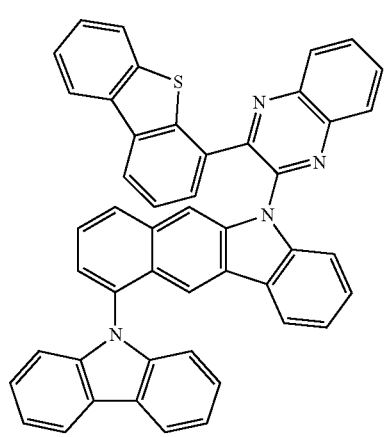
-continued
17
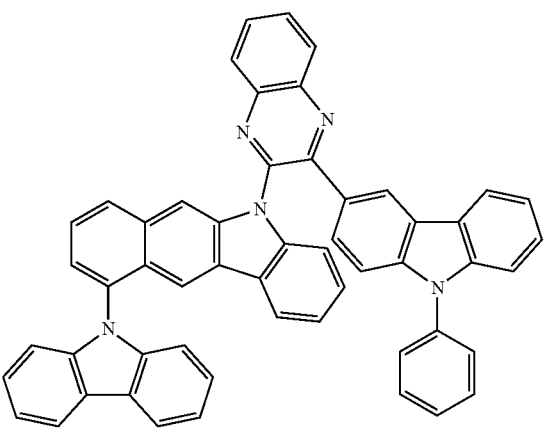
18
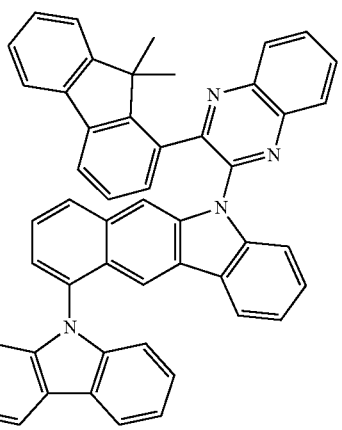
19
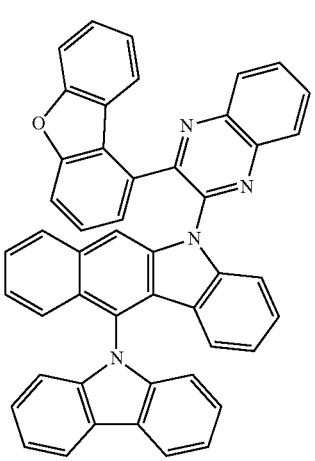

20
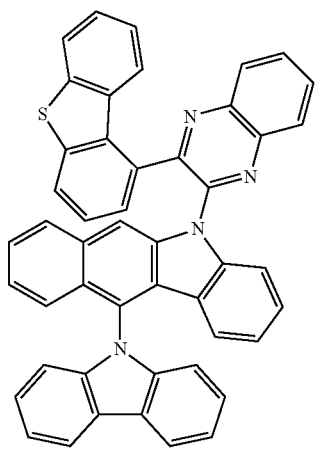
21
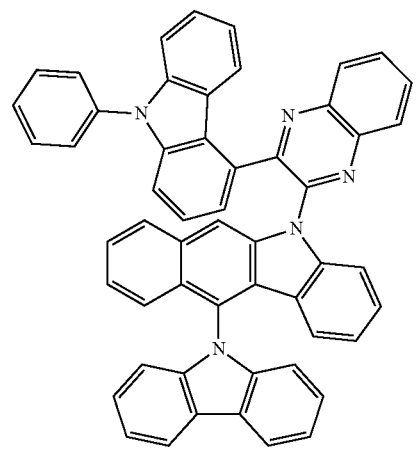
22
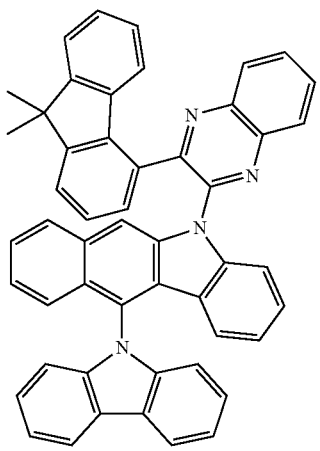
23
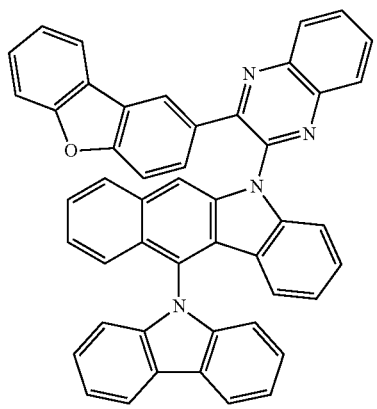
24
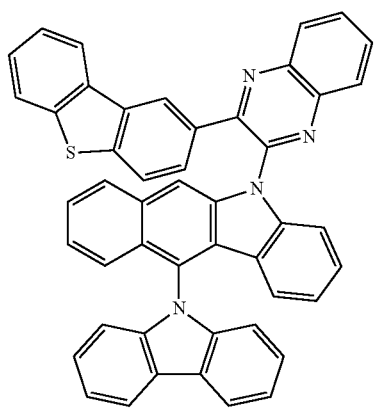
25
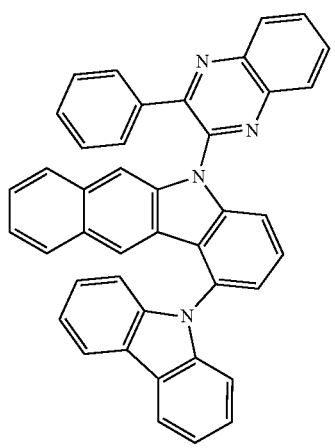

26
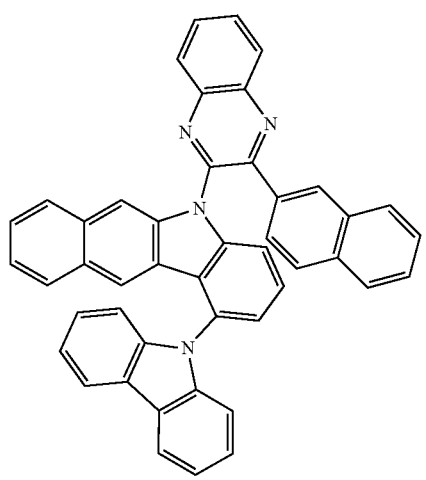
29
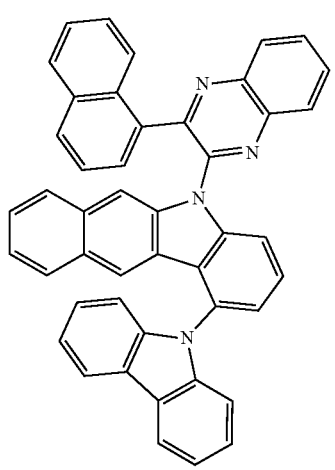
27
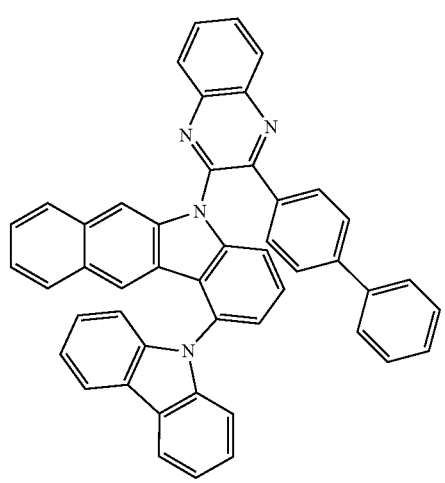
30
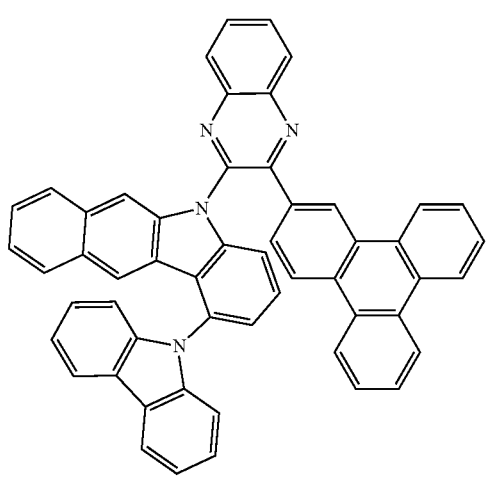
28
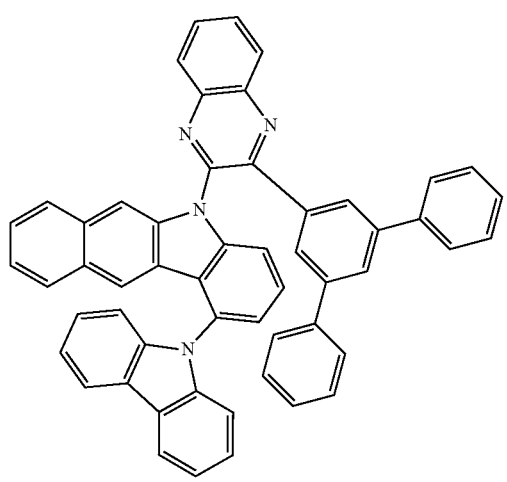
31
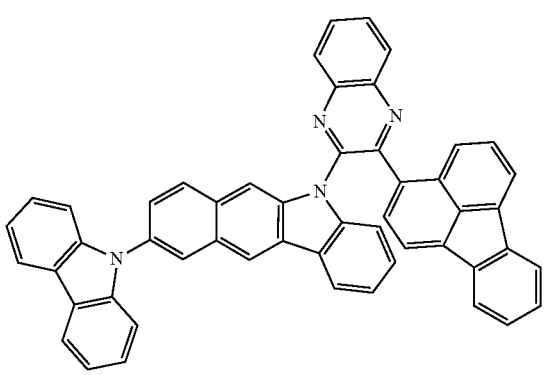

577
-continued
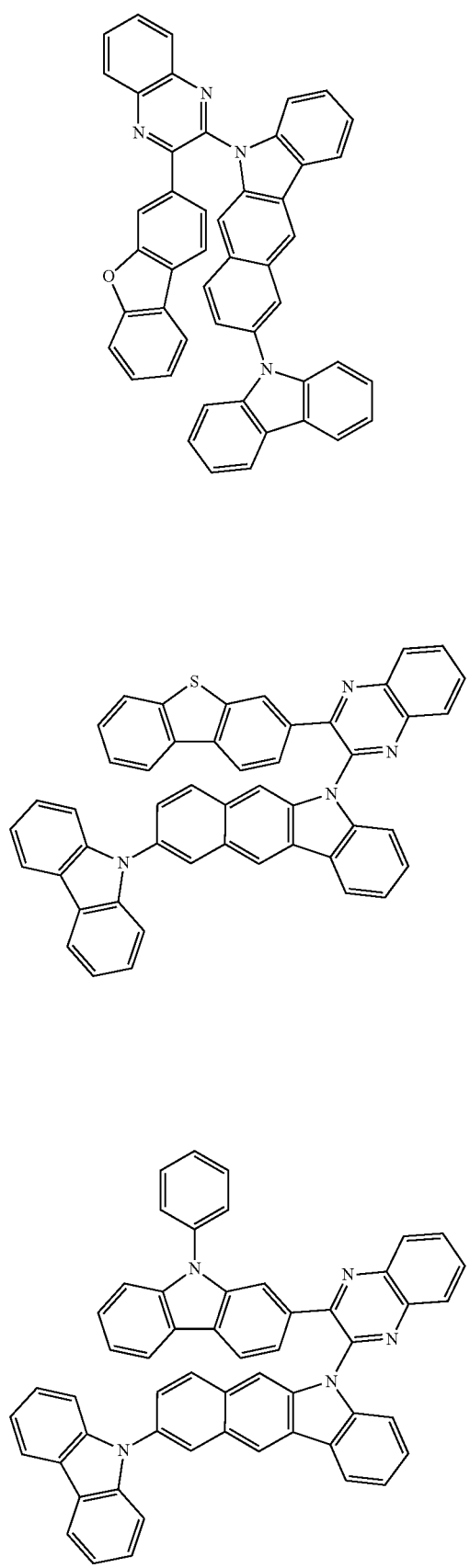
578
-continued
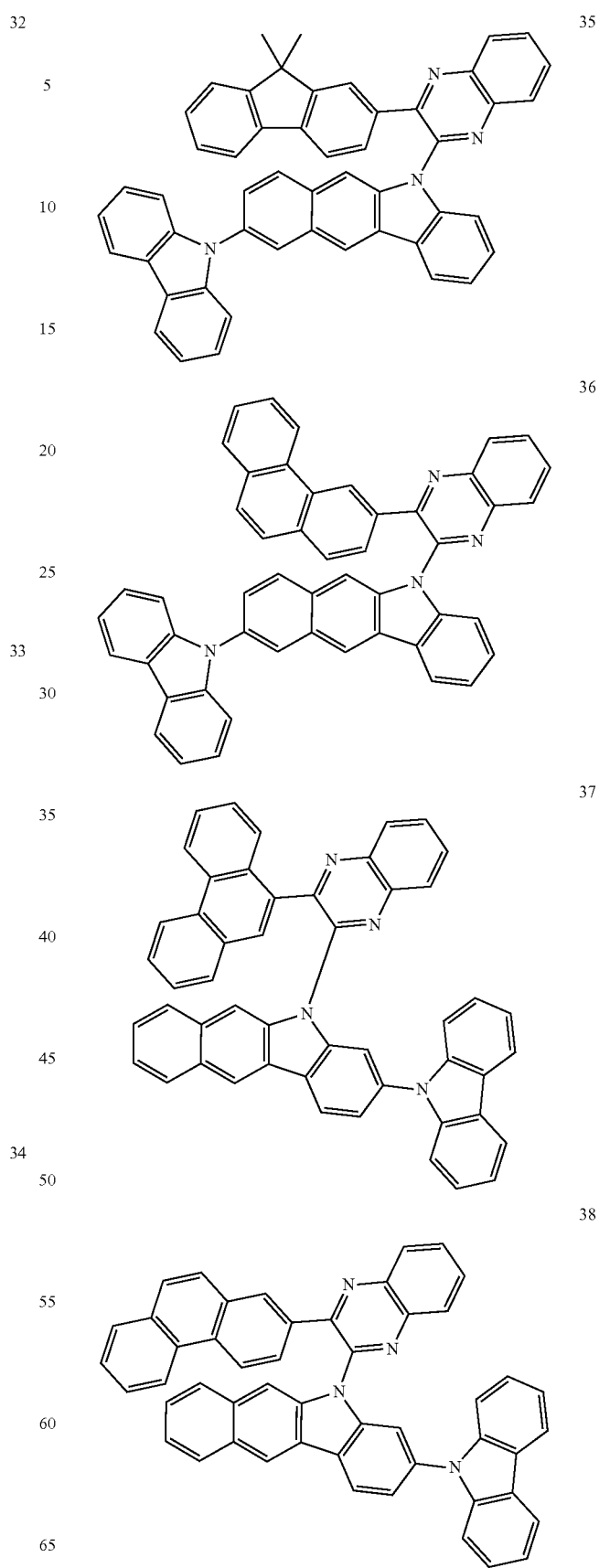

39
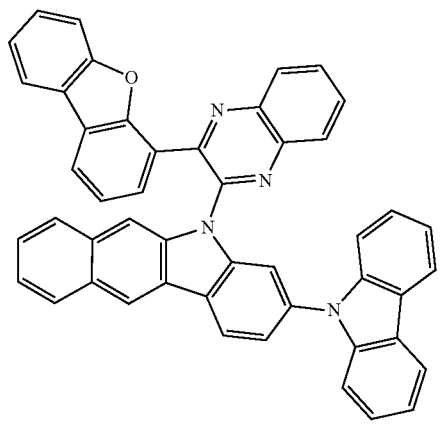
40
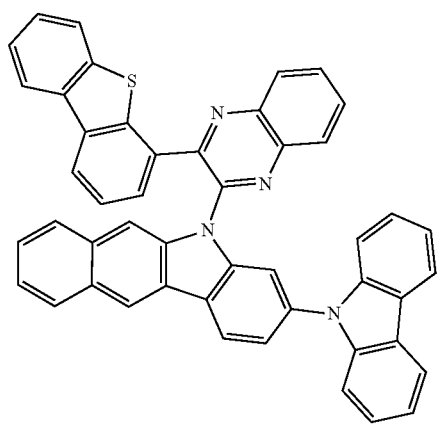
41
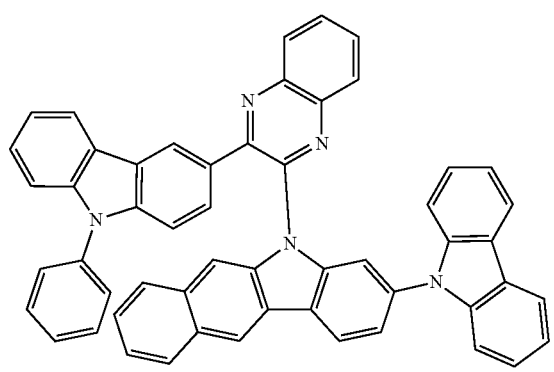
42
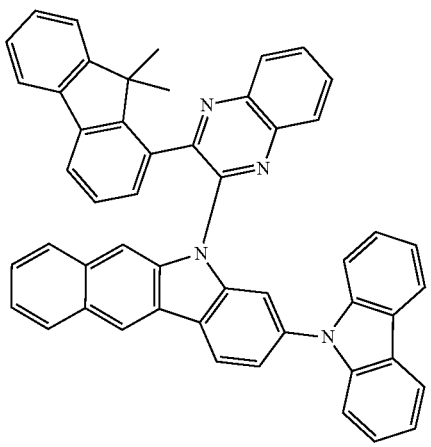
43
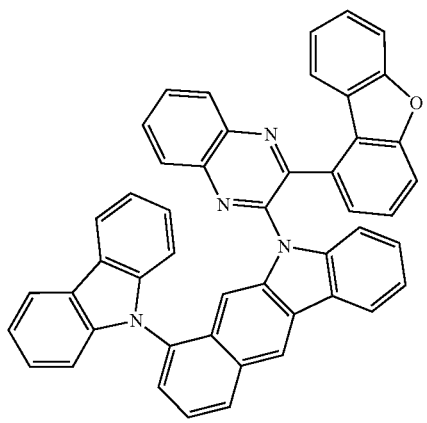
44
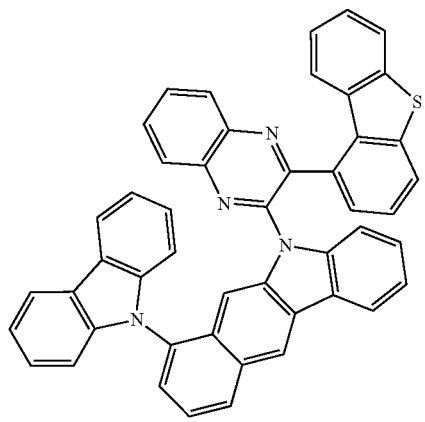

-continued
45
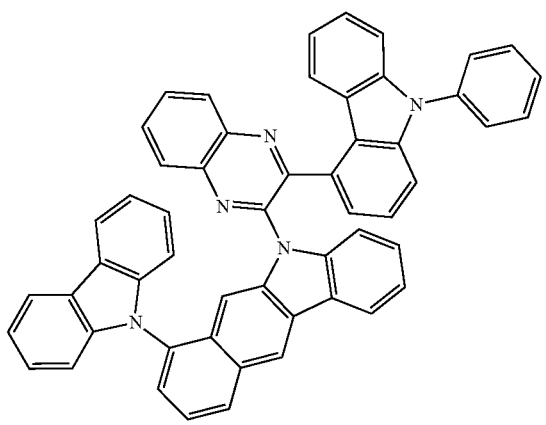
46
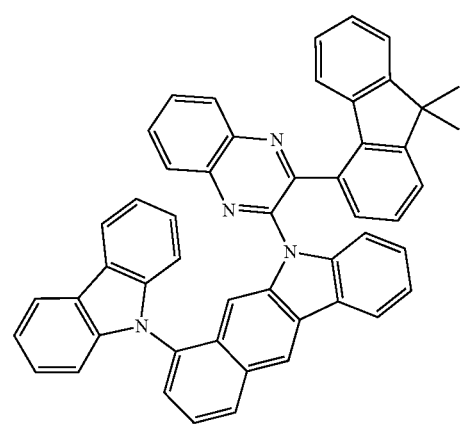
47
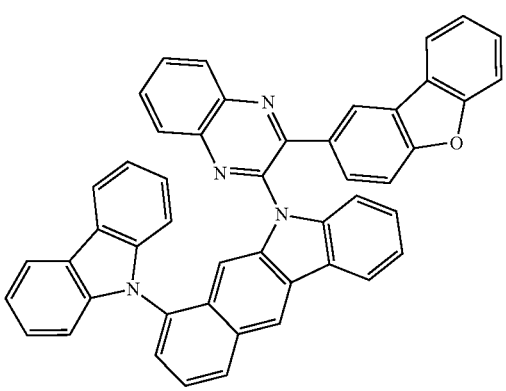
48
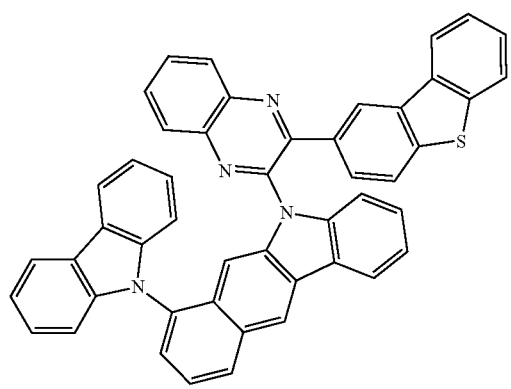
-continued
49
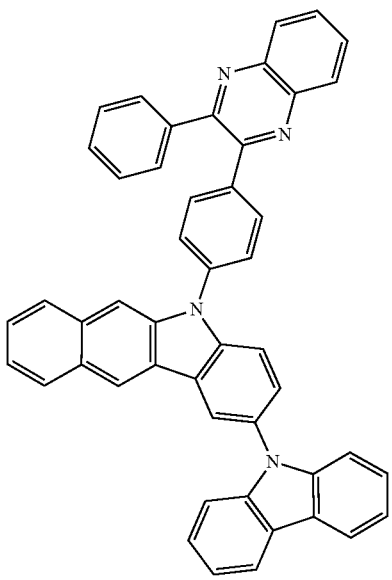
50
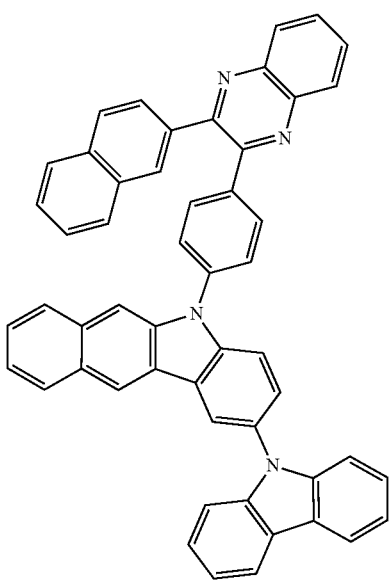

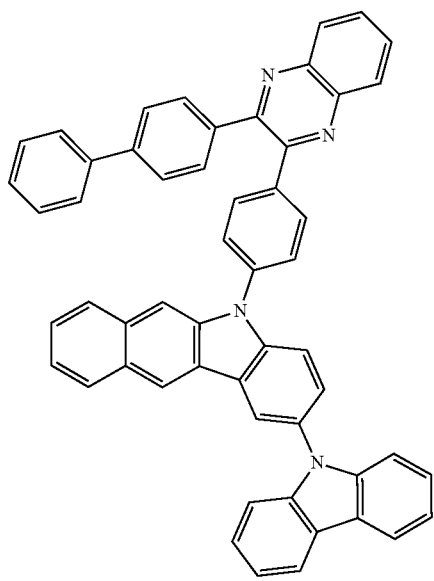
51
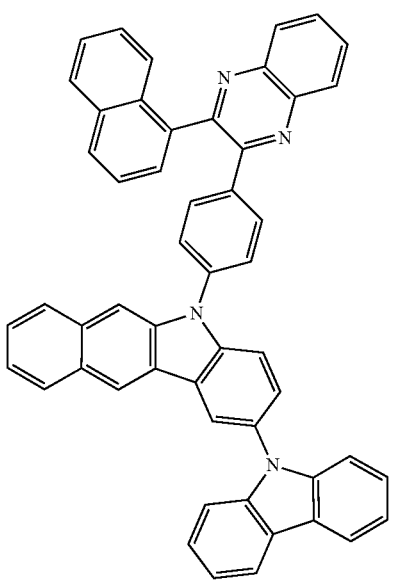
53
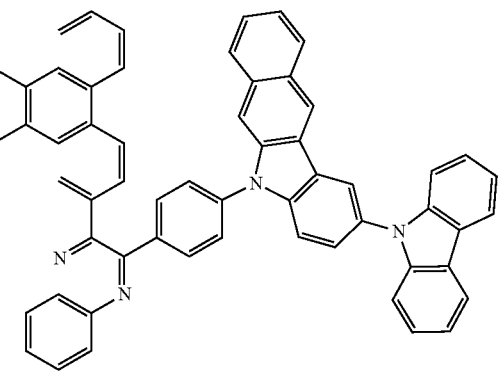
54
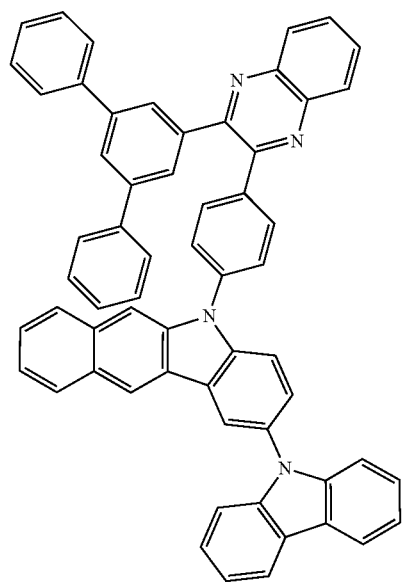
52
55

56
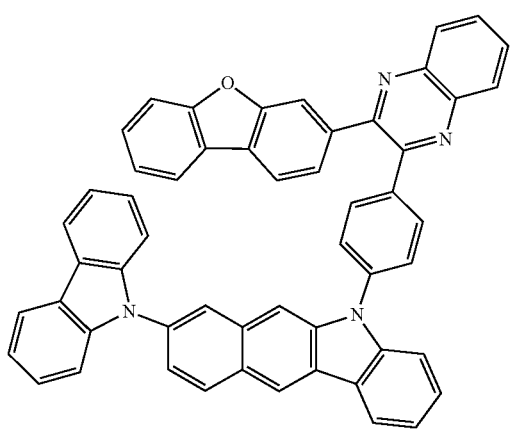
57
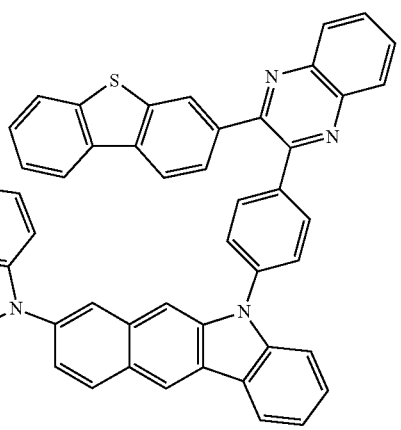
58
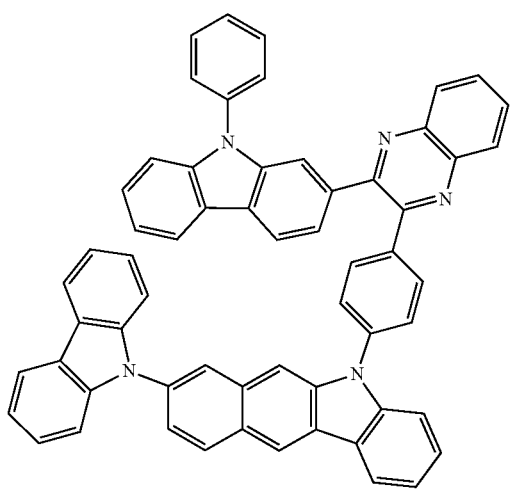
59
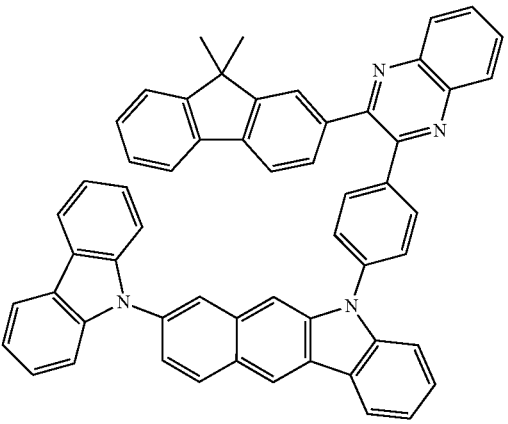
60
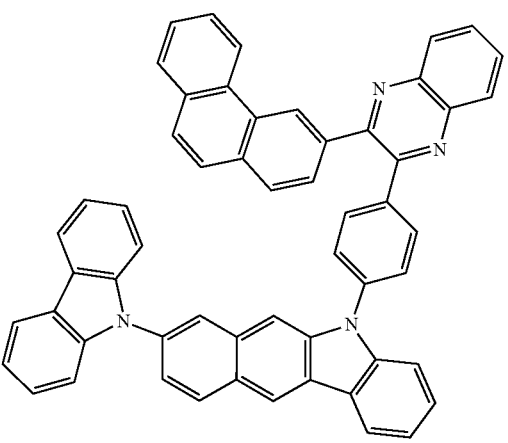
61
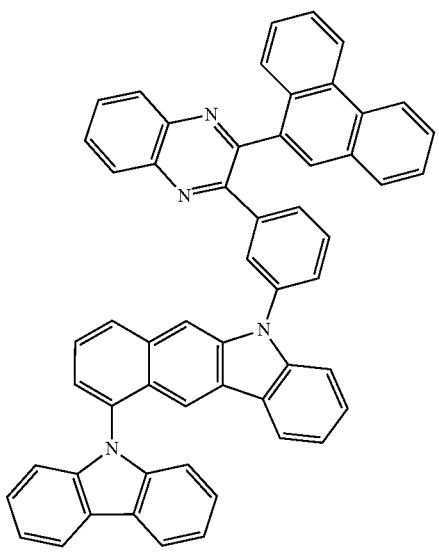

62
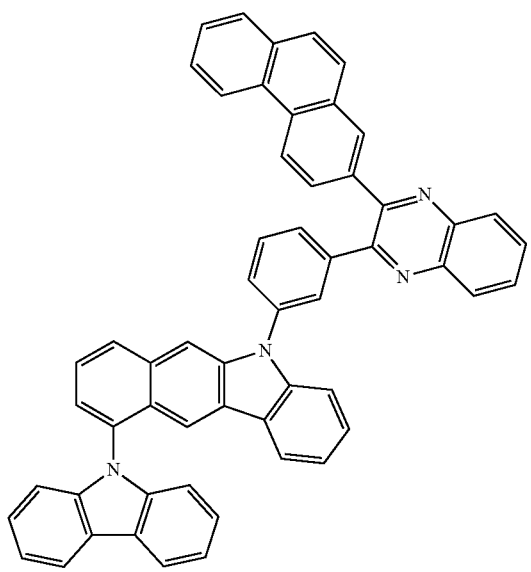
64
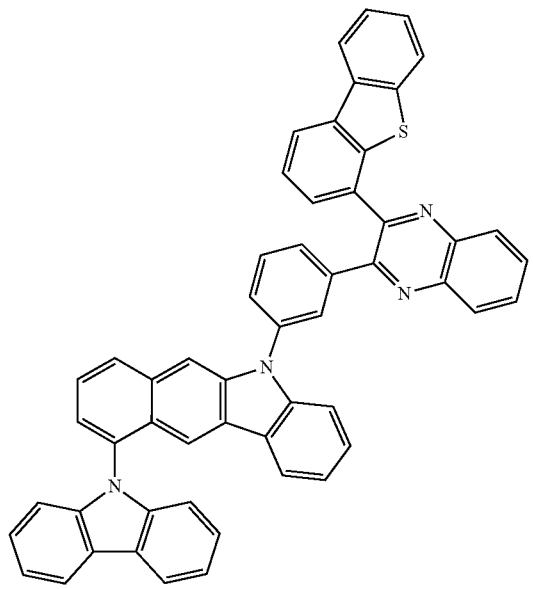
63
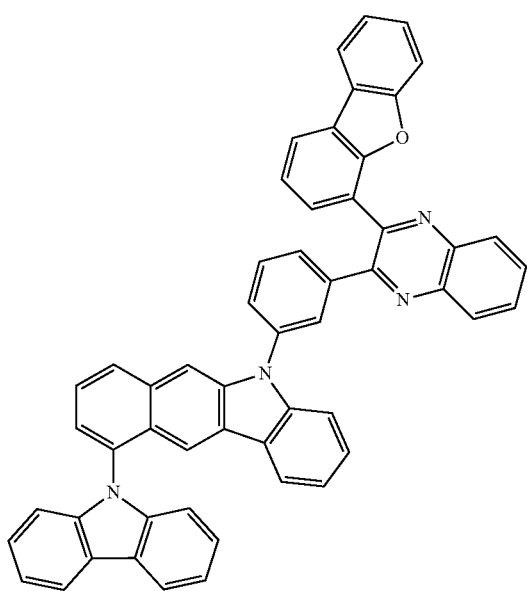
65
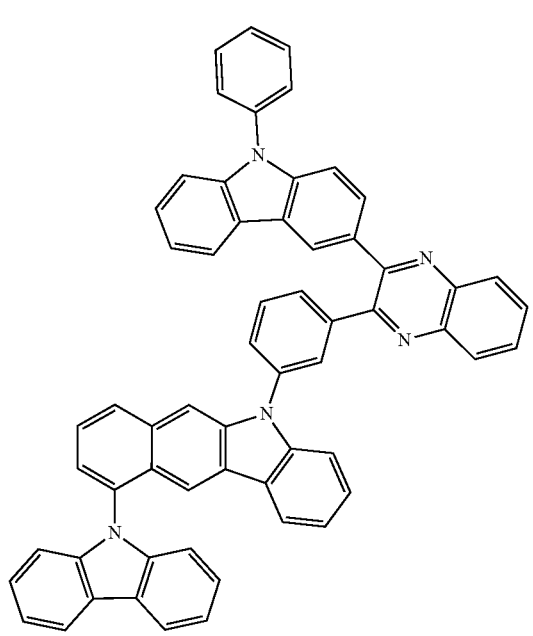

66
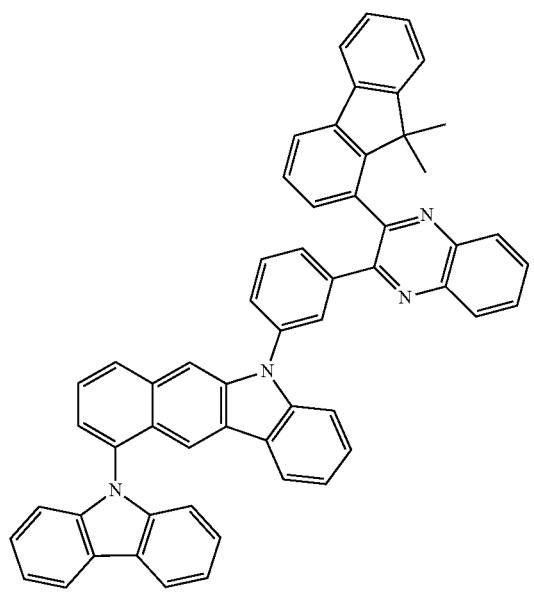
68
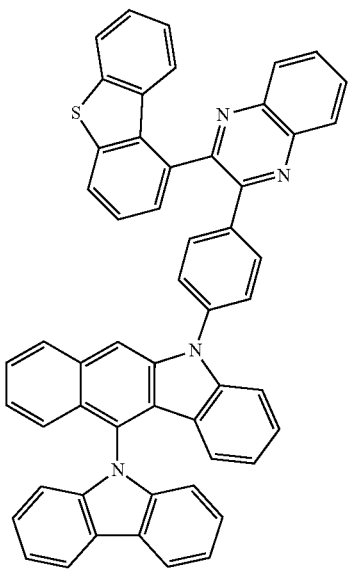
67
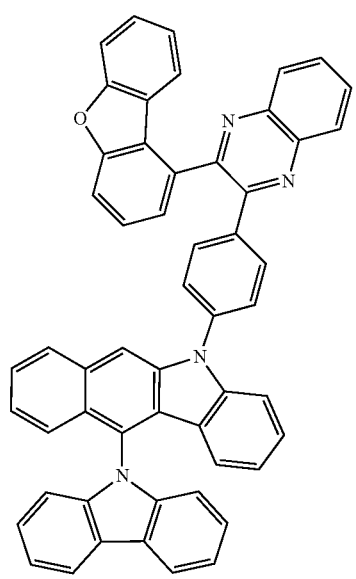
69
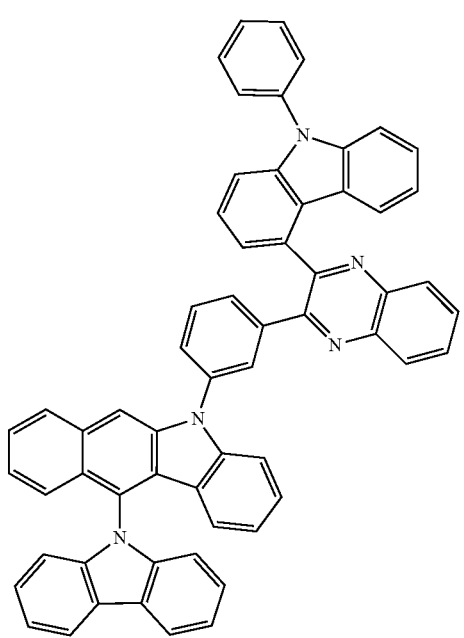

591
-continued
70
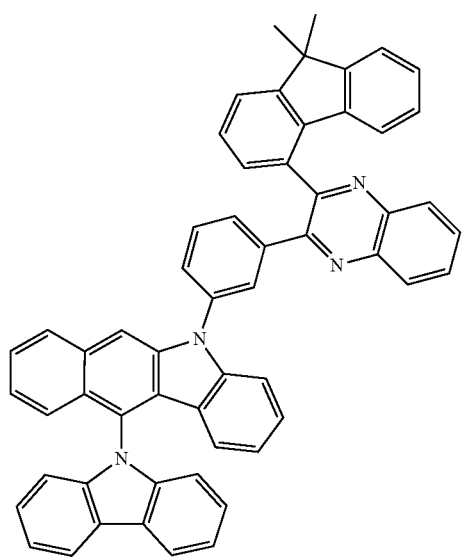
71
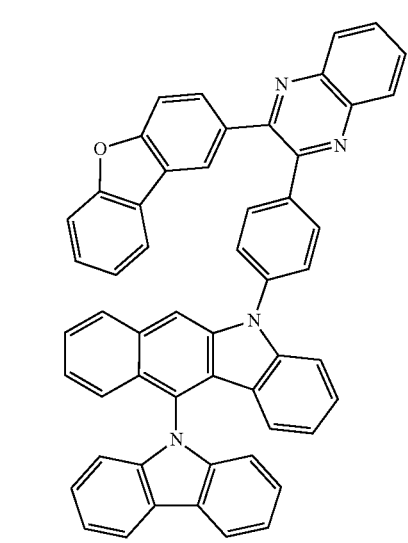
72
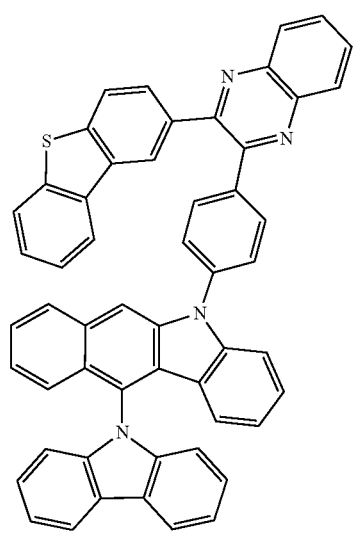
592
-continued
73
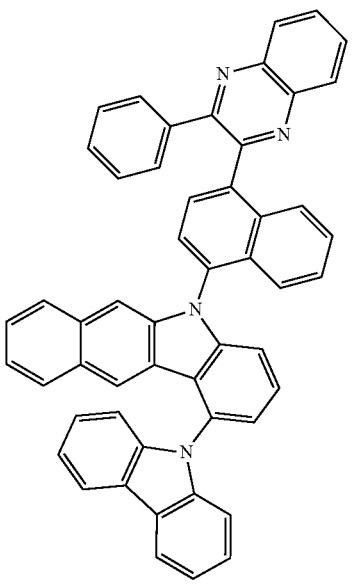
74
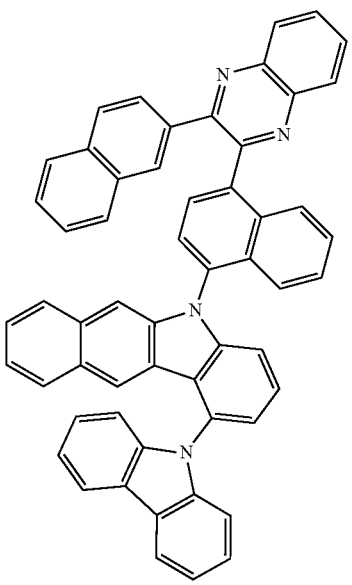

593
-continued
75
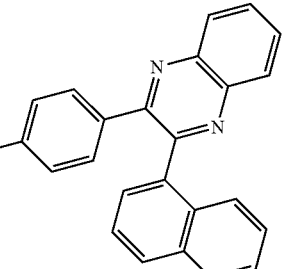
76
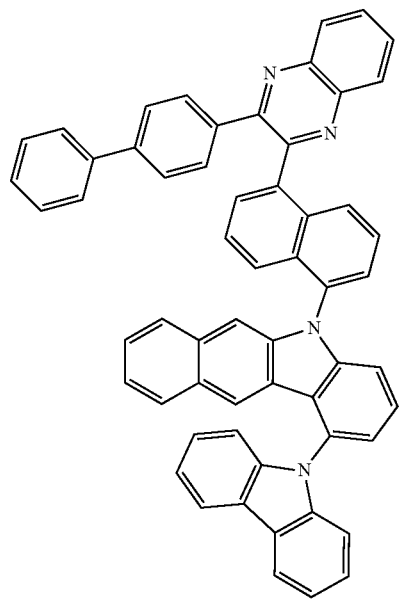
594
-continued
77
78

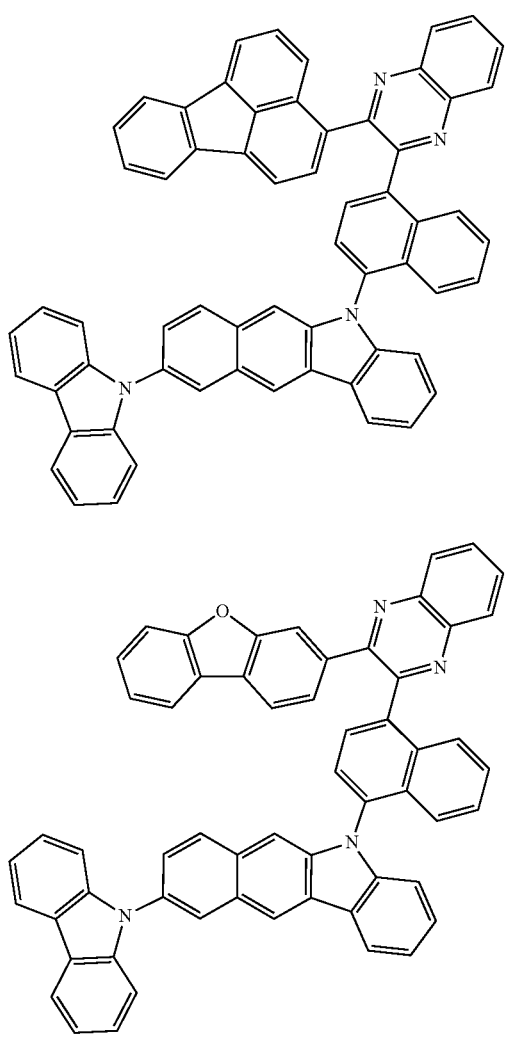
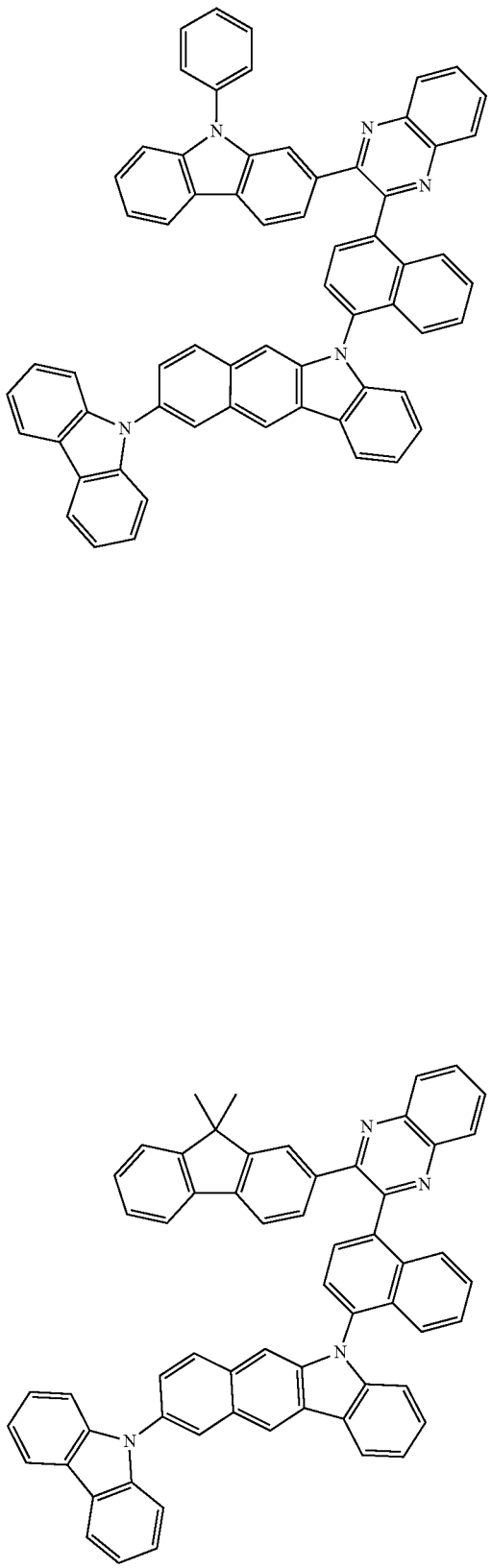

84
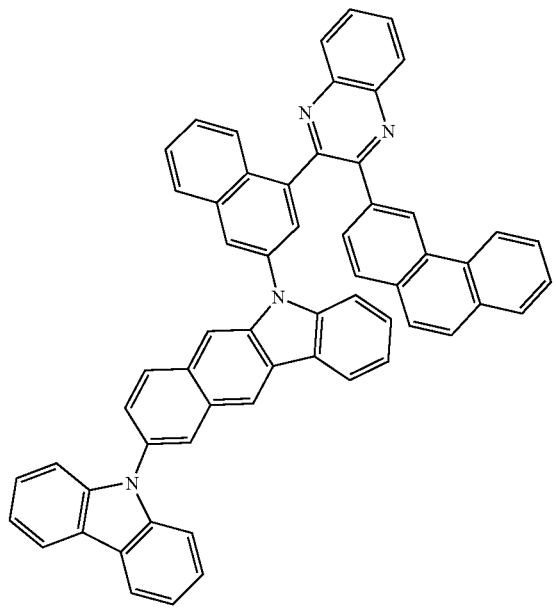
85
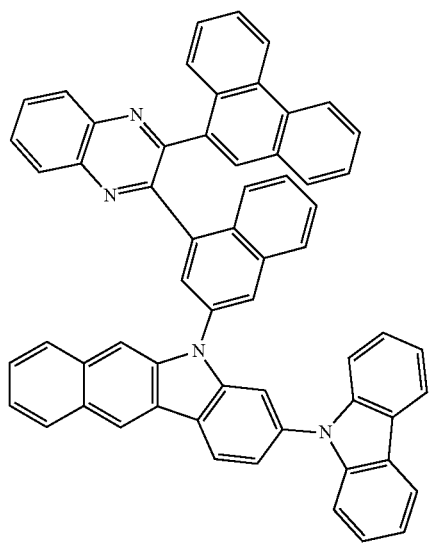
86
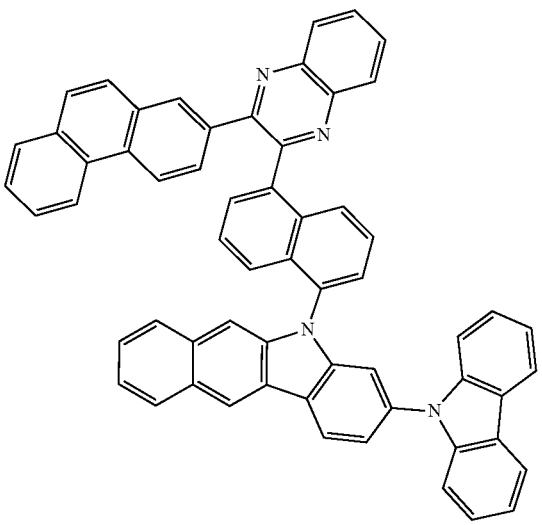
87
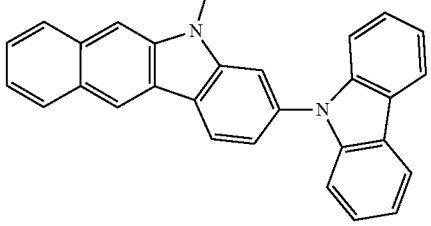
88
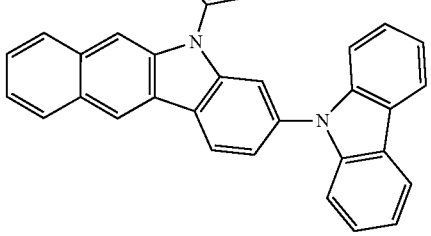

599
-continued
89
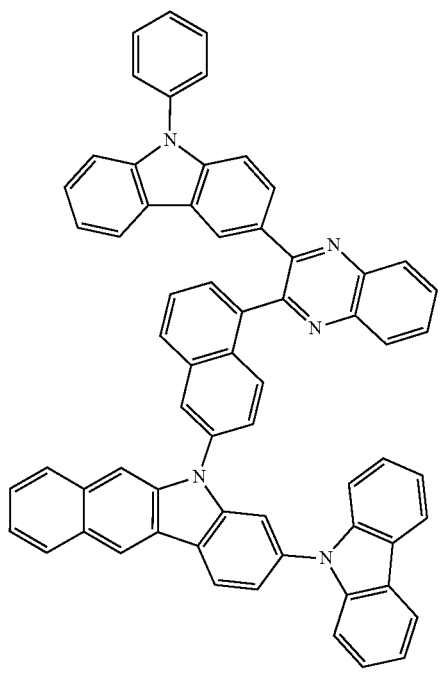
90
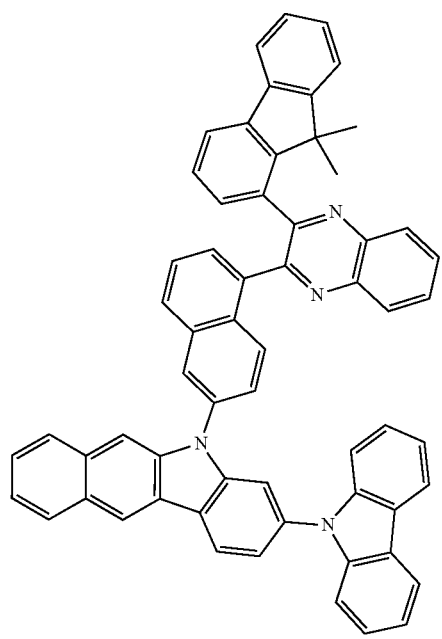
600
-continued
91
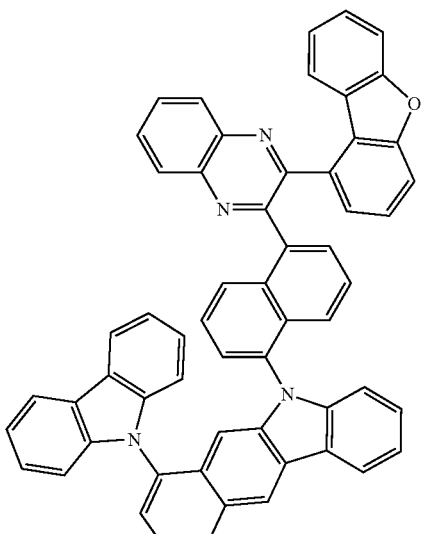
92
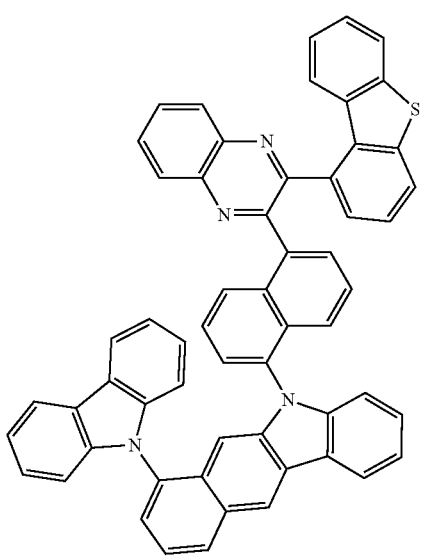

-continued
93
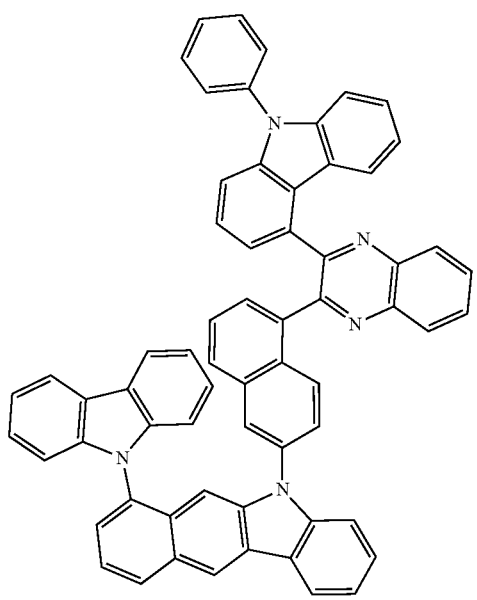
94
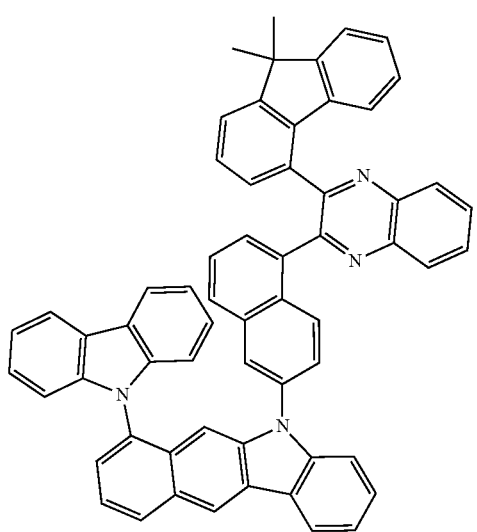
95
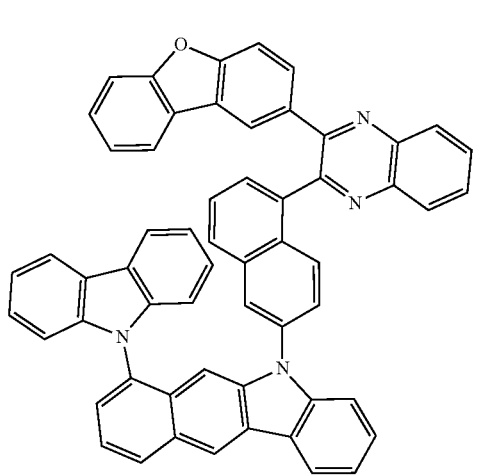
-continued
96
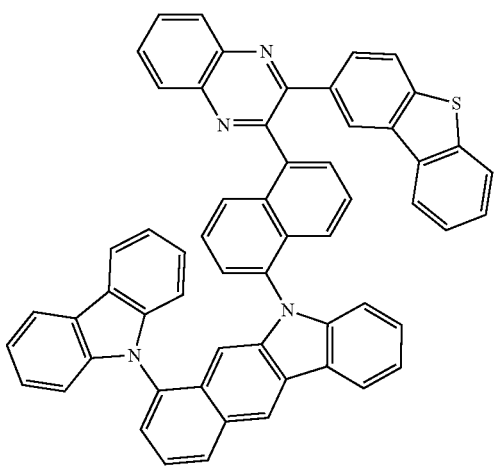
97
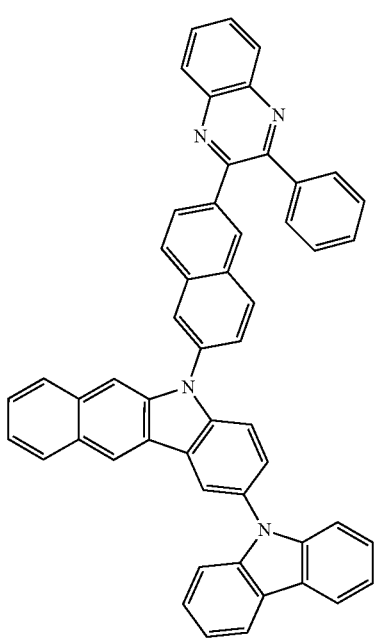

603
-continued
604
-continued
98
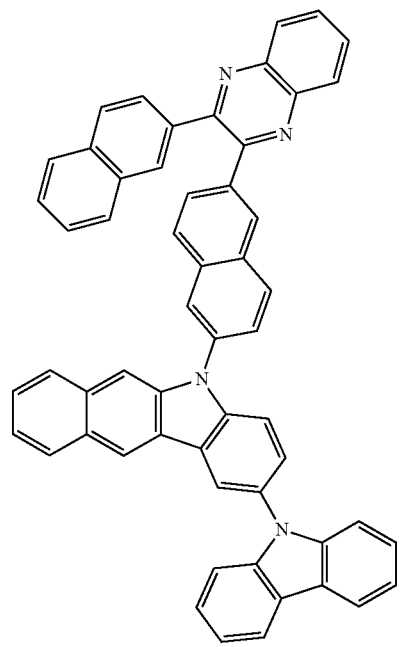
100
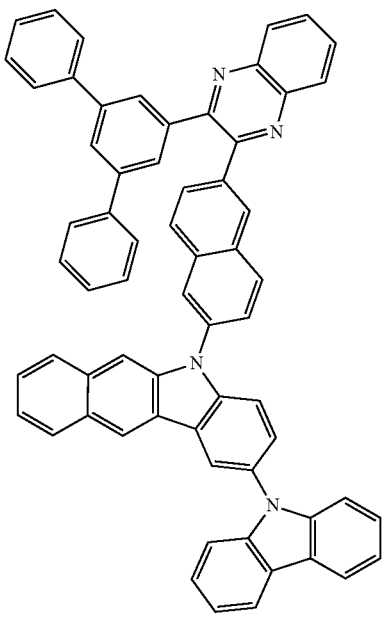
99
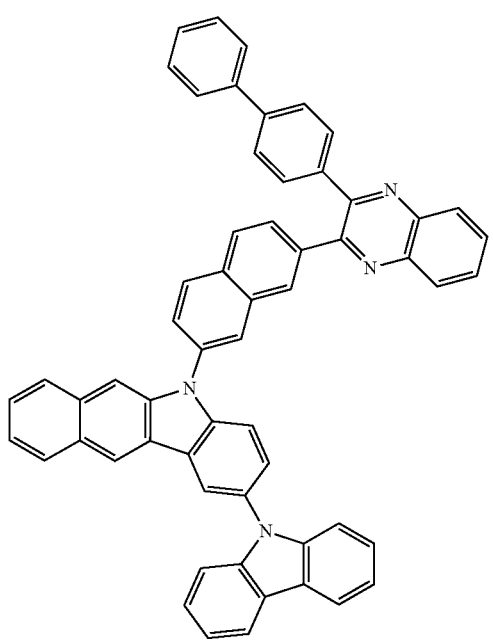
101
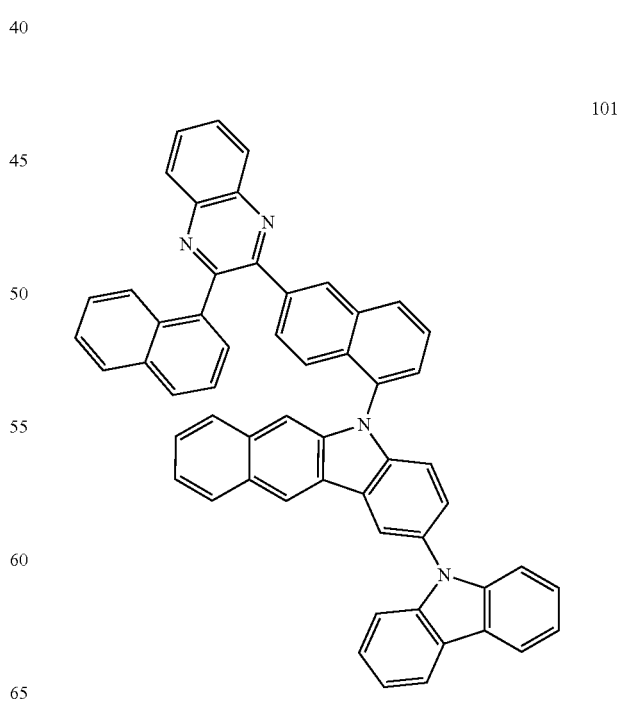

-continued
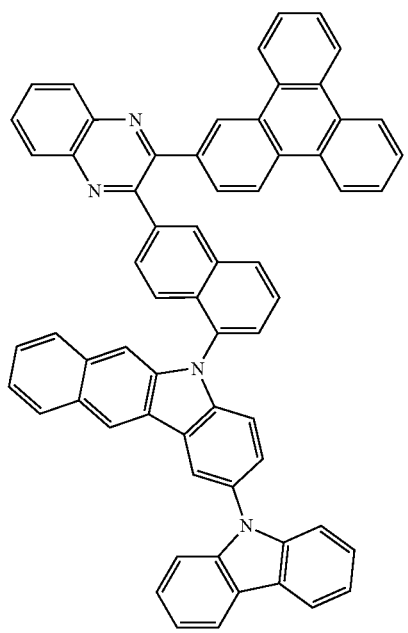
102
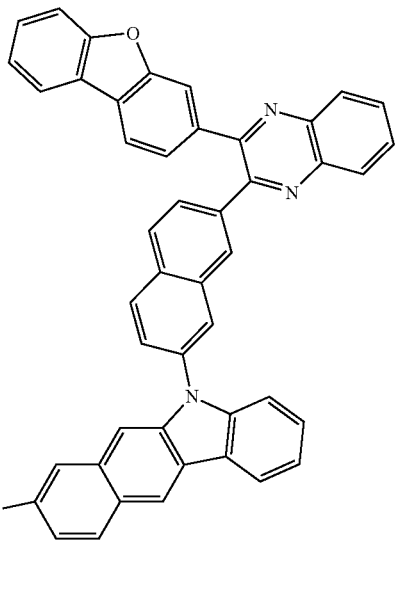
104
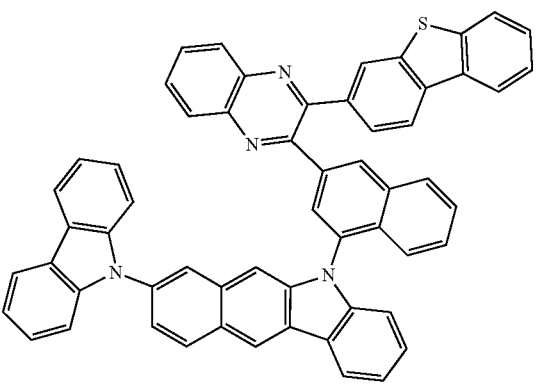
105
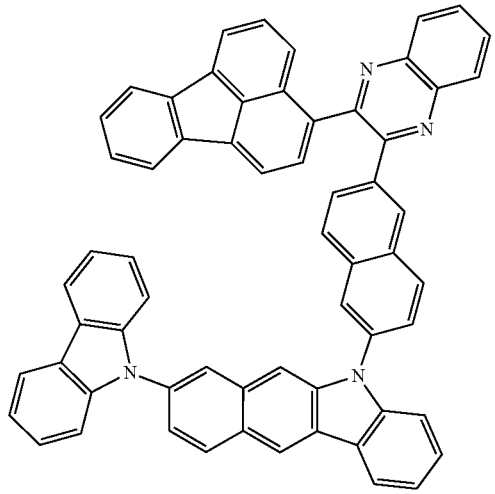
103
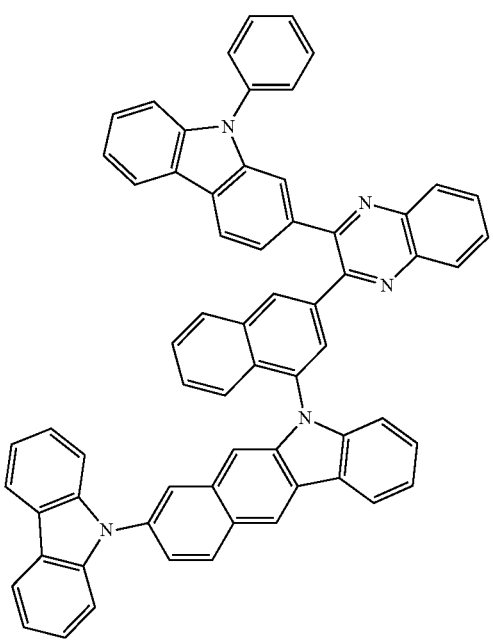
106

607
-continued
108
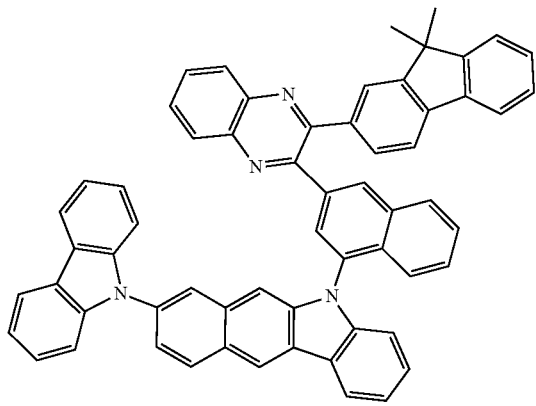
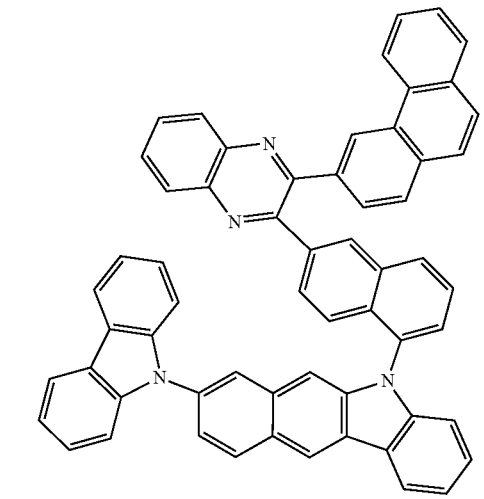
608
-continued
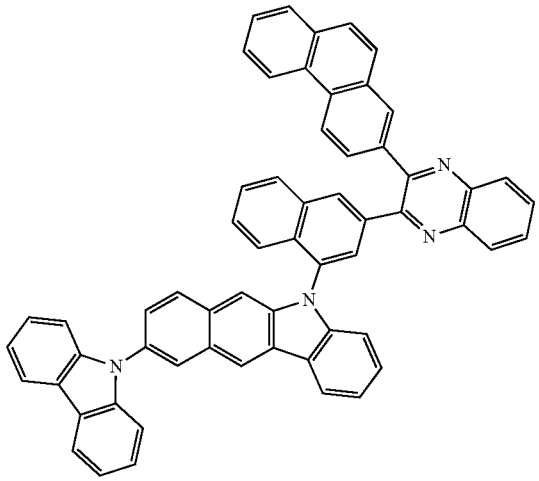
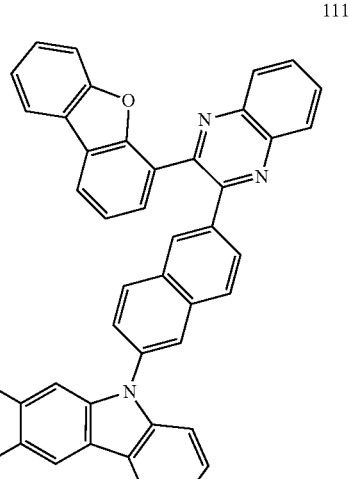
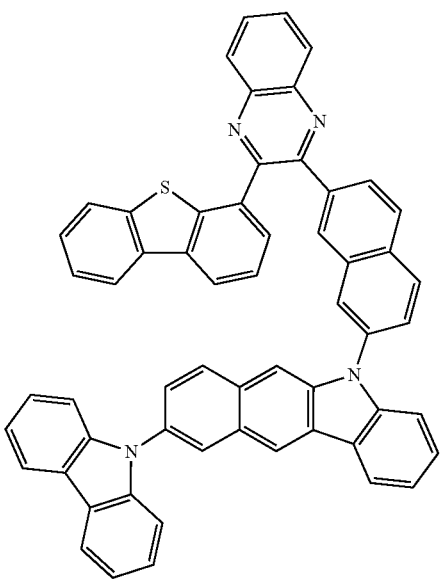

609
-continued
113
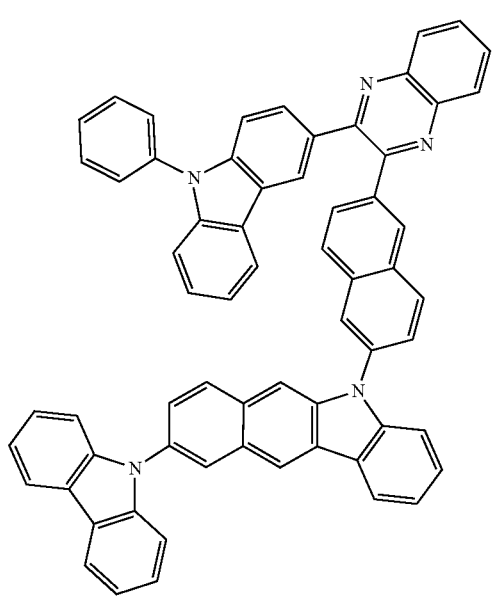
114
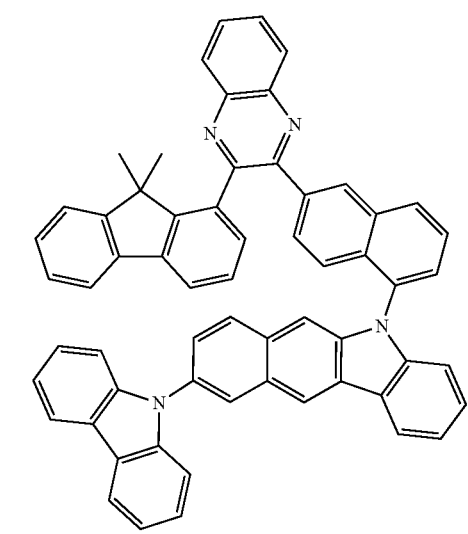
610
-continued
115
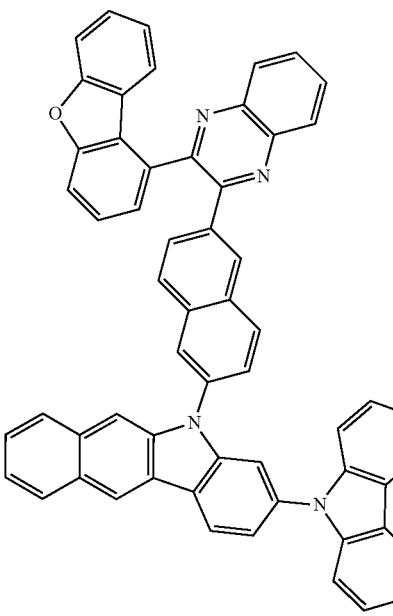
116
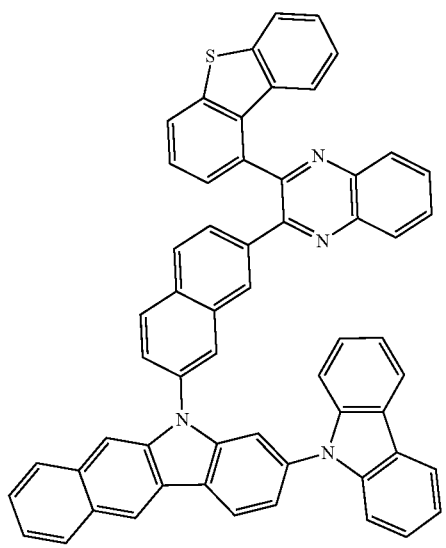

611
-continued
117
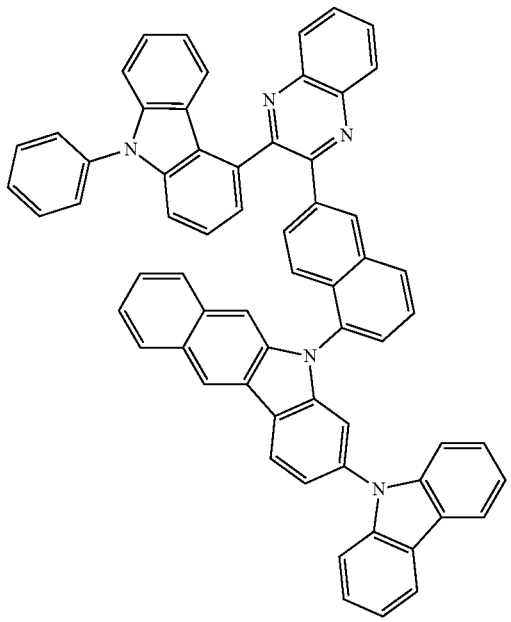
118
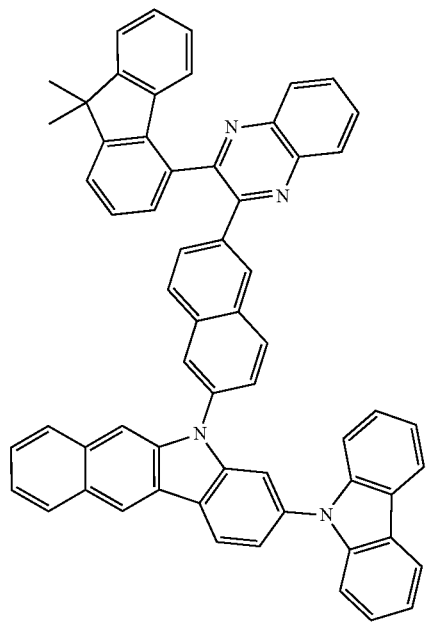
612
-continued
119
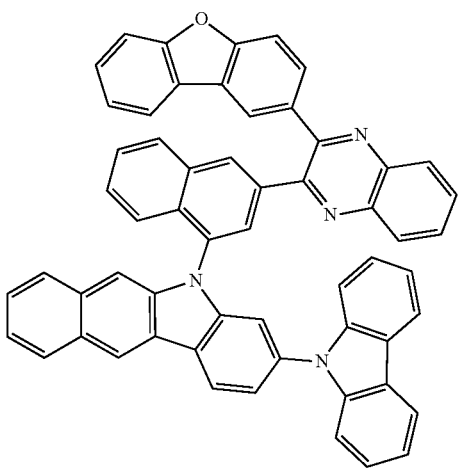
120
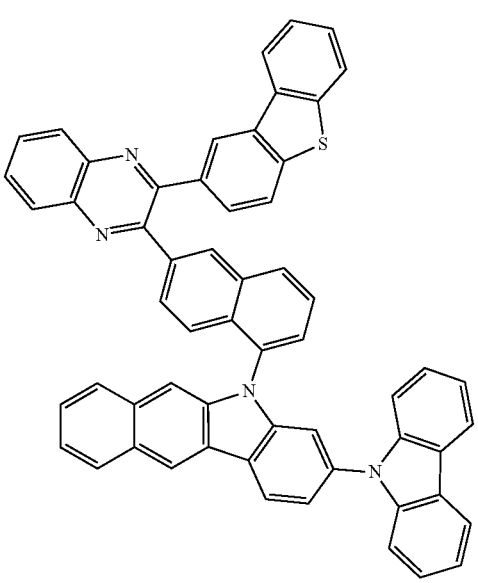
121
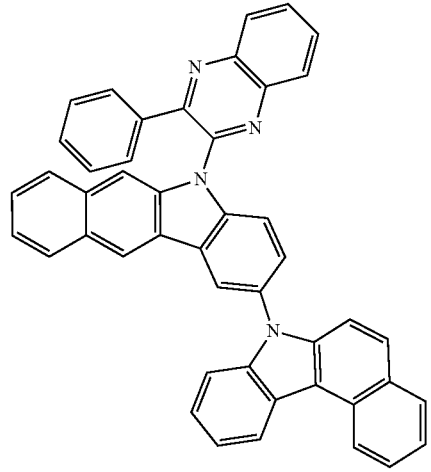

613
-continued
122
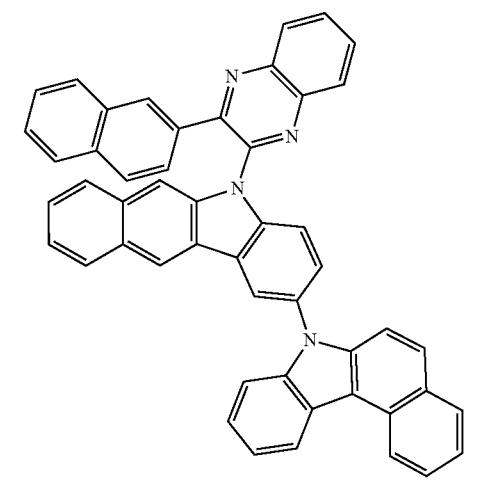
123
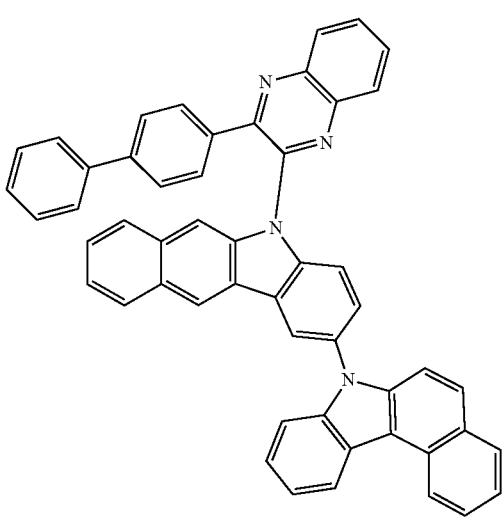
124
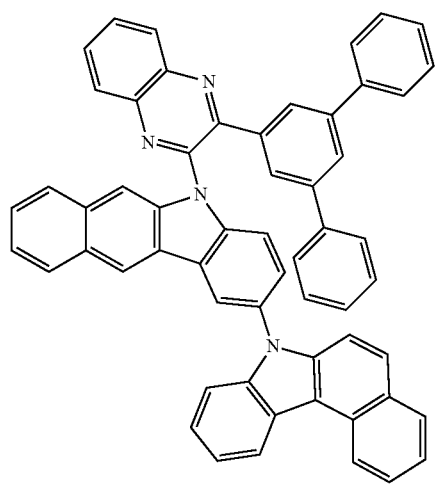
614
-continued
125
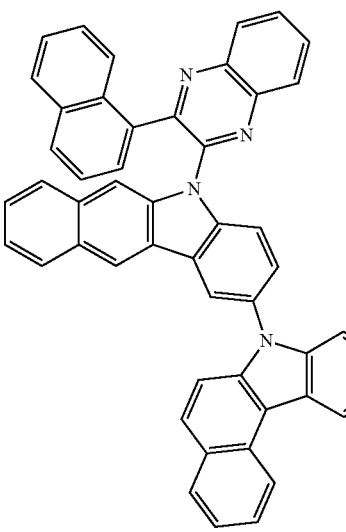
126
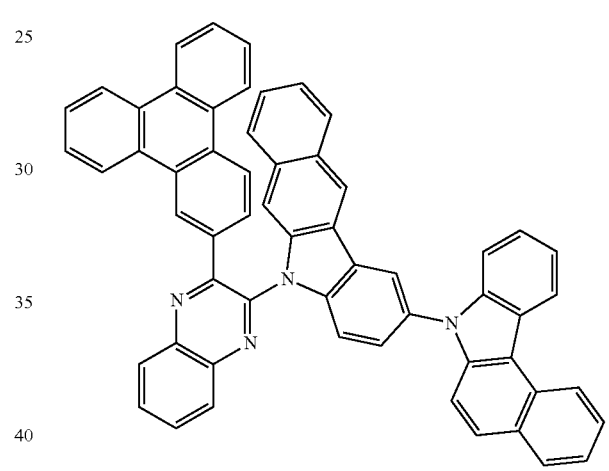
127
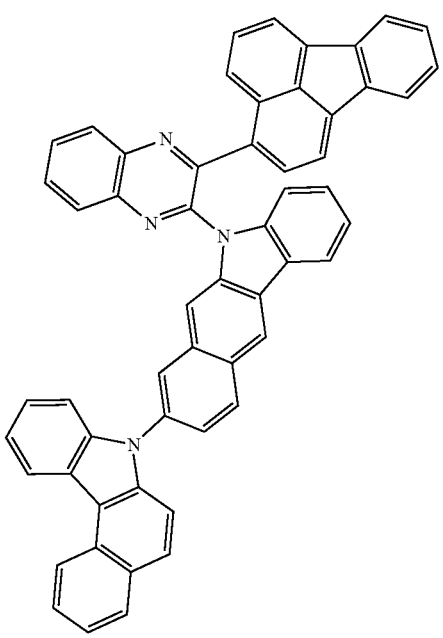

128
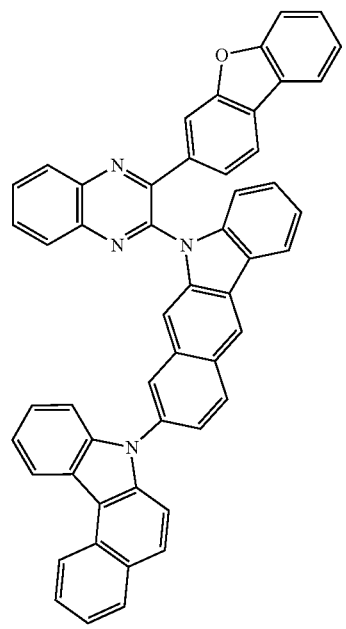
129
130
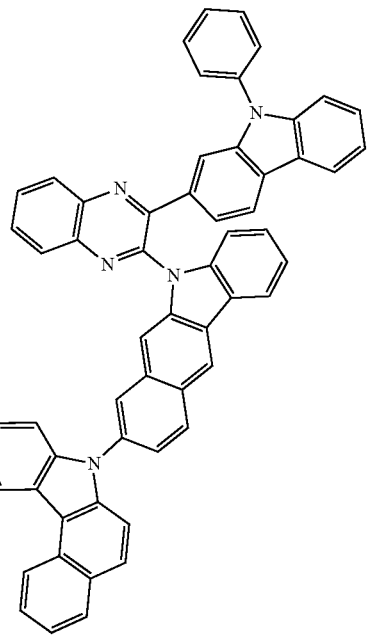
131

132
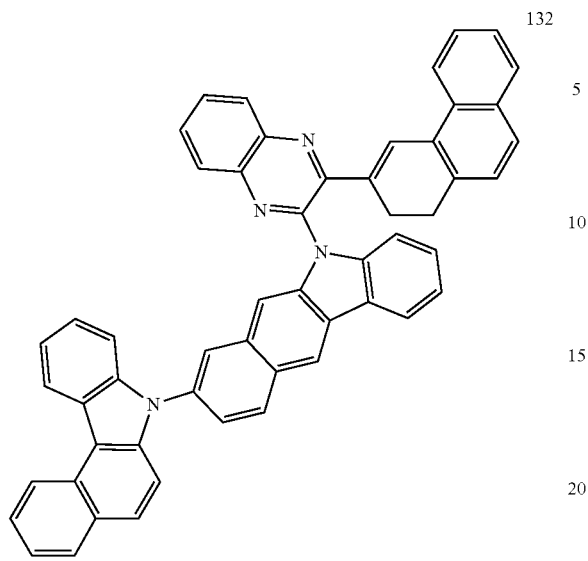
133
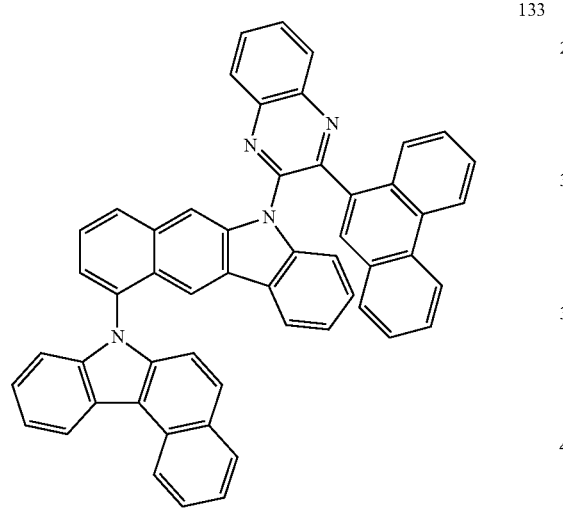
134
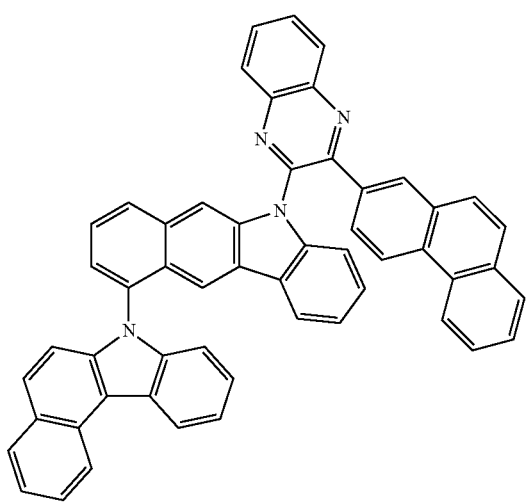
135
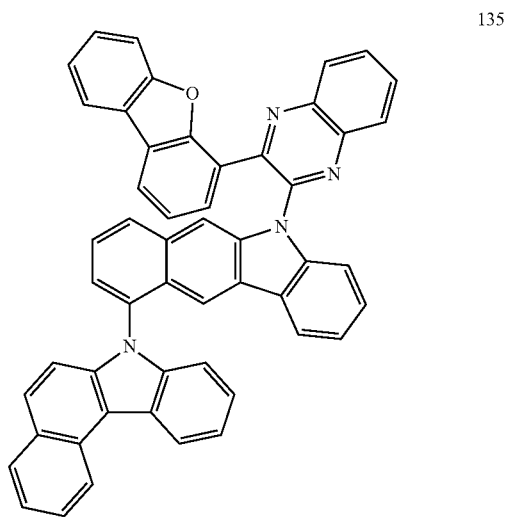
136
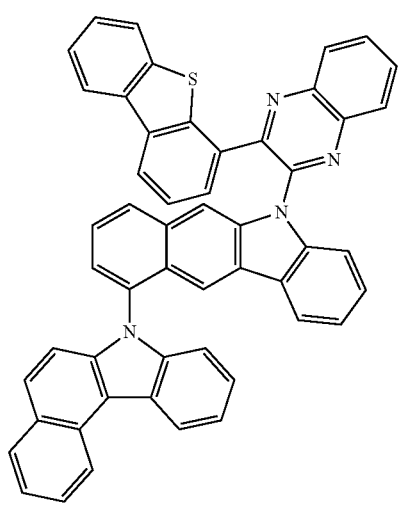
137
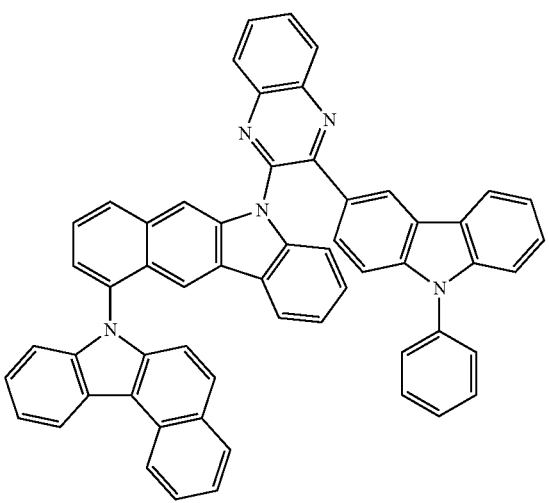

138
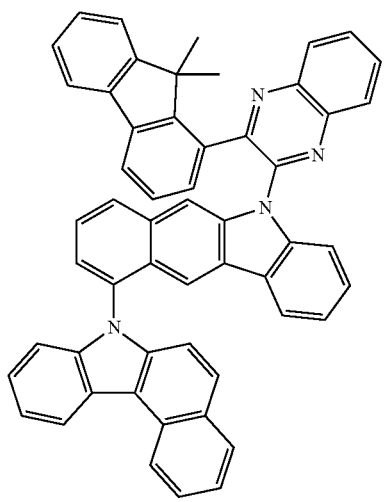
139
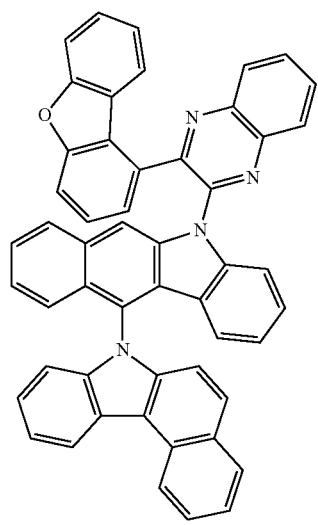
140
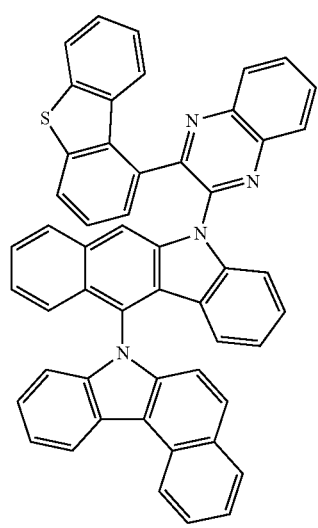
141
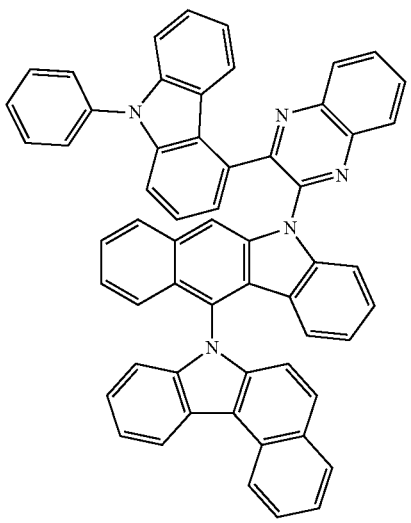
142
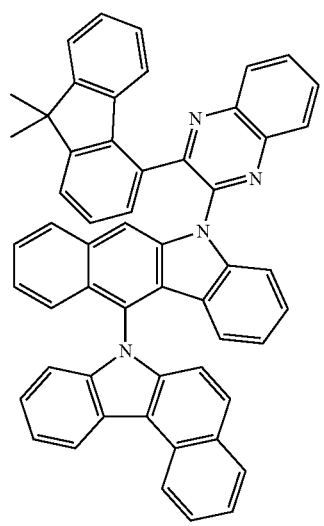
143
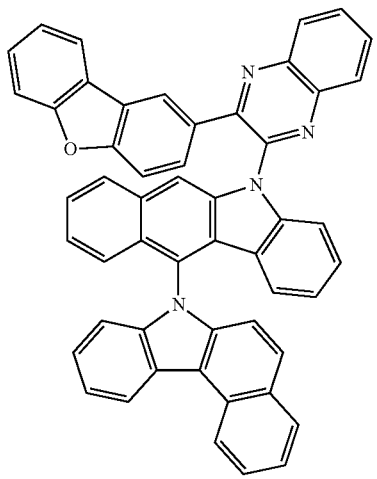

144
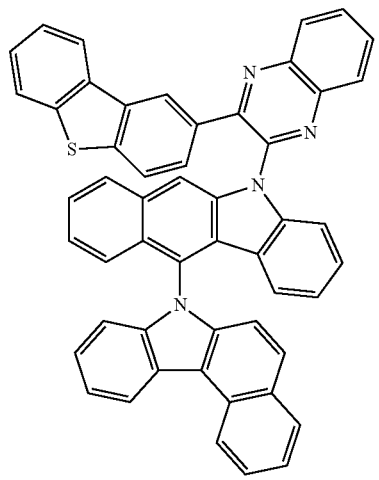
145
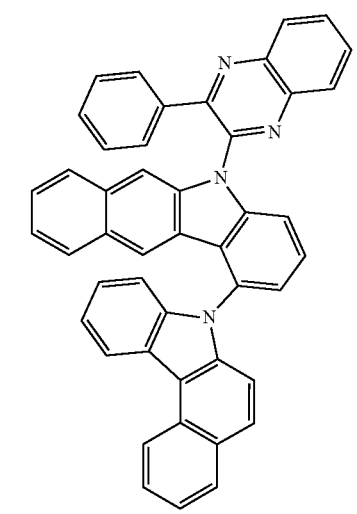
146
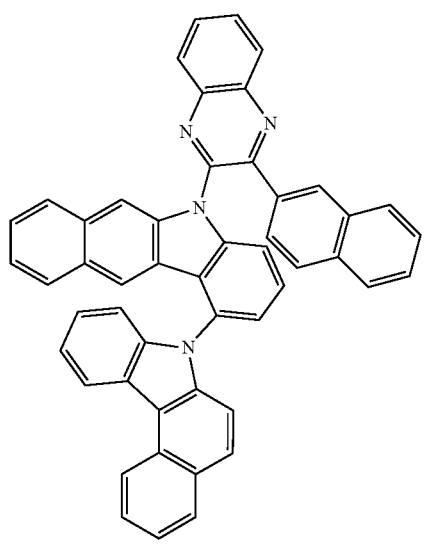
147
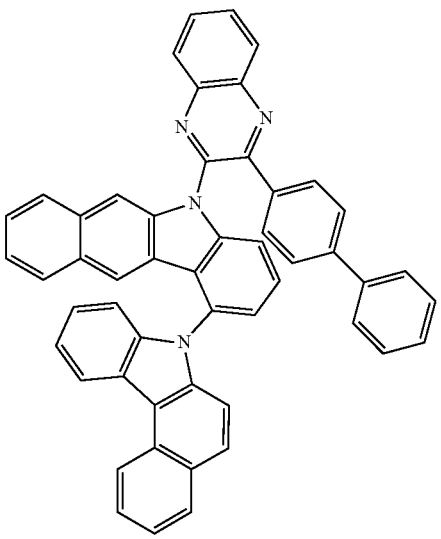
148
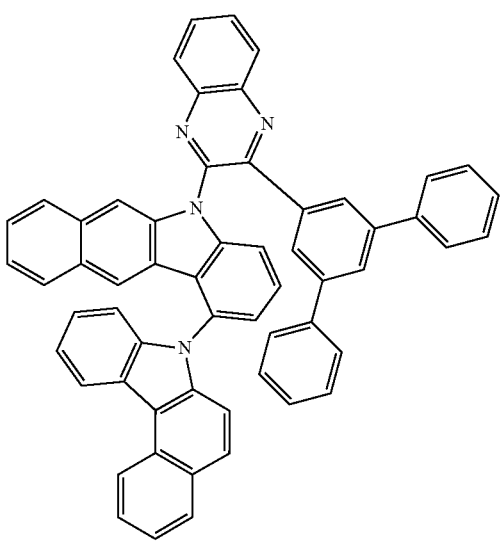
149
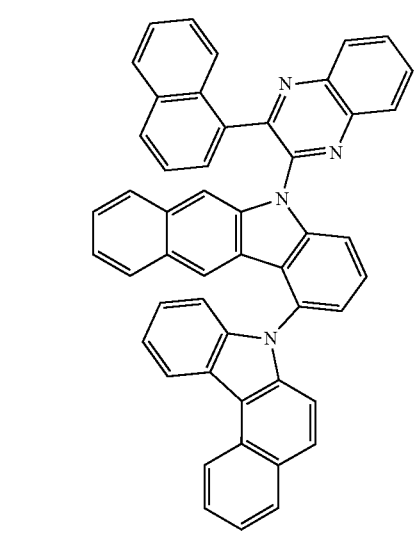

-continued
150
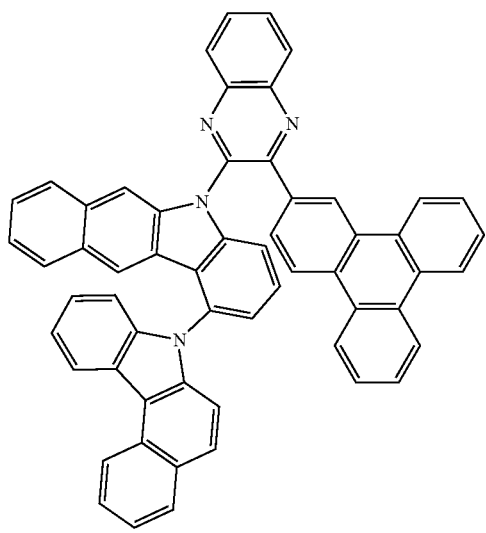
151
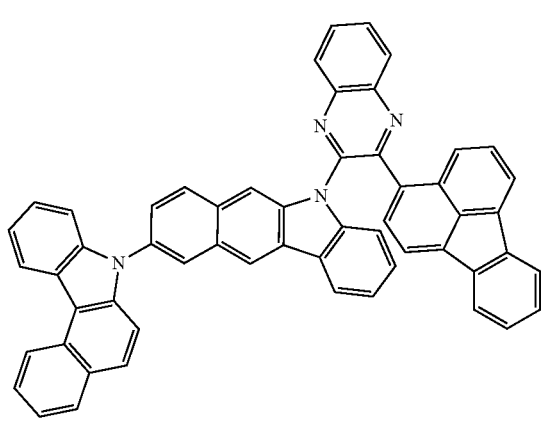
152
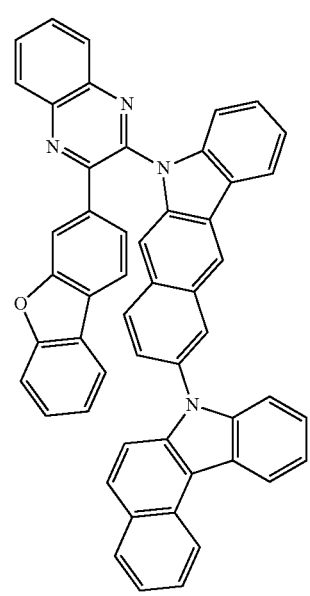
-continued
153
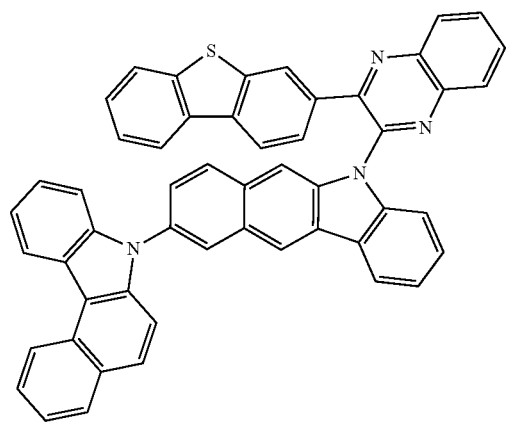
154
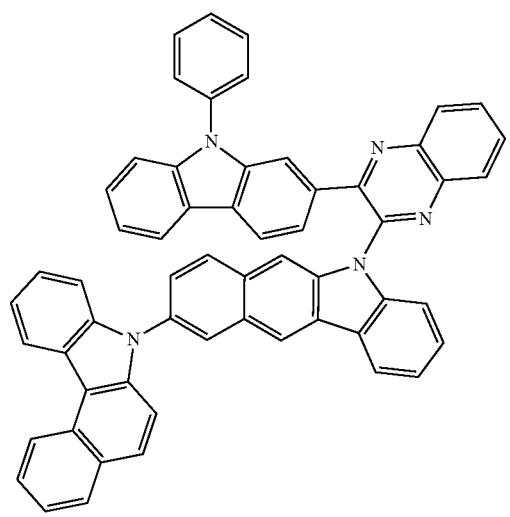
155
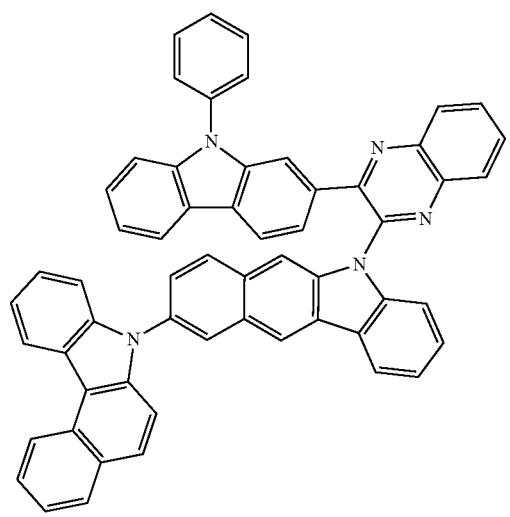

156
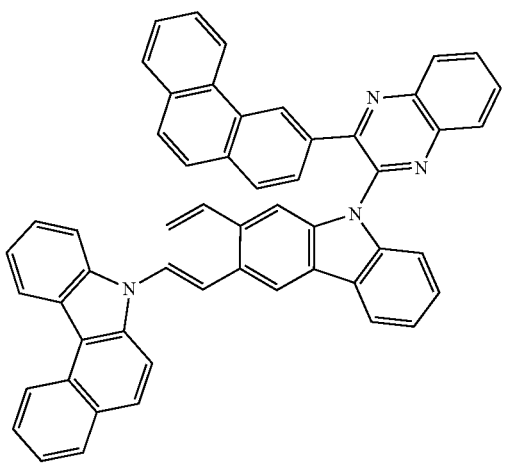
157
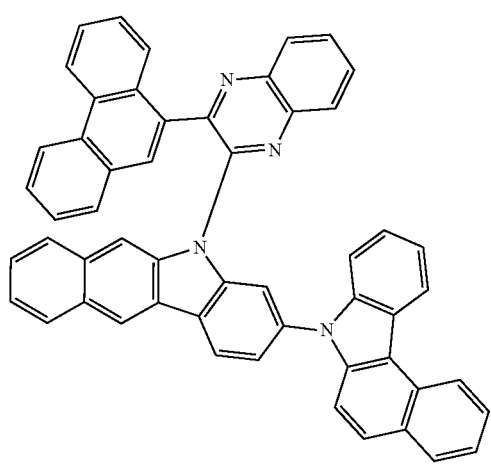
158
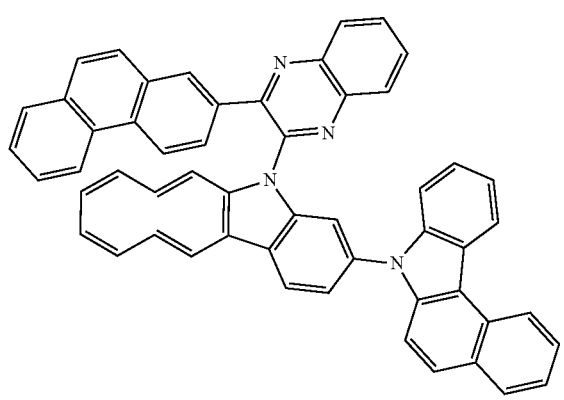
159
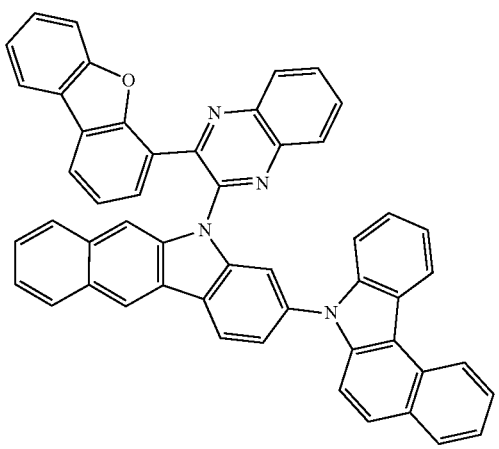
160
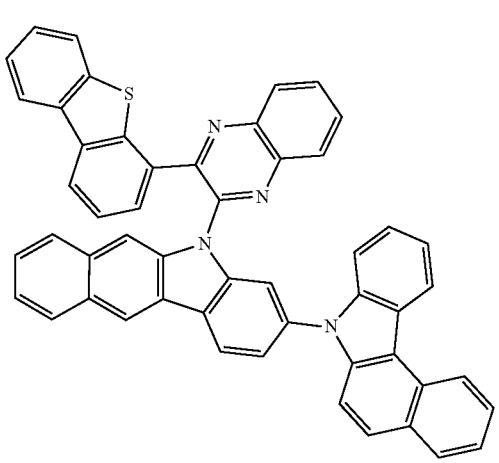
161
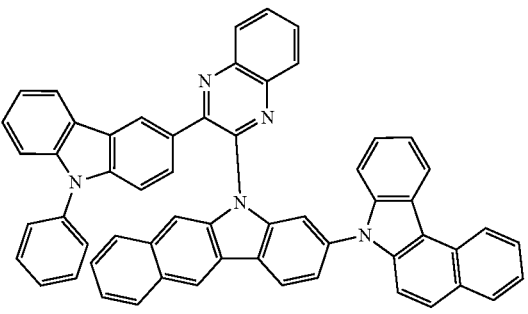

627
-continued
162
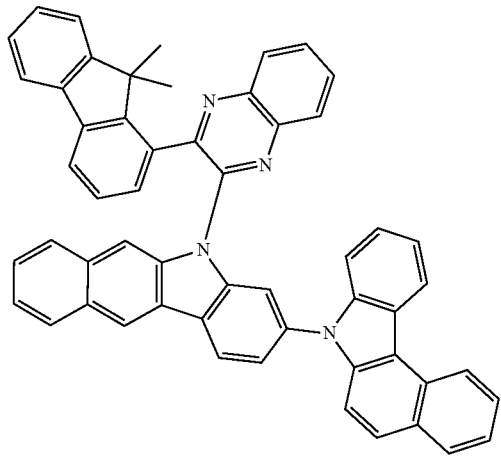
163
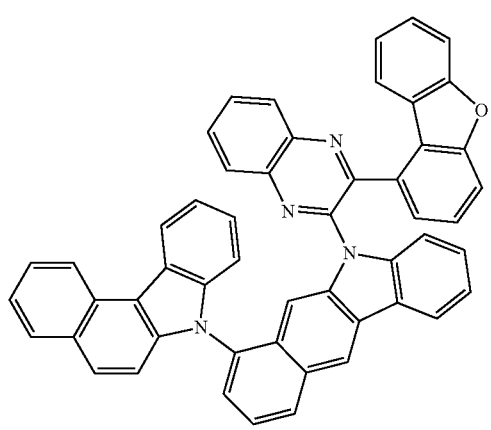
164
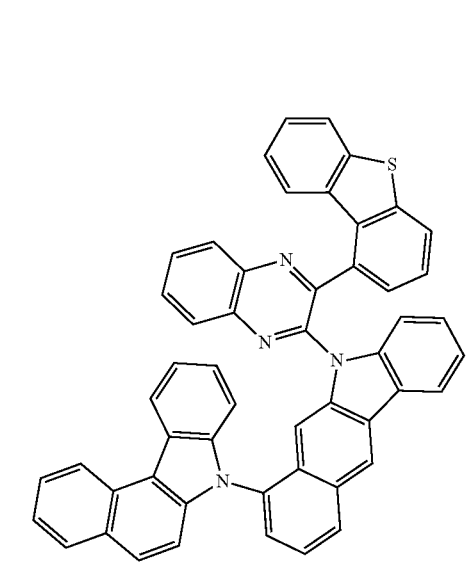
628
-continued
165
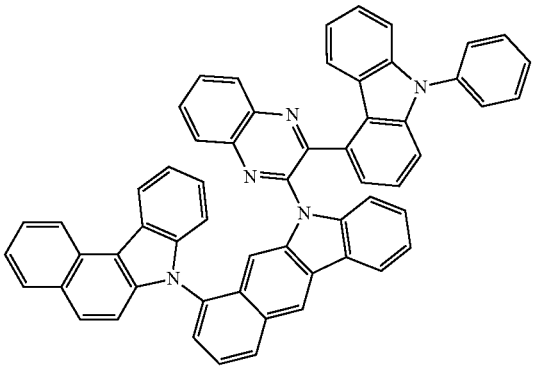
166
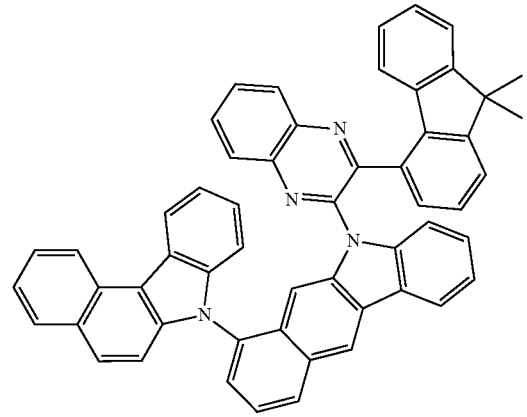
167
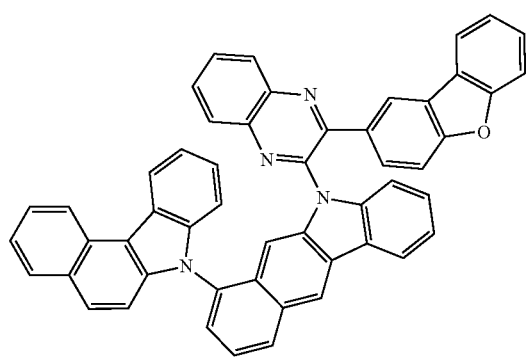
168
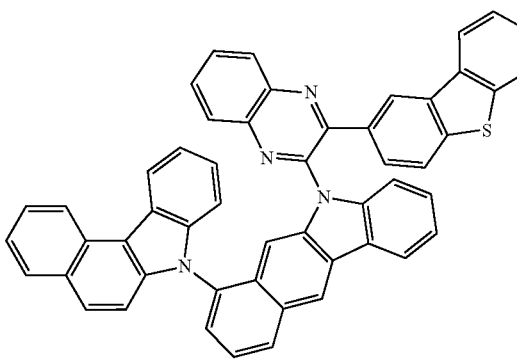

629
-continued
630
-continued
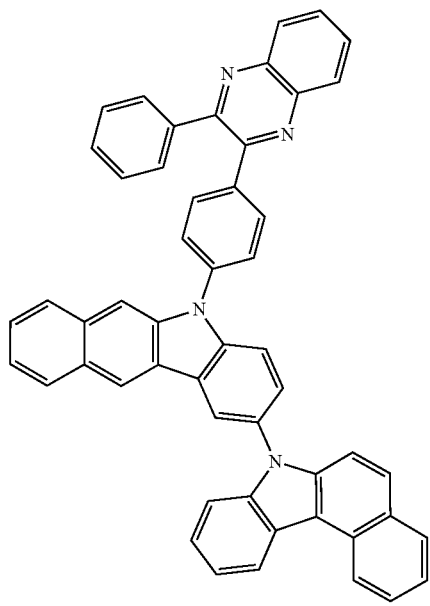
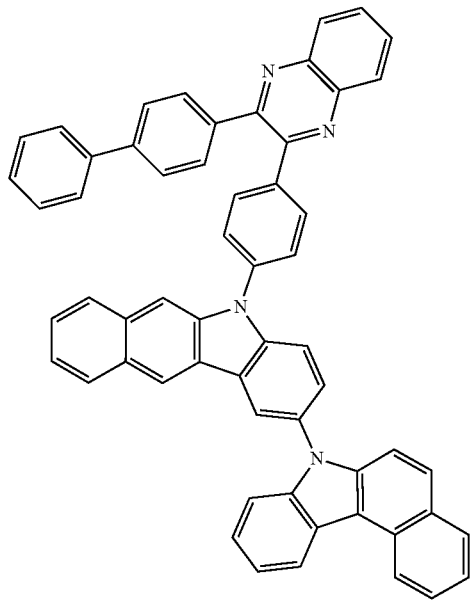

173
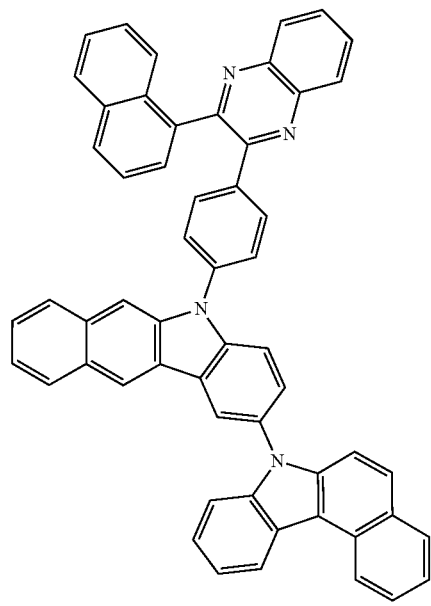
174
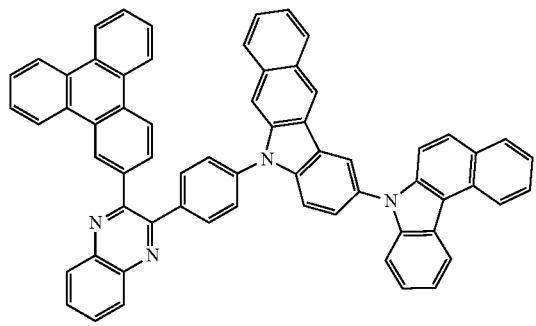
175
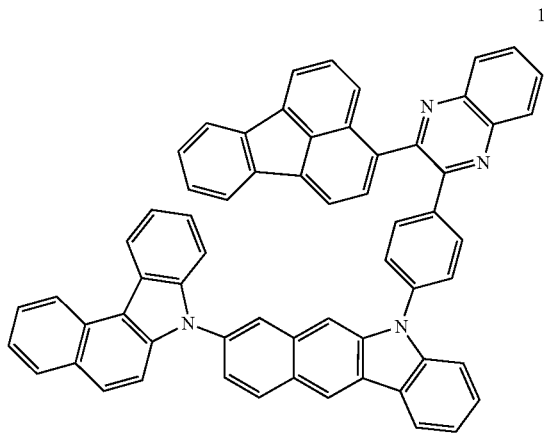
176
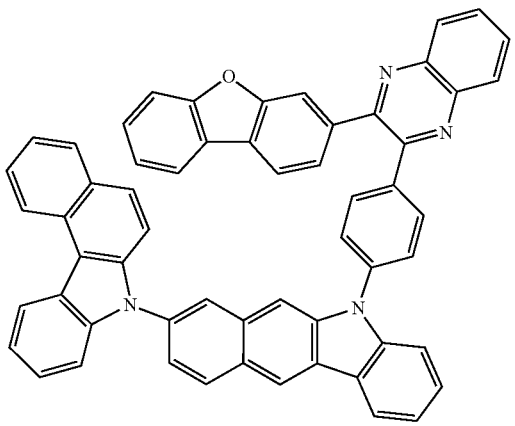
177
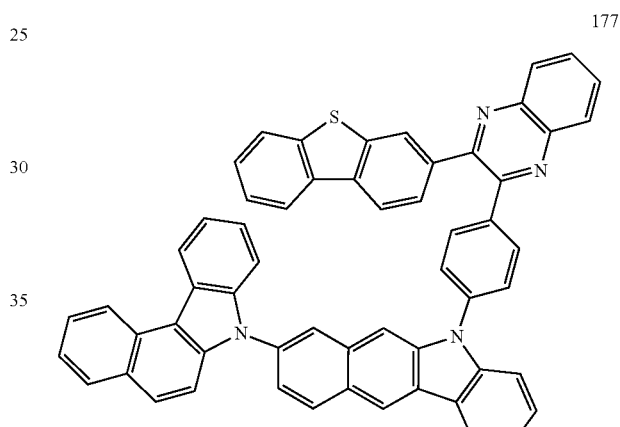
178
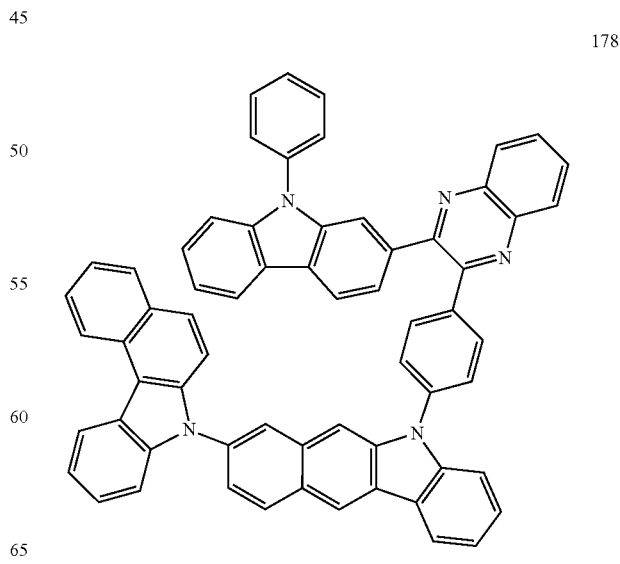

633
-continued
179
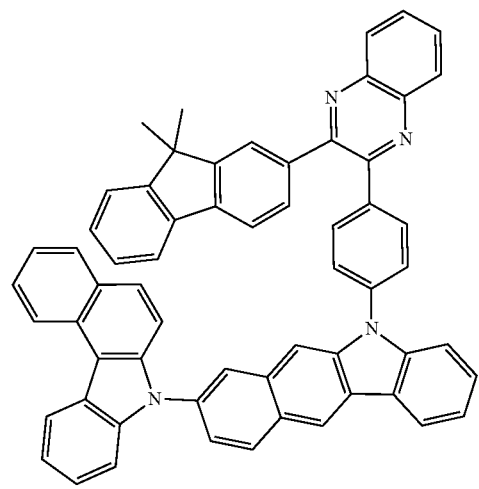
180
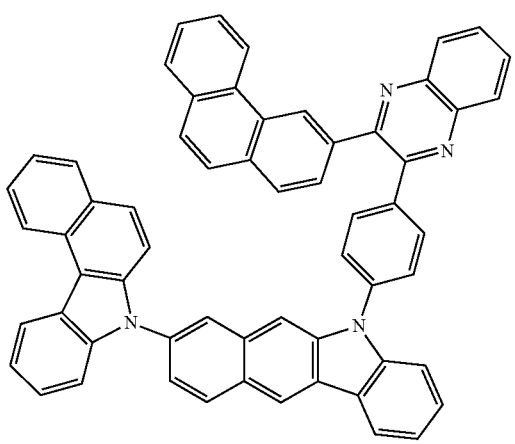
181
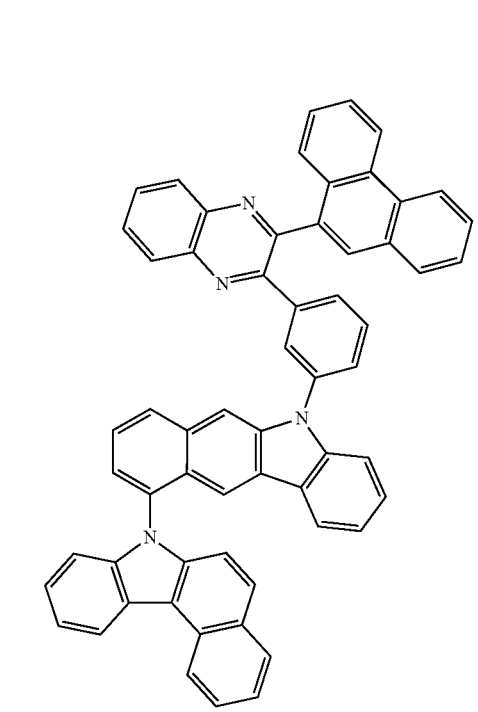
634
-continued
182
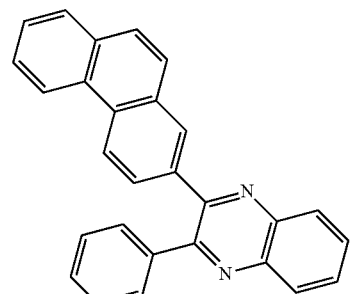
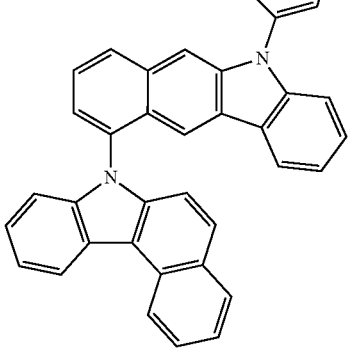
183
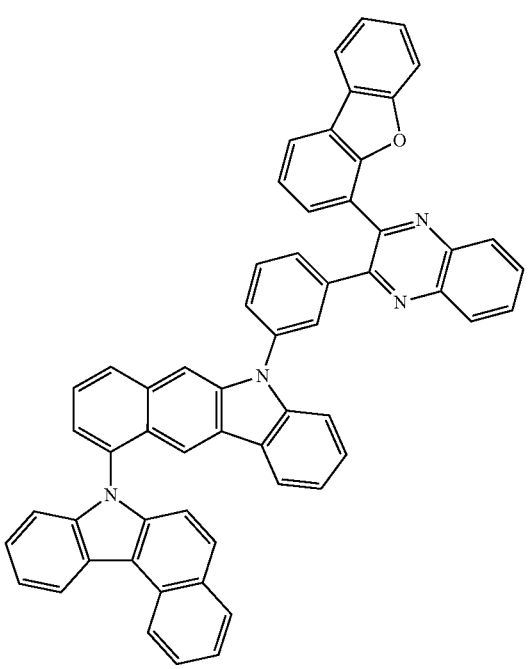

-continued
184
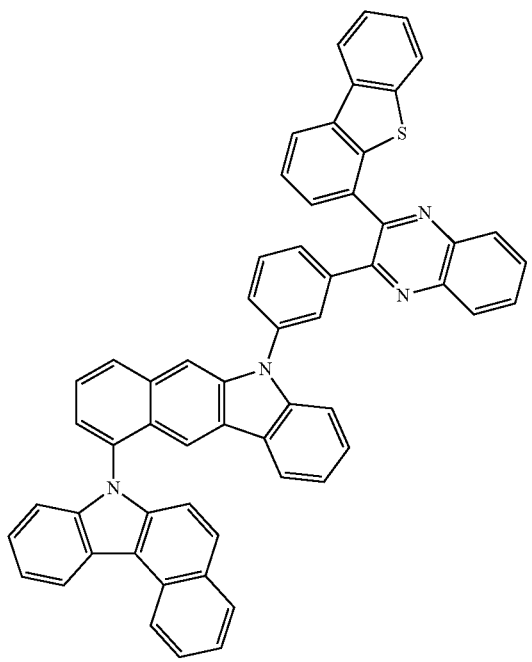
185
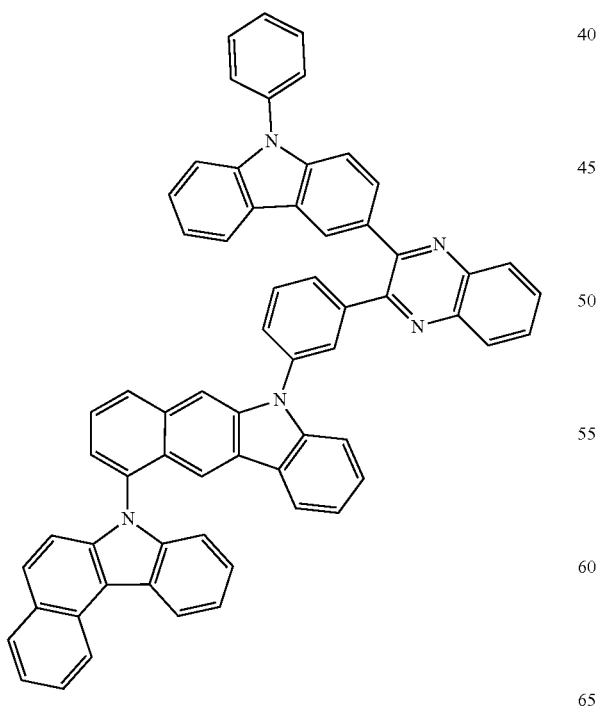
-continued
186
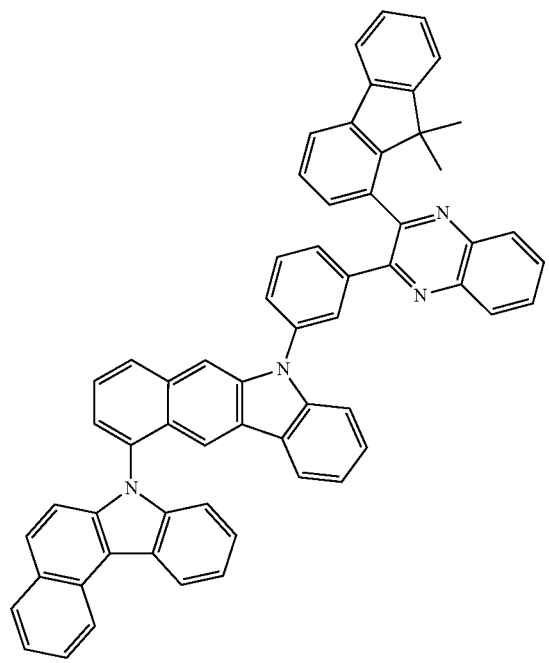
187
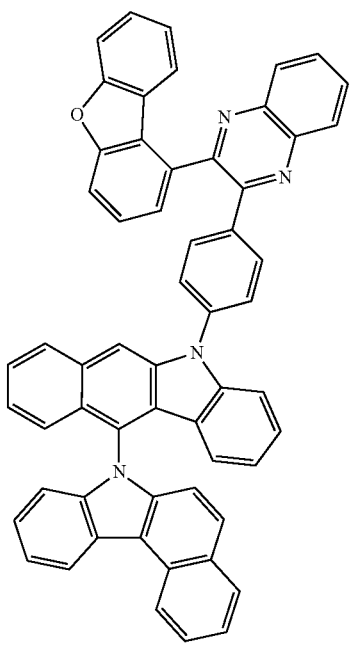

188
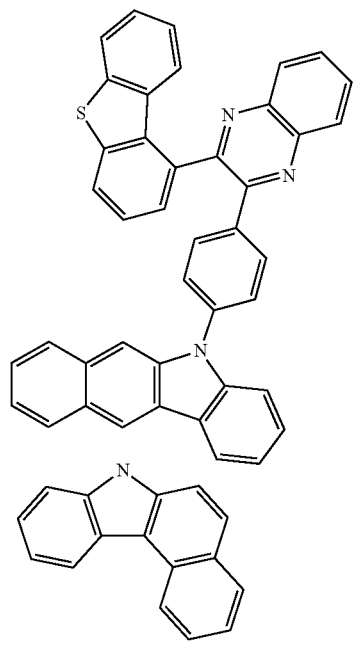
189
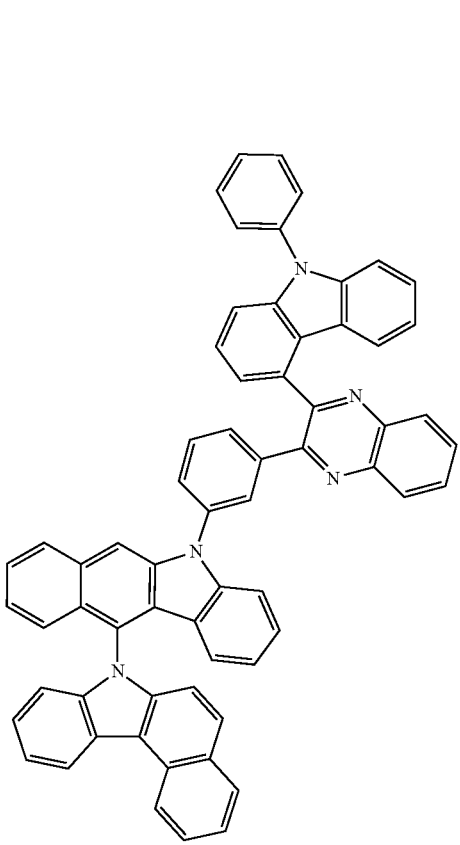
190
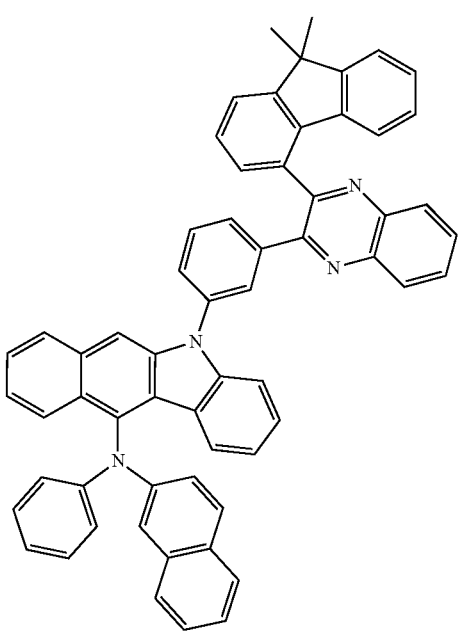
191
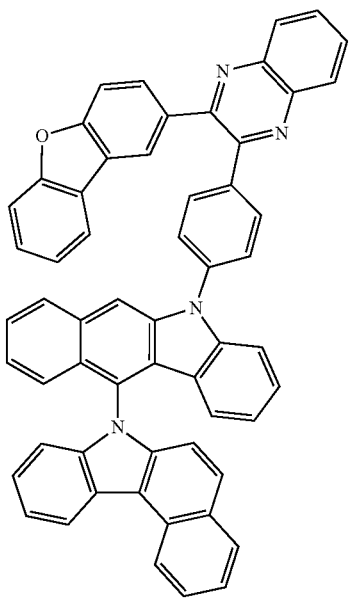

639
-continued
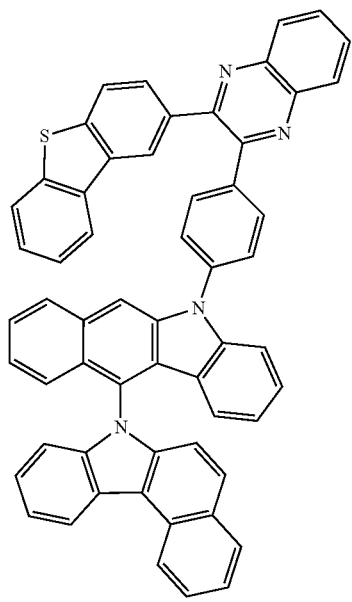
192
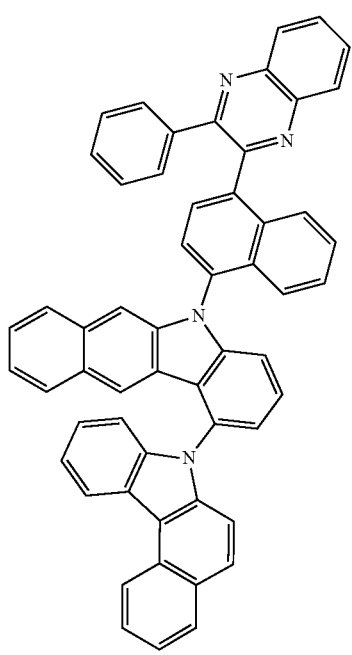
193
640
-continued
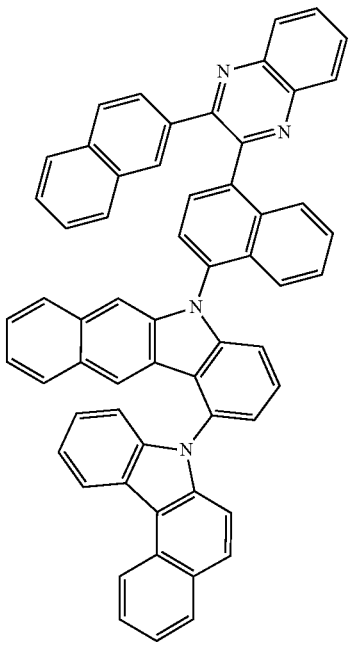
194
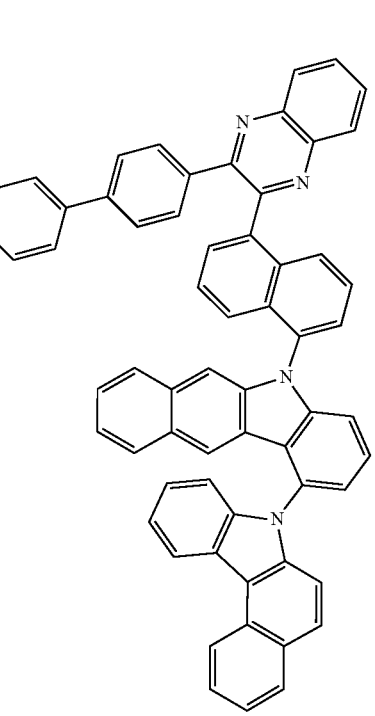
195

196
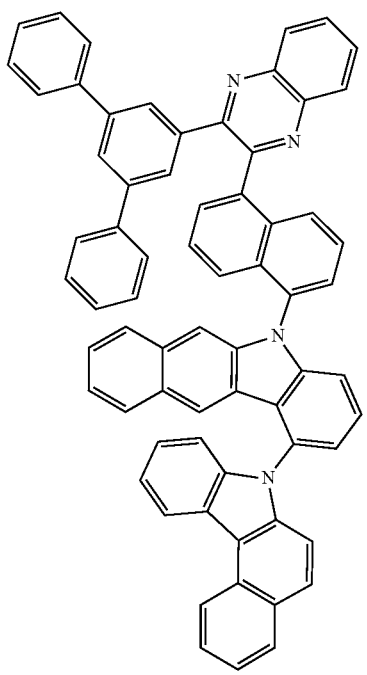
198
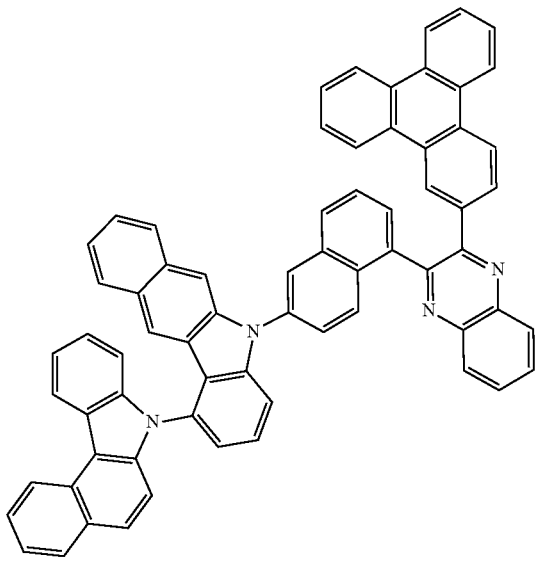
197
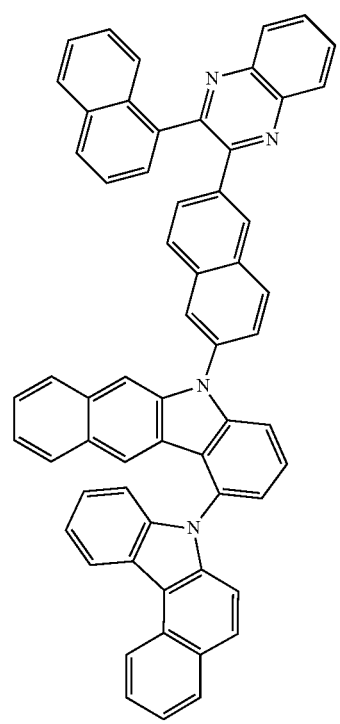
199
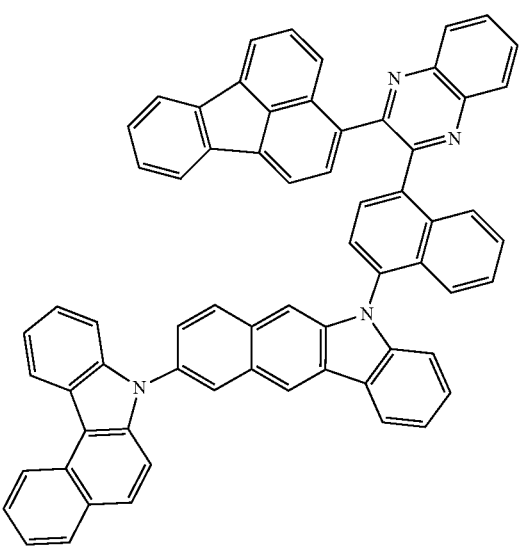

200
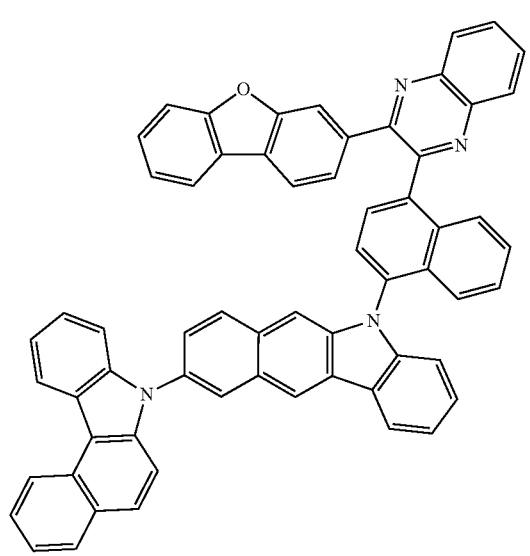
201
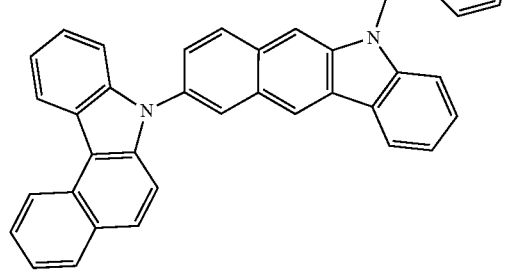
202
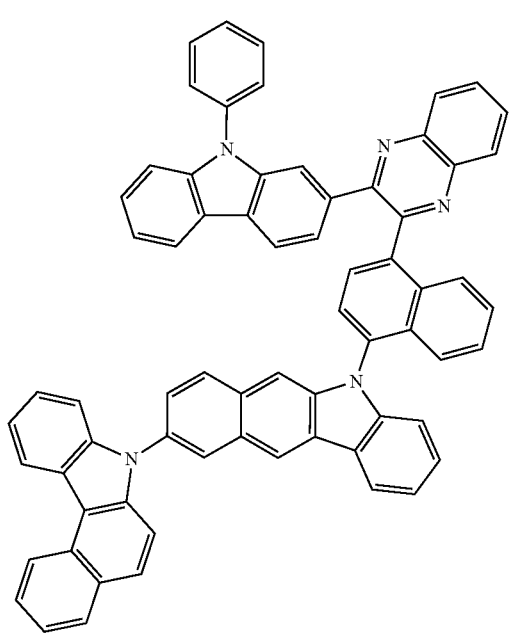
203
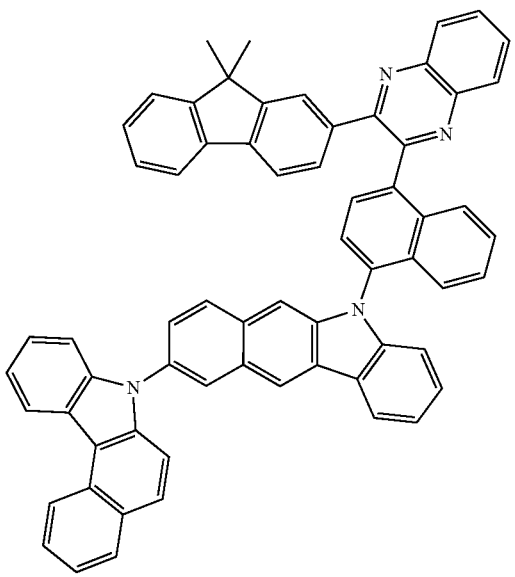

204
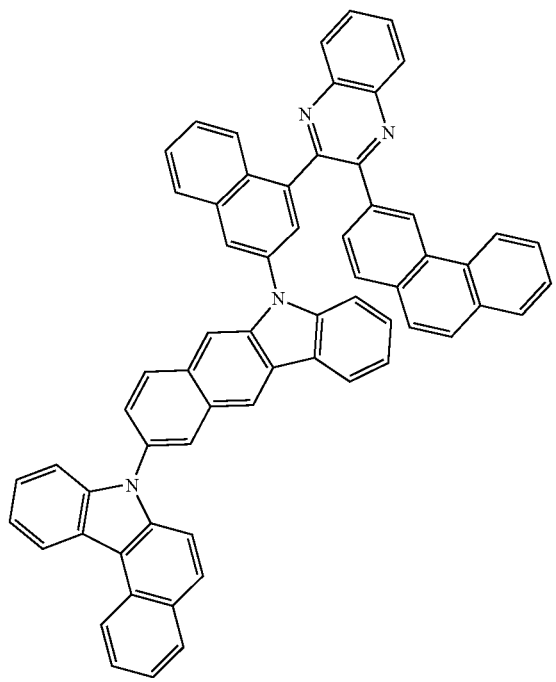
205
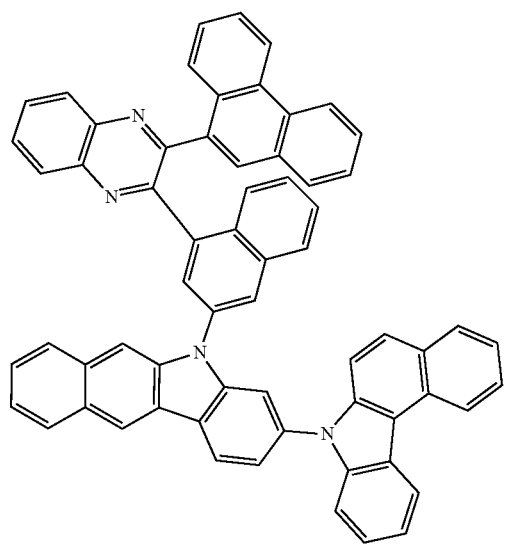
206
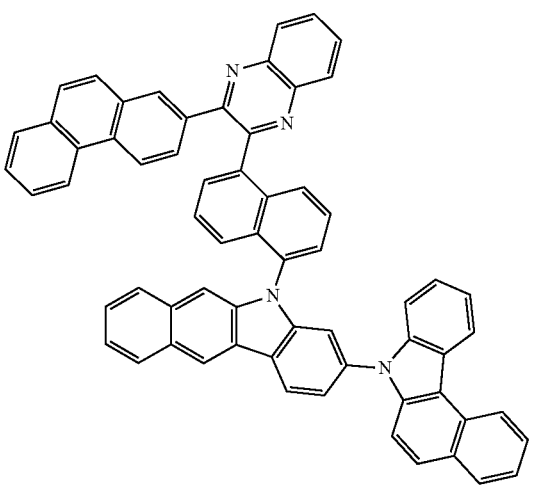
207
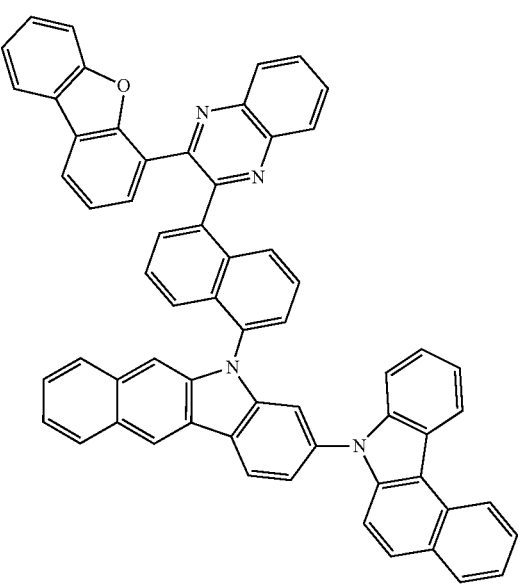

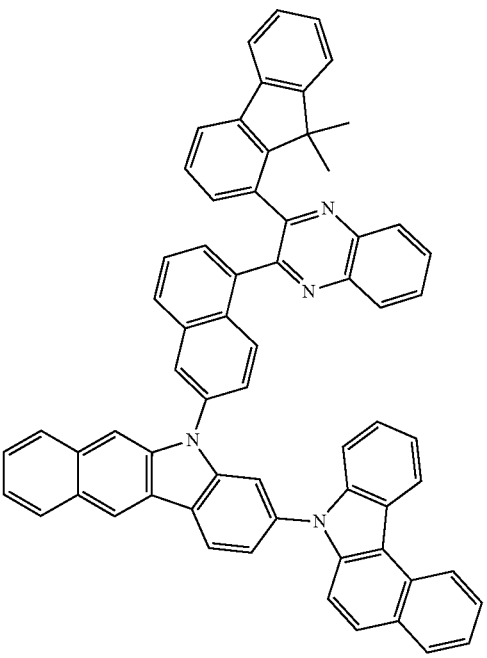
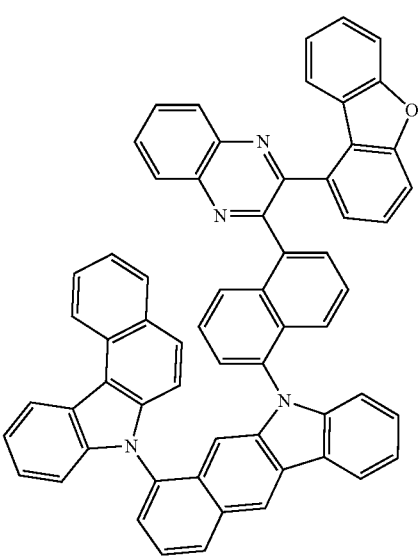

649
-continued
650
-continued
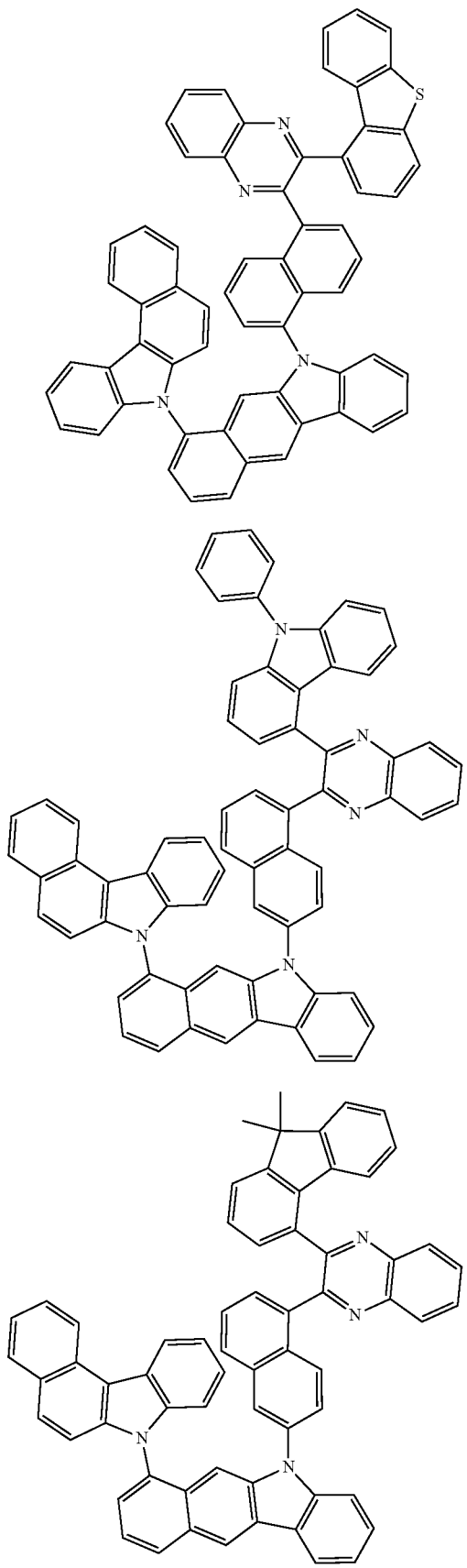
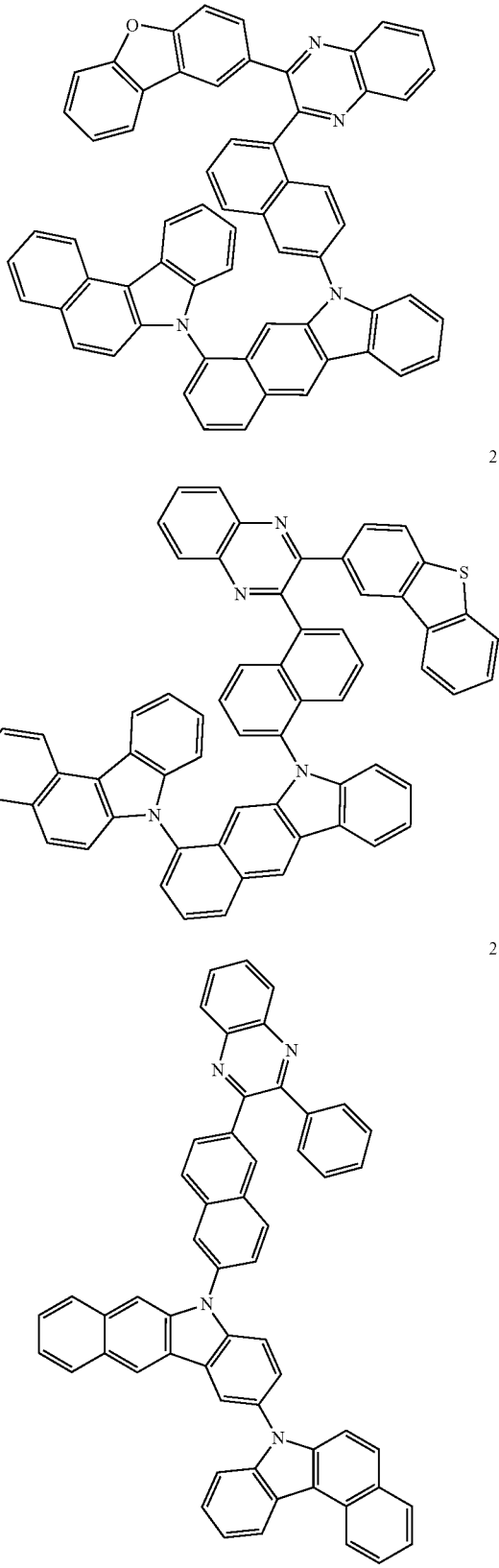

651
-continued
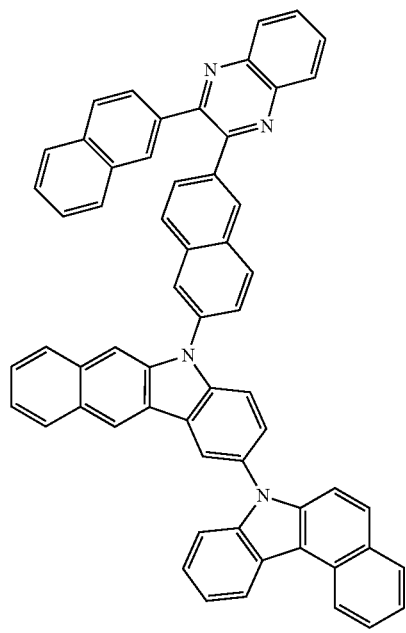
218
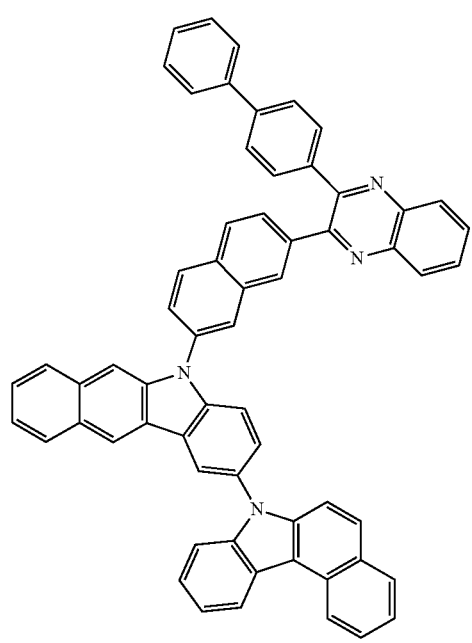
219
652
-continued
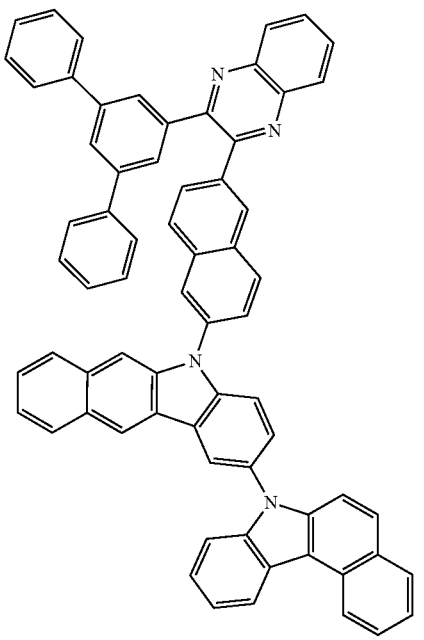
220
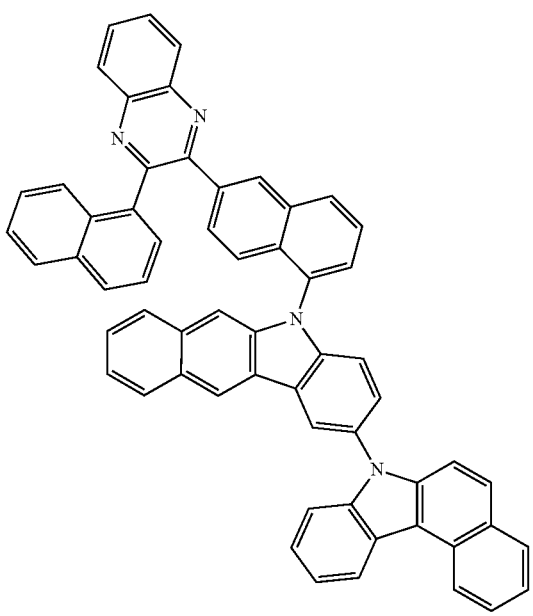
221

653
-continued
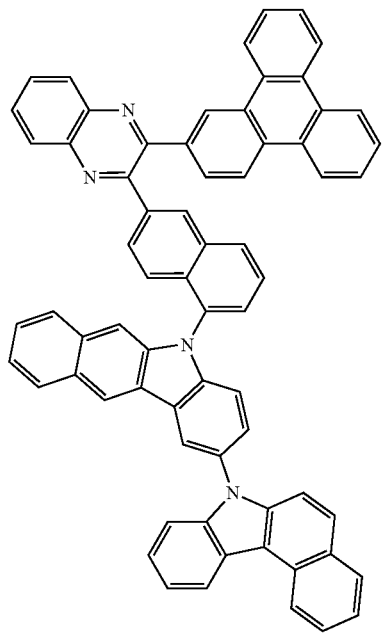
222
654
-continued
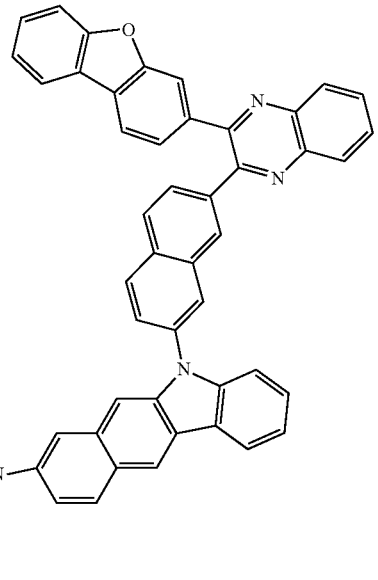
224
223
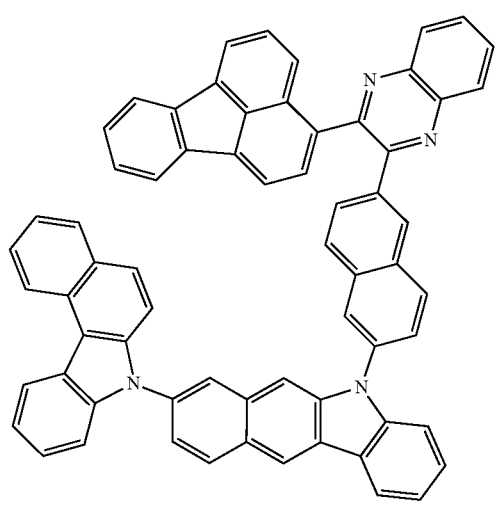
225
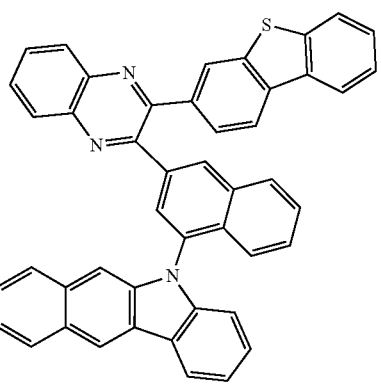

-continued
226
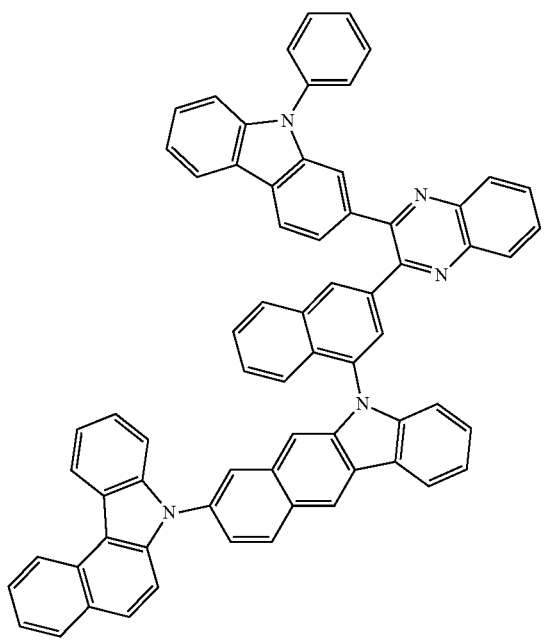
227
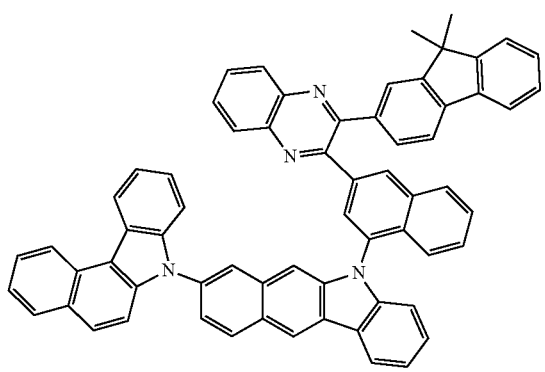
228
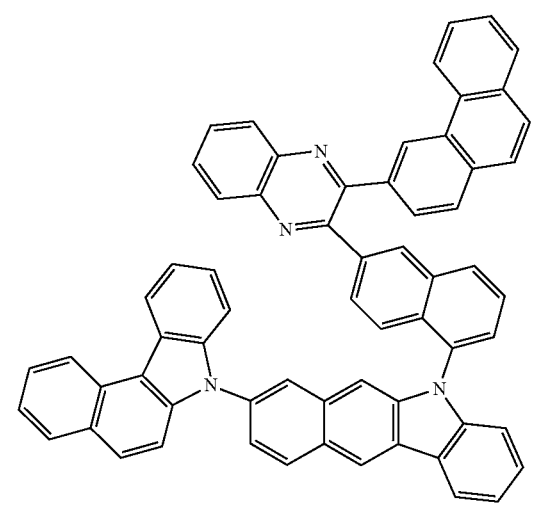
-continued
229
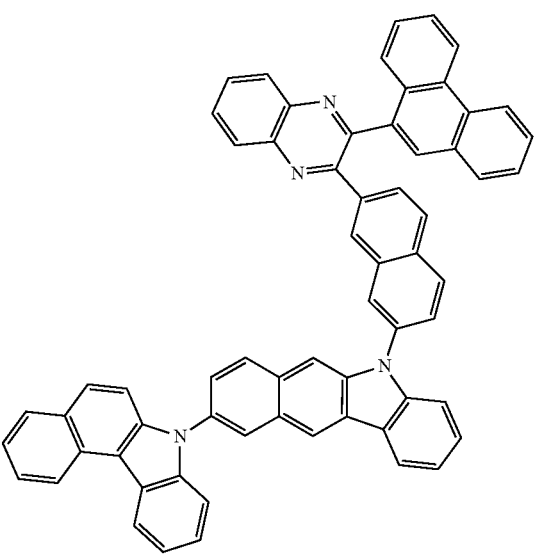
230
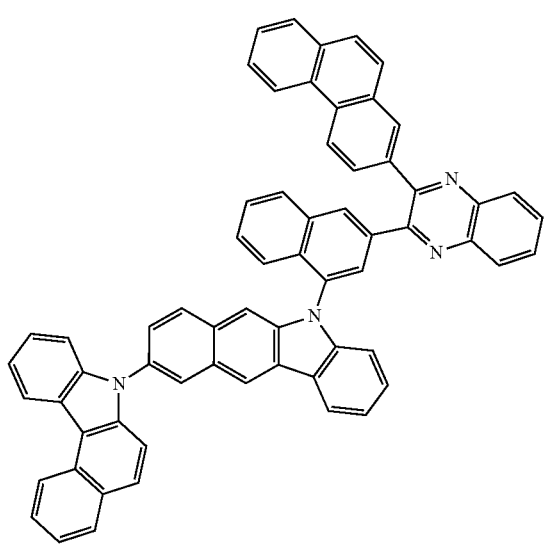

231
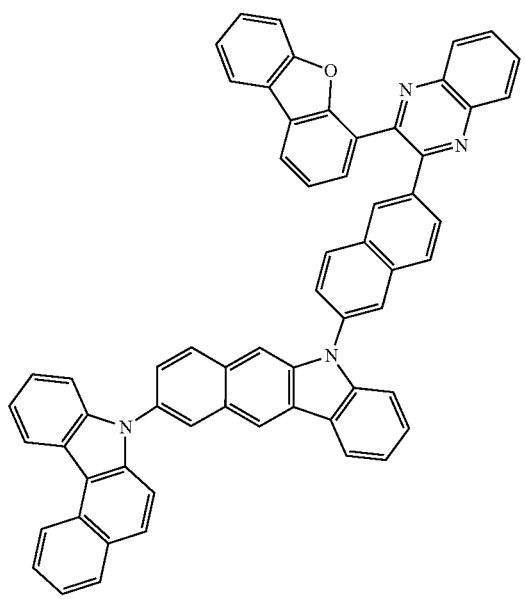
233
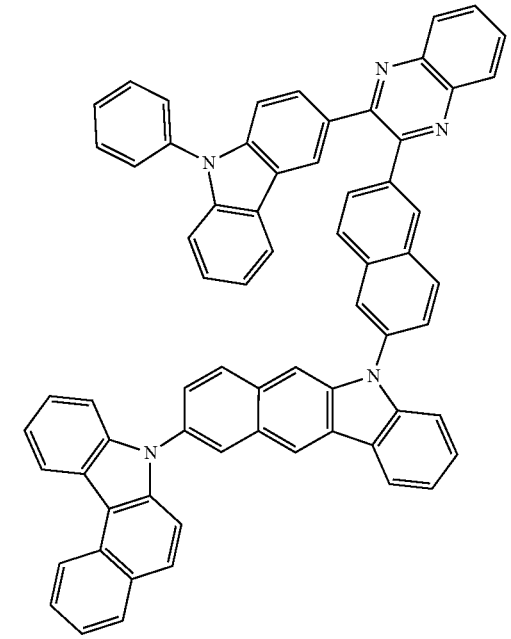
232
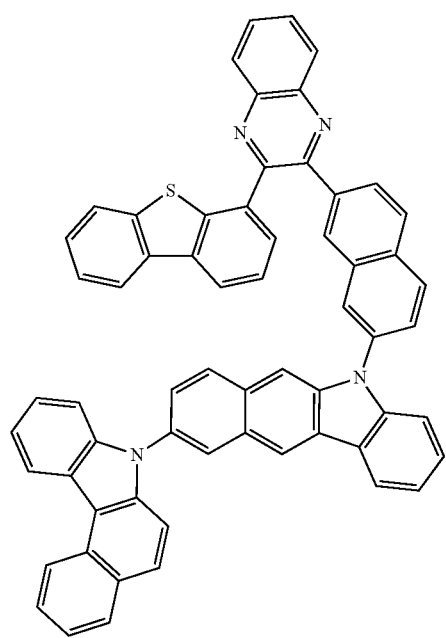
234
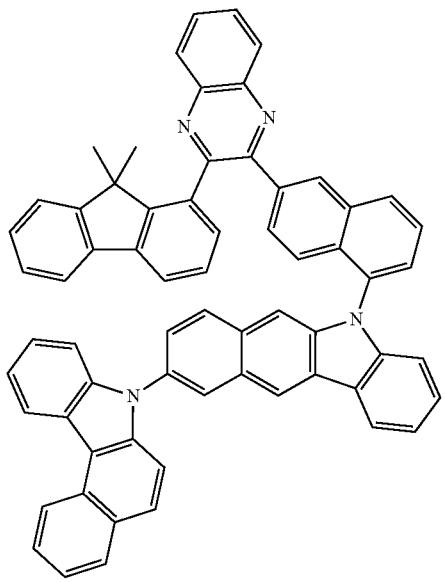

235
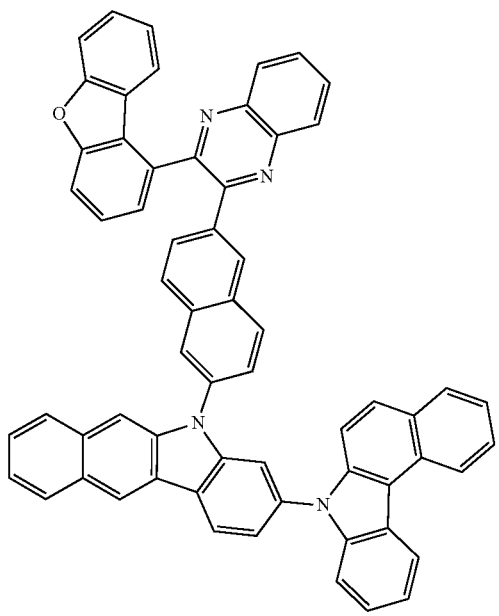
236
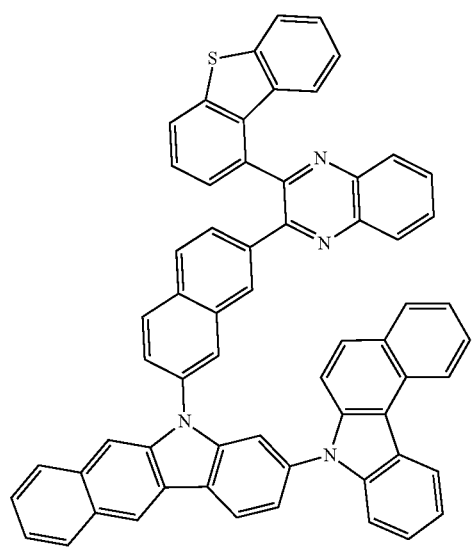
237
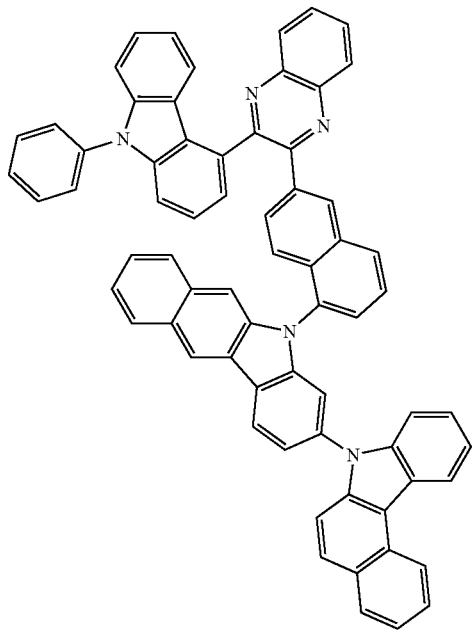
238
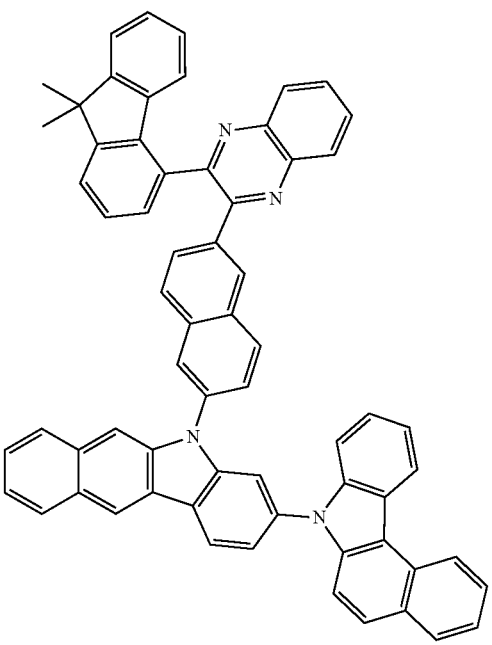

661
-continued
239
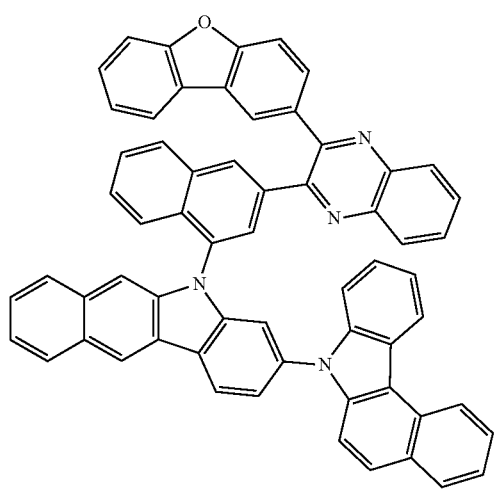
240
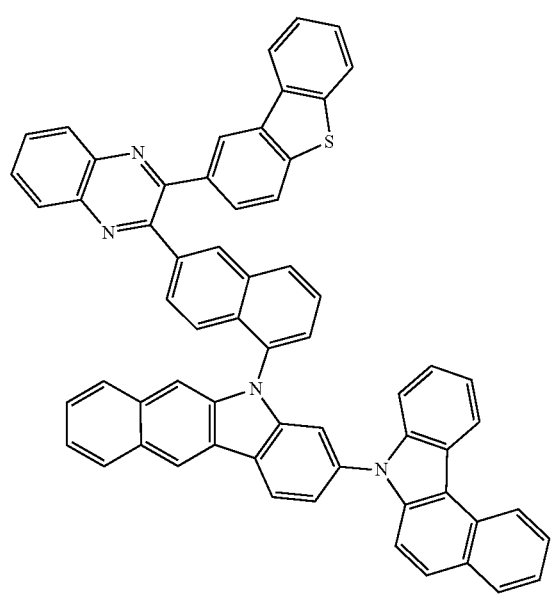
241
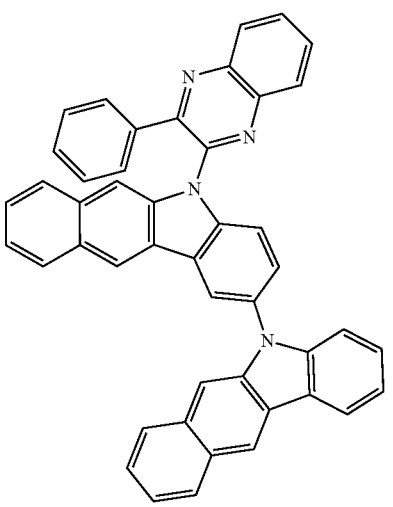
662
-continued
242
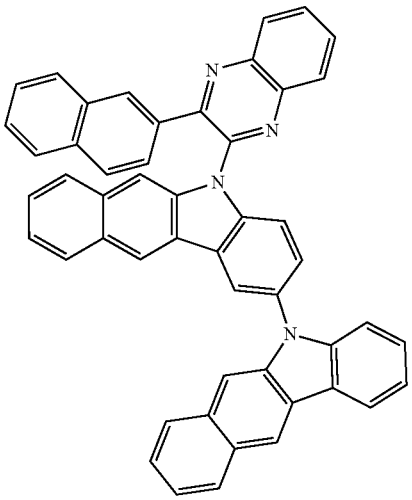
243
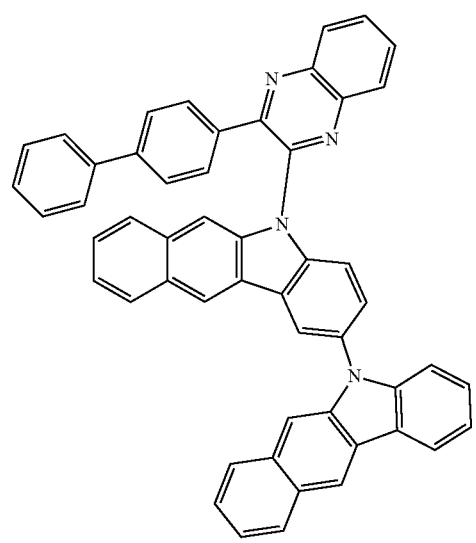
244
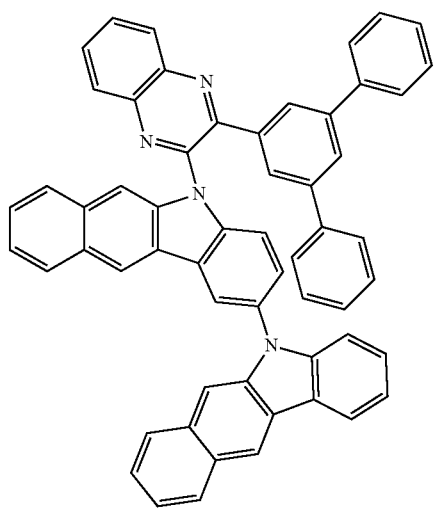

663
-continued
245
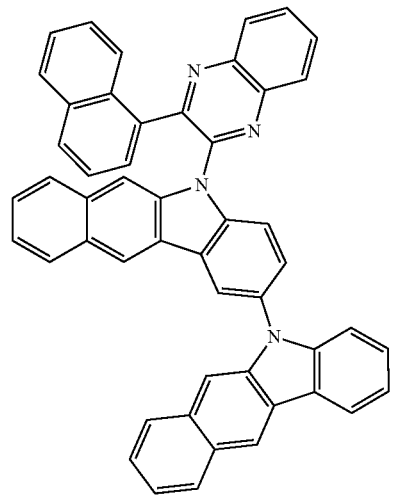
246
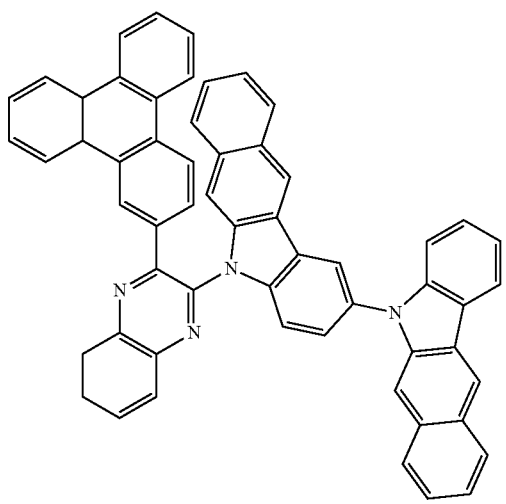
247
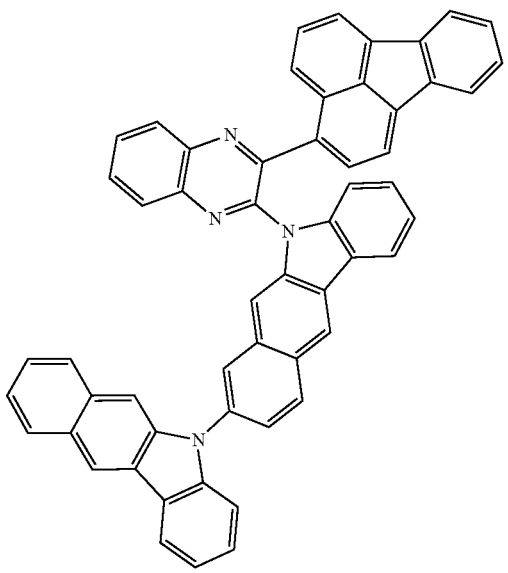
664
-continued
248
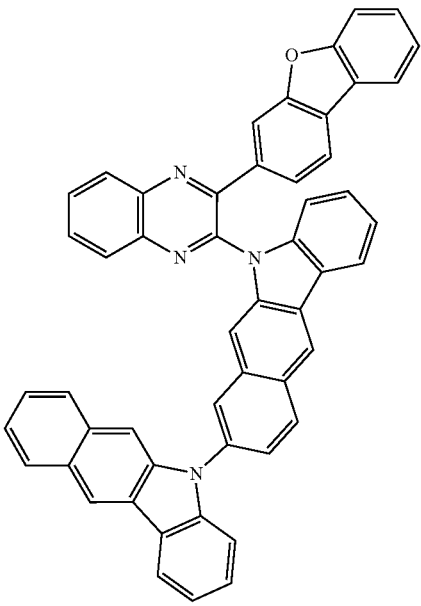
249
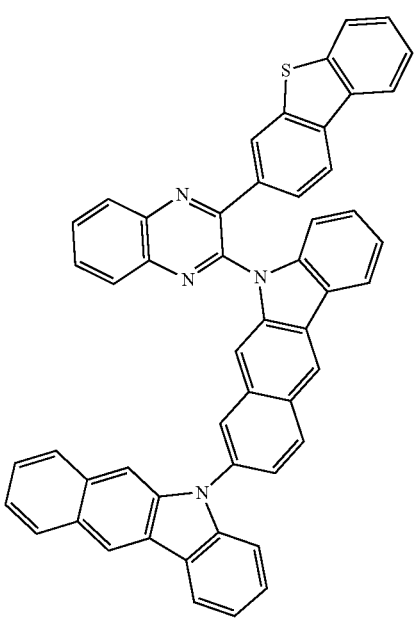

250
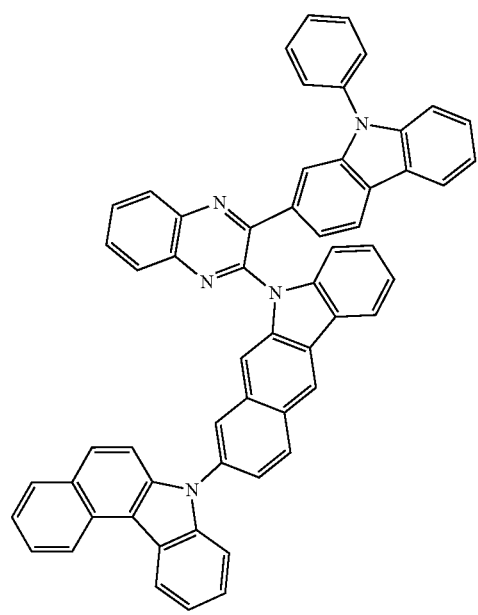
251
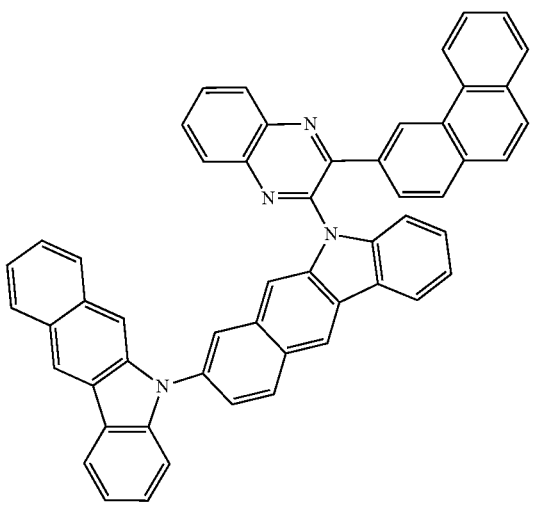
252
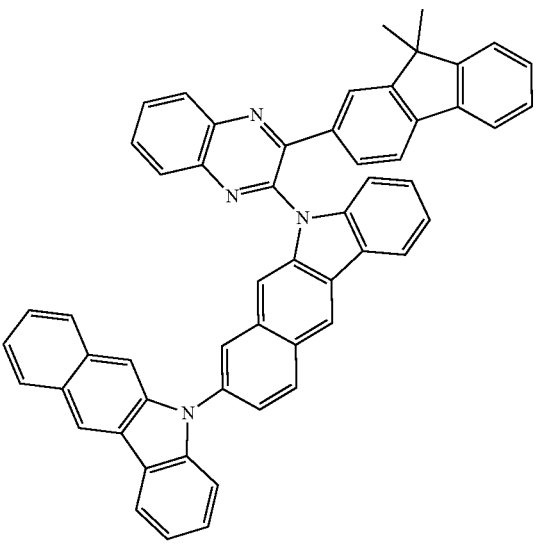
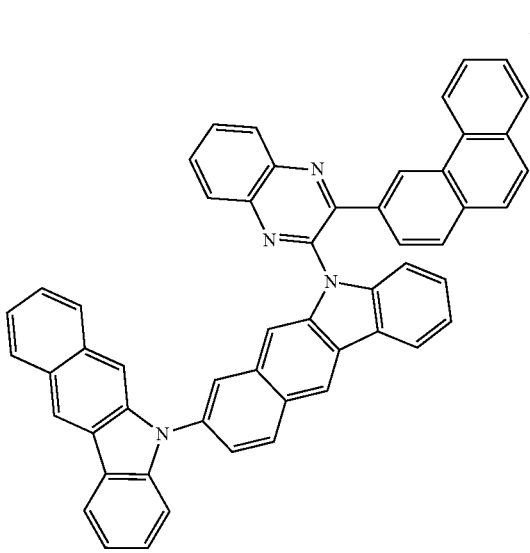

253
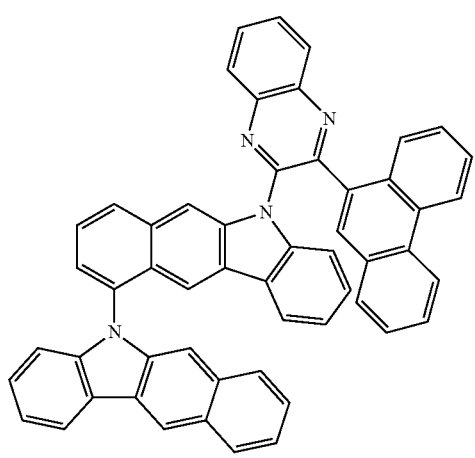
254
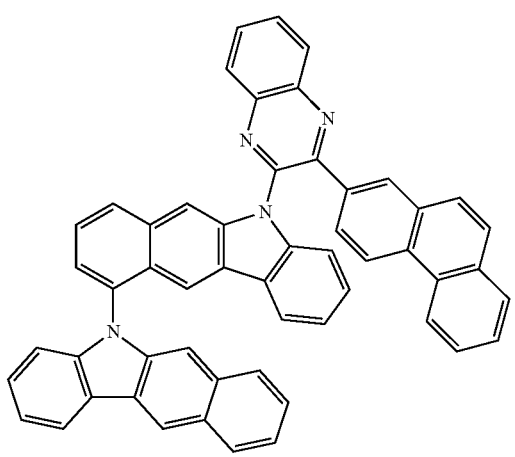
255
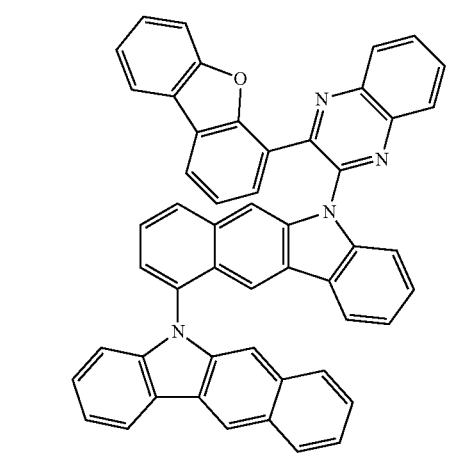
256
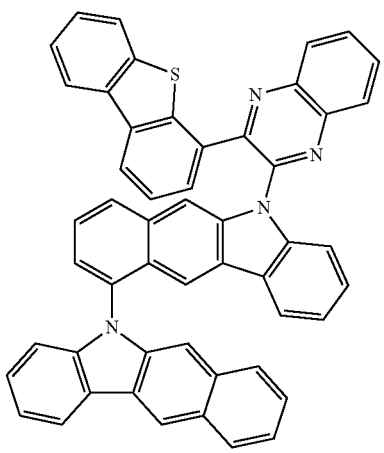
257
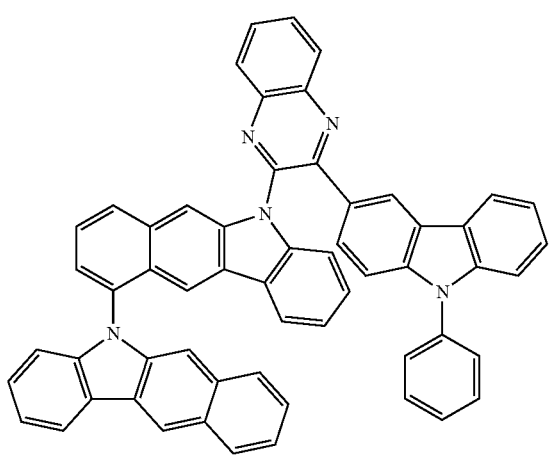
258
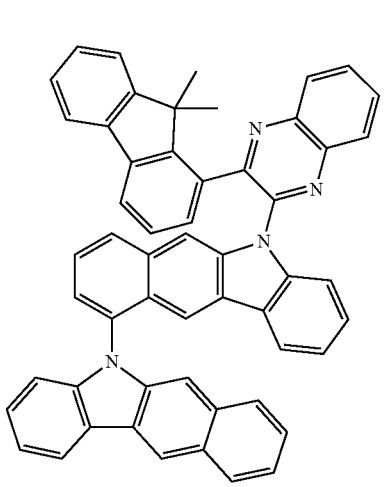

259
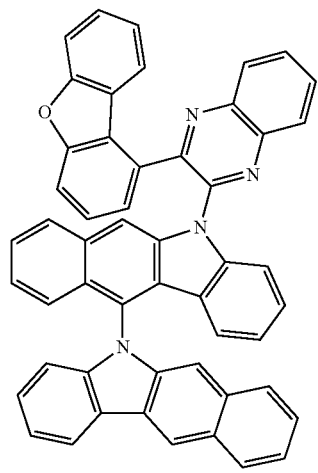
262
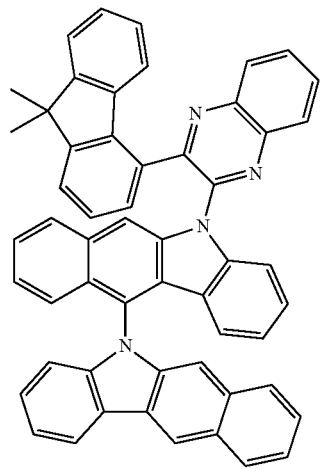
260
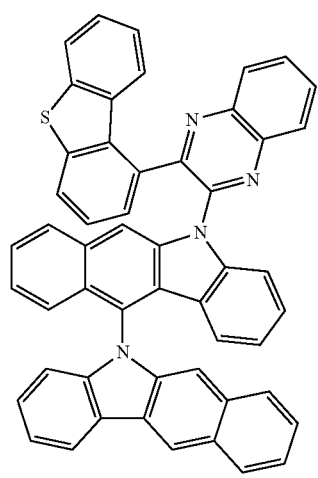
263
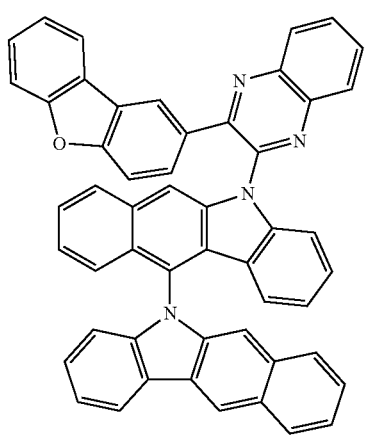
261
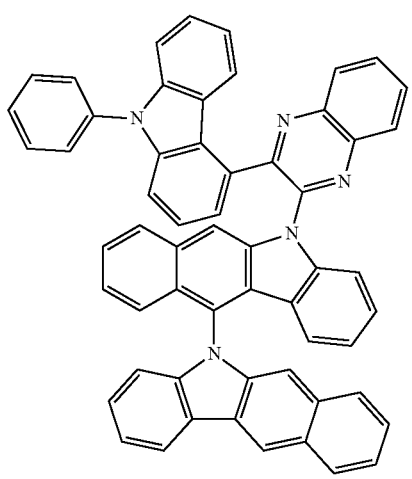
264
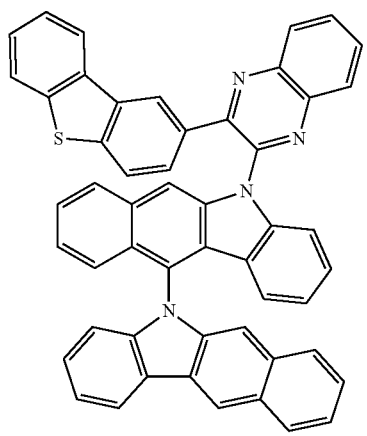

-continued
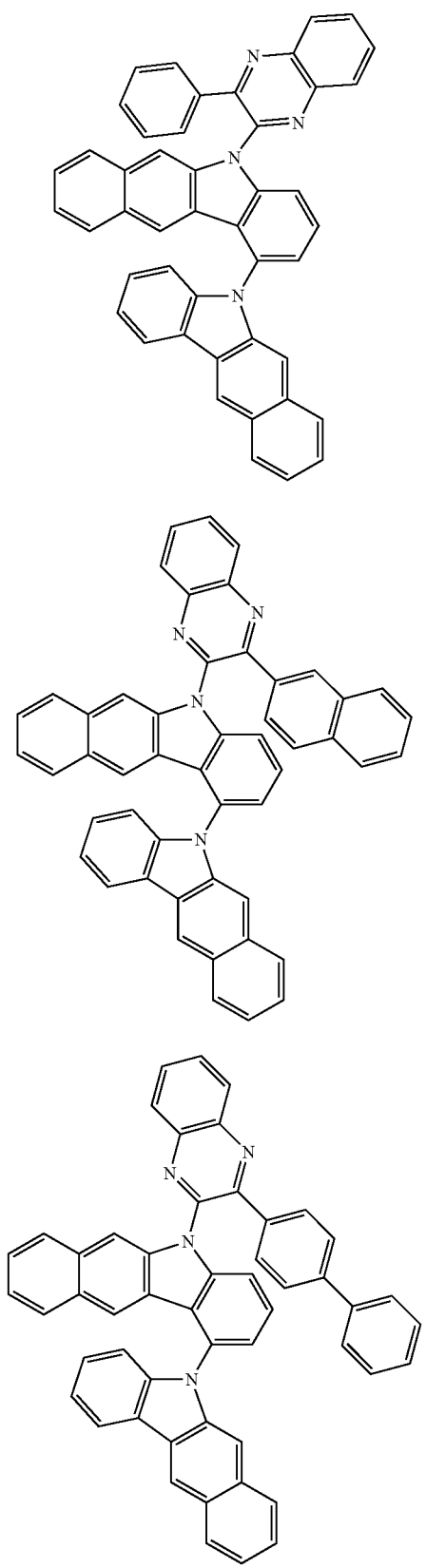
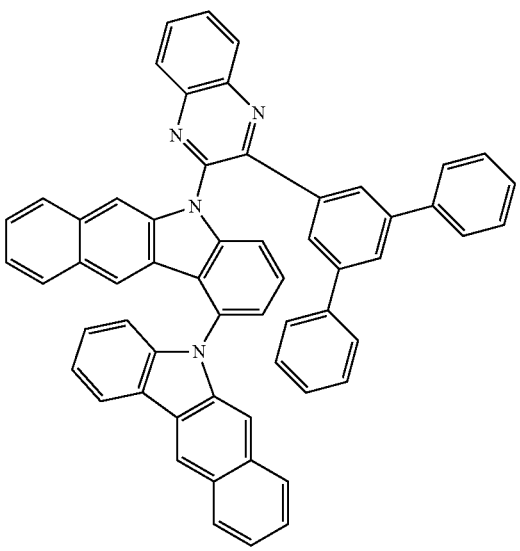
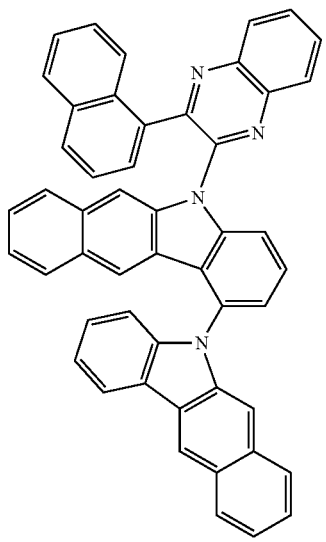
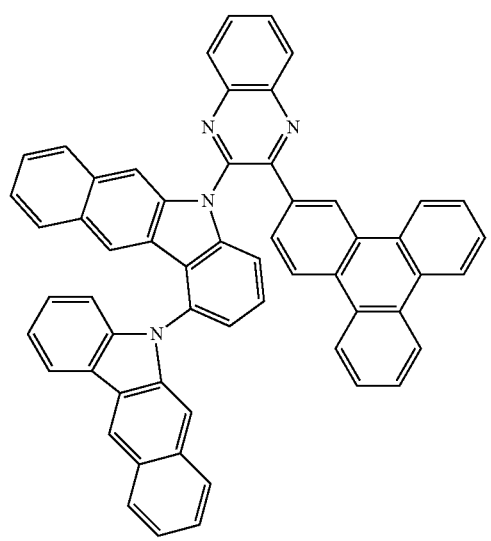

-continued
271
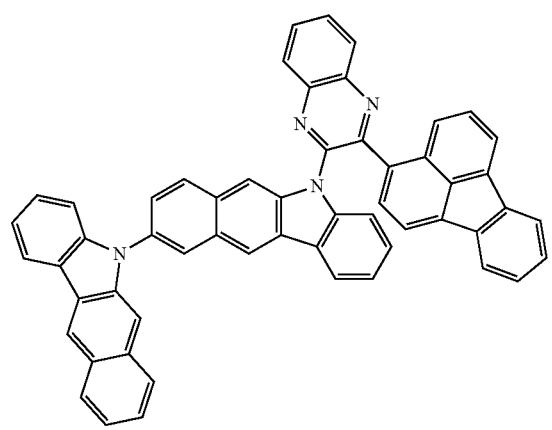
272
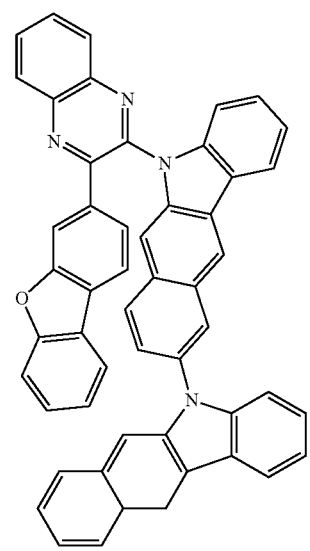
273
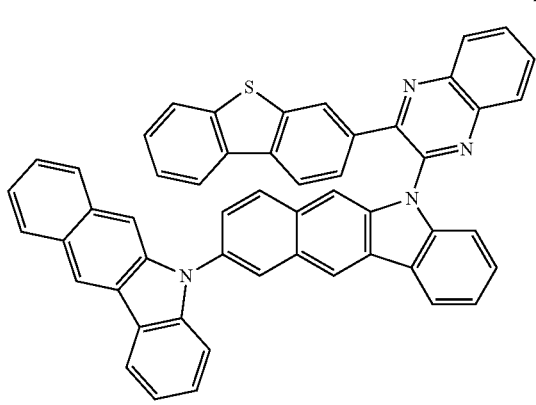
-continued
274
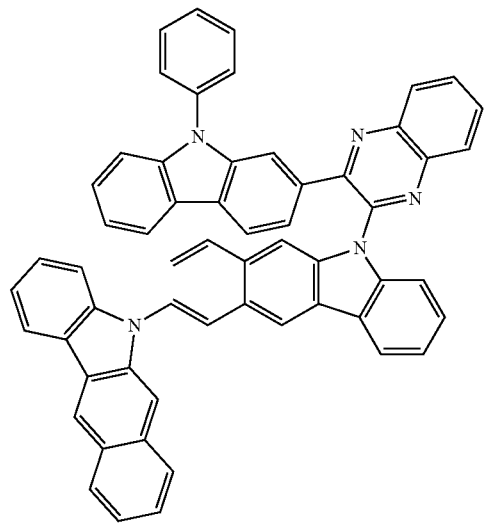
275
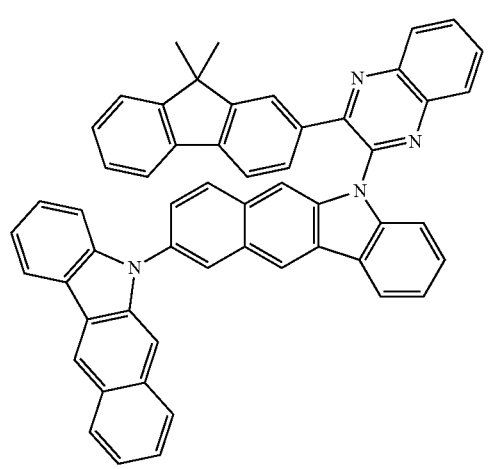
276
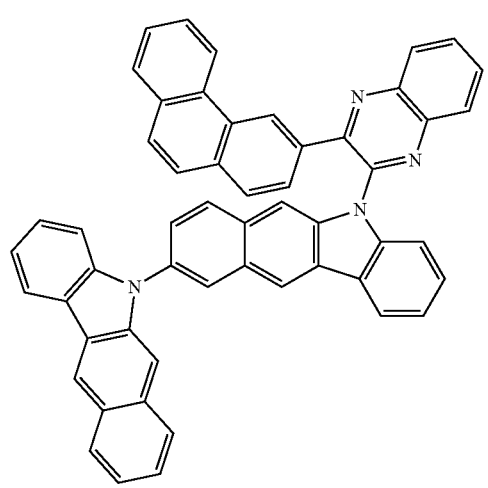

277
278
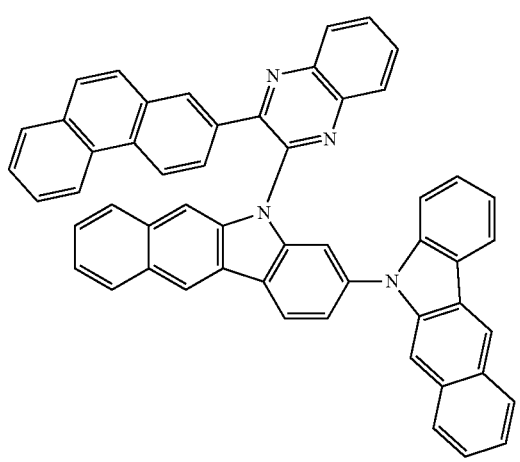
279
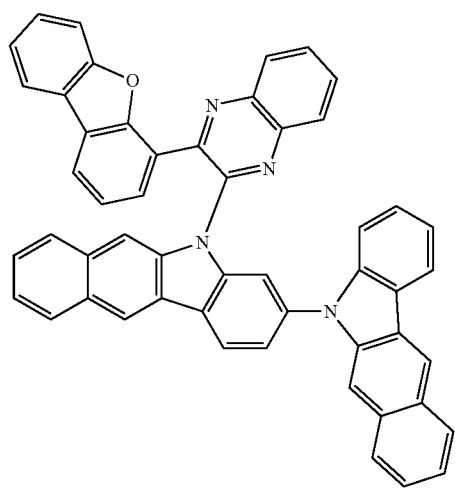
280
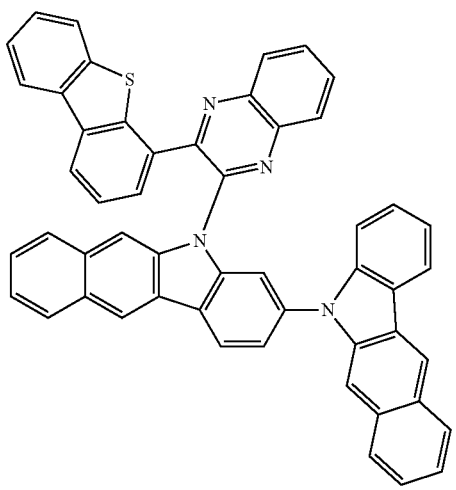
281
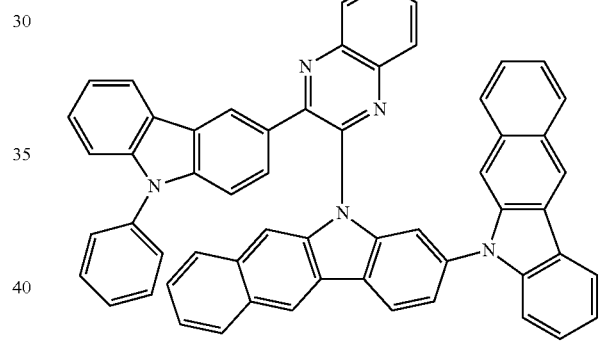
282
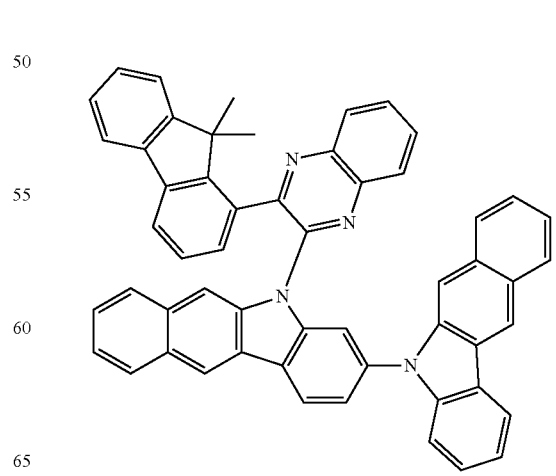

283
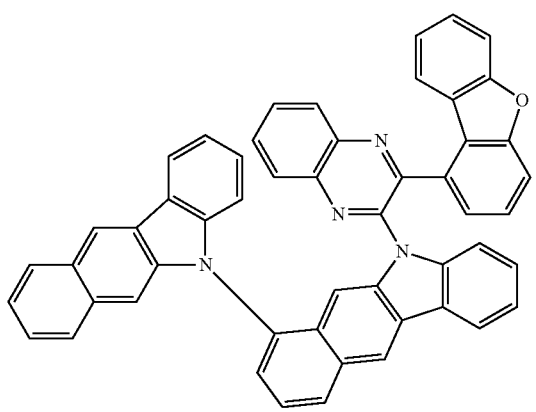
284
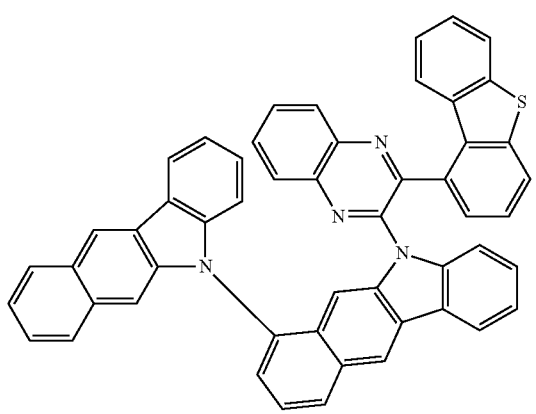
285
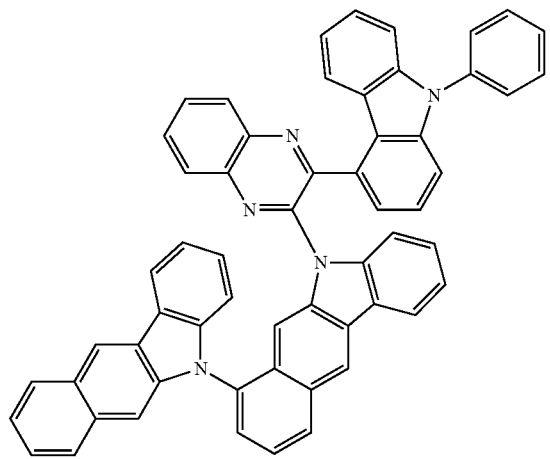
286
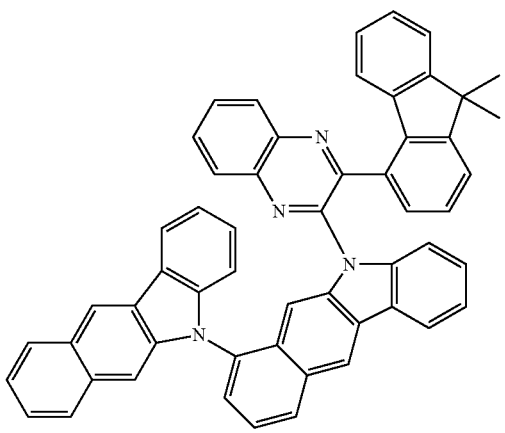
287
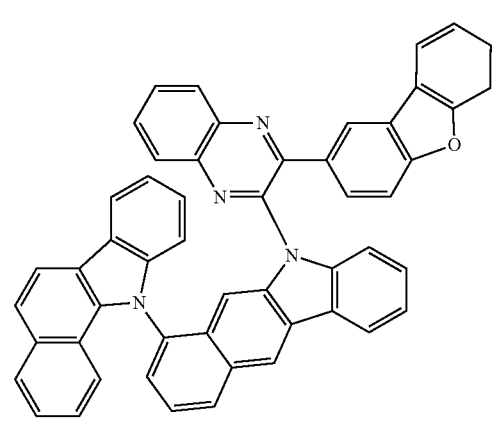
288
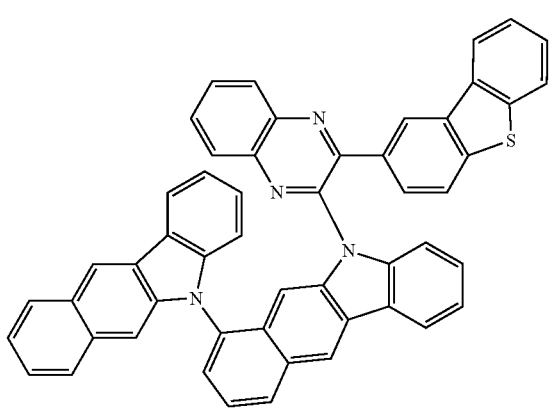

679
-continued
289
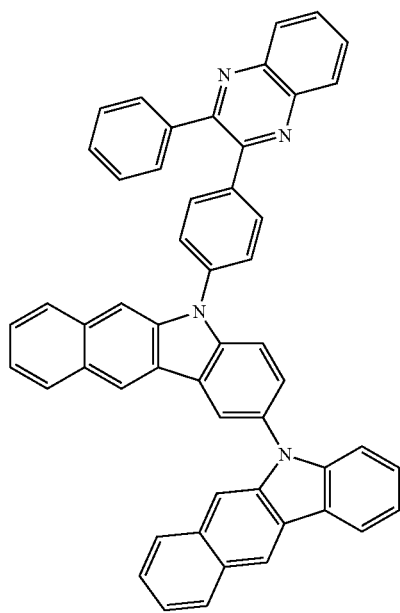
290
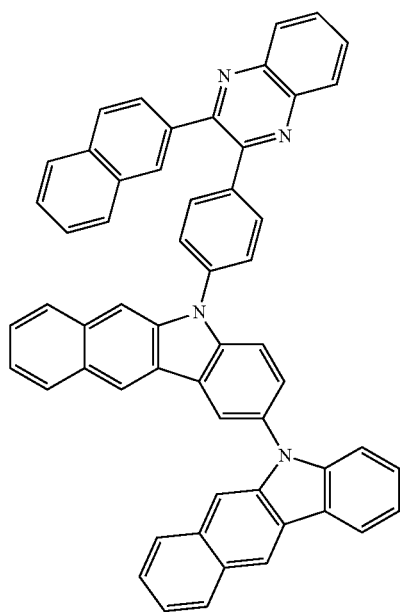
680
-continued
291
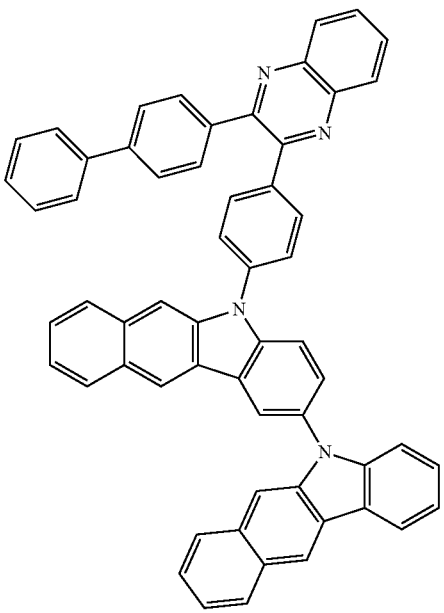
292
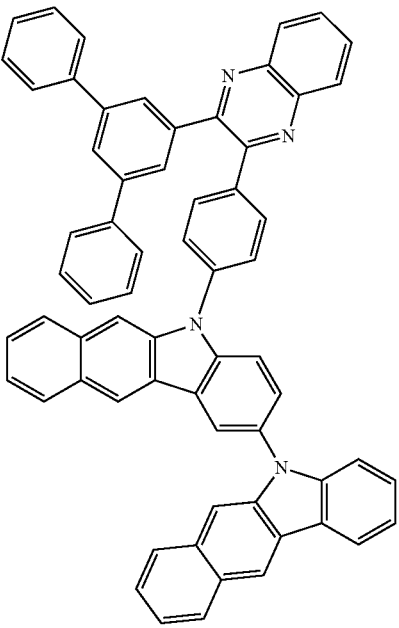

293
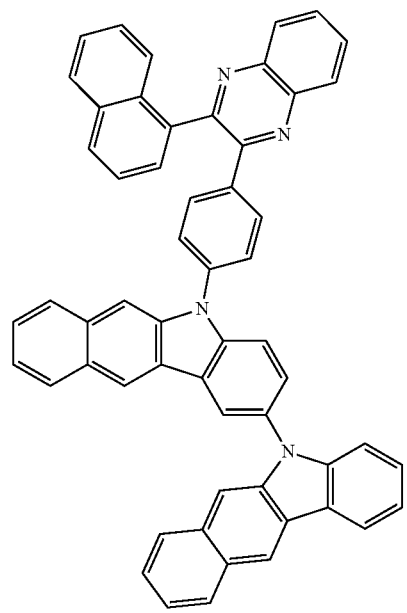
294
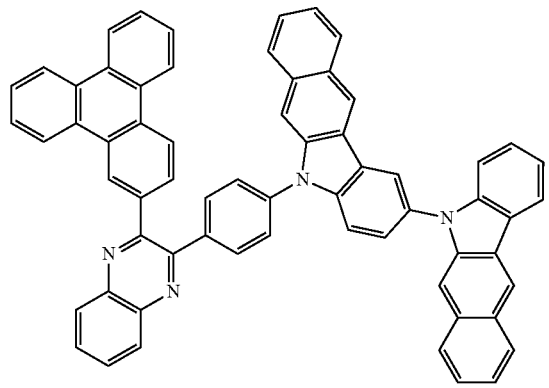
295
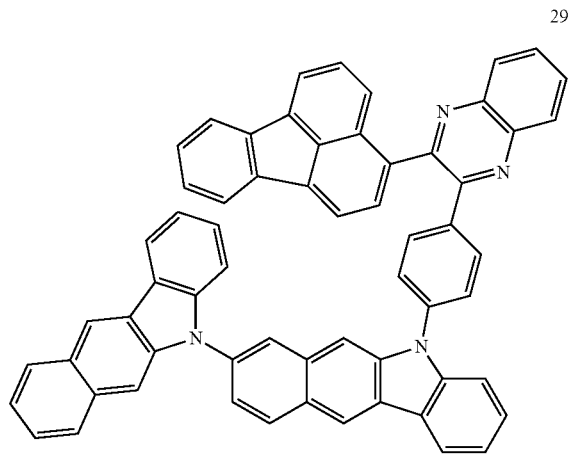
296
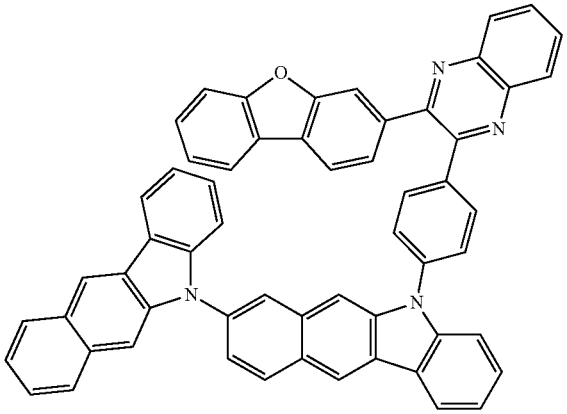
297
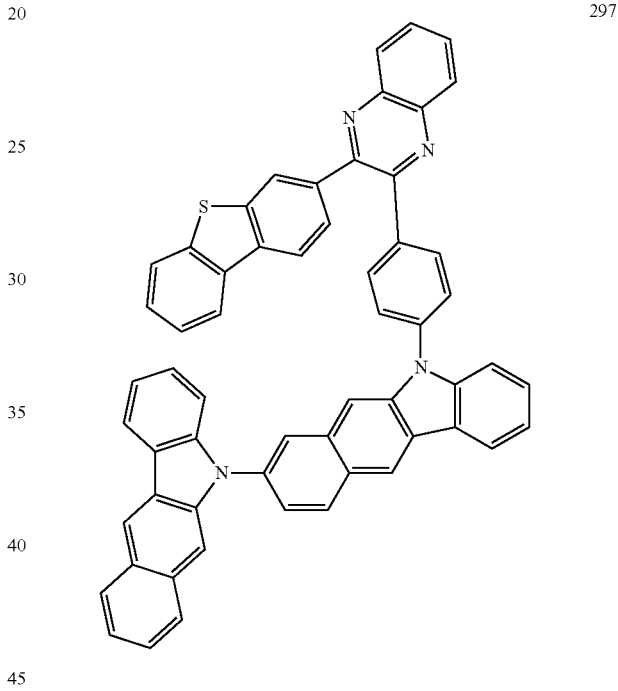
298
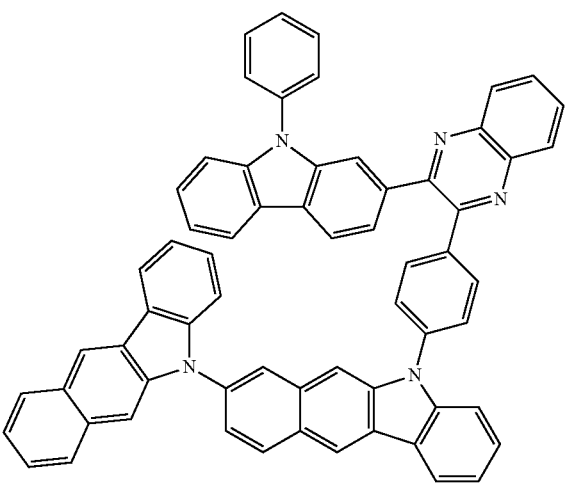

683
-continued
299
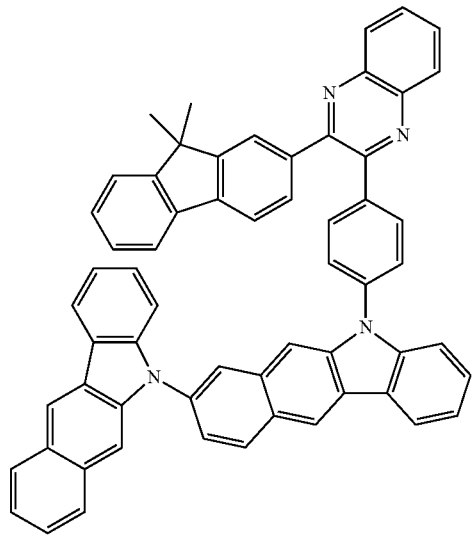
300
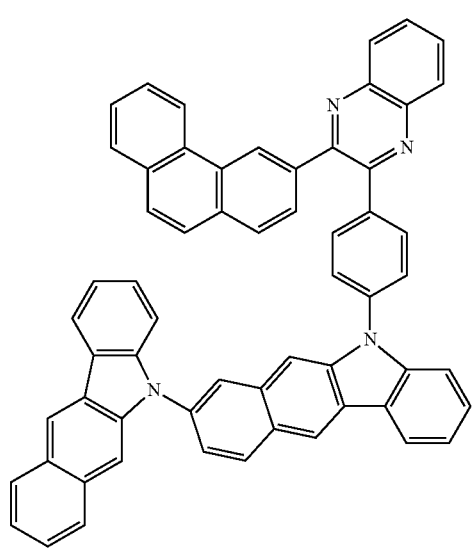
684
-continued
302
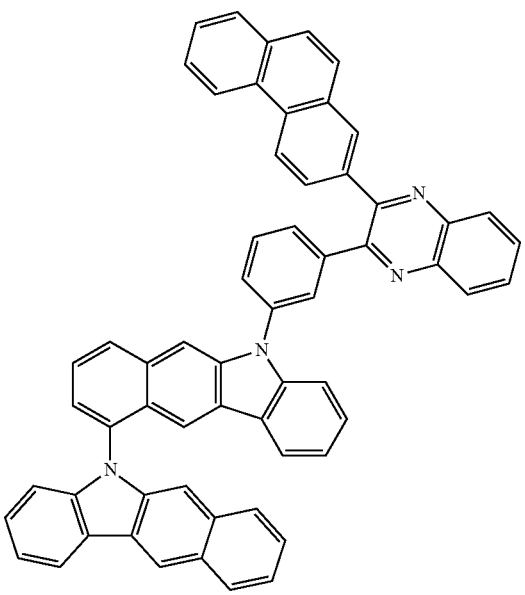
303
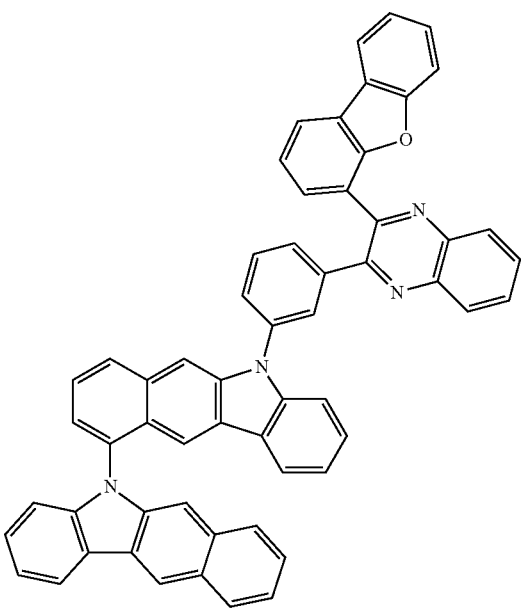

304
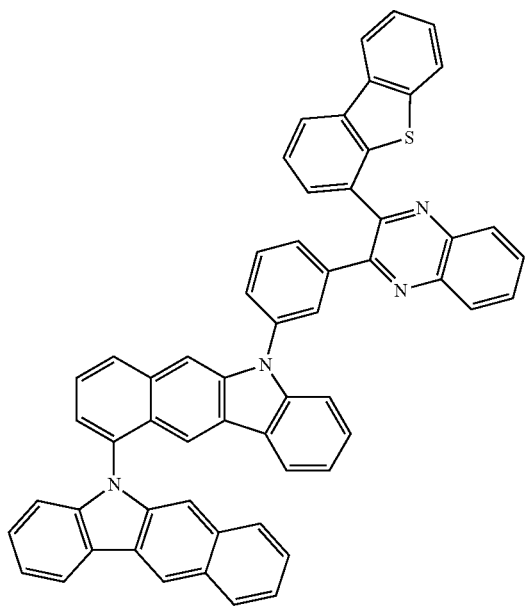
305
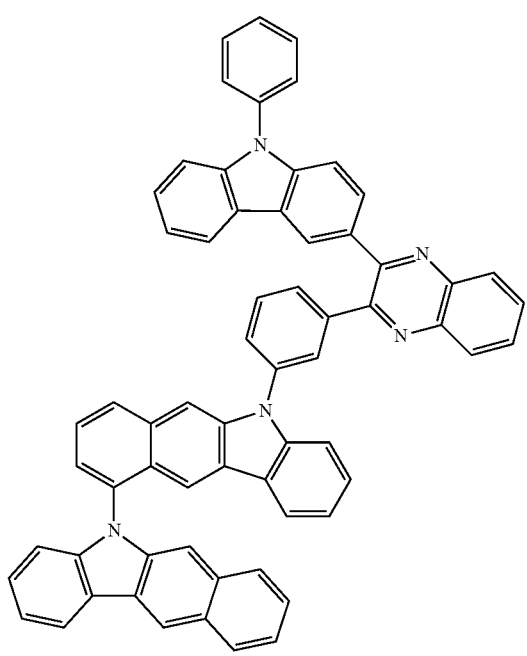
306
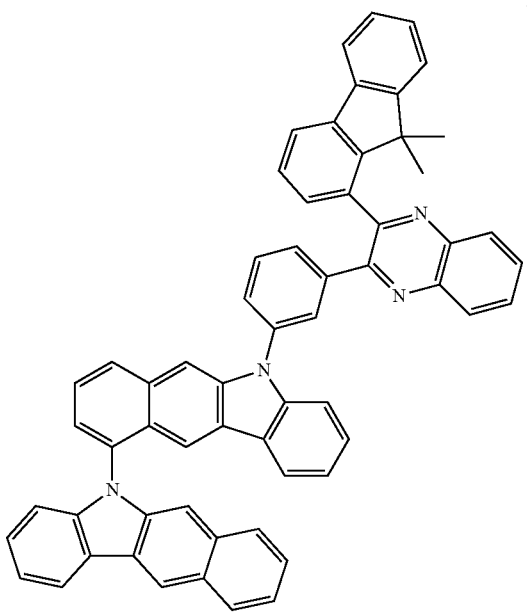
307
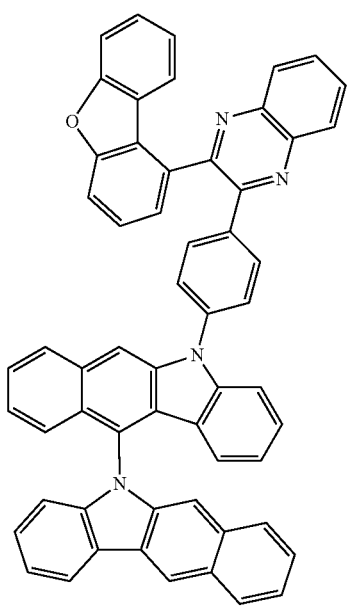

687
-continued
308
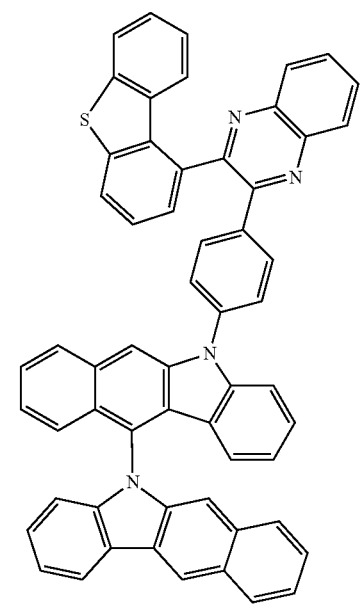
309
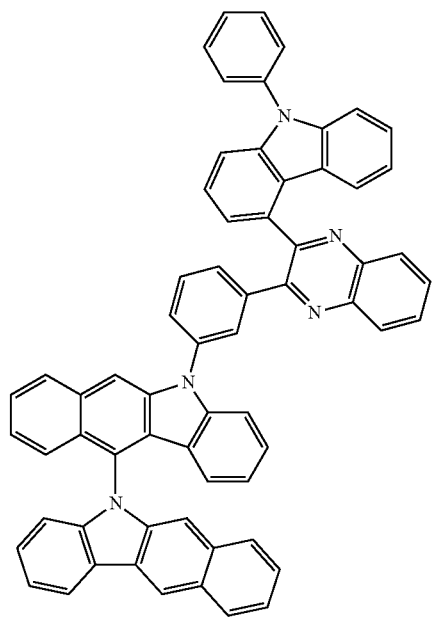
688
-continued
310
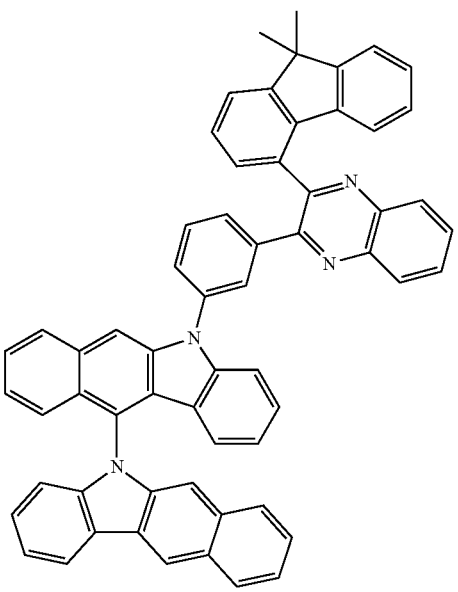
311

689
-continued
312
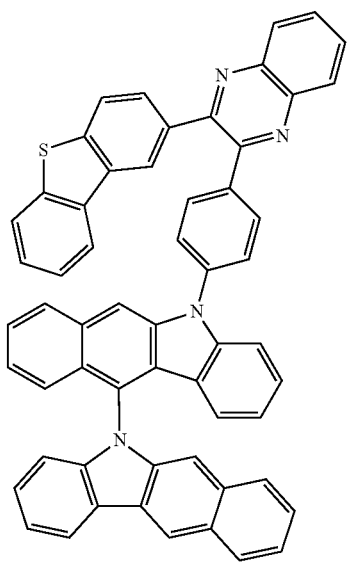
313
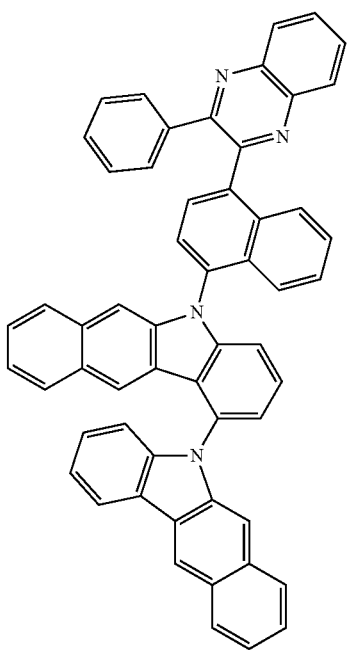
690
-continued
314
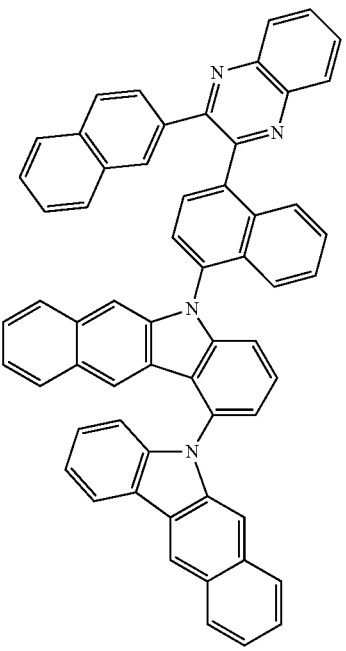
315
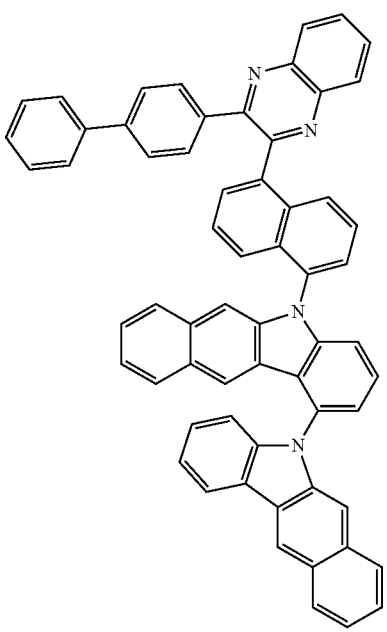

691
-continued
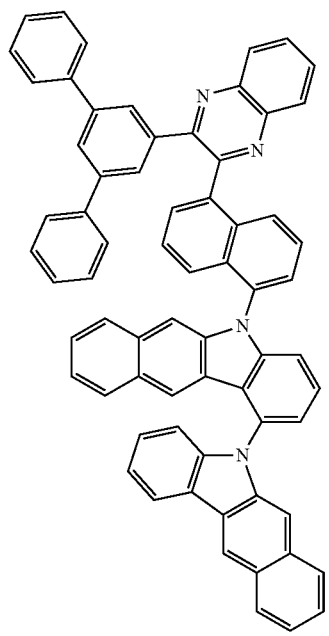
316
692
-continued
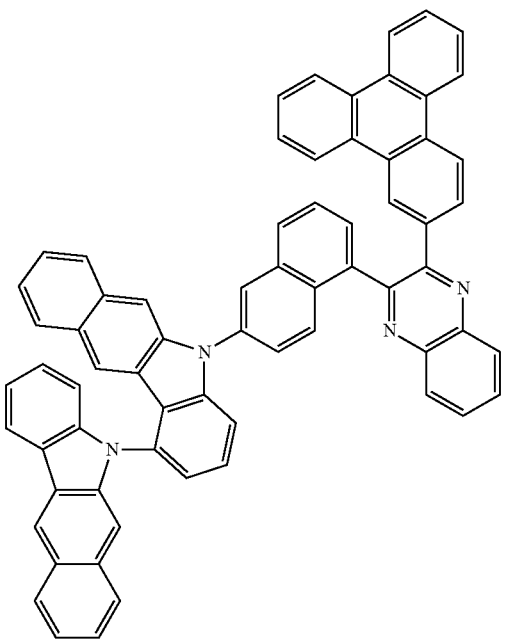
318
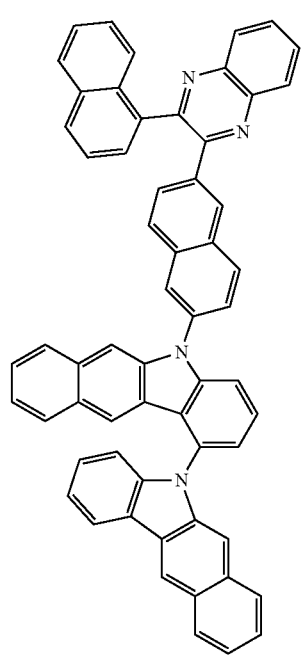
317
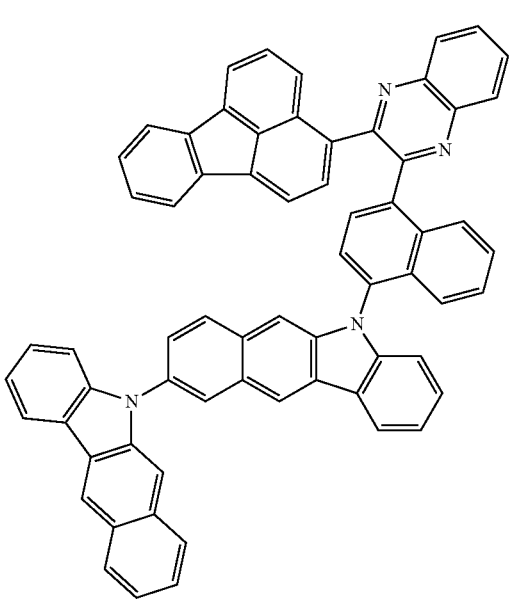
319

693
-continued
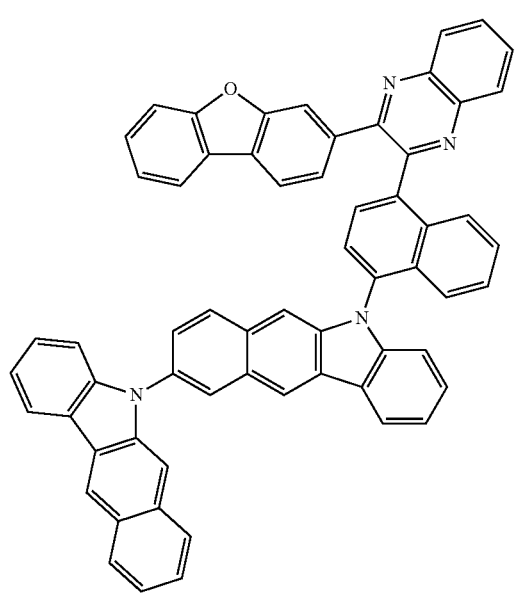
320
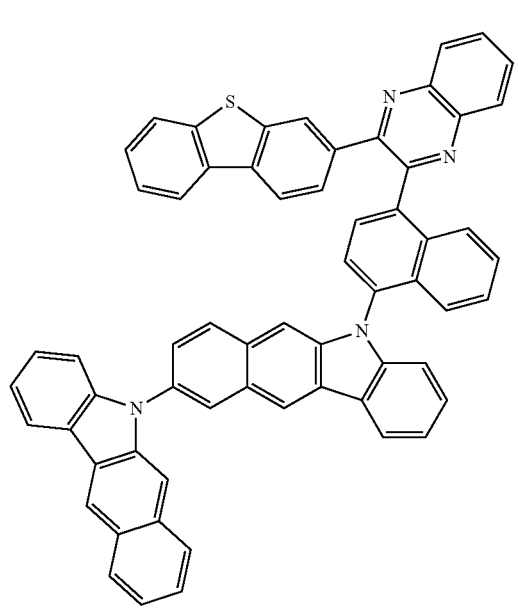
321
694
-continued
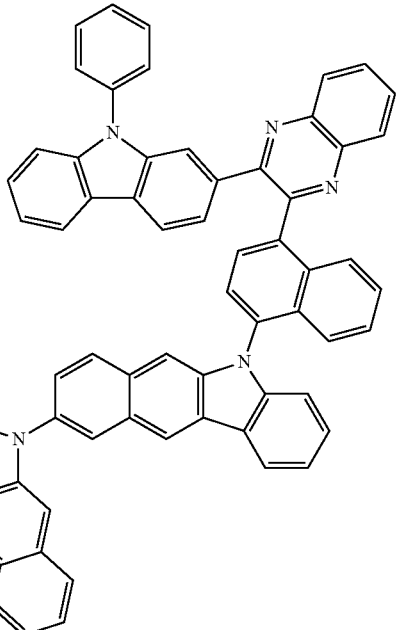
322
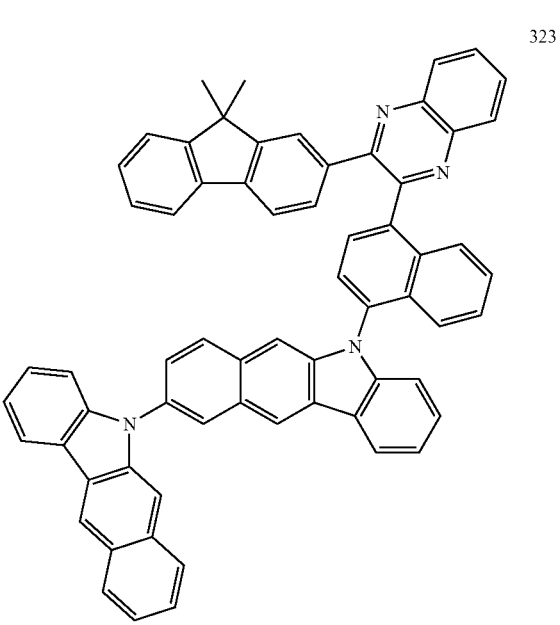
323

-continued
324
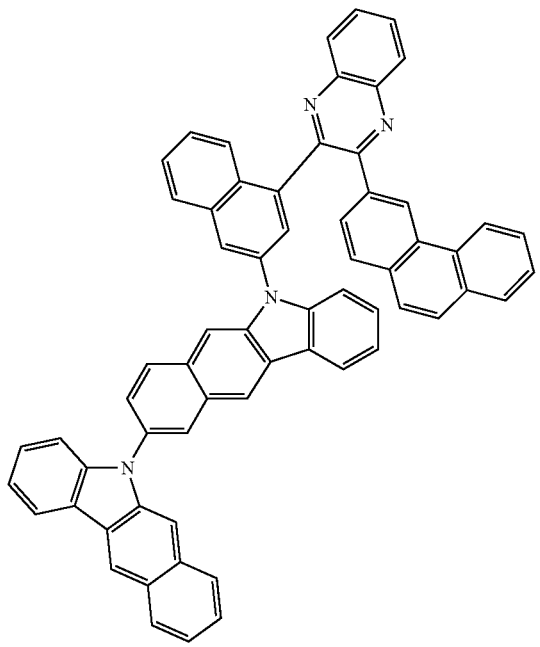
325
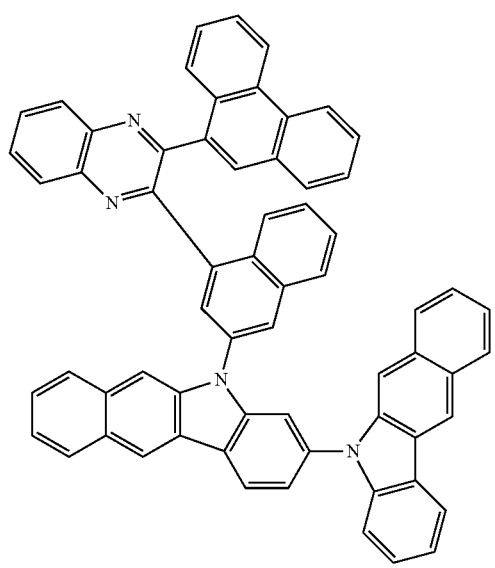
-continued
326
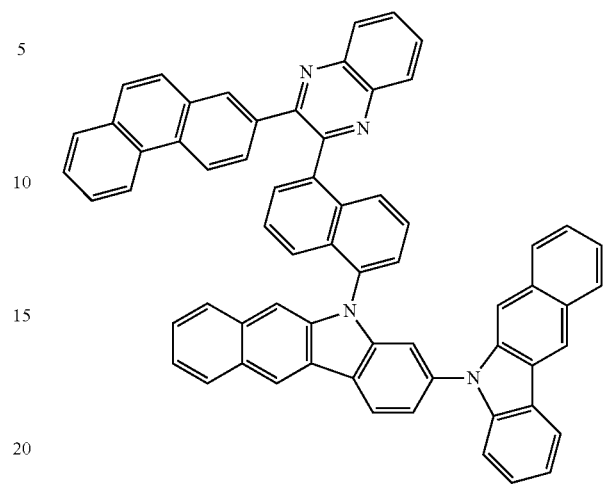
327
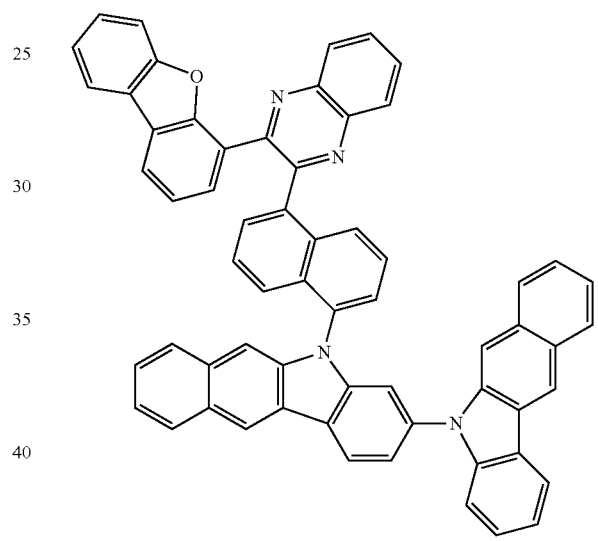
328
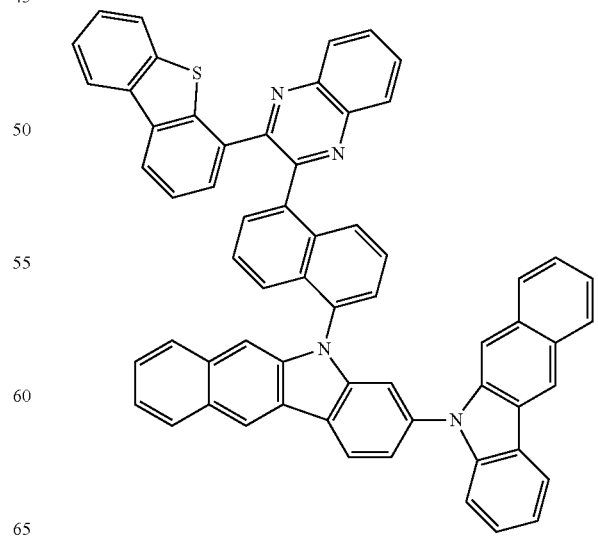

697
-continued
329
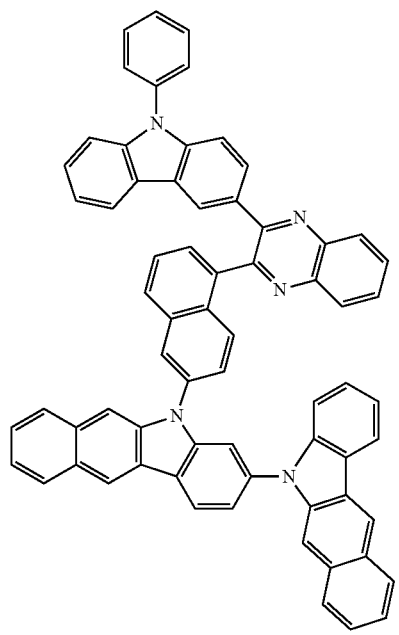
330
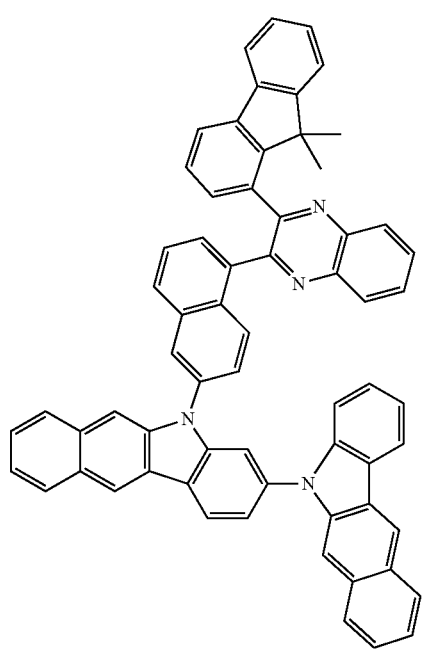
698
-continued
331
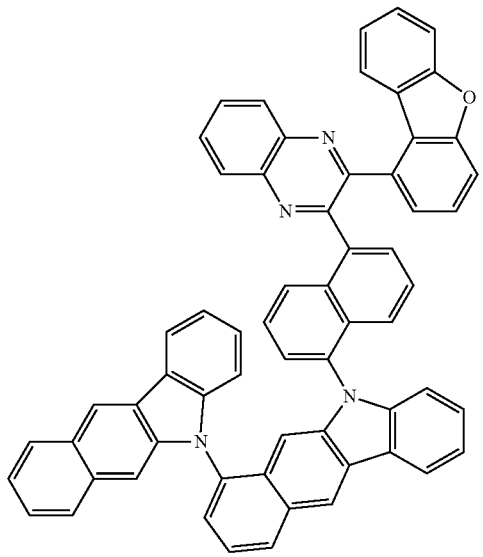
332
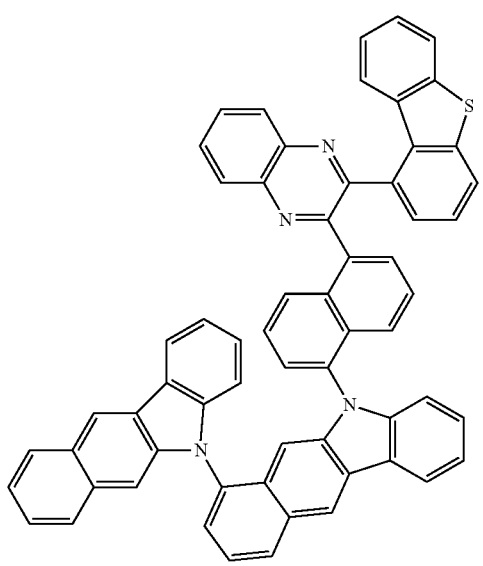

699
-continued
333
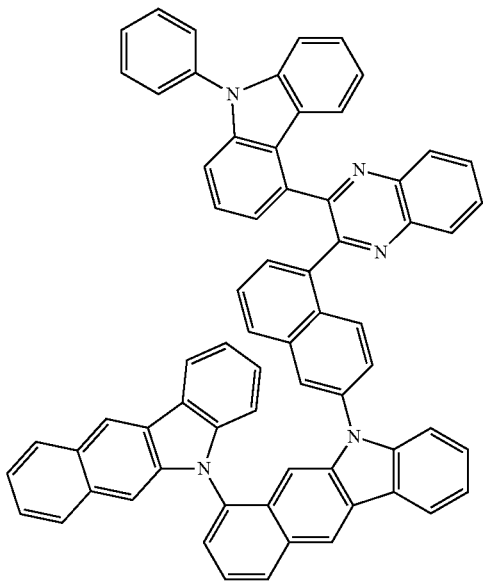
334
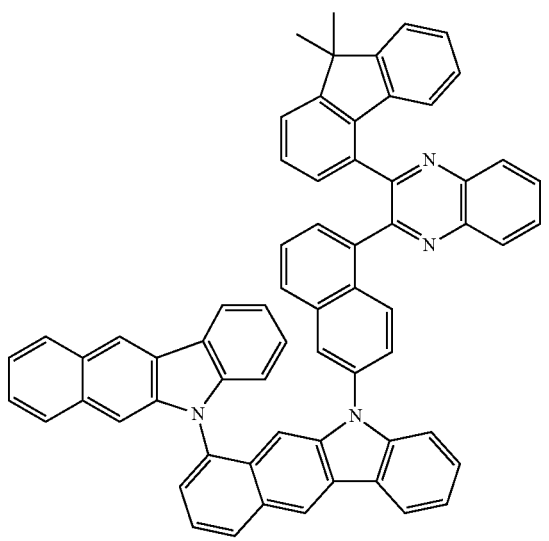
335
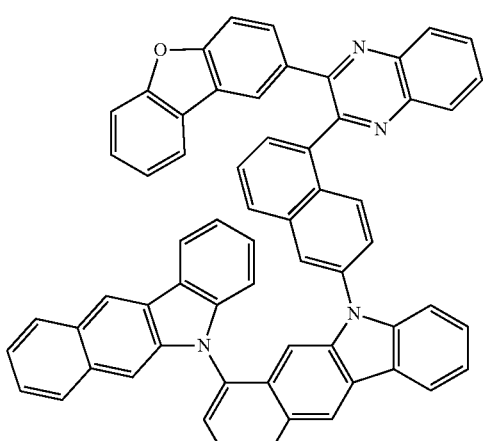
700
-continued
336
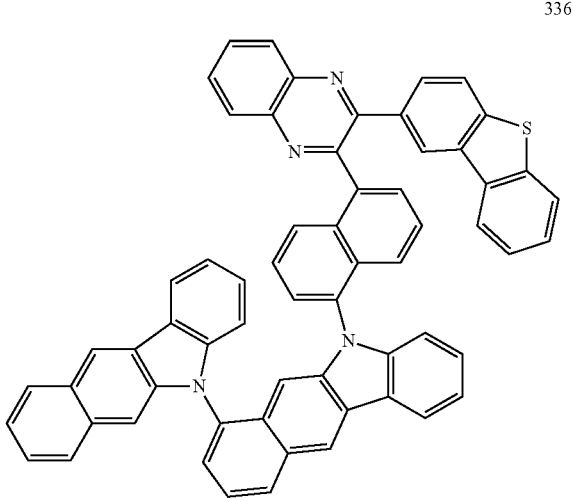
337
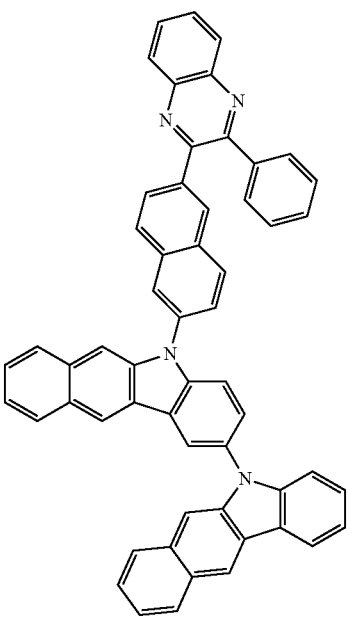

701
-continued
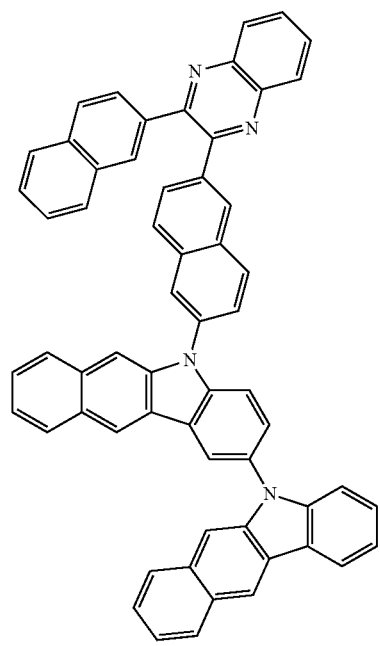
338
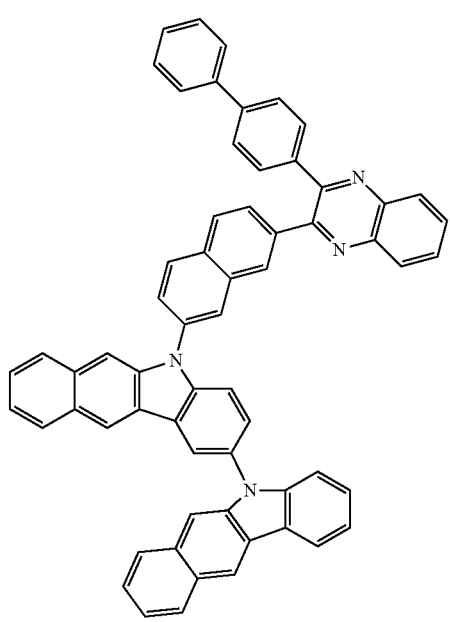
339
702
-continued
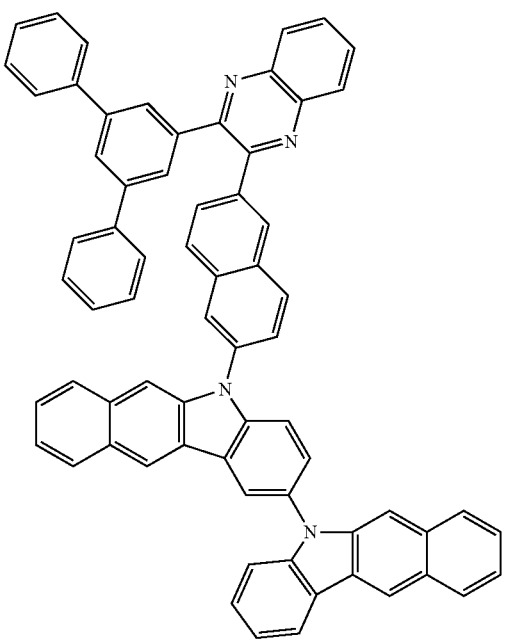
340
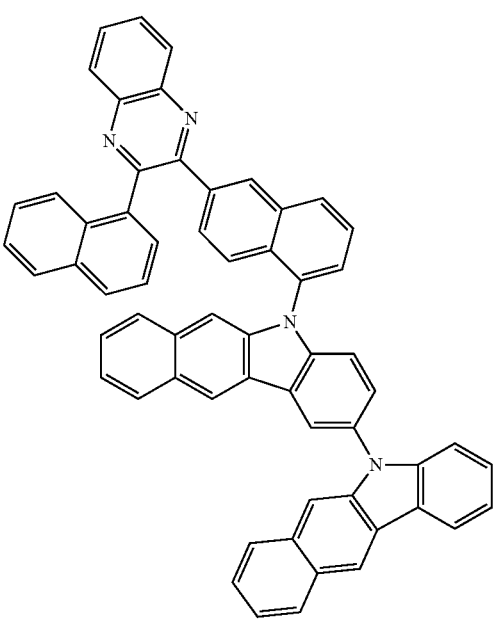
341

703
-continued
342
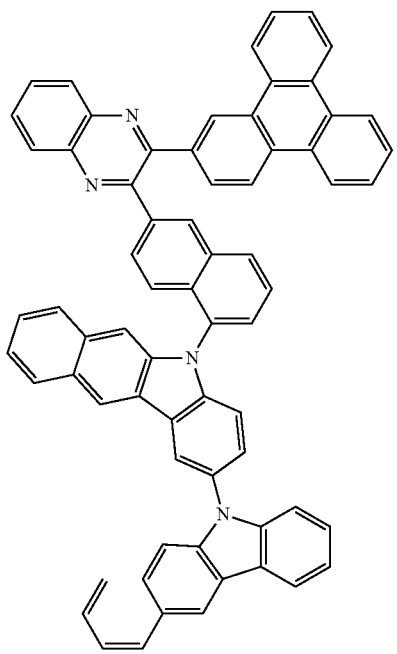
704
-continued
344
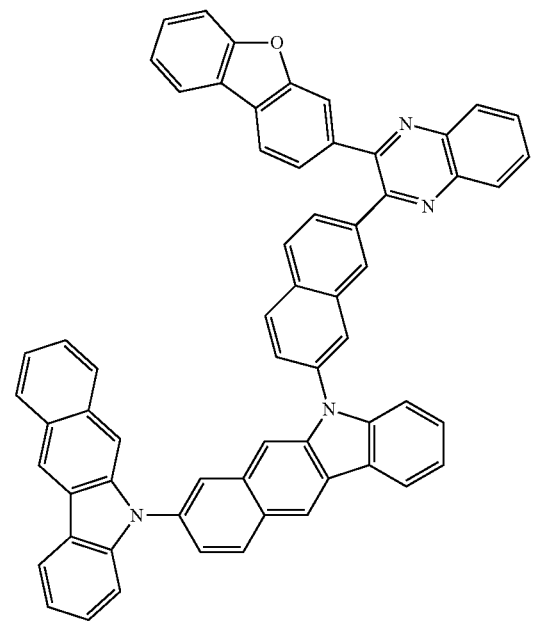
343
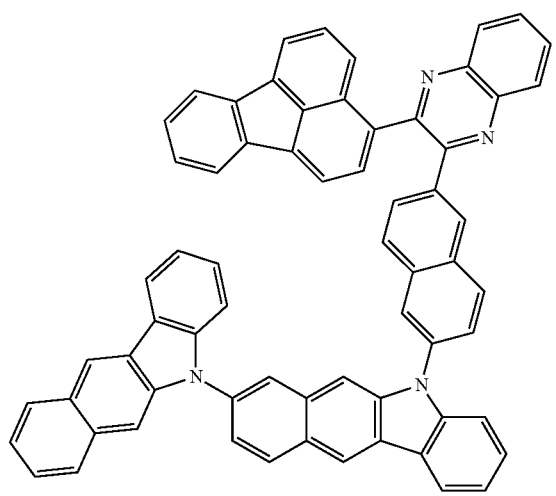
345

705
-continued
706
-continued
346
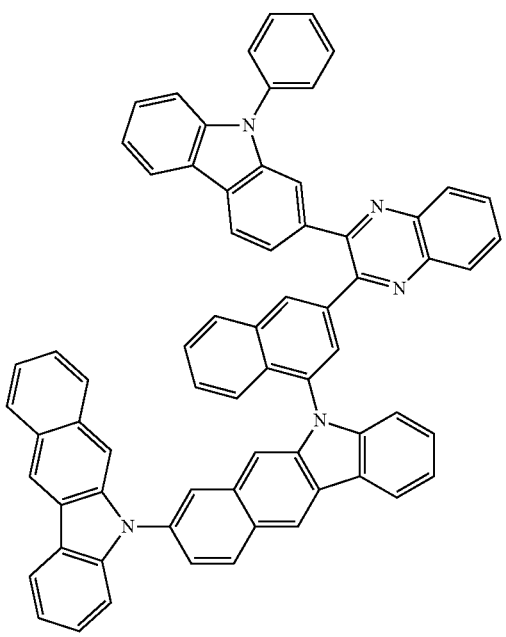
349
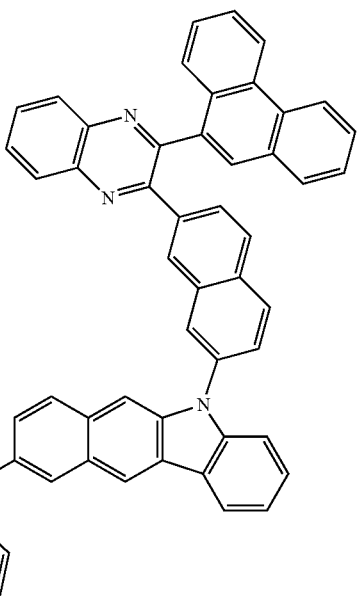
347
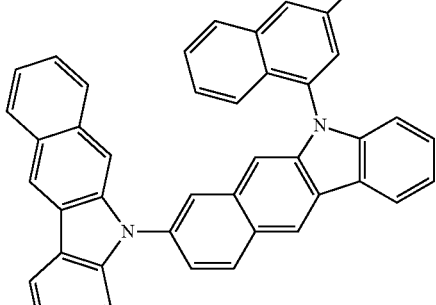
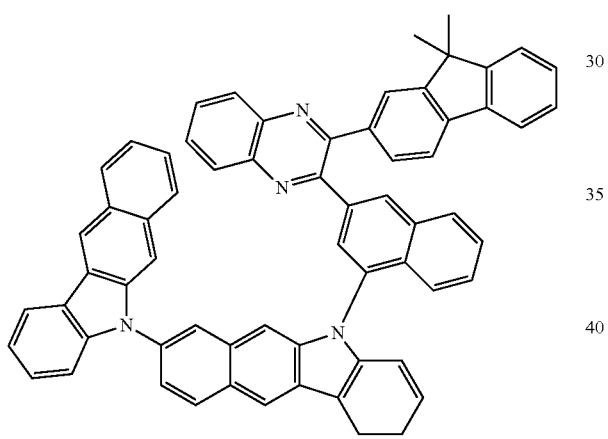
348
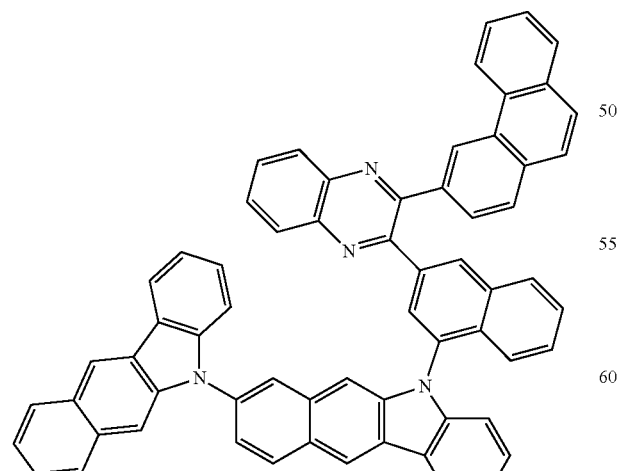
350
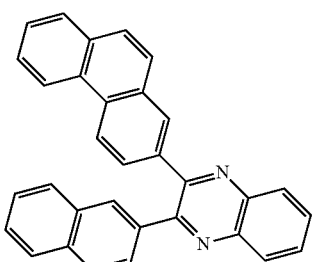
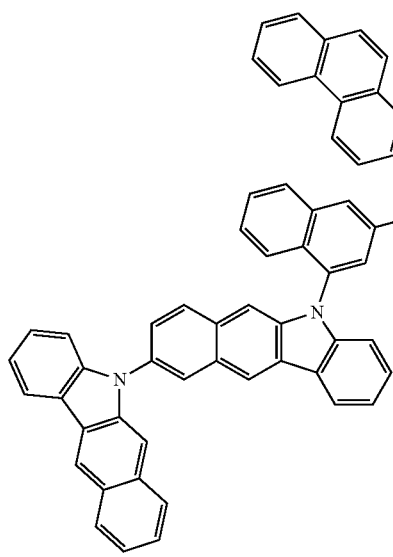

707
-continued
351
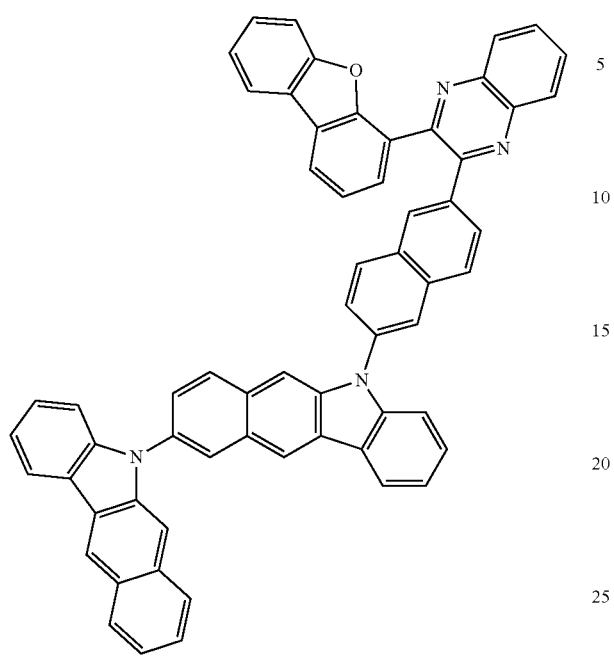
352
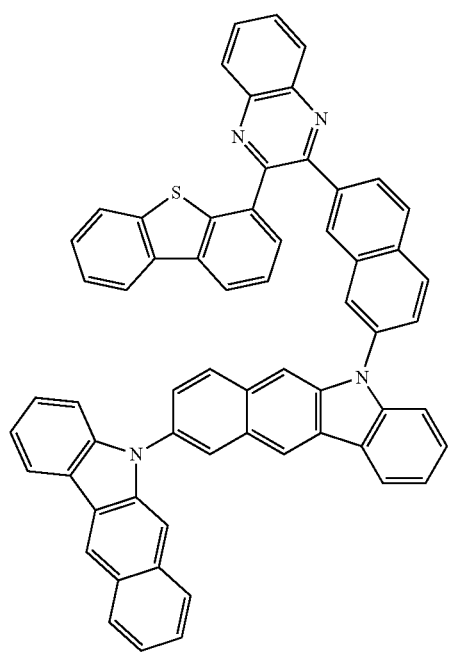
708
-continued
353
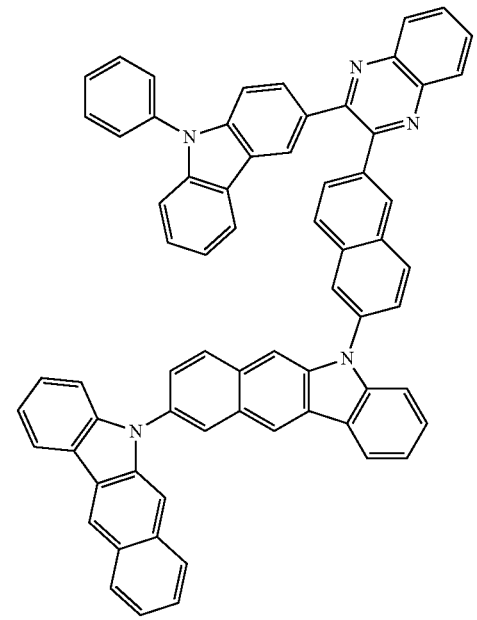
354
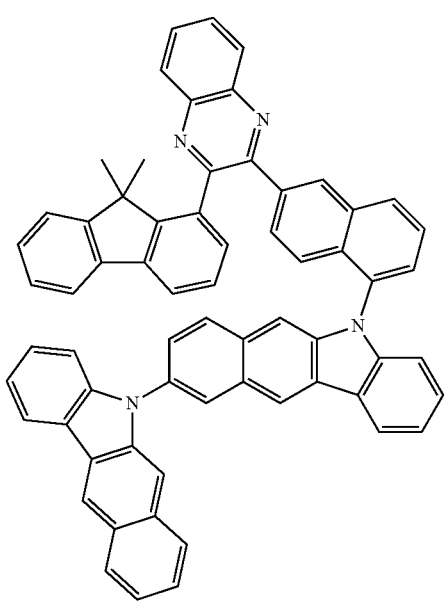

709
-continued
355
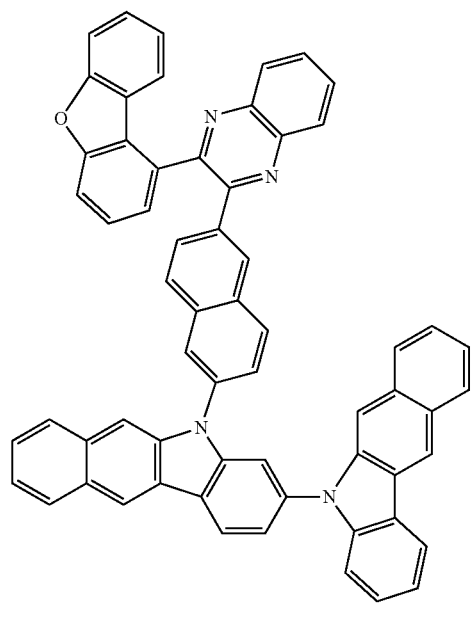
356
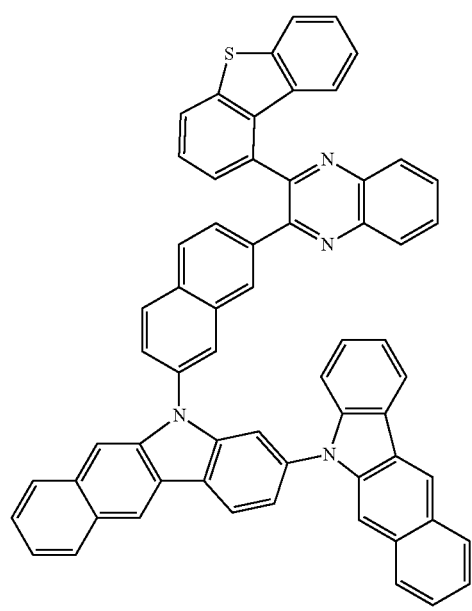
710
-continued
357
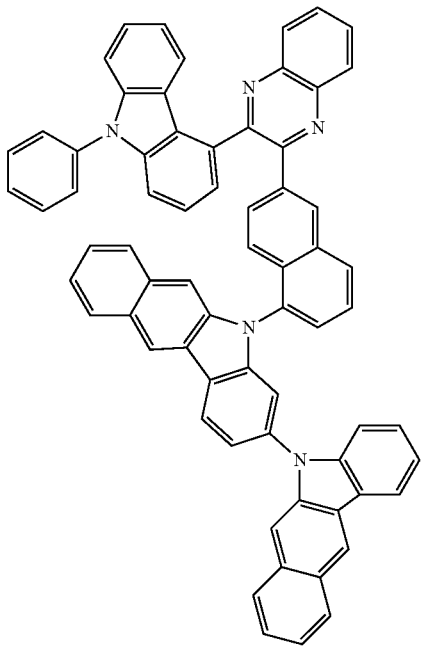
358
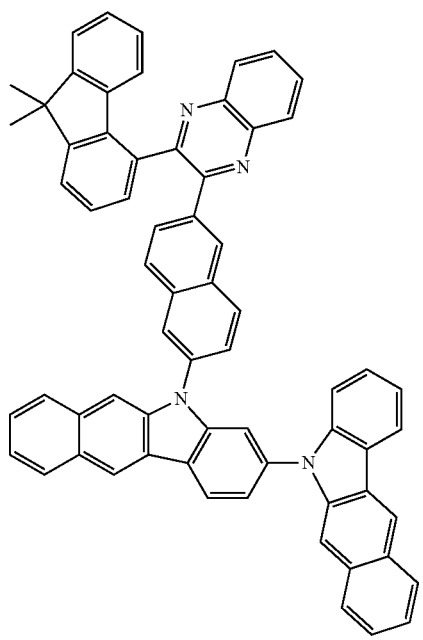

711
-continued
712
-continued
359
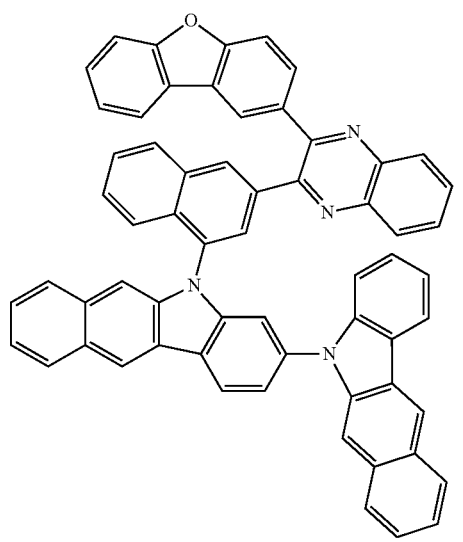
362
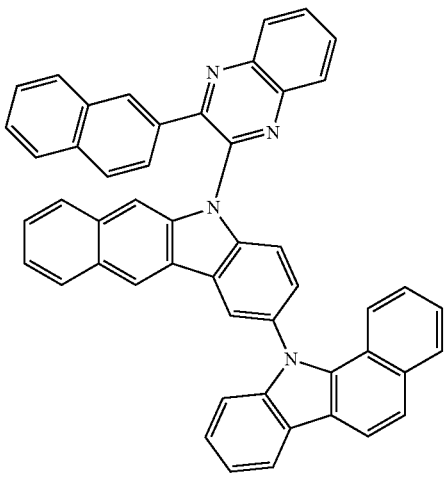
360
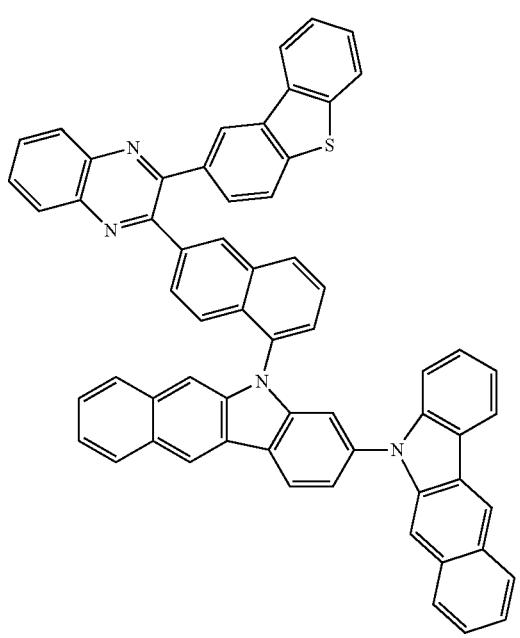
363
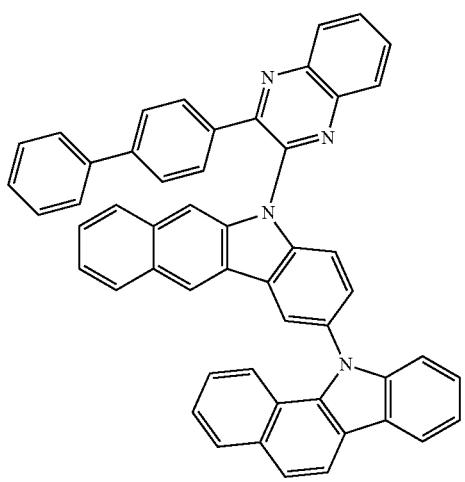
361
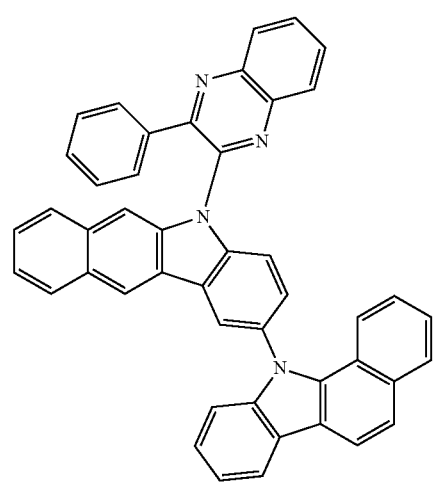
364
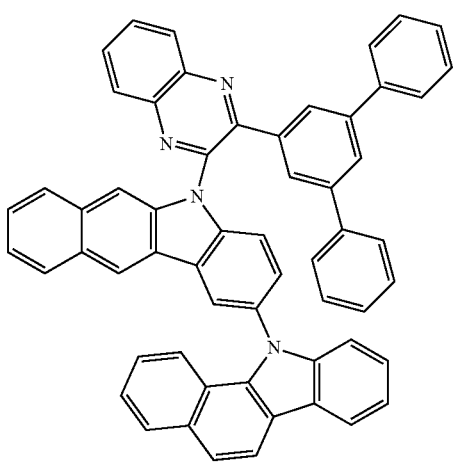

-continued
365
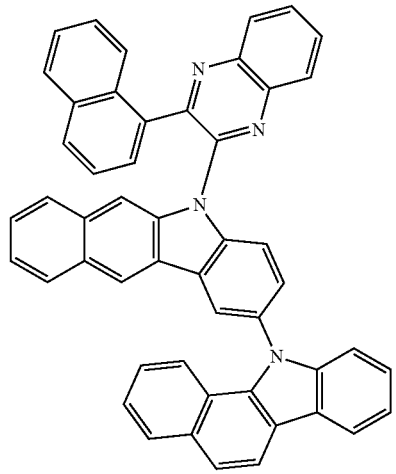
366
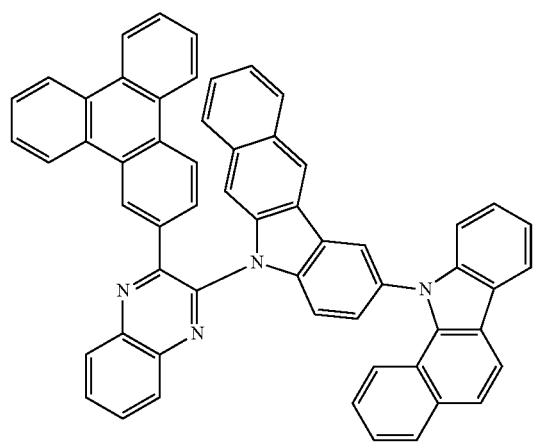
367
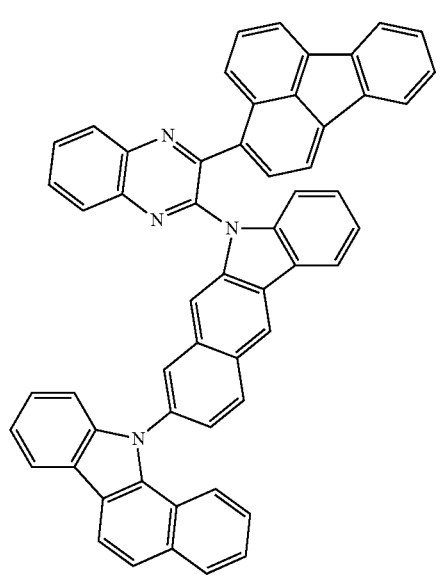
-continued
368
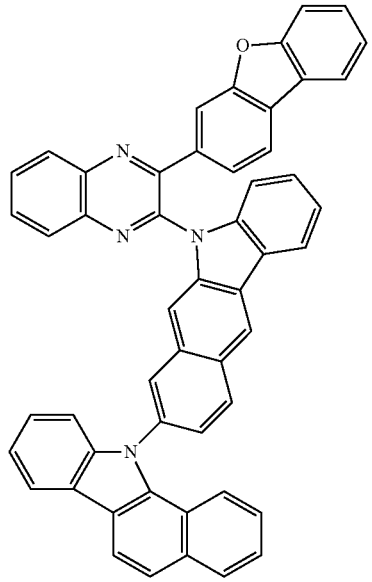
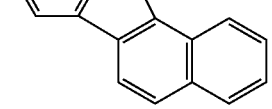
369
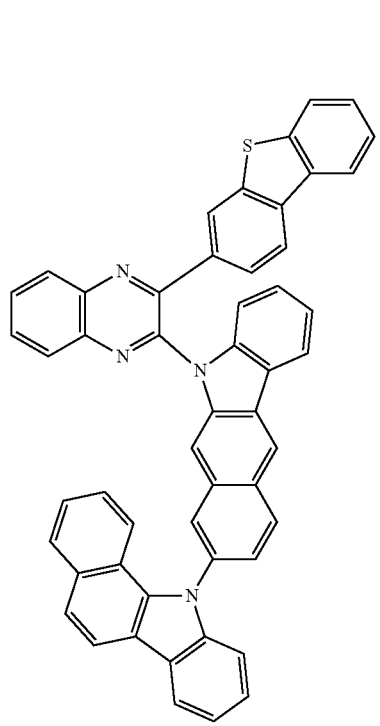

| 370 | 373 |
|---|---|
| 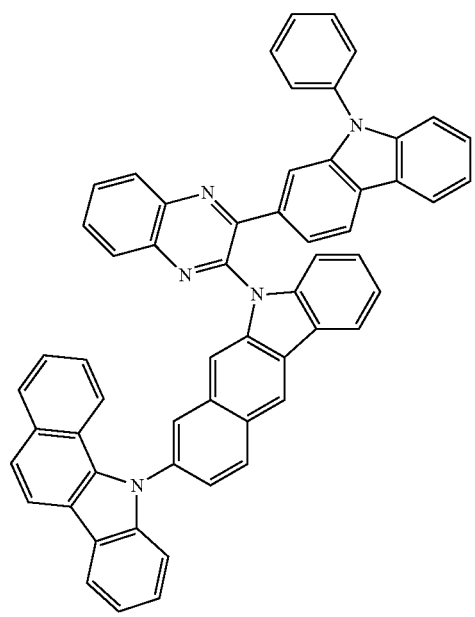 | 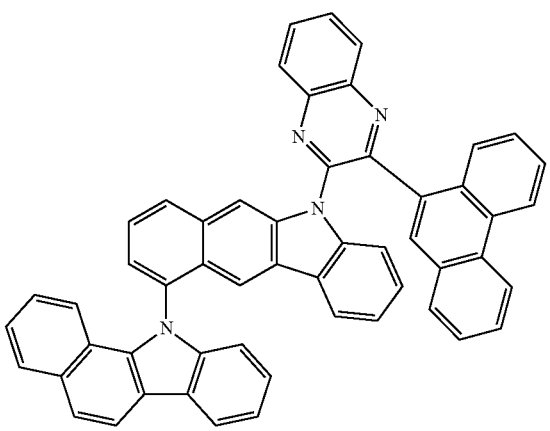 |
| 371 | 374 |
| 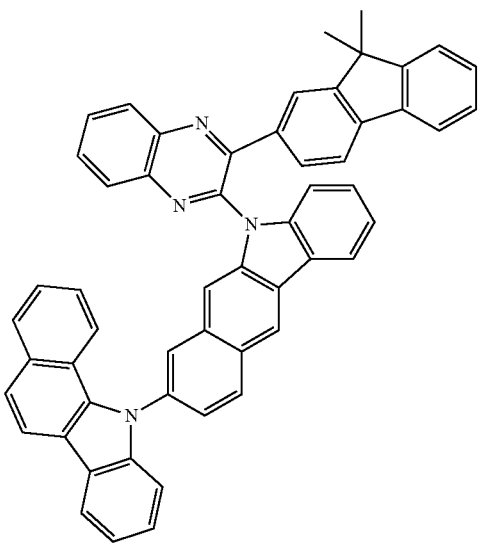 | 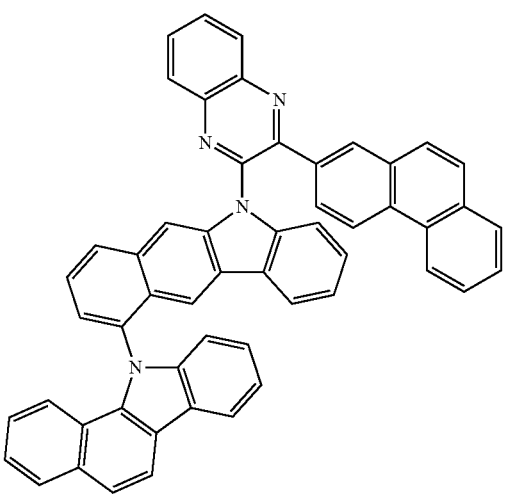 |
| 372 | 375 |
| | 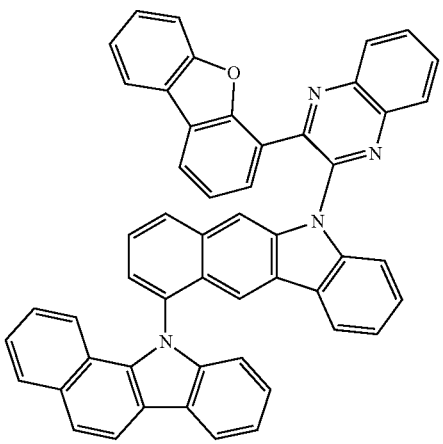 |

376
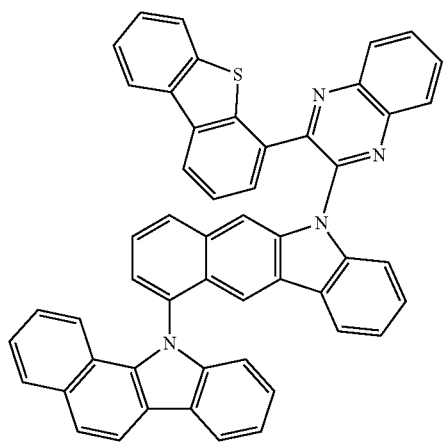
377
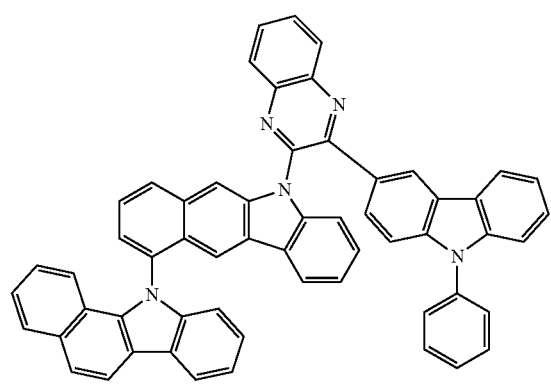
378
379
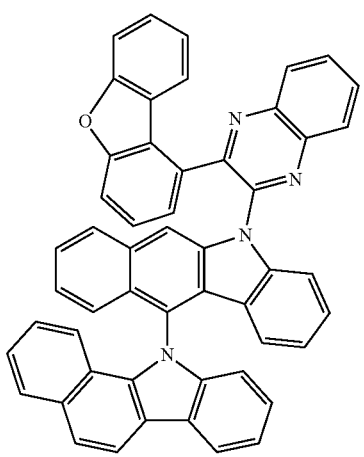
380
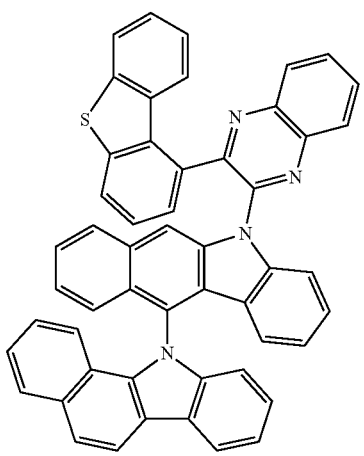
381
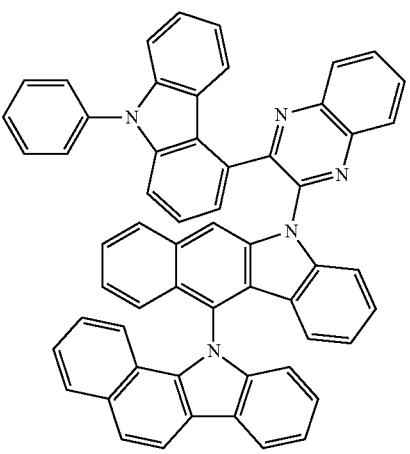

719
-continued
382
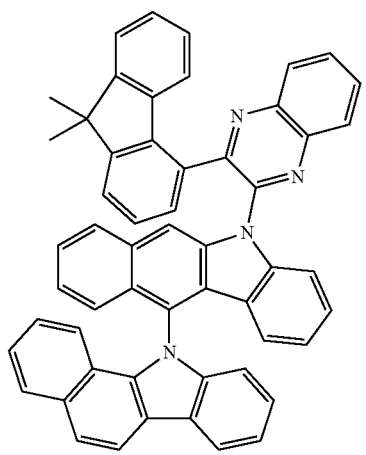
383
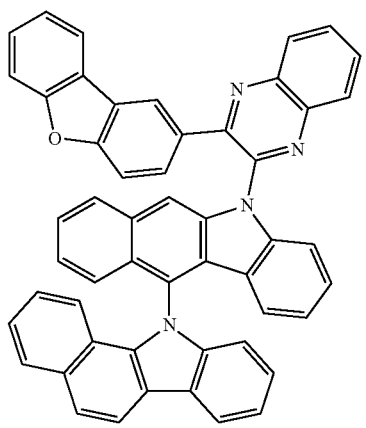
384
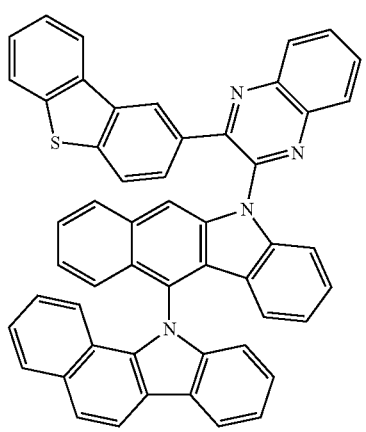
720
-continued
385
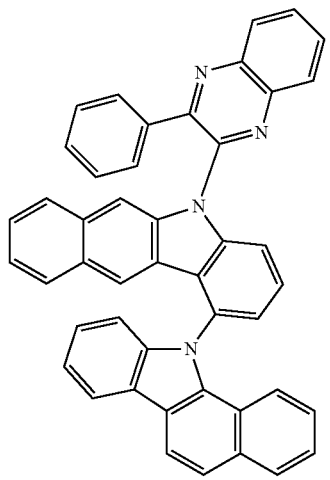
386
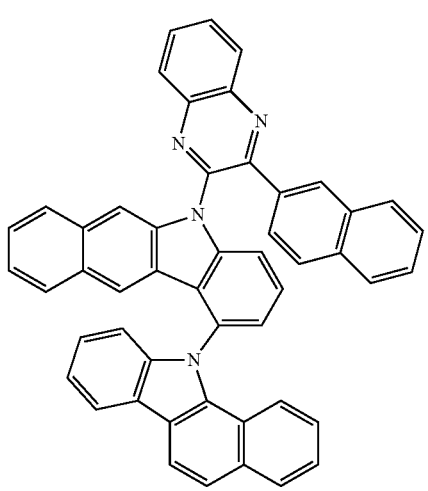
387
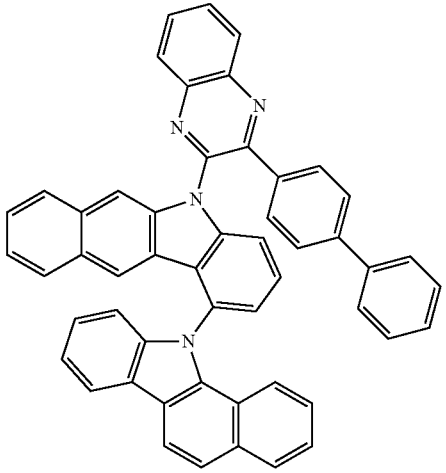

721
-continued
388
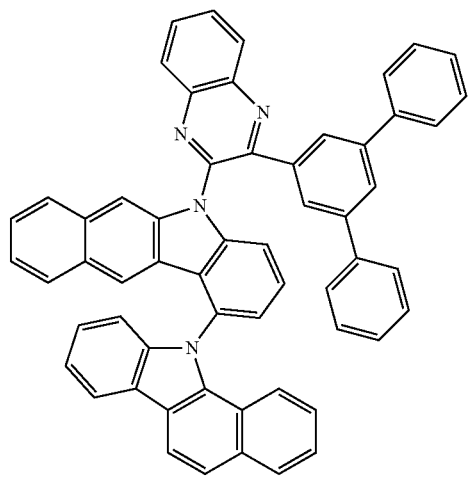
389
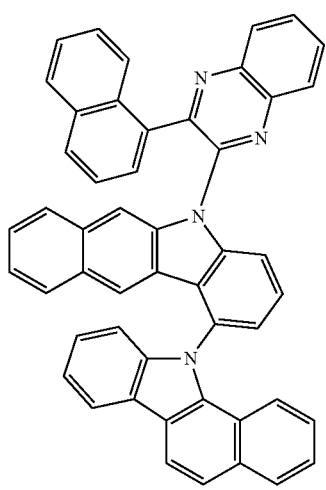
390
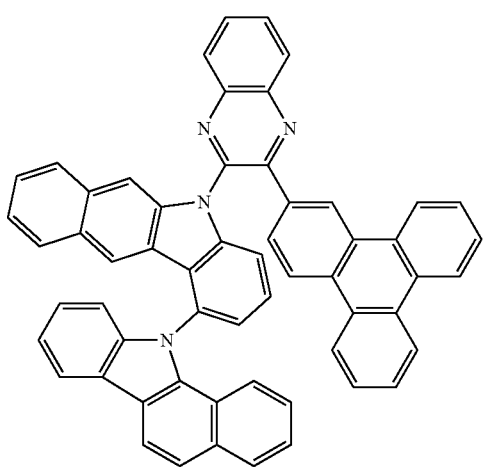
722
-continued
391
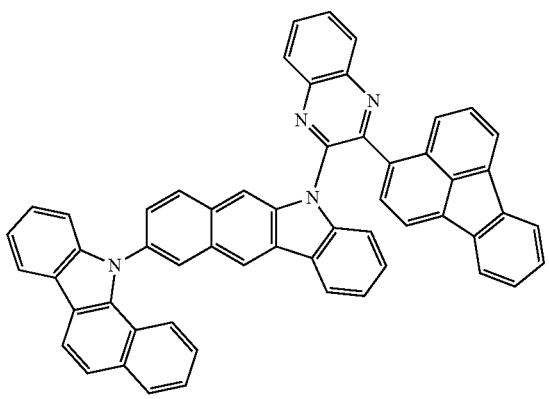
392
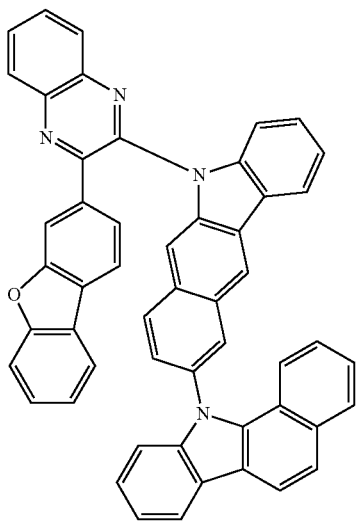
393
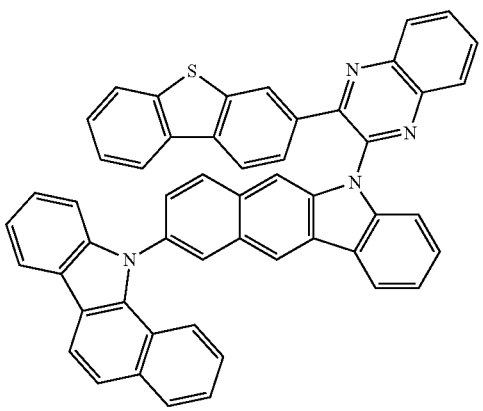

394
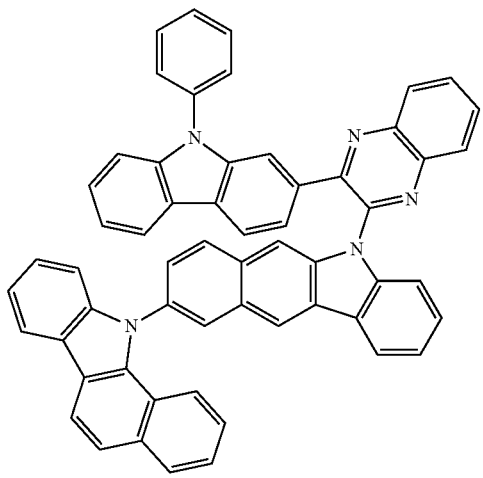
395
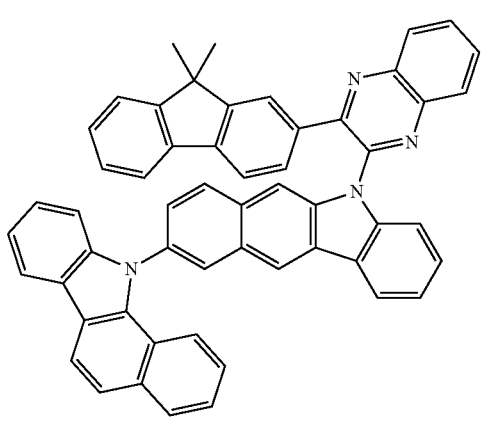
396
397
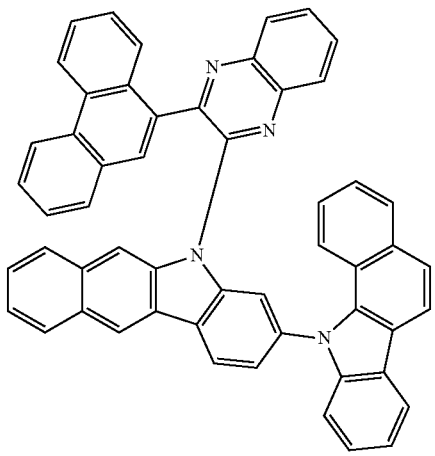
398
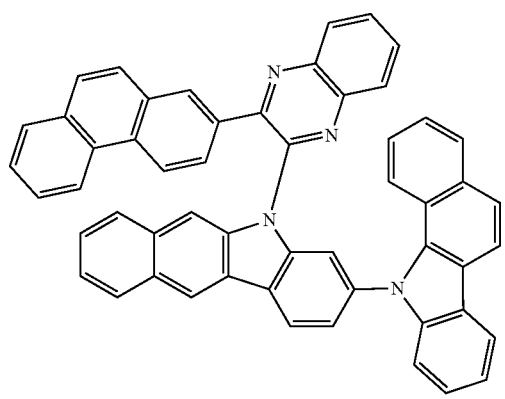
399
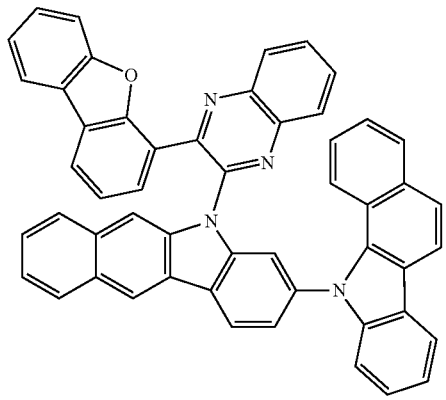
400
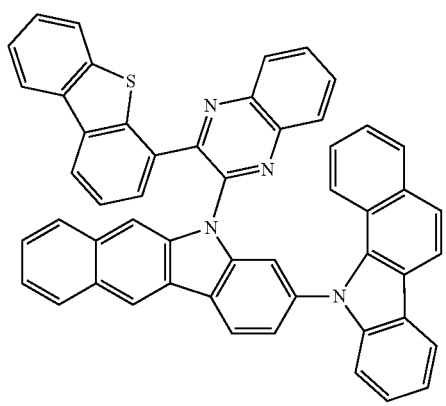

-continued
401
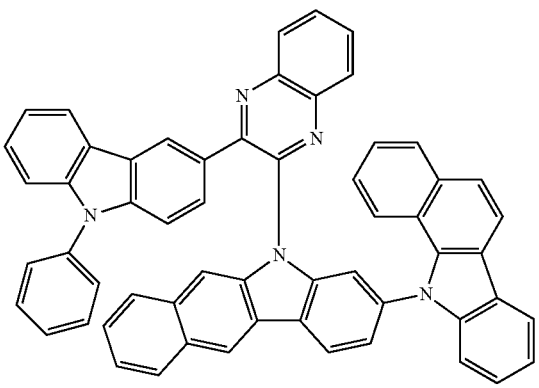
402
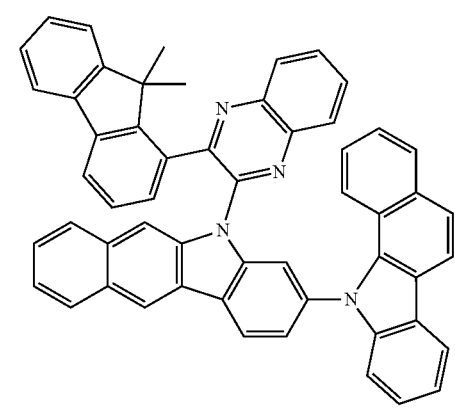
403
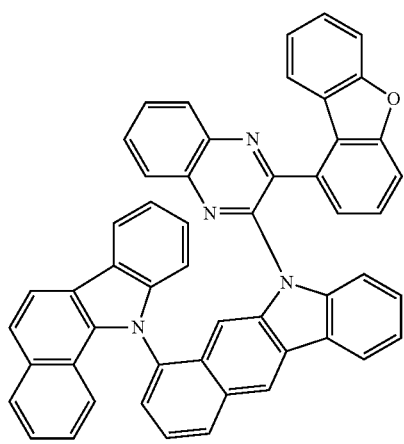
-continued
404
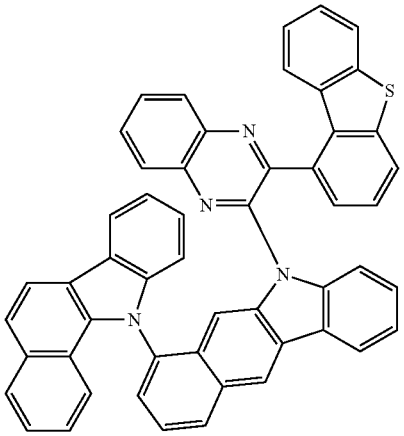
405
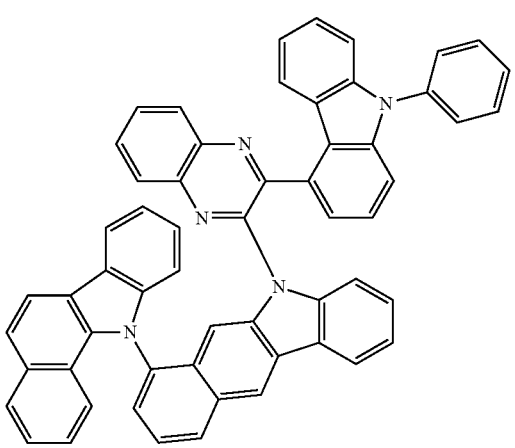
406
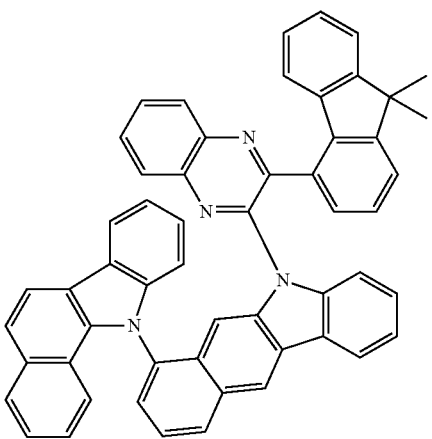

407
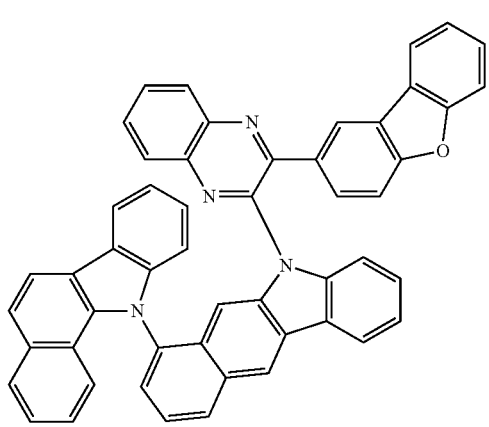
408
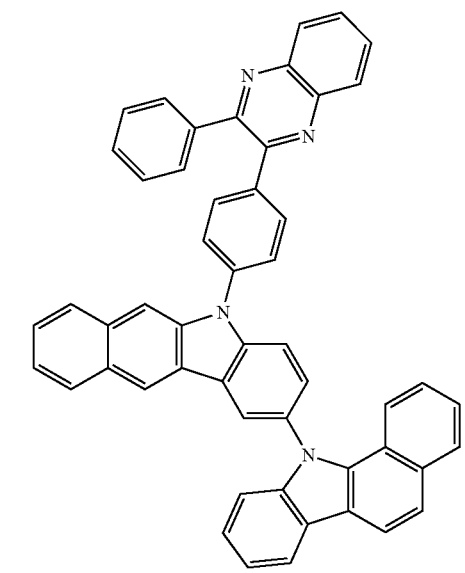
409
410
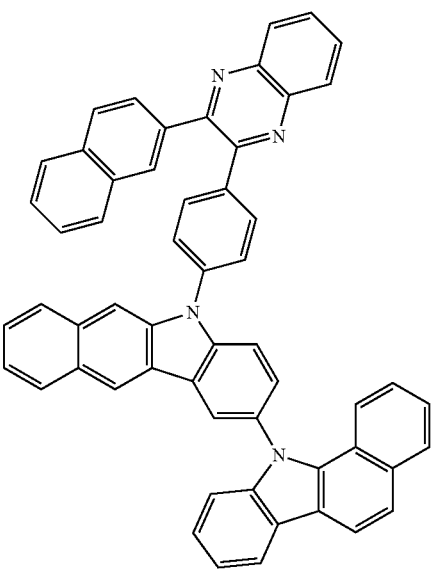
411
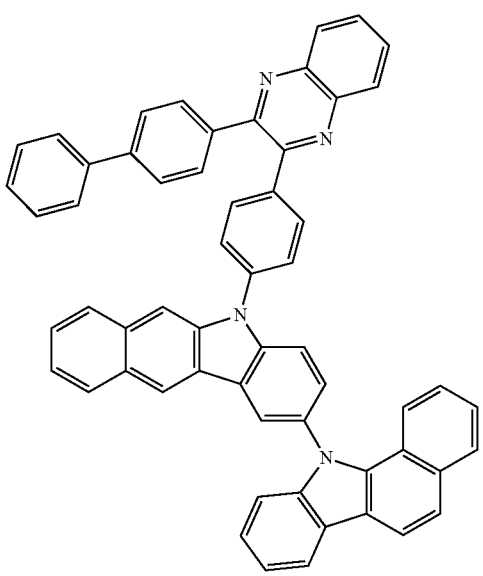

729
-continued
730
-continued
412
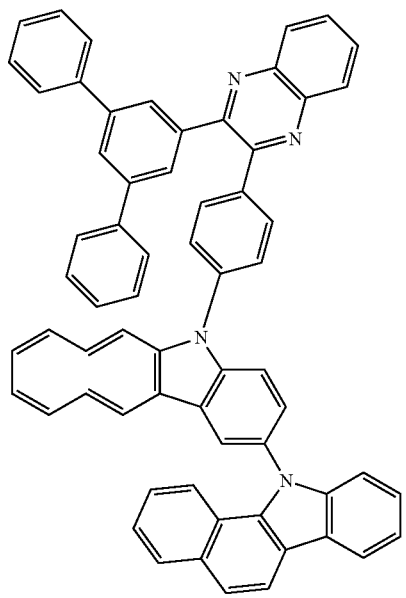
415
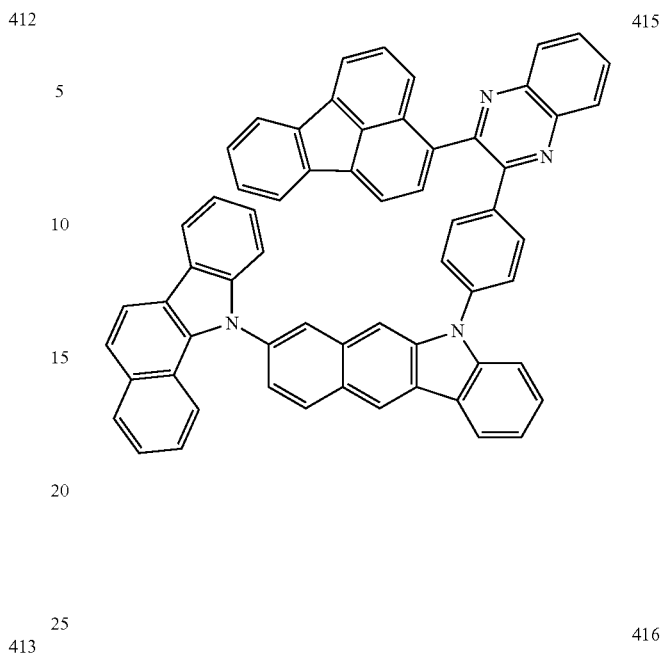
413
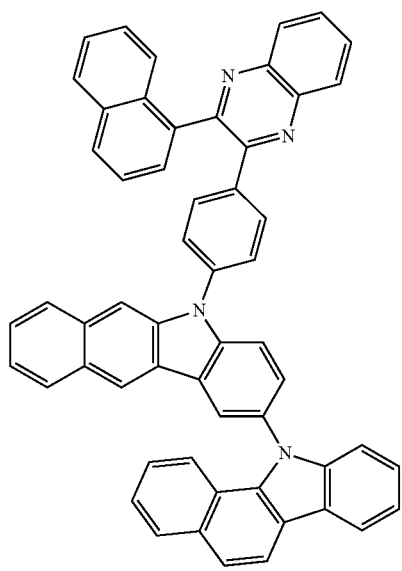
416
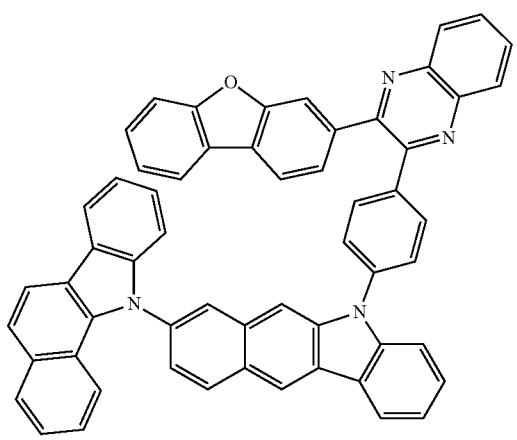
414
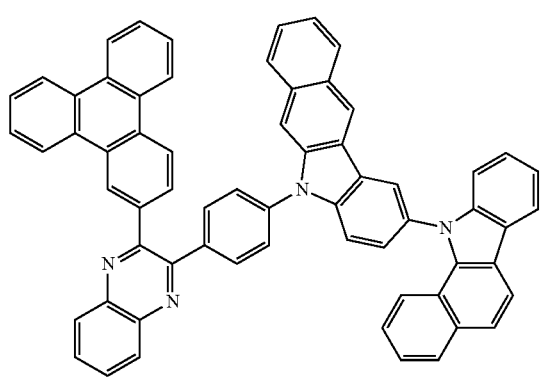
417
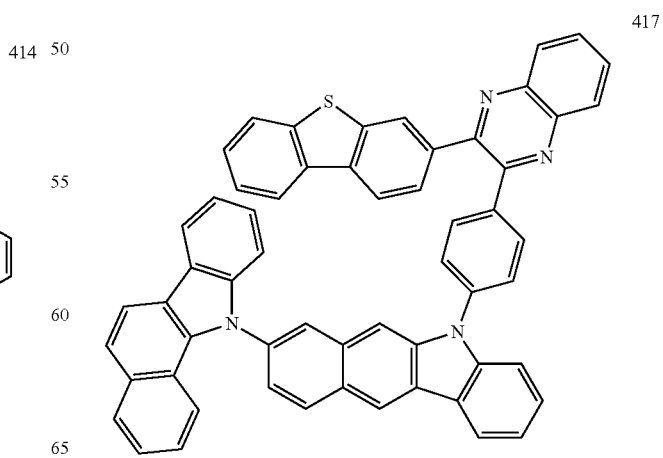

731
-continued
418
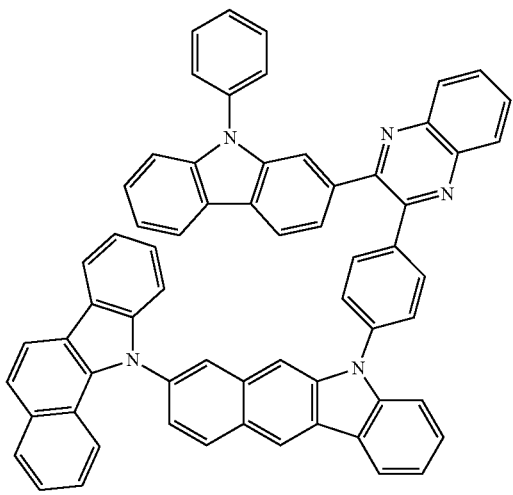
419
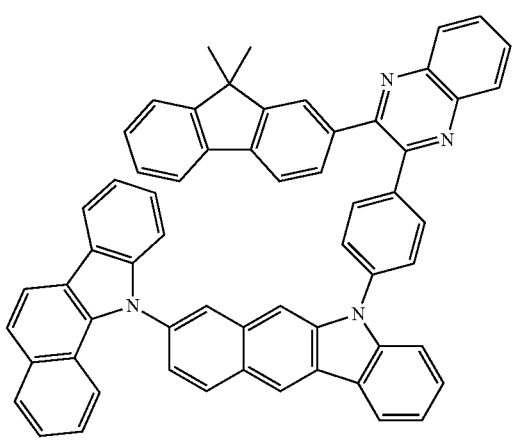
420
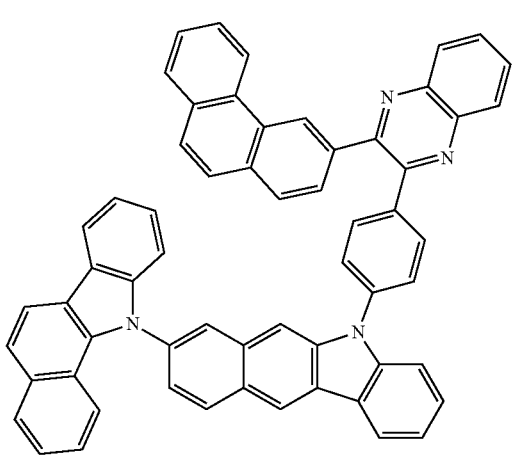
732
-continued
421
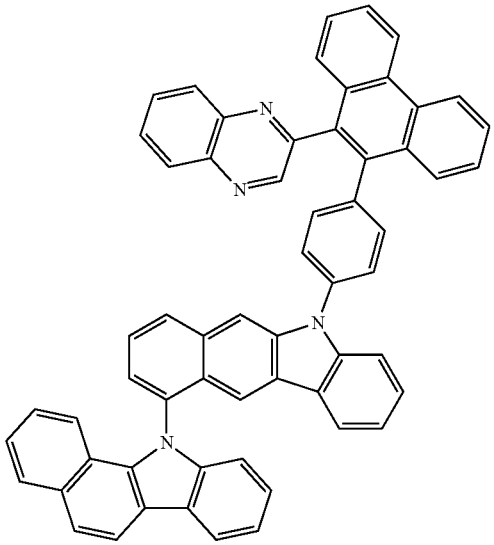
422
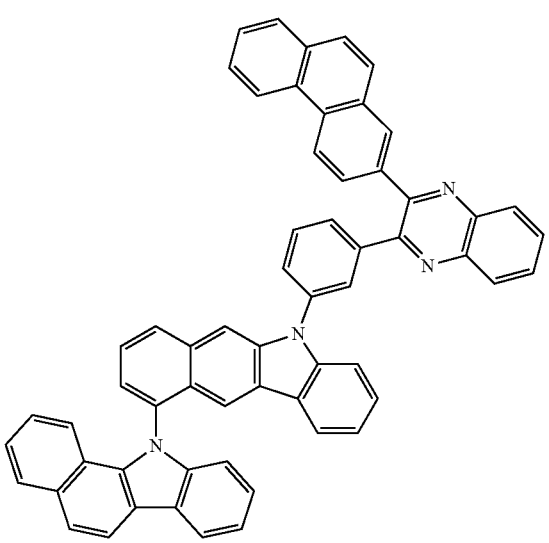
423
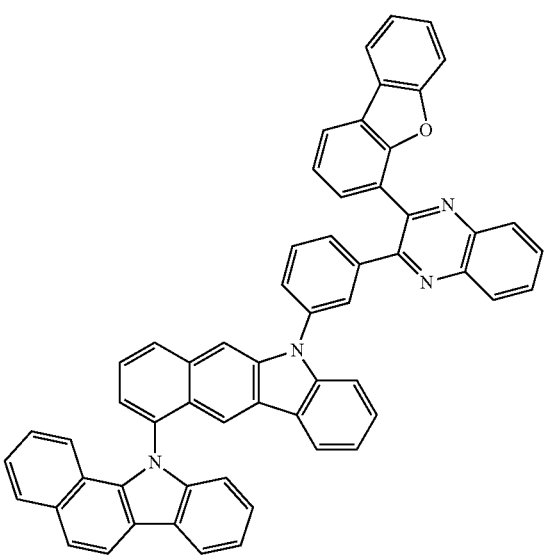

424
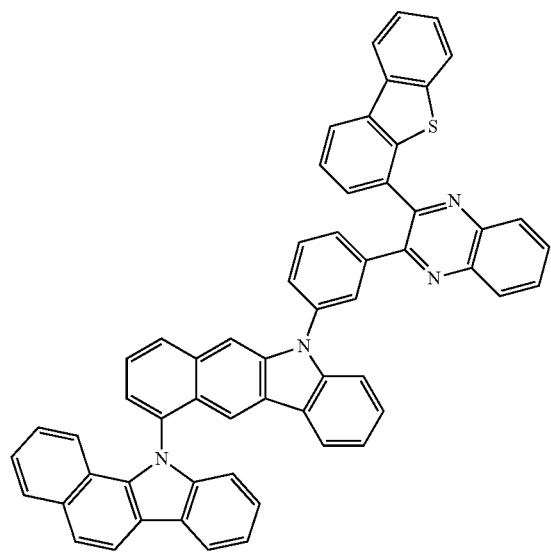
425
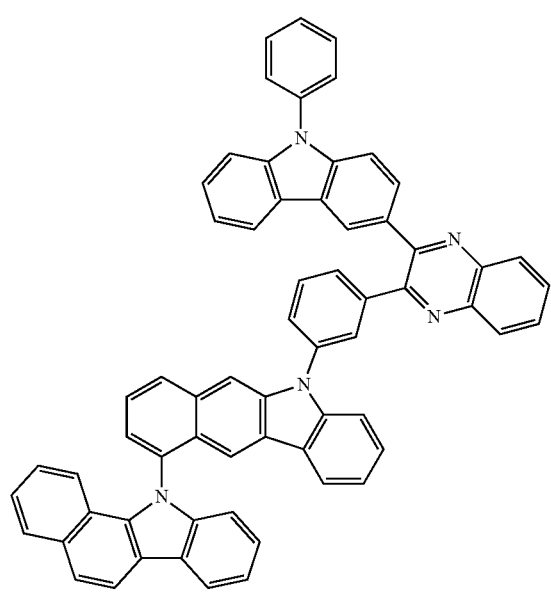
426
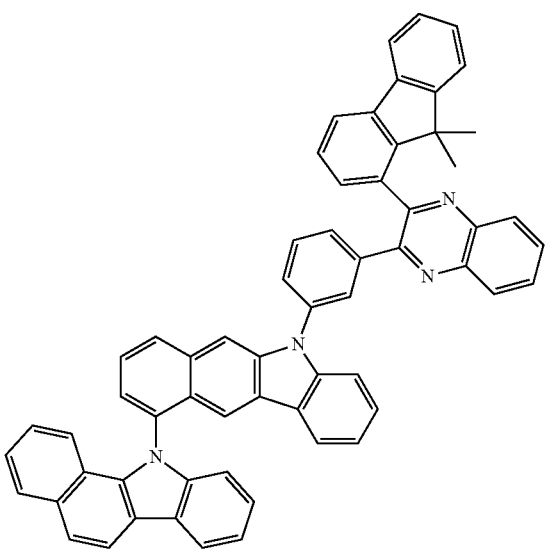
427
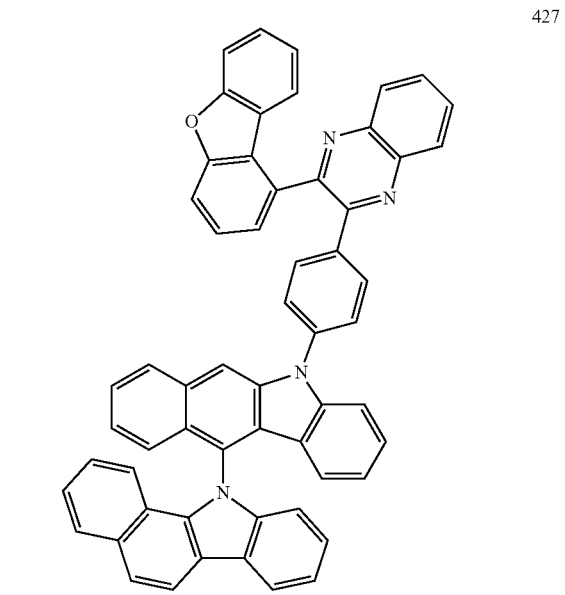

735
-continued
736
-continued
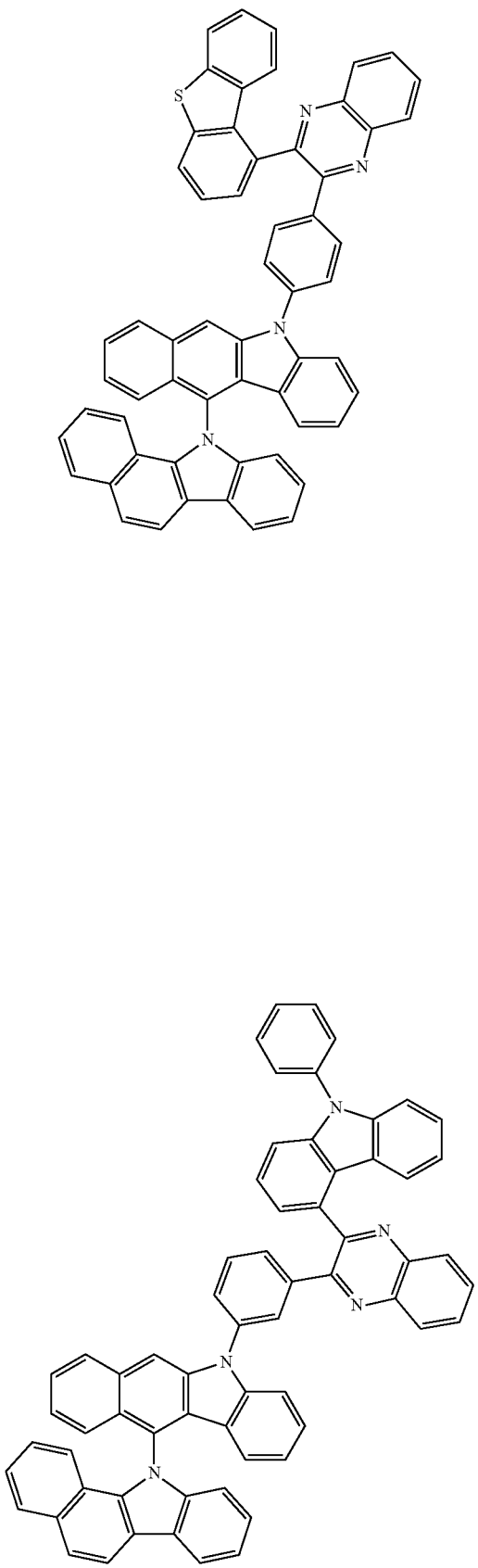
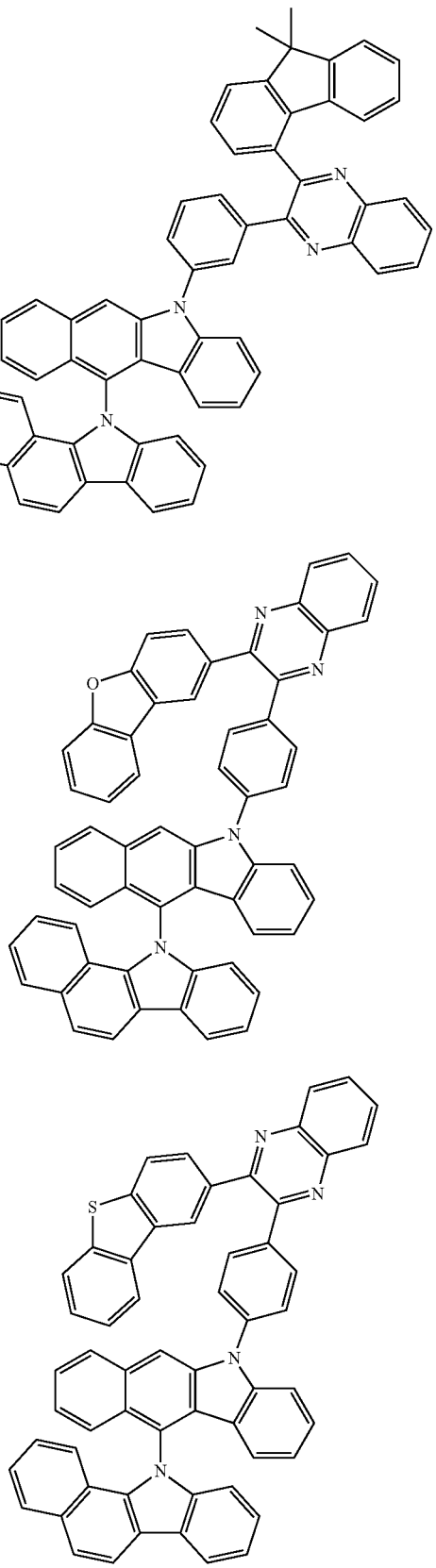

737
-continued
433
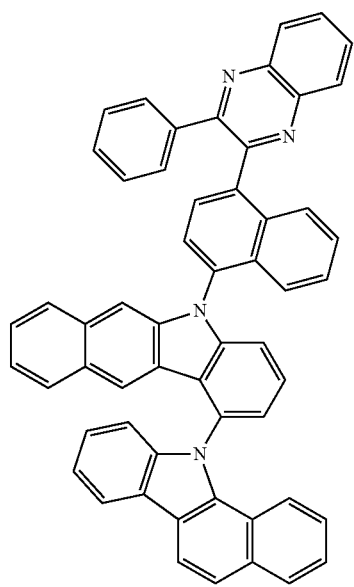
434
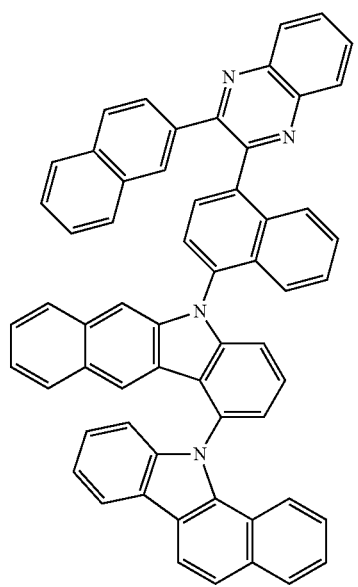
738
-continued
435
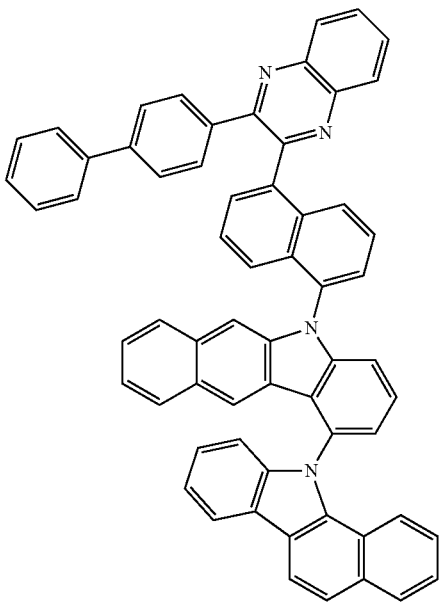
436
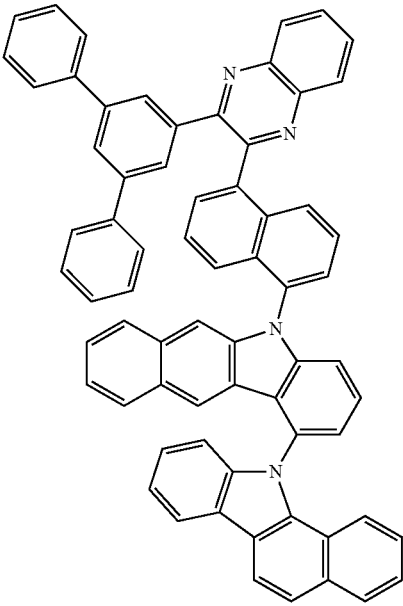

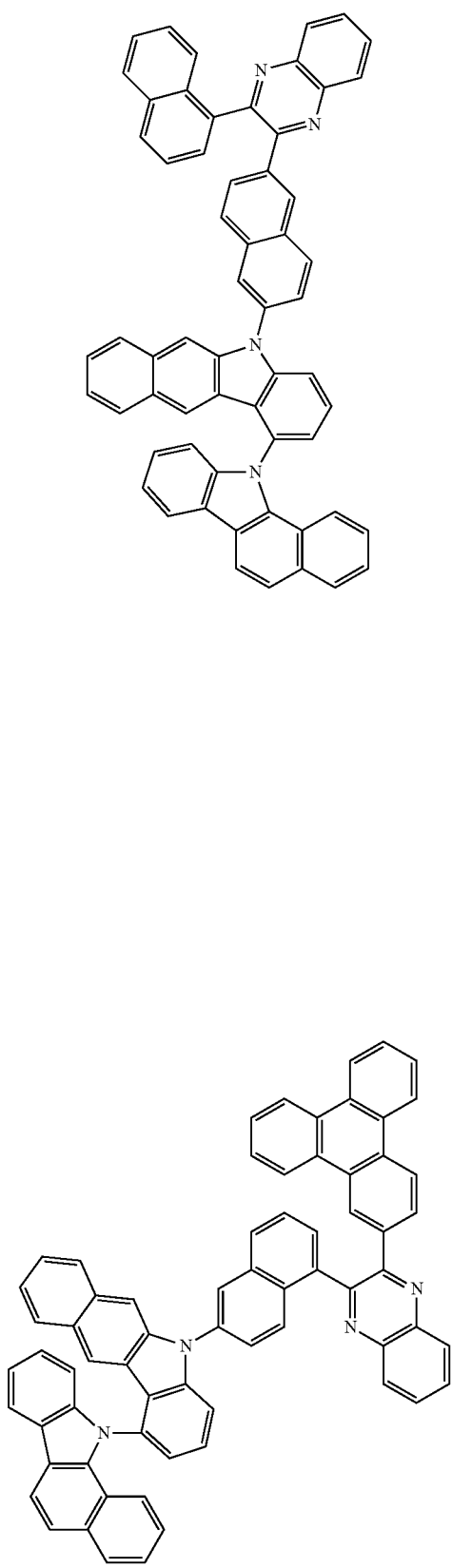
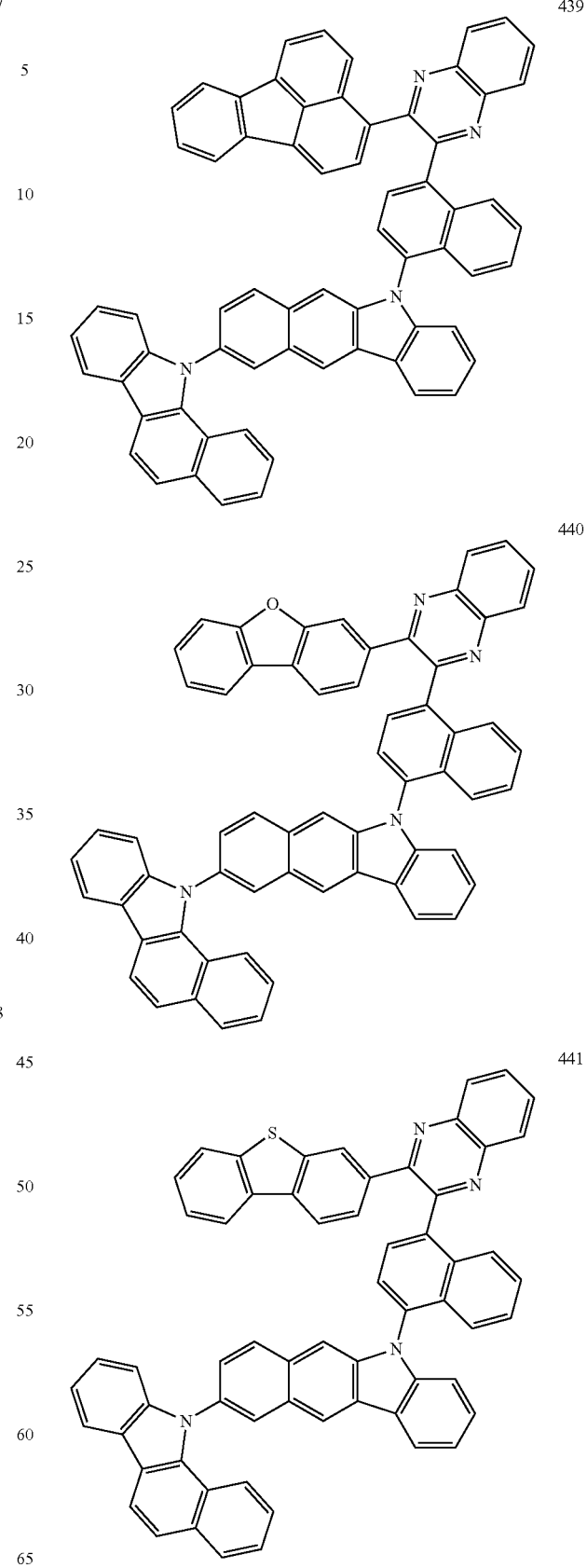

-continued
442
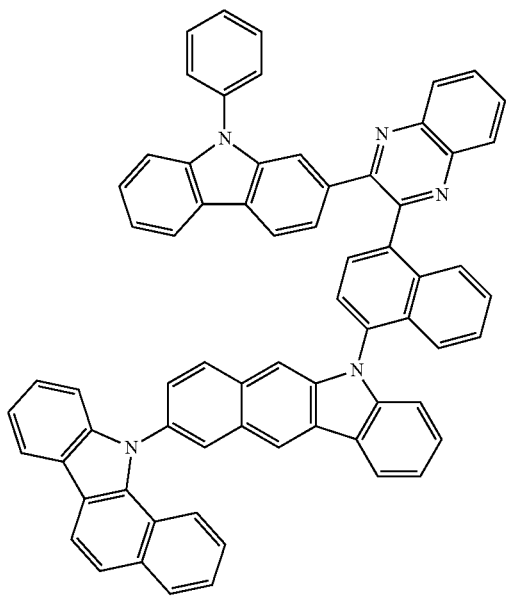
443
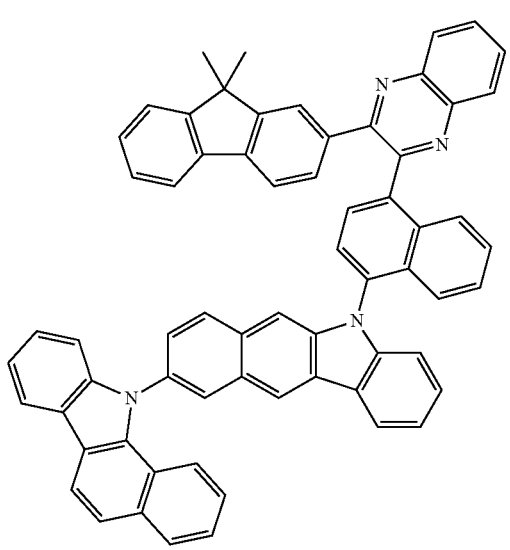
-continued
444
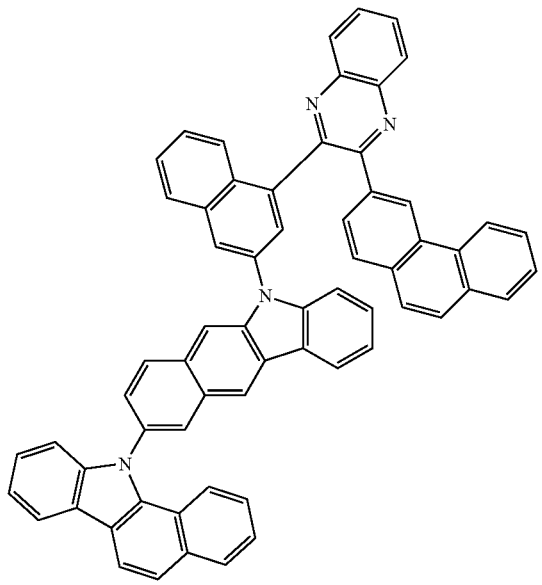
445
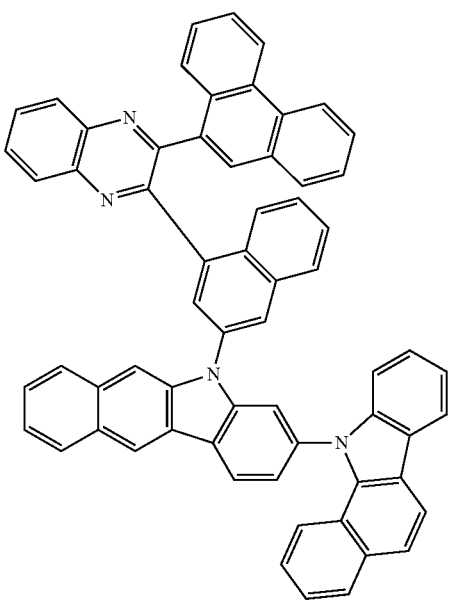

743
-continued
446
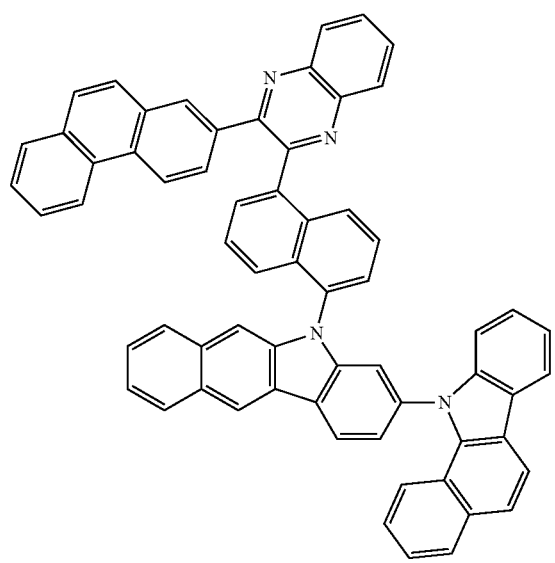
447
744
-continued
448
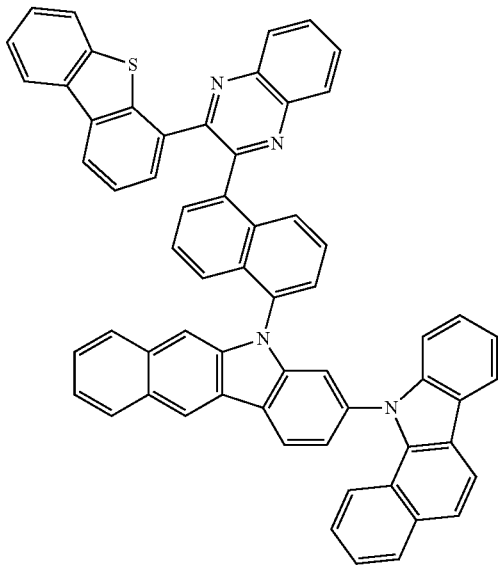
449
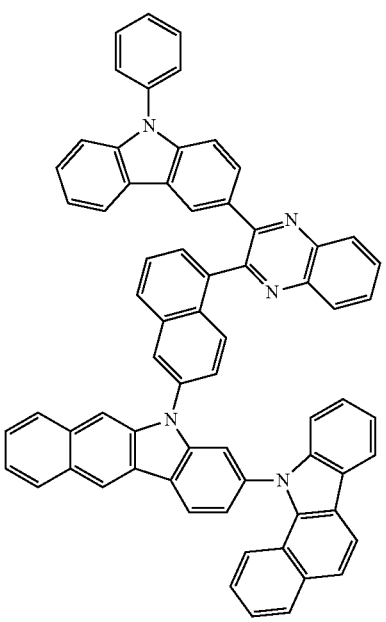

745
-continued
746
-continued
450
452
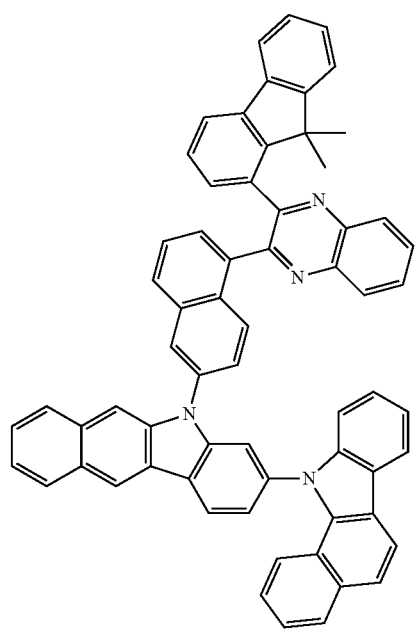
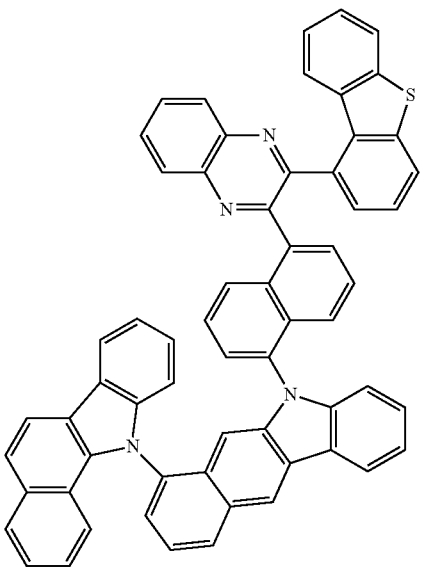
451
453
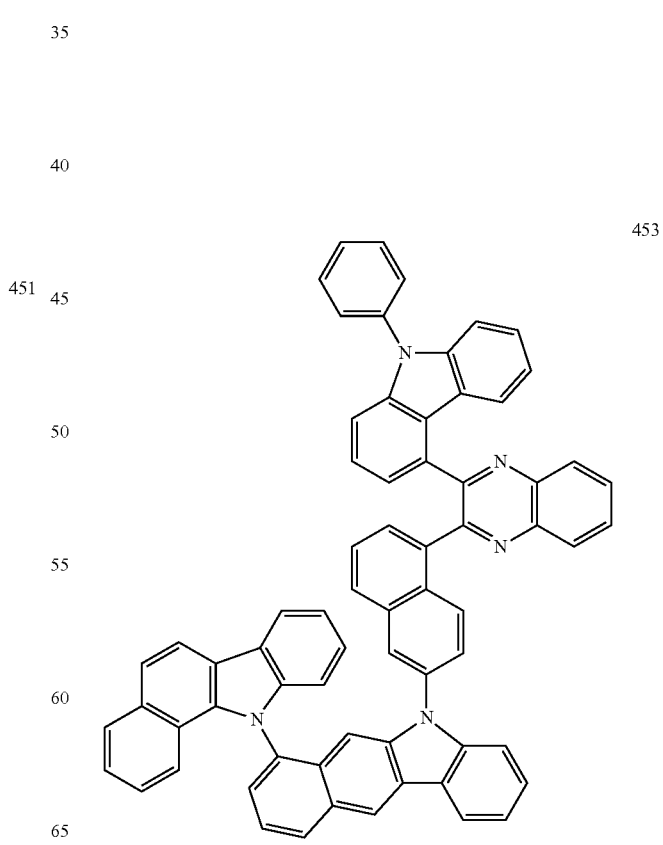

747
-continued
454
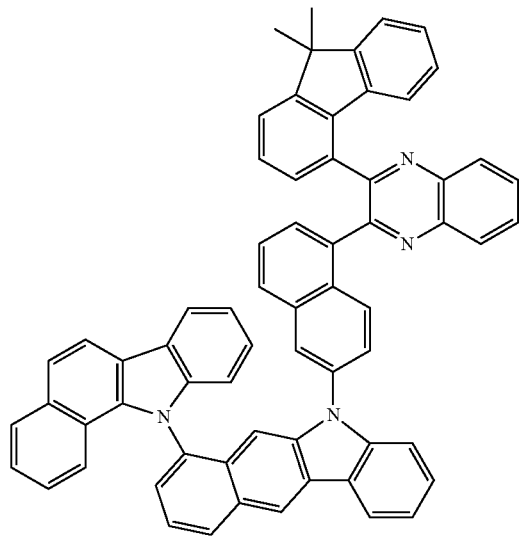
455
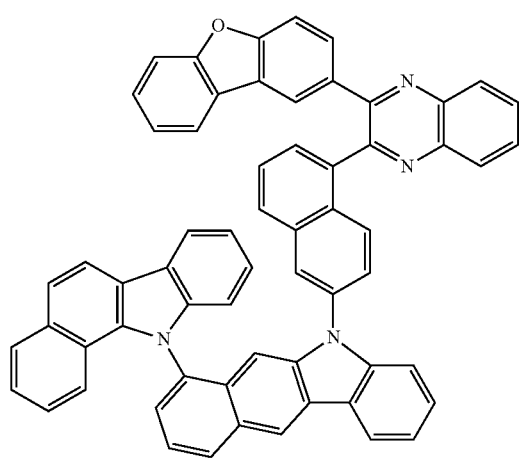
456
748
-continued
457
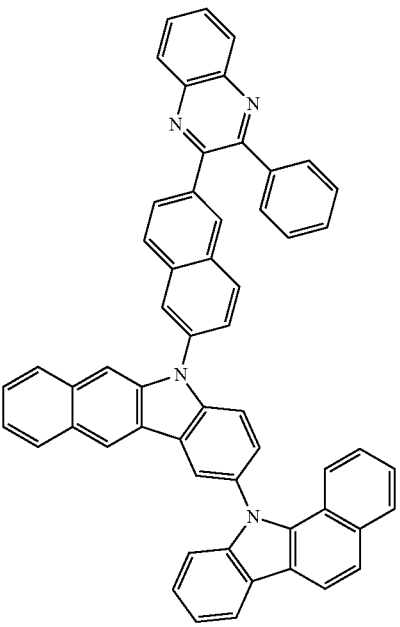
458
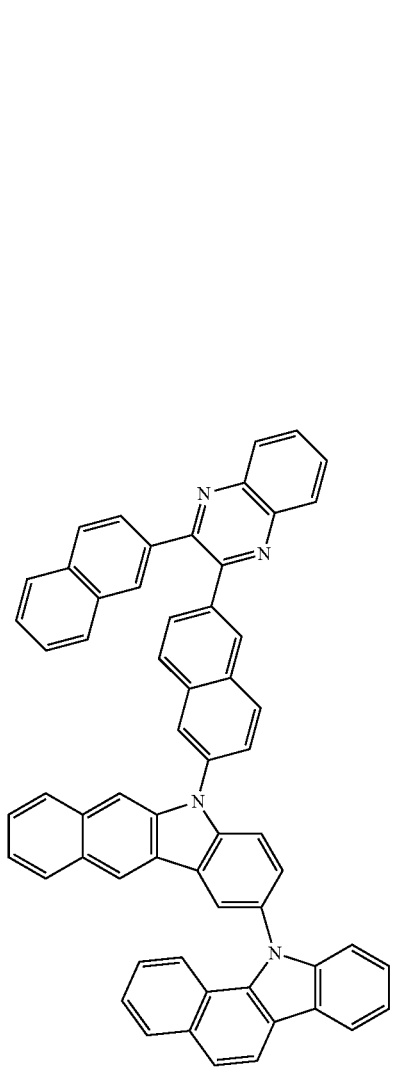

749
-continued
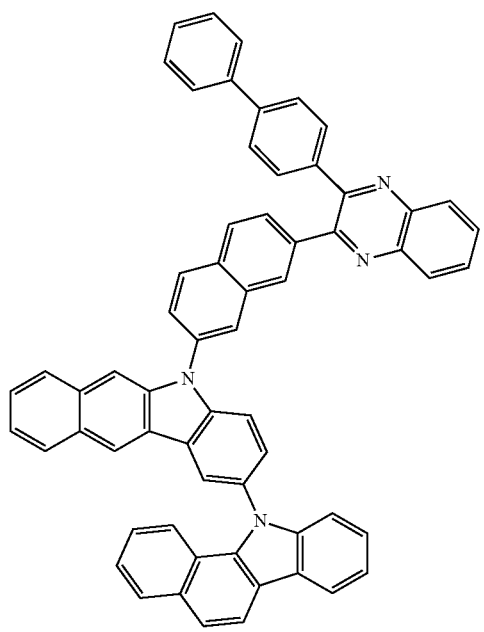
459
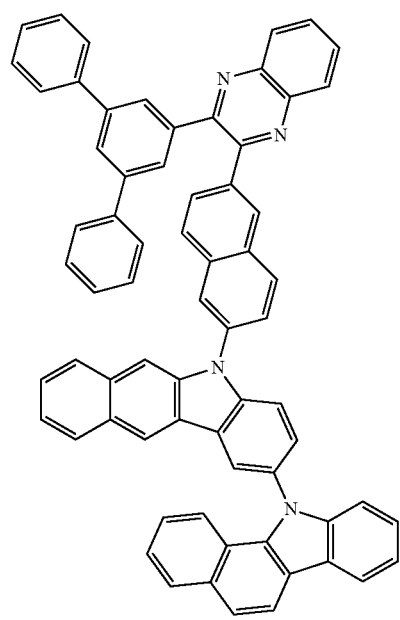
460
750
-continued
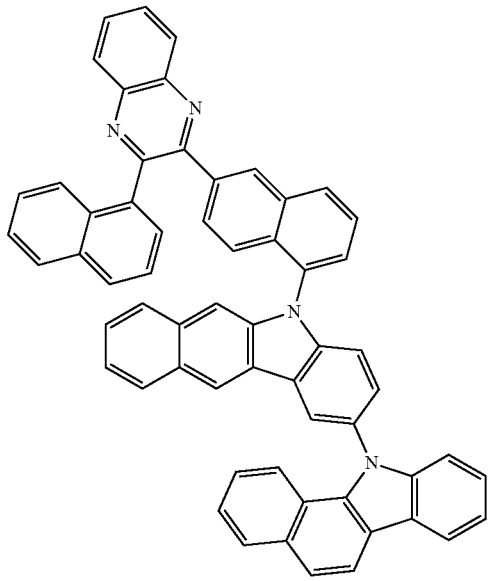
461
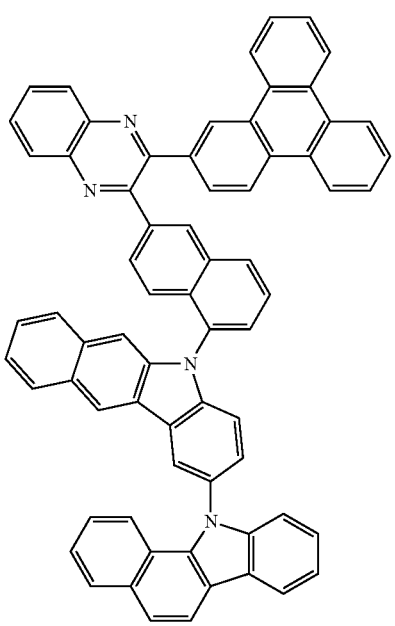
462

751
-continued
752
-continued
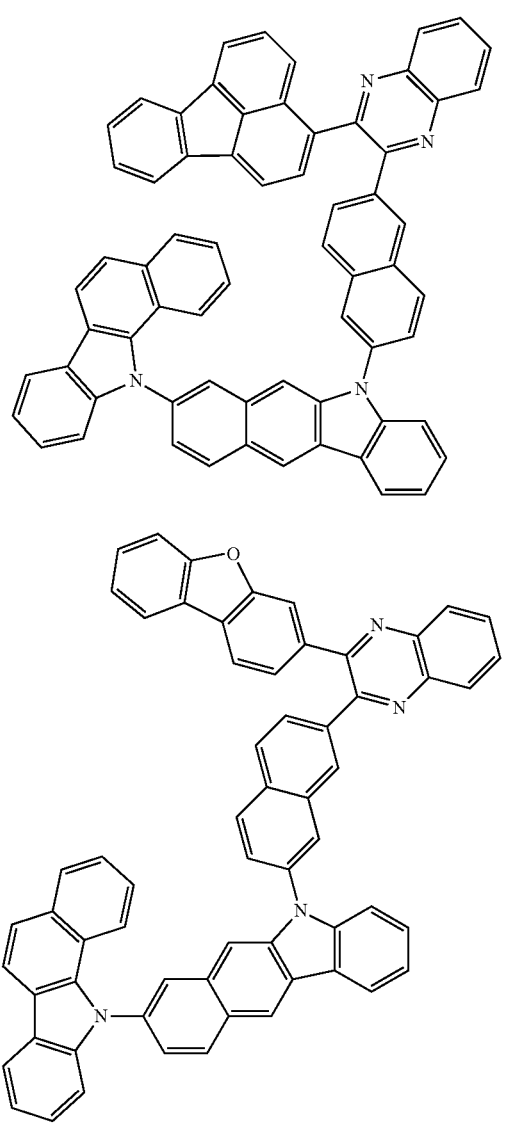
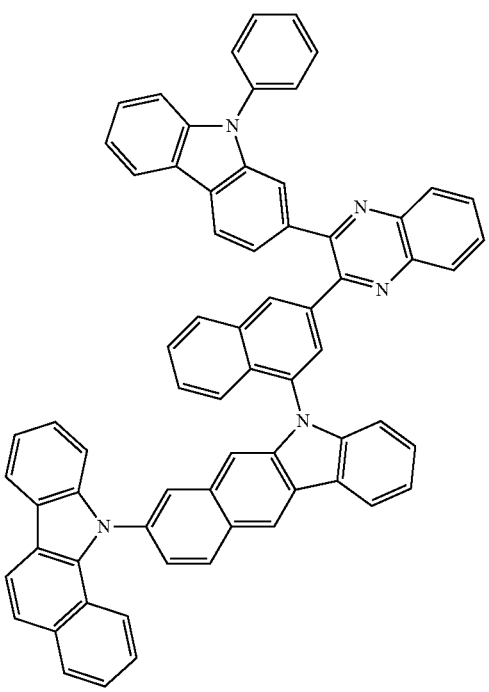

753
-continued
468
469
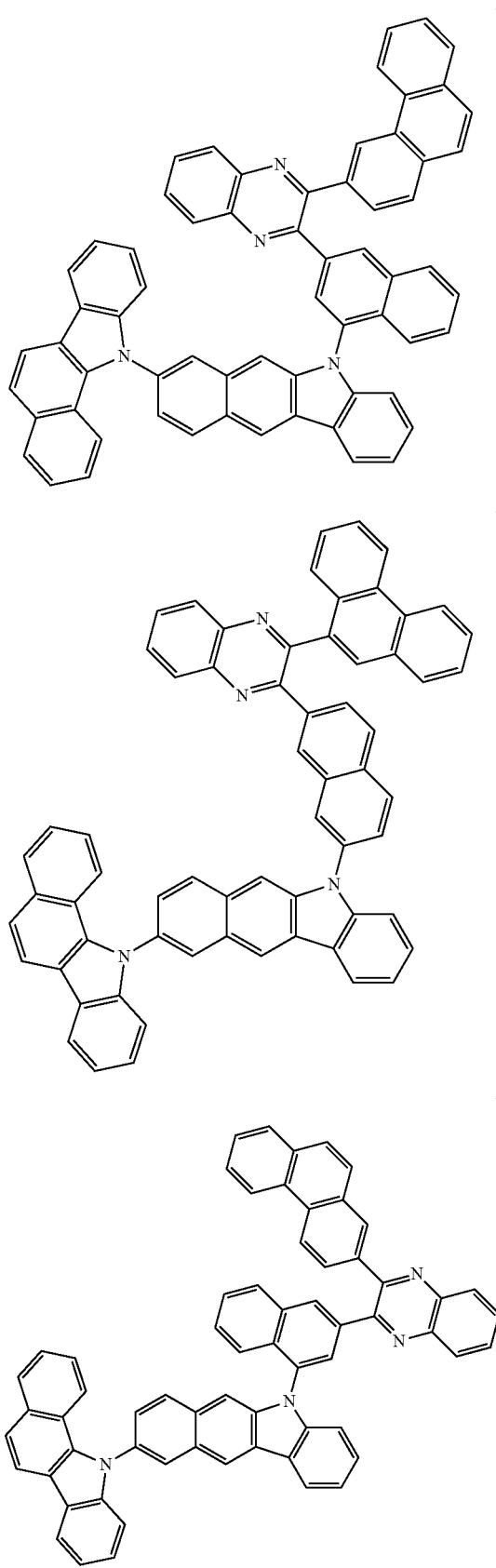
754
-continued
471
472
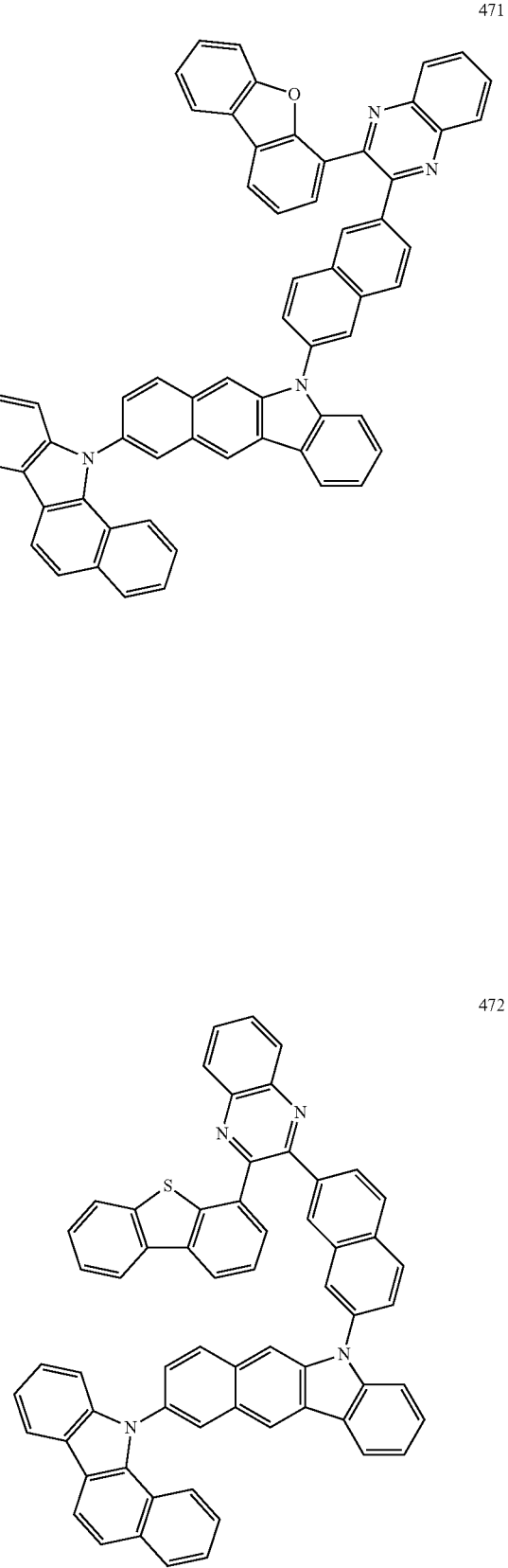

755
-continued
473
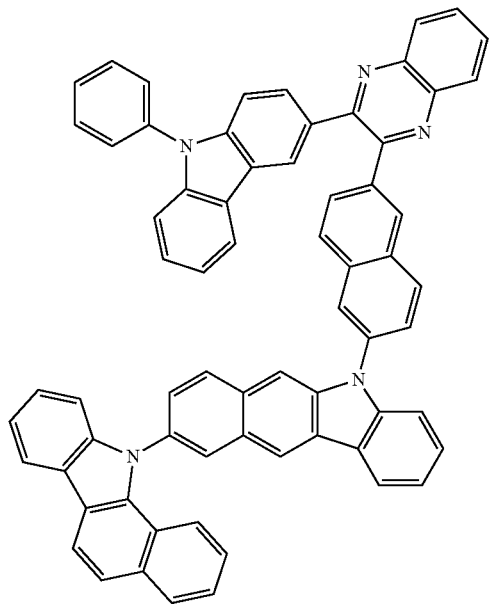
756
-continued
475
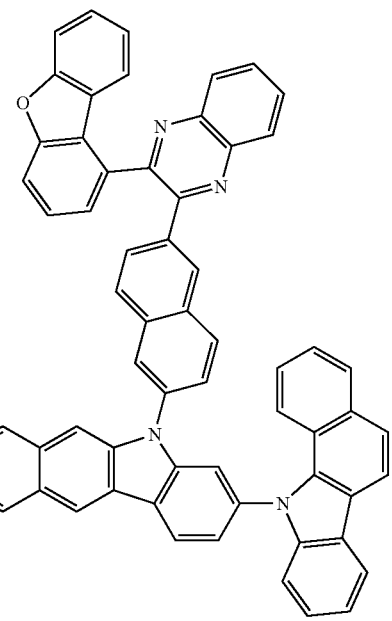
474
476
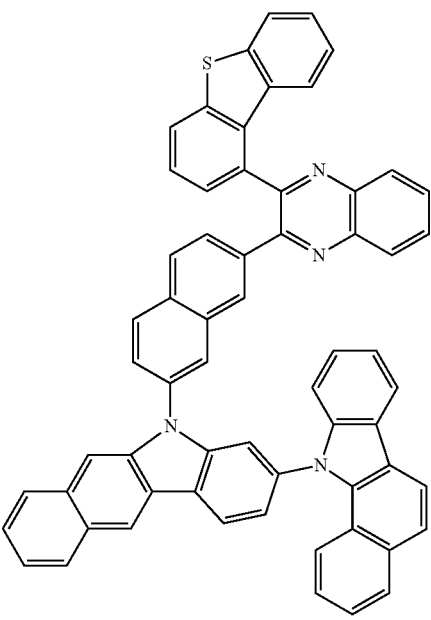

477
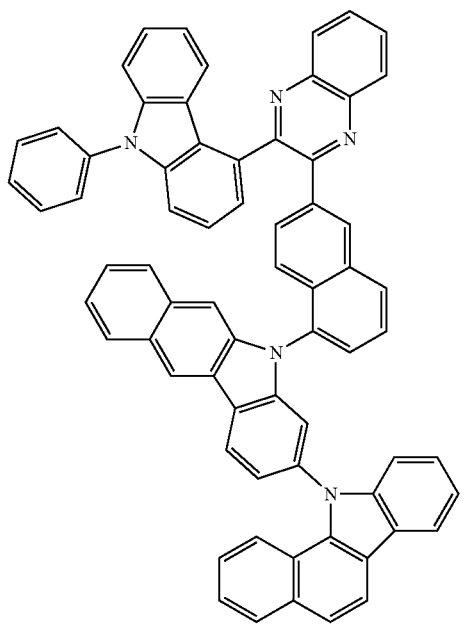
478
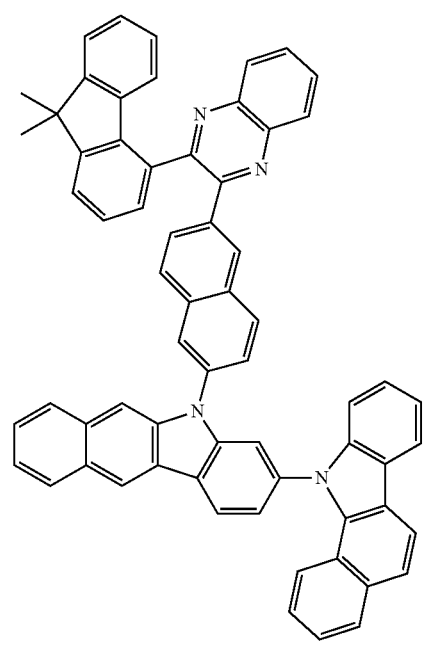
479
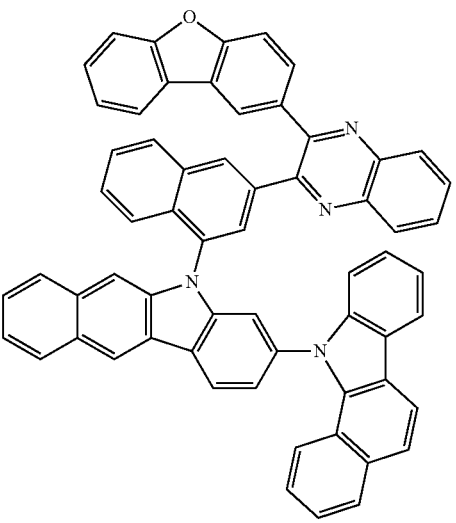
480
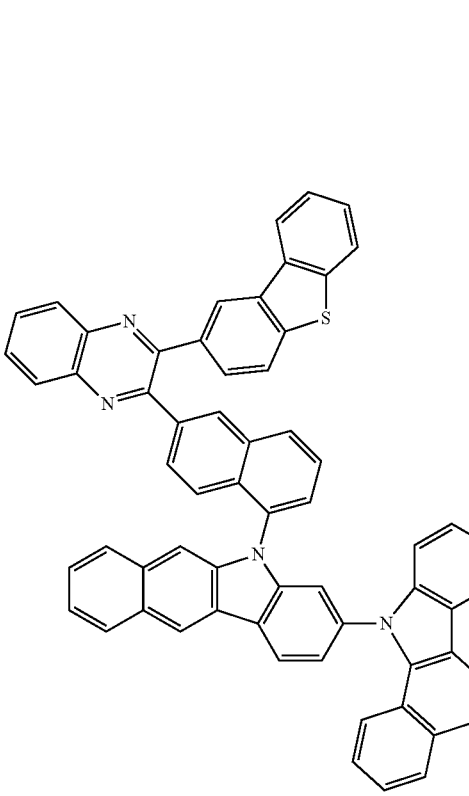

759
-continued
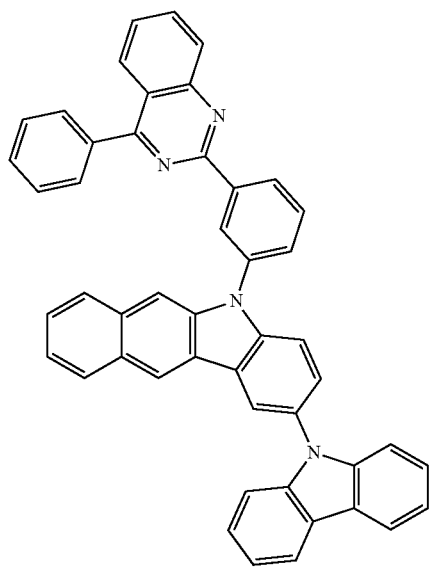
481
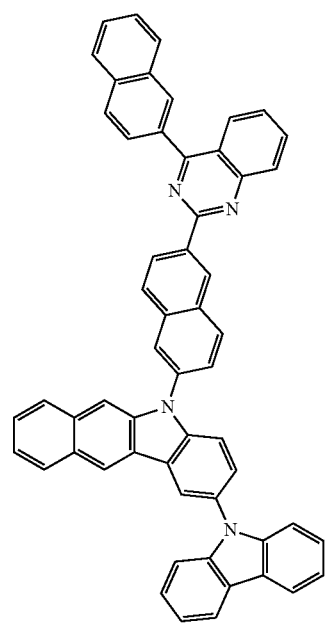
482
760
-continued
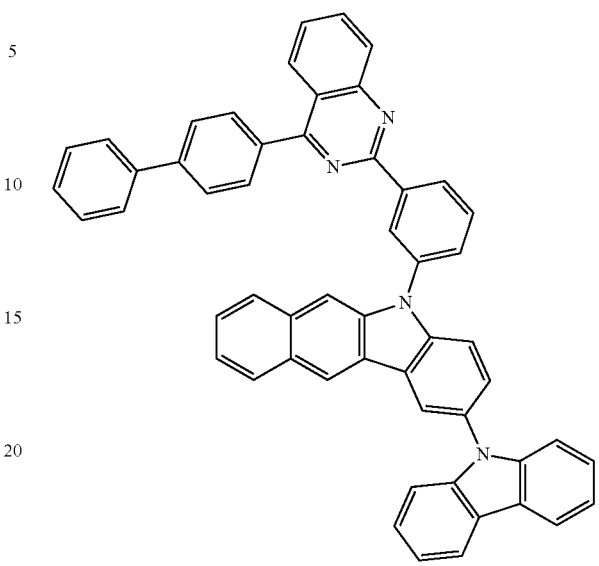
483
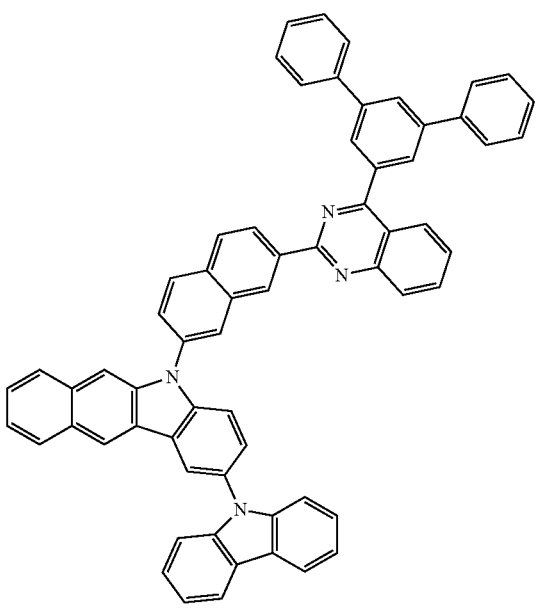
484

761
-continued
485
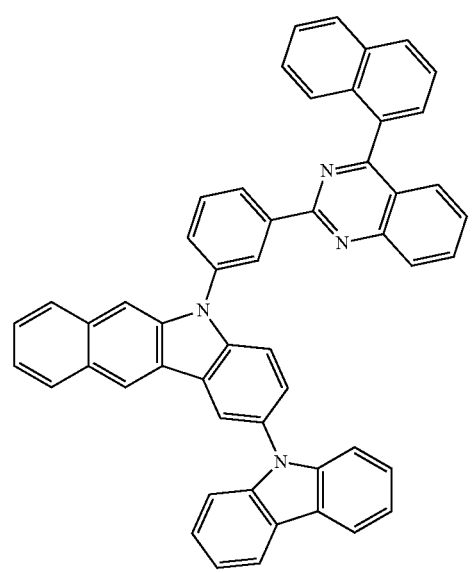
486
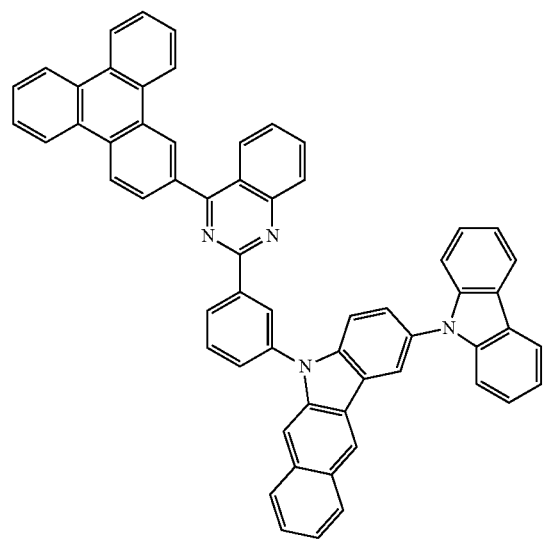
762
-continued
487
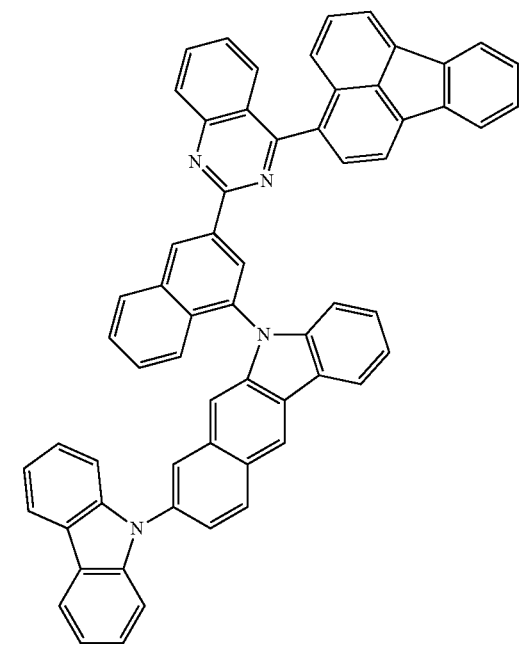
488
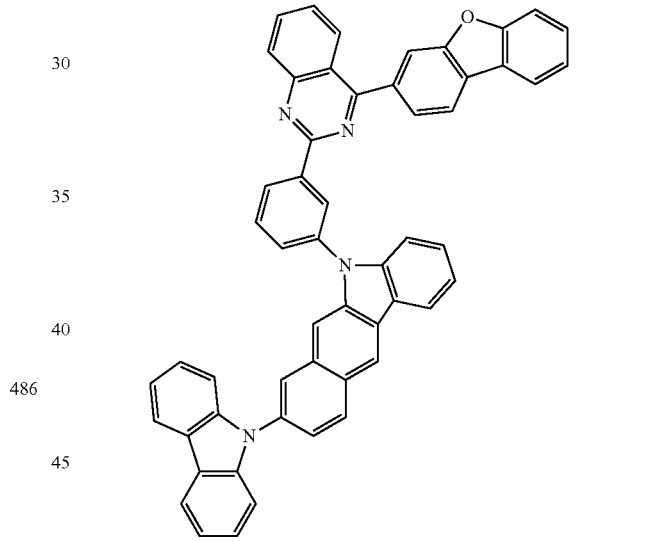
489
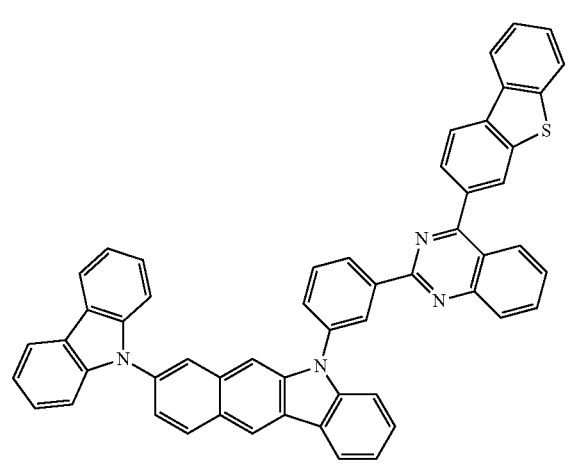

-continued
490
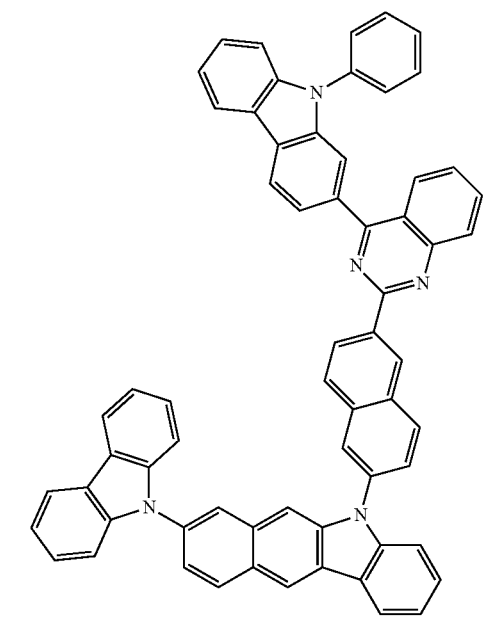
491
494
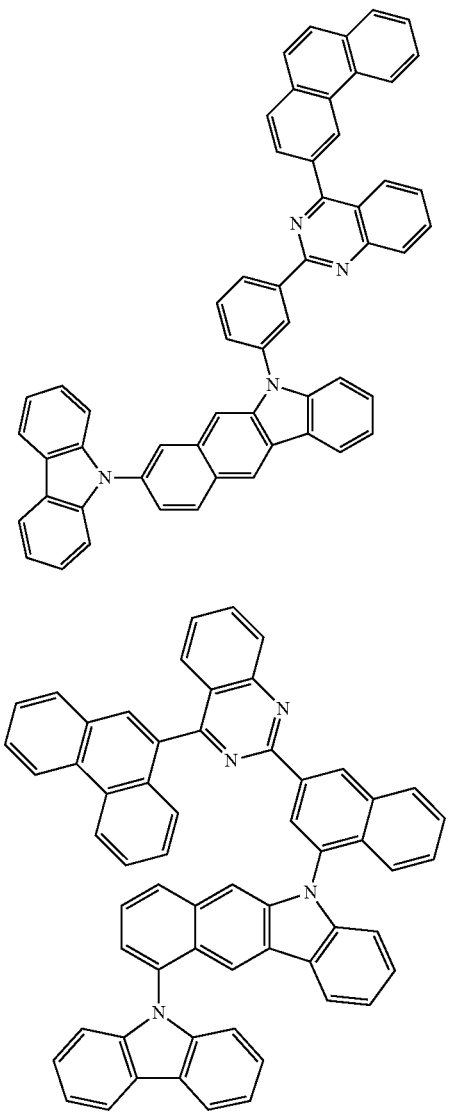

765
-continued
495
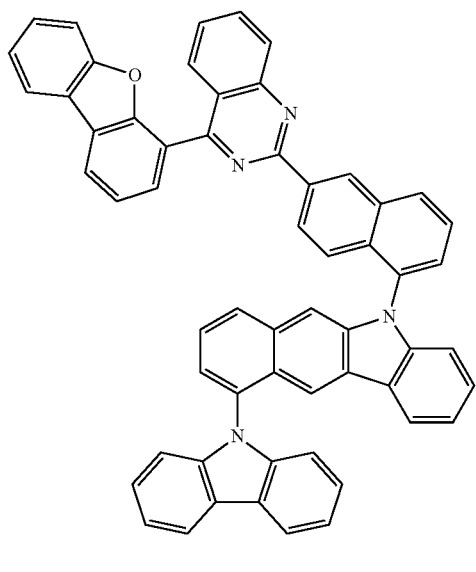
496
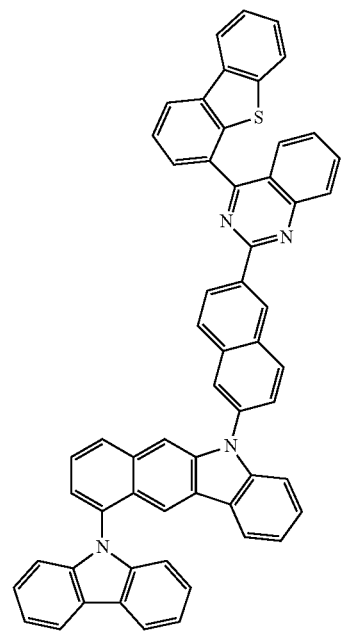
766
-continued
497
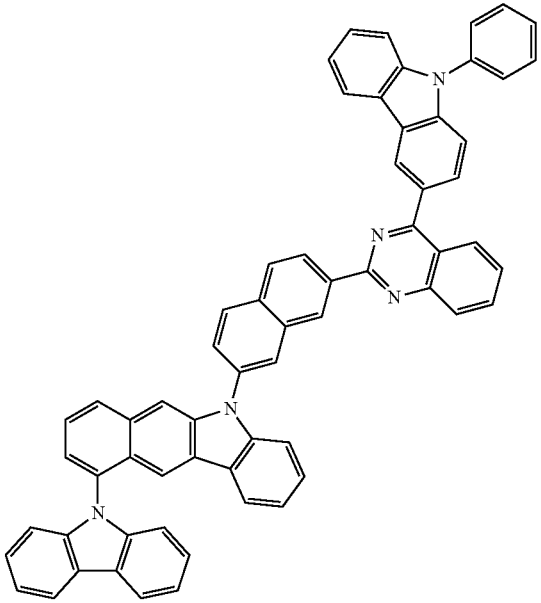
498
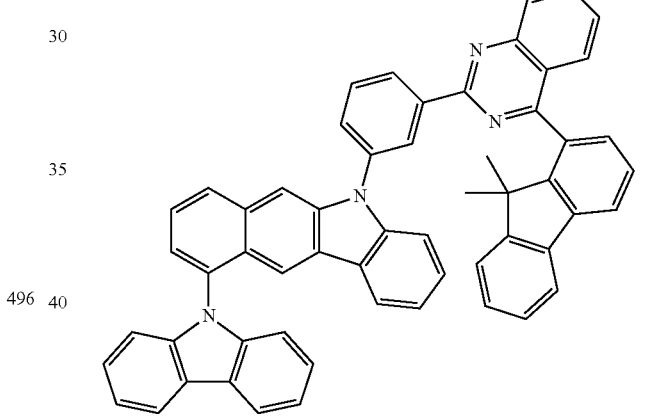
499
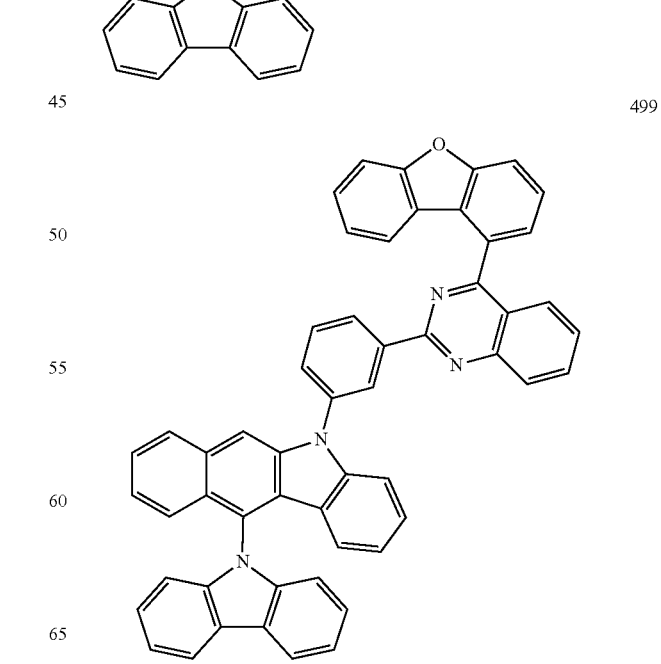

767
-continued
500
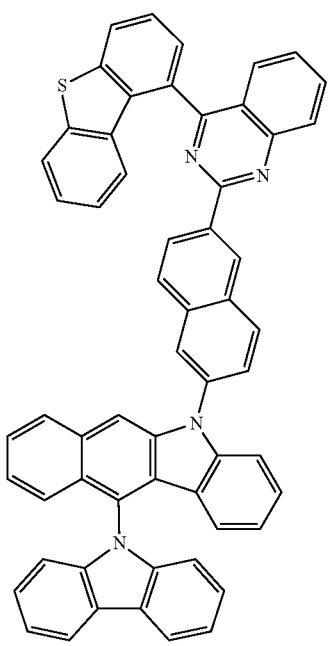
502
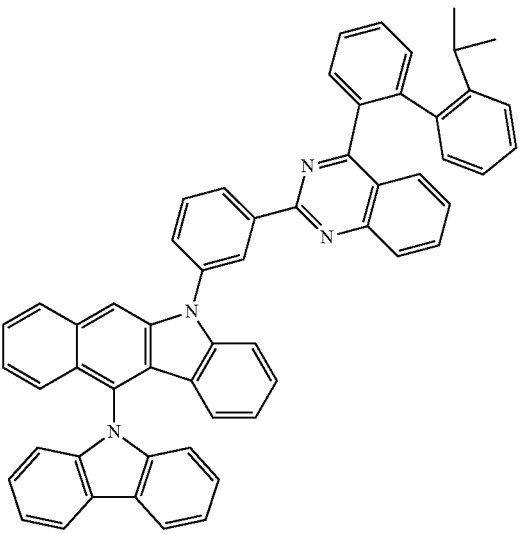
501
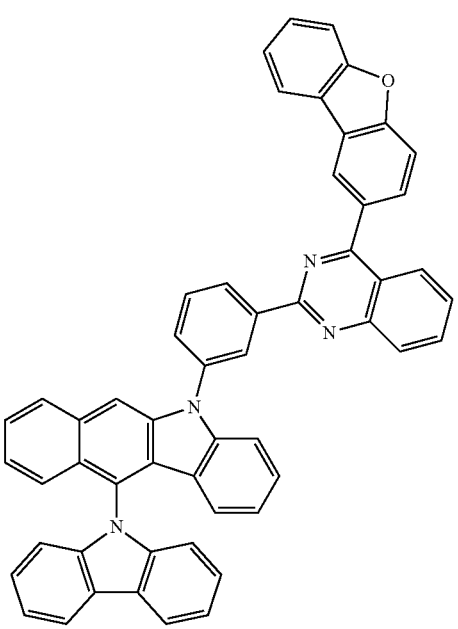
768
-continued
503

769
-continued
504
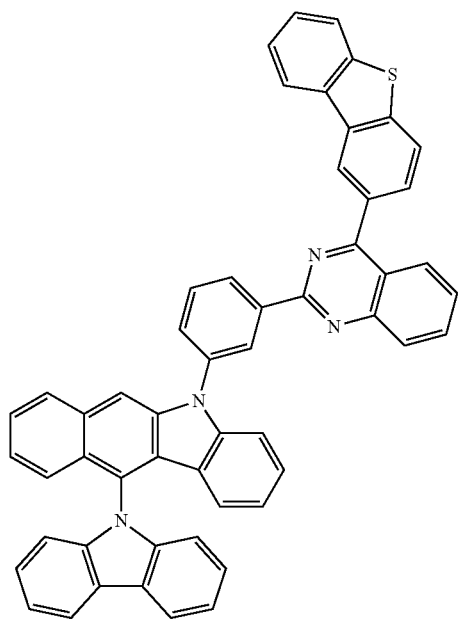
770
-continued
506
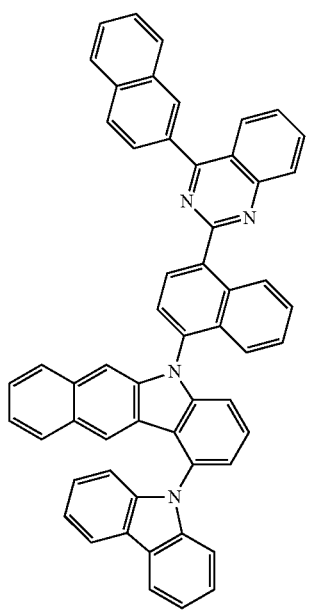
505
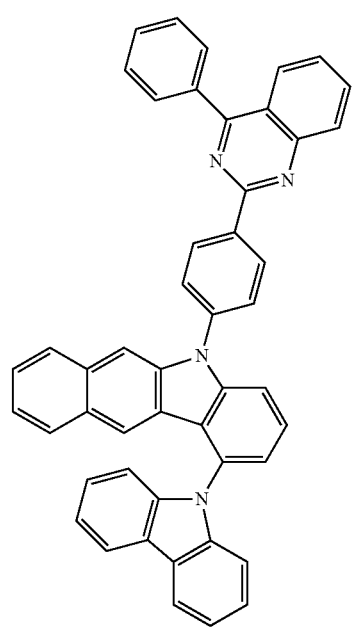
507
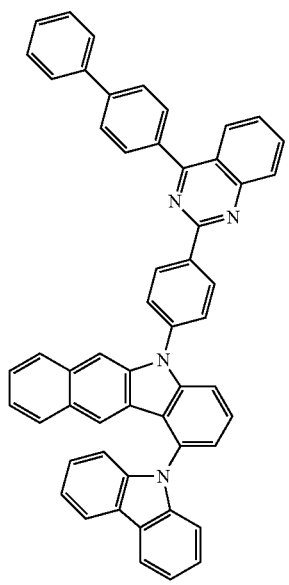

771
-continued
508
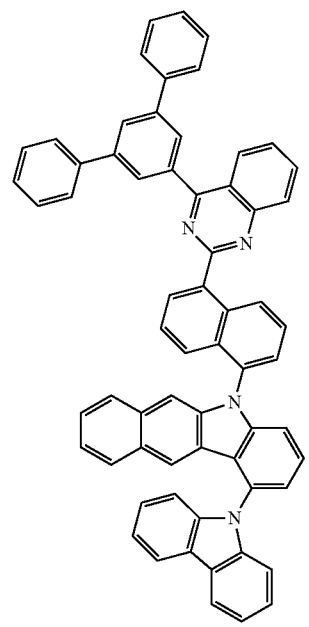
509
772
-continued
510
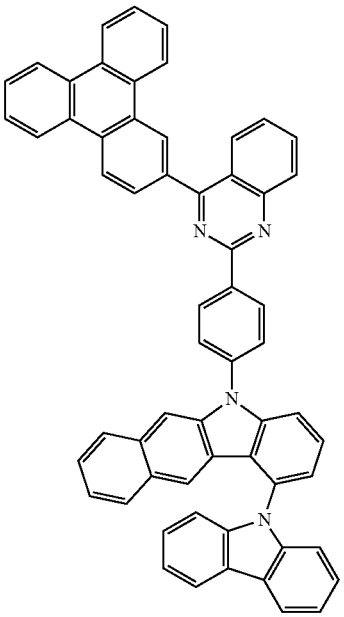
511
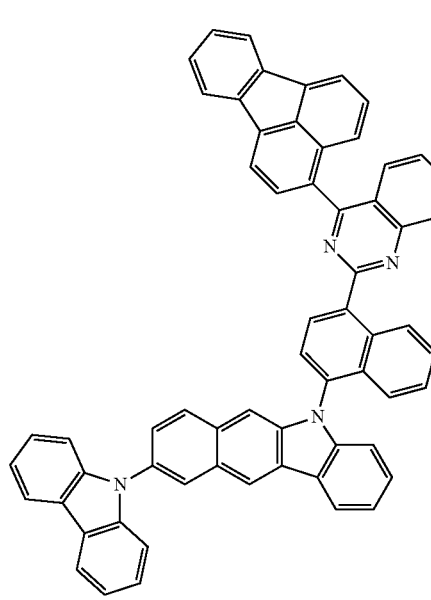

773
-continued
512
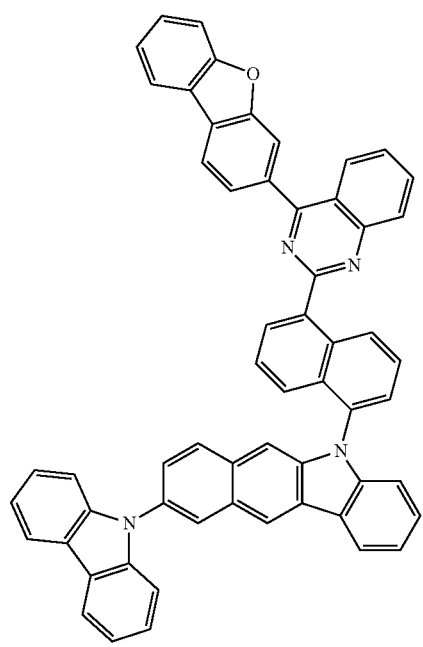
774
-continued
514
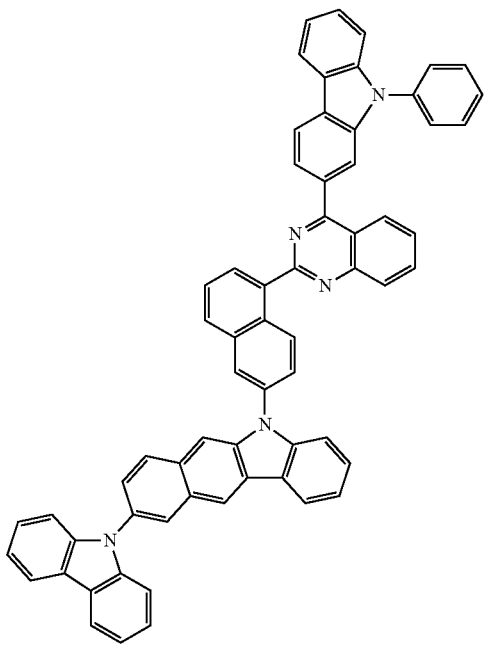
513
515
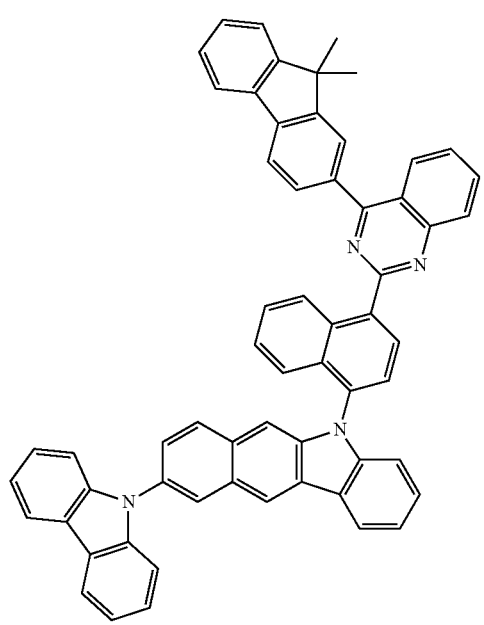

775
-continued
776
-continued
516
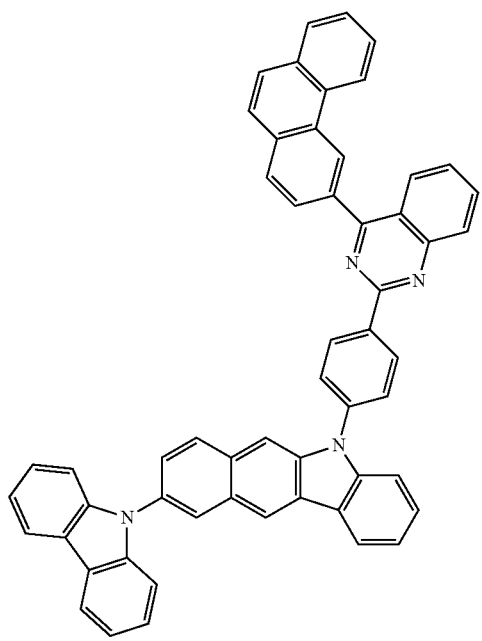
518
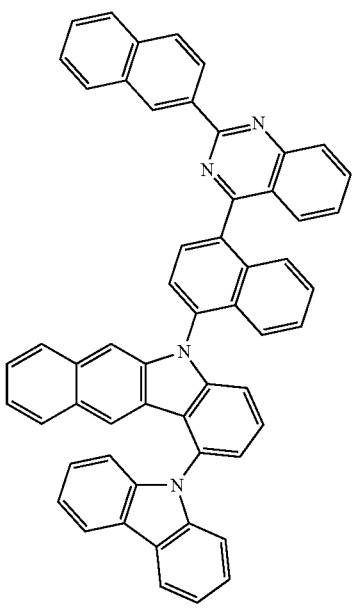
517
519
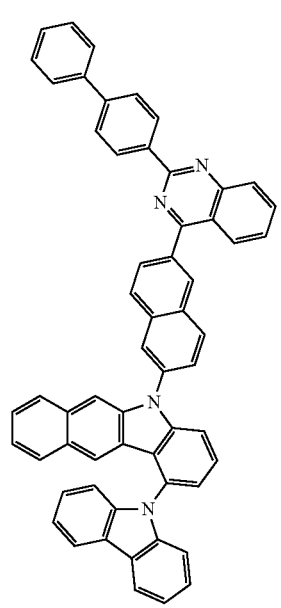

520
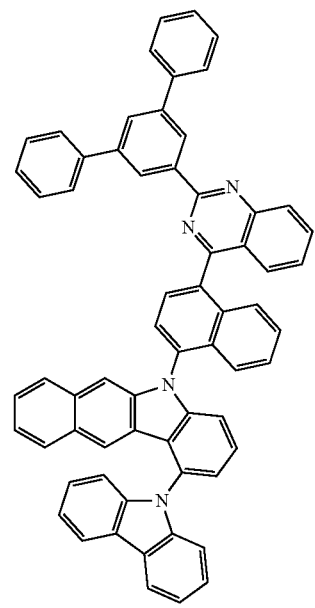
521
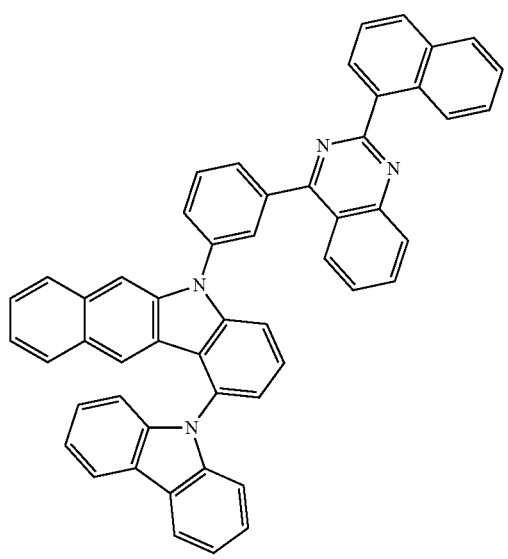
522
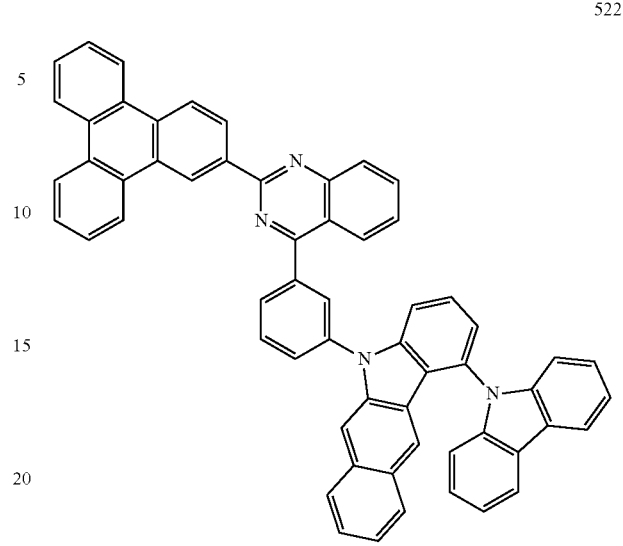
523
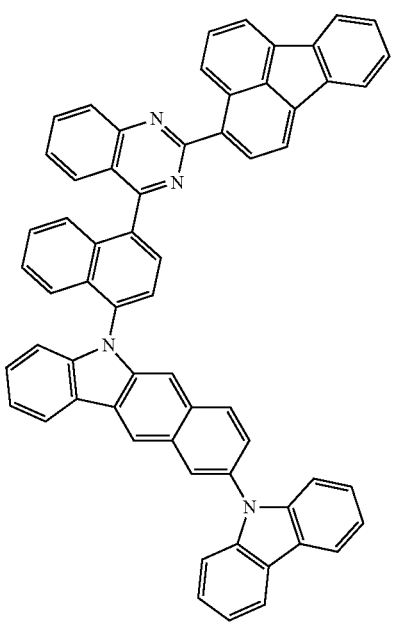

779
-continued
524
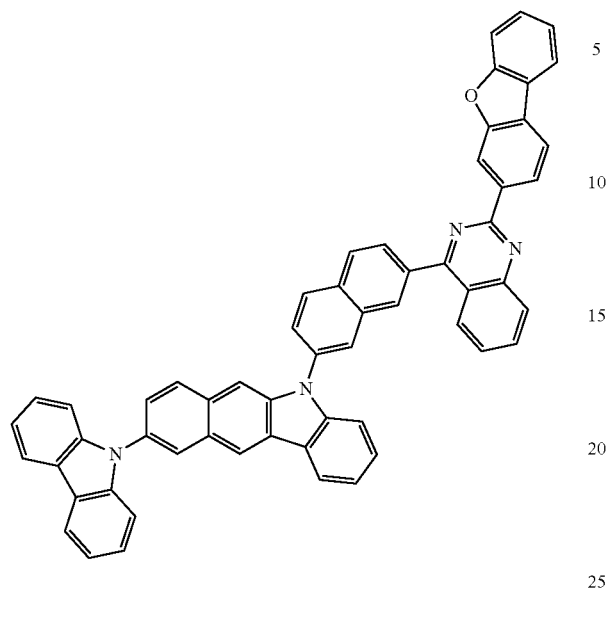
525
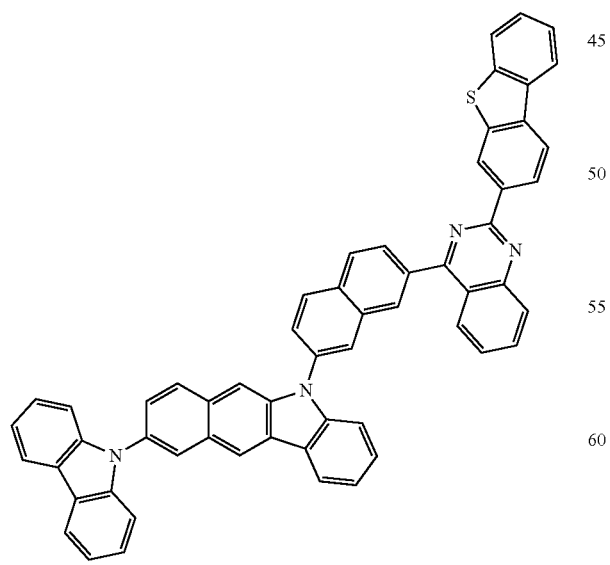
780
-continued
526
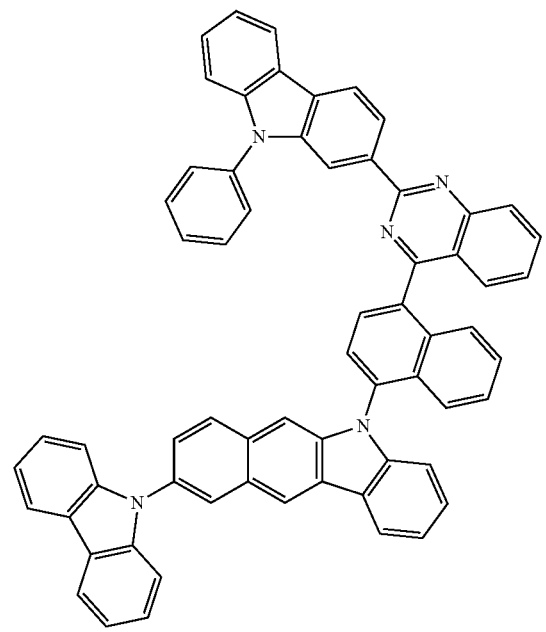
527
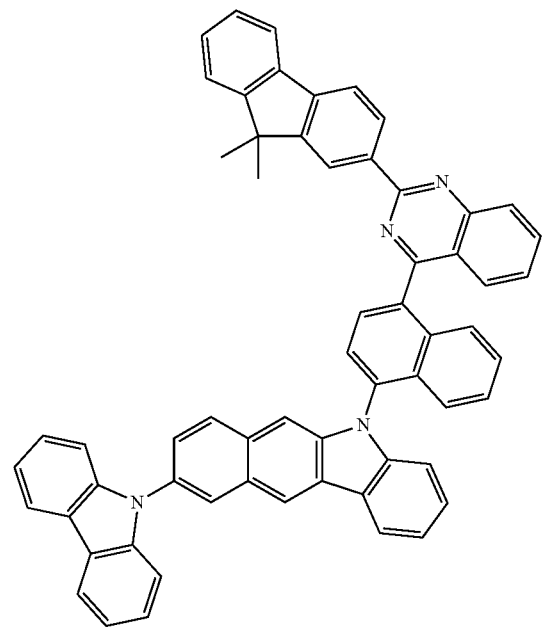

781
-continued
782
-continued
528
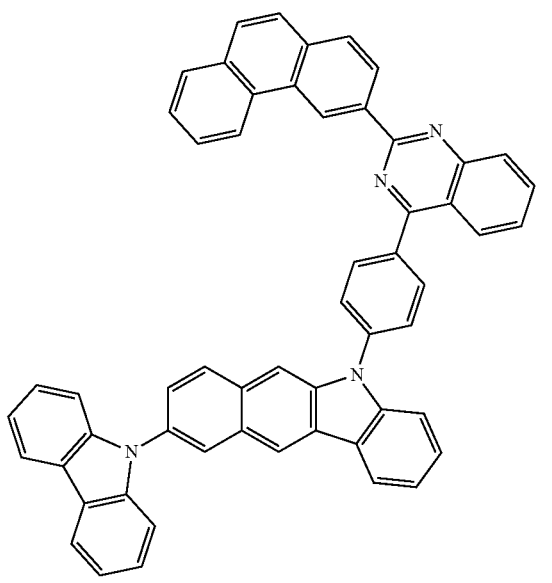
530
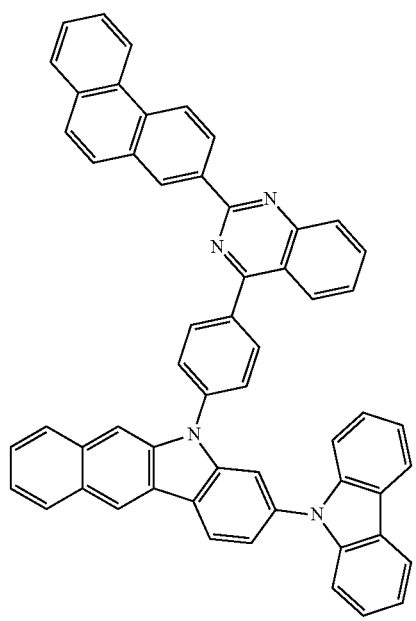
529
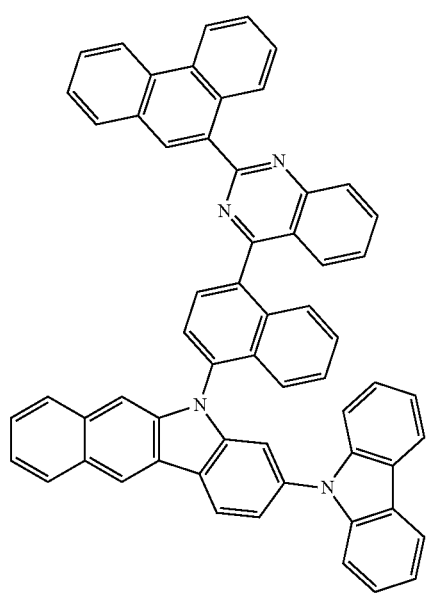
531
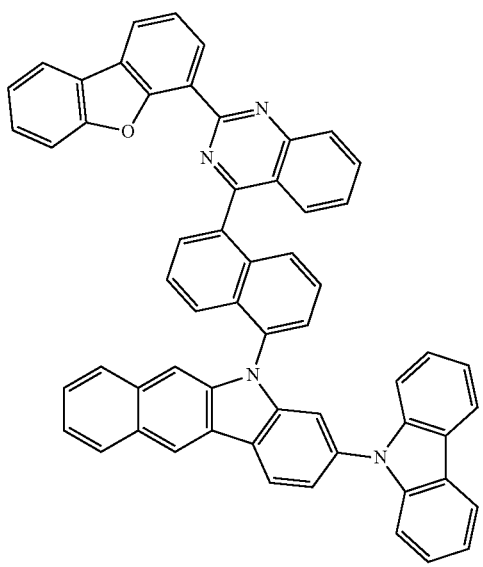

-continued
532
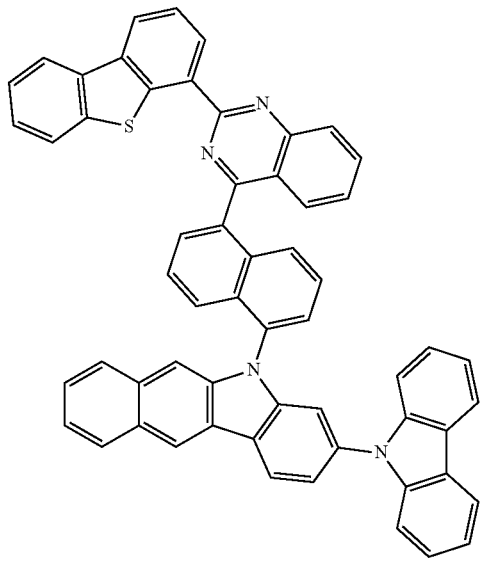
533
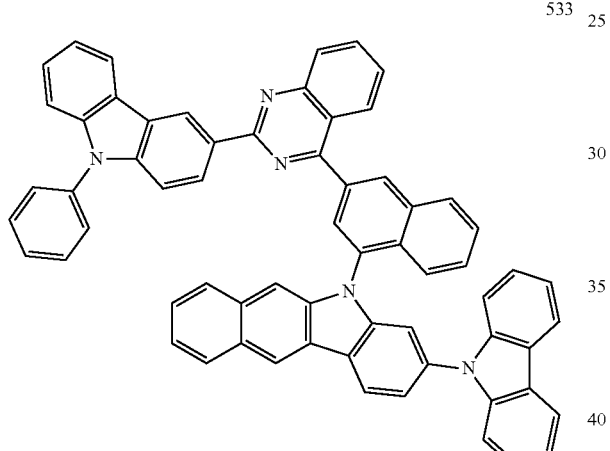
534
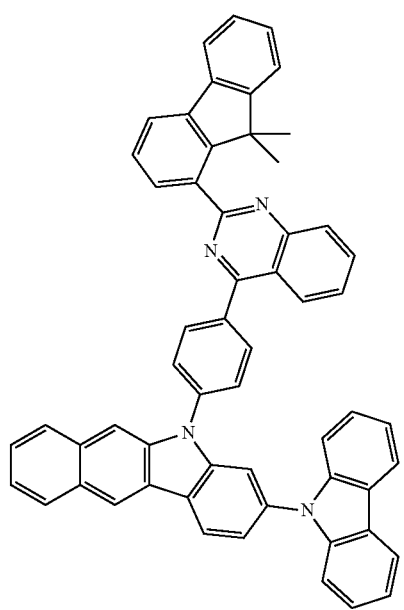
-continued
535
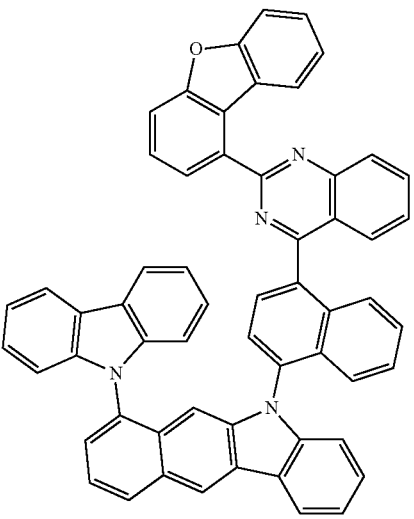
536
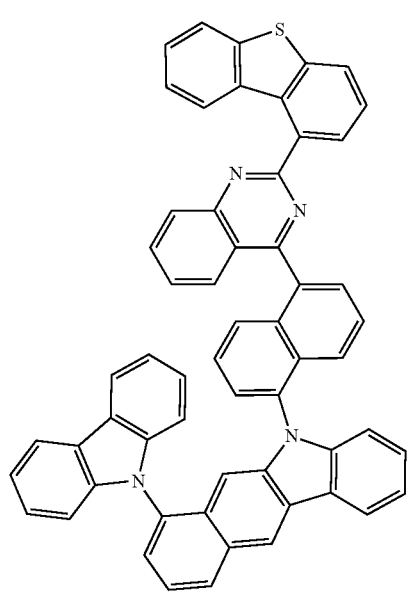

785
-continued
537
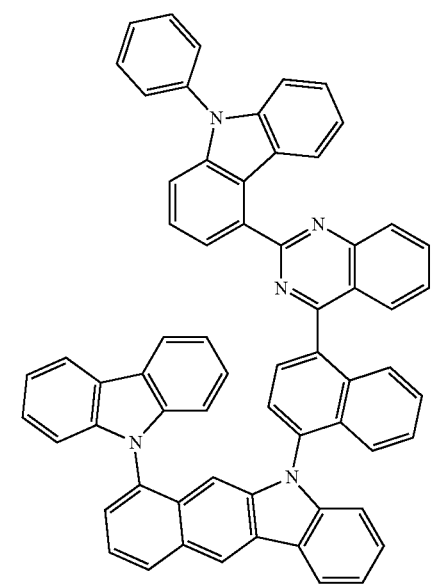
538
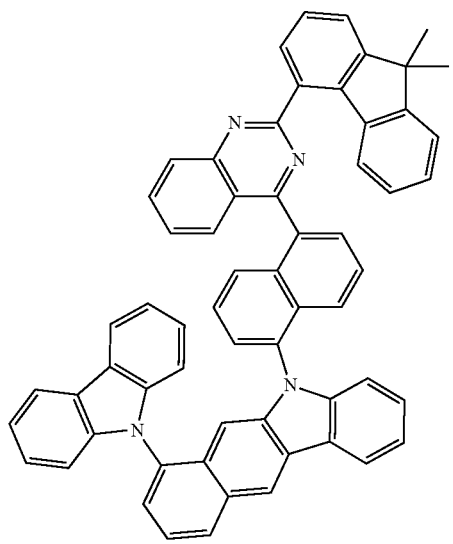
786
-continued
539
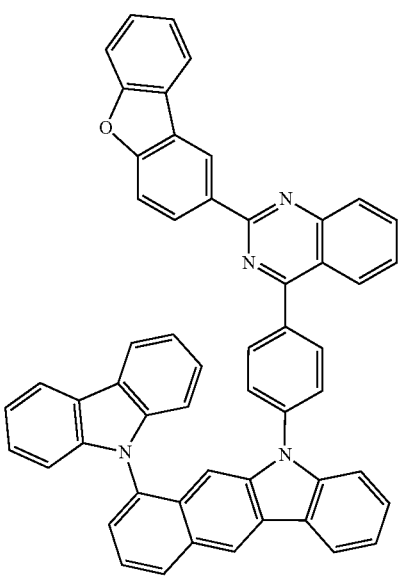
540
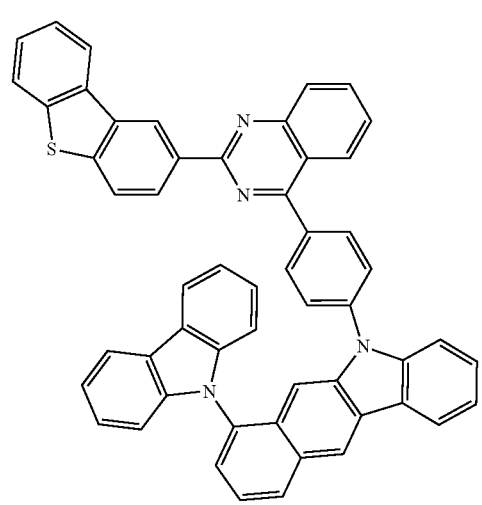
541
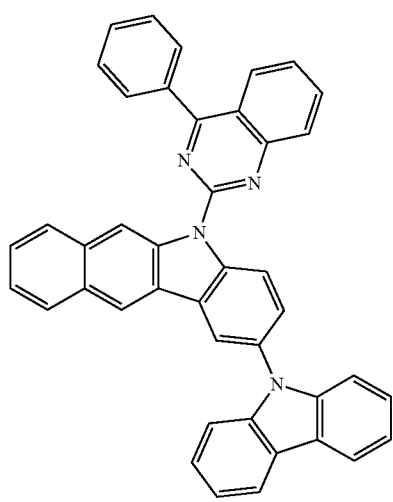

542
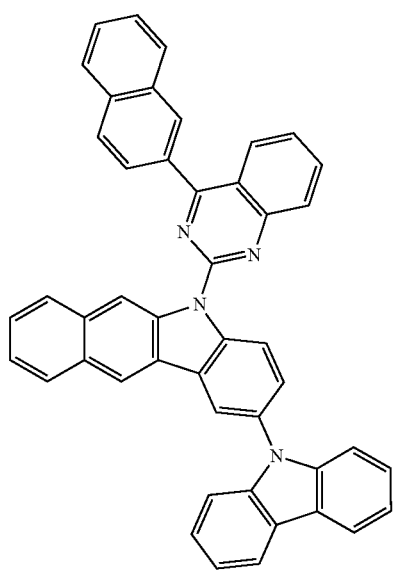
543
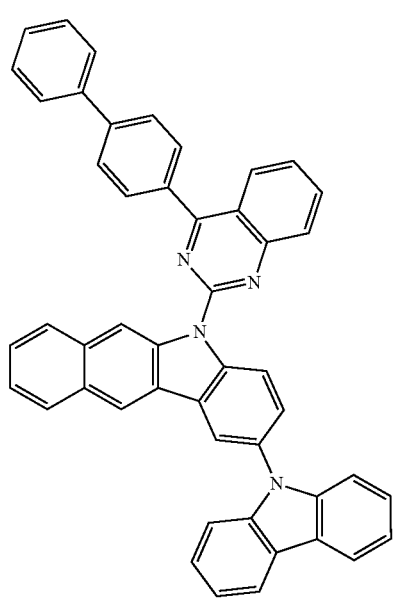
544
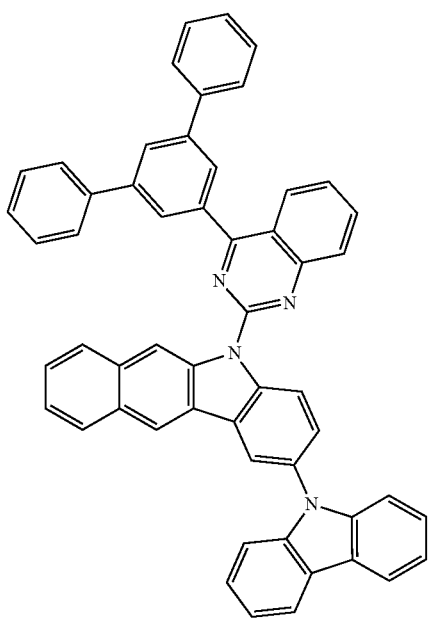
545
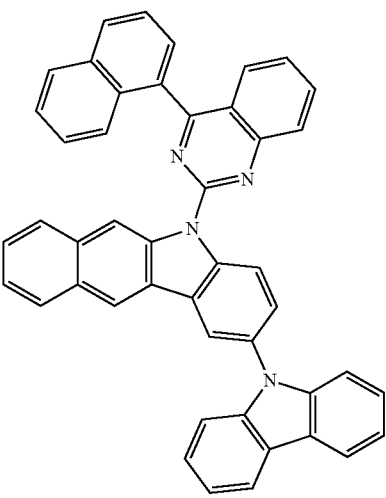

789
-continued
790
-continued
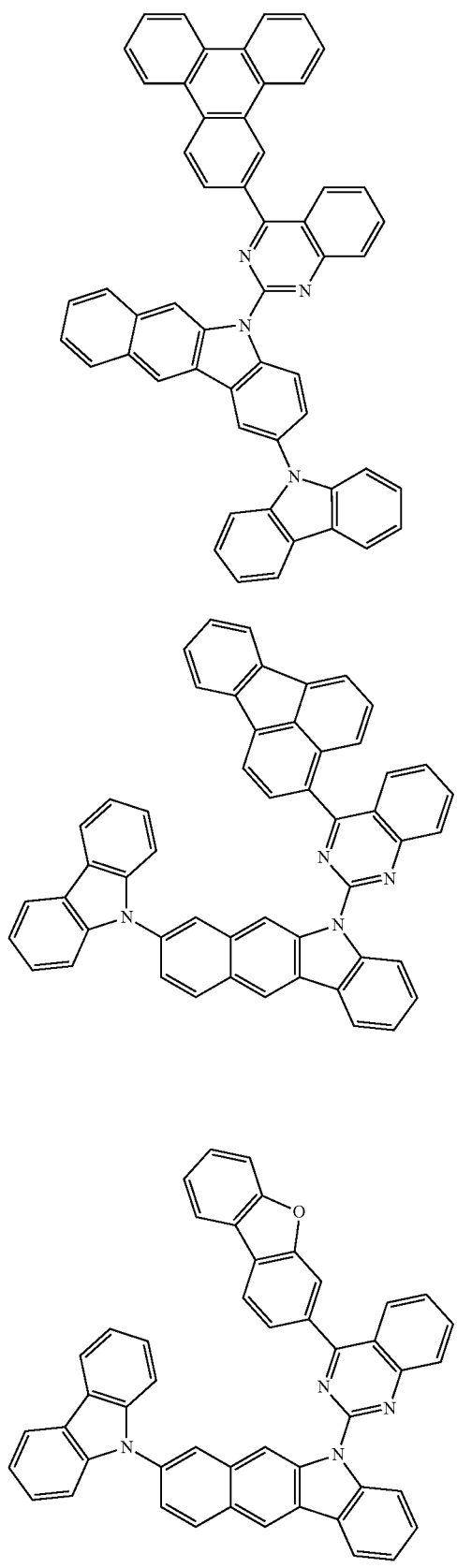
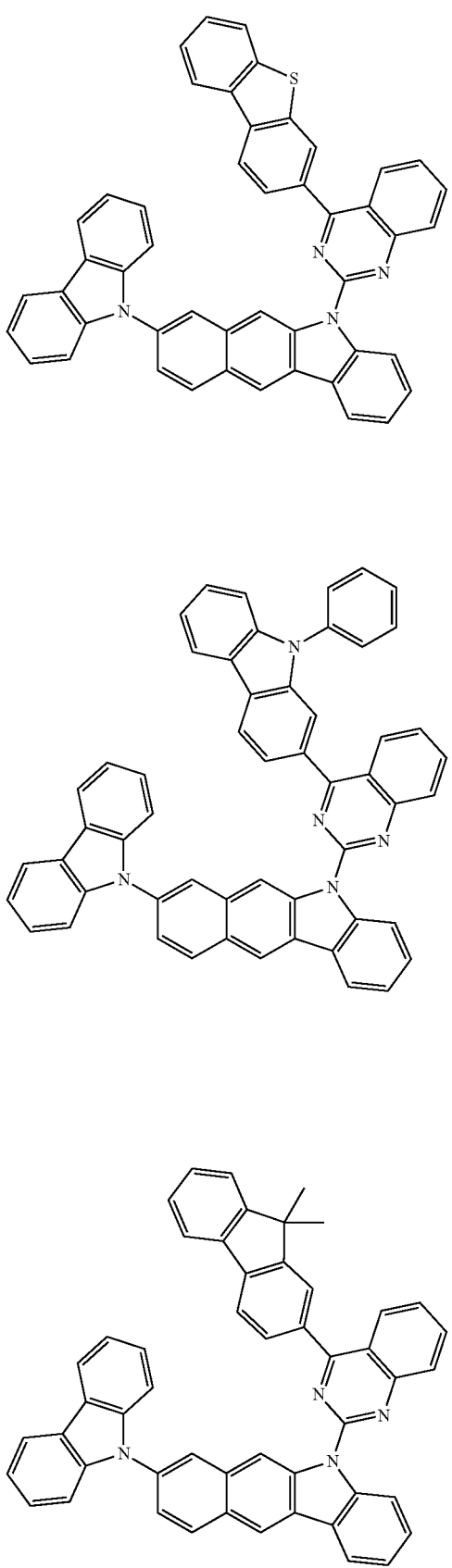

552
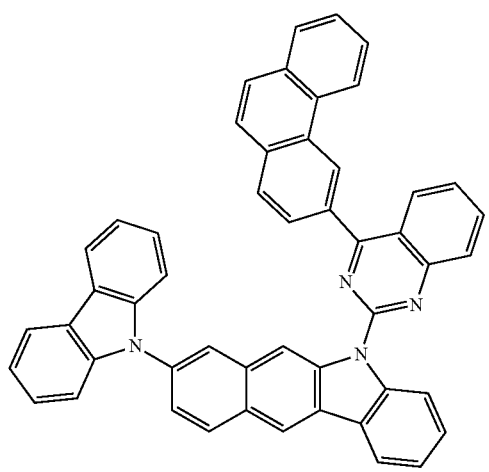
553
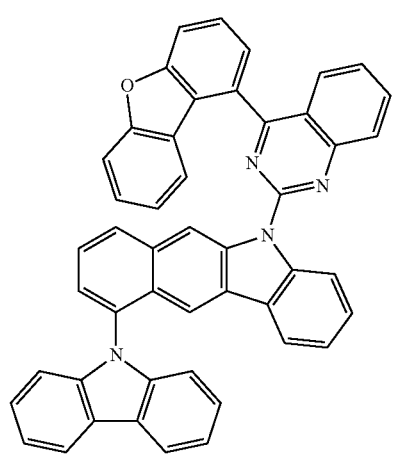
554
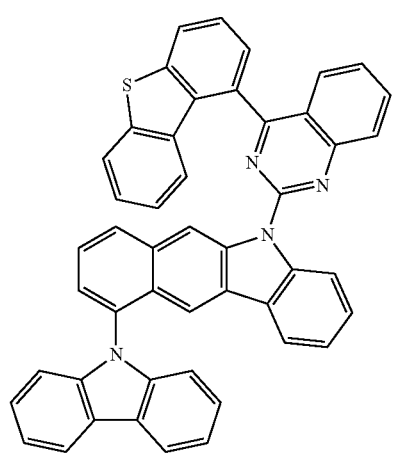
555
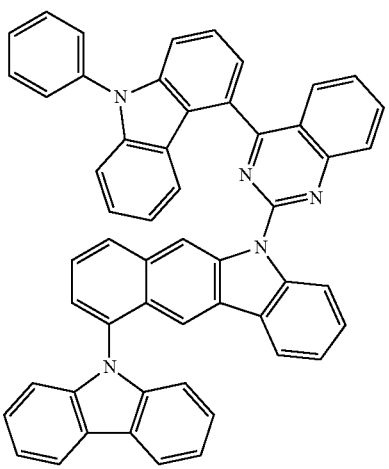
556
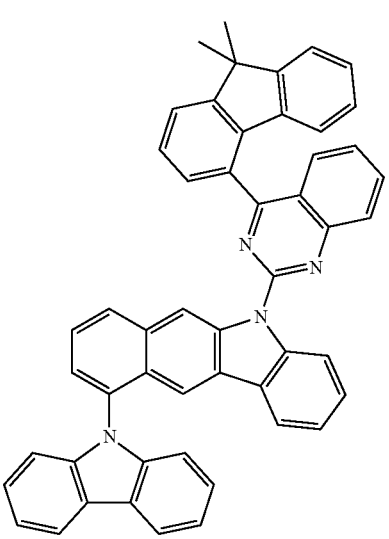
557
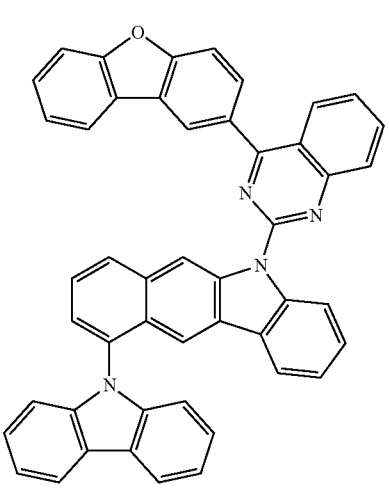

-continued
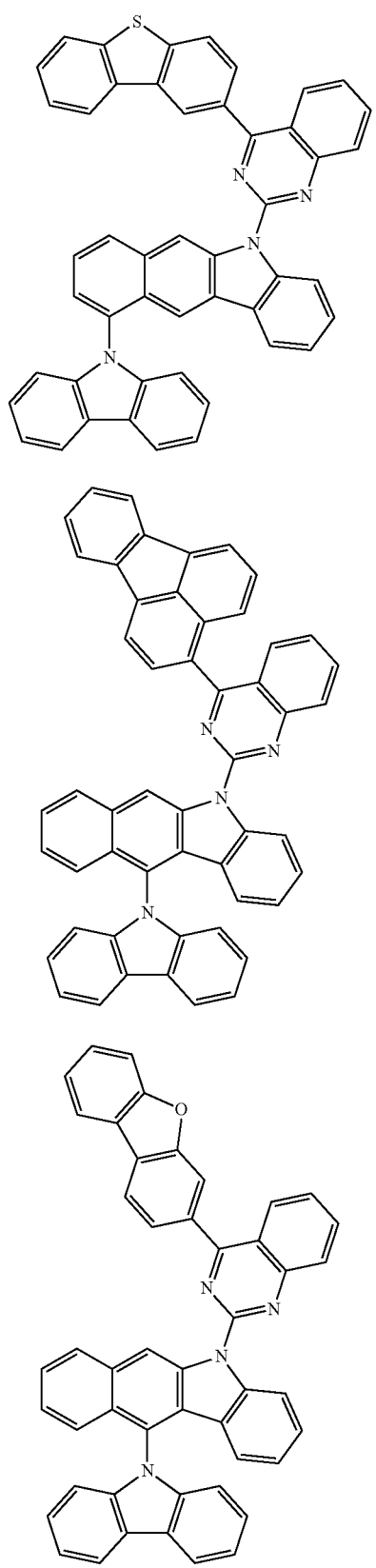
558
559
560
-continued
561
562

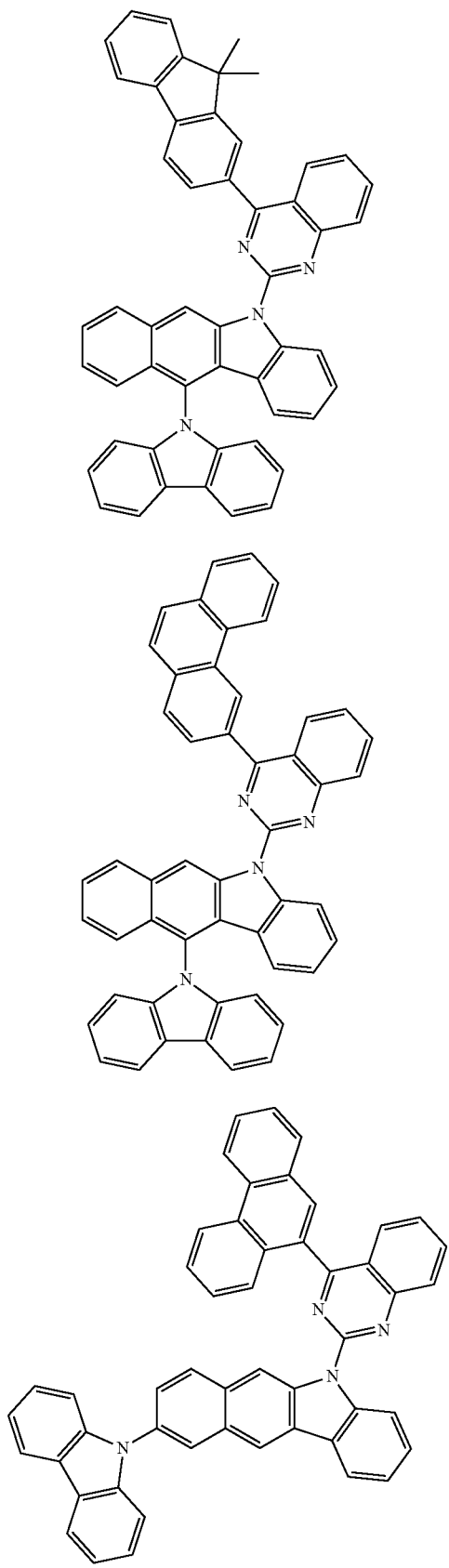
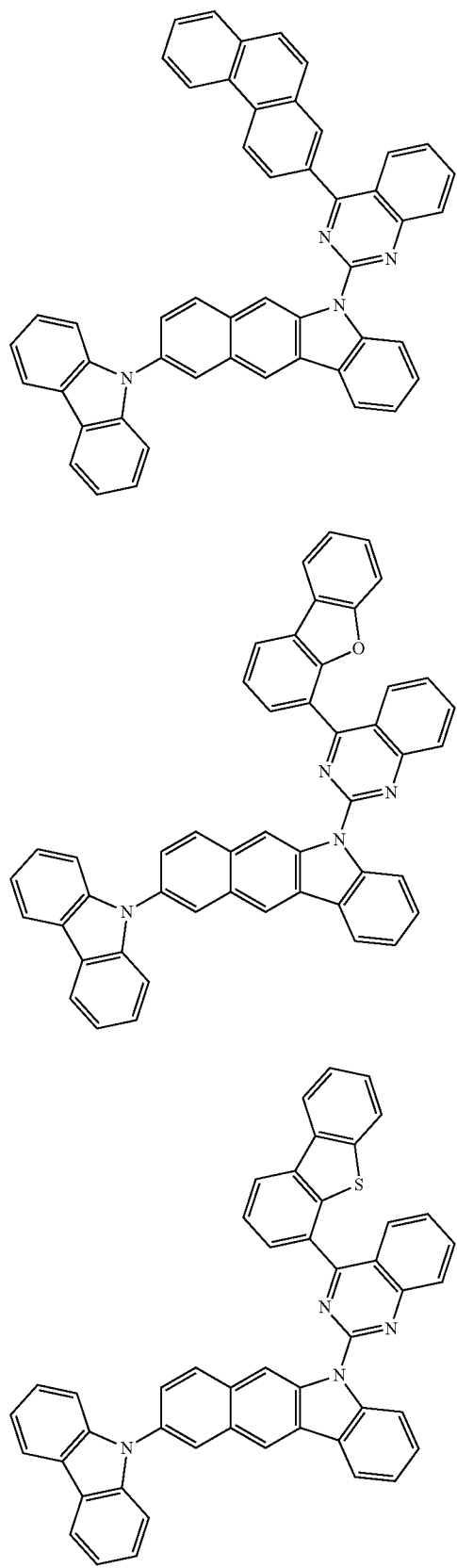

569
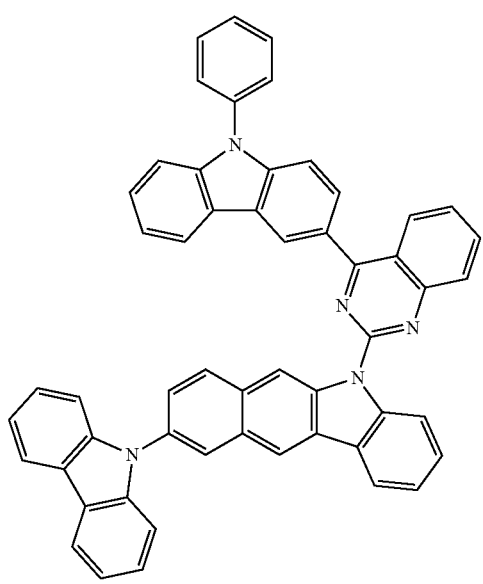
570
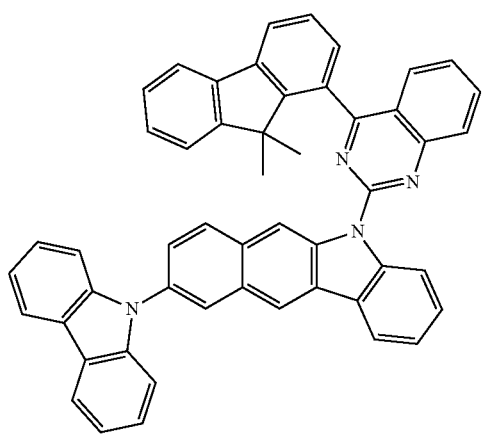
571
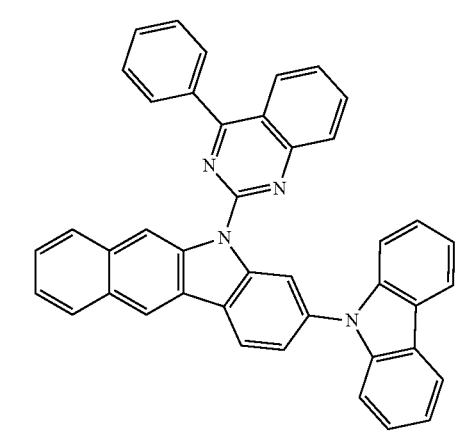
572
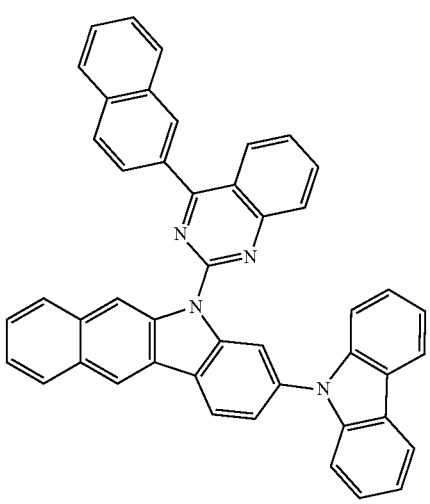
573
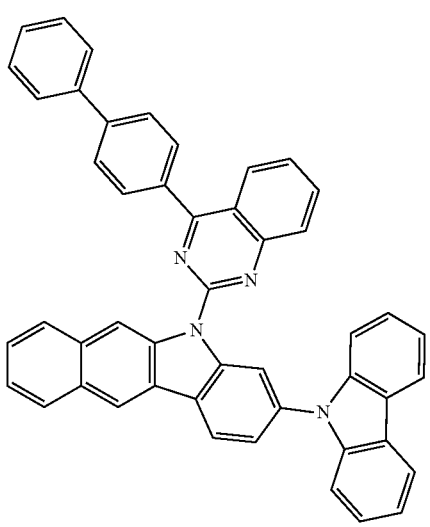
574
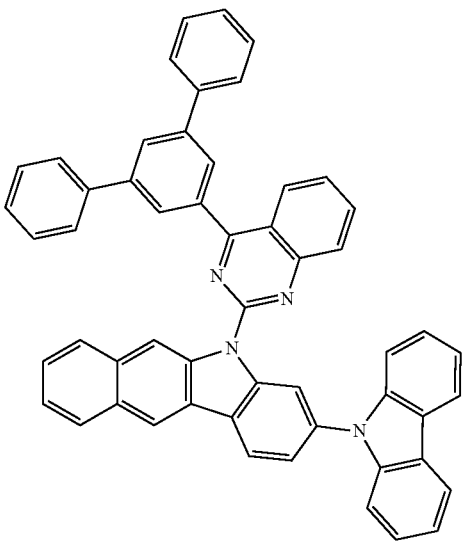

575
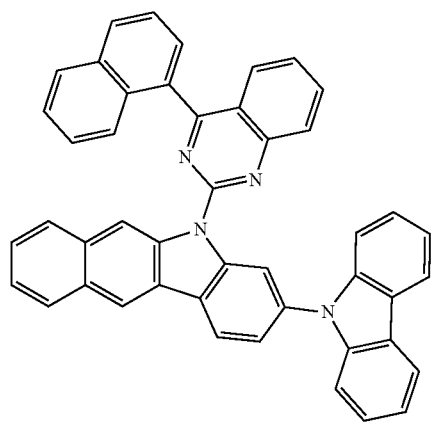
576
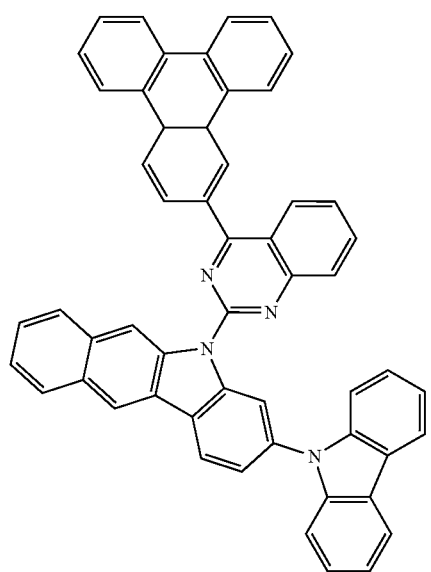
577
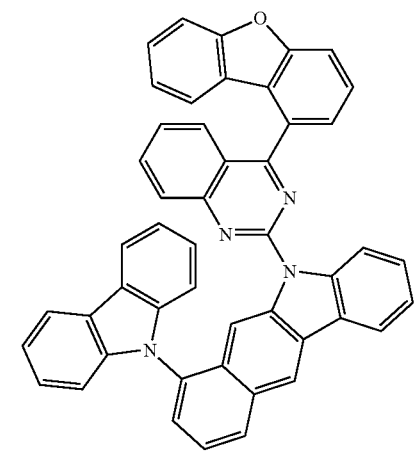
578
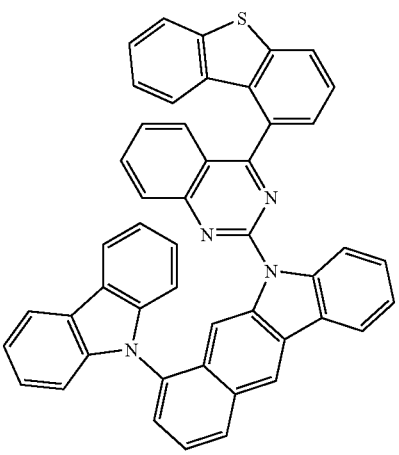
579
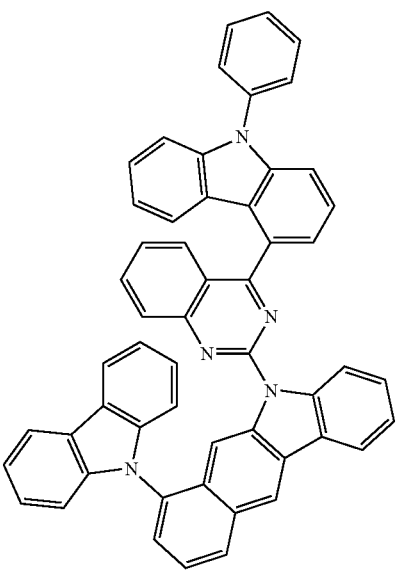
580
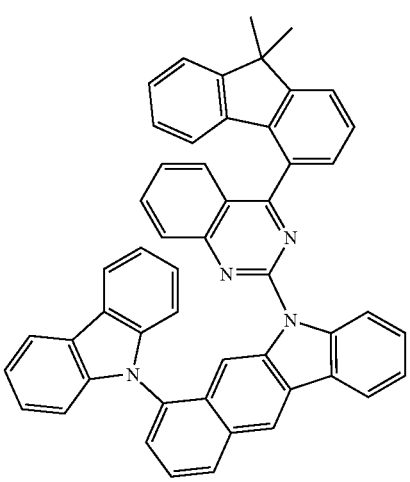

801
-continued
581
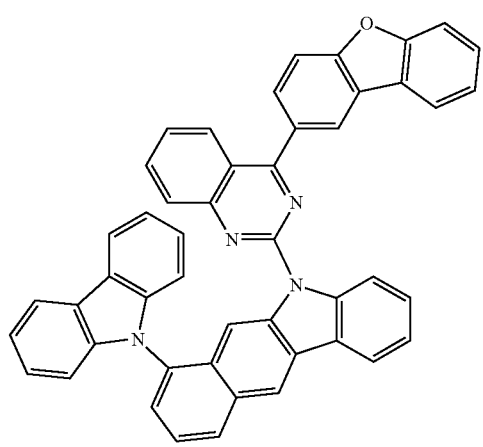
582
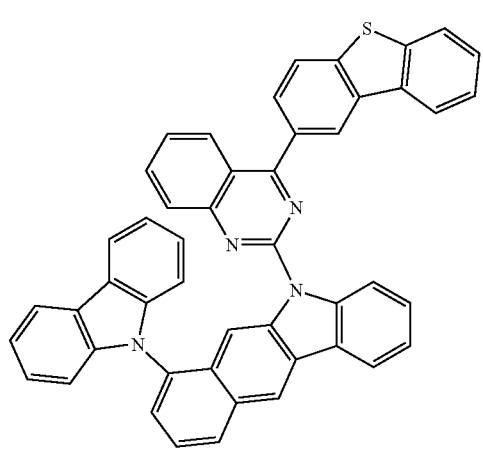
583
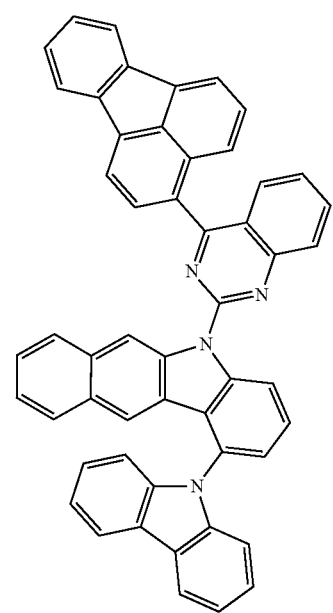
802
-continued
584
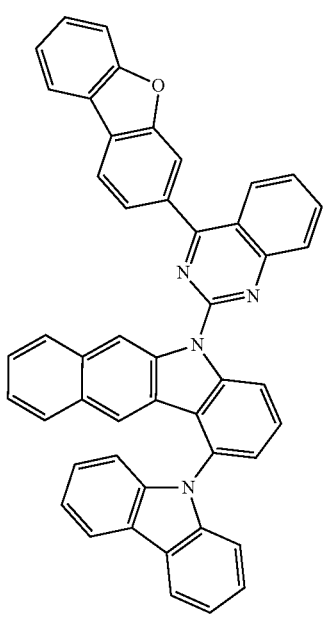
585
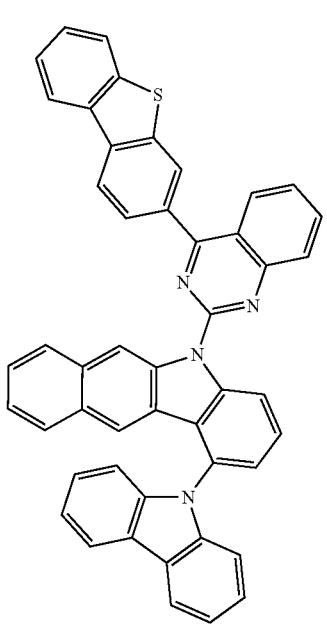

803
-continued
586
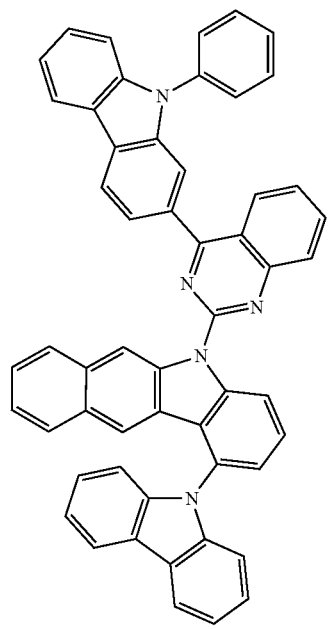
587
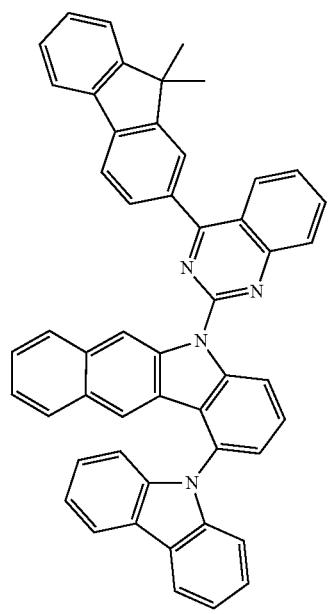
804
-continued
588
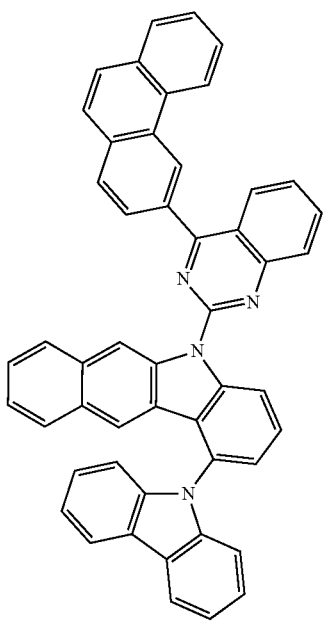
589
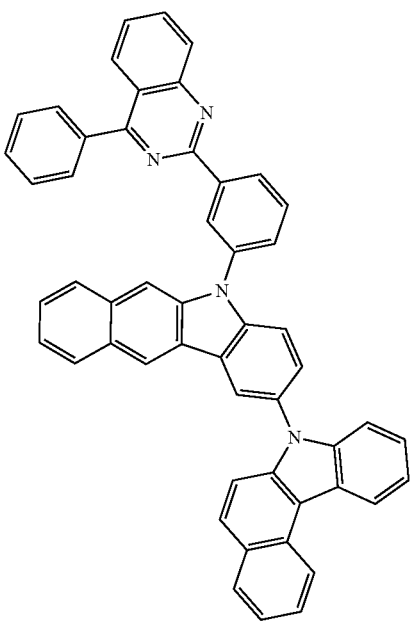

805
-continued
590
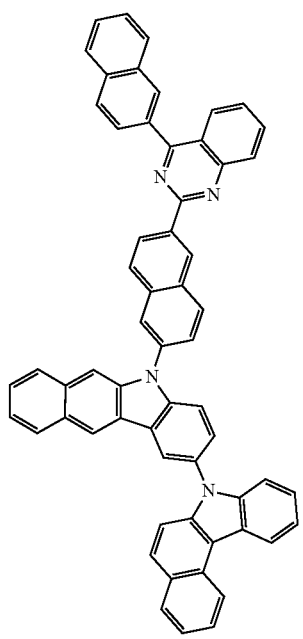
591
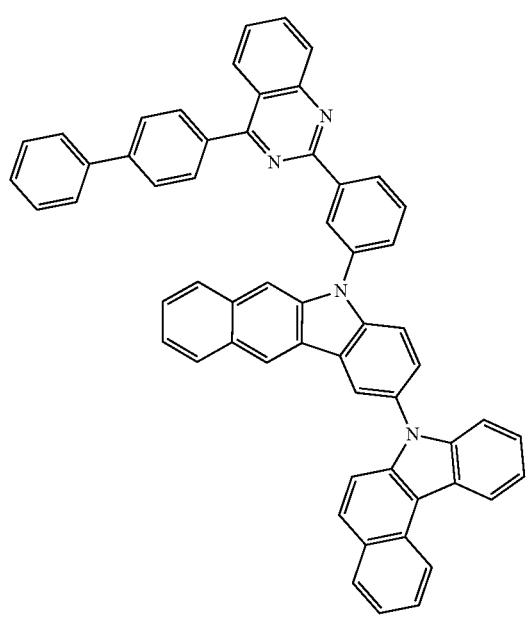
806
-continued
592
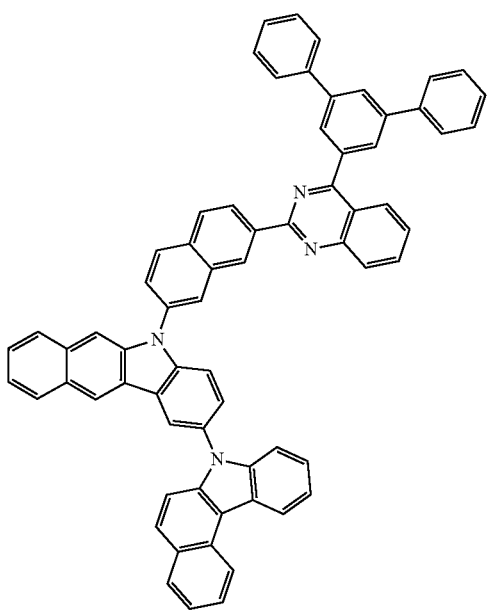
593
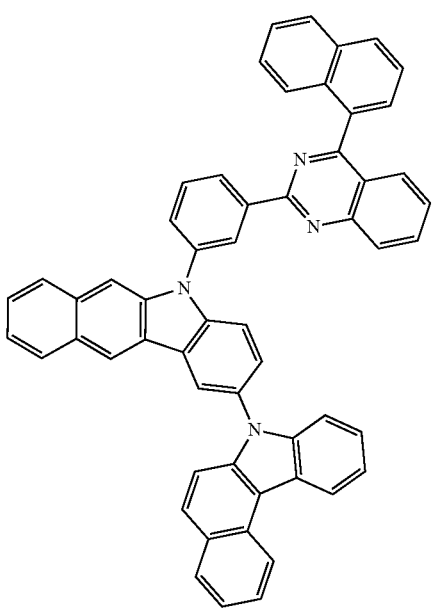

807
-continued
594
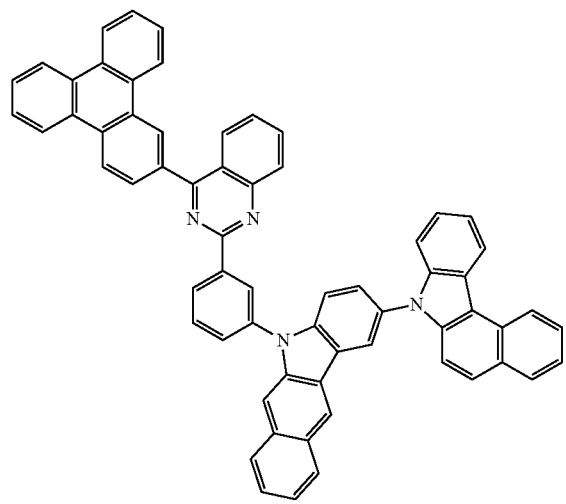
595
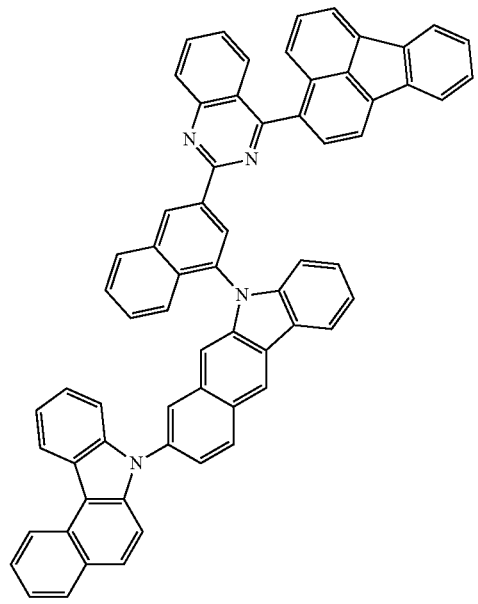
808
-continued
596
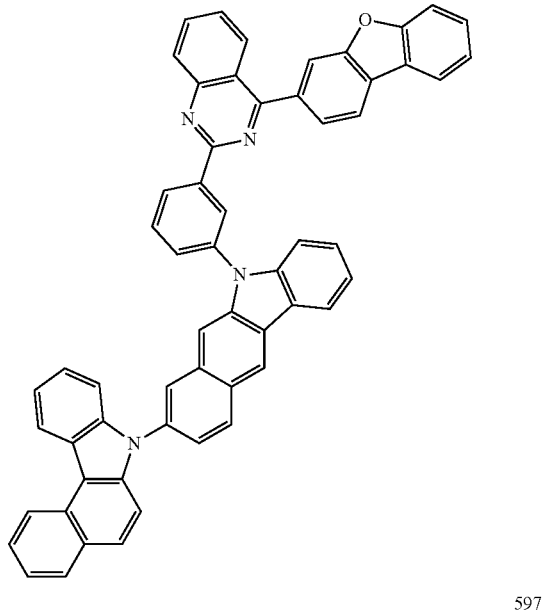
597
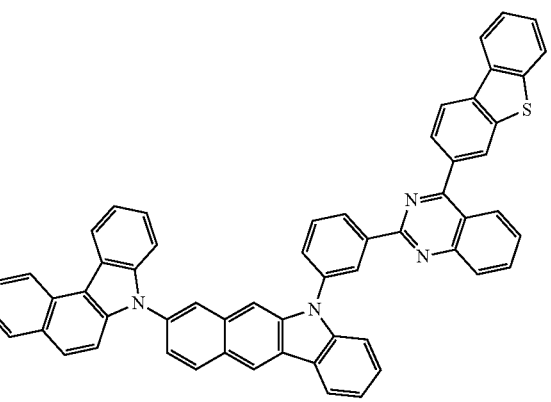
598
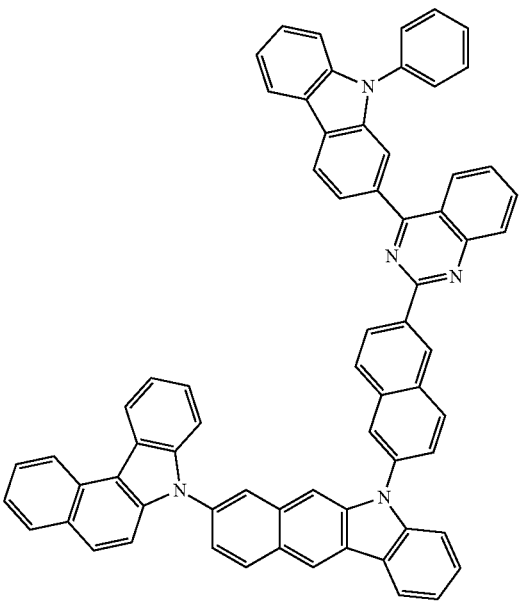

809
-continued
599
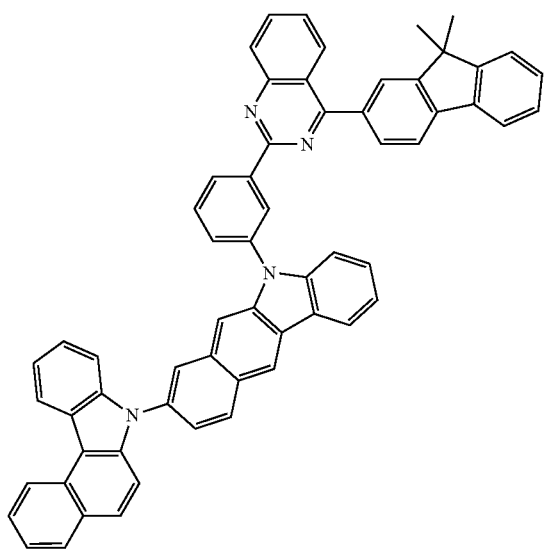
600
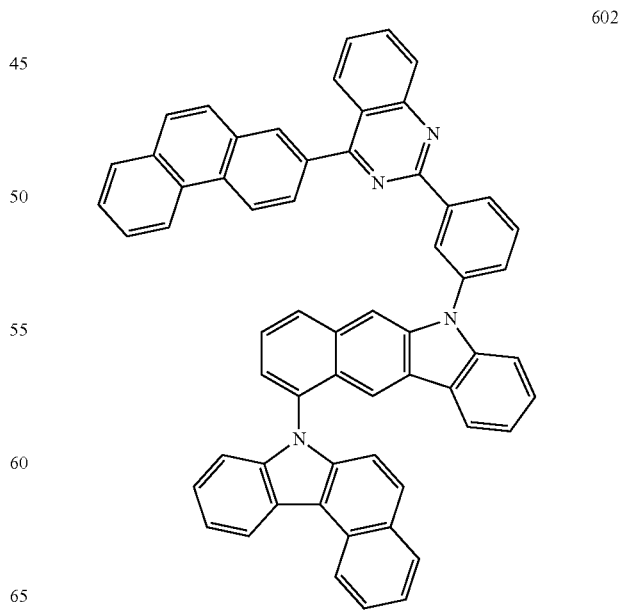
810
-continued
601
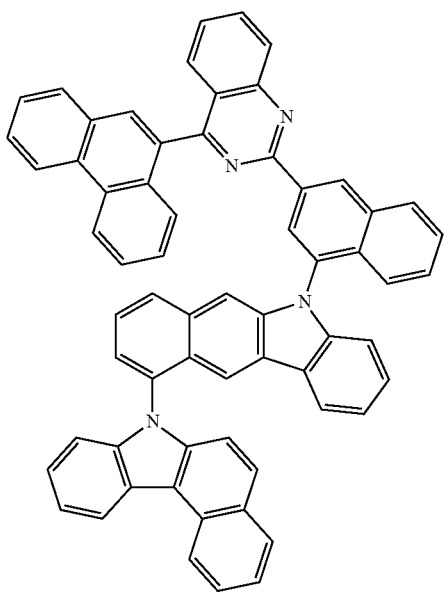
602

811
-continued
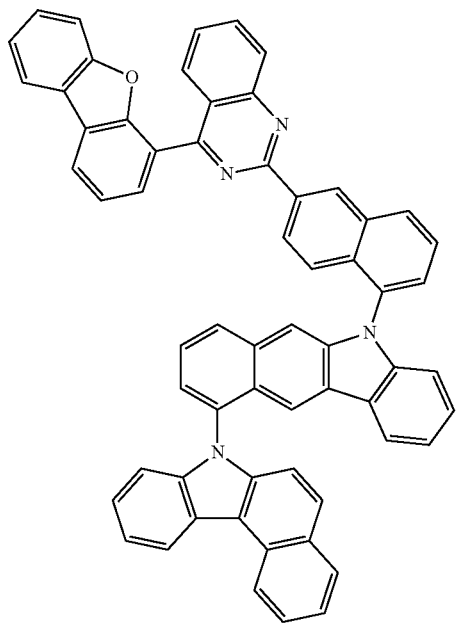
603
812
-continued
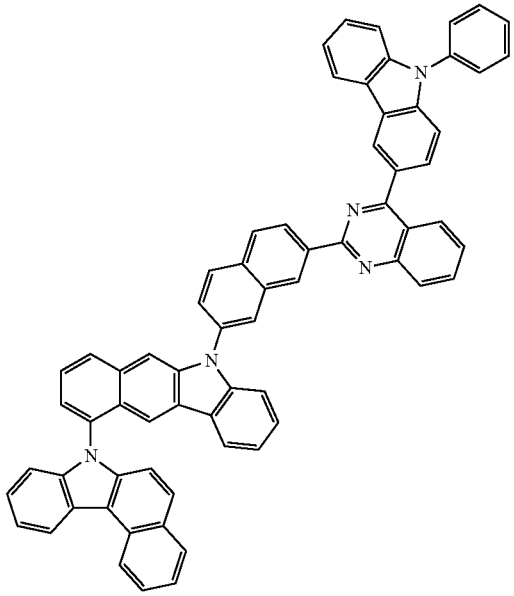
605
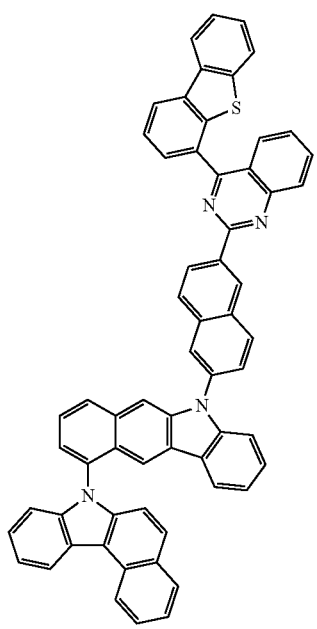
604
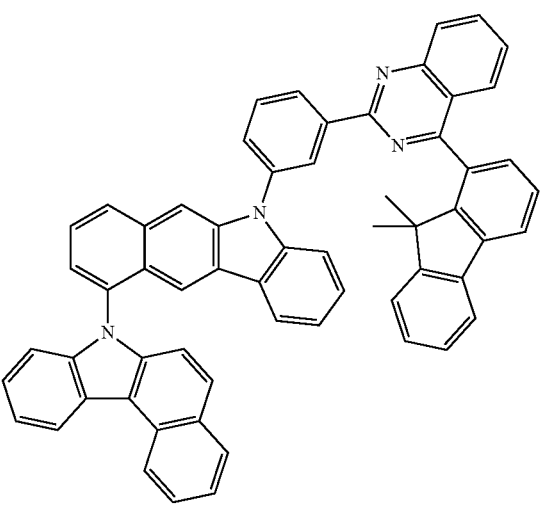
606

813
-continued
607
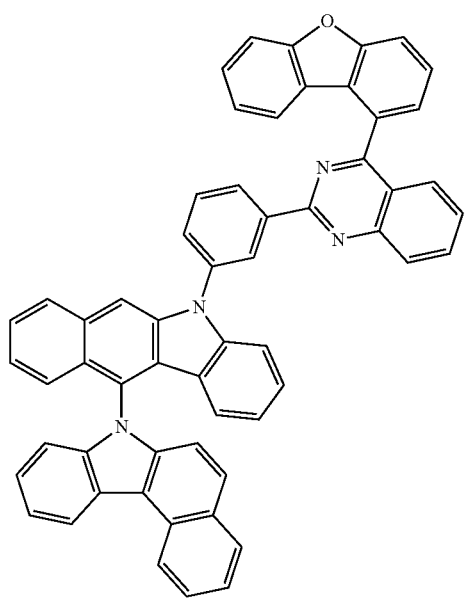
608
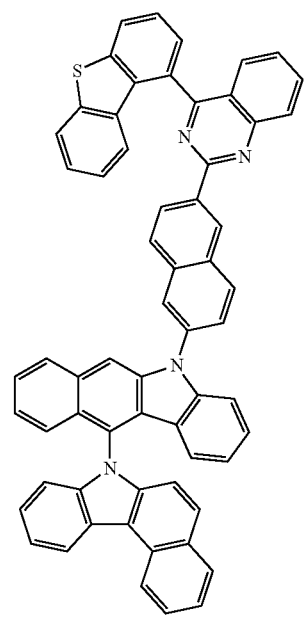
814
-continued
609
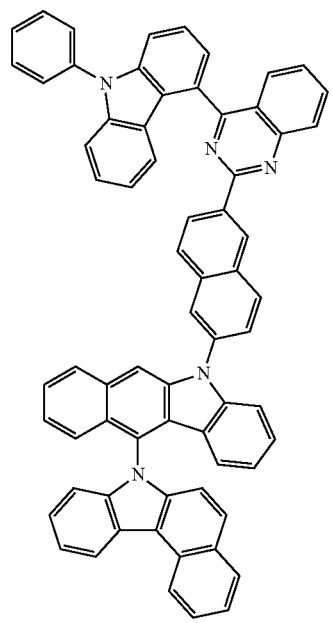
610
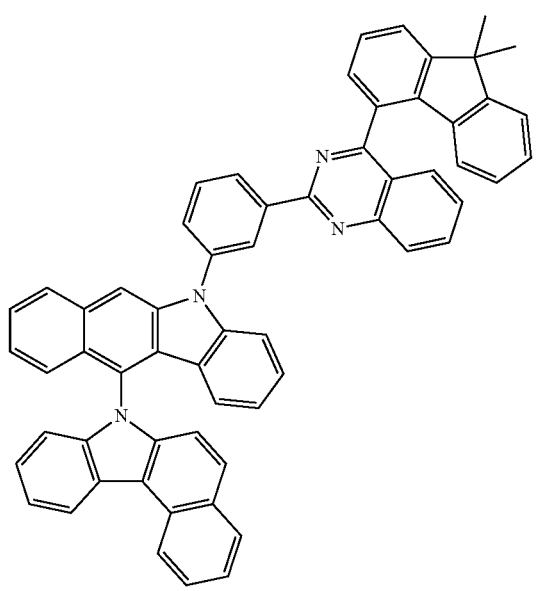

815
-continued
611
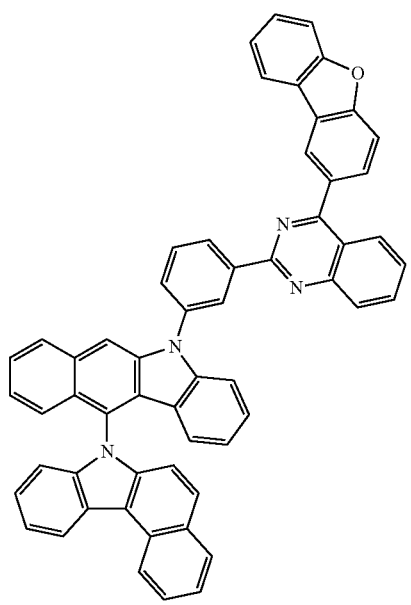
612
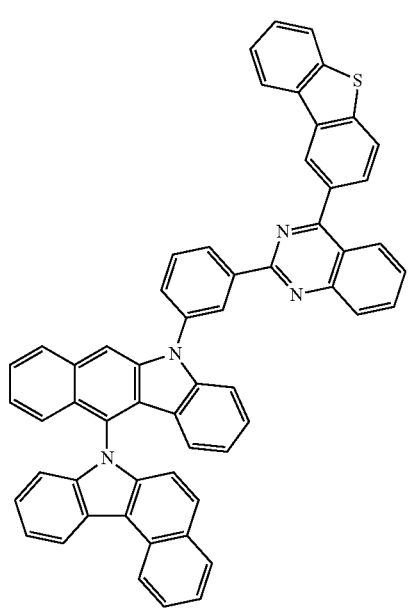
816
-continued
613
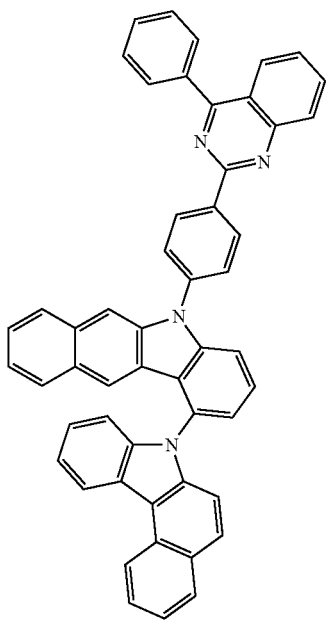
614
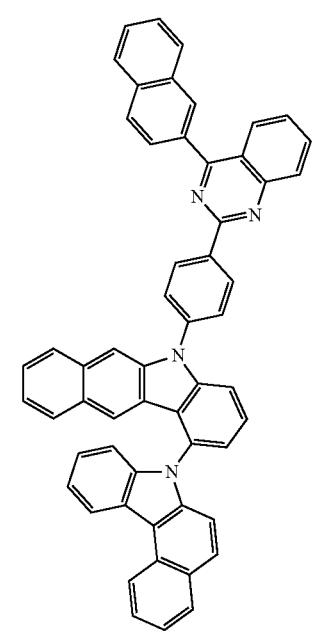

817
-continued
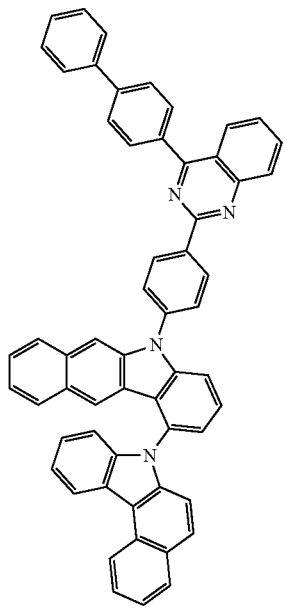
615
818
-continued
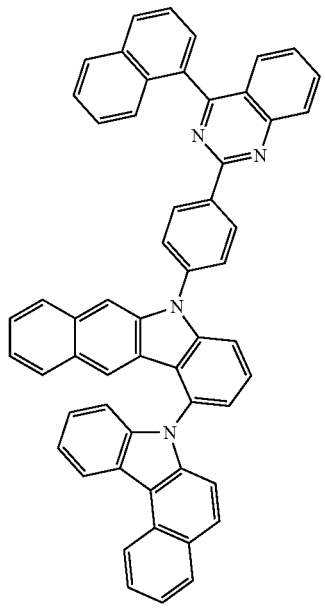
617
616
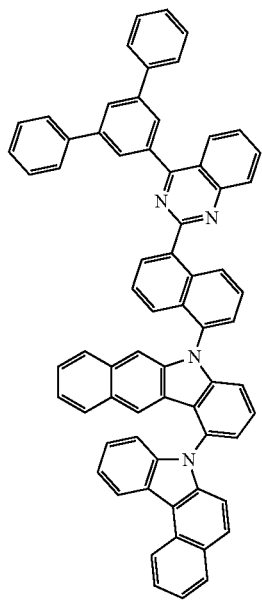
618
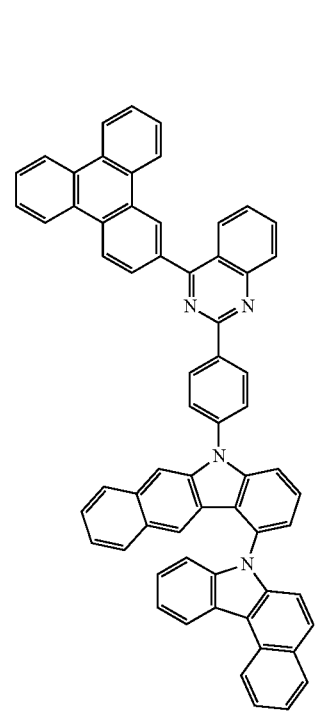

819
-continued
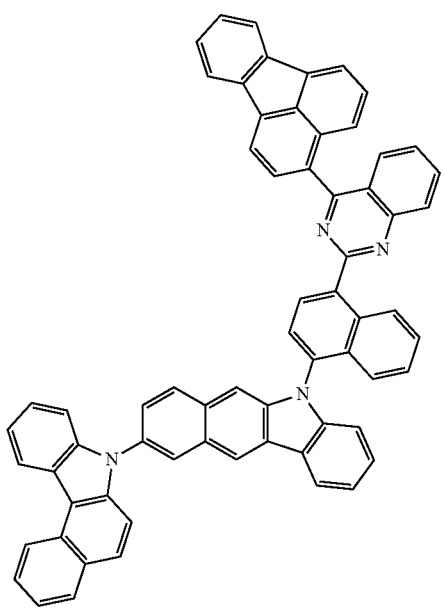
619
820
-continued
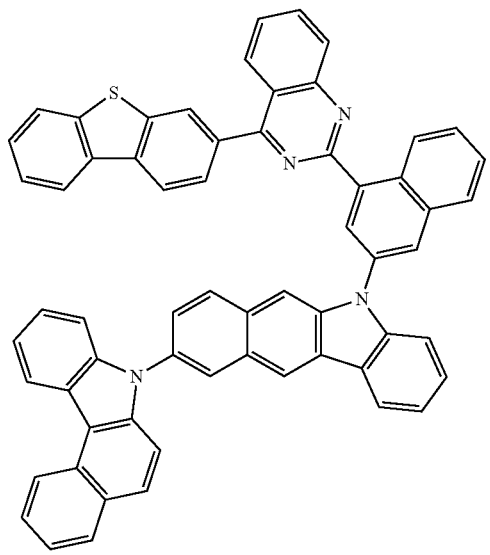
621
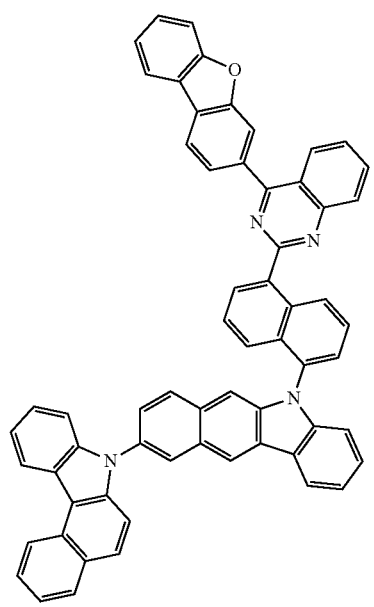
620
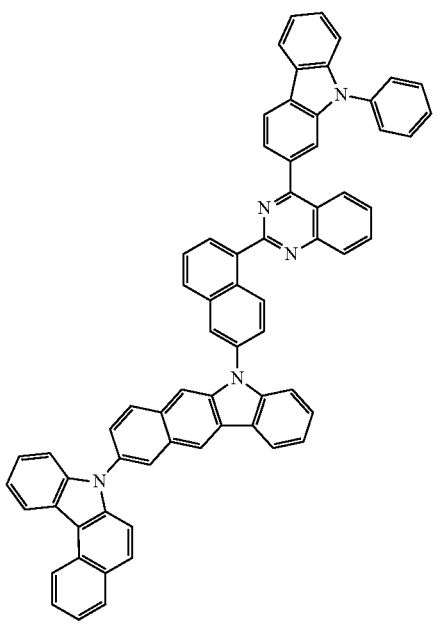
622

821
-continued
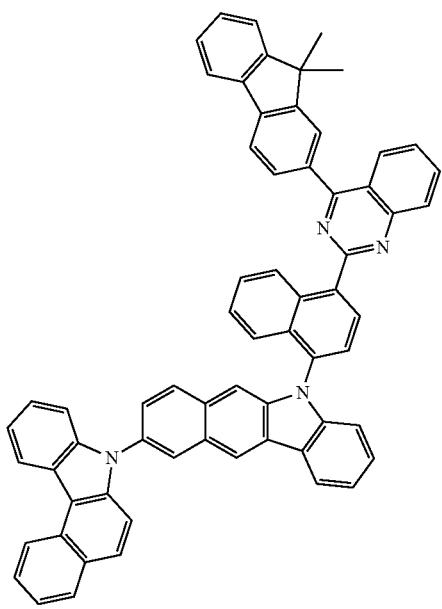
623
822
-continued
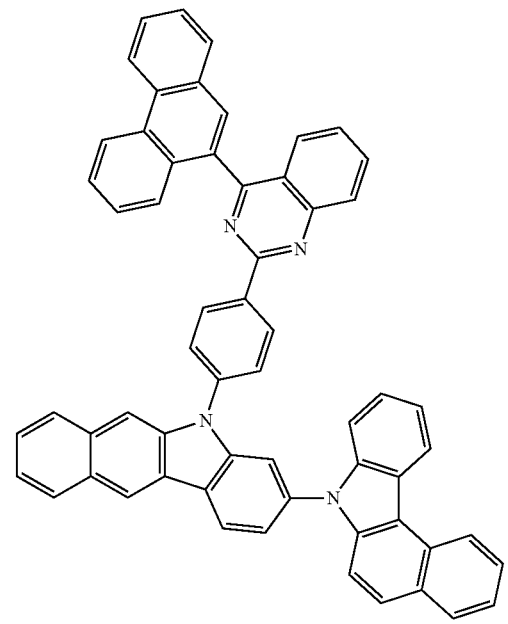
625
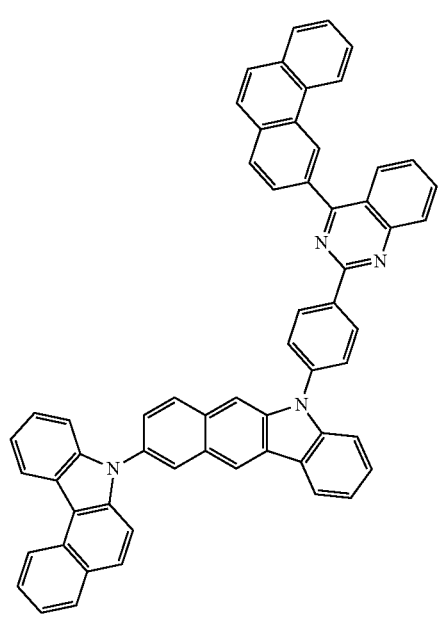
624
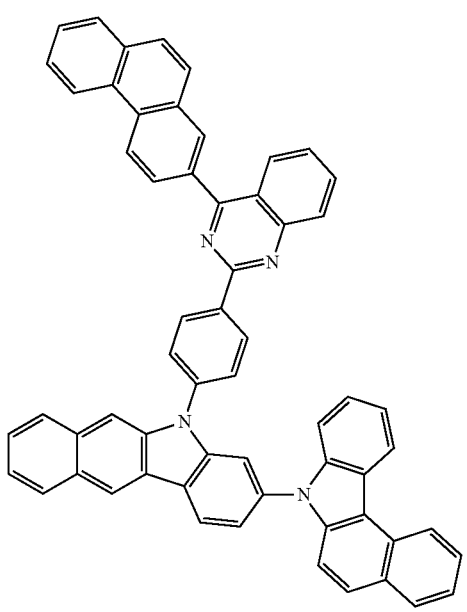
626

823
-continued
627
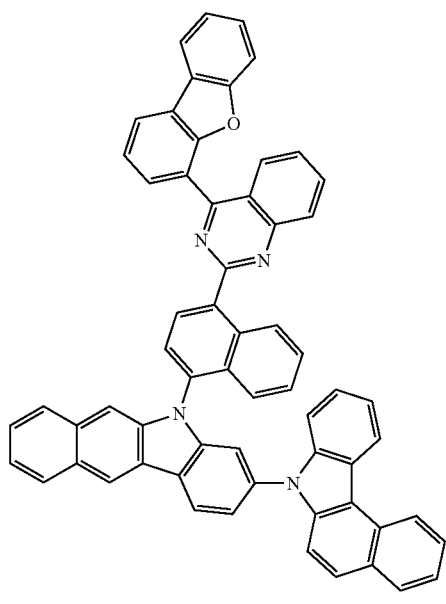
628
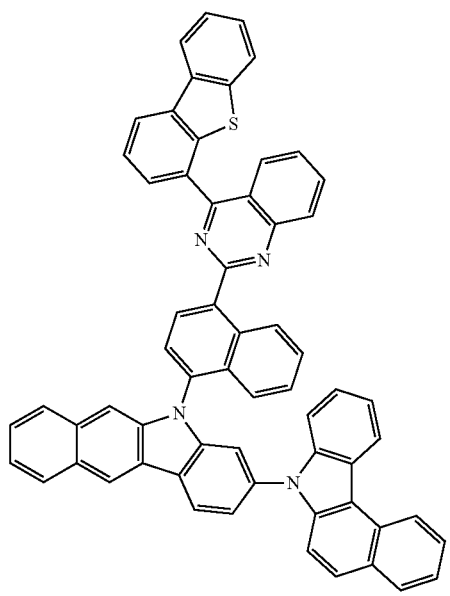
824
-continued
629
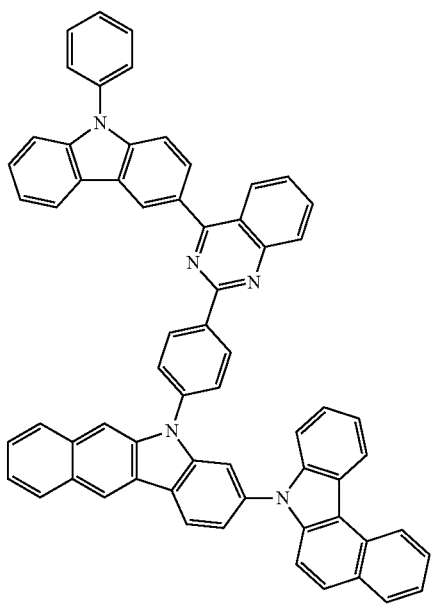
630
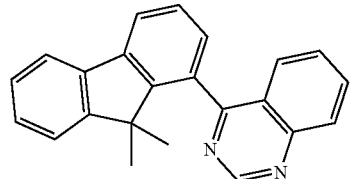
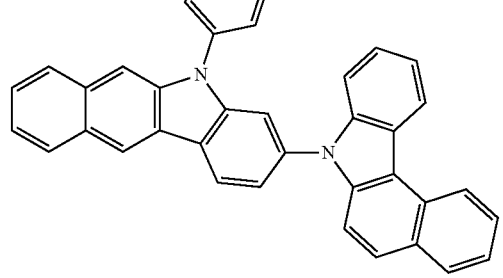

825
-continued
826
-continued
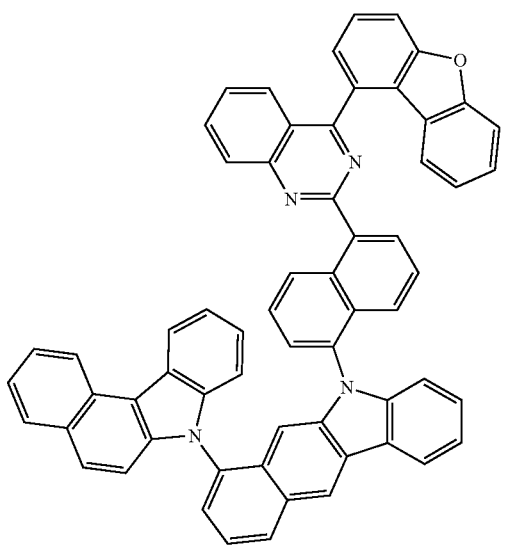
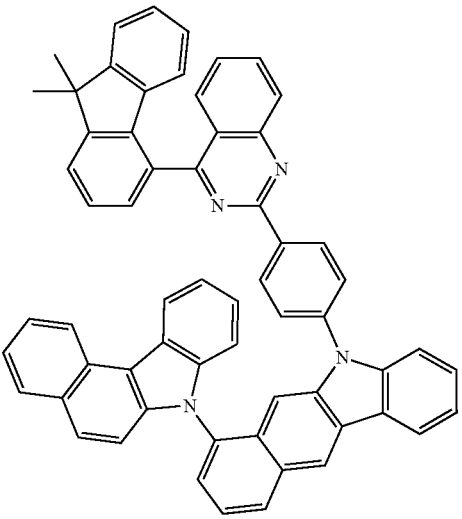

827
-continued
637
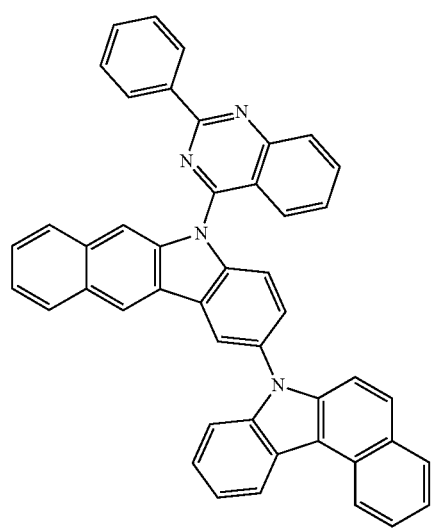
638
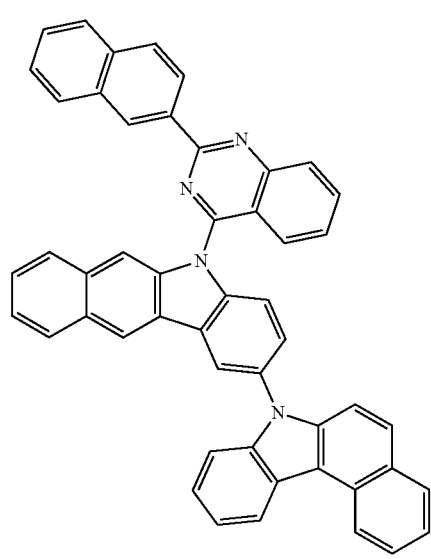
828
-continued
639
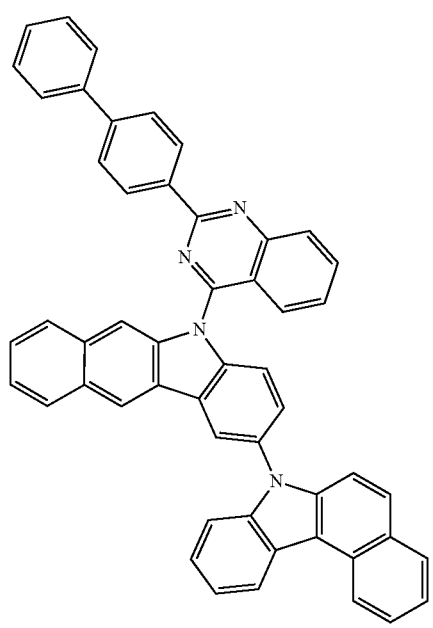
640
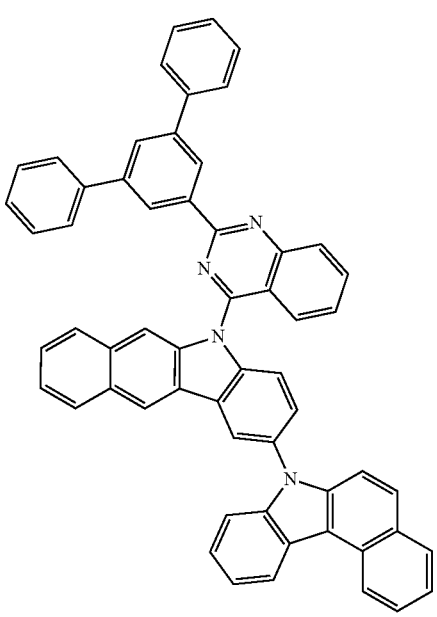

829
-continued
641
642
643
-continued
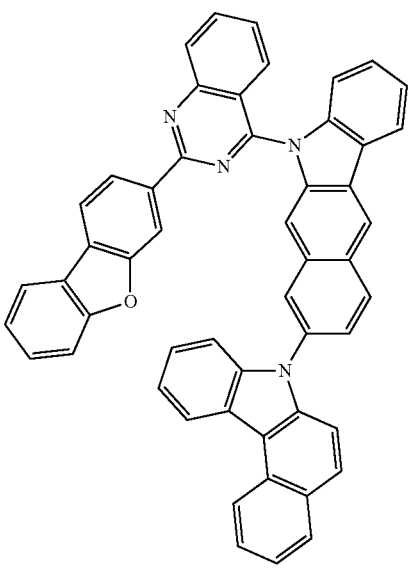
644
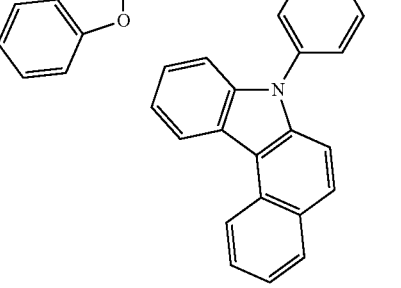
645
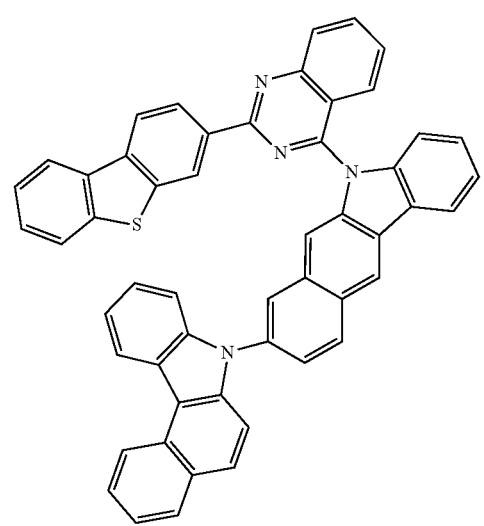

831
-continued
646
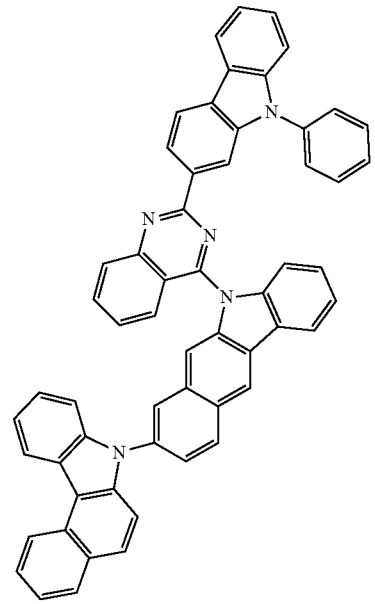
647
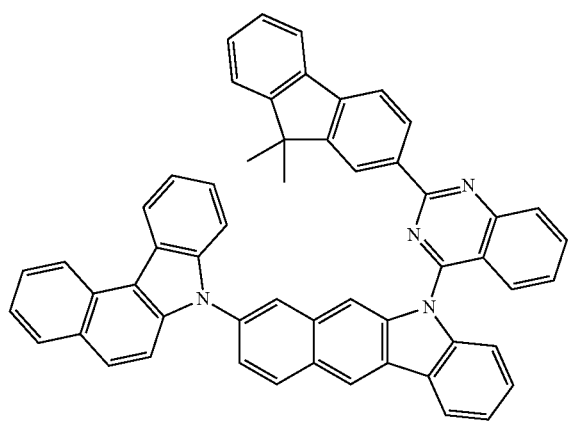
648
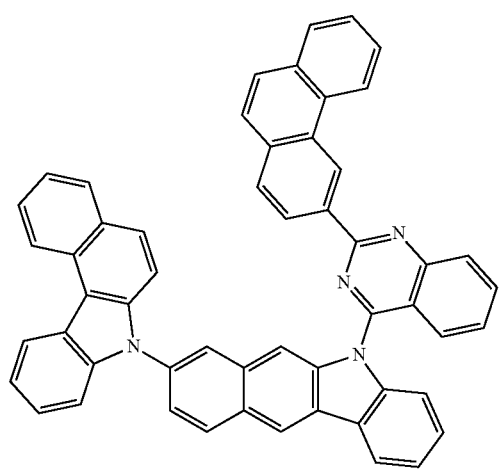
832
-continued
649
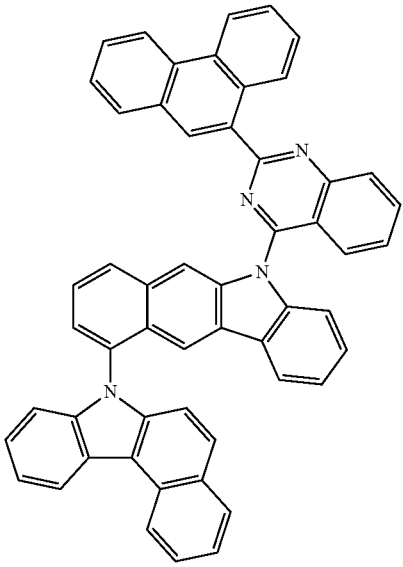
650
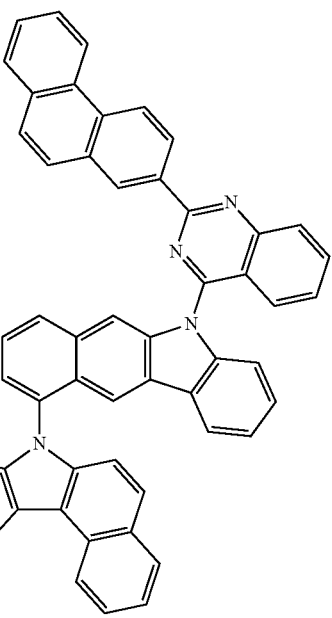

651
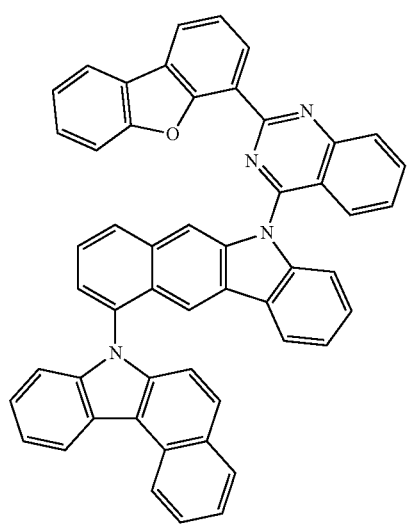
652
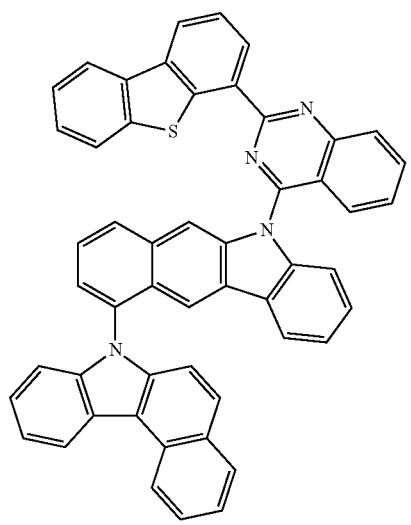
653
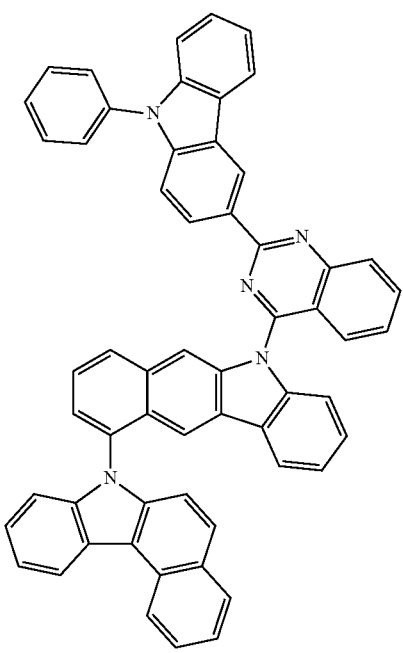
654
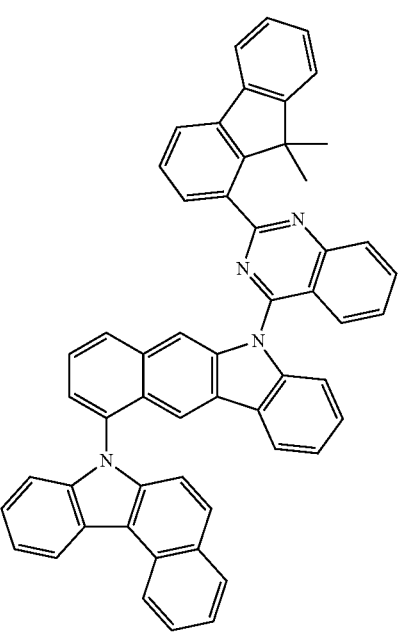

835
-continued
655
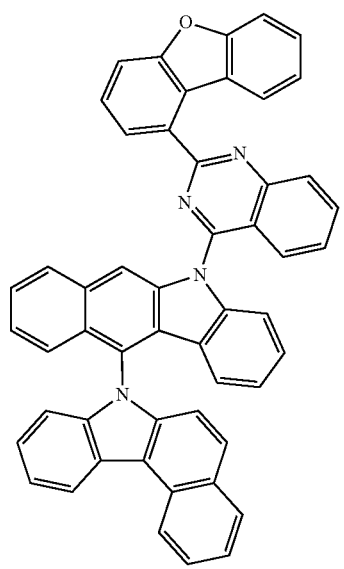
656
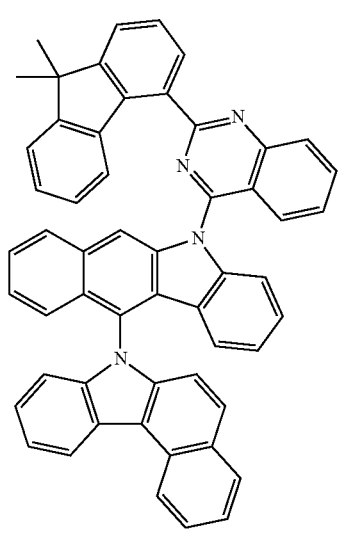
836
-continued
657
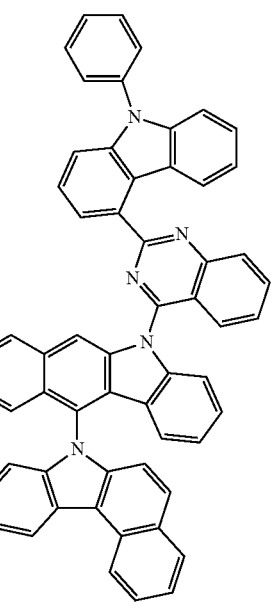
658

837
-continued
659
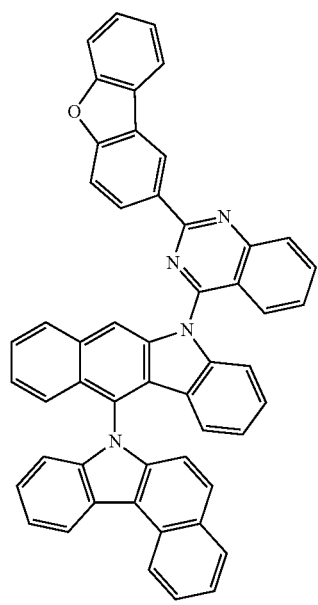
660
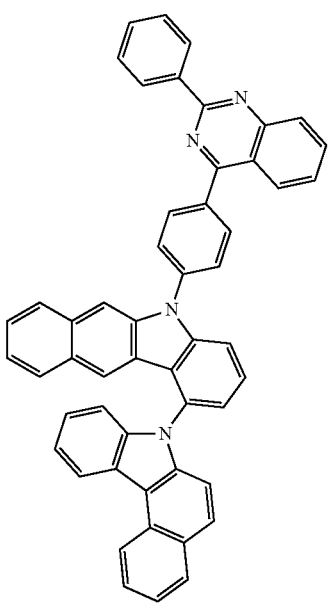
838
-continued
661
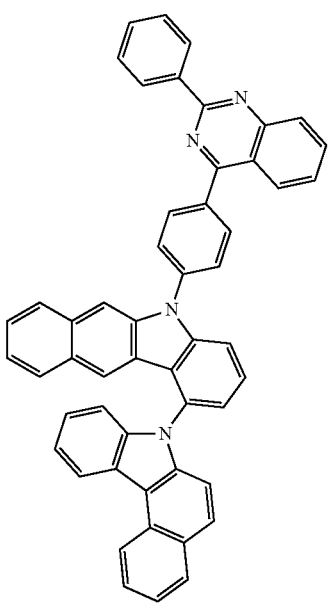
662
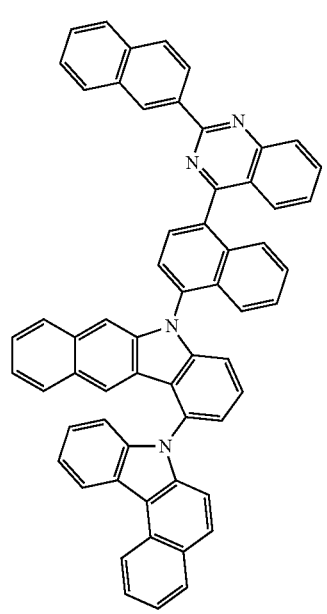

839
-continued
663
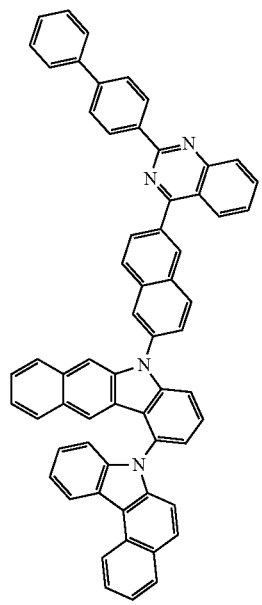
664
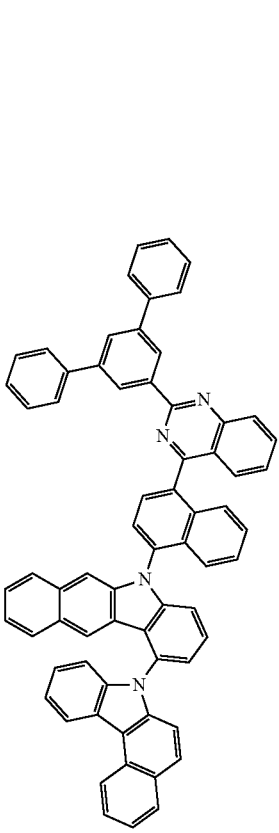
840
-continued
665
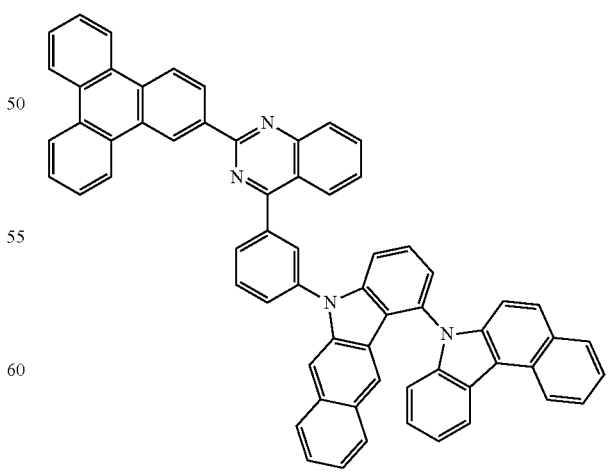
666

667
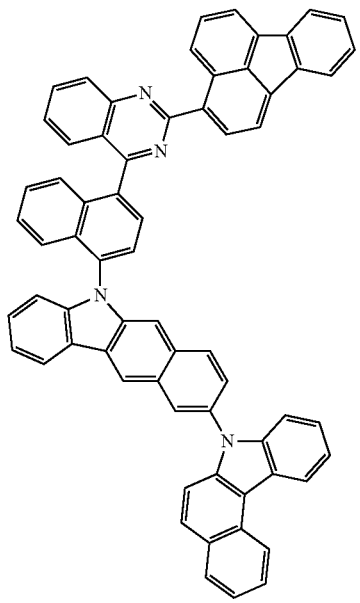
668
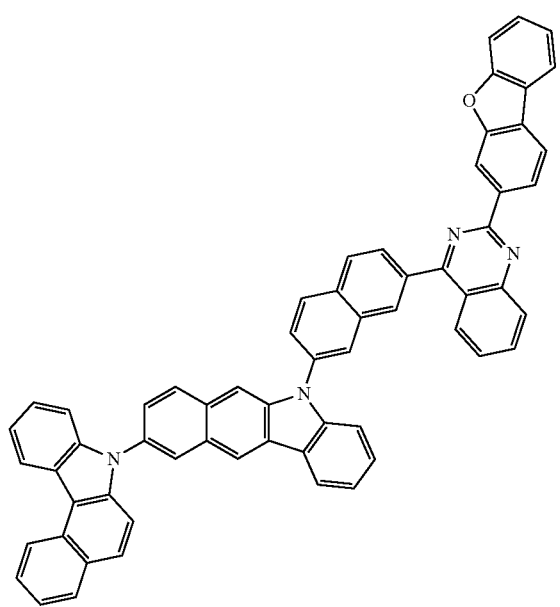
669
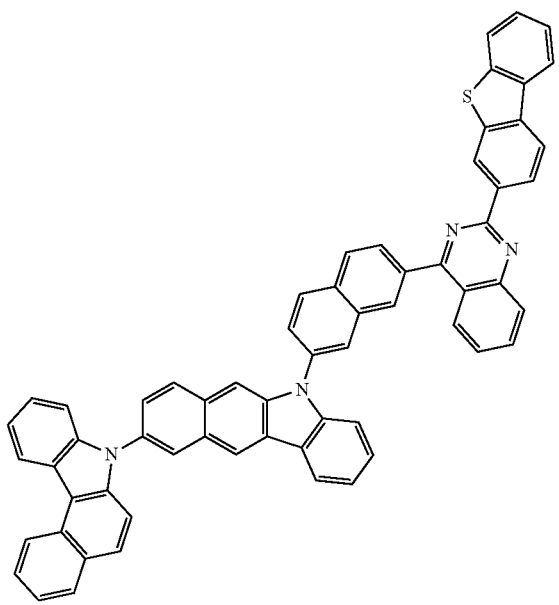
670
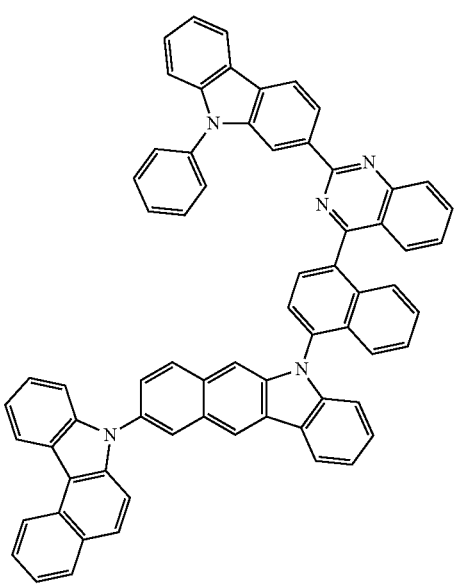

843
-continued
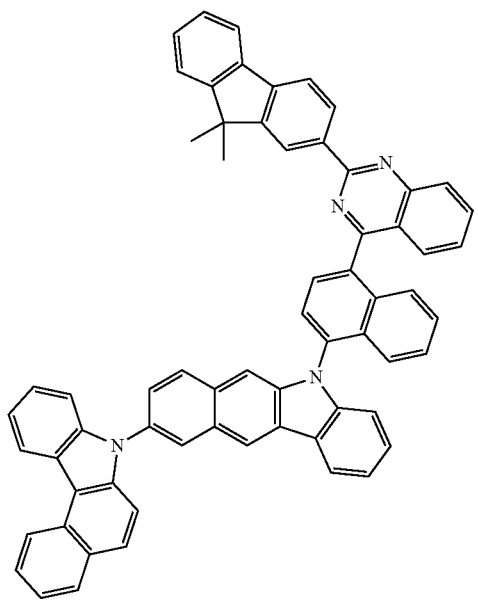
671
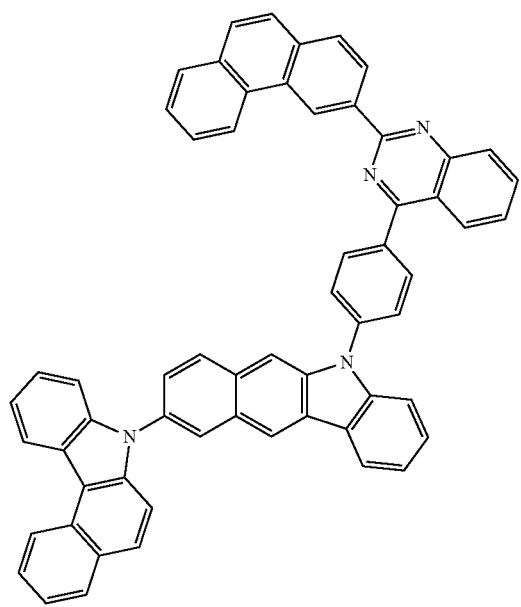
672
844
-continued
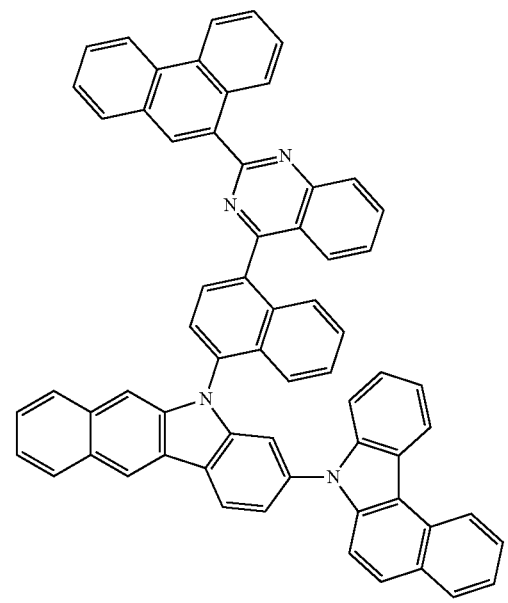
673
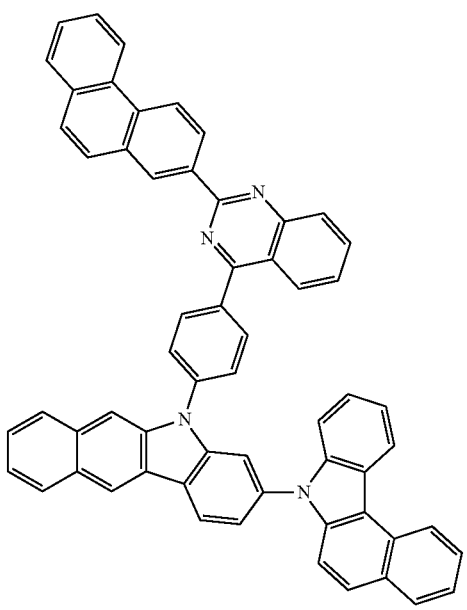
674

845
-continued
846
-continued
675
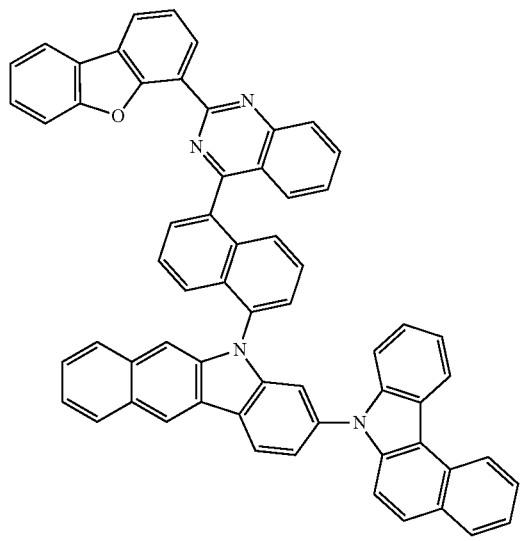
678
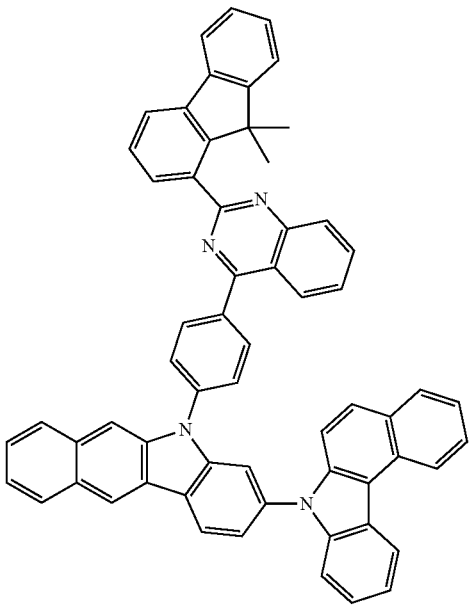
676
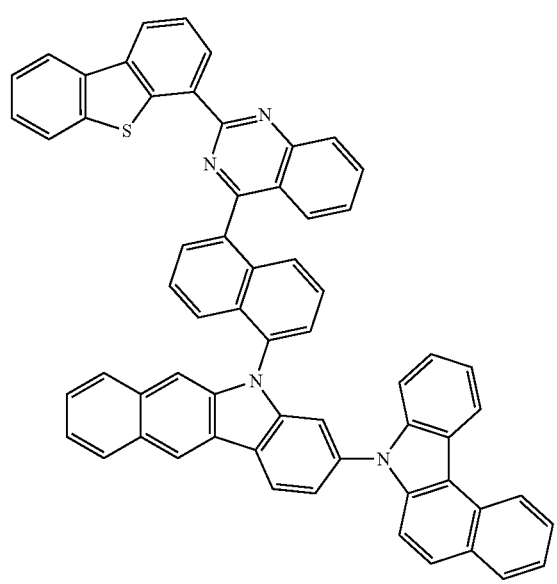
679
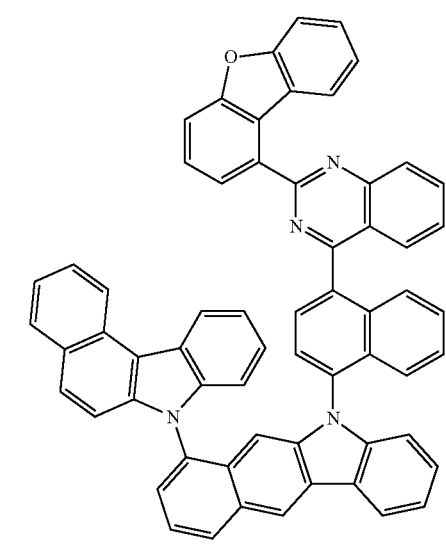
677
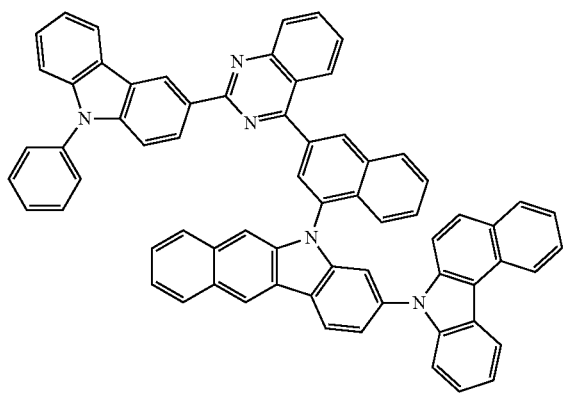

847
-continued
848
-continued
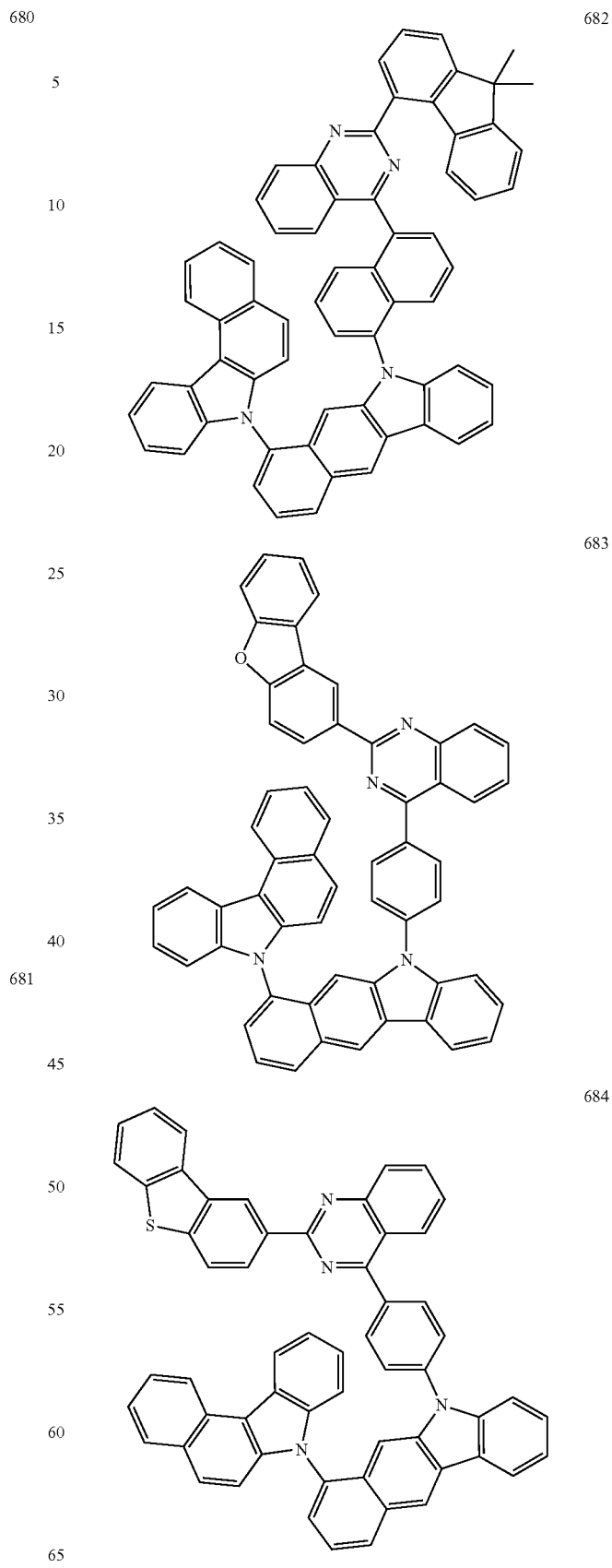

849
-continued
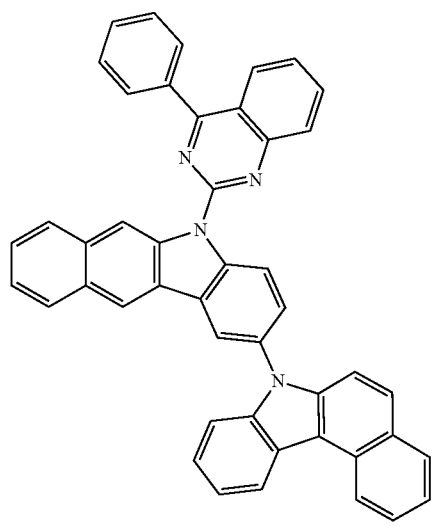
685
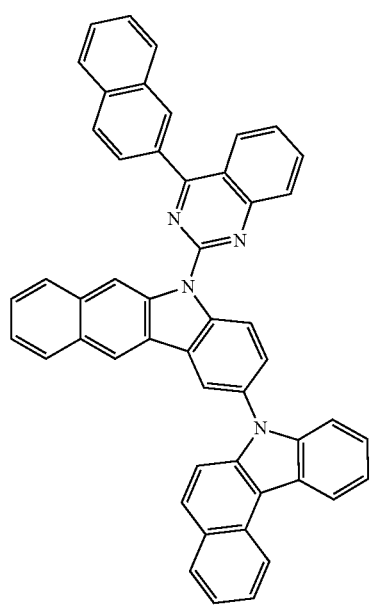
686
850
-continued
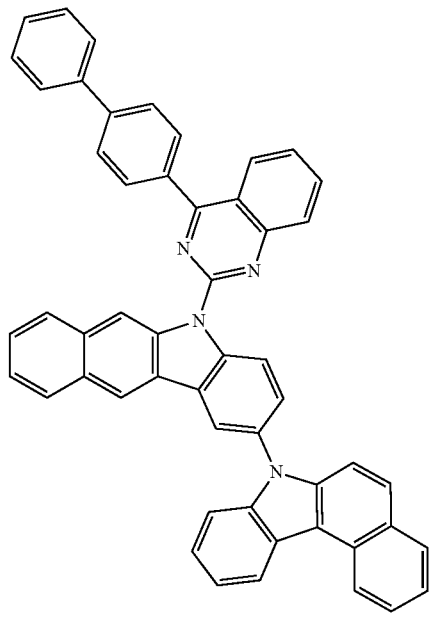
687
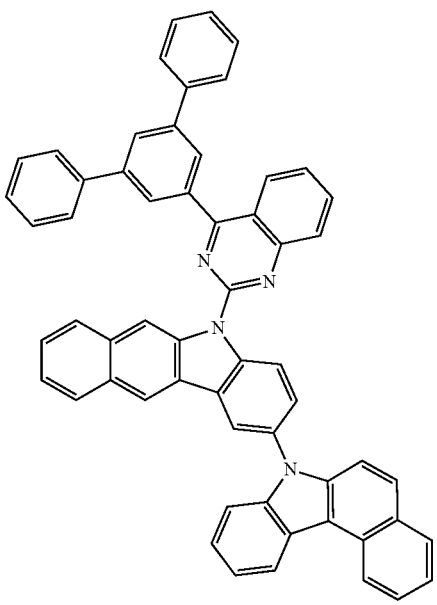
688

851
-continued
689
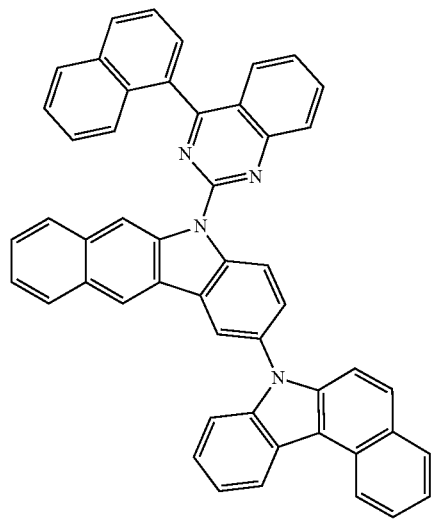
690
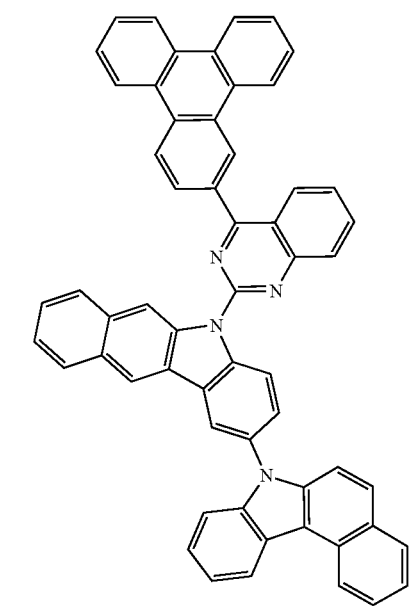
691
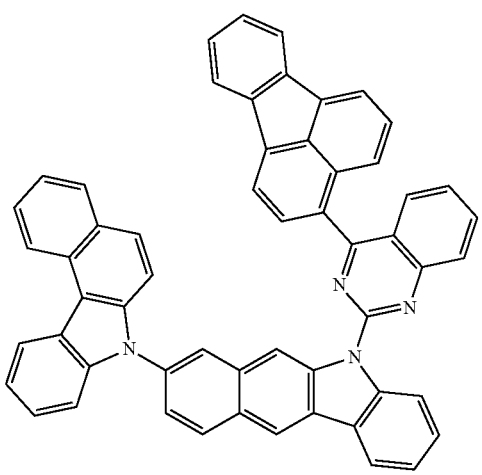
852
-continued
692
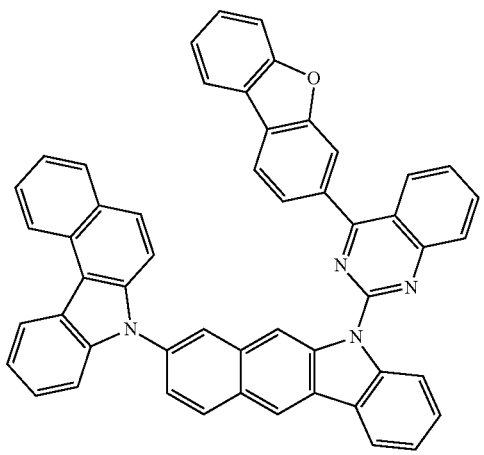
693
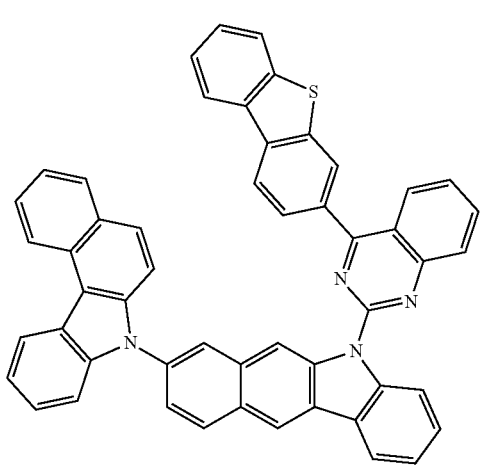
694
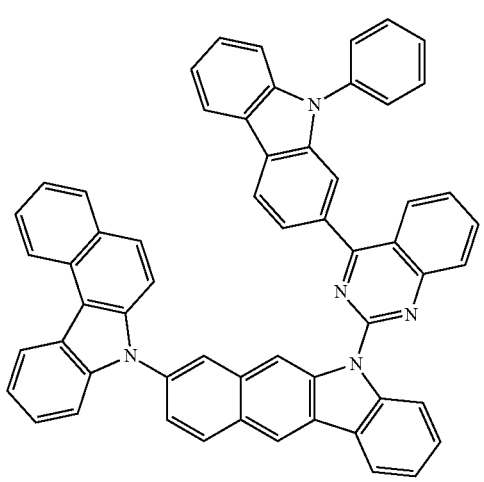

695
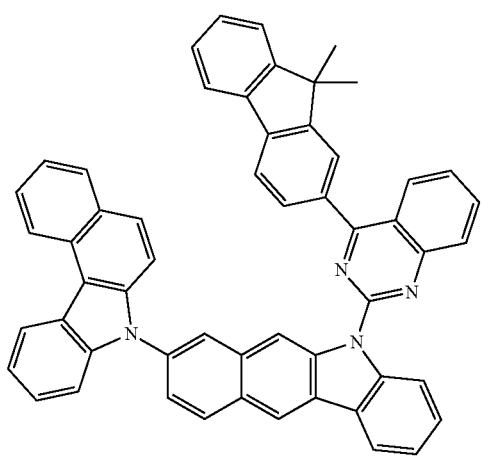
696
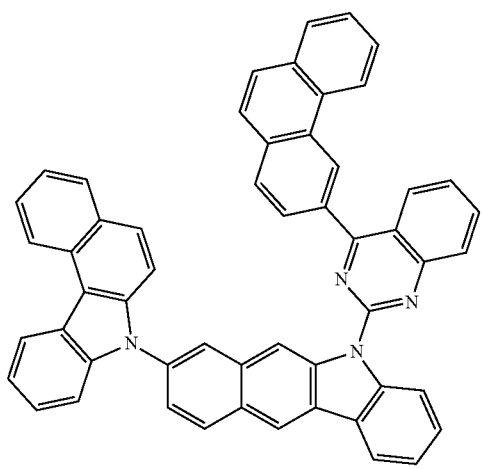
697
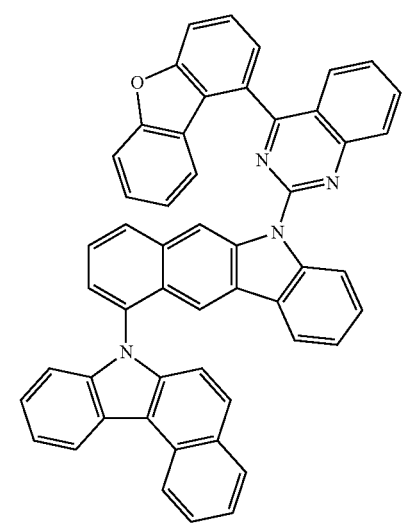
698
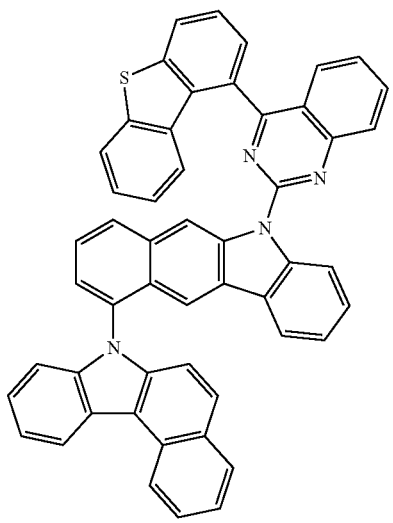
699
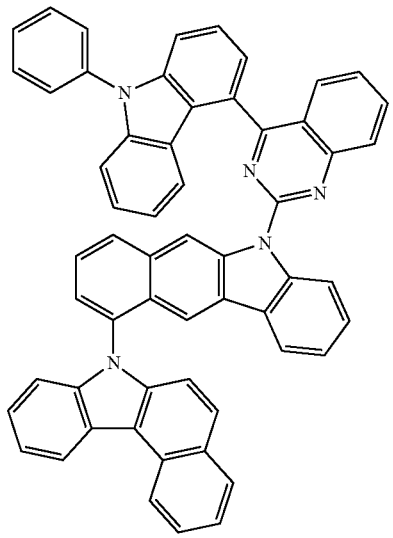
700
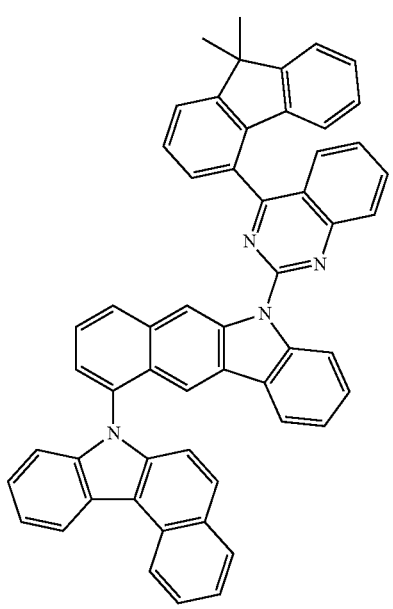

855
-continued
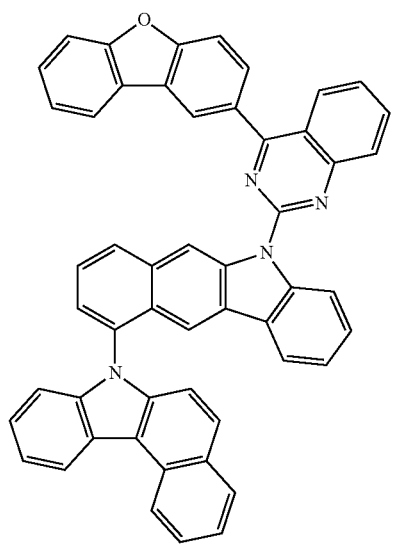
701
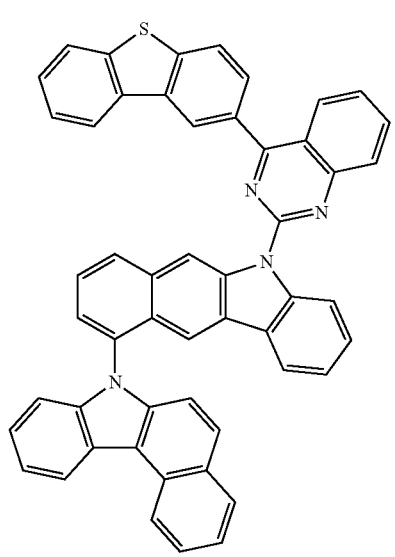
702
856
-continued
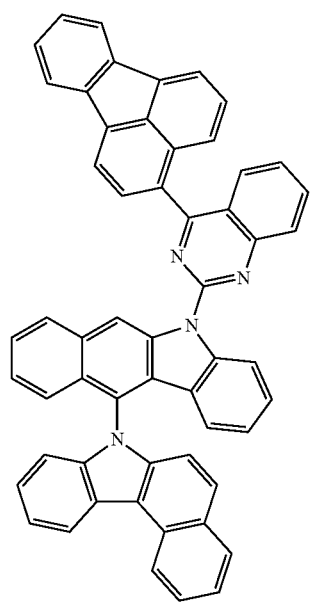
703
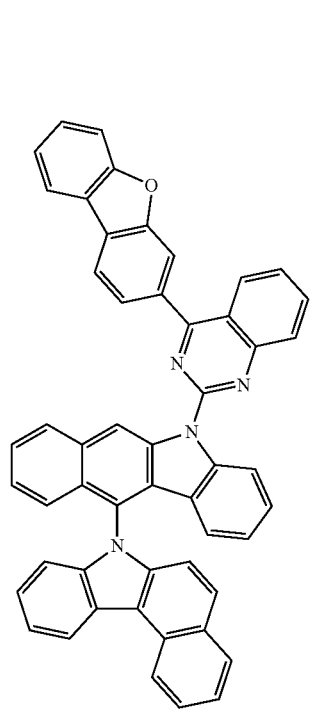
704

857
-continued
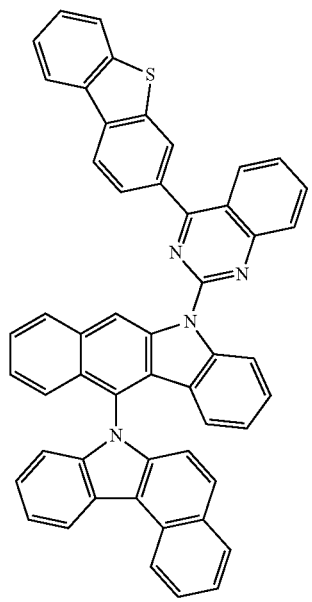
705
858
-continued
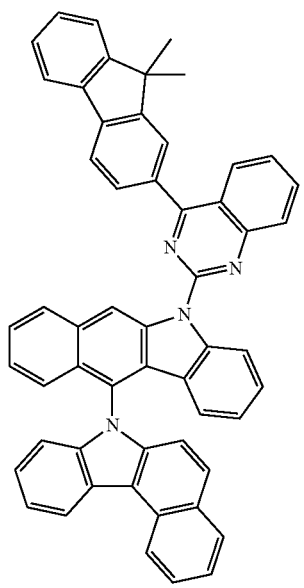
707
706
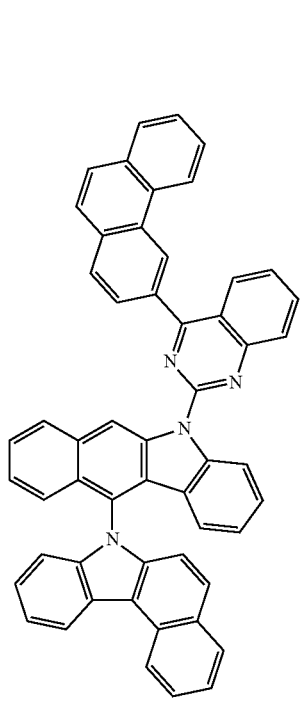
708

859
-continued
709
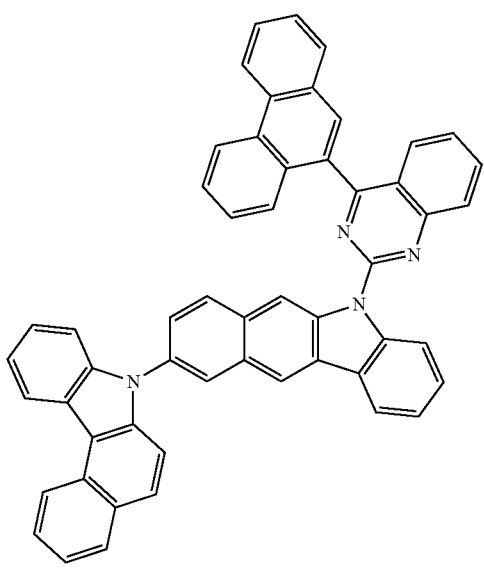
710
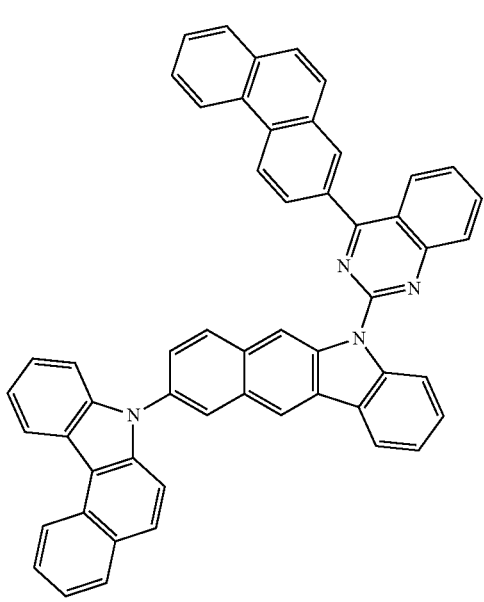
860
-continued
711
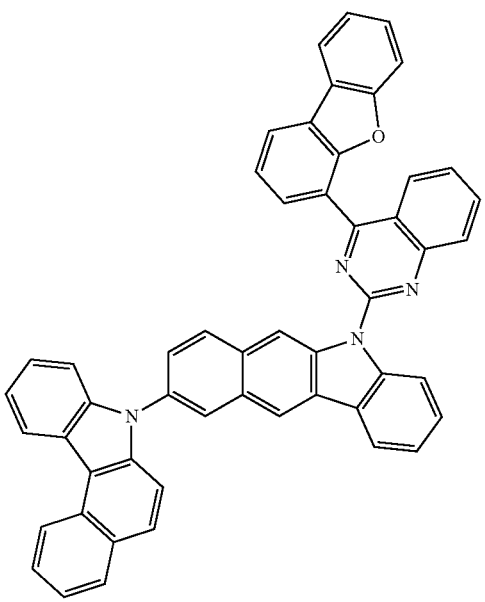
712
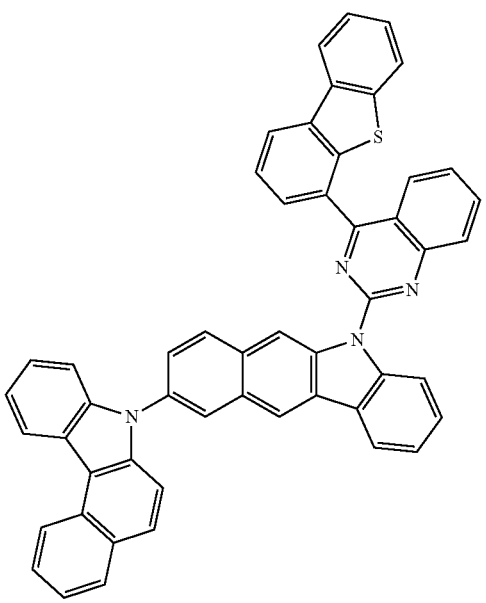

861
-continued
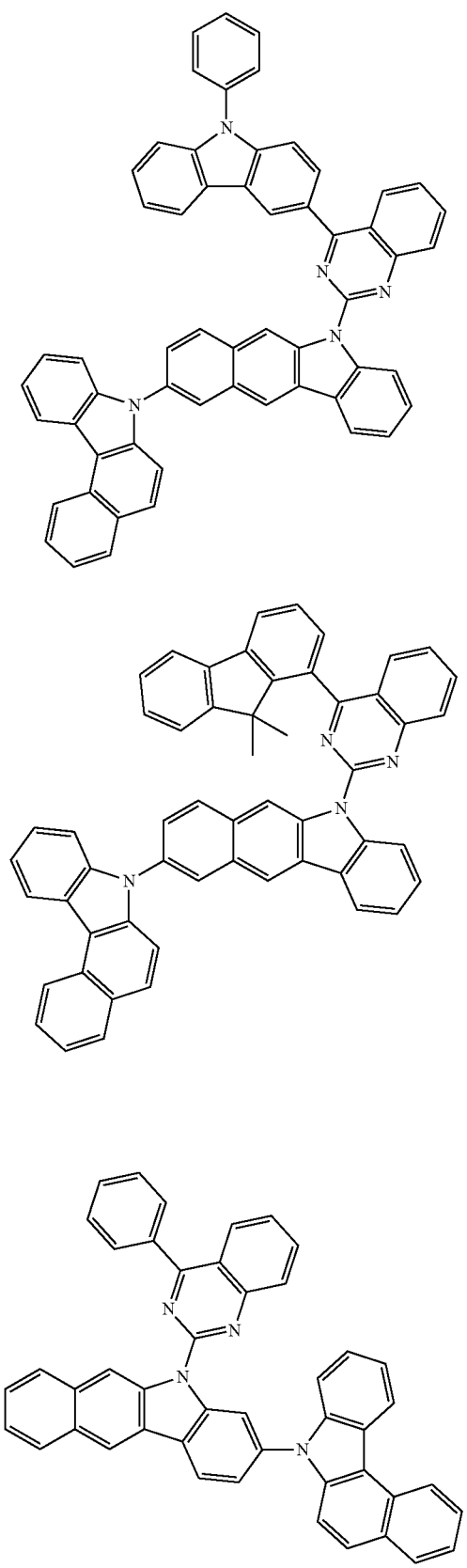
713
714
715
862
-continued
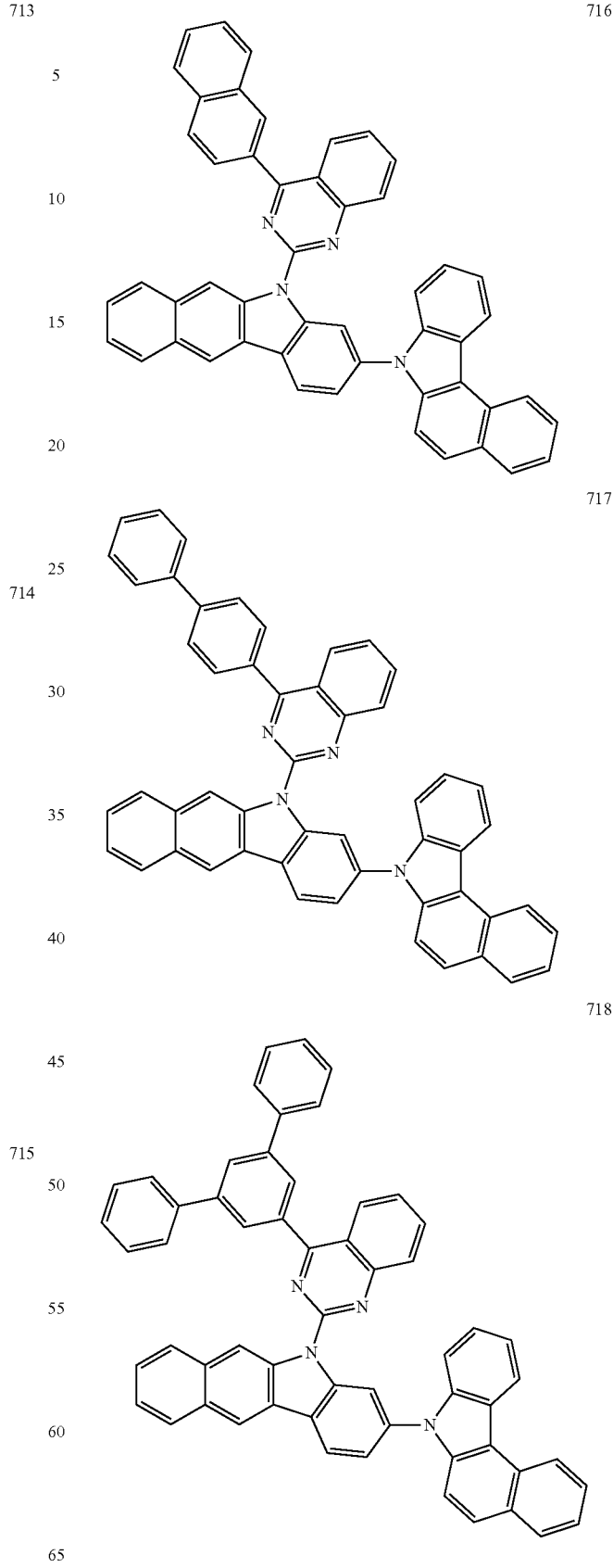
716
717
718

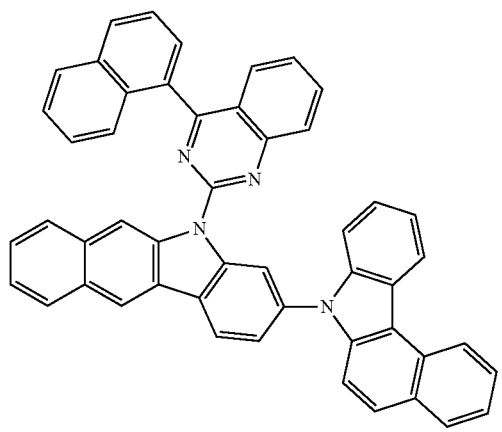
719
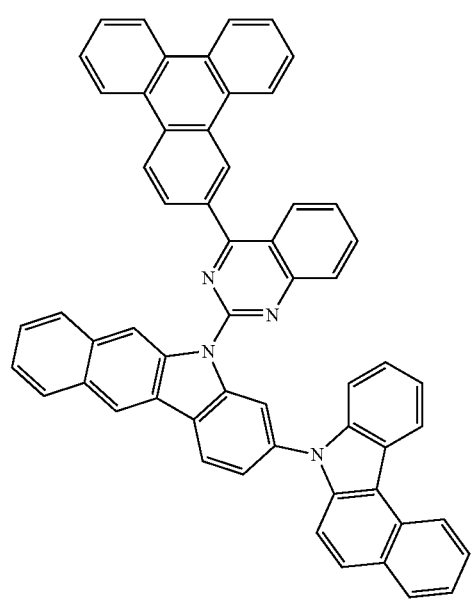
720
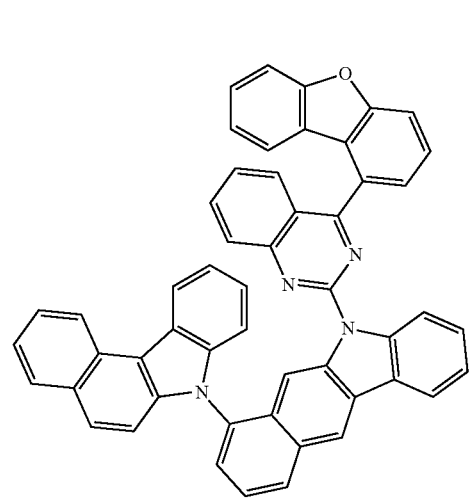
721
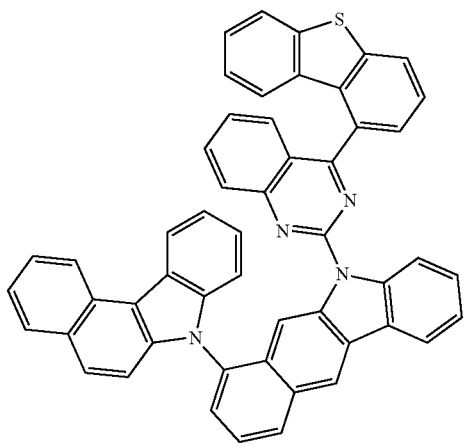
722
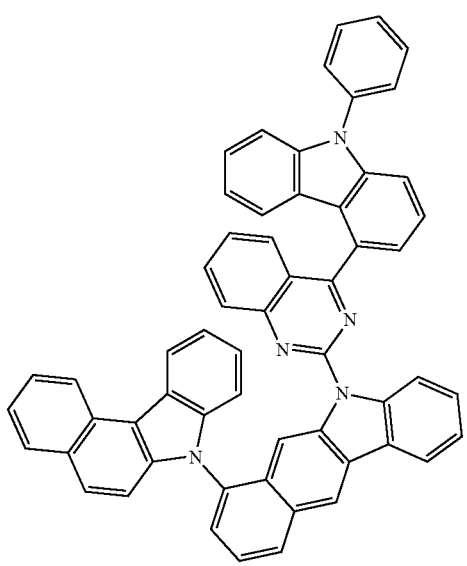
723
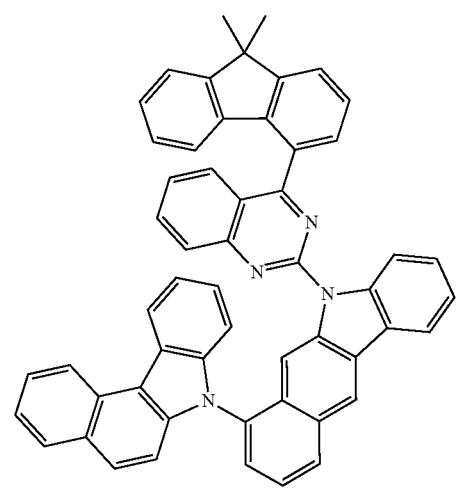
724

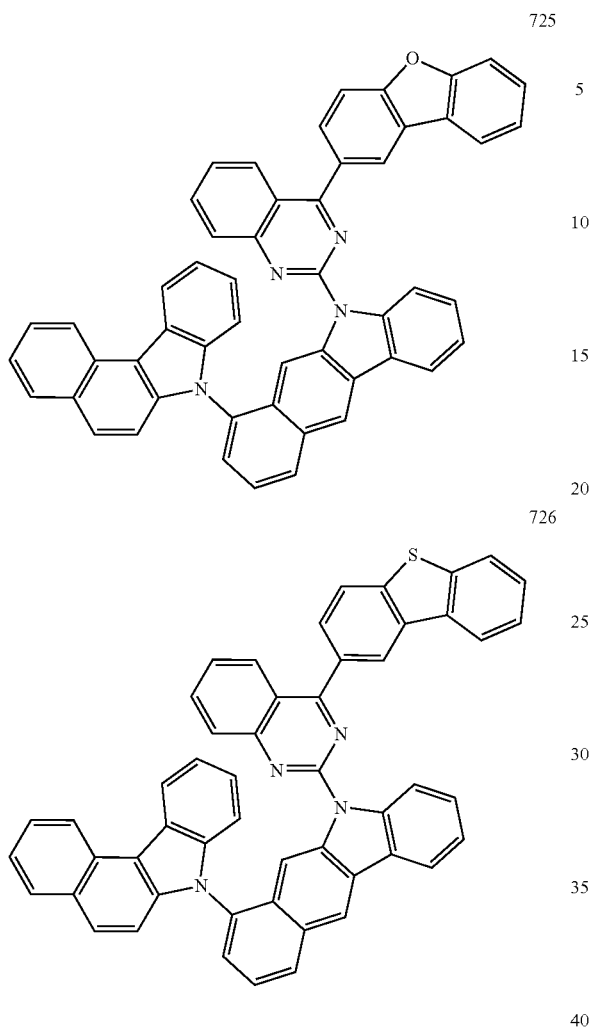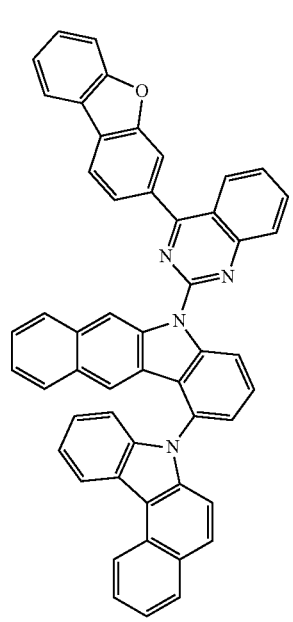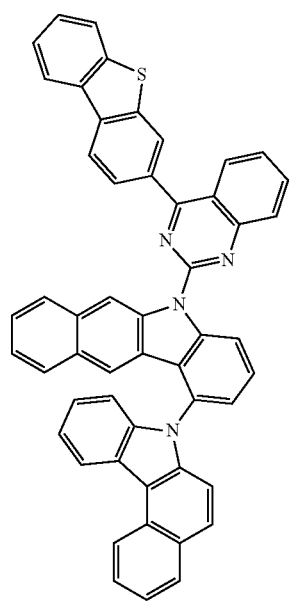

867
-continued
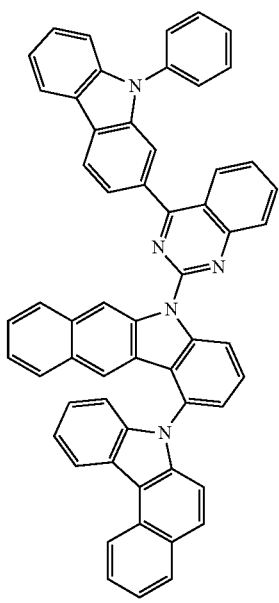
730
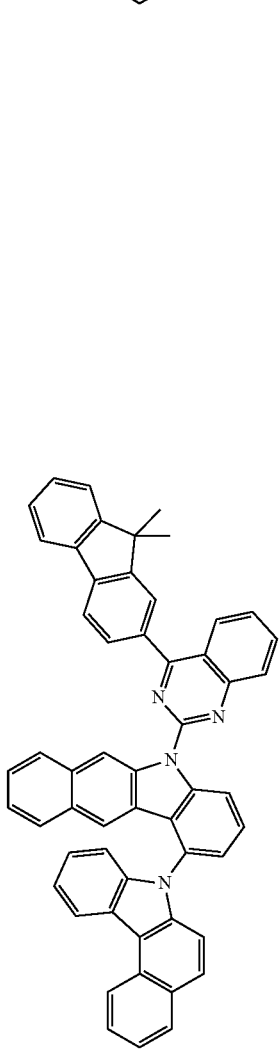
731
868
-continued
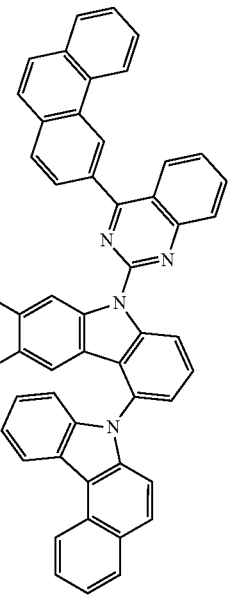
732
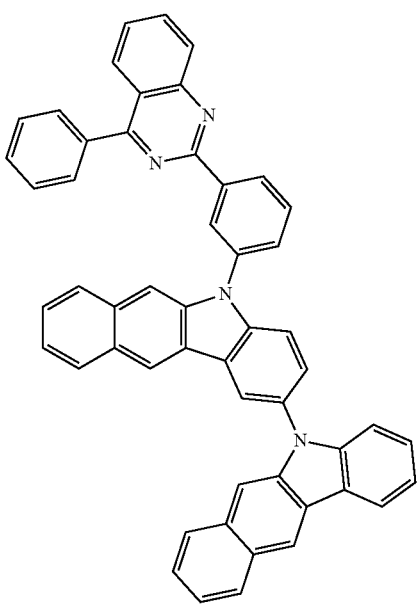
733

869
-continued
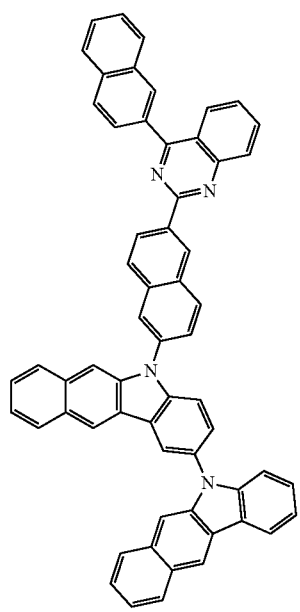
734
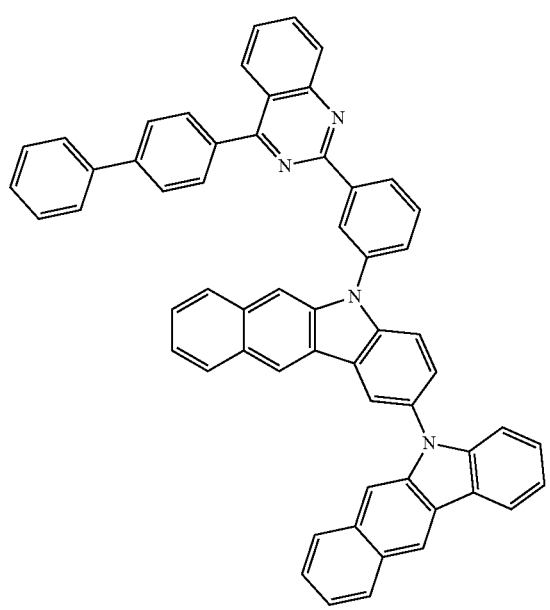
735
870
-continued
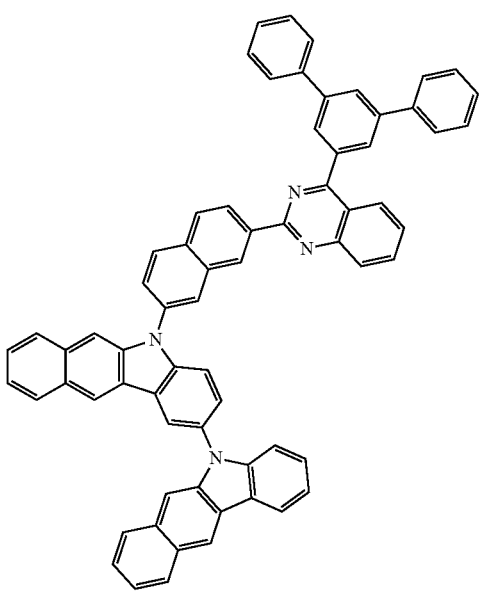
736
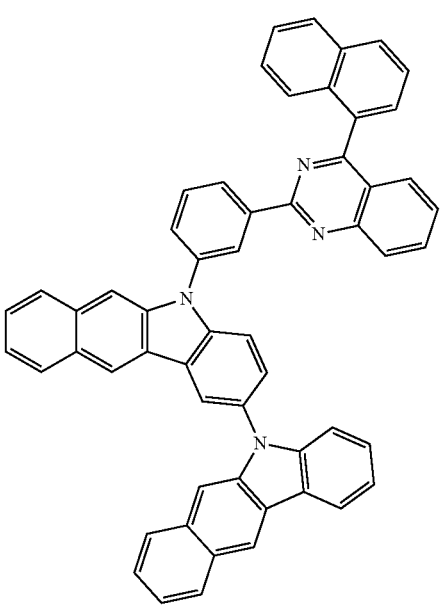
737

871
-continued
738
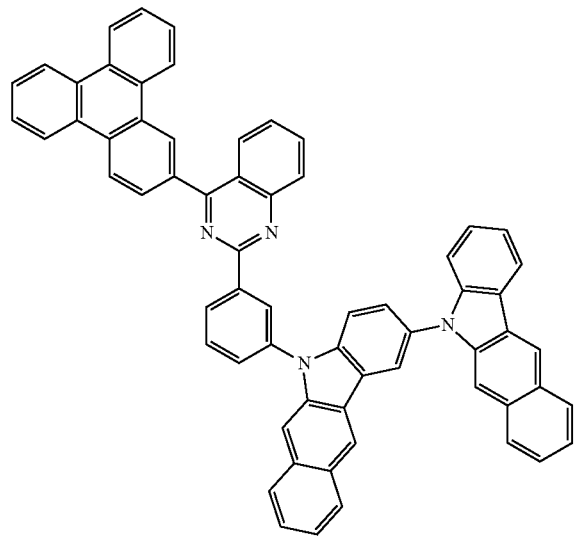
740
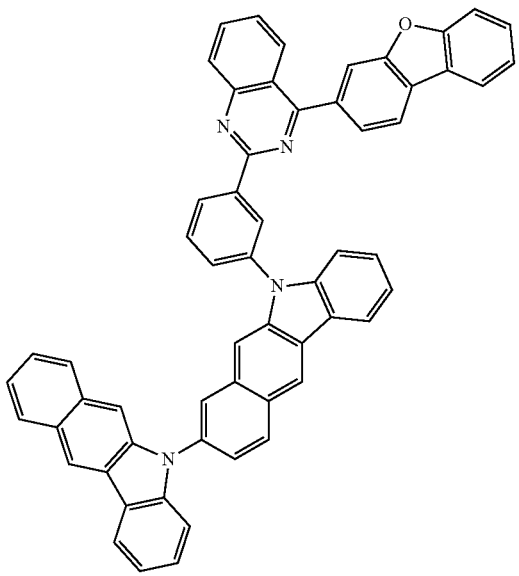
872
-continued
741
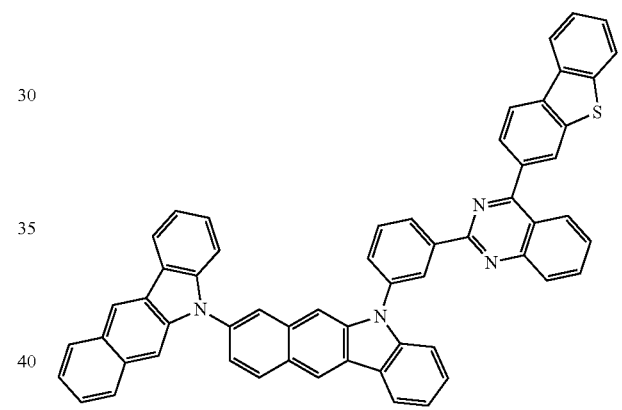
739
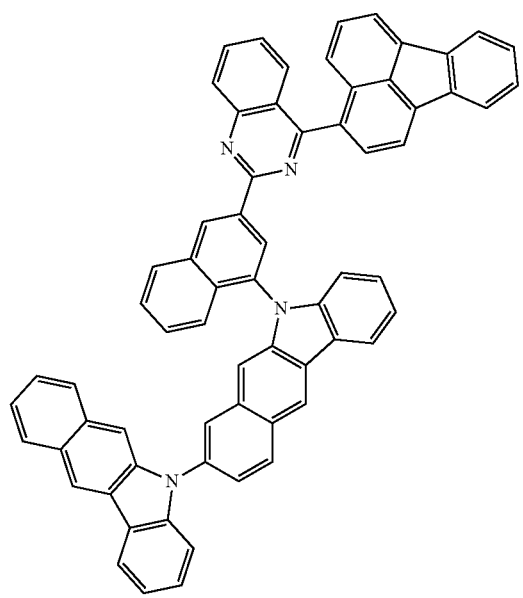
742
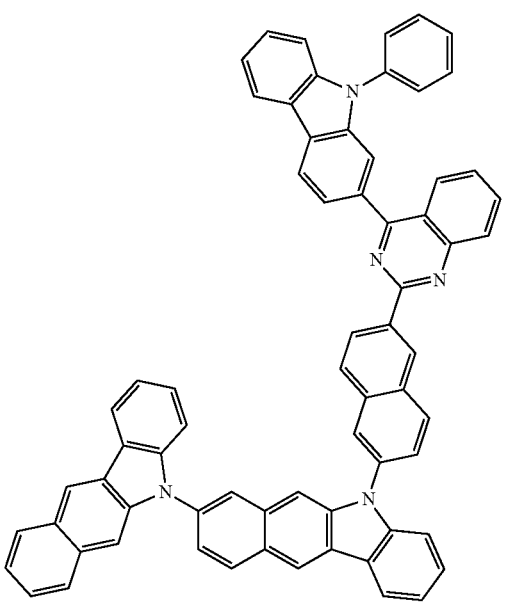

873
-continued
743
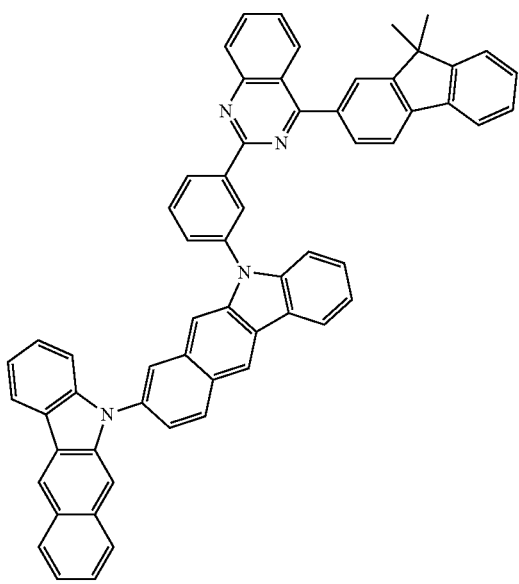
744
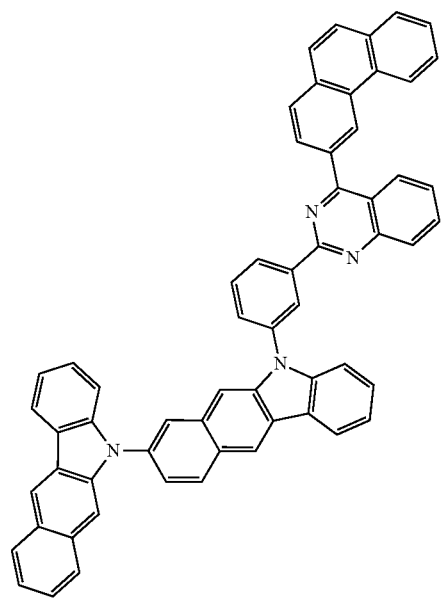
874
-continued
745
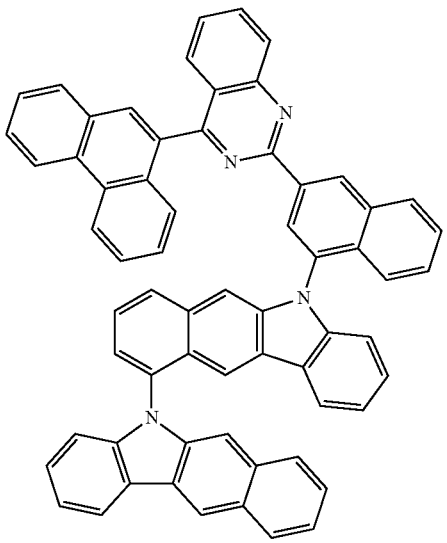
746
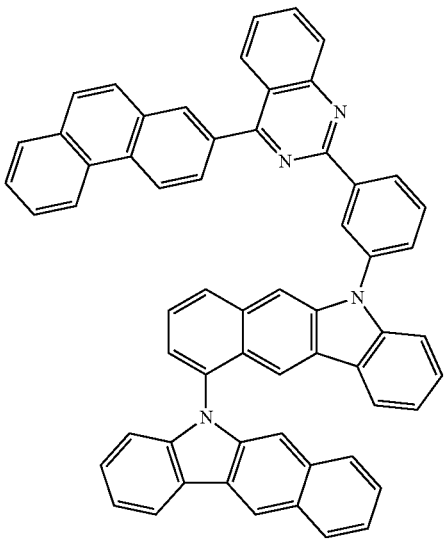
747
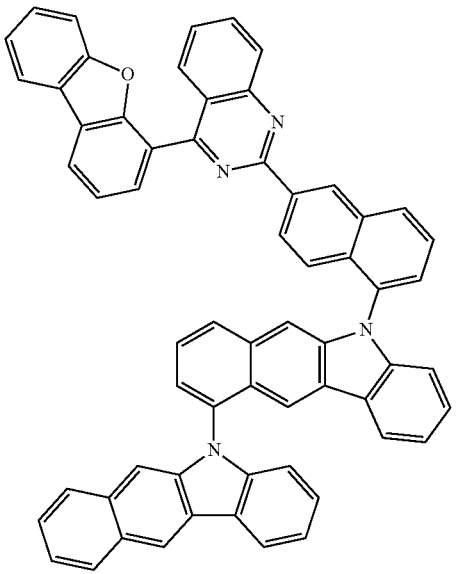

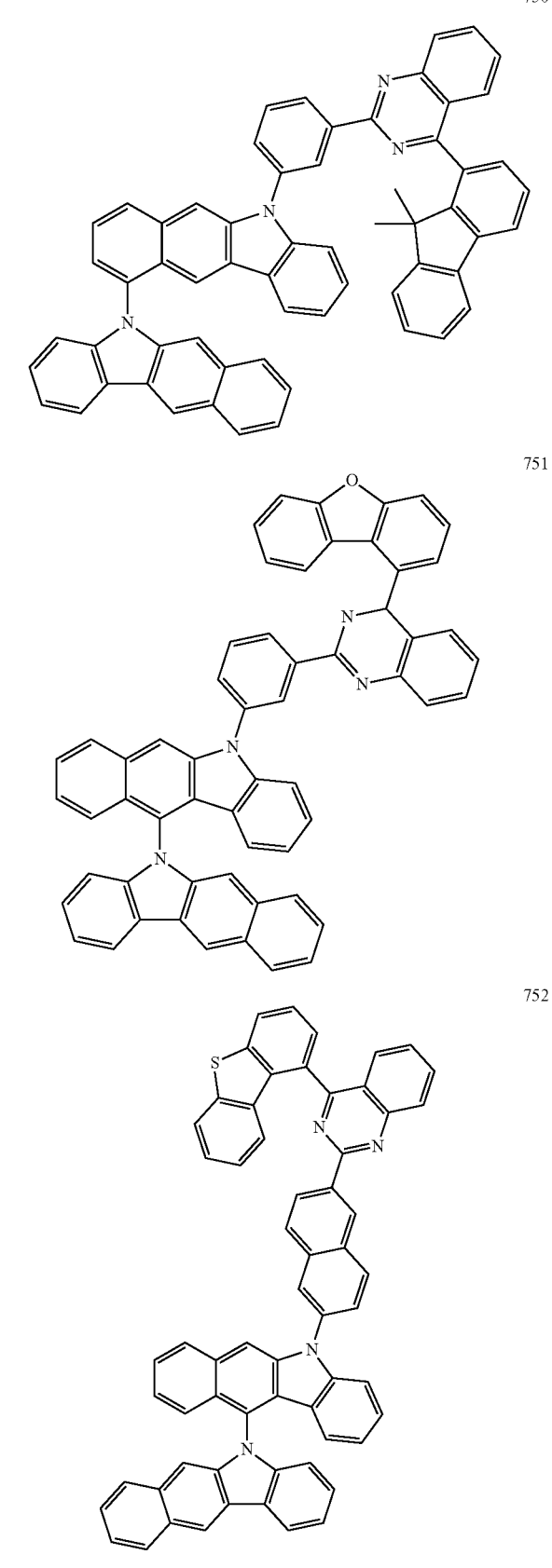

877
-continued
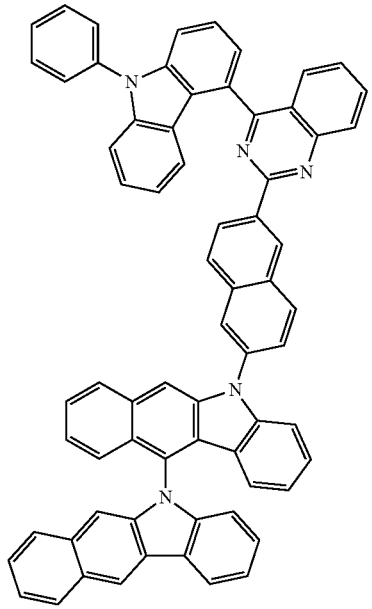
753
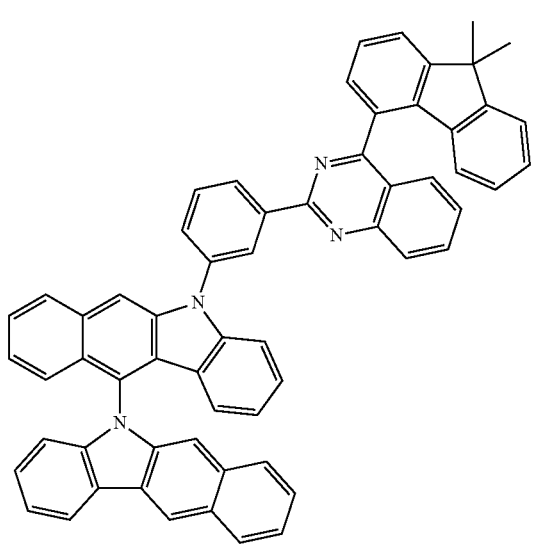
754
878
-continued
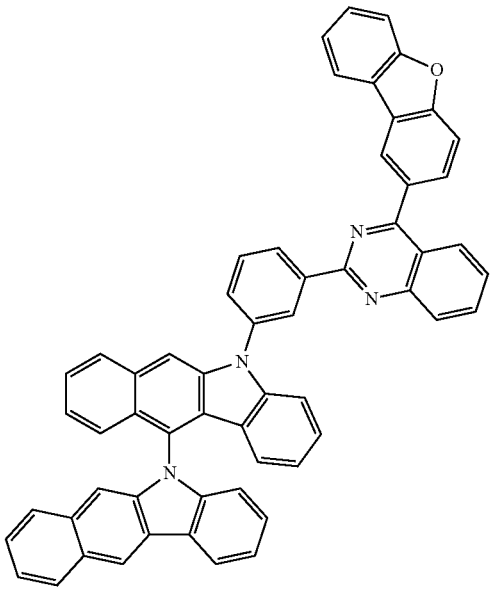
755
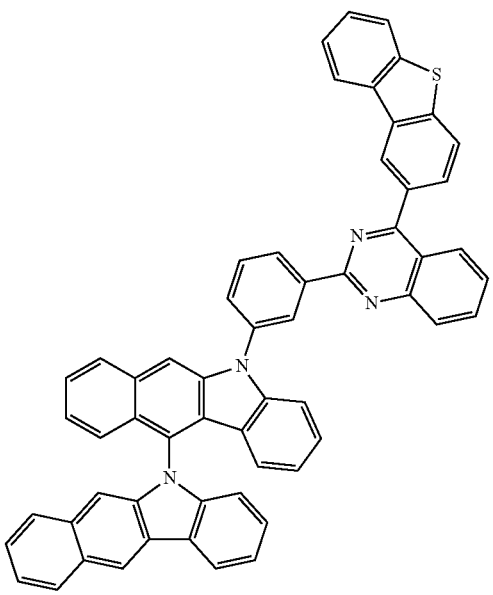
756

879
-continued
757
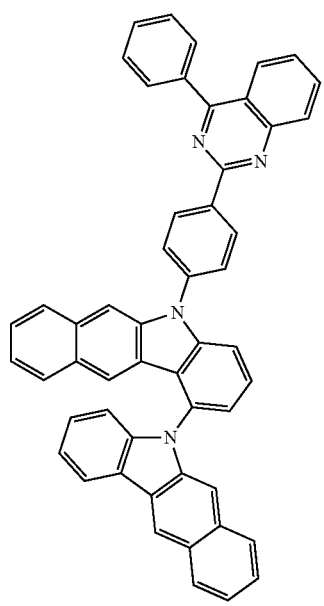
758
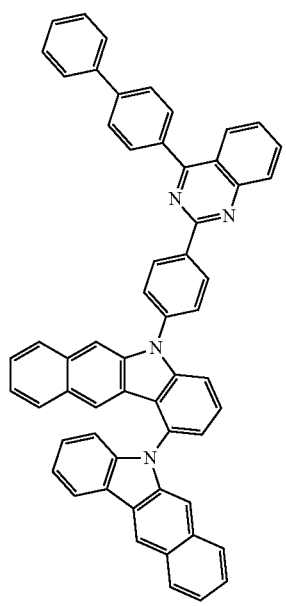
880
-continued
759
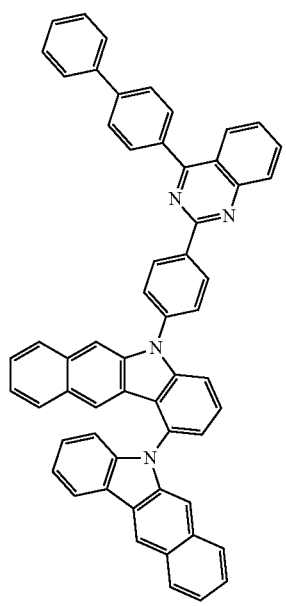
760
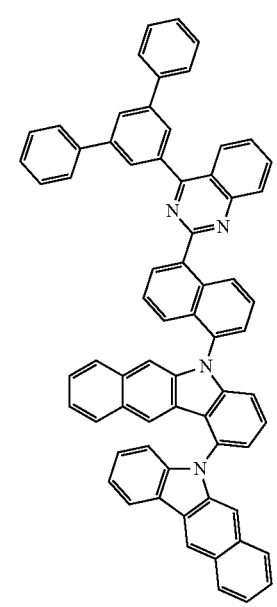

881
-continued
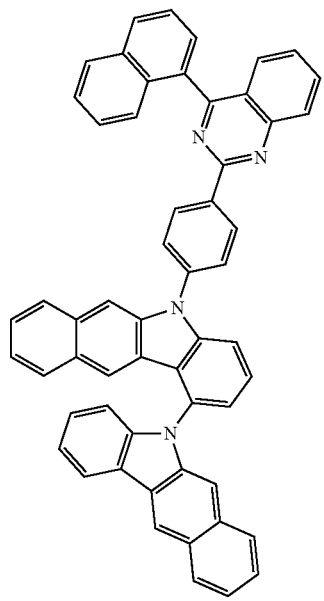
761
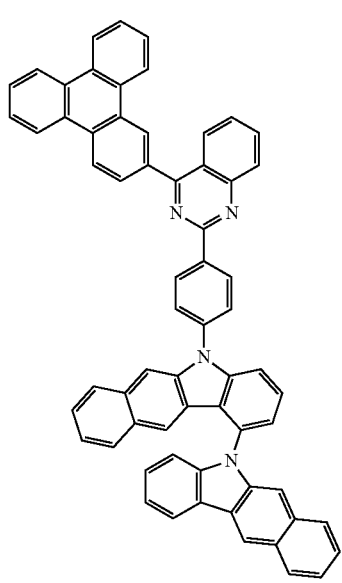
762
882
-continued
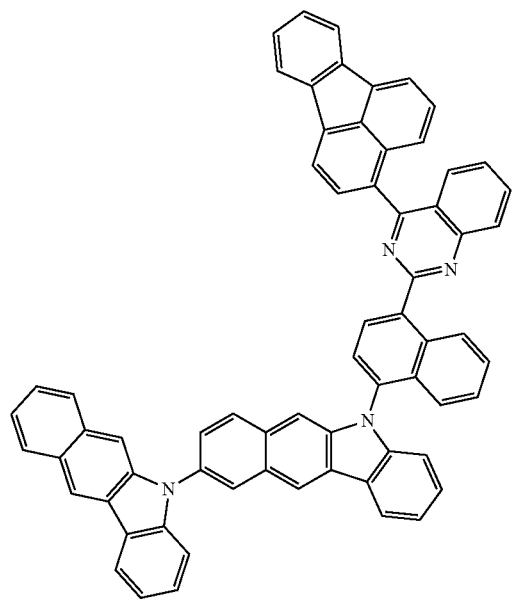
763
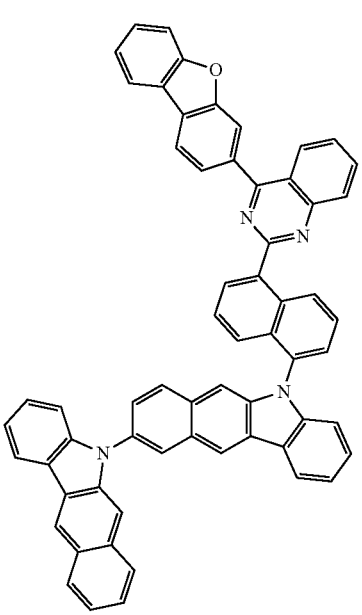
764

765
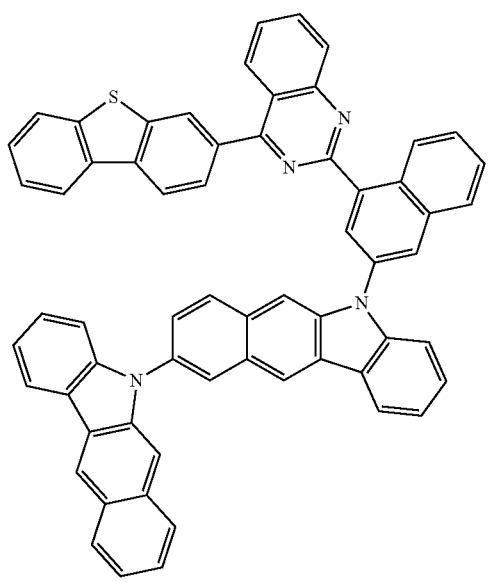
766
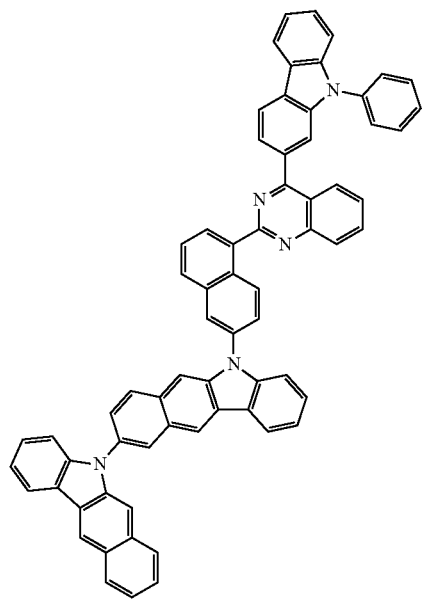
767
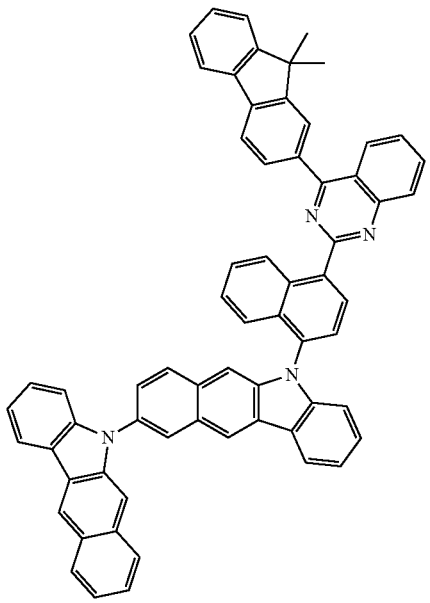
768
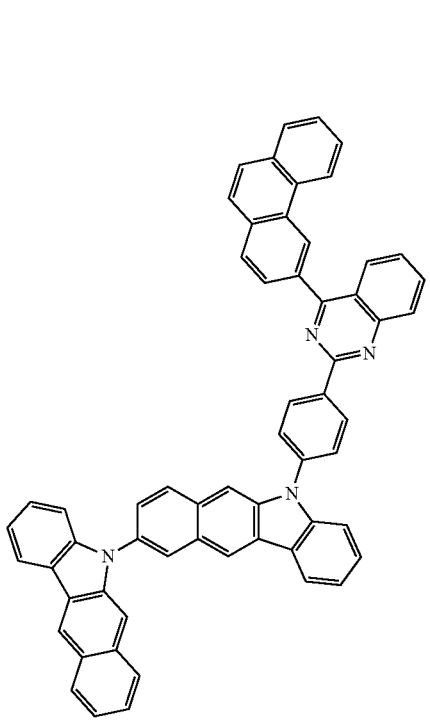

885
-continued
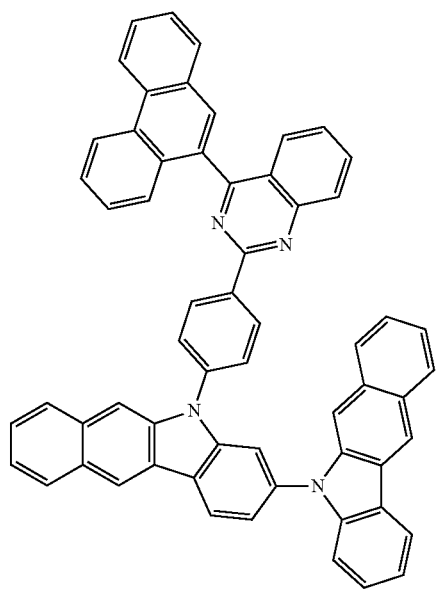
769
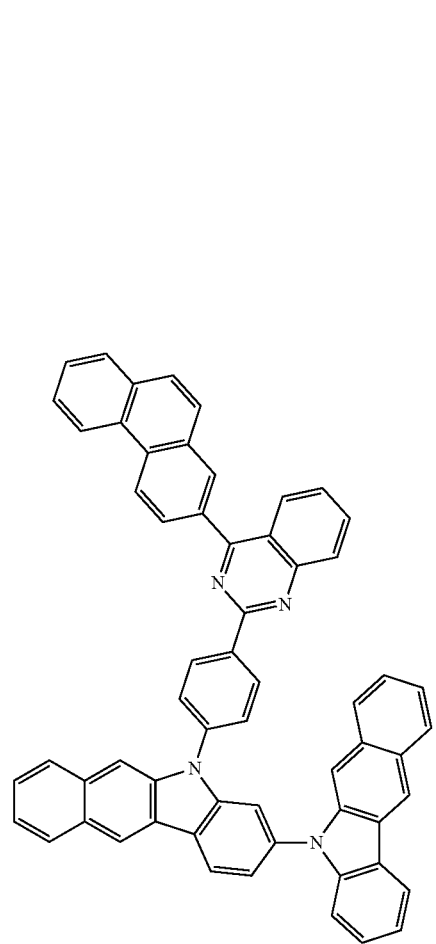
770
886
-continued
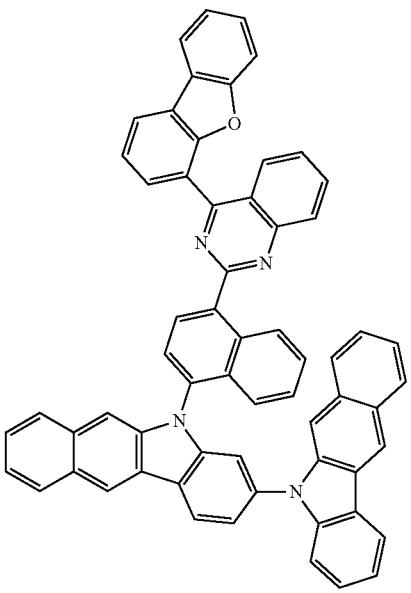
771
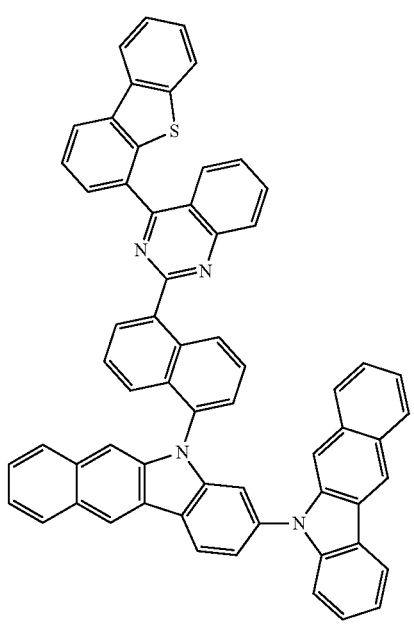
772

887
-continued
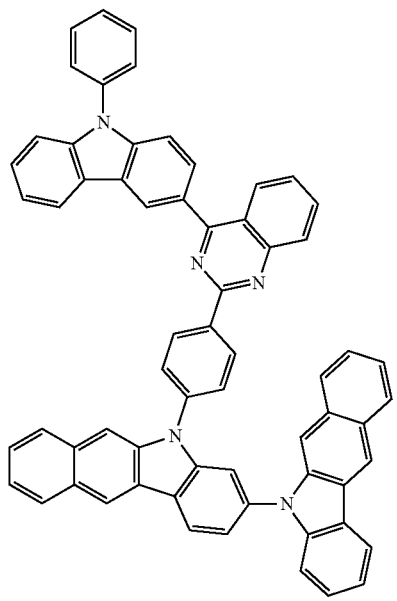
773
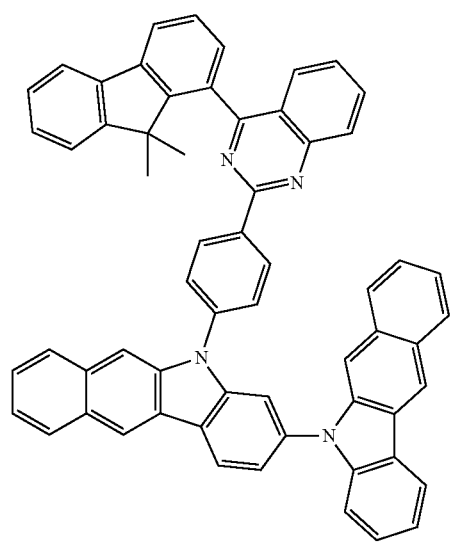
774
888
-continued
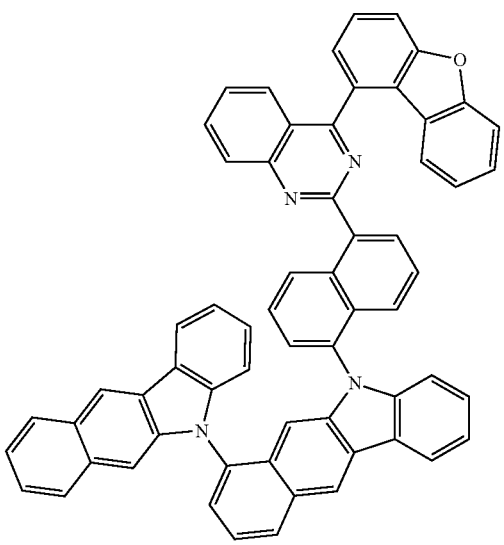
775
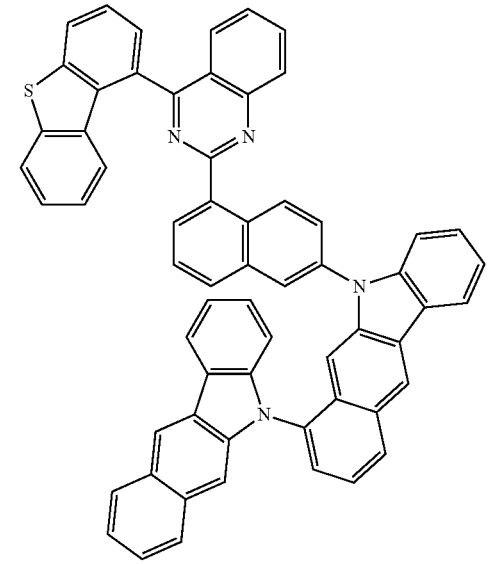
776

889
-continued
777
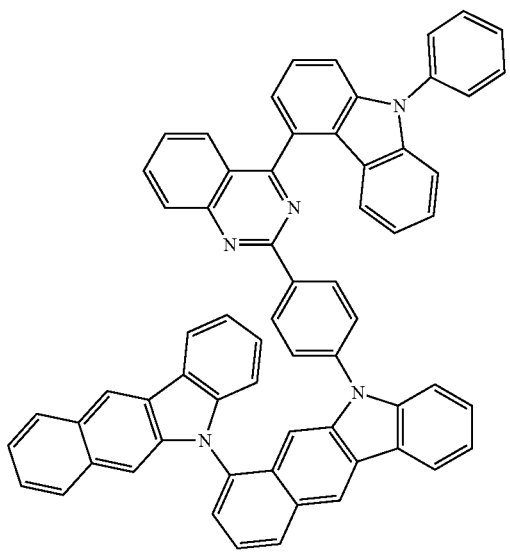
778
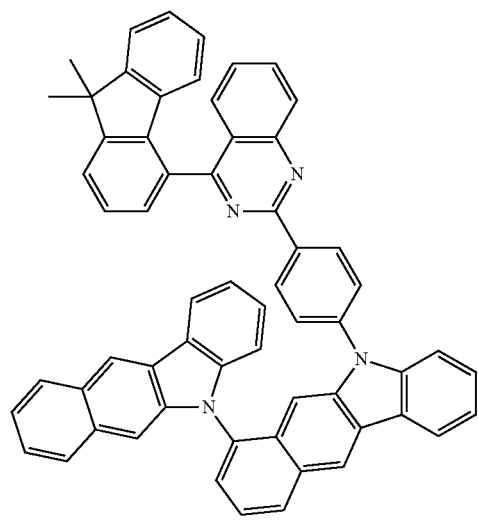
779
890
-continued
780
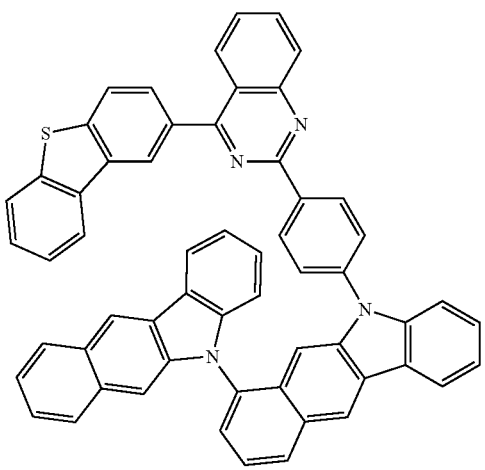
781
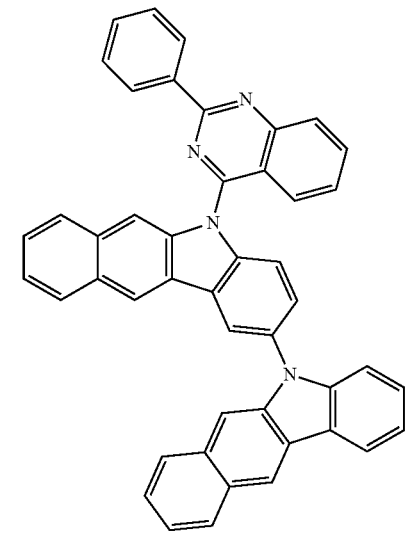
782
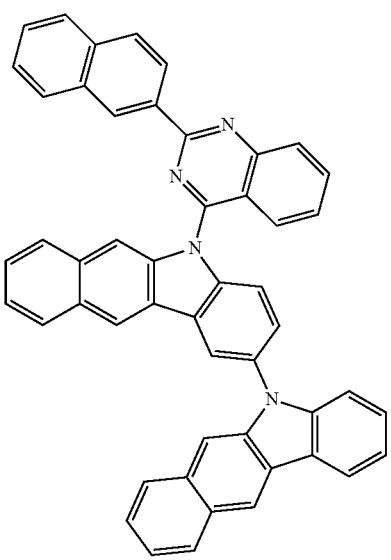

891
-continued
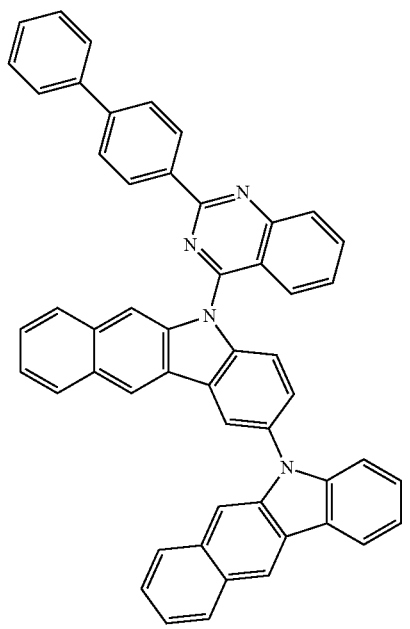
783
892
-continued
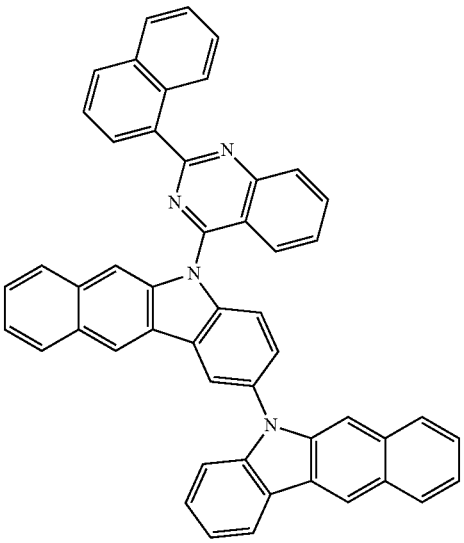
785
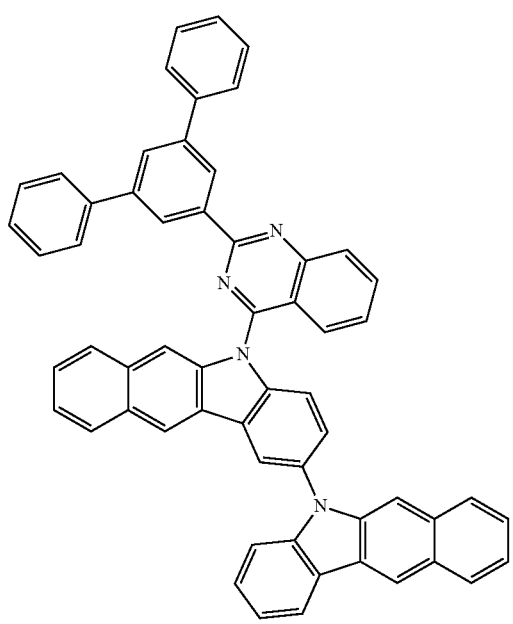
784
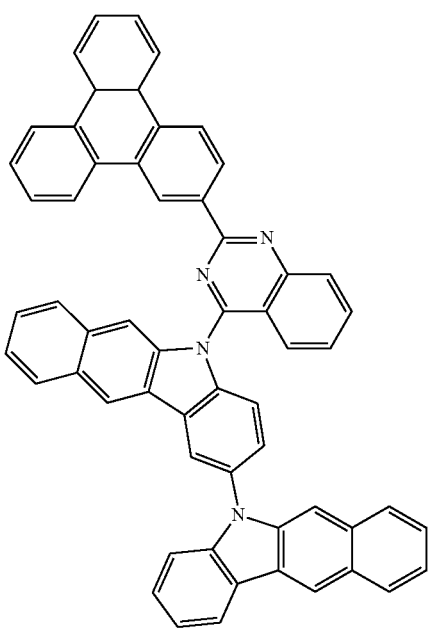
786

893
-continued
787
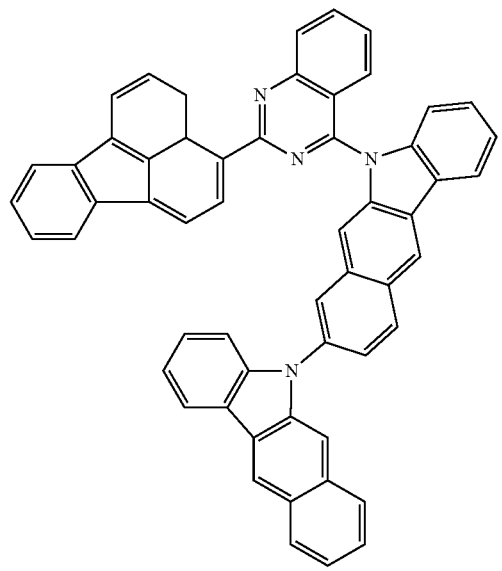
788
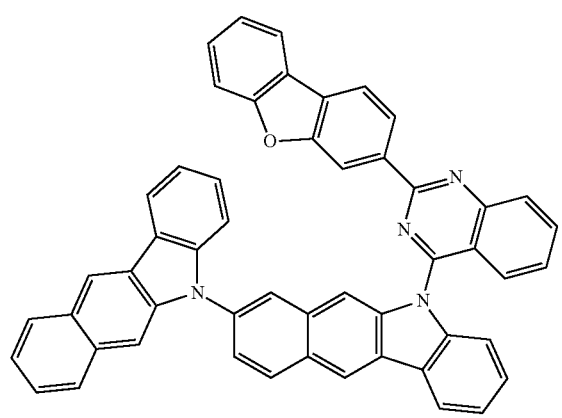
789
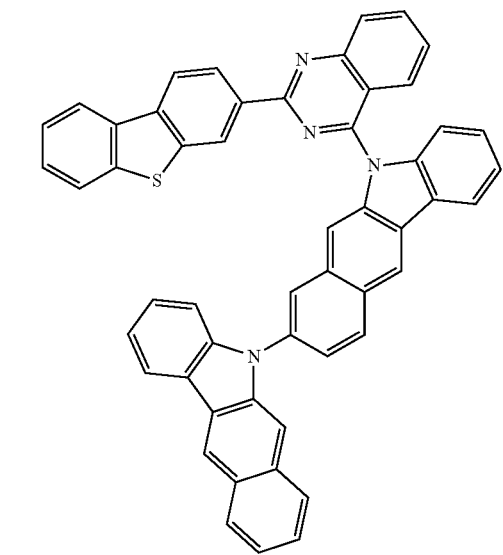
894
-continued
790
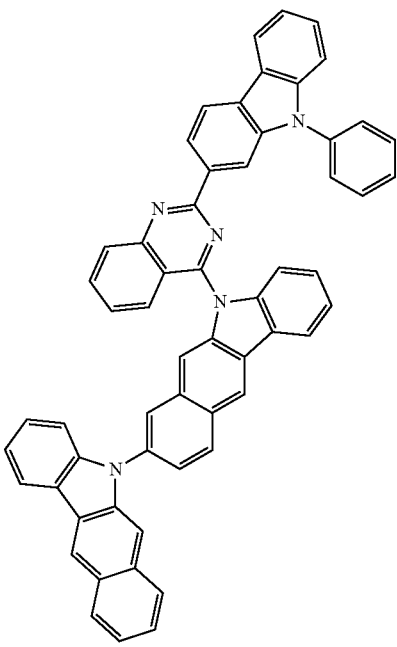
791
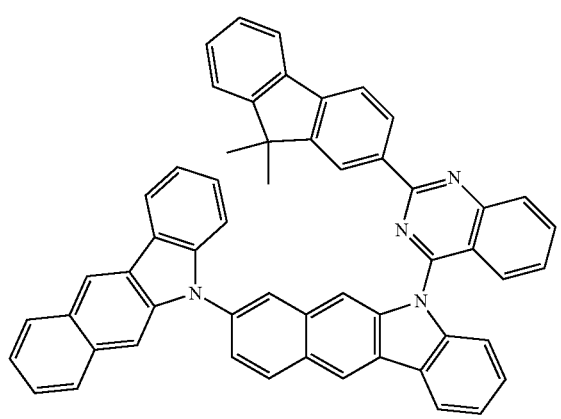
792
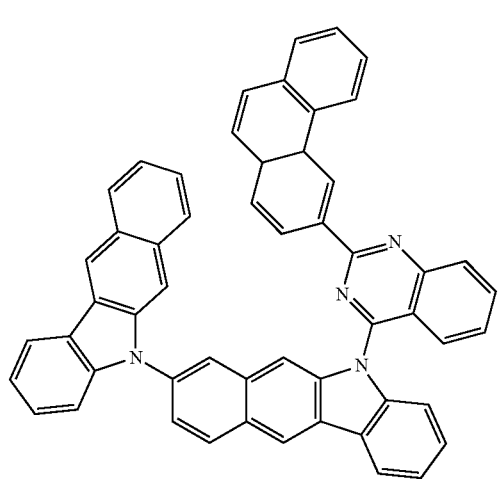

793
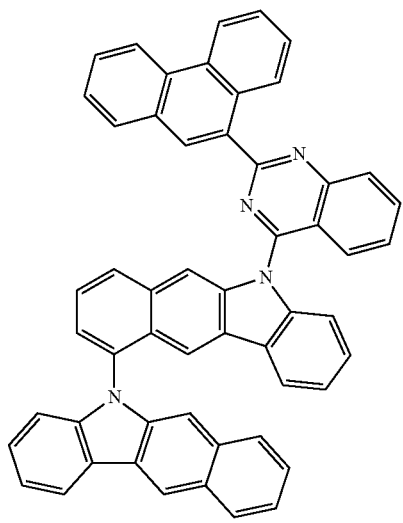
794
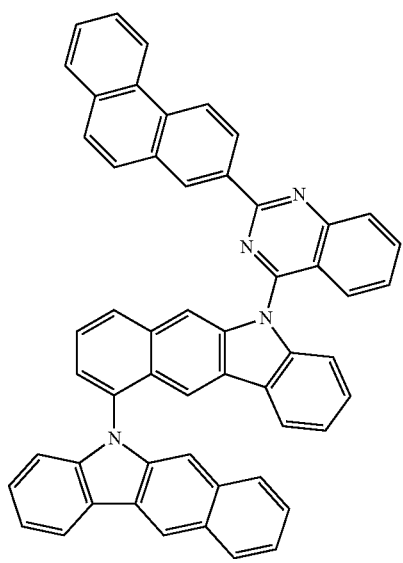
795
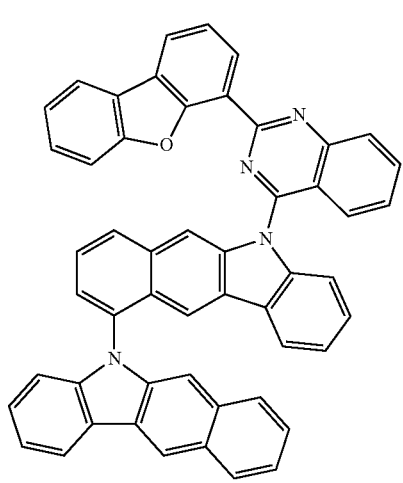
796
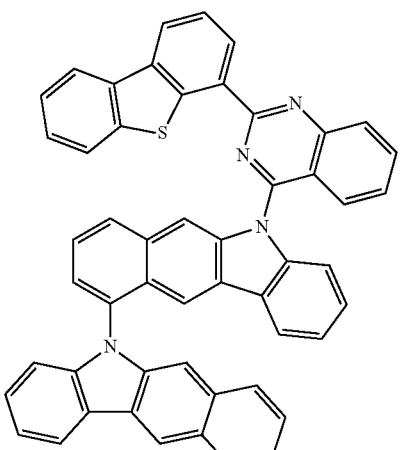
797
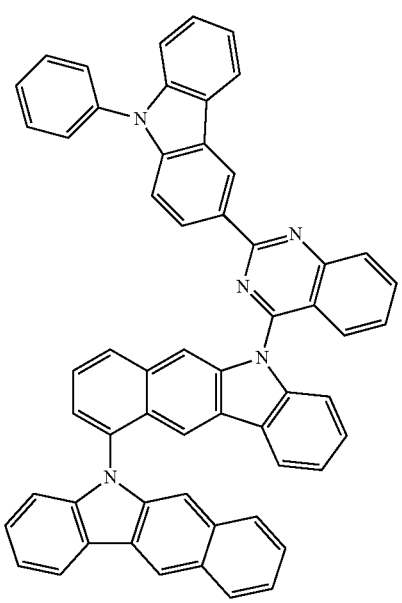
798
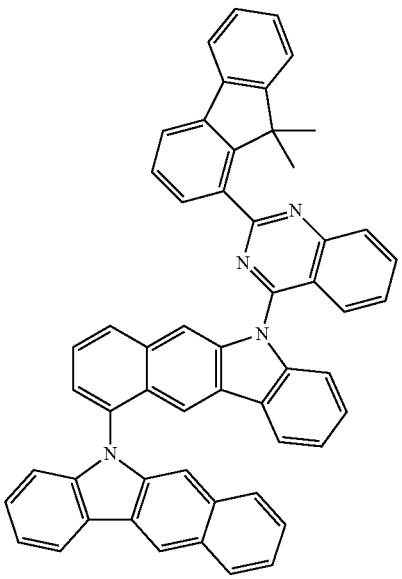

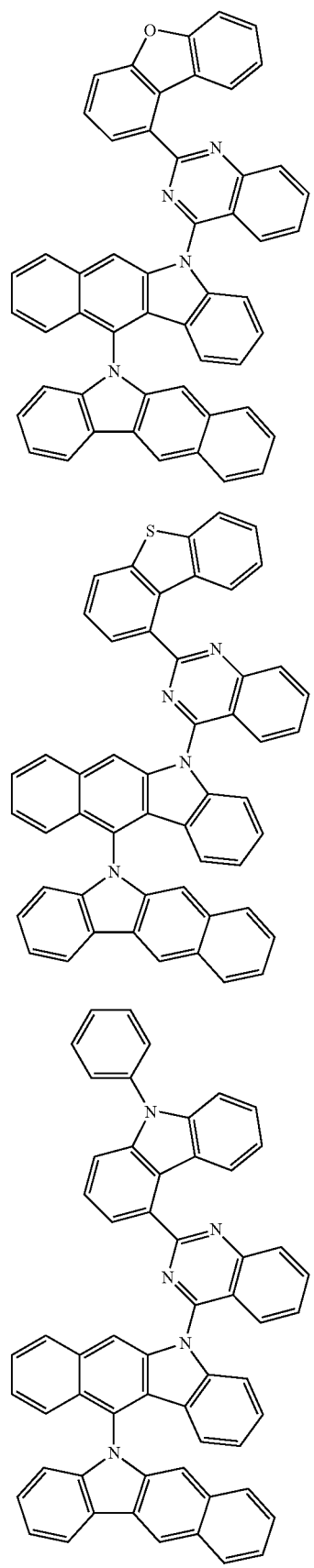

899
-continued
805
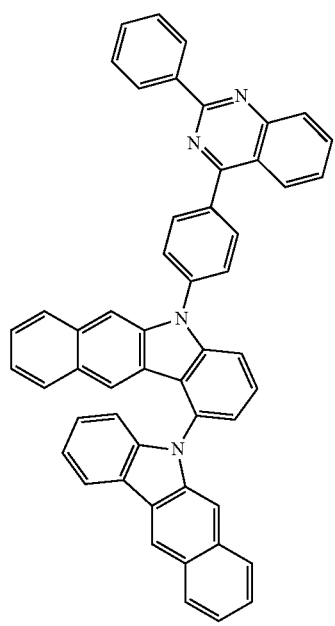
806
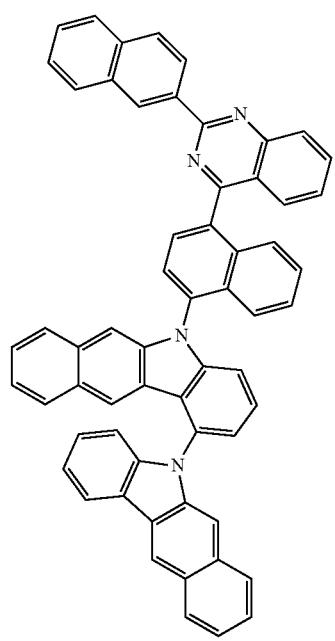
900
-continued
807
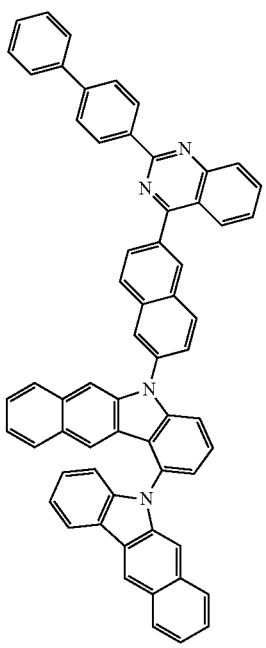
808

901 -continued
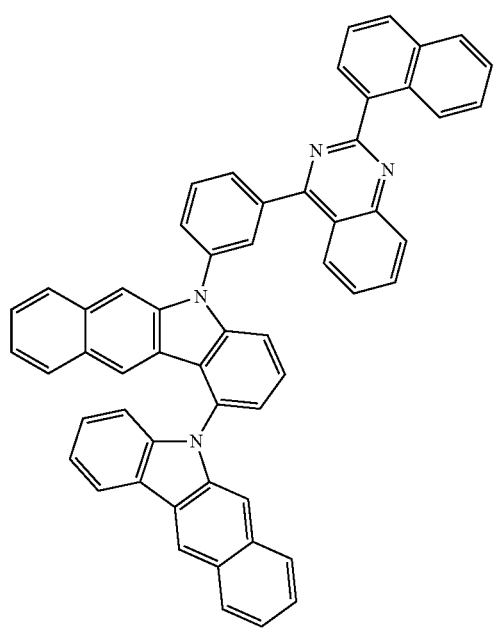
809
902 -continued
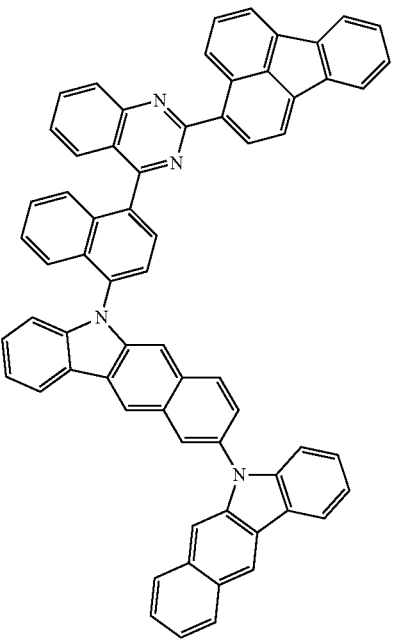
811
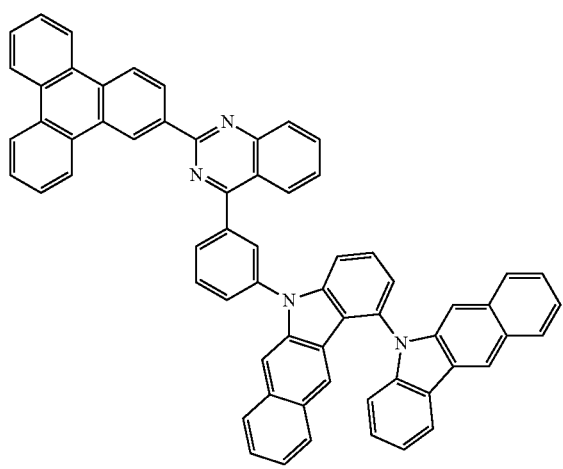
810
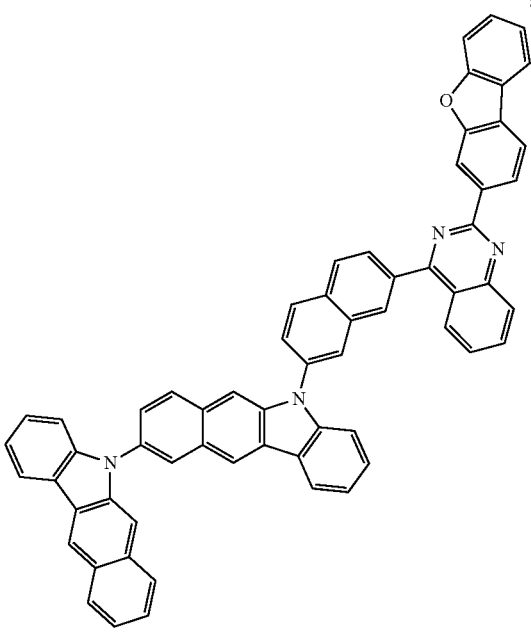
812

903
-continued
813
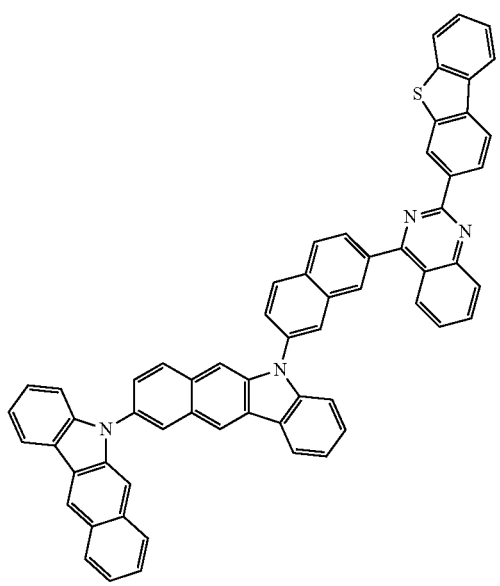
814
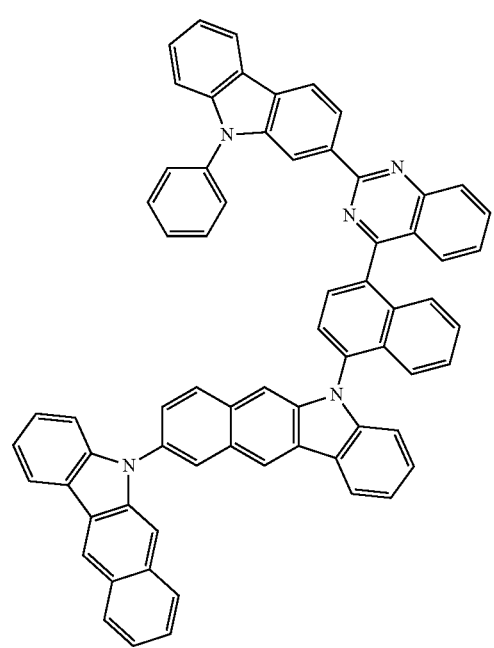
904
-continued
815
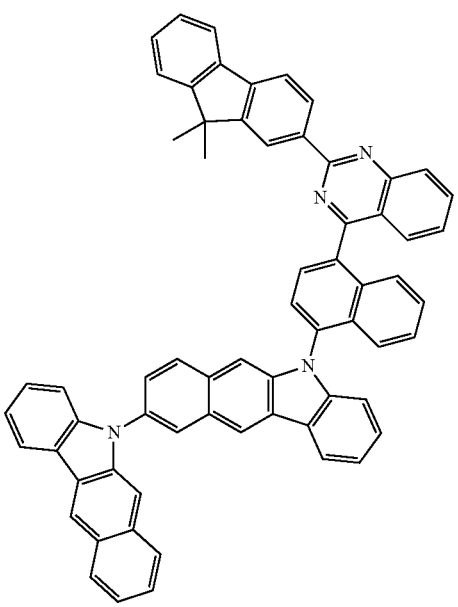
816
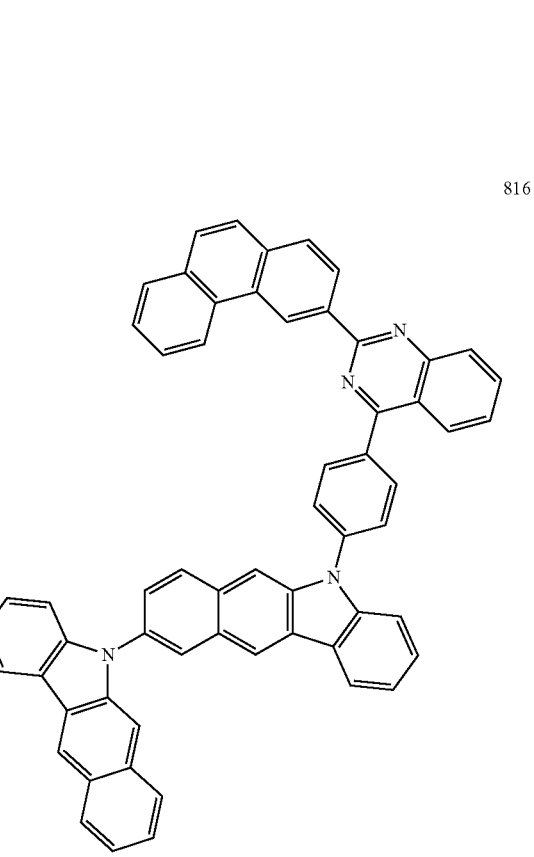

905
-continued
817
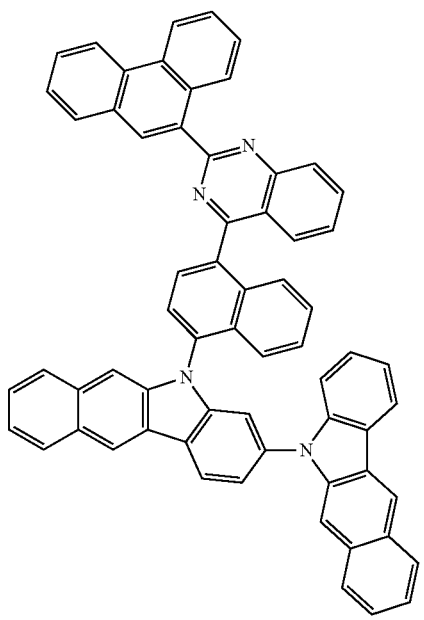
818
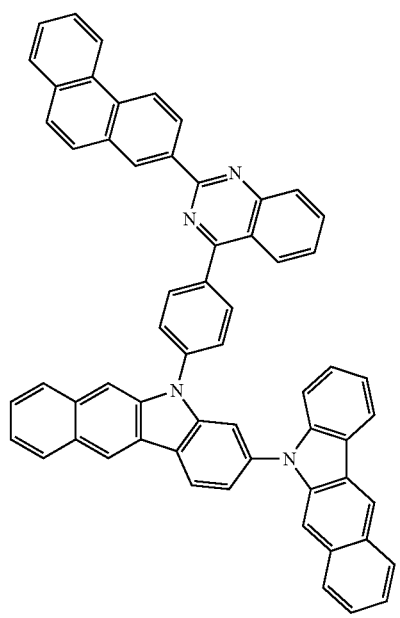
906
-continued
819
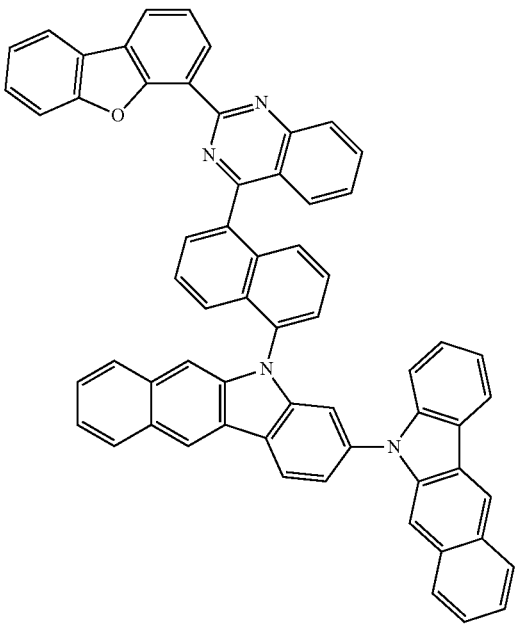
820
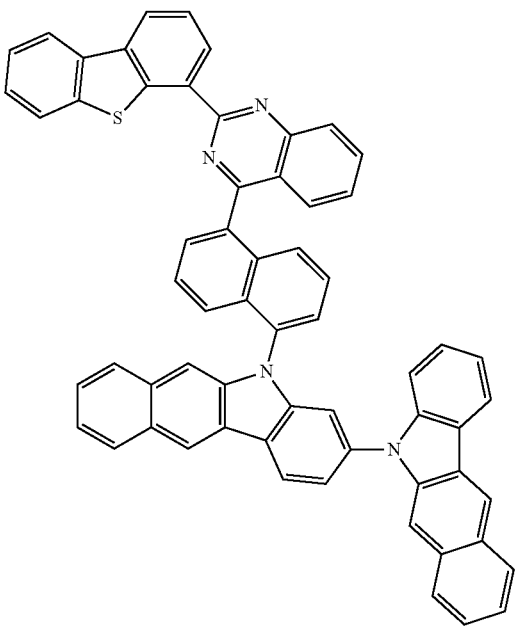

907
-continued
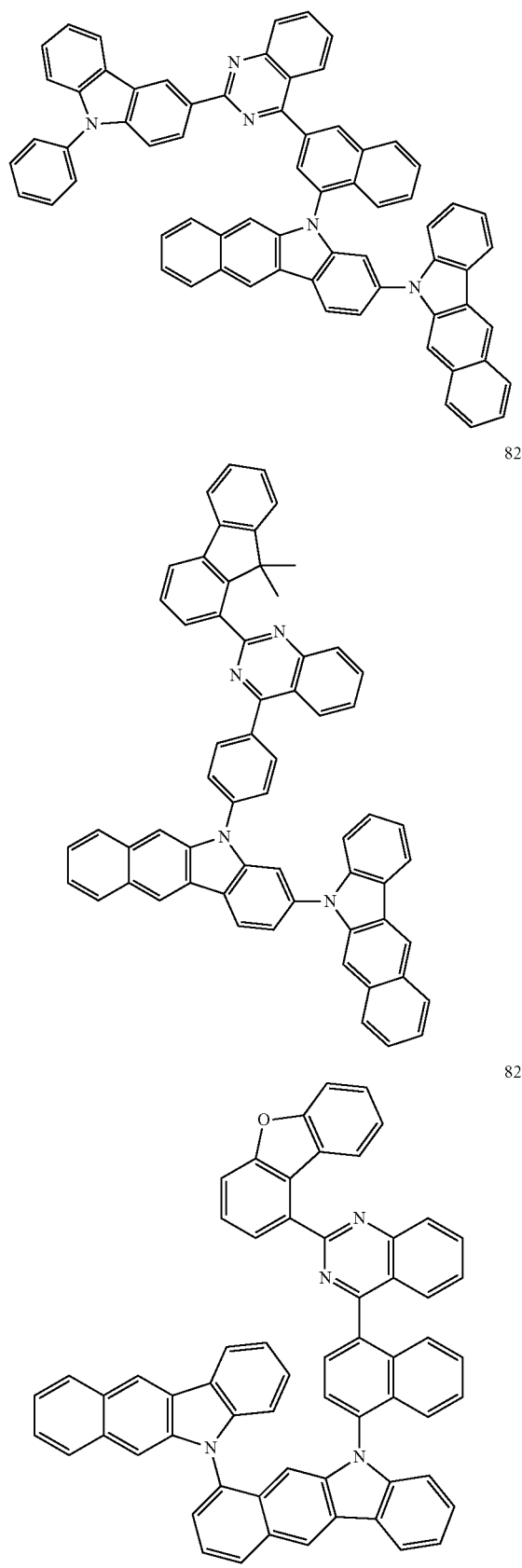
908
-continued

909
-continued
826
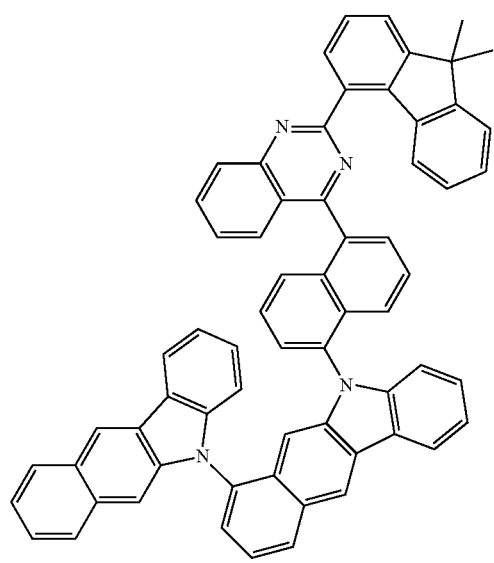
827
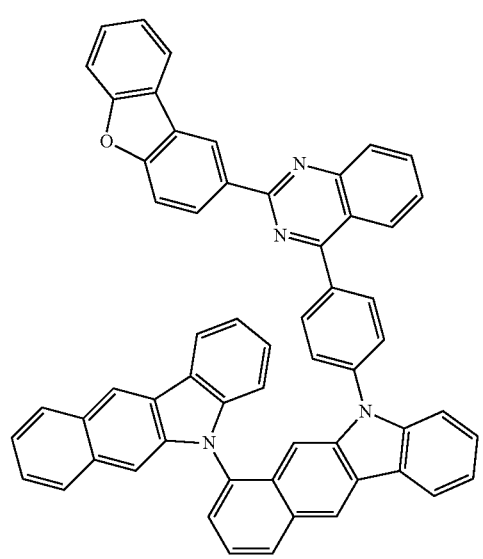
828
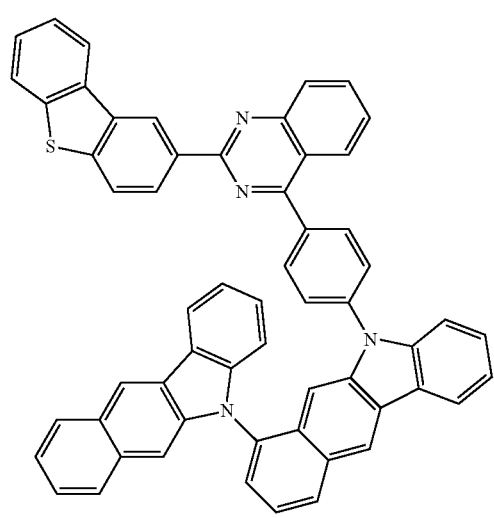
910
-continued
829
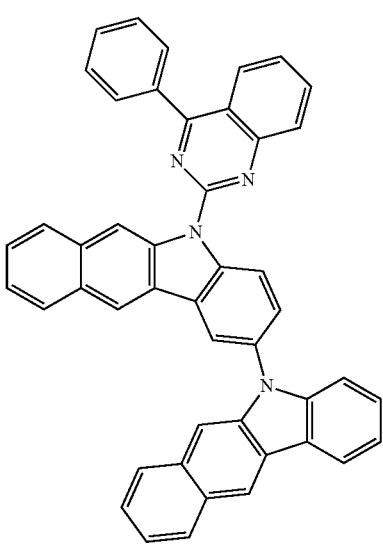
830
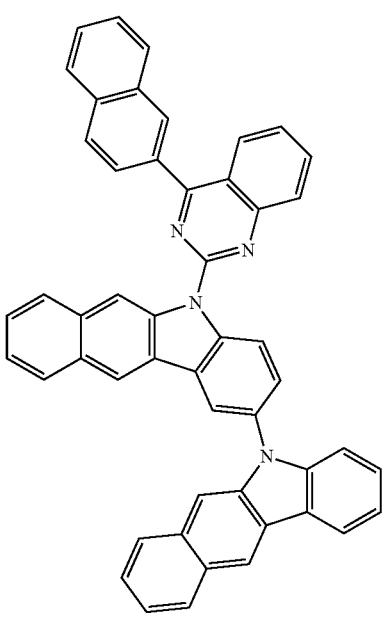

911
-continued
831
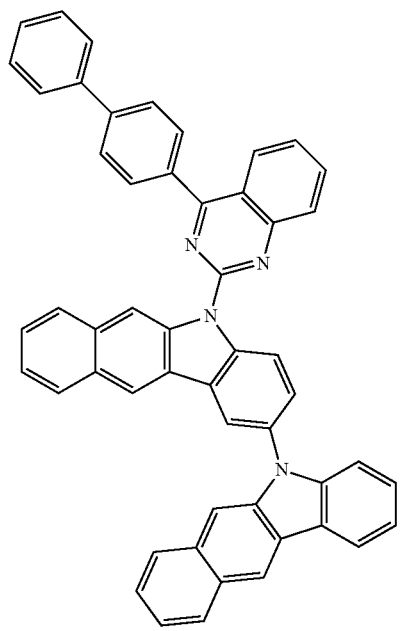
832
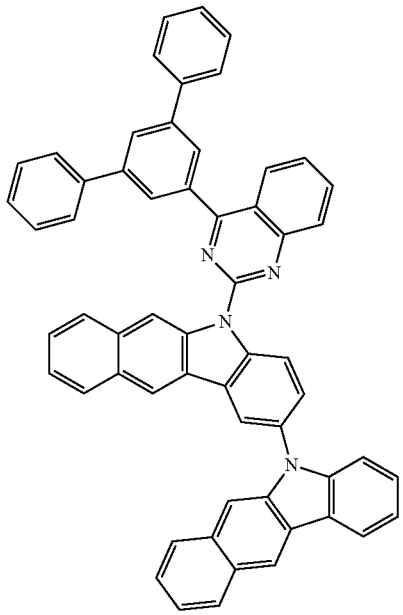
912
-continued
833
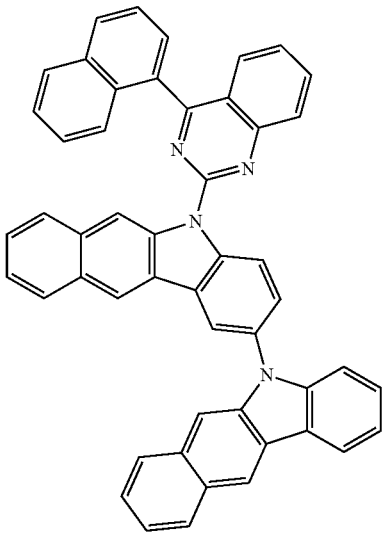
834
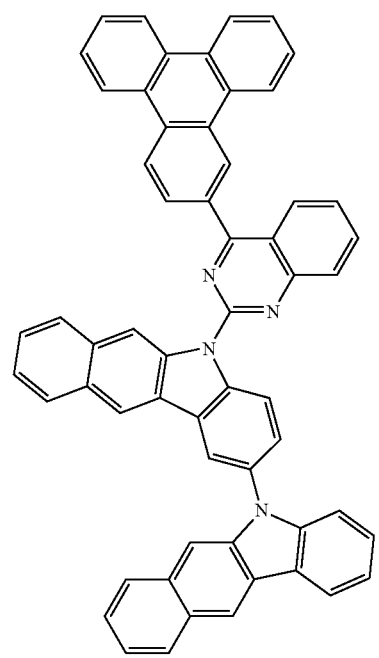
835
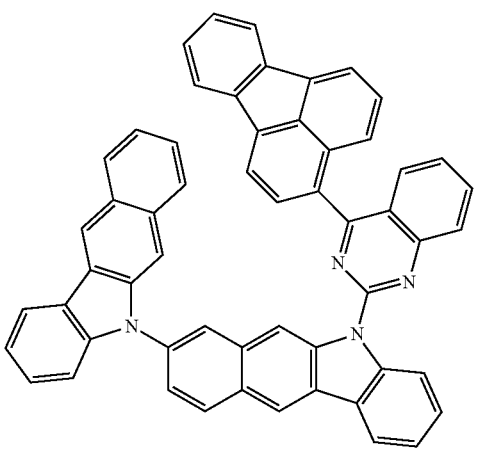

836
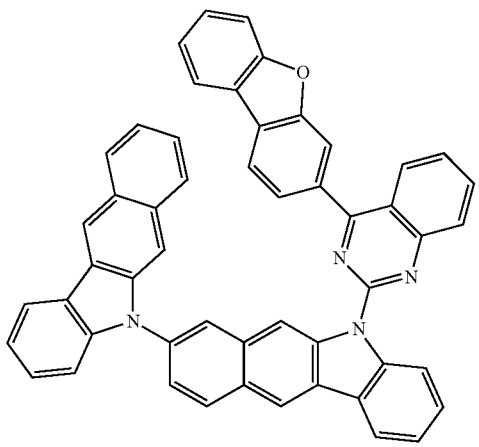
837
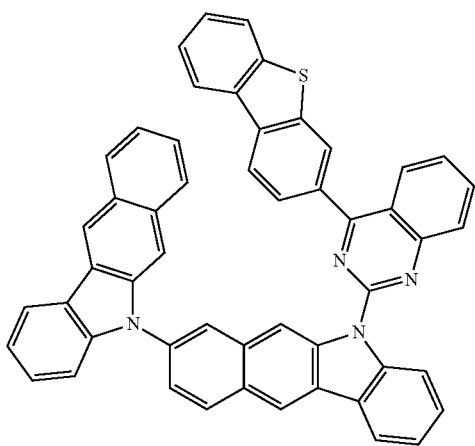
838
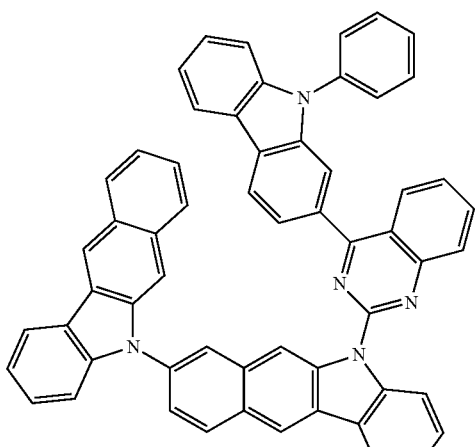
839
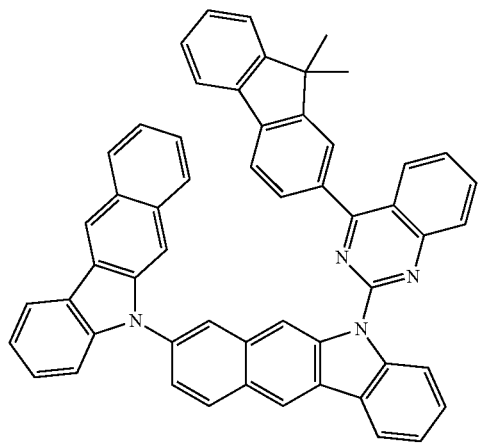
840
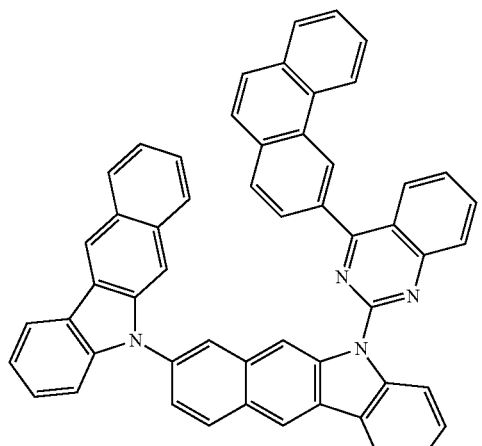
841
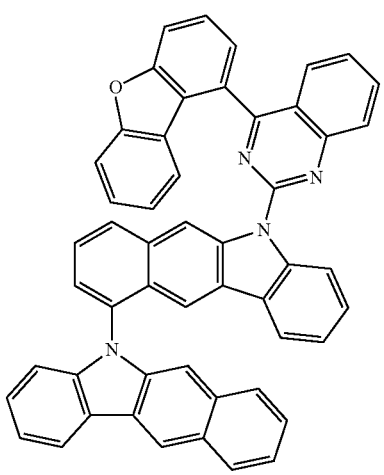

-continued
842
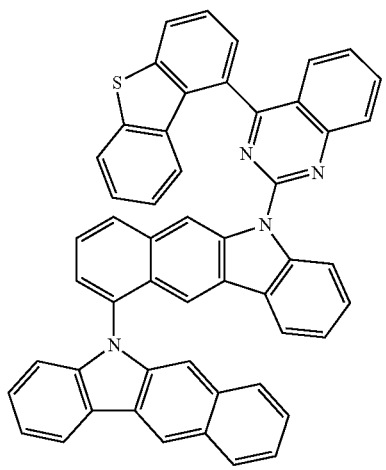
843
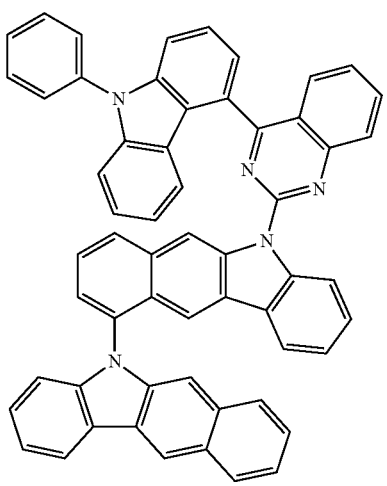
844
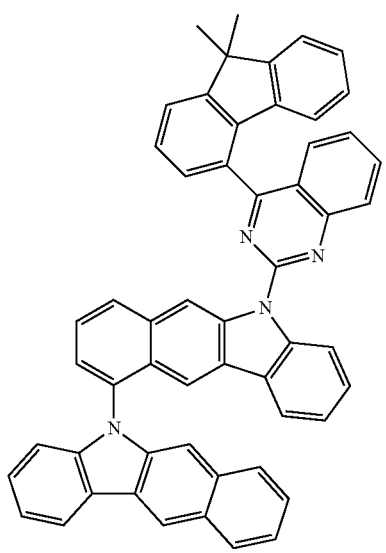
-continued
845
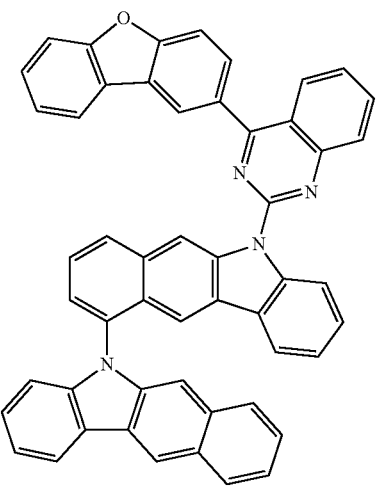
846
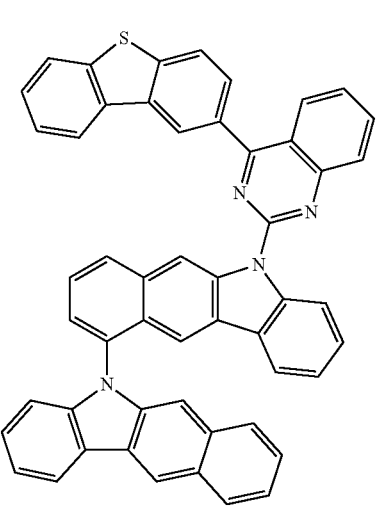
847
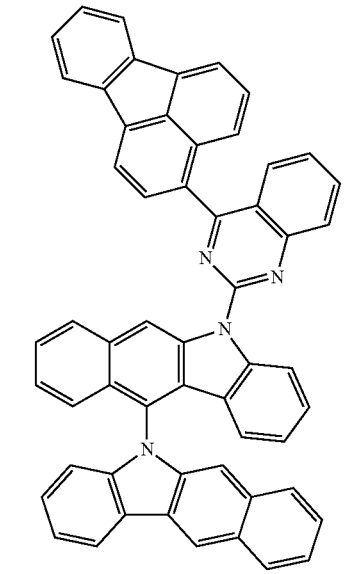

917
-continued
848
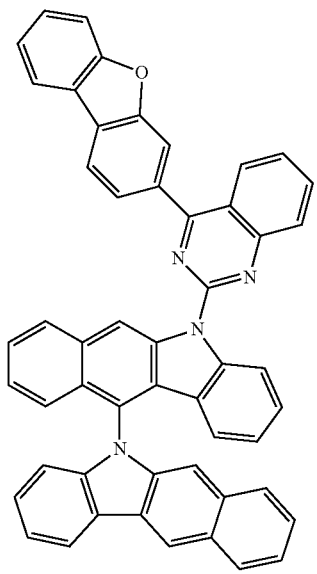
849
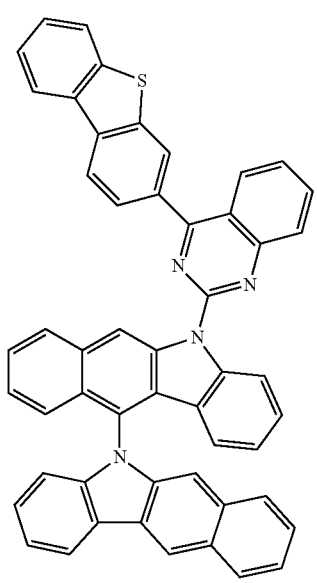
918
-continued
850
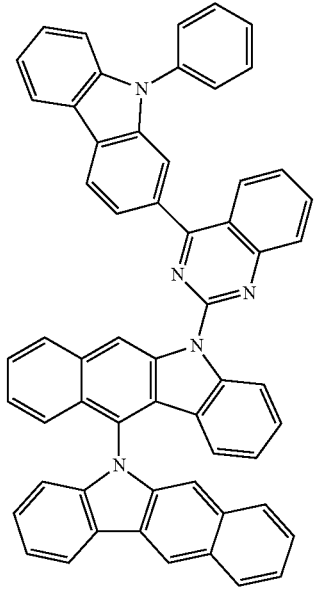
851
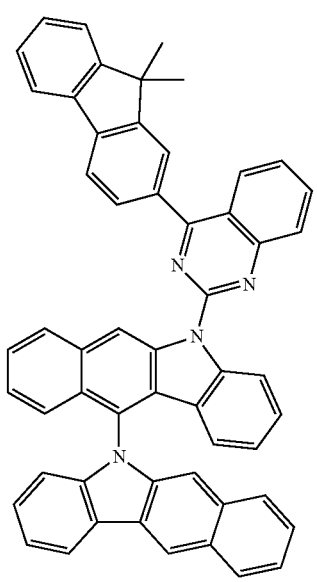

919
-continued
852
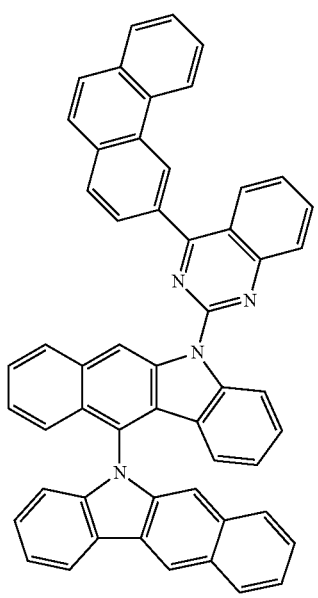
853
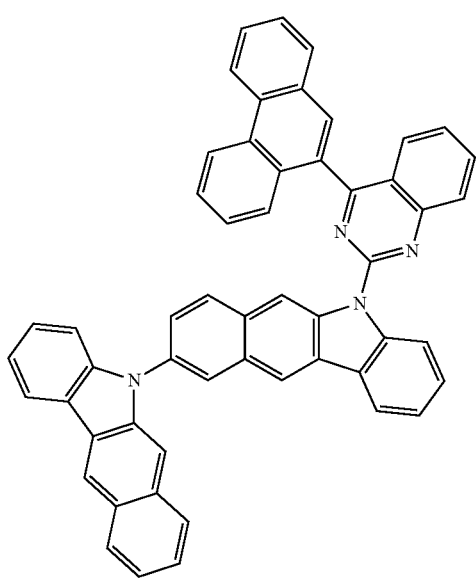
920
-continued
854
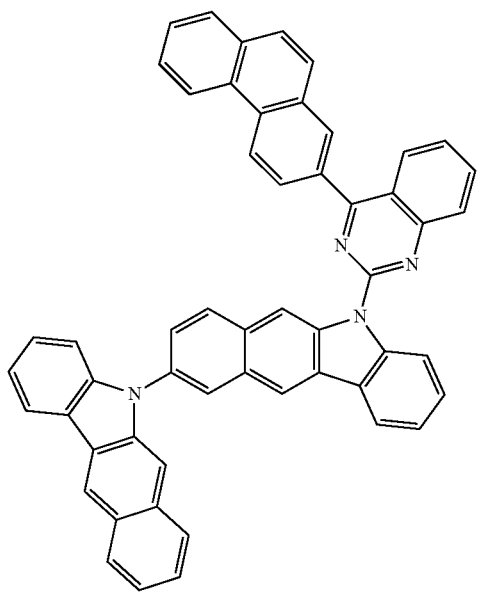
855
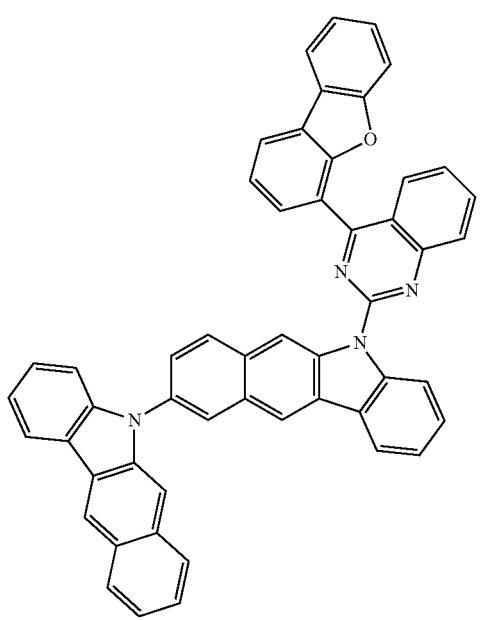

921
-continued
856
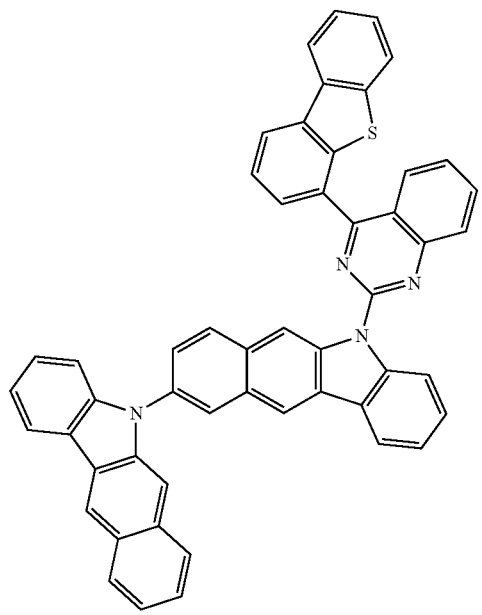
857
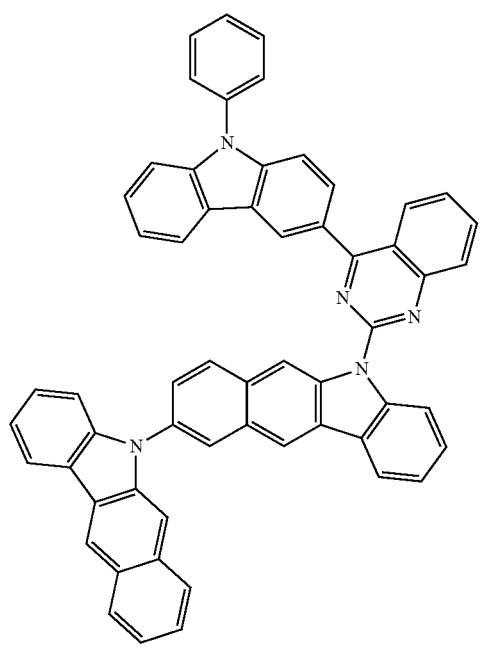
922
-continued
858
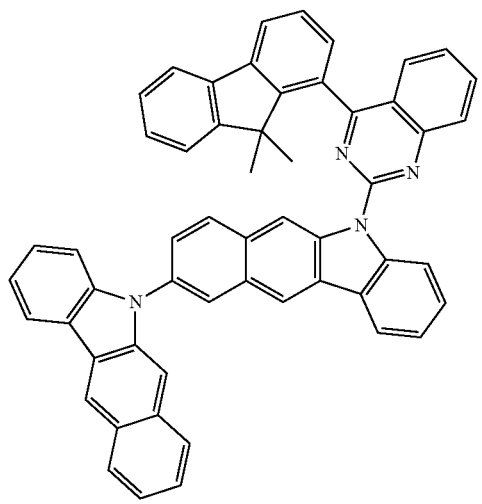
859
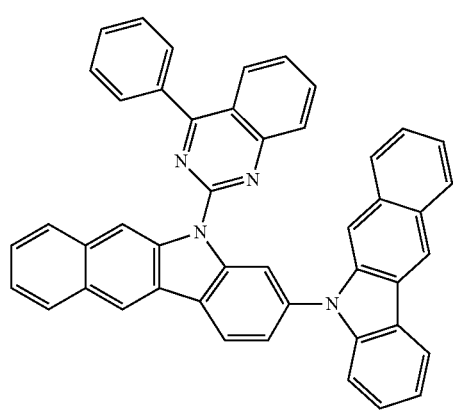
860
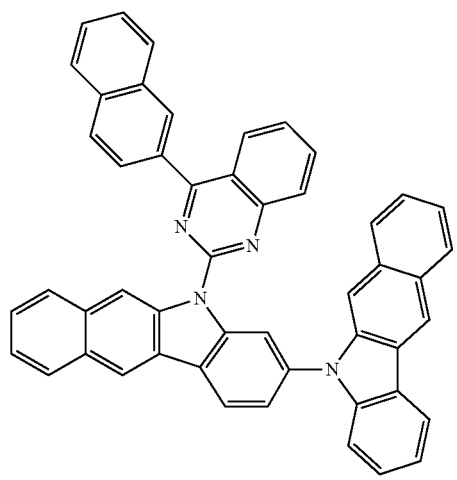

923
-continued
861
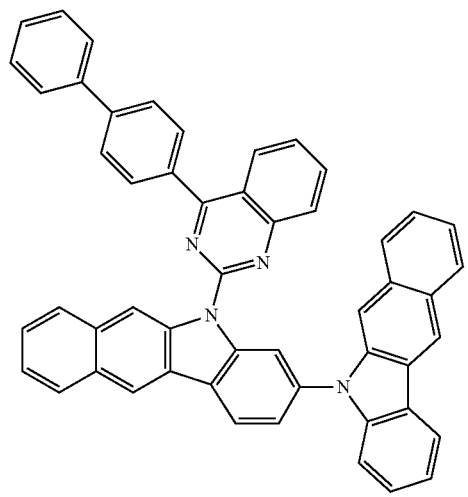
862
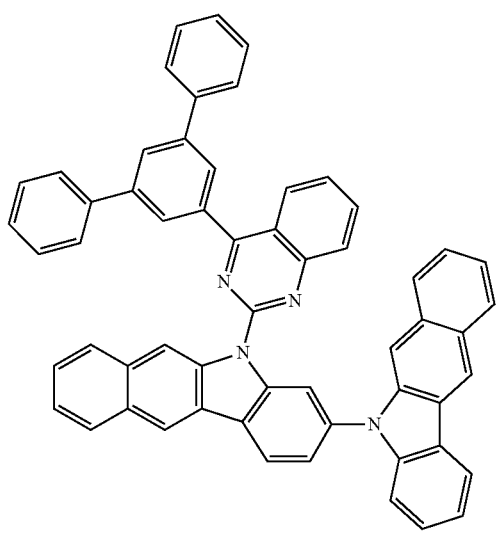
863
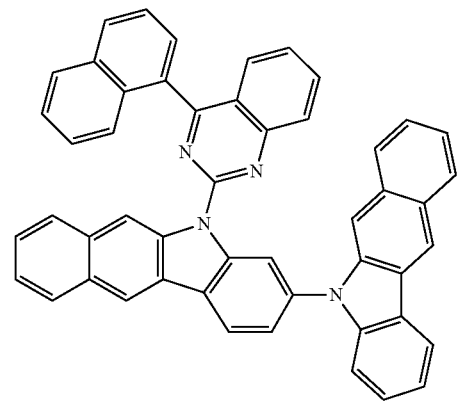
924
-continued
864
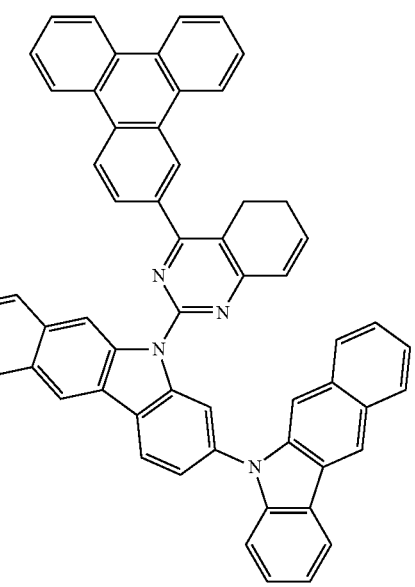
865
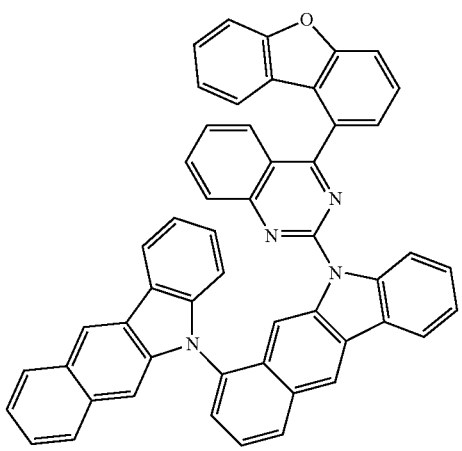
866
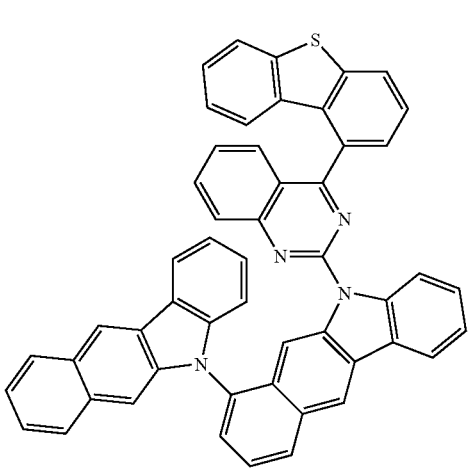

925
-continued
867
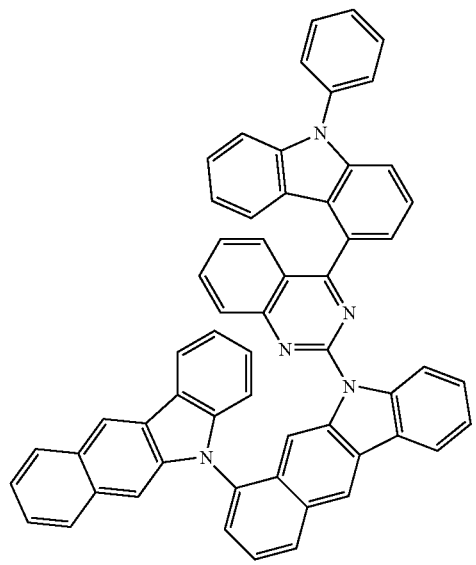
868
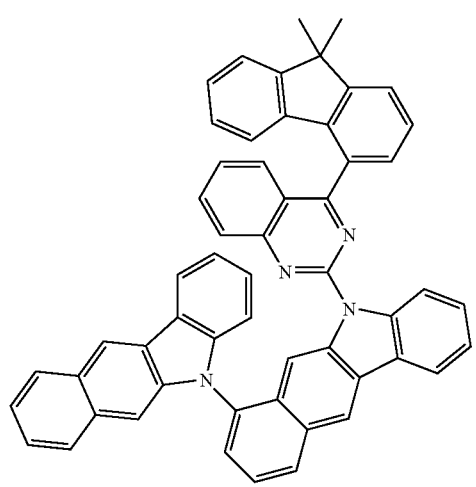
869
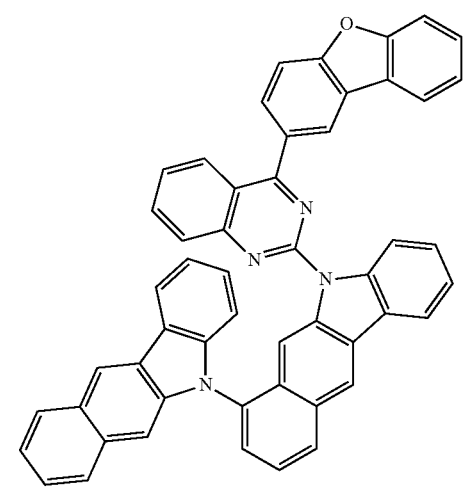
926
-continued
870
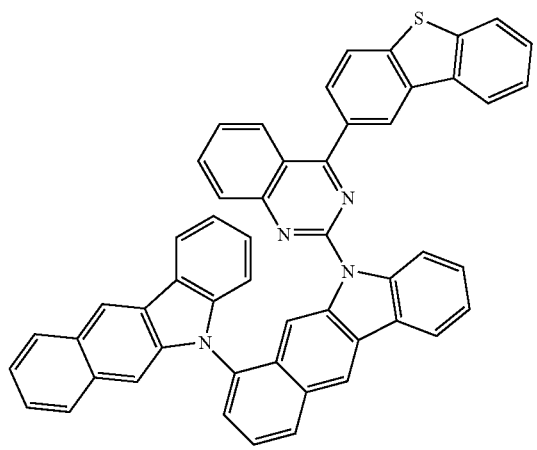
871
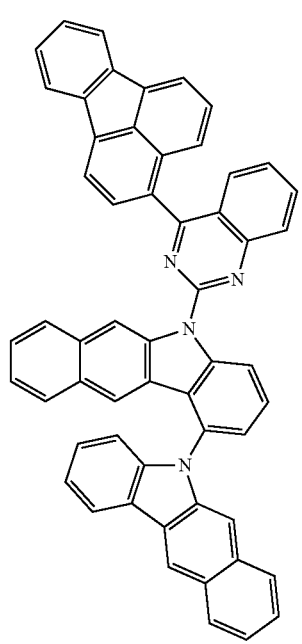

927
-continued
872
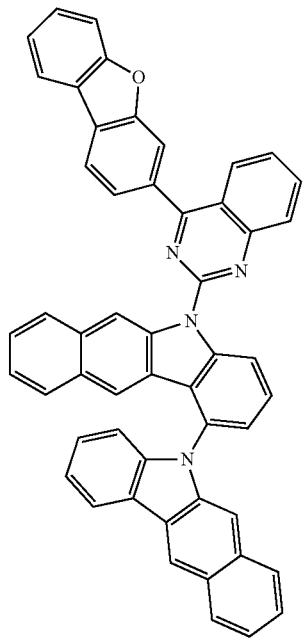
873
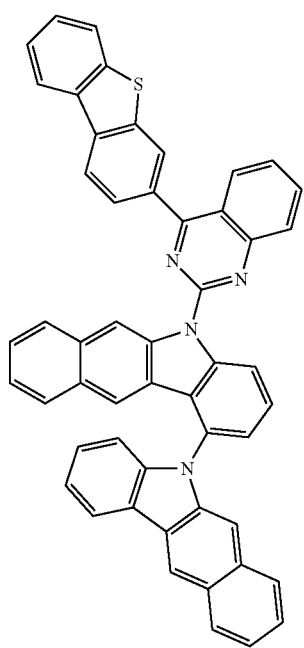
928
-continued
874
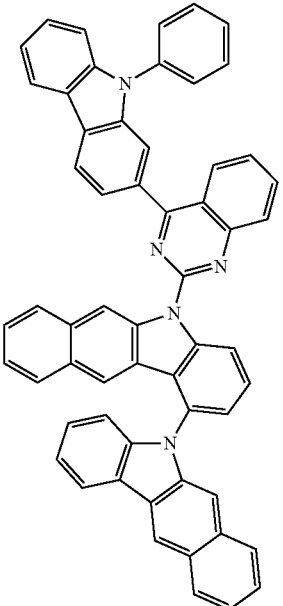
875
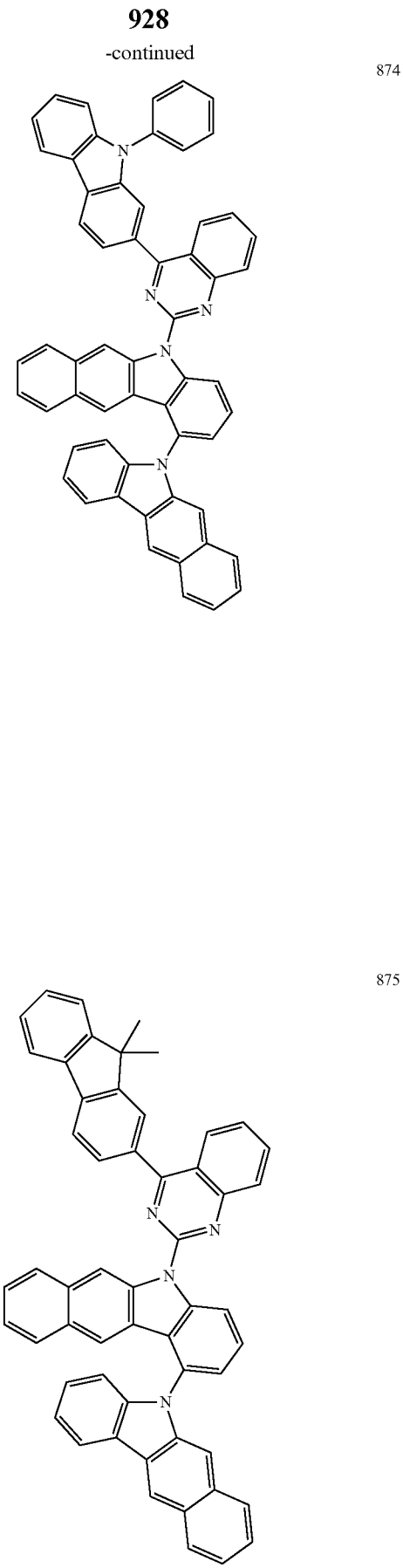

929
-continued
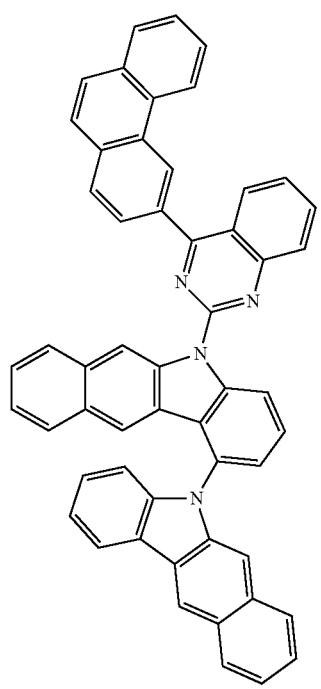
876
930
-continued
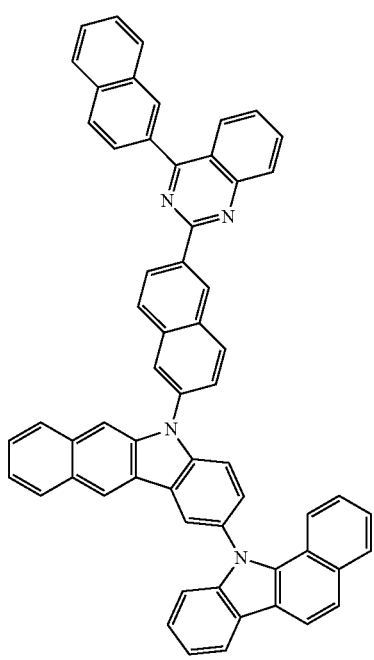
878
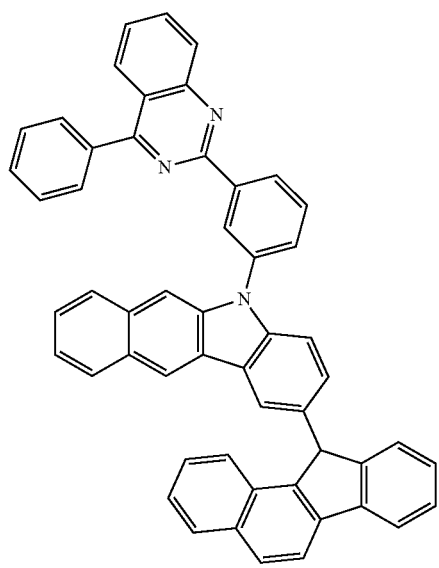
877
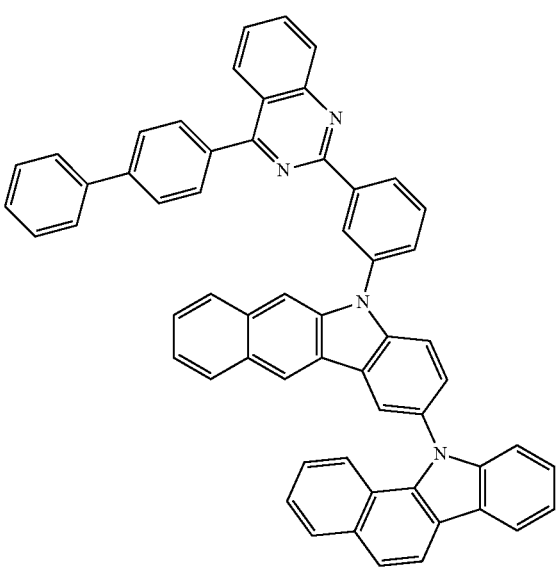
879

931
-continued
880
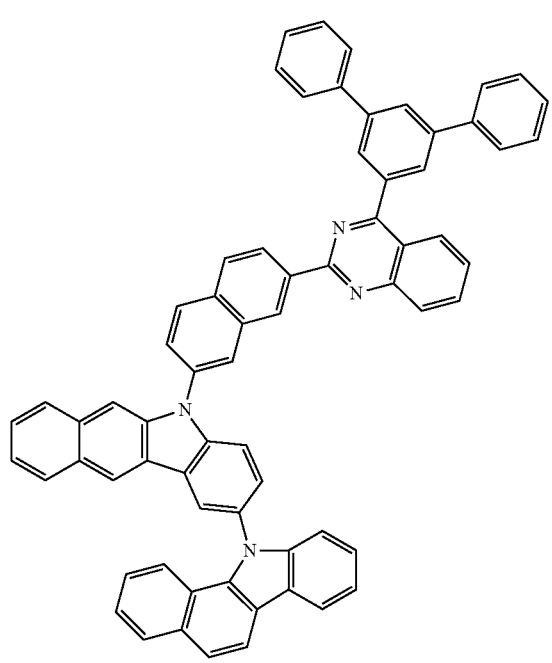
881
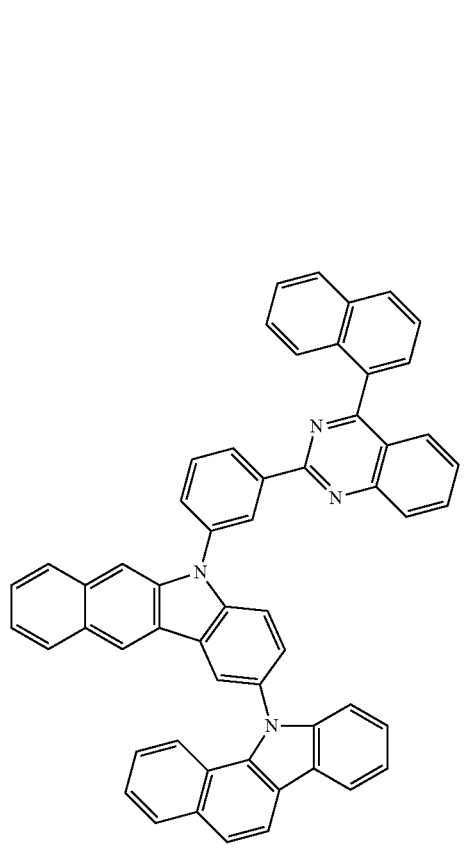
932
-continued
882
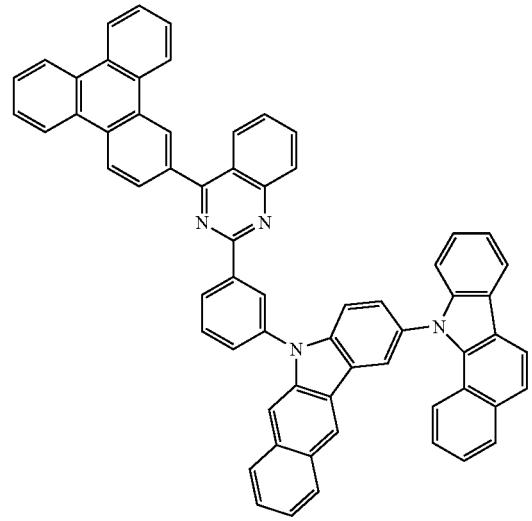
883
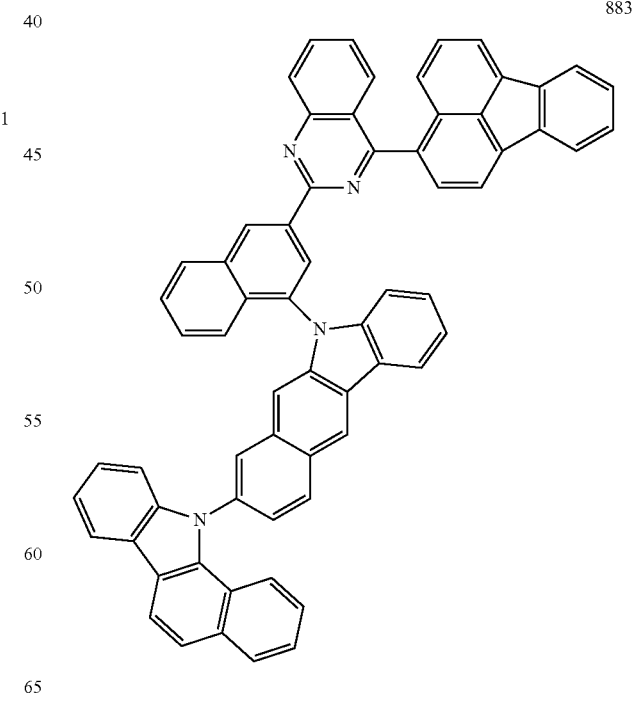

933
-continued
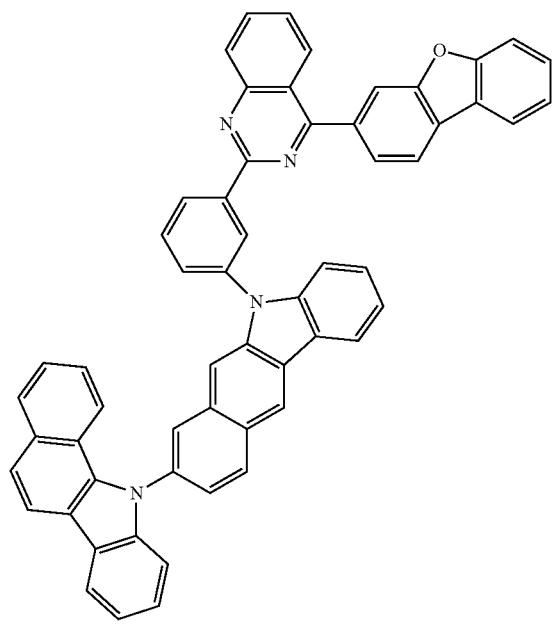
884
934
-continued
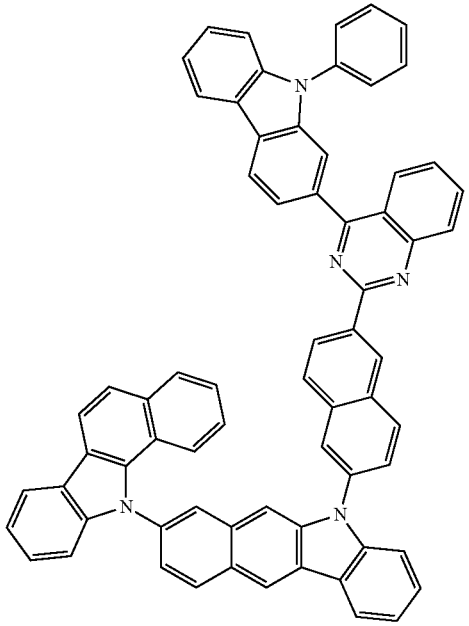
886
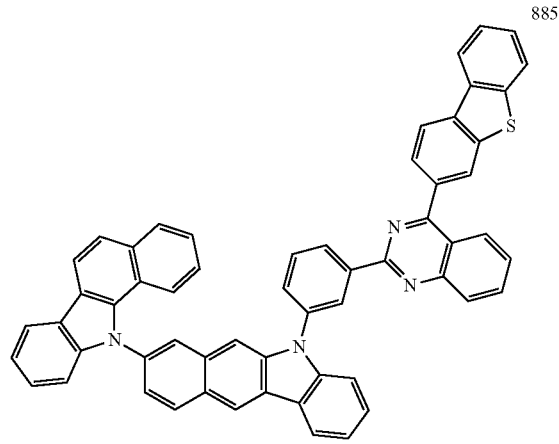
885
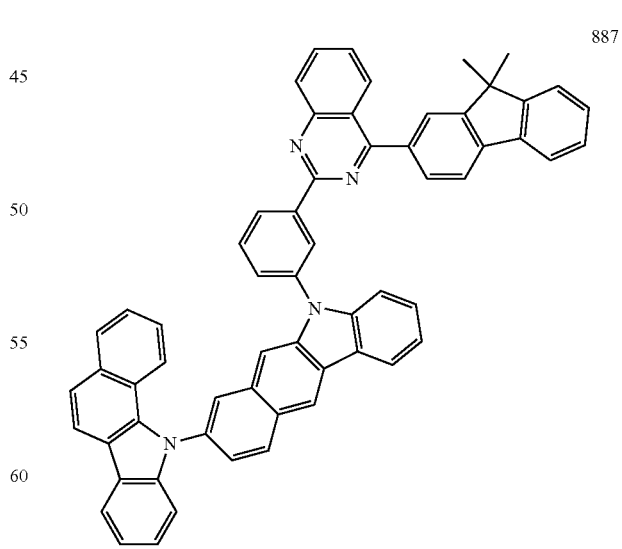
887

-continued
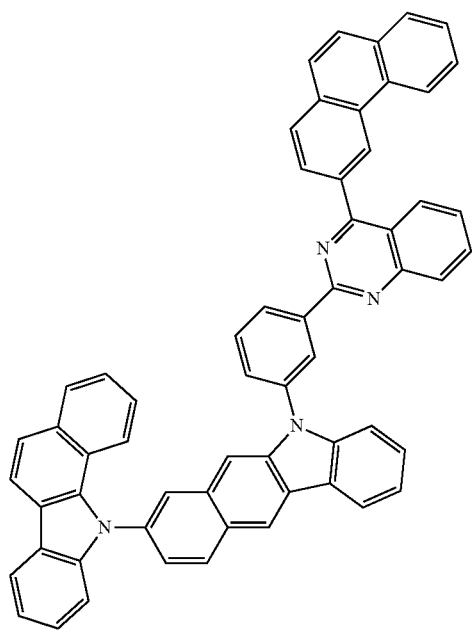
888
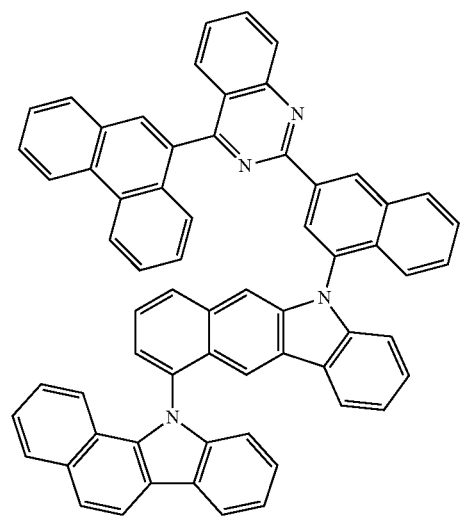
889
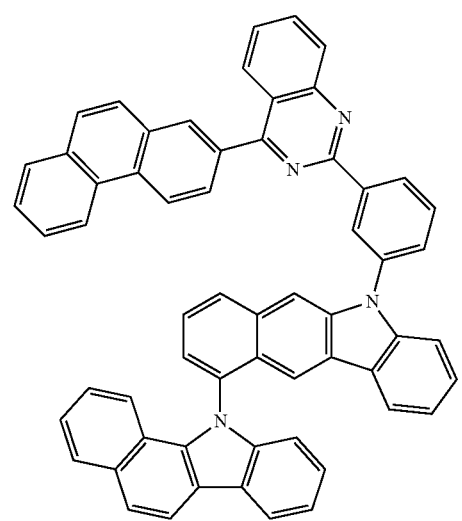
890
-continued
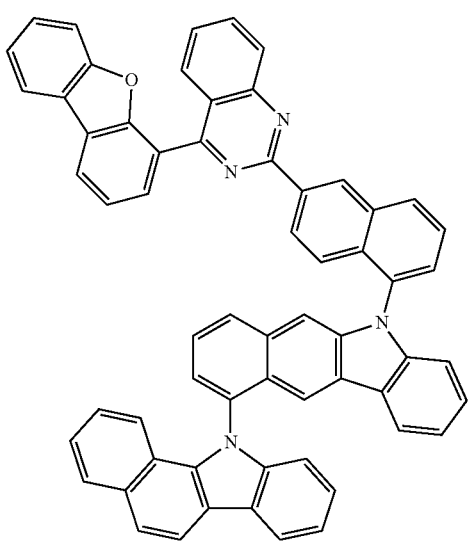
891
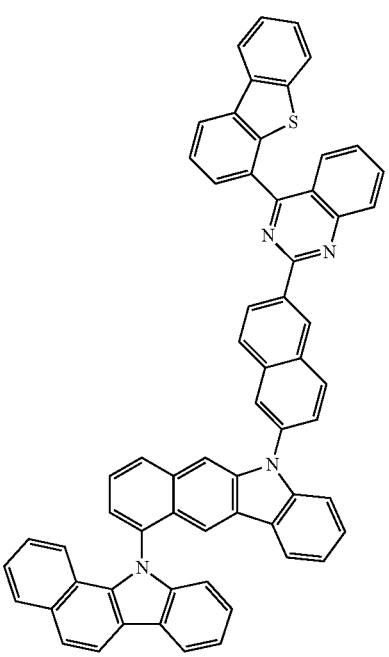
892

937
-continued
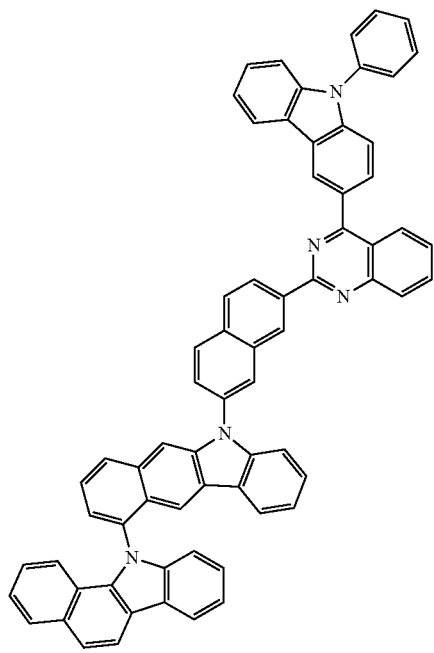
893
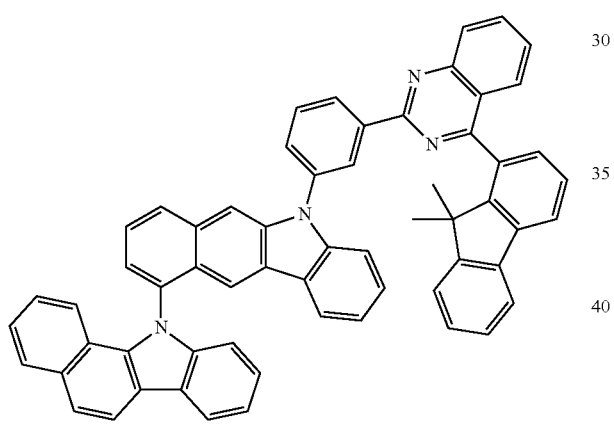
894
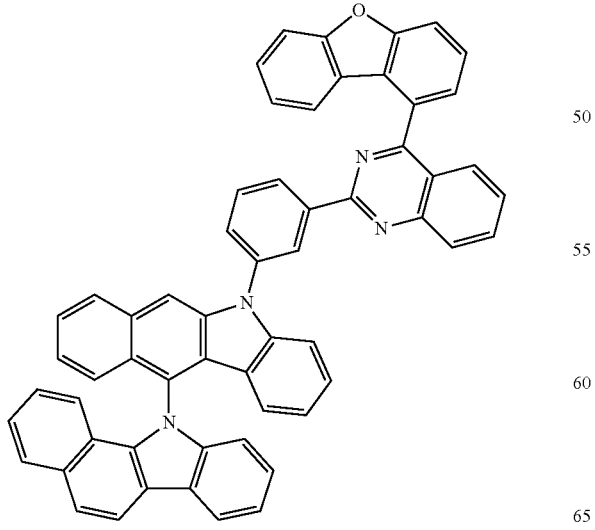
895
938
-continued
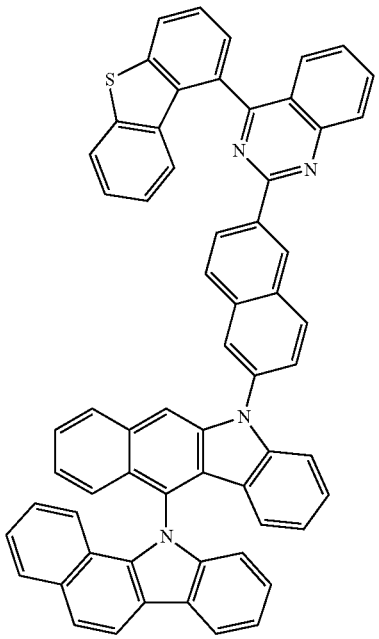
896
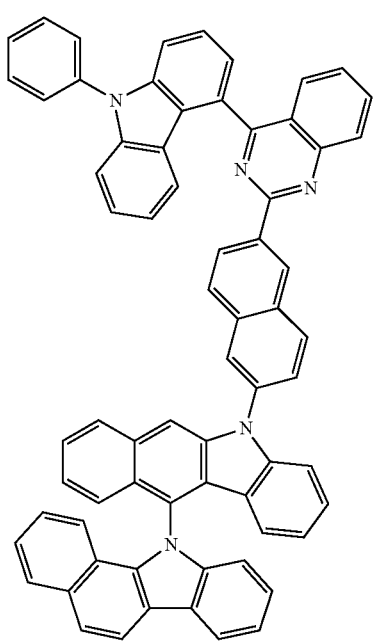
897

939
-continued
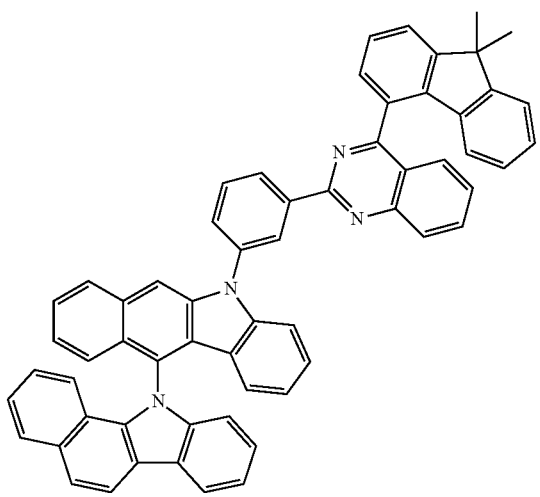
898
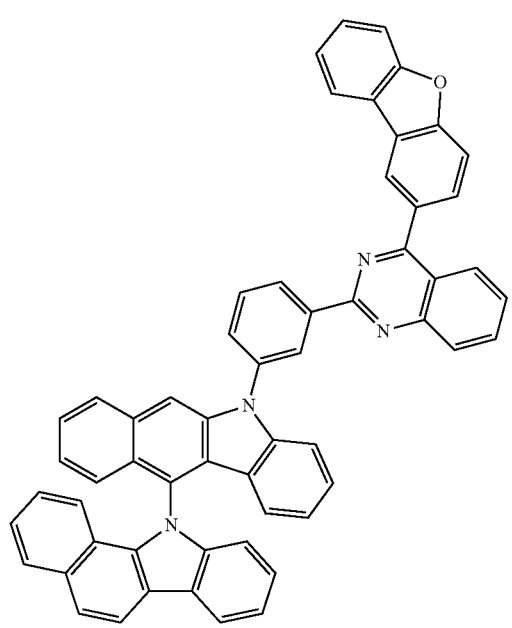
899
940
-continued
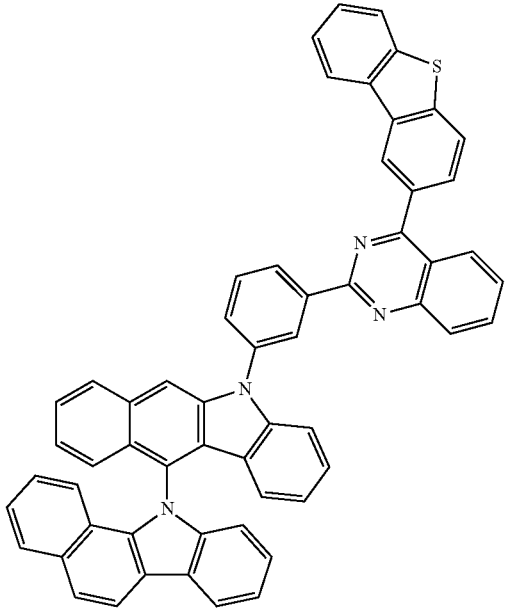
900
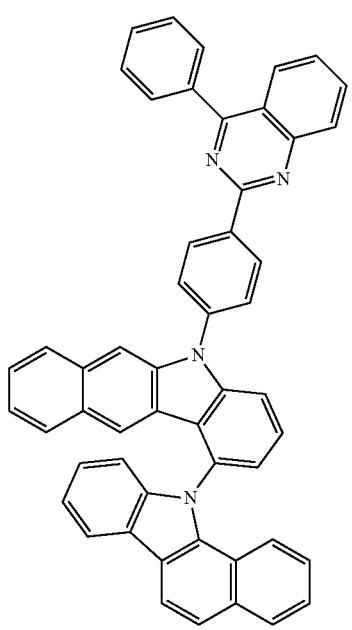
901

941
-continued
942
-continued
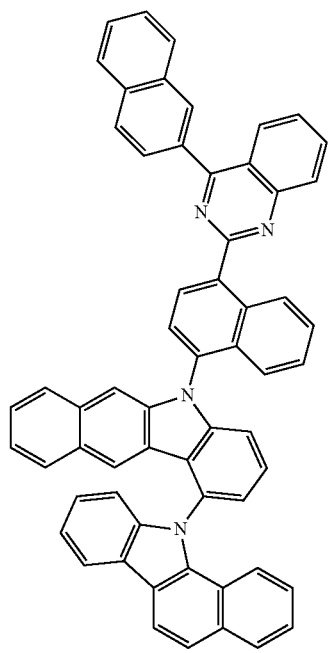
902
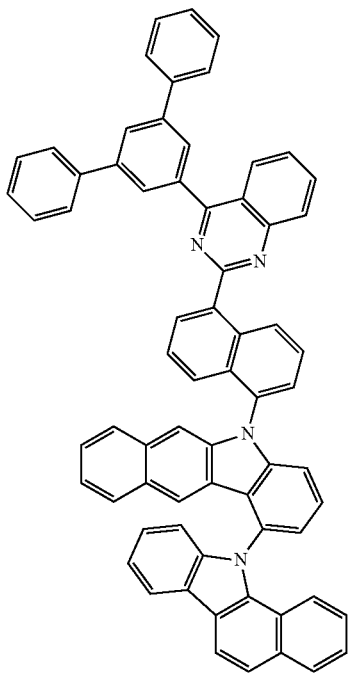
904
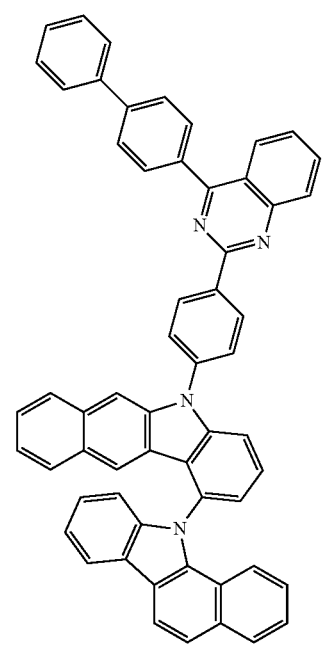
903
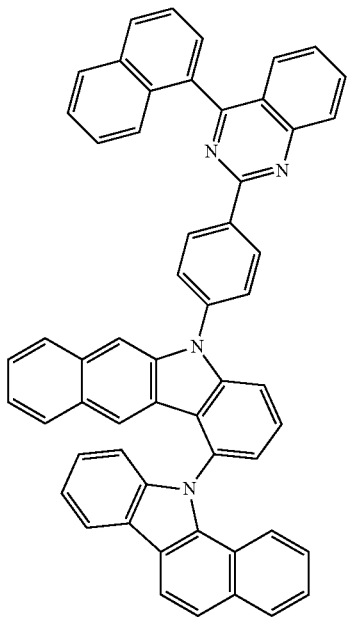
905

943
-continued
906
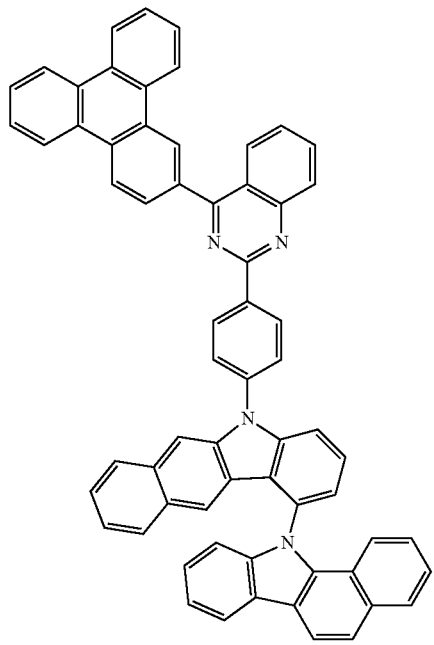
907
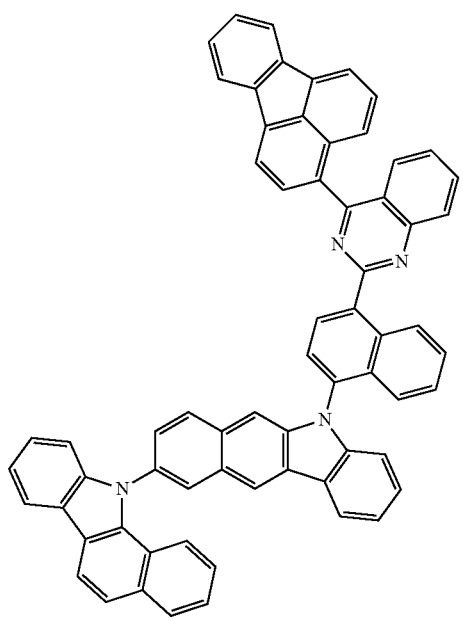
944
-continued
908
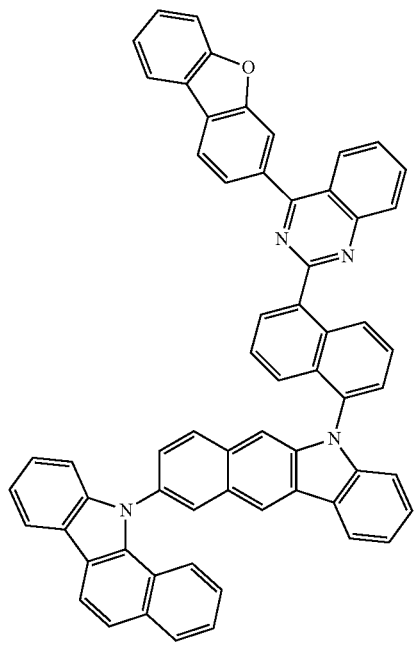
909
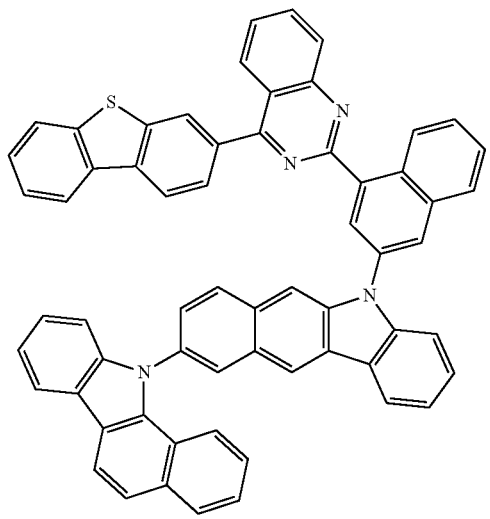

945
-continued
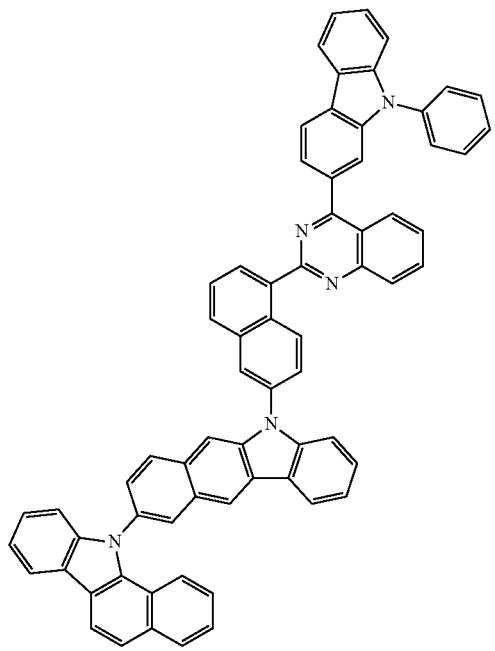
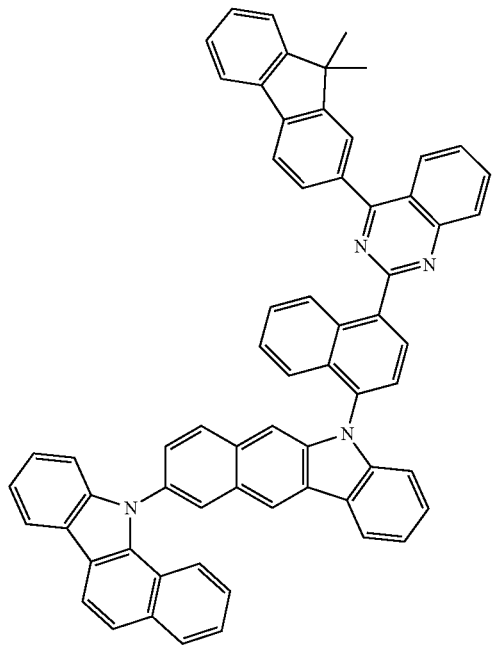
946
-continued
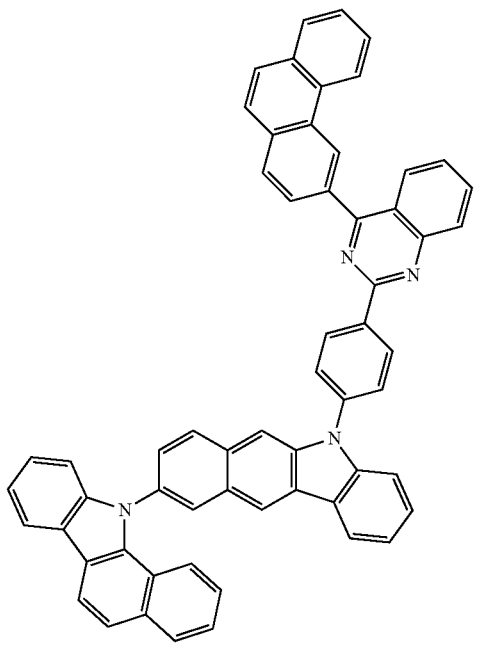
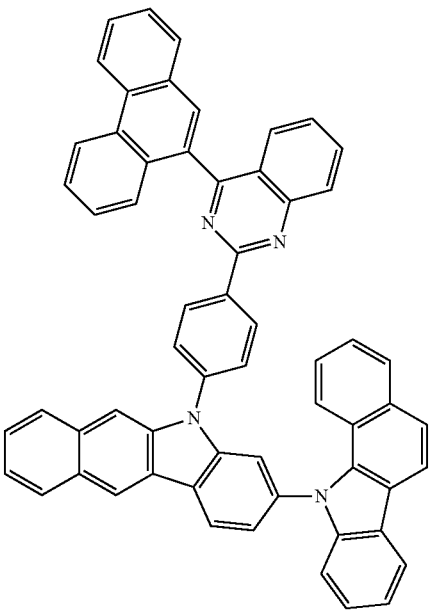

947
-continued
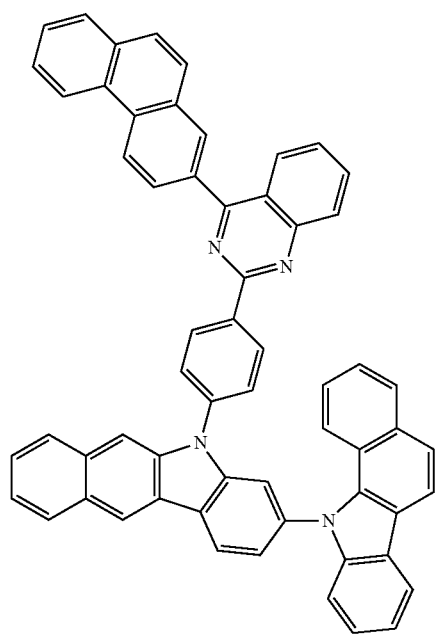
914
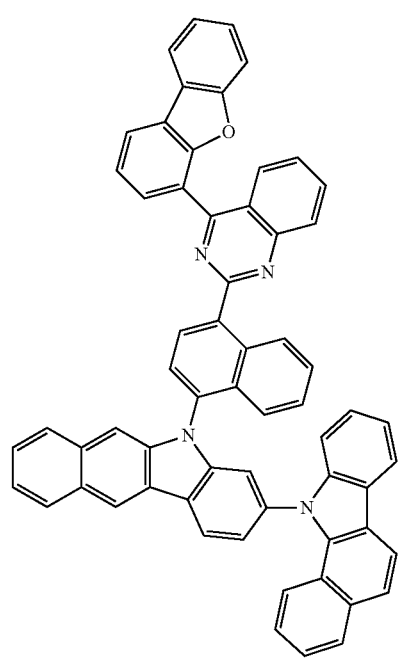
915
948
-continued
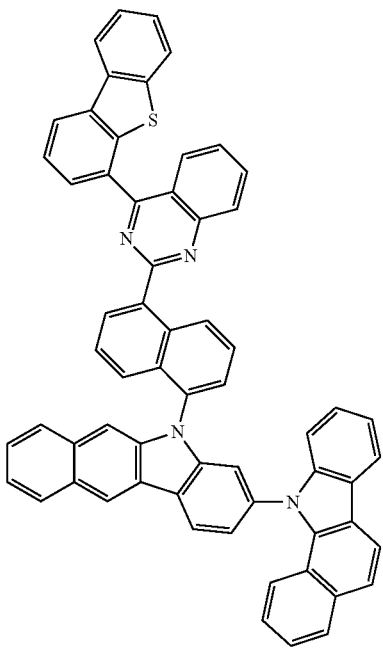
916
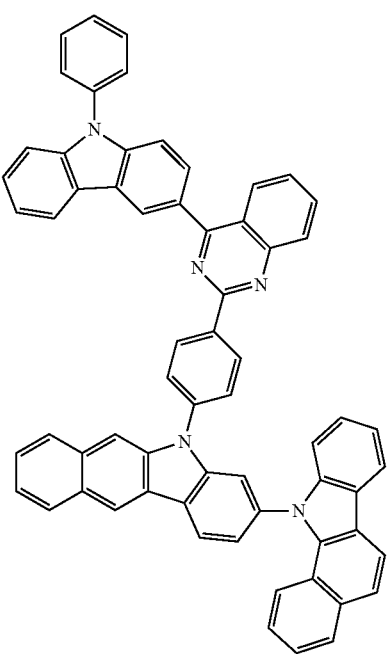
917

949
-continued
950
-continued
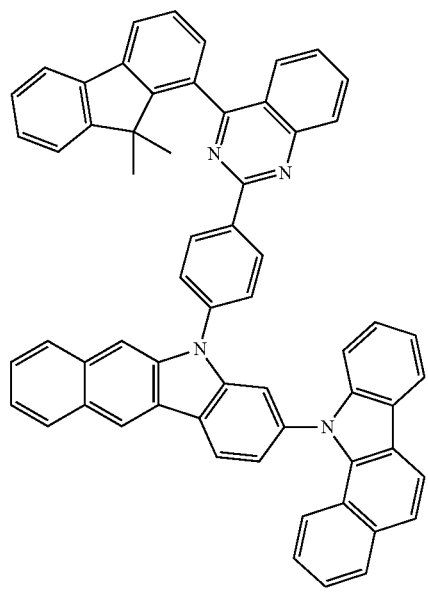
918
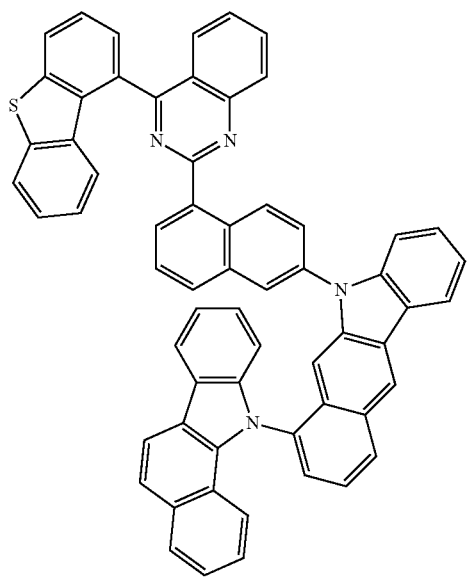
920
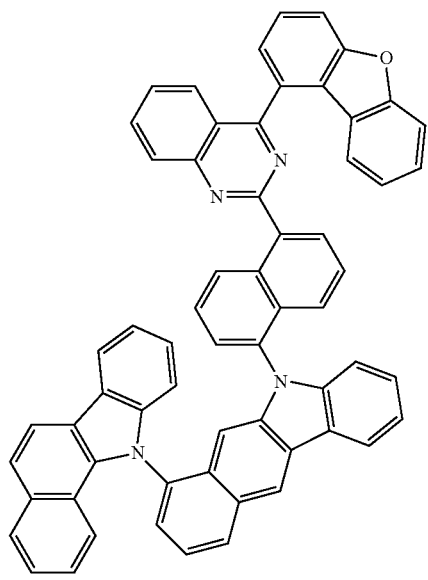
919
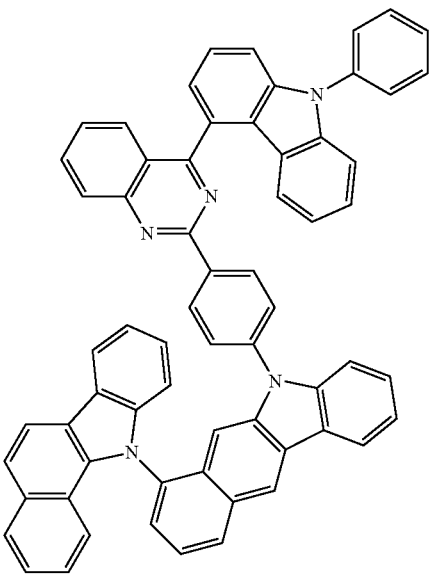
921

922
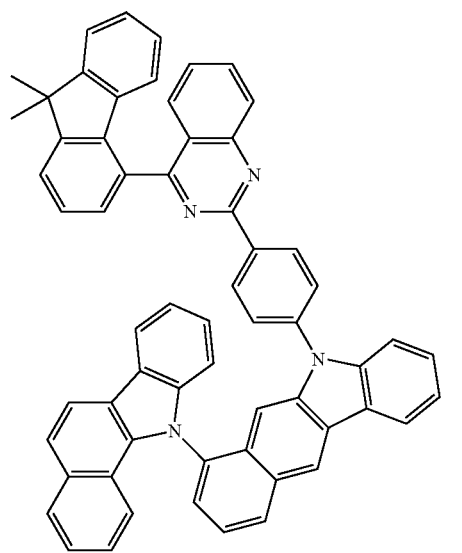
923
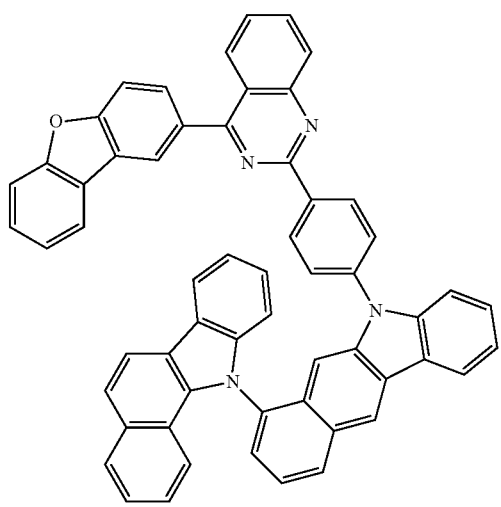
924
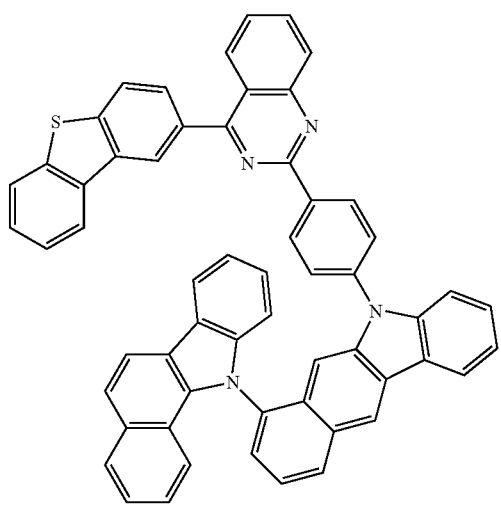
925
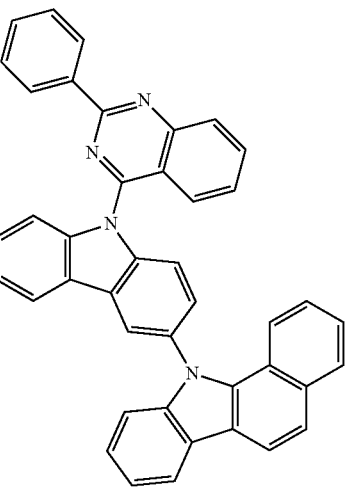
926
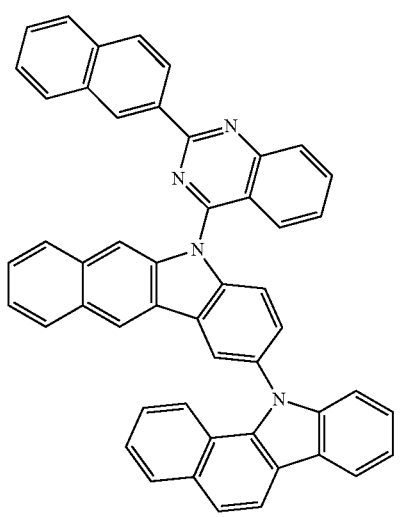
927
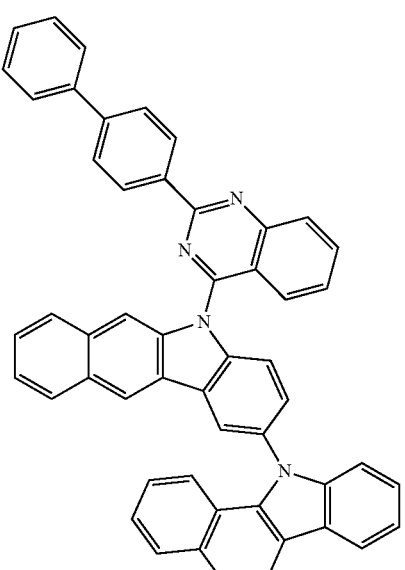

953
-continued
928
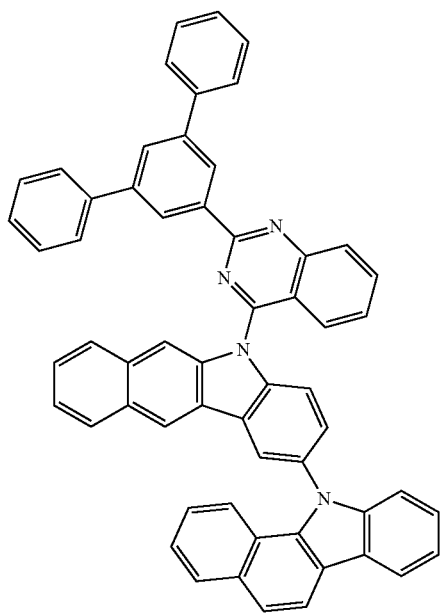
929
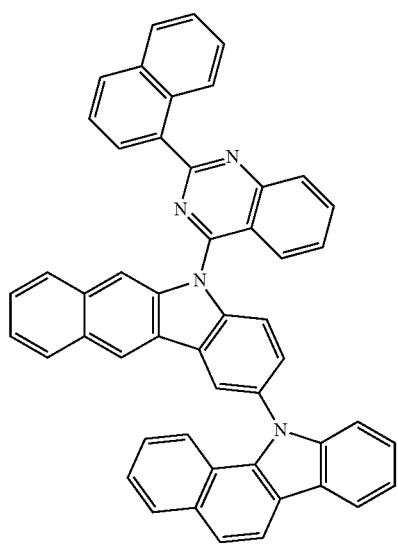
954
-continued
930
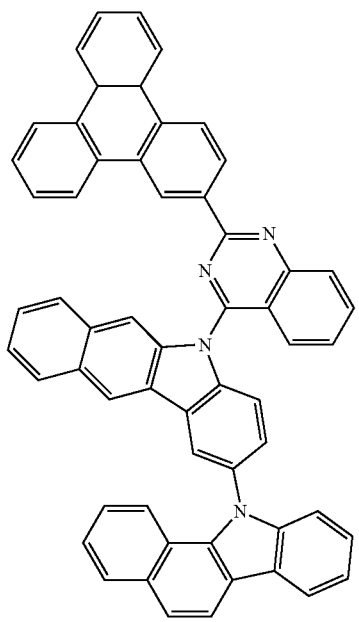
931
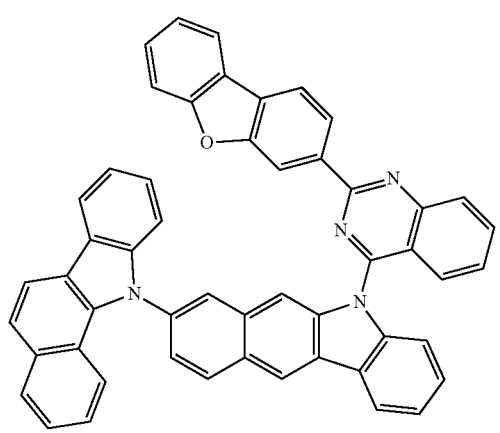
932

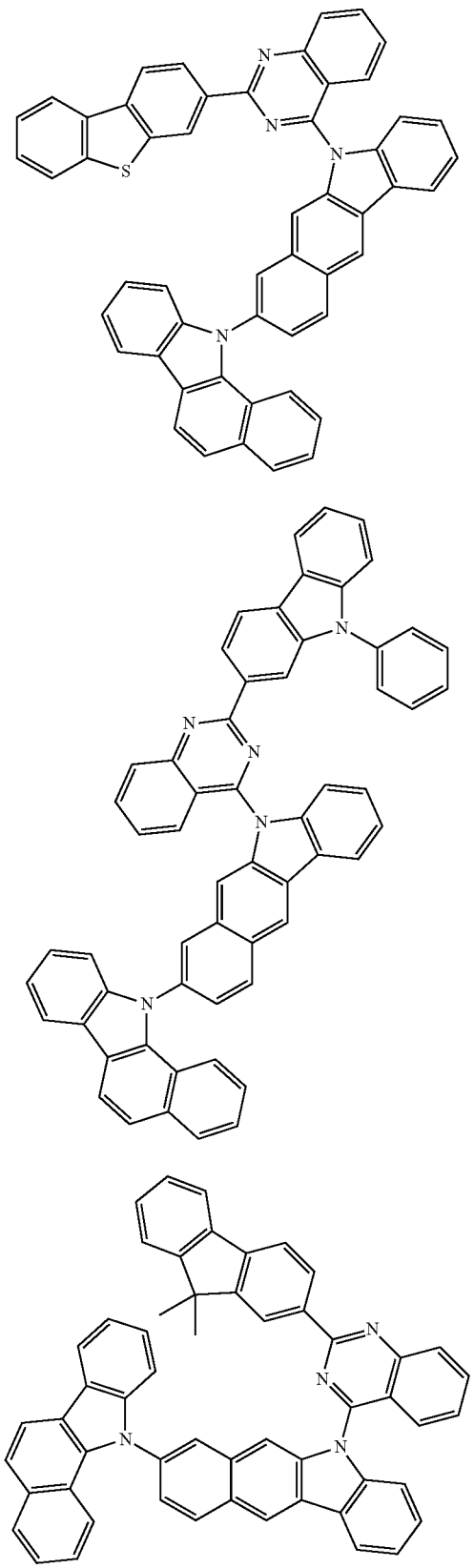
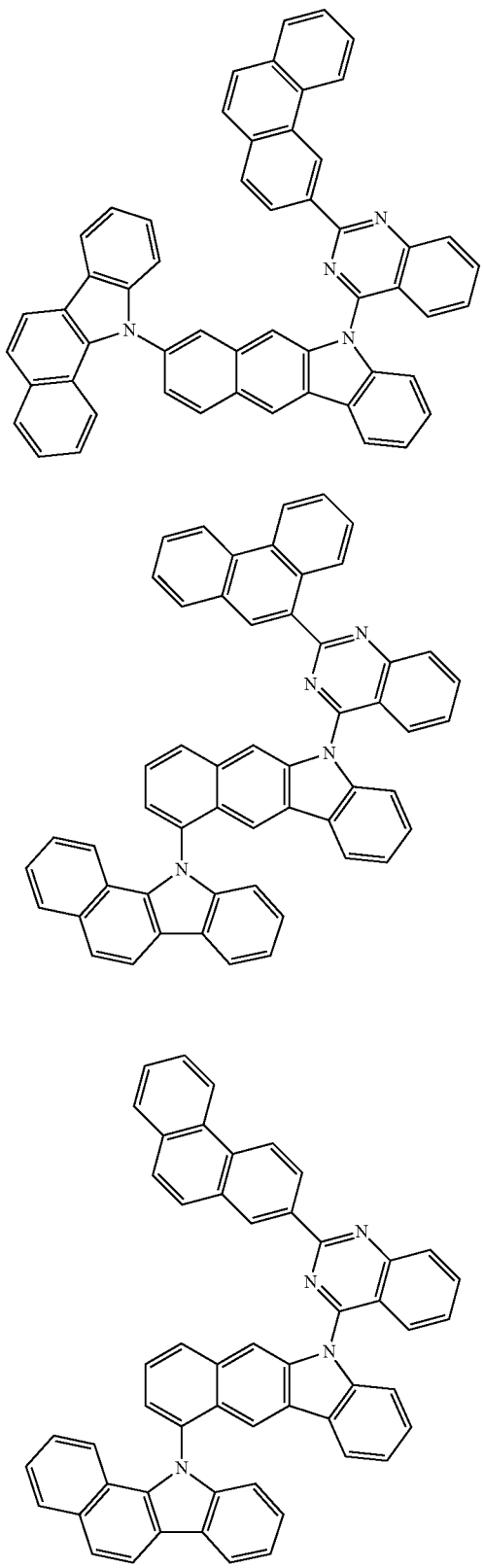

957
-continued
958
-continued
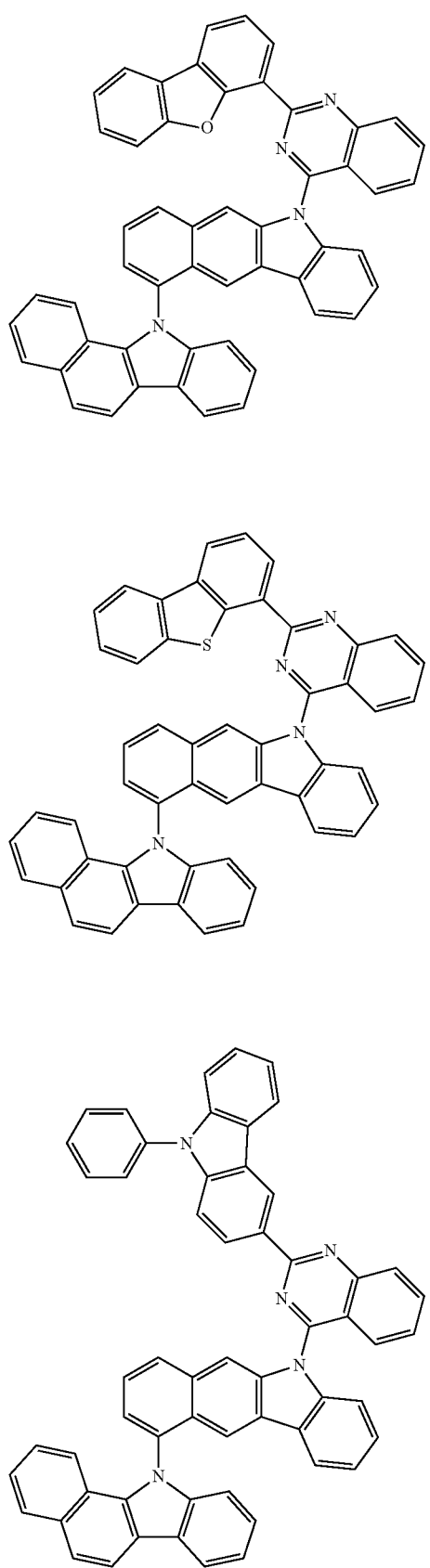
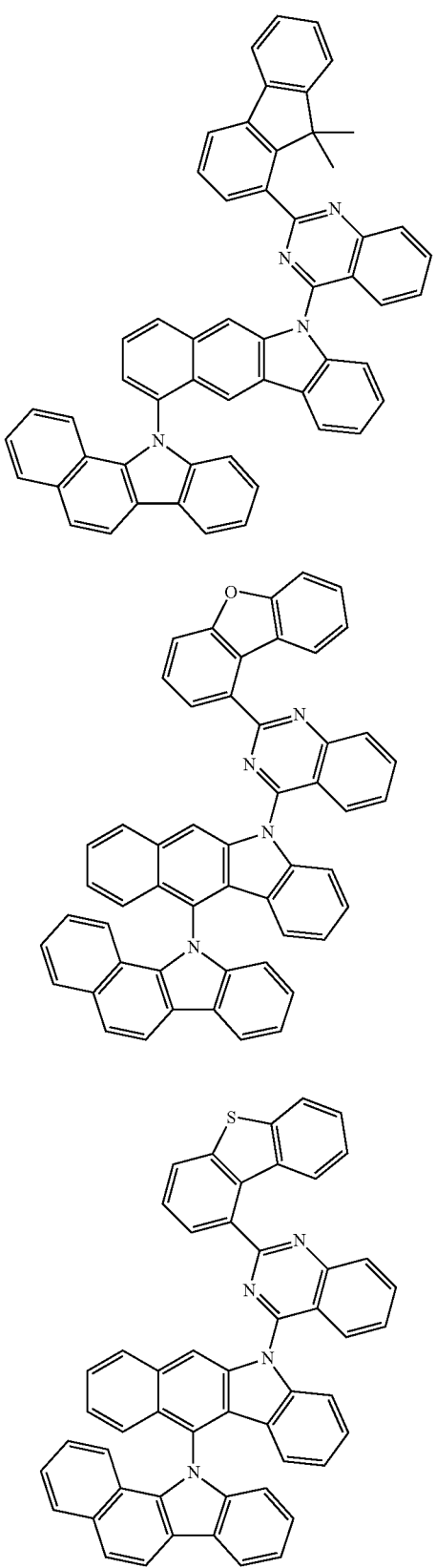

959
-continued
945
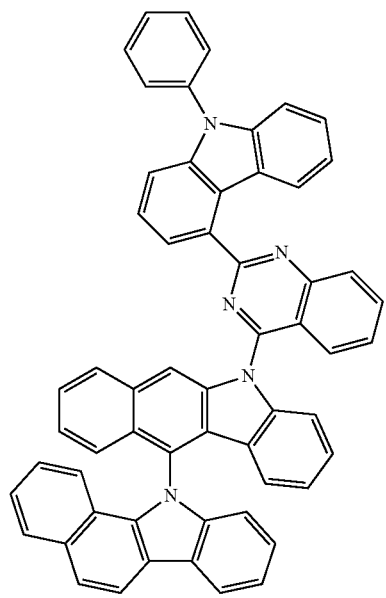
946
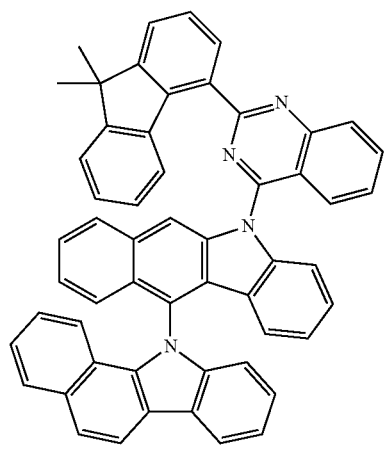
947
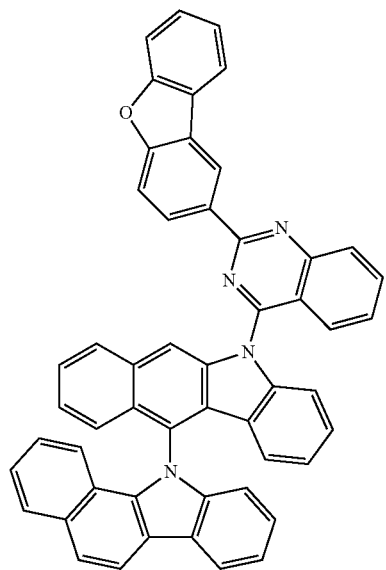
960
-continued
948
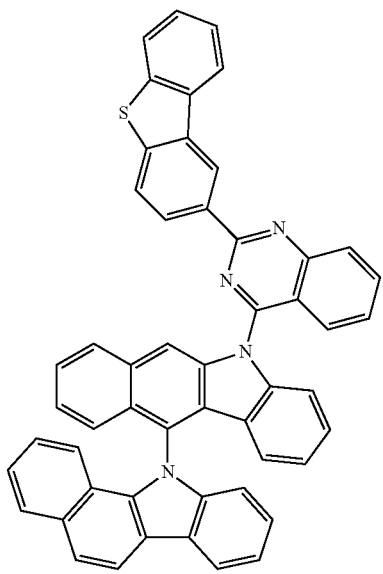
949
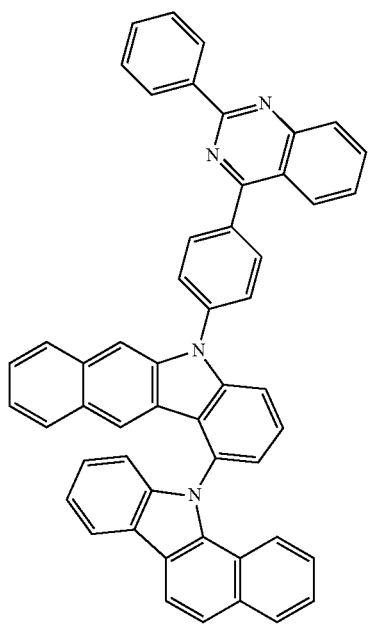

961
-continued
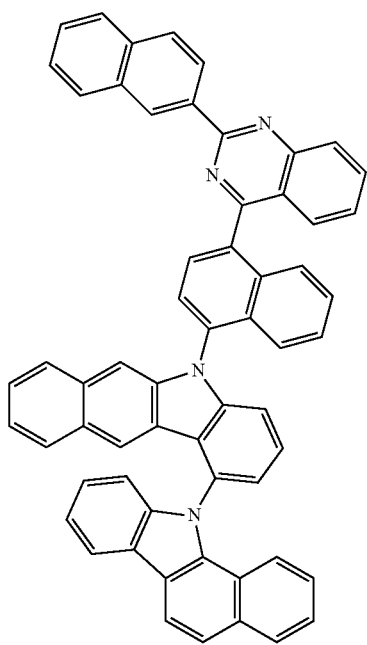
950
962
-continued
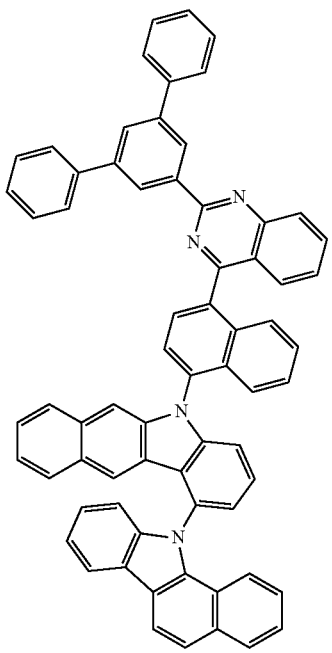
952
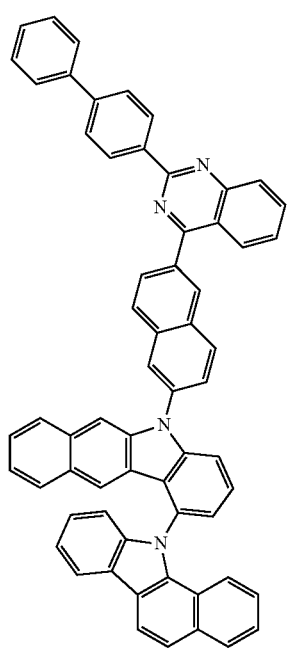
951
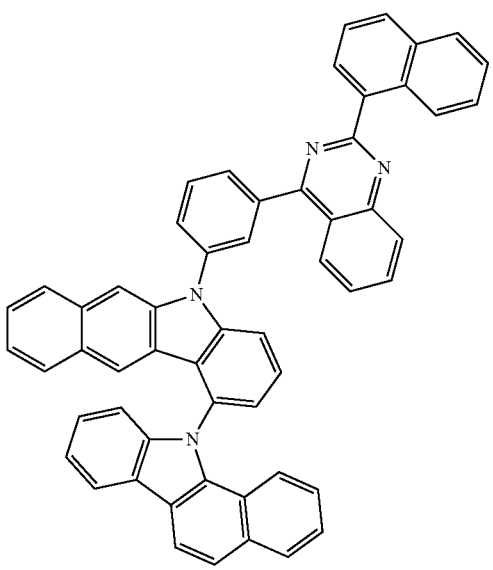
953

963
-continued
964
-continued
954
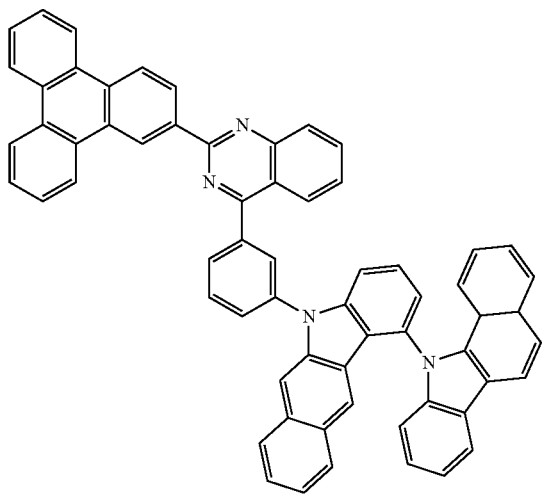
956
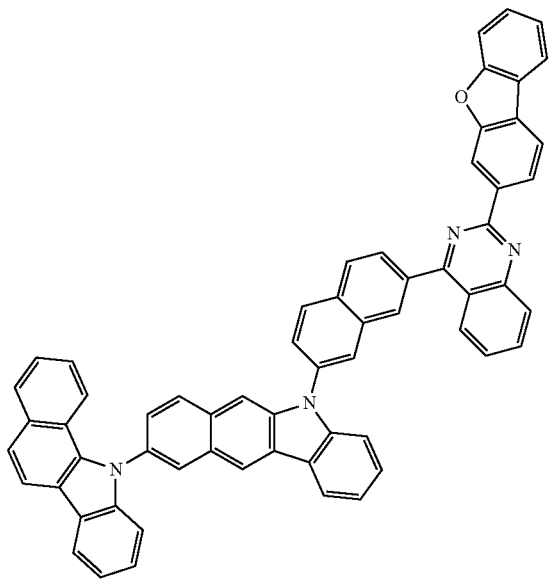
955
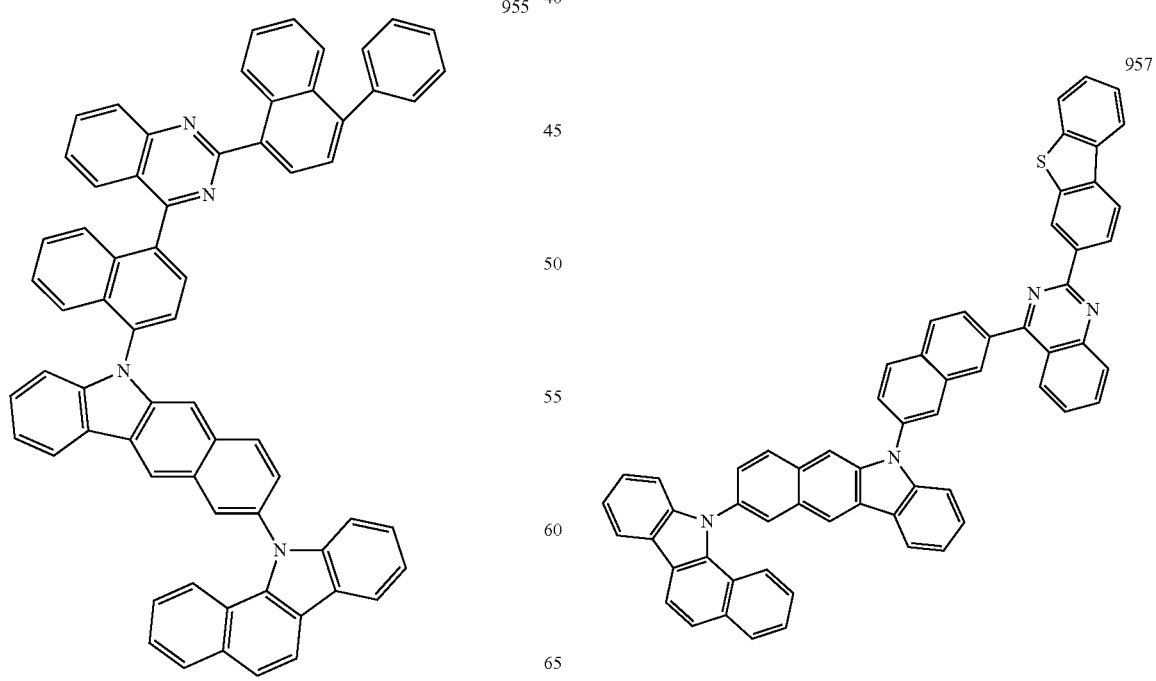
957

965
-continued
958
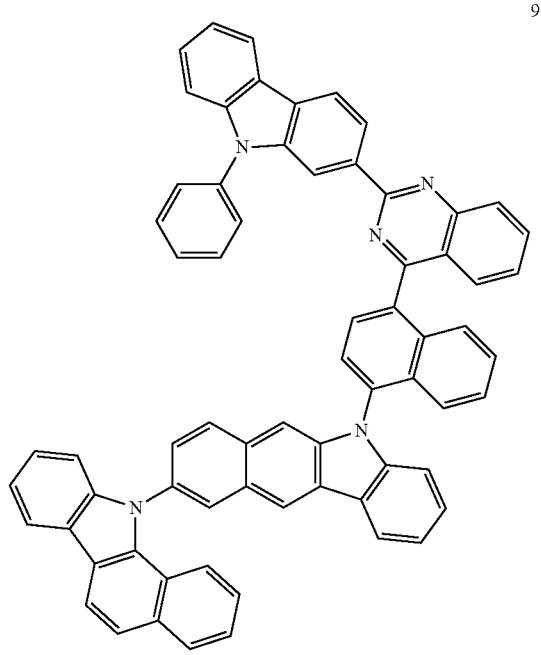
959
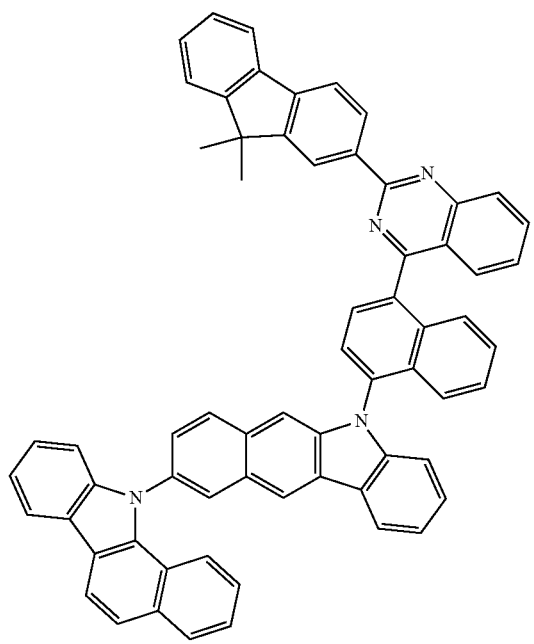
966
-continued
960
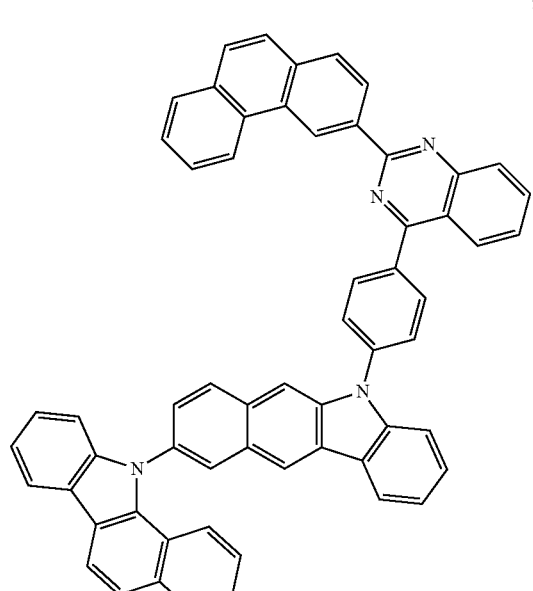
961
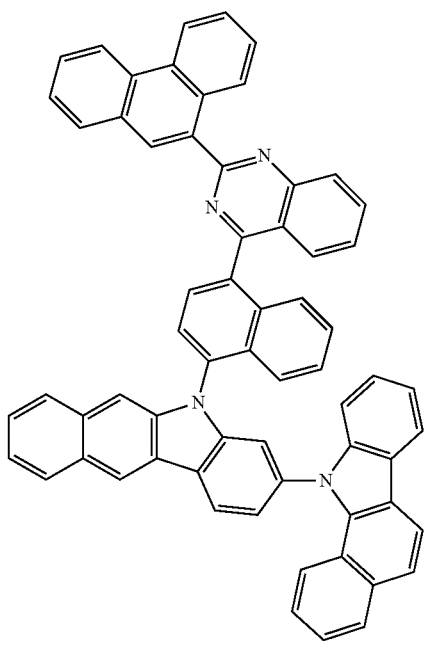

967
-continued
968
-continued
962
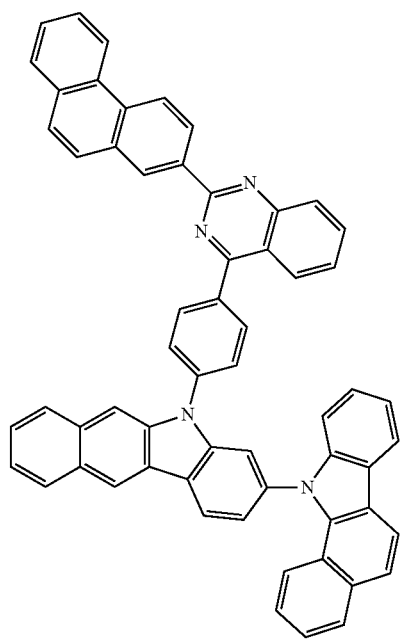
964
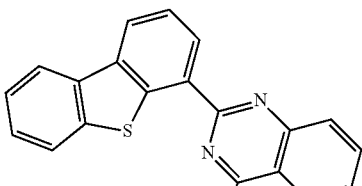
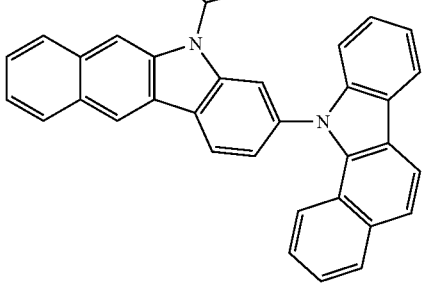
963
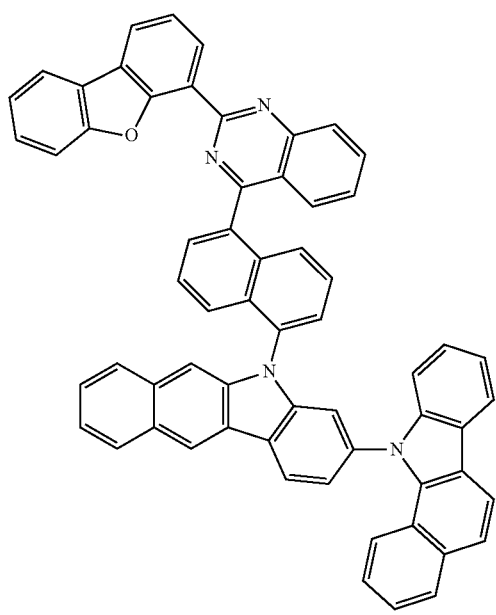
965
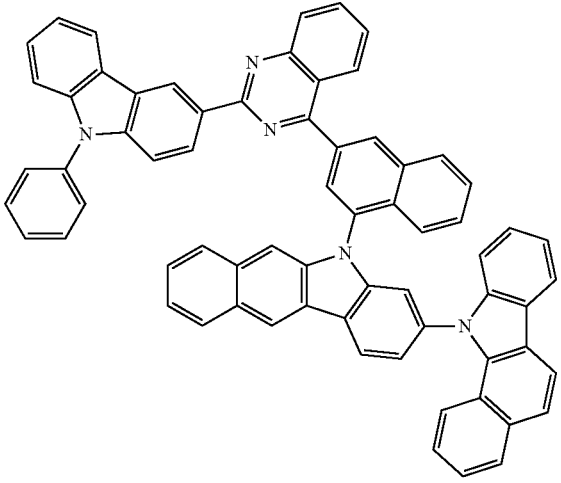

969
-continued
966
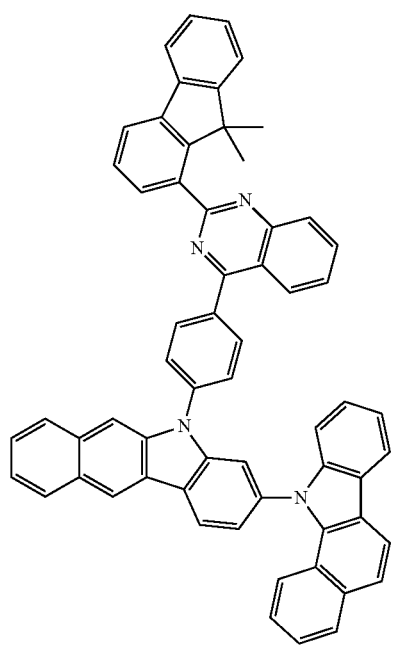
967
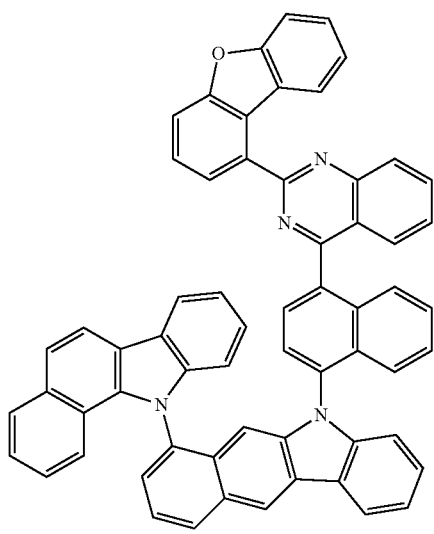
970
-continued
968
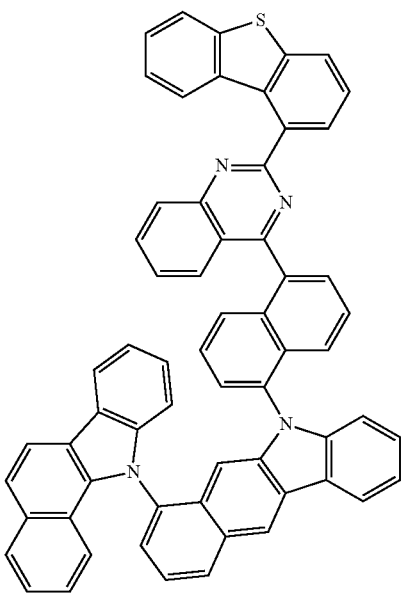
969
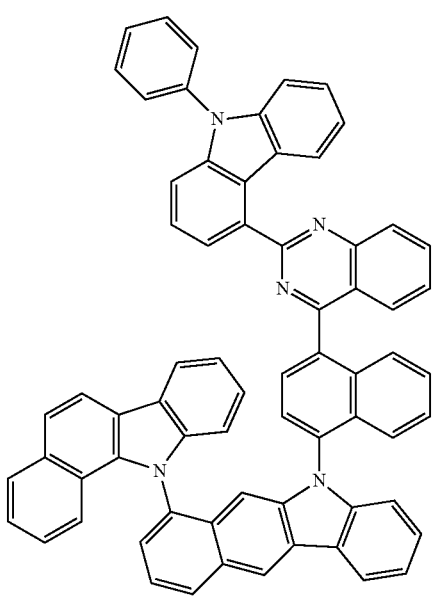

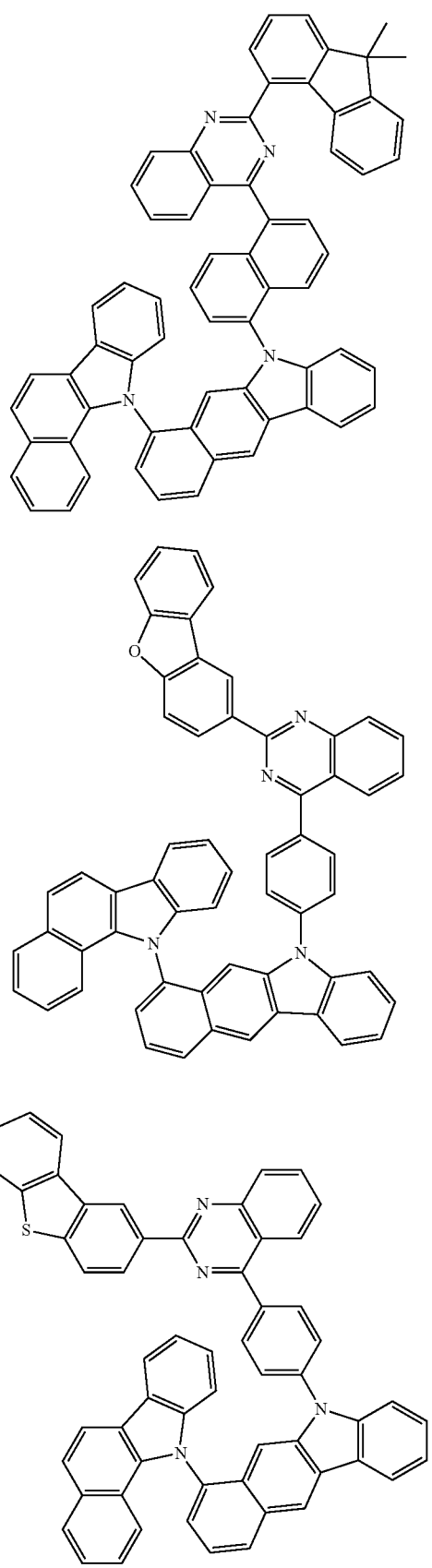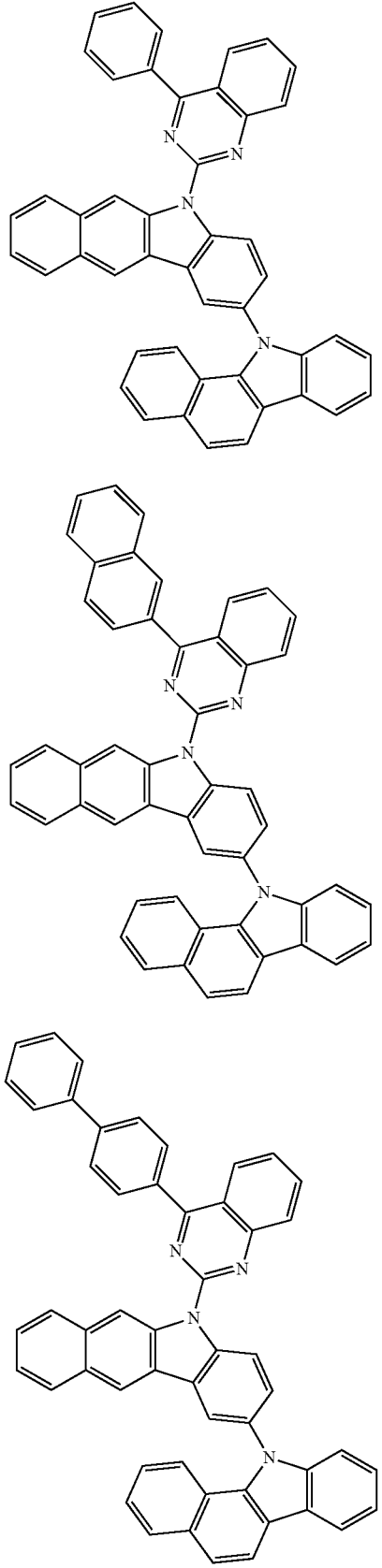

973 -continued
976
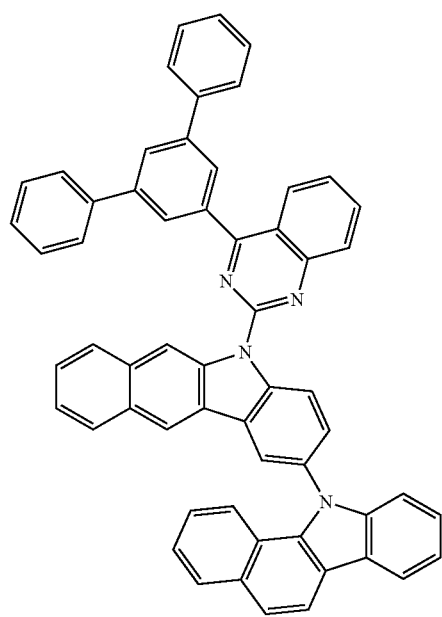
977
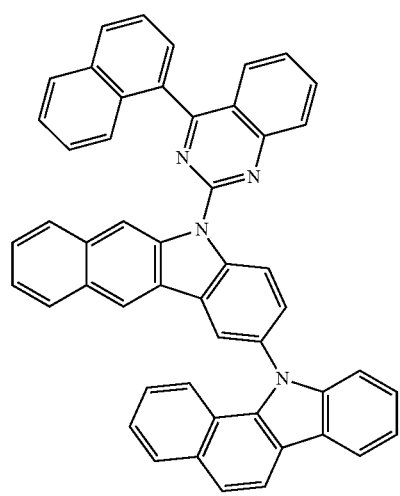
974 -continued
978
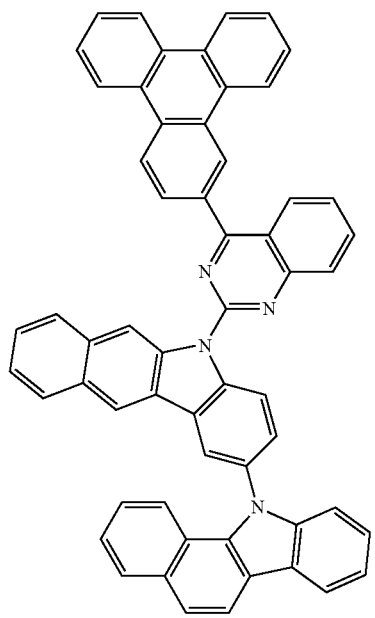
979
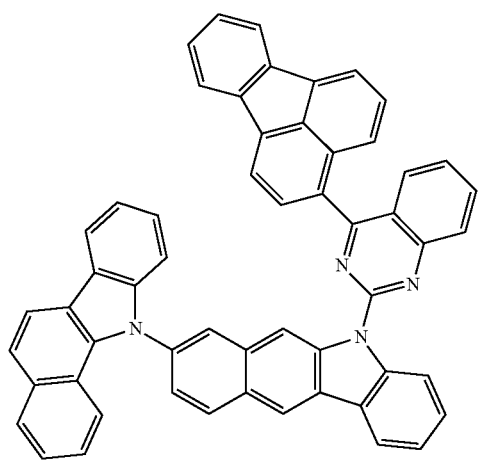
980
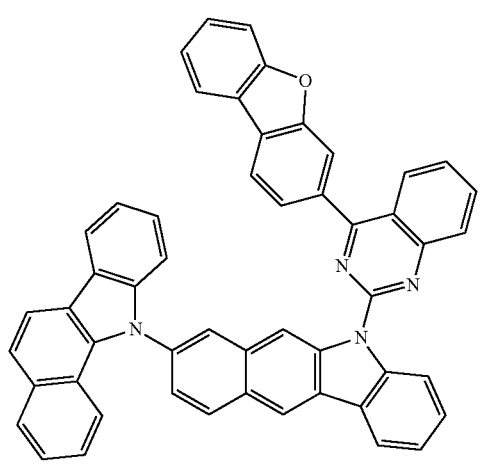

981 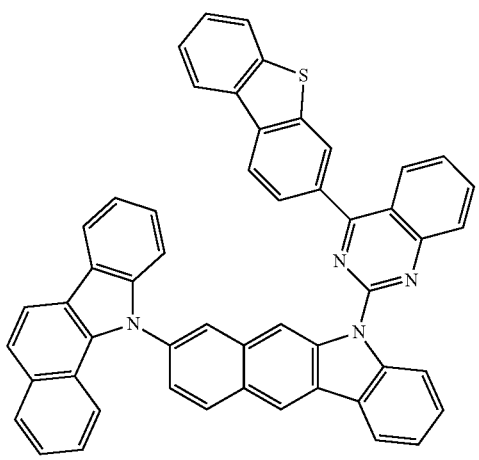
984 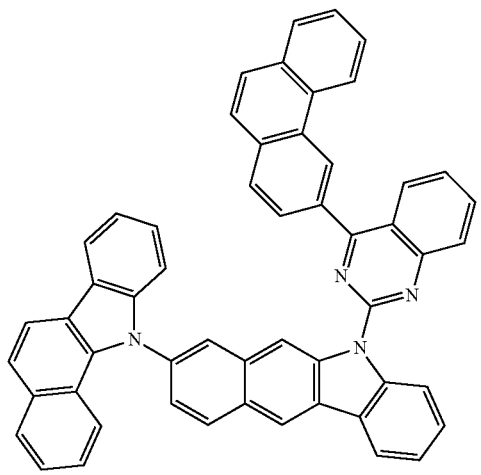
982 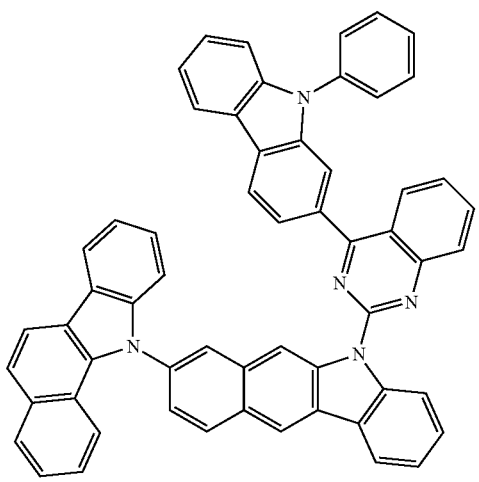
985 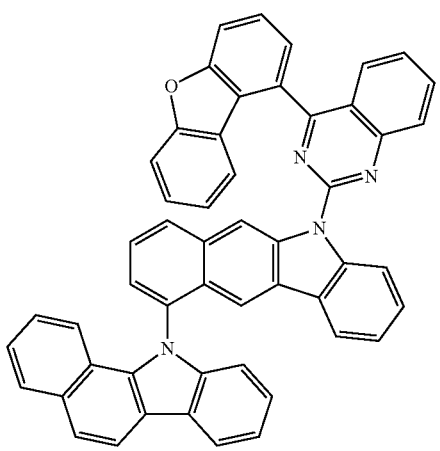
983 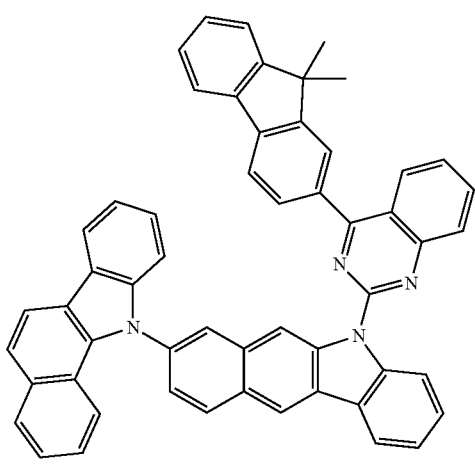
986 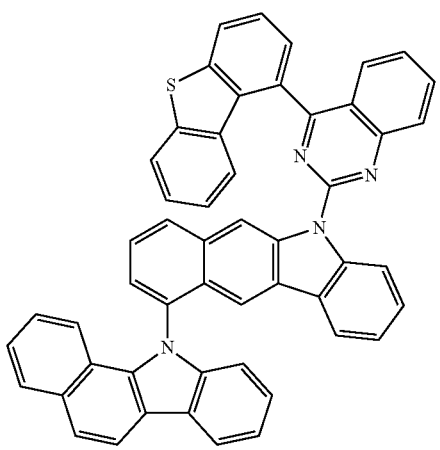

977
-continued
987
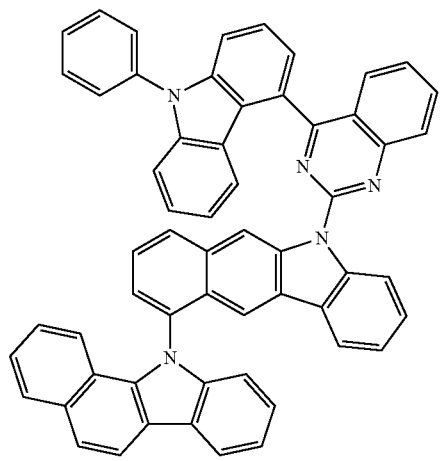
988
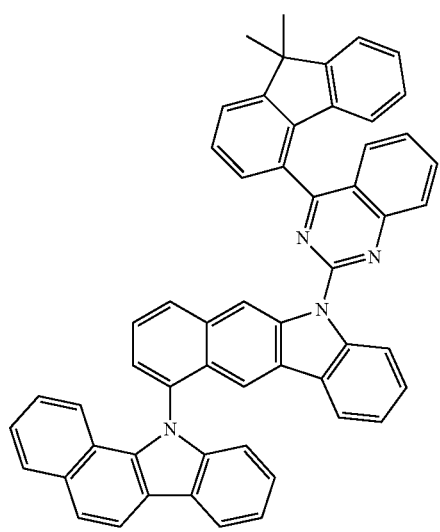
989
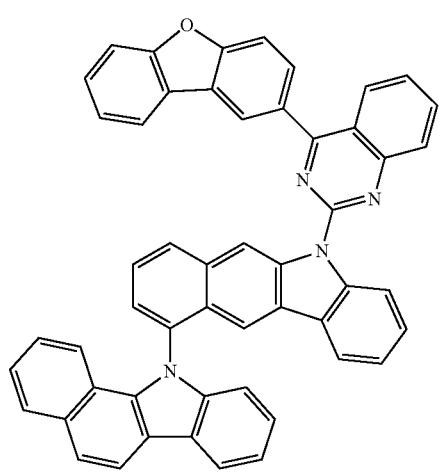
978
-continued
990
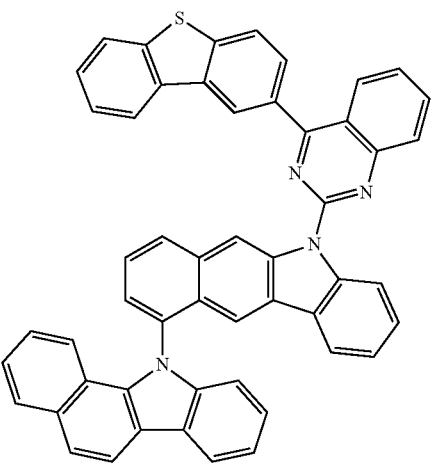
991
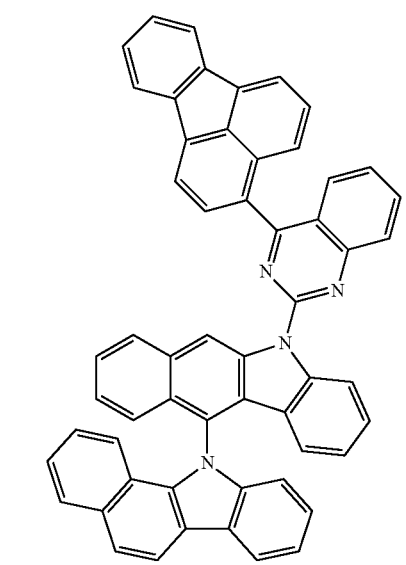
992
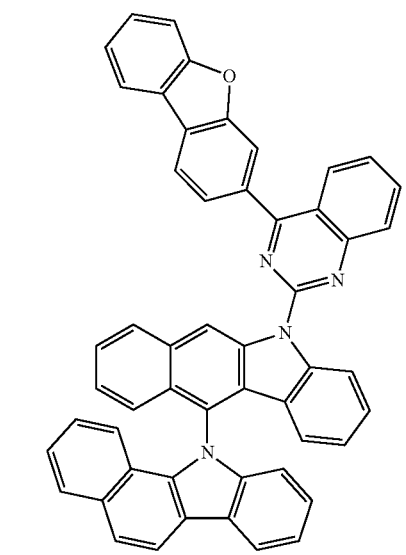

| 979 -continued | 980 -continued |
|---|---|
| 993 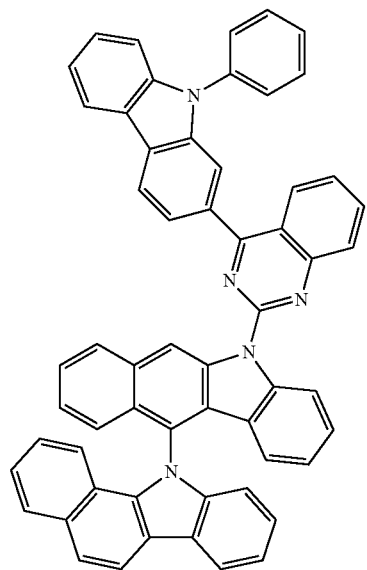 | 996 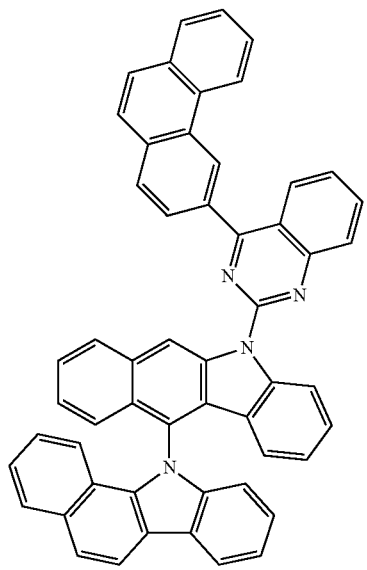 |
| 994 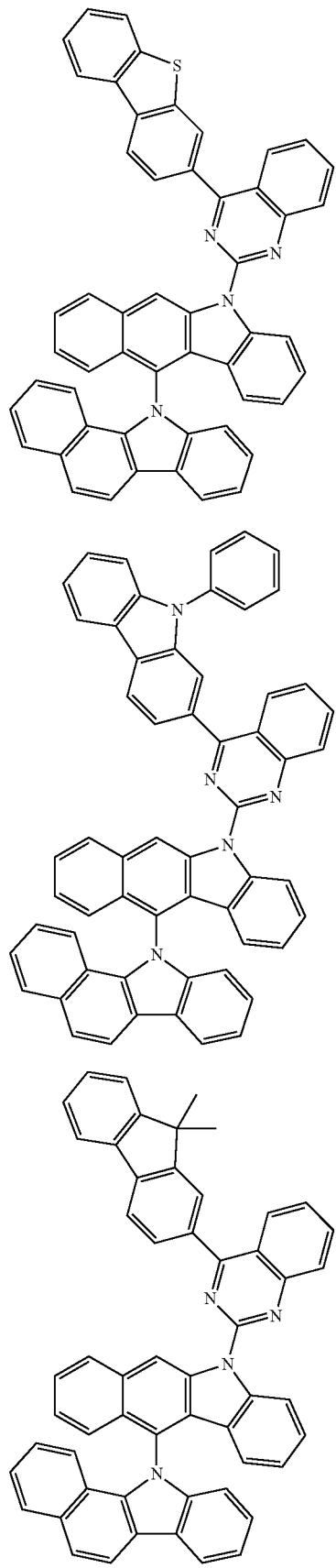 | 997 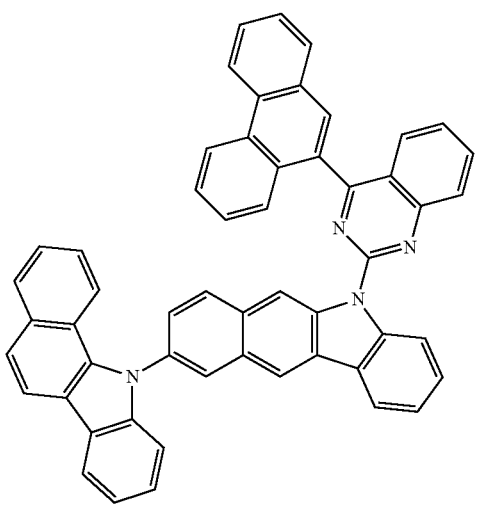 |
| 995 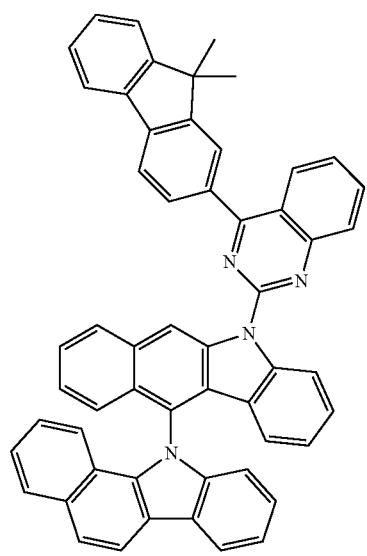 | 998 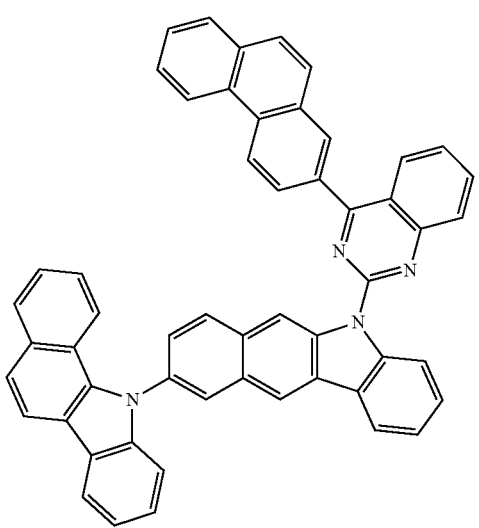 |

981
-continued
999
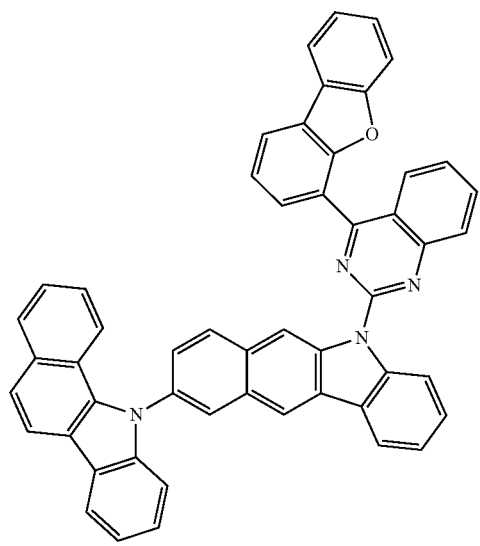
1000
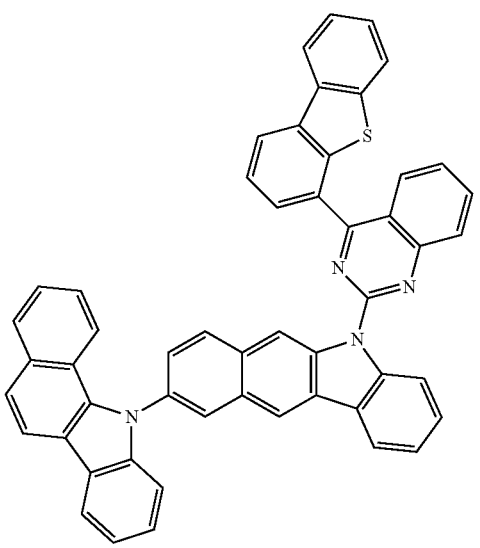
1001
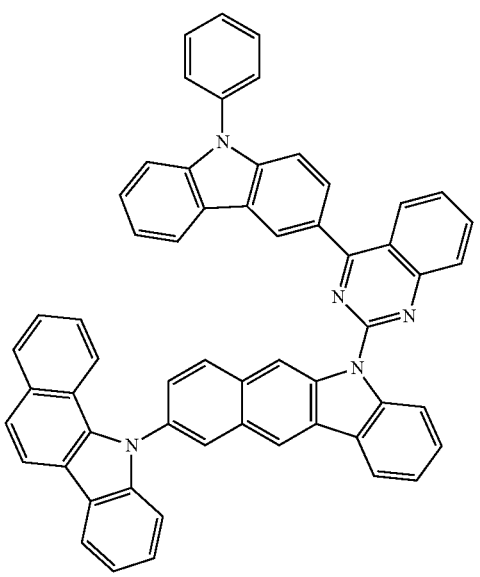
982
-continued
1002
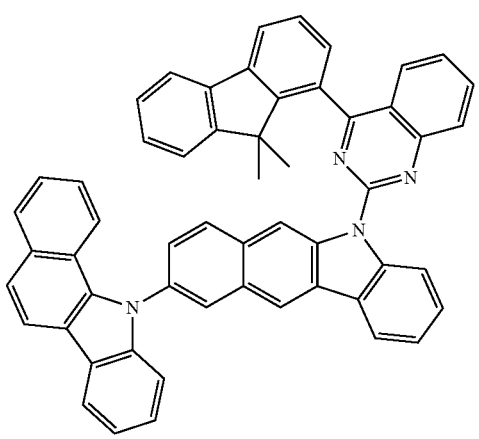
1003
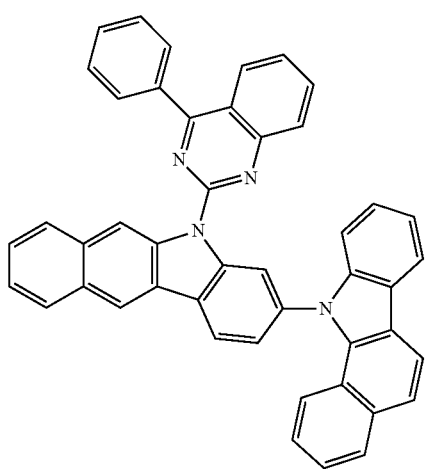
1004
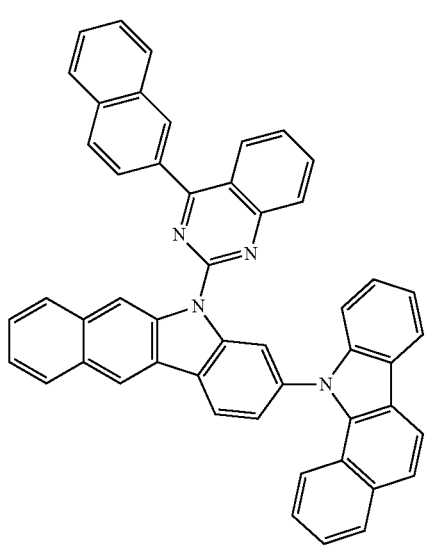

983
-continued
1005
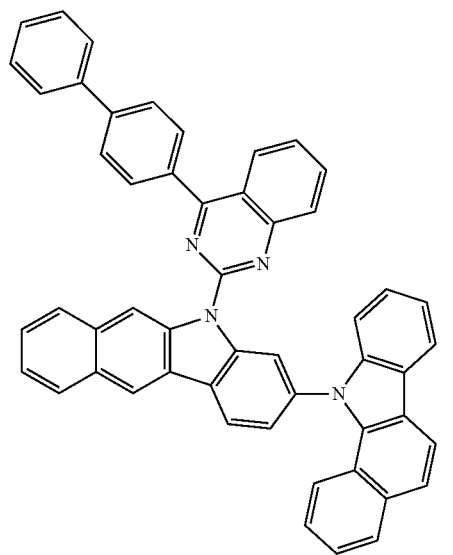
1006
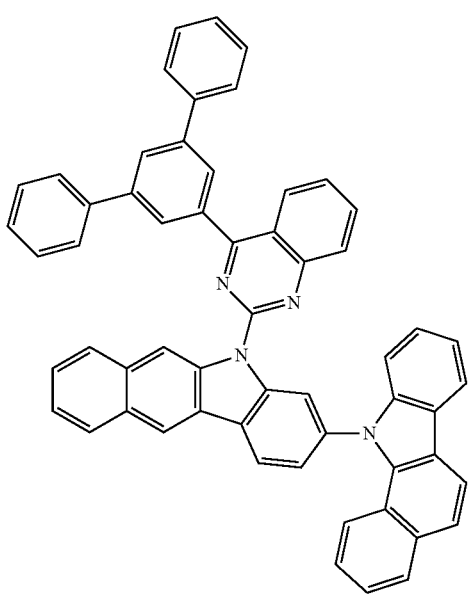
1007
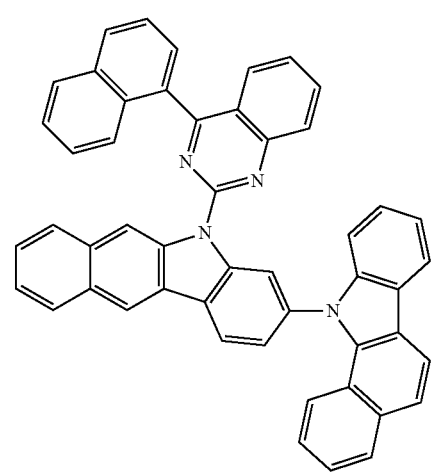
984
-continued
1008
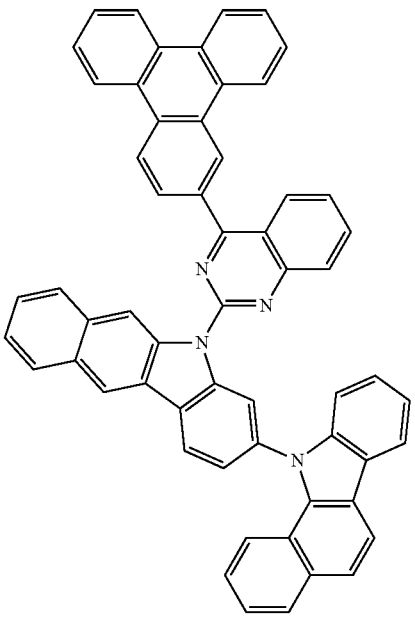
1009
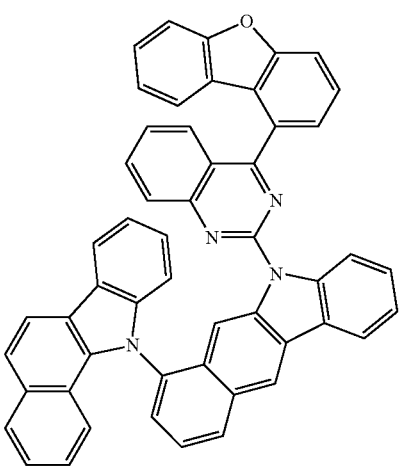
1010
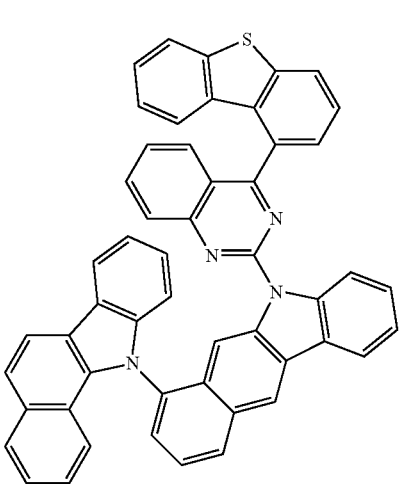

985
-continued
1011
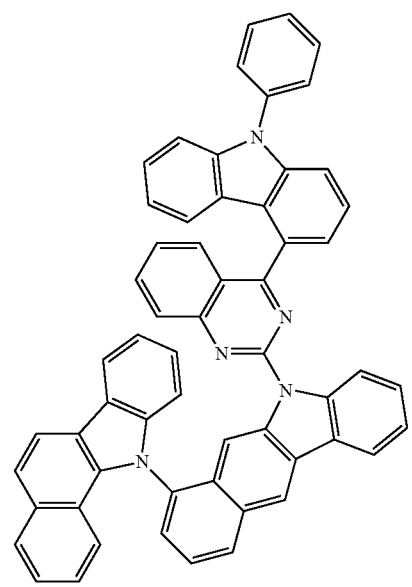
1012
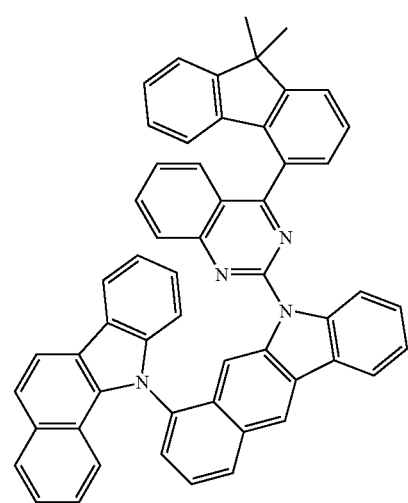
1013
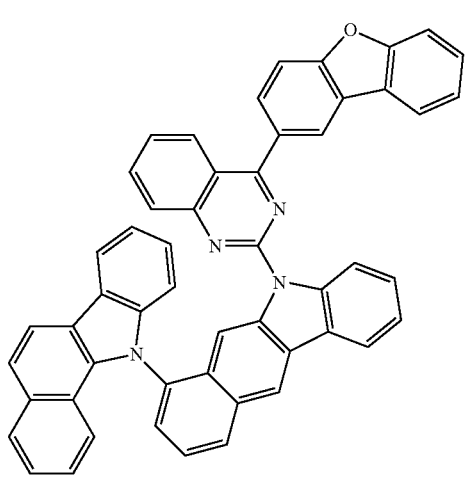
986
-continued
1014
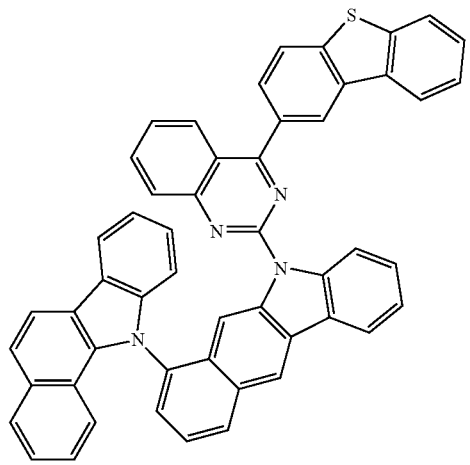
1015
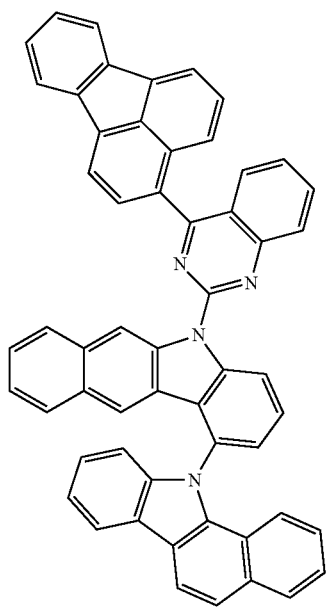
1016
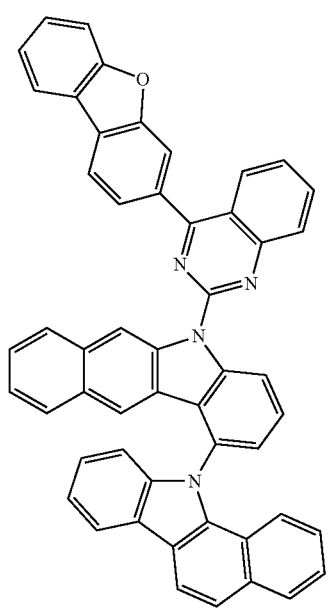

987
-continued
1017
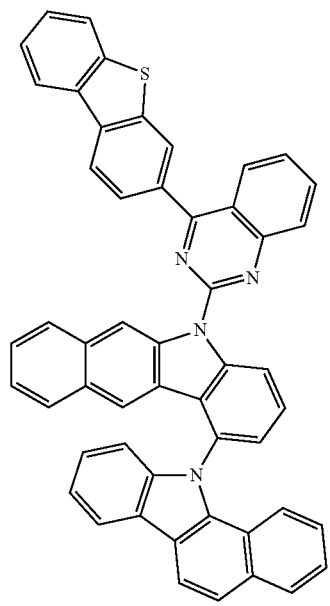
1018
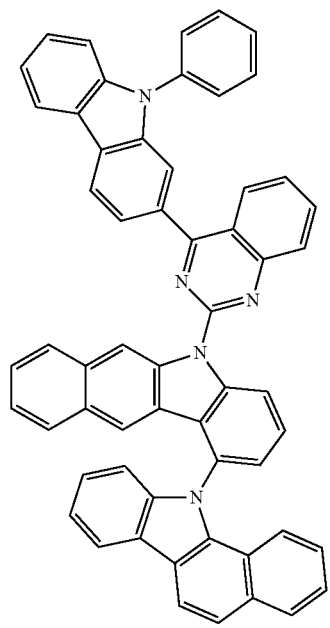
988
-continued
1019
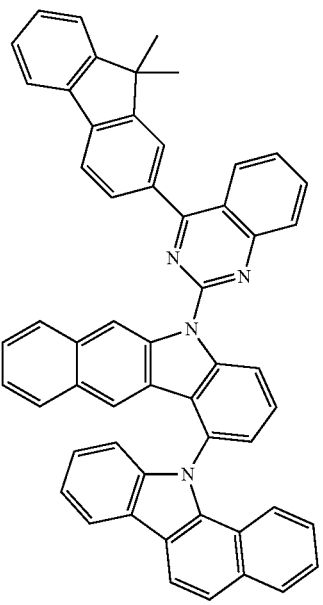
1020
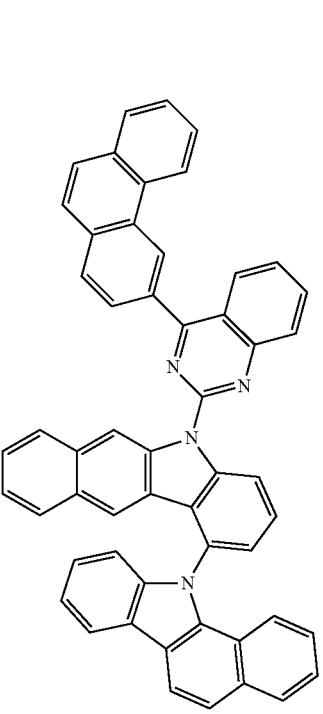

989
-continued
990
-continued
1021
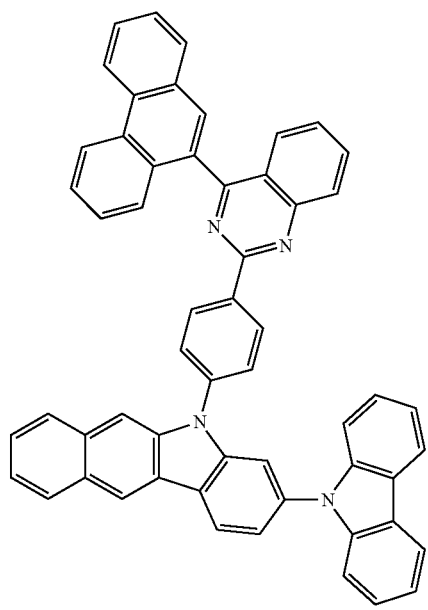
1023
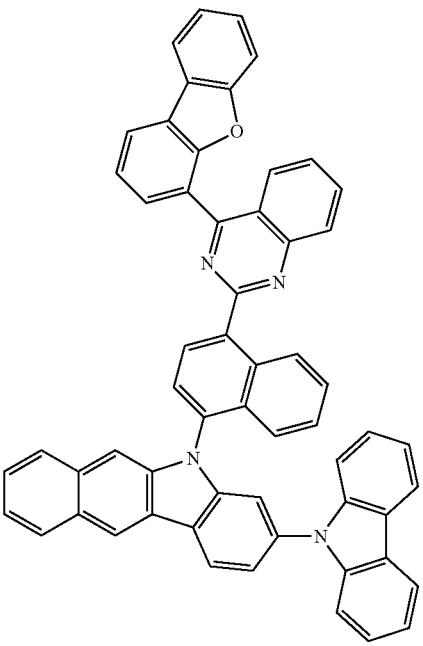
1022
1024
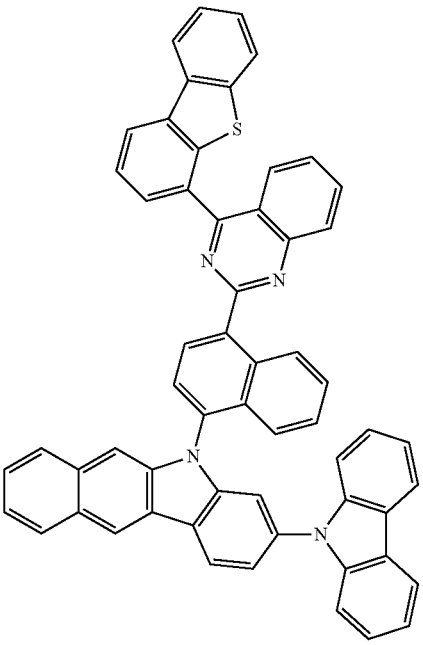

991
-continued
1025
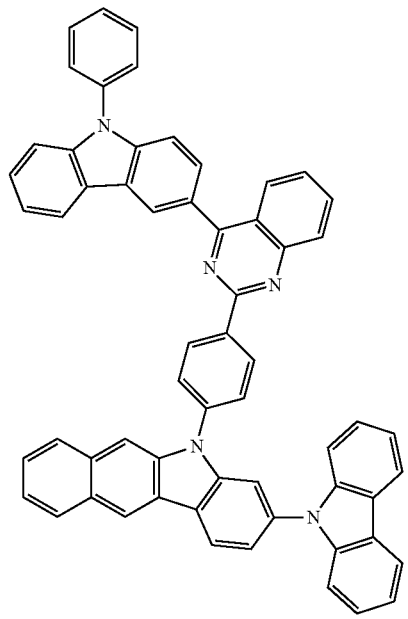
1026
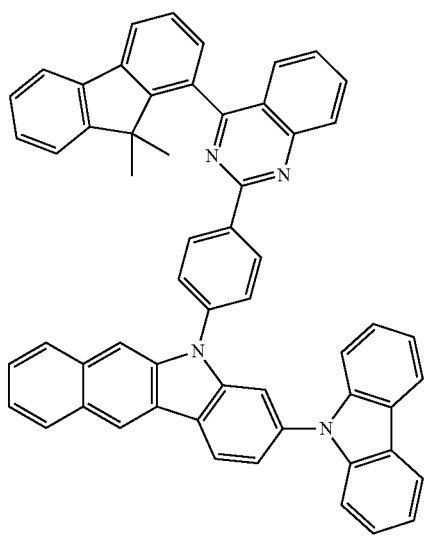
992
-continued
1027
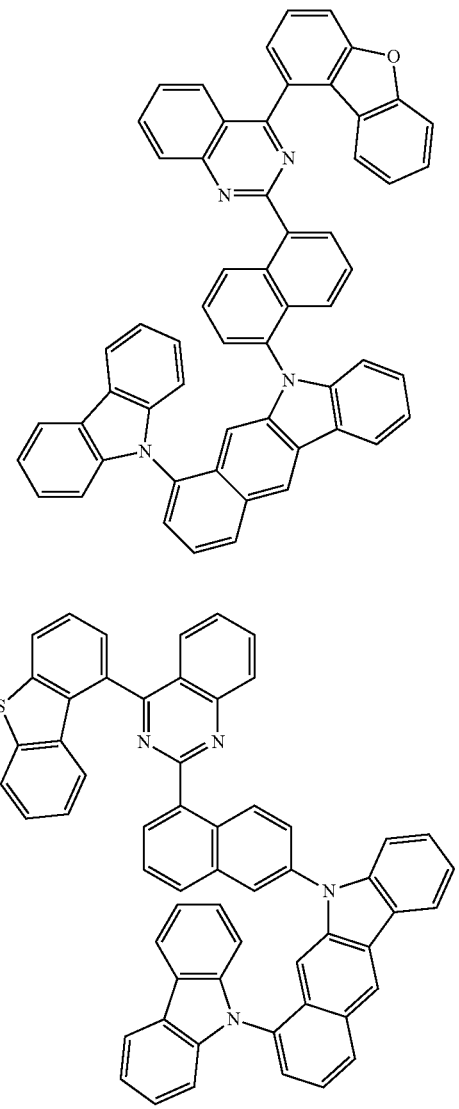
1028
1029
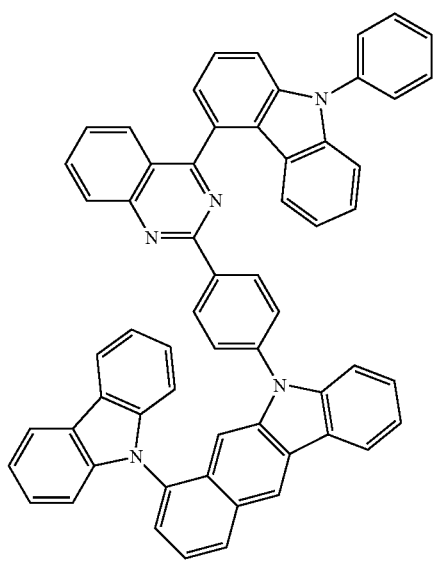

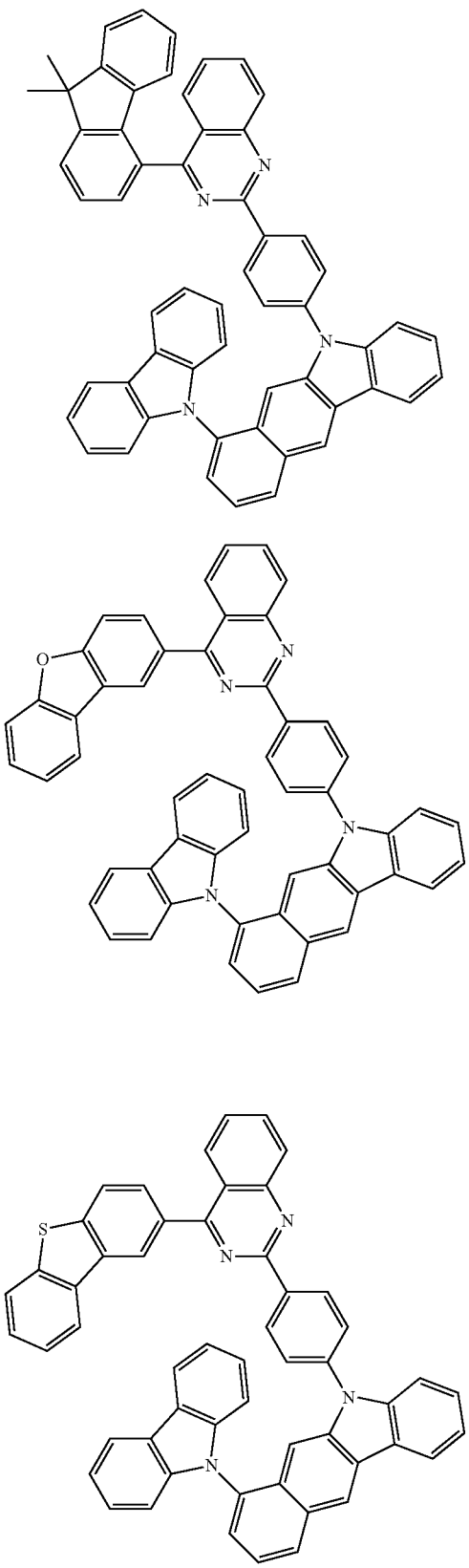
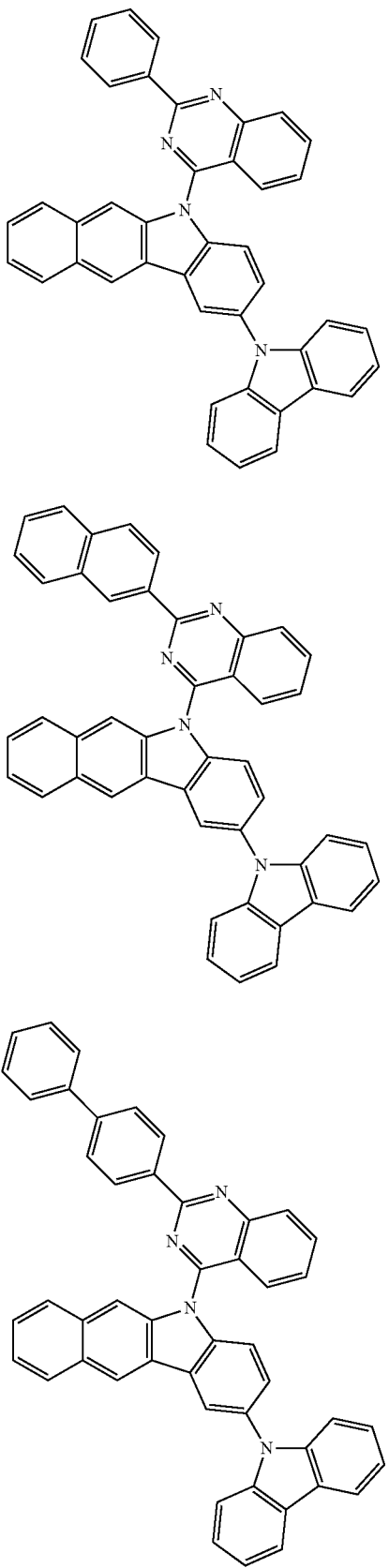

1036
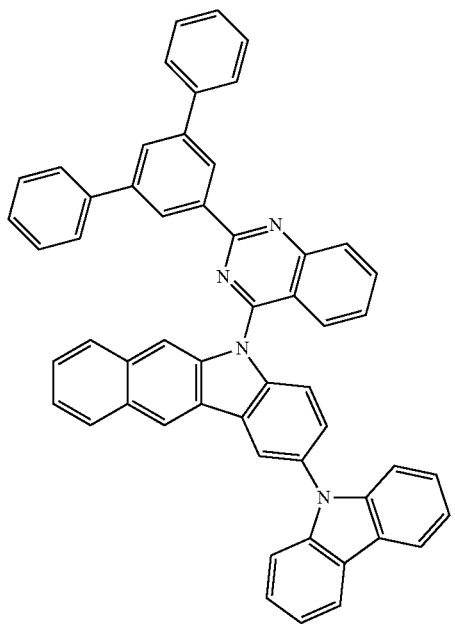
1037
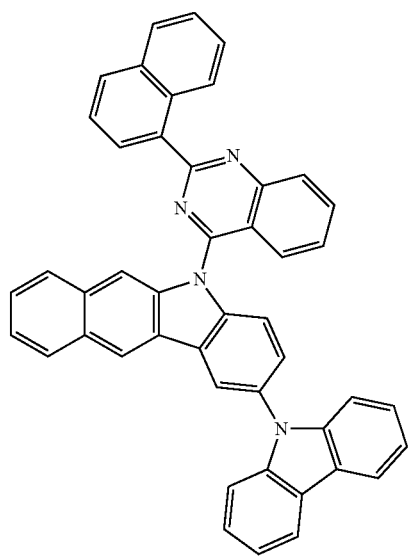
1038
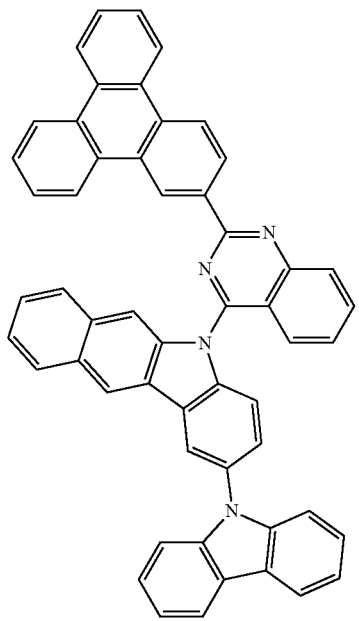
1039
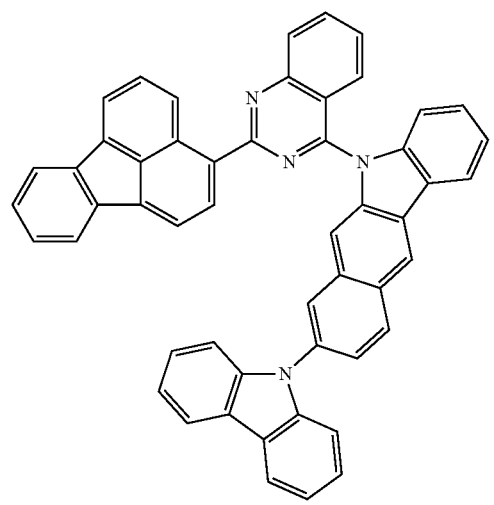
1040
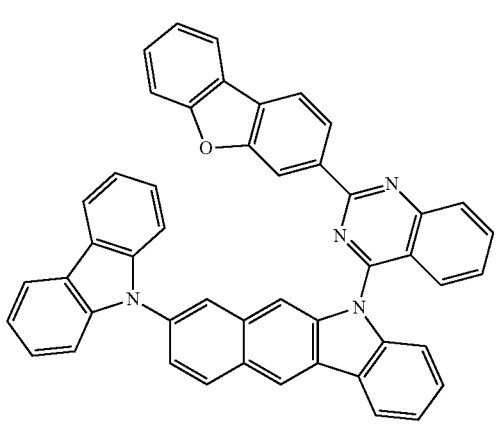

-continued
1041
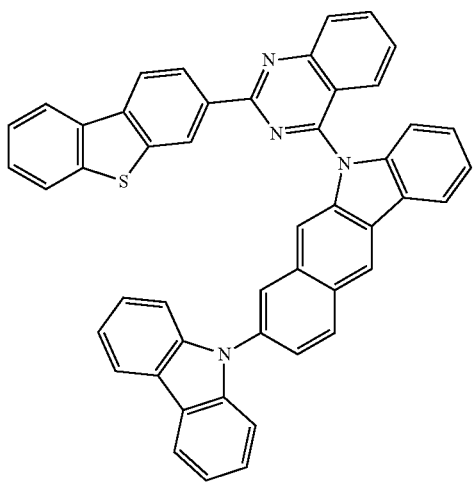
1042
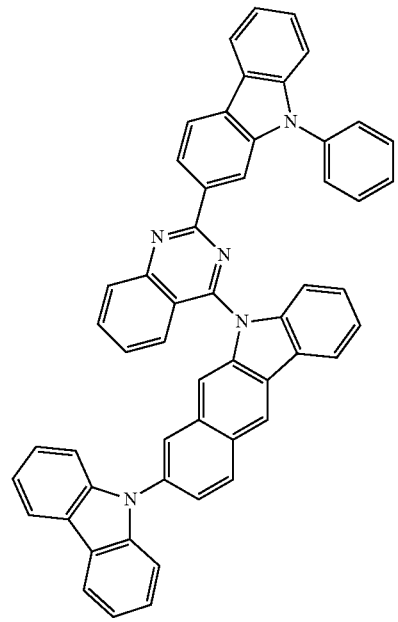
1043
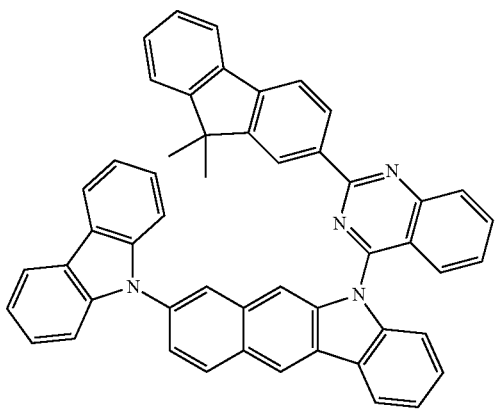
-continued
1044
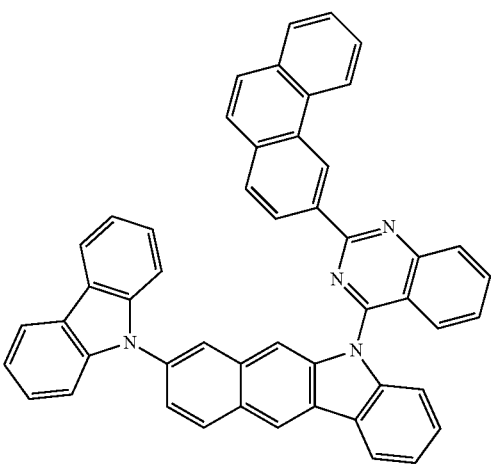
1045
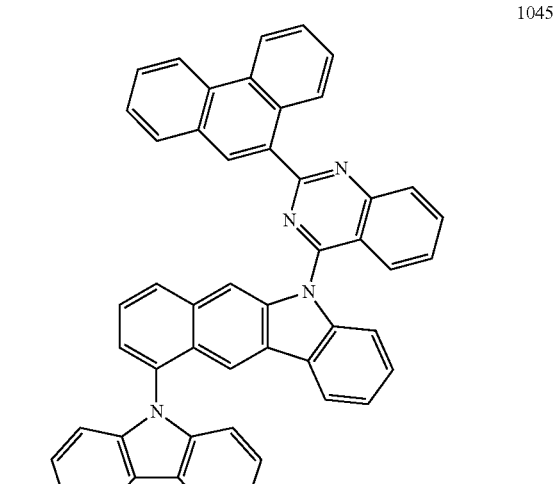
1046
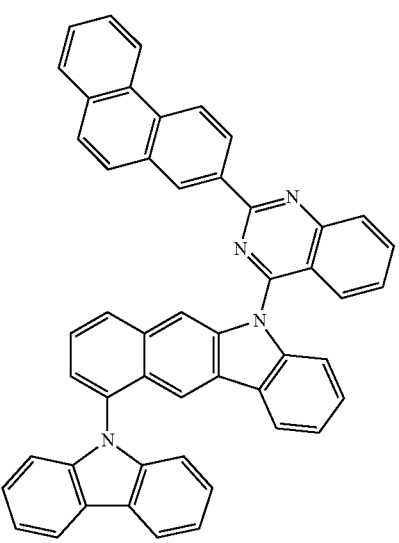

-continued
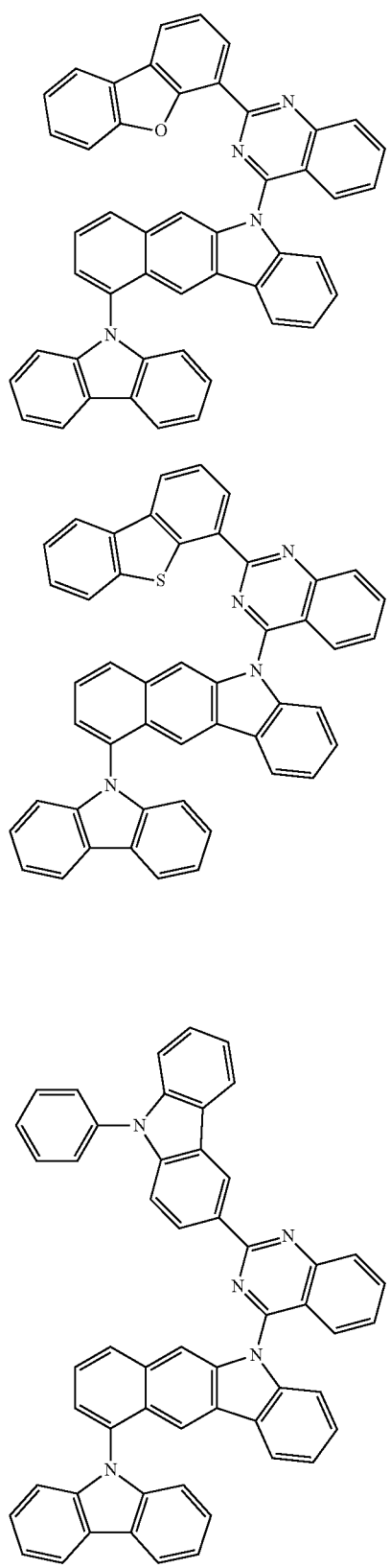
1047
1048
1049
-continued
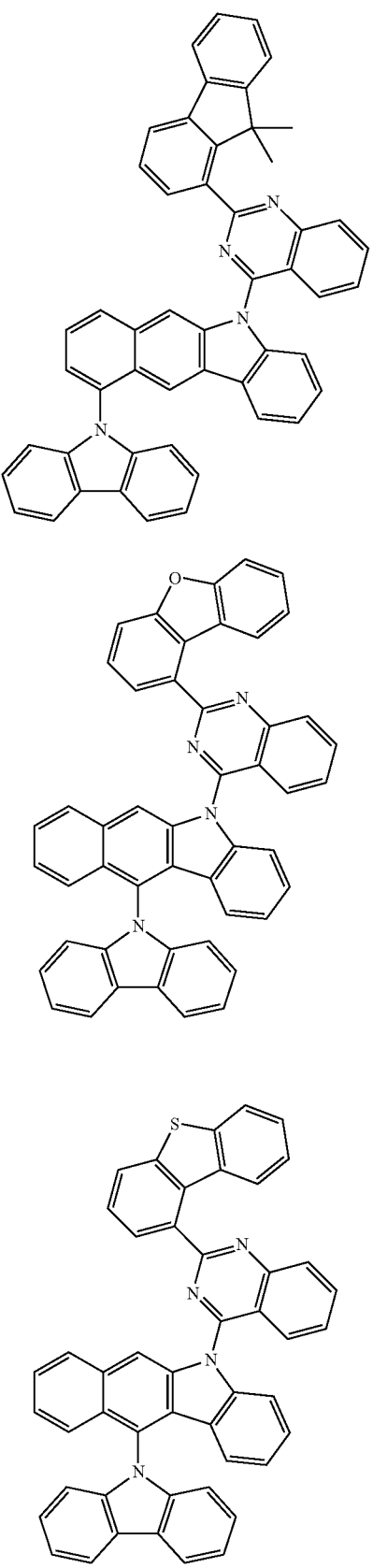
1050
1051
1052

1001
-continued

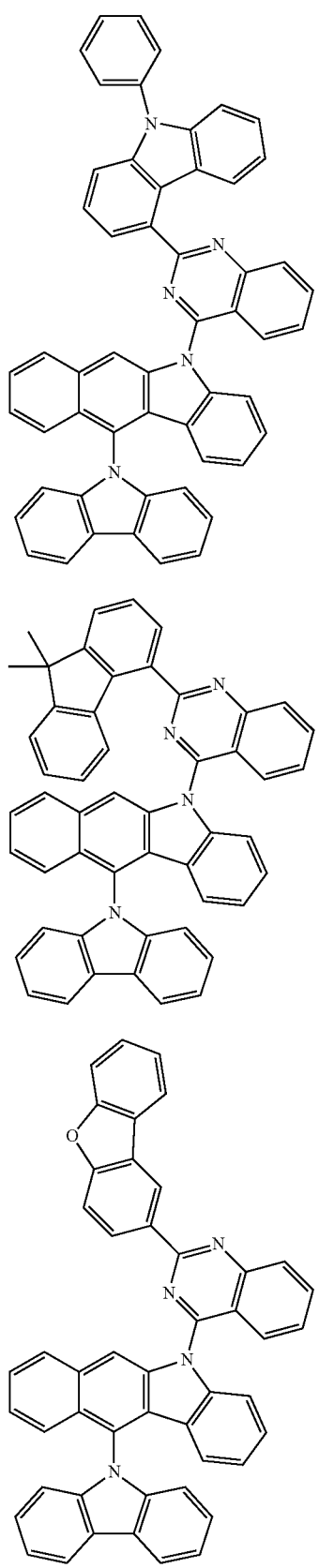

1002
-continued

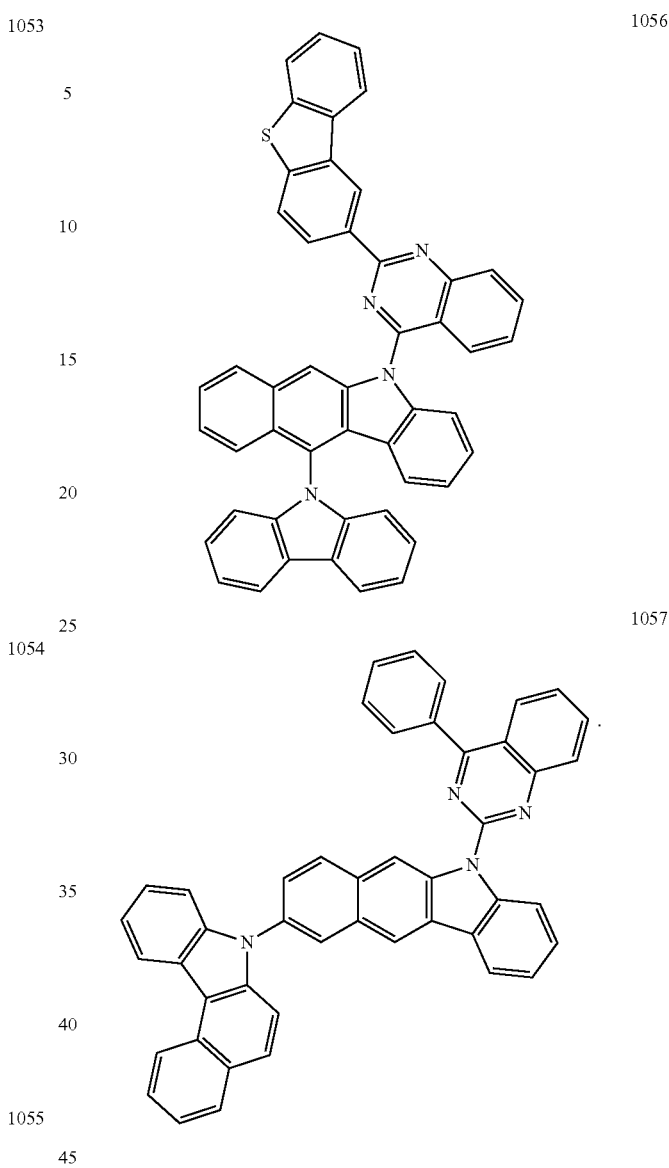

6. An organic light emitting device comprising:
a first electrode,
a second electrode provided opposite to the first electrode, and
one or more organic material layers provided between the first electrode and the second electrode,
wherein one or more layers of the one or more organic material layers comprise the heterocyclic compound of claim 1.

7. The organic light emitting device of claim 6, wherein the one or more organic material layers comprise a hole injection layer or a hole transfer layer, and the hole injection layer or the hole transfer layer comprises the heterocyclic compound.

8. The organic light emitting device of claim 6, wherein the one or more organic material layers comprise an electron transfer layer or an electron injection layer, and the electron transfer layer or the electron injection layer comprises the heterocyclic compound.

9. The organic light emitting device of claim 6, wherein the one or more organic material layers comprise a light emitting layer, and the light emitting layer comprises the heterocyclic compound.

* * * * *